(12) United States Patent
Du et al.

(10) Patent No.: US 10,072,001 B2
(45) Date of Patent: Sep. 11, 2018

(54) TANK-BINDING KINASE INHIBITOR COMPOUNDS

(71) Applicant: Gilead Sciences, Inc., Foster City, CA (US)

(72) Inventors: Zhimin Du, Belmont, CA (US); Juan Arnaldo Guerrero, Concord, CA (US); Joshua Aaron Kaplan, Foster City, CA (US); John Edward Knox, Jr., San Carlos, CA (US); Devan Naduthambi, San Bruno, CA (US); Barton W. Phillips, San Mateo, CA (US); Chandrasekar Venkataramani, Redwood City, CA (US); Peiyuan Wang, San Mateo, CA (US); William J. Watkins, Saratoga, CA (US); Jeff Zablocki, Los Altos, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/728,562

(22) Filed: Jun. 2, 2015

(65) Prior Publication Data

US 2015/0344473 A1      Dec. 3, 2015

Related U.S. Application Data

(60) Provisional application No. 62/007,322, filed on Jun. 3, 2014.

(51) Int. Cl.
| | |
|---|---|
| *C07D 471/04* | (2006.01) |
| *C07D 487/04* | (2006.01) |
| *C07D 519/00* | (2006.01) |
| *C07D 473/00* | (2006.01) |

(52) U.S. Cl.
CPC ......... *C07D 471/04* (2013.01); *C07D 473/00* (2013.01); *C07D 487/04* (2013.01); *C07D 519/00* (2013.01)

(58) Field of Classification Search
CPC .. C07D 471/04; C07D 473/00; C07D 487/04; C07D 519/00
See application file for complete search history.

(56) References Cited

U.S. PATENT DOCUMENTS

| | | | |
|---|---|---|---|
| 8,969,335 | B2 | 3/2015 | Hoelzemann et al. |
| 2012/0238540 | A1 | 9/2012 | Holcombe et al. |
| 2013/0217951 | A1 | 8/2013 | Dorsch et al. |
| 2013/0289017 | A1 | 10/2013 | Dorsch et al. |
| 2014/0275027 | A1 | 9/2014 | Gong et al. |
| 2014/0323481 | A1 | 10/2014 | Dorsch et al. |
| 2015/0005284 | A1 | 1/2015 | Eggenweiler et al. |
| 2015/0352108 | A1 | 12/2015 | Holcomb et al. |
| 2016/0096827 | A1 | 4/2016 | Du et al. |
| 2016/0289684 | A1 | 10/2016 | Feng et al. |
| 2016/0376283 | A1 | 12/2016 | Sherer et al. |
| 2017/0174713 | A1 | 6/2017 | Zhimin et al. |

FOREIGN PATENT DOCUMENTS

| | | |
|---|---|---|
| CN | 103251600 A | 8/2013 |
| WO | WO-2005075465 A1 | 8/2005 |
| WO | WO-2007002433 A1 | 1/2007 |
| WO | WO-2008090181 A1 | 7/2008 |
| WO | WO-2009/030890 A1 | 3/2009 |
| WO | WO-2009/087225 A2 | 7/2009 |
| WO | WO-2009091388 A2 | 7/2009 |
| WO | WO-2009118567 A2 | 10/2009 |
| WO | WO-2009122180 A1 | 10/2009 |
| WO | WO-2010100431 A1 | 9/2010 |
| WO | WO-2010127754 A1 | 11/2010 |
| WO | WO-2011046970 A1 | 4/2011 |
| WO | WO-2011048082 A1 | 4/2011 |
| WO | WO-2012010826 A1 | 1/2012 |
| WO | WO-2012104007 A2 | 8/2012 |
| WO | WO-2012142329 A1 | 10/2012 |
| WO | WO-2012161877 A1 | 11/2012 |
| WO | WO-2012161879 A1 | 11/2012 |
| WO | WO-2012/171337 A1 | 12/2012 |
| WO | WO-2013/026890 A1 | 2/2013 |
| WO | WO-2013024282 A2 | 2/2013 |
| WO | WO-2013026516 A1 | 2/2013 |
| WO | WO-2013026890 A1 | 2/2013 |
| WO | WO-2013034238 A1 | 3/2013 |

(Continued)

OTHER PUBLICATIONS

International Search Report—Written Opinion dated Aug. 20, 2015 for PCT/US2015/033769.

(Continued)

*Primary Examiner* — Rebecca L Anderson
(74) *Attorney, Agent, or Firm* — Morrison & Foerster LLP

(57) ABSTRACT

Compounds having the following formula (I) and methods of their use and preparation are disclosed:

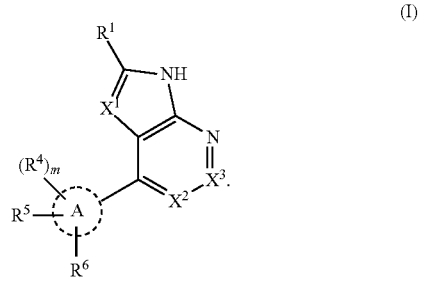

30 Claims, No Drawings

(56) References Cited

FOREIGN PATENT DOCUMENTS

| WO | WO-2013075785 A1 | 5/2013 |
|---|---|---|
| WO | WO-2013/085802 A1 | 6/2013 |
| WO | WO-2013117285 A1 | 8/2013 |
| WO | WO-2014004863 A2 | 1/2014 |
| WO | WO-2014128486 A1 | 8/2014 |
| WO | WO-2014139328 A1 | 9/2014 |
| WO | WO2015089327 | 6/2015 |
| WO | WO-2015134171 A1 | 9/2015 |
| WO | WO-2016049211 A1 | 3/2016 |
| WO | WO-2016057338 A1 | 4/2016 |
| WO | WO-2017003995 A1 | 1/2017 |

OTHER PUBLICATIONS

Bamborough et al (2006) "5-(1H-Benzimidazol-1-yl)-3-alkoxy-2-thiophenecarbonitriles as potent, selective, inhibitors of IKK-e kinase," *Bioorganic & Medicinal Chemistry Letters* 16: 6236-6240.

International Preliminary Report on Patentability dated Dec. 15, 2016 for PCT/US2015/033769.

International Search Report—Written Opinion dated Nov. 13, 2015 for PCT/2015/051757.

Liu, (2013) "Crystal Structure of a Human IkB Kinase β Asymmetric Dimer," *J. Biol. Chem.*, 288:22758-22767.

McIver et al., (2012) "Synthesis and structure-activity relationships of a novel series of pyrimidines as potent inhibitors of TBK1/IKKe kinases," *Bioorganic & Medicinal Chemistry Letters*, 22:7169-7173.

Office Action dated Feb. 3, 2017 for European Application No. 15738156.7.

U.S. Appl. No. 15/380,836, filed Dec. 15, 2016.

Wang et al. (2012) "Discovery of azabenzimidazole derivatives as potent, selective inhibitors of TBK1/IKKe kinases," *Bioorganic & Medicinal Chemistry Letters*; 22: 2063-2069.

Yu et al. (2015) "Regulation of T-Cell Activation and Migration by the Kinase TBK1 During Neuroinflammation" *Nature Communications*, 6:6074; 1-13.

Zhang et al. (2016) "IkB Kinase ∈ is and NFATc1 Kinase That Inhibits T Cell Immune Response" *Cell Reports* 16:1-47.

International Preliminary Report on Patentability dated Mar. 28, 2017 for PCT/US2015/051757.

International Search Report—Written Opinion dated Feb. 3, 2016 for PCT/US2016/067022.

Office Action dated May 24, 2017 for Australian Application No. 2015271837.

Office Action dated May 1, 2017 for New Zealand Application No. 726317.

Office Action dated Oct. 9, 2017 for Chinese Application No. 201580030007.0.

Office Action dated Oct. 9, 2017 for Chinese Application No. 201580030007.0—English Translation.

Office Action dated Nov. 13, 2017 for New Zealand Application No. 726317.

Office Action dated Nov. 14, 2017 for Japanese Application No. 2016-570275.

Office Action dated Nov. 14, 2017 for Japanese Application No. 2016-570275—English translation.

English language abstract of CN 103251600. 2013.

Office Action dated Nov. 16, 2017, for Canadian Patent Application No. 2951126, filed Jun. 2, 2015, 3 pages.

Office Action dated Dec. 22, 2017, for Eurasian Patent Application No. 201692203, filed Jun. 2, 2015, 6 pages (including English translation).

Office Action dated Feb. 27, 2018, for European Office Action 15738156.7, filed Jun. 2, 2015, 4 pages.

Office Action dated Mar. 2, 2018, for Korean Patent Application No. 10-2016-7036819, filed Jun. 2, 2015, 21 pages (including English translation).

Office Action dated Mar. 5, 2018 for Japanese Patent Application No. 2016-570275, filed Jun. 2, 2015, 4 pages (including English translation).

Hideshima, T. et al. (Dec. 1, 2003). "Antitumor Activity of Lysophosphatidic Acid Acyltransferase-β Inhibitors, a Novel Class of Agents, in Multiple Myeloma," *Cancer Research* 63(23):8428-8436.

Office Action dated May 14, 2018 for Australian Patent Application No. 2015271837, filed Jun. 2, 2015, 2 pages.

Korean Office Action dated Jul. 2, 2018, for Patent Application No. 10-2016-7036819, filed Jun. 2, 2015, 14 pages (including English translation).

TANK-BINDING KINASE INHIBITOR COMPOUNDS

CROSS-REFERENCE TO RELATED APPLICATIONS

This application claims the benefit of priority of U.S. Provisional Application No. 62/007,322, filed Jun. 3, 2014, which is hereby incorporated by reference herein in its entirety.

FIELD OF THE INVENTION

This application relates to chemical compounds which may inhibit or otherwise modulate the activity of TANK-binding kinase (TBK1) and I-Kappa-B kinase (IKKε, IKBKE), and to compositions and formulations containing such compounds, and methods of using and making such compounds.

BACKGROUND OF THE INVENTION

TBK1 is a serine/threonine kinase with diverse roles in cancer, inflammation, and the host-pathogen response. Shen, R. R. and W. C. Hahn (2011) Oncogene 30(6): 631-641. TBK1 activates its substrates IRF3 and IRF7 transcription factors by direct phosphorylation of specific sites that induces their localization to the nucleus to drive transcription of type I IFN genes (Sankar, S., H. Chan, et al., (2006) Cell Signal 18(7): 982-993). In addition, NFkB activation can be bolstered by the kinase activity of TBK1 phosphorylating the inhibitors of NFkB, which enables activation of the canonical or non-canonical NFkB transcription factors.

TBK1 has been implicated as being a key gene required for KRAS-dependent cancers, required for HER2+ breast cancers, and contributing to the acquisition of resistance to erlotinib. Depletion of TBK1 by shRNA results in synthetic lethality with KRAS-dependent cancer cell lines and xenograft models (Barbie, D. A., P. Tamayo, et al. (2009) Nature 462(7269): 108-112) and TBK1 is required for RAS-mediated transformation of murine embryonic fibroblasts (Ou, Y. H., M. Torres, et al. (2011) Mol Cell 41(4): 458-470). TBK1 is downstream of RAS and elicits its oncogenic properties via the RALB-NFkB and AKT pathways (Chien, Y., S. Kim, et al. (2006) Cell 127(1): 157-170). In addition, TBK1 directly phosphorylates AKT at S473 and results in the downstream activation of the mTORC1/2 pathway (Ou, Y. H., M. Torres, et al. (2011) Mol Cell 41(4): 458-470). TBK1 was also identified as being important for the survival of HER2+ breast cancer cell lines via an shRNA kinome screen and showed combination effects with the EGFR/HER2 kinase inhibitor, lapatinib (Deng, T., J. C. Liu, et al. (2014) Cancer Res 74(7): 2119-2130). Additionally, integrin alphaVbeta3 was identified as a marker of cells that are resistant to EGFR therapies and have stem-like properties. The signaling cascade required for the survival of these cells was attributed to KRAS-TALB-TBK1-NFkB axis and inhibiting TBK1 was sufficient to block the survival of these cells. Seguin, L, S. Kato, et al. (2014), Nat Cell Biol 16(5): 457-468.

IKKε is a serine/threonine kinase and its gene amplifications have been identified in up to 30% of breast cancers. Depleting IKKε in cell lines with shRNA that have these amplifications results in their decreased viability (Boehm, J. S., J. J. Zhao, et al. (2007) Cell 129(6): 1065-1079). Overexpression of IKKε in ovarian cancer has been demonstrated to mediate resistance to cisplatin and is a poor prognostic factor (Guo, J. P., S. K. Shu, et al. (2009) Am J Pathol 175(1): 324-333).

TBK1 and IKKε are also both implicated in inflammatory responses and associated disorders. IKKε has been shown to be involved in manifestations of rheumatoid arthritis (RA) that include extracellular matrix destruction, synovial inflammation, and activation of the innate immune response (Sweeney, S. E., D. Hammaker, et al. (2005) J Immunol 174(10): 6424-6430). IKKε and IRF3 protein levels are increased in the synovium of RA patients and mice deficient in IKKε show reduced clinical signs of arthritis in a collagen-induced arthritis model as well as associated reduction of inflammation and erosion. Corr, M., D. L. Boyle, et al. (2009), Ann Rheum Dis 68(2): 257-263. Other inflammatory disorders that manifest as a result of Type I IFN response and upstream activation of $TLR^3/TLR^4$ or cytosolic nucleic acid sensors are likely to also rely on a TBK1/IKKε signaling axis to initiate and maintain their pathogenic state such as Sjogrens syndrome, inflammatory bowel disease (IBD), chronic obstructive pulmonary disease (COPD), systemic lupus erythematosus (SLE), dermatomyositis, polymyositis, systemic sclerosis. Baccala, R., K. Hoebe, et al. (2007), Nat Med 13(5): 543-551. Furthermore, both TBK1 and IKKε have been shown to play a role in maintaining macrophages in an activated state in response to IFN. Solis, M., R. Romieu-Mourez, et al. (2007) Eur J Immunol 37(2): 528-539.

In addition to inflammation and cancer, IKKε is implicated in obesity, type 2 and insulin resistance. Mice deficient for IKKε are protected from obesity induced by a high-fat diet, hepatic steatosis, insulin resistance, and chronic inflammation of the liver and fat. Chiang, S. H., M. Bazuine, et al. (2009) Cell 138(5): 961-975. Consistent with this, high levels of NFkB activation have been seen in the liver, adipocytes, and adipose tissue resident macrophages as well as increase levels of IKKε over healthy mice. Treatment with a kinase inhibitor to TBK1/IKKε improved obesity-related metabolic dysfunction in mice fed a high fat diet (Reilly, S. M., S. H. Chiang, et al. (2013) Nat Med 19(3): 313-321).

Accordingly, there is a need for inhibitors of the kinase activity of TBK1 and/or IKKε for treating cancers, inflammatory, and metabolic disorders that may have an active TBK1 and/or IKKε pathway.

SUMMARY OF THE INVENTION

One embodiment provides a compound of formula (I):

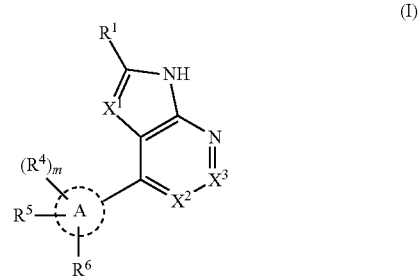

(I)

wherein,
A is a 6 membered aryl or 5-6 membered heteroaryl ring;
$X^1$ is $CR^2$ or N;

$X^2$ and $X^3$ are independently $CR^3$ or N, provided that at most only one of $X^2$ and $X^3$ are N;

$R^1$ is selected from the group consisting of H, $C_{1-6}$ alkyl, $C_{2-6}$ alkenyl, $C_{2-6}$ alkynyl, $-OR^a$, $-C(O)R^a$, $-C(O)OR^a$, $-C(O)NR^aR^b$, $-OC(O)NR^aR^b$, $-NR^aR^b$, $-CN$, $-NR^aC(O)R^b$, $-NR^aC(O)OR^b$, $-S(O)_{0-2}R^a$, $-S(O)_2NR^aR^b$, $-NR^aS(O)_2R^b$, wherein each $C_{1-6}$ alkyl, $C_{2-6}$ alkenyl and $C_{2-6}$ alkynyl is optionally substituted with from one to five $R^{20}$ groups;

or $R^1$ has the following structure:

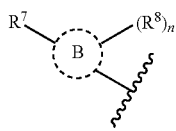

wherein B is selected from the group consisting of $C_{6-10}$ aryl, $C_{3-10}$ cycloalkyl, 5-10 membered heteroaryl and 3-12 membered heterocyclyl;

$R^2$ is selected from the group consisting of H, $C_{1-6}$ alkyl, $C_{3-10}$ cycloalkyl, 3-12 membered heterocyclyl, $C_{1-6}$ heteroalkyl, $C_{1-6}$ haloalkyl, $C_{2-6}$ alkenyl, $C_{2-6}$ alkynyl, $-NR^aR^b$, halogen, $-CN$, $-NO_2$, $-OR^a$, $-C(O)R^a$, $-C(O)OR^a$, $-C(O)NR^aR^b$, $-OC(O)NR^aR^b$, $-NR^aC(O)R^b$, $-NR^aC(O)OR^b$, $-S(O)_{0-2}R^a$, $-S(O)_2NR^aR^b$ and $-NR^aS(O)_2R^b$;

each $R^3$ is independently selected from the group consisting of H, $C_{1-6}$ alkyl, $C_{3-10}$ cycloalkyl, 3-12 membered heterocyclyl, $C_{1-6}$ heteroalkyl, $C_{1-6}$ haloalkyl, $C_{2-6}$ alkenyl, $C_{2-6}$ alkynyl, $-NR^aR^b$, halogen, $-CN$, $-NO_2$, $-OR^a$, $-C(O)R^a$, $-C(O)OR^a$, $-C(O)NR^aR^b$, $-OC(O)NR^aR^b$, $-NR^aC(O)R^b$, $-NR^aC(O)OR^b$, $-S(O)_{0-2}R^a$, $-S(O)_2NR^aR^b$ and $-NR^aS(O)_2R^b$;

each $R^4$ is independently selected from the group consisting of H, $C_{1-6}$ alkyl, $C_{1-6}$ heteroalkyl, $C_{1-6}$ haloalkyl, $C_{2-6}$ alkenyl, $C_{2-6}$ alkynyl, $-NR^aR^b$, halogen, $-C(O)R^a$, $-C(O)OR^a$, $-C(O)NR^aR^b$, $-OC(O)NR^aR^b$, $-NR^aC(O)R^b$, $-NR^aC(O)OR^b$, $-S(O)_{0-2}R^a$, $-S(O)_2NR^aR^b$, $-NR^aS(O)_2R^b$, $-N_3$, $-CN$, $-NO_2$ and $-OR^a$;

$R^5$ is selected from the group consisting of H, $C_{1-6}$ alkyl, $C_{1-6}$ heteroalkyl, $-NR^aR^b$, halogen, $C(O)R^a$, $-C(O)OR^a$, $-C(O)NR^aR^b$, $-OC(O)NR^aR^b$, $-NR^aC(O)R^b$, $-NR^aC(O)OR^b$, $-S(O)_{0-2}R^a$, $-S(O)_2NR^aR^b$, $-NR^aS(O)_2R^b$, $C_{6-10}$ aryl, $C_{3-10}$ cycloalkyl, 5-10 membered heteroaryl, 3-12 membered heterocyclyl and $-O-R^9$ wherein each $C_{1-6}$ alkyl, $C_{1-6}$ heteroalkyl, $C_{6-10}$ aryl, $C_{3-10}$ cycloalkyl, 5-10 membered heteroaryl and 3-12 membered heterocyclyl is optionally substituted with from one to five $R^{20}$ groups;

or $R^5$ and one $R^4$ are taken together to form a fused $C_6$ aryl, 5-10 membered heteroaryl, 5-10 membered heterocyclyl or $C_{3-6}$ cycloalkyl each optionally substituted with one to five $R^{20}$ groups;

$R^6$ is $-CN$ located at the meta (3) position with respect to the point of attachment of the A ring;

$R^7$ is selected from the group consisting of H, $C_{1-6}$ alkyl, $C_{2-6}$ alkenyl, $C_{2-6}$ alkynyl, $C_{1-6}$ heteroalkyl, $-NR^aR^b$, halogen, $C(O)R^a$, $-C(O)OR^a$, $-C(O)NR^aR^b$, $-OC(O)NR^aR^b$, $-NR^aC(O)R^b$, $-NR^aC(O)OR^b$, $-S(O)_{0-2}R^a$, $-S(O)_2NR^aR^b$, $-NR^aS(O)_2R^b$, $-N_3$, $-CN$, $-NO_2$, $-OR^a$, $C_{6-10}$ aryl, $C_{3-10}$ cycloalkyl, 5-10 membered heteroaryl and 3-12 membered heterocyclyl wherein each $C_{1-6}$ alkyl, $C_{2-6}$ alkenyl, $C_{2-6}$ alkynyl, $C_{1-6}$ heteroalkyl, $C_{6-10}$ aryl, $C_{3-10}$ cycloalkyl, 5-10 membered heteroaryl and 3-12 membered heterocyclyl is optionally substituted with 1-5 $R^{20}$ groups;

each $R^8$ is independently selected from the group consisting of H, $C_{1-6}$ alkyl, $C_{1-6}$ heteroalkyl, $C_{1-6}$ haloalkyl, $C_{1-6}$ hydroxyalkyl, $C_{2-6}$ alkenyl, $C_{2-6}$ alkynyl, $C_{6-10}$ aryl, $C_{3-10}$ cycloalkyl, 5-10 membered heteroaryl and 3-12 membered heterocyclyl, $-NR^aR^b$, halogen, $-C(O)R^a$, $-C(O)OR^a$, $-C(O)NR^aR^b$, $-OC(O)NR^aR^b$, $-NR^aC(O)R^b$, $-NR^aC(O)OR^b$, $-S(O)_{0-2}R^c$, $-S(O)_2NR^aR^b$, $-NR^aS(O)_2R^b$, $-N_3$, $-CN$, $-NO_2$ and $-OR^a$, wherein each $C_{1-6}$ alkyl, $C_{1-6}$ heteroalkyl, $C_{6-10}$ aryl, $C_{3-10}$ cycloalkyl, 5-10 membered heteroaryl and 3-12 membered heterocyclyl is optionally substituted with from one to five $R^{20}$ groups; or $R^7$ and $R^8$ are taken together to form a fused, spiro or bridged $C_{3-10}$ cycloalkyl or 3-12 membered heterocyclyl, which are optionally substituted with 1-5 $R^{20}$ groups;

$R^9$ is $C_{1-6}$ alkyl, 3-12 membered heterocyclyl, $C_{6-10}$ aryl, $C_{3-10}$ cycloalkyl, 5-10 membered heteroaryl or 3-12 membered heterocyclyl, each of which is optionally substituted with from one to five $R^{20}$ groups;

n is 0-2;

m is 0-3;

each $R^{20}$ is independently $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, halogen, oxo, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)_2NR^aR^b$, $-NR^aS(O)_2R^b$, $-N_3$, $-CN$, or $-NO_2$, or two $R^{20}$ groups can join together to form a fused, spiro or bridged $C_{3-10}$ cycloalkyl or 3-12 membered heterocyclyl ring, wherein each $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl is optionally substituted with from one to five halogen, oxo, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)_2NR^aR^b$, $-NR^aS(O)_2R^b$, $-N_3$, $-CN$, or $-NO_2$;

$R^{21}$ is independently $C_{1-6}$ alkyl, $C_{3-10}$ cycloalkyl, $C_{1-6}$ heteroalkyl, 3-12 membered heterocyclyl, $C_6$-$C_{10}$ aryl, 5-10 membered heteroaryl, hydroxyl, amino, $C_{1-6}$ alkylamino, $-CN$ or halogen; and each $R^a$ and $R^b$ is independently H; or $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, each of which is optionally substituted with from one to five $R^{21}$; or $R^a$ and $R^b$ together with the atoms to which they are attached form a 3-12 membered heterocyclyl optionally substituted with one to five $R^{21}$ groups;

with the proviso that if $R^1$ is H, then all of $R^2$ and $R^3$ groups are H;

or a pharmaceutically acceptable salt thereof.

In another embodiment A is a phenyl or 6-membered heteroaryl.

Another embodiment provides a compound having the following formula (Ia):

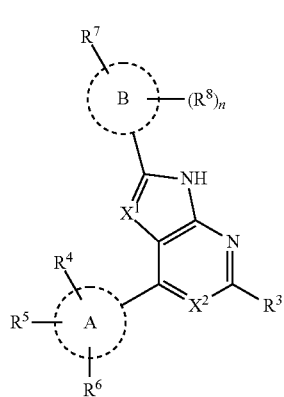
(Ia)

or a pharmaceutically acceptable salt thereof.

Another embodiment provides a compound having the following formula (Ib):

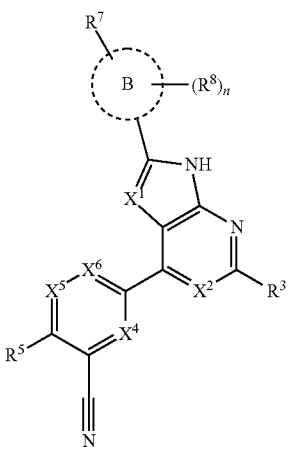
(Ib)

wherein,
$X^4$, $X^5$ and $X^6$ are independently N or $CR^4$;
provided that at least one of $X^4$, $X^5$ and $X^6$ is $CR^4$;
or a pharmaceutically acceptable salt thereof.

Another embodiment provides a compound having the following formula (Ic):

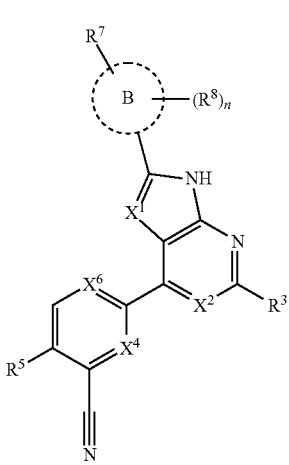
(Ic)

or a pharmaceutically acceptable salt thereof.

Another embodiment provides a compound having the following formula (Id):

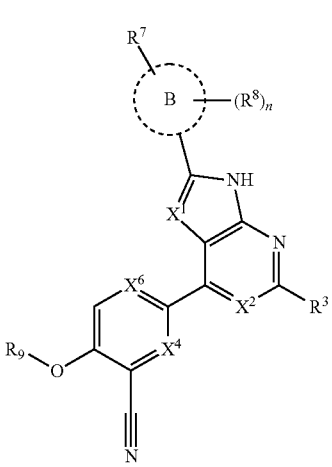
(Id)

or a pharmaceutically acceptable salt thereof.

Another embodiment provides a compound having the following formula (Ie):

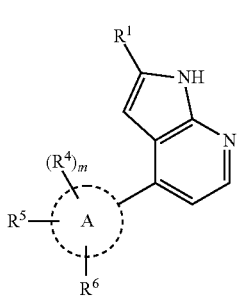
(Ie)

or a pharmaceutically acceptable salt thereof.

Another embodiment provides a compound having the following formula (If):

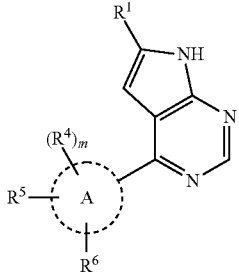
(If)

or a pharmaceutically acceptable salt thereof.

Another embodiment provides a compound having the following formula (Ig):

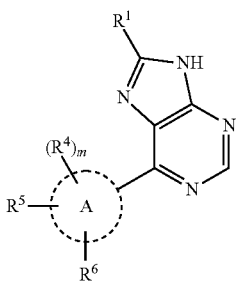
(Ig)

or a pharmaceutically acceptable salt thereof.

Another embodiment provides a compound having the following formula (Ih):

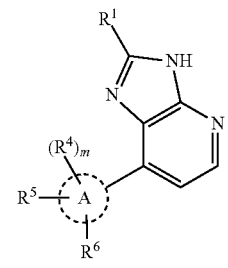
(Ih)

a pharmaceutically acceptable salt thereof.

Another embodiment provides a compound having the following formula (Ij):

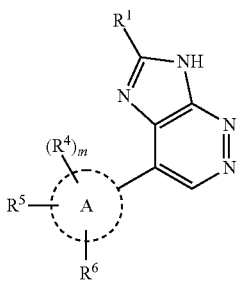
(Ij)

or a pharmaceutically acceptable salt thereof.

Another embodiment provides a compound having the following formula (Ik):

(Ik)

or a pharmaceutically acceptable salt thereof.

In another embodiment, $X^1$ is CH. In another embodiment, $X^1$ is N. In another embodiment, $X^2$ is CH. In another embodiment, $X^2$ is N. In another embodiment, $X^3$ is N. In another embodiment, $X^3$ is CH. In another embodiment, both $X^2$ and $X^3$ are CH.

In another embodiment, $R^1$ is selected from the group consisting of aminocarbonyl, $C_{1-6}$ alkylaminocarbonyl, carboxyl, $C_{3-6}$cycloalkylaminocarbonyl, 5-7 membered heterocyclyl-$C_{1-6}$ alkyl, 5-7 membered heterocyclyl-$C_{2-6}$ alkynyl, $C_{6-10}$ arylaminocarbonyl and $C_{5-7}$ cycloalkenyl optionally substituted with one to three $R^{20}$ groups.

In another embodiment, $R^1$ is selected from the group consisting of:

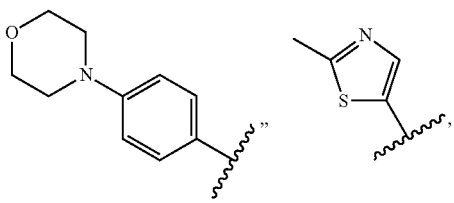

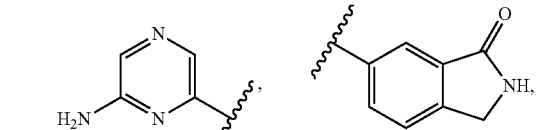

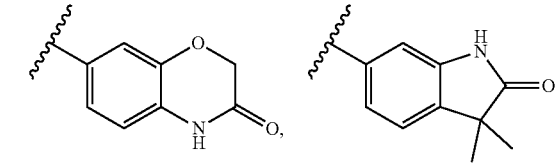

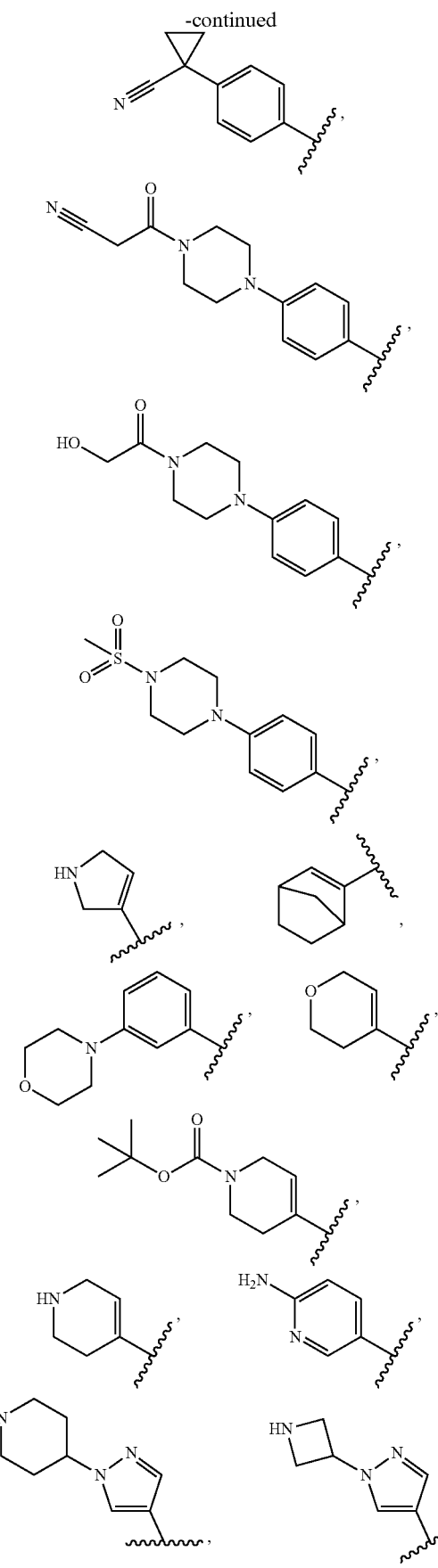
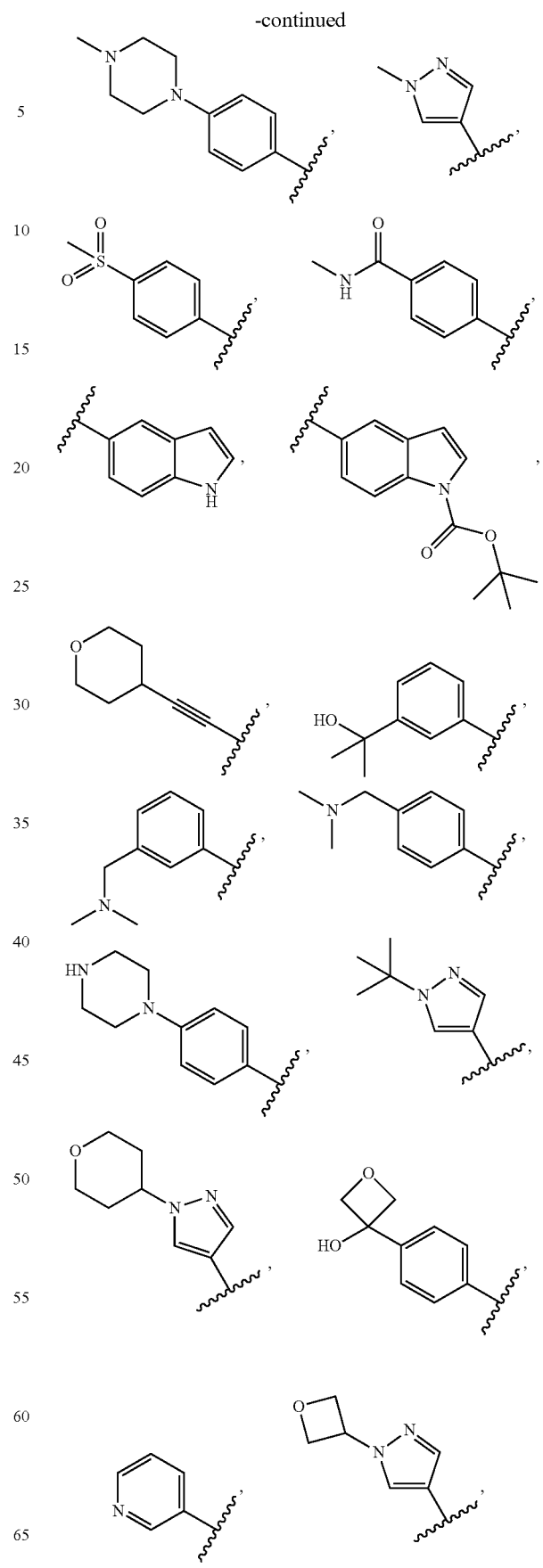

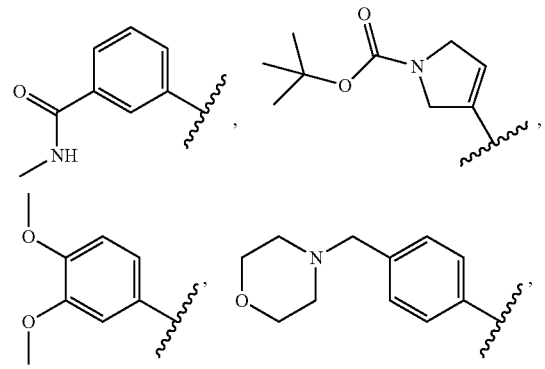
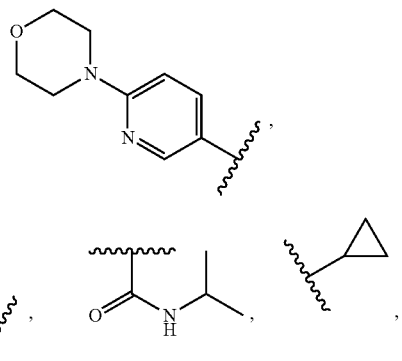
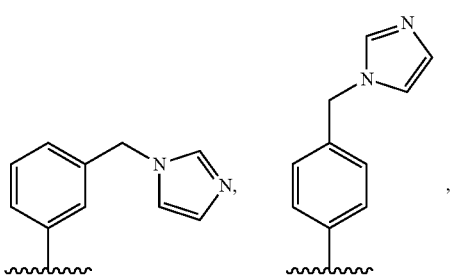
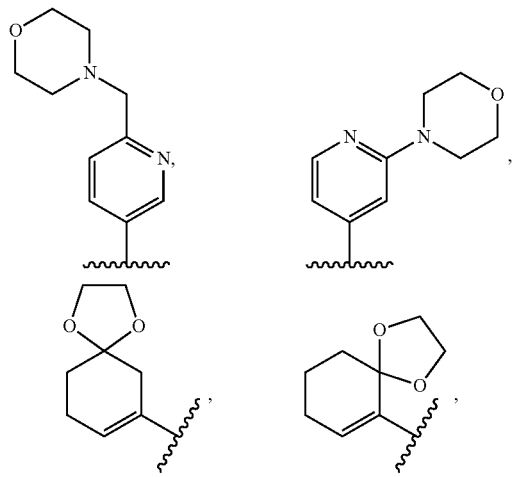
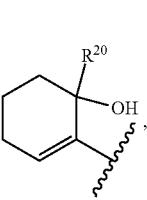
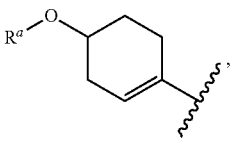
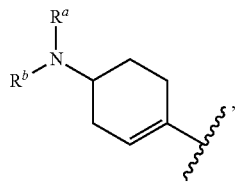

-continued
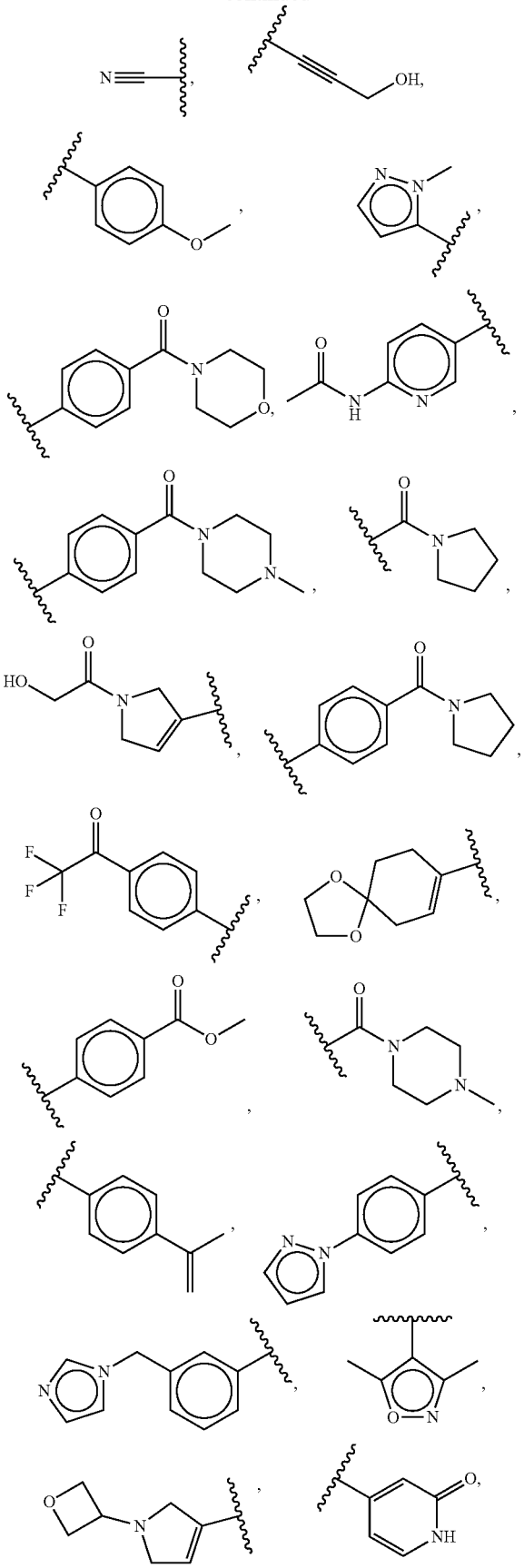
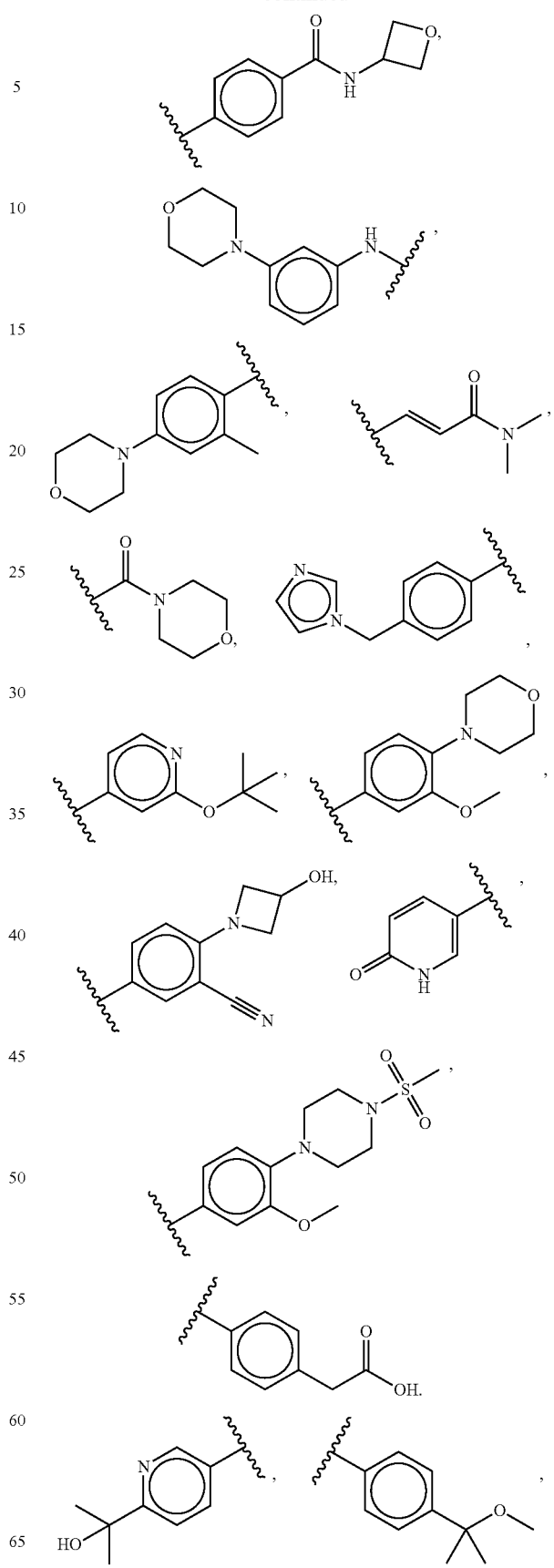

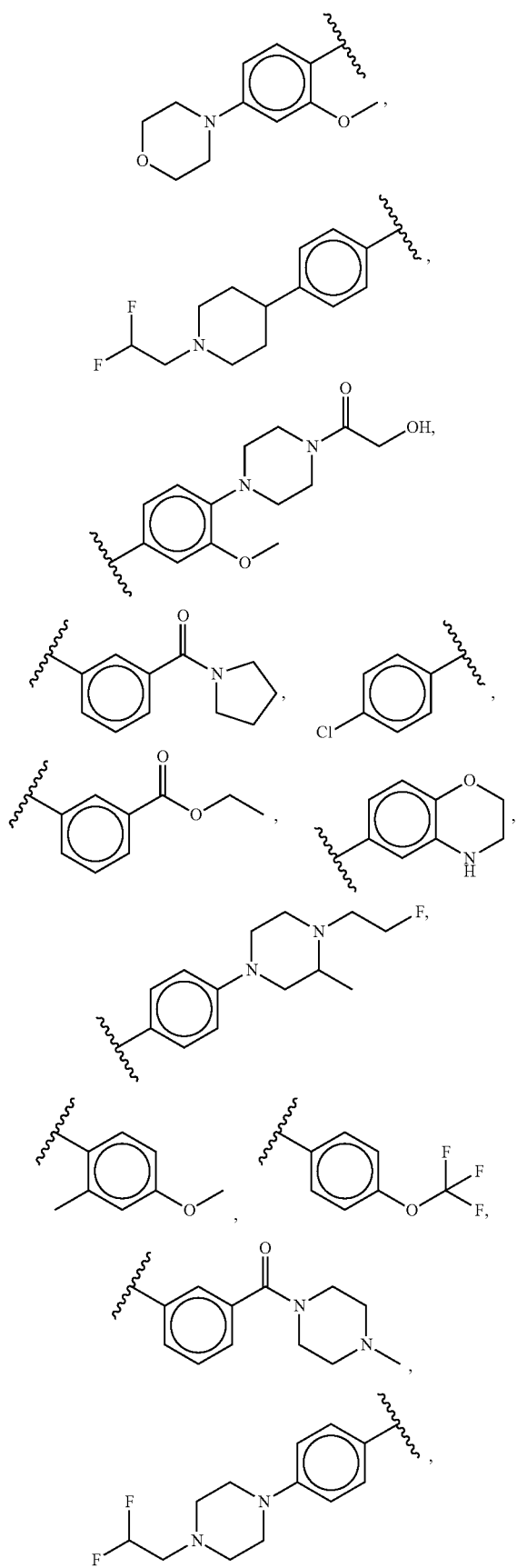

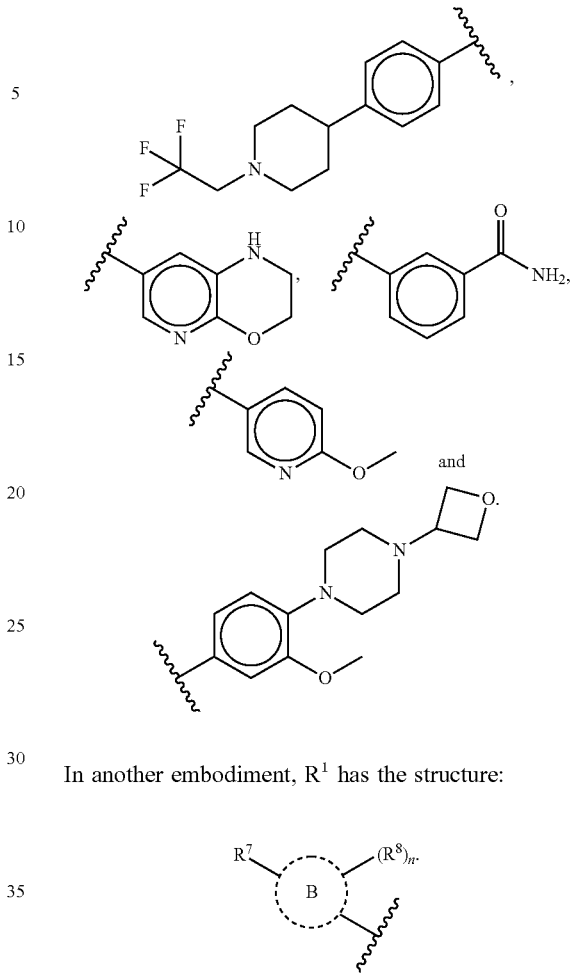

In another embodiment, $R^1$ has the structure:

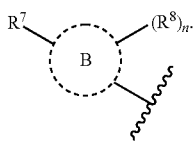

In another embodiment, B is selected from the group consisting of phenyl, pyridyl, pyrazolyl, pyrazinyl, pyrrolyl, thiazolyl, dihydropyrrolyl, piperidenyl, pyrrolidenyl, bicyclo[2.2.1]heptenyl, isoindolinonyl, indolyl, cyclopropyl, cyclohexyl, cyclopentyl and benzoxazinonyl.

In another embodiment, $R^7$ is selected from the group consisting of amino, 3-7 membered heterocyclyl, $C_{1-6}$ alkylamiocarbonyl, $C_{1-6}$ alkoxycarbonyl, $C_{1-6}$ alkoxy, 5-7 membered heterocyclyl-$C_{1-6}$ alkyl, hydroxyl $C_{1-6}$ alkyl, $C_{1-6}$ alkylsulfonyl-5-7 membered heterocyclyl, 5-7 membered heterocyclyl $C_{1-6}$ alkoxy, 5-7 membered heterocyclyloxy, $C_{1-6}$ alkyl, 5-10 membered heteroaryl, and (4-7 membered heterocyclyl)-4-7 membered heterocyclyl. In another embodiment, $R^7$ is a 5-7 membered heterocyclyl.

In another embodiment, $R^7$ is selected from the group consisting of morpholinyl, amino, oxetanyl, hydroxyoxetanyl, azetidinyl, tetrahydropyranyl, tetrahydropyranyloxy, dihydropyranyl, piperidenyl, tetrahydrofuranyl, 1-(methylsulfonyl)piperazinyl, 3-(4-piperazin-1-yl)-3-oxopropanenitrile, tetrahydrofuranyloxy, piperazinyl, 2-oxa-6-azaspiro[3.3]heptanyl and pyrrolidinyl. In another embodiment, $R^7$ is morpholinyl.

In another embodiment, $R^7$ is at the meta (3) or para (4) position with respect to the point of attachment to the B-ring.

In another embodiment, $R^8$ is independently selected from the group consisting of $C_{1-6}$ alkyl, $C_{1-6}$ haloalkyl, —$NR^aR^b$, halogen, —CN, and —$OR^a$.

In another embodiment, $R^8$ is —CN or $C_{1-6}$ alkoxy and n is 1. In another embodiment, n is 0.

In another embodiment, m is 0-2. In another embodiment, m is 0 or 1.

In another embodiment, $R^1$ is not H. In another embodiment, $R^2$, $R^3$ and $R^4$ are H. In another embodiment, $X^5$ is $CR^4$.

In another embodiment, $R^5$ is —$NR^aR^b$. In another embodiment, $R^a$ and $R^b$ on $R^5$ join together with the atoms to which they are attached form a 3-12 membered heterocyclyl which is optionally substituted with one to three of halo, hydroxyl, oxo, $C_{1-6}$ alkyl, $C_{1-6}$ alkoxy, $C_{1-6}$ haloalkyl, $C_{1-6}$ haloalkoxy, CN, amino, or $C_{1-6}$ alkylamino.

In another embodiment, $R^5$ is selected from the group consisting of:

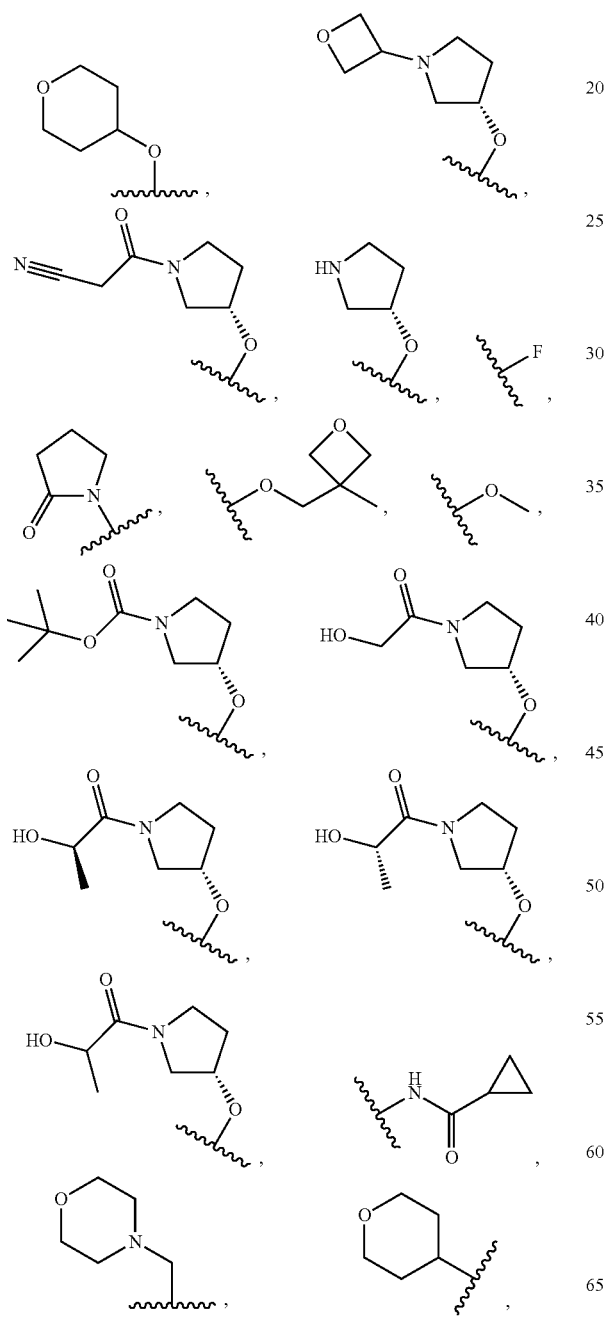

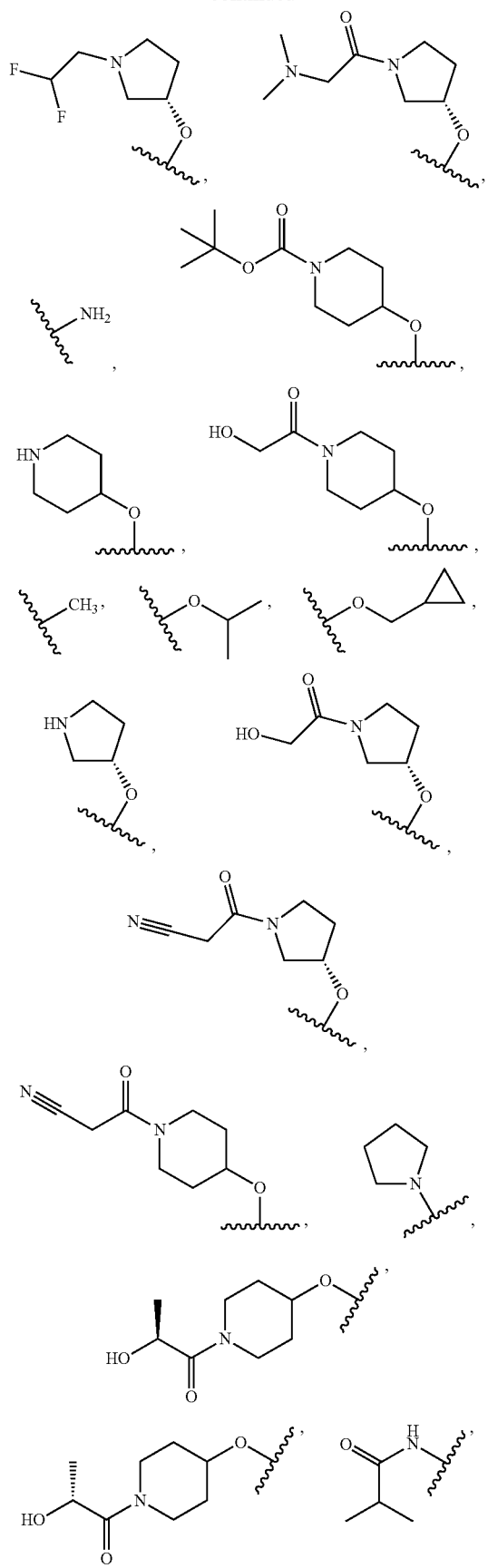

-continued

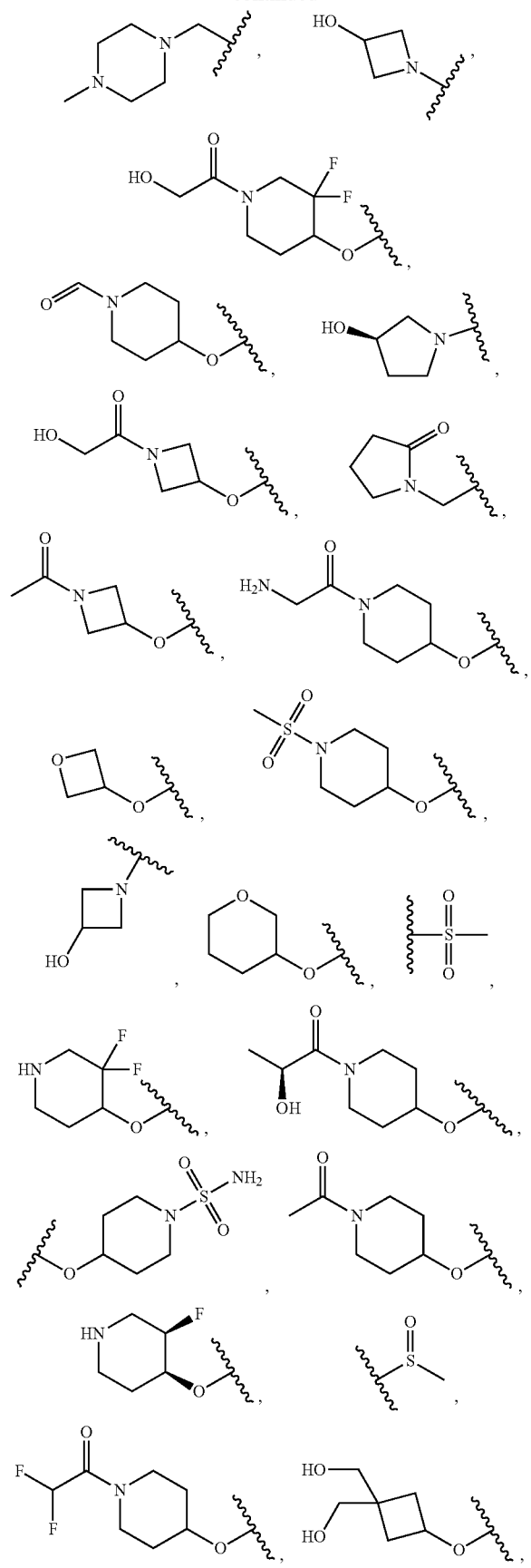

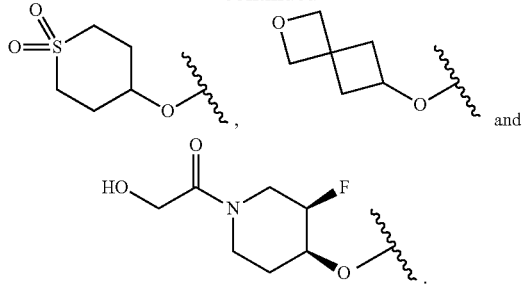

In another embodiment, R⁵ is —OR⁹. In another embodiment, R⁹ is substituted with one R²⁰ group selected from $C_{1-6}$ alkoxycarbonyl, hydroxyl $C_{1-6}$ alkylcarbonyl, $C_{1-6}$ alkoxycarbonyl, cyano $C_{1-6}$ alkylcabonyl or $C_{3-6}$ cycloalkyl-$C_{1-6}$ alkoxy. In another embodiment, R⁹ is selected from the group consisting of tetrahydropyranyl, tetrahydrofuranyl, pyrrolidinyl, oxetanylmethyl, 1-(oxetan-3-yl)pyrrolidinyl, oxo-propanylnitrile-pyrrolinyl and piperidinyl. In another embodiment, R⁹ is unsubstituted tetrahydropyranyl.

In another embodiment, R⁹ is $C_{1-6}$ alkyl or 3-12 membered heterocyclyl, each of which is optionally substituted with from 1-5R²⁰ groups.

In another embodiment, R⁹ is substituted with mono or di-fluoro. More particularly, the mono or di-fluoro is at the ortho position.

In another embodiment, R⁹ is:

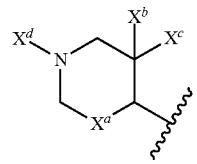

$X^a$ is a bond or $C(R^x)(R^y)$, wherein $R^x$ and $R^y$ are independently selected from the group consisting of H, halo or methyl;

$X^b$ and $X^c$ are independently selected from the group consisting of H, halo or methyl;

$X^d$ is selected from the group consisting of H; or $C_{1-6}$ alkyl, $C_{2-6}$ alkenyl, $C_{3-10}$ cycloalkyl, $C_{1-6}$ heteroalkyl, 3-12 membered heterocyclyl, $C_{6-10}$ aryl, 5-10 membered heteroaryl, each of which is optionally substituted with from one to five groups selected from $C_{1-6}$ alkyl, $C_{3-10}$ cycloalkyl, $C_{1-6}$ heteroalkyl, 3-12 membered heterocyclyl, $C_6$-$C_{10}$ aryl, 5-10 membered heteroaryl, hydroxyl, $C_{1-6}$ alkoxy, amino, —CN, —C(O)H, —C(O)NH₂, —C(O)NH($C_{1-6}$ alkyl), —C(O)N($C_{1-6}$ alkyl)₂, —COOH, —C(O)$C_{1-6}$ alkyl, —C(O)O$C_{1-6}$ alkyl, or halogen.

In another embodiment, $X^d$ is $C_{1-6}$ alkyl substituted with hydroxyl. In another embodiment, $X^a$ is CH₂. In another embodiment, $X^b$ is fluoro. In another embodiment, $X^c$ is H.

In another embodiment, R⁵ is N-pyrrolidinyloxy or N-piperidinyloxy substituted with $C_{1-6}$ alkoxycarbonyl, hydroxyl $C_{1-6}$ alkylcarbonyl, hydroxyl 3-6 membered heterocyclyl, halo 3-6 membered heterocyclyl, $C_{1-6}$ alkoxycarbonyl, cyano $C_{1-6}$ alkylcabonyl or $C_{3-6}$ cycloalkyl-$C_{1-6}$ alkoxy.

In another embodiment, R⁵ is at the para position (4).

In another embodiment, A is phenyl or a 5-6 membered heteroaryl. In another embodiment, A is pyridyl. In another embodiment, A is phenyl.

In another embodiment, $R^5$ and one $R^4$ are taken together to form a fused $C_6$ aryl, 5-10 membered heteroaryl, 5-10 membered heterocyclyl or $C_{3-6}$ cycloalkyl each optionally substituted with one to five $R^{20}$ groups.
Another embodiment provides a compound selected from the group consisting of:
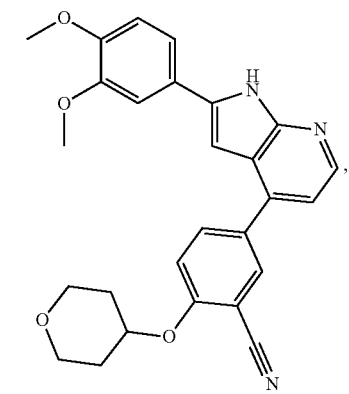
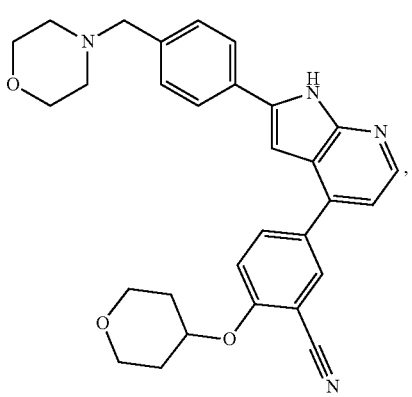
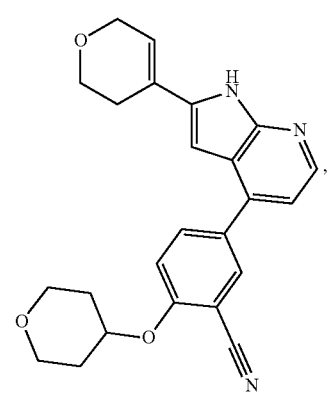
-continued
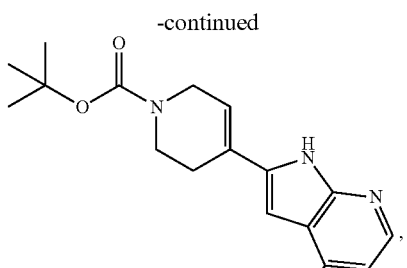
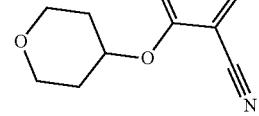
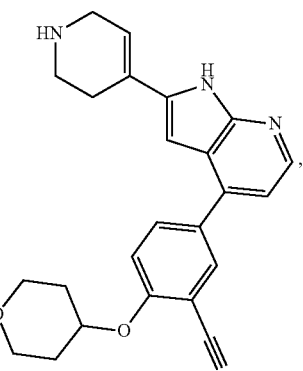
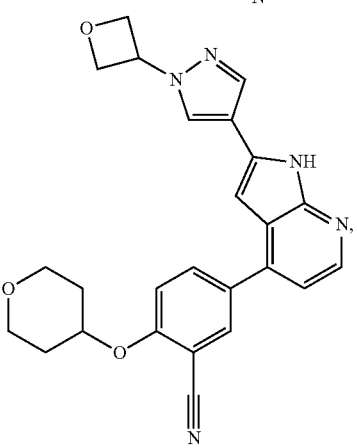
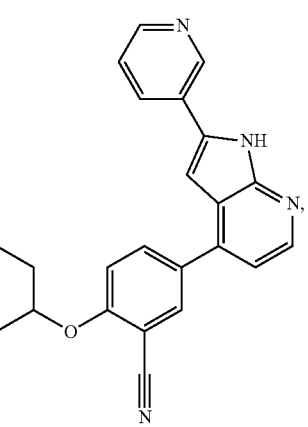

-continued
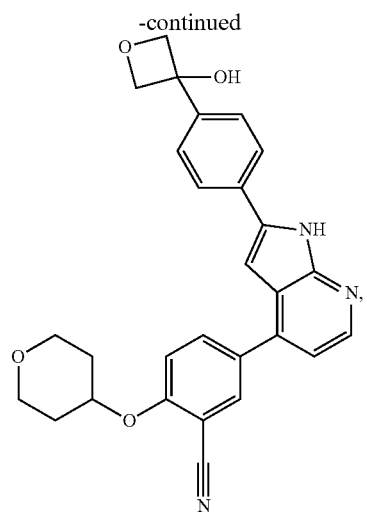
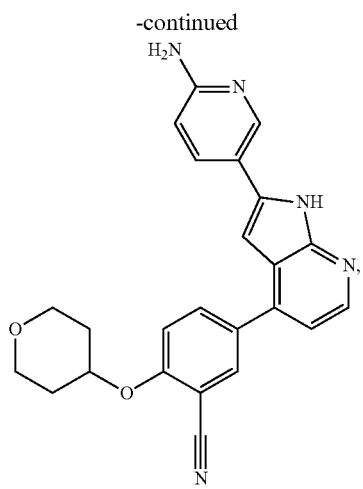
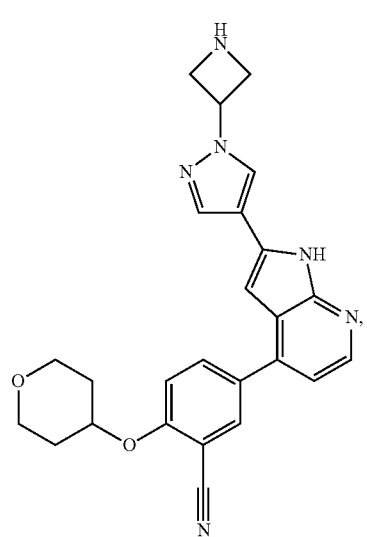
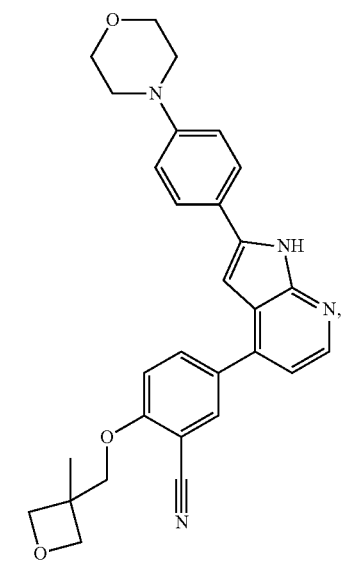
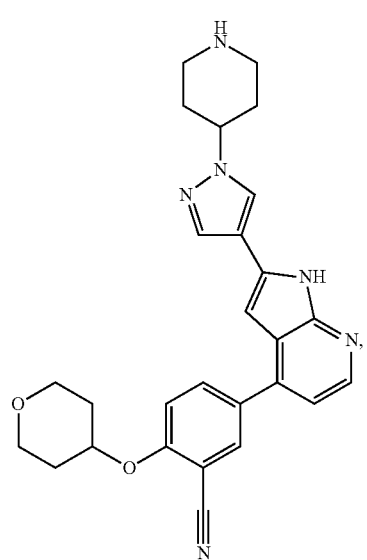
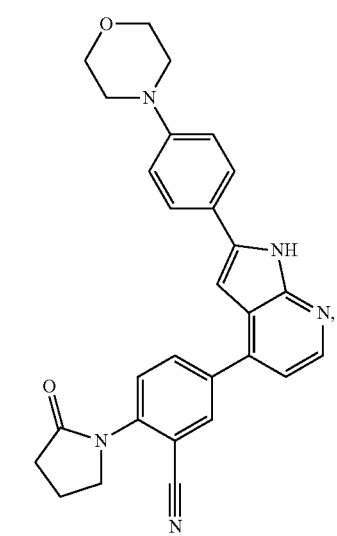

-continued

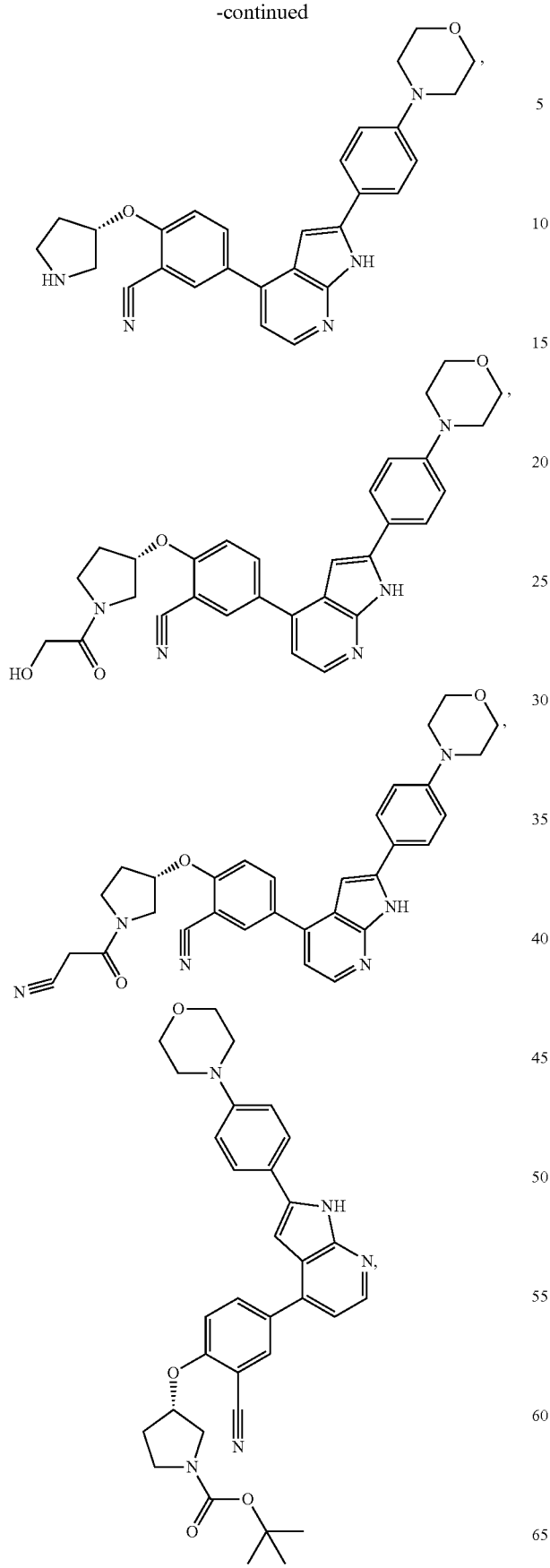
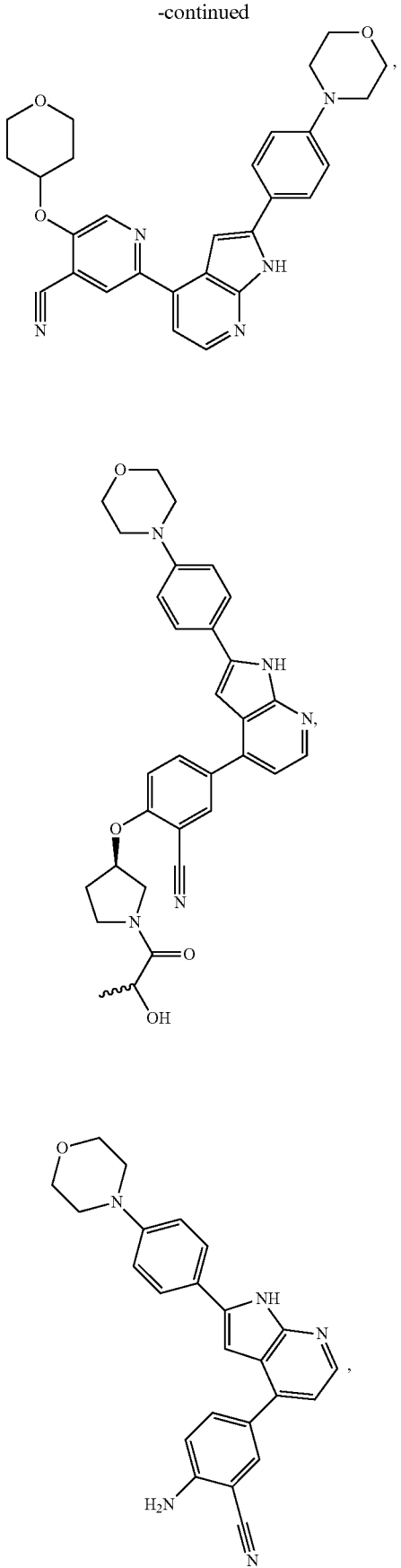

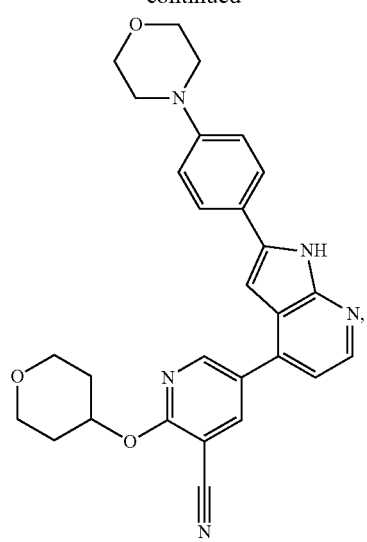
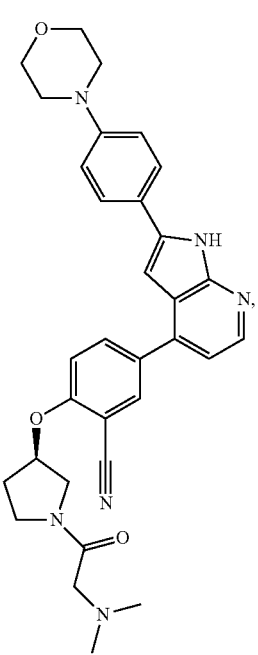
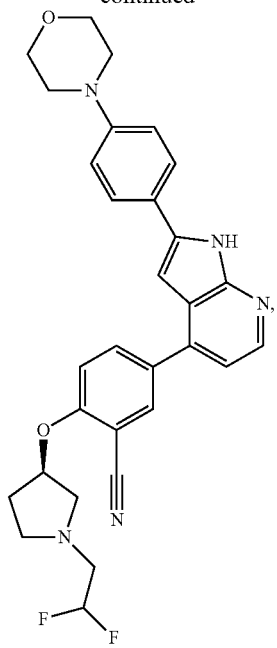
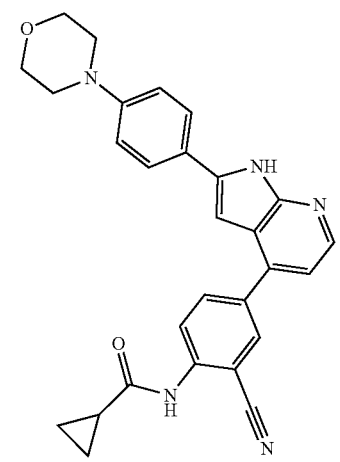
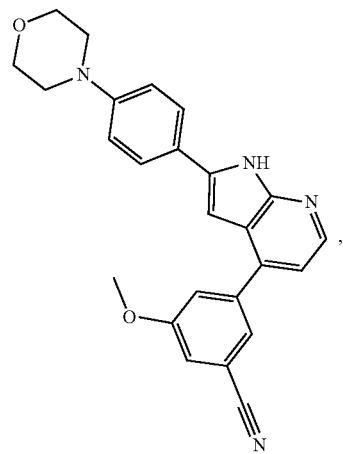

31
-continued
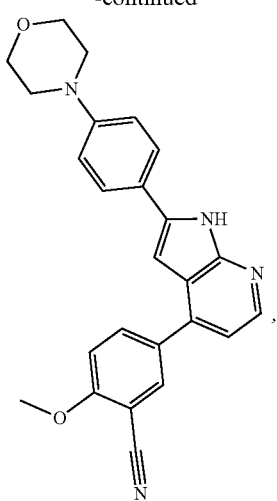
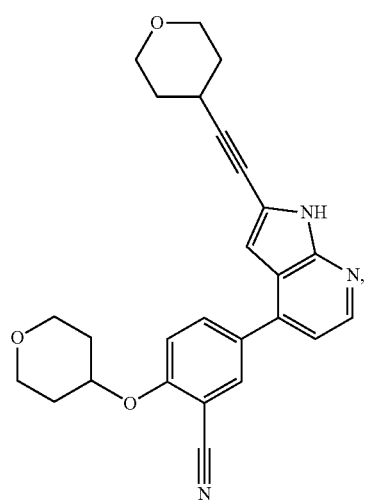
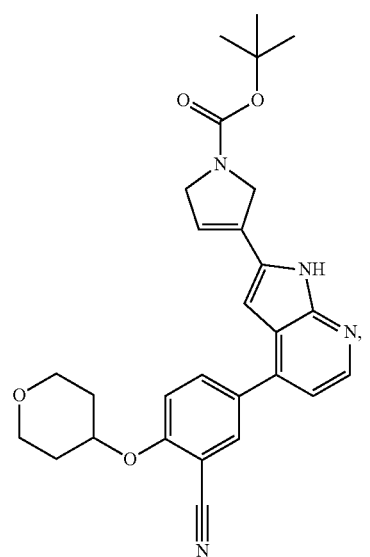
32
-continued
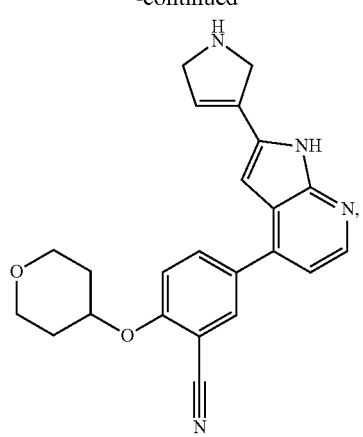
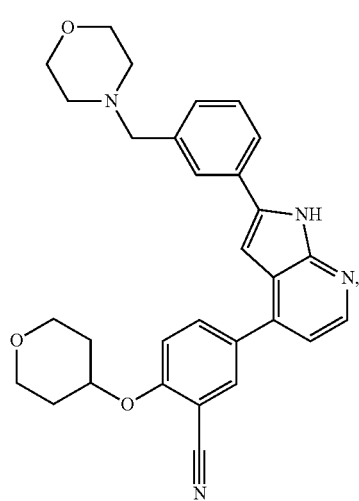

33
-continued
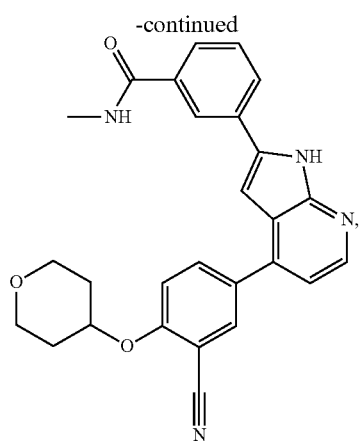
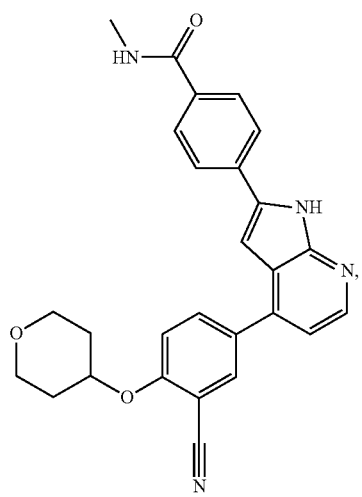
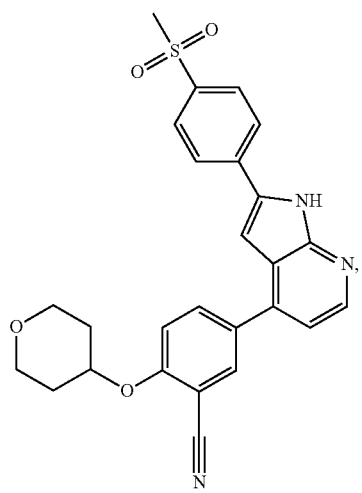
34
-continued
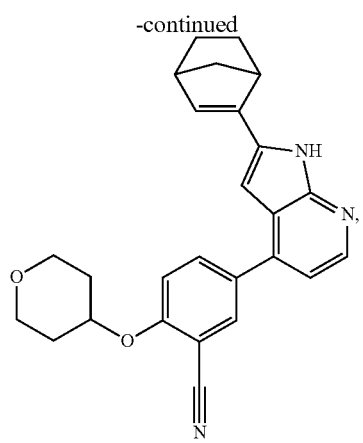
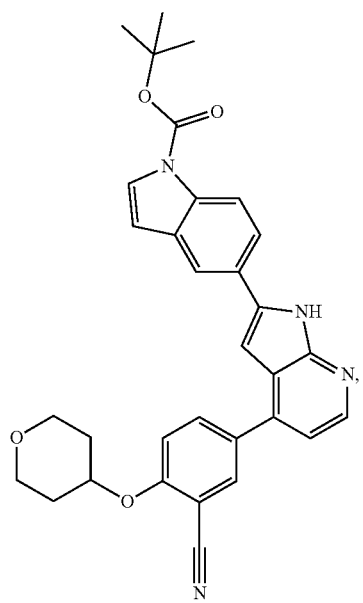
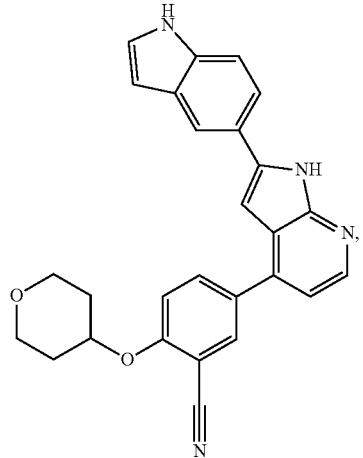

35
-continued
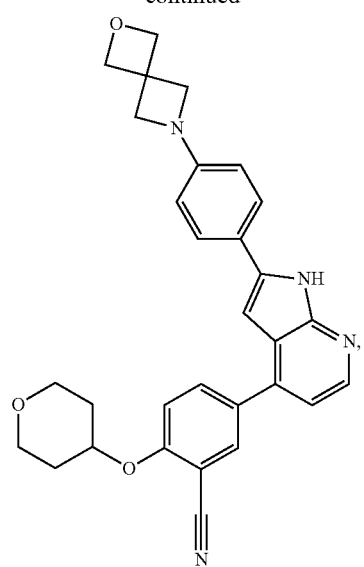
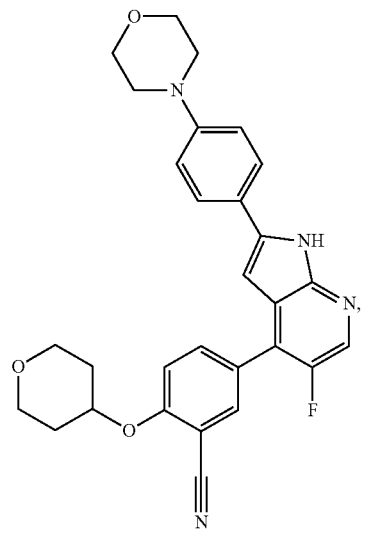
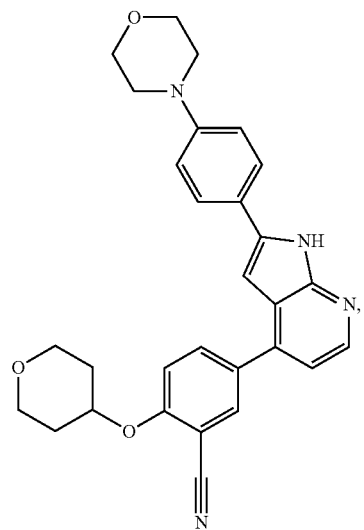
36
-continued
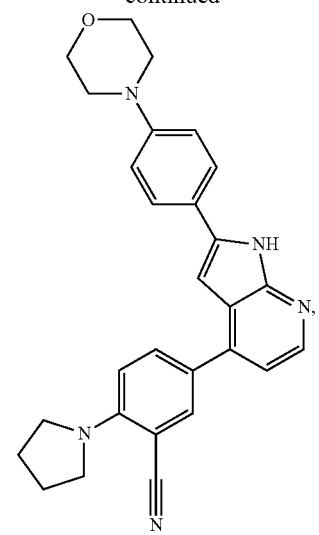
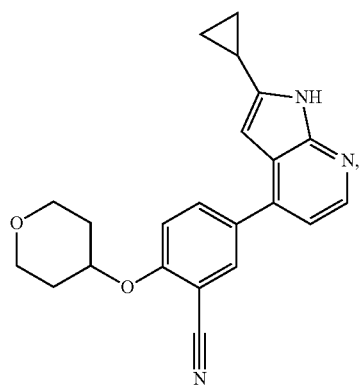
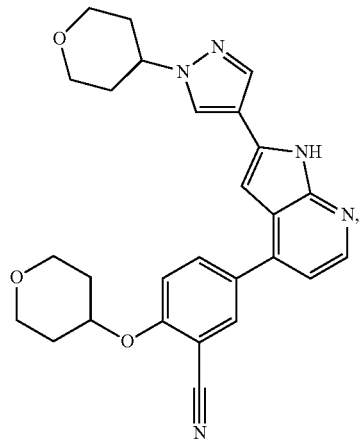

37
-continued
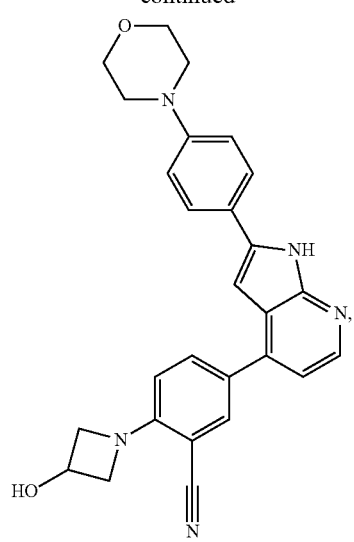
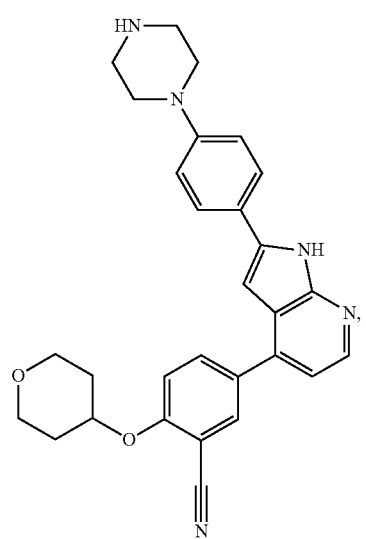
38
-continued
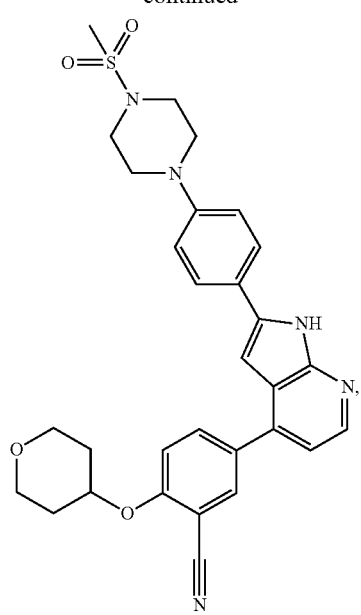

39
-continued
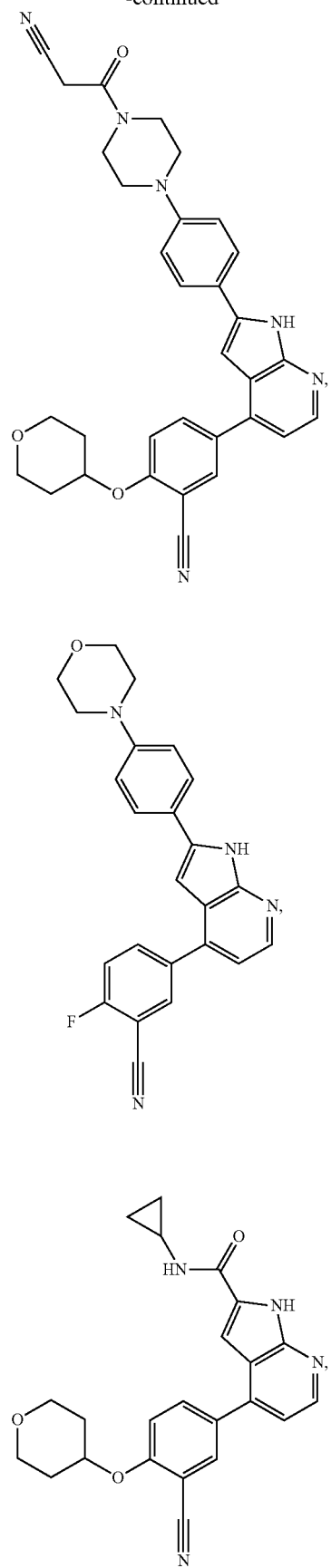
40
-continued
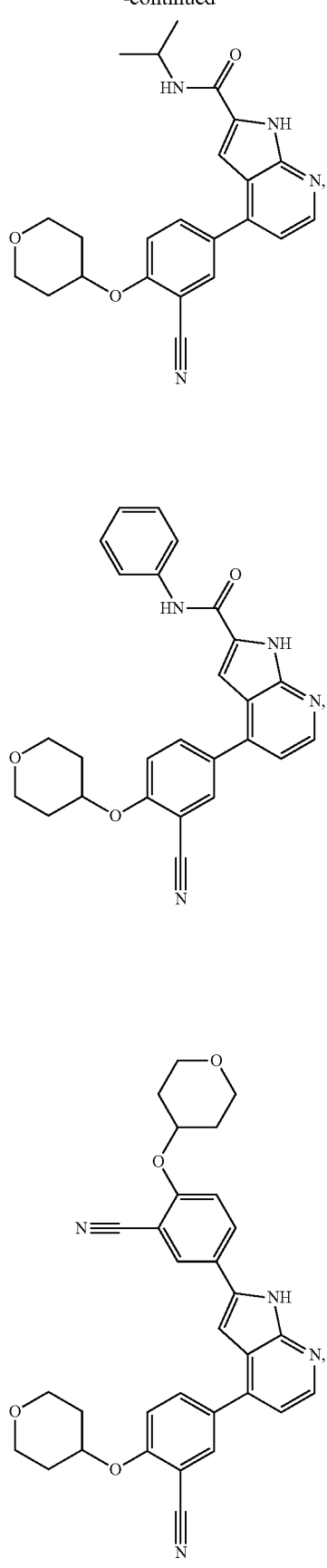

41
-continued
42
-continued
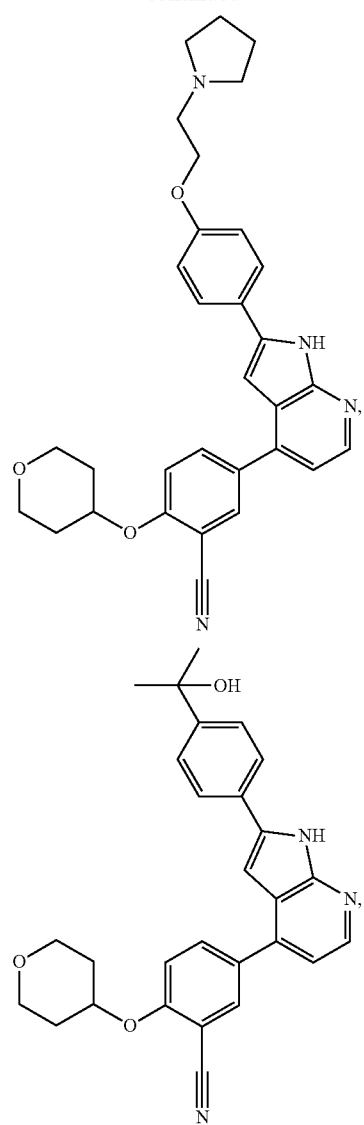
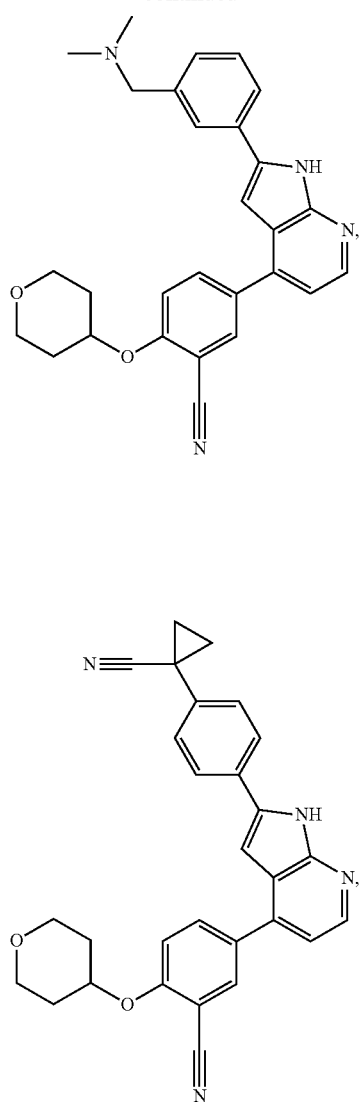
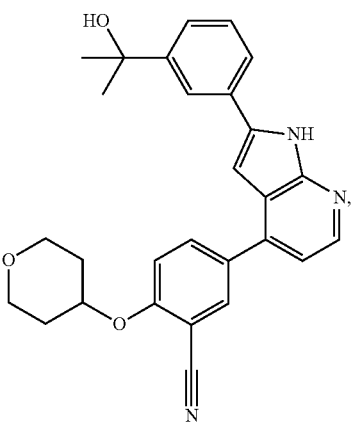

43

-continued

44

-continued

45
-continued
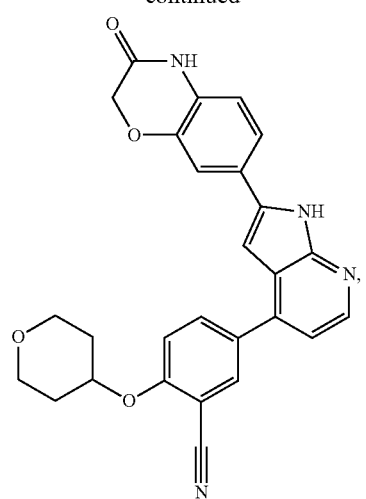
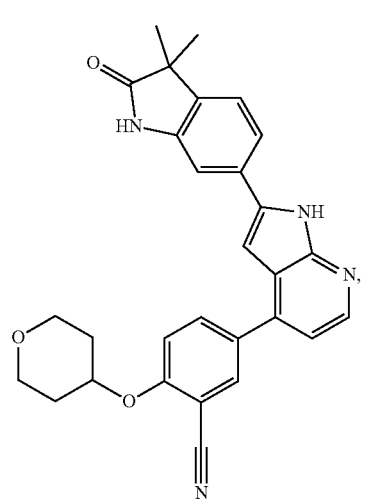
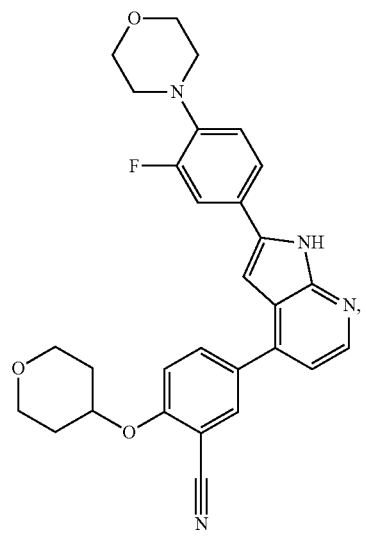
46
-continued
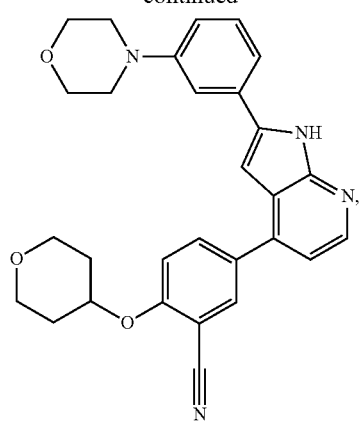
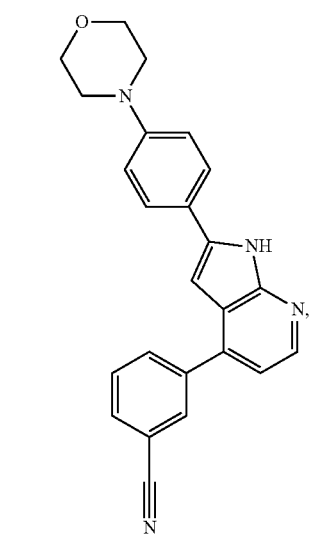
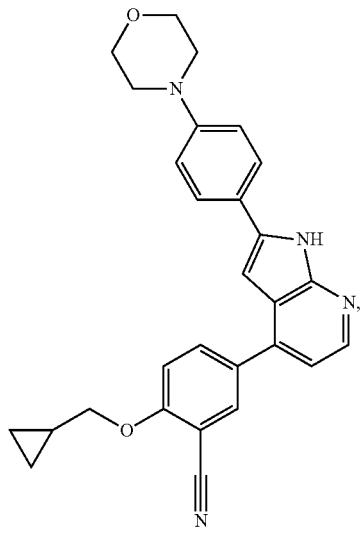

47
-continued
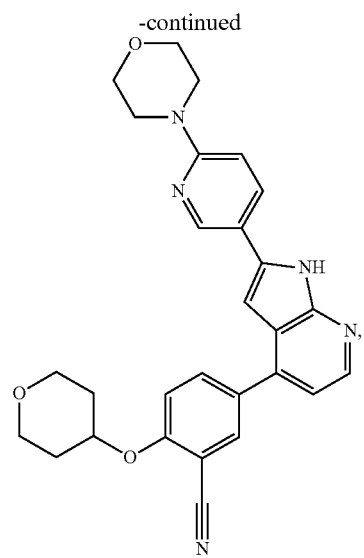
48
-continued
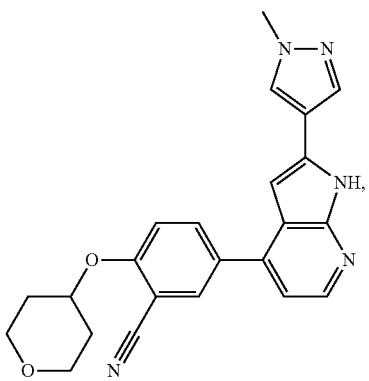
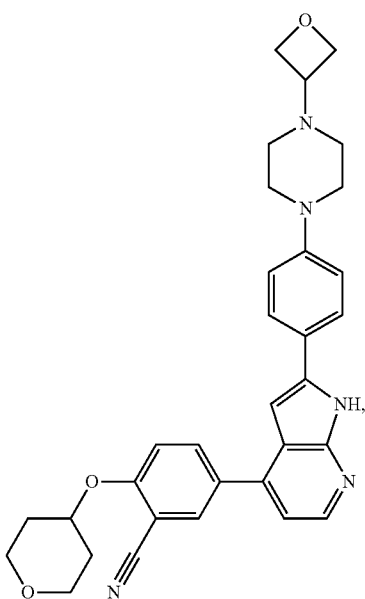
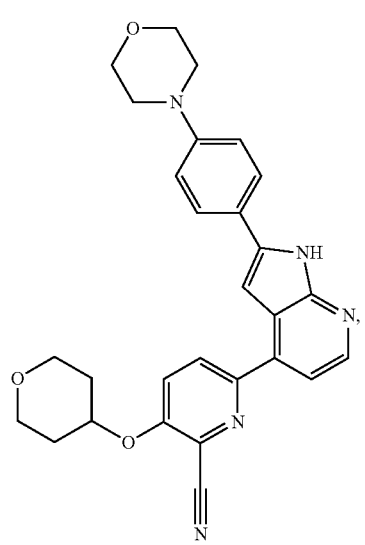

49
-continued
50
-continued
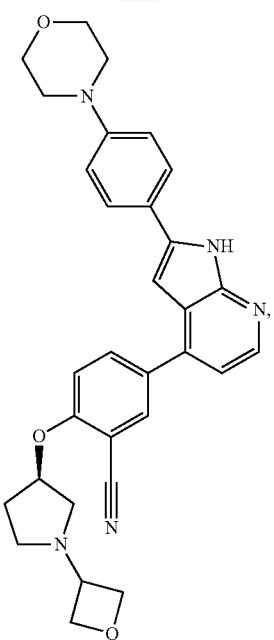
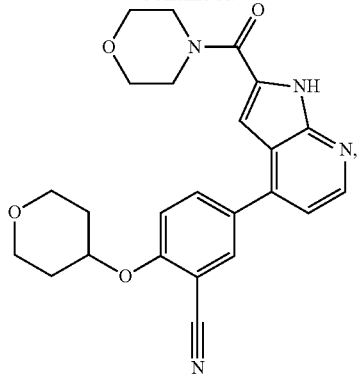
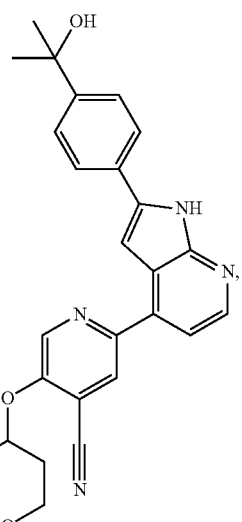
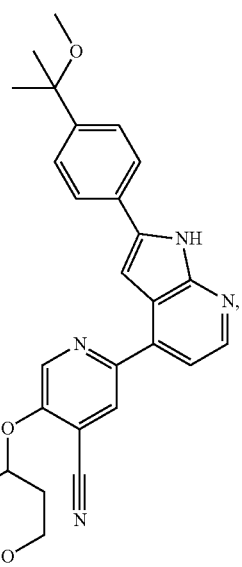

| 51 | 52 |
|---|---|
| -continued | -continued |
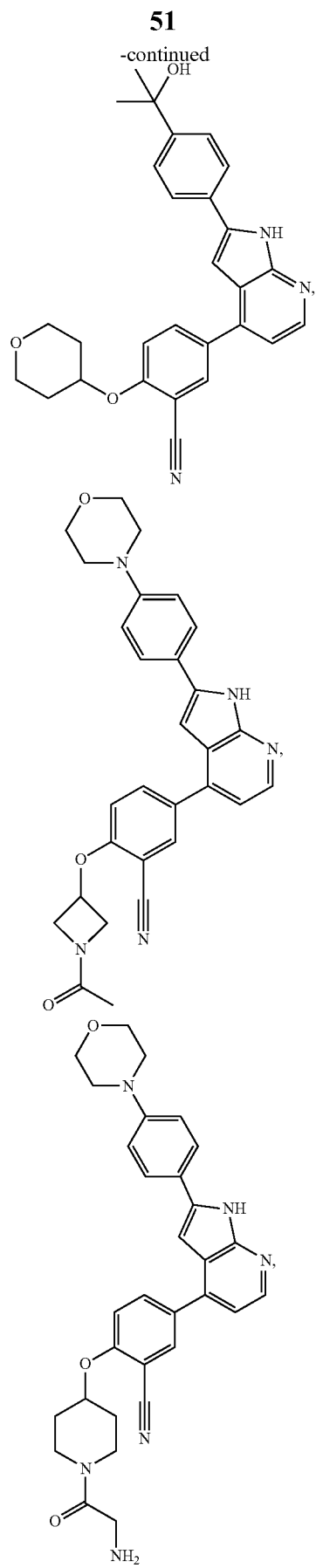
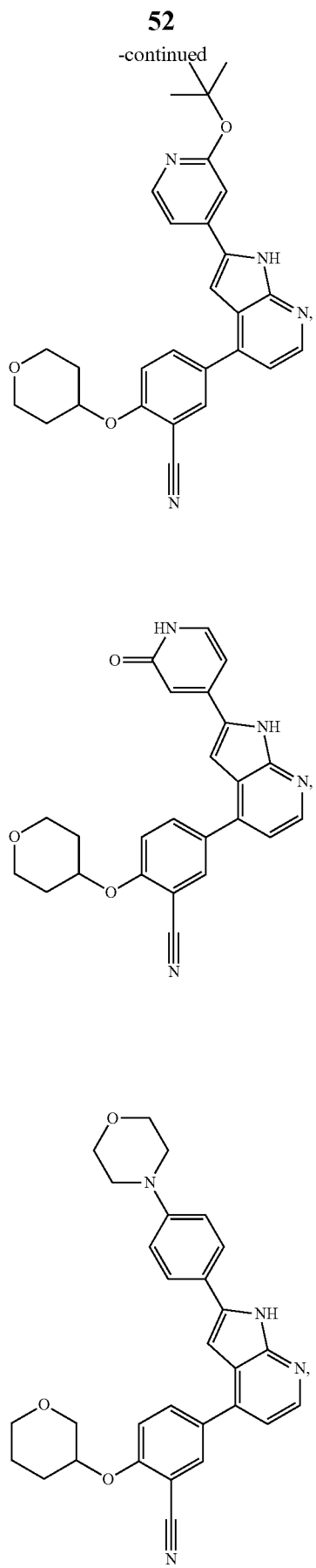

53
-continued
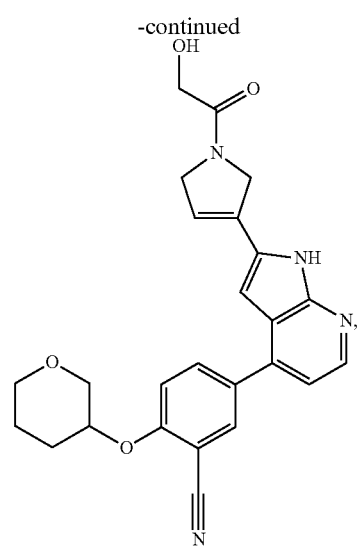
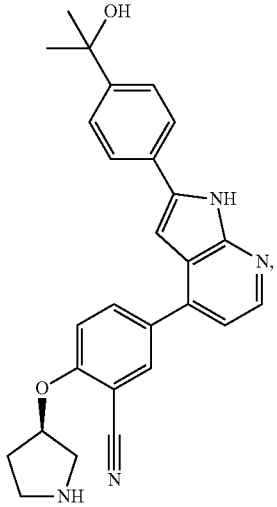
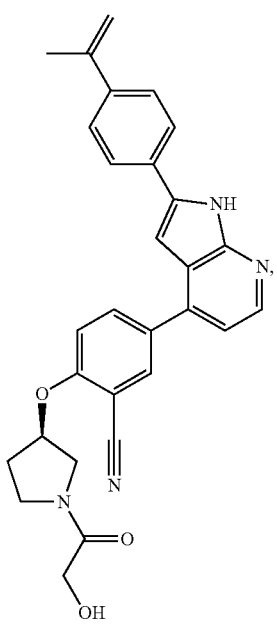
54
-continued
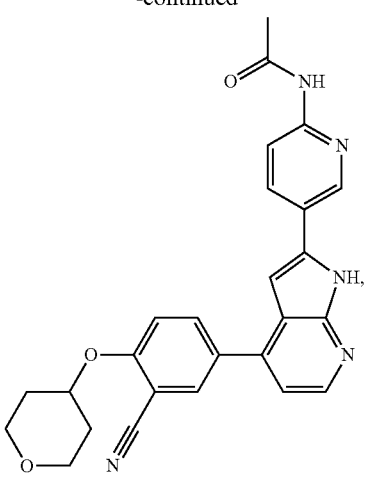
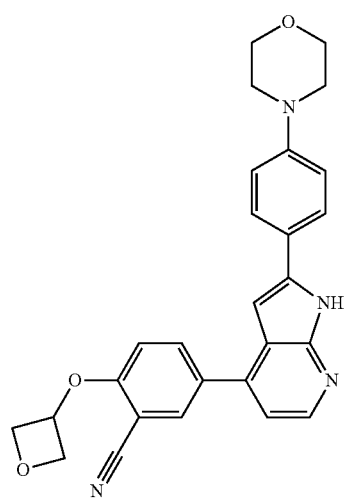
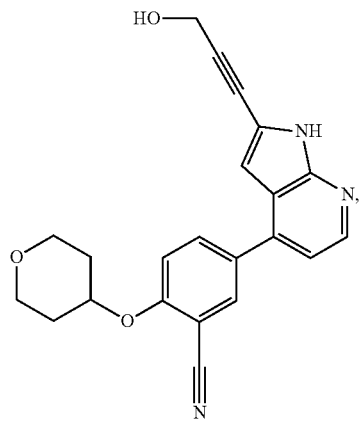

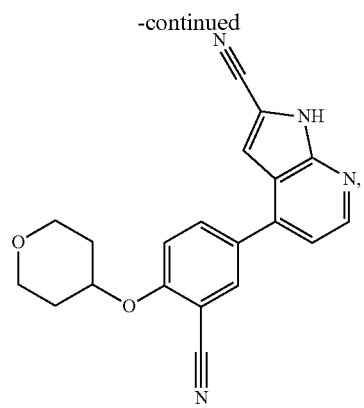
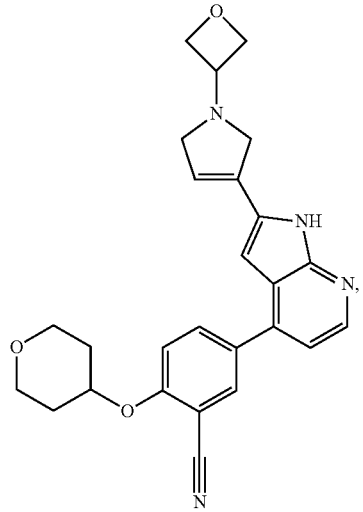
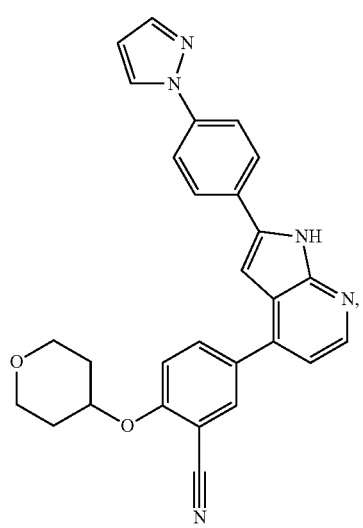
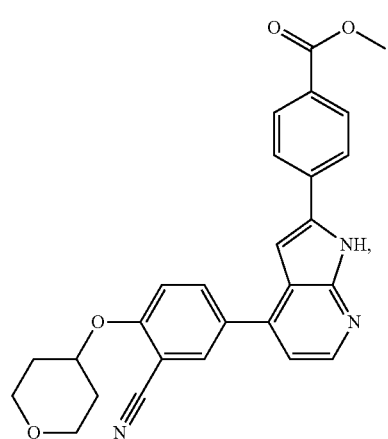

57
-continued
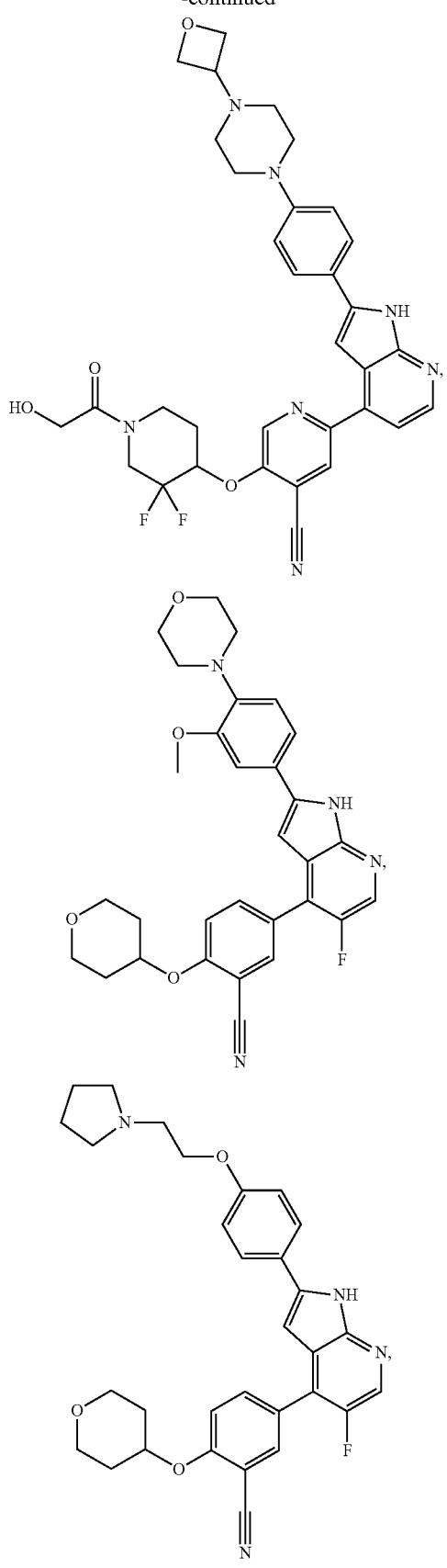
58
-continued
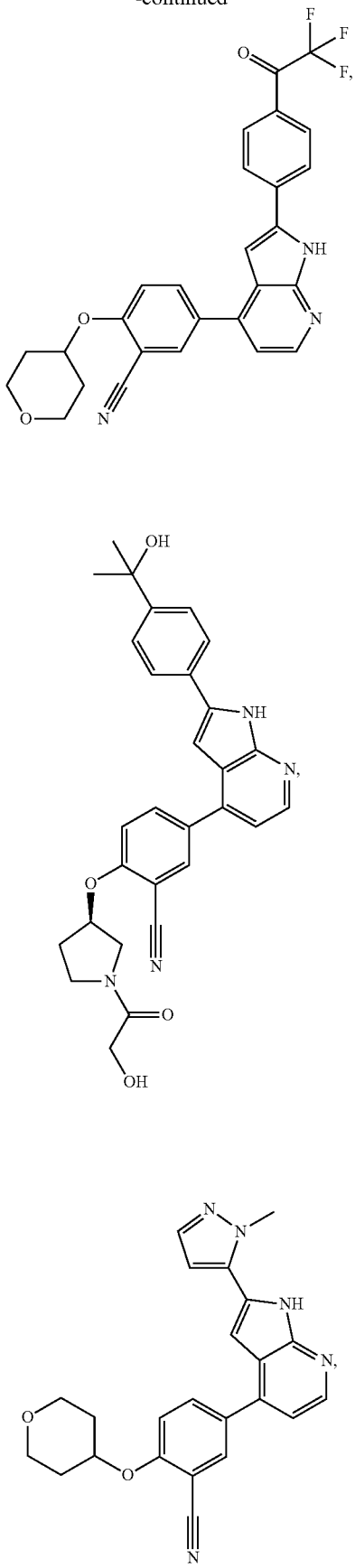

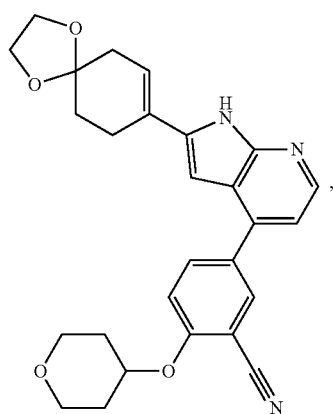
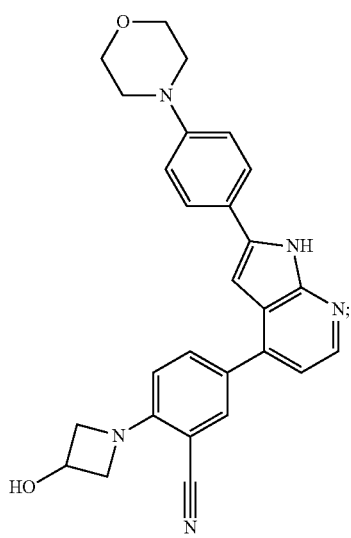
or a pharmaceutically acceptable salt thereof.
Another embodiment provides a compound selected from the group consisting of:
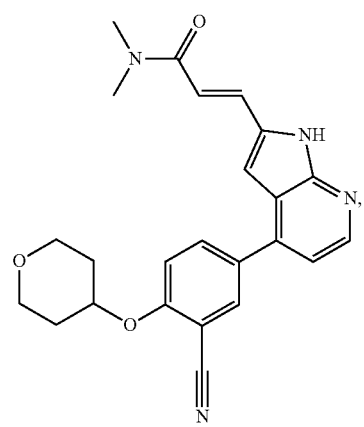
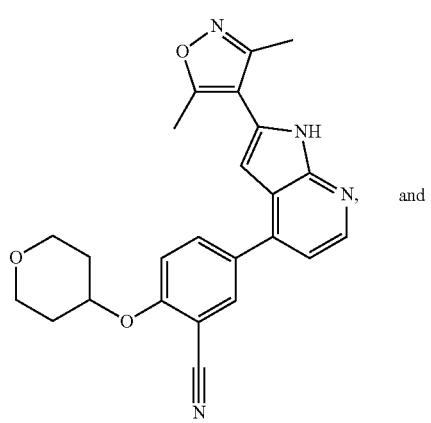
and
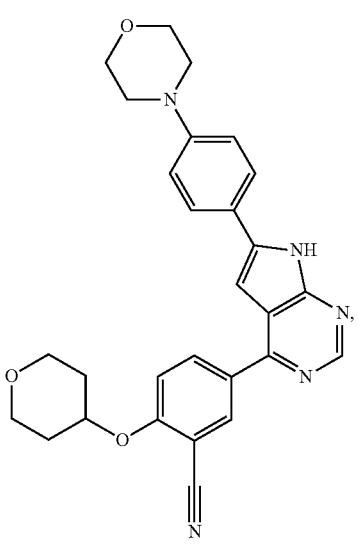

61
-continued
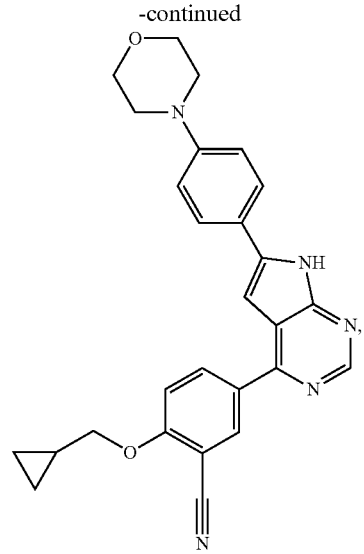
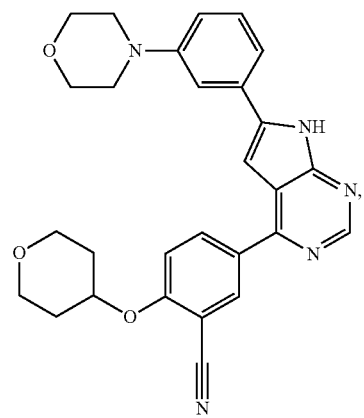
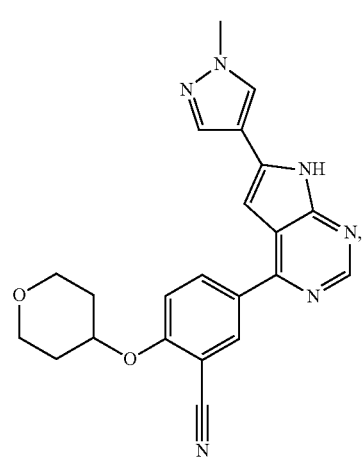
62
-continued
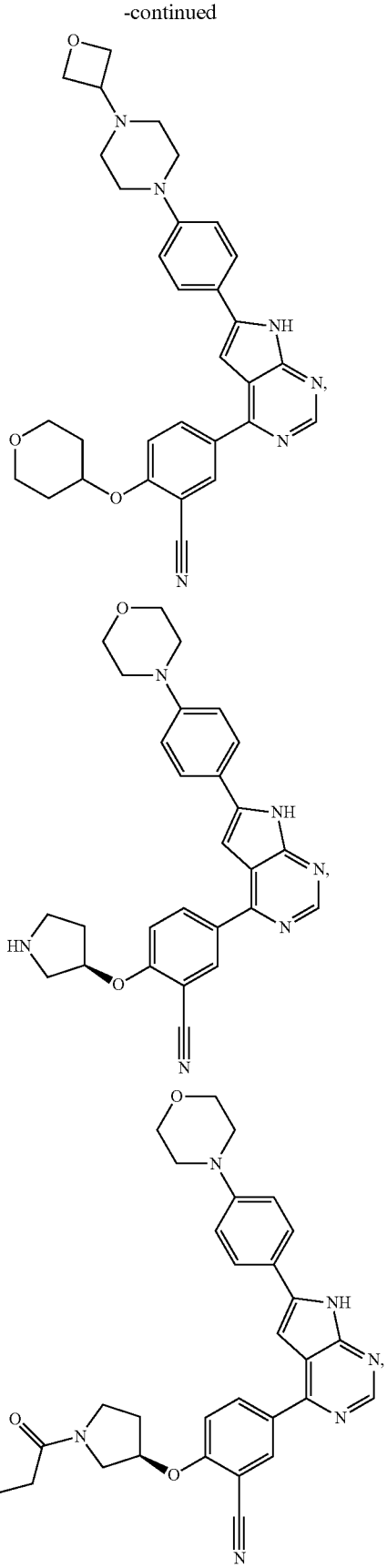

-continued
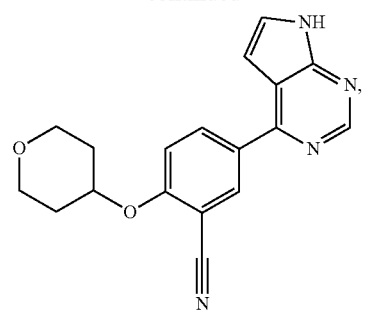
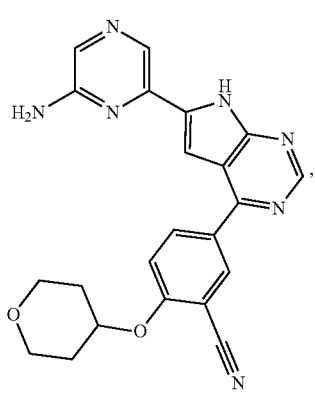
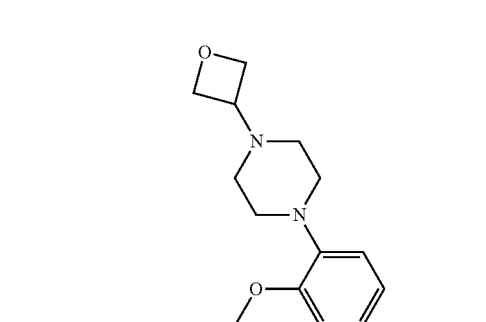
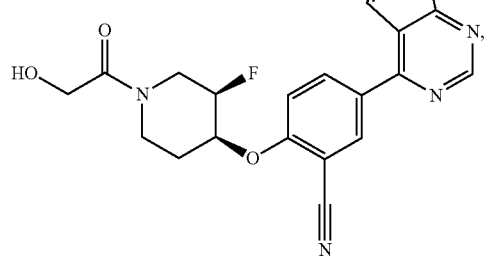
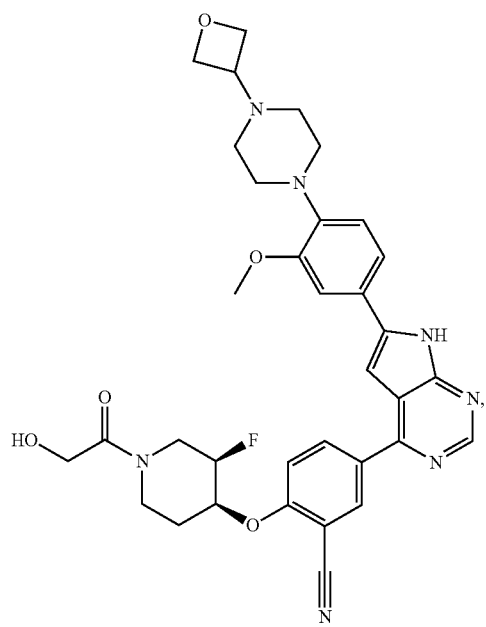
-continued
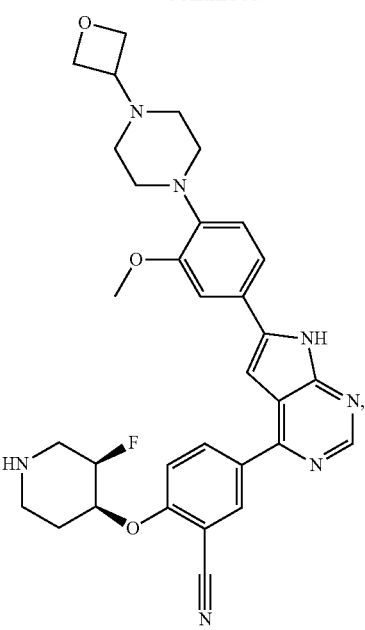
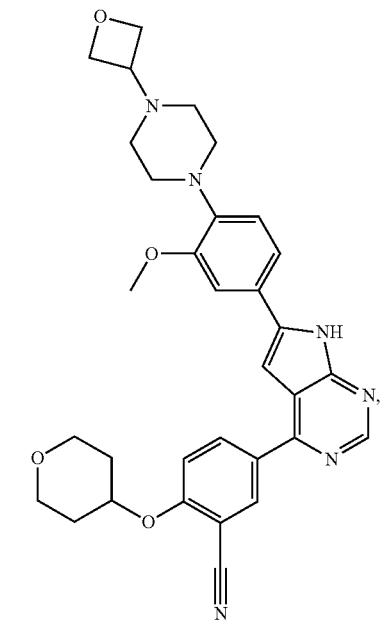

65
-continued
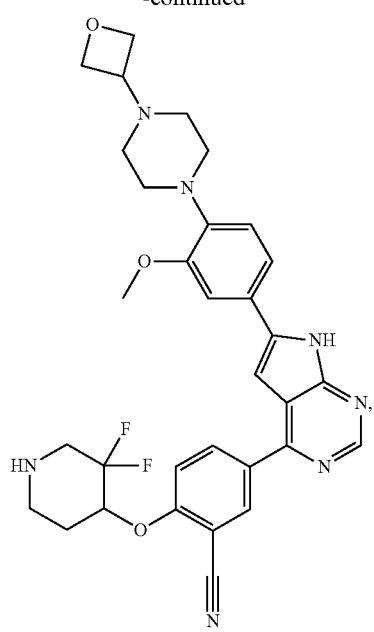
66
-continued
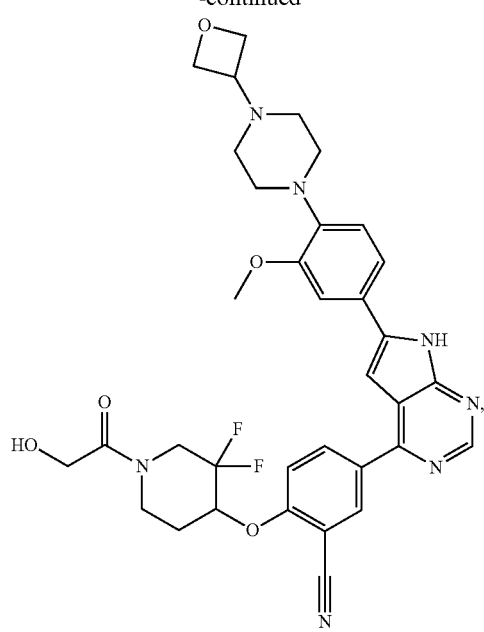
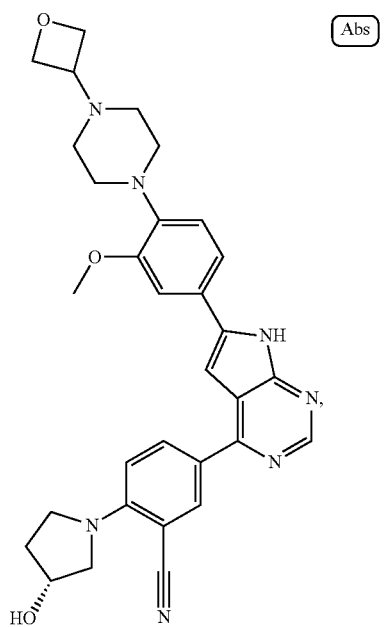
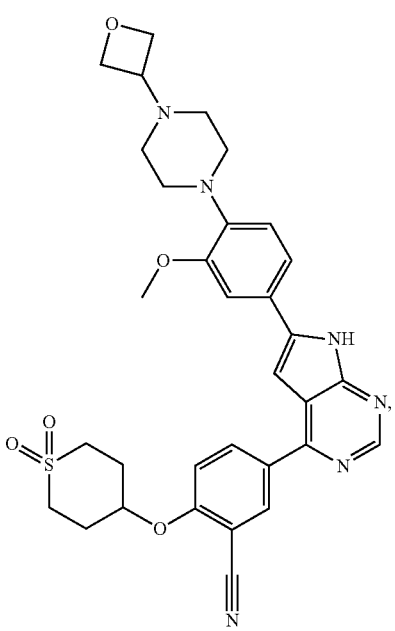

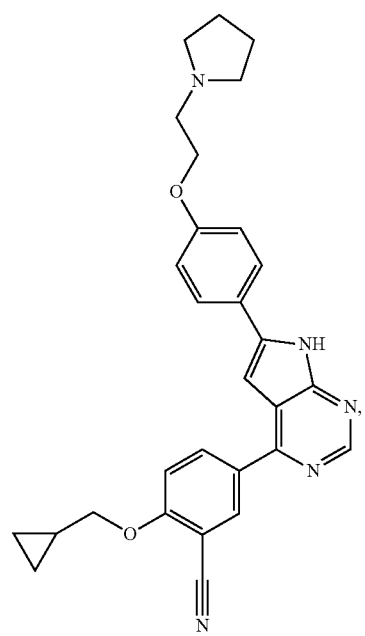
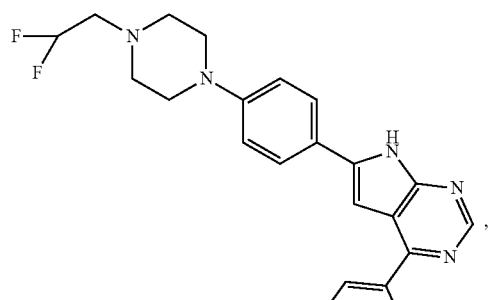
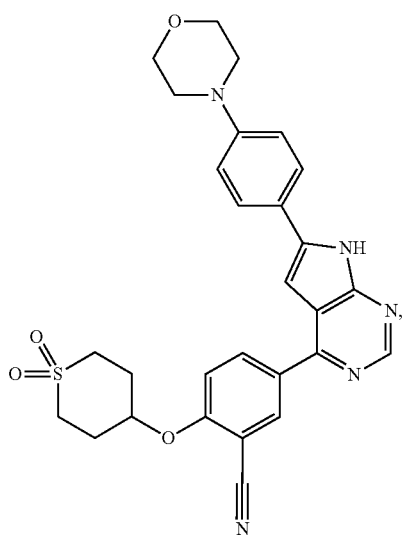
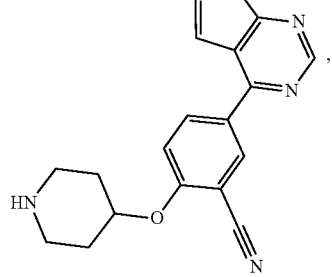
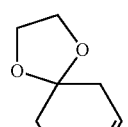
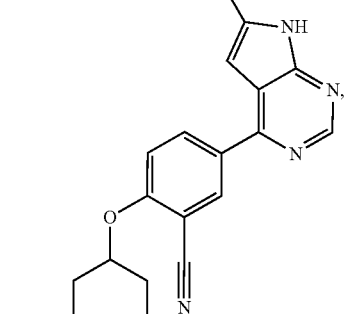
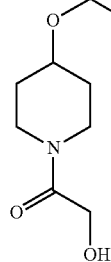

69
-continued
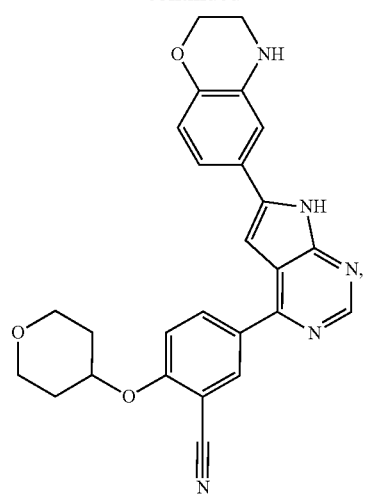
70
-continued
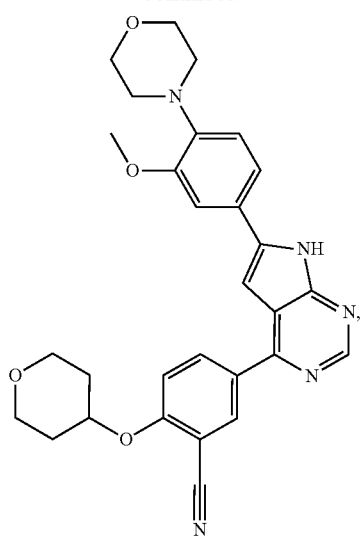
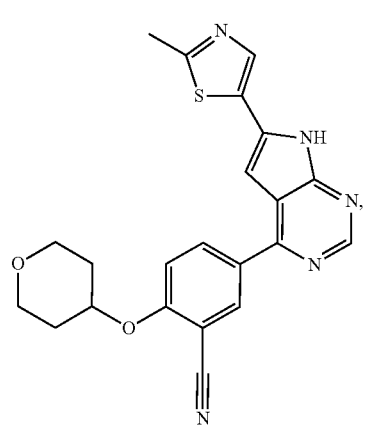
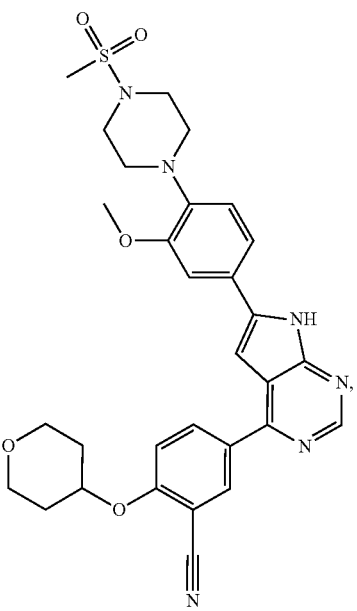

71
-continued
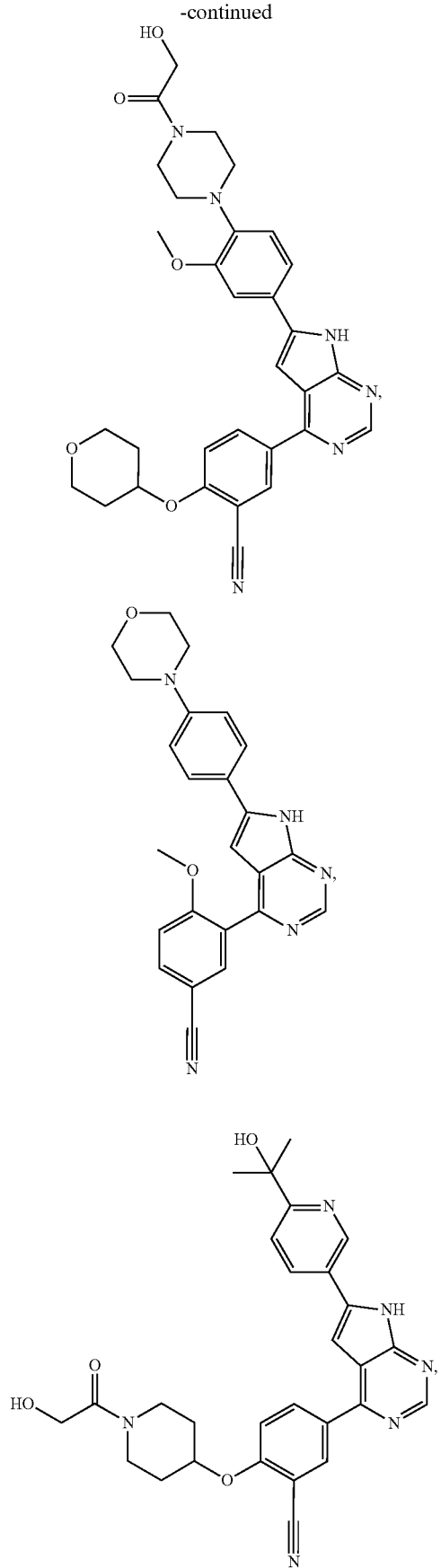
72
-continued
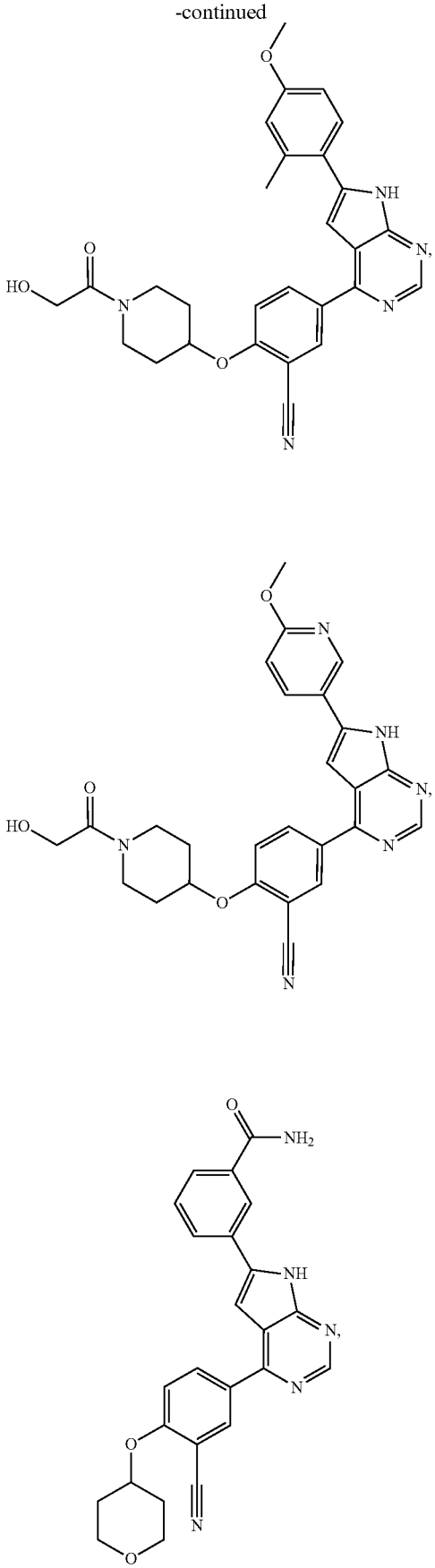

73
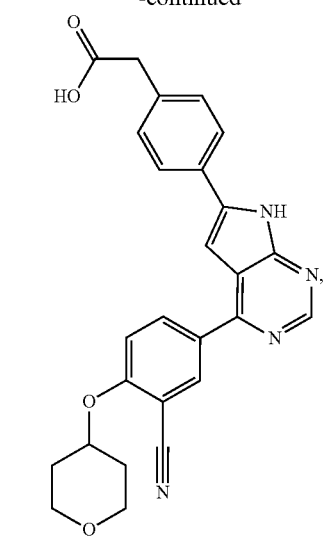
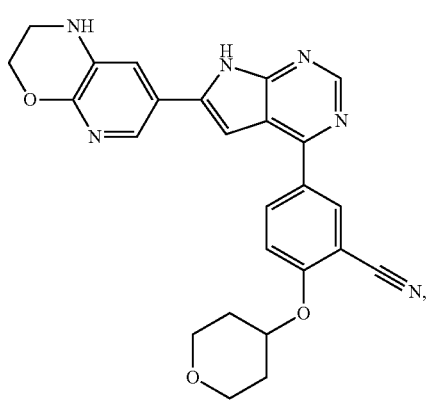
74
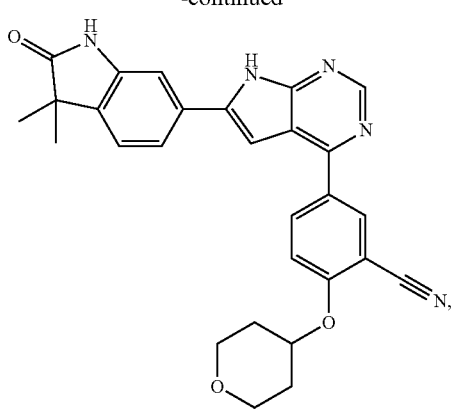
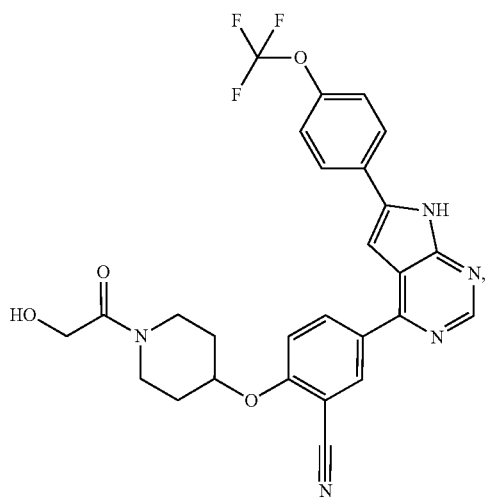
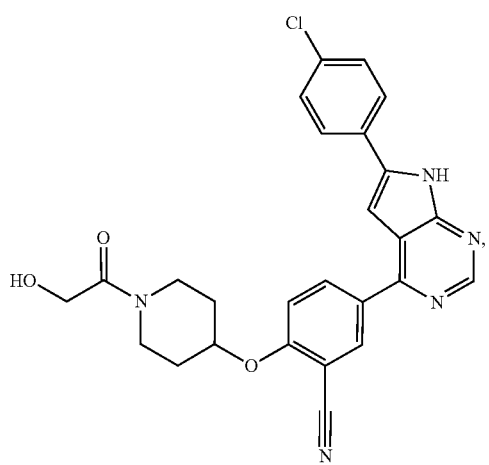

75
-continued
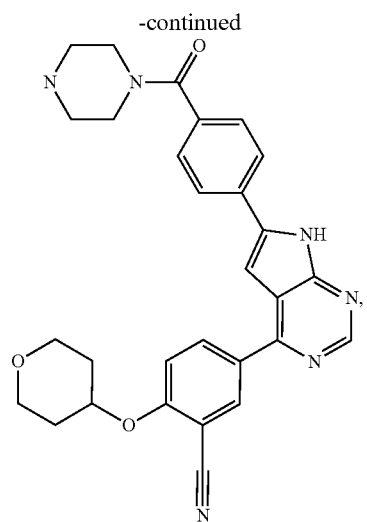
76
-continued
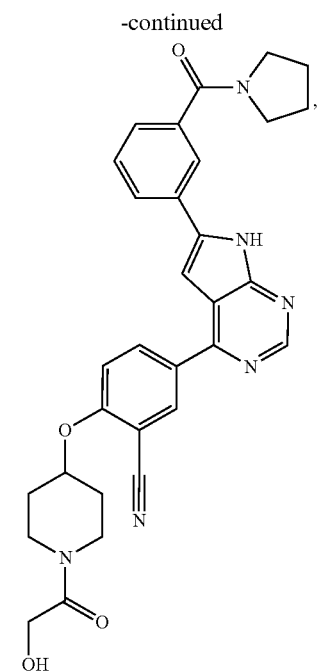
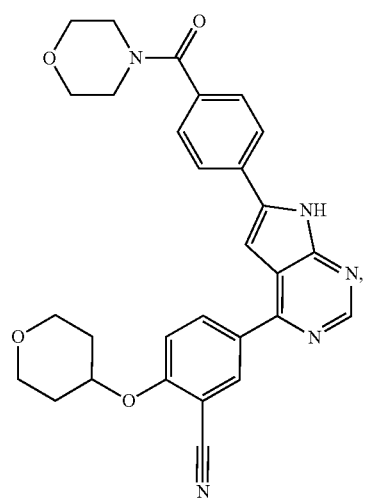
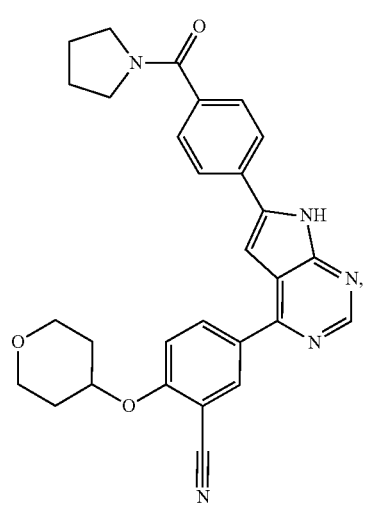
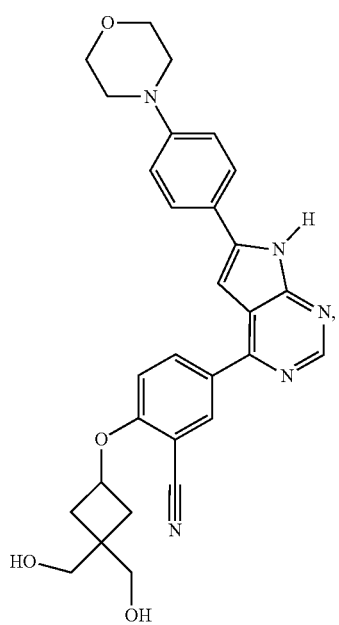

77
-continued
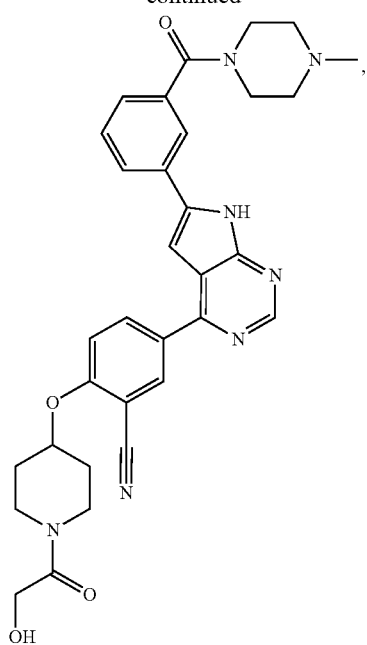
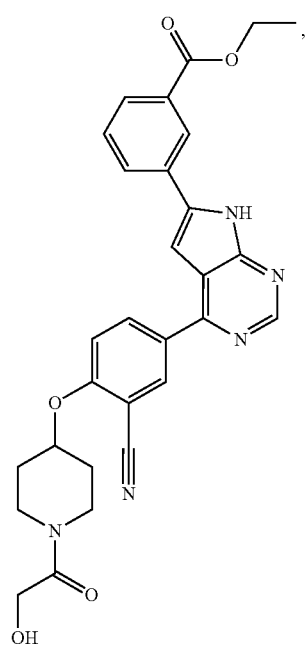
78
-continued
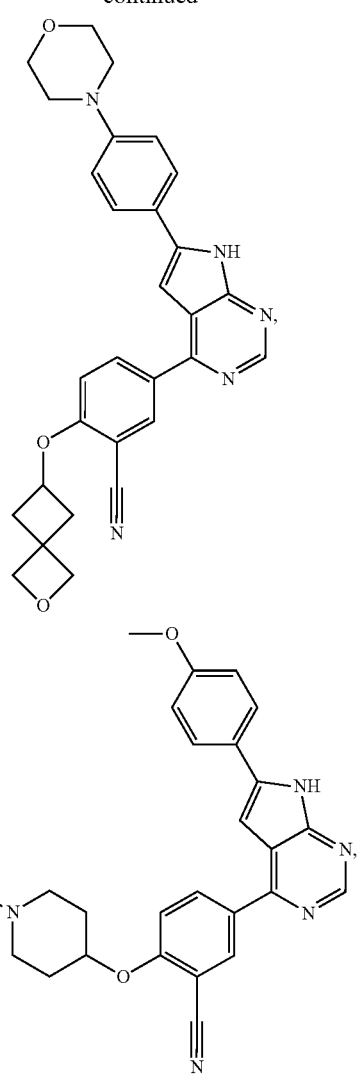
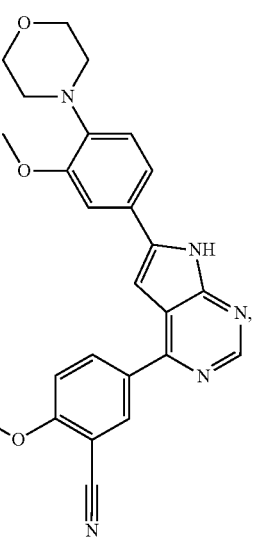

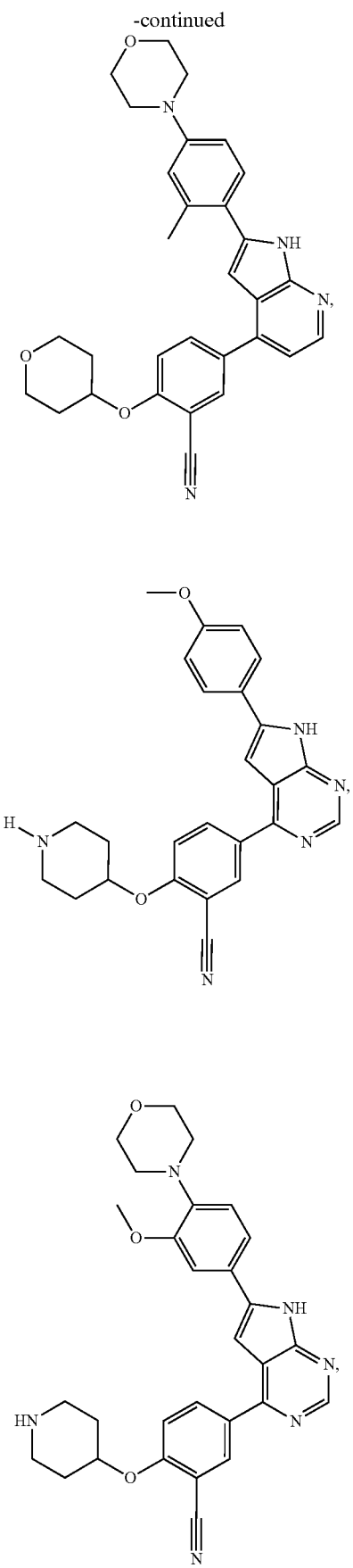
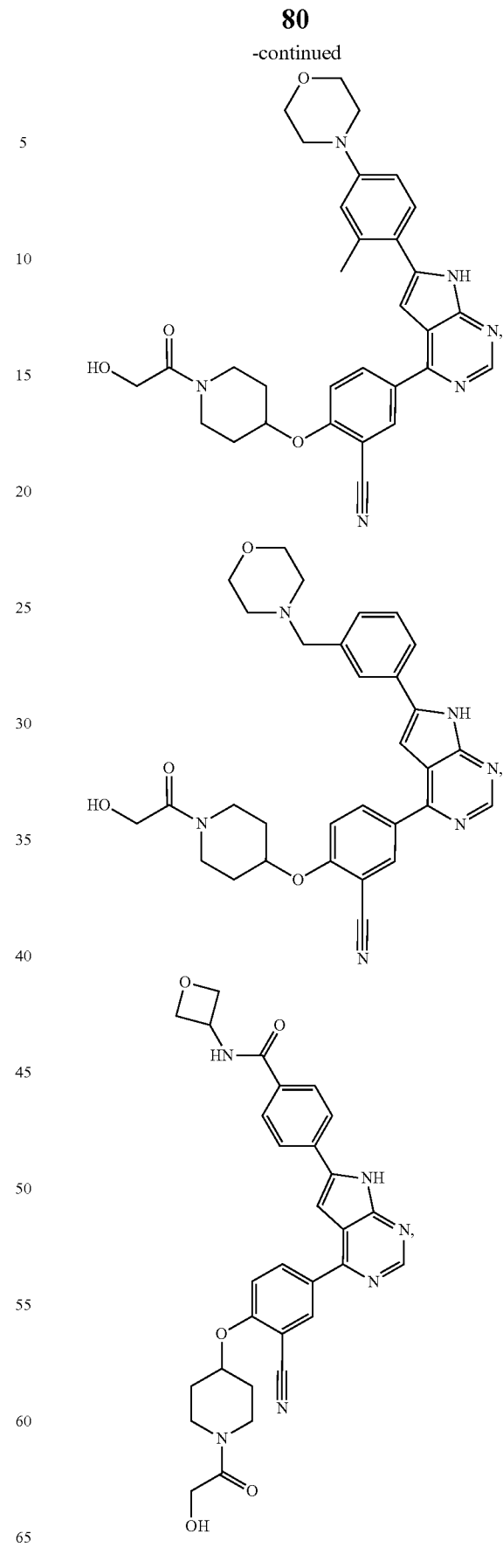

81
-continued
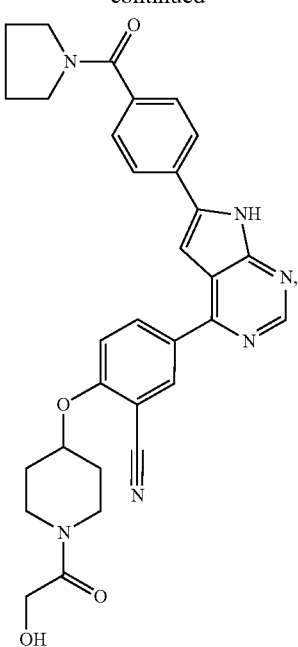
82
-continued
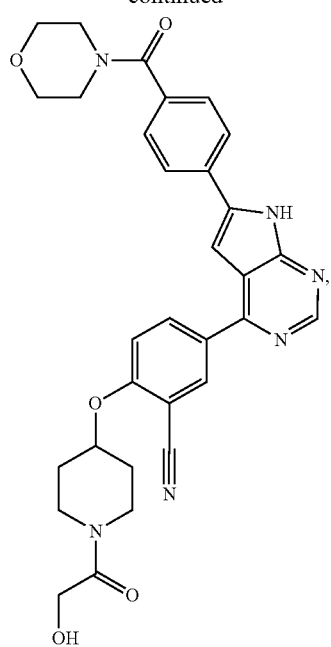
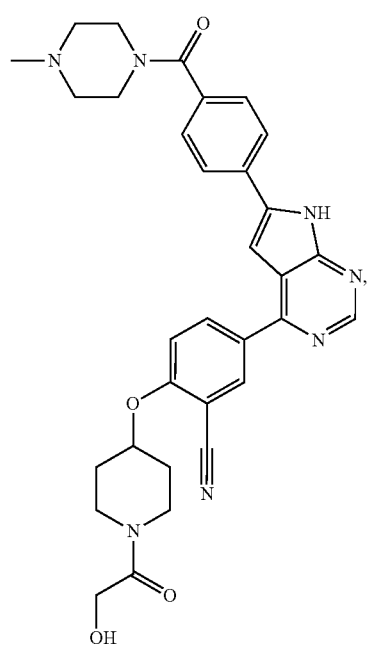
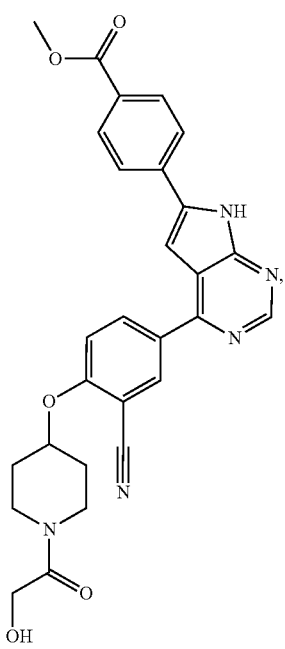

83
-continued
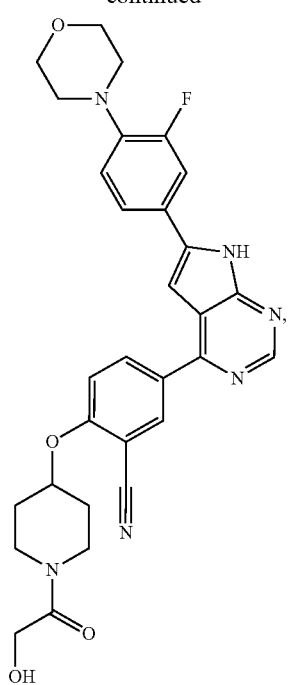
84
-continued
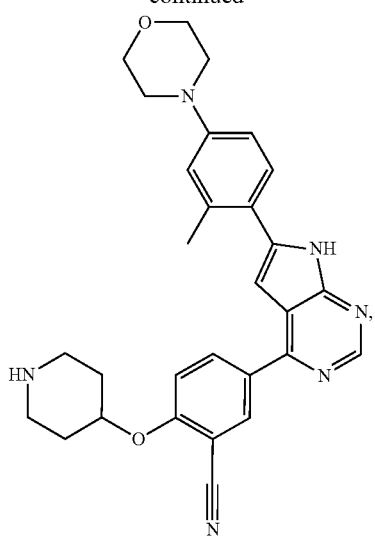
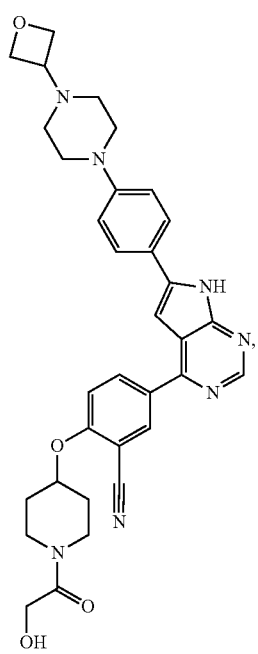
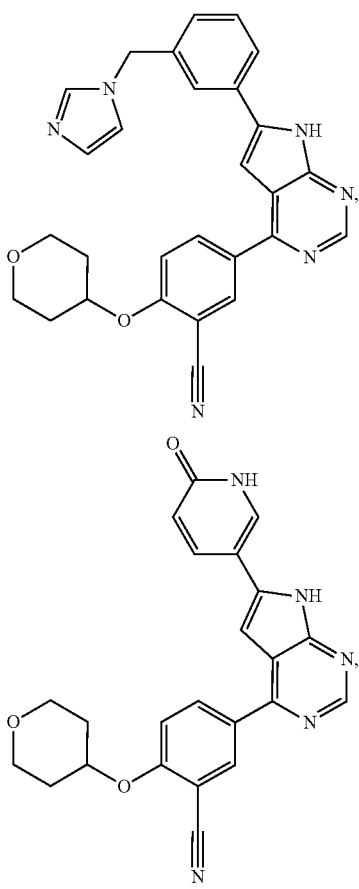

85
-continued
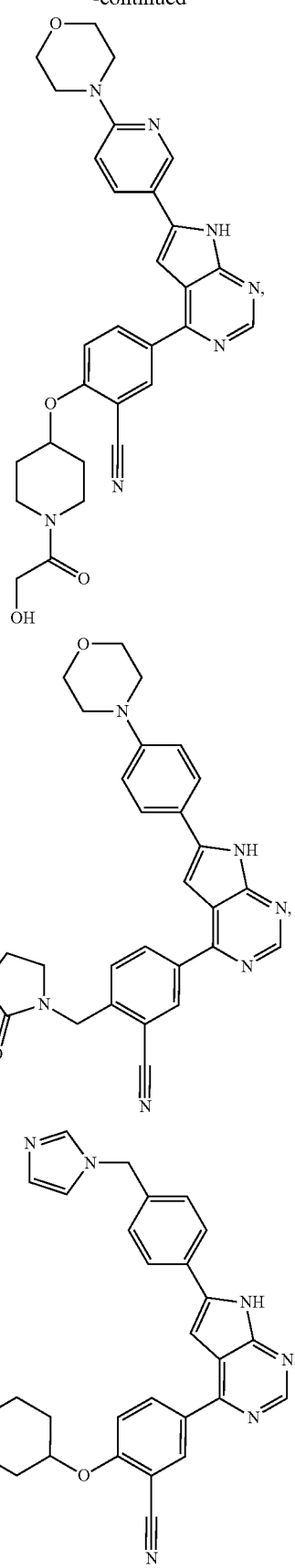
86
-continued
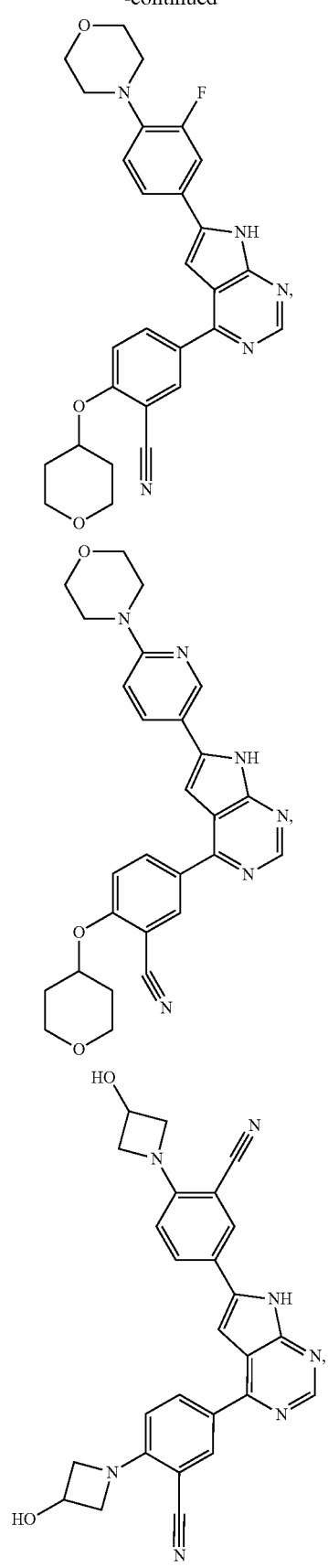

87
-continued
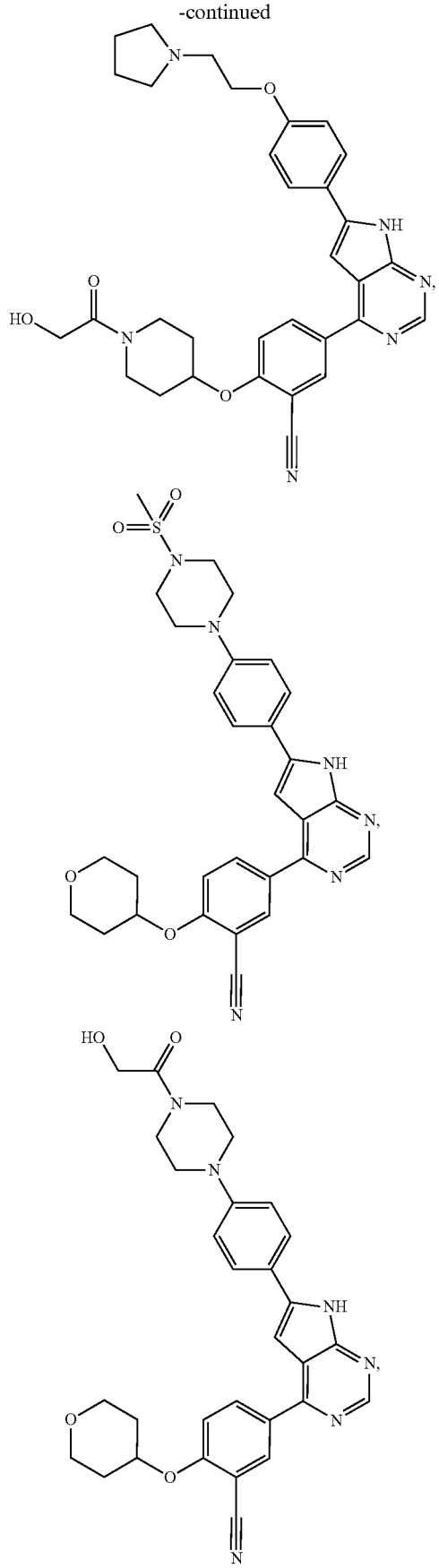
88
-continued
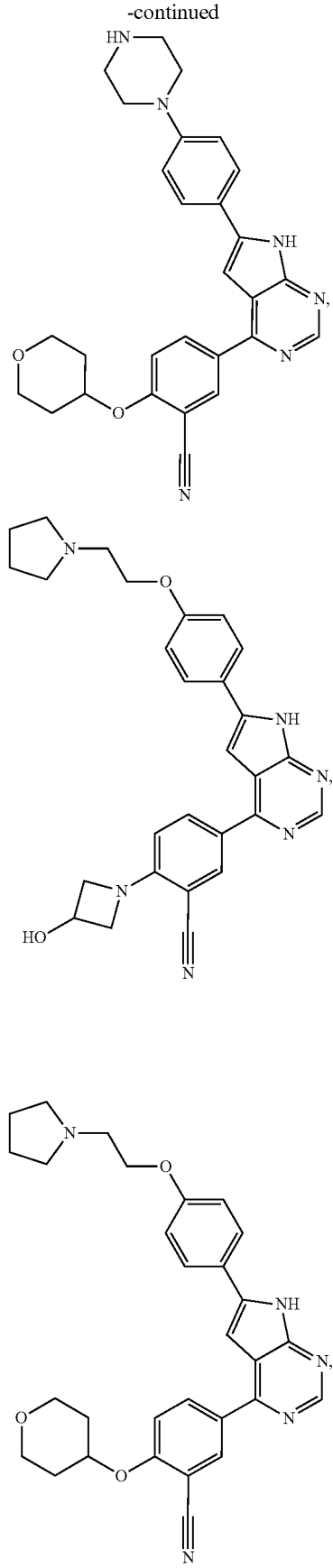

89
-continued
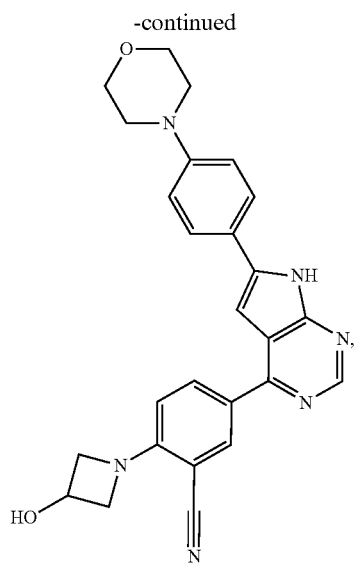
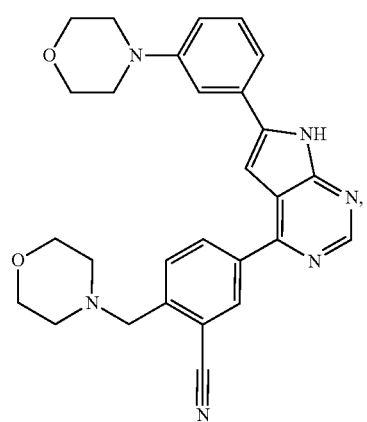
90
-continued
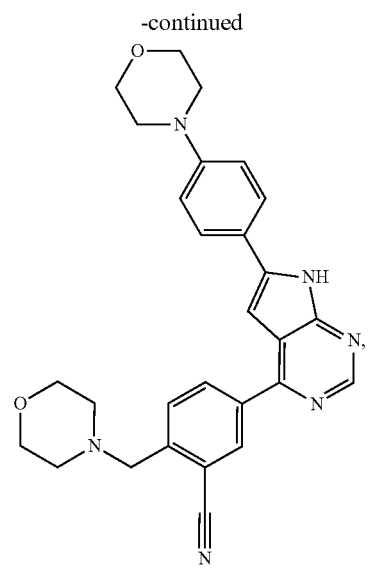
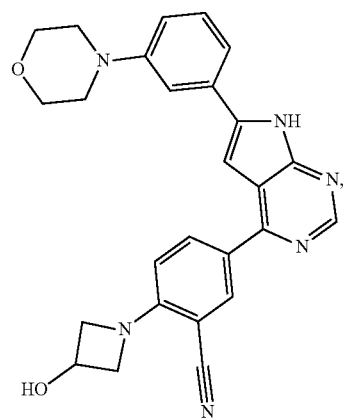

91
-continued
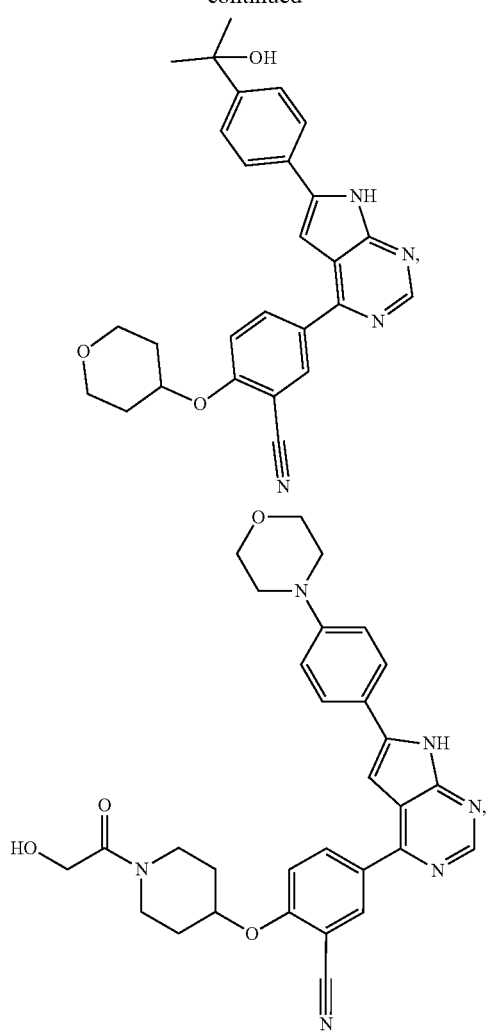
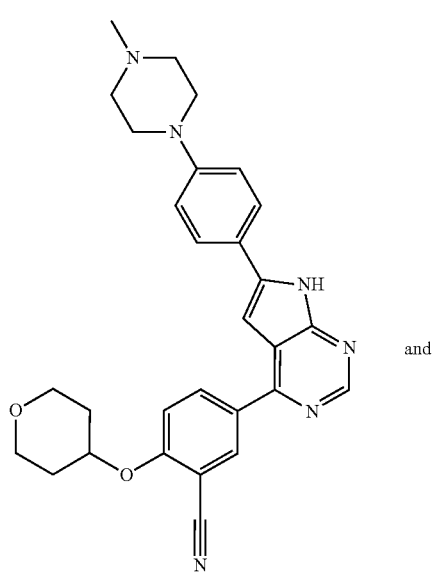
and
92
-continued
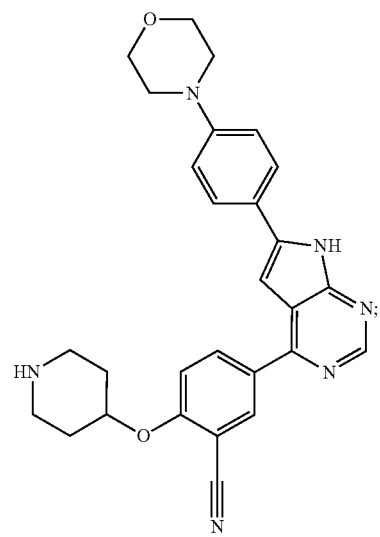
or a pharmaceutically acceptable salt thereof.
Another embodiment provides a compound selected from the group consisting of:
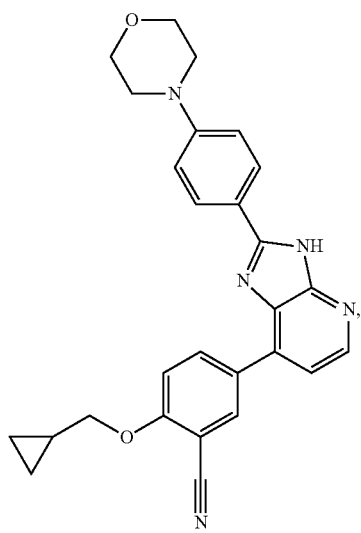

93
-continued
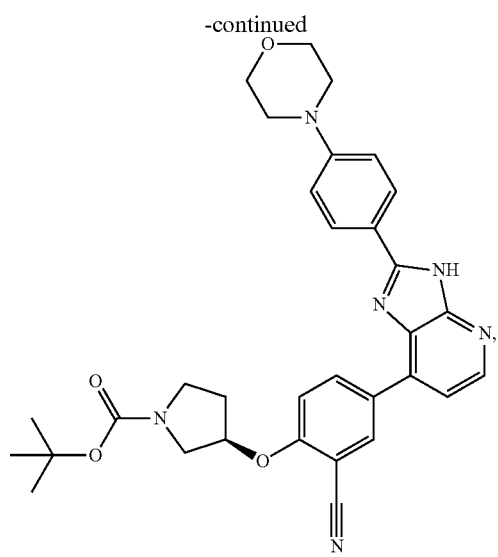
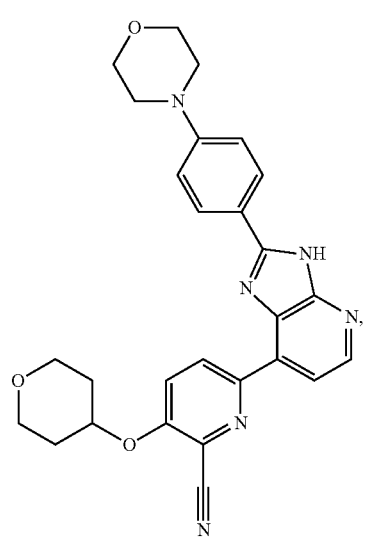
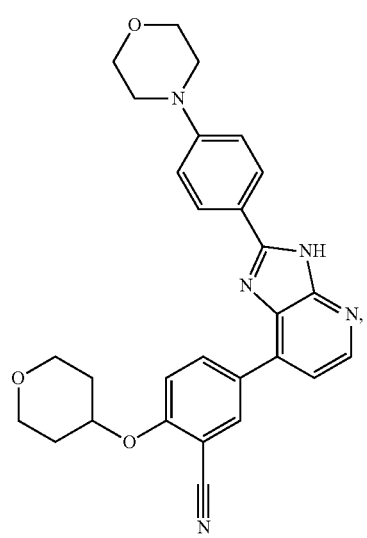
94
-continued
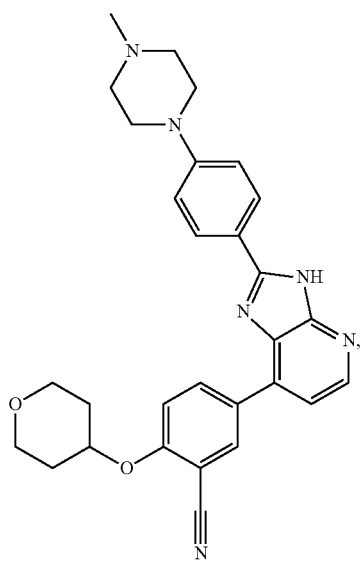
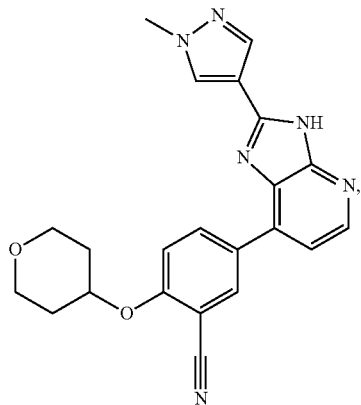
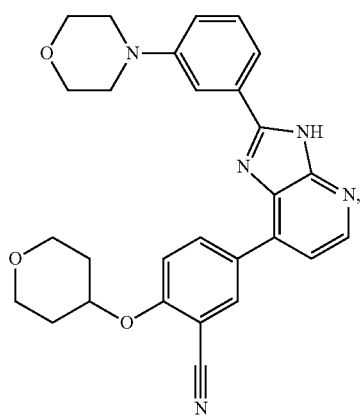

-continued
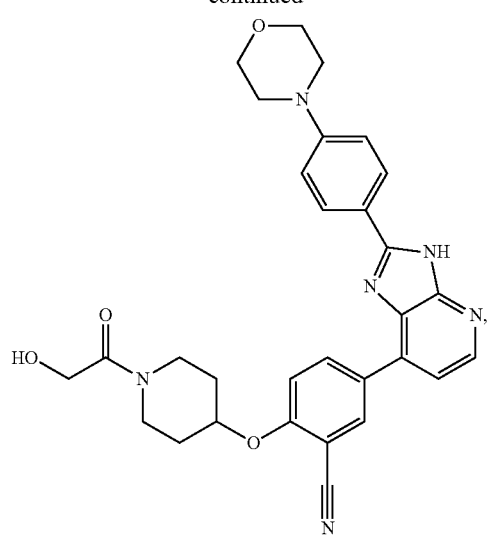
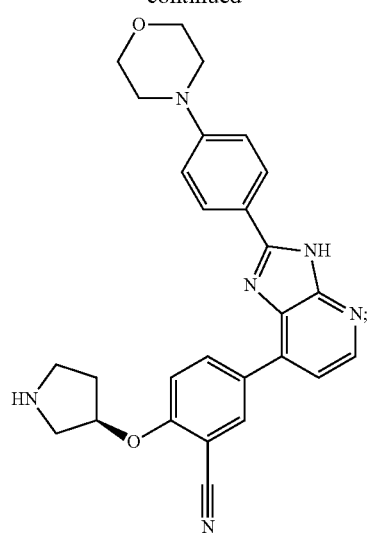
or a pharmaceutically acceptable salt thereof.
Another embodiment provides a compound selected from the group consisting of:
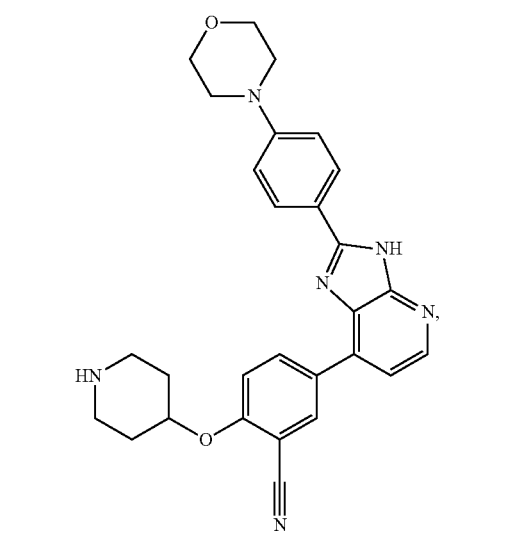
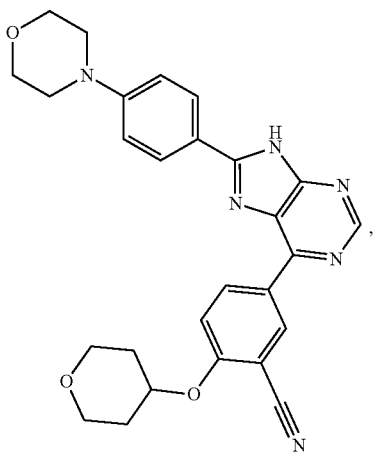
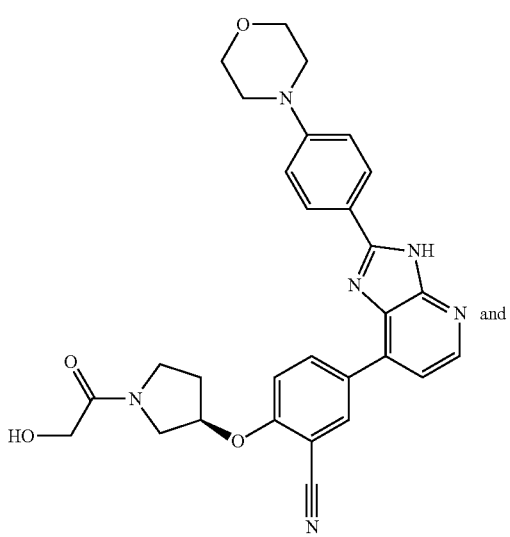
and
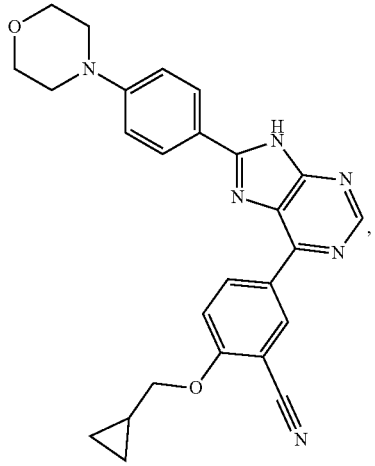

97
-continued
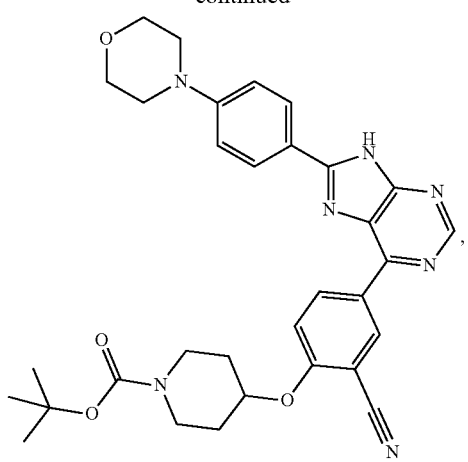
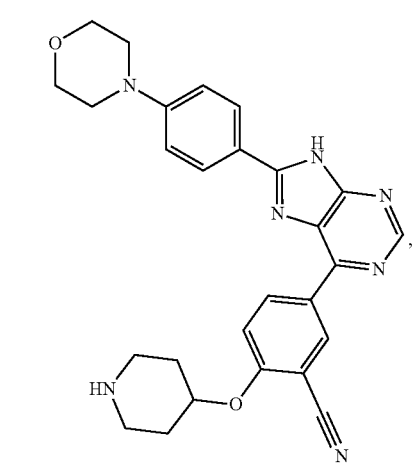
98
-continued
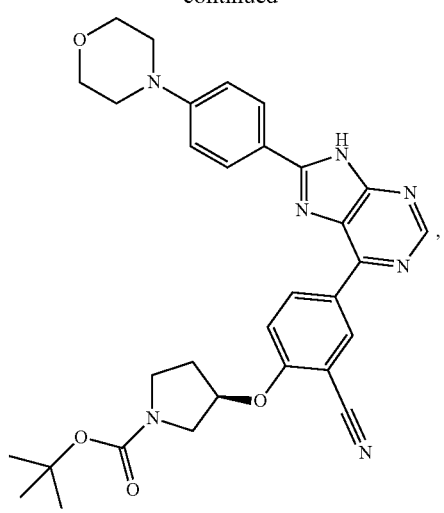
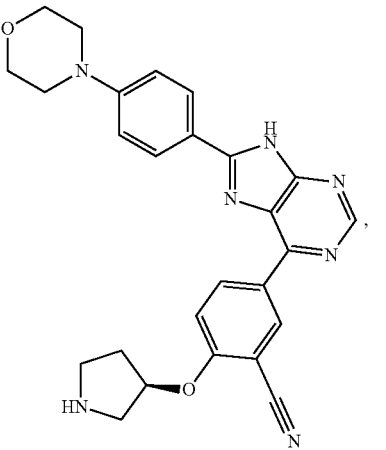

99
-continued
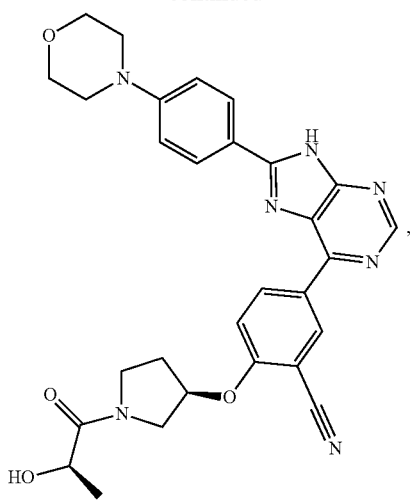
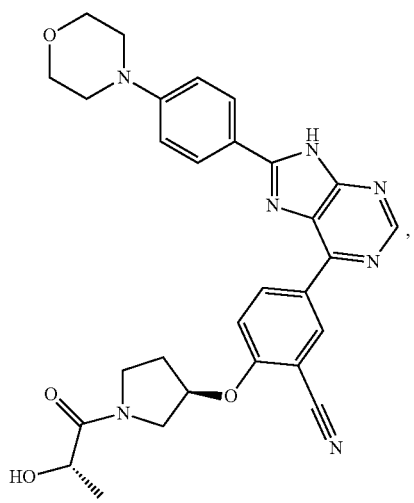
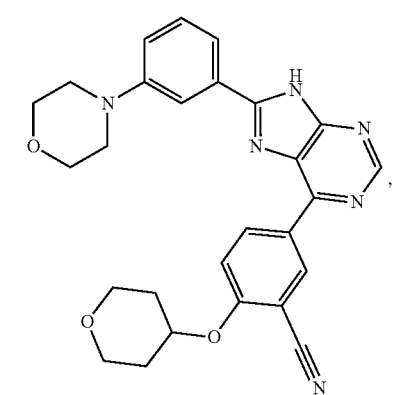
100
-continued
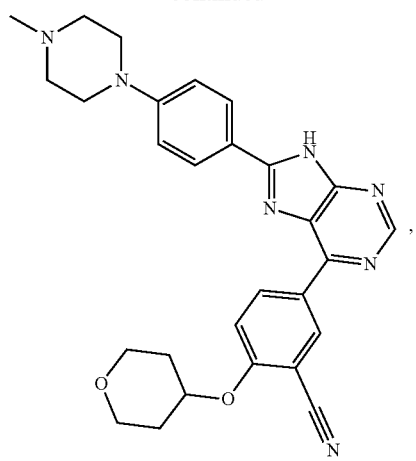
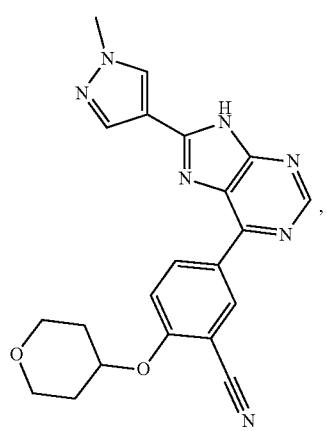
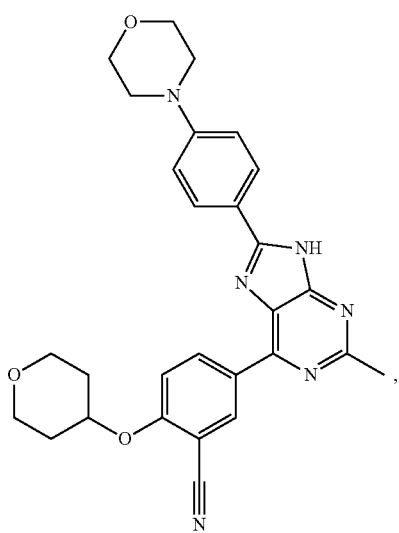

101
-continued
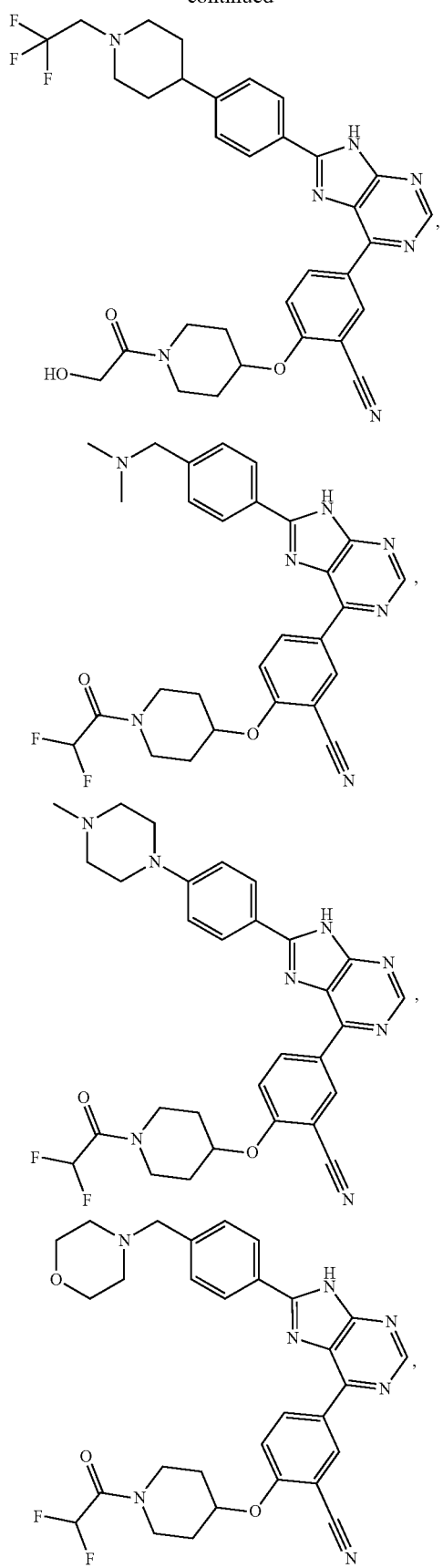
102
-continued
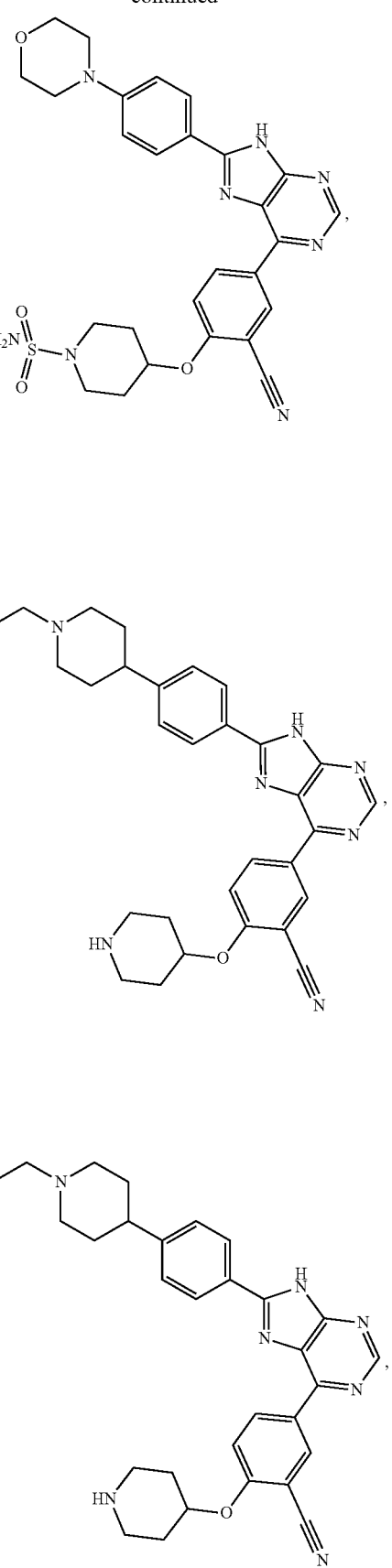

103
-continued
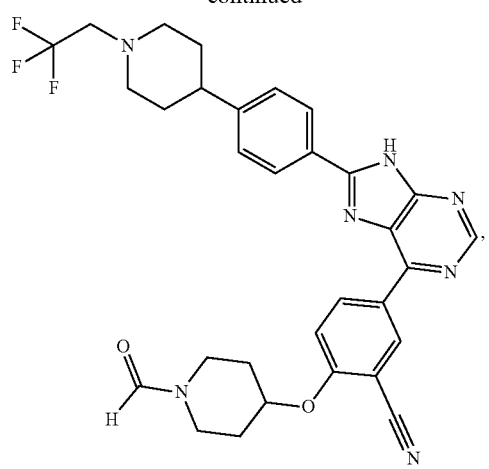
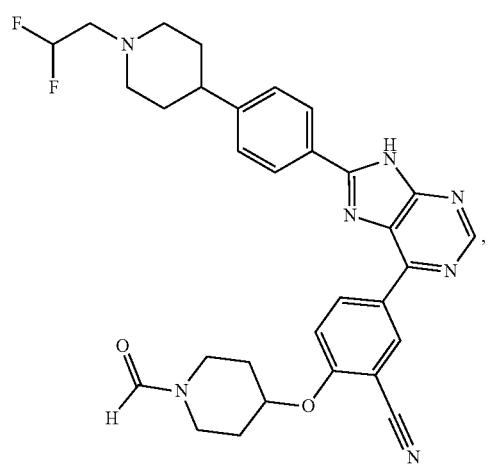
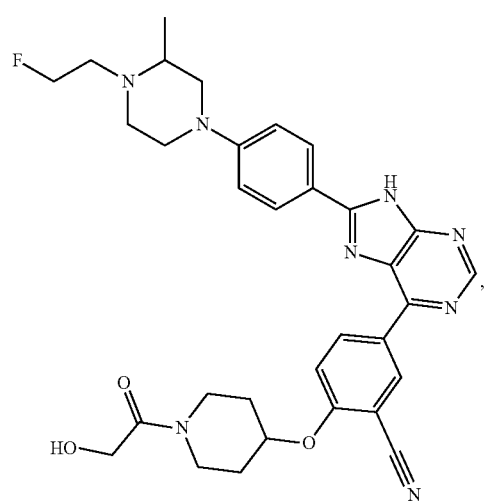
104
-continued
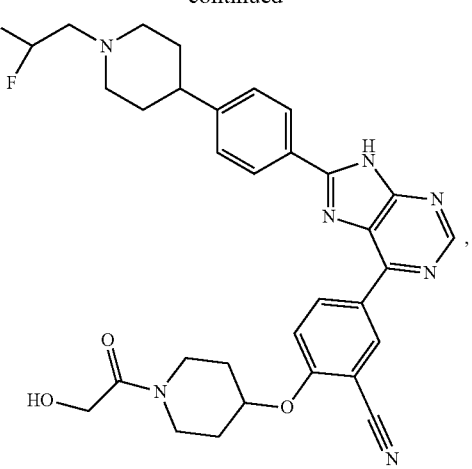
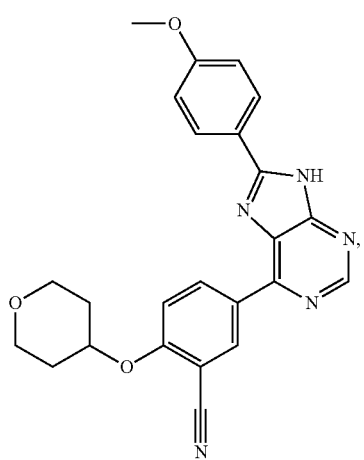
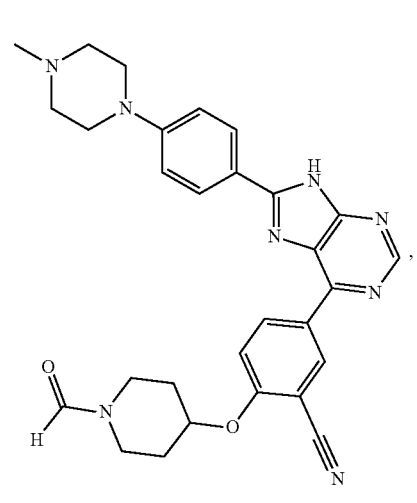

105
-continued
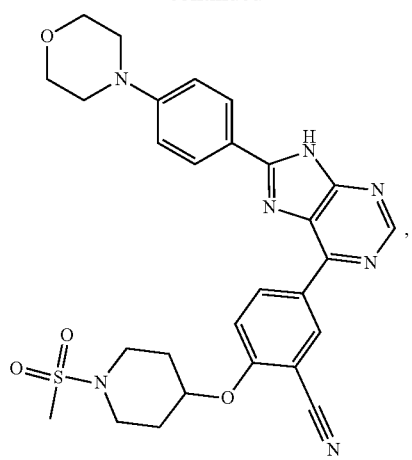
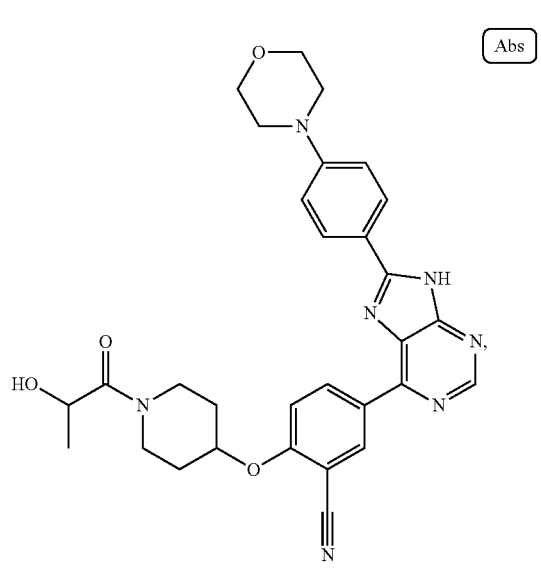
106
-continued
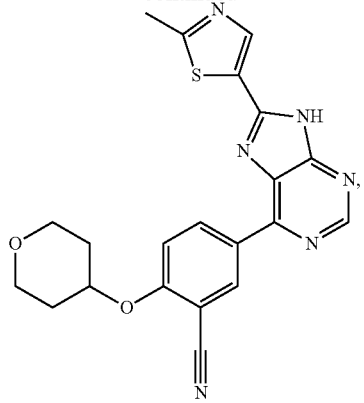
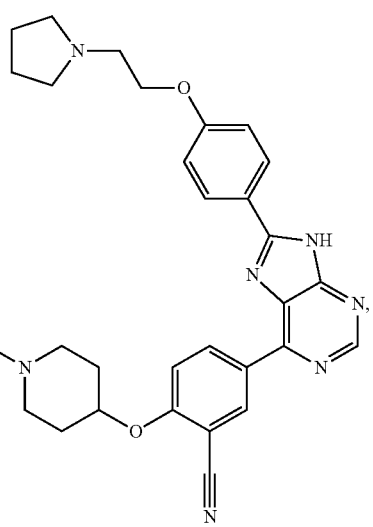
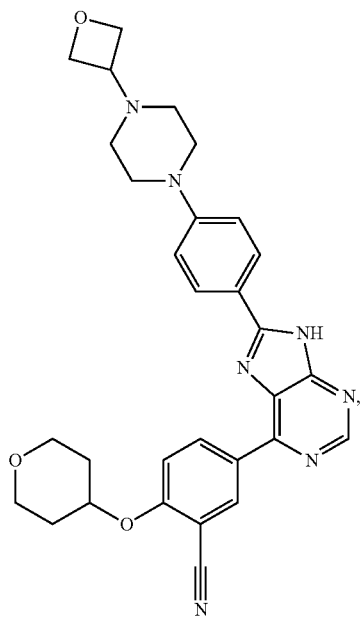

107
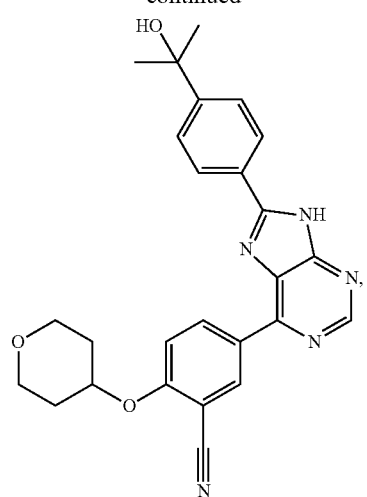
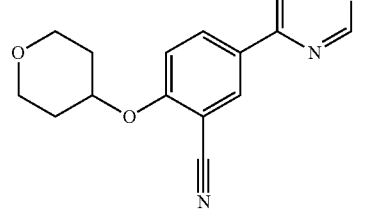
108
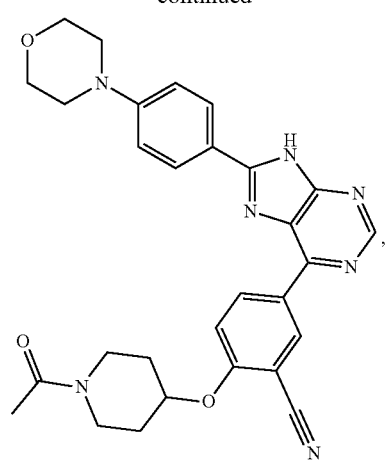
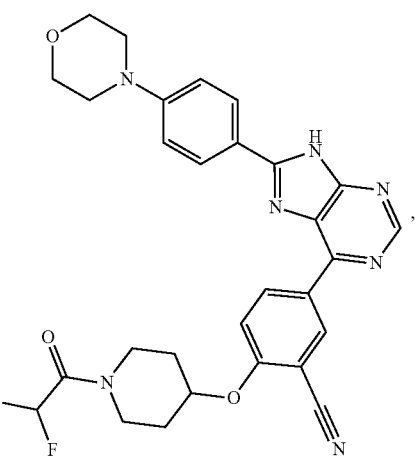
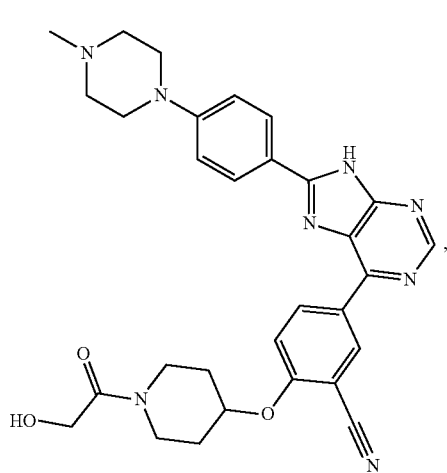
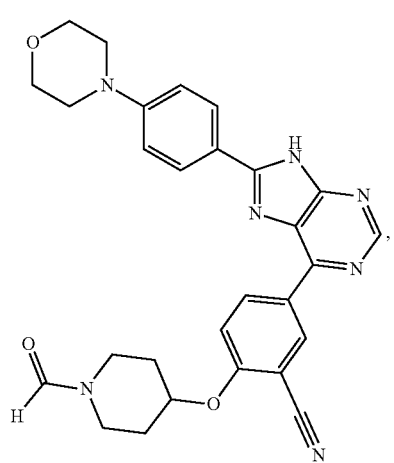
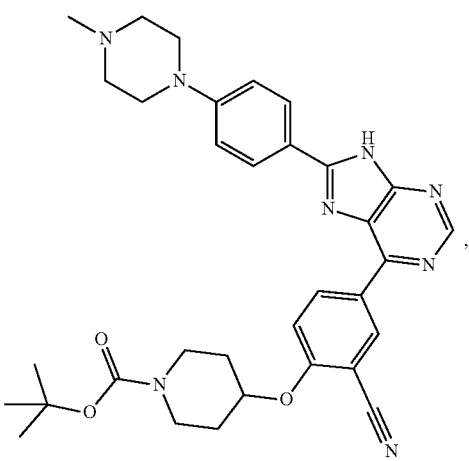

109
-continued
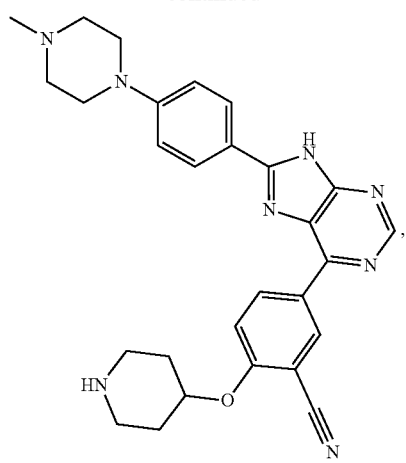
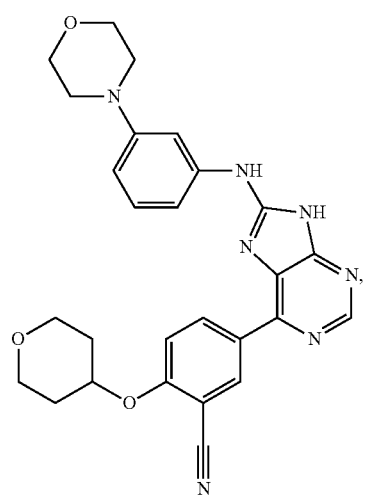
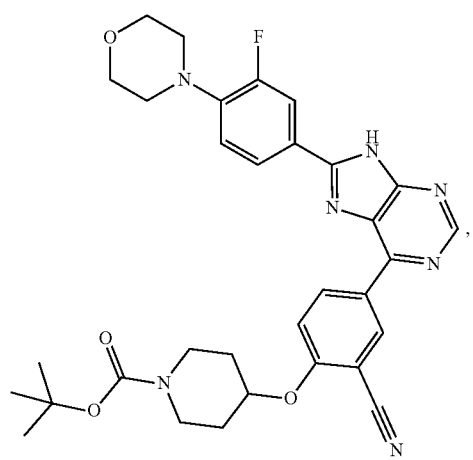
110
-continued
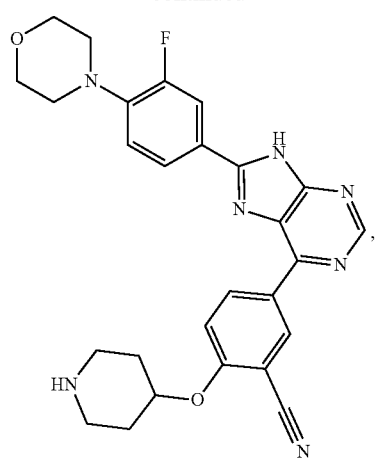
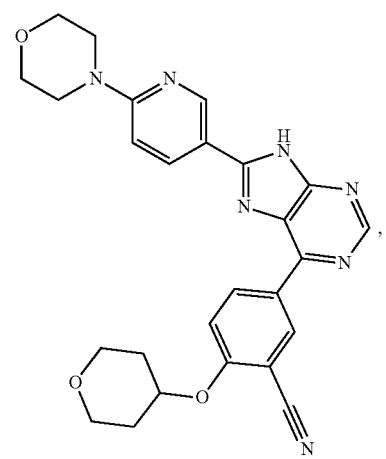
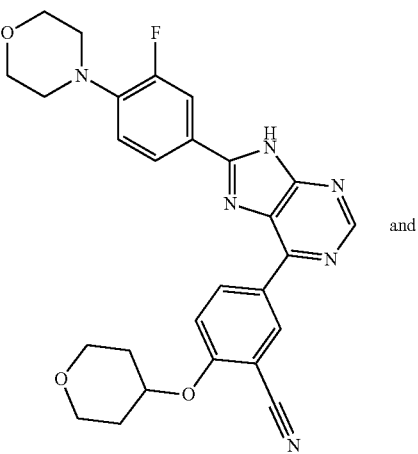
and

111

-continued

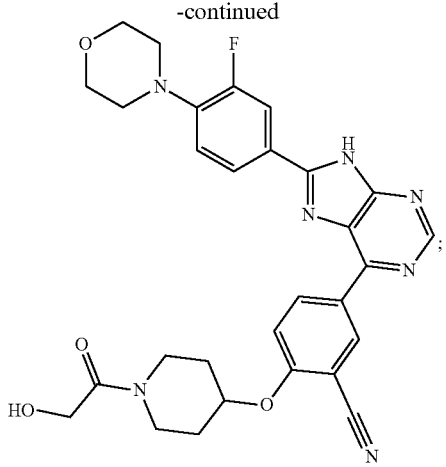

or a pharmaceutically acceptable salt thereof.

Another embodiment provides a compound of the formula:

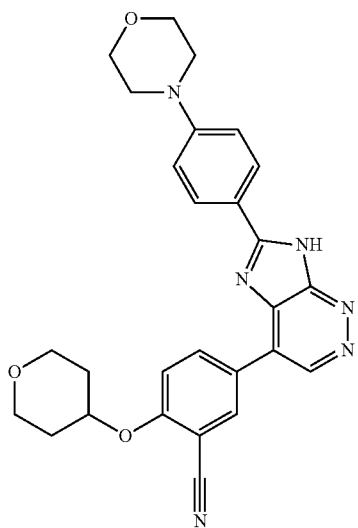

or a pharmaceutically acceptable salt thereof.

Another embodiment provides a pharmaceutical composition comprising a compound as described herein, or a pharmaceutically acceptable salt thereof, and a pharmaceutically acceptable carrier.

Another embodiment provides a method of treating a subject having a disease or condition responsive to the inhibition of TBK1, comprising administering to the subject a therapeutically effective amount of a compound as described herein, or a pharmaceutically acceptable salt thereof. In another embodiment, the disease is cancer. Another embodiment provides a method of treating a subject having a disease or condition responsive to the inhibition of IKKε, comprising administering to the subject a therapeutically effective amount of a compound as described herein, or a pharmaceutically acceptable salt thereof.

Another embodiment provides a method of treating a subject suffering from a RAS-dependent/mutant cancer, comprising administering to the subject a therapeutically effective amount of a compound as described herein. In another embodiment, the RAS-dependent/mutant cancer is selected from the group consisting of non-small cell lung cancer, colorectal cancer, pancreatic cancer, AML, and melanoma.

Another embodiment provides a method of treating a subject suffering from breast or ovarian cancer, comprising administering to the subject a therapeutically effective amount of a compound as described herein. Another embodiment provides a method of treating a subject suffering from cancer resistant to HER2 and EGFR targeted therapies comprising administering to the subject a therapeutically effective amount of a compound as described herein.

Another embodiment provides a method of treating a subject suffering from a disease selected from the group consisting of Rheumatoid arthritis (RA), Inflammatory bowel disease (IBD), Chronic obstructive pulmonary disease (COPD), Systemic lupus erythematosus (SLE), Polymositis, Systemic sclerosis, Type 2 diabetes, Obesity and Hepatic steatosis.

Another embodiment provides a method of inhibiting TBK1 in a subject, comprising administering a compound of a compound described herein, or a pharmaceutically acceptable salt thereof. Another embodiment provides a method of inhibiting IKKε in a subject, comprising administering a compound as described herein, or a pharmaceutically acceptable salt thereof.

Another embodiment provides further administering to the subject an additional active agent.

Another embodiment provides a compound as described herein, or a pharmaceutically acceptable salt thereof, for use in therapy.

Another embodiment provides a compound as described herein, or a pharmaceutically acceptable salt thereof, for use in a method of treating a subject having a disease or condition responsive to the inhibition of TBK1. In an embodiment, the disease is cancer. Another embodiment provides a compound as described herein, or a pharmaceutically acceptable salt thereof for use in a method of treating a subject having a disease or condition responsive to the inhibition of IKKε.

Another embodiment provides a compound as described herein, or a pharmaceutically acceptable salt thereof, for use in a method of treating a subject suffering from a RAS-dependent/mutant cancer. In an embodiment, the RAS-dependent/mutant cancer is selected from the group consisting of non-small cell lung cancer, colorectal cancer, pancreatic cancer, AML, and melanoma.

Another embodiment provides a compound as described herein, or a pharmaceutically acceptable salt thereof, for use in a method of treating a subject suffering from breast or ovarian cancer. Another embodiment provides a compound as described herein, or a pharmaceutically acceptable salt thereof, for use in a method of treating a subject suffering from cancer resistant to HER2 and EGFR targeted therapies.

Another embodiment provides a compound as described herein, or a pharmaceutically acceptable salt thereof, for use in a method of treating a subject suffering from a disease selected from the group consisting of Rheumatoid arthritis (RA), Inflammatory bowel disease (IBD), Chronic obstructive pulmonary disease (COPD), Systemic lupus erythematosus (SLE), Polymositis, Systemic sclerosis, Type 2 Obesity and Hepatic steatosis.

Another embodiment provides a compound as described herein, or a pharmaceutically acceptable salt thereof, for use in a method of treating a subject suffering from cancer.

Another embodiment provides a compound as described herein, or a pharmaceutically acceptable salt thereof, for use in a method of inhibiting TBK1 in a subject. Another embodiment provides a compound as described herein, or a pharmaceutically acceptable salt thereof, for use in a method of inhibiting IKKε in a subject.

Another embodiment provides the use of a compound as described herein, or a pharmaceutically acceptable salt thereof, in the manufacture of a medicament for treating a subject having a disease or condition responsive to the inhibition of TBK1. In an embodiment, the disease is cancer. Another embodiment the use of a compound as described herein, or a pharmaceutically acceptable salt thereof, in the manufacture of a medicament for treating a subject having a disease or condition responsive to the inhibition of IKKε.

Another embodiment provides the use of a compound as described herein, or a pharmaceutically acceptable salt thereof, in the manufacture of a medicament for treating a subject suffering from a RAS-dependent/mutant cancer. In an emobodiment, the RAS-dependent/mutant cancer is selected from the group consisting of non-small cell lung cancer, colorectal cancer, pancreatic cancer, AML, and melanoma.

Another embodiment provides the use of a compound as described herein, or a pharmaceutically acceptable salt thereof, in the manufacture of a medicament for treating a subject suffering from breast or ovarian cancer. Another embodiment provides the use of a compound as described herein, or a pharmaceutically acceptable salt thereof, in the manufacture of a medicament for treating a subject suffering from cancer resistant to HER2 and EGFR targeted therapies.

Another embodiment provides the use of a compound as described herein, or a pharmaceutically acceptable salt thereof, in the manufacture of a medicament for treating a subject suffering from a disease selected from the group consisting of Rheumatoid arthritis (RA), Inflammatory bowel disease (IBD), Chronic obstructive pulmonary disease (COPD), Systemic lupus erythematosus (SLE), Polymositis, Systemic sclerosis, Type 2 diabetes, Obesity and Hepatic steatosis.

Another embodiment provides the use of a compound as described herein, or a pharmaceutically acceptable salt thereof, in the manufacture of a medicament for inhibiting TBK1 in a subject. Another embodiment provides the use of a compound as described herein, or a pharmaceutically acceptable salt thereof, in the manufacture of a medicament for inhibiting IKKε in a subject.

DETAILED DESCRIPTION OF THE INVENTION

The following is a list of abbreviations and acronyms used throughout the application:

| Abbreviation | Meaning |
| --- | --- |
| °C. | Degree Celsius |
| ATP | Adenosine-5'-triphosphate |
| AcOH | Acetic acid |
| ACN | Acetonitrile |
| CAN | Ceric ammonium nitrate |
| CDI | 1,1'-carbonyldiimidazole |
| conc. | Concentrated |
| d | Doublet |
| DABCO | 1,4-Diazabicyclo[2.2.2]octane |
| DAST | (Diethylamino)sulfur trifluoride |
| dd | Doublet of doublets |
| DCE | 1,2-dichloroethane |
| DCM | Dichloromethane |
| DEAD | Diethyl azodicarboxylate |
| DIAD | Diisopropyl azodicarboxylate |
| DIPEA | N,N-diisopropylethylamine |
| DMAP | 4-dimethylaminopyridine |
| DME | 1,2-dimethoxyethane |
| DMF | Dimethylformamide |
| DMSO | Dimethylsulfoxide |
| dppf | 1,1'-Bis(diphenylphosphino)ferrocene |
| EA | Ethyl alcohol |
| ECF | Extracellular fluid |
| EDTA | Ethylenediaminetetraacetic acid |
| EGTA | Ethylene glycol tetraacetic acid |
| ETOAC | Ethyl acetate |
| equiv/eq | Equivalents |
| ESI | Electrospray ionization |
| Ac | Acetate |
| Et | Ethyl |
| g | Grams |
| HATU | 2-(7-Aza-1H-Benzotriazole-1-yl)-1,1,3,3-tetramethyluronium hexafluorophosphate |
| hERG | human Ether-à-go-go Related Gene |
| HMDS | hexamethyldisilazane(azide) |
| HPLC | High-performance liquid chromatography |
| h/hr | Hours |
| Hz | Hertz |
| $IC_{50}$ | The half maximal inhibitory concentration |
| J | Coupling constant |
| Kg | Kilogram |
| LAH | Lithium ammonium hydride |
| LCMS/LC-MS | Liquid chromatography-mass spectrometry |
| LDA | Lithium diisopropylamide |
| M | Molar |
| m | multiplet |
| m/z | mass-to-charge ratio |
| M+ | Mass peak |
| M + H | Mass peak plus hydrogen |
| mCPBA | 3-chloroperoxybenzoic acid |
| Me | Methyl |
| MeOH | Methyl alcohol/methanol |
| mg | Milligram |
| MHz | Megahertz |
| min/m | Minute |
| ml/mL | Milliliter |
| mM | Millimolar |
| mmol | Millimole |
| MS | Mass spectroscopy |
| mw | Microwave |
| N | Normal |
| mol | Mole |
| NMP | N-methylpyrrolidinone |
| NMR | Nuclear magnetic resonance |
| Ph | Phenyl |
| PEPPSI™-IPr | [1,3-Bis(2,6-Diisopropylphenyl)imidazol-2-ylidene](3-chloropyridyl)palladium(II) dichloride |
| ppm | Parts per million |
| prep | Preparative |
| Rf | Retention factor |
| RP | Reverse phase |
| RT/rt | Room temperature |
| s | Second |
| s | Singlet |
| SEM | 2-(Trimethylsilyl)ethoxymethyl |
| t | Triplet |
| TEA | Triethylamine |
| TFA | Trifluoroacetic acid |
| THF | Tetrahydrofuran |
| 2-MeTHF/Me-THF | 2-Methyl Tetrahydrofuran |
| TLC | Thin layer chromatography |
| TMS | trimethylsilyl |
| WT | Wild type |
| δ | Chemical shift |
| μg | Microgram |
| μL/μl | Microliter |
| μM | Micromolar |
| μm | Micrometer |
| μmol | Micromole |

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

A dash at the front or end of a chemical group is a matter of convenience; chemical groups may be depicted with or without one or more dashes without losing their ordinary meaning. A wavy line drawn through a line in a structure indicates a point of attachment of a group, e.g.:

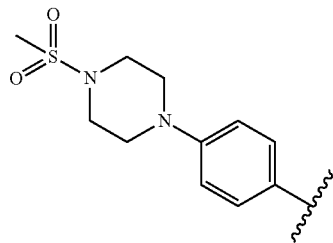 [SMILES: *c1ccc(N2CCN(S(C)(=O)=O)CC2)cc1]

A dashed line indicates an optional bond. Where multiple substituent groups are identified the point of attachment is at the terminal substituent (e.g. for "alkylaminocarbonyl" the point of attachment is at the carbonyl substituent).

The prefix "$C_{x-y}$" indicates that the following group has from x (e.g. 1) to y (e.g. 6) carbon atoms, one or more of which, in certain groups (e.g. heteroalkyl, heteroaryl, heteroarylalkyl, etc.), may be replaced with one or more heteroatoms or heteroatomic groups. For example, "$C_{1-6}$ alkyl" indicates that the alkyl group has from 1 to 6 carbon atoms. Likewise, the term "x-y membered" rings, wherein x and y are numerical ranges, such as "3-12 membered heterocyclyl", refers to a ring containing x-y atoms (e.g. 3-12), of which up to half may be heteroatoms, such as N, O, S, P, and the remaining atoms are carbon.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"Alkyl" refers to any group derived from a linear or branched saturated hydrocarbon. Alkyl groups include, but are not limited to, methyl, ethyl, propyl such as propan-1-yl, propan-2-yl (iso-propyl), butyls such as butan-1-yl, butan-2-yl (sec-butyl), 2-methyl-propan-1-yl (iso-butyl), 2-methyl-propan-2-yl (t-butyl), pentyls, hexyls, octyls, dectyls, and the like. Unless otherwise specified, an alkyl group has from 1 to 10 carbon atoms, for example from 1 to 6 carbon atoms, for example from 1 to 4 carbon atoms.

"Alkenyl" refers to any group derived from a straight or branched hydrocarbon with at least one carbon-carbon double bond. Alkenyl groups include, but are not limited to, ethenyl (vinyl), propenyl (allyl), 1-butenyl, 1,3-butadienyl, and the like. Unless otherwise specified, an alkenyl group has from 2 to 10 carbon atoms, for example from 2 to 6 carbon atoms, for example from 2 to 4 carbon atoms.

"Alkynyl" refers to any group derived from a straight or branched hydrocarbon with at least one carbon-carbon triple bond and includes those groups having one triple bond and one double bond. Examples of alkynyl groups include, but are not limited to, ethynyl (—C≡CH), propargyl (—CH$_2$C≡CH), (E)-pent-3-en-1-ynyl, and the like. Unless otherwise specified, an alkynyl group has from 2 to 10 carbon atoms, for example from 2 to 6 carbon atoms, for example from 2 to 4 carbon atoms.

"Amino" refers to —NH$_2$. Amino groups may also be substituted as described herein, such as with alkyl, carbonyl or other amino groups. The term "alkylamino" refers to an amino group substituted with one or two alkyl substituents (e.g. dimethylamino or propylamino).

"Aryl" refers to any group derived from one or more aromatic rings, that is, a single aromatic ring, a bicyclic or a multicyclic ring system. Aryl groups include, but are not limited to, those groups derived from acenaphthylene, anthracene, azulene, benzene, chrysene, a cyclopentadienyl anion, naphthalene, fluoranthene, fluorene, indane, perylene, phenalene, phenanthrene, pyrene and the like. Unless otherwise specified, an aryl group has from 5 to 20 carbon atoms.

"Arylalkyl" (also "aralkyl") refers to any combination aryl group and an alkyl group. Arylalkyl groups include, but are not limited to, those groups derived from benzyl, tolyl, dimethylphenyl, 2-phenylethan-1-yl, 2-naphthylmethyl, and the like. An arylalkyl group comprises from 6 to 30 carbon atoms, for example the alkyl group can comprise from 1 to 10 carbon atoms and the aryl group can comprise from 5 to 20 atoms.

"Bridged" refers to a ring fusion wherein non-adjacent atoms on a ring are joined by a divalent substituent, such as an alkylenyl or heteroalkylenyl group or a single heteroatom. Quinuclidinyl and admantanyl are examples of bridged ring systems.

"Cycloalkyl" refers to a cyclic alkyl and alkenyl groups. A cycloalkyl group can have one or more cyclic rings and includes fused and bridged groups that are fully saturated or partially unsaturated. Examples include, but are not limited to, cyclopropyl, cyclobutyl, cyclopentyl, cyclohexyl, adamantyl, methylcyclopropyl (cyclopropylmethyl), ethylcyclopropyl, cyclohexenyl and the like. Another example includes $C_{5-7}$ cycloakenyl.

"Halo" and "halogen" refer to fluoro, chloro, bromo and iodo.

"Haloalkyl" refers to an alkyl wherein one or more hydrogen atoms are each replaced by a halogen. Examples include, but are not limited to, —CH$_2$Cl, —CH$_2$F, —CH$_2$Br, —CFClBr, —CH$_2$CH$_2$Cl, —CH$_2$CH$_2$F, —CF$_3$, —CH$_2$CF$_3$, —CH$_2$CCl$_3$, and the like, as well as alkyl groups such as perfluoroalkyl in which all hydrogen atoms are replaced by fluorine atoms.

"Halo 3-6 membered heterocyclyl" refers to a heterocyclyl group substituted at a carbon atom with at least one halogen atom, and may include multiple halogen atoms, such as 3,3-difluoroazetidinyl.

"Heteroalkyl" refers to an alkyl in which one or more of the carbon atoms (and any associated hydrogen atoms) are each independently replaced with the same or heteroatom or heteroatomic group. Heteroatoms include, but are not limited to, N, P, O, S, etc. Heteroatomic groups include, but are not limited to, —NR—, —O—, —S—, —PH—, —P(O)$_2$—, —S(O)—, —S(O)$_2$—, and the like, where R is H, alkyl, aryl, cycloalkyl, heteroalkyl, heteroaryl or cycloheteroalkyl. Heteroalkyl groups include, but are not limited to, —OCH$_3$, —CH$_2$OCH$_3$, —SCH$_3$, —CH$_2$SCH$_3$, —NRCH$_3$, —CH$_2$NRCH$_3$, —CH$_2$OH and the like, where R is hydrogen, alkyl, aryl, arylalkyl, heteroalkyl, or heteroaryl, each of which may be optionally substituted. A heteroalkyl group comprises from 1 to 10 carbon and up to three hetero atoms, e.g., from 1 to 6 carbon and from 1 to 2 hetero atoms.

"Heteroaryl" refers to mono or multicyclic aryl group in which one or more of the aromatic carbon atoms (and any associated hydrogen atoms) are independently replaced with the same or different heteroatom or heteroatomic group, as defined above. Multicyclic ring systems are included in heteroaryl and may be attached at the ring with the heteroatom or the aryl ring. Heteroaryl groups include, but are not limited to, groups derived from acridine, benzoimidazole, benzothiophene, benzofuran, benzoxazole, benzothiazole, carbazole, carboline, cinnoline, furan, imidazole, imidazopyridine, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyridone, pyrimidine, pyrrole, pyrrolizine, quinazoline, quinoline, quinolizine, quinoxaline, tetrazole, thiadiazole, thiazole, thiophene, triazole, xanthene, and the like. Heteroaryl groups may have 5-14 members, 5-10 members, or 5-6 members.

"Heterocycle," "heterocyclic," and "heterocyclyl" refer to a saturated or partially unsaturated non-aromatic ring or a partially non-aromatic multiple-ring system with at least one heteroatom or heteroatomic group, as defined above. Heterocycles include, but are not limited to, groups derived from azetidine, aziridine, imidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, tetrahydro-2H-thiopyran 1,1-dioxide, quinuclidine, N-bromopyrrolidine, N-chloropiperidine, and the like. Heterocyclyl groups also include partially unsaturated ring systems containing one or more double bonds, including fused ring systems with one aromatic ring and one non-aromatic ring, but not fully aromatic ring systems. Examples include dihydroquinolines, e.g. 3,4-dihydroquinoline, dihydroisoquinolines, e.g. 1,2-dihydroisoquinoline, dihydroimidazole, tetrahydroimidazole etc., indoline, isoindoline, isoindolones (e.g. isoindolin-1-one), isatin, dihydrophthalazine, quinolinone, spiro[cyclopropane-1,1'-isoindolin]-3'-one, and the like. Heterocycle groups may have 3-12 members, or 3-10 members, or 3-7 members, or 5-6 members.

"Hydroxyl" and "hydroxy" are used interchangeably and refer to —OH. "Oxo" refers to =O. Where tautomeric forms of the compound exist, hydroxyl and oxo groups are interchangeable.

It is understood that combinations of chemical groups may be used and will be recognized by persons of ordinary skill in the art. For instance, the group "hydroxyalkyl" would refer to a hydroxyl group attached to an alkyl group. A great number of such combinations may be readily envisaged. Additional examples of substituent combinations used herein include: $C_{1-6}$ alkylamiocarbonyl (e.g. $CH_3CH_2NHC(O)—$) $C_{1-6}$ alkoxycarbonyl (e.g. $CH_3O—C(O)—$), 5-7 membered heterocyclyl-$C_{1-6}$ alkyl (e.g. piperazinyl-$CH_2—$), $C_{1-6}$ alkylsulfonyl-5-7 membered heterocyclyl (e.g. $CH_3S(O)_2$-morpholinyl-), 5-7 membered heterocyclyl $C_{1-6}$ alkoxy (e.g. pyrrolidinyl-O—), 5-7 membered heterocyclyloxy, (4-7 membered heterocyclyl)-4-7 membered heterocyclyl (e.g. oxetanyl-pyrrolidinyl-), $C_{3-6}$ cycloalkylaminocarbonyl (e.g. cyclopropyl-NH—C(O)—), 5-7 membered heterocyclyl-$C_{2-6}$ alkynyl (e.g. N-piperazinyl-$CH_2C≡CCH_2$-), and $C_{6-10}$ arylaminocarbonyl (e.g. phenyl-NH—C(O)—).

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents. When substituents (R-groups) are taken together (e.g. when $R^7$ and $R^8$ are taken together) they may be taken from the same point of attachment to form a spiro ring.

The phrase "meta (3) position with respect to the point of attachment of the A ring", refers to the position on the ring where the substituent (e.g. —CN) is adjoined and is shown below with an arrow, wherein z represents a carbon atom or nitrogen:

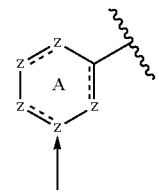

Similarly, para (4) position substitution refers to attachment of a substituent at the position indicated below, with respect to the point of attachment (e.g. of the B ring):

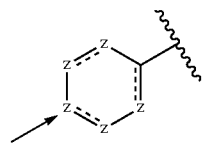

Similarly, ortho or 2-position refers to attachment of a substituent at the position indicated below, with respect to the point of attachment:

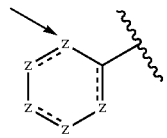

The term "pharmaceutically acceptable" with respect to a substance refers to that substance which is generally regarded as safe and suitable for use without undue toxicity, irritation, allergic response, and the like, commensurate with a reasonable benefit/risk ratio.

The compounds described herein include isomers, stereoisomers and the like. As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound.

The term "fused" refers to a ring which is bound to an adjacent ring.

"Enantiomers" are a pair of stereoisomers that are non-superimposable mirror images of each other. A 1:1 mixture of a pair of enantiomers is a "racemic" mixture.

The term is used to designate a racemic mixture where appropriate. "Diastereoisomers" are stereoisomers that have at least two asymmetric atoms, but which are not mirror-images of each other.

The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

"Subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, pocket pets, rabbits, dogs, and monkeys), and the like.

"Treating" and "treatment" of a disease include the following:
(1) preventing or reducing the risk of developing the disease, i.e., causing the clinical symptoms of the disease not to develop in a subject that may be exposed to or predisposed to the disease but does not yet experience or display symptoms of the disease,
(2) inhibiting the disease, i.e., arresting or reducing the development of the disease or its clinical symptoms, or
(3) relieving the disease, i.e., causing regression of the disease or its clinical symptoms.

"Effective amount" refers to an amount that may be effective to elicit the desired biological, clinical, or medical response, including the amount of a compound that, when administered to a subject for treating a disease, is sufficient to effect such treatment. The effective amount will vary depending on the compound, the disease and its severity and the age, weight, etc., of the subject to be treated. The effective amount can include a range of amounts.

The compounds of the invention include solvates, hydrates, tautomers, stereoisomers and salt forms thereof.

Provided are also compounds in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds exhibit may increase resistance to metabolism, and thus may be useful for increasing the half-life of the compounds when administered to a mammal. See, e.g., Foster, "Deuterium Isotope Effects in Studies of Drug Metabolism," Trends Pharmacol. Sci., 5(12):524-527 (1984). Such compounds are synthesized by means well known in the art, for example by employing starting materials in which one or more hydrogen atoms have been replaced by deuterium.

The pharmaceutical compositions of compounds of Formula (I) (including compounds of Formulae (Ia)-(Ik)) may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

In one aspect, the compounds described herein may be administered orally. Oral administration may be via, for example, capsule or enteric coated tablets. In making the pharmaceutical compositions that include at least one compound of Formula (I), or a pharmaceutically acceptable salt, is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound of Formula (I), or a pharmaceutically acceptable salt, can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions may, in some embodiments, be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, for oral administration, each dosage unit contains from about 10 mg to about 1000 mg of a compound described herein, for example from about 50 mg to about 500 mg, for example about 50 mg, about 75 mg, about 100 mg, about 150 mg, about 200 mg, about 250 mg, or about 300 mg. In other embodiments, for parenteral administration, each dosage unit contains from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, and the severity of the subject's symptoms.

In certain embodiments, dosage levels may be from 0.1 mg to 100 mg per kilogram of body weight per day, for example from about 1 mg to about 50 mg per kilogram, for example from about 5 mg to about 30 mg per kilogram. Such dosage levels may, in certain instances, be useful in the treatment of the above-indicated conditions. In other embodiments, dosage levels may be from about 10 mg to about 2000 mg per subject per day. The amount of active ingredient that may be combined with the vehicle to produce a single dosage form will vary depending upon the host treated and the particular mode of administration. Dosage unit forms may contain from 1 to 500 mg of an active ingredient.

Frequency of dosage may also vary depending on the compound used and the particular disease or condition treated. In some embodiments, for example, for the treatment of an autoimmune and/or inflammatory disease, a dosage regimen of 4 times daily or less is used. In some embodiments, a dosage regimen of 1 or 2 or 3 times daily is used. It will be understood, however, that the specific dose level for any particular subject will depend upon a variety of factors including the activity of the specific compound employed, the age, body weight, general health, sex, diet, time of administration, route of administration, and rate of excretion, drug combination and the severity of the particular disease in the subject undergoing therapy.

For preparing solid compositions such as tablets, the principal active ingredient may be mixed with a pharmaceutical excipient to form a solid preformulation composition containing a homogeneous mixture of a compound of Formula (I), or a pharmaceutically acceptable salt, thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Kits that include a compound of Formula (I), or a pharmaceutically acceptable salt, thereof, and suitable packaging are provided. In one embodiment, a kit further includes instructions for use. In one aspect, a kit includes a compound of Formula (I), or a pharmaceutically acceptable salt thereof, and instructions for use of the compounds in the treatment of the diseases or conditions described herein.

Articles of manufacture that include a compound of Formula (I), or a pharmaceutically acceptable salt thereof, in a suitable container are provided. The container may be a vial, jar, ampoule, preloaded syringe, and intravenous bag.

Compounds of Formula (I) may be combined with one or more additional therapeutic agents. The present application provides methods, compositions, kits and articles of manufacture thereof that use or include one or more therapeutic agents inhibiting one or more targets that relate to, directly or indirectly, to cell growth, proliferation, or apoptosis for treating hyperproliferative disorders such as cancers or myeloproliferative neoplasms. The one or more therapeutic agents are compounds or molecules that is an Abl inhibitor, an ACK inhibitor, an A2B inhibitor, an ASK inhibitor, an Auroa kinase inhibitor, a BTK inhibitor, a BRD inhibitor, a c-Kit inhibitor, a c-Met inhibitor, a CAK inhibitor, a CaMK inhibitor, a CDK inhibitor, a CK inhibitor, a DDR inhibitor, an EGFR inhibitor, a FAK inhibitor, a Flt-3 inhibitor, a FYN inhibitor, a GSK inhibitor, a HCK inhibitor, a HDAC inhibitor, an IKK inhibitor, an IDH inhibitor, an IKK inhibitor, a JAK inhibitor, a KDR inhibitor, a LCK hibitor, a LOX inhibitor, a LOXL inhibitor, a LYN inhibitor, a MMP inhibitor, a MEK inhibitor, a MAPK inhibitor, a NEK9 inhibitor, a NPM-ALK inhibitor, a p38 kinase inhibitor, a PDGF inhibitor, a PI3 kinase (PI3K), a PK inhibitor, a PLK inhibitor, a PK inhibitor, a PYK inhibitor, a SYK inhibitor, a TPL2 inhibitor, a STK inhibitor, a STAT inhibitor, a SRC inhibitor, a TBK inhibitor, a TIE inhibitor, a TK inhibitor, a VEGF inhibitor, a YES inhibitor, a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof. In some embodiment, the therapeutic agents are compounds or molecules that target a PI3 kinase (PI3K), a spleen tyrosine kinase (SYK), a Janus kinase (JAK), a Bruton's tyrosine kinase (BTK), or any combination thereof, resulting in the inhibition of one or more targets. In certain embodiments, the therapeutic agent is a PI3Kδ inhibitor that selectively inhibits PI3K p110 delta isoform (PI3Kδ). In some embodiments, the therapeutic agents are a PI3Kδ inhibitor and a JAK1/2 inhibitor.

The JAK inhibitor binds and inhibits one or more members of JAK family, including JAK1, JAK2, and/or JAK3.

In one embodiment, the JAK inhibitor is Compound A having the structure:

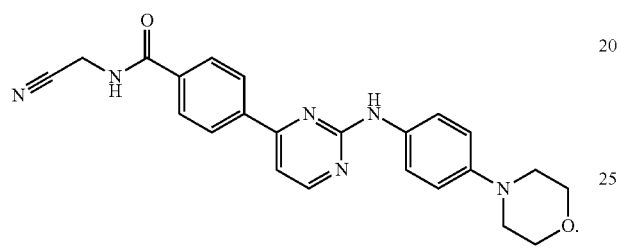

Compound A may be referred to by its compound name: N-(cyanomethyl)-4-[2-(4-morpholinoanilino)pyrimidin-4-yl]benzamide using ChemDraw. Compound A, also referred to as CYT0387 or momelotinib, is a selective inhibitor to JAK2 and JAK1, relative to JAK3. Methods for synthesizing compounds of formula I and Compound A are previously described in U.S. Pat. No. 8,486,941. This reference is hereby incorporated herein by reference in its entirety.

Additional JAK inhibitors include, but are not limited to, ruxolitinib (INCB018424), fedratinib (SAR302503, TG101348), tofacitinib, baricitinib, lestaurtinib, pacritinib (SB1518), XL019, AZD1480, INCB039110, LY2784544, BMS911543, and NS018.

The PI3K inhibitors inhibit one or more isoforms of Class I PI3K, including PI3Kα, PI3Kβ, PI3Kδ, PI3Kγ, or any combination thereof.

In some embodiments, the PI3Kδ inhibitor is Compound B having the structure:

(B)

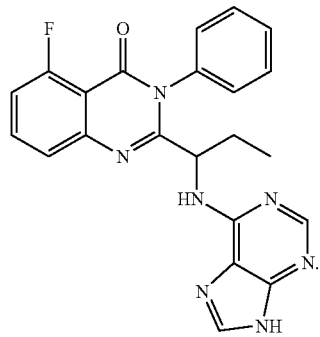

In other embodiments, Compound B is predominantly the S-enantiomer, having the structure:

(B)S

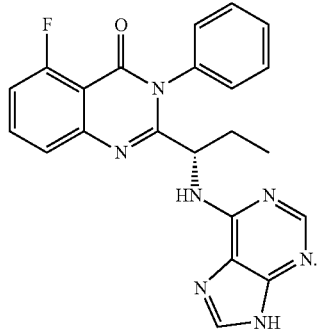

The (S)-enantiomer of Compound B may also be referred to by its compound name: (S)-2-(1-((9H-purin-6-yl)amino)propyl)-5-fluoro-3-phenylquinazolin-4(3H)-one using ChemDraw.

In certain embodiments, the PI3Kδ inhibitor is Compound C having the structure:

(C)

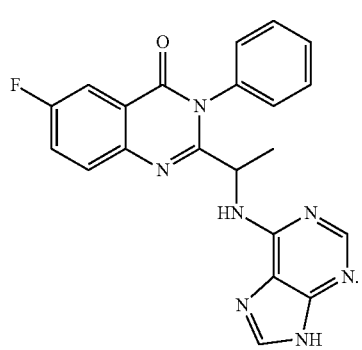

In additional embodiments, Compound C is predominantly the S-enantiomer, having the structure:

(C)S

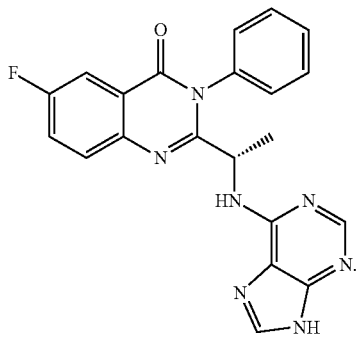

The (S)-enantiomer of Compound C may also be referred to by its compound name: (S)-2-(1-((9H-purin-6-yl)amino)ethyl)-6-fluoro-3-phenylquinazolin-4(3H)-one using ChemDraw.

In another embodiment, the PI3K inhibitor is Compound D, having the structure:

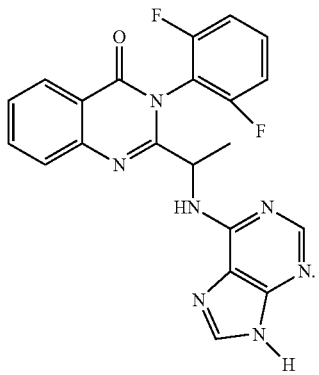

(D)

In one embodiment, Compound D is predominantly the S-enantiomer, having the structure:

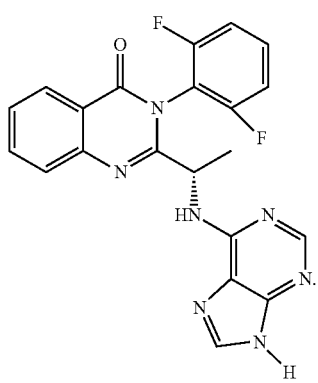

(D)S

The (S)-enantiomer of Compound D may also be referred to by its compound name: (S)-2-(1-((9H-purin-6-yl)amino)ethyl)-3-(2,6-difluorophenyl)quinazolin-4(3H)-one using ChemDraw.

In yet other embodiments, the PI3K inhibitor is Compound E which is named by its compound name: (S)-4-amino-6-((1-(5-chloro-4-oxo-3-phenyl-3,4-dihydroquinazolin-2-yl)ethyl)amino)pyrimidine-5-carbonitrile using ChemDraw. In some other embodiment, the PI3K inhibitor includes the compounds described in U.S. Provisional Application Nos. 61/543,176; 61/581,528; 61/745,429; 61/745,437; and 61/835,333. The references are hereby incorporated herein by reference in their entirety.

Compounds B, C, D, and E are PI3Kδ inhibitors, selectively inhibiting PI3K p110δ compared to other PI3K isoforms. Methods for synthesizing the compounds of formula II, Compounds B, C, D, and E are previously described in U.S. Pat. No. 7,932,260 or U.S. Provisional Application No. 61/581,528. The references are hereby incorporated herein by reference in their entirety.

Additional PI3K inhibitors include but are not limited to XL147, BKM120, GDC-0941, BAY80-6946, PX-866, CH5132799, XL756, BEZ235, and GDC-0980, wortmannin, LY294002, PI3K II, TGR-1202, AMG-319, GSK2269557, X-339, X-414, RP5090, KAR4141, XL499, OXY111A, IPI-145, IPI-443, GSK2636771, BAY 10824391, buparlisib, BYL719, RG7604, MLN1117, WX-037, AEZS-129, PA799, AS252424, TGX221, TG100115, IC87114, and ZSTK474.

The SYK inhibitor includes but is not limited to 6-(1H-indazol-6-yl)-N-(4-morpholinophenyl)imidazo[1,2-a]pyrazin-8-amine, $R^{406}$ (tamatinib), $R^{788}$ (fostamatinib), PRT062607, BAY-61-3606, NVP-QAB 205 AA, $R^{112}$, or $R^{343}$, or a pharmaceutically acceptable salt thereof. See Kaur et al., European Journal of Medicinal Chemistry 67 (2013) 434-446. In one embodiment, the Syk inhibitor is 6-(1H-indazol-6-yl)-N-(4-morpholinophenyl)imidazo[1,2-a]pyrazin-8-amine as described in U.S. Pat. No. 8,450,321.

In various embodiments, compounds of Formula (I) may be combined with one or more IDO1 inhibitors. In one embodiment, the IDO1 inhibitor is INCB24360 having the structure:

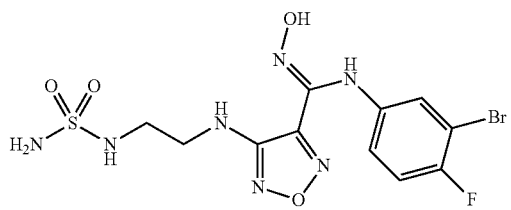 [SMILES: NS(=O)(=O)NCCNc1nonc1/C(=N/O)Nc1ccc(F)c(Br)c1]

In another embodiment, the IDO1 inhibitor is NLG-919 having the following structure:

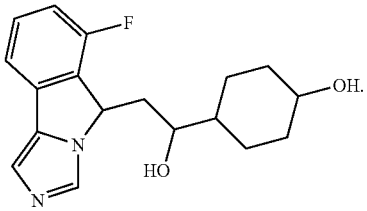 [SMILES: OC1CCC(C(O)CC2c3c(F)cccc3-c3cncn32)CC1]

In another embodiment, the IDO1 inhibitor is indoximod having the following structure:

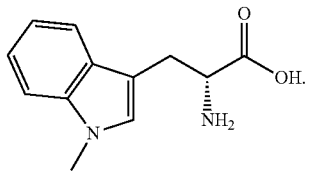 [SMILES: Cn1cc(C[C@@H](N)C(=O)O)c2ccccc21]

Another embodiment provides a compound of formula (I), or a pharmaceutically acceptable salt thereof, in combination with a one or more additional therapeutic agents, for example one or more additional therapeutic agents from the above list of additional therapeutic agents, for use in: therapy; a method of treating a subject having a disease or condition responsive to the inhibition of TBK1, such as cancer; a method of treating a subject having a disease or condition responsive to the inhibition of IKKε; a method of treating a subject suffering from a RAS-dependent/mutant cancer, such as non-small cell lung cancer, colorectal cancer, pancreatic cancer, AML, and melanoma; a method of treating a subject suffering from breast or ovarian cancer; a method of treating a subject suffering from cancer resistant to HER2 and EGFR targeted therapies; a method of treating a subject suffering from a disease selected from the group consisting of Rheumatoid arthritis (RA), Inflammatory bowel disease (IBD), Chronic obstructive pulmonary disease (COPD), Systemic lupus erythematosus (SLE), Polymositis, Systemic sclerosis, Type 2 diabetes, Obesity and Hepatic steatosis; or a method of treating a subject suffering from cancer.

Another embodiment provides the use of a compound of formula (I), or a pharmaceutically acceptable salt thereof, in combination with a one or more additional therapeutic agents, for example one or more additional therapeutic agents from the above list of additional therapeutic agents, in the manufacture of a medicament for: therapy; treating a subject having a disease or condition responsive to the inhibition of TBK1, such as cancer; treating a subject having a disease or condition responsive to the inhibition of IKKε; treating a subject suffering from a RAS-dependent/mutant cancer, such as non-small cell lung cancer, colorectal cancer, pancreatic cancer, AML, and melanoma; treating a subject suffering from breast or ovarian cancer; treating a subject suffering from cancer resistant to HER2 and EGFR targeted therapies; treating a subject suffering from a disease selected from the group consisting of Rheumatoid arthritis (RA), Inflammatory bowel disease (IBD), Chronic obstructive pulmonary disease (COPD), Systemic lupus erythematosus (SLE), Polymositis, Systemic sclerosis, Type 2 diabetes, Obesity and Hepatic steatosis; or treating a subject suffering from cancer.

In an embodiment, the above combinations comprise one additional therapeutic agent, for example one additional therapeutic agent selected from the additional therapeutic agents listed above.

Another embodiment of the invention provides a product comprising a compound of formula (I), or a pharmaceutically acceptable salt thereof, and one or more additional therapeutic agents, such as one or more of the additional therapeutic agents listed above, as a combined preparation for simultaneous, separate or sequential use in therapy.

Synthesis of certain compounds, and intermediates used to prepare compounds, are detailed in the following sections. Example numbers are listed for convenience.

All operations involving moisture and/or oxygen sensitive materials were conducted under an atmosphere of dry nitrogen in pre-dried glassware. Unless noted otherwise, materials were obtained from commercially available sources and used without further purification.

Nuclear magnetic resonance ("NMR") spectra were recorded on a Varian 400 MHz resonance spectrometer. $^1$H NMR chemical shifts are given in parts per million (δ) downfield from tetramethylsilane ("TMS") using TMS or the residual solvent signal (CHCl3=δ 7.24, DMSO=δ 2.50) as internal standard. $^1$H NMR information is tabulated in the following format: multiplicity (s, singlet; d, doublet; t, triplet; q, quartet; m, multiplet), coupling constant(s) (J) in Hertz, number of protons. The prefix app is occasionally applied in cases where the true signal multiplicity was unresolved and br indicates the signal in question was broadened.

The compounds were named using ChemBioDraw Ultra Version 12.0.

When production of starting materials is not particularly described, the compounds are known or may be prepared analogously to methods known in the art or as disclosed in the Examples. One of skill in the art will appreciate that synthetic methodologies described herein are only representative of methods for preparation of the compounds described herein, and that other known methods and variants of methods described herein may be used. The methods or features described in various Examples may be combined or adapted in various ways to provide additional ways of making the compounds described herein.

EXAMPLES

Methods for obtaining the novel compounds described herein will be apparent to those of ordinary skill in the art, with suitable procedures being described, for example, in the reaction schemes and examples below, and in the references cited herein.

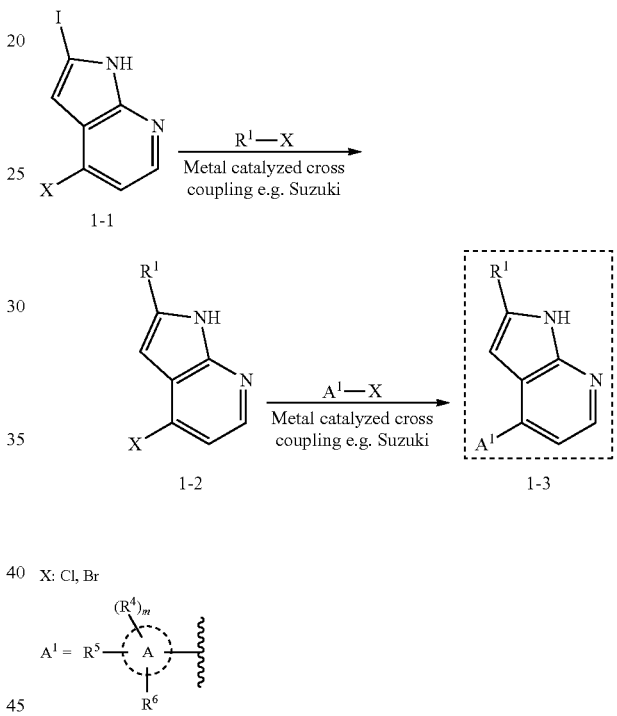

General Scheme 1

Scheme 1 shows a general synthesis of compounds of the invention beginning with metal catalyzed cross coupling reactions (e.g. Suzuki) of $R^1$ group's yields intermediates 1-2, which undergoes another metal catalyzed cross coupling reactions (e.g. Suzuki) of $A^1$ groups to yield final compounds of the type 1-3.

General Scheme 2

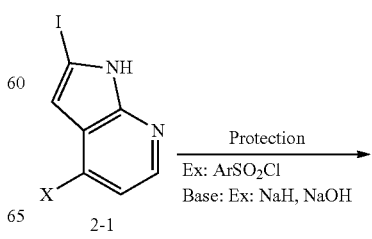

-continued

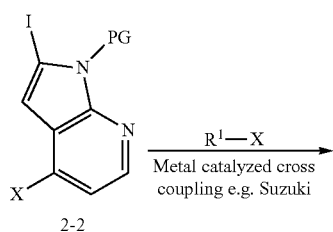
2-2

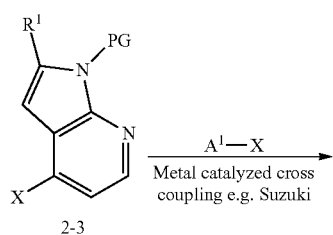
2-3

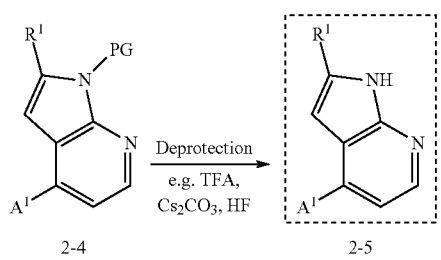
2-4    2-5

X: Cl, Br

-continued

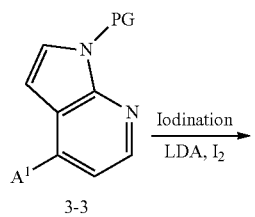
3-3

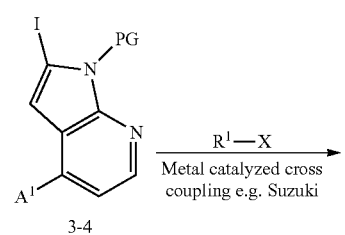
3-4

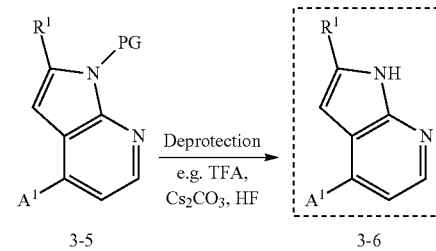
3-5    3-6

X: Cl, Br

Scheme 2 describes a general synthesis of compounds of the invention beginning with protection (SEM-Cl or ArSO$_2$Cl, base e.g. NaH or NaOH) of the azaindole intermediates 2-1 yielding the protected intermediate 2-2. Metal catalyzed cross coupling reactions (e.g. Suzuki) of the intermediate 2-2 with R$^1$ group's yields intermediates 2-3 which undergoes another metal catalyzed cross coupling reactions (e.g. Suzuki) of A$^1$ groups to yield intermediate 2-4. Deprotection of the protecting group, such as a SEM group (e.g. TFA/heat or TBAF) or ArSO$_2$ group (e.g. TFA or Cs$_2$CO$_3$), yields final compounds of the type 2-5.

Scheme 3 describes a general synthesis of compounds of the invention beginning with protection (SEM-Cl or ArSO$_2$Cl, base e.g. NaH or NaOH) of the azaindole intermediates 3-1 yielding the protected intermediate 3-2. Metal catalyzed cross coupling reactions (e.g. Suzuki) of the intermediate 3-2 with A$^1$ group's yields intermediates 3-3. Halogenation (iodination with I2, LDA) gives the iodo intermediate 3-4, which undergoes metal catalyzed cross coupling reactions (e.g. Suzuki) with R$^1$ group's yields intermediates 3-5. Deprotection of the SEM group (e.g. TFA/heat or TBAF) or ArSO$_2$ group (e.g. TFA or Cs$_2$CO$_3$), yields final compounds of the type 3-6.

General Scheme 3

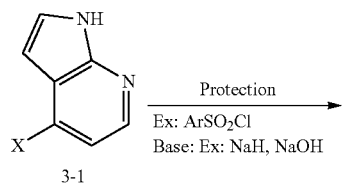
3-1

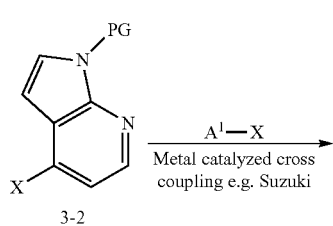
3-2

General Scheme 4:

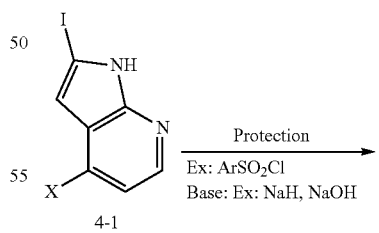
4-1

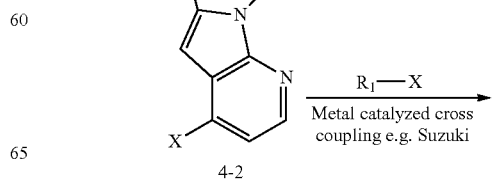
4-2

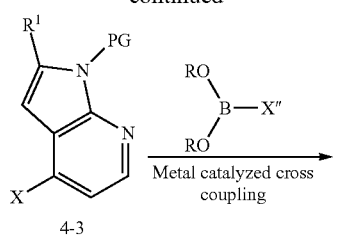

4-3

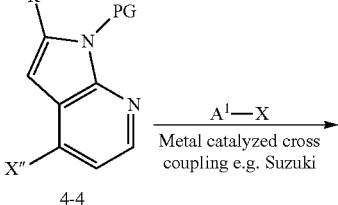

4-4

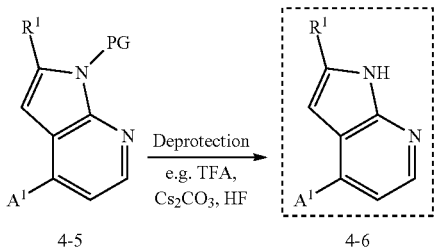

4-5    4-6

X: Cl, Br

X'' = H, —C(CH₃)₂CC(CH₃)₂—

Scheme 4 describes a general synthesis of compounds of the invention beginning with protection (SEM-Cl or ArSO₂Cl, base e.g. NaH or NaOH) of the azaindole intermediates 4-1 yielding the protected intermediate 4-2. Metal catalyzed cross coupling reactions (e.g. Suzuki) of the intermediate 4-2 with R¹ group's yields intermediates 4-3. Conversion of the halogen (X=Cl, Br) to the boronate or boronic acid using metal catalyzed (e.g. Pd(Cl₂(PPh₃)₂, base: KOAc, solvent: dioxane) yields intermediate 4-4, which undergoes another metal catalyzed cross coupling reactions (e.g. Suzuki) with A¹ group's yields intermediates 4-5. Deprotection of the SEM group (e.g. TFA/heat or TBAF) or ArSO₂ group (e.g. TFA or Cs₂CO₃), yields final compounds of the type 4-6.

General Scheme 5

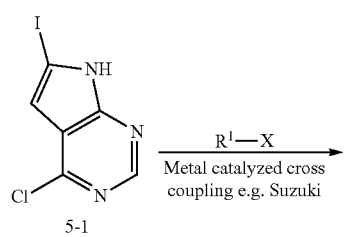

5-1

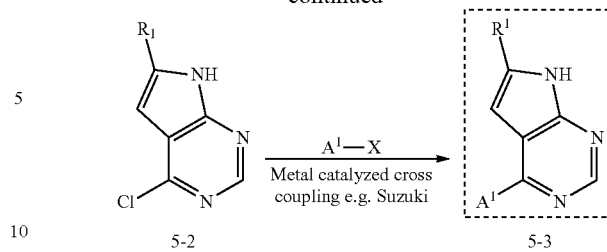

5-2    5-3

Scheme 5 shows a general synthesis of compounds of the invention beginning with metal catalyzed cross coupling reactions (e.g. Suzuki) of R¹ group's yields intermediates 5-2, which undergoes another metal catalyzed cross coupling reactions (e.g. Suzuki) of A¹ groups to yield final compounds of the type 5-3.

General Scheme 6

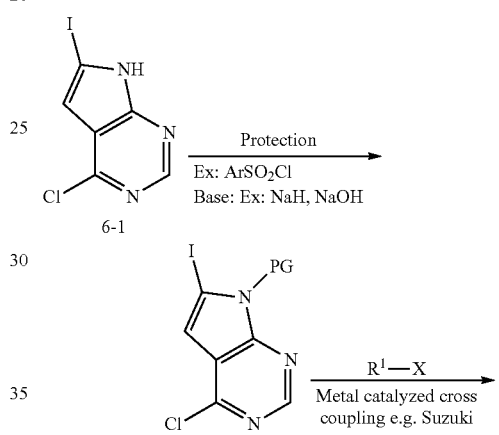

6-1

6-2

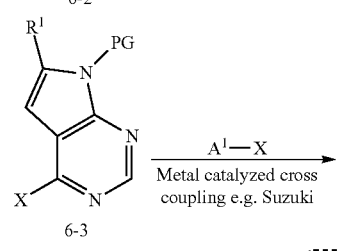

6-3

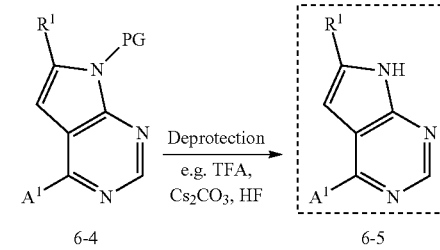

6-4    6-5

Scheme 6 describes a general synthesis of compounds of the invention beginning with protection (SEM-Cl or ArSO₂Cl, base e.g. NaH or NaOH) of the 4-chloro-6-iodo-7H-pyrrolo[2,3-d]pyrimidine intermediate 6-1 yielding the protected intermediate 6-2. Metal catalyzed cross coupling reactions (e.g. Suzuki) of the intermediate 6-2 with R¹ group's yields intermediates 6-3 which undergoes another metal catalyzed cross coupling reactions (e.g. Suzuki) of A¹ groups to yield intermediate 6-4. Deprotection of the SEM group (e.g. TFA/heat or TBAF) or ArSO₂ group (e.g. TFA or Cs₂CO₃), yields final compounds of the type 6-5.

General Scheme 7

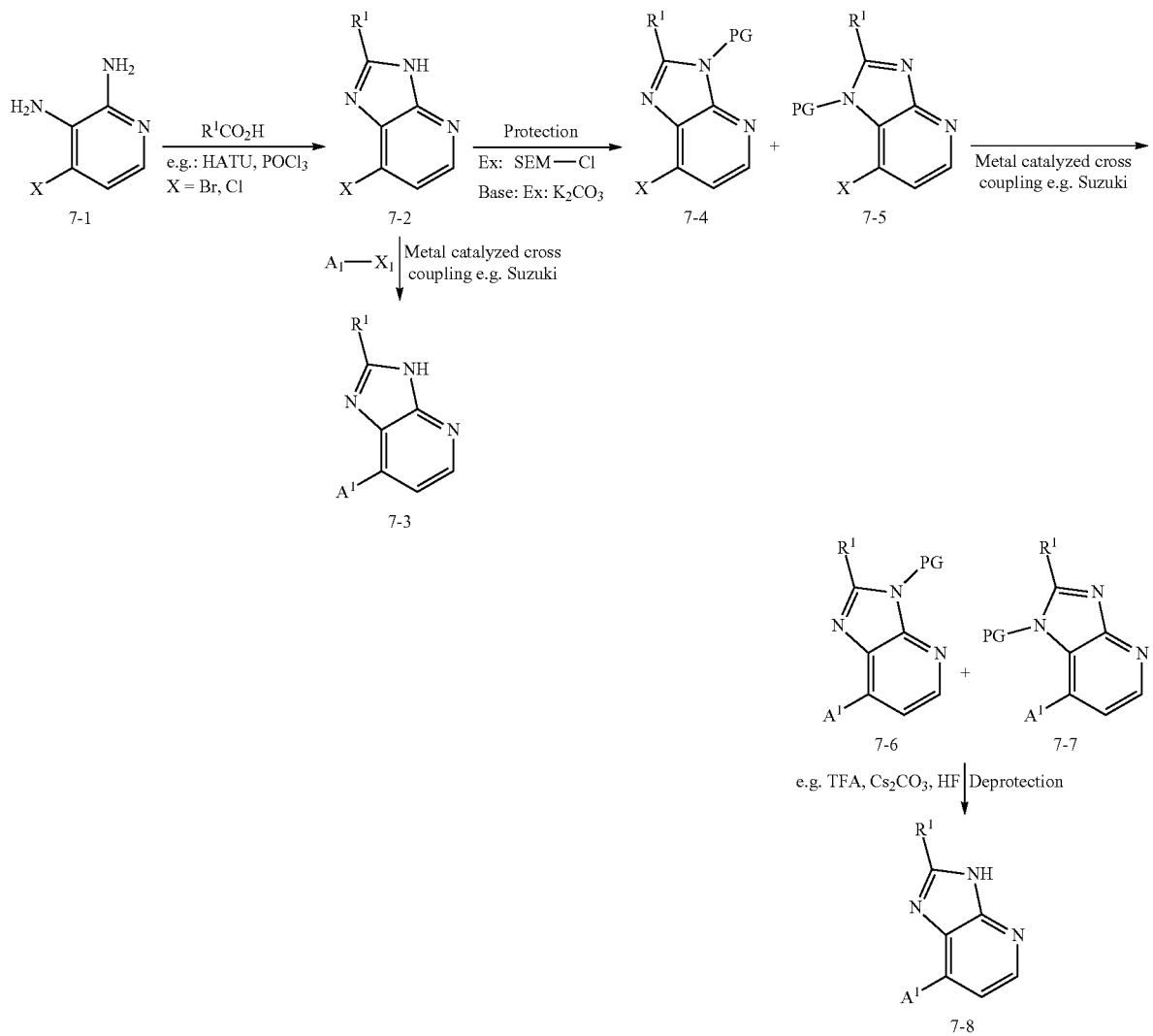

Scheme 7 describes a general synthesis of compounds of the invention beginning with coupling of corresponding acid with 4-halopyridine-2,3-diamine 7-1 (ex: 4-chloropyridine-2,3-diamine or 4-Bromopyridine-2,3-diamine, e.g. HATU or POCl$^3$, e.g. DMF, acetonitrile as solvents, e.g. base: DIPEA or NMM) to give the intermediate 7-2 which undergoes metal catalyzed cross coupling reactions (e.g. Suzuki) of $A^1$ groups to yield final compounds of the type 7-3.

Scheme 7 also describes a general synthesis of compounds of the invention with the protection of the intermediate 7-2 (SEM-Cl, base e.g. $K_2CO_3$) yielding a mixture of intermediates 7-4 and 7-5. Installation of $A_1$ groups under metal catalyzed coupling conditions (e.g. Suzuki), gets to a mixture of intermediates 7-6 and 7-7. Deprotection of the SEM group (e.g. TFA/heat or HF), yields final compounds of the type 7-8.

General Scheme 8

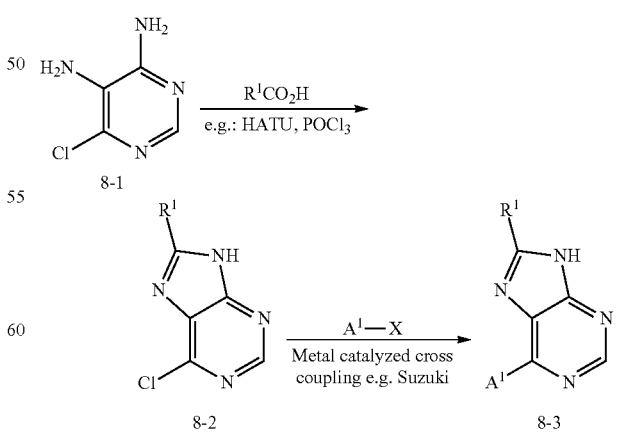

Scheme 8 describes a general synthesis of compounds of the invention beginning with coupling of corresponding acid with 6-chloropyrimidine-4,5-diamine (e.g. HATU or POCl$_3$, e.g. DMF, acetonitrile as solvents, e.g. base: DIPEA or NMM) to give the intermediate 8-2 which undergoes metal catalyzed cross coupling reactions (e.g. Suzuki) of A$^1$ groups to yield final compounds of the type 8-3.

Intermediate A: 5-(2-iodo-1-(phenylsulfonyl)-1H-pyrrolo[2,3-b]pyridin-4-yl)-2-((tetrahydro-2H-pyran-4-yl)oxy)benzonitrile

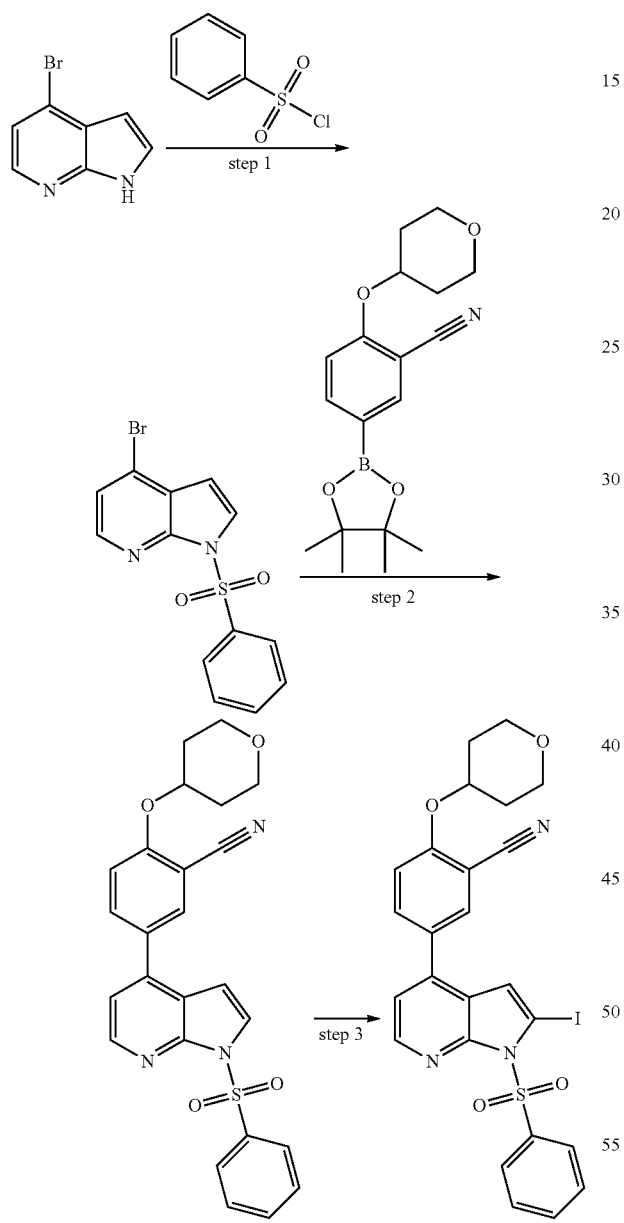

Step 1: 4-Bromo-1H-pyrrolo[2,3-b]pyridine (10 g, 51 mmol) was suspended in a mixture of dichloromethane (200 mL) and 1,4-dioxane (70 mL) and treated with 50% w/w aqueous sodium hydroxide solution (15 mL), followed by tetra-n-butylammonium bisulfate. The mixture was vigorously stirred and cooled in an ice-water bath whilst benzenesulfonyl chloride (9.6 ml, 76 mmol) was added dropwise. The reaction mixture was left stirring vigorously overnight. The mixture was evaporated to dryness and the resulting solid was triturated with water (approximately 100 mL), followed by methanol (approximately 50 mL). The solid was dried in a vacuum oven to give the desired product LCMS-ESI$^+$ (m/z): [M+H]$^+$ calcd for C$_{13}$H$_9$BrN$_2$O$_2$S: 337.0. found: 337.3.

Step 2: A mixture of 4-bromo-1-(phenylsulfonyl)-1H-pyrrolo[2,3-b]pyridine (5.0 g, 15 mmol), 2-((tetrahydro-2H-pyran-4-yl)oxy)-5-(4,4,5,5-tetramethyl-1,3,2-dioxaborolan-2-yl)benzonitrile (5.4 g, 16 mmol), [1,1'-bis(diphenylphosphino)ferrocene]dichloropalladium(II) complex with dichloromethane (0.55 g, 0.74 mmol), and sodium carbonate (3.1 g, 30 mmol) in 1,4-dioxanes (130 mL) and water (40 mL) was heated for approximately 5 hours on a 115° C. heating block. After cooling to room temperature, the mixture was concentrated under reduced pressure. The residue was partitioned between dichloromethane and water. The aqueous phase was extracted three times with dichloromethane. The combined organics were dried over anhydrous magnesium sulfate, filtered, concentrated under reduced pressure. The residue was purified via flash chromatography on silica gel to give 5-(2-iodo-1-(phenylsulfonyl)-1H-pyrrolo[2,3-b]pyridin-4-yl)-2-((tetrahydro-2H-pyran-4-yl)oxy)benzonitrile.

LCMS-ESI$^+$ (m/z): [M+H]$^+$ calcd for C$_{25}$H$_{21}$N$_3$O$_4$S: 460.1. found: 460.2.

Step 3: A solution of diisopropylamine (1.1 mL, 7.9 mmol) in THF (30 mL), under an Argon atmosphere, was cooled in a solid CO$_2$/acetone bath. n-Butyllithium solution (2.5 M in hexanes, 2.7 mL, 6.7 mmol) was added dropwise via syringe. The mixture was transferred to ice-water bath and stirred 15 minutes before re-cooling in the CO$_2$/acetone bath. A solution of 5-(1-(phenylsulfonyl)-1H-pyrrolo[2,3-b]pyridin-4-yl)-2-((tetrahydro-2H-pyran-4-yl)oxy)benzonitrile (1.4 g, 3.4 mmol) in THF (6 mL) was added dropwise. After one hour of stirring at −78° C., a solution of iodine (2.3 g, 9.1 mmol) in THF (8 mL) was added dropwise via syringe. The mixture was allowed to stir in the cooling bath for 15 minutes post-I$_2$ addition before bath was removed, allowing room temperature to be regained. After one hour of stirring at room temperature, the reaction mixture was quenched by the addition of saturated aqueous ammonium chloride solution. The aqueous phase was extracted three times with ethyl acetate. The combined extracts washed once each with 10% aqueous sodium thiosulfate solution and saturated aqueous sodium chloride solution. Organics were dried over anhydrous magnesium sulfate, filtered, concentrated to dryness under reduced pressure to furnish 5-(2-iodo-1-(phenylsulfonyl)-1H-pyrrolo[2,3-b]pyridin-4-yl)-2-((tetrahydro-2H-pyran-4-yl)oxy)benzonitrile. LCMS-ESI$^+$ (m/z): [M+H]$^+$ calcd for C$_{25}$H$_{20}$IN$_3$O$_4$S: 586.0. found: 586.1.

Intermediate B: tert-butyl 4-(2-cyano-4-(4,4,5,5-tetramethyl-1,3,2-dioxaborolan-2-yl)phenoxy)piperidine-1-carboxylate

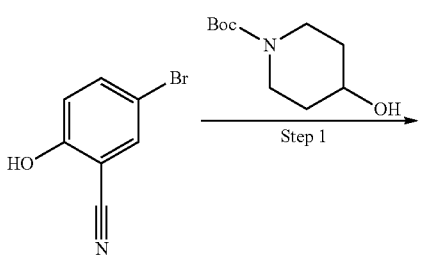

-continued

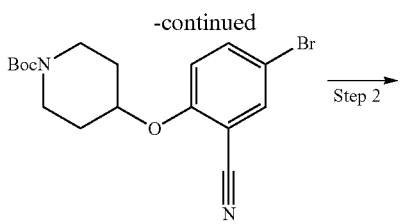

Step 2

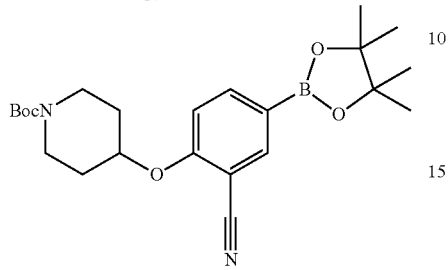

Step 1: 5-bromo-2-hydroxybenzonitrile (45 g, 0.23 mol) in anhydrous THF (1000 mL) was combined with tert-butyl 4-hydroxypiperidine-1-carboxylate (55 g, 0.27 mol), PPh₃ (70.7 g, 0.27 mol), followed by addition of DEAD (47.7 g, 0.27 mol) at r.t. The mixture was stirred at r.t. for 18 hrs. The reaction mixture was concentrated under reduced pressure. The residue was purified by silica gel chromatography (PE/EA=20/1 to 10/1) to give tert-butyl 4-(4-bromo-2-cyanophenoxy)piperidine-1-carboxylate. $^1$H NMR: (CDCl₃, 400 MHz): δ 7.67 (s, 1H), 7.62-7.59 (m, 1H), 6.88 (d, J=9.2 Hz, 1H), 4.62-4.61 (m, 1H), 3.63-3.47 (m, 4H), 1.91-1.85 (m, 4H), 1.47 (s, 9H)

Step 2: To a solution of tert-butyl 4-(4-bromo-2-cyanophenoxy)piperidine-1-carboxylate (46.7 g, 0.12 mol) in dioxane (1000 mL) was added Pd(dppf)Cl₂ (4.4 g, 6 mmol) (Bpin)₂ (37.5 g, 0.14 mol), and KOAc (35.3 g, 0.36 mol). After stirring at 80° C. for 20 hrs under N₂, the mixture was filtered to remove KOAc, and the filtrate was concentrated under reduced pressure. The residue was purified by twice column chromatography (PE/EA=20/1 to 10/1) to give the title compound. $^1$H NMR: (CDCl₃, 400 MHz): δ 8.03 (s, 1H), 7.92 (d, J=8.8 Hz, 1H), 6.95 (d, J=8.8 Hz, 1H), 4.70 (m, 1H), 3.64 (m, 2H), 3.52-3.48 (m, 2H), 1.90-1.84 (m, 4H), 1.59 (s, 9H), 1.47-1.34 (m, 12H).

Intermediate C: (R)-tert-butyl 3-(2-cyano-4-(4,4,5,5-tetramethyl-1,3,2-dioxaborolan-2-yl)phenoxy) pyrrolidine-1-carboxylate

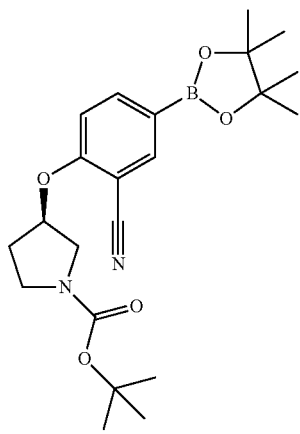 [SMILES: CC(C)(C)OC(=O)N1CC[C@@H](Oc2ccc(B3OC(C)(C)C(C)(C)O3)cc2C#N)C1]

The title compound was prepared following similar procedure to prepare Intermediate B using (S)-tert-butyl 3-hydroxypyrrolidine-1-carboxylate instead of tert-butyl 4-hydroxypiperidine-1-carboxylate in step 1. $^1$H NMR: (CDCl₃, 400 MHz): δ 8.03 (s, 1H), 7.92 (d, J=7.6 Hz, 1H), 6.89 (d, J=8.4 Hz, 1H), 5.02 (s, 1H), 3.71-3.57 (m, 4H), 2.27-2.15 (m, 2H), 1.58 (s, 9H), 1.34 (s, 12H).

Intermediate D: (S)-tert-butyl 3-(2-cyano-4-(4,4,5,5-tetramethyl-1,3,2-dioxaborolan-2-yl)phenoxy)pyrrolidine-1-carboxylate

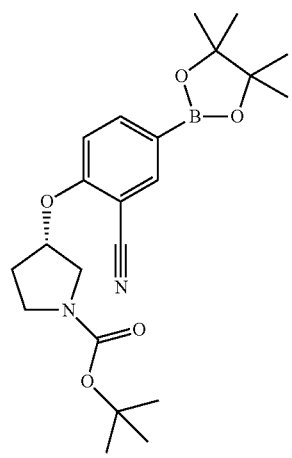 [SMILES: CC(C)(C)OC(=O)N1CC[C@H](Oc2ccc(B3OC(C)(C)C(C)(C)O3)cc2C#N)C1]

The title compound was prepared following similar procedure to prepare Intermediate B using (R)-tert-butyl 3-hydroxypyrrolidine-1-carboxylate instead of tert-butyl 4-hydroxypiperidine-1-carboxylate in step 1. $^1$H NMR: (CDCl₃, 400 MHz): δ 8.04 (s, 1H), 7.94 (d, J=7.2 Hz, 1H), 6.91 (d, J=8.4 Hz, 1H), 5.04 (s, 1H), 3.73-3.59 (m, 4H), 2.29-2.16 (m, 2H), 1.59 (s, 9H), 1.36 (s, 12H).

Intermediate E: 2-(cyclopropylmethoxy)-5-(4,4,5,5-tetramethyl-1,3,2-dioxaborolan-2-yl)benzonitrile

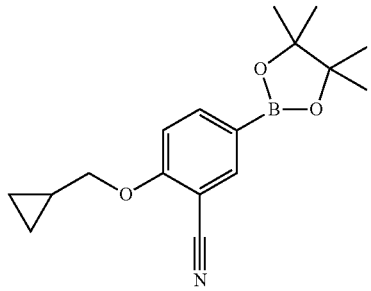 [SMILES: CC1(C)OB(c2ccc(OCC3CC3)c(C#N)c2)OC1(C)C]

Step 1: To a solution of cyclopropylmethanol (2.7 g, 38 mmol, 1.52 equiv.) in dry DMF (100 mL), sodium hydride, 60% suspension in oil (1.5 g, 38 mmol, 1.52 equiv.) at 0° C. under nitrogen. After 30 minutes at 0° C., 5-bromo-2-fluorobenzonitrile (5 g, 25 mmol, 1 equiv.) in dry DMF (20 mL) was added and the reaction mixture was heated to 50° C. for 16 hrs. The reaction mixture is mixed with ice water and ethyl acetate. The organic phases are washed with water and saturated sodium chloride solution and dried with sodium sulfate. After removal of the solvent the crude product was purified by column by chromatography (PE:EA=30:1) to obtain 5-bromo-2-(cyclopropylmethoxy)benzonitrile. $^1$H NMR: (CDCl$_3$): δ 7.65 (d, J=1.6 Hz, 1H), 7.59 (dd, J=8.0, 1.6 Hz, 1H), 6.84 (d, J=8.0 Hz, 1H), 3.92 (d, J=6.8 Hz, 2H), 1.26-1.33 (m, 1H), 0.65-0.69 (m, 2H), 0.37-0.41 (m, 2H).

Step 2: A solution of 5-bromo-2-(cyclopropylmethoxy)benzonitrile (36 g, 0.144 mol, 1 equiv.) in 1,4-Dioxane (600 mL) was degassed for 10 min, then (Bpin)$_2$ (40.2 g, 0.156 mol, 1.08 equiv.), [1,1'-bis (diphenylphosphino) ferrocene] dichloropalladium (II) (2.64 g, 3.6 mmol, 0.025 equiv.), 1,1' bis (diphenylphosphino) ferrocene (1.98 g, 3.6 mmol, 0.025 equiv.) and potassium acetate (28.2 g, 0.288 mol) are added at room temperature and refluxed for 18 h. The reaction mixture is mixed with ice water (200 mL) and ethyl acetate extracted. The organic phases are washed with water and saturated sodium chloride solution and dried with sodium sulfate. After removal of the solvent the crude product was purified by column by chromatography to obtain the title compound. $^1$H NMR: (CDCl$_3$): δ 8.01 (d, J=1.6 Hz, 1H), 7.91 (dd, J=8.4, 1.6 Hz, 1H), 6.91 (d, J=8.4 Hz, 1H), 3.96 (d, J=6.8 Hz, 2H), 1.33 (s, 12H), 1.28-1.34 (m, 1H), 0.65-0.69 (m, 2H), 0.38-0.42 (m, 2H).

Intermediate F: 2-((tetrahydro-2H-pyran-4-yl)oxy)-5-(4,4,5,5-tetramethyl-1,3,2-dioxaborolan-2-yl)benzonitrile

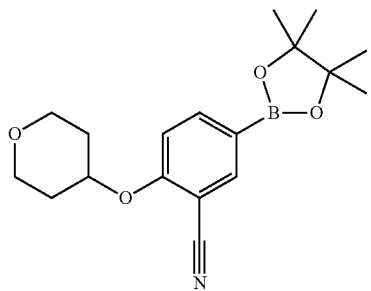 [SMILES: CC1(C)OB(c2ccc(OC3CCOCC3)c(C#N)c2)OC1(C)C]

Step 1: To tetrahyropyranol (30.0 g, 294 mmol) in DMF (400 mL) at 0° C. was added NaH (19.6 g, 294 mmol). 5-bromo-2-fluorobenzonitrile (49.0 g, 245 mmol) was added drop wise as a solution in DMF (100 mL). The reaction was stirred at 45° C. for 16 The reaction was cooled to rt and quenched by pouring the reaction into H$_2$O. The precipitate was filtered and dried under vacuum to 5-bromo-2-((tetrahydro-2H-pyran-4-yl)oxy)benzonitrile which was used further without purification.

Step 2: To 5-Bromo-2-tetrahydropyran-4-yloxy-benzonitrile (57 g, 202 mmol) in dioxane (550 mL) was added bis(pinacolato)diboron (65 g, 256 mmol), KOAc (50.4 g, 606 mmol), and Pd(dppf)Cl$_2$ (6.3 g, 10 mmol). The reaction was heated to 90° C. for 16 The solvent was removed and the residual was quenched with H$_2$O (500 mL), followed by extraction with EtOAc (3×1000 mL). The aqueous and organic layers were separated. The organic layer was washed with aq. saturated NaCl and dried (Na$_2$SO$_4$). Purification by silica gel chromatography (0-100%, EtOAc in Hexanes) provided the title compound. $^1$H NMR: (CDCl$_3$): δ 8.02 (d, 1H), 7.92-7.89 (m, 1H), 6.95-6.93 (d, 1H), 4.71-4.69 (m, 1H), 4.00-3.98 (m, 2H), 3.63-3.60 (m, 2H), 2.04-2.01 (m, 2H), 1.90-1.85 (m, 2H), 1.33 (s, 12H).

Intermediate G: Preparation of 6-bromo-3-((tetrahydro-2H-pyran-4-yl)oxy)picolinonitrile

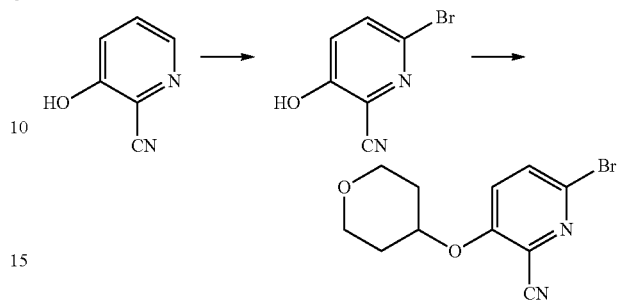

Step 1: 3-hydroxypicolinonitrile (12.5 g, 104 mmol) taken up in 160 mL acetonitrile and 30 mL water. While stirring vigorously, the solution was cooled to −10° C. and treated with N-bromosuccinimide (18.5 g, 104 mmol) in portions over 2 h, then allowed to stir at rt for 16 h. The solution was diluted with EtOAc (700 mL), washed with 5% LiCl (3-times). The organic layer is separated, dried and concentrated to afford crude 6-bromo-3-hydroxypicolinonitrile. LCMS-ESI$^+$ (m/z): [M+H]$^+$ calcd for C$_6$H$_4$BrN$_2$O$_2$: 198.9, 200.9. found: 199.0, 201.0.

Step 2: A solution of 6-bromo-3-hydroxypicolinonitrile (3.5 g, 7.6 mmol) an 5.8 g, 35 mmol) in 50 mL DMF was treated with potassium carbonate (7.29 g, 53 mmol) and sodium iodide (0.262 g, 0.20 mmol) and heated to 85° C. for 18 h. Cooled to rt and diluted with EtOAc and water. Organic layer washed with 5% LiCl. Organic layers were combined, dried and concentrated under reduced pressure. The residue was purified by flash column chromatography on silica gel to afford 6-bromo-3-((tetrahydro-2H-pyran-4-yl)oxy)picolinonitrile. LCMS-ESI$^+$ (m/z): [M+H]$^+$ calcd for C1$_1$H$_{12}$BrN$_2$O$_2$: 283.0, 285.0. found: 282.8, 284.7.

Intermediate H: Preparation 2-((tetrahydro-2H-pyran-4-yl)oxy)-5-(4,4,5,5-tetramethyl-1,3,2-dioxaborolan-2-yl)nicotinonitrile

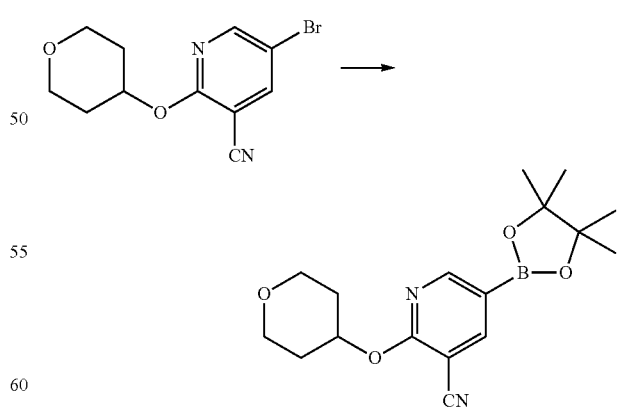

5-bromo-2-((tetrahydro-2H-pyran-4-yl)oxy)nicotinonitrile (1.5 g, 5.3 mmol), 4,4,4',4',5,5,5',5'-octamethyl-2,2'-bi (1,3,2-dioxaborolane) (1.35 g, 5.3 mmol) potassium acetate (1.6 g, 16 mmol) and [1,1-Bis(diphenylphosphino)ferrocene]dichloropalladium(II), complex with dichloromethane (162 mg, 0.27 mmol) were taken up in 30 mL dioxane and heated to 80° C. for 4 h. After cooling to rt the mixture was diluted with ethyl acetate, filtered and concentrated under reduced pressure. The residue was purified by flash column chromatography on silica gel to afford 2-((tetrahydro-2H-pyran-4-yl)oxy)-5-(4,4,5,5-tetramethyl-1,3,2-dioxaborolan-2-yl)nicotinonitrile. LCMS-ESI⁺ (m/z): [M+H]⁺ calcd for $C_{17}H_{23}BN_2O_4$: 331.2. found: 330.9.

Example 1: Preparation of 5-(2-(3,4-dimethoxyphenyl)-1H-pyrrolo[2,3-b]pyridin-4-yl)-2-((tetrahydro-2H-pyran-4-yl)oxy)benzonitrile

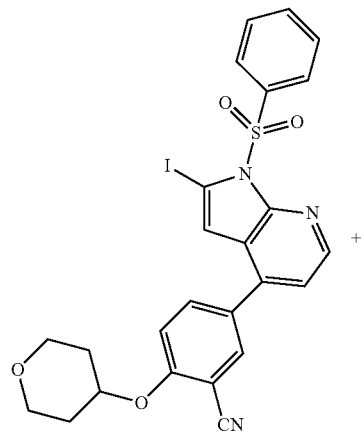

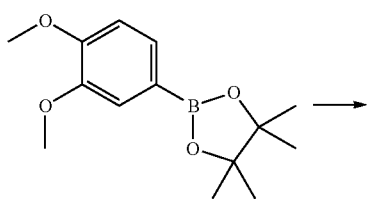

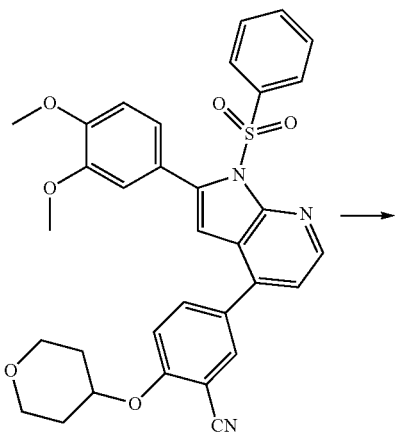

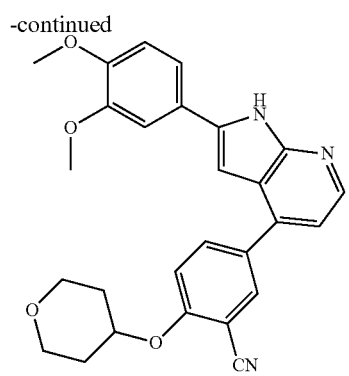

Step 1: A sealed tube containing a suspension of 5-(2-iodo-1-(phenylsulfonyl) 1H-pyrrolo[2,3-b]pyridin-4-yl)-2-((tetrahydro-2H-pyran-4-yl)oxy)benzonitrile (100 mg, 0.171 mmol) and Pd(PPh₃)₄ (9 mg, 0.008 mmol) in a degassed mixture of dioxane/H₂O (1.5 mL, 4/1), was preheated at 85° C. for 5 min. Next, K₂CO₃ (59 mg, 0.427 mmol) and 2-(3,4-dimethoxyphenyl)-4,4,5,5-tetramethyl-1,3,2-dioxaborolane (68 mg, 0.257 mmol), were added to the mixture and the reaction was additionally heated at 100° C. in the sealed tube for 15 hrs. Afterwards, the crude material was allowed to reach room temperature. It was diluted with EtOAc and filtered through a short pad of Celite, washing the solids with EtOAc. The filtrate was washed with saturated aqueous sodium chloride solution and the organic phase separated and dried over anhydrous MgSO₄. After filtration of the solids and evaporation in vacuo, the resulting oily residue was purified by column chromatography over silica gel to afford 5-(2-(3,4-dimethoxyphenyl)-1-(phenylsulfonyl)-1H-pyrrolo[2,3-b]pyridin-4-yl)-2-((tetrahydro-2H-pyran-4-yl)oxy)benzonitrile. LCMS-ESI⁺ (m/z): [M+H]⁺ calcd for $C_{33}H_{29}N_3O_6S$: 596.2. found: 596.4.

Step 2: A mixture of 5-(2-(3,4-dimethoxyphenyl)-1-(phenylsulfonyl)-1H-pyrrolo[2,3-b]pyridin-4-yl)-2-((tetrahydro-2H-pyran-4-yl)oxy)benzonitrile (100.0 mg, 0.169 mmol) and 10% aqueous solution of NaOH (1.7 mL) in abs EtOH (3.5 mL) was refluxed for 3 hours, cooled and diluted with water (10 mL). The reaction mixture was quenched with saturated ammonium chloride (10 mL) and extracted with DCM. The organic extracts were dried (Na₂SO₄), concentrated in vacuo and the residue dissolved in small amount of EtOAc. A precipitate which appeared was filtered off to afford 5-(2-(3,4-dimethoxyphenyl)-1H-pyrrolo[2,3-b]pyridin-4-yl)-2-((tetrahydro-2H-pyran-4-yl)oxy)benzonitrile.

¹H NMR (400 MHz, DMSO-d6) δ 12.24 (s, 1H), 8.22 (d, J=5.0 Hz, 1H), 8.12 (d, J=2.3 Hz, 1H), 8.07-8.13 (m, 1H), 7.62-7.47 (m, 3H), 7.18 (d, J=5.0 Hz, 1H), 7.11-6.97 (m, 2H), 4.92 (m, 1H), 3.95-3.82 (m, 2H), 3.85 (s, 3H), 3.79 (s, 3H), 3.53-3.58 (m, 2H), 2.11-1.99 (m, 2H), 1.71 (m, 2H). LCMS-ESI⁺ (m/z): [M+H]⁺ calcd for $C_{27}H_{25}N_3O_4$: 456.2. found: 456.2.

Example 2: Preparation of 5-(2-(4-(morpholinomethyl)phenyl)-1H-pyrrolo[2,3-b]pyridin-4-yl)-2-((tetrahydro-2H-pyran-4-yl)oxy)benzonitrile

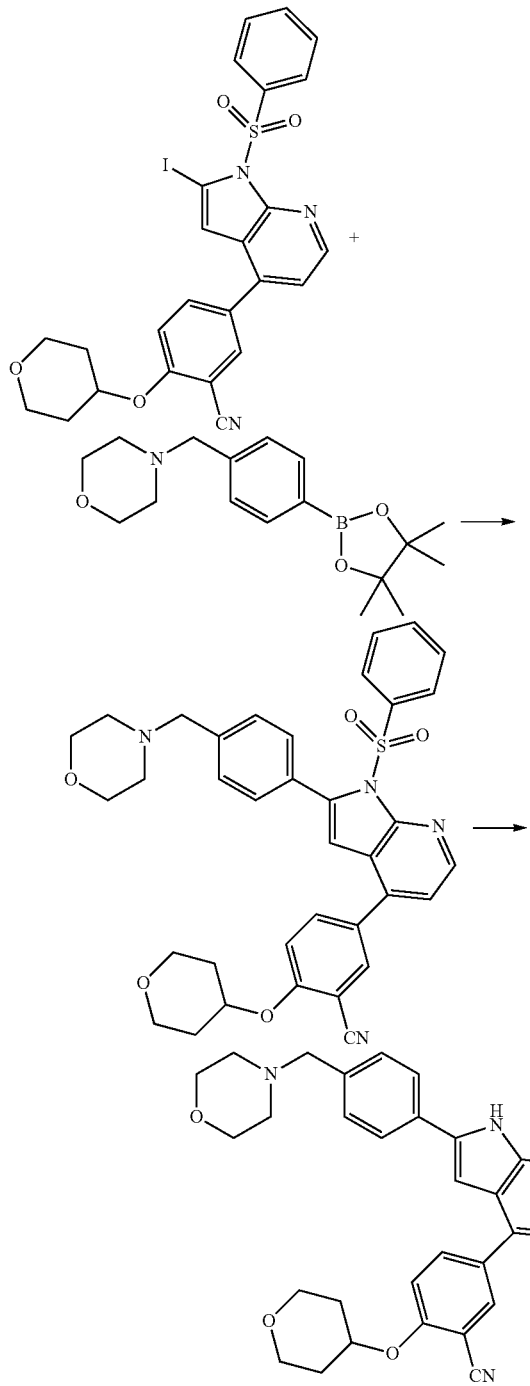

Step 1: A sealed tube containing a suspension of 5-(2-iodo-1-(phenylsulfonyl)-1H-pyrrolo[2,3-b]pyridin-4-yl)-2-((tetrahydro-2H-pyran-4-yl)oxy)benzonitrile (100 mg, 0.171 mmol) and Pd(PPh$_3$) (9 mg, 0.008 mmol) in a degassed mixture of dioxane/H$_2$O (1.5 mL, 4/1), was preheated at 85° C. for 5 min. Next, K$_2$CO$_3$ (59 mg, 0.427 mmol) and 4-(4-(4,4,5,5-tetramethyl-1,3,2-dioxaborolan-2-yl)benzyl)morpholine (78 mg, 0.256 mmol), were added to the mixture and the reaction was additionally heated at 100° C. in the sealed tube for 15 hrs. Afterwards, the crude material was allowed to reach room temperature. It was diluted in MeOH and filtered through a short pad of Celite. The filtrate was concentrate in vacuo. The residue was purified by flash column chromatography on silica gel to give 5-(2-(4-(morpholinomethyl)phenyl)-1-(phenylsulfonyl)-1H-pyrrolo[2,3-b]pyridin-4-yl)-2-((tetrahydro-2H-pyran-4-yl)oxy)benzonitrile. LCMS-ESI$^+$ (m/z): [M+H]$^+$ calcd for C$_{36}$H$_{34}$N$_4$O$_5$S: 635.2. found: 635.5.

Step 2: A mixture of 5-(2-(4-(morpholinomethyl)phenyl)-1-(phenylsulfonyl)-1H-pyrrolo[2,3-b]pyridin-4-yl)-2-((tetrahydro-2H-pyran-4-yl)oxy)benzonitrile (95 mg, 0.15 mmol) and 10 percent aqueous solution of NaOH (1.7 mL) in abs EtOH (3.5 mL) was refluxed for 3 hours, cooled and diluted with water (10 mL). The reaction mixture was quenched with saturated ammonium chloride and extracted with DCM. The organic extracts were dried (Na$_2$SO$_4$), concentrated in vacuo and the residue was purified by flash column chromatography on silica gel to afford 5-(2-(4-(morpholinomethyl)phenyl)-1H-pyrrolo[2,3-b]pyridin-4-yl)-2-((tetrahydro-2H-pyran-4-yl)oxy)benzonitrile. $^1$H NMR (400 MHz, DMSO-d6) δ 12.27 (s, 1H), 8.25 (d, J=5.0 Hz, 1H), 8.13 (d, J=2.3 Hz, 1H), 8.08 (dd, J=8.9, 2.3 Hz, 1H), 7.99-7.86 (m, 2H), 7.52 (d, J=8.9 Hz, 1H), 7.38 (d, J=8.0 Hz, 2H), 7.20 (d, J=5.0 Hz, 1H), 7.12 (d, J=2.0 Hz, 1H), 4.92 (m, 1H), 3.96-3.81 (m, 2H), 3.64-3.51 (m, 6H), 3.48 (s, 2H), 2.36 (t, J=4.6 Hz, 4H), 2.13-1.96 (m, 2H), 1.70 (m, 2H). LCMS-ESI$^+$ (m/z): [M+H]$^+$ calcd for C$_{30}$H$_{30}$N$_4$O$_3$: 495.2. found: 495.1.

Example 3: Preparation of 5-(2-(3,6-dihydro-2H-pyran-4-yl)-1H-pyrrolo[2,3-b]pyridin-4-yl)-2-((tetrahydro-2H-pyran-4-yl)oxy)benzonitrile

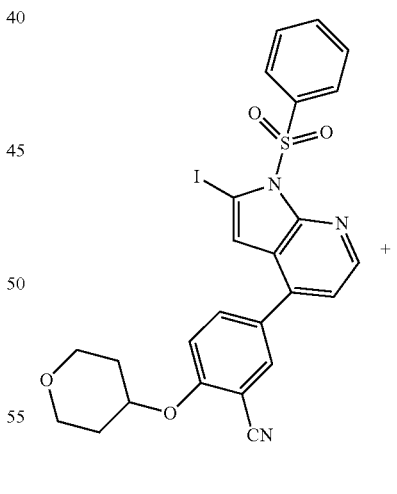

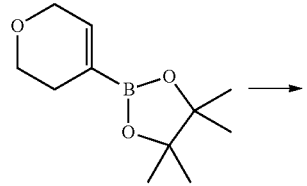

-continued

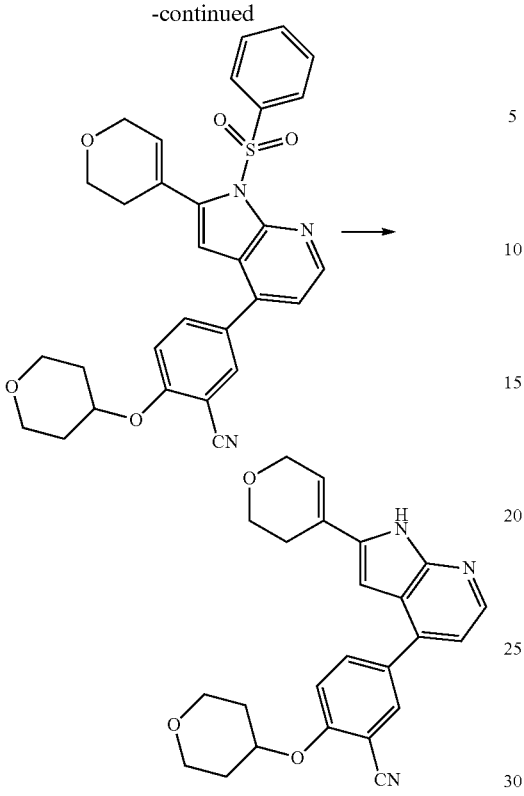

Step 1: A sealed tube containing a suspension of 5-(2-iodo-1-(phenylsulfonyl)-1H-pyrrolo[2,3-b]pyridin-4-yl)-2-((tetrahydro-2H-pyran-4-yl)oxy)benzonitrile (100 mg, 0.171 mmol) and Pd(PPh₃), (9 mg, 0.008 mmol) in a degassed mixture of dioxane/H₂O (1.5 mL, 4/1), was preheated at 85° C. for 5 min. Next, K₂CO₃ (59 mg, 0.43 mmol) and 2-(3,6-dihydro-2H-pyran-4-yl)-4,4,5,5-tetramethyl-1,3,2-dioxaborolane (54 mg, 0.257 mmol), were added to the mixture and the reaction was additionally heated at 100° C. in the sealed tube for 15 hrs. Afterwards, the crude material was allowed to reach room temperature. It was concentrated to dryness; the residue was triturated with EtOH and filtered through a short pad of Celite, washing the solids with CH₂Cl₂. The filtrate was concentrated to dryness. The residue was purified by flash column chromatography on silica gel to afford 5-(2-(3,6-dihydro-2H-pyran-4-yl)-1-(phenylsulfonyl)-1H-pyrrolo[2,3-b]pyridin-4-yl)-2-((tetrahydro-2H-pyran-4-yl)oxy)benzonitrile. LCMS-ESI⁺ (m/z): [M+H]⁺ calcd for $C_{30}H_{27}N_3O_5S$: 542.2. found: 542.2.

Step 2: A mixture of 5-(2-(3,6-dihydro-2H-pyran-4-yl)-1-(phenylsulfonyl)-1H-pyrrolo[2,3-b]pyridin-4-yl)-2-((tetrahydro-2H-pyran-4-yl)oxy)benzonitrile (88.0 mg, 0.162 mmol) and 10 percent aqueous solution of NaOH (1.7 mL) in abs EtOH (3.5 mL) was refluxed for 3 hours, cooled and diluted with water (10 mL). The reaction mixture was quenched with saturated ammonium chloride (10 mL) and extracted with DCM. The organic extracts were dried (Na₂SO₄), concentrated in vacuo and the residue was purified by flash column chromatography on silica gel to afford 5-(2-(3,6-dihydro-2H-pyran-4-yl)-1H-pyrrolo[2,3-b]pyridin-4-yl)-2-((tetrahydro-2H-pyran-4-yl)oxy)benzonitrile.
¹H NMR (400 MHz, DMSO-d6) δ 11.95 (s, 1H), 8.22 (d, J=5.0 Hz, 1H), 8.14-7.92 (m, 2H), 7.69-7.41 (m, 3H), 7.16 (d, J=5.0 Hz, 1H), 6.74-6.44 (m, 2H), 4.90 (m, 1H), 4.26 (m, 2H), 3.98-3.70 (m, 4H), 3.54 (m, 2H), 2.17-1.89 (m, 2H), 1.69 (m, 2H). LCMS-ESI⁺ (m/z): [M+H]⁺ calcd for $C_{24}H_{23}N_3O_3$: 402.2. found: 402.2.

Example 4: Preparation of tert-butyl 4-(4-(3-cyano-4-((tetrahydro-2H-pyran-4-yl)oxy)phenyl)-1H-pyrrolo[2,3-b]pyridin-2-yl)-5,6-dihydropyridine-1(2H)-carboxylate

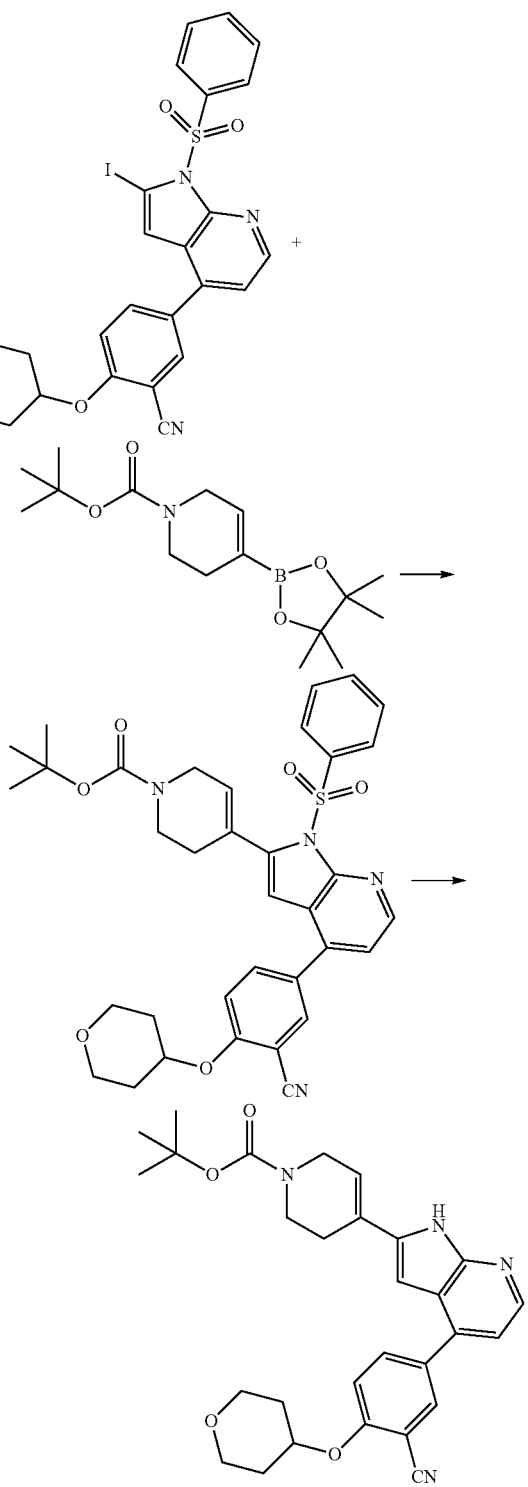

Step 1: A sealed tube containing a suspension of 5-(2-iodo-1-(phenylsulfonyl)-1H-pyrrolo[2,3-b]pyridin-4-yl)-2-((tetrahydro-2H-pyran-4-yl)oxy)benzonitrile (300 mg, 0.512 mmol) and Pd(PPh3)4 (27 mg, 0.023 mmol) in a degassed mixture of dioxane/H2O (4.5 mL, 4/1), was preheated at 85° C. for 5 min. Next, K2CO3 (177 mg, 1.28 mmol) and tert-butyl 4-(4,4,5,5-tetramethyl-1,32-dioxaborolan-2-yl)-5,6-dihydropyridine-1(2H)-carboxylate (238 mg, 0.77 mmol), were added to the mixture and the reaction was additionally heated at 100° C. in the sealed tube for 15 hrs. Afterwards, the crude material was allowed to reach room temperature. It was concentrated to dryness; the residue was triturated with EtOH and filtered through a short pad of Celite, washing the solids with CH2Cl2. The filtrate was concentrated to dryness. The residue was purified by flash column chromatography on silica gel to afford tert-butyl 4-(4-(3-cyano-4-((tetrahydro-2H-pyran-4-yl)oxy)phenyl)-1-(phenylsulfonyl)-1H-pyrrolo[2,3-b]pyridin-2-yl)-5,6-dihydropyridine-(2H)-carboxylate. LCMS-ESI+ (m/z): [M+H]+ calcd for $C_{35}H_{36}N_4O_6S$:641.2. found: 641.1.

Step 2: A mixture of tert-butyl 4-(4-(3-cyano-4-((tetrahydro-2H-pyran-4-yl)oxy)phenyl)-1-(phenylsulfonyl)-1H-pyrrolo[2,3-b]pyridin-2-yl)-5,6-dihydropyridine-1(2H)-carboxylate (320 mg, 0.499 mmol) and 10% aqueous solution of NaOH (4 mL) in abs EtOH (8.5 mL) was refluxed for 3 hours, cooled and diluted with water (25 mL). The reaction mixture was quenched with saturated ammonium chloride and extracted with DCM. The organic extracts were dried (Na2SO4), concentrated in vacuo and the residue was purified by flash column chromatography on silica gel to afford tert-butyl 4-(4-(3-cyano-4-((tetrahydro-2H-pyran-4-yl)oxy)phenyl)-1H-pyrrolo[2,3-b]pyridin-2-yl)-5,6-dihydropyridine-1(2H)-carboxylate.

1H NMR (400 MHz, DMSO-d6) δ 8.34-8.11 (m, 1H), 8.12-7.90 (m, 1H), 7.70-7.40 (m, 2H), 7.15 (m, 1H), 6.64 (m, 1H), 6.50 (s, 1H), 6.39-6.21 (m, 1H), 4.89 (m, 1H), 4.04 (s, 1H), 3.97-3.80 (m, 2H), 3.76-3.39 (m, 4H), 2.04 (m, 2H), 1.68 (m, 2H), 1.53-1.25 (m, 9H). LCMS-ESI+ (m/z): [M+H]+ calcd for $C_{29}H_{32}N_4O_4$: 501.2. found: 501.1.

Example 5: Preparation of 2-((tetrahydro-2H-pyran-4-yl)oxy)-5-(2-(1,2,3,6-tetrahydropyridin-4-yl)-1H-pyrrolo[2,3-b]pyridin-4-yl)benzonitrile

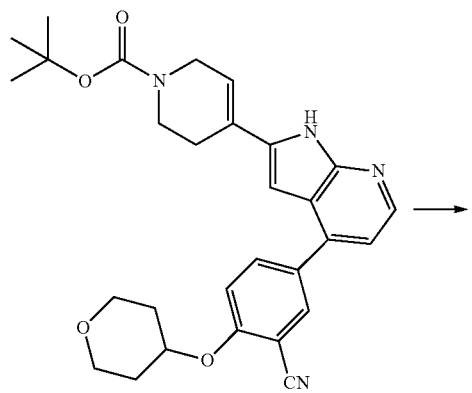

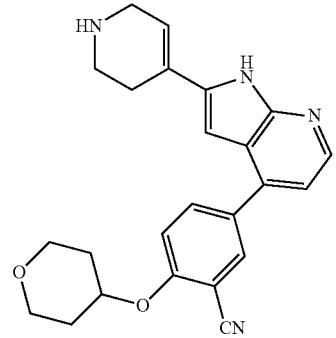

A solution of tert-butyl 4-(4-(3-cyano-4-((tetrahydro-2H-pyran-4-yl)oxy)phenyl)-1H-pyrrolo[2,3-b]pyridin-2-yl)-5,6-dihydropyridine-1(2H)-carboxylate (70 mg, 0.14 mmol) in CH2Cl2 (4 mL) and trifluoroacetic acid (1.5 mL) was stirred at rt for 4 hr. The solvent was evaporated under reduced pressure. The reaction mixture was then concentrated to dryness, the residue was purified by flash column chromatography on silica gel to afford 2-((tetrahydro-2H-pyran-4-yl)oxy)-5-(2-(1,2,3,6-tetrahydropyridin-4-yl)-1H-pyrrolo[2,3-b]pyridin-4-yl)benzonitrile.

1H NMR (400 MHz, DMSO-d6) δ 12.09 (s, 1H), 8.82 (s, 1H), 8.26 (d, J=5.0 Hz, 1H), 8.16-7.93 (m, 2H), 7.51 (d, J=8.9 Hz, 1H), 7.19 (d, J=5.0 Hz, 1H), 6.74 (s, 1H), 6.51 (m, 1H), 4.91 (m, 1H), 3.85 (m, 4H), 3.70-3.44 (m, 4H), 2.75 (m, 1H), 2.18-1.92 (m, 2H), 1.69 (m, 2H). LCMS-ESI+ (m/z): [M+H]+ calcd for $C_{24}H_{24}N_4O_2$: 401.2. found: 401.1.

Example 6: 5-(2-(1-(oxetan-3-yl)-1H-pyrazol-4-yl)-1H-pyrrolo[2,3-b]pyridin-4-yl)-2-((tetrahydro-2H-pyran-4-yl)oxy)benzonitrile

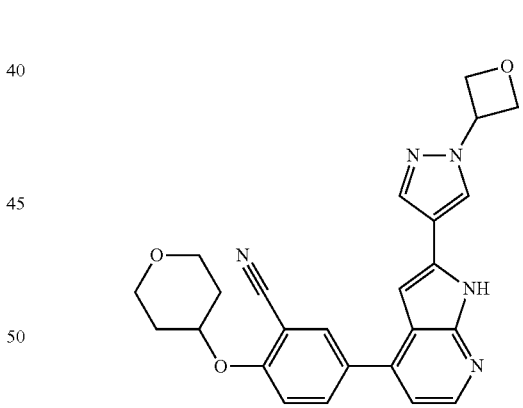

Step 1: Preparation of 5-(2-(1-(oxetan-3-yl)-1H-pyrazol-4-yl)-1-(phenylsulfonyl)-1H-pyrrolo[2,3-b]pyridin-4-yl)-2-((tetrahydro-2H-pyran-4-yl)oxy)benzonitrile A mixture of 5-(2-iodo-1-(phenylsulfonyl)-1H-pyrrolo[2,3-b]pyridin-4-yl)-2-((tetrahydro-2H-pyran-4-yl)oxy)benzonitrile (0.33 g, 0.56 mmol), 1-(oxetan-3-yl)-4-(4,4,5,5-tetramethyl-1,3,2-dioxaborolan-2-yl)-1H-pyrazole (Synthonix, 0.17 g, 0.67 mmol), Cesium carbonate (0.46 g, 1.4 mmol), and bis(triphenylphosphine)palladium(II) dichloride (0.02 g, 0.03 mmol) in 1,4-dioxanes (3 mL) and water (1 mL), was heated overnight on an 85° C. block. After cooling to room temperature, the mixture was purified via flash chromatography on silica gel to give the desired material. LCMS-ESI+ (m/z): [M+H]+ calcd for $C_{31}H_{27}N_5O_5S$: 582.2. found: 582.5.

Step 2: Preparation of 5-(2-(1-(oxetan-3-yl)-1H-pyrazol-4-yl)-1H-pyrrolo[2,3-b]pyridin-4-yl)-2-((tetrahydro-2H-pyran-4-yl)oxy)benzonitrile 5-(2-(1-(oxetan-3-yl)-1H-pyrazol-4-yl)-1-(phenylsulfonyl)-1H-pyrrolo[2,3-b]pyridin-4-yl)-2-((tetrahydro-2H-pyran-4-yl)oxy)benzonitrile (0.31 g, 0.54 mmol) was taken up in 1,4-dioxanes (2 mL) in a microwave vial. Cesium carbonate (0.53 g, 1.6 mmol) was added, followed by 2,2,2-trifluoroethanol (1 mL). The mixture was heated in a Biotage microwave reactor for 30 minutes at 100° C. After cooling to room temperature, the mixture was diluted with methanol/dichloromethane and concentrated to dryness under reduced pressure. The residue was purified via prep HPLC (10-70% acetonitrile in water, 0.1% trifluoroacetic acid buffer) to furnish 5-(2-(1-(oxetan-3-yl)-1H-pyrazol-4-yl)-1H-pyrrolo[2,3-b]pyridin-4-yl)-2-((tetrahydro-2H-pyran-4-yl)oxy)benzonitrile.

LCMS-ESI+ (m/z): [M+H]+ calcd for $C_{25}H_{23}N_5O_3$: 442.2. found: 442.2. 1H NMR (400 MHz, DMSO-d6) δ 12.32 (s, 1H), 8.54 (s, 1H), 8.27 (d, J=5.1 Hz, 1H), 8.25 (s, 1H), 8.17 (d, J=2.4 Hz, 1H), 8.11 (dd, J=8.7, 2.5 Hz, 1H), 7.59 (d, J=9.0 Hz, 1H), 7.28 (d, J=5.2 Hz, 1H), 6.95 (d, J=1.9 Hz, 1H), 5.67 (m, 1H), 5.05-4.92 (m, 5H), 3.93 (m, 2H), 3.61 (m, 2H), 2.10 (m, 2H), 1.76 (m, 2H).

Example 7: 5-(2-(pyridin-3-yl)-1H-pyrrolo[2,3-b]pyridin-4-yl)-2-((tetrahydro-2H-pyran-4-yl)oxy)benzonitrile

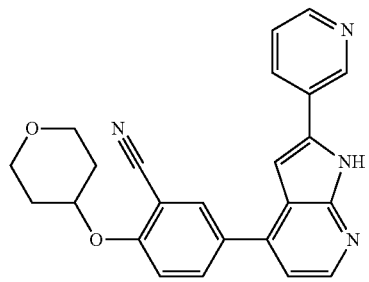 [SMILES: N#Cc1cc(-c2ccnc3[nH]c(-c4cccnc4)cc23)ccc1OC1CCOCC1]

Step 1: Preparation of 5-(1-(phenylsulfonyl)-2-(pyridin-3-yl)-1H-pyrrolo[2,3-b]pyridin-4-yl)-2-((tetrahydro-2H-pyran-4-yl)oxy)benzonitrile: A mixture of 5-(2-iodo-1-(phenylsulfonyl)-1H-pyrrolo[2,3-b]pyridin-4-yl)-2-((tetrahydro-2H-pyran-4-yl)oxy)benzonitrile (0.37 g, 0.62 mmol), pyridine-3-boronic acid (0.09 g, 0.75 mmol), Cesium carbonate (0.51 g, 1.6 mmol), and bis(triphenylphosphine)palladium(I) dichloride (0.03 g, 0.04 mmol) in 1,4-dioxanes (3 mL) and water (1 mL), was heated for two hours on an 85° C. block. After cooling to room temperature, the mixture was purified via flash chromatography on silica gel to give the desired material. LCMS-ESI+ (m/z): [M+H]+ calcd for $C_{30}H_{24}N_4O_4S$: 537.2. found: 537.5.

Step 2: Preparation of 5-(2-(pyridin-3-yl)-1H-pyrrolo[2,3-b]pyridin-4-yl)-2-((tetrahydro-2H-pyran-4-yl)oxy)benzonitrile: 5-(1-(phenylsulfonyl)-2-(pyridin-3-yl)-1H-pyrrolo[2,3-b]pyridin-4-yl)-2-((tetrahydro-2H-pyran-4-yl)oxy)benzonitrile (0.28 g, 0.53 mmol) was taken up in 1,4-dioxanes (2 mL) in a microwave vial. Cesium carbonate (0.51 g, 1.6 mmol) was added, followed by 2,2,2-trifluoroethanol (1 mL). The mixture was heated in a Biotage microwave reactor for 30 minutes at 100° C. After cooling to room temperature, the mixture was diluted with methanol/dichloromethane and concentrated to dryness under reduced pressure. The residue was purified via prep HPLC (10-65% acetonitrile in water, 0.1% trifluoroacetic acid buffer) to furnish 5-(2-(pyridin-3-yl)-1H-pyrrolo[2,3-b]pyridin-4-yl)-2-((tetrahydro-2H-pyran-4-yl)oxy)benzonitrile. LCMS-ESI+ (m/z): [M+H]+ calcd for $C_{24}H_{20}N_4O_2$: 397.2. found: 397.2. 1H NMR (400 MHz, DMSO-d6) δ 12.67 (s, 1H), 9.38 (d, J=1.6 Hz, 1H), 8.72-8.69 (m, 2H), 8.40 (d, J=5.0 Hz, 1H), 8.22 (d, J=2.3 Hz, 1H), 8.15 (dd, J=8.8, 2.4 Hz, 1H), 7.81 (dd, J=8.1, 5.2 Hz, 1H), 7.59 (d, J=8.9 Hz, 1H), 7.52 (s, 1H), 7.33 (d, J=5.0 Hz, 1H), 4.99 (tt, J=7.8, 3.8 Hz, 1H), 3.94 (m, 2H), 3.62 (m, 2H), 2.33-1.91 (m, 2H), 1.76 (m, 2H).

Example 8: 5-(2-(4-(3-hydroxyoxetan-3-yl)phenyl)-1H-pyrrolo[2,3-b]pyridin-4-yl)-2-((tetrahydro-2H-pyran-4-yl)oxy)benzonitrile

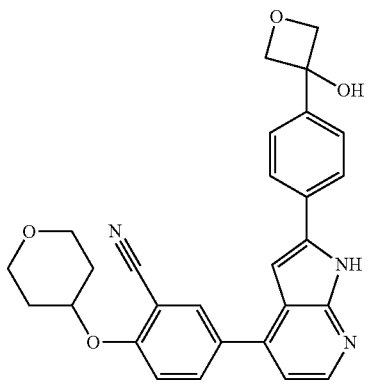 [SMILES: N#Cc1cc(-c2ccnc3[nH]c(-c4ccc(C5(O)COC5)cc4)cc23)ccc1OC1CCOCC1]

Step 1: Preparation of 3-(4-bromophenyl)oxetan-3-ol: n-BuLi (Aldrich, 1.6 M in hexanes, 2.9 mL, 4.6 mmol) was added dropwise at room temperature to a solution of 1-bromo-4-iodobenzene (1.3 g, 4.6 mmol) in pentane (14 mL). The mixture was stirred for 1 hr. A white precipitate was allowed to settle. The pentane was removed by pipette. The solid was diluted with pentane (14 mL) and then added to a solution of 3-oxetanone (0.63 g, 8.7 mmol) in THF (14 mL) that was cooled in an ice-water bath. The resulting suspension was stirred for three day at room temperature. The mixture was quenched by the addition of saturated aqueous ammonium chloride solution and allowed to stir for 30 minutes. Ethyl acetate was added and the layers separated. The aqueous layer was then extracted three times with ethyl acetate. The combined organic layers were washed with saturated aqueous sodium chloride solution, dried over anhydrous magnesium sulfate, filtered, and concentrated under reduced pressure. The waxy solid was taken up in a minimum of dichloromethane and precipitated with hexanes. The solid was collected by filtration and washed with hexanes to provide the desired material. 1H NMR (400 MHz, DMSO-d6) δ 7.77-7.47 (m, 4H), 6.49 (s, 1H), 4.80 (d, J=6.5 Hz, 2H), 4.68 (d, J=6.5 Hz, 2H).

Step 2: Preparation of 5-(2-(4-(3-hydroxyoxetan-3-yl)phenyl)-1-(phenylsulfonyl)-1H-pyrrolo[2,3-b]pyridin-4-yl)-2-((tetrahydro-2H-pyran-4-yl)oxy)benzonitrile: A mixture of 3-(4-bromophenyl)oxetan-3-ol (0.22 g, 0.97 mmol), bis(pinacolato)diboron (0.32 g, 1.3 mmol), potassium acetate (0.29 g, 2.9 mmol), and [1,1'-bis(diphenylphosphino)ferrocene]dichloropalladium(II) complex with dichloromethane (0.04 g, 0.05 mmol) in 1,4-dioxane (5 mL) was heated overnight at 85° C. After cooling to room temperature, the reaction mixture was charged with 5-(2-iodo-1-(phenylsulfonyl)-1H-pyrrolo[2,3-b]pyridin-4-yl)-2-((tetrahydro-2H-pyran-4-yl)oxy)benzonitrile (0.25 g, 0.43 mmol), Cesium carbonate (0.35 g, 1.1 mmol), bis(triphenylphosphine)palladium(II) dichloride (0.02 g, 0.03 mmol) and water (2 mL). The mixture was heated for 30 minutes on an 85° C. block. After cooling to room temperature, the mixture was purified via flash chromatography on silica gel to give the desired material. LCMS-ESI+ (m/z): [M+H]+ calcd for $C_{34}H_{29}N_3O_6S$: 608.2. found: 608.2.

Step 3: Preparation of 5-(2-(4-(3-hydroxyoxetan-3-yl)phenyl)-1H-pyrrolo[2,3-b]pyridin-4-yl)-2-((tetrahydro-2H-pyran-4-yl)oxy)benzonitrile: 5-(2-(4-(3-hydroxyoxetan-3-yl)phenyl)-1-(phenylsulfonyl)-1H-pyrrolo[2,3-b]pyridin-4-yl)-2-((tetrahydro-2H-pyran-4-yl)oxy)benzonitrile (0.22 g, 0.36 mmol) was taken up in 1,4-dioxanes (2 mL) in a microwave vial. Cesium carbonate (0.35 g, 1.1 mmol) was added, followed by 2,2,2-trifluoroethanol (1 mL). The mixture was heated in a Biotage microwave reactor for 30 minutes at 100° C. After cooling to room temperature, the mixture was diluted with methanol/dichloromethane and concentrated to dryness under reduced pressure. The residue was purified via prep HPLC (10-65% acetonitrile in water, 0.1% trifluoroacetic acid buffer) to furnish 5-(2-(4-(3-hydroxyoxetan-3-yl)phenyl)-1H-pyrrolo[2,3-b]pyridin-4-yl)-2-((tetrahydro-2H-pyran-4-yl)oxy)benzonitrile.

LCMS-ESI+ (m/z): [M+H]+ calcd for $C_{28}H_{25}N_3O_4$: 468.2. found: 468.2. ¹H NMR (400 MHz, DMSO-$d_6$) δ 12.45 (s, 1H), 8.33 (d, J=5.0 Hz, 1H), 8.21 (d, J=2.3 Hz, 1H), 8.16 (dd, J=8.8, 2.4 Hz, 1H), 8.08 (d, J=8.4 Hz, 2H), 7.73 (m, 2H), 7.59 (d, J=8.9 Hz, 1H), 7.30 (d, J=5.1 Hz, 1H), 7.24 (d, J=2.0 Hz, 1H), 4.98 (tt, J=8.0, 4.0 Hz, 1H), 4.84 (d, J=6.5 Hz, 2H), 4.77 (d, J=6.5 Hz, 2H), 3.94 (m, 2H), 3.62 (m, 2H), 2.10 (m, 2H), 1.76 (m, 2H).

Example 9: 5-(2-(1-(azetidin-3-yl)-1H-pyrazol-4-yl)-1H-pyrrolo[2,3-b]pyridin-4-yl)-2-((tetrahydro-2H-pyran-4-yl)oxy)benzonitrile

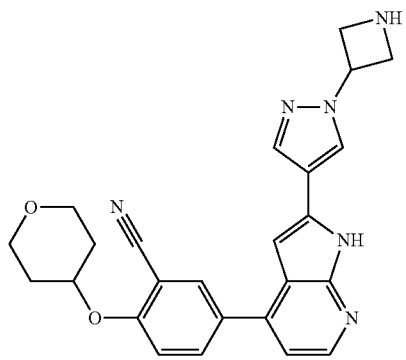 [SMILES: N#Cc1cc(-c2ccnc3[nH]c(-c4cnn(C5CNC5)c4)cc23)ccc1OC1CCOCC1]

Step 1: Preparation of tert-butyl 3-(4-(4-(3-cyano-4-((tetrahydro-2H-pyran-4-yl)oxy)phenyl)-1-(phenylsulfonyl)-1H-pyrrolo[2,3-b]pyridin-2-yl)-1H-pyrazol-1-yl)azetidine-1-carboxylate A mixture of 5-(2-iodo-1-(phenylsulfonyl)-1H-pyrrolo[2,3-b]pyridin-4-yl)-2-((tetrahydro-2H-pyran-4-yl)oxy)benzonitrile (0.29 g, 0.50 mmol), tert-butyl 3-(4-(4,4,5,5-tetramethyl-1,3,2-dioxaborolan-2-yl)-1H-pyrazol-1-yl)azetidine-1-carboxylate (PharmaBlock, 0.21 g, 0.60 mmol), Cesium carbonate (0.41 g, 1.2 mmol), and bis(triphenylphosphine) palladium(II) dichloride (0.02 g, 0.03 mmol) in 1,4-dioxanes (3 mL) and water (1 mL), was heated overnight on an 85° C. block. After cooling to room temperature, the mixture was purified via flash chromatography on silica gel to give the desired material. LCMS-ESI+ (m/z): [M+H]+ calcd for $C_{36}H_{36}N_6O_6S$: 681.2. found: 681.2.

Step 2: Preparation of tert-butyl 3-(4-(4-(3-cyano-4-((tetrahydro-2H-pyran-4-yl)oxy)phenyl)-1H-pyrrolo[2,3-b]pyridin-2-yl)-1H-pyrazol-1-yl)azetidine-1-carboxylate: tert-butyl 3-(4-(4-(3-cyano-4-((tetrahydro-2H-pyran-4-yl)oxy)phenyl)-1-(phenylsulfonyl)-1H-pyrrolo[2,3-b]pyridin-2-yl)-1H-pyrazol-1-yl)azetidine-1-carboxylate (0.28 g, 0.42 mmol) was taken up in 1,4-dioxanes (2 mL) in a microwave vial. Cesium carbonate (0.41 g, 1.3 mmol) was added, followed by 2,2,2-trifluoroethanol (1 mL). The mixture was heated in a Biotage microwave reactor for 30 minutes at 100° C. After cooling to room temperature, the mixture was diluted with dichloromethane, filtered, and concentrated to dryness under reduced pressure to give the crude intermediate. LCMS-ESI+ (m/z): [M+H]+ calcd for $C_{30}H_{32}N_6O_4$: 541.3. found: 541.2.

Step 3: Preparation of 5-(2-(1-(azetidin-3-yl)-1H-pyrazol-4-yl)-1H-pyrrolo[2,3-b]pyridin-4-yl)-2-((tetrahydro-2H-pyran-4-yl)oxy)benzonitrile: The concentrated residue (0.42 mmol assumed) was taken up in dichloromethane (5 mL) and treated with trifluoroacetic acid (2.6 mL). The mixture was allowed to stand overnight at room temperature before being concentrated and purified via flash chromatography on silica gel to furnish 5-(2-(1-(azetidin-3-yl)-1H-pyrazol-4-yl)-1H-pyrrolo[2,3-b]pyridin-4-yl)-2-((tetrahydro-2H-pyran-4-yl)oxy)benzonitrile. LCMS-ESI+ (m/z): [M+H]+ calcd for $C_{25}H_{24}N_6O_2$: 441.2. found: 441.2.

¹H NMR (400 MHz, DMSO-$d_6$) δ 12.18 (s, 1H), 8.46 (s, 1H), 8.26 (s, 1H), 8.25 (d, J=4.8 Hz, 1H), 8.15 (d, J=2.3 Hz, 1H), 8.09 (dd, J=8.8, 2.3 Hz, 1H), 7.58 (d, J=8.9 Hz, 1H), 7.22 (d, J=5.0 Hz, 1H), 6.89 (s, 1H), 5.39 (p, J=7.4 Hz, 1H), 4.97 (tt, J=8.0, 4.0 Hz, 1H), 4.22 (d, J=7.4 Hz, 4H), 3.93 (m, 2H), 3.61 (m, 2H), 2.09 (m, 2H), 1.76 (m, 2H).

Example 10: 5-(2-(1-(piperidin-4-yl)-1H-pyrazol-4-yl)-1H-pyrrolo[2,3-b]pyridin-4-yl)-2-((tetrahydro-2H-pyran-4-yl)oxy)benzonitrile

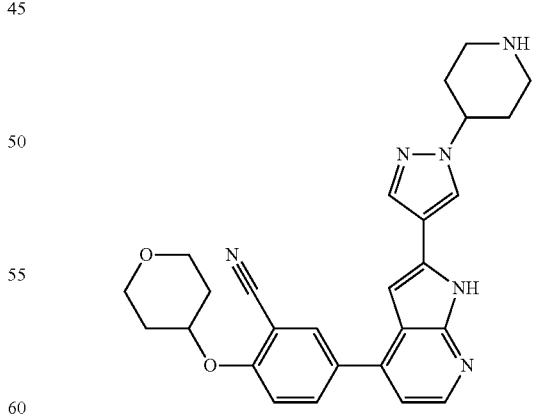

Step 1: Preparation of tert-butyl 4-(4-(4-(3-cyano-4-((tetrahydro-2H-pyran-4-yl)oxy)phenyl)-1-(phenylsulfonyl)-1H-pyrrolo[2,3-b]pyridin-2-yl)-1H-pyrazol-1-yl)piperidine-1-carboxylate A mixture of 5-(2-iodo-1-(phenylsulfonyl)-1H-pyrrolo[2,3-b]pyridin-4-yl)-2-((tetrahydro-2H-pyran-4-yl)oxy)benzonitrile (0.27 g, 0.46 mmol), tert-butyl 4-(4-(4,4,5,5-tetramethyl-1,3,2-dioxaborolan-2-yl)-1H-pyrazol-1-yl)piperidine-1-carboxylate (Combi-Blocks, 0.21 g, 0.55 mmol), Cesium carbonate (0.38 g, 1.2 mmol), and bis(triphenylphosphine)palladium(II) dichloride (0.02 g, 0.03 mmol) in 1,4-dioxanes (3 mL) and water (1 mL), was heated overnight on an 85° C. block. After cooling to room temperature, the mixture was purified via flash chromatography on silica gel to give the desired material. LCMS-ESI$^+$ (m/z): [M+H]$^+$ calcd for $C_{38}H_{40}N_6O_6S$: 709.3. found: 709.2.

Step 2: Preparation of tert-butyl 4-(4-(4-(3-cyano-4-((tetrahydro-2H-pyran-4-yl)oxy)phenyl)-1H-pyrrolo[2,3-b]pyridin-2-yl)-1H-pyrazol-1-yl)piperidine-1-carboxylate: tert-butyl 4-(4-(4-(3-cyano-4-((tetrahydro-2H-pyran-4-yl)oxy)phenyl)-1-(phenylsulfonyl)-1H-pyrrolo[2,3-b]pyridin-2-yl)-1H-pyrazol-1-yl)piperidine-1-carboxylate (0.29 g, 0.41 mmol) was taken up in 1,4-dioxanes (2 mL) in a microwave vial. Cesium carbonate (0.40 g, 1.2 mmol) was added, followed by 2,2,2-trifluoroethanol (1 mL). The mixture was heated in a Biotage microwave reactor for 30 minutes at 100° C. After cooling to room temperature, the mixture was diluted with dichloromethane, filtered, and concentrated to dryness under reduced pressure to give the crude intermediate. LCMS-ESI$^+$ (m/z): [M+H]$^+$ calcd for $C_{32}H_{36}N_6O_4$: 569.3. found: 569.4.

Step 3: Preparation of 5-(2-(1-(piperidin-4-yl)-1H-pyrazol-4-yl)-1H-pyrrolo[2,3-b]pyridin-4-yl)-2-((tetrahydro-2H-pyran-4-yl)oxy)benzonitrile: The concentrated residue (0.41 mmol assumed) was taken up in dichloromethane (5 mL) and treated with trifluoroacetic acid (2.5 mL). The mixture was allowed to stand overnight at room temperature before being concentrated and purified via flash chromatography on silica gel to furnish 5-(2-(1-(piperidin-4-yl)-1H-pyrazol-4-yl)-1H-pyrrolo[2,3-b]pyridin-4-yl)-2-((tetrahydro-2H-pyran-4-yl)oxy)benzonitrile.

LCMS-ESI$^+$ (m/z): [M+H]$^+$ calcd for $C_{27}H_{28}N_6O_2$: 469.2. found: 469.2. $^1$H NMR (400 MHz, DMSO-d$_6$) 12.16 (s, 1H), 8.40 (s, 1H), 8.24 (d, J=5.0 Hz, 1H), 8.16 (s, 1H), 8.14 (d, J=2.3 Hz, 1H), 8.09 (dd, J=8.9, 2.3 Hz, 1H), 7.58 (d, J=8.9 Hz, 1H), 7.22 (d, J=5.0 Hz, 1H), 6.89 (d, J=2.0 Hz, 1H), 4.97 (tt, J=8.0, 3.9 Hz, 1H), 4.59 (tt, J=10.9, 4.2 Hz, 1H), 3.93 (m, 2H), 3.61 (m, 2H), 3.48 (m, 2H), 3.17 (m, 2H), 2.29 (m, 2H), 2.24-2.04 (m, 4H), 1.76 (m, 2H).

Example 11: 5-(2-(6-aminopyridin-3-yl)-1H-pyrrolo[2,3-b]pyridin-4-yl)-2-((tetrahydro-2H-pyran-4-yl)oxy)benzonitrile

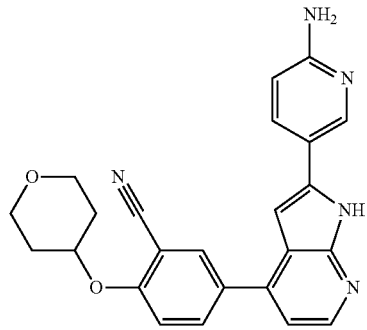 [SMILES: N#Cc1cc(-c2ccnc3[nH]c(-c4ccc(N)nc4)cc23)ccc1OC1CCOCC1]

Step 1: Preparation of 5-(2-(6-aminopyridin-3-yl)-1-(phenylsulfonyl)-1H-pyrrolo[2,3-b]pyridin-4-yl)-2-((tetrahydro-2H-pyran-4-yl)oxy)benzonitrile: A mixture of 5-(2-iodo-1-(phenylsulfonyl)-1H-pyrrolo[2,3-b]pyridin-4-yl)-2-((tetrahydro-2H-pyran-4-yl)oxy)benzonitrile (0.33 g, 0.56 mmol), 2-Aminopyridine-5-boronic acid pinacol ester (0.15 g, 0.68 mmol), Cesium carbonate (0.46 g, 1.4 mmol) and bis(triphenylphosphine)palladium(II) dichloride (0.02 g, 0.03 mmol) in 1,4-dioxanes (3 mL) and water (1 mL), was heated for one hour on an 85° C. block. After cooling to room temperature, the mixture was purified via flash chromatography on silica gel to give the desired material. LCMS-ESI$^+$ (m/z): [M+H]$^+$ calcd for $C_{30}H_{25}N_5O_4S$: 552.2. found: 552.2.

Step 2: Preparation of 5-(2-(6-aminopyridin-3-yl)-1H-pyrrolo[2,3-b]pyridin-4-yl)-2-((tetrahydro-2H-pyran-4-yl)oxy)benzonitrile: 5-(2-(6-aminopyridin-3-yl)-1-(phenylsulfonyl)-1H-pyrrolo[2,3-b]pyridin-4-yl)-2-((tetrahydro-2H-pyran-4-yl)oxy)benzonitrile (0.38 g, 0.50 mmol) was taken up in 1,4-dioxanes (2 mL) in a microwave vial. Cesium carbonate (0.49 g, 1.5 mmol) was added, followed by 2,2,2-trifluoroethanol (1 mL). The mixture was heated in a Biotage microwave reactor for 30 minutes at 100° C. After cooling to room temperature, the mixture was diluted with methanol/dichloromethane and concentrated to dryness under reduced pressure. The residue was purified via prep HPLC (10-50% acetonitrile in water, 0.1% trifluoroacetic acid buffer) to furnish 5-(2-(6-aminopyridin-3-yl)-1H-pyrrolo[2,3-b]pyridin-4-yl)-2-((tetrahydro-2H-pyran-4-yl)oxy)benzonitrile.

LCMS-ESI$^+$ (m/z): [M+H]$^+$ calcd for $C_{24}H_{21}N_5O_2$: 412.2. found: 412.2. $^1$H NMR (400 MHz, DMSO-d$_6$) δ 12.42 (s, 1H), 8.56 (m, 2H), 8.34 (d, J=5.0 Hz, 1H), 8.20 (bs, 2H), 8.19 (d, J=2.3 Hz, 1H), 8.11 (dd, J=8.8, 2.3 Hz, 1H), 7.58 (d, J=9.0 Hz, 1H), 7.29 (d, J=5.0 Hz, 1H), 7.25 (s, 1H), 7.10 (m, 1H), 4.98 (tt, J=7.8, 3.8 Hz, 1H), 3.93 (m, 2H), 3.61 (m, 2H), 2.10 (m, 2H), 1.76 (m, 2H).

Example 12: 2-((3-methyloxetan-3-yl)methoxy)-5-(2-(4-morpholinophenyl)-1H-pyrrolo[2,3-b]pyridin-4-yl)benzonitrile

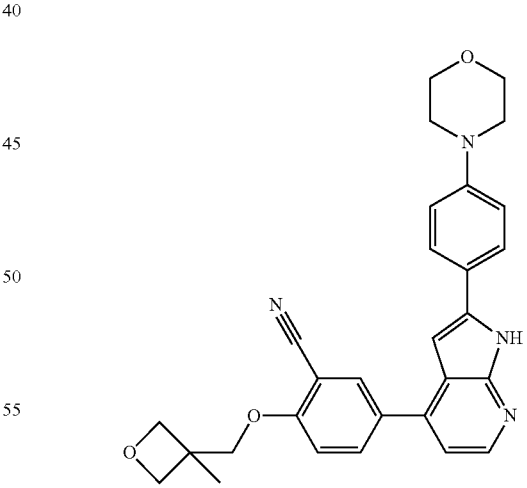

Step 1: Preparation of 5-bromo-2-((3-methyloxetan-3-yl)methoxy)benzonitrile: A solution of 3-methyl-3-oxetanemethanol (Aldrich, 2.0 g, 20 mmol) in N,N-dimethylformamide (40 mL) was stirred in an ice-water bath under an atmosphere of Argon. Sodium hydride (60% in mineral oil, 0.78 g, 20 mmol) was added in a single portion. Mixture was stirred at 0° C. for 10 minutes and then the cooling bath was removed. The mixture was stirred overnight at room temperature. To the mixture was added via syringe 5-bromo-2-fluorobenzonitrile (4.7 g, 24 mmol) as a solution in N,N-dimethylformamide (20 mL) at room temperature. Mixture was stirred for 8 hours at 50° C. block, and then allowed to cool to room temperature. Water was added and the resulting suspension was extracted three times with ethyl acetate. The combined extracts were washed once each with water and saturated aqueous sodium chloride solution, dried over anhydrous magnesium sulfate, filtered, and concentrated to dryness under reduced pressure. The crude material was purified via flash chromatography on silica gel to give the desired material. LCMS-ESI$^+$ (m/z): [M+H]$^+$ calcd for $C_{12}H_{12}BrNO_2$: 282.0. found: 281.9.

Step 2: Preparation of 2-((3-methyloxetan-3-yl)methoxy)-5-(4,4,5,5-tetramethyl-1,3,2-dioxaborolan-2-yl)benzonitrile: A mixture of 5-bromo-2-((3-methyloxetan-3-yl)methoxy)benzonitrile (0.17 g, 0.59 mmol), bis(pinacolato)diboron (0.19 g, 0.76 mmol), potassium acetate (0.17 g, 1.8 mmol), and [1,1'-bis(diphenylphosphino)ferrocene]dichloropalladium(II) complex with dichloromethane (0.02 g, 0.03 mmol) in 1,4-dioxane (3 mL) was heated for 30 minutes at 85° C. The analysis of an aliquot of reaction mixture by LC/MS confirmed the consumption of starting material and presence of the desired product. The reaction mixture was carried on without further purification. LCMS-ESI$^+$ (m/z): [M+H]$^+$ calcd for $C_{18}H_{24}BNO_4$: 330.2. found: 330.0.

Step 3: Preparation of 2-((3-methyloxetan-3-yl)methoxy)-5-(2-(4-morpholinophenyl)-1-(phenylsulfonyl)-1H-pyrrolo[2,3-b]pyridin-4-yl)benzonitrile: The reaction mixture containing 2-((3-methyloxetan-3-yl)methoxy)-5-(4,4,5,5-tetramethyl-1,3,2-dioxaborolan-2-yl)benzonitrile (0.59 mmol assumed) was charged with 4-(4-(4-bromo-1-(phenylsulfonyl)-1H-pyrrolo[2,3-b]pyridin-2-yl)phenyl)morpholine (0.07 g, 0.14 mmol), Cesium carbonate (0.14 g, 0.43 mmol), [1,1'-bis(diphenylphosphino)ferrocene]dichloropalladium(II) complex with dichloromethane (0.005 g, 0.007 mmol) and water (1 mL). The mixture was heated overnight on an 85° C. block. After cooling to room temperature, the mixture was purified via flash chromatography on silica gel to give the desired material. LCMS-ESI$^+$ (m/z): [M+H]$^+$ calcd for $C_{35}H_{32}N_4O_5S$: 621.2. found: 621.1.

Step 4: Preparation of 2-((3-methyloxetan-3-yl)methoxy)-5-(2-(4-morpholinophenyl)-1H-pyrrolo[2,3-b]pyridin-4-yl)benzonitrile: 2-((3-methyloxetan-3-yl)methoxy)-5-(2-(4-morpholinophenyl)-1-(phenylsulfonyl)-1H-pyrrolo[2,3-b]pyridin-4-yl)benzonitrile (0.09 g, 0.14 mmol) was taken up in 1,4-dioxanes (2 mL) in a microwave vial. Cesium carbonate (0.14 g, 0.43 mmol) was added, followed by 2,2,2-trifluoroethanol (1 mL). The mixture was heated in a Biotage microwave reactor for 30 minutes at 100° C. After cooling to room temperature, the mixture was diluted with methanol/dichloromethane and concentrated to dryness under reduced pressure. The residue was purified via prep HPLC (10-75% acetonitrile in water, 0.1% trifluoroacetic acid buffer) to furnish 2-((3-methyloxetan-3-yl)methoxy)-5-(2-(4-morpholinophenyl)-1H-pyrrolo[2,3-b]pyridin-4-yl)benzonitrile.

LCMS-ESI$^+$ (m/z): [M+H]$^+$ calcd for $C_{29}H_{28}N_4O_3$: 481.2. found: 481.3. $^1$H NMR (400 MHz, DMSO-$d_6$) δ 12.33 (s, 1H), 8.27 (d, J=5.1 Hz, 1H), 8.24-8.12 (m, 2H), 7.92 (d, J=8.8 Hz, 2H), 7.54 (d, J=8.6 Hz, 1H), 7.28 (d, J=5.2 Hz, 1H), 7.07 (m, 3H), 4.60 (d, J=5.9 Hz, 2H), 4.40 (d, J=5.6 Hz, 2H), 4.39 (s, 2H), 3.80 (dd, J=6.1, 3.6 Hz, 4H), 3.24 (dd, J=5.9, 3.7 Hz, 4H), 1.48 (s, 3H).

Example 13: 5-(2-(4-morpholinophenyl)-1H-pyrrolo[2,3-b]pyridin-4-yl)-2-(2-oxopyrrolidin-1-yl)benzonitrile

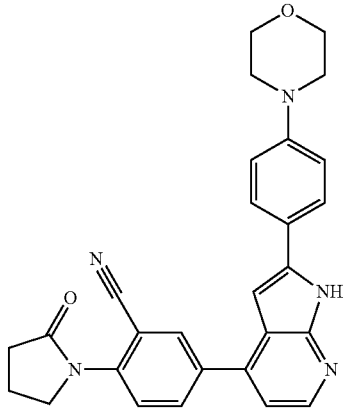 [SMILES: N#Cc1cc(-c2ccnc3[nH]c(-c4ccc(N5CCOCC5)cc4)cc23)ccc1N1CCCC1=O]

Step 1: Preparation of N-(4-bromo-2-cyanophenyl)-4-chlorobutanamide: To a solution of 2-amino-5-bromobenzonitrile (1.5 g, 7.6 mmol) in pyridine (15 mL) was added dropwise 4-chlorobutanoyl chloride (1.0 mL, 9.1 mmol) at 0° C. The ice-water bath was allowed to regain room temperature and was stirred overnight. The reaction mixture was poured into water and extracted with ethyl acetate. The organic layers were combined, and the mixture was washed with saturated aqueous sodium chloride solution, dried over anhydrous magnesium sulfate, filtered, and concentrated to dryness under reduced pressure. The residue was analyzed by LC/MS, confirming the presence of N-(4-bromo-2-cyanophenyl)-4-chlorobutanamide, and carried forward without further purification.

LCMS-ESI$^+$ (m/z): [M+H]$^+$ calcd for $C_{11}H_{10}BrClN_2O$: 303.0. found: 303.0.

Step 2: Preparation of 5-bromo-2-(2-oxopyrrolidin-1-yl)benzonitrile: To a solution of crude N-(4-bromo-2-cyanophenyl)-4-chlorobutanamide (7.6 mmol assumed) in 2-methyltetrahydrofuran was added sodium hydride (60% in mineral oil, 0.61 g, 15 mmol) at 0° C., and the mixture was warmed to room temperature and stirred overnight. The reaction was quenched with glacial acetic acid (approximately 5 mL) and poured into water. The mixture was extracted with ethyl acetate. The organic layers were combined, and mixture was washed with saturated aqueous sodium chloride solution and dried over anhydrous magnesium sulfate. The solvent was evaporated under reduced pressure. Residue was purified via flash chromatography on silica gel to give the desired product.

LCMS-ESI$^+$ (m/z): [M+H]$^+$ calcd for $C_{11}H_9BrN_2O$: 265.0. found: 265.1.

Step 3: Preparation of (3-cyano-4-(2-oxopyrrolidin-1-yl)phenyl)boronic acid: A mixture of 5-bromo-2-(2-oxopyrrolidin-1-yl)benzonitrile (0.19 g, 0.70 mmol), bis(pinacolato)diboron (0.36 g, 1.4 mmol), potassium acetate (0.21 g, 2.1 mmol), and [1,1'-bis(diphenylphosphino)ferrocene]dichloropalladium(II) complex with dichloromethane (0.03 g, 0.04 mmol) in 1,4-dioxane (3 mL) was heated overnight at 85° C. The analysis of an aliquot of reaction mixture by LC/MS confirmed the consumption of starting material and presence of the desired product. The reaction mixture was carried on without further purification. LCMS-ESI$^+$ (m/z): [M+H]$^+$ calcd for $C_{11}H_{11}BN_2O_3$: 231.1. found: 231.4.

Step 4: Preparation of 5-(2-(4-morpholinophenyl)-1-(phenylsulfonyl)-1H-pyrrolo[2,3-b]pyridin-4-yl)-2-(2-oxopyrrolidin-1-yl)benzonitrile: To a mixture of 4-(4-(4-bromo-1-(phenylsulfonyl)-1H-pyrrolo[2,3-b]pyridin-2-yl)phenyl)morpholine (0.09 g, 0.17 mmol) and [1,1'-bis(diphenylphosphino)ferrocene]dichloropalladium(II) complex with dichloromethane (0.006 g, 0.009 mmol) was added the reaction mixture containing (3-cyano-4-(2-oxopyrrolidin-1-yl)phenyl)boronic acid (0.70 mmol assumed), 1,4-dioxane rinsate (3 mL), and 2M aqueous sodium carbonate solution (2 mL). The mixture was heated overnight for three hours at 90° C. After cooling to room temperature, the mixture was purified via flash chromatography on silica gel to give the desired material.

LCMS-ESI+ (m/z): [M+H]+ calcd for $C_{34}H_{29}N_5O_4S$: 604.2. found: 604.2.

Step 5: Preparation of 5-(2-(4-morpholinophenyl)-1H-pyrrolo[2,3-b]pyridin-4-yl)-2-(2-oxopyrrolidin-1-yl)benzonitrile: 5-(2-(4-morpholinophenyl)-1-(phenylsulfonyl)-1H-pyrrolo[2,3-b]pyridin-4-yl)-2-(2-oxopyrrolidin-1-yl)benzonitrile (0.08 g, 0.14 mmol) was taken up in 1,4-dioxanes (2 mL) in a microwave vial. Cesium carbonate (0.13 g, 0.41 mmol) was added, followed by 2,2,2-trifluoroethanol (1 mL). The mixture was heated in a Biotage microwave reactor for 30 minutes at 100° C. After cooling to room temperature, the mixture was diluted with methanol/dichloromethane and concentrated to dryness under reduced pressure. The residue was purified via flash chromatography on silica gel to afford the desired material. $^1$H NMR (400 MHz, DMSO-$d_6$) δ 12.37 (s, 1H), 8.32-8.30 (m, 2H), 8.26 (dd, J=8.4, 2.2 Hz, 1H), 7.94 (d, J=8.8 Hz, 2H), 7.77 (d, J=8.5 Hz, 1H), 7.34 (d, J=5.1 Hz, 1H), 7.11-7.07 (m, 3H), 3.99 (t, J=6.9 Hz, 2H), 3.80 (m, 4H), 3.25 (m, 4H), 2.58 (m, 2H), 2.24 (m, 2H). LCMS-ESI+ (m/z): [M+H]+ calcd for $C_{28}H_{25}N_5O_2$: 464.2. found: 464.4.

Example 14: Preparation of (R)-5-(2-(4-morpholinophenyl)-1H-pyrrolo[2,3-b]pyridin-4-yl)-2-(pyrrolidin-3-yloxy)benzonitrile

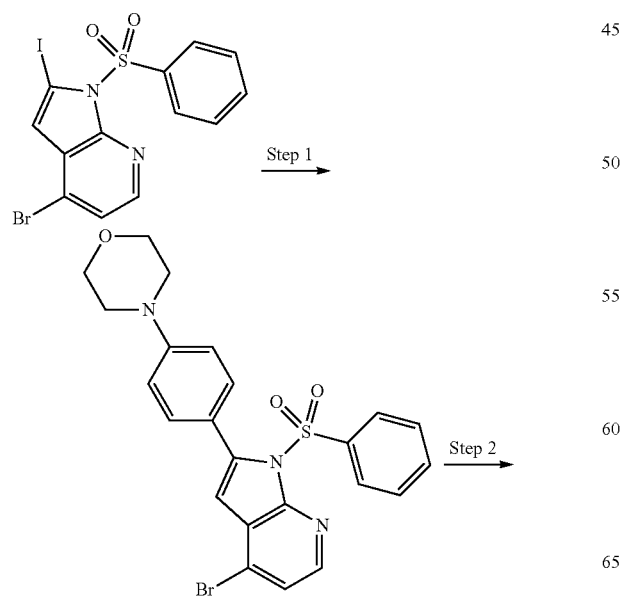

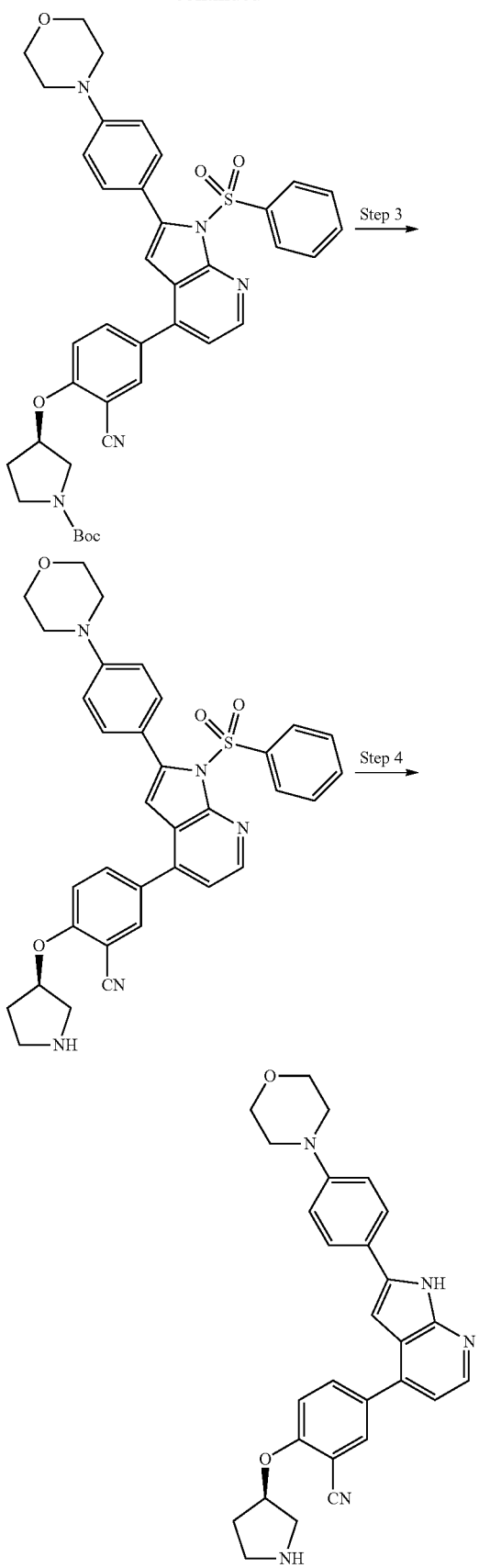

Step 1: 4-bromo-2-iodo-1-(phenylsulfonyl)-1H-pyrrolo[2,3-b]pyridine (4.50 g, 9.72 mmol) and 4-(4-(4,4,5,5-tetramethyl-1,3,2-dioxaborolan-2-yl)phenyl)morpholine (2.81 g, 9.72 mmol) were taken up in 55 mL dioxane in a 250 mL rbf. The flask was evacuated and stirred vigorously under vacuum for 5 min. Bis(triphenylphosphine)palladium(II) dichloride (479 mg, 0.68 mmol) and 1N NaHCO$_3$ (19.4 mL, 19.4 mmol) and the reaction heated to 80° C. for 6 hrs. The reaction was then cooled to rt and diluted with 100 mL EtOAc. After 5 min vigorous stirring the mixture was filtered thru Celite® and extracted with EtOAc. The combined organic layers were washed with saturated aqueous sodium chloride solution, dried, filtered and concentrated under reduced pressure. The residue was purified by flash column chromatography on silica gel to afford 4-(4-(4-bromo-1-(phenylsulfonyl)-1H-pyrrolo[2,3-b]pyridin-2-yl)phenyl)morpholine.

LCMS-ESI$^+$ (m/z): [M+H]$^+$ calcd for C$_{23}$H$_{20}$BrN$_3$O$_3$S: 498.0, 500.0. found: 498.1, 500.0.

Step 2: 4-(4-(4-bromo-1-(phenylsulfonyl)-1H-pyrrolo[2,3-b]pyridin-2-yl)phenyl)morpholine (1.028 g, 2.06 mmol) and (R)-tert-butyl 3-(2-cyano-4-(4,4,5,5-tetramethyl-1,3,2-dioxaborolan-2-yl)phenoxy)pyrrolidine-1-carboxylate (0.94 g, 2.27 mmol) were taken up in 20 mL MeCN and treated with [1,1'-Bis(diphenylphosphino)ferrocene]dichloropalladium(II), complex with CH$_2$Cl$_2$ (0.14 g, 0.17 mmol), 2N Na$_2$CO$_3$ (3.44 mL, 6.88 mmol) and 1N NaHCO$_3$ (0.859 mL, 0.86 mmol). The reaction mixture was heated at 85° C. for 1 h. After cooling to room temperature, the mixture was poured into a saturated aqueous solution of NaHCO$_3$ and extracted with ethyl acetate. The combined organic layers were washed with saturated aqueous sodium chloride solution, dried, filtered and concentrated under reduced pressure. The residue was purified by flash column chromatography on silica gel to afford (R)-tert-butyl 3-(2-cyano-4-(2-(4-morpholinophenyl)-1-(phenylsulfonyl)-1H-pyrrolo[2,3-b]pyridin-4-yl)phenoxy)pyrrolidine-1-carboxylate. LCMS-ESI$^+$ (m/z): [M+H]$^+$ calcd for C$_{39}$H$_{39}$N$_5$O$_6$S: 706.3. found: 706.6.

Step 3: A solution of (R)-tert-butyl 3-(2-cyano-4-(2-(4-morpholinophenyl)-1-(phenylsulfonyl)-1H-pyrrolo[2,3-b]pyridin-4-yl)phenoxy)pyrrolidine-1-carboxylate (162 mg, 0.234 mmol) in 10 mL CH$_2$Cl$_2$ and 10 mL TFA. After stirring 30 min at rt the reaction was concentrated under reduced pressure and the residue partitioned between EtOAc and 2N Na$_2$CO$_3$. The combined organic layers were washed with saturated aqueous sodium chloride solution, dried, filtered and concentrated under reduced pressure to provide (R)-5-(2-(4-morpholinophenyl)-1-(phenylsulfonyl)-1H-pyrrolo[2,3-b]pyridin-4-yl)-2-(pyrrolidin-3-yloxy)benzonitrile. LCMS-ESI$^+$ (m/z): [M+H]$^+$ calcd for C$_{34}$H$_{31}$N$_5$O$_4$S: 606.2. found: 606.5.

Step 4: In an appropriate sized microwave vial, a solution of (R)-5-(2-(4-morpholinophenyl)-1-(phenylsulfonyl)-1H-pyrrolo[2,3-b]pyridin-4-yl)-2-(pyrrolidin-3-yloxy)benzonitrile (0.14 g, 0.23 mmol) and 2N LiOH (0.29 mL, 0.58 mmol) in 2 mL THF was heated at 100° C. for 2 h). The cooled reaction mixture was diluted with DCM, dried with sodium sulfate, filtered and concentrated under reduced pressure. The residue was purified via prep HPLC (2-95% acetonitrile in water, 0.1% trifluoroacetic acid buffer) to give (R)-5-(2-(4-morpholinophenyl)-1H-pyrrolo[2,3-b]pyridin-4-yl)-2-(pyrrolidin-3-yloxy)benzonitrile as the trifluoroacetic acid salt. 1H NMR (400 MHz, DMSO-d$_6$) δ 12.18 (s, 1H), 8.19 (d, J=2.4 Hz, 1H), 8.21 (d, J=4.8 Hz, 1H), 8.13 (dd, J=8.8, 2.4 Hz, 1H), 7.85 (d, J=8.5 Hz, 2H), 7.46 (d, J=8.9 Hz, 1H), 7.19 (d, J=5.1 Hz, 1H), 7.01 (d, J=8.8 Hz, 2H), 6.96 (m, 1H), 5.41 (s, 1H), 3.74 (t, J=4.8 Hz, 4H), 3.18 (t, J=4.8 Hz, 4H), 3.01 (m, 1H), 2.89 (m, 2H), 2.71 (m, 1H), 2.27 (m, 2H). LCMS-ESI$^+$ (m/z): [M+H]$^+$ calcd for C$_{28}$H$_{27}$N$_5$O$_2$: 466.2. found: 466.4.

Example 15: Preparation of (R)-2-((1-(2-hydroxyacetyl)pyrrolidin-3-yl)oxy)-5-(2-(4-morpholinophenyl)-1H-pyrrolo[2,3-b]pyridin-4-yl)benzonitrile

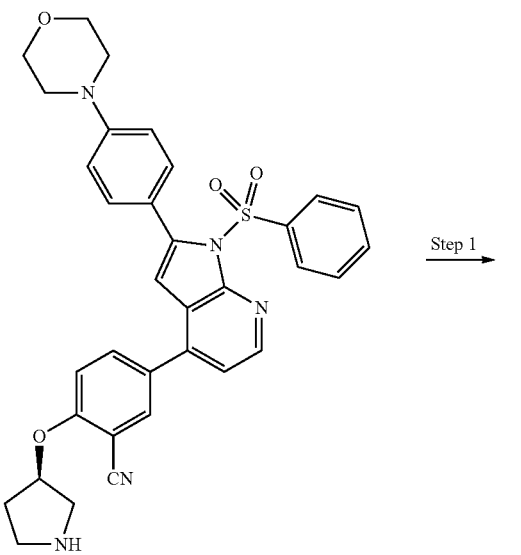

Step 1

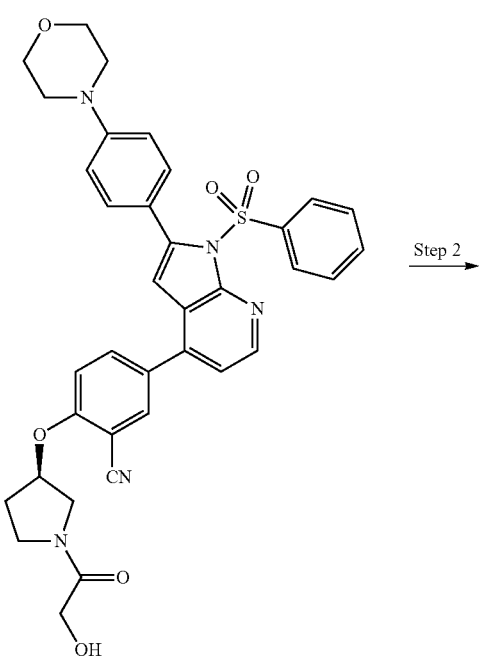

Step 2

-continued

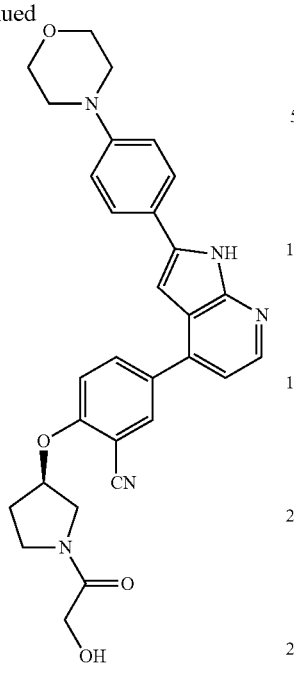

Example 16: Preparation of (R)-2-((1-(2-cyanoacetyl)pyrrolidin-3-yl)oxy)-5-(2-(4-morpholinophenyl)-1H-pyrrolo[2,3-b]pyridin-4-yl)benzonitrile

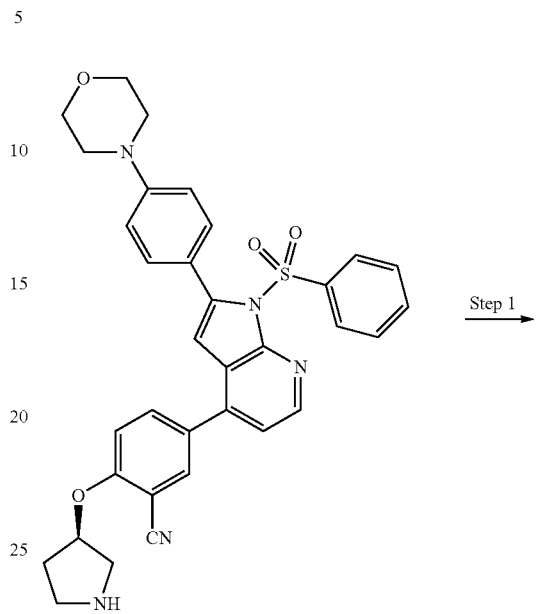

Step 1: To an appropriate sized microwave vial, 6-(R)-5-(2-(4-morpholinophenyl)-1-(phenylsulfonyl)-1H-pyrrolo[2,3-b]pyridin-4-yl)-2-(pyrrolidin-3-yloxy)benzonitrile (100 mg, 0.165 mmol), hydroxyacetic acid (38 mg, 0.495 mmol), HATU (75 mg, 0.198 mmol), TEA (0.046 mL, 0.33 mmol) and DMF (2 mL) were added. The mixture was stirred at rt for 16 h. The mixture was poured into water and extracted with ethyl acetate. The combined organic layers were washed with 1N citric acid, sodium bicarbonate and saturated aqueous sodium chloride solution, dried, filtered and concentrated under reduced pressure to provide (R)-2-((1-(2-hydroxyacetyl)pyrrolidin-3-yl)oxy)-5-(2-(4-morpholinophenyl)-1-(phenylsulfonyl)-1H-pyrrolo[2,3-b]pyridin-4-yl)benzonitrile. LCMS-ESI+ (m/z): [M+H]+ calcd for $C_{36}H_{33}N_5O_6S$: 664.2. found: 664.5.

Step 2: To an appropriate sized microwave vial, a mixture of (R)-2-((1-(2-hydroxyacetyl)pyrrolidin-3-yl)oxy)-5-(2-(4-morpholinophenyl)-1-(phenylsulfonyl)-1H-pyrrolo[2,3-b]pyridin-4-yl)benzonitrile (107 mg, 0.16 mmol) and 2N NaOH (0.161 mL, 0.322 mmol) in THF (2 mL) and MeOH (0.5 mL) was heated at 60° C. for 18 h. The reaction was concentrated under reduced pressure. The residue was purified via prep HPLC (2-95% acetonitrile in water, 0.1% trifluoroacetic acid buffer) to isolate (R)-2-((1-(2-hydroxyacetyl)pyrrolidin-3-yl)oxy)-5-(2-(4-morpholinophenyl)-1H-pyrrolo[2,3-b]pyridin-4-yl)benzonitrile as the trifluoroacetic acid salt. $^1$H NMR (400 MHz, DMSO-d6) δ 12.17 (s, 1H), 8.20 (d, J=5.2 Hz, 1H), 8.15-8.10 (m, 2H), 7.90-7.82 (m, 2H), 7.49 (d, J=8.8 Hz, 1H), 7.19 (d, J=5.1 Hz, 1H), 7.05-6.93 (m, 3H), 5.39 (s, 1H, rotamer 1), 5.32 (s, 1H, rotamer 2), 4.13-3.93 (m, 2H), 3.81 (dd, J=12.1, 4.4 Hz, 1H), 3.74 (t, J=4.9 Hz, 4H), 3.70-3.57 (m, 1H), 3.40-3.43 (m, 2H), 3.18 (t, J=4.9 Hz, 4H), 2.27 (m, 1H), 2.16 (m, H). LCMS-ESI+ (m/z): [M+H]+ calcd for $C_{30}H_{29}N_5O_4$: 524.2. found: 524.3.

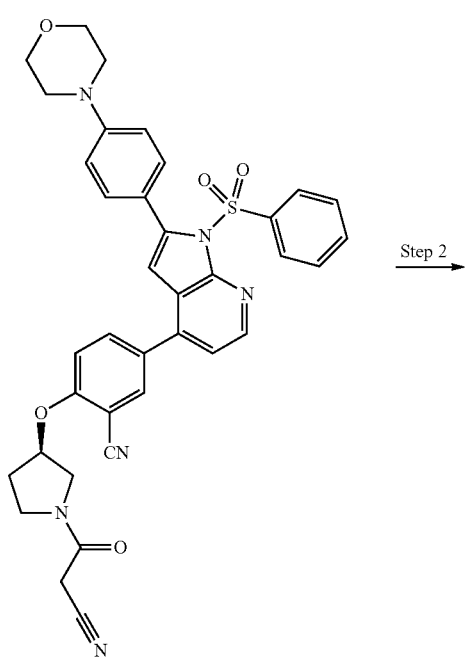

164

Example 17: Preparation of (R)-tert-butyl 3-(2-cyano-4-(2-(4-morpholinophenyl)-1H-pyrrolo[2,3-b]pyridin-4-yl)phenoxy)pyrrolidine-1-carboxylate

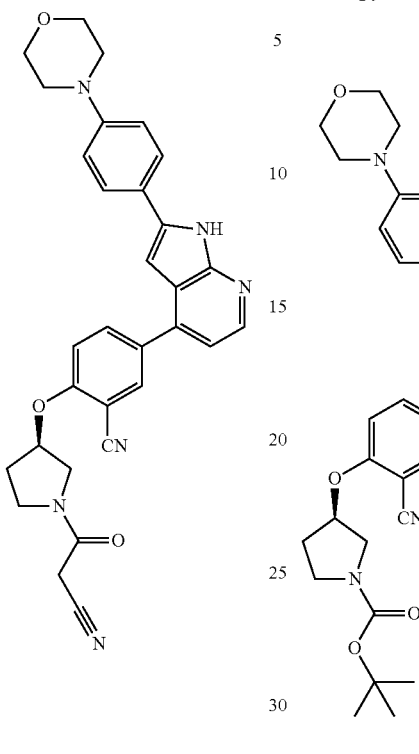

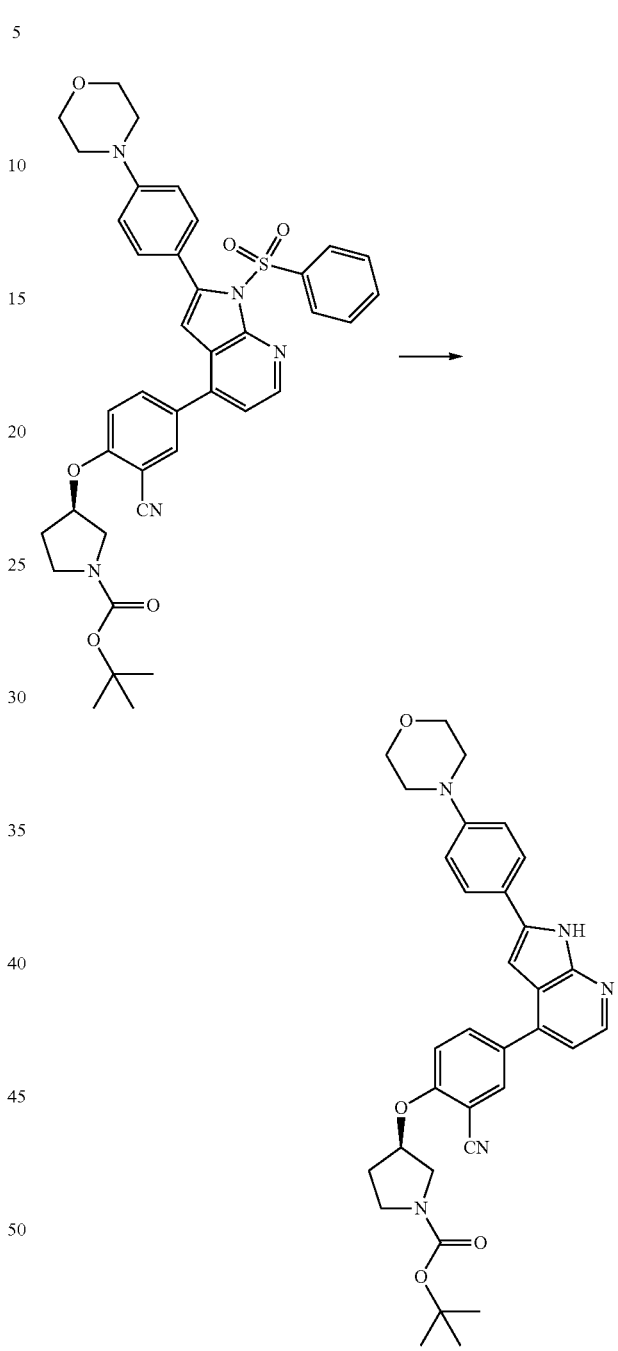

Step 1: (R)-2-((1-(2-cyanoacetyl)pyrrolidin-3-yl)oxy)-5-(2-(4-morpholinophenyl)-1-(phenylsulfonyl)-1H-pyrrolo[2,3-b]pyridin-4-yl)benzonitrile was prepared by the same procedure used for Example 15-step 1, by substituting α-cyanoacetic acid for α-hydroxyacetic acid. LCMS-ESI⁺ (m/z): [M+H]⁺ calcd for $C_{37}H_{32}N_6O_5S$: 673.2. found: 673.5.

Step 2: Following similar procedure to synthesize Example 15-step 2, (R)-2-((1-(2-cyanoacetyl)pyrrolidin-3-yl)oxy)-5-(2-(4-morpholinophenyl)-1H-pyrrolo[2,3-b]pyridin-4-yl)benzonitrile was prepared. ¹H NMR (400 MHz, DMSO-d6) δ 8.21 (d, 5.2 Hz, 1H), 8.17-8.10 (m, 2H), 7.86 (dd, J=8.8, 2.4 Hz, 1H), 7.48 (dd, J=8.8, 2.4 Hz, 1H), 7.21 (dd, J=5.2, 1.6 Hz, 1H), 7.01 (d, J=8.8 Hz, 2H), 6.98-7.01 (m, 1H), 3.90-3.83 (m, 1H), 3.74 (m, 4H), 3.70-3.38 (m, 3H), 3.18 (m, 4H), 2.34-2.14 (m, 2H). LCMS-ESI⁺ (m/z): [M+H]⁺ calcd for $C_{31}H_{28}N_6O_3$: 533.2. found: 533.3.

To an appropriate sized microwave vial, (R)-tert-butyl 3-(2-cyano-4-(2-(4-morpholinophenyl)-1-(phenylsulfonyl)-1H-pyrrolo[2,3-b]pyridin-4-yl)phenoxy)pyrrolidine-1-carboxylate (101 mg, 0.143 mmol), 1N NaOH (172 µL, 0.172 mmol) and EtOH were added. The mixture was heated to 120° C. for 0.5 hrs. After cooling to room temperature, the mixture was filtered and concentrated under reduced pressure. The residue was purified by RP HPLC (2-95% acetonitrile in water, 0.1% trifluoroacetic acid buffer) to provide (R)-tert-butyl-3-(2-cyano-4-(2-(4-morpholinophenyl)-1H-pyrrolo[2,3-b]pyridin-4-yl)phenoxy)pyrrolidine-1-carboxylate. $^1$H NMR (400 MHz, DMSO-d$_6$) δ 12.21 (s, 1H), 8.20 (d, J=5.1 Hz, 1H), 8.17-8.07 (m, 2H), 7.86 (d, J=8.4 Hz, 2H), 7.47 (d, J=8.8 Hz, 1H), 7.20 (d, J=5.1 Hz, 1H), 7.04-6.96 (m, 3H), 5.29 (m, 1H), 3.78-3.70 (m, 4H), 3.66-3.35 (m, 4H), 3.18 (t, J=4.9 Hz, 4H), 2.25-2.14 (m, 2H), 1.40 (s, 9H).

LCMS-ESI$^+$ (m/z): [M+H]$^+$ calcd for C$_{33}$H$_{35}$N$_5$O$_4$: 566.3. found: 566.3.

Example 18: Preparation of 5-(2-(4-morpholinophenyl)-1H-pyrrolo[2,3-b]pyridin-4-yl)-2-(piperidin-4-yloxy)benzonitrile

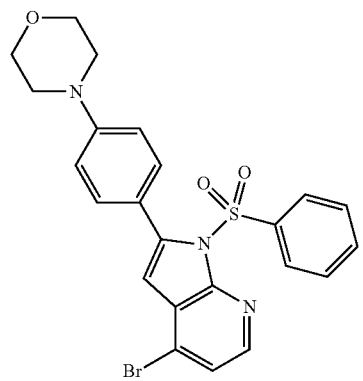

Step 1

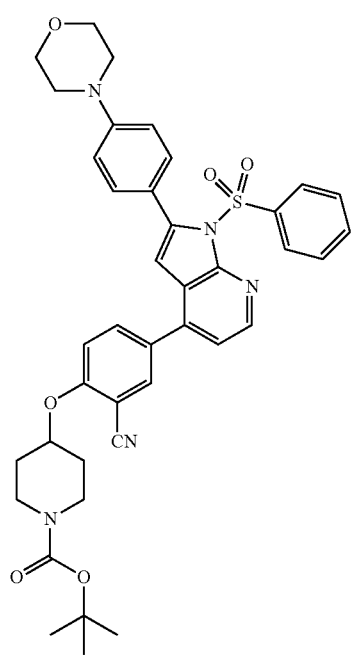

Step 2

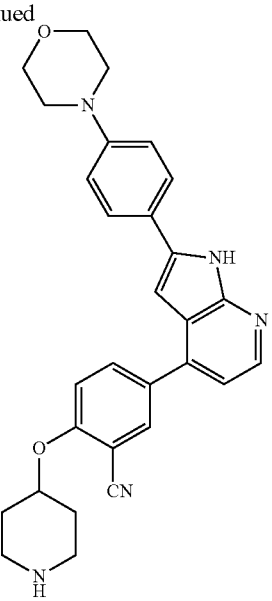

Step 1: tert-butyl 4-(2-cyano-4-(2-(4-morpholinophenyl)-1-(phenylsulfonyl)-1H-pyrrolo[2,3-b]pyridin-4-yl)phenoxy)piperidine-1-carboxylate was prepared using the same procedure reported in Example 14-step 2 by substituting tert-butyl 4-(2-cyano-4-(4,4,5,5-tetramethyl-1,3,2-dioxaborolan-2-yl)phenoxy)piperidine-1-carboxylate. LCMS-ESI$^+$ (m/z): [M+H]$^+$ calcd for C$_{40}$H$_{41}$N$_5$O$_6$S: 720.3. found: 720.5.

Step 2: To an appropriate sized microwave vial, a mixture of tert-butyl 4-(2-cyano-4-(2-(4-morpholinophenyl)-1-(phenylsulfonyl)-1H-pyrrolo[2,3-b]pyridin-4-yl)phenoxy)piperidine-1-carboxylate (150 mg, 0.21 mmol) and Cs$_2$CO$_3$ (204 mg, 0.63 mmol) in THF (0.5 mL) and trifluoroethanol (0.2 mL) was heated at 100° C. for 0.5 hrs. The reaction was diluted with DCM and filtered. The residue was acidified with several drops of 10% TFA in DCM and concentrated under reduced pressure. The residue was purified via prep HPLC (2-95% acetonitrile in water, 0.1% trifluoroacetic acid buffer) to isolate 5-(2-(4-morpholinophenyl)-1H-pyrrolo[2,3-b]pyridin-4-yl)-2-(piperidin-4-yloxy)benzonitrile as the trifluoroacetic acid salt. $^1$H NMR (400 MHz, DMSO-d$_6$) δ 12.18 (s, 1H), 8.20 (d, J=5.2 Hz, 1H), 8.16 (d, J=2.4 Hz, 1H), 8.11 (dd, J=8.8, 2.4 Hz, 2H), 7.53 (d, J=8.9 Hz, 3H), 7.18 (d, J=5.2 Hz, 3H), 7.01 (d, J=8.8 Hz, 2H), 6.97 (d, J=2 Hz, 1H), 4.99 (dq, J=7.2, 3.6 Hz, 1H), 3.74 (t, J=5.2 Hz, 4H), 3.31-3.20 (m, 4H), 3.18 (t, J=5.2 Hz, 4H), (s, 4H), 2.20-2.11 (m, 2H), 2.00-1.96 (m, 2H). LCMS-ESI$^+$ (m/z): [M+H]$^+$ calcd for C$_{29}$H$_{29}$N$_5$O$_2$: 480.2. found: 480.3.

Example 19: Preparation of 2-((1-(2-hydroxyacetyl)piperidin-4-yl)oxy)-5-(2-(4-morpholinophenyl)-1H-pyrrolo[2,3-b]pyridin-4-yl)benzonitrile

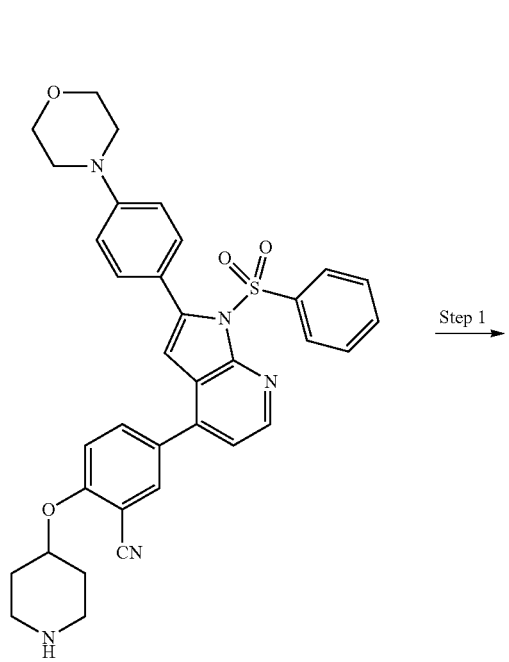

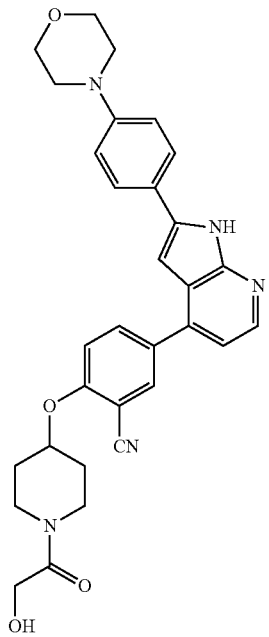

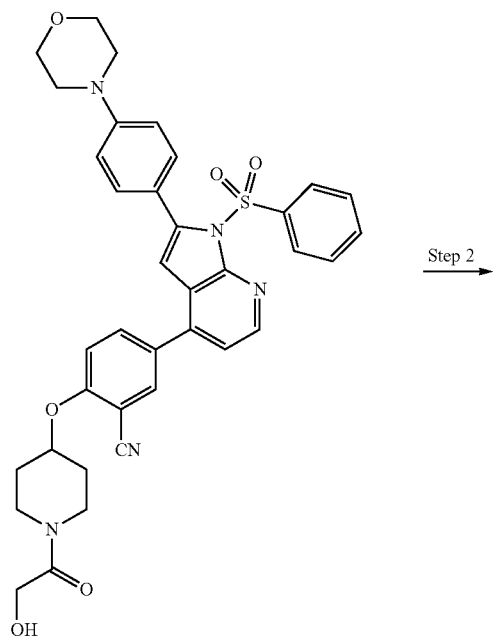

Step 1: 2-((1-(2-hydroxyacetyl)piperidin-4-yl)oxy)-5-(2-(4-morpholinophenyl)-1-(phenylsulfonyl)-1H-pyrrolo[2,3-b]pyridin-4-yl)benzonitrile was prepared using the same procedure reported in Example 15-step 1. LCMS-ESI$^+$ (m/z): [M+H]$^+$ calcd for $C_{37}H_{35}N_5O_6S$: 678.2. found: 678.5.

Step 2: 2-((1-(2-hydroxyacetyl)piperidin-4-yl)oxy)-5-(2-(4-morpholinophenyl)-1H-pyrrolo[2,3-b]pyridin-4-yl)benzonitrile was prepared using the procedure reported in Example 18-step 2. $^1$H NMR (400 MHz, DMSO-d$_6$) δ 12.24 (s, 1H), 8.21 (dd, J=5.2, 0.8 Hz, 1H), 8.15 (d, J=2.4 Hz, 1H), 8.12 (dd, J=8.8, 2.4 Hz, 1H), 7.86 (d, J=8.6 Hz, 2H), 7.53 (d, J=8.8 Hz, 1H), 7.21 (d, J=5.0 Hz, 1H), 7.05-6.98 (m, 3H), 5.01-4.95 (m, 1H), 4.12 (s, 2H), 3.70-3.77 (m, 5H), 3.61-3.45 (m, 2H), 3.40-3.31 (m, 1H), 3.18 (t, J=4.8 Hz, 4H), a.64-1.81 (m, 2H), 2.06-1.93 (m, 2H). LCMS-ESI$^+$ (m/z): [M+H]$^+$ calcd for $C_{31}H_{31}N_5O_4$: 538.2. found: 538.5.

Example 20: Preparation of 2-((1-(2-cyanoacetyl)piperidin-4-yl)oxy)-5-(2-(4-morpholinophenyl)-1H-pyrrolo[2,3-b]pyridin-4-yl)benzonitrile

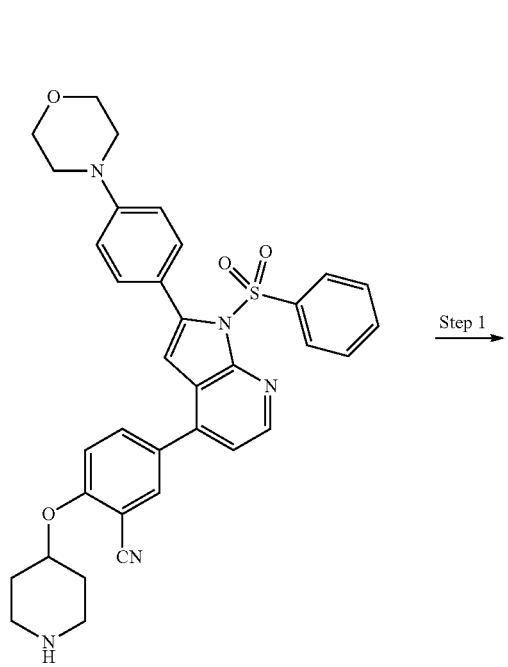

Step 1 →

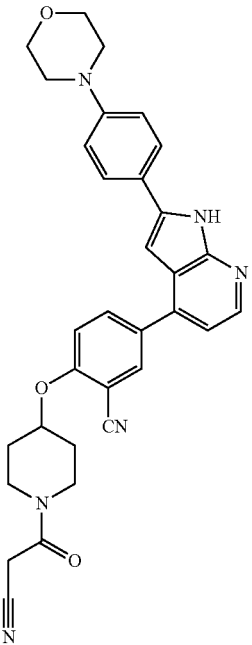

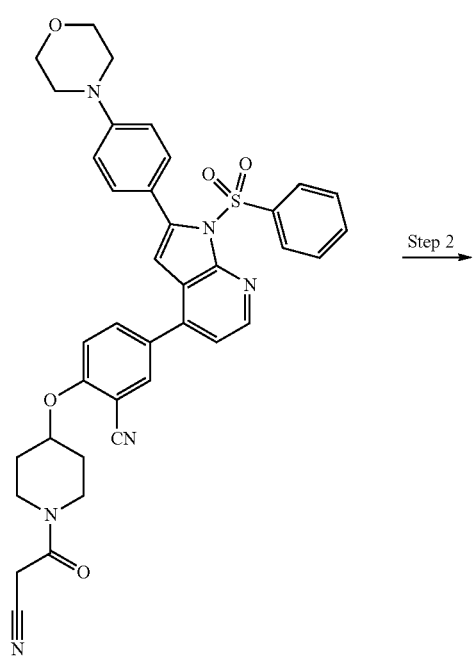

Step 2 →

Step 1: 2-((1-(2-cyanoacetyl)piperidin-4-yl)oxy)-5-(2-(4-morpholinophenyl)-1-(phenylsulfonyl)-1H-pyrrolo[2,3-b]pyridin-4-yl)benzonitrile was prepared using similar procedure reported in Example 15-step 1, substituting α-cyanoacetic acid for α-hydroxyacetic acid. LCMS-ESI+ (m/z): [M+H]+ calcd for $C_{38}H_{34}N_6O_5S$: 687.2. found: 687.5.

Step 2: 2-((1-(2-cyanoacetyl)piperidin-4-yl)oxy)-5-(2-(4-morpholinophenyl)-1H-pyrrolo[2,3-b]pyridin-4-yl)benzonitrile was prepared using the same procedure reported in Example 18 step 2. $^1$H NMR (400 MHz, DMSO-$d_6$) δ 12.24 (s, 1H), 8.21 (d, J=5.1 Hz, 1H), 8.15 (d, J=2.4 Hz, 1H), 8.10 (dd, J=8.8, 2.4 Hz, 1H), 7.86 (d, J=8.6 Hz, 2H), 7.53 (d, J=8.9 Hz, 1H), 7.24-7.18 (m, 1H), 7.04-6.98 (m, 3H), 5.02-4.95 (m, 1H), 4.09 (s, 2H), 3.74 (t, J=4.8 Hz, 4H), 3.72-3.64 (m, 1H), 3.62-3.47 (m, 2H), 3.43-3.33 (m, 1H), 3.18 (t, J=4.8 Hz, 4H), 2.09-2.01 (m, 1H), 2.01-1.93 (m, 1H), 1.86-1.76 (m, 1H), 1.76-1.65 (m, 1H). LCMS-ESI+ (m/z): [M+H]+ calcd for $C_{32}H_{30}N_6O_3$: 547.2. found: 547.7.

Example 21: Preparation of tert-butyl 4-(2-cyano-4-(2-(4-morpholinophenyl)-1H-pyrrolo[2,3-b]pyridin-4-yl)phenoxy)piperidine-1-carboxylate

Example 22: Preparation of (S)-5-(2-(4-morpholinophenyl)-1H-pyrrolo[2,3-b]pyridin-4-yl)-2-(pyrrolidin-3-yloxy)benzonitrile

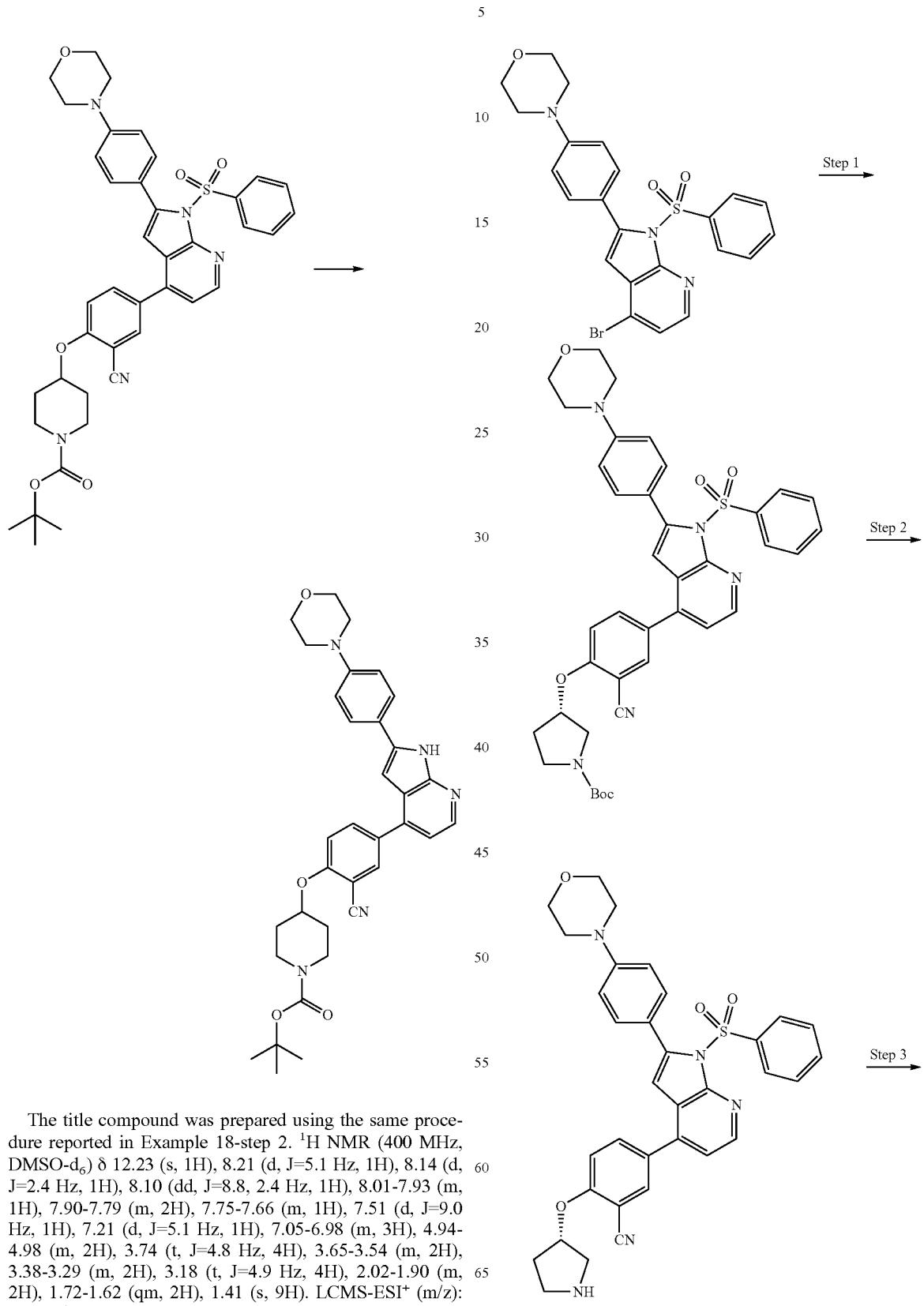

The title compound was prepared using the same procedure reported in Example 18-step 2. $^1$H NMR (400 MHz, DMSO-d$_6$) δ 12.23 (s, 1H), 8.21 (d, J=5.1 Hz, 1H), 8.14 (d, J=2.4 Hz, 1H), 8.10 (dd, J=8.8, 2.4 Hz, 1H), 8.01-7.93 (m, 1H), 7.90-7.79 (m, 2H), 7.75-7.66 (m, 1H), 7.51 (d, J=9.0 Hz, 1H), 7.21 (d, J=5.1 Hz, 1H), 7.05-6.98 (m, 3H), 4.94-4.98 (m, 2H), 3.74 (t, J=4.8 Hz, 4H), 3.65-3.54 (m, 2H), 3.38-3.29 (m, 2H), 3.18 (t, J=4.9 Hz, 4H), 2.02-1.90 (m, 2H), 1.72-1.62 (qm, 2H), 1.41 (s, 9H). LCMS-ESI$^+$ (m/z): [M+H]$^+$ calcd for C$_{34}$H$_{37}$N$_5$O$_4$: 580.3. found: 580.6.

Example 23: Preparation of (S)-2-((1-(2-hydroxyacetyl)pyrrolidin-3-yl)oxy)-5-(2-(4-morpholinophenyl)-1H-pyrrolo[2,3-b]pyridin-4-yl)benzonitrile

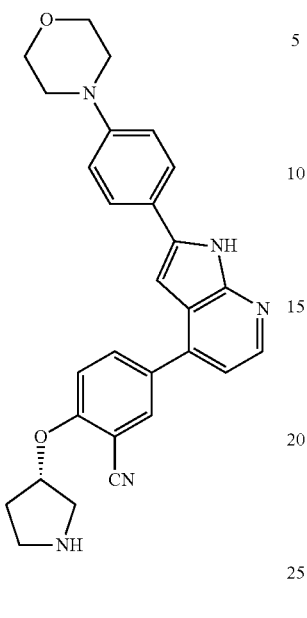

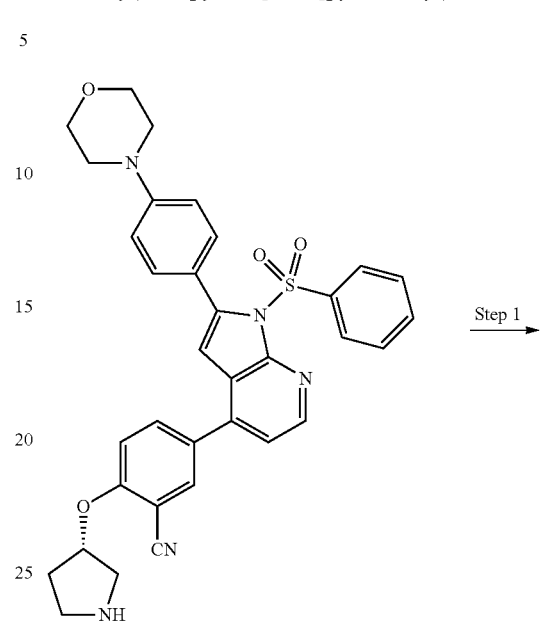

Step 1: (S)-tert-butyl 3-(2-cyano-4-(2-(4-morpholinophenyl)-1-(phenylsulfonyl)-1H-pyrrolo[2,3-b]pyridin-4-yl)phenoxy)pyrrolidine-1-carboxylate was prepared using the same procedure reported in Example 14-step 2. LCMS-ESI$^+$ (m/z): [M+H]$^+$ calcd for $C_{39}H_{39}N_5O_6S$: 706.3. found: 706.6.

Step 2: (S)-5-(2-(4-morpholinophenyl)-1-(phenylsulfonyl)-1H-pyrrolo[2,3-b]pyridin-4-yl)-2-(pyrrolidin-3-yloxy)benzonitrile was prepared using the procedure reported in Example 14 step-3. LCMS-ESI$^+$ (m/z): [M+H]$^+$ calcd for $C_{34}H_{31}N_5O_4S$: 606.2. found: 606.3.

Step 3: (S)-5-(2-(4-morpholinophenyl)-1H-pyrrolo[2,3-b]pyridin-4-yl)-2-(pyrrolidin-3-yloxy)benzonitrile was prepared using the same procedure reported in Example 18-step 2.

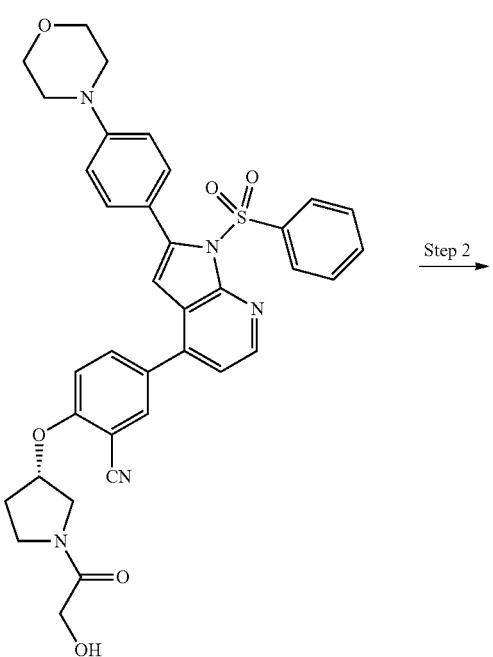

$^1$H NMR (400 MHz, DMSO-d$_6$) δ 8.10-8.06 (m, 3H), 7.87 (d, J=8.8 Hz, 2H), 7.34 (d, J=8.6 Hz, 1H), 6.96 (m, 3H), 6.86 (s, 1H), 5.09 (s, 1H), 3.74 (t, J=4.7 Hz, 3H), 3.57 (dd, J=12.2, 5.0 Hz, 1H), 3.41-3.19 (m, 4H), 3.18 (t, J=4.8 Hz, 4H), 2.07 (ddd, J=13.7, 9.1, 5.1 Hz, 1H), 1.99-1.91 (m, 1H). LCMS-ESI$^+$ (m/z): [M+H]$^+$ calcd for $C_{28}H_{27}N_5O_2$: 466.2. found: 466.3.

Example 24: Preparation of (S)-2-((1-(2-cyanoacetyl)pyrrolidin-3-yl)oxy)-5-(2-(4-morpholinophenyl)-1H-pyrrolo[2,3-b]pyridin-4-yl)benzonitrile

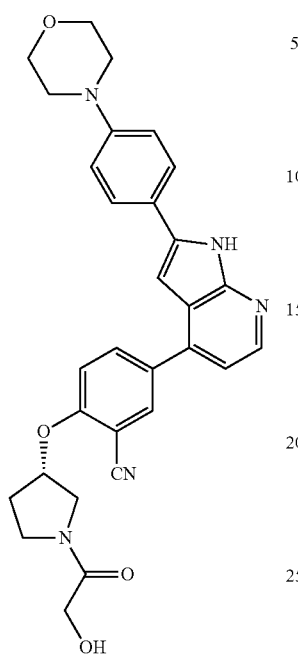

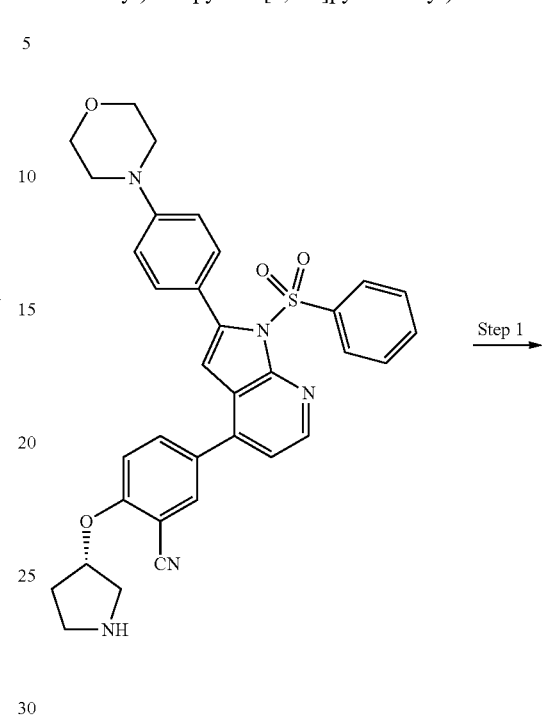

Step 1: (S)-2-((1-(2-hydroxyacetyl)pyrrolidin-3-yl)oxy)-5-(2-(4-morpholinophenyl)-1-(phenylsulfonyl)-1H-pyrrolo[2,3-b]pyridin-4-yl)benzonitrile was prepared using the same procedure reported in Example 15 step-1. LCMS-ESI+ (m/z): [M+H]+ calcd for $C_{36}H_{33}N_5O_6S$: 664.2. found: 664.5.

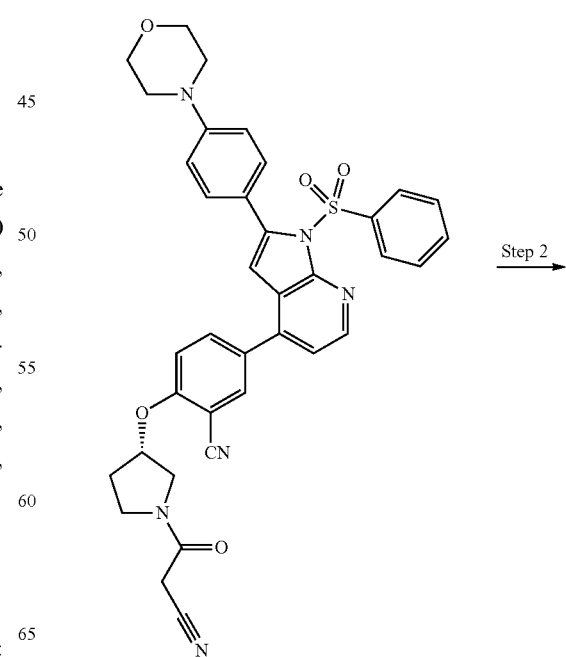

Step 2: The title compound was prepared using the same procedure reported for Example 18 step 2. $^1$H NMR (400 MHz, DMSO-$d_6$) δ 8.22-8.07 (m, 2H), 8.19 (d, J=4.8 Hz, 1H), 7.86 (d, J=8.8 Hz, 2H), 7.49 (d, J=8.7 Hz, 1H), 7.17 (d, J=5.1 Hz, 1H), 7.04-6.94 (m, 3H), 5.41-5.31 (m, 1H), 4.64 (td, J=5.7, 3.6 Hz, 1H), 4.05 (t, J=5.6 Hz, 1H), 4.01 (dd, J=9.6, 5.2 Hz, 1H), 3.81 (dd, J=12, 4.4 Hz, 1H), 3.79 (t, 4H), 3.69-3.58 (m, 2H), 3.55-3.40 (m, 2H), 3.18 (t, J=5.0 Hz, 8H), 2.33-2.24 (m, 1H), 2.20-2.08 (m, 1H).

LCMS-ESI+ (m/z): [M+H]+ calcd for $C_{30}H_{29}N_5O_4$: 524.2. found: 524.3.

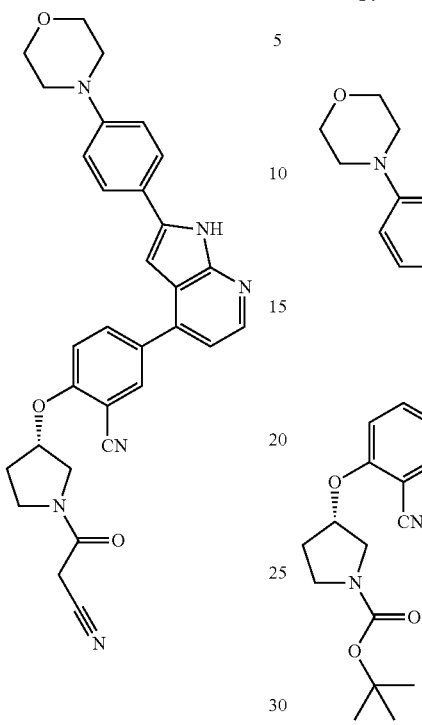

Step 1: (S)-2-((1-(2-cyanoacetyl)pyrrolidin-3-yl)oxy)-5-(2-(4-morpholinophenyl)-1-(phenylsulfonyl)-1H-pyrrolo[2,3-b]pyridin-4-yl)benzonitrile was prepared using the procedure reported in Example 15-step 1, substituting α-cyanoacetic acid for α-hydroxyacetic acid. LCMS-ESI+ (m/z): [M+H]+ calcd for $C_{37}H_{33}N_6O_5S$: 673.2. found: 673.7.

Step 2: The title compound was prepared using the same procedure reported in Example 18-Step 2. $^1$H NMR (400 MHz, DMSO-d$_6$) δ 8.22 (d, J=5.1 Hz, 1H), 8.19-8.06 (m, 2H), 7.86 (dd, J=8.9, 2.8 Hz, 2H), 7.48 (dd, J=8.9, 1.8 Hz, 1H), 7.23 (dd, J=5.2, 2.2 Hz, 1H), 7.09-6.95 (m, 3H), 5.43-5.28 (m, 1H), 4.02 (s, 2H), 3.90-3.83 (m, 1H), 3.79-3.71 (m, 4H), 3.81-3.35 (m, 3H), 3.19 (t, J=4.9 Hz, 4H), 2.44-2.04 (m, 2H). LCMS-ESI+ (m/z): [M+H]+ calcd for $C_{31}H_{28}N_6O_3$: 533.2. found: 533.4.

Example 25: Preparation of (S)-tert-butyl 3-(2-cyano-4-(2-(4-morpholinophenyl)-1H-pyrrolo[2,3-b]pyridin-4-yl)phenoxy)pyrrolidine-1-carboxylate

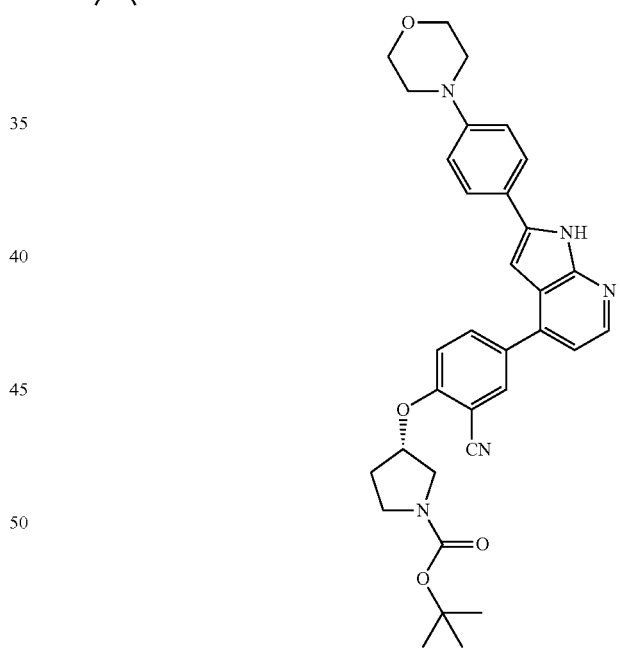

The title compound was prepared using the same procedure reported in Example 18-step 2.

$^1$H NMR (400 MHz, DMSO-d$_6$) δ 12.24 (s, 1H), 8.21 (d, J=5.1 Hz, 1H), 8.15 (s, 1H), 8.11 (dd, J=8.8, 2 Hz, 1H), 7.86 (d, J=6.8 Hz, 2H), 7.47 (d, J=8.8 Hz, 1H), 7.21 (d, J=5.1 Hz, 1H), 7.05-6.98 (m, 1H), 7.01 (d, J=6.8 Hz, 2H), 5.29 (s, 1H), 3.74 (m, 4H), 3.57-3.67 (m, 1H), 3.45-3.53 (m, 2H), 3.35-3.45 (m, 1H), 3.18 (m, 4H), 2.08-2.28 (m, 2H), 1.40 (s, 9H). LCMS-ESI+ (m/z): [M+H]+ calcd for $C_{33}H_{35}N_5O_4$: 566.3. found: 566.6.

Example 26: Preparation of 2-(2-(4-morpholinophenyl)-1H-pyrrolo[2,3-b]pyridin-4-yl)-5-((tetrahydro-2H-pyran-4-yl)oxy)isonicotinonitrile

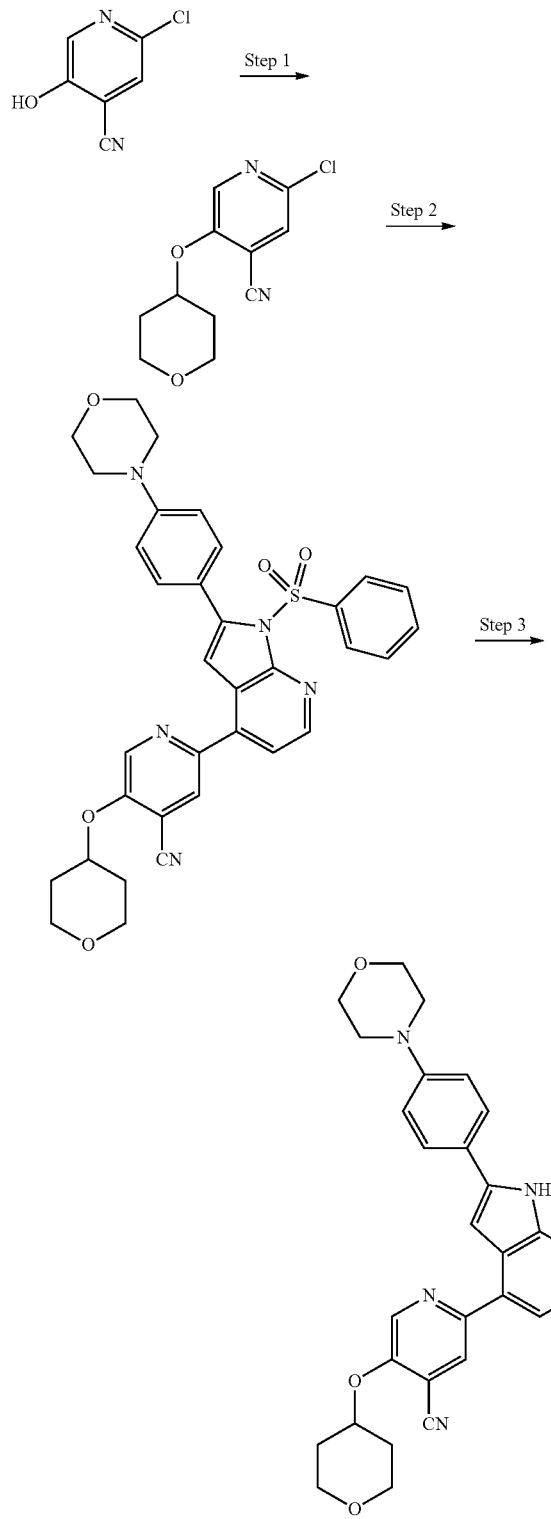

Step 1: 2-chloro-5-hydroxyisonicotinonitrile (WO201391096) (1.22 g, 7.89 mmol) weighed into 20 mL microwave vial and taken up in 10 mL DMF. While stirring vigorously, the solution was treated with 325-mesh $K_2CO_3$ (3.27 g, 24 mmol), tetrahydro-2H-pyran-4-yl 4-methylbenzenesulfonate (3.04 g, 12 mmol) and potassium iodide (0.13 g, 0.79 mmol). The mixture was stirred under $N_2$ in a reaction block at 100° C. for 1 h. After cooling to room temperature, the mixture was diluted with EtOAc and poured into water, then extracted with ethyl acetate. The combined organic layers were washed with saturated aqueous sodium chloride solution, dried, filtered and concentrated under reduced pressure. The residue was purified by flash column chromatography on silica gel to afford 2-chloro-5-((tetrahydro-2H-pyran-4-yl)oxy)isonicotinonitrile as a yellow solid. LCMS-ESI$^+$ (m/z): [M+H]$^+$ calcd for $C_{11}H_{11}ClN_2O_2$: 239.1. found: 238.9.

Step 2: 2-(2-(4-morpholinophenyl)-1-(phenylsulfonyl)-1H-pyrrolo[2,3-b]pyridin-4-yl)-5-((tetrahydro-2H-pyran-4-yl)oxy)isonicotinonitrile was prepared from 2-chloro-5-((tetrahydro-2H-pyran-4-yl)oxy)isonicotinonitrile using the method reported for Example 14-step 2, by substituting 4-(4-(1-(phenylsulfonyl)-4-(4,4,5,5-tetramethyl-1,3,2-dioxaborolan-2-yl)-1H-pyrrolo[2,3-b]pyridin-2-yl)phenyl)morpholine for (R)-tert-butyl-3-(2-cyano-4-(4,4,5,5-tetramethyl-1,3,2-dioxaborolan-2-yl)phenoxy)pyrrolidine-1-carboxylate. LCMS-ESI$^+$ (m/z): [M+H]$^+$ calcd for $C_{34}H_{31}N_5O_5S$: 622.2. found: 622.50.

Step 3: 2-(2-(4-morpholinophenyl)-1H-pyrrolo[2,3-b]pyridin-4-yl)-5-((tetrahydro-2H-pyran-4-yl)oxy)isonicotinonitrile was prepared using the same procedure reported in Example 18-step 2. $^1$H NMR (400 MHz, DMSO-d$_6$) δ 12.13 (d, J=2.3 Hz, 1H), 9.01 (s, 1H), 8.49 (d, J=0.7 Hz, 1H), 8.22 (d, J=5.1 Hz, 1H), 7.85 (d, J=8.8 Hz, 2H), 7.57 (d, J=5.1 Hz, 1H), 7.38 (d, J=2.1 Hz, 1H), 7.11-6.95 (m, 2H), 5.09 (m, 1H), 3.99-3.83 (m, 2H), 3.74 (dd, J=6.1, 3.6 Hz, 4H), 3.66-3.51 (m, 3H), 3.19 (dd, J=6.1, 3.7 Hz, 4H), 2.24-2.03 (m, 2H), 1.73 (dtd, J=12.7, 8.5, 3.9 Hz, 2H). LCMS-ESI$^+$ (m/z): [M+H]$^+$ calcd for $C_{28}H_{27}N_5O_3$: 482.2. found: 482.0.

Example 27: Preparation of 2-(((3R)-1-(2-hydroxypropanoyl)pyrrolidin-3-yl)oxy)-5-(2-(4-morpholinophenyl)-1H-pyrrolo[2,3-b]pyridin-4-yl)benzonitrile

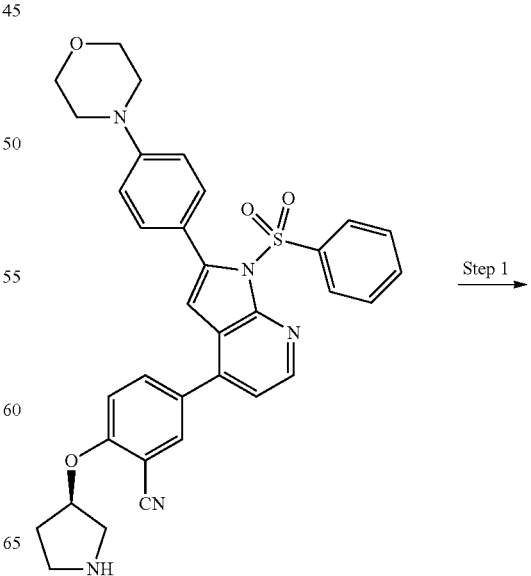

-continued

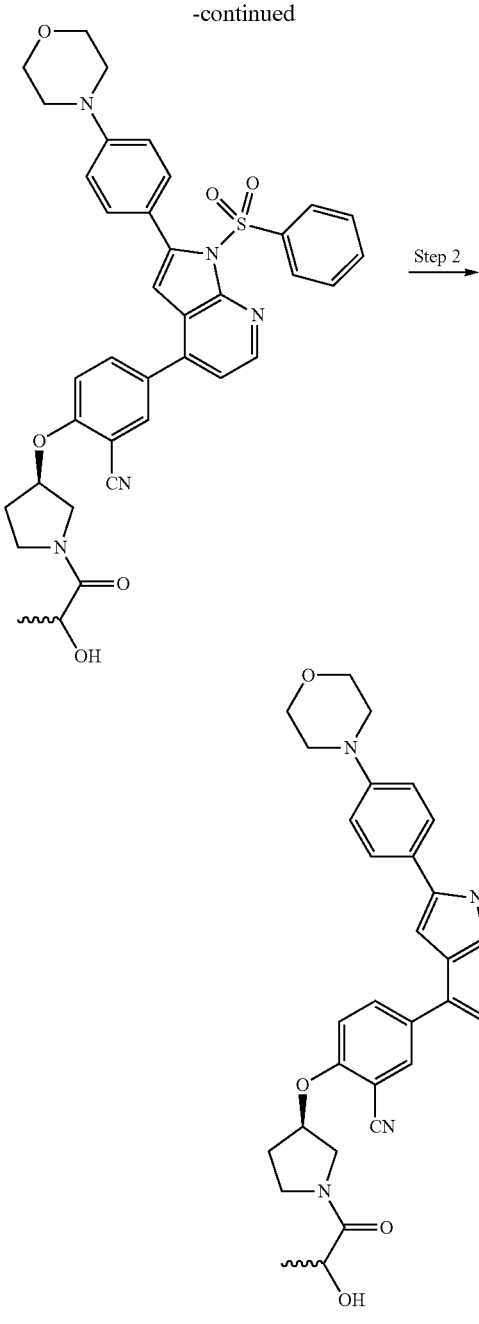

Step 2

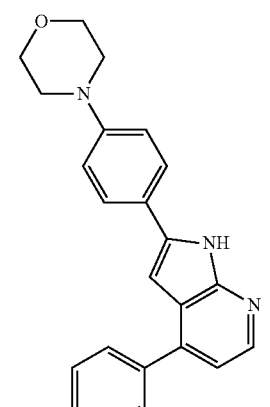

Step 1: 2-(((3R)-1-(2-hydroxypropanoyl)pyrrolidin-3-yl)oxy)-5-(2-(4-morpholinophenyl)-1-(phenylsulfonyl)-1H-pyrrolo[2,3-b]pyridin-4-yl)benzonitrile was prepared using the same procedure reported in Example 15-step 1, substituting L-lactic acid for α-hydroxyacetic acid. LCMS-ESI⁺ (m/z): [M+H]⁺ calcd for $C_{37}H_{35}N_5O_6S$: 678.2. found: 678.1.

Step 2: 2-(((3R)-1-(2-hydroxypropanoyl)pyrrolidin-3-yl)oxy)-5-(2-(4-morpholinophenyl)-1H-pyrrolo[2,3-b]pyridin-4-yl)benzonitrile was prepared using the same procedure reported in Example 18-Step 2. ¹H NMR (400 MHz, DMSO-d₆) δ 8.23 (d, J=5.2 Hz, 1H), 8.19-8.08 (m, 2H), 7.87 (d, J=8.8 Hz, 2H), 7.51 (dd, J=8.9, 4.6 Hz, 1H), 7.26 (d, J=4.8 Hz, 1H), 7.11-6.93 (m, 3H), 5.36 (d, J=16.2 Hz, 1H), 4.33 (q, J=6.5 Hz, 1H-epimer A), 4.25 (q, J=6.7 Hz, 1H-epimer B), 3.99-3.80 (m, 1H), 3.70-3.40 (m, 6H), 3.28-3.07 (m, 4H), 2.38-2.05 (m, 2H), 1.20 (d, J=6.4 Hz, 3H-epimer A), 1.17 (d, J=6.8 Hz, 1H-epimer B). LCMS-ESI⁺ (m/z): [M+H]⁺ calcd for $C_{31}H_{31}N_5O_4$: 538.2. found: 538.3.

Example 28: Preparation of 2-amino-5-(2-(4-morpholinophenyl)-1H-pyrrolo[2,3-b]pyridin-4-yl)benzonitrile

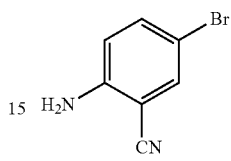

Step 1

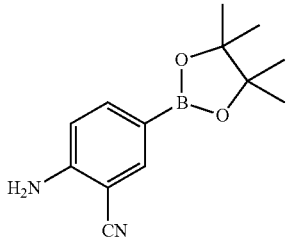

Step 2

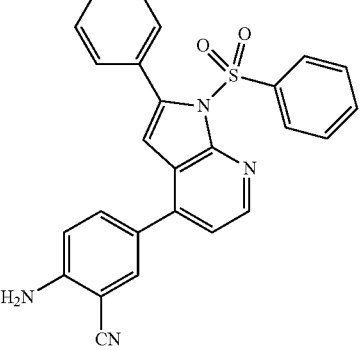

Step 3

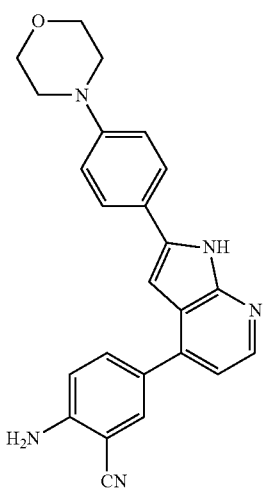

Step 1: To a solution of 2-amino-5-bromobenzonitrile (2.5 g, 12.7 mmol) in-dioxane (12 mL), bis(pinacolato)diborane (1.95 g, 48.8 mmol), potassium acetate (4.5 g, 38.1 mmol), and [1,1'-Bis(diphenylphosphino)ferrocene]dichloropalladium(II), complex with dichloromethane (1.03 g, 1.27 mmol) were added. The resulting mixture was stirred for 1 hr at 80° C. The cooled reaction mixture was diluted with EtOAc, washed with $H_2O$ and saturated aqueous sodium chloride solution, dried ($Na_2SO_4$), filtered, and concentrated in vacuo. The residue was purified by column chromatography on silica gel (Hexanes/EtOAc) to afford 2-amino-5-(4,4,5,5-tetramethyl-1,3,2-dioxaborolan-2-yl)benzonitrile. LCMS-ESI$^+$ (m/z): [M+H]$^+$ calcd for $C_{13}H_{17}BN_2O_2$: 245.1. found: 245.1.

Step 2: 2-amino-5-(2-(4-morpholinophenyl)-1-(phenylsulfonyl)-1H-pyrrolo[2,3-b]pyridin-4-yl)benzonitrile was prepared using the same procedure reported in Example 14-step 2. LCMS-ESI$^+$ (m/z): [M+H]$^+$ calcd for $C_{30}H_{25}N_5O_3S$: 536.2. found: 536.2.

Step 3: 2-amino-5-(2-(4-morpholinophenyl)-1H-pyrrolo[2,3-b]pyridin-4-yl)benzonitrile was prepared using the same procedure reported in Example 18-step 2.

$^1$H NMR (400 MHz, DMSO-d$_6$) δ 12.35 (s, 1H), 8.17 (d, J=5.4 Hz, 1H), 7.94-7.76 (m, 4H), 7.21 (d, J=5.4 Hz, 1H), 7.15-6.89 (m, 4H), 3.74 (dd, J=5.8, 3.9 Hz, 4H), 3.26-3.11 (m, 4H). LCMS-ESI$^+$ (m/z): [M+H]$^+$ calcd for $C_{24}H_{21}N_5O$: 396.2. found: 396.3.

Example 29: Preparation of 5-(2-(4-morpholinophenyl)-1H-pyrrolo[2,3-b]pyridin-4-yl)-2-((tetrahydro-2H-pyran-4-yl)oxy)nicotinonitrile

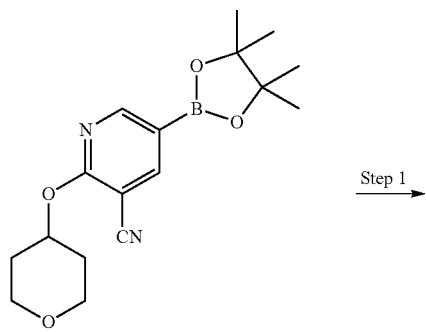

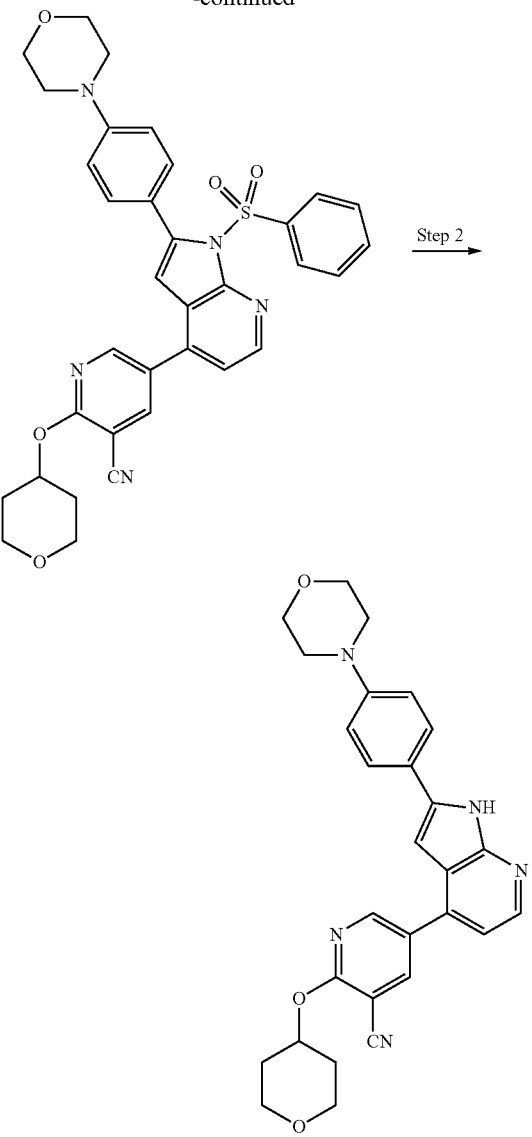

Step 1: 5-(2-(4-morpholinophenyl)-1-(phenylsulfonyl)-1H-pyrrolo[2,3-b]pyridin-4-yl)-2-((tetrahydro-2H-pyran-4-yl)oxy)nicotinonitrile was prepared using the same procedure reported in Example 14-step 2. LCMS-ESI$^+$ (m/z): [M+H]$^+$ calcd for $C_{34}H_{31}N_5O_5S$: 622.2. found: 622.2.

Step 2: 5-(2-(4-morpholinophenyl)-1H-pyrrolo[2,3-b]pyridin-4-yl)-2-((tetrahydro-2H-pyran-4-yl)oxy)nicotinonitrile was prepared using the same procedure reported in Example 18-step 2. $^1$H NMR (400 MHz, DMSO-d$_6$) δ 8.90 (d, J=2.5 Hz, 1H), 8.68 (d, J=2.5 Hz, 1H), 8.23 (d, J=5.1 Hz, 1H), 7.89 (d, J=8.8 Hz, 2H), 7.87-7.82 (m, 1H), 7.26 (dd, J=6.5, 5.1 Hz, 1H), 7.08 (d, J=2.0 Hz, 1H), 7.02 (d, J=8.8 Hz, 2H), 5.43 (m, 1H), 3.89 (dt, J=11.3, 4.6 Hz, 2H), 3.56 (ddd, J=11.7, 8.7, 3.0 Hz, 2H), 3.19 (t, J=4.9 Hz, 4H), 2.08 (dq, J=13.2, 3.8 Hz, 2H), 1.76 (dtd, J=12.8, 8.7, 4.0 Hz, 2H). LCMS-ESI$^+$ (m/z): [M+H]$^+$ calcd for $C_{28}H_{27}N_5O_3$: 482.2. found: 482.2.

Example 30: Preparation of (R)-2-((1-(2-(dimethyl-amino)acetyl)pyrrolidin-3-yl)oxy)-5-(2-(4-morpholinophenyl)-1H-pyrrolo[2,3-b]pyridin-4-yl)benzonitrile

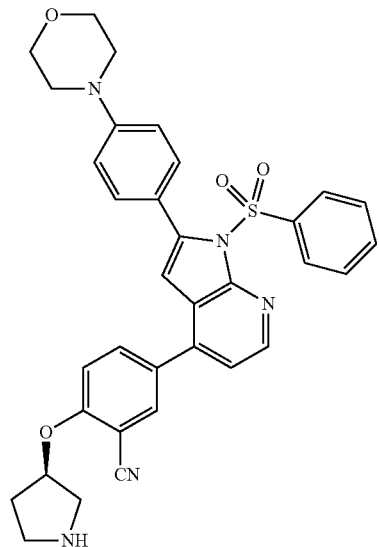

Step 1 →

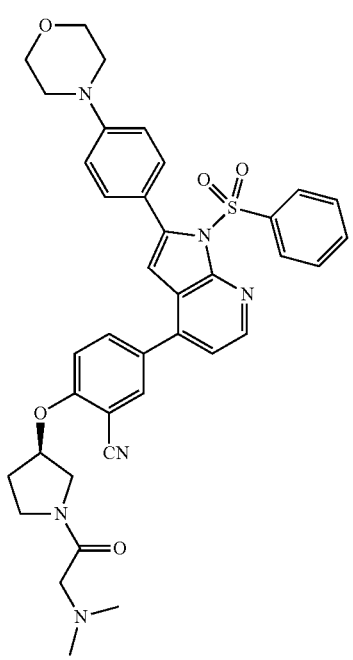

Step 2 →

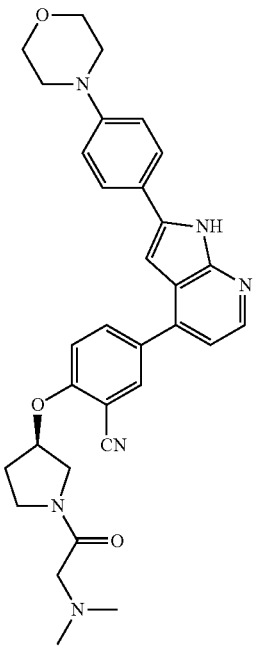

Step 1: (R)-2-((1-(2-(dimethylamino)acetyl)pyrrolidin-3-yl)oxy)-5-(2-(4-morpholinophenyl)-1-(phenylsulfonyl)-1H-pyrrolo[2,3-b]pyridin-4-yl)benzonitrile was prepared by the same procedure used for Example 15-step 1 by substituting N,N-dimethylglycine for α-hydroxyacetic acid. LCMS-ESI$^+$ (m/z): [M+H]$^+$ calcd for $C_{38}H_{38}N_6O_5S$: 691.3. found: 691.2.

Step 2: (R)-2-((1-(2-(dimethylamino)acetyl)pyrrolidin-3-yl)oxy)-5-(2-(4-morpholinophenyl)-1H-pyrrolo[2,3-b]pyridin-4-yl)benzonitrile was prepared using the same procedure reported in Example 18-step 2. $^1$H NMR (400 MHz, DMSO-d$_6$) δ 8.21 (dd, J=5.1, 0.9 Hz, 1H), 8.19-8.10 (m, 2H), 7.86 (dd, J=8.9, 2.0 Hz, 2H), 7.51 (d, J=8.7 Hz, 1H), 7.20 (dd, J=5.1, 1.4 Hz, 1H), 7.06-6.93 (m, 3H), 5.48 (d, J=3.9 Hz, 1H), 4.34-4.05 (m, 2H), 3.84 (dd, J=11.9, 4.3 Hz, 1H), 3.80-3.63 (m, 6H), 3.63-3.44 (m, 2H), 3.24-3.12 (m, 4H), 2.90-2.76 (m, 6H), 2.53 (t, J=5.6 Hz, 1H), 2.34 (m, 1H), 2.22 (m, 1H). LCMS-ESI$^+$ (m/z): [M+H]$^+$ calcd for $C_{32}H_{34}N_6O_3$: 551.3. found: 551.2.

Example 31: Preparation of (R)-2-((1-(2,2-difluoro-ethyl)pyrrolidin-3-yl)oxy)-5-(2-(4-morpholinophenyl)-1H-pyrrolo[2,3-b]pyridin-4-yl)benzonitrile

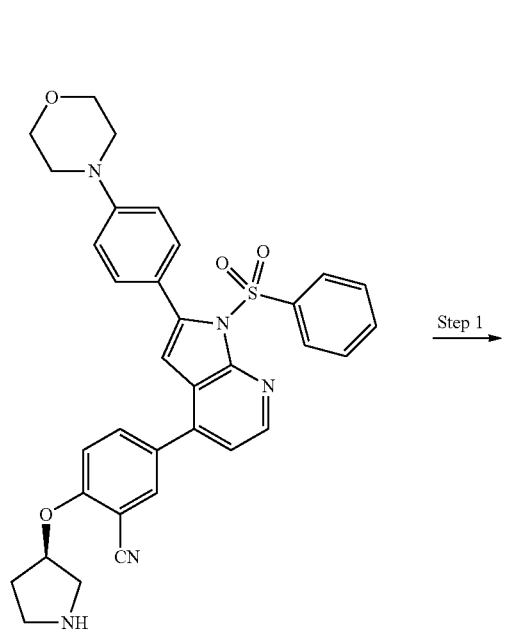

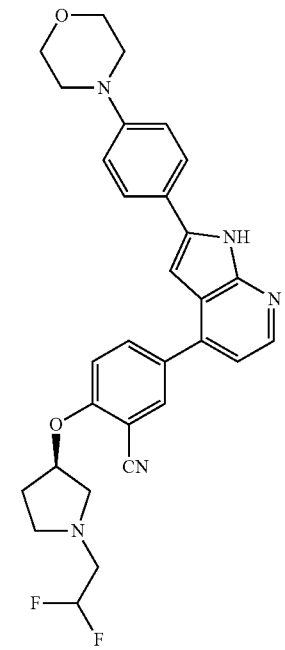

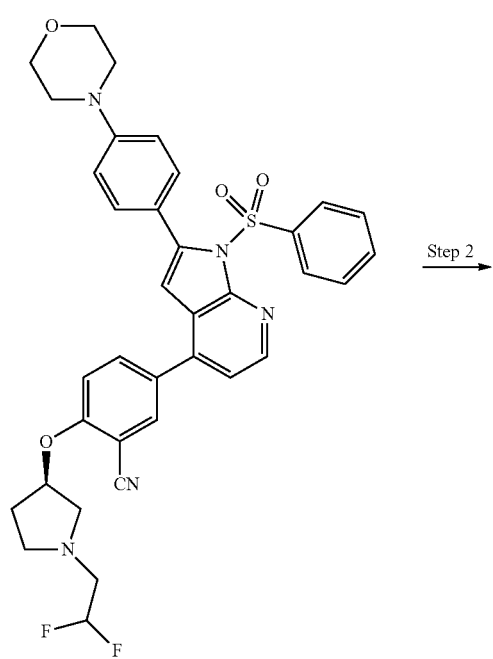

Step 1: To an appropriate sized microwave vial, (R)-5-(2-(4-morpholinophenyl)-1-(phenylsulfonyl)-1H-pyrrolo[2,3-b]pyridin-4-yl)-2-(pyrrolidin-3-yloxy)benzonitrile (150 mg, 0.28 mmol), (153 mg, 0.612 mmol), potassium carbonate (68 mg, 0.50 mmol) and DMF (0.5 mL) mL) were added. The mixture was stirred at 80° C. for 18 hr. After cooling to room temperature, the mixture was poured into water, neutralized to pH 7 and extracted with ethyl acetate. The combined organic layers were washed with saturated aqueous sodium chloride solution, dried, filtered and concentrated under reduced pressure. The residue was purified by flash column chromatography on silica gel.

LCMS-ESI$^+$ (m/z): [M+H]$^+$ calcd for $C_{36}H_{33}F_2N_5O_4S$: 670.2. found: 670.2.

Step 2: (R)-2-((1-(2,2-difluoroethyl)pyrrolidin-3-yl)oxy)-5-(2-(4-morpholinophenyl)-1H-pyrrolo[2,3-b]pyridin-4-yl)benzonitrile was prepared using the same procedure reported in Example 18-step 2. $^1$H NMR (400 MHz, DMSO-d$_6$) δ 8.21 (d, J=5.2 Hz, 1H), 8.18 (d, J=2 Hz, 1H), 8.13 (dd, J=8.8, 2.4 Hz, 1H), 7.86 (d, J=8.8 Hz, 2H), 7.42 (d, J=8.9 Hz, 1H), 7.20 (d, J=5.1 Hz, 1H), 7.02 (d, J=8.8 Hz, 1H), 6.97 (d, J=2.0 Hz, 1H), 6.41 (t, J=54 Hz, 1H), 5.35 (s, 1H), 3.74 (t, J=4.9 Hz, 4H), 3.82-3.24 (m, 6H), 3.18 (t, J=4.9 Hz, 2H), 2.53 (t, J=5.5 Hz, 1H), 2.22-2.10 (m, 1H). LCMS-ESI$^+$ (m/z): [M+H]$^+$ calcd for $C_{30}H_{29}F_2N_5O_2$: 530.2. found: 530.2.

Example 32: Preparation of N-(2-cyano-4-(2-(4-morpholinophenyl)-1H-pyrrolo[2,3-b]pyridin-4-yl)phenyl)cyclopropanecarboxamide

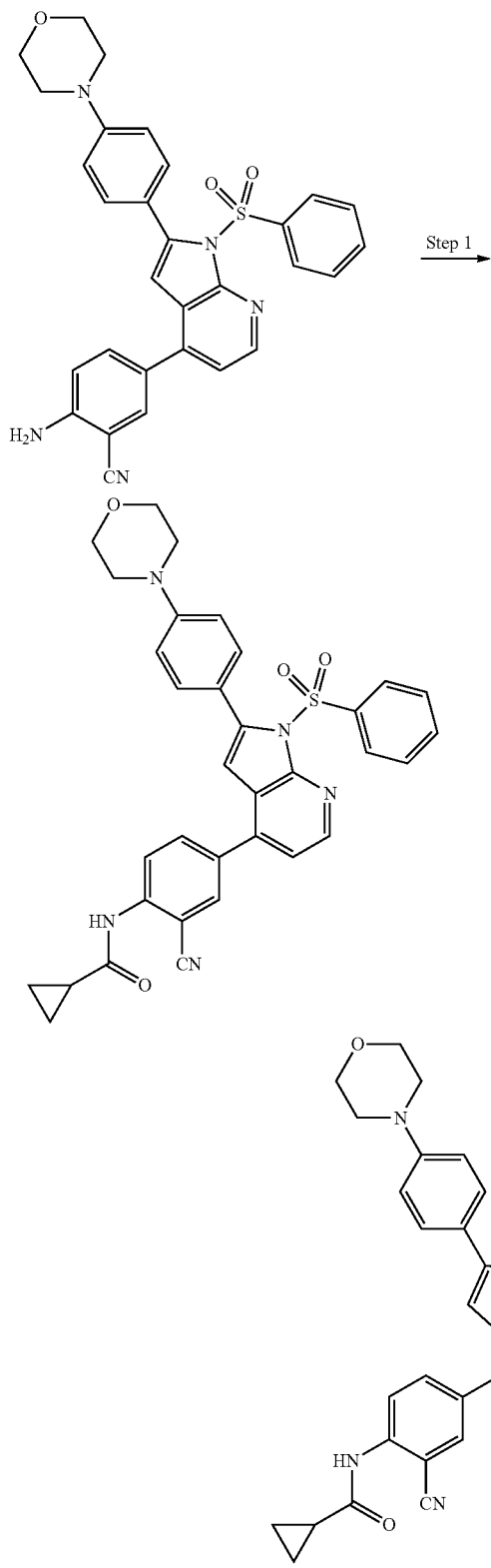

Step 1: To an appropriate sized microwave vial, 2-amino-5-(2-(4-morpholinophenyl)-1-(phenylsulfonyl)-1H-pyrrolo[2,3-b]pyridin-4-yl)benzonitrile (104 mg, 0.19 mmol) was taken up in 2 mL DCM and cooled to 0° C. Pyridine (47 μL, 0.50 mmol) and cyclopropanecarbonyl chloride (18 μL, 0.24 mmol) were added. After 1 h the reaction was warmed to rt, poured into pH 6 citrate buffer and extracted with $CH_2Cl_2$.

The combined organic layers were washed with saturated aqueous sodium chloride solution, dried, filtered and concentrated under reduced pressure. The residue was purified by flash column chromatography on silica gel to afford N-(2-cyano-4-(2-(4-morpholinophenyl)-1-(phenylsulfonyl)-1H-pyrrolo[2,3-b]pyridin-4-yl)phenyl)cyclopropanecarboxamide. LCMS-ESI$^+$ (m/z): [M+H]$^+$ calcd for $C_{34}H_{29}N_5O_4S$: 604.2. found: 604.2.

Step 2: N-(2-cyano-4-(2-(4-morpholinophenyl)-1H-pyrrolo[2,3-b]pyridin-4-yl)phenyl)cyclopropanecarboxamide was prepared using the same procedure reported in Example 18-step 2. $^1$H NMR (400 MHz, DMSO-d$_6$) δ 8.21 (d, J=5.0 Hz, 1H), 8.17 (d, J=2.1 Hz, 1H), 8.12 (dd, J=8.6, 2.2 Hz, 1H), 7.92-7.84 (m, 2H), 7.79 (d, J=8.5 Hz, 1H), 7.21 (d, J=5.0 Hz, 1H), 7.05-6.96 (m, 3H), 3.76-3.71 (m, 4H), 3.63-3.52 (m, 1H), 3.22-3.12 (m, 4H), 2.02-1.89 (m, 1H), 1.81-1.65 (m, 2H), 0.96-0.80 (m, 4H). LCMS-ESI$^+$ (m/z): [M+H]$^+$ calcd for $C_{28}H_{25}N_5O_2$: 464.2. found: 464.3.

Example 33: Preparation of 3-methoxy-5-(2-(4-morpholinophenyl)-1H-pyrrolo[2,3-b]pyridin-4-yl)benzonitrile

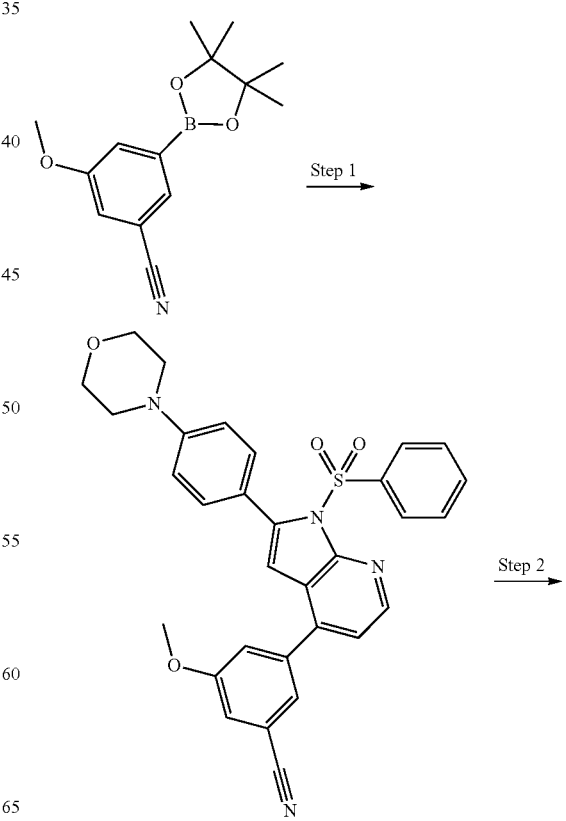

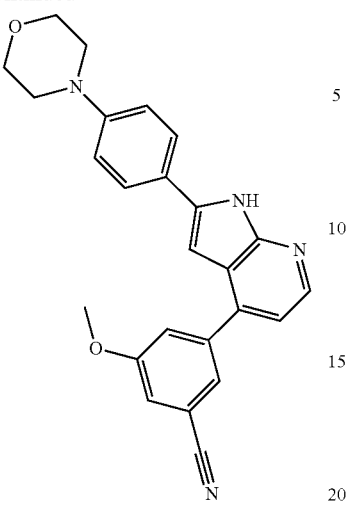
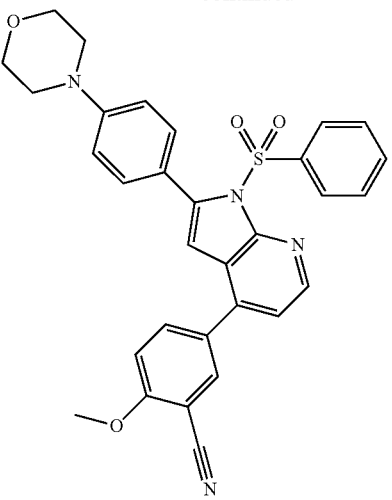

Step 1: 3-methoxy-5-(4,4,5,5-tetramethyl-1,3,2-dioxaborolan-2-yl)benzonitrile was prepared using the same procedure reported in Example 14-step 2. LCMS-ESI⁺ (m/z): [M+H]⁺ calcd for $C_{31}H_{26}N_4O_4S$: 551.1. found: 551.5.

Step 2: 3-methoxy-5-(2-(4-morpholinophenyl)-1H-pyrrolo[2,3-b]pyridin-4-yl)benzonitrile was prepared using the same procedure reported in Example 18-step 2. ¹H NMR (400 MHz, DMSO-d6) δ 8.23 (d, J=5.0 Hz, 1H), 7.88 (d, J=9.2 Hz, 2H), 7.78 (t, J=1.4 Hz, 1H), 7.61 (dd, J=2.6, 1.5 Hz, 1H), 7.54 (dd, J=2.6, 1.3 Hz, 1H), 7.24 (d, J=5.1 Hz, 1H), 7.06-6.96 (m, 3H), 3.92 (s, 3H), 3.76-3.71 (m, 4H), 3.23-3.12 (m, 4H). LCMS-ESI⁺ (m/z): [M+H]⁺ calcd for $C_{25}H_{22}N_4O_2$: 411.2. found: 411.2.

Example 34: Preparation of 2-methoxy-5-(2-(4-morpholinophenyl)-1H-pyrrolo[2,3-b]pyridin-4-yl)benzonitrile

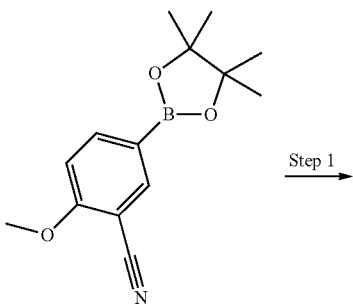

Step 1 →

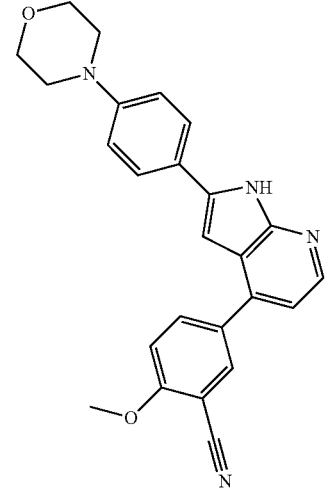

Step 1: 2-methoxy-5-(4,4,5,5-tetramethyl-1,3,2-dioxaborolan-2-yl)benzonitrile was prepared using the same procedure reported in Example 14-step 2. LCMS-ESI⁺ (m/z): [M+H]⁺ calcd for $C_{31}H_{26}N_4O_4S$: 551.1. found: 551.4.

Step 2: 2-methoxy-5-(2-(4-morpholinophenyl)-1H-pyrrolo[2,3-b]pyridin-4-yl)benzonitrile was prepared using the same procedure reported in Example 18-step 2. ¹H NMR (400 MHz, DMSO-d6) δ 8.19 (d, J=5.0 Hz, 1H), 8.16-8.09 (m, 2H), 7.86 (d, J=8.8 Hz, 2H), 7.42 (d, J=9.5 Hz, 1H), 7.16 (d, J=5.0 Hz, 1H), 7.07-6.92 (m, 3H), 4.00 (s, 3H), 3.74 (dd, J=6.1, 3.6 Hz, 4H), 3.23-3.14 (m, 4H). LCMS-ESI⁺ (m/z): [M+H]⁺ calcd for $C_{25}H_{22}N_4O_2$: 411.2. found: 411.3.

Example 35: Preparation of 5-(2-((tetrahydro-2H-pyran-4-yl)ethynyl)-1H-pyrrolo[2,3-b]pyridin-4-yl)-2-((tetrahydro-2H-pyran-4-yl)oxy)benzonitrile

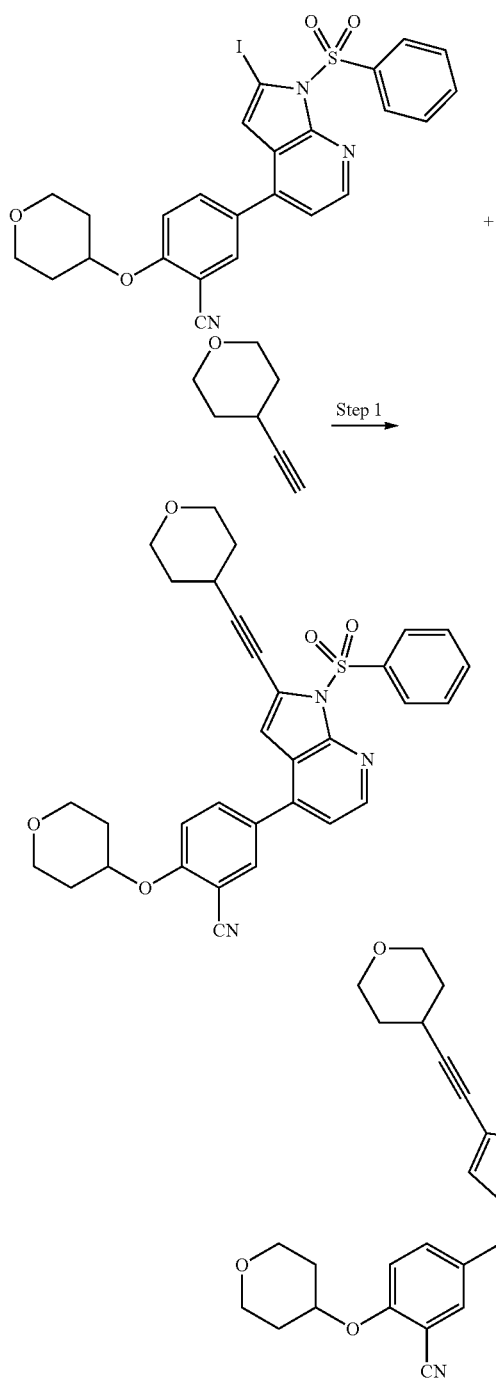

Step 1: To an appropriate sized microwave vial, 5-(2-iodo-1-(phenylsulfonyl)-1H-pyrrolo[2,3-b]pyridin-4-yl)-2-((tetrahydro-2H-pyran-4-yl)oxy)benzonitrile (161 mg, 0.275 mmol), 4-ethynyltetrahydro-2H-pyran (30 mg, 0.275 mmol), Bis(triphenylphosphine)palladium(II) dichloride (6.8 mg, 0.009 mmol) and copper(I) iodide (6.5 mg, 0.034 mmol), TEA (0.35 mL) and THF (0.65 mL). The mixture was stirred at rt for 20 h, then diluted with CH₂Cl₂ and filtered thru Celite®. The resulting brown oil was purified by flash column chromatography on silica gel to afford 5-(1-(phenylsulfonyl)-2-((tetrahydro-2H-pyran-4-yl)ethynyl)-1H-pyrrolo[2,3-b]pyridin-4-yl)-2-((tetrahydro-2H-pyran-4-yl)oxy)benzonitrile. LCMS-ESI⁺ (m/z): [M+H]⁺ calcd for $C_{32}H_{29}N_3O_5S$: 568.2. found: 568.2.

Step 2: 5-(2-((tetrahydro-2H-pyran-4-yl)ethynyl)-1H-pyrrolo[2,3-b]pyridin-4-yl)-2-((tetrahydro-2H-pyran-4-yl)oxy)benzonitrile was prepared using the same procedure reported in Example 18-step 2. ¹H NMR (400 MHz, DMSO-d6) δ 8.30 (d, J=5.0 Hz, 1H), 8.09 (d, J=2.3 Hz, 1H), 8.02 (dd, J=8.9, 2.4 Hz, 1H), 7.49 (d, J=8.9 Hz, 1H), 7.24 (d, J=5.1 Hz, 1H), 6.85 (d, J=1.8 Hz, 1H), 4.90 (dt, J=8.0, 4.0 Hz, 1H), 3.84 (ddt, J=22.0, 11.5, 4.2 Hz, 4H), 3.55 (ddd, J=11.5, 8.3, 3.1 Hz, 2H), 3.45 (ddd, J=11.7, 9.1, 2.7 Hz, 2H), 2.97 (dt, J=9.1, 4.8 Hz, 1H), 2.03 (ddt, J=12.2, 5.9, 3.1 Hz, 2H), 1.85 (dq, J=12.3, 3.7 Hz, 2H), 1.65 (ddtd, J=26.4, 13.0, 9.1, 8.7, 3.8 Hz, 4H). LCMS-ESI⁺ (m/z): [M+H]⁺ calcd for $C_{26}H_{25}N_3O_3$: 428.2. found: 428.2.

Example 36: Preparation of tert-butyl 3-(4-(3-cyano-4-((tetrahydro-2H-pyran-4-yl)oxy)phenyl)-1H-pyrrolo[2,3-b]pyridin-2-yl)-2,5-dihydro-1H-pyrrole-1-carboxylate

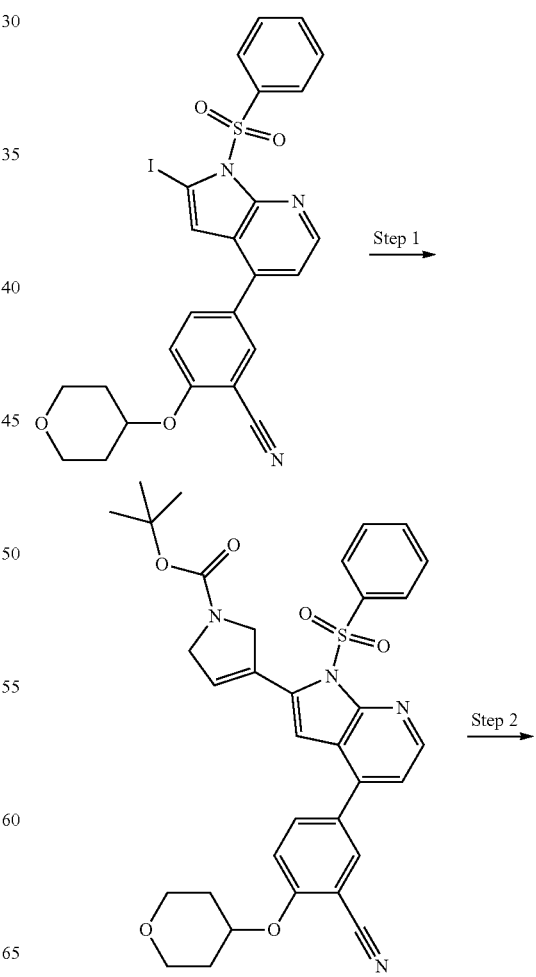

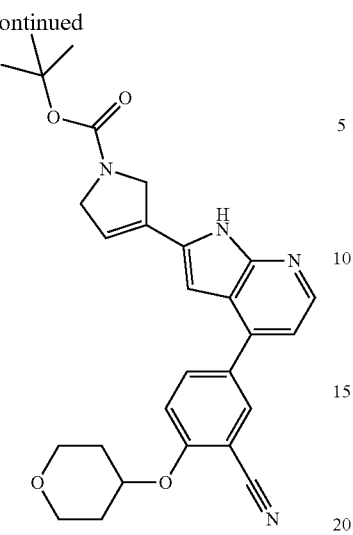

Step 1: To 5-(2-iodo-1-(methylsulfonyl)-1H-pyrrolo[2,3-b]pyridin-4-yl)-2-((tetrahydro-2H-pyran-4-yl)oxy)benzonitrile (77 mg, 0.132 mmol) in dioxane (2 mL), tert-butyl 3-(4,4,5,5-tetramethyl-1,3,2-dioxaborolan-2-yl)-2,5-dihydro-1H-pyrrole-1-carboxylate (39 mg, 0.132 mmol), Cesium carbonate (128 mg, 0.393 mmol) dissolved in water (1 mL), and PEPPSI-iPr catalyst (10 mg, 0.015 mmol) were added. The reaction mixture was heated at 85° C. for 3 h. After cooling to room temperature, the mixture was poured into water and extracted with ethyl acetate. The combined organic layers were washed with saturated aqueous sodium chloride solution, dried, filtered and concentrated under reduced pressure. The residue was purified by flash column chromatography on silica gel to afford tert-butyl 3-(4-(3-cyano-4-((tetrahydro-2H-pyran-4-yl)oxy)phenyl)-1-(methylsulfonyl)-1H-pyrrolo[2,3-b]pyridin-2-yl)-2,5-dihydro-1H-pyrrole-1-carboxylate.

Step 2: To an appropriate sized microwave vial, a solution of tert-butyl 3-(4-(3-cyano-4-((tetrahydro-2H-pyran-4-yl)oxy)phenyl)-1-(methylsulfonyl)-1H-pyrrolo[2,3-b]pyridin-2-yl)-2,5-dihydro-1H-pyrrole-1-carboxylate (25 mg, 0.040 mmol) in 2-methyltetrahydrofuran (1 mL), 2,2,2-trifluoroethanol (0.5 mL) and Cesium carbonate (66 mg, 0.203 mmol) were added. The reaction mixture was heated in a microwave reactor at 110° C. for 35 min. After cooling to room temperature, the mixture was poured into water and extracted with ethyl acetate. The combined organic layers were washed with saturated aqueous sodium chloride solution, dried, filtered and concentrated under reduced pressure. The residue was purified via prep HPLC to isolate tert-butyl 3-(4-(3-cyano-4-((tetrahydro-2H-pyran-4-yl)oxy)phenyl)-1H-pyrrolo[2,3-b]pyridin-2-yl)-2,5-dihydro-1H-pyrrole-1-carboxylate. $^1$H NMR (400 MHz, DMSO-d6) δ 12.22 (s, 1H), 8.27 (d, J=5.1 Hz, 1H), 8.10 (m, 1H), 8.04 (m, 1H), 7.51 (dd, J=8.9, 4.1 Hz, 1H), 7.21 (dd, J=8.0, 5.1 Hz, 1H), 6.70 (d, J=32 Hz, 1H), 6.52 (d, J=16.2 Hz, 1H), 4.91 (m, 1H), 4.44 (m, 2H), 4.24 (m, 2H), 3.87 (m, 2H), 3.54 (m, 2H), 2.04 (m, 2H), 1.69 (m, 2H), 1.44 (d, J=5.0 Hz, 9H). LCMS-ESI$^+$ (m/z): [M+H]$^+$ calcd for $C_{28}H_{30}N_4O_4$: 487.2. found: 487.1.

Example 37: Preparation of 5-(2-(2,5-dihydro-1H-pyrrol-3-yl)-1H-pyrrolo[2,3-b]pyridin-4-yl)-2-((tetrahydro-2H-pyran-4-yl)oxy)benzonitrile

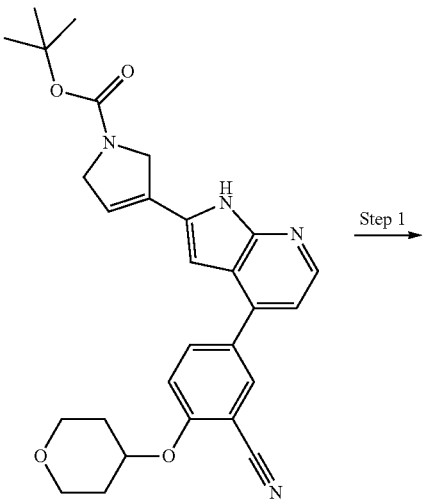

Step 1

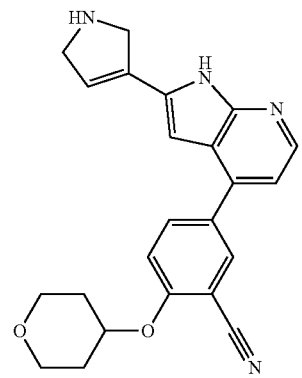

To a solution of tert-butyl 3-(4-(3-cyano-4-((tetrahydro-2H-pyran-4-yl)oxy)phenyl)-1H-pyrrolo[2,3-b]pyridin-2-yl)-2,5-dihydro-1H-pyrrole-1-carboxylate (10 mg, 0.021 mmol) in dichloromethane (1.5 mL) was added trifluoroacetic acid (300 μL). The reaction mixture was stirred at room temperature overnight and then concentrated. The residue was dissolved in ethyl acetate and washed with saturated sodium bicarbonate solution. The combined organic layers were washed with saturated aqueous sodium chloride solution, dried, filtered and concentrated under reduced pressure. The residue was purified via prep HPLC to isolate 5-(2-(2,5-dihydro-1H-pyrrol-3-yl)-1H-pyrrolo[2,3-b]pyridin-4-yl)-2-((tetrahydro-2H-pyran-4-yl)oxy)benzonitrile. $^1$H NMR (400 MHz, DMSO-d6) δ 12.08 (s, 1H), 8.24 (d, J=5.0 Hz, 1H), 8.07 (d, J=2.3 Hz, 1H), 8.02 (dd, J=8.8, 2.4 Hz, 1H), 7.51 (d, J=9.0 Hz, 1H), 7.17 (d, J=5.0 Hz, 1H), 6.55 (m, 2H), 4.95-4.85 (m, 1H), 4.02 (m, 2H), 3.88 (m, 4H), 3.55 (m, 2H), 2.03 (m, 2H), 1.75-1.63 (m, 2H). LCMS-ESI$^+$ (m/z): [M+H]$^+$ calcd for $C_{23}H_{22}N_4O_2$: 387.2. found: 387.2.

Example 38: Preparation of 5-(2-(4-(1H-indol-2-yl)phenyl)-1H-pyrrolo[2,3-b]pyridin-4-yl)-2-((tetrahydro-2H-pyran-4-yl)oxy)benzonitrile

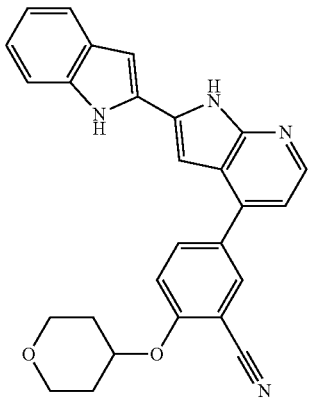 [SMILES: N#Cc1cc(-c2ccnc3[nH]c(-c4cc5ccccc5[nH]4)cc23)ccc1OC1CCOCC1]

Following similar procedure to synthesize Example 36, (2-(4-(1H-indol-2-yl)phenyl)-1H-pyrrolo[2,3-b]pyridin-4-yl)-2-((tetrahydro-2H-pyran-4-yl)oxy)benzonitrile was synthesized.

$^1$H NMR (400 MHz, DMSO-d6) δ 12.38 (s, 1H), 11.62 (s, 1H), 8.26 (d, J=5.0 Hz, 1H), 8.15 (d, J=2.3 Hz, 1H), 8.08 (dd, J=8.9, 2.3 Hz, 1H), 7.56 (m, 2H), 7.39 (m, 1H), 7.22 (d, J=5.0 Hz, 1H), 7.18 (m, 1H), 7.11 (m, 2H), 7.00 (m, 1H), 4.95 (m, 1H), 3.93-3.84 (m, 2H), 3.57 (m, 2H), 2.04 (m, 2H), 1.70 (m, 2H). LCMS-ESI$^+$ (m/z): [M+H]$^+$ calcd for $C_{27}H_{22}N_4O_2$: 435.2. found: 435.2.

Example 39: Preparation of 5-(2-(3-(morpholinomethyl)phenyl)-1H-pyrrolo[2,3-b]pyridin-4-yl)-2-((tetrahydro-2H-pyran-4-yl)oxy)benzonitrile

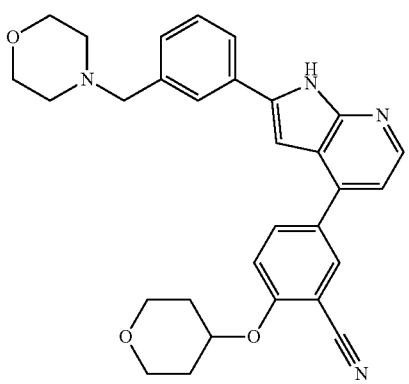 [SMILES: N#Cc1cc(-c2ccnc3[nH]c(-c4cccc(CN5CCOCC5)c4)cc23)ccc1OC1CCOCC1]

Following similar procedure to synthesize Example 36, 5-(2-(3-(morpholinomethyl)phenyl)-1H-pyrrolo[2,3-b]pyridin-4-yl)-2-((tetrahydro-2H-pyran-4-yl)oxy)benzonitrile was synthesized. $^1$H NMR (400 MHz, DMSO-d6) δ 12.43 (s, 1H), 9.88 (s, 1H), 8.30 (d, J=5.0 Hz, 1H), 8.13 (d, J=2.3 Hz, 1H), 8.09-8.03 (m, 2H), 7.61-7.51 (m, 2H), 7.48 (m, 1H), 7.22 (d, J=5.0 Hz, 1H), 7.11 (d, J=2.0 Hz, 1H), 4.96-4.88 (m, 1H), 4.38 (s, 2H), 3.97 (m, 2H), 3.91-3.82 (m, 2H), 3.64 (m, 2H), 3.56 (m, 4H), 3.17 (m, 2H), 2.09-1.99 (m, 2H), 1.71 (m, 2H). LCMS-ESI$^+$ (m/z): [M+H]$^+$ calcd for $C_{30}H_{30}N_4O_3$: 495.2. found: 495.2.

Example 40: Preparation of 3-(4-(3-cyano-4-((tetrahydro-2H-pyran-4-yl)oxy)phenyl)-1H-pyrrolo[2,3-b]pyridin-2-yl)-N-methylbenzamide

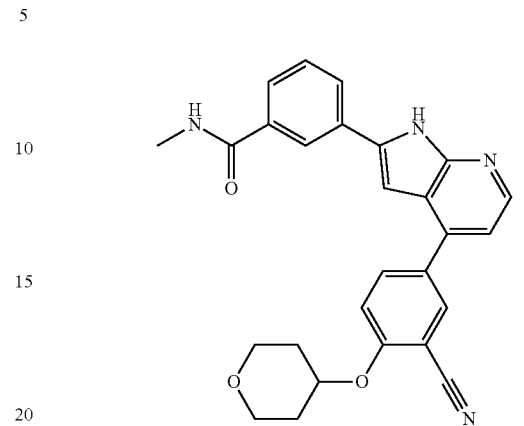

The title compound was prepared following similar procedure to synthesize Example 36.

$^1$H NMR (400 MHz, DMSO-d6) δ 12.41 (s, 1H), 8.47 (d, J=4.8 Hz, 1H), 8.40 (s, 1H), 8.29 (d, J=5.0 Hz, 1H), 8.16 (m, 1H), 8.13-8.05 (m, 2H), 7.77 (d, J=7.7 Hz, 1H), 7.55 (dt, J=7.8, 3.3, 3.3 Hz, 2H), 7.24 (d, J=5.0 Hz, 1H), 7.21 (d, J=2.0 Hz, 1H), 4.93 (m, 1H), 3.88 (m, 2H), 3.56 (m, 2H), 2.81 (d, J=4.4 Hz, 3H), 2.05 (m, 2H), 1.71 (m, 2H). LCMS-ESI$^+$ (m/z): [M+H]$^+$ calcd for $C_{27}H_{24}N_4O_3$: 453.2. found: 453.2.

Example 41: Preparation of 4-(4-(3-cyano-4-((tetrahydro-2H-pyran-4-yl)oxy)phenyl)-1H-pyrrolo[2,3-b]pyridin-2-yl)-N-methylbenzamide

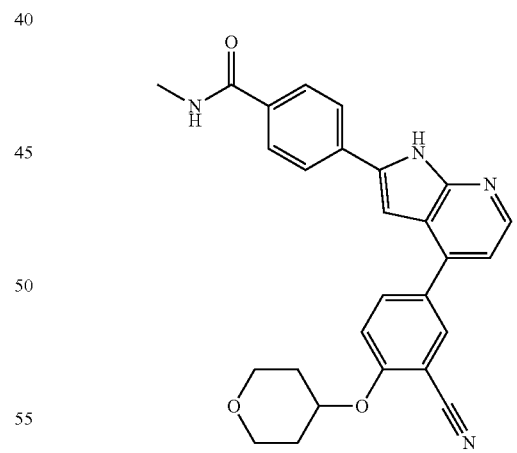

The title compound was prepared following similar procedure to synthesize Example 36.

$^1$H NMR (400 MHz, DMSO-d6) δ 12.42 (s, 1H), 8.47 (m, 1H), 8.29 (d, J=5.0 Hz, 1H), 8.16 (d, J=2.3 Hz, 1H), 8.08 (d, J=7.7 Hz, 2H), 7.91 (d, J=8.3 Hz, 2H), 7.53 (d, J=9.0 Hz, 1H), 7.29 (d, J=2.0 Hz, 1H), 7.24 (d, J=5.0 Hz, 1H), 4.96-4.89 (m, 1H), 3.88 (m, 2H), 3.56 (m, 2H), 2.79 (d, J=4.5 Hz, 3H), 2.05 (m, 2H), 1.71 (m, 2H). LCMS-ESI$^+$ (m/z): [M+H]$^+$ calcd for $C_{27}H_{24}N_4O_3$: 453.2. found: 453.1.

Example 42: Preparation of 5-(2-(4-(methylsulfonyl)phenyl)-1H-pyrrolo[2,3-b]pyridin-4-yl)-2-((tetrahydro-2H-pyran-4-yl)oxy)benzonitrile

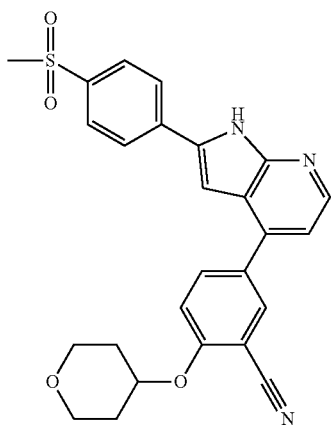 [SMILES: CS(=O)(=O)c1ccc(-c2cc3c(-c4ccc(OC5CCOCC5)c(C#N)c4)ccnc3[nH]2)cc1]

The title compound was prepared following similar procedure to synthesize Example 36.

$^1$H NMR (400 MHz, DMSO-d6) δ 12.56 (s, 1H), 8.33 (d, J=5.0 Hz, 1H), 8.29-8.22 (m, 2H), 8.16 (d, J=2.3 Hz, 1H), 8.10 (dd, J=8.8, 2.4 Hz, 1H), 8.00-7.95 (m, 2H), 7.53 (d, J=9.0 Hz, 1H), 7.40 (d, J=1.9 Hz, 1H), 7.26 (d, J=5.0 Hz, 1H), 4.92 (m, 1H), 3.88 (m, 5.9, 3.9 Hz, 2H), 3.56 (m, 2H), 3.25 (s, 3H), 2.10-1.99 (m, 2H), 1.71 (m, 2H). LCMS-ESI$^+$ (m/z): [M+H]$^+$ calcd for $C_{26}H_{23}N_3O_4S$: 474.1. found: 474.1.

Example 43: Preparation of 5-(2-(bicyclo[2.2.1]hept-2-en-2-yl)-1H-pyrrolo[2,3-b]pyridin-4-yl)-2-((tetrahydro-2H-pyran-4-yl)oxy)benzonitrile

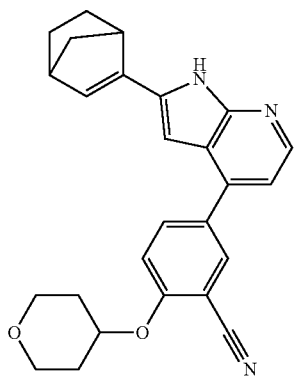 [SMILES: N#Cc1cc(-c2ccnc3[nH]c(C4=CC5CCC4C5)cc23)ccc1OC1CCOCC1]

The title compound was prepared following similar procedure to synthesize Example 36.

$^1$H NMR (400 MHz, DMSO-d6) δ 11.91 (s, 1H), 8.20 (d, J=5.1 Hz, 1H), 8.09 (d, J=2.3 Hz, 1H), 8.04 (dd, J=8.8, 2.3 Hz, 1H), 7.52 (d, J=8.9 Hz, 1H), 7.17 (d, J=5.1 Hz, 1H), 6.66 (d, J=1.9 Hz, 1H), 6.64 (d, J=3.1 Hz, 1H), 4.95-4.85 (m, 1H), 3.87 (m, 2H), 3.56 (m, 2H), 3.35 (s, 1H), 3.01 (s, 1H), 2.08-1.98 (m, 2H), 1.77 (m, 2H), 1.73-1.63 (m, 2H), 1.44 (d, J=8.1 Hz, 1H), 1.23 (d, J=8.2 Hz, 1H), 1.08 (m, 1H), 1.01 (m, 1H). LCMS-ESI$^+$ (m/z): [M+H]$^+$ calcd for $C_{26}H_{25}N_3O_2$: 412.2. found: 412.2.

Example 44 and Example 45

Preparation of tert-butyl 5-(4-(3-cyano-4-((tetrahydro-2H-pyran-4-yl)oxy)phenyl)-1H-pyrrolo[2,3-b]pyridin-2-yl)-1H-indole-1-carboxylate and 5-(2-(1H-indol-5-yl)-1H-pyrrolo[2,3-b]pyridin-4-yl)-2-((tetrahydro-2H-pyran-4-yl)oxy)benzonitrile

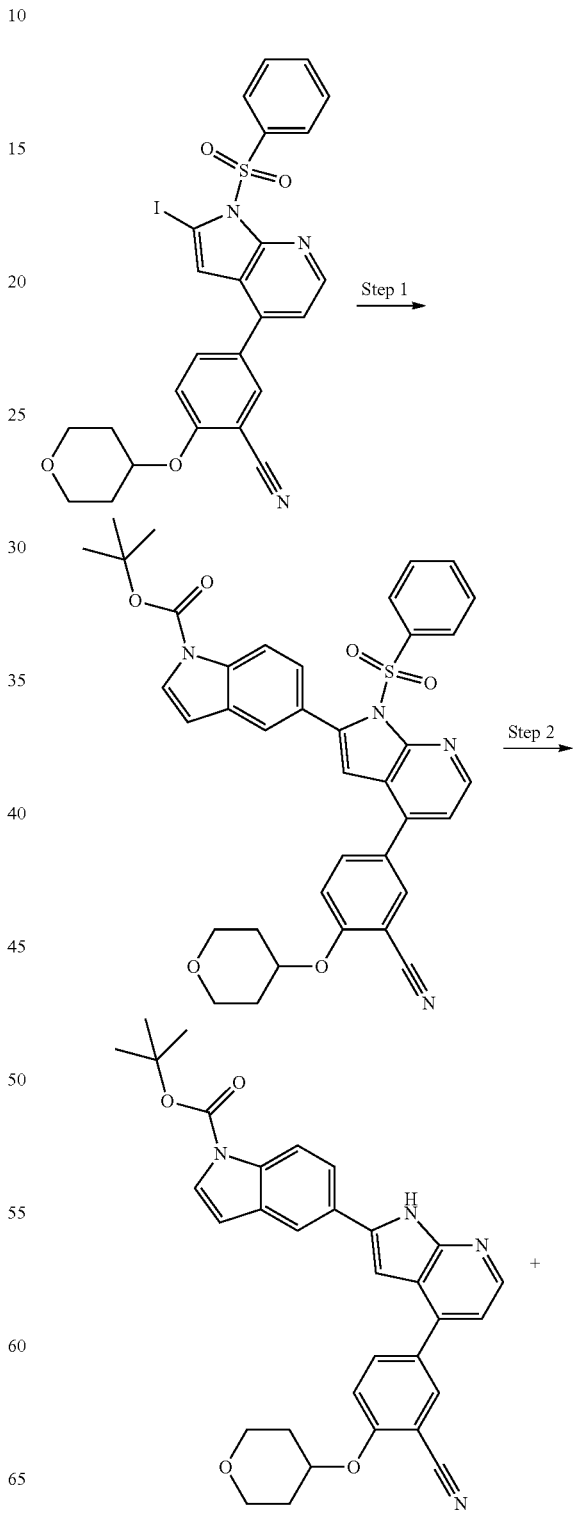

-continued

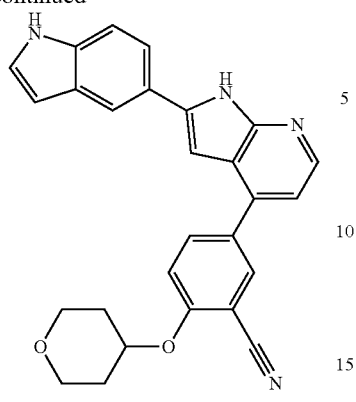

Step 1: Following similar procedure to synthesize Example 36 tert-butyl 5-(4-(3-cyano-4-((tetrahydro-2H-pyran-4-yl)oxy)phenyl)-1-(phenylsulfonyl)-1H-pyrrolo[2,3-b]pyridin-2-yl)-1H-indole-1-carboxylate was prepared.

Step 2: To an appropriate sized microwave vial, a solution of tert-butyl 5-(4-(3-cyano-4-((tetrahydro-2H-pyran-4-yl)oxy)phenyl)-1-(phenylsulfonyl)-1H-pyrrolo[2,3-b]pyridin-2-yl)-1H-indole-1-carboxylate (54 mg, 0.080 mmol) in 2-methyltetrahydrofuran (1 mL), 2,2,2-trifluoroethanol (0.5 mL), and Cesium carbonate (66 mg, 0.203 mmol) were added. The reaction mixture was heated at 110° C. for 35 min. After cooling to room temperature, the mixture was poured into water and extracted with ethyl acetate. The combined organic layers were washed with saturated aqueous sodium chloride solution, dried, filtered and concentrated under reduced pressure. The residue was purified via prep HPLC to isolate tert-butyl 5-(4-(3-cyano-4-((tetrahydro-2H-pyran-4-yl)oxy)phenyl)-1H-pyrrolo[2,3-b]pyridin-2-yl)-1H-indole-1-carboxylate and 5-(2-(1H-indol-5-yl)-1H-pyrrolo[2,3-b]pyridin-4-yl)-2-((tetrahydro-2H-pyran-4-yl)oxy)benzonitrile.

Example 44

$^1$H NMR (400 MHz, DMSO-d6) δ 12.38 (s, 1H), 8.26 (m, 2H), 8.17 (d, J=2.3 Hz, 1H), 8.14-8.08 (m, 2H), 7.98 (dd, J=8.7, 1.8 Hz, 1H), 7.71 (d, J=3.7 Hz, 1H), 7.53 (d, J=9.0 Hz, 1H), 7.23 (d, J=5.1 Hz, 1H), 7.17 (d, J=2.0 Hz, 1H), 6.76 (d, J=3.7 Hz, 1H), 4.93 (m, 1H), 3.88 (m, 2H), 3.56 (m, 2H), 2.09-2.00 (m, 2H), 1.71 (m, 2H), 1.64 (s, 9H).

LCMS-ESI$^+$ (m/z): [M+H]$^+$ calcd for C$_{32}$H$_{30}$N$_4$O$_4$: 535.2. found: 535.1.

Example 45

$^1$H NMR (400 MHz, DMSO-d6) δ 12.28 (s, 1H), 11.21 (s, 1H), 8.23-8.18 (m, 2H), 8.16 (m, 1H), 8.12 (dd, J=8.8, 2.4 Hz, 1H), 7.73 (dd, J=8.5, 1.7 Hz, 1H), 7.53 (d, J=8.9 Hz, 1H), 7.45 (d, J=8.5 Hz, 1H), 7.38 (t, J=2.8, 2.8 Hz, 1H), 7.22 (d, J=5.1 Hz, 1H), 7.05 (m, 1H), 6.49 (m, 1H), 4.97-4.87 (m, 1H), 3.88 (m, 2H), 3.58 (m, 2H), 2.06 (m, 2H), 1.71 (m, 2H). LCMS-ESI$^+$ (m/z): [M+H]$^+$ calcd for C$_{27}$H$_{22}$N$_4$O$_2$: 435.2; found: 435.1.

Example 46: Preparation of 5-(2-(4-(2-oxa-6-azaspiro[3.3]heptan-6-yl)phenyl)-1H-pyrrolo[2,3-b]pyridin-4-yl)-2-((tetrahydro-2H-pyran-4-yl)oxy)benzonitrile

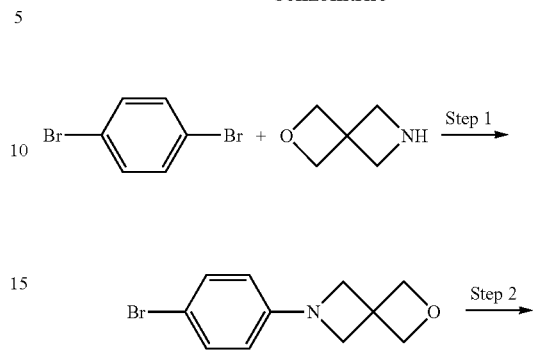

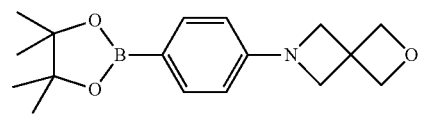

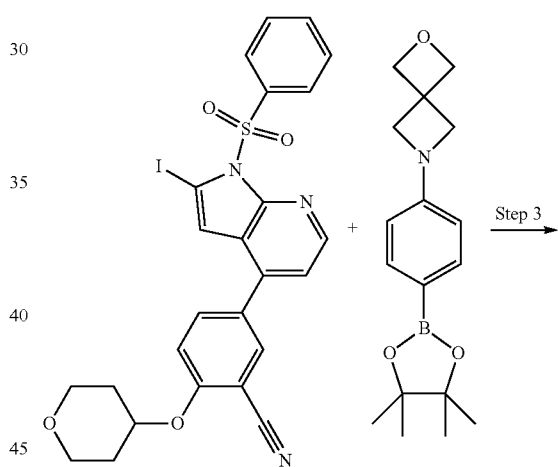

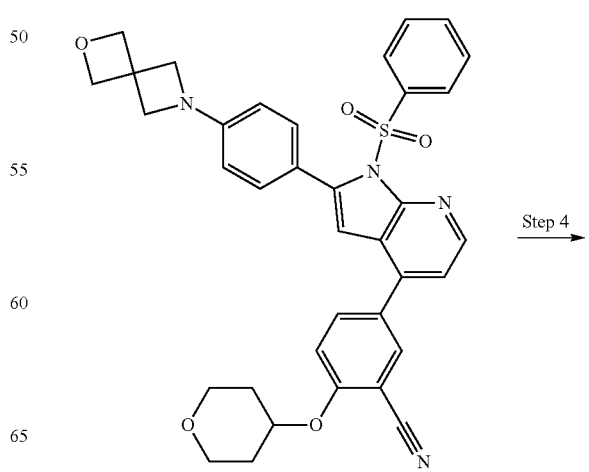

-continued

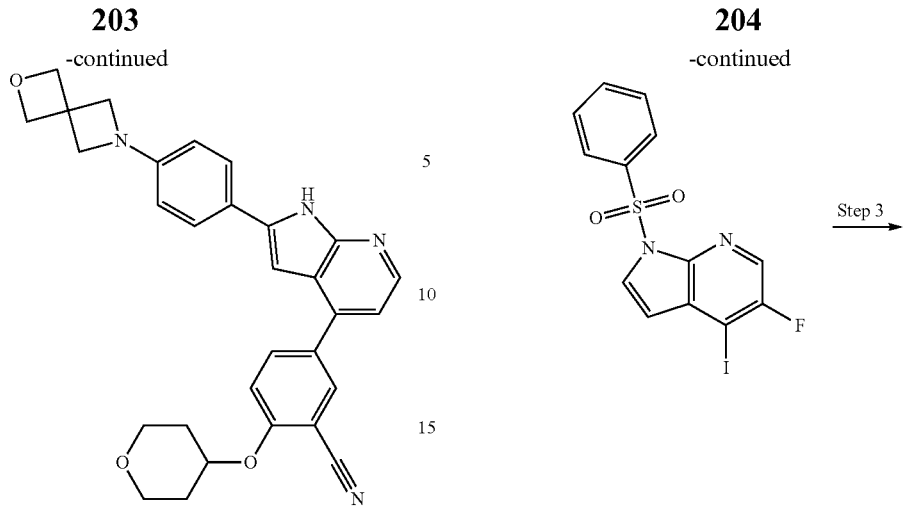

Step 1: To 1,4-Dibromobenzene (400 mg, 1.696 mmol) in toluene (2 mL) was added 2-oxa-6-azaspiro[3.3]heptane (100 μL, 1.140 mmol), 2,2'-bis(diphenylphosphino)-1,1'-binaphthyl (21 mg, 0.030 mmol), Cesium carbonate (552 mg, 1.694 mmol), and Tris(dibenzylideneacetone)dipalladium(0) (15 mg, 0.016 mmol). The reaction mixture was heated at 100° C. for 1 h. After cooling to room temperature, the reaction mixture was filtered through Celite, washed with DCM. The filtrate was concentrated and purified by flash column chromatography on silica gel to afford 6-(4-bromophenyl)-2-oxa-6-azaspiro[3.3]heptane.

Step 2: To 6-(4-bromophenyl)-2-oxa-6-azaspiro[3.3]heptane (173 mg, 0.681 mmol) in dioxane (4 mL) was added bis(pinacolato)diboron (344 mg, 1.355 mmol), [1,1'-Bis(diphenylphosphino)ferrocene]dichloropalladium(II) (56 mg, 0.069 mmol), and potassium acetate (200 mg, 2.038 mmol). The reaction mixture was heated at 80° C. for 2 h. After cooling to room temperature, the mixture was poured into water and extracted with ethyl acetate. The combined organic layers were washed with saturated aqueous sodium chloride solution, dried, filtered and concentrated under reduced pressure. The residue was purified by flash column chromatography on silica gel to afford 6-(4-(4,4,5,5-tetramethyl-1,3,2-dioxaborolan-2-yl)phenyl)-2-oxa-6-azaspiro[3.3]heptane.

Step 3 and Step 4: The title compound was prepared by following similar procedure to synthesize Example 36.

$^1$H NMR (400 MHz, DMSO-d6) δ 12.13 (s, 1H), 8.18 (m, 1H), 8.12 (m, 1H), 8.07 (dd, J=8.7, 2.5 Hz, 1H), 7.80 (d, J=8.5 Hz, 2H), 7.52 (d, J=8.9 Hz, 1H), 7.18 (d, J=5.1 Hz, 1H), 6.93 (d, J=2.2 Hz, 1H), 6.49 (d, J=8.3 Hz, 2H), 4.97-4.86 (m, 1H), 4.72 (s, 4H), 4.02 (s, 4H), 3.88 (m, 2H), 3.55 (m, 2H), 2.10-1.99 (m, 2H), 1.70 (m, 2H). LCMS-ESI$^+$ (m/z): [M+H]$^+$ calcd for $C_{30}H_{28}N_4O_3$: 493.2. found: 493.2.

Example 47: Preparation of 5-(5-fluoro-2-(4-morpholinophenyl)-1H-pyrrolo[2,3-b]pyridin-4-yl)-2-((tetrahydro-2H-pyran-4-yl)oxy)benzonitrile

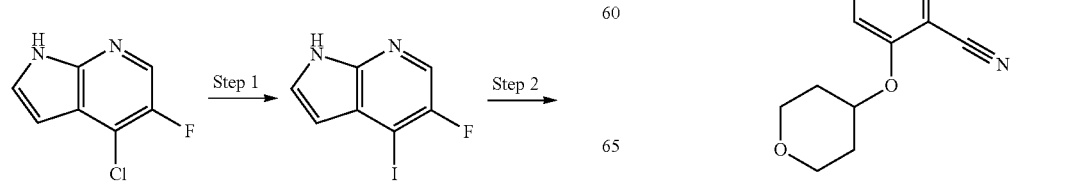

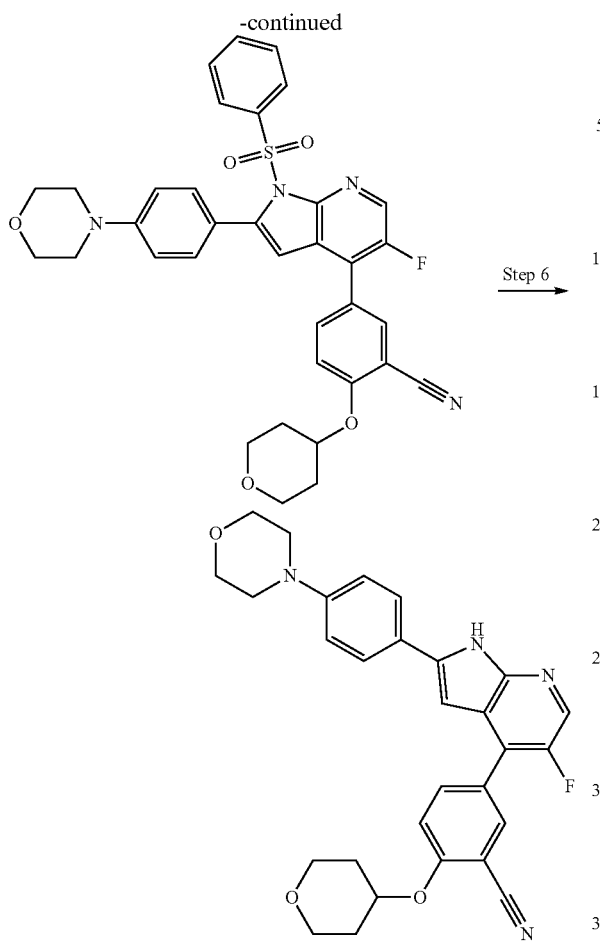

Step 1: 4-chloro-5-fluoro-1H-pyrrolo[2,3-b]pyridine (500 mg, 2.931 mmol) in dioxane (12 mL) was warmed to 40° C. until a solution resulted. 4M HCl in dioxane solution (800 µL, 3.224 mmol) was added dropwise. The reaction mixture was cooled to room temperature and filtered. The solid was washed with diethyl ether and dried. It was then suspended in acetonitrile (10 mL) and treated with sodium iodide (2.63 g, 17.55 mmol). The reaction mixture was heated at 80° C. overnight. After cooling to room temperature, reaction mixture was treated with 1N sodium hydroxide solution until it was basic. It was then extracted with ethyl acetate and washed with water. The combined organic layers were washed with saturated aqueous sodium chloride solution, dried, filtered and concentrated under reduced pressure to afford 5-fluoro-4-iodo-1H-indole.

Step 2: To 5-fluoro-4-iodo-1H-indole (160 mg, 0.611 mmol) in dichloromethane (10 mL) was added benzenesulfonyl chloride (120 µL, 0.94 mmol), tetrabutylammonium hydrogen sulfate (31 mg, 0.09 mmol), and sodium hydroxide (610 mg, 15.25 mmol) dissolved in water (2 mL). The reaction mixture was stirred at room temperature for 2 h. The reaction mixture was washed with saturated aqueous sodium chloride solution. The organic layer was dried, filtered and concentrated under reduced pressure. The residue was purified by flash column chromatography on silica gel to afford 5-fluoro-4-iodo-1-(phenylsulfonyl)-1H-indole.

Step 3: To 5-fluoro-4-iodo-1-(phenylsulfonyl)-1H-indole (162 mg, 0.403 mmol) in acetonitrile (4 mL), 2-((tetrahydro-2H-pyran-4-yl)oxy)-5-(4,4,5,5-tetramethyl-1,3,2-dioxaborolan-2-yl)benzonitrile (140 mg, 0.425 mmol), [1,1'-Bis (diphenylphosphino)ferrocene]dichloropalladium(II) (32 mg, 0.039 mmol), and 2M sodium carbonate solution (690 µL, 1.38 mmol) were added. The reaction mixture was heated at 85° C. for 1 h. After cooling to room temperature, the mixture was poured into water and extracted with ethyl acetate. The combined organic layers were washed with saturated aqueous sodium chloride solution, dried, filtered and concentrated under reduced pressure. The residue was purified by flash column chromatography on silica gel to afford 5-(5-fluoro-1-(phenylsulfonyl)-1H-indol-4-yl)-2-((tetrahydro-2H-pyran-4-yl)oxy)benzonitrile.

Step 4: 5-(5-fluoro-1-(phenylsulfonyl)-1H-indol-4-yl)-2-((tetrahydro-2H-pyran-4-yl)oxy)benzonitrile (50 mg, 0.105 mmol) in 2-methyltetrahydrofuran (1 mL) was cooled to 0° C. and treated with 1M lithium diisopropylamide solution (160 µL, 0.157 mmol). The reaction was stirred at 0° C. for 30 min, and then iodine (37 mg, 0.146 mmol) dissolved in 2-methyltetrahydrofuran (0.5 mL) was added. Reaction mixture was stirred at 0° C. for another 20 min and then warmed to room temperature. It was then quenched with saturated ammonium chloride solution and extracted with ethyl acetate. The combined organic layers were washed with saturated aqueous sodium chloride solution, dried, filtered and concentrated under reduced pressure. The residue was purified by flash column chromatography on silica gel to afford 5-(5-fluoro-2-iodo-1-(phenylsulfonyl)-1H-indol-4-yl)-2-((tetrahydro-2H-pyran-4-yl)oxy)benzonitrile.

Step 5 and Step 6: The title compound was prepared by following similar procedure to synthesize Example 36.

$^1$H NMR (400 MHz, DMSO-d6) δ 12.20 (s, 1H), 8.18 (d, J=3.1 Hz, 1H), 8.02 (m, 1H), 7.95 (dd, J=9.0, 1.9 Hz, 1H), 7.83 (d, J=8.7 Hz, 2H), 7.54 (d, J=9.0 Hz, 1H), 7.00 (d, J=8.8 Hz, 2H), 6.81 (d, J=2.1 Hz, 1H), 4.92 (m, 1H), 3.88 (m, 2H), 3.73 (m, 4H), 3.55 (m, 2H), 3.18 (m, 4H), 2.05 (m, 2H), 1.71 (m, 2H). LCMS-ESI$^+$ (m/z): [M+H]$^+$ calcd for $C_{29}H_{27}FN_4O_3$: 499.2. found: 499.2.

Example 48: Preparation of 5-(2-(4-morpholinophenyl)-1H-pyrrolo[2,3-b]pyridin-4-yl)-2-((tetrahydro-2H-pyran-4-yl)oxy)benzonitrile

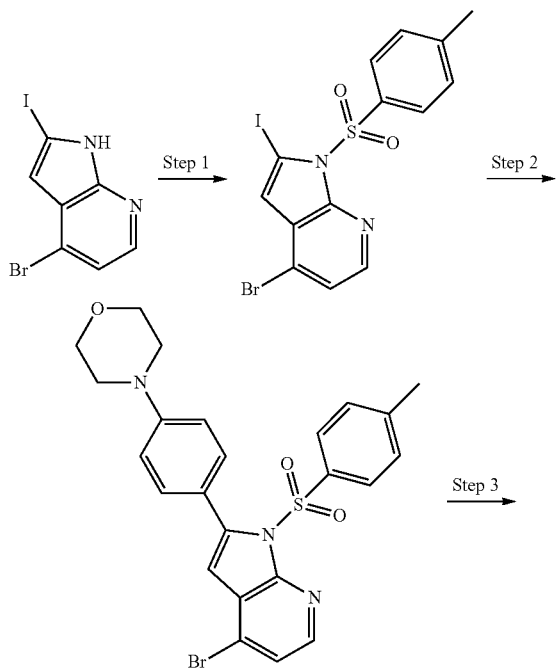

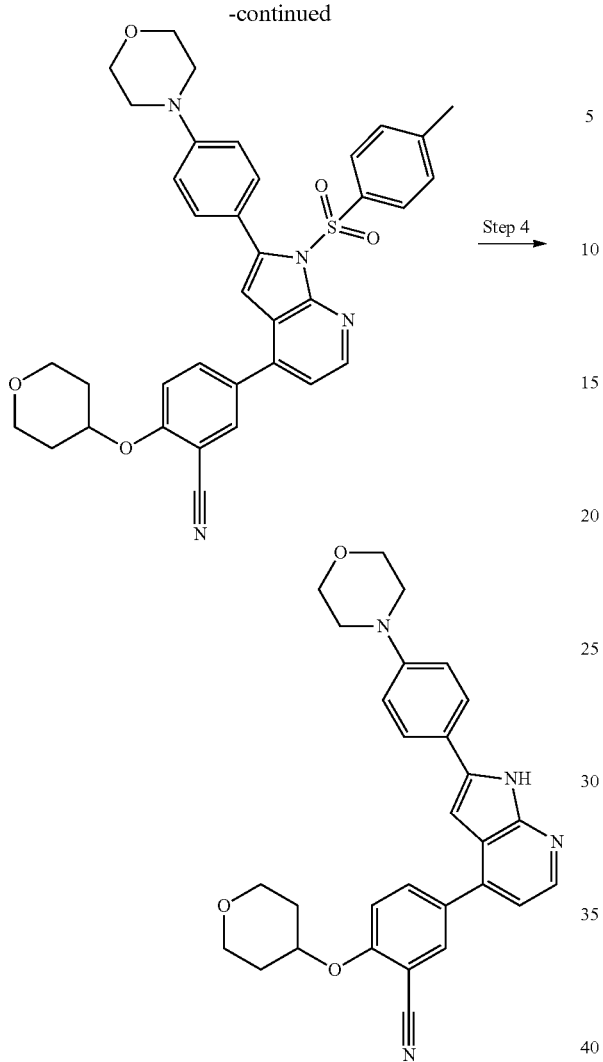

Step 1: To a solution of reagent 4-bromo-2-iodo-1H-pyrrolo[2,3-b]pyridine (1 g, 3.09 mmol) in DMF (6 mL) was added NaH (142 mg, 60% in mineral oil) at room temperature and stirred for 30 min. To this mixture was added 4-methylbenzene-1-sulfonyl chloride (649.5 mg, 3.1 mmol) at once and stirred overnight. The reaction mixture was added water drop wish (5 mL), the solid particle was filtered and washed with water. The residue was purified by flash column chromatography on silica gel to afford 4-bromo-2-iodo-1-tosyl-1H-pyrrolo[2,3-b]pyridine. LCMS-ESI+ (m/z): [M+H]+ calcd for $C_{14}H_{10}BrIN_2O_2S$: 478.1. found: 478.9.

Step 2: To stirring solution of 4-bromo-2-iodo-1-tosyl-1H-pyrrolo[2,3-b]pyridine (700 mg, 1.46 mmol), 4-(4-(4,4,5,5-tetramethyl-1,3,2-dioxaborolan-2-yl)phenyl)morpholine (636.4 mg, 2.20 mmol), and PdCl$_2$(Ph$_3$P)$_2$ (1.3 mg, 0.14 mmol) in DMF (15 mL) were added solution of NaHCO$_3$ (370 mg, 4.40 mmol) in water (7 mL). The reaction was stirred at 100° C. for 1 h. The reaction mixture was diluted with dichloromethane and filtered through pad of silica gel washed with 10% MeOH/DCM (100 mL) and solvent was concentrated to dryness. The residue was purified by flash column chromatography on silica gel to afford 4-(4-(4-bromo-1-tosyl-1H-pyrrolo[2,3-b]pyridin-2-yl)phenyl)morpholine. LCMS-ESI+ (m/z): [M+H]+ calcd for $C_{24}H_{22}BrN_3O_3S$: 512.1. found: 512.10.

Step 3: To stirred mixture of 4-(4-(4-bromo-1-tosyl-1H-pyrrolo[2,3-b]pyridin-2-yl)phenyl)morpholine (100 mg, 0.19 mmol), 2-((tetrahydro-2H-pyran-4-yl)oxy)-5-(4,4,5,5-tetramethyl-1,3,2-dioxaborolan-2-yl)benzonitrile (77.1 mg, 0.23 mmol), PEPPSI-iPr catalyst (26.6 mg, 0.039 mmol) in dioxane (4 mL) was added solution of Cs$_2$CO$_3$ (190.3 mg, 0.69 mmol) in Water (2 mL) and heated at 100° C. for 2 h. The reaction mixture was cooled to room temperature, diluted with dichloromethane and poured in to water. The organic layer separated, dried over Na$_2$SO$_4$ and the solvent was concentrated to dryness. The residue was purified by flash column chromatography on silica gel to afford 5-(2-(4-morpholinophenyl)-1-tosyl-1H-pyrrolo[2,3-b]pyridin-4-yl)-2-((tetrahydro-2H-pyran-4-yl)oxy)benzonitrile.
cLCMS-ESI+ (m/z): [M+H]+ calcd for $C_{36}H_{34}N_4O_5S$: 512.1. found: 512.10.

Step 4: To 5-(2-(4-morpholinophenyl)-1-tosyl-1H-pyrrolo[2,3-b]pyridin-4-yl)-2-((tetrahydro-2H-pyran-4-yl)oxy)benzonitrile (120 mg, 0.189 mmol) in MeOH (5 mL) was added fine powder of K$_2$CO$_3$. This mixture was heated at 85° C. for 4 h. The solvent was concentrated and the crude product was purified by flash column chromatography on silica gel to afford 5-(2-(4-morpholinophenyl)-1H-pyrrolo[2,3-b]pyridin-4-yl)-2-((tetrahydro-2H-pyran-4-yl)oxy)benzonitrile.
$^1$H NMR (400 MHz, DMSO-d6) δ 12.18 (s, —NH), 8.19 (br s, 1H), 8.13 (d, J=2 Hz, 1H), 8.09 (dd, J=8.8, 2.0 Hz, 1H), 7.86 (d, J=8.4 Hz, 2H), 7.53 (d, J=8.8 Hz, 1H), 7.19, (d, J=5.2 Hz, 1H), 7.02 (s, 1H), 7.00 (d, J=4.4 Hz, 1H), 4.92 (m, 1H), 3.90-3.72 (m, 8H), 3.57-3.52 (m, 4H), 3.19-3.17 (m, 4H), 2.06-2.03 (m, 2H), 1.73-1.66 (m, 2H). LCMS-ESI+ (m/z): [M+H]+ calcd for $C_{29}H_{28}N_4O_3$: 481.2. found: 481.2.

Example 49: Preparation of 5-(2-(4-morpholinophenyl)-1H-pyrrolo[2,3-b]pyridin-4-yl)-2-(pyrrolidin-1-yl)benzonitrile

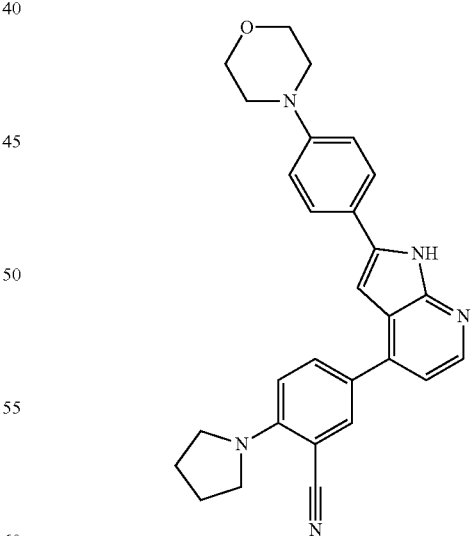

Following similar procedure to synthesize Example 48, 5-(2-(4-morpholinophenyl)-1H-pyrrolo[2,3-b]pyridin-4-yl)-2-(pyrrolidin-1-yl)benzonitrile was synthesized.
$^1$H NMR (400 MHz, DMSO-d6) δ 12.32 (s, —NH), 8.18 (d, J=5.2 Hz, 1H), 7.94-7.92 (m, 2H), 7.86 (d, J=8.4 Hz, 2H), 7.23 (d, J=5.2 Hz, 1H), 7.03-7.01 (m, 3H), 6.96, (d, J=9.6

Hz, 1H), 3.72-3.61 (m, 8H), 3.19-3.17 (m, 4H), 1.98-1.96 (m, 4H). LCMS-ESI⁺ (m/z): [M+H]⁺ calcd for C₂₈H₂₇N₅O: 450.6. found: 450.5.

Example 50: Preparation of 5-(2-cyclopropyl-1H-pyrrolo[2,3-b]pyridin-4-yl)-2-((tetrahydro-2H-pyran-4-yl)oxy)benzonitrile

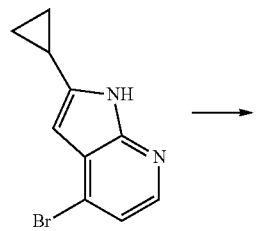

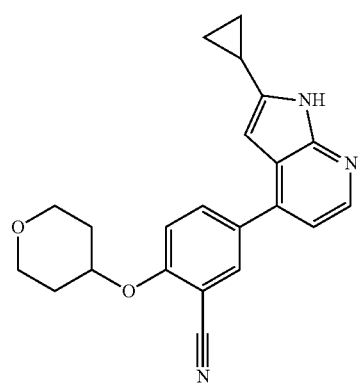

To stirred mixture of 4-bromo-2-cyclopropyl-1H-pyrrolo[2,3-b]pyridine (200 mg, 0.84 mmol), 2-((tetrahydro-2H-pyran-4-yl)oxy)-5-(4,4,5,5-tetramethyl-1,3,2-dioxaborolan-2-yl)benzonitrile (333.2 mg, 1.01 mmol), PEPPSI-iPr catalyst (115.0 mg, 0.169 mmol) in dioxane (6 mL) was added solution of Cs₂CO₃ (822.5 mg, 2.53 mmol) in water (3 mL) and heated at 85° C. for 3 h. The reaction mixture was cooled to room temperature, diluted with dichloromethane and poured in to water. The organic layer separated, dried over Na₂SO₄ and the solvent was concentrated to dryness. The residue was purified via prep HPLC (5-95% acetonitrile in water, 0.1% trifluoroacetic acid buffer) to isolate 5-(2-cyclopropyl-1H-pyrrolo[2,3-b]pyridin-4-yl)-2-((tetrahydro-2H-pyran-4-yl)oxy)benzonitrile.

¹H NMR (400 MHz, DMSO-d6) δ 11.78 (s, —NH), 8.15 (d, J=5.2 Hz, 1H), 8.05 (d, J=2.4, 1H), 8.01 (dd, J=8.8, 2.4 Hz, 2H), 7.50 (d, J=8.8 Hz, 1H), 7.17 (d, J=5.2 Hz, 1H), 6.3 (d, J=1.2 Hz, 1H), 4.90-4.88 (m, 1H), 3.89-3.83 (m, 2H), 3.57-3.51 (m, 2H), 2.07-2.01 (m, 3H), 1.71-1.66 (m, 2H), 1.02-0.97 (m, 2H) 0.89-0.86 (m, 2H). LCMS-ESI⁺ (m/z): [M+H]⁺ calcd for C₂₂H₂₁N₃O₂: 360.4. found: 360.2.

Example 51: Preparation of 5-(2-(1-(tetrahydro-2H-pyran-4-yl)-1H-pyrazol-4-yl)-1H-pyrrolo[2,3-b]pyridin-4-yl)-2-((tetrahydro-2H-pyran-4-yl)oxy)benzonitrile

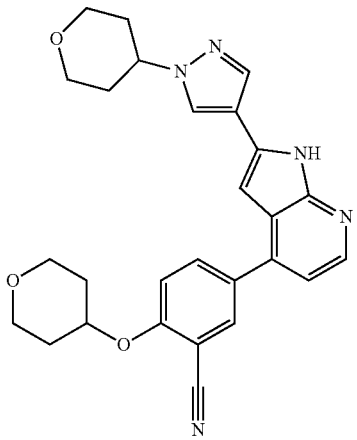 [SMILES: N#Cc1cc(-c2ccnc3[nH]c(-c4cnn(C5CCOCC5)c4)cc23)ccc1OC1CCOCC1]

Following similar procedure to synthesize Example 48, 5-(2-(1-(tetrahydro-2H-pyran-4-yl)-1H-pyrazol-4-yl)-1H-pyrrolo[2,3-b]pyridin-4-yl)-2-((tetrahydro-2H-pyran-4-yl)oxy)benzonitrile was synthesized.

¹H NMR (400 MHz, DMSO-d6) δ 12.07 (s, —NH), 8.36 (s, 1H), 8.16 (t, J=3.6 Hz, 1H), 8.09 (d, J=2 Hz, 1H), 8.06 (dd, J=10.4, 2.6 Hz, 2H), 7.83 (d, J=7.2 Hz, 1H), 7.53 (d, J=9.2 Hz, 1H), 7.15 (d, J=5.2 Hz, 1H), 6.80 (d, J=1.6 Hz, 1H) 4.93-4.46 (m, 1H), 4.45-4.39 (m, 1H), 4.03-3.95 (m, 2H), 3.89-3.81 (m, 2H), 3.57-3.52 (m, 4H), 2.01-1.69 (m, 8H). LCMS-ESI⁺ (m/z): [M+H]⁺ calcd for C₂₇H₂₇N₅O₃: 470.6. found: 470.2.

Example 52: Preparation of 2-(3-hydroxyazetidin-1-yl)-5-(2-(4-morpholinophenyl)-1H-pyrrolo[2,3-b]pyridin-4-yl)benzonitrile

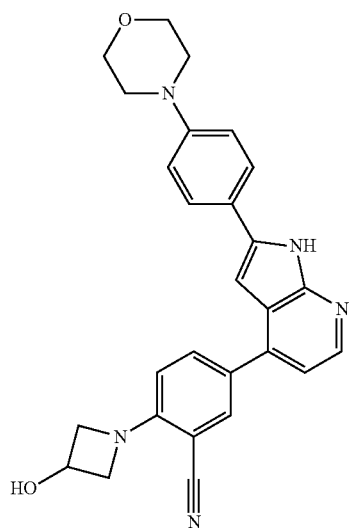

The title compound was prepared from Intermediate 2-fluoro-5-(2-(4-morpholinophenyl)-1-(phenylsulfonyl)-

1H-pyrrolo[2,3-b]pyridin-4-yl)benzonitrile (Example 58) by displacing the fluoro substituent with azetidin-3-ol and followed by deprotection $^1$H NMR (400 MHz, DMSO-d$_6$) δ 12.05 (s, 1H), 8.14 (d, J=5.0 Hz, 1H), 7.94-7.87 (m, 2H), 7.87-7.80 (m, 2H), 7.11 (d, J=5.1 Hz, 1H), 7.05-6.95 (m, 2H), 6.92 (d, J=2.1 Hz, 1H), 6.74 (d, J=8.6 Hz, 1H), 5.76 (d, J=6.3 Hz, 1H), 4.71-4.51 (m, 1H), 4.52-4.29 (m, 2H), 4.01-3.82 (m, 2H), 3.74 (t, J=4.8 Hz, 4H), 3.17 (t, J=4.8 Hz, 4H). LCMS-ESI$^+$ (m/z): [M+H]$^+$ calcd for C$_{27}$H$_{25}$N$_5$O$_2$: 452.5. found: 452.3.

Example 53: Preparation of 5-(2-(1-(tert-butyl)-1H-pyrazol-4-yl)-1H-pyrrolo[2,3-b]pyridin-4-yl)-2-((tetrahydro-2H-pyran-4-yl)oxy)benzonitrile

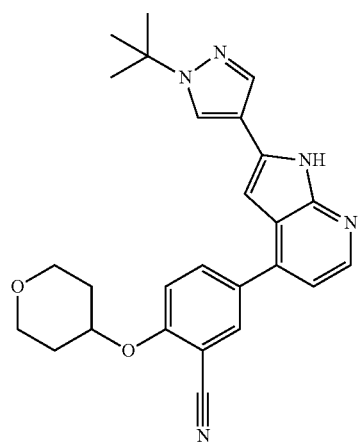 [SMILES: CC(C)(C)n1cc(-c2cc3c(-c4ccc(OC5CCOCC5)c(C#N)c4)ccnc3[nH]2)cn1]

Following similar procedure to synthesize Example 48, 5-(2-(1-(tert-butyl)-1H-pyrazol-4-yl)-1H-pyrrolo[2,3-b]pyridin-4-yl)-2-((tetrahydro-2H-pyran-4-yl)oxy)benzonitrile was synthesized.

$^1$H NMR (400 MHz, DMSO-d6) δ 12.01 (s, —NH), 8.43 (d, J=4.0 Hz, 1H), 8.16 (d, J=4 Hz, 1H), 8.08 (d, J=8 Hz, 1H), 8.05-8.02 (m, 2H), 7.53 (d, J=4 Hz, 1H), 7.35 (d, J=4.0 Hz, 1H), 6.81 (d, J=4.0 Hz, 1H), 4.93-4.89 (m, 1H) 3.90-3.85 (m, 2H), 3.58-3.52 (m, 2H), 2.06-2.02 (m, 2H), 1.74-1.65 (m, 2H), 1.55 (s, 9H). LCMS-ESI$^+$ (m/z): [M+H]$^+$ calcd for C$_{26}$H$_{27}$N$_5$O$_2$: 442.5. found: 442.2.

Example 54: Preparation of 5-(2-(4-(piperazin-1-yl)phenyl)-1H-pyrrolo[2,3-b]pyridin-4-yl)-2-((tetrahydro-2H-pyran-4-yl)oxy)benzonitrile

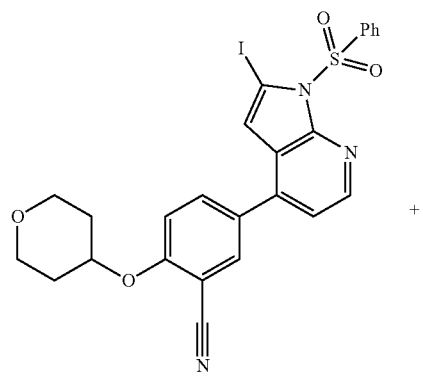

+

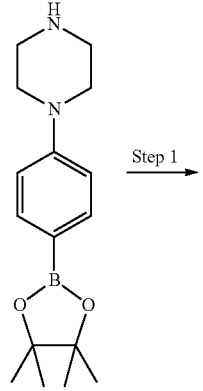

Step 1

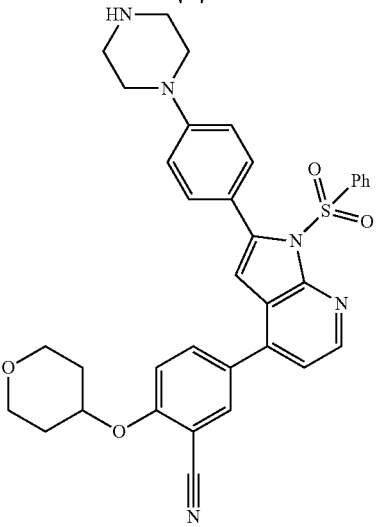

Step 2

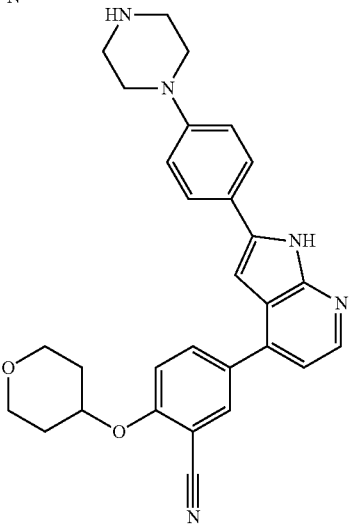

Step 1: To stirring solution of 5-(2-iodo-1-(phenylsulfonyl)-1H-pyrrolo[2,3-b]pyridin-4-yl)-2-((tetrahydro-2H-pyran-4-yl)oxy)benzonitrile (500 mg, 0.85 mmol), 1-(4-(4,4,5,5-tetramethyl-1,3,2-dioxaborolan-2-yl)phenyl)piperazine (270.7 mg, 0.94 mmol), and PdCl$_2$(Ph$_3$P)$_2$ (60 mg, 0.085 mmol) in DMF (12 mL) were added solution of NaHCO$_3$ (215 mg, 2.56 mmol) in water (6 mL). The reaction was stirred at 100° C. for 1 h. The reaction mixture was diluted with dichloromethane, filtered through pad of silica gel washed with 10% MeOH/DCM and the solvent concentrated to dryness. The residue was purified by flash column chromatography on silica gel to afford 5-(1-(phenylsulfo-nyl)-2-(4-(piperazin-1-yl)phenyl)-1H-pyrrolo[2,3-b]pyridin-4-yl)-2-((tetrahydro-2H-pyran-4-yl)oxy)benzonitrile.

LCMS-ESI⁺ (m/z): [M+H]⁺ calcd for $C_{35}H_{33}N_5O_4S$: 620.7. found: 620.2.

Step 2: The 5-(1-(phenylsulfonyl)-2-(4-(piperazin-1-yl)phenyl)-1H-pyrrolo[2,3-b]pyridin-4-yl)-2-((tetrahydro-2H-pyran-4-yl)oxy)benzonitrile (35.2 mg, 0.05 mmol) was dissolved in a mixture of 2,2,2,-Trifluoroethanol, Me-THF (2:1) and added $Cs_2CO_3$ (55.2 mg, 0.17 mmol). This mixture was heated at 100° C. for 12 h. The reaction mixture was cooled to room temperature, diluted with dichloromethane and filtered through pad of silica gel and washed with 10% MeOH/DCM. The solvent was concentrated to dryness. The residue was purified via prep HPLC (5-95% acetonitrile in water, 0.1% trifluoroacetic acid buffer) to isolate 5-(2-(4-(piperazin-1-yl)phenyl)-1H-pyrrolo[2,3-b]pyridin-4-yl)-2-((tetrahydro-2H-pyran-4-yl)oxy)benzonitrile.

¹H NMR (400 MHz, CDCl₃) b 9.72 (s, —NH), 8.11 (d, J=6 Hz, 1H), 8.05 (d, J=2.4 Hz, 1H), 7.97 (dd, J=8.8, 2.0 Hz, 1H), 7.84 (d, J=8.8 Hz, 2H), 7.31 (d, J=6.0 Hz, 1H), 7.24, (d, J=9.2 Hz, 1H), 7.05 (d, J=8.8 Hz, 2H), 6.94 (s, 1H), 4.82-4.79 (m, 1H), 4.09-4.04 (m, 2H), 3.72-3.66 (m, 2H), 3.57-3.56 (m, 4H), 3.40-3.39 (m, 4H), 2.16-2.11 (m, 2H), 2.01-1.95 (m, 2H). LCMS-ESI⁺ (m/z): [M+H]⁺ calcd for $C_{29}H_{29}N_5O_2$: 480.6. found: 480.2.

Example 55: Preparation of 5-(2-(4-(4-(methylsulfonyl)piperazin-1-yl)phenyl)-1H-pyrrolo[2,3-b]pyridin-4-yl)-2-((tetrahydro-2H-pyran-4-yl)oxy)benzonitrile

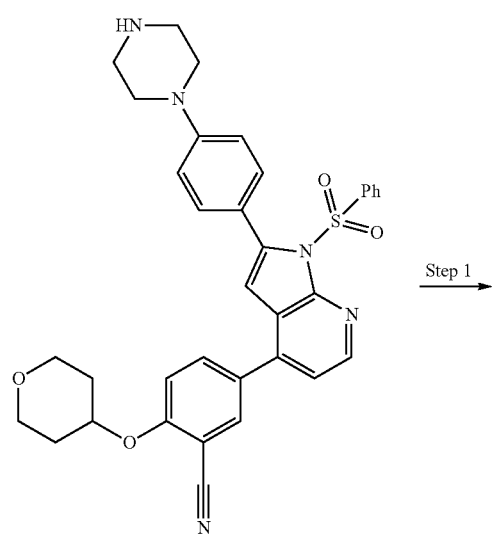

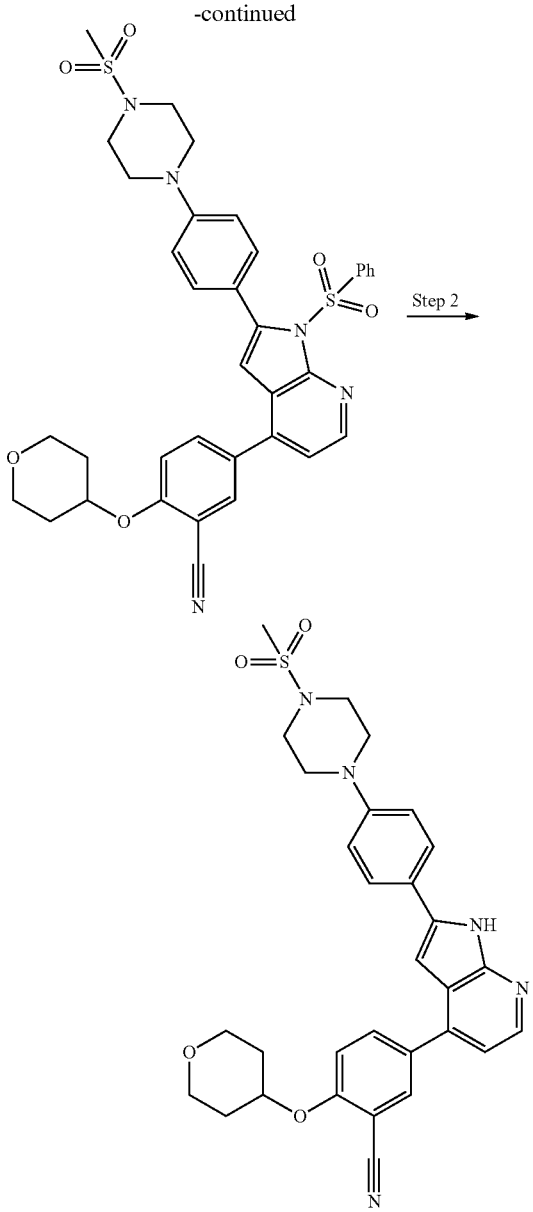

To solution of compound 5-(1-(phenylsulfonyl)-2-(4-(piperazin-1-yl)phenyl)-1H-pyrrolo[2,3-b]pyridin-4-yl)-2-((tetrahydro-2H-pyran-4-yl)oxy)benzonitrile (50 mg, 0.08 mmol) in dichloromethane (2 mL) were added pyridine (31.9 mg, 0.40 mmol) followed by methane sulfonyl chloride (18.5 mg, 0.16 mmol) in a 10 mL microwave vial and sealed. This reaction mixture was stirred at room temperature overnight. The solvent was concentrated to dryness. The crude product was dissolved in a mixture of 2,2,2,-Trifluoroethanol, Me-THF (2:1) and added $Cs_2CO_3$ (63 mg, 0.19 mmol). This mixture was heated at 100° C. for 12 h. The reaction mixture was cooled to room temperature, diluted with dichloromethane and filtered through pad of silica gel and washed with 10% MeOH/DCM. The solvent was concentrated and the crude product was purified by flash column chromatography on silica gel to afford 5-(2-(4-(4-(methylsulfonyl)piperazin-1-yl)phenyl)-1H-pyrrolo[2,3-b]pyridin-4-yl)-2-((tetrahydro-2H-pyran-4-yl)oxy)benzonitrile. ¹H NMR (400 MHz, DMSO-d6) δ 12.12 (s, —NH), 8.19 (d, J=5.2 Hz, 1H), 8.12 (d, J=2.4 Hz, 1H), 8.06 (dd, J=8.8, 2.0 Hz, 1H), 7.88 (d, J=8.8 Hz, 2H), 7.52 (d, J=9.2 Hz, 1H), 7.17, (d, J=5.2 Hz, 1H), 7.05 (d, J=9.2 Hz, 2H), 6.98 (d, J=2.4 Hz, 1H), 4.92-4.89 (m, 1H), 3.91-3.85 (m, 2H), 3.58-3.53 (m, 2H), 3.34-3.32 (m, 4H), 3.25-3.32 (m, 4H), 2.91 (s, 3H), 2.05-2.03 (m, 2H), 1.74-1.67 (m, 2H). LCMS-ESI+ (m/z): [M+H]+ calcd for $C_{30}H_{31}N_5O_4S$: 558.7. found: 558.2.

Example 56: Preparation of 5-(2-(4-(4-(2-hydroxyacetyl)piperazin-1-yl)phenyl)-1H-pyrrolo[2,3-b]pyridin-4-yl)-2-((tetrahydro-2H-pyran-4-yl)oxy)benzonitrile

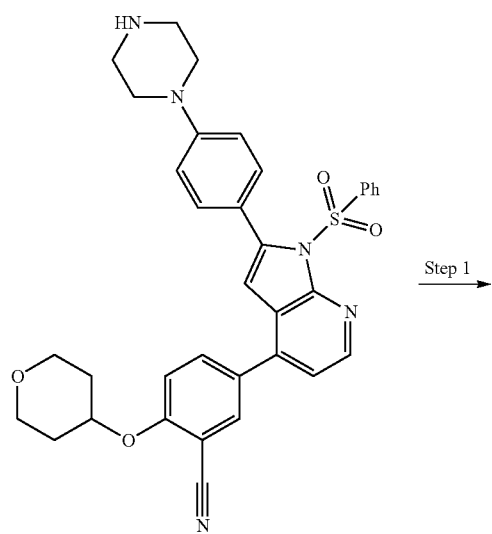

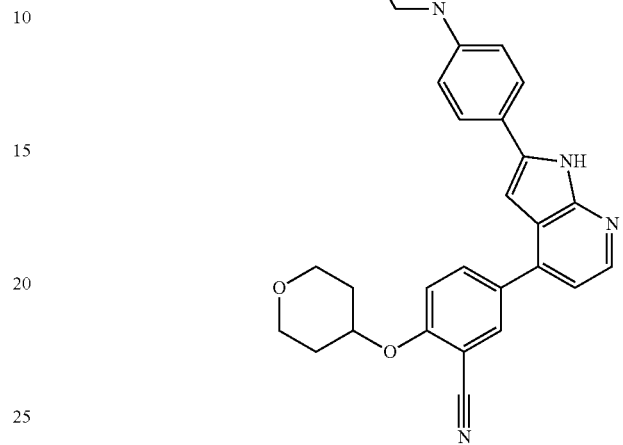

To solution of compound 5-(1-(phenylsulfonyl)-2-(4-(piperazin-1-yl)phenyl)-1H-pyrrolo[2,3-b]pyridin-4-yl)-2-((tetrahydro-2H-pyran-4-yl)oxy)benzonitrile (50 mg, 0.08 mmol), glycolic acid (12.3 mg, 0.16 mmol), HATU (61.4 mg, 0.16 mmol) in dichloromethane (2 mL) was added DIPEA (168.7 mg, 0.96 mmol) in a 10 mL microwave vial and sealed. This reaction mixture was stirred at room temperature overnight. The solvent was concentrated to dryness. The crude product was dissolved in a mixture of 2,2,2,-Trifluoroethanol, Me-THF (2:1) and added $Cs_2CO_3$ (63 mg, 0.19 mmol). This mixture was heated at 100° C. for 12 h. The reaction mixture was cooled to room temperature, diluted with dichloromethane and filtered through pad of silica gel and washed with 10% MeOH/DCM. The solvent was concentrated and the crude product was purified by flash column chromatography on silica gel to afford 5-(2-(4-(4-(2-hydroxyacetyl)piperazin-1-yl)phenyl)-1H-pyrrolo[2,3-b]pyridin-4-yl)-2-((tetrahydro-2H-pyran-4-yl)oxy)benzonitrile.

$^1$H NMR (400 MHz, DMSO-d6) δ 12.11 (s, —NH), 8.19 (d, J=4.8 Hz, 1H), 8.12 (d, J=2.0 Hz, 1H), 8.08 (dd, J=9.2, 2.4 Hz, 1H), 7.86 (d, J=8.4 Hz, 2H), 7.52 (d, J=9.2 Hz, 1H), 7.16, (d, J=5.2 Hz, 1H), 7.05 (d, J=8.8 Hz, 2H), 6.97 (d, J=2 Hz, 1H), 4.93-4.90 (m, 1H), 4.61 (t, J=5.6 Hz, 1H) 4.13 (d, J=5.6 Hz, 2H), 3.90-3.85 (m, 2H), 3.62-3.56 (m, 4H), 3.55-3.52 (m, 2H), 3.15-3.11 (m, 4H), 2.05-2.03 (m, 2H), 1.73-1.68 (m, 2H).

LCMS-ESI+ (m/z): [M+H]+ calcd for $C_{31}H_{31}N_5O_4$: 538.6. found: 538.2.

Example 57: Preparation of 5-(2-(4-(4-(2-cyanoacetyl)piperazin-1-yl)phenyl)-1H-pyrrolo[2,3-b]pyridin-4-yl)-2-((tetrahydro-2H-pyran-4-yl)oxy)benzonitrile

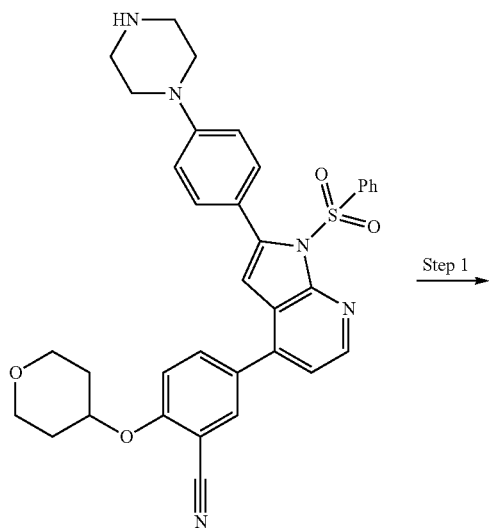

Step 1 →

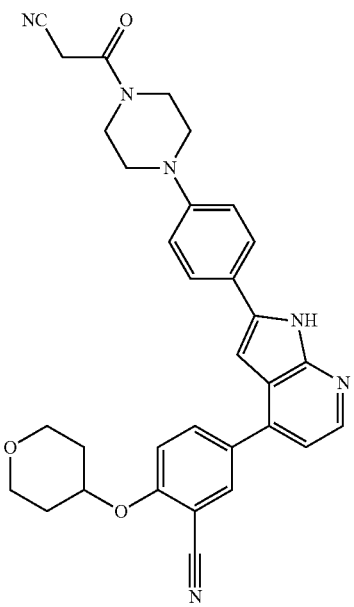

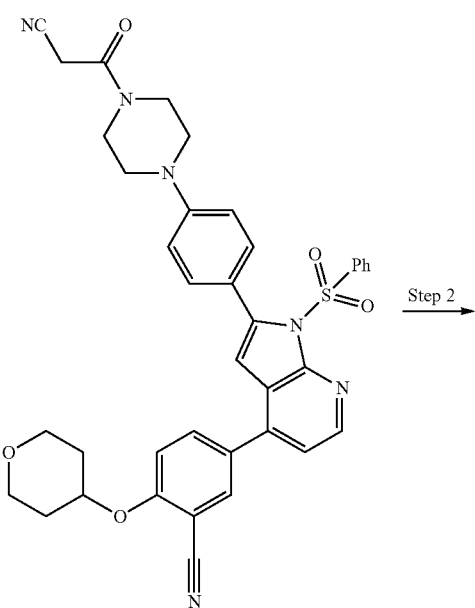

Step 2 →

To solution of compound 5-(1-(phenylsulfonyl)-2-(4-(piperazin-1-yl)phenyl)-1H-pyrrolo[2,3-b]pyridin-4-yl)-2-((tetrahydro-2H-pyran-4-yl)oxy)benzonitrile (50 mg, 0.08 mmol), 2-cyanoacetic acid (13.7 mg, 0.16 mmol), HATU (61.4 mg, 0.16 mmol) in dichloromethane (2 mL) was added DIPEA (168.7 mg, 0.96 mmol) in a 10 mL microwave vial and sealed. This reaction mixture was stirred at room temperature overnight. The solvent was concentrated to dryness. The crude product was dissolved in a mixture of 2,2,2,-Trifluoroethanol, Me-THF (2:1) and added $Cs_2CO_3$ (63 mg, 0.19 mmol). This mixture was heated at 100° C. for 12 h. The reaction mixture was cooled to room temperature, diluted with dichloromethane and filtered through pad of silica gel and washed with 10% MeOH/DCM. The solvent was concentrated and the crude product was purified by flash column chromatography on silica gel to afford 5-(2-(4-(4-(2-cyanoacetyl)piperazin-1-yl)phenyl)-1H-pyrrolo[2,3-b]pyridin-4-yvl)-2-((tetrahydro-2H-pyran-4-yl)oxy)benzonitrile.

$^1$H NMR (400 MHz, DMSO-d6) δ 12.11 (s, —NH), 8.19 (d, J=4.8 Hz, 1H), 8.12 (d, J=2.0 Hz, 1H), 8.08 (dd, J=9.2, 2.4 Hz, 1H), 7.86 (d, J=8.4 Hz, 2H), 7.52 (d, J=9.2 Hz, 1H), 7.16, (d, J=5.2 Hz, 1H), 7.03 (d, J=8.8 Hz, 2H), 6.97 (d, J=2.0 Hz, 1H), 4.93-4.89 (m, 1H), 4.09 (s, 2H), 3.90-3.85 (m, 2H), 3.62-3.55 (m, 4H), 3.54-3.48 (m, 2H), 3.23-3.21 (m, 4H), 2.05-2.03 (m, 2H), 1.74-1.66 (m, 2H). LCMS-ESI$^+$ (m/z): [M+H]$^+$ calcd for $C_{32}H_{30}N_6O_3$: 547.6; found: 547.3.

Example 58: Preparation of 2-fluoro-5-(2-(4-morpholinophenyl)-1H-pyrrolo[2,3-b]pyridin-4-yl)benzonitrile

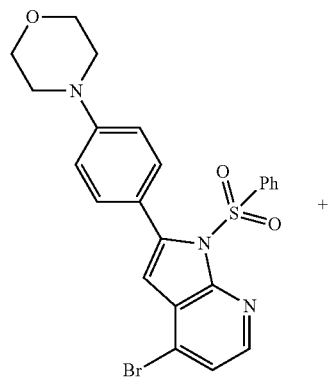

+

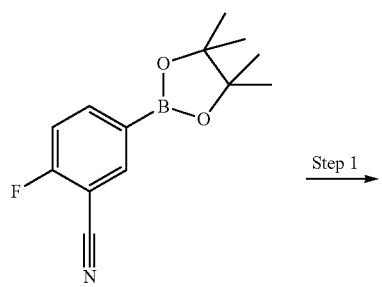

→ Step 1

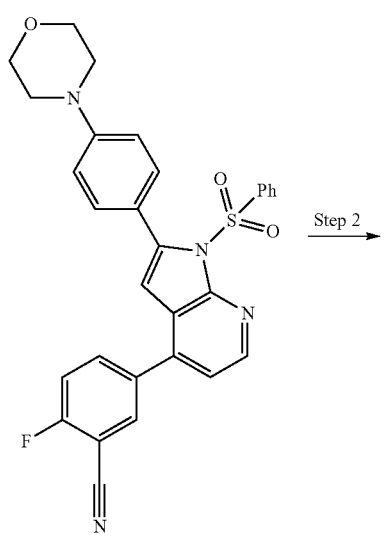

→ Step 2

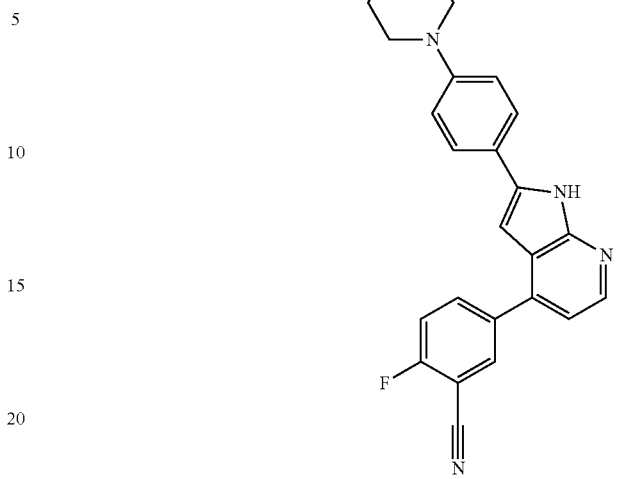

Step 1: To stirring solution of 4-(4-(4-bromo-1-(phenylsulfonyl)-1H-pyrrolo[2,3-b]pyridin-2-yl)phenyl)morpholine (500 mg, 1.0 mmol), 2-fluoro-5-(4,4,5,5-tetramethyl-1,3,2-dioxaborolan-2-yl)benzonitrile (272.6 mg, 1.1 mmol), and PdCl$_2$(Ph$_3$P)$_2$ (70.4 mg, 0.07 mmol) in DMF (12 mL) were added solution of NaHCO$_3$ (233 mg, 3.01 mmol) in water (6 mL). The reaction was stirred at 100° C. for 1 h. The reaction mixture was diluted with dichloromethane, filtered through pad of silica gel washed with 10% MeOH/DCM and the solvent concentrated to dryness. The residue was purified by flash column chromatography on silica gel to afford 2-fluoro-5-(2-(4-morpholinophenyl)-1-(phenylsulfonyl)-1H-pyrrolo[2,3-b]pyridin-4-yl)benzonitrile.

LCMS-ESI$^+$ (m/z): [M+H]$^+$ calcd for C$_{30}$H$_{23}$FN$_4$O$_3$S: 538.6. found: 539.2.

Step 2: The 2-fluoro-5-(2-(4-morpholinophenyl)-1-(phenylsulfonyl)-1H-pyrrolo[2,3-b]pyridin-4-yl)benzonitrile (40 mg, 0.06 mmol) was dissolved in a mixture of 2,2,2,-Trifluoroethanol, Me-THF (2:1) and added Cs$_2$CO$_3$ (63 mg, 0.19 mmol). This mixture was heated at 100° C. for 12 h. The reaction mixture was cooled to room temperature, diluted with dichloromethane and filtered through pad of silica gel and washed with 10% MeOH/DCM. The solvent was concentrated to dryness. The residue was purified via prep HPLC (5-95% acetonitrile in water, 0.1% trifluoroacetic acid buffer) to isolate 2-fluoro-5-(2-(4-morpholinophenyl)-1H-pyrrolo[2,3-b]pyridin-4-yl)benzonitrile. $^1$H NMR (400 MHz, DMSO-d6) δ 12.13 (s, —NH), 8.20 (d, J=4.8 Hz, 1H), 8.19 (d, J=2.0 Hz, 1H), 8.16 (dd, J=9.2, 2.4 Hz, 1H), 7.86 (d, J=8.4 Hz, 2H), 7.56 (d, J=8.8 Hz, 1H), 7.19 (d, J=5.2 Hz, 1H), 7.02 (d, J=9.2 Hz, 2H), 6.99 (d, J=2.0 Hz, 1H), 3.73 (t, J=4.4 Hz, 4H), 3.19 (t, J=4.8 Hz, 4H). LCMS-ESI$^+$ (m/z): [M+H]$^+$ calcd for C$_{24}$H$_{19}$FN$_4$O: 399.4. found: 399.2.

Example 59: Preparation of 4-(3-cyano-4-((tetrahydro-2H-pyran-4-yl)oxy)phenyl)-N-cyclopropyl-1H-pyrrolo[2,3-b]pyridine-2-carboxamide

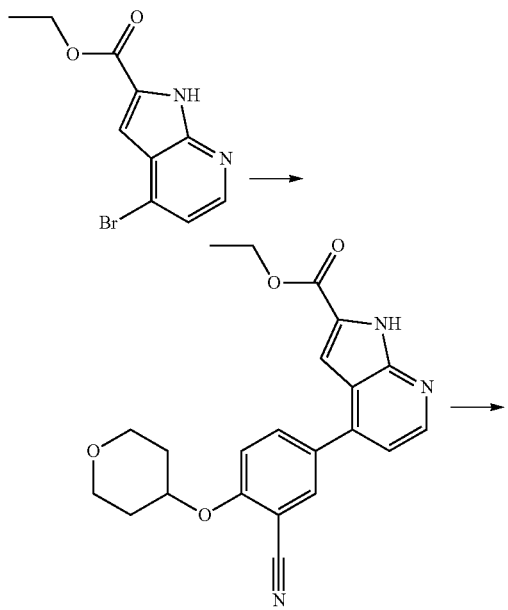

Step 1: To a mixture ethyl 4-bromo-1H-pyrrolo[2,3-b]pyridine-2-carboxylate (500 mgs, 1.86 mmol) and 2-((tetrahydro-2H-pyran-4-yl)oxy)-5-(4,4,5,5-tetramethyl-1,3,2-dioxaborolan-2-yl)benzonitrile (673 mgs, 2.0 mmol) in DME (6 mL) was 2.0 M aqueous $Na_2CO_3$ (2.0 mL, 4 mmol) and $Pd(PPh_3)_4$ (107 mgs, 0.09 mmol). The reaction mixture was heated at 140° C. for 1 hr. After cooling to rt, ethyl acetate (10 mL) and water (20 mL) was added and the solids were filtered and washed with water and dried to give ethyl 4-(3-cyano-4-((tetrahydro-2H-pyran-4-yl)oxy)phenyl)-1H-pyrrolo[2,3-b]pyridine-2-carboxylate (500 mgs) LCMS-ESI$^+$ (m/z): [M+H]$^+$ calcd for $C_{22}H_{21}N_3O_4$ as (M+H)$^+$ 392.4. found: 392.1.

Step 2: To a stirred solution of ethyl 4-(3-cyano-4-((tetrahydro-2H-pyran-4-yl)oxy)phenyl)-1H-pyrrolo[2,3-b]pyridine-2-carboxylate (500 mgs, 1.27 mmol) in Ethanol/Tetrahydrofuran (10 mL, 1:1) was added 2M aqueous lithium hydroxide (1.27 mmL, 2 equiv.). After 1 h at 60° C., the reaction mixture was concentrated in vacuo, diluted into water, washed with ether (2x) and the aq layer pH adjusted to ~7 with 1N aqueous hydrochloric acid, the solids formed were collected by filtration and dried in vacuo to give 4-(3-cyano-4-((tetrahydro-2H-pyran-4-yl)oxy)phenyl)-1H-pyrrolo[2,3-b]pyridine-2-carboxylic acid (203 mgs). LCMS-ESI$^+$ (m/z): [M+H]$^+$ calcd for $C_{20}H_{17}N_3O_4$ as (M+H)$^+$ 364.4. found: 364.1.

Step 3: To a mixture of 4-(3-cyano-4-((tetrahydro-2H-pyran-4-yl)oxy)phenyl)-1H-pyrrolo[2,3-b]pyridine-2-carboxylic acid (30 mgs, 0.083 mmol), cyclopropylamine (0.012 mL, 0.165 mmol) and HATU (48 mgs, 0.132 mmol) in DMF (1 mL) was added DIPEA (0.05 mL, 0.25 mmol) and the resulting solution was stirred at 55° C. for 3 hr. Additional cyclopropyl amine (0.1 mL) was added and stirred at 55° C. After 16 h, the crude mixture was concentrated and purified by reverse phase chromatography to give the title compound as TFA salt. LCMS-ESI$^+$ (m/z): [M+H]$^+$ calcd for $C_{23}H_{22}N_4O_3$ as (M+H)$^+$ 403.4. found: 403.1 $^1$H NMR (400 MHz, DMSO-$d_6$) δ 12.21 (s, 1H), 8.47 (d, J=4.0 Hz, 1H), 8.31 (d, J=4.9 Hz, 1H), 8.05 (d, J=2.3 Hz, 1H), 7.97 (dd, J=8.8, 2.4 Hz, 1H), 7.49 (d, J=8.9 Hz, 1H), 7.25-7.18 (m, 2H), 4.90-4.85 (m, 1H), 3.85-3.79 (m, 2H), 3.64-3.47 (m, 2H), 2.82-2.77 (m, 1H), 2.02-1.95 (m, 2H), 1.68-1.60 (m, 2H), 0.69-0.65 (m, 2H), 0.54-0.50 (m, 2H)

Example 60: Preparation of 4-(3-cyano-4-((tetrahydro-2H-pyran-4-yl)oxy)phenyl)-N-isopropyl-1H-pyrrolo[2,3-b]pyridine-2-carboxamide

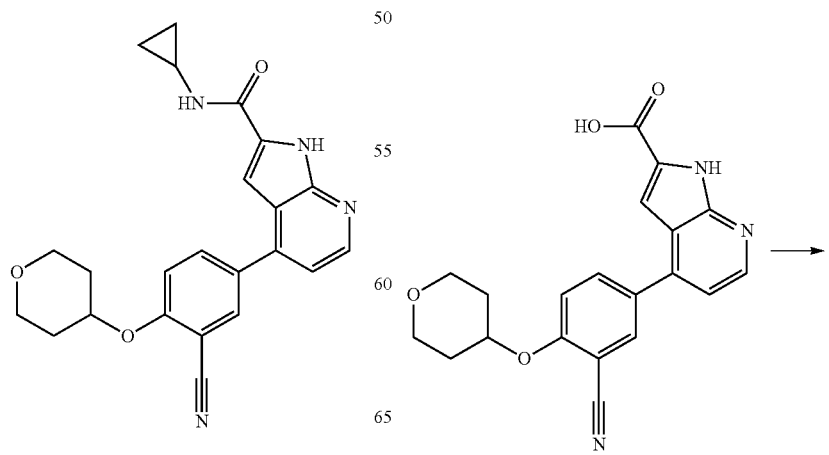

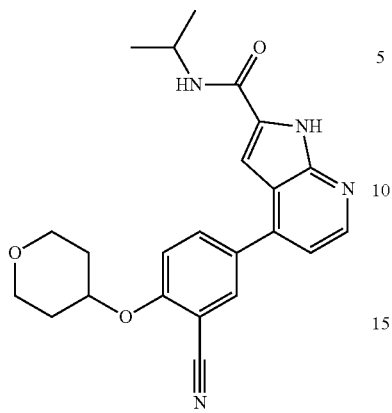

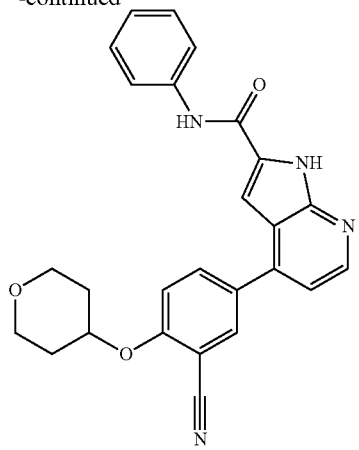

To a mixture of 4-(3-cyano-4-((tetrahydro-2H-pyran-4-yl)oxy)phenyl)-1H-pyrrolo[2,3-b]pyridine-2-carboxylic acid (30 mgs, 0.083 mmol), isopropylamine (0.012 mL, 0.165 mmol) and HATU (48 mgs, 0.132 mmol) in DMF (1 mL) was added DIPEA (0.05 mL, 0.25 mmol) and the resulting solution was stirred at 55° C. for 3 hr. Additional isopropyl amine (0.1 mL) was and stirred at 55° C. After 16 h, the crude mixture was concentrated and purified by reverse phase chromatography to give the title compound as TFA salt. LCMS-ESI$^+$ (m/z): [M+H]$^+$ calcd for $C_{23}H_{24}N_4O_3$ as (M+H)$^+$ 405.4. found: 405.1 $^1$H NMR (400 MHz, DMSO-d$_6$) δ 12.19 (s, 1H), 8.31 (d, J=4.9 Hz, 1H), 8.24 (d, J=7.7 Hz, 1H), 8.06 (d, J=2.3 Hz, 1H), 7.98 (dd, J=8.8, 2.3 Hz, 1H), 7.51 (d, J=8.9 Hz, 1H), 7.27 (d, J=2.0 Hz, 1H), 7.20 (d, J=4.9 Hz, 1H), 4.91-4.85 (m, 1H), 4.10-3.99 (m, 1H), 3.85-3.77 (m, 2H), 3.53-3.47 (m, 2H), 2.02-1.95 (m, 2H), 1.68-1.60 (m, 2H), 1.13 (d, J=6.6 Hz, 6H).

Example 61: Preparation of 4-(3-cyano-4-((tetrahydro-2H-pyran-4-yl)oxy)phenyl)-N-phenyl-1H-pyrrolo[2,3-b]pyridine-2-carboxamide

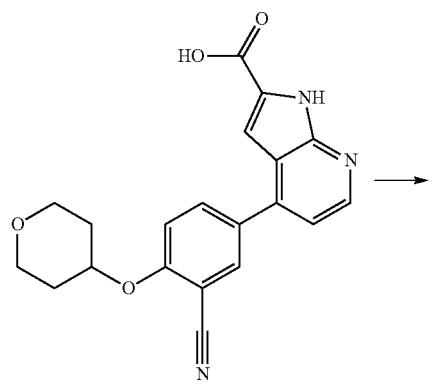

To a mixture of 4-(3-cyano-4-((tetrahydro-2H-pyran-4-yl)oxy)phenyl)-1H-pyrrolo[2,3-b]pyridine-2-carboxylic acid (30 mgs, 0.083 mmol) in DCE (1 mL) was added oxalyl-chloride (0.01 mL) and 1 drop of DMF and the reactions mixture was stirred at rt. After 2 h, the reaction mixture was concentrated to dryness and to the resulting solids was added DMAP (10 mgs, 0.083 mmol), DCM (2 mL) and aniline (100 mgs, 1.0 mmol). After 16 h at rt, the acetonitrile/water (1:1, 5 mL) was added and the solids were filtered and washed with acetonitrile. The filtrate was then concentrated and purified by reverse phase chromatography to give the title compound as TFA salt. LCMS-ESI$^+$ (m/z): [M+H]$^+$ calcd for $C_{26}H_{22}N_4O_3$ as (M+H)$^+$ 439.5. found: 439.1.

Example 62: Preparation of 5,5'-(1H-pyrrolo[2,3-b]pyridine-2,4-diyl)bis(2-((tetrahydro-2H-pyran-4-yl)oxy)benzonitrile)

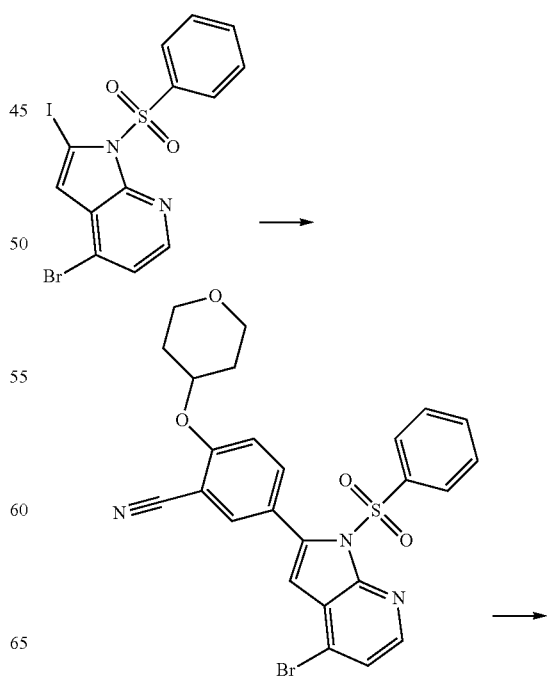

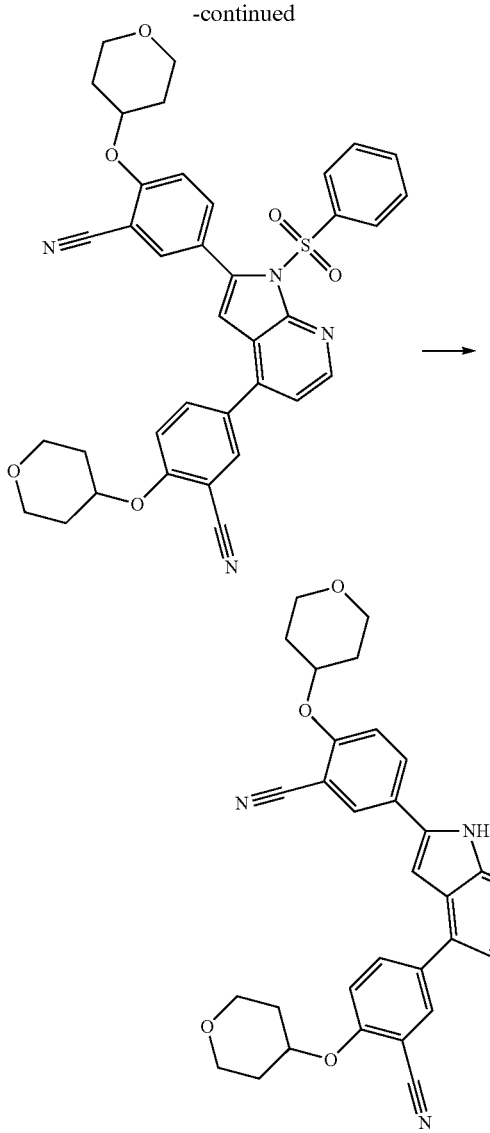

next step without purification. LCMS-ESI⁺ (m/z): [M+H]⁺ calcd for $C_{37}H_{36}N_4O_5S$: 649.8. found: 649.2.

Step 3: A mixture of 5,5'-(1-(phenylsulfonyl)-1H-pyrrolo[2,3-b]pyridine-2,4-diyl)bis(2-((tetrahydro-2H-pyran-4-yl)oxy)benzonitrile) and $Cs_2CO_3$ (211 mg, 0.65 mmol) in THF/2,2,2,-Trifluoroethanol (1:1, 3 mL) was heated at 100° C. for 48 h. The mixture was then concentrated and purified twice by reverse phase chromatography to give the title compound as TFA salt. LCMS-ESI⁺ (m/z): [M+H]⁺ calcd for $C_{31}H_{28}N_4O_4$ as (M+H)⁺ 521.6. found: 521.2 ¹H NMR (400 MHz, DMSO-d₆) δ 12.31 (s, 1H), 8.37 (d, J=2.3 Hz, 1H), 8.23-8.18 (m, 2H), 8.10 (d, J=2.3 Hz, 1H), 8.04 (dd, J=8.8, 2.4 Hz, 1H), 7.44 (dd, J=21.8, 9.0 Hz, 2H), 7.22-7.16 (m, 2H), 4.90-4.82 (m, 2H), 3.87-3.78 (m, 4H), 3.54-3.46 (m, 4H), 2.02-1.94 (m, 4H), 1.68-1.59 (m, 4H).

Example 63: Preparation of 5-(2-(4-(2-(pyrrolidin-1-yl)ethoxy)phenyl)-1H-pyrrolo[2,3-b]pyridin-4-yl)-2-((tetrahydro-2H-pyran-4-yl)oxy)benzonitrile

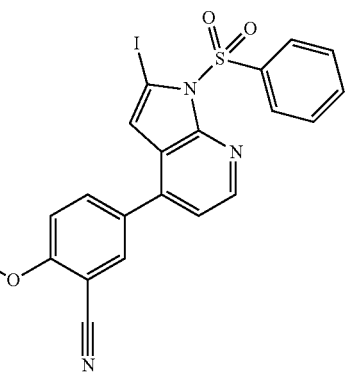

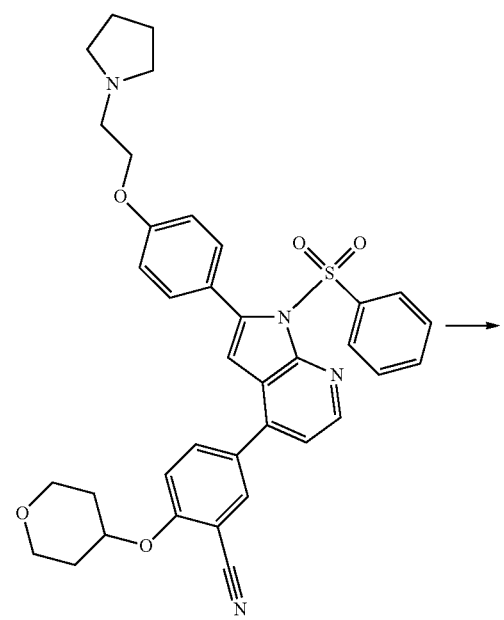

Step 1: To a solution of 4-bromo-2-iodo-1-(phenylsulfonyl)-1H-pyrrolo[2,3-b]pyridine (100 mgs, 0.216 mmol) and 2-((tetrahydro-2H-pyran-4-yl)oxy)-5-(4,4,5,5-tetramethyl-1,3,2-dioxaborolan-2-yl)benzonitrile (85 mgs, 0.260 mmol) in DME (1 mL), was added 2.0 M aqueous $Na_2CO_3$ (0.21 mL, 0.42 mmol) and Pd(PPh₃)₄ (12 mgs, 0.011 mmol) and the reaction mixture was heated at 140° C. for 1 hr. The mixture was then cooled to room temperature and concentrated and used for next step without purification.

Step 2: To the above crude mixture in DMF (2 mL) was added 2-((tetrahydro-2H-pyran-4-yl)oxy)-5-(4,4,5,5-tetramethyl-1,3,2-dioxaborolan-2-yl)benzonitrile (92 mgs, 0.281 mmol), 2.0 M aqueous $Na_2CO_3$ (0.32 mL, 0.65 mmol) and Pd(PPh₃)₄ (12 mgs, 0.011 mmol) and the reaction mixture was heated at 140° C. for 30 min. The reactions mixture was cooled to rt and diluted with acetonitrile/water (1:1, 5 mL) and the resulting mixture was stirred at rt for 2 h which resulted in gummy solids. The supernatant layer was decanted the gummy solids were taken into DCM and dried. Filtration, followed by concentration gave 5,5'-(1-(phenylsulfonyl)-1H-pyrrolo[2,3-b]pyridine-2,4-diyl)bis(2-((tetrahydro-2H-pyran-4-yl)oxy)benzonitrile) which was used for -continued

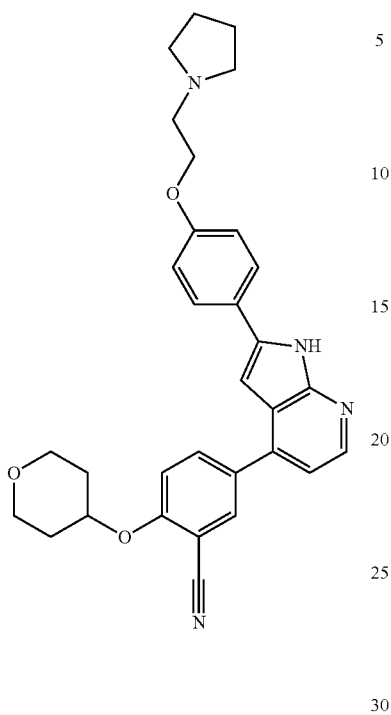

Step 1: To a solution of 5-(2-iodo-1-(phenylsulfonyl)-1H-pyrrolo[2,3-b]pyridin-4-yl)-2-((tetrahydro-2H-pyran-4-yl)oxy)benzonitrile (75 mgs, 0.128 mmol) and 1-(2-(4-(4,4,5,5-tetramethyl-1,3,2-dioxaborolan-2-yl)phenoxy)ethyl)pyrrolidine (49 mgs, 0.154 mmol) in DME (2 mL), was added 2.0 M aqueous Na$_2$CO$_3$ (0.2 mL, 0.4 mmol) and Pd(PPh$_3$)$_4$ (7 mgs, 0.006 mmol) and the reaction mixture was heated at 140° C. for 1 hr. The mixture was then cooled to rt and concentrated and used for next step without purification. LCMS-ESI$^+$ (m/z): [M+H]$^+$ calcd for C$_{37}$H$_{36}$O$_5$SN$_4$: 649.7. found: 649.2.

Step 2: To the above crude mixture in THF/2,2,2,-Trifluoroethanol (1:1, 3 mL) was added Cs$_2$CO$_3$ (211 mg, 0.65 mmol) was the reaction mixture was heated at 100° C. for 16 h. The mixture was then concentrated and purified by reverse phase chromatography to give the title compound as TFA salt. The TFA salt was dissolved in methanol and passed through MP-carbonate resin to give the title compound. LCMS-ESI$^+$ (m/z): [M+H]$^+$ calcd for C$_{31}$H$_{32}$N$_4$O$_3$ as (M+H)$^+$ 509.6. found: 509.5. $^1$H NMR (400 MHz, DMSO-d$_6$) δ 12.18 (s, 1H), 8.21 (d, J=5.0 Hz, 1H), 8.13 (d, J=2.3 Hz, 1H), 8.08 (dd, J=8.8, 2.4 Hz, 1H), 7.91 (d, J=8.8 Hz, 2H), 7.52 (d, J=8.9 Hz, 1H), 7.18 (d, J=5.0 Hz, 1H), 7.04-7.00 (m, 3H), 4.94-4.90 (m, 1H), 4.11 (t, J=5.9 Hz, 2H), 3.90-3.85 (m, 2H), 3.58-3.52 (m, 2H), 2.78 (t, J=5.9 Hz, 2H), 2.53-2.50 (m, 4H), 2.08-2.03 (m, 2H), 1.75-1.65 (m, 6H).

Example 64: Preparation of 5-(2-(4-(2-hydroxypropan-2-yl)phenyl)-1H-pyrrolo[2,3-b]pyridin-4-yl)-2-((tetrahydro-2H-pyran-4-yl)oxy)benzonitrile

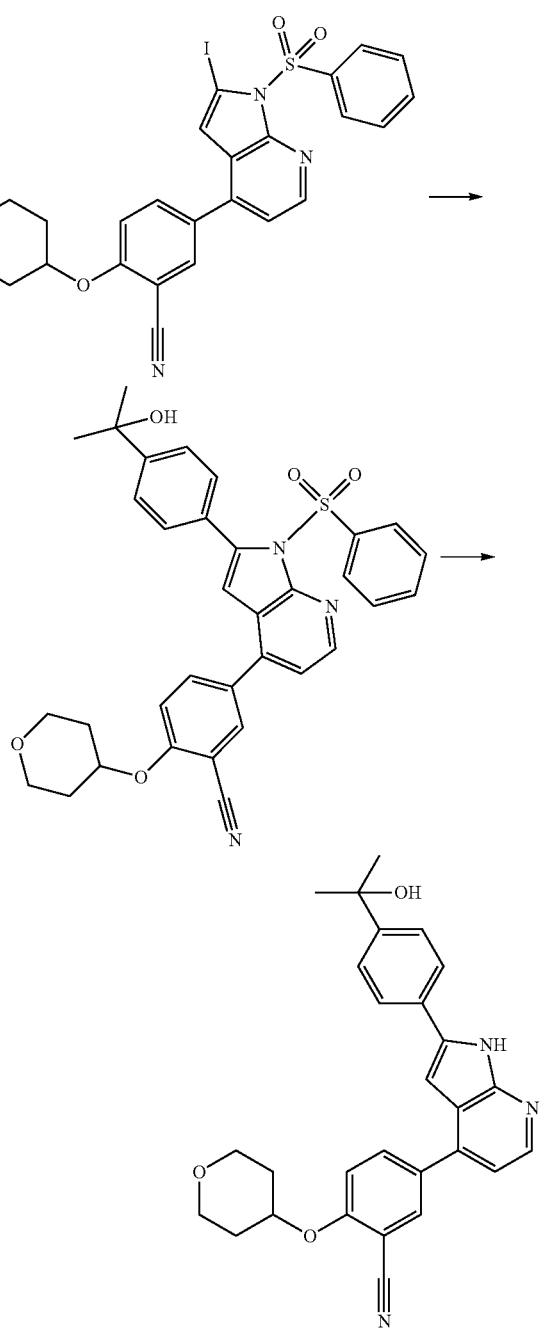

Step 1: To a solution of 5-(2-iodo-1-(phenylsulfonyl)-1H-pyrrolo[2,3-b]pyridin-4-yl)-2-((tetrahydro-2H-pyran-4-yl)oxy)benzonitrile (75 mgs, 0.128 mmol) and 2-(4-(4,4,5,5-tetramethyl-1,3,2-dioxaborolan-2-yl)phenyl)propan-2-ol (40 mgs, 0.154 mmol) in DME (2 mL), was added 2.0 M aqueous Na$_2$CO$_3$ (0.2 mL, 0.4 mmol) and Pd(PPh$_3$)$_4$ (7 mgs, 0.006 mmol) and the reaction mixture was heated at 140° C. for 1 hr. The mixture was then cooled to rt and concentrated and used for next step without purification.

LCMS-ESI+ (m/z): [M+H]+ calcd for $C_{34}H_{31}O_5SN_3$: 594.6. found: 594.2.

Step 2: To the above crude mixture in THF/2,2,2,-Trifluoroethanol (1:1, 3 mL) was added $Cs_2CO_3$ (125 mg, 0.38 mmol) was the reaction mixture was heated at 100° C. for 16 h. The mixture was then concentrated and purified by reverse phase chromatography to give the title compound as TFA salt. LCMS-ESI+ (m/z): [M+H]+ calcd for $C_{28}H_{27}N_3O_3$ as (M+H)+ 454.5. found: 454.2. $^1$H NMR (400 MHz, DMSO-$d_6$) δ 12.31 (s, 1H), 8.25 (d, J=5.0 Hz, 1H), 8.14 (d, J=2.3 Hz, 1H), 8.09 (dd, J=8.8, 2.4 Hz, 1H), 7.91 (d, J=8.4 Hz, 2H), 7.54-7.52 (m, 3H), 7.22 (d, J=5.0 Hz, 1H), 7.11 (d, J=2.1 Hz, 1H), 4.95-4.89 (m, 1H), 3.91-3.85 (m, 2H), 3.59-3.53 (m, 2H), 2.10-1.99 (m, 2H), 1.75-1.66 (m, 2H), 1.44 (s, 6H).

Example 65: Preparation of 5-(2-(4-((dimethylamino)methyl)phenyl)-1H-pyrrolo[2,3-b]pyridin-4-yl)-2-((tetrahydro-2H-pyran-4-yl)oxy)benzonitrile

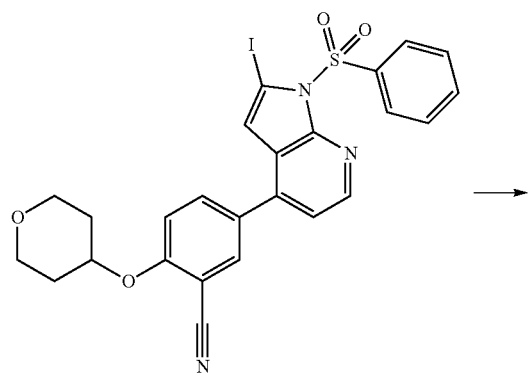

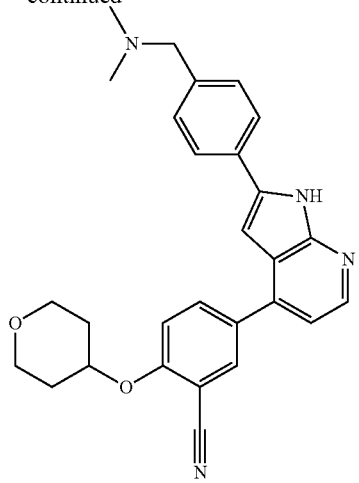

Step 1: To a solution of 5-(2-iodo-1-(phenylsulfonyl)-1H-pyrrolo[2,3-b]pyridin-4-yl)-2-((tetrahydro-2H-pyran-4-yl)oxy)benzonitrile (75 mgs, 0.128 mmol) and N,N-dimethyl-1-(4-(4,4,5,5-tetramethyl-1,3,2-dioxaborolan-2-yl)phenyl)methanamine.HCl (46 mgs, 0.154 mmol) in DME (2 mL) was added 2.0 M aqueous $Na_2CO_3$ (0.2 mL, 0.4 mmol) and Pd(PPh$_3$)$_4$ (7 mgs, 0.006 mmol) and the reaction mixture was heated at 140° C. for 1 hr. The mixture was then cooled to rt and concentrated and used for next step without purification. LCMS-ESI+ (m/z): [M+H]+ calcd for $C_{34}H_{32}O_4SN_4$: 593.7. found: 593.2.

Step 2: To the above crude mixture in THF/2,2,2,-Trifluoroethanol (1:1, 3 mL) was added $Cs_2CO_3$ (125 mg, 0.38 mmol) was the reaction mixture was heated at 100° C. for 16 h. The mixture was then concentrated and purified twice by reverse phase chromatography to give the title compound as TFA salt. LCMS-ESI+ (m/z): [M+H]+ calcd for $C_{28}H_{28}N_4O_2$ as (M+H)+ 453.6. found: 453.1 $^1$H NMR (400 MHz, DMSO-$d_6$) 12.42 (s, 1H), 9.75 (brs, 1H), 8.30 (d, J=5.0 Hz, 1H), 8.16 (d, J=2.3 Hz, 1H), 8.13-8.06 (m, 3H), 7.58-7.53 (m, 3H), 7.27 (d, J=2.1 Hz, 1H), 7.24 (d, J=4.9 Hz, 1H), 4.97-4.91 (m, 1H), 4.31 (d, J=5.1 Hz, 2H), 3.91-3.86 (m, 2H), 3.60-3.53 (m, 2H), 2.76 (d, J=4.5 Hz, 6H), 2.10-1.99 (m, 2H), 1.75-1.67 (m, 2H).

Example 66: Preparation of 5-(2-(3-((dimethylamino)methyl)phenyl)-1H-pyrrolo[2,3-b]pyridin-4-yl)-2-((tetrahydro-2H-pyran-4-yl)oxy)benzonitrile

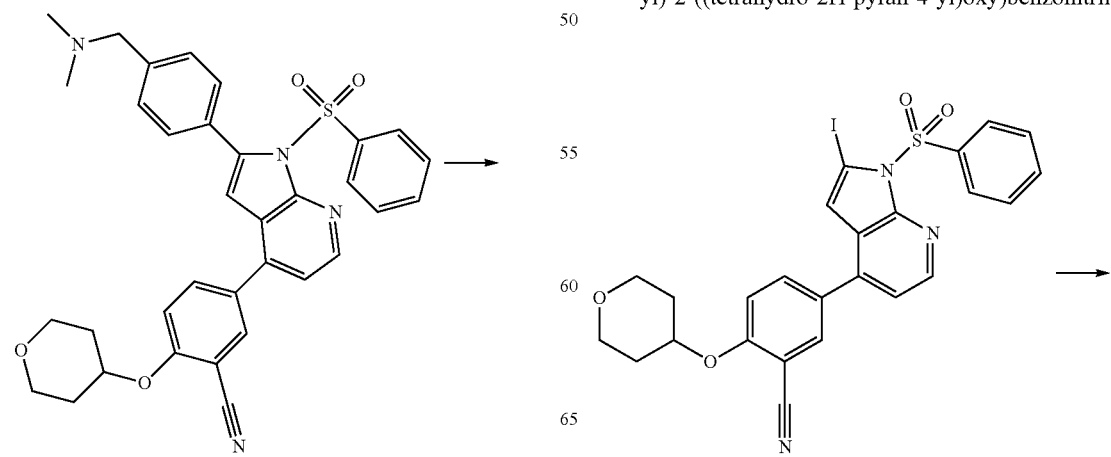

232

Example 67: Preparation of 5-(2-(4-(1-cyanocyclo-propyl)phenyl)-1H-pyrrolo[2,3-b]pyridin-4-yl)-2-((tetrahydro-2H-pyran-4-yl)oxy)benzonitrile

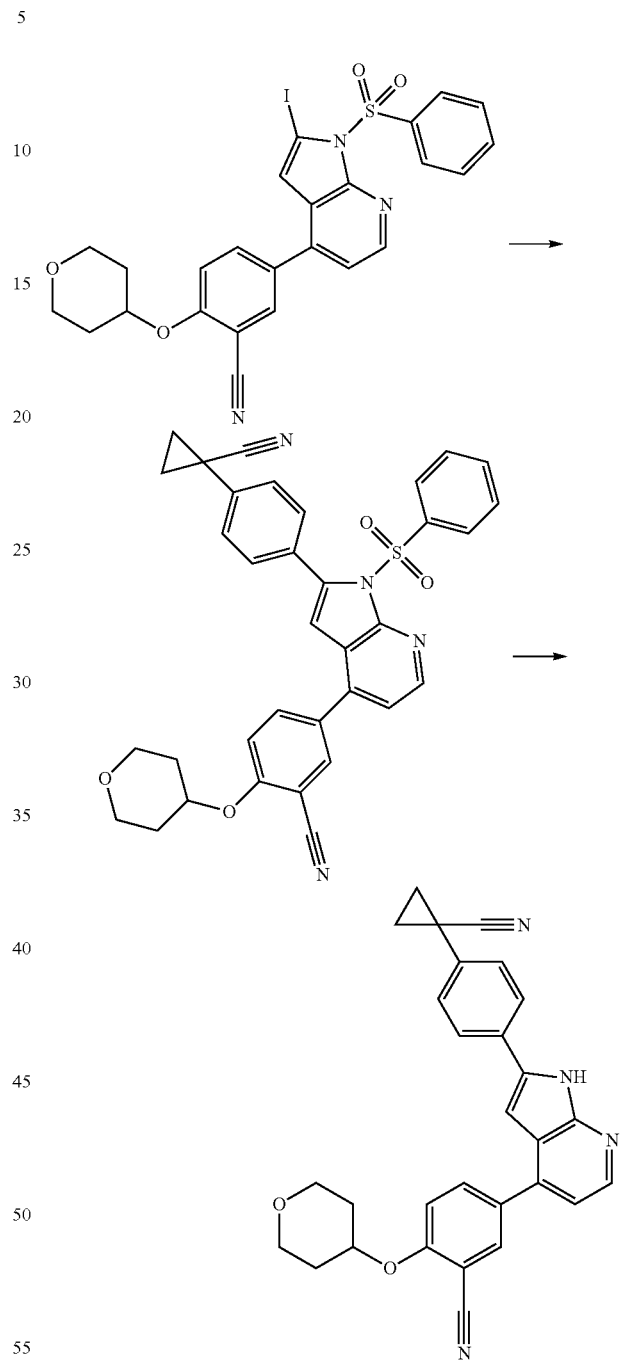

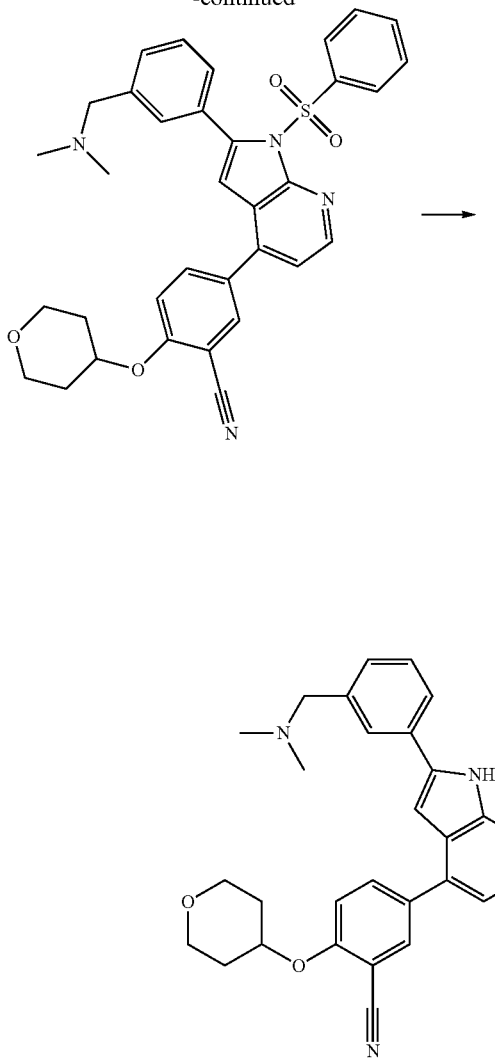

Step 1: To a solution of 5-(2-iodo-1-(phenylsulfonyl)-1H-pyrrolo[2,3-b]pyridin-4-yl)-2-((tetrahydro-2H-pyran-4-yl)oxy)benzonitrile (75 mgs, 0.128 mmol) and N,N-dimethyl-1-(3-(4,4,5,5-tetramethyl-1,3,2-dioxaborolan-2-yl)phenyl)methanamine (46 mgs, 0.154 mmol) in DME (2 mL) was added 2.0 M aqueous $Na_2CO_3$ (0.2 mL, 0.4 mmol) and $Pd(PPh_3)_4$ (7 mgs, 0.006 mmol) and the reaction mixture was heated at 140° C. for 1 hr. The mixture was then cooled to rt and concentrated and used for next step without purification. LCMS-ESI$^+$ (m/z): [M+H]$^+$ calcd for $C_{34}H_{32}O_4SN_4$: 593.7. found: 593.2.

Step 2: To the above crude mixture in THF/2,2,2,-Trifluoroethanol (1:1, 3 mL) was added $Cs_2CO_3$ (125 mg, 0.38 mmol) was the reaction mixture was heated at 100° C. for 16 h. The mixture was then concentrated and purified twice by reverse phase chromatography to give the title compound as TFA salt. LCMS-ESI$^+$ (m/z): [M+H]$^+$ calcd for $C_{28}H_{28}N_4O_2$ as (M+H)$^+$ 453.6. found: 453.1 $^1$H NMR (400 MHz, DMSO-$d_6$) δ 12.44 (s, 1H), 9.72 (brs, 1H), 8.30 (d, J=5.0 Hz, 1H), 8.16 (d, J=2.3 Hz, 1H), 8.13-8.06 (m, 3H), 7.60-7.45 (m, 3H), 7.23 (d, J=5.0 Hz, 1H), 7.11 (d, J=2.0 Hz, 1H), 4.96-4.90 (m, 1H), 4.31 (d, J=5.0 Hz, 2H), 3.91-3.85 (m, 2H), 3.59-3.53 (m, 2H), 2.78 (d, J=4.6 Hz, 6H), 2.08-2.01 (m, 2H), 1.74-1.66 (m, 2H).

Step 1: To a solution of 5-(2-iodo-1-(phenylsulfonyl)-1H-pyrrolo[2,3-b]pyridin-4-yl)-2-((tetrahydro-2H-pyran-4-yl)oxy)benzonitrile (75 mgs, 0.128 mmol) and (4-(1-cyanocyclopropyl)phenyl)boronic acid (28 mgs, 0.154 mmol) in DME (2 mL) was added 2.0 M aqueous $Na_2CO_3$ (0.2 mL, 0.4 mmol) and $Pd(PPh_3)_4$ (7 mgs, 0.006 mmol) and the reaction mixture was heated at 140° C. for 1 hr. The mixture was then cooled to rt and concentrated and used for next step without purification. LCMS-ESI$^+$ (m/z): [M+H]$^+$ calcd for $C_{35}H_{28}O_4SN_4$: 601.7. found: 601.2.

Step 2: To the above mixture in THF/2,2,2,-Trifluoroethanol (1:1, 3 mL) was added Cs$_2$CO$_3$ (125 mg, 0.38 mmol) was the reaction mixture was heated at 100° C. for 16 h. The mixture was then concentrated and purified twice by reverse phase chromatography to give the title compound as TFA salt. LCMS-ESI$^+$ (m/z): [M+H]$^+$ calcd for C$_{29}$H$_{24}$N$_4$O$_2$ as (M+H)$^+$ 461.5. found: 461.1 $^1$H NMR (400 MHz, DMSO-d$_6$) 12.32 (s, 1H), 8.22 (d, J=5.0 Hz, 1H), 8.09 (d, J=2.3 Hz, 1H), 8.04 (dd, J=8.8, 2.4 Hz, 1H), 7.96 (d, J=8.4 Hz, 2H), 7.48 (d, J=8.9 Hz, 1H), 7.35 (d, J=8.4 Hz, 2H), 7.17 (d, J=5.0 Hz, 1H), 7.13 (d, J=2.1 Hz, 1H), 4.91-4.83 (m, 1H), 3.86-3.80 (m, 2H), 3.57-3.42 (m, 2H), 2.03-1.96 (m, 2H), 1.75-1.71 (m, 2H), 1.69-1.61 (m, 2H), 1.55-1.48 (m, 2H).

Example 68: Preparation of 5-(2-(3-(2-hydroxypropan-2-yl)phenyl)-1H-pyrrolo[2,3-b]pyridin-4-yl)-2-((tetrahydro-2H-pyran-4-yl)oxy)benzonitrile

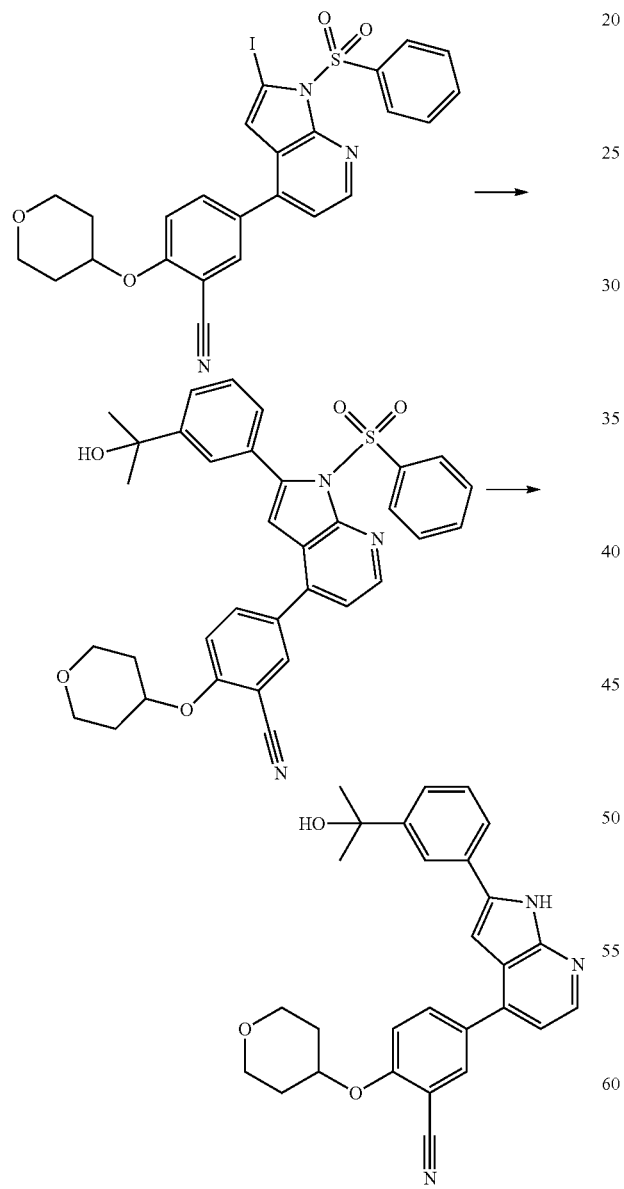

Step 1: To a solution of 5-(2-iodo-1-(phenylsulfonyl)-1H-pyrrolo[2,3-b]pyridin-4-yl)-2-((tetrahydro-2H-pyran-4-yl)oxy)benzonitrile (75 mgs, 0.128 mmol) and (2-(3-(4,4,5,5-tetramethyl-1,3,2-dioxaborolan-2-yl)phenyl)propan-2-ol (35 mgs, 0.154 mmol) in DME (2 mL) was added 2.0 M aqueous Na$_2$CO$_3$ (0.2 mL, 0.4 mmol) and Pd(PPh$_3$)$_4$ (7 mgs, 0.006 mmol) and the reaction mixture was heated at 140° C. for 1 hr. The mixture was then cooled to rt and concentrated and used for next step without purification. LCMS-ESI$^+$ (m/z): [M+H]$^+$ calcd for C$_{34}$H$_{31}$O$_5$SN$_3$: 594.6. found: 594.2.

Step 2: To the above crude mixture in THF/2,2,2,-Trifluoroethanol (1:1, 3 mL) was added Cs$_2$CO$_3$ (125 mg, 0.38 mmol) was the reaction mixture was heated at 100° C. for 16 h. The mixture was then concentrated and purified twice by reverse phase chromatography to give the title compound as TFA salt. LCMS-ESI$^+$ (m/z): [M+H]$^+$ calcd for C$_{28}$H$_{27}$N$_3$O$_3$ as (M+H)$^+$ 454.5. found: 454.2. $^1$H NMR (400 MHz, DMSO-d$_6$) δ 12.34 (s, 1H), 8.26 (d, J=5.0 Hz, 1H), 8.14 (d, J=2.3 Hz, 1H), 8.09 (dd, J=8.8, 2.4 Hz, 1H), 8.02 (t, J=1.8 Hz, 1H), 7.81 (d, J=7.7 Hz, 1H), 7.54 (d, J=8.9 Hz, 1H), 7.49-7.45 (m, 1H), 7.38 (t, J=7.7 Hz, 1H), 7.21 (d, J=5.0 Hz, 1H), 7.09 (d, J=2.1 Hz, 1H), 4.94-4.90 (m, 1H), 3.90-3.85 (m, 2H), 3.58-3.52 (m, 2H), 2.07-2.03 (m, 2H), 1.74-1.66 (m, 2H), 1.48 (s, 6H).

Example 69: Preparation of 2-methyl-5-(2-(4-morpholinophenyl)-1H-pyrrolo[2,3-b]pyridin-4-yl)benzonitrile

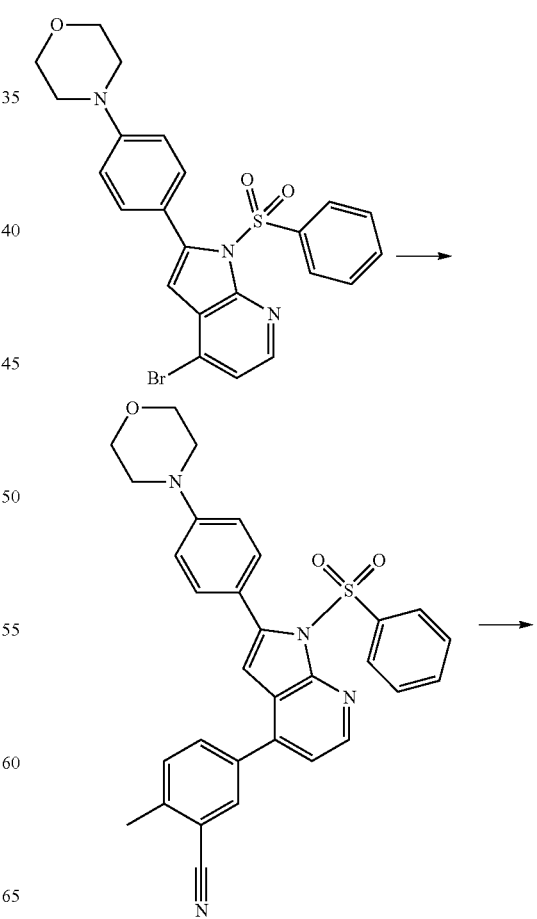

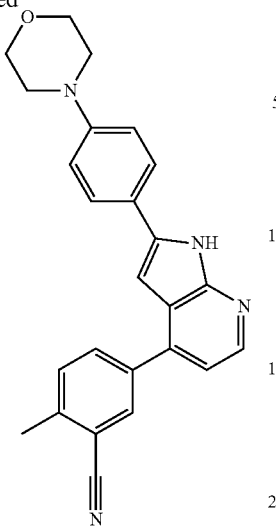

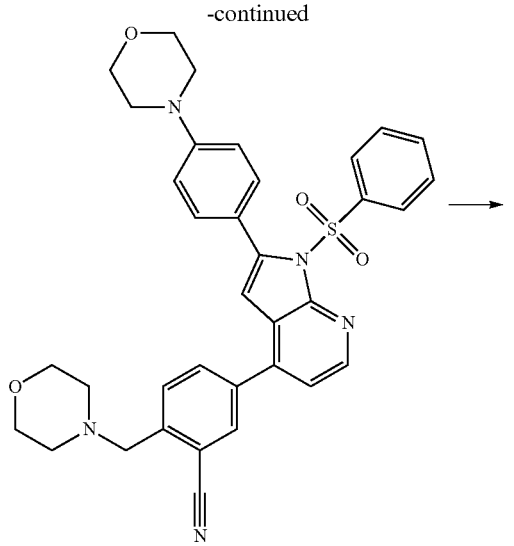

Step 1: To a solution of 4-(4-(4-bromo-1-(phenylsulfonyl)-1H-pyrrolo[2,3-b]pyridin-2-yl)phenyl)morpholine (75 mgs, 0.150 mmol) and 2-methyl-5-(4,4,5,5-tetramethyl-1,3,2-dioxaborolan-2-yl)benzonitrile (40 mgs, 0.166 mmol) in DME (2 mL) was added 2.0 M aqueous $Na_2CO_3$ (0.2 mL, 0.4 mmol) and $Pd(PPh_3)_4$ (9 mgs, 0.008 mmol) and the reaction mixture was heated at 140° C. for 1 hr. The mixture was then cooled to rt and concentrated and used for next step without purification. LCMS-ESI$^+$ (m/z): [M+H]$^+$ calcd for $C_{31}H_{26}O_3SN_4$: 535.1. found: 535.1.

Step 2: To the above crude mixture in THF/2,2,2,-Trifluoroethanol (1:1, 3 mL) was added $Cs_2CO_3$ (146 mg, 0.45 mmol) was the reaction mixture was heated at 100° C. for 16 h. The mixture was then concentrated and purified twice by reverse phase chromatography to give the title compound as TFA salt. LCMS-ESI$^+$ (m/z): [M+H]$^+$ calcd for $C_{25}H_{22}N_4O$ as (M+H)$^+$ 395.5. found: 395.3. $^1$H NMR (400 MHz, DMSO-$d_6$) 12.15 (s, 1H), 8.21 (d, J=5.0 Hz, 1H), 8.15 (d, J=1.9 Hz, 1H), 8.05 (dd, J=8.0, 2.0 Hz, 1H), 7.86 (d, J=8.8 Hz, 2H), 7.64 (d, J=8.1 Hz, 1H), 7.19 (d, J=5.0 Hz, 1H), 7.03-6.95 (m, 3H), 3.75-3.73 (m, 4H), 3.21-3.15 (m, 4H), 2.57 (s, 3H).

Example 70: Preparation of 2-(morpholinomethyl)-5-(2-(4-morpholinophenyl)-1H-pyrrolo[2,3-b]pyridin-4-yl)benzonitrile

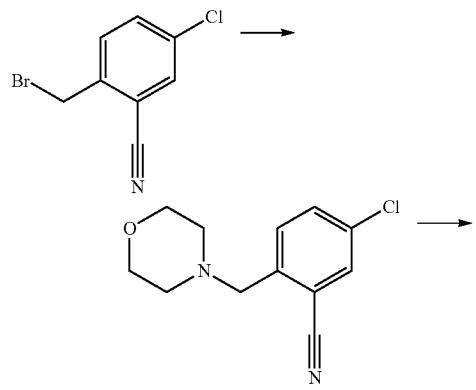

Step 1: Solid 2-(bromomethyl)-5-chlorobenzonitrile (500 mgs, 2.17 mmol) was added in two portions to a stirred solution of morpholine (0.2 mL, 2.3 mmol) and triethylamine (0.3 mL, 2.17 mmol) in methanol (1 mL). After 6 hr at rt, the solvent was removed and the residue was dissolved in ethylacetate and washed with 1N NaOH, water, saturated aqueous sodium chloride solution and dried ($MgSO_4$). Filtration and concentration gave 5-chloro-2-(morpholinomethyl)benzonitrile which was used without purification for next step. LCMS-ESI$^+$ (m/z): [M+H]$^+$ calcd for $C_{12}H_{13}N_2O$ as (M+H)$^+$ 237.7. found: 237.2. $^1$H NMR (400 MHz, Chloroform-d) δ 8.61 (d, J=8.7 Hz, 1H), 7.80-7.67 (m, 2H), 4.37 (s, 2H), 4.33-4.23 (m, 2H), 3.99 (m, 2H), 3.33 (m, 2H), 3.12-2.99 (m, 2H).

Step 2: To a mixture of 4-(4-(1-(phenylsulfonyl)-4-(4,4,5,5-tetramethyl-1,3,2-dioxaborolan-2-yl)-1H-pyrrolo[2,3-b]pyridin-2-yl)phenyl)morpholine (60 mgs, 0.11 mmol) and 5-chloro-2-(morpholinomethyl)benzonitrile (50 mgs, 0.21 mmol) in DME/water 4 (3 mL, 2:1) was $Cs_2CO_3$ (133 mL, 0.41 mmol) and PEPSI-iPr (11 mgs, 0.016 mmol) and the reaction mixture was heated at 140° C. for 1 hr. The mixture was then cooled to rt and concentrated and used for next step without purification. LCMS-ESI$^+$ (m/z): [M+H]$^+$ calcd for $C_{35}H_{33}O_4SN_5$: 620.7. found: 620.2.

Step 3: To the above crude mixture in THF/2,2,2,-Trifluoroethanol (1:1, 3 mL) was added Cs$_2$CO$_3$ (120 mg, 0.37 mmol) was the reaction mixture was heated at 100° C. for 16 h. The mixture was then concentrated and purified by reverse phase chromatography to give the title compound as TFA salt. LCMS-ESI$^+$ (m/z): [M+H]$^+$ calcd for C$_{29}$H$_{29}$N$_5$O$_2$ as (M+H)$^+$ 480.6. found: 480.1 $^1$H NMR (400 MHz, DMSO-d$_6$) 12.26 (s, 1H), 8.36 (s, 1H), 8.26 (d, J=5.1 Hz, 2H), 7.94 (d, J=8.2 Hz, 1H), 7.86 (d, J=8.8 Hz, 2H), 7.26 (d, J=5.0 Hz, 1H), 7.04-7.00 (m, 3H), 4.53 (brs, 2H), 3.75-3.73 (m, 8H), 3.20-3.17 (m, 8H).

Example 71: Preparation of 2-isopropoxy-5-(2-(4-morpholinophenyl)-1H-pyrrolo[2,3-b]pyridin-4-yl)benzonitrile

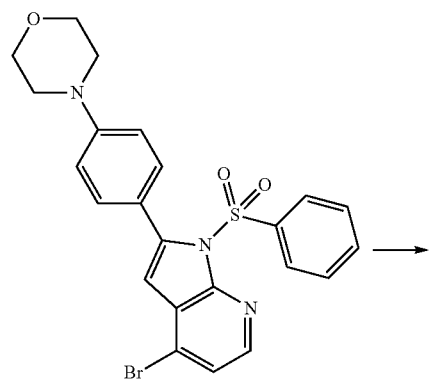

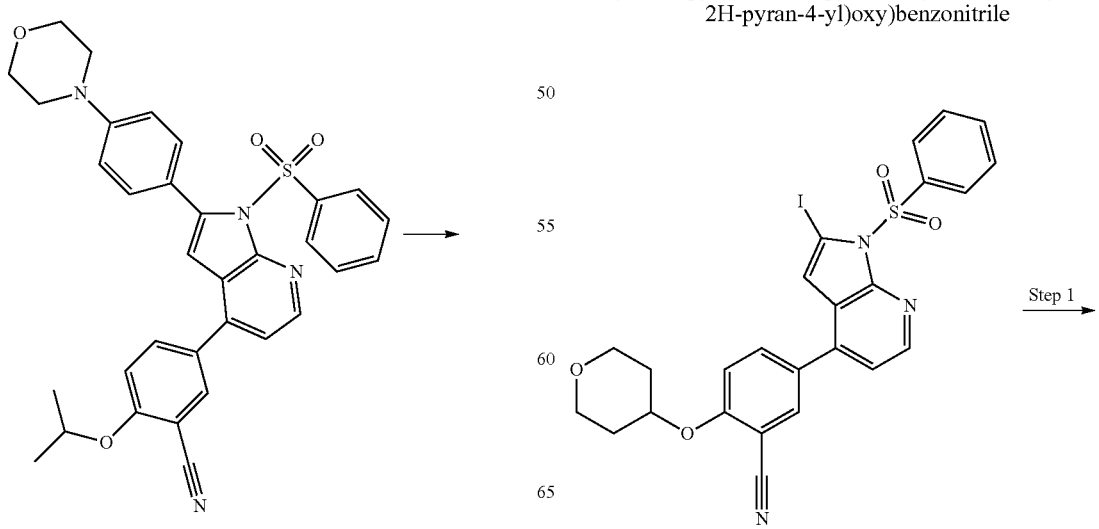

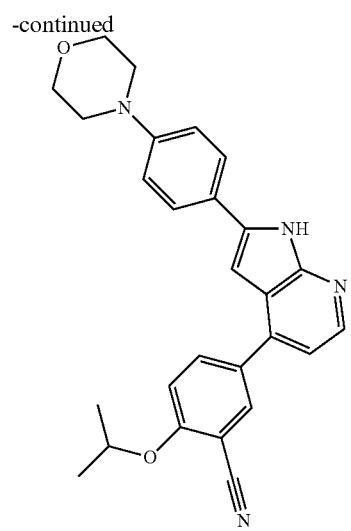

Step 1: To a solution of 4-(4-(4-bromo-1-(phenylsulfonyl)-1H-pyrrolo[2,3-b]pyridin-2-yl)phenyl)morpholine (75 mgs, 0.150 mmol) and 2-isopropoxy-5-(4,4,5,5-tetramethyl-1,3,2-dioxaborolan-2-yl)benzonitrile (48 mgs, 0.166 mmol) in DME (2 mL) was added 2.0 M aqueous Na$_2$CO$_3$ (0.16 mL, 0.3 mmol) and Pd(PPh$_3$)$_4$ (9 mgs, 0.008 mmol) and the reaction mixture was heated at 140° C. for 1 hr. The mixture was then cooled to rt and concentrated and used for next step without purification. LCMS-ESI$^+$ (m/z): [M+H]$^+$ calcd for C$_{33}$H$_{30}$O$_4$SN$_4$: 579.7. found: 579.2.

Step 2: To the above crude mixture in THF/2,2,2,-Trifluoroethanol (1:1, 3 mL) was added Cs$_2$CO$_3$ (146 mg, 0.45 mmol) was the reaction mixture was heated at 100° C. for 16 h. The mixture was then concentrated and purified twice by reverse phase chromatography to give the title compound as TFA salt. LCMS-ESI$^+$ (m/z): [M+H]$^+$ calcd for C$_{27}$H$_{26}$N$_4$O$_2$ as (M+H)$^+$ 439.5. found: 439.2. $^1$H NMR (400 MHz, DMSO-d$_6$) 12.26 (s, 1H), 8.21 (d, J=5.1 Hz, 1H), 8.13-8.06 (m, 2H), 7.86 (d, J=8.8 Hz, 2H), 7.44 (d, J=8.8 Hz, 1H), 7.21 (d, J=5.1 Hz, 1H), 7.05-6.98 (m, 3H), 4.92-4.86 (m, 1H), 3.74 (dd, J=6.1, 3.5 Hz, 4H), 3.18 (dd, J=5.9, 3.7 Hz, 4H), 1.37 (d, J=6.0 Hz, 6H).

Example 72: Synthesis of 5-(2-(2-methylthiazol-5-yl)-1H-pyrrolo[2,3-b]pyridin-4-yl)-2-((tetrahydro-2H-pyran-4-yl)oxy)benzonitrile -continued

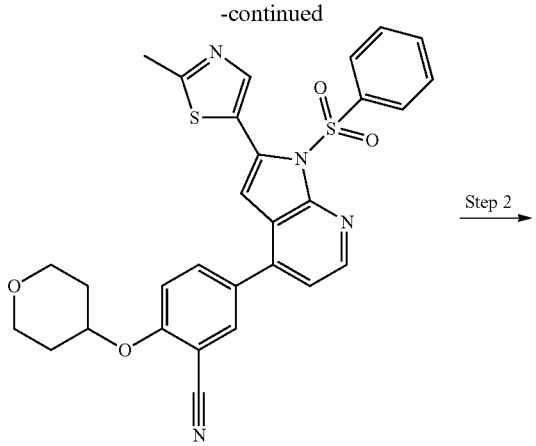

Step 1: To an appropriate sized microwave vial, 5-(2-iodo-1-(phenylsulfonyl)-1H-pyrrolo[2,3-b]pyridin-4-yl)-2-((tetrahydro-2H-pyran-4-yl)oxy)benzonitrile (80 mg, 0.137 mmol), 2-methyl-5-(4,4,5,5-tetramethyl-1,3,2-dioxaborolan-2-yl)thiazole (34 mg, 0.150 mmol), Cesium carbonate (133 mg, 0.41 mmol), dioxane (3 mL) and water (1.5 mL) were added. The mixture was degassed with nitrogen for 10 minutes. PEPPSI-iPr catalyst (9 mg, 0.014 mmol) was added and the solution was heated at 105° C. for 2 h. After cooling to room temperature, the mixture was poured into water, and extracted with dichloromethane. The combined organic layers were washed with saturated aqueous sodium chloride solution, dried with magnesium sulfate, filtered and concentrated under reduced pressure. The residue 5-(2-(2-methylthiazol-5-yl)-1-(phenylsulfonyl)-1H-pyrrolo[2,3-b]pyridin-4-yl)-2-((tetrahydro-2H-pyran-4-yl)oxy)benzonitrile was used for next step. LCMS-ESI$^+$ (m/z): [M+H]$^+$ calcd for $C_{29}H_{24}N_4O_4S_2$: 557.66. found: 557.1.

Step 2: To an appropriate sized microwave vial, the crude material 5-(2-(2-methylthiazol-5-yl)-1-(phenylsulfonyl)-1H-pyrrolo[2,3-b]pyridin-4-yl)-2-((tetrahydro-2H-pyran-4-yl)oxy)benzonitrile (50 mg, 0.09 mmol) in a THF (4 mL) and 2,2,2-trifluoroethanol (2 mL) was heated at 105° C. for 6 h. After cooling down to room temperature, the mixture was poured into water, and extracted with dichloromethane. The combined organic layers were washed with saturated aqueous sodium chloride solution, dried with magnesium sulfate, filtered and concentrated under reduced pressure. The residue was purified via prep HPLC (10-95% acetonitrile in water, 0.1% trifluoroacteic acid buffer). Clean fractions poured into a saturated solution of sodium bicarbonate in water and extracted with dichloromethane to yield the product 5-(2-(2-methylthiazol-5-yl)-1H-pyrrolo[2,3-b]pyridin-4-yl)-2-((tetrahydro-2H-pyran-4-yl)oxy)benzonitrile.
$^1$H NMR (400 MHz, DMSO-d6) δ 12.45 (s, 1H), 8.27 (d, J=5.0 Hz, 1H), 8.17 (s, 1H), 8.11 (d, J=2.3 Hz, 1H), 8.04 (dd, J=8.9, 2.3 Hz, 1H), 7.52 (d, J=8.9 Hz, 1H), 7.21 (d, J=5.0 Hz, 1H), 6.85 (s, 1H), 4.96-4.86 (m, 1H), 3.91-3.81 (m, 2H), 3.6-3.5 (m, 2H), 2.68 (s, 3H), 2.13-1.94 (m, 2H), 1.75-1.65 (m, 2H). LCMS-ESI$^+$ (m/z): [M+H]$^+$ calcd for $C_{23}H_{20}N_4O_2S$: 417.50. found: 417.1.

Example 73: Synthesis of 5-(2-(6-aminopyrazin-2-yl)-1H-pyrrolo[2,3-b]pyridin-4-yl)-2-((tetrahydro-2H-pyran-4-yl)oxy)benzonitrile

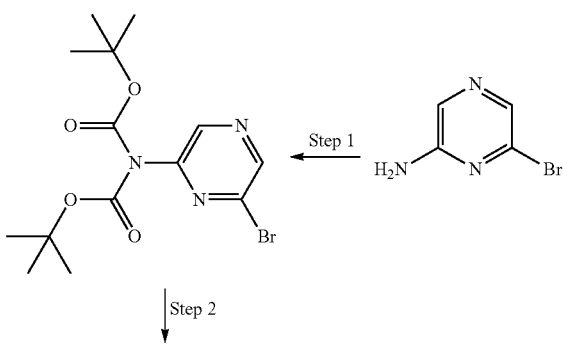

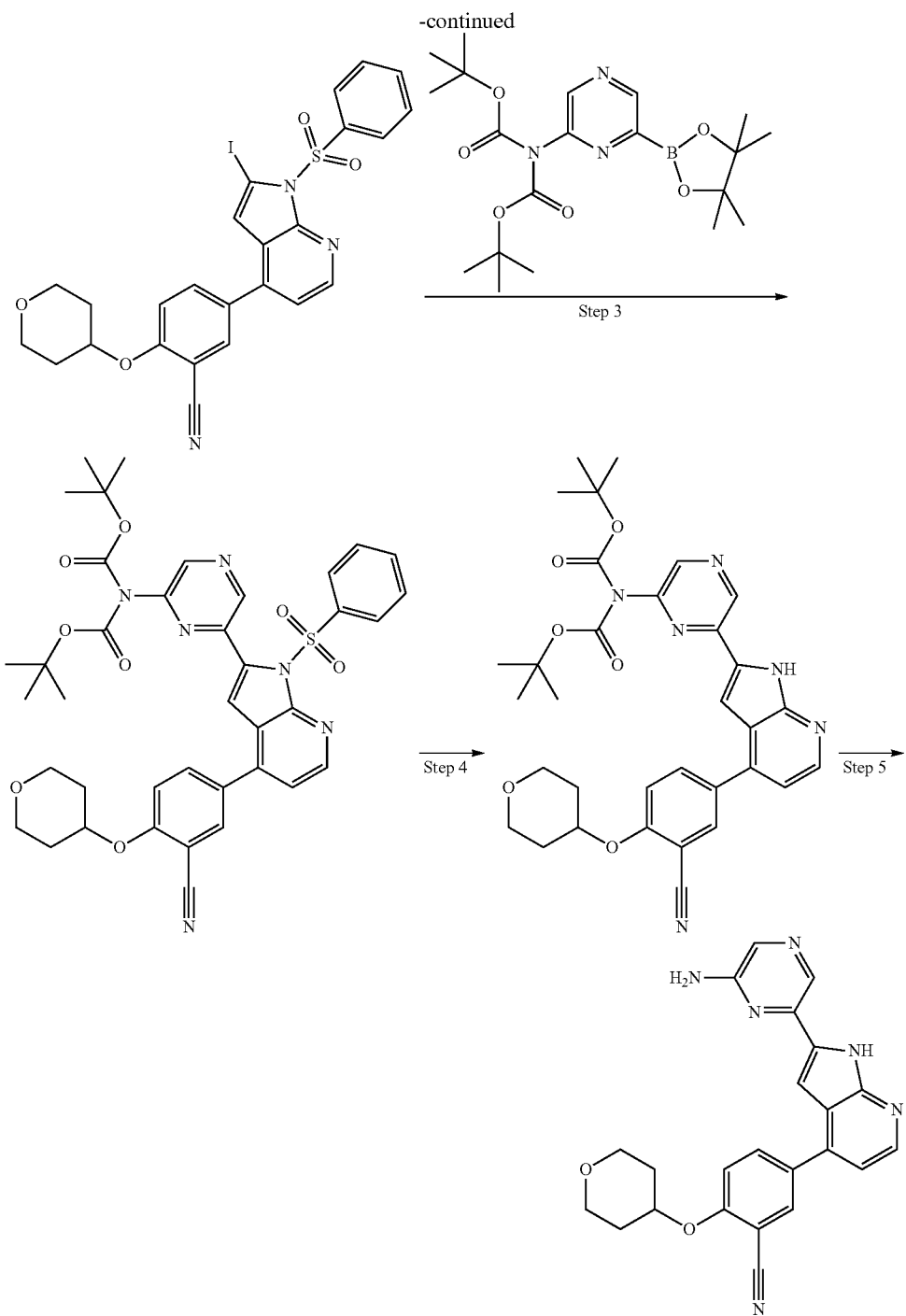

Step 1: N,N-Diisopropylethylamine (2.1 mL) was added to 6-bromopyrazin-2-amine (1.0 g, 6 mmol), di-tert-butyl dicarbonate (2.63 g, 12 mmol) and N,N-dimethylpyridin-4-amine (1.4 g) in a solution of dichloromethane (15 mL). The resulting solution was stirred at room temperature 3 hours, then evaporated to dryness and re-dissolved in dichloromethane, and washed sequentially with water and saturated saturated aqueous sodium chloride solution. The organic layer was dried over $Mg_2SO_4$, filtered and evaporated under reduced pressure to afford crude product. The crude product was purified by flash silica chromatography (elution gradient 40 to 60% ethyl acetate in hexane). Pure fractions were evaporated to yield 6-bromo-N,N-Di-Boc-pyrazin-2-amine. LCMS-ESI$^+$ (m/z): [M+H]$^+$ calcd for $C_{14}H_{20}BrN_3O_4$: 375.2. found: 374.1.

Step 2: To a mixture of 6-bromo-N,N-Di-Boc-pyrazin-2-amine (700 mg, 1.8 mmol), potassium acetate (551 mg, 6.0 mmol), 4,4,5,5,-tetramethyl-2-(4,4,5,5,-tetramethyl-1,3,2-dioxaborolan-2-yl)-1,3,2-dioxaborolane (475 mg, 2.0 mmol) and 1,1'-bis(diphenylphosphino)ferrocene palladium (II) chloride dichloromethane adduct (228 mg, 0.12 mmol) was added 1,4-dioxane (15 mL). The mixture was heated in a microwave at 105° C. for 1 h. After cooling to room temperature, the solids were filtered off and the volatiles were removed in vacuo to yield crude N,N-Di-Boc-6-(4,4,5,5-tetramethyl-1,3,2-dioxaborolan-2-yl)pyrazin-2-amine which was used further without further purification. LCMS-ESI⁺ (m/z): [M+H]⁺ calcd for C$_{20}$H$_{32}$BN$_3$O$_6$: 422.3. found: 422.2.

Step 3: Following similar procedure to synthesize Example 72 step 1, beginning with 5-(2-iodo-1-(phenylsulfonyl)-1H-pyrrolo[2,3-b]pyridin-4-yl)-2-((tetrahydro-2H-pyran-4-yl)oxy)benzonitrile (150 mg, 0.35 mmol) and N,N-di-Boc-6-(4,4,5,5-tetramethyl-1,3,2-dioxaborolan-2-yl)pyrazin-2-amine (207 mg, 0.35 mmol), 5-(2-(6-(Di-Boc-amino)pyrazin-2-yl)-1-(phenylsulfonyl)-1H-pyrrolo[2,3-b]pyridin-4-yl)-2-((tetrahydro-2H-pyran-4-yl)oxy)benzonitrile was synthesized. LCMS-ESI⁺ (m/z): [M+H]⁺ calcd for C$_{39}$H$_{40}$N$_6$O$_8$S: 753.8. found 753.2.

Step 4: Following similar procedure to synthesize Example 72 step 2, beginning with 5-(2-(6-(Di-Boc-amino)pyrazin-2-yl)-1-(phenylsulfonyl)-1H-pyrrolo[2,3-b]pyridin-4-yl)-2-((tetrahydro-2H-pyran-4-yl)oxy)benzonitrile (150 mg, 0.19 mmol), 5-(2-(6-(Di-Boc-amino)pyrazin-2-yl)-1H-pyrrolo[2,3-b]pyridin-4-yl)-2-((tetrahydro-2H-pyran-4-yl)oxy)benzonitrile was synthesized. LCMS-ESI⁺ (m/z): [M+H]⁺ calcd for C$_{33}$H$_{36}$N$_6$O$_6$: 613.7. found 613.2.

Step 5: To a 100 mL round bottle flask, the compound 5-(2-(6-(Di-Boc-amino)pyrazin-2-yl)-1H-pyrrolo[2,3-b]pyridin-4-yl)-2-((tetrahydro-2H-pyran-4-yl)oxy)benzonitrile (80 mg, 0.13 mmol) in TFA (5 mL) was stirred at room temperature for 1 hr. The reaction was concentrated under reduced pressure. The residue was purified via prep HPLC (2-95% acetonitrile in water, 0.1% trifluoroacteic acid buffer). Clean fractions were poured into a saturated solution of sodium bicarbonate in water and extracted with dichloromethane to yield the product 5-(2-(6-aminopyrazin-2-yl)-1H-pyrrolo[2,3-b]pyridin-4-yl)-2-((tetrahydro-2H-pyran-4-yl)oxy)benzonitrile. ¹H NMR (400 MHz, DMSO-d6) δ 12.31 (s, 1H), 8.44 (s, 1H), 8.32 (d, J=5.0 Hz, 1H), 8.13 (d, J=2.3 Hz, 1H), 8.06 (dd, J=8.8, 2.3 Hz, 1H), 7.83 (s, 1H), 7.55 (d, J=8.9 Hz, 1H), 7.24 (d, J=5.0 Hz, 1H), 7.22 (s, 1H), 6.50 (s, 2H), 4.97-4.87 (m, 1H), 3.93-3.79 (m, 2H), 3.6-3.5 (m, 2H), 2.11-1.96 (m, 2H), 1.75-1.65 (m, 2H). LCMS-ESI⁺ (m/z): [M+H]⁺ calcd for C$_{23}$H$_{20}$N$_6$O$_2$: 413.4. found: 413.1.

Example 74: Synthesis of 5-(2-(3-oxoisoindolin-5-yl)-1H-pyrrolo[2,3-b]pyridin-4-yl)-2-((tetrahydro-2H-pyran-4-yl)oxy)benzonitrile

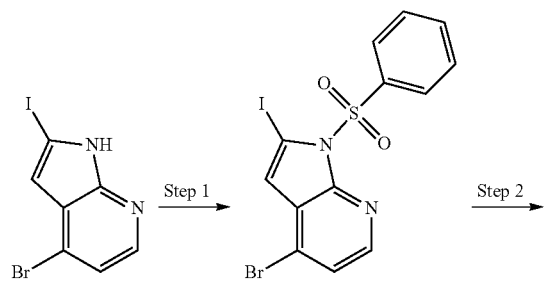

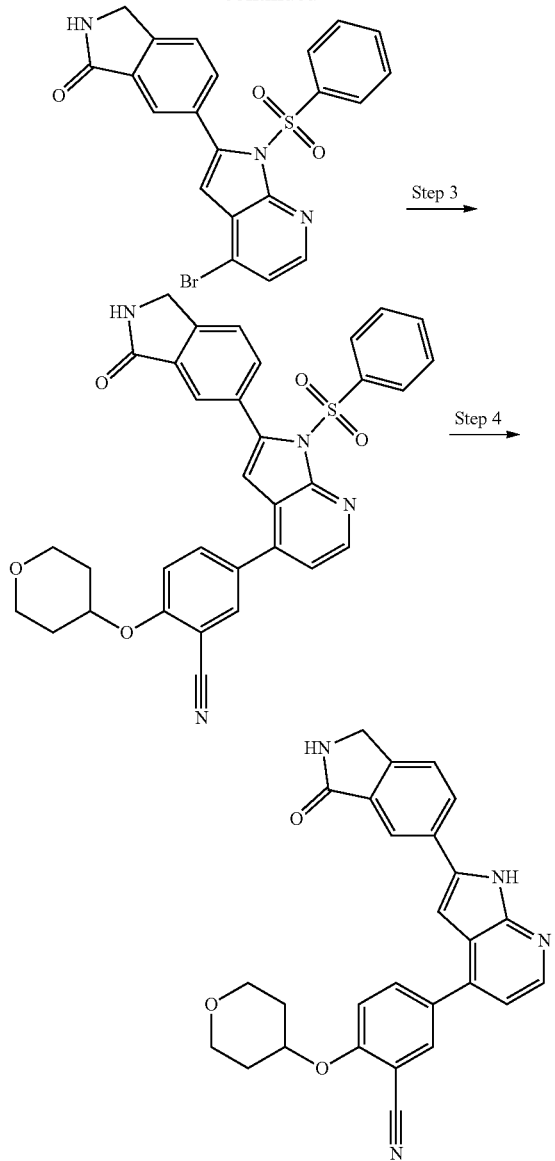

Step 1: Benzenesulfonyl chloride (4.8 g, 27 mmol) was added dropwise into a solution of 4-bromo-2-iodo-1H-pyrrolo[2,3-b]pyridine (8.0 g, 24.7 mmol), and 4-(Dimethylamino)pyridine (6.0 g, 50 mmol) in DCM (150 mL) at room temperature. The mixture was stirred for 24 hrs. The organic layer was washed with 1N HCl aqueous solution and then dried over magnesium sulfate and evaporated under reduced pressure. The solids formed were then suspended in suspended in acetonitrile, followed by filtration gave 4-bromo-2-iodo-1-(phenylsulfonyl)-1H-pyrrolo[2,3-b]pyridine. LCMS-ESI⁺ (m/z): [M+H]⁺ calcd for C$_{13}$H$_8$BrIN$_2$O$_2$S: 464.1. found: 464.9.

Step 2: To an appropriate sized microwave vial, 4-bromo-2-iodo-1-(phenylsulfonyl)-1H-pyrrolo[2,3-b]pyridine (200 mg, 0.43 mmol), 6-(4,4,5,5-tetramethyl-1,3,2-dioxaborolan-2-yl)isoindolin-1-one (123 mg, 0.47 mmol), sodium bicarbonate (127 mg, 1.23 mmol), 1,4-dioxane (3 mL) and water (1.5 mL) were added. The mixture was degassed with nitrogen for 10 minutes. Bis(triphenylphosphine)palladium (II)dichloride (48 mg, 0.043 mmol) was added and the solution heated at 105° C. for 2 h. After cooling to room temperature, the mixture was poured into water, and extracted with dichloromethane. The combined organic layers were washed with saturated aqueous sodium chloride solution, dried with magnesium sulfate, filtered and concentrated under reduced pressure. The residue 6-(4-bromo-1-(phenylsulfonyl)-1H-pyrrolo[2,3-b]pyridin-2-yl)isoindolin-1-one was used for next step. LCMS-ESI+ (m/z): [M+H]+ calcd for $C_{21}H_{14}BrN_3O_3S$: 469.3. found: 469.9.

Step 3: Following similar procedure to synthesize Example 72 step 1, beginning with 6-(4-bromo-1-(phenylsulfonyl)-1H-pyrrolo[2,3-b]pyridin-2-yl)isoindolin-1-one (200 mg, 0.43 mmol) and 2-((tetrahydro-2H-pyran-4-yl)oxy)-5-(4,4,5,5-tetramethyl-1,3,2-dioxaborolan-2-yl)benzonitrile (154 mg, 0.47 mmol), 5-(2-(3-oxoisoindolin-5-yl)-1-(phenylsulfonyl)-1H-pyrrolo[2,3-b]pyridin-4-yl)-2-((tetrahydro-2H-pyran-4-yl)oxy)benzonitrile was synthesized. LCMS-ESI+ (m/z): [M+H]+ calcd for $C_{33}H_{26}N_4O_5S$: 591.6. found 591.2.

Step 4: Following similar procedure to synthesize compound Example 72 step 2, beginning with 5-(2-(3-oxoisoindolin-5-yl)-1-(phenylsulfonyl)-1H-pyrrolo[2,3-b]pyridin-4-yl)-2-((tetrahydro-2H-pyran-4-yl)oxy)benzonitrile (100 mg, 0.169 mmol), 5-(2-(3-oxoisoindolin-5-yl)-1H-pyrrolo[2,3-b]pyridin-4-yl)-2-((tetrahydro-2H-pyran-4-yl)oxy)benzonitrile was synthesized. $^1$H NMR (400 MHz, DMSO-d6) δ 12.40 (d, J=2.0 Hz, 1H), 8.61 (s, 1H), 8.35-8.30 (m, 1H), 8.27 (d, J=5.0 Hz, 1H), 8.22 (dd, J=8.0, 1.7 Hz, 1H), 8.17 (d, J=2.3 Hz, 1H), 8.12 (dd, J=8.8, 2.4 Hz, 1H), 7.65 (d, J=8.0 Hz, 1H), 7.52 (d, J=9.0 Hz, 1H), 7.29 (d, J=1.9 Hz, 1H), 7.23 (d, J=5.0 Hz, 1H), 4.97-4.87 (m, 1H), 4.41 (s, 2H), 3.96-3.79 (m, 2H), 3.61-3.51 (m, 2H), 2.11-1.95 (m, 2H), 1.76-1.66 (m, 2H). LCMS-ESI+ (m/z): [M+H]+ calcd for $C_{27}H_{22}N_4O_3$: 451.5. found 451.2.

Example 75: Synthesis of 5-(2-(3-oxo-3,4-dihydro-2H-benzo[b][1,4]oxazin-7-yl)-1H-pyrrolo[2,3-b]pyridin-4-yl)-2-((tetrahydro-2H-pyran-4-yl)oxy)benzonitrile

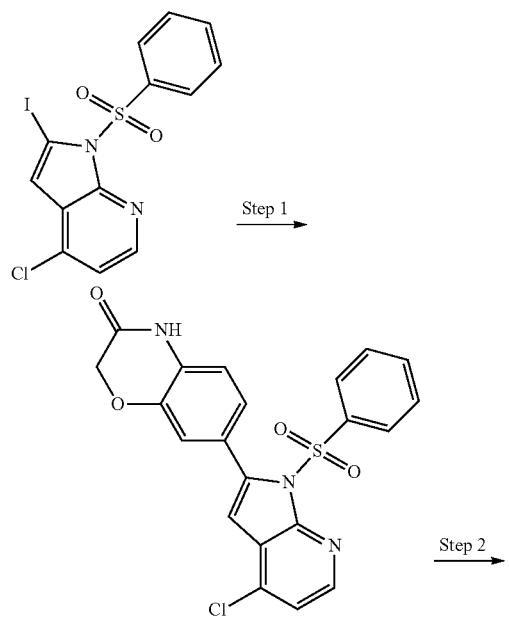

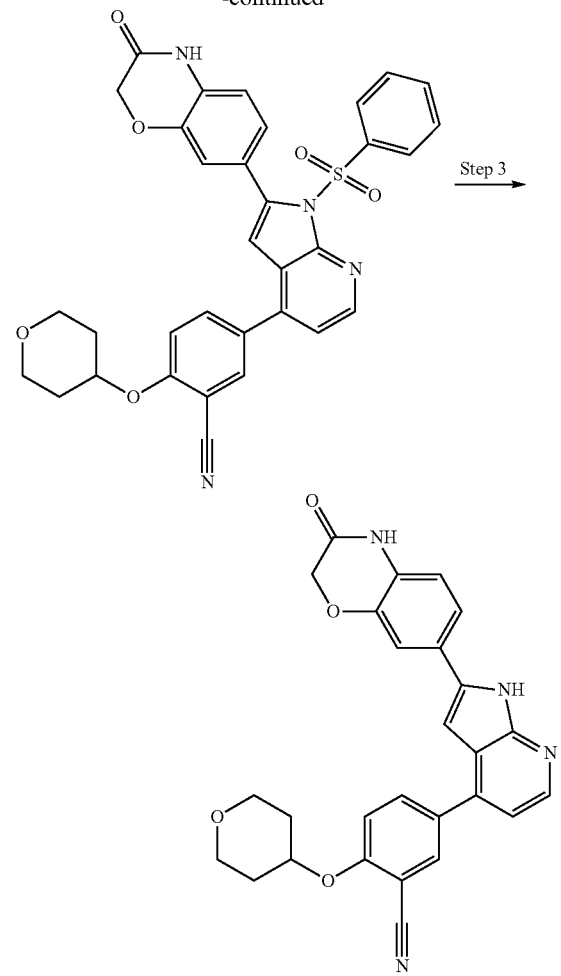

Step 1: Following similar general procedure to synthesize compound Example 74 step 2, beginning with 4-chloro-2-iodo-1-(phenylsulfonyl)-1H-pyrrolo[2,3-b]pyridine (200 mg, 0.47 mmol) and 7-(4,4,5,5-tetramethyl-1,3,2-dioxaborolan-2-yl)-2H-benzo[b][1,4]oxazin-3(4H)-one (144 mg, 0.52 mmol), 7-(4-chloro-1-(phenylsulfonyl)-1H-pyrrolo[2,3-b]pyridin-2-yl)-2H-benzo[b][1,4]oxazin-3(4H)-one was synthesized. LCMS-ESI+ (m/z): [M+H]+ calcd for $C_{21}H_{14}ClN_3O_4S$: 440.9. found 440.1.

Step 2: Following similar procedure to synthesize Example 72 step 1, beginning with 7-(4-chloro-1-(phenylsulfonyl)-1H-pyrrolo[2,3-b]pyridin-2-yl)-2H-benzo[b][1,4]oxazin-3(4H)-one (150 mg, 0.34 mmol) and 2-((tetrahydro-2H-pyran-4-yl)oxy)-5-(4,4,5,5-tetramethyl-1,3,2-dioxaborolan-2-yl)benzonitrile (123 mg, 0.37 mmol), 5-(2-(3-oxo-3,4-dihydro-2H-benzo[b][1,4]oxazin-7-yl)-1-(phenylsulfonyl)-1H-pyrrolo[2,3-b]pyridin-4-yl)-2-((tetrahydro-2H-pyran-4-yl)oxy)benzonitrile was synthesized. LCMS-ESI+ (m/z): [M+H]+ calcd for $C_{33}H_{26}N_4O_6S$: 607.7. found 607.2.

Step 3: Following similar procedure to synthesize compound Example 72 step 2, beginning with 5-(2-(3-oxo-3,4-dihydro-2H-benzo[b][1,4]oxazin-7-yl)-1-(phenylsulfonyl)-1H-pyrrolo[2,3-b]pyridin-4-yl)-2-((tetrahydro-2H-pyran-4-yl)oxy)benzonitrile (50 mg, 0.082 mmol), 5-(2-(3-oxo-3,4-dihydro-2H-benzo[b][1,4]oxazin-7-yl)-1H-pyrrolo[2,3-b]pyridin-4-yl)-2-((tetrahydro-2H-pyran-4-yl)oxy)benzonitrile was synthesized. $^1$H NMR (400 MHz, DMSO-d6) δ 12.21 (d, J=2.2 Hz, 1H), 10.81 (s, 1H), 8.23 (d, J=5.0 Hz, 1H), 8.13 (d, J=2.3 Hz, 1H), 8.07 (dd, J=8.8, 2.4 Hz, 1H), 7.63 (d, J=1.8 Hz, 1H), 7.62-7.57 (m, 1H), 7.51 (d, J=8.9 Hz, 1H), 7.19 (d, J=5.0 Hz, 1H), 7.09 (d, J=2.1 Hz, 1H), 6.97-6.91 (m, 1H), 4.97-4.87 (m, 1H), 4.67-4.57 (m, 2H), 3.93-3.84 (m, 2H), 3.6-3.5 (m, 2H), 2.10-1.98 (m, 2H), 1.75-1.65 (m, 2H). LCMS-ESI+ (m/z): [M+H]+ calcd for C27H22N4O4: 467.5. found 467.2.

Example 76: Synthesis of 5-(2-(3,3-dimethyl-2-oxoindolin-6-yl)-1H-pyrrolo[2,3-b]pyridin-4-yl)-2-((tetrahydro-2H-pyran-4-yl)oxy)benzonitrile

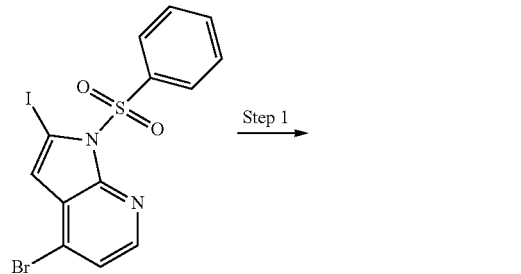

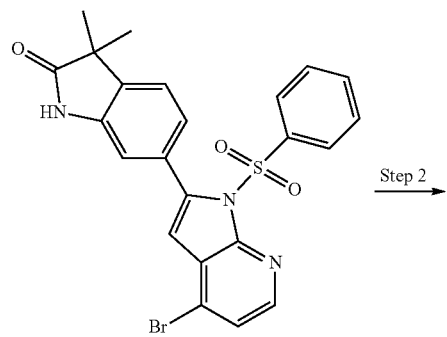

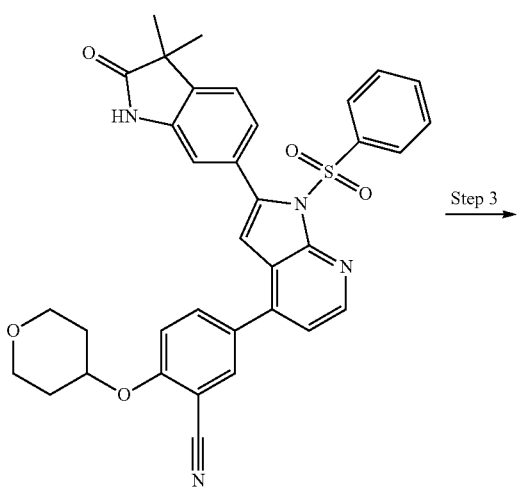

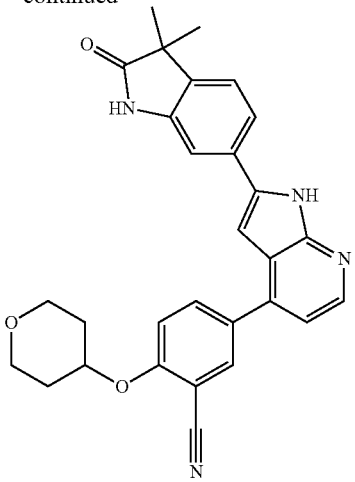

Step 1: Following similar procedure to synthesize compound Example 74 step 2, beginning with 4-bromo-2-iodo-1-(phenylsulfonyl)-1H-pyrrolo[2,3-b]pyridine (100 mg, 0.35 mmol) and 3,3-dimethyl-6-(4,4,5,5-tetramethyl-1,3,2-dioxaborolan-2-yl)indolin-2-one (204 mg, 0.35 mmol), 6-(4-bromo-1-(phenylsulfonyl)-1H-pyrrolo[2,3-b]pyridin-2-yl)-3,3-dimethylindolin-2-one was synthesized. LCMS-ESI+ (m/z): [M+H]+ calcd for C23H18BrN3O3S: 497.4. found 498.3.

Step 2: Following similar procedure to synthesize Example 72 step 1, beginning with 6-(4-bromo-1-(phenylsulfonyl)-1H-pyrrolo[2,3-b]pyridin-2-yl)-3,3-dimethylindolin-2-one (132 mg, 0.26 mmol) and 2-((tetrahydro-2H-pyran-4-yl)oxy)-5-(4,4,5,5-tetramethyl-1,3,2-dioxaborolan-2-yl)benzonitrile (105 mg, 0.319 mmol), 5-(2-(3,3-dimethyl-2-oxoindolin-6-yl)-1-(phenylsulfonyl)-1H-pyrrolo[2,3-b]pyridin-4-yl)-2-((tetrahydro-2H-pyran-4-yl)oxy)benzonitrile was synthesized. LCMS-ESI+ (m/z): [M+H]+ calcd for C35H30N4O5S: 619.7. found 619.2.

Step 3: Following similar procedure to synthesize compound Example 72 step 2, beginning with 5-(2-(3,3-dimethyl-2-oxoindolin-6-yl)-1-(phenylsulfonyl)-1H-pyrrolo[2,3-b]pyridin-4-yl)-2-((tetrahydro-2H-pyran-4-yl)oxy)benzonitrile (100 mg, 0.162 mmol), 5-(2-(3,3-dimethyl-2-oxoindolin-6-yl)-1H-pyrrolo[2,3-b]pyridin-4-yl)-2-((tetrahydro-2H-pyran-4-yl)oxy)benzonitrile was synthesized. 1H NMR (400 MHz, DMSO-d6) δ 12.29 (s, 1H), 10.50 (s, 1H), 8.25 (d, J=5.0 Hz, 1H), 8.14 (d, J=2.3 Hz, 1H), 8.08 (dd, J=8.8, 2.3 Hz, 1H), 7.60 (dd, J=7.8, 1.6 Hz, 1H), 7.52 (d, J=8.9 Hz, 1H), 7.40 (d, J=1.6 Hz, 1H), 7.36 (d, J=7.8 Hz, 1H), 7.20 (d, J=5.0 Hz, 1H), 7.03 (s, 1H), 4.97-4.87 (m, 1H), 3.92-3.82 (m, 2H), 3.6-3.5 (m, 2H), 2.11-1.97 (m, 2H), 1.75-1.65 (m, 2H), 1.27 (s, 6H).

LCMS-ESI+ (m/z): [M+H]+ calcd for C29H26N4O3: 479.5. found 479.2.

Example 77: Synthesis of 5-(2-(3-fluoro-4-morpholinophenyl)-1H-pyrrolo[2,3-b]pyridin-4-yl)-2-((tetrahydro-2H-pyran-4-yl)oxy)benzonitrile

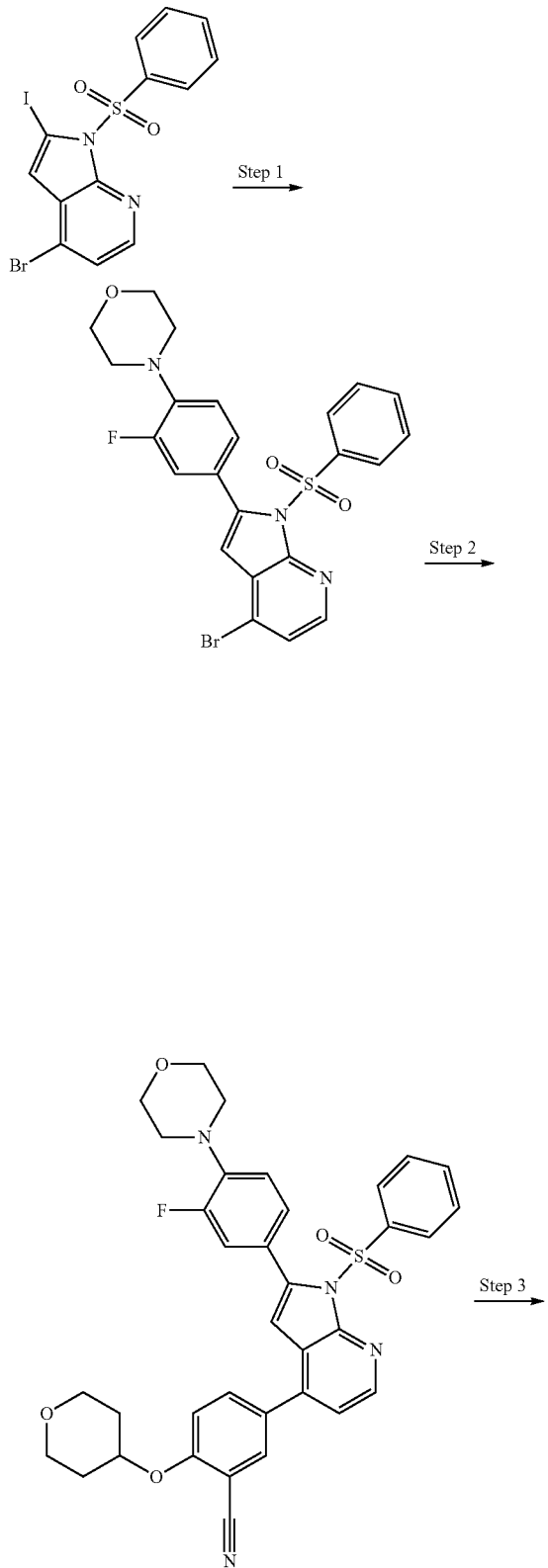

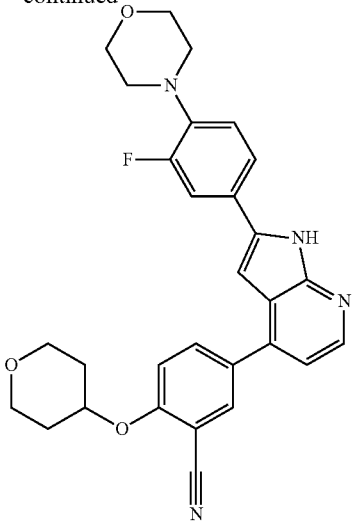

Step 1: Following similar procedure to synthesize compound Example 74 step 2, beginning with 4-bromo-2-iodo-1-(phenylsulfonyl)-1H-pyrrolo[2,3-b]pyridine (150 mg, 0.32 mmol) and (3-fluoro-4-morpholinophenyl)boronic acid (77 mg, 0.34 mmol), 4-(4-(4-bromo-1-(phenylsulfonyl)-1H-pyrrolo[2,3-b]pyridin-2-yl)-2-fluorophenyl)morpholine was synthesized. LCMS-ESI$^+$ (m/z): [M+H]$^+$ calcd for $C_{23}H_{19}BrFN_3O_3S$: 517.4. found 518.1.

Step 2: Following similar procedure to synthesize Example 72 step 1, beginning with 4-(4-(4-bromo-1-(phenylsulfonyl)-1H-pyrrolo[2,3-b]pyridin-2-yl)-2-fluorophenyl)morpholine (133 mg, 0.26 mmol) and 2-((tetrahydro-2H-pyran-4-yl)oxy)-5-(4,4,5,5-tetramethyl-1,3,2-dioxaborolan-2-yl)benzonitrile (101 mg, 0.31 mmol), 5-(2-(3-fluoro-4-morpholinophenyl)-1-(phenylsulfonyl)-1H-pyrrolo[2,3-b]pyridin-4-yl)-2-((tetrahydro-2H-pyran-4-yl)oxy)benzonitrile was synthesized. LCMS-ESI$^+$ (m/z): [M+H]$^+$ calcd for $C_{35}H_{31}FN_4O_5S$: 639.7. found 639.3.

Step 3: Following similar procedure to synthesize compound Example 72 step 2, beginning with 5-(2-(3-fluoro-4-morpholinophenyl)-1-(phenylsulfonyl)-1H-pyrrolo[2,3-b]pyridin-4-yl)-2-((tetrahydro-2H-pyran-4-yl)oxy)benzonitrile (120 mg, 0.188 mmol), 5-(2-(3-fluoro-4-morpholinophenyl)-1H-pyrrolo[2,3-b]pyridin-4-yl)-2-((tetrahydro-2H-pyran-4-yl)oxy)benzonitrile was synthesized. $^1$H NMR (400 MHz, DMSO-d6) δ 12.23 (d, J=2.2 Hz, 1H), 8.23 (d, J=5.0 Hz, 1H), 8.13 (d, J=2.3 Hz, 1H), 8.08 (dd, J=8.8, 2.4 Hz, 1H), 7.84 (dd, J=14.6, 2.1 Hz, 1H), 7.76 (dd, J=8.5, 2.1 Hz, 1H), 7.51 (d, J=8.9 Hz, 1H), 7.19 (d, J=5.0 Hz, 1H), 7.14 (d, J=2.1 Hz, 1H), 7.09 (t, J=8.9 Hz, 1H), 4.96-4.86 (m, 1H), 3.93-3.83 (m, 2H), 3.74 (dd, J=5.9, 3.4 Hz, 4H), 3.61-3.51 (m, 2H), 3.06 (dd, J=5.8, 3.5 Hz, 4H), 2.1-2.01 (m, 2H), 1.75-1.65 (m, 2H). LCMS-ESI$^+$ (m/z): [M+H]$^+$ calcd for $C_{29}H_{27}FN_4O_3$: 499.5. found 499.2.

251

Example 78: Synthesis of 5-(2-(3-morpholinophenyl)-1H-pyrrolo[2,3-b]pyridin-4-yl)-2-((tetrahydro-2H-pyran-4-yl)oxy)benzonitrile

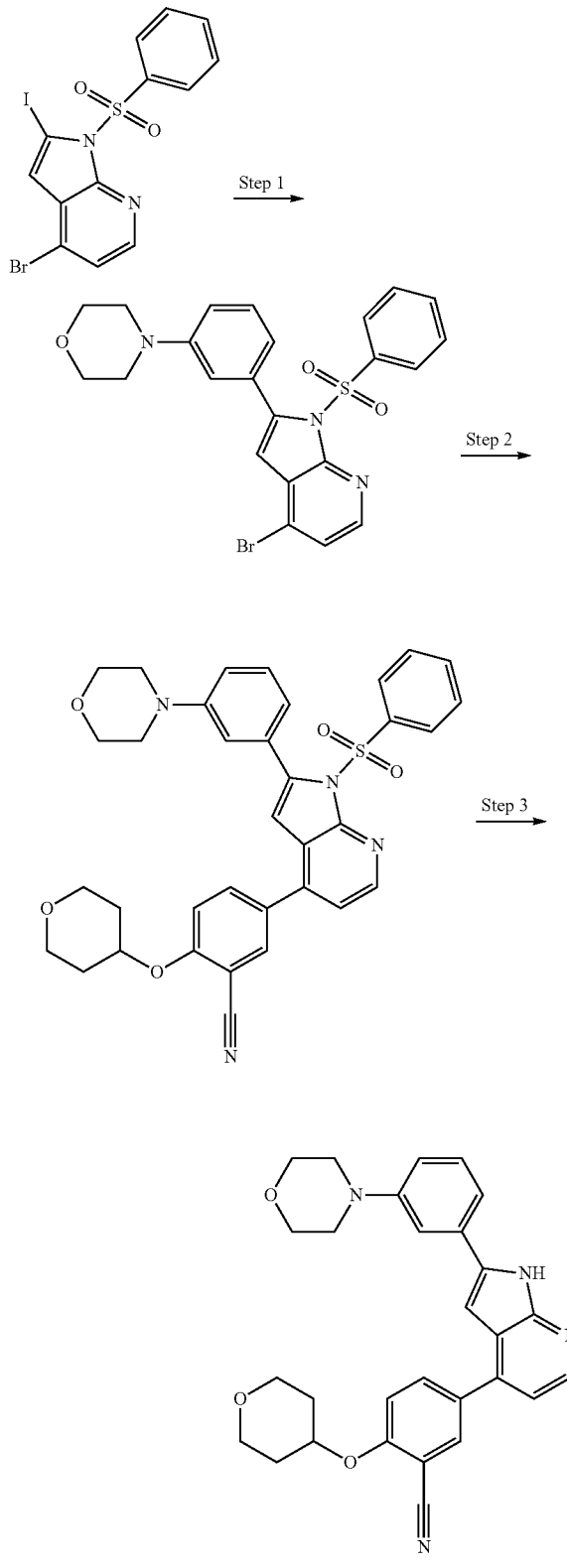

252

Step 1: Following similar procedure to synthesize compound Example 74 step 2, beginning with 4-bromo-2-iodo-1-(phenylsulfonyl)-1H-pyrrolo[2,3-b]pyridine (200 mg, 0.43 mmol) and 4-(3-(4,4,5,5-tetramethyl-1,3,2-dioxaborolan-2-yl)phenyl)morpholine (131 mg, 0.45 mmol), 4-(3-(4-bromo-1-(phenylsulfonyl)-1H-pyrrolo[2,3-b]pyridin-2-yl)phenyl)morpholine was synthesized. LCMS-ESI+ (m/z): [M+H]+ calcd for $C_{23}H_{20}BrN_3O_3S$: 499.4. found 500.0.

Step 2: Following similar procedure to synthesize Example 72 step 1, beginning with 4-(3-(4-bromo-1-(phenylsulfonyl)-1H-pyrrolo[2,3-b]pyridin-2-yl)phenyl)morpholine (112 mg, 0.26 mmol) and 2-((tetrahydro-2H-pyran-4-yl)oxy)-5-(4,4,5,5-tetramethyl-1,3,2-dioxaborolan-2-yl)benzonitrile (104 mg, 0.31 mmol), 5-(2-(3-morpholinophenyl)-1-(phenylsulfonyl)-1H-pyrrolo[2,3-b]pyridin-4-yl)-2-((tetrahydro-2H-pyran-4-yl)oxy)benzonitrile was synthesized. LCMS-ESI+ (m/z): [M+H]+ calcd for $C_{35}H_{32}N_4O_5S$: 621.7. found 621.2.

Step 3: Following similar procedure to synthesize compound Example 72 step 2, beginning with 5-(2-(3-morpholinophenyl)-1-(phenylsulfonyl)-1H-pyrrolo[2,3-b]pyridin-4-yl)-2-((tetrahydro-2H-pyran-4-yl)oxy)benzonitrile (120 mg, 0.188 mmol), 5-(2-(3-morpholinophenyl)-1H-pyrrolo[2,3-b]pyridin-4-yl)-2-((tetrahydro-2H-pyran-4-yl)oxy)benzonitrile was synthesized. 1H NMR (400 MHz, DMSO-d6) δ 12.26 (d, J=2.1 Hz, 1H), 8.25 (d, J=5.0 Hz, 1H), 8.12 (d, J=2.3 Hz, 1H), 8.08 (dd, J=8.8, 2.3 Hz, 1H), 7.57-7.49 (m, 2H), 7.43 (dd, J=7.5, 1.5 Hz, 1H), 7.29 (t, J=7.9 Hz, 1H), 7.19 (d, J=5.0 Hz, 1H), 7.13 (d, J=2.0 Hz, 1H), 6.91 (dd, J=8.1, 2.3 Hz, 1H), 4.97-4.87 (m, 1H), 3.91-3.81 (m, 2H), 3.79-3.71 (m, 4H), 3.61-3.51 (m, 2H), 3.25-3.18 (m, 4H), 2.18-2.00 (m, 2H), 1.75-1.65 (m, 2H). LCMS-ESI+ (m/z): [M+H]+ calcd for $C_{29}H_{28}N_4O_3$: 481.6. found 481.2.

Example 79: Synthesis of 3-(2-(4-morpholinophenyl)-1H-pyrrolo[2,3-b]pyridin-4-yl)benzonitrile

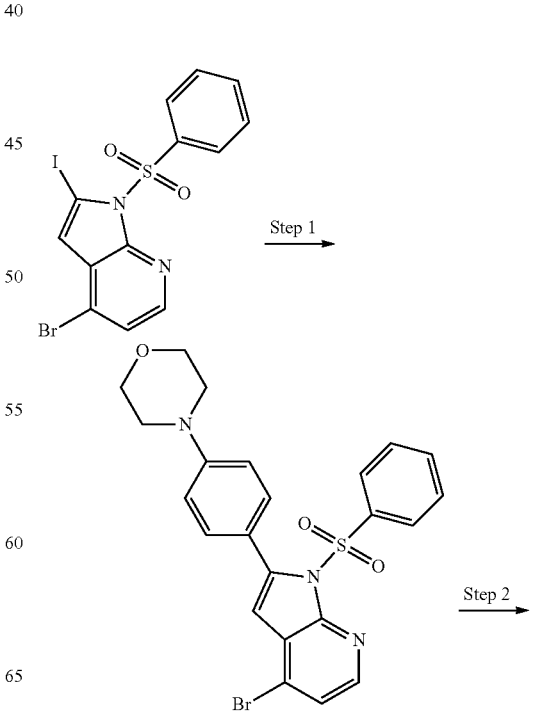

253

-continued

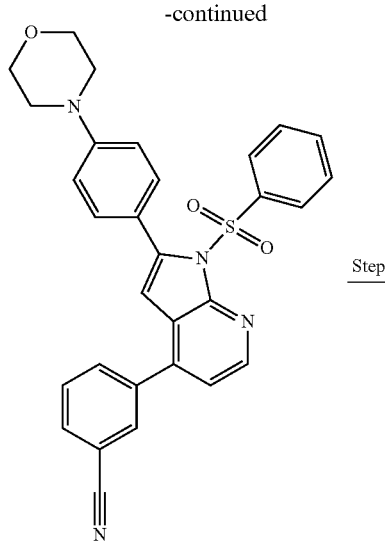

Step 3 →

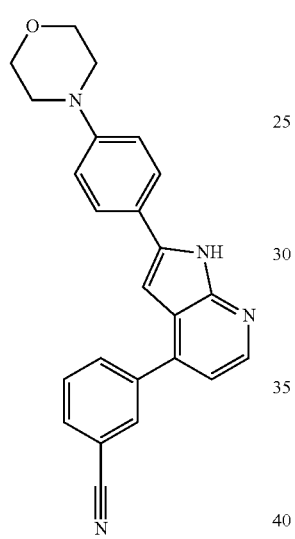

Step 1: Following similar procedure to synthesize compound Example 74 step 2, beginning with 4-bromo-2-iodo-1-(phenylsulfonyl)-1H-pyrrolo[2,3-b]pyridine (5.0 g, 10.8 mmol) and 4-(4-(4,4,5,5-tetramethyl-1,3,2-dioxaborolan-2-yl)phenyl)morpholine (3.4 g, 11.88 mmol), 4-(4-(4-bromo-1-(phenylsulfonyl)-1H-pyrrolo[2,3-b]pyridin-2-yl)phenyl)morpholine was synthesized. LCMS-ESI⁺ (m/z): [M+H]⁺ calcd for $C_{23}H_{20}BrN_3O_3S$: 499.4. found 500.0.

Step 2: Following similar procedure to synthesize Example 72 step 1, beginning with 4-(4-(4-bromo-1-(phenylsulfonyl)-1H-pyrrolo[2,3-b]pyridin-2-yl)phenyl)morpholine (100 mg, 0.20 mmol) and 3-(4,4,5,5-tetramethyl-1,3,2-dioxaborolan-2-yl)benzonitrile (55 mg, 0.24 mmol), 3-(2-(4-morpholinophenyl)-1-(phenylsulfonyl)-1H-pyrrolo[2,3-b]pyridin-4-yl)benzonitrile was synthesized. LCMS-ESI⁺ (m/z): [M+H]⁺ calcd for $C_{30}H_{24}N_4O_3S$: 521.6. found 521.2.

Step 3: Following similar procedure to synthesize compound Example 72 step 2, beginning with 3-(2-(4-morpholinophenyl)-1-(phenylsulfonyl)-1H-pyrrolo[2,3-b]pyridin-4-yl)benzonitrile (90 mg, 0.173 mmol), 3-(2-(4-morpholinophenyl)-1H-pyrrolo[2,3-b]pyridin-4-yl)benzonitrile was synthesized. ¹H NMR (400 MHz, DMSO-d6) δ 12.18 (d, J=2.1 Hz, 1H), 8.26-8.19 (m, 2H), 8.16 (dt, J=7.9, 1.4 Hz, 1H), 7.92 (dt, J=7.8, 1.3 Hz, 1H), 7.87 (d,

254

J=8.7 Hz, 2H), 7.76 (t, J=7.8 Hz, 1H), 7.22 (d, J=5.0 Hz, 1H), 7.04-6.96 (m, 3H), 3.74 (t, J=4.8 Hz, 4H), 3.18 (t, J=4.9 Hz, 4H). LCMS-ESI⁺ (m/z): [M+H]⁺ calcd for $C_{24}H_{20}N_4O$: 381.4. found 381.1.

Example 80: Synthesis of 2-(cyclopropylmethoxy)-5-(2-(4-morpholinophenyl)-1H-pyrrolo[2,3-b]pyridin-4-yl)benzonitrile

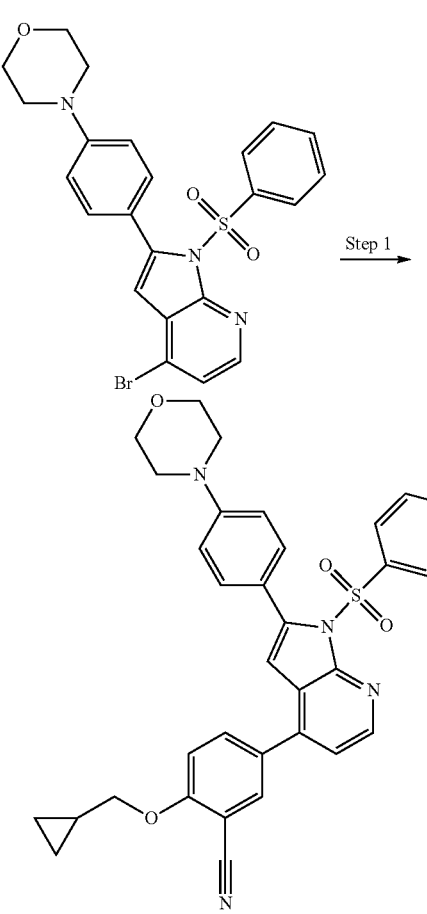

Step 1: Following similar procedure to synthesize Example 72 step 1, beginning with 4-(4-(4-bromo-1-(phenylsulfonyl)-1H-pyrrolo[2,3-b]pyridin-2-yl)phenyl)morpholine (150 mg, 0.30 mmol) and 2-(cyclopropylmethoxy)-5-(4,4,5,5-tetramethyl-1,3,2-dioxaborolan-2-yl)benzonitrile (108 mg, 0.36 mmol), 2-(cyclopropylmethoxy)-5-(2-(4-morpholinophenyl)-1-(phenylsulfonyl)-1H-pyrrolo[2,3-b]pyridin-4-yl)benzonitrile was synthesized. LCMS-ESI⁺ (m/z): [M+H]⁺ calcd for $C_{34}H_{30}N_4O_4S$: 591.7. found 591.2.

Step 2: Following similar procedure to synthesize compound Example 72 step 2, beginning with 2-(cyclopropylmethoxy)-5-(2-(4-morpholinophenyl)-1-(phenylsulfonyl)-1H-pyrrolo[2,3-b]pyridin-4-yl)benzonitrile (90 mg, 0.173 mmol), 2-(cyclopropylmethoxy)-5-(2-(4-morpholinophenyl)-1H-pyrrolo[2,3-b]pyridin-4-yl)benzonitrile was synthesized. ¹H NMR (400 MHz, DMSO-d6) δ 12.12 (d, J=2.0 Hz, 1H), 8.18 (d, J=5.0 Hz, 1H), 8.14-8.03 (m, 2H), 7.92-7.77 (m, 2H), 7.39 (d, J=8.8 Hz, 1H), 7.16 (d, J=5.0 Hz, 1H), 7.04-6.97 (m, 2H), 6.95 (d, J=2.0 Hz, 1H), 4.09 (d, J=7.0 Hz, 2H), 3.82-3.65 (m, 4H), 3.21-3.14 (m, 4H), 1.36-1.26 (m, 1H), 0.70-0.54 (m, 2H), 0.47-0.31 (m, 2H). LCMS-ESI⁺ (m/z): [M+H]⁺ calcd for $C_{28}H_{26}N_4O_2$: 451.5. found 451.3.

Example 81: Synthesis of 5-(2-(6-morpholinopyridin-3-yl)-1H-pyrrolo[2,3-b]pyridin-4-yl)-2-((tetrahydro-2H-pyran-4-yl)oxy)benzonitrile

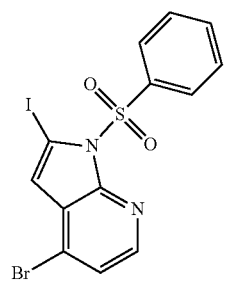

Step 1 →

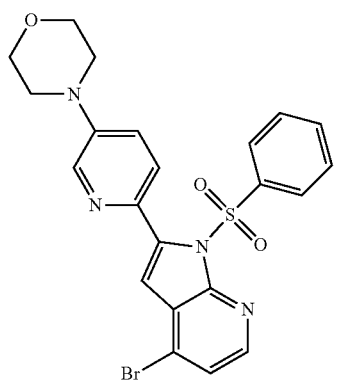

Step 2 →

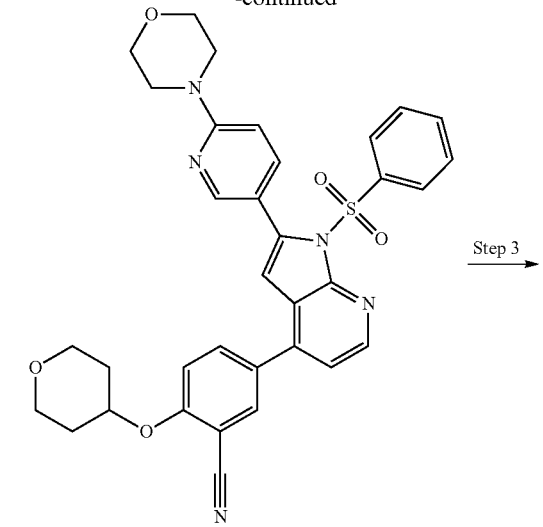

Step 3 →

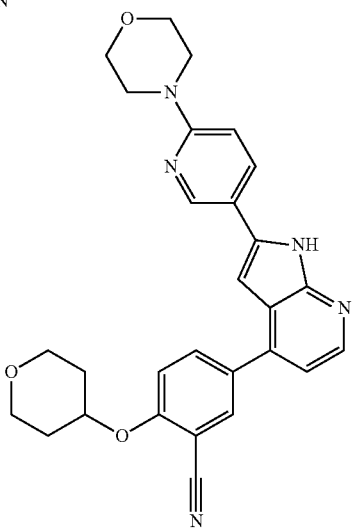

Step 1: Following similar procedure to synthesize compound Example 74 step 2, beginning with 4-bromo-2-iodo-1-(phenylsulfonyl)-1H-pyrrolo[2,3-b]pyridine (200 mg, 0.43 mmol) and 4-(5-(4,4,5,5-tetramethyl-1,3,2-dioxaborolan-2-yl)pyridin-2-yl)morpholine (132 mg, 0.45 mmol), 4-(5-(4-bromo-1-(phenylsulfonyl)-1H-pyrrolo[2,3-b]pyridin-2-yl)pyridin-2-yl)morpholine was synthesized. LCMS-ESI⁺ (m/z): [M+H]⁺ calcd for $C_{22}H_{19}BrN_4O_3S$: 500.4. found 501.1.

Step 2: Following similar procedure to synthesize Example 72 step 1, beginning with 4-(5-(4-bromo-1-(phenylsulfonyl)-1H-pyrrolo[2,3-b]pyridin-2-yl)pyridin-2-yl)morpholine (130 mg, 0.26 mmol) and 2-((tetrahydro-2H-pyran-4-yl)oxy)-5-(4,4,5,5-tetramethyl-1,3,2-dioxaborolan-2-yl)benzonitrile (102 mg, 0.31 mmol), 5-(2-(6-morpholinopyridin-3-yl)-1-(phenylsulfonyl)-1H-pyrrolo[2,3-b]pyridin-4-yl)-2-((tetrahydro-2H-pyran-4-yl)oxy)benzonitrile was synthesized. LCMS-ESI⁺ (m/z): [M+H]⁺ calcd for $C_{34}H_{31}N_5O_5S$: 622.7. found 622.2.

Step 3: Following general similar to synthesize compound Example 72 step 2, beginning with 5-(2-(6-morpholinopyridin-3-yl)-1-(phenylsulfonyl)-1H-pyrrolo[2,3-b]pyridin-4-yl)-2-((tetrahydro-2H-pyran-4-yl)oxy)benzonitrile (85 mg, 0.137 mmol), 5-(2-(6-morpholinopyridin-3-yl)-1H-pyrrolo[2,3-b]pyridin-4-yl)-2-((tetrahydro-2H-pyran-4-yl)oxy)benzonitrile was synthesized. ¹H NMR (400 MHz, DMSO-d6) δ 12.29-12.09 (m, 1H), 8.77 (d, J=2.4 Hz, 1H), 8.20 (d, J=5.0 Hz, 1H), 8.14 (dd, J=10.5, 2.3 Hz, 2H), 8.07 (dd, J=8.8, 2.4 Hz, 1H), 7.51 (d, J=9.0 Hz, 1H), 7.18 (d, J=5.0 Hz, 1H), 7.04 (d, J=2.0 Hz, 1H), 6.92 (d, J=8.9 Hz, 1H), 4.96-4.85 (m, 1H), 3.92-3.83 (m, 2H), 3.73-3.68 (m, 4H), 3.60-3.46 (m, 6H), 2.09-1.98 (m, 2H), 1.74-1.65 (m, 2H). LCMS-ESI⁺ (m/z): [M+H]⁺ calcd for $C_{28}H_{27}N_5O_3$: 482.5. found 482.3.

Example 82: Synthesis of 5-(2-(4-(4-methylpiperazin-1-yl)phenyl)-1H-pyrrolo[2,3-b]pyridin-4-yl)-2-((tetrahydro-2H-pyran-4-yl)oxy)benzonitrile

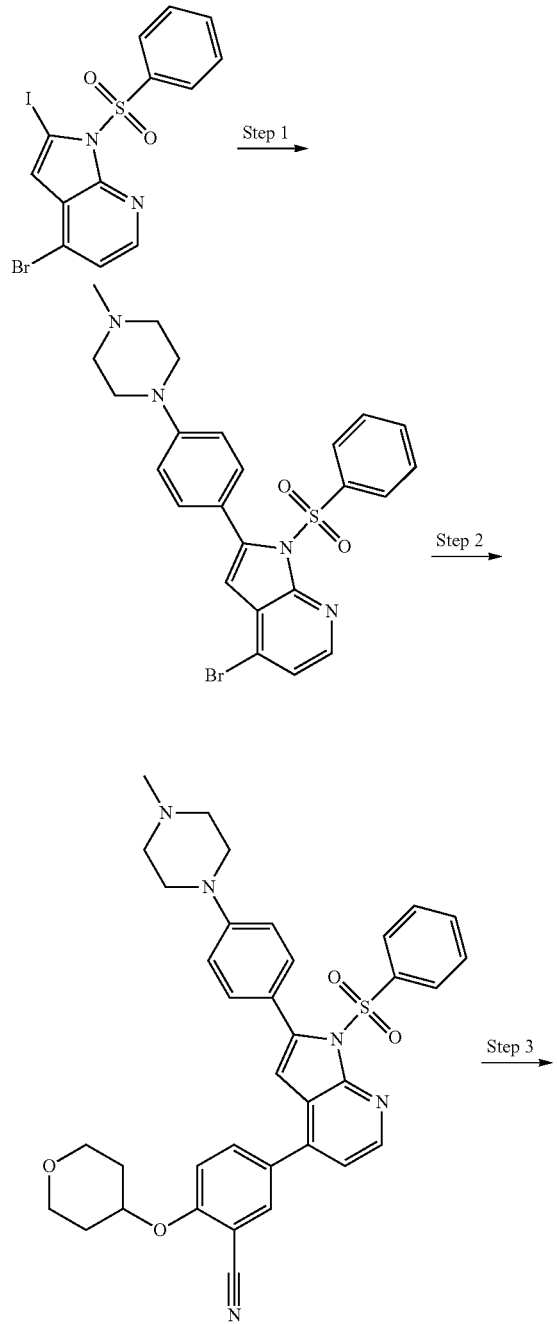

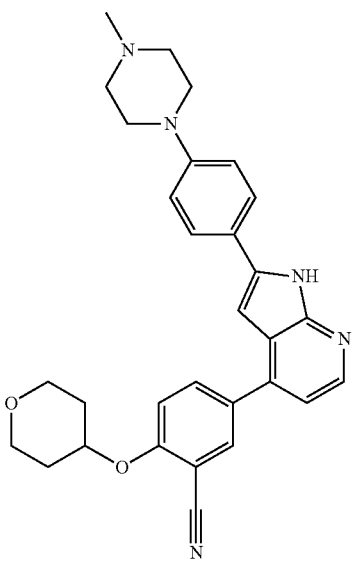

Step 1: Following similar procedure to synthesize compound Example 74 step 2, beginning with 4-bromo-2-iodo-1-(phenylsulfonyl)-1H-pyrrolo[2,3-b]pyridine (200 mg, 0.43 mmol) and 1-methyl-4-(4-(4,4,5,5-tetramethyl-1,3,2-dioxaborolan-2-yl)phenyl)piperazine (137 mg, 0.45 mmol), 4-bromo-2-(4-(4-methylpiperazin-1-yl)phenyl)-1-(phenylsulfonyl)-1H-pyrrolo[2,3-b]pyridine was synthesized. LCMS-ESI⁺ (m/z): [M+H]⁺ calcd for $C_{24}H_{23}BrN_4O_2S$: 511.43. found 513.0.

Step 2: Following similar procedure to synthesize Example 72 step 1, beginning with 4-bromo-2-(4-(4-methylpiperazin-1-yl)phenyl)-1-(phenylsulfonyl)-1H-pyrrolo[2,3-b]pyridine (220 mg, 0.43 mmol) and 2-((tetrahydro-2H-pyran-4-yl)oxy)-5-(4,4,5,5-tetramethyl-1,3,2-dioxaborolan-2-yl)benzonitrile (169 mg, 0.51 mmol), 5-(2-(4-(4-methylpiperazin-1-yl)phenyl)-1-(phenylsulfonyl)-1H-pyrrolo[2,3-b]pyridin-4-yl)-2-((tetrahydro-2H-pyran-4-yl)oxy)benzonitrile was synthesized. LCMS-ESI⁺ (m/z): [M+H]⁺ calcd for $C_{36}H_{35}N_5O_4S$: 634.8. found 634.2.

Step 3: Following similar procedure to synthesize compound Example 72, beginning with 5-(2-(4-(4-methylpiperazin-1-yl)phenyl)-1-(phenylsulfonyl)-1H-pyrrolo[2,3-b]pyridin-4-yl)-2-((tetrahydro-2H-pyran-4-yl)oxy)benzonitrile (85 mg, 0.137 mmol), 5-(2-(4-(4-methylpiperazin-1-yl)phenyl)-1H-pyrrolo[2,3-b]pyridin-4-yl)-2-((tetrahydro-2H-pyran-4-yl)oxy)benzonitrile was synthesized. ¹H NMR (400 MHz, DMSO-d6) δ 12.10 (s, 1H), 8.18 (d, J=5.0 Hz, 1H), 8.12 (d, J=2.3 Hz, 1H), 8.07 (dd, J=8.8, 2.4 Hz, 1H), 7.83 (d, J=8.8 Hz, 2H), 7.51 (d, J=8.9 Hz, 1H), 7.16 (d, J=5.0 Hz, 1H), 7.04-6.96 (m, 2H), 6.95 (d, J=2.1 Hz, 1H), 4.96-4.87 (m, 1H), 3.92-3.85 (m, 2H), 3.59-3.50 (m, 2H), 3.20 (t, J=5.0 Hz, 4H), 2.44 (t, J=5.0 Hz, 4H), 2.21 (s, 3H), 2.10-1.95 (m, 2H), 1.73-1.65 (m, 2H). LCMS-ESI⁺ (m/z): [M+H]⁺ calcd for $C_{30}H_{31}N_5O_2$: 494.6. found 494.3.

259

Example 83: Synthesis of 5-(2-phenyl-1H-pyrrolo[2,3-b]pyridin-4-yl)-2-((tetrahydro-2H-pyran-4-yl)oxy)benzonitrile

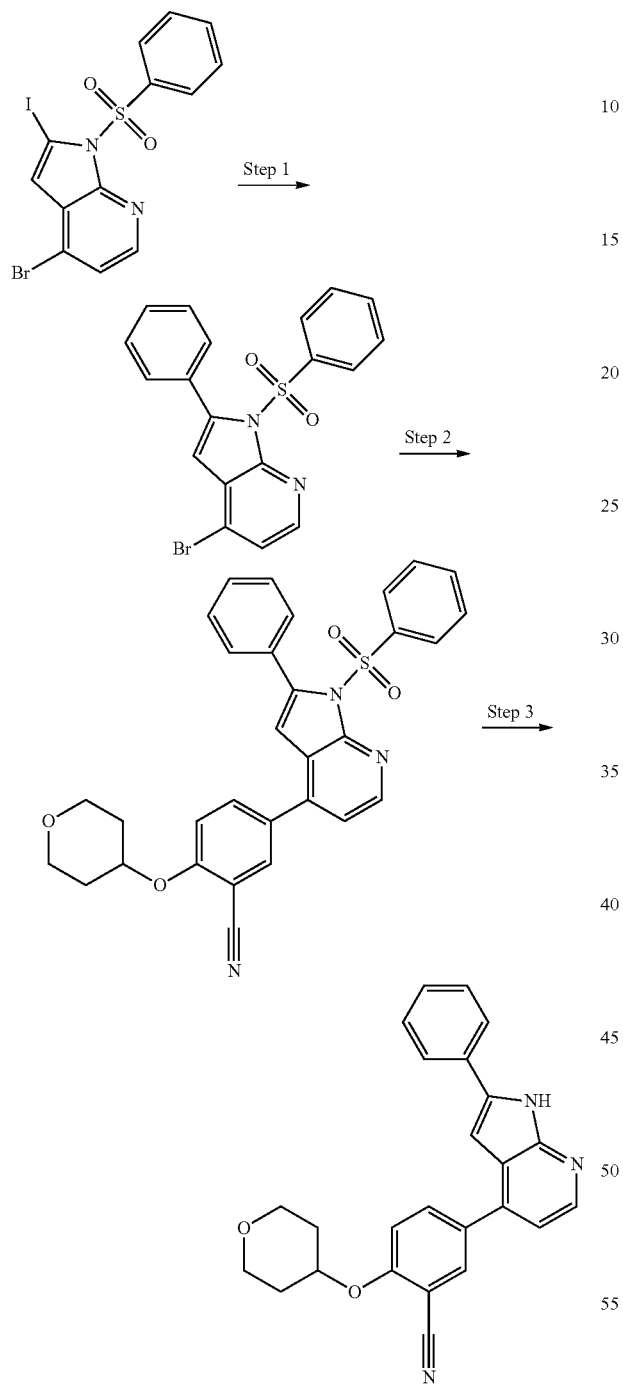

Step 1: Following similar procedure to synthesize compound Example 74 step 2, beginning with 4-bromo-2-iodo-1-(phenylsulfonyl)-1H-pyrrolo[2,3-b]pyridine (200 mg, 0.43 mmol) and 4,4,5,5-tetramethyl-2-phenyl-1,3,2-dioxaborolane (92 mg, 0.45 mmol), 4-bromo-2-phenyl-1-(phenylsulfonyl)-1H-pyrrolo[2,3-b]pyridine was synthesized. LCMS-ESI$^+$ (m/z): [M+H]$^+$ calcd for C$_{19}$H$_{13}$BrN$_2$O$_2$S: 414.3. found 414.9.

260

Step 2: Following similar procedure to synthesize Example 72 step 1, beginning with 4-bromo-2-phenyl-1-(phenylsulfonyl)-1H-pyrrolo[2,3-b]pyridine (111 mg, 0.26 mmol) and 2-((tetrahydro-2H-pyran-4-yl)oxy)-5-(4,4,5,5-tetramethyl-1,3,2-dioxaborolan-2-yl)benzonitrile (106 mg, 0.32 mmol), 5-(2-phenyl-1-(phenylsulfonyl)-1H-pyrrolo[2,3-b]pyridin-4-yl)-2-((tetrahydro-2H-pyran-4-yl)oxy)benzonitrile was synthesized. LCMS-ESI$^+$ (m/z): [M+H]$^+$ calcd for C$_{31}$H$_{25}$N$_3$O$_4$S: 536.6. found 536.2.

Step 3: Following similar procedure to synthesize compound Example 72 step 2, beginning with 5-(2-phenyl-1-(phenylsulfonyl)-1H-pyrrolo[2,3-b]pyridin-4-yl)-2-((tetrahydro-2H-pyran-4-yl)oxy)benzonitrile (60 mg, 0.112 mmol), 5-(2-phenyl-1H-pyrrolo[2,3-b]pyridin-4-yl)-2-((tetrahydro-2H-pyran-4-yl)oxy)benzonitrile was synthesized. LCMS-ESI$^+$ (m/z): [M+H]$^+$ calcd for C$_{25}$H$_{21}$N$_3$O$_2$: 396.4. found 396.2.

Example 84: Synthesis of 5-(2-(1-methyl-1H-pyrazol-4-yl)-1H-pyrrolo[2,3-b]pyridin-4-yl)-2-((tetrahydro-2H-pyran-4-yl)oxy)benzonitrile

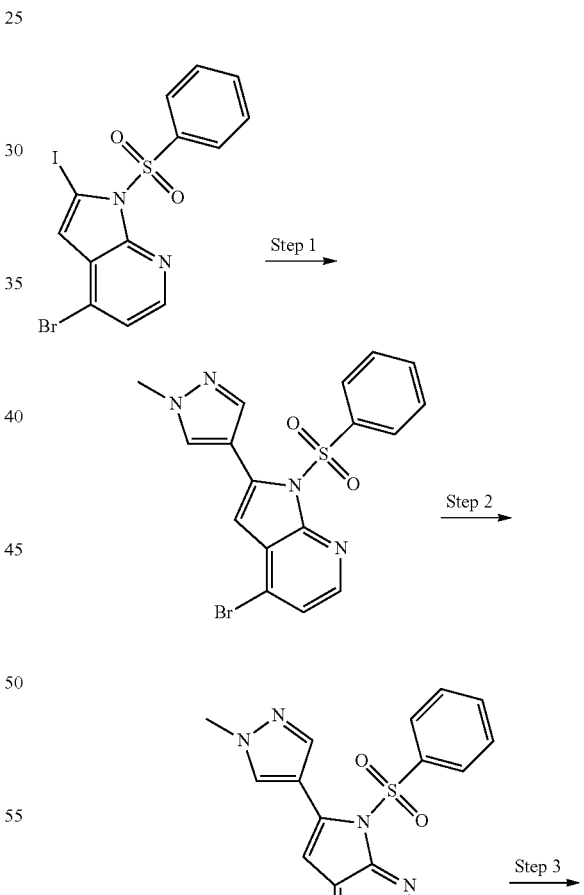

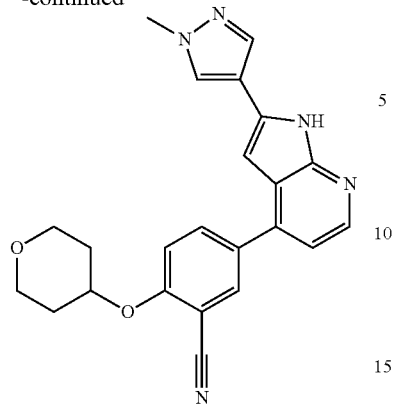

Step 1: Following similar procedure to synthesize compound Example 74 step 2, beginning with 4-bromo-2-iodo-1-(phenylsulfonyl)-1H-pyrrolo[2,3-b]pyridine (200 mg, 0.43 mmol) and 1-methyl-4-(4,4,5,5-tetramethyl-1,3,2-dioxaborolan-2-yl)-1H-pyrazole (92 mg, 0.45 mmol), 4-bromo-2-(1-methyl-1H-pyrazol-4-yl)-1-(phenylsulfonyl)-1H-pyrrolo[2,3-b]pyridine was synthesized. LCMS-ESI[+] (m/z): [M+H][+] calcd for $C_{17}H_{13}BrN_4O_2S$: 418.3. found 418.9.

Step 2: Following similar procedure to synthesize Example 72 step 1, beginning with 4-bromo-2-(1-methyl-1H-pyrazol-4-yl)-1-(phenylsulfonyl)-1H-pyrrolo[2,3-b]pyridine (121 mg, 0.29 mmol) and 2-((tetrahydro-2H-pyran-4-yl)oxy)-5-(4,4,5,5-tetramethyl-1,3,2-dioxaborolan-2-yl)benzonitrile (114.5 mg, 0.34 mmol), 5-(2-(1-methyl-1H-pyrazol-4-yl)-1-(phenylsulfonyl)-1H-pyrrolo[2,3-b]pyridin-4-yl)-2-((tetrahydro-2H-pyran-4-yl)oxy)benzonitrile was synthesized. LCMS-ESI[+] (m/z): [M+H][+] calcd for $C_{29}H_{25}N_5O_4S$: 540.6. found 540.2.

Step 3: Following similar procedure to synthesize compound Example 72 step 2, beginning with 5-(2-(1-methyl-1H-pyrazol-4-yl)-1-(phenylsulfonyl)-1H-pyrrolo[2,3-b]pyridin-4-yl)-2-((tetrahydro-2H-pyran-4-yl)oxy)benzonitrile (55 mg, 0.102 mmol), 5-(2-(1-methyl-1H-pyrazol-4-yl)-1H-pyrrolo[2,3-b]pyridin-4-yl)-2-((tetrahydro-2H-pyran-4-yl)oxy)benzonitrile was synthesized. $^1$H NMR (400 MHz, DMSO-d6) δ 12.07 (d, J=2.4 Hz, 1H), 8.21 (s, 1H), 8.17 (d, J=5.0 Hz, 1H), 8.09 (d, J=2.3 Hz, 1H), 8.06-7.98 (m, 2H), 7.52 (d, J=8.9 Hz, 1H), 7.15 (d, J=5.0 Hz, 1H), 6.78 (d, J=2.0 Hz, 1H), 4.96-4.87 (m, 1H), 3.94-3.81 (m, 5H), 3.59-3.51 (m, 2H), 2.1-2.01 (m, 2H), 1.73-1.65 (m, 2H). LCMS-ESI[+] (m/z): [M+H][+] calcd for $C_{23}H_{21}N_5O_2$: 400.4. found 400.2.

Example 85: Synthesis of 5-(2-(4-(4-(oxetan-3-yl)piperazin-1-yl)phenyl)-1H-pyrrolo[2,3-b]pyridin-4-yl)-2-((tetrahydro-2H-pyran-4-yl)oxy)benzonitrile

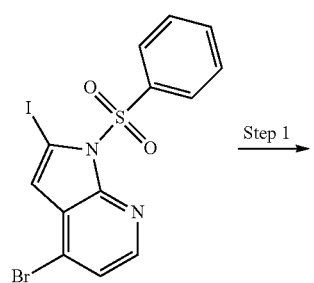

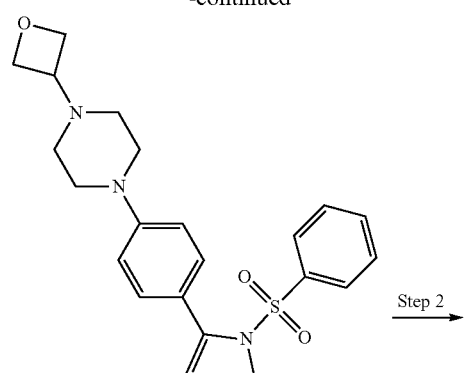

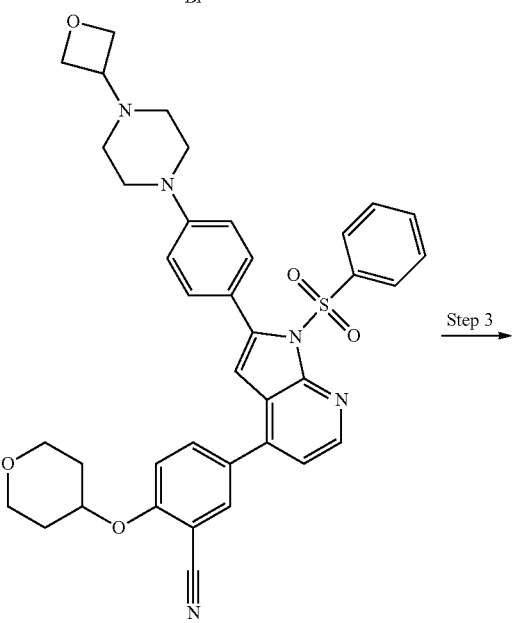

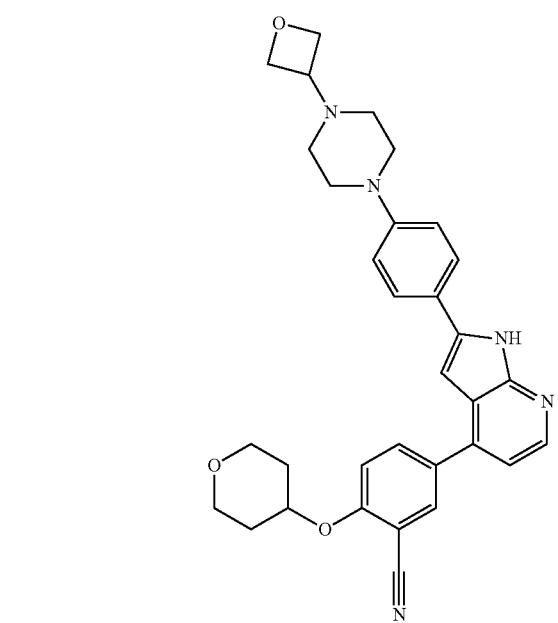 [SMILES: N#Cc1cc(-c2ccnc3[nH]c(-c4ccc(N5CCN(C6COC6)CC5)cc4)cc23)ccc1OC1CCOCC1]

Step 1: Following similar procedure to synthesize compound Example 74 step 2, beginning with 4-bromo-2-iodo-1-(phenylsulfonyl)-1H-pyrrolo[2,3-b]pyridine (300 mg, 0.64 mmol) and 1-(oxetan-3-yl)-4-(4-(4,4,5,5-tetramethyl-1,3,2-dioxaborolan-2-yl)phenyl)piperazine (267 mg, 0.77 mmol), 4-bromo-2-(1-methyl-1H-pyrazol-4-yl)-1-(phenylsulfonyl)-1H-pyrrolo[2,3-b]pyridine was synthesized. LCMS-ESI+ (m/z): [M+H]+ calcd for $C_{26}H_{25}BrN_4O_3S$: 554.4. found 555.0.

Step 2: Following similar procedure to synthesize Example 72 step 1, beginning with 4-bromo-2-(4-(4-(oxetan-3-yl)piperazin-1-yl)phenyl)-1-(phenylsulfonyl)-1H-pyrrolo[2,3-b]pyridine (100 mg, 0.18 mmol) and 2-((tetrahydro-2H-pyran-4-yl)oxy)-5-(4,4,5,5-tetramethyl-1,3,2-dioxaborolan-2-yl)benzonitrile (71 mg, 0.217 mmol), 5-(2-(4-(4-(oxetan-3-yl)piperazin-1-yl)phenyl)-1-(phenylsulfonyl)-1H-pyrrolo[2,3-b]pyridin-4-yl)-2-((tetrahydro-2H-pyran-4-yl)oxy)benzonitrile was synthesized. LCMS-ESI+ (m/z): [M+H]+ calcd for $C_{38}H_{37}N_5O_5S$: 676.8. found 676.2.

Step 3: Following similar procedure to synthesize compound Example 72 step 2, beginning with 5-(2-(4-(4-(oxetan-3-yl)piperazin-1-yl)phenyl)-1-(phenylsulfonyl)-1H-pyrrolo[2,3-b]pyridin-4-yl)-2-((tetrahydro-2H-pyran-4-yl)oxy)benzonitrile (85 mg, 0.126 mmol), 5-(2-(4-(4-(oxetan-3-yl)piperazin-1-yl)phenyl)-1H-pyrrolo[2,3-b]pyridin-4-yl)-2-((tetrahydro-2H-pyran-4-yl)oxy)benzonitrile was synthesized. $^1$H NMR (400 MHz, DMSO-d6) δ 12.11 (s, 1H), 8.18 (d, J=5.0 Hz, 1H), 8.12 (d, J=2.3 Hz, 1H), 8.07 (dd, J=8.8, 2.3 Hz, 1H), 7.83 (d, J=8.7 Hz, 2H), 7.52 (d, J=8.9 Hz, 1H), 7.16 (d, J=5.0 Hz, 1H), 7.00 (d, J=8.8 Hz, 2H), 6.95 (d, J=2.1 Hz, 1H), 4.96-4.88 (m, 1H), 4.56 (t, J=6.5 Hz, 2H), 4.46 (t, J=6.1 Hz, 2H), 3.97-3.80 (m, 2H), 3.6-3.51 (m, 2H), 3.49-3.41 (m, 1H), 3.29-3.19 (m, 4H), 2.44-2.37 (m, 4H), 2.10-1.97 (m, 2H), 1.75-1.66 (m, 2H). LCMS-ESI+ (m/z): [M+H]+ calcd for $C_{32}H_{33}N_5O_3$: 536.6. found 536.3.

Example 86: Preparation of 6-(2-(4-morpholinophenyl)-1H-pyrrolo[2,3-b]pyridin-4-yl)-3-((tetrahydro-2H-pyran-4-yl)oxy)picolinonitrile

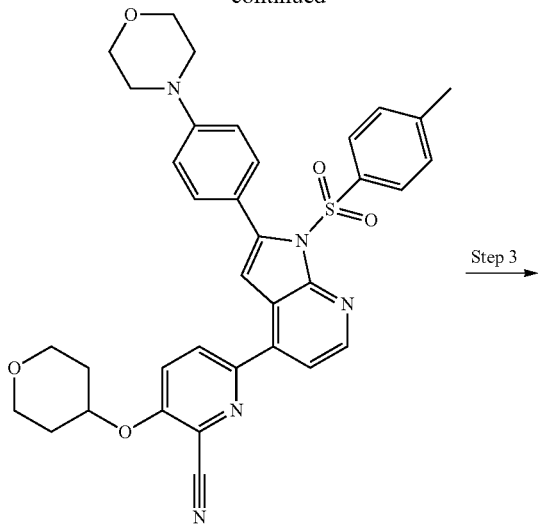

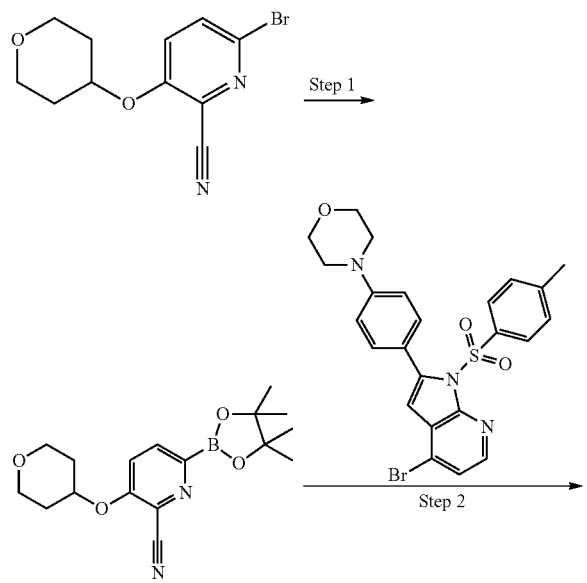

Step 1: 6-bromo-3-((tetrahydro-2H-pyran-4-yl)oxy)picolinonitrile (200 mg, 0.71 mmol) was dissolved in dioxane (15 mL), vacuumed and back filled with argon. The solution in positive argon flow was added mixture of 4,4,4',4',5,5,5',5'-octamethyl-2,2'-bi(1,3,2-dioxaborolane) (179 mg, 0.71 mmol), KOAc (208 mg, 2.12 mmol) and Pd-dppf (21 mg, 0.03 mmol). This mixture was vacuumed and back filled with argon and heated at 80° C. for 2 h. The reaction was cooled to room temperature, diluted with ethyl acetate (25 mL) and stirred for 10 min. The solid particle was filtered through pad of silica gel, washed with ethyl acetate and the solvent was concentrated to dryness to afford product 3-((tetrahydro-2H-pyran-4-yl)oxy)-6-(4,4,5,5-tetramethyl-1,3,2-dioxaborolan-2-yl)picolinonitrile. This crude product was used for next step without further purification.

Step 2: To stirred mixture of 4-(4-(4-bromo-1-tosyl-1H-pyrrolo[2,3-b]pyridin-2-yl)phenyl)morpholine (140 mg, 0.27 mmol), 3-((tetrahydro-2H-pyran-4-yl)oxy)-6-(4,4,5,5-tetramethyl-1,3,2-dioxaborolan-2-yl)picolinonitrile (108 mg, 0.32 mmol), and PEPPSI-iPr catalyst (37 mg, 0.05 mmol) in Dioxane (4 mL) was added solution of $Cs_2CO_3$ (266 mg, 0.82 mmol) in Water (2 mL) and heated at 100° C. for 1 h. The mixture was diluted with dichloromethane and water. The organic layer was separated, and dried over $Na_2SO_4$. The solvent was concentrated to afford product 6-(2-(4-morpholinophenyl)-1-tosyl-1H-pyrrolo[2,3-b]pyridin-4-yl)-3-((tetrahydro-2H-pyran-4-yl)oxy)picolinonitrile and used for nest step without purification. LCMS-ESI$^+$ (m/z): [M+H]$^+$ calcd for $C_{35}H_{33}N_5O_5S$: 636.7. found: 636.2.

Step 3: To a solution of 6-(2-(4-morpholinophenyl)-1-(phenylsulfonyl)-1H-pyrrolo[2,3-b]pyridin-4-yl)-3-((tetrahydro-2H-pyran-4-yl)oxy)picolinonitrile (150 mg, 0.23 mmol) 2,2,2,-Trifluoroethanol, Me-THF (2:1) was added $Cs_2CO_3$ (230 mg, 0.71 mmol). This mixture was heated at 85° C. for 12 h. The reaction mixture was cooled to room temperature, diluted with dichloromethane and poured in to water. The organic layer separated, dried over $Na_2SO_4$ and the solvent was concentrated to dryness. The residue was purified via prep HPLC (5-95% acetonitrile in water, 0.1% trifluoroacetic acid buffer) to isolate 6-(2-(4-morpholinophenyl)-1H-pyrrolo[2,3-b]pyridin-4-yl)-3-((tetrahydro-2H-pyran-4-yl)oxy)picolinonitrile. $^1$H NMR (400 MHz, DMSO-d6) δ 12.26 (s, —NH), 8.42 (d, J=8.8 Hz, 1H), 8.26 (d, J=5.6 Hz, 1H), 8.05 (d, J=9.2 Hz, 1H), 7.85 (d, J=9.2 Hz, 2H), 7.57 (d, J=5.2 Hz, 1H), 7.26 (d, J=1.2 Hz, 1H), 7.06 (d, J=9.2 Hz, 2H), 5.01-4.96 (m, 1H), 3.94-3.85 (m, 2H), 3.75-3.73 (m, 4H), 3.58-3.52 (m, 2H), 3.20-3.15 (m, 4H), 2.06-2.03 (m, 2H), 1.75-1.68 (m, 2H). LCMS-ESI$^+$ (m/z): [M+H]$^+$ calcd for $C_{28}H_{27}N_5O_3$: 482.6. found: 482.2.

Example 87: Preparation of (R)-5-(2-(4-morpholinophenyl)-1H-pyrrolo[2,3-b]pyridin-4-yl)-2-((1-(oxetan-3-yl)pyrrolidin-3-yl)oxy)benzonitrile

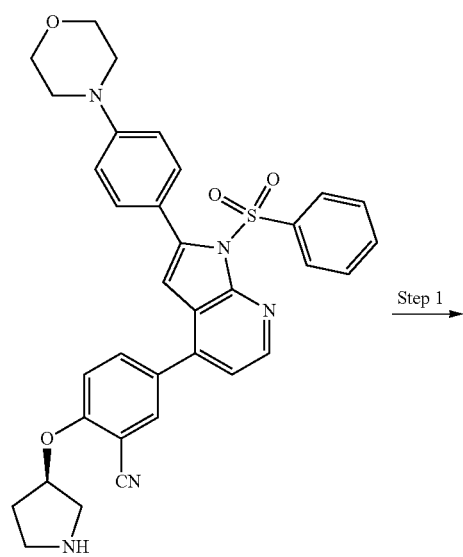

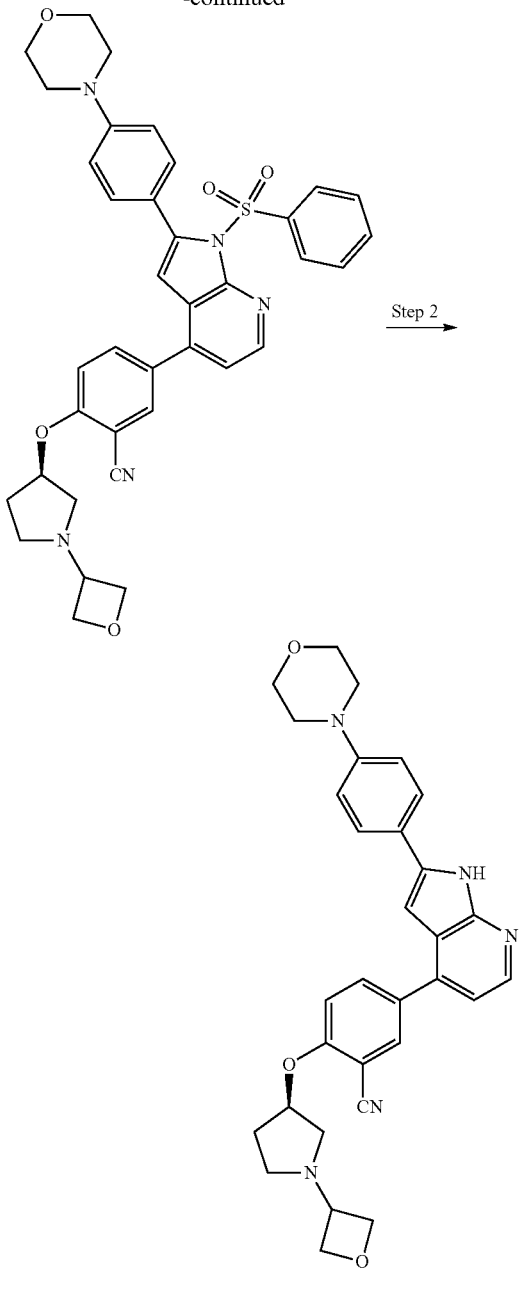

Step 1: To an appropriate sized microwave vial, ((R)-5-(2-(4-morpholinophenyl)-1-(phenylsulfonyl)-1H-pyrrolo[2,3-b]pyridin-4-yl)-2-(pyrrolidin-3-yloxy)benzonitrile (162 mg, 0.267 mmol) and 2 mL THF were added, then cooled to 100° C. Oxetan-3-one (386 mg, 5.35 mmol), sodium triacetoxyborohydride (1.13 g, 5.35 mmol) and acetic acid (0.15 mL, 2.67 mmol) were added in 5 portions every 2 hrs. After 8 h, the reaction was allowed to warm to rt and stir overnight. The mixture was poured into $CH_2Cl_2$, washed with 1N sodium carbonate. The organic layer was washed with saturated aqueous sodium chloride solution, dried, filtered and concentrated under reduced pressure to afford (R)-5-(2-(4-morpholinophenyl)-1-(phenylsulfonyl)-1H-pyrrolo[2,3-b]pyridin-4-yl)-2-((1-(oxetan-3-yl)pyrrolidin-3-yl)oxy)benzonitrile. LCMS-ESI$^+$ (m/z): [M+H]$^+$ calcd for $C_{37}H_{36}N_5O_5S$: 662.2. found: 662.1.

Step 2: (R)-5-(2-(4-morpholinophenyl)-1H-pyrrolo[2,3-b]pyridin-4-yl)-2-((1-(oxetan-3-yl)pyrrolidin-3-yl)oxy)benzonitrile was prepared using the same procedure reported in Example 18-step 2. $^1$H NMR (400 MHz, DMSO-d6) δ 8.29-8.19 (m, 2H), 8.15 (dd, J=8.8, 2.3 Hz, 1H), 7.85 (d, J=8.7 Hz, 2H), 7.45 (d, J=8.9 Hz, 1H), 7.22 (d, J=5.1 Hz, 1H), 7.07-6.96 (m, 3H), 5.47 (s, 1H), 4.83-4.76 (m, 2H), 4.70 (dd, J=8.1, 5.1 Hz, 2H), 4.65-4.56 (m, 1H), 3.78-3.69 (m, 4H), 3.25-3.12 (m, 4H). LCMS-ESI$^+$ (m/z): [M+H]$^+$ calcd for $C_{31}H_{32}N_5O_3$: 521.2. found: 522.3.

Example 101: Preparation of 5-(6-(4-morpholinophenyl)-7H-pyrrolo[2,3-d]pyrimidin-4-yl)-2-((tetrahydro-2H-pyran-4-yl)oxy)benzonitrile

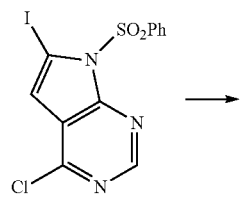

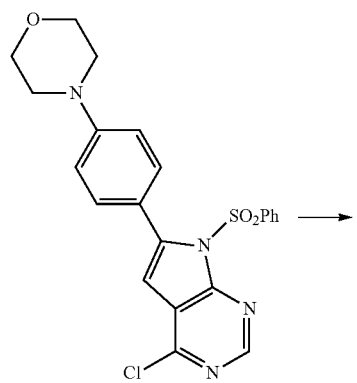

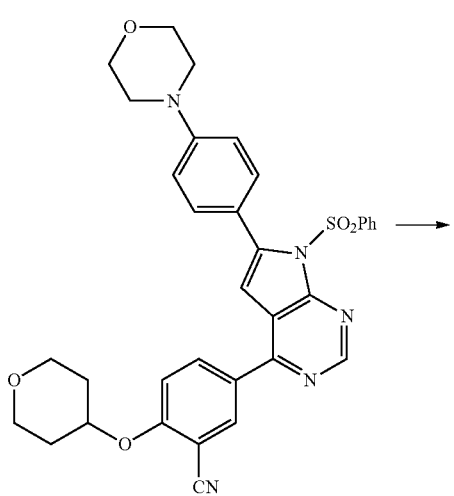

-continued

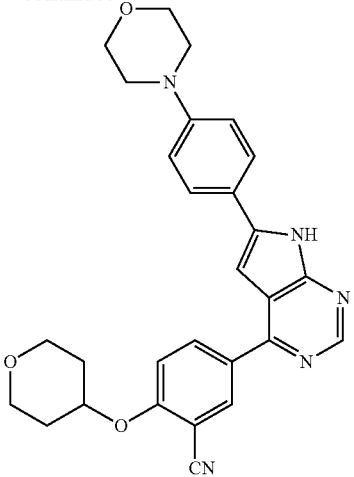

Step 1: To a mixture 4-chloro-6-iodo-7-(phenylsulfonyl)-7H-pyrrolo[2,3-d]pyrimidine (200 mgs, 0.477 mmol) and 4-(4-(4,4,5,5-tetramethyl-1,3,2-dioxaborolan-2-yl)phenyl)morpholine (145 mgs, 0.5 mmol), in DME (3 mL) was added 2.0 M aqueous Na$_2$CO$_3$ (0.5 mL, 1 mmol) and Pd(PPh$_3$)$_4$ catalyst (28 mgs, 0.025 mmol). The reaction mixture was heated at 100° C. for 1 hr. The mixture was then concentrated and purified by flash chromatography (25-100% Ethyl acetate/hexanes) to give 4-(4-(4-chloro-7-(phenylsulfonyl)-7H-pyrrolo[2,3-d]pyrimidin-6-yl)phenyl)morpholine. LCMS-ESI$^+$ (m/z): [M+H]$^+$ calcd for $C_{22}H_{19}ClN_4O_3S$: 455.9. found: 455.1.

Step 2: To a mixture 4-(4-(4-chloro-7-(phenylsulfonyl)-7H-pyrrolo[2,3-d]pyrimidin-6-yl)phenyl)morpholine (43 mgs, 0.095 mmol) and 2-((tetrahydro-2H-pyran-4-yl)oxy)-5-(4,4,5,5-tetramethyl-1,3,2-dioxaborolan-2-yl)benzonitrile (34 mgs, 0.5 mmol) in DME (2 mL) was 2.0 M aqueous Na$_2$CO$_3$ (0.1 mL, 0.2 mmol) and Pd(PPh$_3$)$_4$ (5 mgs, 0.005 mmol). The reaction mixture was heated at 140° C. for 1 hr. The mixture was then concentrated and used for next step without purification. LCMS-ESI$^+$ (m/z): [M+H]$^+$ calcd for $C_{34}H_{31}ClN_5O_5S$: 622.7. found: 622.2.

Step 3: To the crude product from step 2 in THF/2,2,2,-Trifluoroethanol (1:1, 2 mL) was added Cs$_2$CO$_3$ (93 mg, 0.285 mmol). The mixture was stirred at 100° C. for 2 hr. Acetonitrile/Water (1:1, 5 mL) was added and the solids were filtered and washed with acetonitrile. The solids were then purified by reverse phase chromatography to give the title compound as TFA salt. LCMS-ESI$^+$ (m/z): [M+H]$^+$ calcd for $C_{28}H_{27}N_5O_3$ as (M+H)$^+$ 482.5. found: 482.2 $^1$H NMR (400 MHz, DMSO-d$_6$) δ 12.97 (s, 1H), 8.84 (s, 1H), 8.50-8.46 (m, 2H), 7.95 (d, J=8.4 Hz, 2H), 7.57 (d, J=9.2 Hz, 1H), 7.39 (d, J=1.9 Hz, 1H), 7.05 (d, J=9.2 Hz, 2H), 5.00-4.94 (m, 1H), 3.90-3.85 (m, 2H), 3.75-3.73 (m, 4H), 3.59-3.53 (m, 2H), 3.23-3.21 (m, 4H), 2.09-2.02 (m, 2H), 1.75-1.67 (m, 2H).

Example 102: Preparation of 2-(cyclopropyl-methoxy)-5-(6-(4-morpholinophenyl)-7H-pyrrolo[2,3-d]pyrimidin-4-yl)benzonitrile

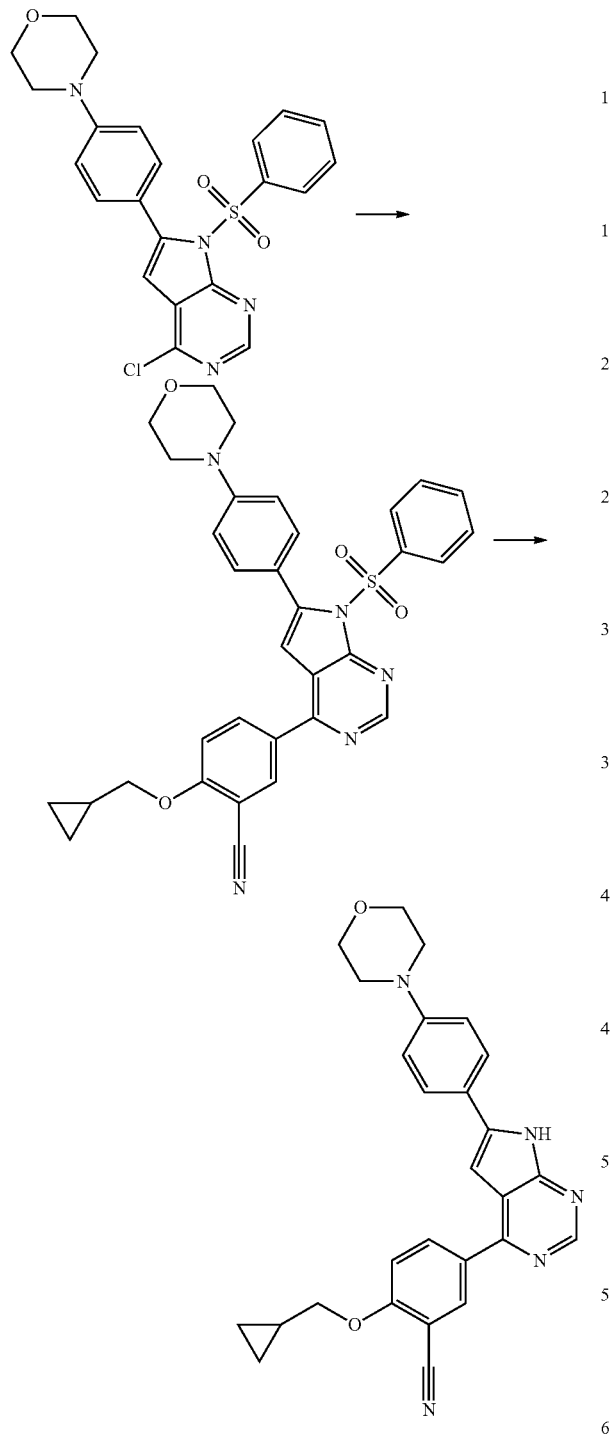

Step 1: To a mixture 4-(4-(4-chloro-7-(phenylsulfonyl)-7H-pyrrolo[2,3-d]pyrimidin-6-yl)phenyl)morpholine (45 mgs, 0.095 mmol) and 2-(cyclopropylmethoxy)-5-(4,4,5,5-tetramethyl-1,3,2-dioxaborolan-2-yl)benzonitrile (43 mgs, 0.14 mmol) (WO2013034238), in DME (2 mL) was added 2.0 M aqueous Na$_2$CO$_3$ (0.1 mL, 0.2 mmol) and Pd(PPh$_3$)$_4$ catalyst (5 mgs, 0.005 mmol) and the reaction mixture was heated to 140° C. for 1 hr. The mixture was then concentrated and used for next step without purification.

Step 2: To the crude product from step 2 in THF/2,2,2,-Trifluoroethanol (1:1, 2 mL) was added Cs$_2$CO$_3$ (98 mg, 0.3 mmol). The mixture was stirred at 100° C. for 14 hr. Acetonitrile/Water (1:1, 5 mL) was added and the solids were filtered and washed with acetonitrile. The solids were then purified by reverse phase chromatography to give the title compound as TFA salt. LCMS-ESI$^+$ (m/z): [M+H]$^+$ calcd for C$_{27}$H$_{25}$N$_5$O$_2$ as (M+H)$^+$ 452.5. found: 452.2 $^1$H NMR (400 MHz, DMSO-d$_6$) δ 12.85 (s, 1H), 8.78 (s, 1H), 8.47-8.42 (m, 2H), 7.90 (d, J=8.8 Hz, 2H), 7.42-7.37 (m, 1H), 7.35 (d, J=1.9 Hz, 1H), 7.01 (d, J=8.8 Hz, 1H), 4.09 (d, J=7.0 Hz, 2H), 3.71-3.68 (m, 4H), 3.19-3.16 (m, 4H), 1.31-1.23 (m, 1H), 0.62-0.55 (m, 2H), 0.39-0.34 (m, 2H).

Example 103: Preparation of 5-(6-(3-morpholinophenyl)-7H-pyrrolo[2,3-d]pyrimidin-4-yl)-2-((tetrahydro-2H-pyran-4-yl)oxy)benzonitrile

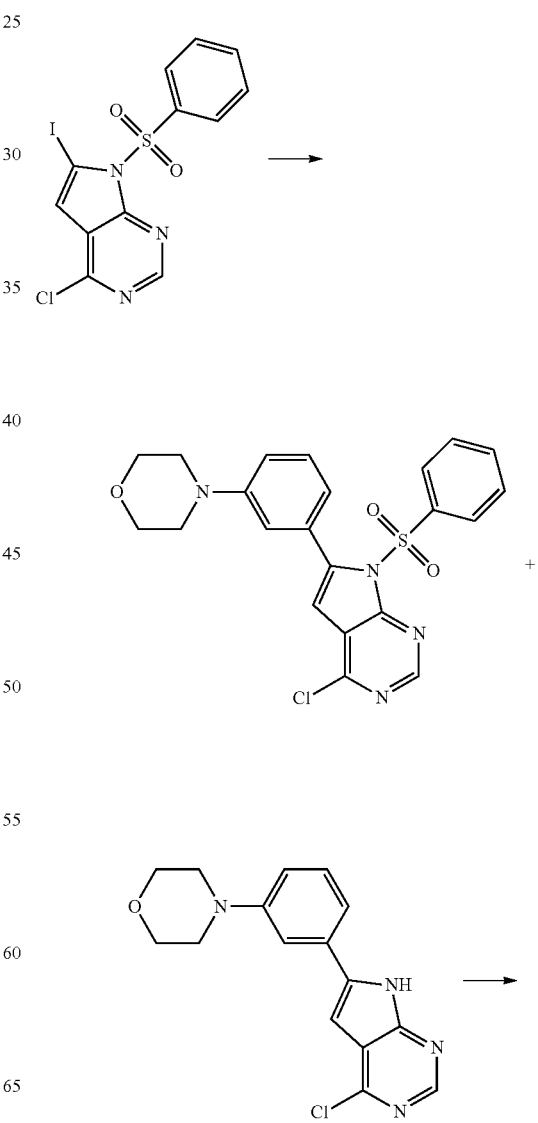

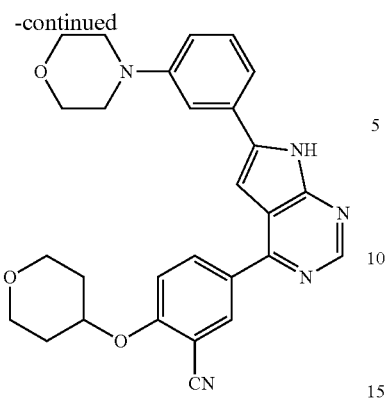

Step 1: To a solution of 4-chloro-6-iodo-7-(phenylsulfonyl)-7H-pyrrolo[2,3-d]pyrimidine (200 mgs, 0.44 mmol) and 3-(4-(4,4,5,5-tetramethyl-1,3,2-dioxaborolan-2-yl)phenyl)morpholine (151 mgs, 0.52 mmol) in DME (3 mL), was added 2.0 M aqueous Na$_2$CO$_3$ (0.7 mL, 1.43 mmol) and Pd(PPh$_3$)$_4$ (28 mgs, 0.025 mmol) and the reaction mixture was heated at 100° C. for 1 hr. The mixture was then concentrated and purified by flash chromatography (25-100% Ethyl acetate/hexanes) to give 4-(3-(4-chloro-7-(phenylsulfonyl)-7H-pyrrolo[2,3-d]pyrimidin-6-yl)phenyl)morpholine (29 mgs) LCMS-ESI$^+$ (m/z): [M+H]$^+$ calcd for C$_{22}$H$_{19}$ClN$_4$O$_3$S: 455.9. found: 455.1 and 4-(3-(4-chloro-7H-pyrrolo[2,3-d]pyrimidin-6-yl)phenyl)morpholine (75 mgs) LCMS-ESI$^+$ (m/z): [M+H]$^+$ calcd for C$_{16}$H$_{15}$ClN$_4$O: 314.7. found: 315.1.

Step 2: To a mixture of 4-(3-(4-chloro-7H-pyrrolo[2,3-d]pyrimidin-6-yl)phenyl)morpholine (30 mgs, 0.095 mmol) and 2-((tetrahydro-2H-pyran-4-yl)oxy)-5-(4,4,5,5-tetramethyl-1,3,2-dioxaborolan-2-yl)benzonitrile (50 mgs, 0.15 mmol) in DMF (1 mL) was added 2.0 M aqueous Na$_2$CO$_3$ (0.1 mL, 0.2 mmol) and Pd(PPh$_3$)$_4$ catalyst (5 mgs, 0.005 mmol). The reaction mixture was heated to 130° C. for 30 min. The mixture was then concentrated and then purified by reverse phase chromatography followed by flash chromatography (neat Ethyl acetate) to give the title compound as TFA salt.

LCMS-ESI$^+$ (m/z): [M+H]$^+$ calcd for C$_{28}$H$_{27}$N$_5$O$_3$ as (M+H)$^+$ 482.5 found 482.3. $^1$H NMR (400 MHz, DMSO-d$_6$) δ 12.71 (s, 1H), 8.80 (s, 1H), 8.52 (s, 1H), 7.61-7.47 (m, 5H), 7.34 (t, J=8.0 Hz, 1H), 6.99-6.94 (m, 1H), 4.99-4.93 (m, 1H), 3.91-3.84 (m, 2H), 3.79-3.76 (m, 4H), 3.59-3.53 (m, 2H), 3.24-3.21 (m, 4H), 2.09-2.02 (m, 2H), 1.75-1.67 (m, 2H).

Example 104: Preparation of 5-(6-(1-methyl-1H-pyrazol-4-yl)-7H-pyrrolo[2,3-d]pyrimidin-4-yl)-2-((tetrahydro-2H-pyran-4-yl)oxy)benzonitrile

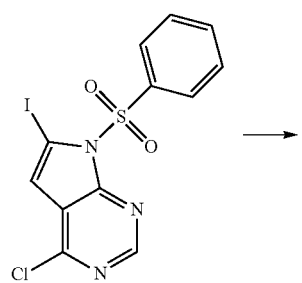

Step 1: To a solution of 4-chloro-6-iodo-7-(phenylsulfonyl)-7H-pyrrolo[2,3-d]pyrimidine (200 mgs, 0.44 mmol) and 1-methyl-4-(4,4,5,5-tetramethyl-1,3,2-dioxaborolan-2-yl)-1H-pyrazole (109 mgs, 0.52 mmol) in DME (3 mL), was added 2.0 M aqueous Na$_2$CO$_3$ (0.7 mL, 1.43 mmol) and Pd(PPh$_3$)$_4$ (28 mgs, 0.025 mmol) and the reaction mixture was heated at 100° C. for 1 hr. The mixture was then concentrated and purified by flash chromatography (40-100% Ethyl acetate/hexanes) to give 4-chloro-6-(1-methyl-1H-pyrazol-4-yl)-7H-pyrrolo[2,3-d]pyrimidine (83 mgs) LCMS-ESI$^+$ (m/z): [M+H]$^+$ calcd for C$_{10}$H$_8$ClN$_5$: 234.7. found: 234.1.

Step 2: To a mixture of 4-chloro-6-(1-methyl-1H-pyrazol-4-yl)-7H-pyrrolo[2,3-d]pyrimidine (30 mgs, 0.095 mmol) and 2-((tetrahydro-2H-pyran-4-yl)oxy)-5-(4,4,5,5-tetramethyl-1,3,2-dioxaborolan-2-yl)benzonitrile (60 mgs, 0.21 mmol) in DMF (1 mL) was added 2.0 M aqueous Na$_2$CO$_3$ (0.2 mL, 0.4 mmol) and Pd(PPh$_3$)$_4$ catalyst (8 mgs, 0.007 mmol). The reaction mixture was heated to 130° C. for 30 min.

Acetonitrile/Water (1:1, 5 mL) was added and the solids formed were filtered and washed with acetonitrile and methanol to give the title compound. LCMS-ESI$^+$ (m/z): [M+H]$^+$ calcd for C$_{22}$H$_{20}$N$_6$O$_2$ as (M+H)$^+$ 401.4. found: 401.1 $^1$H NMR (400 MHz, DMSO-d$_6$) δ 12.55 (s, 1H), 8.73 (s, 1H), 8.50-8.44 (m, 2H), 8.28 (s, 1H), 8.08 (s, 1H), 7.54 (d, J=8.9 Hz, 1H), 7.13 (d, J=1.8 Hz, 1H), 4.98-4.92 (m, 1H), 3.90 (s, 3H), 3.90-3.85 (m, 2H), 3.59-3.53 (m, 2H), 2.08-2.01 (m, 2H), 1.74-1.66 (m, 2H).

Example 105: Preparation of 5-(6-(4-(4-(oxetan-3-yl)piperazin-1-yl)phenyl)-7H-pyrrolo[2,3-d]pyrimidin-4-yl)-2-((tetrahydro-2H-pyran-4-yl)oxy)benzonitrile

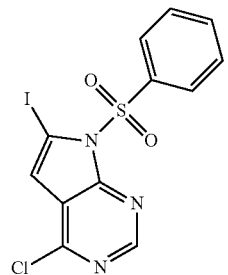

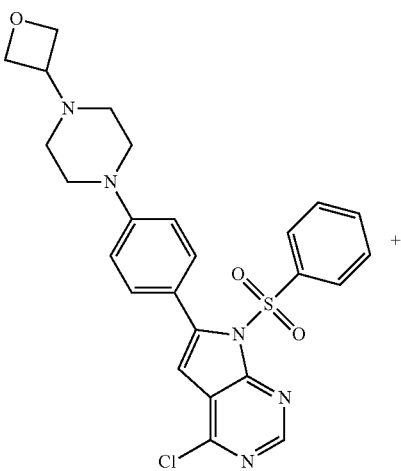
+

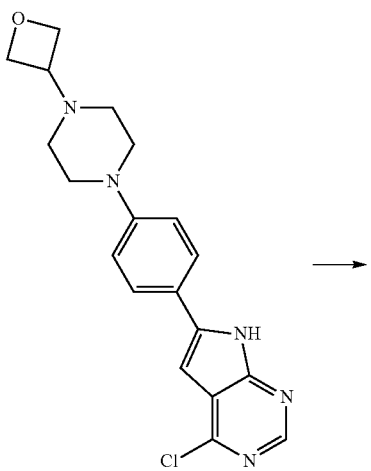

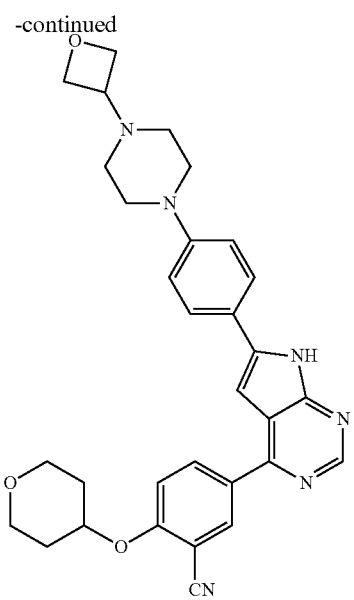

Step 1: To a solution of 4-chloro-6-iodo-7-(phenylsulfonyl)-7H-pyrrolo[2,3-d]pyrimidine (200 mgs, 0.44 mmol) and 1-(oxetan-3-yl)-4-(4-(4,4,5,5-tetramethyl-1,3,2-dioxaborolan-2-yl)phenyl)piperazine (181 mgs, 0.52 mmol) in DME (3 mL), was added 2.0 M aqueous $Na_2CO_3$ (0.7 mL, 1.43 mmol) and $Pd(PPh_3)_4$ (28 mgs, 0.025 mmol) and the reaction mixture was heated at 100° C. for 1 hr. Acetonitrile/Water (1:1, 5 mL) was added and the solids formed were filtered and washed with DCM and dried to give 4-chloro-6-(4-(4-(oxetan-3-yl)piperazin-1-yl)phenyl)-7H-pyrrolo[2,3-d]pyrimidine (80 mgs). LCMS-ESI⁺ (m/z): [M+H]⁺ calcd for $C_{19}H_{20}ClNO_5O$: 369.9. found 370.1 The filtrate was then extracted with ethyl acetate (3×) and the organic layer was then concentrated and purified by flash chromatography (25-100% Ethyl acetate/hexanes) to give 4-chloro-6-(4-(4-(oxetan-3-yl)piperazin-1-yl)phenyl)-7-(phenylsulfonyl)-7H-pyrrolo[2,3-d]pyrimidine (34 mgs) LCMS-ESI⁺ (m/z): [M+H]⁺ calcd for $C_{25}H_{24}ClN_5O_3S$: 511.0. found: 510.1.

Step 2: To a mixture of 4-chloro-6-(4-(4-(oxetan-3-yl)piperazin-1-yl)phenyl)-7H-pyrrolo[2,3-d]pyrimidine (30 mgs, 0.081 mmol) and 2-((tetrahydro-2H-pyran-4-yl)oxy)-5-(4,4,5,5-tetramethyl-1,3,2-dioxaborolan-2-yl)benzonitrile (43 mgs, 0.13 mmol) in DMF (1 mL) was added 2.0 M aqueous $Na_2CO_3$ (0.09 mL, 0.17 mmol) and $Pd(PPh_3)_4$ catalyst (4 mgs, 0.004 mmol). The reaction mixture was heated to 130° C. for 30 min. Acetonitrile/Water (1:1, 5 mL) was added and the solids formed were filtered and washed with acetonitrile and methanol and dried to give the title compound. LCMS-ESI⁺ (m/z): [M+H]⁺ calcd for $C_{31}H_{32}N_6O_3$ as (M+H)⁺ 537.6. found: 537.2. ¹H NMR (400 MHz, DMSO-$d_6$) δ 12.56 (s, 1H), 8.74 (s, 1H), 8.54-8.53 (m, 2H), 7.92 (d, J=8.7 Hz, 2H), 7.53 (d, J=8.8 Hz, 1H), 7.31 (s, 1H), 7.04 (d, J=8.9 Hz, 2H), 4.99-4.91 (m, 1H), 4.56 (t, J=6.1 Hz, 2H), 4.47 (t, J=6.1 Hz, 2H), 3.90-3.85 (m, 2H), 3.59-3.53 (m, 2H), 3.46-3.43 (m, 1H), 3.28-3.26 (m, 4H), 2.42-2.39 (m, 4H), 2.08-2.03 (m, 2H), 1.74-1.66 (m, 2H).

Example 106: Preparation of (R)-5-(6-(4-morpholinophenyl)-7H-pyrrolo[2,3-d]pyrimidin-4-yl)-2-(pyrrolidin-3-yloxy)benzonitrile

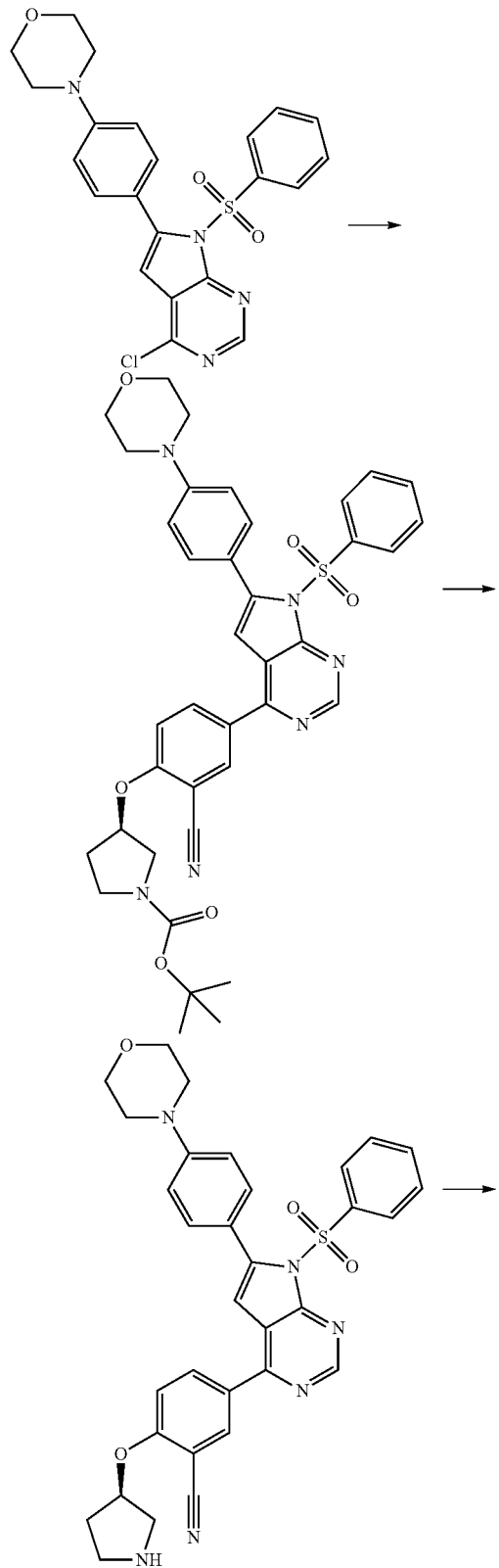

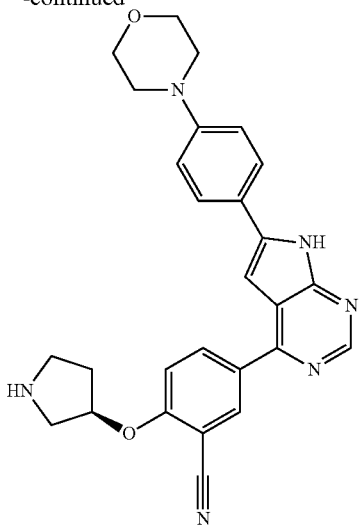

Step 1: To a solution of 4-chloro-6-iodo-7-(phenylsulfonyl)-7H-pyrrolo[2,3-d]pyrimidine (190 mgs, 0.42 mmol) and (R)-tert-butyl 3-(2-cyano-4-(4,4,5,5-tetramethyl-1,3,2-dioxaborolan-2-yl)phenoxy)pyrrolidine-1-carboxylate (208 mgs, 0.52 mmol) in DME (4 mL), was added 2.0 M aqueous $Na_2CO_3$ (0.4 mL, 0.8 mmol) and $Pd(PPh_3)_4$ (24 mgs, 0.021 mmol) and the reaction mixture was heated at 100° C. for 1 hr. The mixture was then concentrated and purified by flash chromatography (40-100% Ethyl acetate/hexanes) to give (R)-tert-butyl 3-(2-cyano-4-(6-(4-morpholinophenyl)-7-(phenylsulfonyl)-7H-pyrrolo[2,3-d]pyrimidin-4-yl)phenoxy)pyrrolidine-1-carboxylate (290 mgs). LCMS-ESI$^+$ (m/z): [M+H]$^+$ calcd for $C_{38}H_{38}N_6O_6S$: 707.8. found: 707.1.

Step 2: To a solution of (R)-tert-butyl 3-(2-cyano-4-(6-(4-morpholinophenyl)-7-(phenylsulfonyl)-7H-pyrrolo[2,3-d]pyrimidin-4-yl)phenoxy)pyrrolidine-1-carboxylate (290 mgs, 0.41 mmol) in DCM (3 mL) was added 4.0 M HCl in dioxane (0.5 mL) and stirred at rt. After 1 h, another 0.5 mL of 4.0 M HCl in dioxane was added and stirred at rt for 1 h. The reaction mixture was then diluted with diethyl ether (20 mL) and stirred at rt for 30 min. The solids were then filtered and washed with diethyl ether and dried to give (R)-5-(6-(4-morpholinophenyl)-7-(phenylsulfonyl)-7H-pyrrolo[2,3-d]pyrimidin-4-yl)-2-(pyrrolidin-3-yloxy)benzonitrile as HCl salt. LCMS-ESI$^+$ (m/z): [M+H]$^+$ calc'd for $C_{33}H_{30}N_6O_4S$: 607.8. found: 607.1.

Step 3: A mixture of (R)-5-(6-(4-morpholinophenyl)-7-(phenylsulfonyl)-7H-pyrrolo[2,3-d]pyrimidin-4-yl)-2-(pyrrolidin-3-yloxy)benzonitrile (30 mgs, 0.05 mmol) and $Cs_2CO_3$ (98 mg, 0.3 mmol) in THF/2,2,2,-Trifluoroethanol (1:1, 1 mL) was heated in microwave at 100 C for 30 min. The mixture was then concentrated and purified by reverse phase chromatography to give the title compound as TFA salt. LCMS-ESI$^+$ (m/z): [M+H]$^+$ calcd for $C_{27}H_{26}N_6O_2$ as (M+H)$^+$ 467.5. found: 467.1 $^1$H NMR (400 MHz, DMSO-$d_6$) δ 12.61 (s, 1H), 9.13 (brs, 1H), 8.91 (brs, 1H), 8.76 (s, 1H), 8.58-8.56 (m, 2H), 7.93 (d, J=8.6 Hz, 2H), 7.48 (d, J=8.8 Hz, 1H), 7.33 (d, J=1.9 Hz, 1H), 7.05 (d, J=8.6 Hz, 2H), 5.44-5.43 (m, 1H), 3.75-3.73 (m, 2H), 3.58-3.44 (m, 8H), 3.22-3.20 (m, 2H), 2.66-2.64 (m, 1H), 2.33-2.28 (m, 1H).

Example 107: Preparation of (R)-2-((1-(2-cyano-acetyl)pyrrolidin-3-yl)oxy)-5-(6-(4-morpholinophenyl)-7H-pyrrolo[2,3-d]pyrimidin-4-yl)benzonitrile

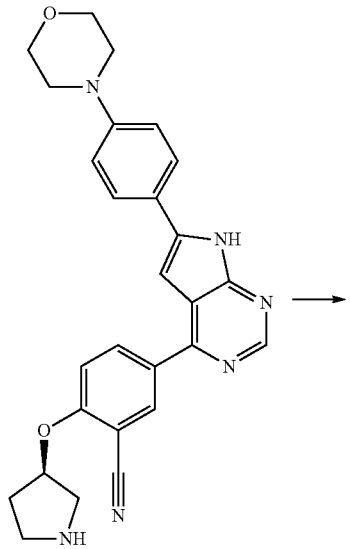

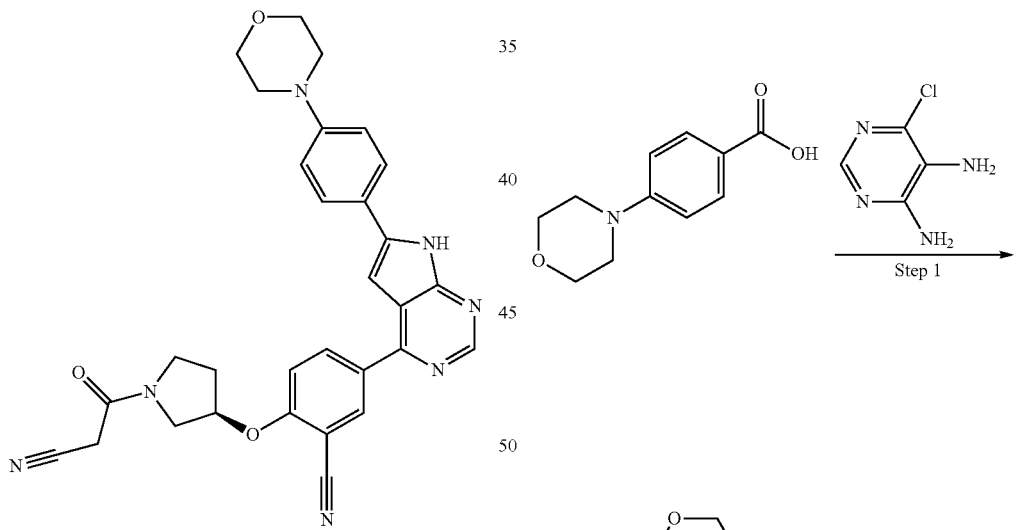

To a mixture of (R)-5-(6-(4-morpholinophenyl)-7H-pyrrolo[2,3-d]pyrimidin-4-yl)-2-(pyrrolidin-3-yloxy)benzonitrile (30 mgs, 0.064 mmol), 2-cyanoacetic acid (30 mgs, 0.35 mmol) and HATU (49 mgs, 0.13 mmol) in DMF (1 mL) was added DIPEA (0.1 mL, 0.57 mmol) and the resulting solution was stirred at rt. After 16 h, the crude mixture was concentrated and purified by reverse phase chromatography to give the title compound as TFA salt. LCMS-ESI+ (m/z): [M+H]+ calcd for $C_{30}H_{27}N_7O_3$ as (M+H)+ 534.6. found: 534.2. $^1$H NMR (400 MHz, DMSO-d$_6$) δ 12.66 (s, 1H), 8.77 (s, 1H), 8.57-8.52 (m, 2H), 7.94 (d, J=8.7 Hz, 2H), 7.50 (dd, J=8.9, 1.3 Hz, 1H), 7.36 (d, J=1.9 Hz, 1H), 3.18 (m, 2H), 2.34-2.25 (m, 2H).

Example 108: Synthesis of 5-(7H-pyrrolo[2,3-d]pyrimidin-4-yl)-2-((tetrahydro-2H-pyran-4-yl)oxy)benzonitrile

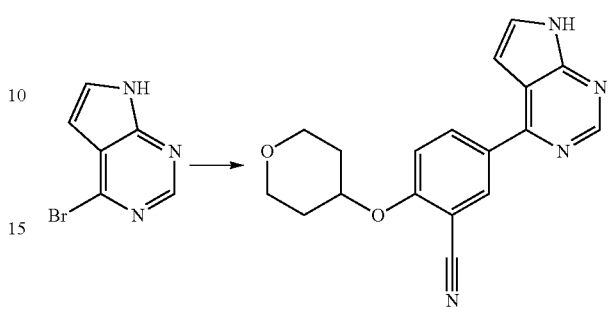

Following similar procedure to synthesize Example 72 step 1, beginning with 4-bromo-7H-pyrrolo[2,3-d]pyrimidine (100 mg, 0.65 mmol) and 2-((tetrahydro-2H-pyran-4-yl)oxy)-5-(4,4,5,5-tetramethyl-1,3,2-dioxaborolan-2-yl)benzonitrile (257 mg, 0.78 mmol), 5-(7H-pyrrolo[2,3-d]pyrimidin-4-yl)-2-((tetrahydro-2H-pyran-4-yl)oxy)benzonitrile was synthesized. LCMS-ESI+ (m/z): [M+H]+ calcd for $C_{18}H_{16}N_4O_2$: 321.3. found 321.2.

Example 201: Preparation of 5-(8-(4-morpholinophenyl)-9H-purin-6-yl)-2-((tetrahydro-2H-pyran-4-yl)oxy)benzonitrile

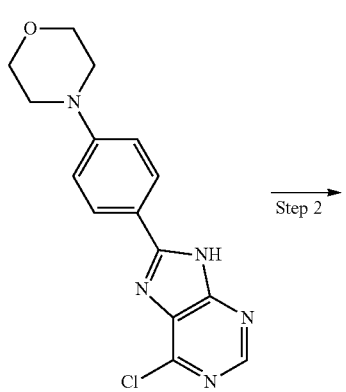

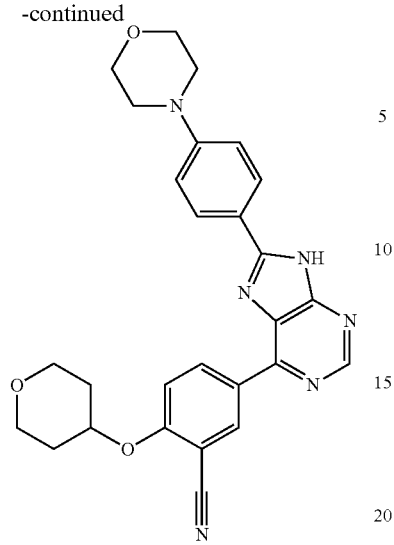

Step 1: A mixture of 6-chloro-4,5-diaminopyrimidine (349 mg, 2.41 mmol), 4-morpholinobenzoic acid (500 mg, 2.41 mmol) and ammonium chloride (774 mg, 14.47 mmol) in $POCl_3$ (8 mL) was heated at 110° C. for 16 hrs. The reaction mixture was cooled and the residue was washed several times with ether. The residue was dissolved in $CH_2Cl_2$ and aqueous $NaHCO_3$. The layers were separated and the aqueous was extracted with $CH_2Cl_2$. The combined organics were washed with saturated $NaHCO_3$, saturated aqueous sodium chloride solution, and dried ($Na_2SO_4$), filtered, and collected in vacuo to give crude 4-(4-(6-chloro-9H-purin-8-yl)phenyl)morpholine. LCMS-ESI$^+$ (m/z): [M+H]$^+$ calcd for $C_{15}H_{14}ClNO_5$: 316.1. found: 316.1.

Step 2: A sealed tube containing a suspension of 4-(4-(6-chloro-9H-purin-8-yl)phenyl)morpholine (60 mg, 0.19 mmol) and Pd(PPh$_3$), (22 mg, 0.019 mmol) in a degassed mixture of dioxane/H$_2$O (2 mL, 4/1), was preheated at 85° C. for 5 min. Next, K$_2$CO$_3$ (80 mg, 0.58 mmol) and (3-cyano-4-((tetrahydro-2H-pyran-4-yl)oxy)phenyl)boronic acid (70 mg, 0.284 mmol), was added to the mixture and the reaction was additionally heated at 100° C. in the sealed tube for 15 hr. Afterwards, the crude material was allowed to reach room temperature. It was diluted with EtOAc and filtered through a short pad of Celite and washed the solids with EtOAc. The filtrate was washed with saturated aqueous sodium chloride solution and the organic phase separated and dried over anhydrous MgSO$_4$. After filtration of the solids and evaporation in vacuo, the resulting oily residue was purified by column chromatography over silica gel, using MeOH/CH$_2$Cl$_2$ mixtures as eluent. The purification gave the desired 5-(8-(4-morpholinophenyl)-9H-purin-6-yl)-2-((tetrahydro-2H-pyran-4-yl)oxy)benzonitrile. LCMS-ESI$^+$ (m/z): [M+H]$^+$ calcd for $C_{27}H_{26}N_6O_3$: 483.2. found: 483.3.

$^1$H NMR (400 MHz, DMSO-d6): δ 9.21 (s, 1H), 9.17 (s, 1H), 8.79 (s, 1H), 8.17 (d, J=8.7 Hz, 2H), 7.61 (m, 1H), 7.13 (d, J=8.6 Hz, 2H), 4.95 (m, 1H), 3.88 (m, 2H), 3.81-3.65 (m, 4H), 3.53-3.58 (m, 2H), 3.27-3.57 (m, 2H), 2.15-1.97 (m, 2H), 1.70 (m, 2H).

Example 202: Preparation of 2-(cyclopropyl-methoxy)-5-(8-(4-morpholinophenyl)-9H-purin-6-yl) benzonitrile

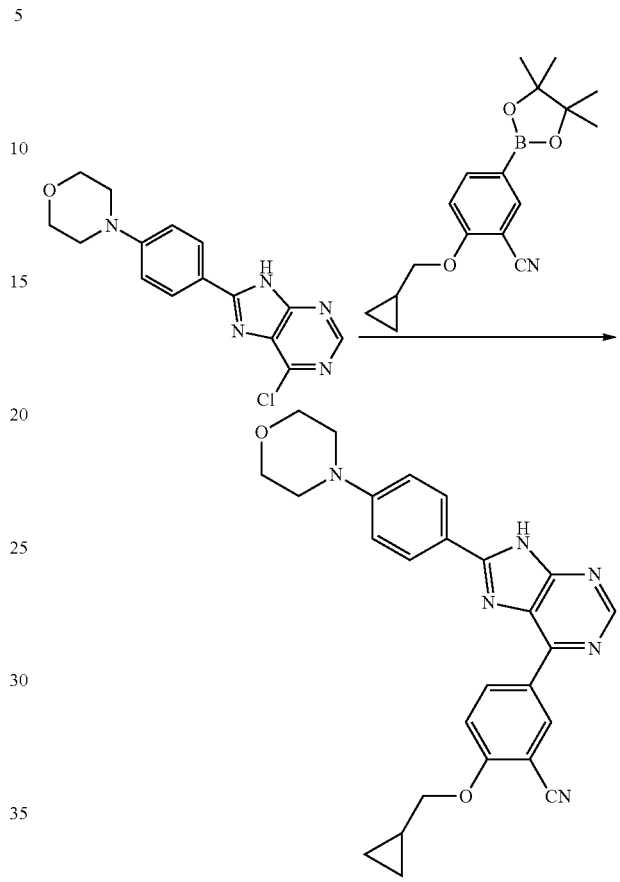

A sealed tube containing a suspension of 4-(4-(6-chloro-9H-purin-8-yl)phenyl)morpholine (30 mg, 0.095 mmol) and Pd(PPh$_3$), (6 mg, 0.005 mmol) in a degassed mixture of dioxane/H$_2$O (1 mL, 4/1), was preheated at 85° C. for 5 min. Next, K$_2$CO$_3$ (30 mg, 0.217 mmol) and 2-(cyclopropyl-methoxy)-5-(4,4,5,5-tetramethyl-1,3,2-dioxaborolan-2-yl) benzonitrile (43 mg, 0.143 mmol), was added to the mixture and the reaction was additionally heated at 100° C. in the sealed tube for 15 hrs. Afterwards, the crude material was allowed to reach room temperature. It was diluted with EtOAc and filtered through a short pad of Celite and washed the solids with MeOH. The filtrate was concentrated to dryness. The residue column chromatography over silica gel, using MeOH/CH$_2$Cl$_2$ mixtures as eluent to afford 2-(cyclopropylmethoxy)-5-(8-(4-morpholinophenyl)-9H-purin-6-yl)benzonitrile.

$^1$H NMR (400 MHz, DMSO-d6) δ 9.36-9.02 (m, 2H), 8.81 (s, 1H), 8.17 (d, J=8.3 Hz, 2H), 7.48 (d, J=9.0 Hz, 1H), 7.13 (d, J=8.4 Hz, 2H), 4.12 (d, J=7.0 Hz, 2H), 3.90-3.63 (m, 4H), 1.27 (m, 1H), 0.63 (d, J=7.6 Hz, 2H), 0.41 (d, J=5.1 Hz, 2H). LCMS-ESI$^+$ (m/z): [M+H]$^+$ calcd for $C_{26}H_{24}N_6O_2$: 453.2. found: 453.2.

Example 203: Preparation of tert-butyl 4-(2-cyano-4-(8-(4-morpholinophenyl)-9H-purin-6-yl)phenoxy)piperidine-1-carboxylate

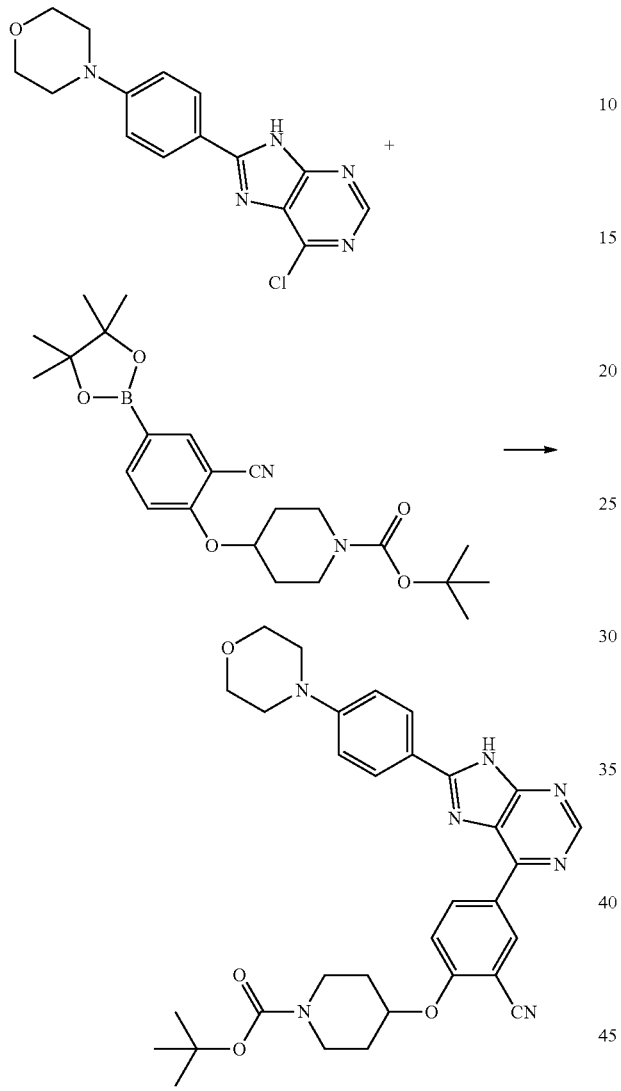

A sealed tube containing a suspension of 4-(4-(6-chloro-9H-purin-8-yl)phenyl)morpholine (30 mg, 0.095 mmol) and Pd(PPh$_3$)$_4$ (6 mg, 0.005 mmol) in a degassed mixture of dioxane/H$_2$O (1 mL, 4/1), was preheated at 85° C. for 5 min. Next, K$_2$CO$_3$ (31 mg, 0.224 mmol) and tert-butyl 4-(2-cyano-4-(4,4,5,5-tetramethyl-1,3,2-dioxaborolan-2-yl)phenoxy)piperidine-1-carboxylate (61 mg, 0.224 mmol), were added to the mixture and the reaction was additionally heated at 100° C. in the sealed tube for hrs. Afterwards, the crude material was allowed to reach room temperature. It was concentrated to dryness. The residue was triturated with MeOH and filtered through a short pad of Celite, and washed the solids with MeOH. The filtrate was concentrated to dryness and the residue was purified by flash column chromatography on silica gel to give tert-butyl 4-(2-cyano-4-(8-(4-morpholinophenyl)-9H-purin-6-yl)phenoxy)piperidine-1-carboxylate.

$^1$H NMR (400 MHz, DMSO-d6) δ 13.80 (s, 1H), 9.18 (m, 2H), 8.82 (s, 1H), 8.32-8.04 (m, 2H), 7.60 (m, 1H), 7.30-7.00 (m, 2H), 5.08-4.78 (m, 1H), 3.93-3.65 (m, 6H), 3.70-3.47 (m, 2H), 3.30 (m, 4H), 1.97 (m, 2H), 1.67 (m, 2H), 1.41 (s, 9H). LCMS-ESI$^+$ (m/z): [M+H]$^+$ calcd for C$_{32}$H$_{35}$N$_7$O$_4$: 582.2. found: 582.0.

Example 204: Preparation of 5-(8-(4-morpholinophenyl)-9H-purin-6-yl)-2-(piperidin-4-yloxy)benzonitrile

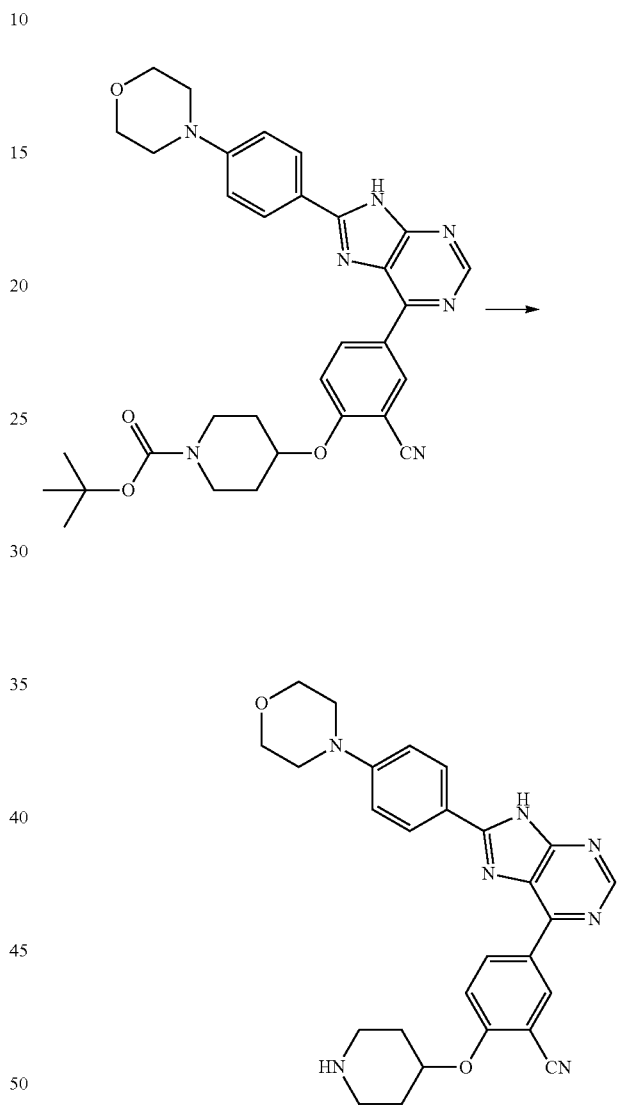

A solution of tert-butyl 4-(2-cyano-4-(8-(4-morpholinophenyl)-9H-purin-6-yl)phenoxy)piperidine-1-carboxylate (30 mg, 0.052 mmol) in CH$_2$Cl$_2$ (2 mL) and trifluoroacetic acid (1 mL) was stirred at rt for 4 hrs. The solvent was evaporated under reduced pressure. The reaction mixture was then concentrated to dryness, the residue was purified by flash column chromatography on silica gel to give 5-(8-(4-morpholinophenyl)-9H-purin-6-yl)-2-(piperidin-4-yloxy)benzonitrile.

$^1$H NMR (400 MHz, DMSO-d6) δ 9.22 (s, 1H), 9.20 (s, 1H), 8.84 (s, 1H), 8.16 (d, J=8.8 Hz, 2H), 7.63 (d, J=8.7 Hz, 1H), 7.14 (d, J=8.9 Hz, 2H), 5.02 (m, 1H), 3.81-3.65 (m, 4H), 3.26 (m, H), 3.16 (m, 2H), 2.17 (m, 2H), 1.96 (m, 2H). LCMS-ESI$^+$ (m/z): [M+H]$^+$ calcd for C$_{27}$H$_{27}$N$_7$O$_2$: 482.2. found: 482.2.

Example 205: Preparation of 2-((1-(2-hydroxyacetyl)piperidin-4-yl)oxy)-5-(8-(4-morpholinophenyl)-9H-purin-6-yl)benzonitrile

Example 206: Preparation of (R)-tert-butyl 3-(2-cyano-4-(8-(4-morpholinophenyl)-9H-purin-6-yl)phenoxy)pyrrolidine-1-carboxylate

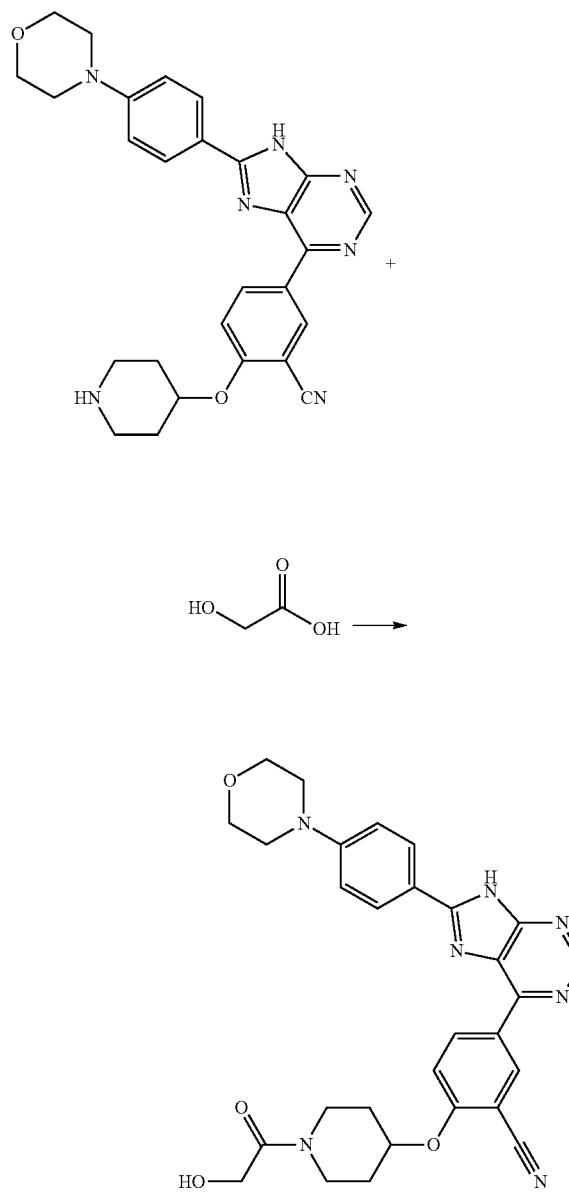

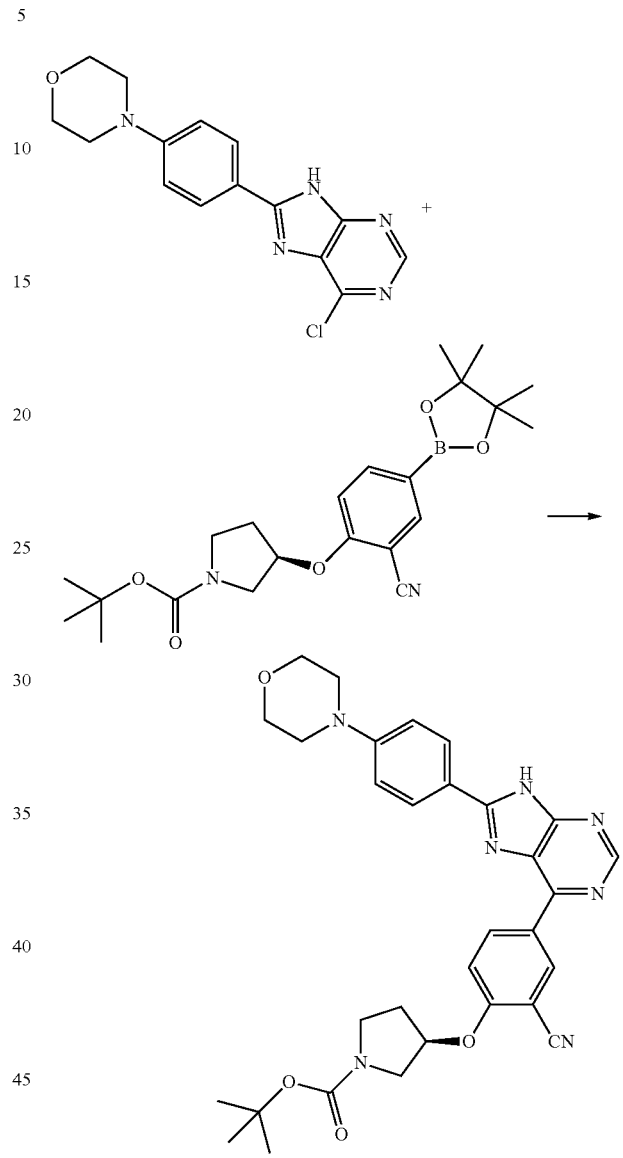

To a mixture of 5-(8-(4-morpholinophenyl)-9H-purin-6-yl)-2-(piperidin-4-yloxy)benzonitrile (12 mg, 0.025 mmol), hydroxyacetic acid (3 mg, 0.039 mmol) and DIPEA (4 mg, 0.031 mmol) in DMF (0.5 mL) was added HATU (11 mg, 0.029 mmol). The reaction mixture was stirred at rt for 16 hrs. The mixture was concentrated in vacuo. The residue was purified by flash column chromatography on silica gel to give 2-((1-(2-hydroxyacetyl)piperidin-4-yl)oxy)-5-(8-(4-morpholinophenyl)-9H-purin-6-yl)benzonitrile. $^1$H NMR (400 MHz, DMSO-d6) δ 13.82 (s, 1H), 9.20 (s, 1H), 9.18 (s, 1H), 8.83 (s, 1H), 8.16 (d, J=8.8 Hz, 2H), 7.65 (m, 1H), 7.14 (d, J=8.8 Hz, 2H), 5.01 (m, 1H), 4.21-4.04 (m, 2H), 3.83-3.70 (m, 4H), 3.30-3.56 (m, 6H), 2.13-1.91 (m, 2H), 1.87-1.60 (m, 2H). LCMS-ESI$^+$ (m/z): [M+H]$^+$ calcd for $C_{29}H_{29}N_7O_4$: 540.2. found: 540.2.

A sealed tube containing a suspension of 4-(4-(6-chloro-9H-purin-8-yl)phenyl)morpholine (132 mg, 0.42 mmol) and Pd(PPh$_3$)$_4$ (24 mg, 0.021 mmol) in a degassed mixture of dioxane/H$_2$O (4.5 mL, 4/1), was preheated at 85° C. for 5 min. Next, K$_2$CO$_3$ (145 mg, 1.05 mmol) and (R)-tert-butyl 3-(2-cyano-4-(4,4,5,5-tetramethyl-1,3,2-dioxaborolan-2-yl)phenoxy)pyrrolidine-1-carboxylate (346 mg, 0.84 mmol), were added to the mixture and the reaction was additionally heated at 100° C. in the sealed tube for 15 hrs. Afterwards, the crude material was allowed to reach room temperature. It was concentrated to dryness, the residue was triturated with EtOH and filtered through a short pad of Celite, washed the solids with CH$_2$Cl$_2$. The filtrate was concentrated to dryness. The residue was purified by flash column chromatography on silica gel to afford (R)-tert-butyl 3-(2-cyano-4-(8-(4-morpholinophenyl)-9H-purin-6-yl)phenoxy)pyrrolidine-1-carboxylate. $^1$H NMR (400 MHz, DMSO-d6) δ 9.21 (br s, 2H), 8.83 (s, 1H), 8.17 (d, J=8.7 Hz, 2H), 7.58 (d, J=9.4 Hz, 1H), 7.14 (d, J=8.8 Hz, 2H), 5.31 (br s, 1H), 3.83-3.68 (m, 4H), 3.63 (m, 2H), 3.54-3.42 (m, 2H), 3.39 (s, 2H), 2.37-2.05 (m, 2H), 1.51-1.31 (m, 9H), 1.05 (s, 2H). LCMS-ESI⁺ (m/z): [M+H]⁺ calcd for $C_{31}H_{33}N_7O_4$: 568.3. found: 567.9.

Example 207: Preparation of (R)-5-(8-(4-morpholinophenyl)-9H-purin-6-yl)-2-(pyrrolidin-3-yloxy)benzonitrile

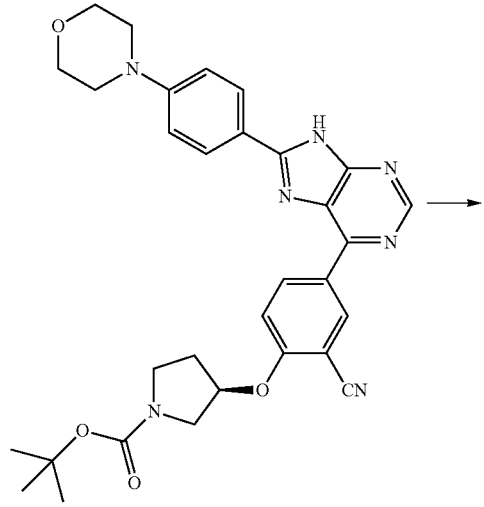

A solution of (R)-tert-butyl 3-(2-cyano-4-(8-(4-morpholinophenyl)-9H-purin-6-yl)phenoxy)pyrrolidine-1-carboxylate (95 mg, 0.167 mmol) in CH₂Cl₂ (5 mL) and trifluoroacetic acid (2 mL) was stirred at rt for 4 hrs. The solvent was evaporated under reduced pressure. The reaction mixture was then concentrated to dryness, the residue was purified by flash column chromatography on silica gel to afford (R)-5-(8-(4-morpholinophenyl)-9H-purin-6-yl)-2-(pyrrolidin-3-yloxy)benzonitrile. ¹H NMR (400 MHz, DMSO-d6) δ 9.31-9.09 (m, 2H), 8.84 (s, 1H), 8.24-8.08 (m, 2H), 7.65-7.49 (m, 1H), 7.24-7.01 (m, 2H), 5.43 (m, 1H), 3.75 (m, 4H), 3.60 (m, 2H), 3.49 (m, 2H), 3.35-3.20 (m, 2H), 2.48 (m, 2H), 2.42-2.16 (m, 2H). LCMS-ESI⁺ (m/z): [M+H]⁺ calcd for $C_{26}H_{25}N_7O_2$: 468.2. found: 468.2.

Example 208: Preparation of (R)-2-((1-(2-hydroxyacetyl)pyrrolidin-3-yl)oxy)-5-(8-(4-morpholinophenyl)-9H-purin-6-yl)benzonitrile

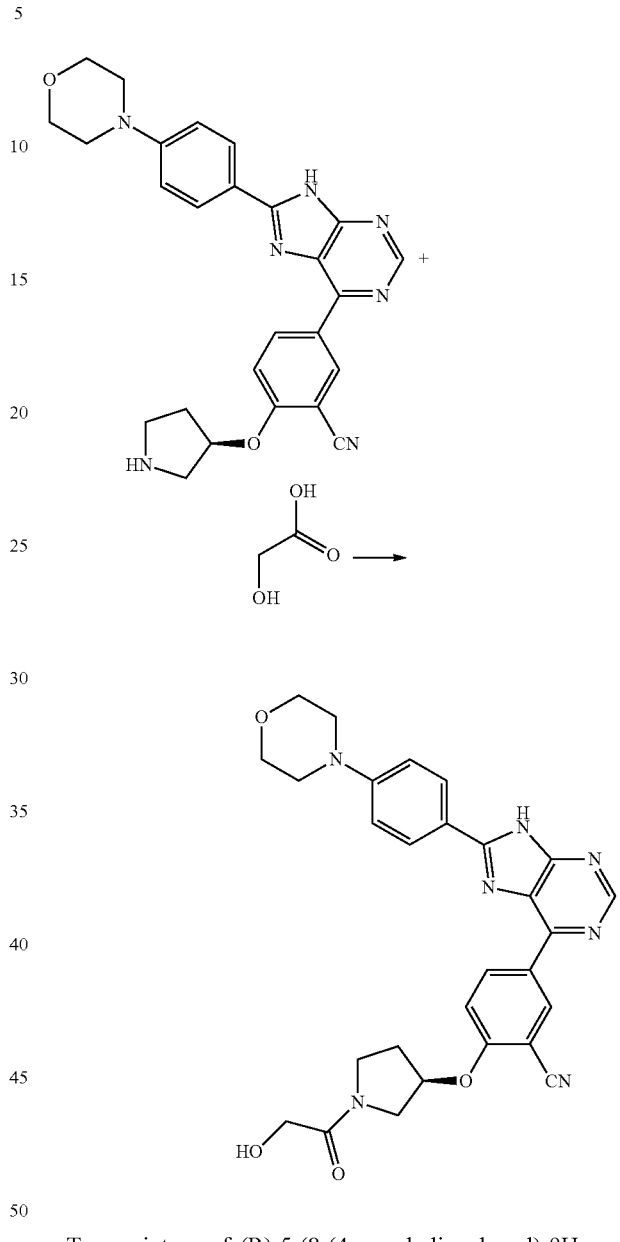

To a mixture of (R)-5-(8-(4-morpholinophenyl)-9H-purin-6-yl)-2-(pyrrolidin-3-yloxy)benzonitrile (18 mg, 0.039 mmol), 2-hydroxyacetic acid (4.5 mg, 0.059 mmol) and DIPEA (8 mg, 0.062 mmol) in DMF (0.8 mL) was added HATU (18 mg, 0.047 mmol). The reaction mixture was stirred at rt for 16 hrs. The mixture was concentrated under vacuum. The residue was purified by flash column chromatography on silica gel to give (R)-2-((1-(2-hydroxyacetyl)pyrrolidin-3-yl)oxy)-5-(8-(4-morpholinophenyl)-9H-purin-6-yl)benzonitrile.

¹H NMR (400 MHz, DMSO-d6) δ 13.81 (s, 1H), 9.21 (m, 2H), 8.83 (s, 1H), 8.17 (d, J=8.5 Hz, 2H), 7.60 (d, J=9.3 Hz, 1H), 7.14 (d, J=8.5 Hz, 2H), 5.38 (d, J=31.0 Hz, 1H), 4.62 (m, 1H), 4.06 (m, 3H), 3.92-3.36 (m, 6H), 2.23 (m, 2H). LCMS-ESI⁺ (m/z): [M+H]⁺ calcd for $C_{28}H_{27}N_7O_4$: 526.2. found: 526.3.

Example 209: Preparation of 2-(((R)-1-((R)-2-hydroxypropanoyl)pyrrolidin-3-yl)oxy)-5-(8-(4-morpholinophenyl)-9H-purin-6-yl)benzonitrile

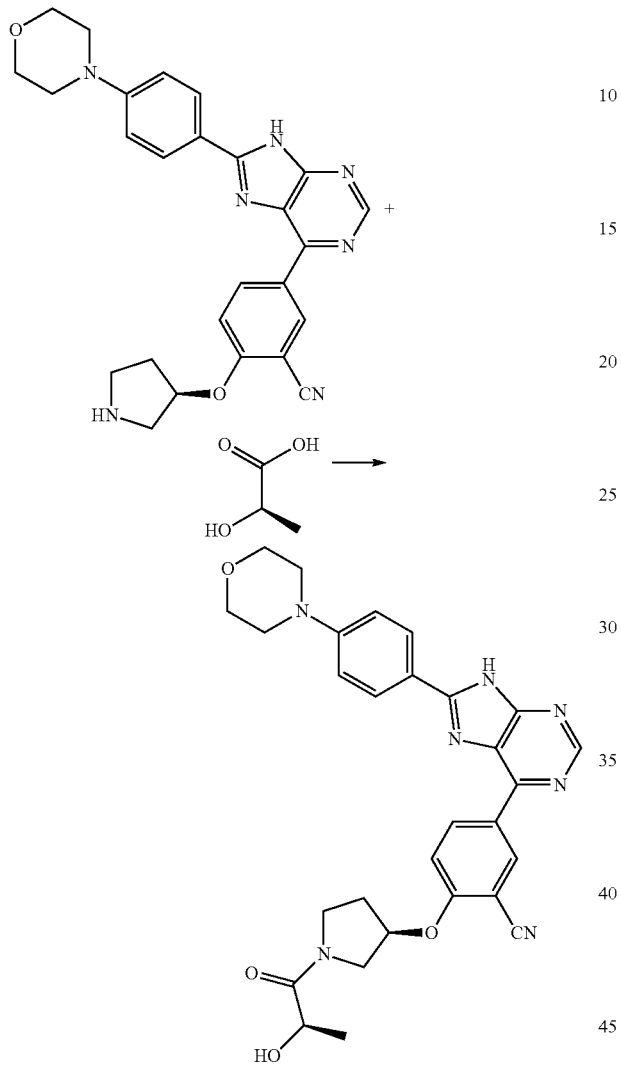

Example 210: Preparation of 2-(((R)-1-((S)-2-hydroxypropanoyl)pyrrolidin-3-yl)oxy)-5-(8-(4-morpholinophenyl)-9H-purin-6-yl)benzonitrile

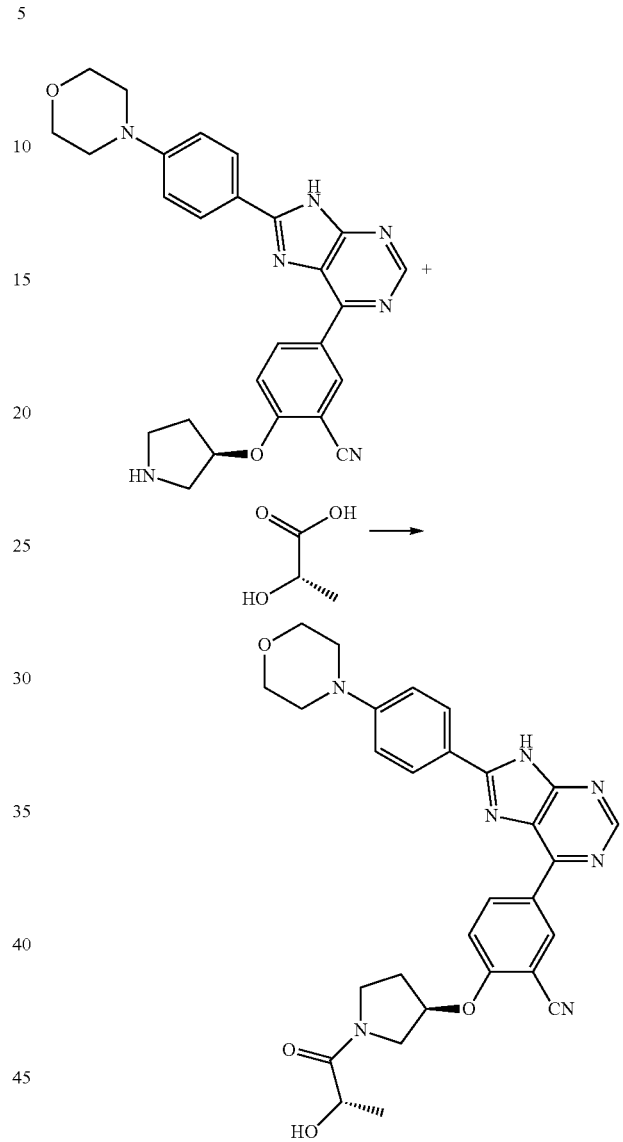

To a mixture of (R)-5-(8-(4-morpholinophenyl)-9H-purin-6-yl)-2-(pyrrolidin-3-yloxy)benzonitrile (19 mg, 0.061 mmol), (R)-2-hydroxypropanoic acid (5.5 mg, 0.061 mmol) and DIPEA (8 mg, 0.062 mmol) in DMF (0.8 mL) was added HATU (19 mg, 0.05 mmol). The reaction mixture was stirred at rt for 16 hrs. The mixture was concentrated under vacuum. The residue was purified by flash column chromatography on silica gel to give 2-(((R)-1-((R)-2-hydroxypropanoyl)pyrrolidin-3-yl)oxy)-5-(8-(4-morpholinophenyl)-9H-purin-6-yl)benzonitrile.

$^1$H NMR (400 MHz, DMSO-d6) δ 13.81 (s, 1H), 9.21 (d, 2H), 8.83 (s, 1H), 8.17 (d, J=8.5 Hz, 2H), 7.60 (dd, J=8.8, 4.2 Hz, 1H), 7.14 (d, J=8.8 Hz, 2H), 5.38 (d, J=17.9 Hz, 1H), 4.92 (dd, J=18.7, 6.7 Hz, 1H), 4.28 (dt, J=34.8, 6.6 Hz, 1H), 4.04-3.82 (m, 2H), 3.81-3.68 (m, 5H), 3.67-3.42 (m, 4H), 2.37-2.05 (m, 2H), 1.18 (dd, J=13.9, 6.6 Hz, 3H). LCMS-ESI$^+$ (m/z): [M+H]$^+$ calcd for $C_{29}H_{29}N_7O_4$: 540.2. found: 540.3.

To a mixture of (R)-5-(8-(4-morpholinophenyl)-9H-purin-6-yl)-2-(pyrrolidin-3-yloxy)benzonitrile (17 mg, 0.036 mmol), (S)-2-hydroxypropanoic acid (5 mg, 0.055 mmol) and DIPEA (7 mg, 0.054 mmol) in DMF (0.8 mL) was added HATU (19 mg, 0.05 mmol). The reaction mixture was stirred at rt for 16 hrs. The mixture was concentrated under vacuum. The residue was purified by flash column chromatography on silica gel to afford 2-(((R)-1-((S)-2-hydroxypropanoyl)pyrrolidin-3-yl)oxy)-5-(8-(4-morpholinophenyl)-9H-purin-6-yl)benzonitrile.

$^1$H NMR (400 MHz, DMSO-d6) δ 13.81 (s, 1H), 9.21 (d, J=9.3 Hz, 2H), 8.83 (s, 1H), 8.17 (d, J=8.5 Hz, 2H), 7.59 (dd, J=9.1, 4.1 Hz, 1H), 7.14 (d, J=8.9 Hz, 2H), 5.37 (d, J=30.6 Hz, 1H), 4.95 (dd, J=9.9, 7.0 Hz, 1H), 4.27 (dt, J=27.5, 6.6 Hz, 1H), 4.06-3.89 (m, 2H), 3.83-3.38 (m, 9H), 2.41-2.04 (m, 2H), 1.31-1.03 (m, 3H). LCMS-ESI$^+$ (m/z): [M+H]$^+$ calcd for $C_{29}H_{29}N_7O_4$: 540.2. found: 540.3.

Example 211: Preparation of 5-(8-(3-morpholinophenyl)-9H-purin-6-yl)-2-((tetrahydro-2H-pyran-4-yl)oxy)benzonitrile

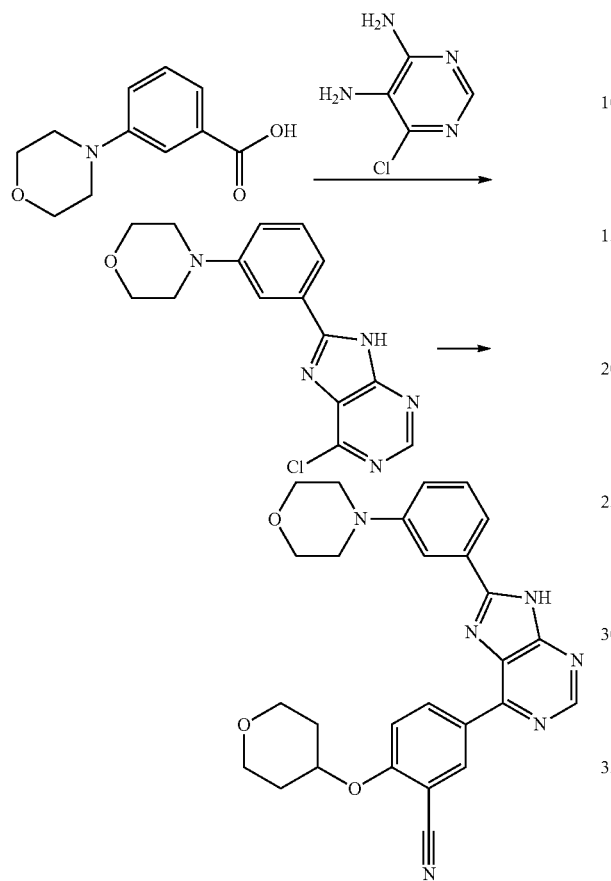

Step 1: A mixture of 6-chloro-4,5-diaminopyrimidine (349 mg, 2.41 mmol), 3-morpholinobenzoic acid (500 mg, 2.41 mmol) and ammonium chloride (774 mg, 14.47 mmol) in POCl$_3$ (7 mL) was heated at 110° C. for 16 hrs. The reaction mixture was cooled and the residue was washed several times with ether. The residue was dissolved in CH$_2$Cl$_2$ and aqueous NaHCO$_3$. The layers were separated and the aqueous was extracted with CH$_2$Cl$_2$. The combined organics were washed with saturated NaHCO$_3$, saturated aqueous sodium chloride solution, and dried (Na$_2$SO$_4$), filtered, and collected in vacuo to give crude 4-(3-(6-chloro-9H-purin-8-yl)phenyl)morpholine. LCMS-ESI$^+$ (m/z): [M+H]$^+$ calcd for C$_{15}$H$_{14}$ClN$_5$O: 316.1. found: 316.1.

Step 2: A sealed tube containing a suspension of 4-(3-(6-chloro-9H-purin-8-yl)phenyl)morpholine (100 mg, 0.317 mmol) and Pd(PPh$_3$)$_4$ (18 mg, 0.016 mmol) in a degassed mixture of dioxane/H$_2$O (2.5 mL, 4/1), was preheated at 85° C. for 5 min. Next, K$_2$CO$_3$ (110 mg, 0.789 mmol) and 2-((tetrahydro-2H-pyran-4-yl)oxy)-5-(4,4,5,5-tetramethyl-1,3,2-dioxaborolan-2-yl)benzonitrile (209 mg, 0.634 mmol), were added to the mixture and the reaction was heated at 100° C. in the sealed tube for 15 hrs. Afterwards, the crude material was allowed to reach room temperature. It was concentrated to dryness. The residue was diluted in MeOH and filtered through a short pad of Celite, washed the solids with MeOH. The filtrate was concentrated to dryness. The residue was purified by flash column chromatography on silica gel to afford 5-(8-(3-morpholinophenyl)-9H-purin-6-yl)-2-((tetrahydro-2H-pyran-4-yl)oxy)benzonitrile. $^1$H NMR (400 MHz, DMSO-d6) δ 11.98 (s, 1H), 9.19 (m, 2H), 8.89 (s, 1H), 7.89-7.81 (m, 1H), 7.78 (m, 1H), 7.62 (m, 1H), 7.46 (m, 1H), 7.17 (m, 1H), 4.96 (m, 1H), 3.94-3.82 (m, 2H), 3.83-3.68 (m, 4H), 3.56 (m, 2H), 3.29 (m, 2H), 2.06 (m, 2H), 1.71 (m, 2H). LCMS-ESI$^+$ (m/z): [M+H]$^+$ calcd for C$_{27}$H$_{26}$N$_6$O$_3$: 483.2. found: 483.2.

Example 212: Preparation of 5-(8-(4-(4-methylpiperazin-1-yl)phenyl)-9H-purin-6-yl)-2-((tetrahydro-2H-pyran-4-yl)oxy)benzonitrile

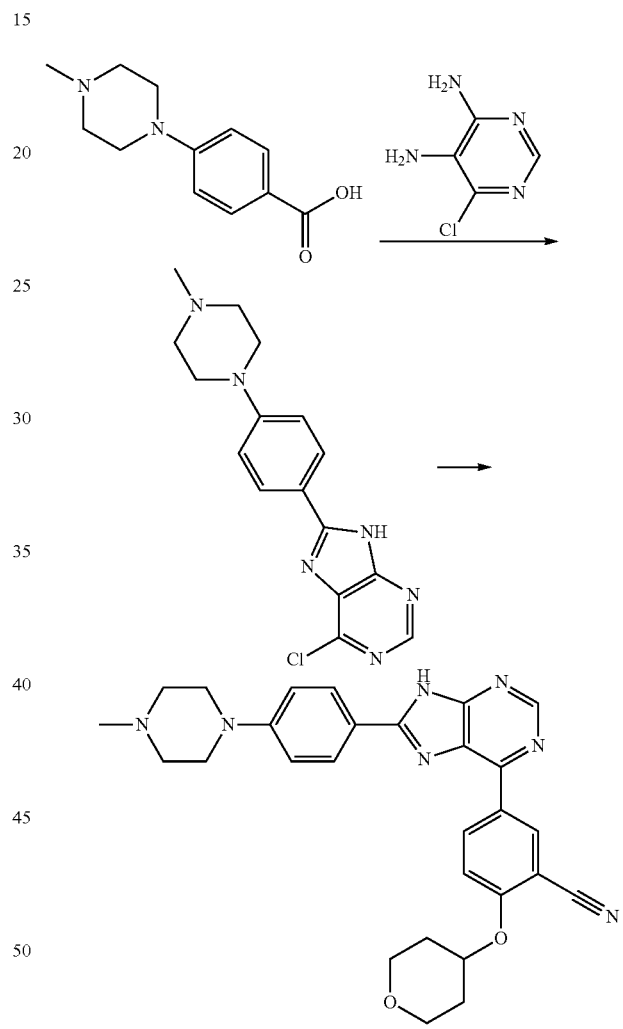

Step 1: A mixture of 6-chloro-4,5-diaminopyrimidine (500 mg, 3.459 mmol), 4-(4-methylpiperazin-1-yl) benzoic acid (762 mg, 3.459 mmol) in POCOl$_3$ (8 mL) was heated at 110° C. for 16 hrs. After it was cooled to room temperature, the residue was washed several times with ether. Then the residue was dissolved in small amount of MeOH, purified by flash column chromatography on silica gel to give 6-chloro-8-(4-(4-methylpiperazin-1-yl)phenyl)-9H-purine. LCMS-ESI$^+$ (m/z): [M+H]$^+$ calcd for C$_{16}$H$_{17}$ClN$_6$: 329.1. found: 329.2.

Step 2: A sealed tube containing a suspension of 6-chloro-8-(4-(4-methylpiperazin-1-yl)phenyl)-9H-purine (55 mg, 0.167 mmol) and Pd(PPh$_3$)$_4$ (10 mg, 0.009 mmol) in a degassed mixture of dioxane/H₂O (1.5 mL, 4/1), was preheated at 85° C. for 5 min. Next, K₂CO₃ (58 mg, 0.42 mmol) and 2-((tetrahydro-2H-pyran-4-yl)oxy)-5-(4,4,5,5-tetramethyl-1,3,2-dioxaborolan-2-yl)benzonitrile (110 mg, 0.334 mmol), were added to the mixture and the reaction was additionally heated at 100° C. in the sealed tube for 15 hrs. Afterwards, the crude material was allowed to reach room temperature. It was diluted in MeOH and filtered through a short pad of Celite, washed with MeOH.

The filtrate was concentrated to dryness. The residue was purified by flash column chromatography on silica gel to afford 5-(8-(4-(4-methylpiperazin-1-yl)phenyl)-9H-purin-6-yl)-2-((tetrahydro-2H-pyran-4-yl)oxy)benzonitrile. ¹H NMR (400 MHz, DMSO-d6) δ 13.76 (s, 1H), 9.18 (br s, 2H), 8.82 (s, 1H), 8.28-8.04 (m, 2H), 7.73-7.51 (m, 1H), 7.27-6.98 (m, 2H), 4.95 (m, 1H), 3.88 (m, 2H), 3.55 (m, 2H), 3.29 (m, 4H), 2.62-2.33 (m, 4H), 2.22 (s, 3H), 2.06 (m, 2H), 1.71 (m, 2H). LCMS-ESI⁺ (m/z): [M+H]⁺ calcd for C₂₈H₂₉N₇O₂: 496.2. found: 496.2.

Example 213: Preparation of 5-(8-(1-methyl-1H-pyrazol-4-yl)-9H-purin-6-yl)-2-((tetrahydro-2H-pyran-4-yl)oxy)benzonitrile

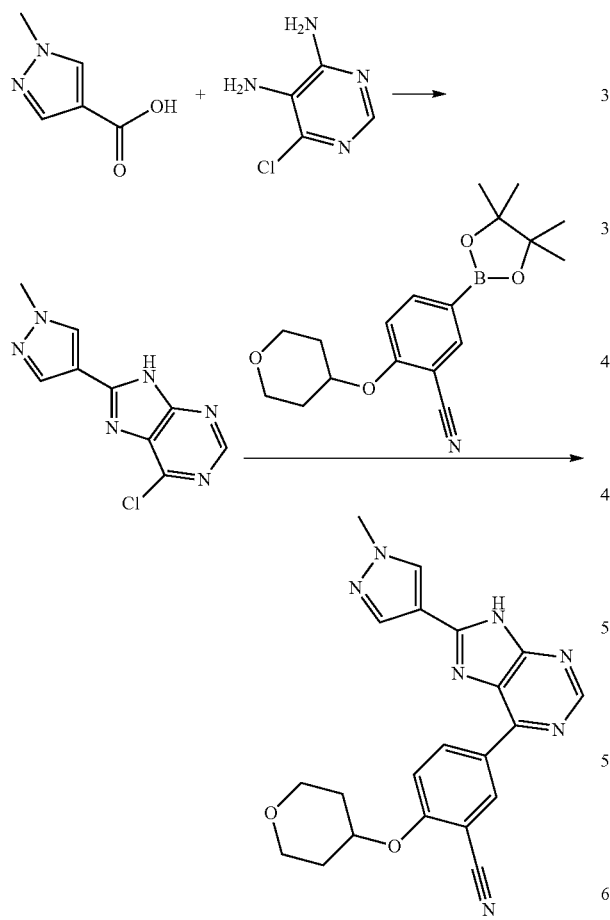

Step 1: A mixture of 6-chloro-4,5-diaminopyrimidine (573 mg, 3.96 mmol), 1-methyl-1H-pyrazole-4-carboxylic acid (500 mg, 3.96 mmol) and ammonium chloride (1.272 g, 23.78 mmol) in POCl₃ (12 mL) was heated at 100° C. for 24 hrs. After it was cooled to room temperature, the mixture was poured into ice/water and neutralized with an ammonia solution. it was extracted with DCE and the organic layers were combined and dried over sodium sulfate. After evaporation under vacuum, the crude material was purified by flash column chromatography on silica gel to afford 6-chloro-8-(1-methyl-1H-pyrazol-4-yl)-9H-purine. LCMS-ESI⁺ (m/z): [M+H]⁺ calcd for C₉H₇ClN₆: 235.0. found: 235.2.

Step 2: A sealed tube containing a suspension of 6-chloro-8-(1-methyl-1H-pyrazol-4-yl)-9H-purine (110 mg, 0.469 mmol) and Pd(PPh₃)₄ (27 mg, 0.023 mmol) in a degassed mixture of dioxane/H₂O (4 mL, 4/1), was preheated at 85° C. for 5 min. Next, K₂CO₃ (162 mg, 1.17 mmol) and 2-((tetrahydro-2H-pyran-4-yl)oxy)-5-(4,4,5,5-tetramethyl-1,3,2-dioxaborolan-2-yl)benzonitrile (308 mg, 0.935 mmol), were added to the mixture and the reaction was additionally heated at 100° C. in the sealed tube for 15 hrs. Afterwards, the crude material was allowed to reach room temperature. It was diluted in MeOH and filtered through a short pad of Celite, washed the solids with MeOH. The filtrate was concentrated to dryness. The residue was purified by flash column chromatography on silica gel to give 5-(8-(1-methyl-1H-pyrazol-4-yl)-9H-purin-6-yl)-2-((tetrahydro-2H-pyran-4-yl)oxy)benzonitrile.

¹H NMR (400 MHz, DMSO-d6) δ 13.79 (s, 1H), 9.26-8.98 (m, 2H), 8.82 (s, 1H), 8.49 (s, 1H), 8.17 (d, J=0.8 Hz, 1H), 7.58 (d, J=9.1 Hz, 1H), 4.95 (m, 1H), 3.96 (s, 3H), 3.87 (m, 2H), 3.55 (m, 2H), 2.19-1.97 (m, 2H), 1.70 (m, 2H). LCMS-ESI⁺ (m/z): [M+H]⁺ calcd for C₂₁H₁₉N₇O₂: 402.2. found: 402.1.

Example 214: Synthesis of 5-(2-methyl-8-(4-morpholinophenyl)-9H-purin-6-yl)-2-((tetrahydro-2H-pyran-4-yl)oxy)benzonitrile

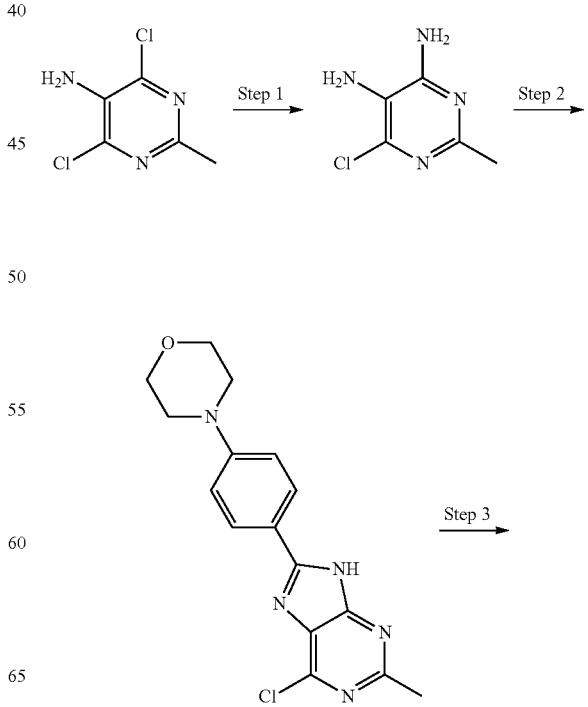

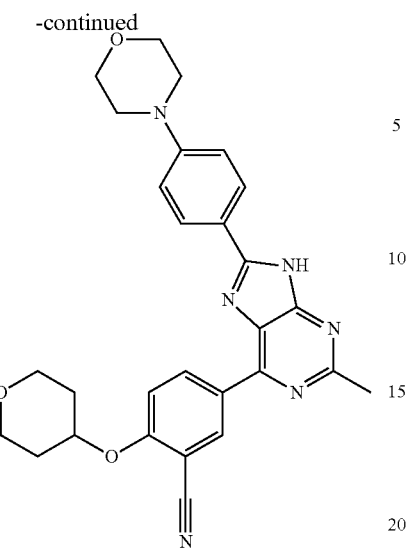

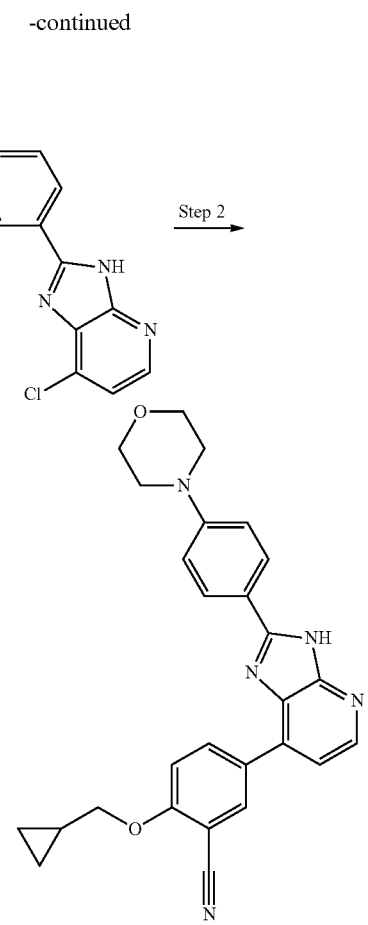

Step 1: 4,6-dichloro-2-methylpyrimidin-5-amine (1.0 g, 5.6 mmol) was added into a solution of ammonia 2N in isopropanol (15 mL) in a high pressure vial and stirred at 150° C. for 18 h. Reaction mixture was evaporated under reduced pressure. Solids were suspended in methanol and filtered to yield 6-chloro-2-methylpyrimidine-4,5-diamine which was used for next step without further purification. LCMS-ESI+ (m/z): [M+H]+ calcd for $C_5H_7ClN_4$: 159.6. found 159.1.

Step 2: Following similar procedure to synthesize Example 305 step 1, beginning with 6-chloro-2-methylpyrimidine-4,5-diamine (500 mg, 3.15 mmol) and 4-morpholinobenzoic acid (718 mg, 3.46 mmol), 4-(4-(6-chloro-2-methyl-9H-purin-8-yl)phenyl)morpholine was synthesized. LCMS-ESI+ (m/z): [M+H]+ calcd for $C_{16}H_{16}ClN_5O$: 330.8. found 330.1.

Step 3: Following similar procedure to synthesize Example 305 step 3, beginning with 4-(4-(6-chloro-2-methyl-9H-purin-8-yl)phenyl)morpholine (400 mg, 1.2 mmol), and 2-((tetrahydro-2H-pyran-4-yl)oxy)-5-(4,4,5,5-tetramethyl-1,3,2-dioxaborolan-2-yl)benzonitrile (439 mg, 1.33 mmol), 5-(2-methyl-8-(4-morpholinophenyl)-9H-purin-6-yl)-2-((tetrahydro-2H-pyran-4-yl)oxy)benzonitrile was synthesized. LCMS-ESI+ (m/z): [M+H]+ calcd for $C_{28}H_{28}N_6O_3$: 497.5. found 497.2.

Example 301: Preparation of 2-(cyclopropylmethoxy)-5-(2-(4-morpholinophenyl)-3H-imidazo[4,5-b]pyridin-7-yl)benzonitrile

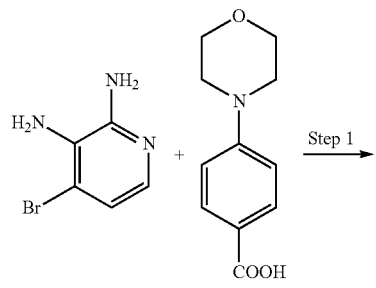

Step 1: To mixture of 4-bromopyridine-2,3-diamine (1 g, 5.31 mmol), 4-morpholinobenzoic acid (1.21 g, 5.85 mmol) in a 20 mL microwave vial was added $POCl_3$ (15 mL). The reaction was stirred at 150° C. for 2 h. The excess $POCl_3$ was removed by distillation. The residue was purified by flash column chromatography on silica gel to afford 4-(4-(7-chloro-3H-imidazo[4,5-b]pyridin-2-yl)phenyl)morpholine. LCMS-ESI+ (m/z): [M+H]+ calcd for $C_{16}H_{15}ClN_4O$: 315.8. found: 315.3.

Step 2: To stirred mixture of 4-(4-(7-chloro-3H-imidazo[4,5-b]pyridin-2-yl)phenyl)morpholine (100 mg, 0.31 mmol), 2-(cyclopropylmethoxy)-5-(4,4,5,5-tetramethyl-1,3,2-dioxaborolan-2-yl)benzonitrile (114 mg, 0.38 mmol), PEPPSI-iPr catalyst (43.0 mg, 0.064 mmol) in dioxane (3 mL) microwave vial was added solution of $Cs_2CO_3$ (309.7 mg, 0.95 mmol) in water (1.5 mL) and heated at 105° C. for 1 h. The reaction mixture was cooled to room temperature, diluted with dichloromethane and filtered through pad of silica gel and washed with 10% MeOH/DCM. The solvent was concentrated and the crude product was purified by flash column chromatography on silica gel to afford 2-(cyclopropylmethoxy)-5-(2-(4-morpholinophenyl)-3H-imidazo[4,5-b]pyridin-7-yl)benzonitrile. $^1$H NMR (400 MHz, DMSO-d6) δ 13.43 (s, —NH), 8.84 (d, J=2.4 Hz, 1H), 8.78 (dd, J=8.8, 2.0 Hz, 1H), 8.27 (d, J=5.6 Hz, 1H), 8.13 (d, J=9.2 Hz, 2H), 7.57 (d, J=5.6 Hz, 1H), 7.44 (d, J=9.2 Hz, 1H), 7.12 (d, J=9.2 Hz, 2H), 4.12 (d, J=7.2 Hz, 2H), 3.76 (t, J=4.4 Hz, 4H), 3.27 (t, J=8.0 Hz, 4H), 1.34-1.28 (m, 1H), 0.65-0.60 (m, 2H), 0.42-0.38 (m, 2H). LCMS-ESI+ (m/z): [M+H]+ calcd for $C_{27}H_{25}N_5O_2$: 452.5. found: 452.3.

Example 302: Preparation of (R)-tert-butyl 3-(2-cyano-4-(2-(4-morpholinophenyl)-3H-imidazo[4,5-b]pyridin-7-yl)phenoxy)pyrrolidine-1-carboxylate

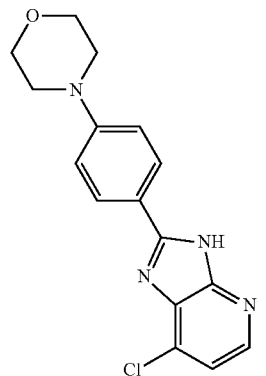

To stirred mixture of 4-(4-(7-chloro-3H-imidazo[4,5-b]pyridin-2-yl)phenyl)morpholine (150 mg, 0.47 mmol), (R)-tert-butyl 3-(2-cyano-4-(4,4,5,5-tetramethyl-1,3,2-dioxaborolan-2-yl)phenoxy)pyrrolidine-1-carboxylate (236.9 mg, 0.57 mmol), PEPPSI-iPr catalyst (64.9 mg, 0.095 mmol) in dioxane (6 mL) was added solution of $Cs_2CO_3$ (464.6 mg, 1.43 mmol) in water (3 mL) and heated at 105° C. for 1 h. The reaction mixture was cooled to room temperature, diluted with dichloromethane and filtered through pad of silica gel and washed with 10% MeOH/DCM. The solvent was concentrated and the crude product was purified by flash column chromatography on silica gel to afford (R)-tert-butyl 3-(2-cyano-4-(2-(4-morpholinophenyl)-3H-imidazo[4,5-b]pyridin-7-yl)phenoxy)pyrrolidine-1-carboxylate.

$^1$H NMR (400 MHz, DMSO-d6) δ 13.42 (s, —NH), 8.84 (s, 1H), 8.82 (d, J=10 Hz, 1H), 8.27 (d, J=5.2 Hz, 1H), 8.13 (d, J=9.2 Hz, 2H), 7.58 (d, J=5.2 Hz, 1H), 7.53 (d, J=9.2 Hz, 1H), 7.12 (d, J=9.2 Hz, 2H), 5.30 (m, 1H), 3.76 (t, J=4.8 Hz, 4H), 3.63 (m, 1H), 3.50-3.39 (m, 3H), 3.25 (t, J=4.8 Hz, 4H), 2.22-2.15 (m, 2H). LCMS-ESI$^+$ (m/z): [M+H]$^+$ calcd for $C_{32}H_{34}N_6O_4$: 567.7. found: 567.2.

Example 303: Preparation of (R)-2-((1-(2-cyano-acetyl)pyrrolidin-3-yl)oxy)-5-(2-(4-morpholinophenyl)-3H-imidazo[4,5-b]pyridin-7-yl)benzonitrile

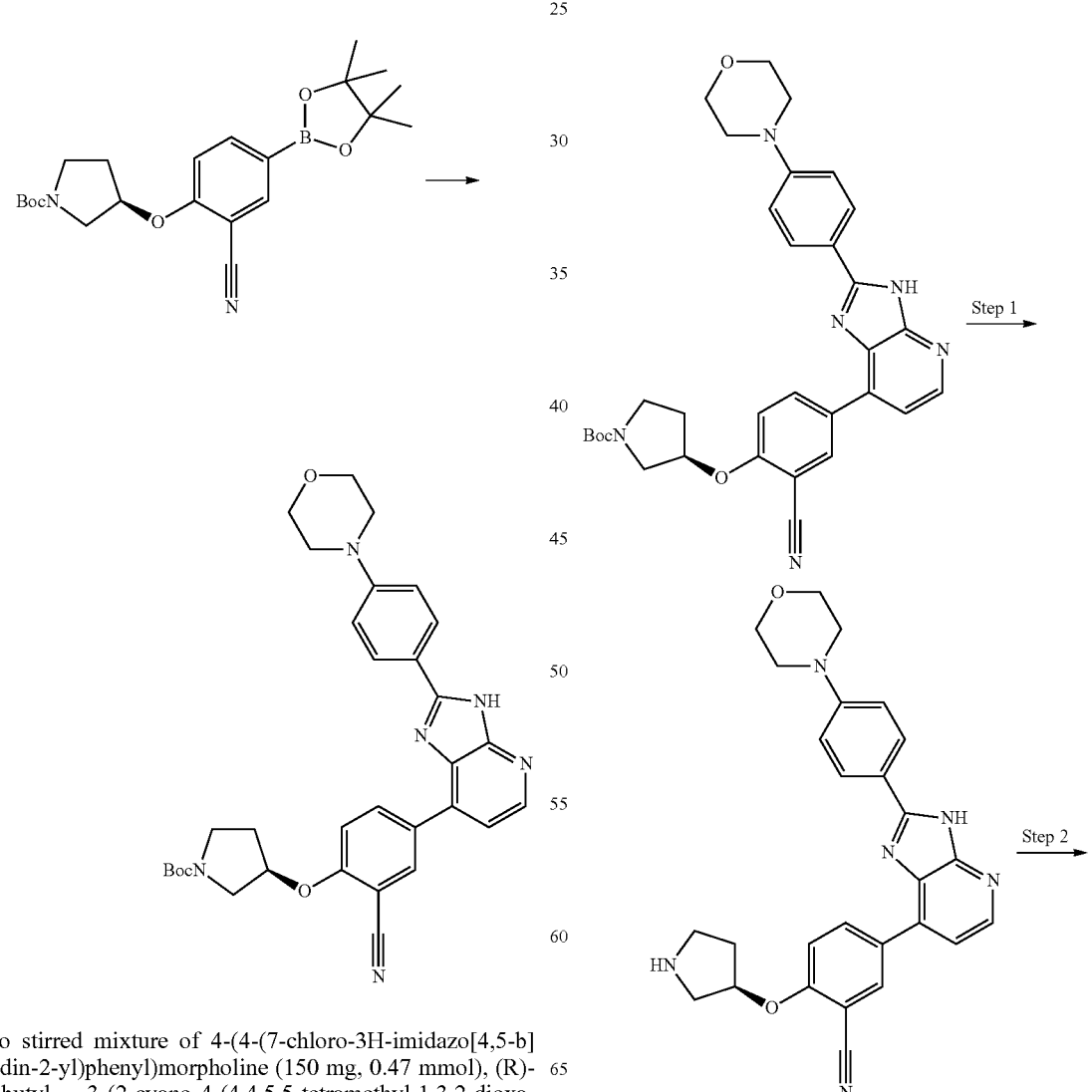

Example 304: Preparation of 6-(2-(4-morpholinophenyl)-3H-imidazo[4,5-b]pyridin-7-yl)-3-((tetrahydro-2H-pyran-4-yl)oxy)picolinonitrile

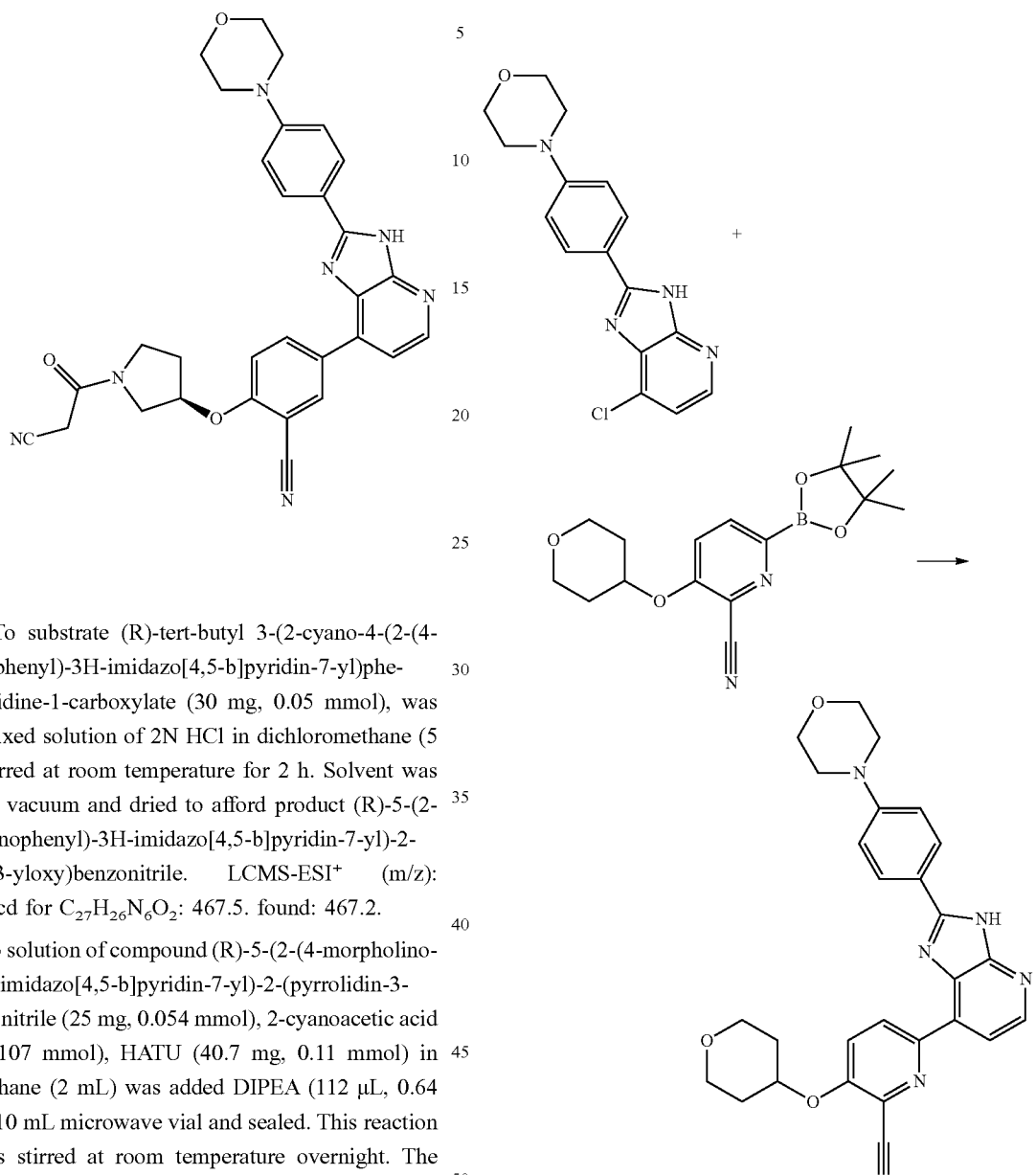

Step 1: To substrate (R)-tert-butyl 3-(2-cyano-4-(2-(4-morpholinophenyl)-3H-imidazo[4,5-b]pyridin-7-yl)phenoxy)pyrrolidine-1-carboxylate (30 mg, 0.05 mmol), was added premixed solution of 2N HCl in dichloromethane (5 mL) and stirred at room temperature for 2 h. Solvent was removed by vacuum and dried to afford product (R)-5-(2-(4-morpholinophenyl)-3H-imidazo[4,5-b]pyridin-7-yl)-2-(pyrrolidin-3-yloxy)benzonitrile. LCMS-ESI$^+$ (m/z): [M+H]$^+$ calcd for $C_{27}H_{26}N_6O_2$: 467.5. found: 467.2.

Step 2: To solution of compound (R)-5-(2-(4-morpholinophenyl)-3H-imidazo[4,5-b]pyridin-7-yl)-2-(pyrrolidin-3-yloxy)benzonitrile (25 mg, 0.054 mmol), 2-cyanoacetic acid (9.2 mg, 0.107 mmol), HATU (40.7 mg, 0.11 mmol) in dichloromethane (2 mL) was added DIPEA (112 µL, 0.64 mmol) in a 10 mL microwave vial and sealed. This reaction mixture was stirred at room temperature overnight. The solvent was concentrated and the crude product was purified by flash column chromatography on silica gel to afford (R)-2-((1-(2-cyanoacetyl)pyrrolidin-3-yl)oxy)-5-(2-(4-morpholinophenyl)-3H-imidazo[4,5-b]pyridin-7-yl)benzonitrile.

$^1$H NMR (400 MHz, DMSO-d6) δ 13.44 (s, —NH), 8.84 (s, 1H), 8.81 (d, J=11.2 Hz, 1H), 8.27 (d, J=4.8 Hz, 1H), 8.13 (d, J=8.0 Hz, 2H), 7.58 (d, J=4.8 Hz, 1H), 7.53 (d, J=8.8 Hz, 2H), 7.12 (d, J=9.2 Hz, 2H), 5.42-5.32 (m, 1H), 4.03-3.83 (m, 2H), 3.74 (t, J=5.2 Hz, 4H), 3.67-3.61 (m, 2H), 3.59-3.43 (m, 2H), 3.26 (t, J=4.8 Hz, 4H), 2.31-2.16 (m, 2H). LCMS-ESI$^+$ (m/z): [M+H]$^+$ calcd for $C_{30}H_{27}N_7O_3$: 534.6. found: 534.3.

To stirred mixture of 4-(4-(7-chloro-3H-imidazo[4,5-b]pyridin-2-yl)phenyl)morpholine (140 mg, 0.44 mmol), 3-((tetrahydro-2H-pyran-4-yl)oxy)-6-(4,4,5,5-tetramethyl-1,3,2-dioxaborolan-2-yl)picolinonitrile (176.2 mg, 0.53 mmol), PEPPSI-iPr catalyst (60.6 mg, 0.09 mmol) in dioxane (6 mL) was added solution of $Cs_2CO_3$ (433.6 mg, 1.33 mmol) in water (3 mL) and heated at 105° C. for 12 h. The reaction mixture was cooled to room temperature, diluted with dichloromethane and filtered through pad of silica gel and washed with 10% MeOH/DCM. The solvent was concentrated and the crude product was purified by flash column chromatography on silica gel to afford 6-(2-(4-morpholinophenyl)-3H-imidazo[4,5-b]pyridin-7-yl)-3-((tetrahydro-2H-pyran-4-yl)oxy)picolinonitrile.

$^1$H NMR (400 MHz, DMSO-d6) δ 9.57 (s, —NH), 8.34 (d, J=5.6 Hz, 1H), 8.19-8.15 (m, 1H), 7.91 (d, J=4.8 Hz, 1H), 7.12-7.08 (m, 2H), 6.65-6.52 (m, 2H), 4.96-4.95 (m, 1H), 3.90-3.85 (m, 2H), 3.77-3.74 (m, 2H), 3.57-3.51 (m, 4H), 3.28-3.26 (m, 4H), 2.07-2.05 (m, 2H), 1.73-1.68 (m, 2H). LCMS-ESI$^+$ (m/z): [M+H]$^+$ calcd for $C_{27}H_{26}N_6O_3$: 483.5; found: 483.2.

Example 305: Synthesis of 5-(2-4-morpholinophenyl)-3H-imidazo[4,5-b]pyridin-7-yl)-2-((tetrahydro-2H-pyran-4-yl)oxy)benzonitrile

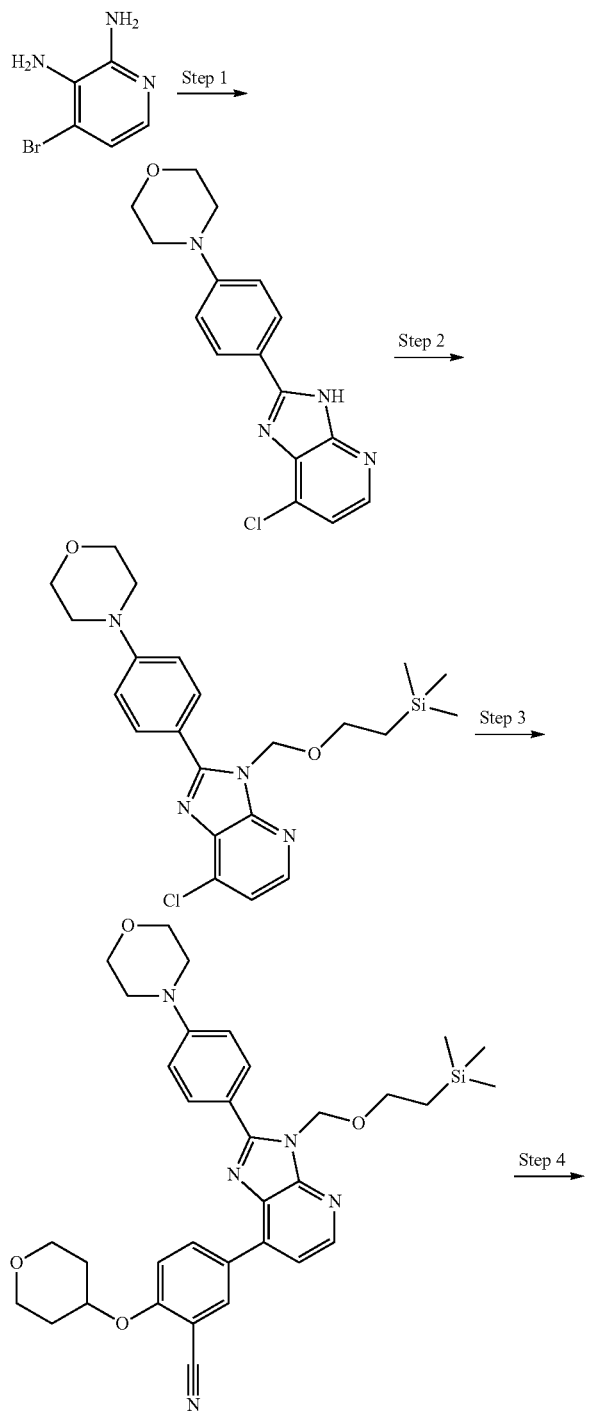

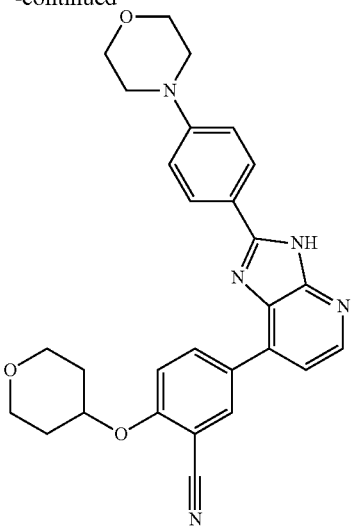

Step 1: 4-bromopyridine-2,3-diamine (143 mg, 1.0 mmol) and 4-morpholinobenzoic acid (1.0-1.1 mmol) were dissolved in phosphoryl chloride (10 mL) in a 20 mL microwave vial. The reaction mixture was stirred at 150° C. for 45 min in a microwave reactor. After cooling down to room temperature the mixture was poured slowly into water under vigorous stirring, and extracted with dichloromethane. The combined organic layers were washed with saturated aqueous sodium chloride solution, dried with magnesium sulfate, filtered and concentrated under reduced pressure to yield 4-(4-(7-chloro-3H-imidazo[4,5-b]pyridin-2-yl)phenyl)morpholine that was used for next step without further purification. LCMS-ESI$^+$ (m/z): [M+H]$^+$ calcd for $C_{16}H_{15}ClN_4O$: 315.7. found 315.1.

Step 2: To a solution of 4-(4-(7-chloro-3H-imidazo[4,5-b]pyridin-2-yl)phenyl)morpholine (120.0 mg, 0.38 mmol) in DMF (6 mL) was added Cesium carbonate (310 mg, 0.95 mmol) and 2-(Trimethylsilyl)-ethoxymethyl chloride (67 mg, 0.4 mmol) and reaction mixture stirred overnight at room temperature. Mixture was poured into water, and extracted with dichloromethane. The combined organic layers were washed with saturated aqueous sodium chloride solution, dried with magnesium sulfate, filtered and concentrated under reduced pressure to give 4-(4-(7-chloro-3-((2-(trimethylsilyl)ethoxy)methyl)-3H-imidazo[4,5-b]pyridin-2-yl)phenyl)morpholine (tentatively assigned regioisomer) which was used for next step without further purification. LCMS-ESI$^+$ (m/z): [M+H]$^+$ calcd for $C_{22}H_{29}ClN_4O_2Si$: 446. found 445.1.

Step 3: Following similar procedure to synthesize EXAMPLE 72 step 1, beginning with the tentatively assigned regioisomer 4-(4-(7-chloro-3-((2-(trimethylsilyl)ethoxy)methyl)-3H-imidazo[4,5-b]pyridin-2-yl)phenyl)morpholine (132 mg, 0.29 mmol) and 2-((tetrahydro-2H-pyran-4-yl)oxy)-5-(4,4,5,5-tetramethyl-1,3,2-dioxaborolan-2-yl)benzonitrile (117 mg, 0.35 mmol), the tentatively assigned regioisomer 5-(2-(4-morpholinophenyl)-3-((2-(trimethylsilyl)ethoxy)methyl)-3H-imidazo[4,5-b]pyridin-7-yl)-2-((tetrahydro-2H-pyran-4-yl)oxy)benzonitrile was synthesized. LCMS-ESI$^+$ (m/z): [M+H]$^+$ calcd for $C_{34}H_{41}N_5O_4Si$: 612.8. found 612.2.

Step 4: Following similar procedure to synthesize EXAMPLE 73 step 5, beginning with the tentatively assigned regioisomer 5-(2-(4-morpholinophenyl)-3-((2-

(trimethylsilyl)ethoxy)methyl)-3H-imidazo[4,5-b]pyridin-7-yl)-2-((tetrahydro-2H-pyran-4-yl)oxy)benzonitrile (132 mg, 0.29 mmol), 5-(2-(4-morpholinophenyl)-3H-imidazo[4,5-b]pyridin-7-yl)-2-((tetrahydro-2H-pyran-4-yl)oxy)benzonitrile was synthesized. $^1$H NMR (400 MHz, DMSO-d6) δ 13.38 (s, 1H), 8.86 (d, J=2.3 Hz, 1H), 8.78 (dd, J=9.1, 2.4 Hz, 1H), 8.20 (d, J=5.2 Hz, 1H), 8.14 (d, J=8.7 Hz, 2H), 7.54 (d, J=9.0 Hz, 1H), 7.45 (d, J=5.2 Hz, 1H), 7.08 (d, J=8.7 Hz, 2H), 4.97-4.85 (m, 1H), 3.95-3.81 (m, 2H), 3.75 (t, J=4.8 Hz, 4H), 3.60-3.50 (m, 2H), 3.23 (d, J=9.7 Hz, 4H), 2.09-2.0 (m, 2H), 1.74-1.65 (m, 2H). LCMS-ESI$^+$ (m/z): [M+H]$^+$ calcd for $C_{28}H_{27}N_5O_3$: 482.5. found 482.3.

Example 306: 5-(2-(4-(4-methylpiperazin-1-yl)phenyl)-3H-imidazo[4,5-b]pyridin-7-yl)-2-((tetrahydro-2H-pyran-4-yl)oxy)benzonitrile

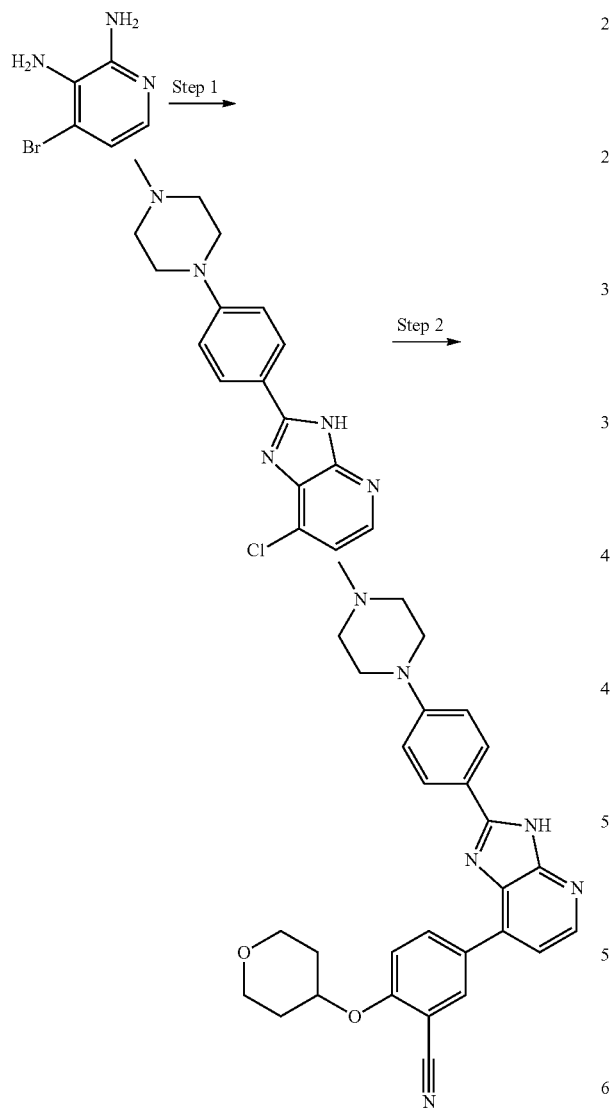

Step 1: Following similar procedure to synthesize Example 305 step 1, beginning with 4-bromopyridine-2,3-diamine (400 mg, 2.12 mmol) and 4-(4-methylpiperazin-1-yl)benzoic acid (515 mg, 2.34 mmol), 7-chloro-2-(4-(4-methylpiperazin-1-yl)phenyl)-3H-imidazo[4,5-b]pyridine was synthesized. LCMS-ESI$^+$ (m/z): [M+H]$^+$ calcd for $C_{17}H_{18}ClN_5$: 328.8. found 328.2.

Step 2: Following similar procedure to synthesize Example 305 step 3, beginning with 7-chloro-2-(4-(4-methylpiperazin-1-yl)phenyl)-3H-imidazo[4,5-b]pyridine (200 mg, 0.61 mmol) and 2-((tetrahydro-2H-pyran-4-yl)oxy)-5-(4,4,5,5-tetramethyl-1,3,2-dioxaborolan-2-yl)benzonitrile (241 mg, 0.0.73 mmol), 5-(2-(4-(4-methylpiperazin-1-yl)phenyl)-3H-imidazo[4,5-b]pyridin-7-yl)-2-((tetrahydro-2H-pyran-4-yl)oxy)benzonitrile was synthesized. $^1$H NMR (400 MHz, DMSO-d6) δ 13.2 (s, 1H), 8.84 (s, 1H), 8.78 (d, J=9.0 Hz, 1H), 8.20 (d, J=5.2 Hz, 1H), 8.11 (d, J=8.9 Hz, 2H), 7.55 (d, J=9.1 Hz, 1H), 7.46 (s, 1H), 7.07 (d, J=8.8 Hz, 2H), 4.97-4.86 (m, 1H), 3.93-3.84 (m, 2H), 3.6-6.51 (m, 2H), 3.31-3.25 (m, 4H), 2.51-2.41 (m, 4H), 2.22 (s, 3H), 2.11-1.94 (m, 2H), 1.80-1.57 (m, 2H). LCMS-ESI$^+$ (m/z): [M+H]$^+$ calcd for $C_{29}H_{30}N_6O_2$: 495.6. found 495.2.

Example 307: Synthesis of 5-(2-(1-methyl-1H-pyrazol-4-yl)-3H-imidazo[4,5-b]pyridin-7-yl)-2-((tetrahydro-2H-pyran-4-yl)oxy)benzonitrile

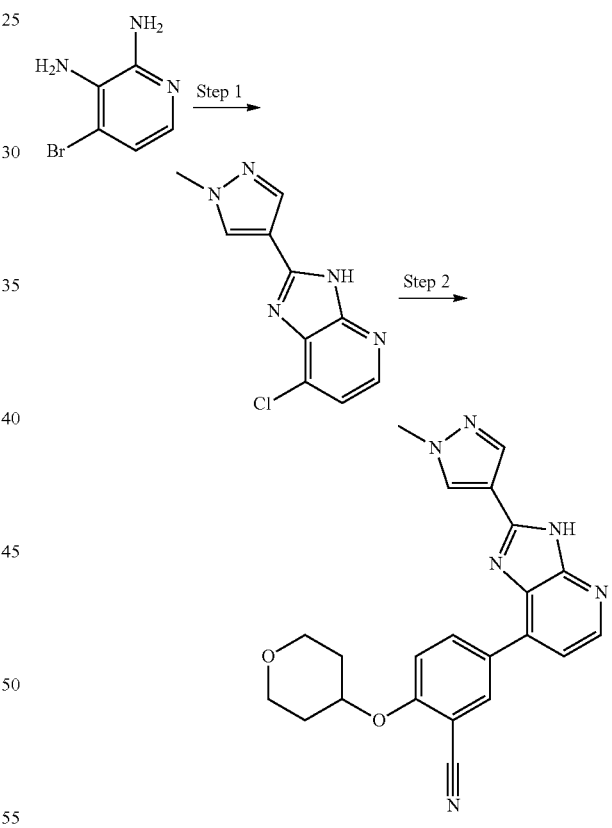

Step 1: Following similar procedure to synthesize Example 305 step 1, beginning with 4-bromopyridine-2,3-diamine (500 mg, 2.66 mmol) and 1-methyl-1H-pyrazole-4-carboxylic acid (368 mg, 2.92 mmol), 7-chloro-2-(1-methyl-1H-pyrazol-4-yl)-3H-imidazo[4,5-b]pyridine was synthesized. LCMS-ESI$^+$ (m/z): [M+H]$^+$ calcd for $C_{10}H_8ClN_5$: 234.6. found 234.2.

Step 2: Following similar procedure to synthesize Example 305 step 3, beginning with 7-chloro-2-(1-methyl-1H-pyrazol-4-yl)-3H-imidazo[4,5-b]pyridine (200 mg, 0.85 mmol) and 2-((tetrahydro-2H-pyran-4-yl)oxy)-5-(4,4,5,5- tetramethyl-1,3,2-dioxaborolan-2-yl)benzonitrile (338 mg, 1.02 mmol), 5-(2-(1-methyl-1H-pyrazol-4-yl)-3H-imidazo[4,5-b]pyridin-7-yl)-2-((tetrahydro-2H-pyran-4-yl)oxy)benzonitrile was synthesized. ¹H NMR (400 MHz, DMSO-d6) δ 13.38 (s, 1H), 8.80-8.73 (m, 1H), 8.70 (dd, J=9.0, 2.4 Hz, 1H), 8.40 (s, 1H), 8.26 (d, J=5.2 Hz, 1H), 8.11 (s, 1H), 7.59-7.47 (m, 2H), 4.99-4.88 (m, 1H), 3.94 (s, 3H), 3.91-3.81 (m, 2H), 3.6-3.5 (m, 2H), 2.1-2.01 (m, 2H), 1.74-1.64 (m, 2H). LCMS-ESI⁺ (m/z): [M+H]⁺ calcd for $C_{22}H_{20}N_6O_2$: 401.4. found 401.2.

Example 308: Synthesis of 5-(2-(3-morpholinophenyl)-3H-imidazo[4,5-b]pyridin-7-yl)-2-((tetrahydro-2H-pyran-4-yl)oxy)benzonitrile

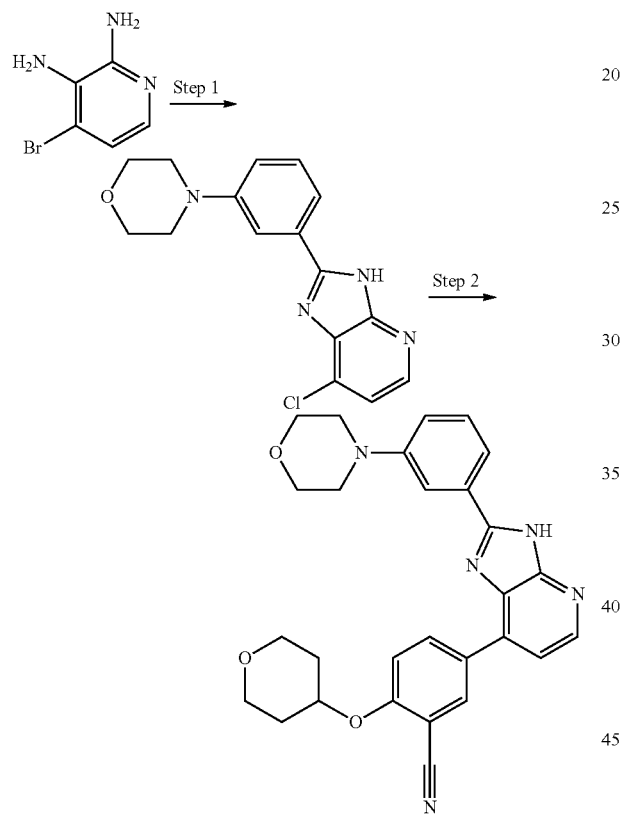

Step 1: Following similar procedure to synthesize Example 305 step 1, beginning with 4-bromopyridine-2,3-diamine (500 mg, 2.66 mmol) and 3-morpholinobenzoic acid (606 mg, 2.92 mmol), 4-(3-(7-chloro-3H-imidazo[4,5-b]pyridin-2-yl)phenyl)morpholine was synthesized. LCMS-ESI⁺ (m/z): [M+H]⁺ calcd for $C_{16}H_{15}ClN_4O$: 315.7. found 315.2.

Step 2: Following similar procedure to synthesize Example 305 step 3, beginning with 4-(3-(7-chloro-3H-imidazo[4,5-b]pyridin-2-yl)phenyl)morpholine (200 mg, 0.64 mmol), and 2-((tetrahydro-2H-pyran-4-yl)oxy)-5-(4,4,5,5-tetramethyl-1,3,2-dioxaborolan-2-yl)benzonitrile (251 mg, 0.762 mmol), 5-(2-(3-morpholinophenyl)-3H-imidazo[4,5-b]pyridin-7-yl)-2-((tetrahydro-2H-pyran-4-yl)oxy)benzonitrile was synthesized. ¹H NMR (400 MHz, DMSO-d6) δ 13.59 (s, 1H), 8.90-8.71 (m, 2H), 8.33 (d, J=5.2 Hz, 1H), 7.82 (t, J=2.0 Hz, 1H), 7.74 (dt, J=7.8, 1.1 Hz, 1H), 7.62-7.52 (m, 2H), 7.41 (t, J=7.9 Hz, 1H), 7.16-7.03 (m, 1H), 4.99-4.89 (m, 1H), 3.91-3.83 (m, 2H), 3.81-3.75 (m, 4H), 3.58-3.50 (m, 2H), 3.27-3.17 (m, 4H), 2.13-1.99 (m, 2H), 1.75-1.65 (m, 2H). LCMS-ESI⁺ (m/z): [M+H]⁺ calcd for $C_{28}H_{27}N_5O_3$: 482.5. found 482.2.

Example 401: Synthesis of 5-(8-(4-morpholinophenyl)-9H-imidazo[4,5-c]pyridazin-6-yl)-2-((tetrahydro-2H-pyran-4-yl)oxy)benzonitrile

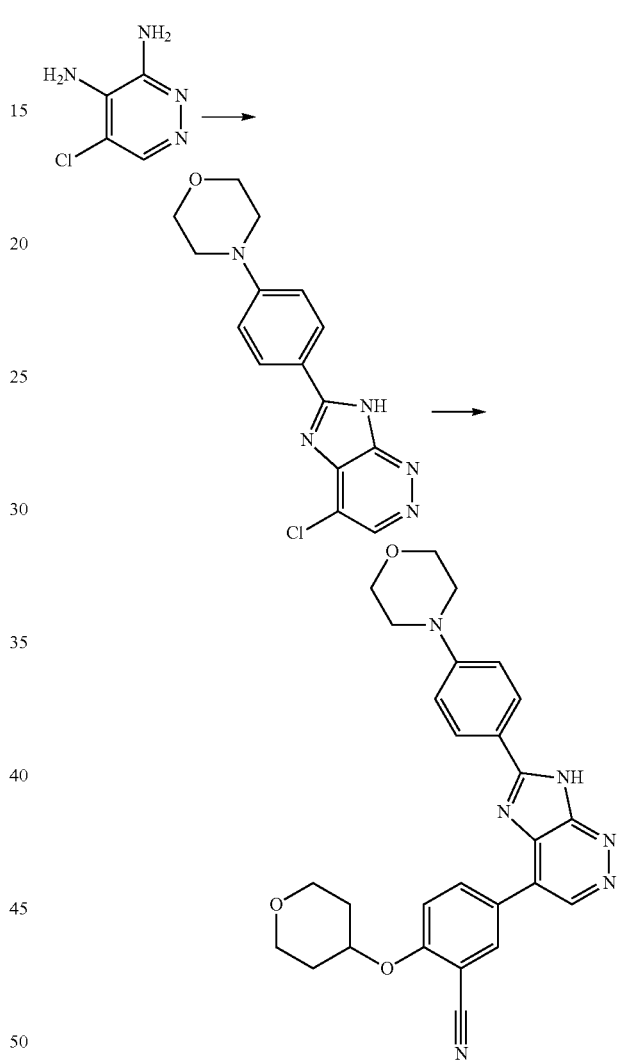

Step 1: Following similar procedure to synthesize Example 305 step 1, beginning with 5-chloropyridazine-3,4-diamine (600 mg, 4.15 mmol) and 4-morpholinobenzoic acid (946 mg, 4.56 mmol), 4-(4-(6-chloro-9H-imidazo[4,5-c]pyridazin-8-yl)phenyl)morpholine was synthesized. LCMS-ESI⁺ (m/z): [M+H]⁺ calcd for $C_{15}H_{15}ClN_5O$: 316.7. found 316.1.

Step 2: To an appropriate sized microwave vial, 4-(4-(6-chloro-9H-imidazo[4,5-c]pyridazin-8-yl)phenyl)morpholine (100 mg, 0.317 mmol), 2-((tetrahydro-2H-pyran-4-yl)oxy)-5-(4,4,5,5-tetramethyl-1,3,2-dioxaborolan-2-yl)benzonitrile (114.7 mg, 0.35 mmol), cesium carbonate (309 mg, 0.95 mmol), dioxane (3 mL) and water (1.5 mL) were added. The mixture was degassed with nitrogen for 10 minutes. PEPPSI-iPr catalyst (21 mg, 0.032 mmol) was added and the solution was heated at 105° C. for 2 h. After cooling to room temperature, the mixture was poured into water, and extracted with dichloromethane. The combined organic layers were washed with 1N HCL aqueous solution and brine. Organic phase was dried over $Mg_2SO_4$ and evaporated under reduced pressure. Solids were suspended in hot acetonitrile and stirred for 1 h. Solids were collected and purified via prep HPLC (10-95% acetonitrile in water, 0.1% trifluoroacteic acid buffer). Clean fractions poured into a saturated solution of sodium bicarbonate in water and extracted with dichloromethane to yield the product 5-(8-(4-morpholinophenyl)-9H-imidazo[4,5-c]pyridazin-6-yl)-2-((tetrahydro-2H-pyran-4-yl)oxy)benzonitrile. LCMS-ESI$^+$ (m/z): [M+H]$^+$ calcd for $C_{27}H_{27}N_6O_3$:483.53. found: 483.2.

Example 109: 5-(6-(4-(2-hydroxypropan-2-yl)phenyl)-7H-pyrrolo[2,3-d]pyrimidin-4-yl)-2-((tetrahydro-2H-pyran-4-yl)oxy)benzonitrile

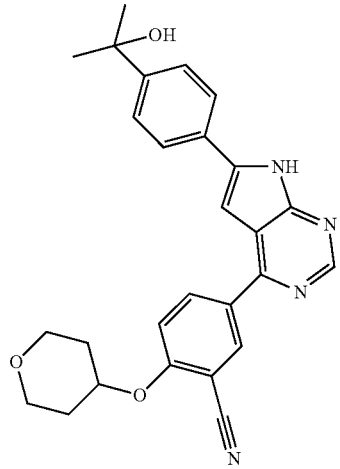 [SMILES: CC(C)(O)c1ccc(-c2cc3c(-c4ccc(OC5CCOCC5)c(C#N)c4)ncnc3[nH]2)cc1]

Step 1: To a solution of 4-chloro-6-iodo-7-(phenylsulfonyl)-7H-pyrrolo[2,3-d]pyrimidine (550 mgs, 1.31 mmol) and (4-(2-hydroxypropan-2-yl)phenyl)boronic acid (286 mgs, 1.21 mmol) in DME (5 mL), was added 2.0 M aq $Na_2CO_3$ (1.7 mL, 3.28 mmol) and Pd(PPh$_3$)$_4$ (75 mgs, 0.066 mmol) and the reaction mixture was heated at 110° C. for 2 hr. The mixture was then diluted with water and acetonitrile and the resulting solid was filtered and washed with ether and dried to give 2-(4-(4-chloro-7H-pyrrolo[2,3-d]pyrimidin-6-yl)phenyl)propan-2-ol which was used further without purification. LCMS-ESI$^+$ (m/z): [M+H]$^+$ calcd for $C_{21}H_{18}ClN_3O_3S$: 428.9. found: 428.2.

Step 2: To a mixture of 2-(4-(4-chloro-7H-pyrrolo[2,3-d]pyrimidin-6-yl)phenyl)propan-2-ol (80 mgs, 0.187 mmol) and 2-((tetrahydro-2H-pyran-4-yl)oxy)-5-(4,4,5,5-tetramethyl-1,3,2-dioxaborolan-2-yl)benzonitrile (68 mgs, 0.21 mmol) in DME (2 mL) was added 2.0 M aq $Na_2CO_3$ (0.21 mL, 0.4 mmol) and Pd(PPh$_3$)$_4$ catalyst (11 mgs, 0.009 mmol). The reaction mixture was heated to 140° C. for 20 min in microwave. The reaction mixture was then concentrated and used for next step without purification. LCMS-ESI$^+$ (m/z): [M+H]$^+$ calcd for $C_{33}H_{30}N_4O_5S$: 595.7. found: 595.2 Step 3: To the crude product from step 2 in THF/2,2,2-Trifluoroethanol (1:1, 2 mL) was added $Cs_2CO_3$ (305 mgs, 0.93 mmol). The mixture was stirred at 100° C. for 30 min.

The reaction mixture was then concentrated and purified by reverse phase chromatography to give the title compound as TFA salt which was then treated with $NaHCO_3$ and extracted with ethylacetate and dried give the free base. LCMS-ESI$^+$ (m/z): [M+H]$^+$ calcd for $C_{27}H_{26}N_4O_3$ as (M+H)$^+$ 455.5. found: 455.2; $^1$H NMR (400 MHz, DMSO-d$_6$) δ 12.72 (s, 1H), 8.79 (s, 1H), 8.52 (m, 2H), 7.99 (d, J=8.3 Hz, 2H), 7.56 (m, 3H), 7.46 (s, 1H), 5.08 (s, 1H), 4.96 (dt, J=8.2, 4.2 Hz, 1H), 3.88 (dt, J=10.4, 4.6 Hz, 2H), 3.56 (ddd, J=11.5, 8.3, 3.1 Hz, 2H), 2.10-2.00 (m, 2H), 1.71 (dtd, J=12.3, 8.2, 3.9 Hz, 2H), 1.45 (s, 6H).

Example 110: 2-(3-hydroxyazetidin-1-yl)-5-(6-(3-morpholinophenyl)-7H-pyrrolo[2,3-d]pyrimidin-4-yl)benzonitrile

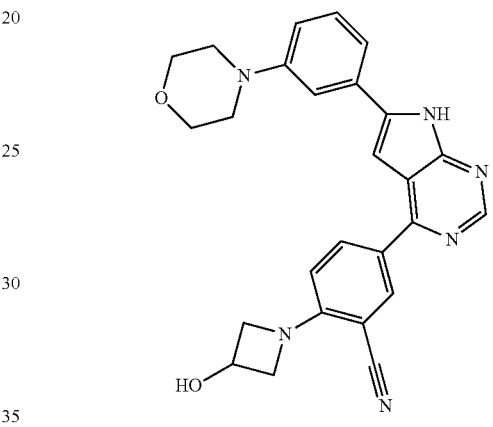

Step 1: To a solution of 4-chloro-6-iodo-7-(phenylsulfonyl)-7H-pyrrolo[2,3-d]pyrimidine (200 mgs, 0.44 mmol) and 3-(4-(4,4,5,5-tetramethyl-1,3,2-dioxaborolan-2-yl)phenyl)morpholine (151 mgs, 0.52 mmol) in DME (3 mL), was added 2.0 M aq $Na_2CO_3$ (0.7 mL, 1.43 mmol) and Pd(PPh$_3$)$_4$ (28 mgs, 0.025 mmol) and the reaction mixture was heated at 100° C. for 1 hr. The mixture was then concentrated and purified by flash chromatography (25-100% Ethyl acetate/hexanes) to give 4-(3-(4-chloro-7-(phenylsulfonyl)-7H-pyrrolo[2,3-d]pyrimidin-6-yl)phenyl)morpholine (29 mgs) LCMS-ESI$^+$ (m/z): [M+H]$^+$ calcd for $C_{22}H_{19}ClN_4O_3S$: 455.9. found: 455.1 and 4-(3-(4-chloro-7H-pyrrolo[2,3-d]pyrimidin-6-yl)phenyl)morpholine (75 mgs) LCMS-ESI$^+$ (m/z): [M+H]$^+$ calcd for $C_{16}H_{15}ClN_4O$: 314.7. found: 315.1.

Step 2: Step 2: To a mixture of 4-(3-(4-chloro-7H-pyrrolo[2,3-d]pyrimidin-6-yl)phenyl)morpholine (27 mgs, 0.095 mmol) and 2-(3-hydroxyazetidin-1-yl)-5-(4,4,5,5-tetramethyl-1,3,2-dioxaborolan-2-yl)benzonitrile (52 mgs, 0.17 mmol) in DMF (1 mL) was added 2.0 M aq $Na_2CO_3$ (0.1 mL, 0.2 mmol) and Pd(PPh$_3$)$_4$ catalyst (4 mgs, 0.004 mmol). The reaction mixture was heated to 125° C. for 30 min in microwave. Acetonitrile/Water (1:1, 5 mL) was added and the solids formed were filtered and washed with acetonitrile and methanol to give the title compound. LCMS-ESI$^+$ (m/z): [M+H]$^+$ calcd for $C_{26}H_{24}N_6O_2$ as (M+H)$^+$ 453.5. found: 453.2; $^1$H NMR (400 MHz, DMSO-d$_6$) δ 8.62 (s, 1H), 8.33 (m, 2H), 7.61-7.50 (m, 2H), 7.29 (m, 2H), 6.96-6.63 (m, 2H), 4.60 (m, 1H), 4.46 (m, 2H), 3.93 (m, 2H), 3.76 (m, 4H), 3.20 (m, 4H).

Example 111: 5-(6-(4-(2-hydroxypropan-2-yl)phenyl)-7H-pyrrolo[2,3-d]pyrimidin-4-yl)-2-(morpholinomethyl)benzonitrile

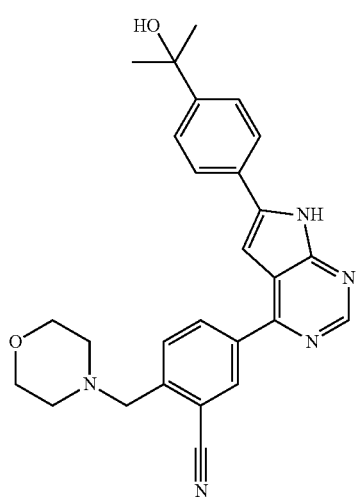 [SMILES: CC(C)(O)c1ccc(-c2cc3c(-c4ccc(CN5CCOCC5)c(C#N)c4)ncnc3[nH]2)cc1]

Step 1: To a mixture of 2-(4-(4-chloro-7H-pyrrolo[2,3-d]pyrimidin-6-yl)phenyl)propan-2-ol (80 mgs, 0.187 mmol) and 2-(morpholinomethyl)-5-(4,4,5,5-tetramethyl-1,3,2-dioxaborolan-2-yl)benzonitrile (68 mgs, 0.21 mmol) in DME (2 mL) was added 2.0 M aq $Na_2CO_3$ (0.21 mL, 0.4 mmol) and $Pd(PPh_3)_4$ catalyst (11 mgs, 0.009 mmol). The reaction mixture was heated to 125° C. for 25 min in microwave. The reaction mixture was then concentrated and used for next step without purification.

Step 2: To the crude product from step 1 in THF/2,2,2,-Trifluoroethanol (1:1, 2 mL) was added $Cs_2CO_3$ (305 mg, s 0.93 mmol). The mixture was stirred at 100° C. for 30 min. The reaction mixture was then concentrated and purified by reverse phase chromatography to give the title compound as TFA salt which was then treated with $NaHCO_3$ and extracted with ethylacetate and dried to give the free base. LCMS-ESI$^+$ (m/z): [M+H]$^+$ calcd for $C_{27}H_{27}N_5O_2$ as (M+H)+ 454.5. found: 454.1.

Example 112: 2-(morpholinomethyl)-5-(6-(4-morpholinophenyl)-7H-pyrrolo[2,3-d]pyrimidin-4-yl)benzonitrile

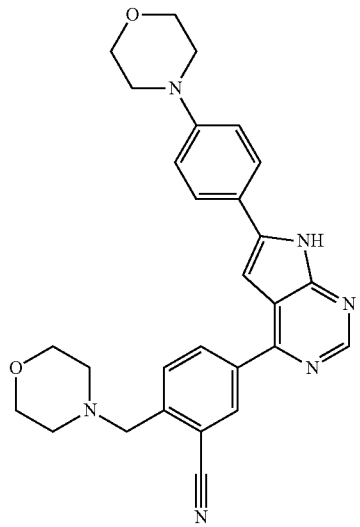 [SMILES: N#Cc1cc(-c2ncnc3[nH]c(-c4ccc(N5CCOCC5)cc4)cc23)ccc1CN1CCOCC1]

To a mixture of 4-(4-(4-chloro-7H-pyrrolo[2,3-d]pyrimidin-6-yl)phenyl)morpholine (50 mgs, 0.16 mmol) and 2-(morpholinomethyl)-5-(4,4,5,5-tetramethyl-1,3,2-dioxaborolan-2-yl)benzonitrile (83 mgs, 0.25 mmol) in DMF (1 mL) was added 2.0 M aq $Na_2CO_3$ (0.2 mL, 0.4 mmol) and $Pd(PPh_3)_4$ catalyst (9 mgs, 0.01 mmol). The reaction mixture was heated to 125° C. for 30 min in microwave. Acetonitrile/Water (1:1, 5 mL) was added and the solids formed were filtered and washed with acetonitrile and methanol to give the title compound. LCMS-ESI$^+$ (m/z): [M+H]$^+$ calcd for $C_{28}H_{28}N_6O_2$ as (M+H)$^+$ 481.6 found: 481.2; $^1$H NMR (400 MHz, DMSO-d$_6$) δ 12.61 (s, 1H), 8.76 (s, 1H), 8.62-8.45 (m, 2H), 7.95 (d, J=8.7 Hz, 2H), 7.78 (d, J=8.1 Hz, 1H), 7.33 (s, 1H), 7.04 (d, J=8.7 Hz, 2H), 3.75 (m, 10H), 3.60 (m, 4H), 3.21 (m, 4H).

Example 113: 2-(morpholinomethyl)-5-(6-(3-morpholinophenyl)-7H-pyrrolo[2,3-d]pyrimidin-4-yl)benzonitrile

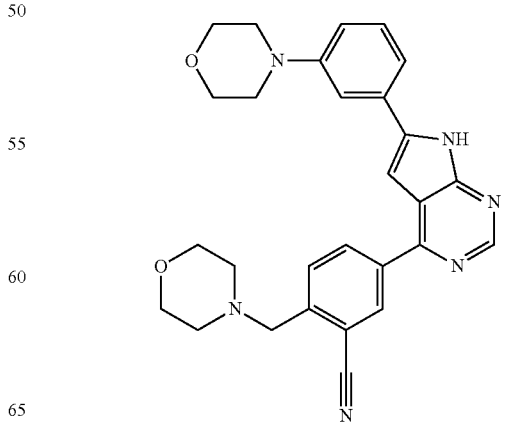

The title compound was prepared following similar procedure to Example 110. LCMS-ESI+ (m/z): [M+H]+ calcd for $C_{28}H_{28}N_6O_2$ as (M+H)+ 481.6. found: 481.2.

Example 114: 5-(6-(4-((1H-imidzol-1-yl)methyl)phenyl)-7H-pyrrolo[2,3-d]pyrimidin-4-yl)-2-((tetrahydro-2H-pyran-4-yl)oxy)benzonitrile

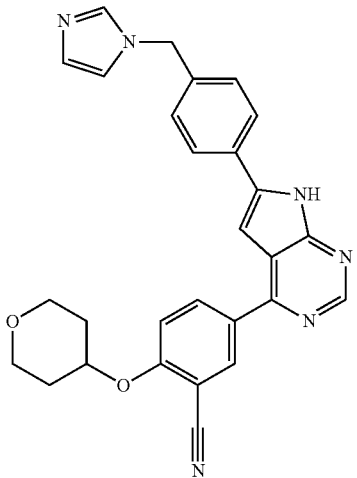 [SMILES: N#Cc1cc(-c2ncnc3[nH]c(-c4ccc(Cn5ccnc5)cc4)cc23)ccc1OC1CCOCC1]

Step 1: To a mixture 4-chloro-6-iodo-7-((2-(trimethylsilyl)ethoxy)methyl)-7H-pyrrolo[2,3-d]pyrimidine (75 mgs, 0.18 mmol) and 1-(4-(4,4,5,5-tetramethyl-1,3,2-dioxaborolan-2-yl)benzyl)-1H-imidazole (57 mgs, 0.20 mmol), in DME (3 mL) was added 2.0 M aq $Na_2CO_3$ (0.25 mL, 0.5 mmol) and Pd(PPh$_3$)$_4$ catalyst (11 mgs, 0.009 mmol). The reaction mixture was heated at 100° C. for 16 hr. Cooled to rt and to the mixture was added 2-((tetrahydro-2H-pyran-4-yl)oxy)-5-(4,4,5,5-tetramethyl-1,3,2-dioxaborolan-2-yl)benzonitrile (73 mgs, 0.2 mmol), 2.0 M aq $Na_2CO_3$ (0.2 mL, 0.37 mmol) and Pd(PPh$_3$)$_4$ (21 mgs, 0.018 mmol) and the reaction mixture was further heated at 100° C. for 16 hr. The mixture was then concentrated and purified by flash chromatography (0-20% Ethyl acetate/Methanol) to give 6-(4-((1H-imidazol-1-yl)methyl)phenyl)-4-chloro-7-((2-(trimethylsilyl)ethoxy)methyl)-7H-pyrrolo[2,3-d]pyrimidine. LCMS-ESI+ (m/z): [M+H]+ calcd for $C_{34}H_{38}N_6O_3Si$: 607.9. found: 607.3.

Step 2: To a mixture 4-(4-(4-chloro-7-(phenylsulfonyl)-7H-pyrrolo[2,3-d]pyrimidin-6-yl)phenyl)morpholine (43 mgs, 0.095 mmol) and 2-((tetrahydro-2H-pyran-4-yl)oxy)-5-(4,4,5,5-tetramethyl-1,3,2-dioxaborolan-2-yl)benzonitrile (34 mgs, 0.5 mmol) in DME (2 mL) was 2.0 M aq $Na_2CO_3$ (0.1 mL, 0.2 mmol) and Pd(PPh$_3$)$_4$ (5 mgs, 0.005 mmol). The reaction mixture was heated at 140° C. for 1 hr. The mixture was then concentrated and used for next step without purification. LCMS-ESI+ (m/z): [M+H]+ calcd for $C_{34}H_{31}ClN_5O_5S$: 622.7. found: 622.2.

Step 3: A solution of 6-(4-((1H-imidazol-1-yl)methyl)phenyl)-4-chloro-7-((2-(trimethylsilyl)ethoxy)methyl)-7H-pyrrolo[2,3-d]pyrimidine (49 mgs, 0.08 mmol) in TFA (1.5 mL) and DCM (1.5 mL) was stirred at room temperature for 1.5 hours. The volatiles were removed under reduce pressure. The residue was dissolved in MeOH (2 mL) and treated with ethane-1,2-diamine (0.3 mL) at room temperature overnight. The volatiles were then removed under reduced pressure and the solids formed were treated with acetonitrile/water, stirred at rt for 15 min, filtered and washed with acetonitrile to give the title compound. LCMS-ESI+ (m/z): [M+H]+ calcd for $C_{28}H_{24}N_6O_2$ as (M+H)+ 477.5 found: 477.1; $^1$H NMR (400 MHz, DMSO-d$_6$) δ 12.81 (s, 1H), 8.82 (s, 1H), 8.56-8.45 (m, 2H), 8.17-7.92 (m, 2H), 7.80 (s, 1H), 7.62-7.37 (m, 3H), 7.31-7.16 (m, 2H), 6.91 (s, 1H), 5.25 (s, 2H), 4.96 (dq, J=7.8, 4.0 Hz, 1H), 3.88 (m, 2H), 3.56 (m, 2H), 2.06 (d, J=13.1 Hz, 2H), 1.71 (dtd, J=12.4, 8.1, 3.8 Hz, 2H).

Example 115: 5-(6-(4-morpholinophenyl)-7H-pyrrolo[2,3-d]pyrimidin-4-yl)-2-((2-oxopyrrolidin-1-yl)methyl)benzonitrile

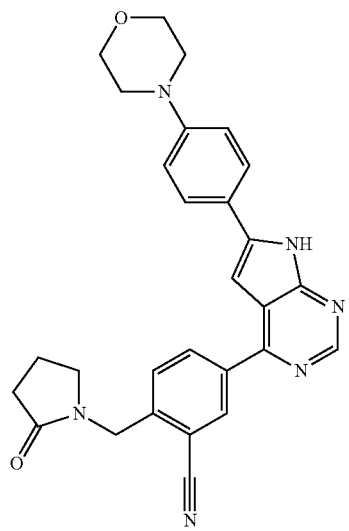 [SMILES: N#Cc1cc(-c2ncnc3[nH]c(-c4ccc(N5CCOCC5)cc4)cc23)ccc1CN1CCCC1=O]

Step 1: Sodium hydride (176 mgs, 4.41 mmol) was added to pyrrolidin-2-one (0.31 mL, 4.0 mmol) in DMF (10 mL) at 0° C. under nitrogen. The resulting solution was stirred at rt for 30 minutes and cooled again to 0° C. 5-bromo-2-(chloromethyl)benzonitrile (921 mgs, 4.00 mmol) was added and the reaction stirred at 20° C. for 2 hours. The residue was poured onto ice/water and extracted into ethyl acetate and the combined organics washed with saturated brine (100 mL), dried over Na2SO4, filtered and evaporated to give crude product. The crude product was purified by flash silica chromatography (30% EtOAc in hexanes). Pure fractions were evaporated to dryness to give 5-chloro-2-((2-oxopyrrolidin-1-yl)methyl)benzonitrile. LCMS-ESI+ (m/z): [M+H]+ calcd for $C_{12}H_{11}ClN_2O$ as (M+H)+ 235.7. found: 235.2.

Step 2: A solution of 5-chloro-2-((2-oxopyrrolidin-1-yl)methyl)benzonitrile (154 mg, 0.66 mmol), Pd$_2$(dba) (23 mg, 0.04 mmol), PCy$_3$ (44 mg, 0.16 mmol), diboron pinacol ester (200 mgs, 0.79 mmol) and KOAc (194 mgs, 1.97 mmol) in 3 mL dioxane was heated in microwave at 150° C. for 15 minutes. The resulting mixture was diluted with DCM, filtered vis a celite pad and concentrated to give 2-((2-oxopyrrolidin-1-yl)methyl)-5-(4,4,5,5-tetramethyl-1,3,2-dioxaborolan-2-yl)benzonitrile which was used further without purification.

Step 3: To a mixture of 4-(4-(4-chloro-7H-pyrrolo[2,3-d]pyrimidin-6-yl)phenyl)morpholine (50 mgs, 0.16 mmol) and 2-((2-oxopyrrolidin-1-yl)methyl)-5-(4,4,5,5-tetramethyl-1,3,2-dioxaborolan-2-yl)benzonitrile (83 mgs, 0.25 mmol) in DMF (1 mL) was added 2.0 M aq $Na_2CO_3$ (0.2 mL, 0.4 mmol) and PdCl$_2$(dppf) catalyst (7 mgs, 0.01 mmol). The reaction mixture was heated to 125° C. for 30 min in microwave. Acetonitrile/Water (1:1, 5 mL) was added and the solids formed were filtered and washed with acetonitrile and methanol to give the title compound. LCMS-ESI$^+$ (m/z): [M+H]$^+$ calcd for C$_{28}$H$_{26}$N$_6$O$_2$ as (M+H)$^+$ 479.6. found: 479.2.

Example 116: 5-(2-(morpholine-4-carbonyl)-1H-pyrrolo[2,3-b]pyridin-4-yl)-2-((tetrahydro-2H-pyran-4-yl)oxy)benzonitrile

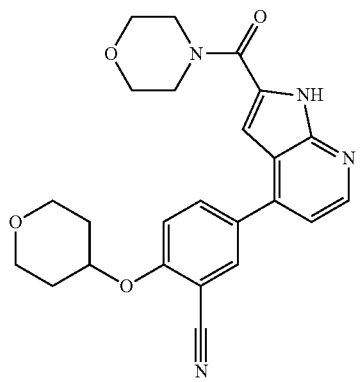 [SMILES: N#Cc1cc(-c2ccnc3[nH]c(C(=O)N4CCOCC4)cc23)ccc1OC1CCOCC1]

To a mixture of 4-(3-cyano-4-((tetrahydro-2H-pyran-4-yl)oxy)phenyl)-1H-pyrrolo[2,3-b]pyridine-2-carboxylic acid (22 mgs, 0.083 mmol), morpholine (0.012 mL, 0.121 mmol) and HATU (35 mgs, 0.132 mmol) in DMF (1 mL) was added DIPEA (0.03 mL, 0.18 mmol) and the resulting solution was stirred at 50° C. for 48 hr. The crude mixture was concentrated and purified by reverse phase chromatography to give the title compound as TFA salt. LCMS-ESI$^+$ (m/z): [M+H]$^+$ calcd for C$_{24}$H$_{24}$N$_4$O$_4$ as (M+H)$^+$ 433.5. found: 433.1.

Example 117: 5-(2-(pyrrolidine-1-carbonyl)-1H-pyrrolo[2,3-b]pyridin-4-yl)-2-((tetrahydro-2H-pyran-4-yl)oxy)benzonitrile

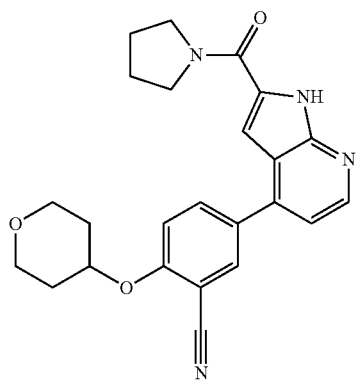 [SMILES: N#Cc1cc(-c2ccnc3[nH]c(C(=O)N4CCCC4)cc23)ccc1OC1CCOCC1]

To a mixture of 4-(3-cyano-4-((tetrahydro-2H-pyran-4-yl)oxy)phenyl)-1H-pyrrolo[2,3-b]pyridine-2-carboxylic acid (22 mgs, 0.083 mmol), pyrrolidine (0.01 mL, 0.121 mmol) and HATU (35 mgs, 0.132 mmol) in DMF (1 mL) was added DIPEA (0.03 mL, 0.18 mmol) and the resulting solution was stirred at 50° C. for 48 hr. The crude mixture was concentrated and purified by reverse phase chromatography to give the title compound as TFA salt. LCMS-ESI$^+$ (m/z): [M+H]$^+$ calcd for C$_{24}$H$_{24}$N$_4$O$_3$ as (M+H)$^+$ 417.5. found: 417.1.

Example 118: 5-(2-(4-methylpiperazine-1-carbonyl)-1H-pyrrolo[2,3-b]pyridin-4-yl)-2-((tetrahydro-2H-pyran-4-yl)oxy)benzonitrile

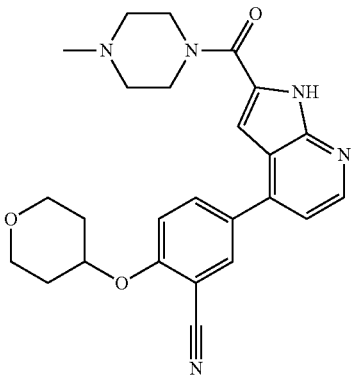 [SMILES: CN1CCN(C(=O)c2cc3c(-c4ccc(OC5CCOCC5)c(C#N)c4)ccnc3[nH]2)CC1]

To a mixture of 4-(3-cyano-4-((tetrahydro-2H-pyran-4-yl)oxy)phenyl)-1H-pyrrolo[2,3-b]pyridine-2-carboxylic acid (22 mgs, 0.083 mmol), N-methylpiperazine (0.006 mL, 0.121 mmol) and HATU (35 mgs, 0.132 mmol) in DMF (1 mL) was added DIPEA (0.03 mL, 0.18 mmol) and the resulting solution was stirred at 50° C. for 48 hr. The crude mixture was concentrated and purified by reverse phase chromatography to give the title compound as TFA salt. LCMS-ESI$^+$ (m/z): [M+H]$^+$ calcd for C$_{25}$H$_{27}$N$_5$O$_3$ as (M+H)$^+$ 446.5. found: 446.1.

Example 119: 5-(6-(3-((1H-imidazol-1-yl)methyl)phenyl)-7H-pyrrolo[2,3-d]pyrimidin-4-yl)-2-((tetrahydro-2H-pyran-4-yl)oxy)benzonitrile

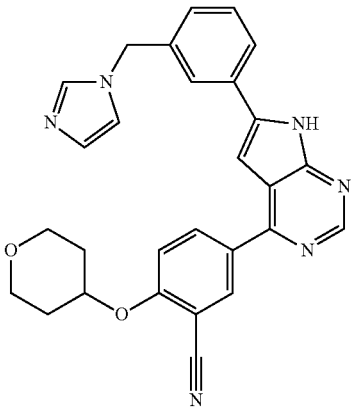 [SMILES: N#Cc1cc(-c2ncnc3[nH]c(-c4cccc(Cn5ccnc5)c4)cc23)ccc1OC1CCOCC1]

The title compound was prepared in similar manner to Example 114 using (3-((1H-imidazol-1-yl)methyl)phenyl) boronic acid instead of 1-(4-(4,4,5,5-tetramethyl-1,3,2-dioxaborolan-2-yl)benzyl)-1H-imidazole. LCMS-ESI$^+$ (m/z): [M+H]$^+$ calcd for C$_{28}$H$_{24}$N$_6$O$_2$ as (M+H)$^+$ 477.5. found: 477.1; $^1$H NMR (400 MHz, DMSO-d$_6$) δ 8.80 (s, 1H), 8.53 (m, 2H), 8.15-7.95 (m, 2H), 7.78 (d, J=1.1 Hz, 1H), 7.60-7.49 (m, 2H), 7.37 (d, J=8.2 Hz, 2H), 7.22 (t, J=1.3 Hz, 1H), 6.91 (s, 1H), 5.24 (s, 2H), 4.96 (dq, J=7.9, 3.9 Hz, 1H), 3.93-3.77 (m, 2H), 3.56 (ddd, J=11.5, 8.3, 3.2 Hz, 2H), 2.05 (d, J=12.4 Hz, 2H), 1.71 (dtd, J=12.3, 8.1, 3.9 Hz, 2H).

Example 120: 5-(6-(2-methyl-4-morpholinophenyl)-7H-pyrrolo[2,3-d]pyrimidin-4-yl)-2-(piperidin-4-yloxy)benzonitrile

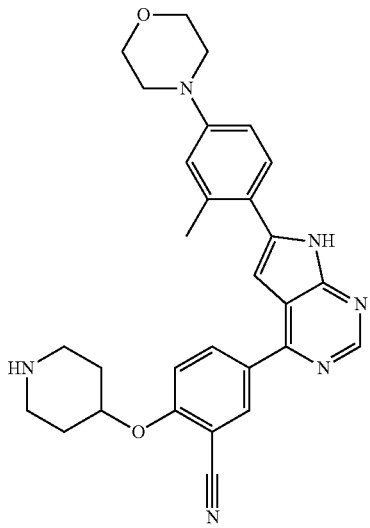 [SMILES: Cc1cc(N2CCOCC2)ccc1-c1cc2c(-c3ccc(OC4CCNCC4)c(C#N)c3)ncnc2[nH]1]

Step 1: To a mixture 4-chloro-6-iodo-7-((2-(trimethylsilyl)ethoxy)methyl)-7H-pyrrolo[2,3-d]pyrimidine (75 mgs, 0.18 mmol) and 4-(3-methyl-4-(4,4,5,5-tetramethyl-1,3,2-dioxaborolan-2-yl)phenyl)morpholine (61 mgs, 0.20 mmol), in DME (3 mL) was added 2.0 M aq $Na_2CO_3$ (0.25 mL, 0.5 mmol), $Pd(PPh_3)_4$ catalyst (11 mgs, 0.009 mmol) and potassium acetate (35 mgs, 0.36 mmol). The reaction mixture was heated at 100° C. for 3 hr. Cooled to rt and to the mixture was added (4-((1-(tert-butoxycarbonyl)piperidin-4-yl)oxy)-3-cyanophenyl)boronic acid (73 mgs, 0.2 mmol), 2.0 M aq $Na_2CO_3$ (0.2 mL, 0.37 mmol) and $Pd(PPh_3)_4$ (21 mgs, 0.018 mmol) and the reaction mixture was further heated at 100° C. for 16 hr. The mixture was then concentrated and purified by flash chromatography (40% Ethyl acetate/hexanes) to give tert-butyl 4-(2-cyano-4-(6-(2-methyl-4-morpholinophenyl)-7-((2-(trimethylsilyl)ethoxy)methyl)-7H-pyrrolo[2,3-d]pyrimidin-4-yl)phenoxy)piperidine-1-carboxylate. LCMS-ESI$^+$ (m/z): [M+H]$^+$ calcd for $C_{40}H_{52}N_6O_5Si$: 725.9. found: 725.3.

Step 2: To a solution of tert-butyl 4-(2-cyano-4-(6-(2-methyl-4-morpholinophenyl)-7-((2-(trimethylsilyl)ethoxy)methyl)-7H-pyrrolo[2,3-d]pyrimidin-4-yl)phenoxy)piperidine-1-carboxylate (116 mgs, 0.160 mmol) in DCM (1.5 mL) was added TFA (1.5 mL) and stirred at room temperature for 1 h. The volatiles were removed under reduce pressure and azeotrope three times with acetonitrile. The residue was dissolved in MeOH (2 mL) and treated with ethane-1,2-diamine (0.5 mL) at room temperature for 2 h. The mixture was then diluted with acetonitrile/water, stirred at rt for 15 min and the resulting solids were filtered and washed with water, acetonitrile, hexanes and ether to give the title compound. LCMS-ESI$^+$ (m/z): [M+H]$^+$ calcd for $C_{29}H_{30}N_6O_2$ as (M+H)$^+$ 495.6. found: 495.2.

Example 121: 2-((1-(2-hydroxyacetyl)piperidin-4-yl)oxy)-5-(6-(2-methyl-4-morpholinophenyl)-7H-pyrrolo[2,3-d]pyrimidin-4-yl)benzonitrile

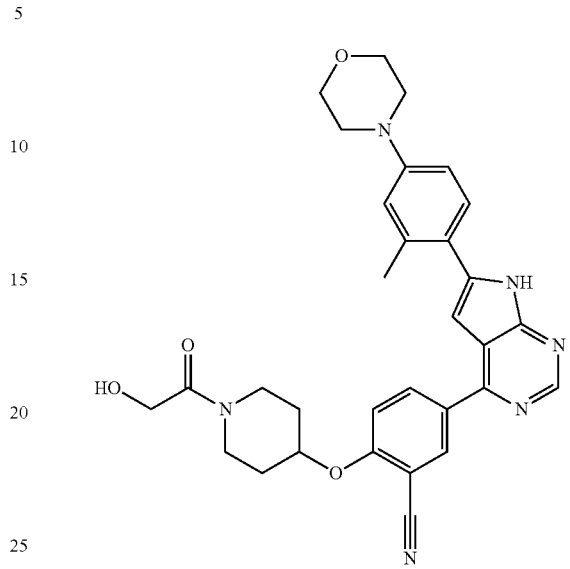

To a mixture of 5-(6-(2-methyl-4-morpholinophenyl)-7H-pyrrolo[2,3-d]pyrimidin-4-yl)-2-(piperidin-4-yloxy)benzonitrile (25 mgs, 0.051 mmol), glycolic acid (5 mgs, 0.06 mmol) and HATU (28 mgs, 0.07 mmol) in DMF (0.5 mL) was added DIPEA (0.03 mL, 0.15 mmol) and the resulting solution was stirred at rt for 2 hrs. The crude mixture was concentrated and purified by reverse phase chromatography to give the title compound as TFA salt. LCMS-ESI$^+$ (m/z): [M+H]$^+$ calcd for $C_{31}H_{32}N_6O_4$ as (M+H)$^+$ 553.6. found: 553.2; $^1$H NMR (400 MHz, DMSO-d$_6$) δ 12.45 (s, 1H), 8.81 (s, 1H), 8.48 (m, 2H), 7.57-7.47 (m, 2H), 6.99-6.81 (m, 3H), 5.00 (m, 1H), 4.12 (s, 2H), 3.92-3.63 (m, 8H), 3.20-3.17 (m, 4H), 2.45 (s, 3H), 2.10-1.90 (m, 2H), 1.80-1.65 (m, 2H).

Example 122: 5-(6-(3-methoxy-4-morpholinophenyl)-7H-pyrrolo[2,3-d]pyrimidin-4-yl)-2-(piperidin-4-yloxy)benzonitrile

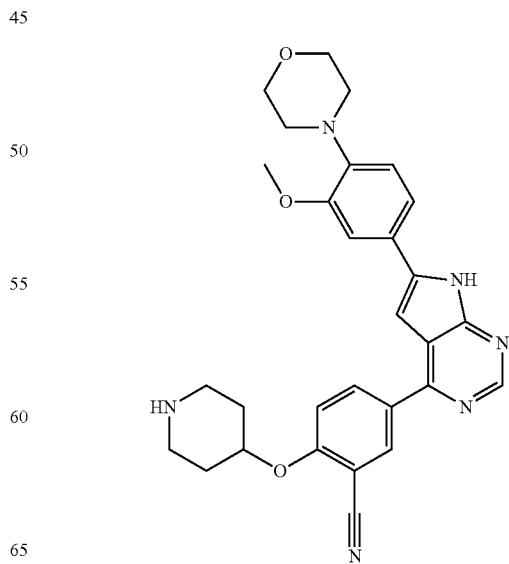

The title compound was prepared in similar manner to Example 120 using 4-(2-methoxy-4-(4,4,5,5-tetramethyl-1,3,2-dioxaborolan-2-yl)phenyl)morpholine instead of 4-(3-methyl-4-(4,4,5,5-tetramethyl-1,3,2-dioxaborolan-2-yl)phenyl)morpholine. LCMS-ESI⁺ (m/z): [M+H]⁺ calcd for $C_{29}H_{30}N_6O_3$ as (M+H)⁺ 511.6. found: 511.2.

Example 123: 5-(6-(4-methoxyphenyl)-7H-pyrrolo[2,3-d]pyrimidin-4-yl)-2-(piperidin-4-yloxy)benzonitrile

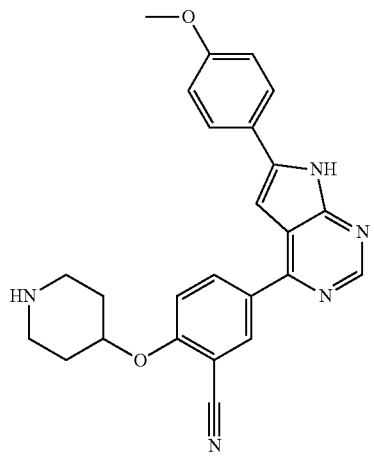 [SMILES: COc1ccc(-c2cc3c(-c4ccc(OC5CCNCC5)c(C#N)c4)ncnc3[nH]2)cc1]

The title compound was prepared in similar manner to Example 120 using (4-methoxyphenyl)boronic acid instead of 4-(3-methyl-4-(4,4,5,5-tetramethyl-1,3,2-dioxaborolan-2-yl)phenyl)morpholine. LCMS-ESI⁺ (m/z): [M+H]⁺ calcd for $C_{25}H_{23}N_5O_2$ as (M+H)+426.5. found: 426.2.

Example 124: 5-(2-(2-methyl-4-morpholinophenyl)-1H-pyrrolo[2,3-b]pyridin-4-yl)-2-((tetrahydro-2H-pyran-4-yl)oxy)benzonitrile

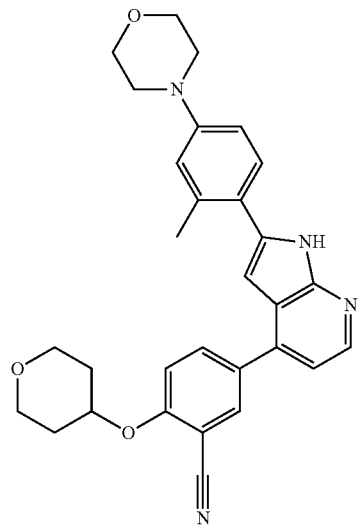 [SMILES: Cc1cc(N2CCOCC2)ccc1-c1cc2c(-c3ccc(OC4CCOCC4)c(C#N)c3)ccnc2[nH]1]

Step 1: To a solution of 5-(2-iodo-1-(phenylsulfonyl)-1H-pyrrolo[2,3-b]pyridin-4-yl)-2-((tetrahydro-2H-pyran-4-yl)oxy)benzonitrile (57 mgs, 0.097 mmol) and 4-(3-methyl-4-(4,4,5,5-tetramethyl-1,3,2-dioxaborolan-2-yl)phenyl)morpholine (35 mgs, 0.12 mmol) in DME (2 mL), was added 2.0 M aq $Na_2CO_3$ (0.2 mL, 0.4 mmol), KOAc (29 mgs, 0.029 mmol) and Pd(PPh₃)₄ (6 mgs, 0.006 mmol) and the reaction mixture was heated at 120° C. for 3 hrs. The mixture was then cooled to rt and purified by flash chromatography (50-100% Ethyl acetate/hexanes) to give 5-(2-(2-methyl-4-morpholinophenyl)-1-(phenylsulfonyl)-1H-pyrrolo[2,3-b]pyridin-4-yl)-2-((tetrahydro-2H-pyran-4-yl)oxy)benzonitrile. LCMS-ESI⁺ (m/z): [M+H]⁺ calcd for $C_{36}H_{34}O_5SN_4$: 635.7. found: 635.2.

Step 2: To 5-(2-(2-methyl-4-morpholinophenyl)-1-(phenylsulfonyl)-1H-pyrrolo[2,3-b]pyridin-4-yl)-2-((tetrahydro-2H-pyran-4-yl)oxy)benzonitrile (43 mgs, 0.068 mmol) in THF/2,2,2,-Trifluoroethanol (1:1, 3 mL) was added $Cs_2CO_3$ (211 mg, 0.65 mmol) was the reaction mixture was heated at 100 C for 16 hrs. The mixture was then concentrated and purified by reverse phase chromatography to give the title compound as TFA salt which was then treated with $NaHCO_3$ and extracted with DCM and dried give the free base. LCMS-ESI⁺ (m/z): [M+H]⁺ calcd for $C_{30}H_{30}N_4O_3$ as (M+H)⁺ 495.6. found: 495.2; ¹H NMR (400 MHz, DMSO-d₆) δ 11.90 (s, 1H), 8.22 (d, J=4.9 Hz, 1H), 8.15-7.97 (m, 2H), 7.48 (dd, J=26.3, 8.7 Hz, 2H), 7.19 (d, J=5.0 Hz, 1H), 7.01-6.78 (m, 2H), 6.61 (d, J=1.9 Hz, 1H), 4.90 (dd, J=8.2, 4.2 Hz, 1H), 3.87 (dt, J=10.5, 4.6 Hz, 2H), 3.74 (t, J=4.8 Hz, 4H), 3.59-3.46 (m, 2H), 3.16 (t, J=4.8 Hz, 4H), 2.43 (s, 3H), 2.04 (d, J=14.1 Hz, 2H), 1.70 (ddd, J=12.9, 8.4, 4.0 Hz, 2H).

Example 125: 2-((1-(2-hydroxyacetyl)piperidin-4-yl)oxy)-5-(6-(3-methoxy-4-morpholinophenyl)-7H-pyrrolo[2,3-d]pyrimidin-4-yl)benzonitrile

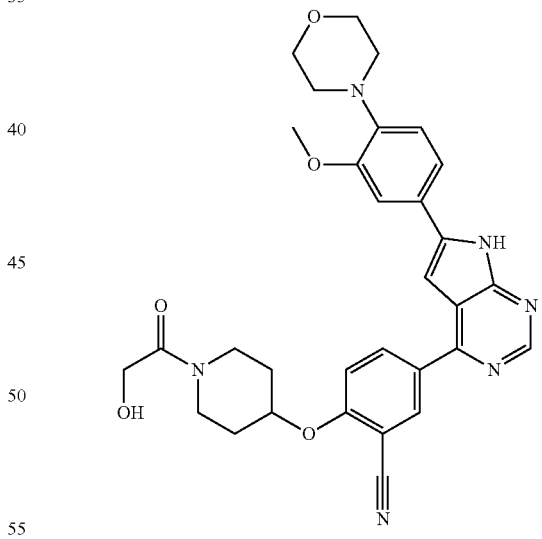

To a solution of 5-(6-(3-methoxy-4-morpholinophenyl)-7H-pyrrolo[2,3-d]pyrimidin-4-yl)-2-(piperidin-4-yloxy)benzonitrile (25 mgs, 0.051 mmol), glycolic acid (5 mgs, 0.06 mmol) and HATU (24 mgs, 0.06 mmol) in DMF (0.5 mL) was added DIPEA (0.03 mL, 0.15 mmol) and the resulting solution was stirred at rt for 2 hrs. The crude mixture was concentrated and purified by reverse phase chromatography to give the title compound as TFA salt which was then treated with $NaHCO_3$ and extracted with DCM and dried give the free base. LCMS-ESI⁺ (m/z): [M+H]⁺ calcd for $C_{31}H_{32}N_6O_5$ as (M+H)⁺ 569.6 found:

569.2; ¹H NMR (400 MHz, DMSO-d₆) δ 12.68 (s, 1H), 8.77 (s, 1H), 8.54-8.52 (m, 2H), 7.71-7.52 (m, 3H), 7.41 (d, J=1.9 Hz, 1H), 6.97 (d, J=8.1 Hz, 1H), 5.05-4.98 (m, 1H), 4.12 (d, J=5.6 Hz, 2H), 3.91 (s, 3H), 3.73 (m, 4H), 3.56-3.45 (m, 4H), 3.08-3.00 (m, 4H), 2.05-1.95 (m, 2H), 1.80-1.75 (m, 2H).

Example 126: 2-((1-(2-hydroxyacetyl)piperidin-4-yl)oxy)-5-(6-(4-methoxyphenyl)-7H-pyrrolo[2,3-d]pyrimidin-4-yl)benzonitrile

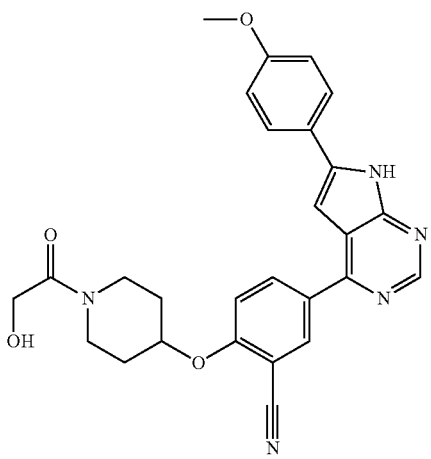 [SMILES: COc1ccc(-c2cc3c(-c4ccc(OC5CCN(C(=O)CO)CC5)c(C#N)c4)ncnc3[nH]2)cc1]

To a solution of 5-(6-(4-methoxyphenyl)-7H-pyrrolo[2,3-d]pyrimidin-4-yl)-2-(piperidin-4-yloxy)benzonitrile (27 mgs, 0.063 mmol), glycolic acid (6 mgs, 0.08 mmol) and HATU (30 mgs, 0.08 mmol) in DMF (0.5 mL) was added DIPEA (0.03 mL, 0.15 mmol) and the resulting solution was stirred at rt for 2 hrs. The crude mixture was concentrated and purified by reverse phase chromatography to give the title compound as TFA salt which was then treated with NaHCO₃ and extracted with DCM and dried give the free base. LCMS-ESI⁺ (m/z): [M+H]⁺ calcd for C₂₇H₂₅N₅O₄ as (M+H)⁺ 484.5. found: 484.1; ¹H NMR (400 MHz, DMSO-d₆) δ 12.65 (s, 1H), 8.77 (s, 1H), 8.55-8.53 (m, 2H), 8.02 (m, 2H), 7.56 (d, J=8.8 Hz, 1H), 7.39 (s, 1H), 7.07-7.05 (m, 2H), 5.05-4.98 (m, 1H), 4.58 (m, 1H), 4.1.3 (d, J=5.6 Hz, 2H), 4.11 (s, 3H), 3.73 (m, 2H), 3.56-3.45 (m, 2H), 2.05-1.97 (m, 2H), 1.82-1.77 (m, 2H).

Example 127: 5-(6-(4-chlorophenyl)-7H-pyrrolo[2,3-d]pyrimidin-4-yl)-2-((1-(2-hydroxyacetyl)piperidin-4-yl)oxy)benzonitrile

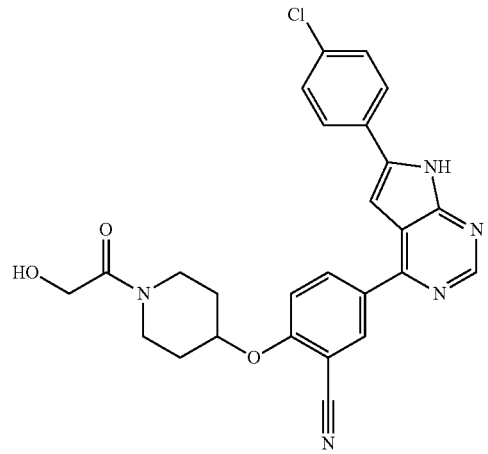 [SMILES: N#Cc1cc(-c2ncnc3[nH]c(-c4ccc(Cl)cc4)cc23)ccc1OC1CCN(C(=O)CO)CC1]

The title compound was prepared in similar manner to Example 120 and Example 126 using (4-Chlorophenyl)boronic acid. LCMS-ESI⁺ (m/z): [M+H]⁺ calcd for C₂₆H₂₂ClN₅O₃ as (M+H)⁺ 488.5. found: 488.1; ¹H NMR (400 MHz, DMSO-d₆) δ 12.88 (s, 1H), 8.82 (s, 1H), 8.56-8.54 (m, 2H), 8.11 (d, J=8.4 Hz, 2H), 7.59-7.54 (m, 4H), 5.05-4.99 (m, 1H), 4.12 (s, 2H), 3.77-3.70 (m, 2H), 3.45-3.35 (m, 2H), 2.05-1.97 (m, 2H), 1.79-1.65 (m, 2H).

Example 128: 2-((1-(2-hydroxyacetyl)piperidin-4-yl)oxy)-5-(6-(4-(trifluoromethoxy)phenyl)-7H-pyrrolo[2,3-d]pyrimidin-4-yl)benzonitrile

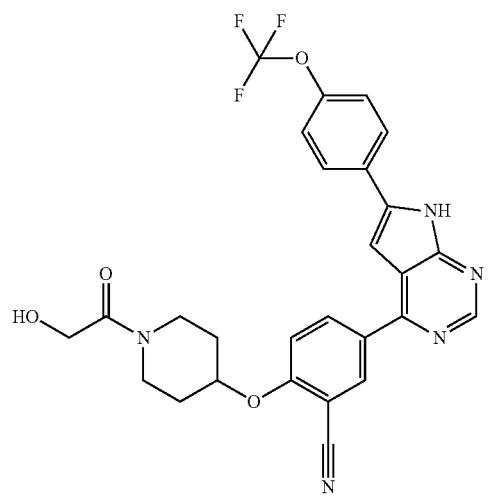 [SMILES: N#Cc1cc(-c2ncnc3[nH]c(-c4ccc(OC(F)(F)F)cc4)cc23)ccc1OC1CCN(C(=O)CO)CC1]

The title compound was prepared in similar manner to Example 120 and Example 126 using (4-trifluoromethoxyphenyl)boronic acid. LCMS-ESI⁺ (m/z): [M+H]⁺ calcd for C₂₇H₂₂F₃N₅O₄ as (M+H)⁺ 538.5. found: 538.2; ¹H NMR (400 MHz, DMSO-d₆) δ 12.89 (s, 1H), 8.84 (s, 1H), 8.56-8.54 (m, 2H), 8.20 (d, J=8.8 Hz, 2H), 7.60-7.51 (m, 4H), 5.07-5.01 (m, 1H), 4.12 (s, 2H), 3.73 (m, 2H), 3.54 (m, 2H), 2.05-2.00 (m, 2H), 1.80-1.70 (m, 2H).

Example 129: 5-(6-(6-(2-hydroxypropan-2-yl)pyridin-3-yl)-7H-pyrrolo[2,3-d]pyrimidin-4-yl)-2-((tetrahydro-2H-pyran-4-yl)oxy)benzonitrile

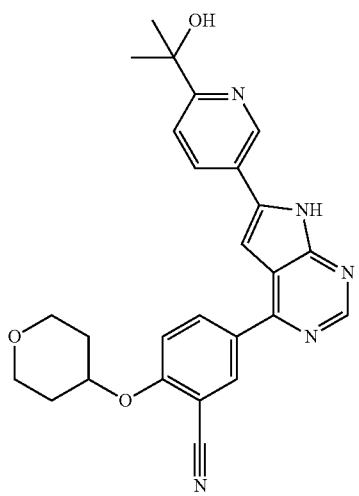 [SMILES: CC(C)(O)c1ccc(-c2cc3c(-c4ccc(OC5CCOCC5)c(C#N)c4)ncnc3[nH]2)cn1]

The title compound was prepared in similar manner to Example 114 using 2-(5-(4,4,5,5-tetramethyl-1,3,2-dioxaborolan-2-yl)pyridin-2-yl)propan-2-ol. LCMS-ESI+ (m/z): [M+H]+ calcd for $C_{26}H_{25}N_5O_3$ as (M+H)+ 456.5. found: 456.1; $^1$H NMR (400 MHz, DMSO-d$_6$) δ 12.96 (s, 1H), 9.13 (dd, J=2.4, 0.8 Hz, 1H), 8.82 (s, 1H), 8.48 (tt, J=6.0, 2.9 Hz, 3H), 7.80 (d, J=8.4 Hz, 1H), 7.64 (d, J=1.9 Hz, 1H), 7.52 (d, J=9.7 Hz, 1H), 4.93 (m, 1H), 3.83 (m, 2H), 3.52 (m, 3H), 2.07-1.90 (m, 2H), 1.66 (m, 2H), 1.44 (s, 6H).

Example 130: 2-((1-(2-hydroxyacetyl)piperidin-4-yl)oxy)-5-(6-(6-methoxypyridin-3-yl)-7H-pyrrolo[2,3-d]pyrimidin-4-yl)benzonitrile

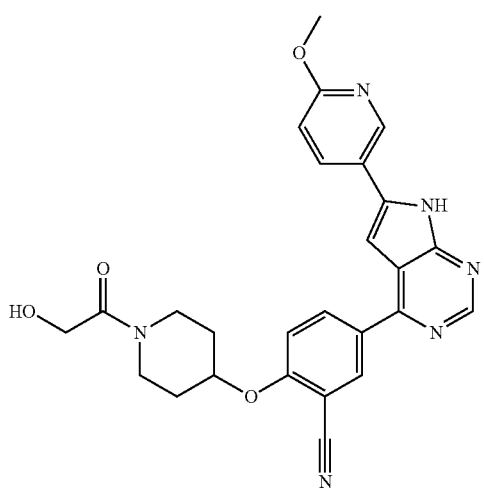 [SMILES: COc1ccc(-c2cc3c(-c4ccc(OC5CCN(C(=O)CO)CC5)c(C#N)c4)ncnc3[nH]2)cn1]

The title compound was prepared in similar manner to Example 114 and Example 126 using (6-methoxypyridin-3-yl)boronic acid. LCMS-ESI+ (m/z): [M+H]+ calcd for $C_{26}H_{24}N_6O_4$ as (M+H)+ 485.5. found: 485.1; $^1$H NMR (400 MHz, DMSO-d$_6$) δ 12.85 (s, 1H), 8.88-8.82 (m, 2H), 8.56-8.52 (m, 2H), 8.39-8.36 (m, 1H), 7.57-7.53 (m, 2H), 6.98 (d, J=8.0 Hz, 1H), 5.07-5.01 (m, 1H), 4.12 (s, 2H), 3.91 (s, 3H), 3.73 (m, 2H), 3.39 (m, 2H), 2.02-1.97 (m, 2H), 1.77-1.70 (m, 2H).

Example 131: 2-((1-(2-hydroxyacetyl)piperidin-4-yl)oxy)-5-(6-(4-methoxy-2-methylphenyl)-7H-pyrrolo[2,3-d]pyrimidin-4-yl)benzonitrile

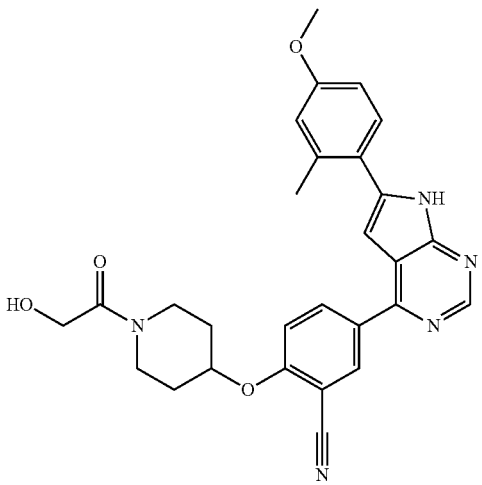 [SMILES: COc1ccc(-c2cc3c(-c4ccc(OC5CCN(C(=O)CO)CC5)c(C#N)c4)ncnc3[nH]2)c(C)c1]

The title compound was prepared in similar manner to Example 120 and Example 126 using (4-methoxy-2-methylphenyl)boronic acid. LCMS-ESI+ (m/z): [M+H]+ calcd for $C_{28}H_{27}N_5O_4$ as (M+H)+ 498.5. found: 498.1; $^1$H NMR (400 MHz, DMSO-d$_6$) δ 12.55 (s, 1H), 8.84 (s, 1H), 8.60-8.37 (m, 2H), 7.54 (dd, J=17.3, 9.1 Hz, 2H), 7.05-6.81 (m, 3H), 5.01 (dt, J=7.4, 3.8 Hz, 1H), 4.12 (s, 2H), 3.95 (s, 1H), 3.80 (s, 3H), 3.52 (m, 4H), 2.45 (s, 3H), 2.00 (s, 2H), 1.73 (d, J=29.7 Hz, 2H).

Example 132: 2-((1-(2-hydroxyacetyl)piperidin-4-yl)oxy)-5-(6-(6-(2-hydroxypropan-2-yl)pyridin-3-yl)-7H-pyrrolo[2,3-d]pyrimidin-4-yl)benzonitrile

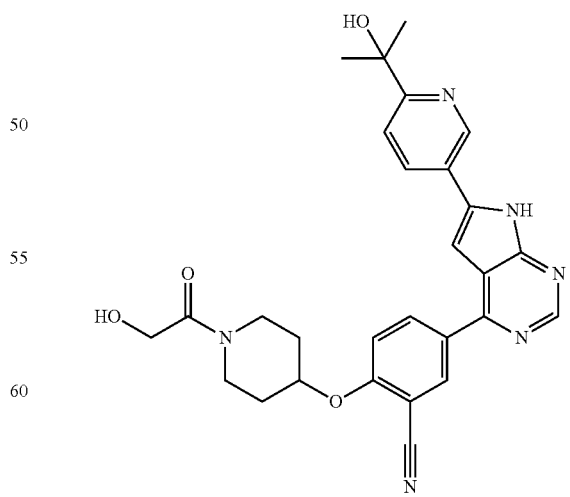

The title compound was prepared in similar manner to Example 120 and Example 126 using (6-methoxypyridin- 3-yl)boronic acid. LCMS-ESI⁺ (m/z): [M+H]⁺ calcd for C$_{28}$H$_{28}$N$_6$O$_4$ as (M+H)⁺ 513.6. found: 513.1; ¹H NMR (400 MHz, DMSO-d$_6$) δ 13.11 (s, 1H), 9.21 (s, 1H), 8.88 (s, 1H), 8.75-8.41 (m, 3H), 7.92 (m, 1H), 7.75 (m, 1H), 7.60 (d, J=9.1 Hz, 1H), 5.05 (m, 1H), 4.13 (s, 2H), 3.82-3.24 (m, 5H), 2.01 (s, 2H), 1.74 (m, 2H), 1.51 (d, J=2.0 Hz, 6H).

Example 133: 4-methoxy-3-(6-(4-morpholinophenyl)-7H-pyrrolo[2,3-d]pyrimidin-4-yl)benzonitrile

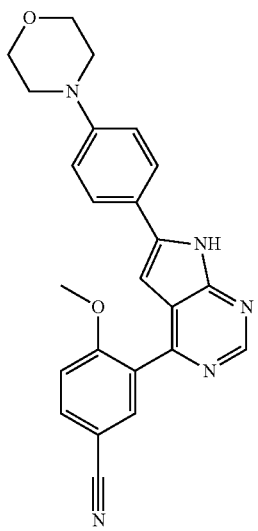 [SMILES: COc1ccc(C#N)cc1-c1ncnc2[nH]c(-c3ccc(N4CCOCC4)cc3)cc12]

To a mixture of 4-(4-(4-chloro-7H-pyrrolo[2,3-d]pyrimidin-6-yl)phenyl)morpholine (50 mgs, 0.16 mmol) and (5-cyano-2-methoxyphenyl)boronic acid (31 mgs, 0.18 mmol) in DMF (1 mL) was added 2.0 M aq Na$_2$CO$_3$ (0.17 mL, 0.3 mmol) and PdCl$_2$dppf catalyst (6 mgs, 0.01 mmol). The reaction mixture was heated to 125° C. for 30 min in heating clock. Acetonitrile/Water (1:1, 5 mL) was added and the solids formed were filtered and washed with acetonitrile, methanol and ether and dried to give the title compound. LCMS-ESI⁺ (m/z): [M+H]⁺ calcd for C$_{24}$H$_{21}$N$_5$O$_2$ as (M+H)⁺ 412.6. found: 412.1.

Example 134: 5-(6-(4-(4-(2-hydroxyacetyl)piperazin-1-yl)-3-methoxyphenyl)-7H-pyrrolo[2,3-d]pyrimidin-4-yl)-2-((tetrahydro-2H-pyran-4-yl)oxy)benzonitrile

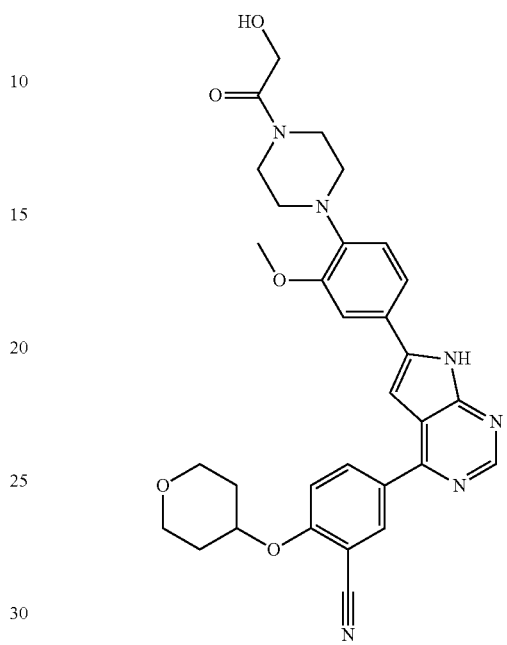

Step 1: 5-Bromo-2-Iodoanisole (4 g, 14.09 mmol), Boc-Piperazine (2.5 g, 13.42 mmol), Pd$_2$(dba)$_3$ (368 mg, 0.4 mmol), XantPhos (699 mg, 1.21 mmol), Sodium t-butoxide (3.8 g, 40.27 mmol) were combined in toluene (36 mL), heated to 60° C. for 3 h. The reaction was diluted with water, extracted with EtOAc, dried (MgSO$_4$), filtered and concentrated. The crude product was purified by flash silica chromatography (10% MeOH in DCM). Pure fractions were evaporated to dryness to give tert-butyl 4-(4-bromo-2-methoxyphenyl)piperazine-1-carboxylate]

Step 2: tert-butyl 4-(4-bromo-2-methoxyphenyl)piperazine-1-carboxylate (1.3 g, 3.4 mmol), Bis (Pinacolato) Diboron (1.5 g, 5.78 mmol), POTASSIUM ACETATE (1.5 g, 15.3 mmol), Dichloro 1,1'-bis(diphenylphosphino)ferrocene palladium (II) dichloromethane (140 mg, 0.17 mmol) were combined in dioxane (30 mL), flushed with N2 and stirred at 110° C. for 3 h. The reaction was diluted with EtOAC, filtered over celite, washed with EtOAc and concentrated. The crude material was purified by Silica gel column chromatography (5-50% EtOAc:Hexanes) to give tert-butyl 4-(2-methoxy-4-(4,4,5,5-tetramethyl-1,3,2-dioxaborolan-2-yl)phenyl)piperazine-1-carboxylate Step 3: To a mixture of 4-chloro-6-iodo-7-((2-(trimethylsilyl)ethoxy)methyl)-7H-pyrrolo[2,3-d]pyrimidine (88 mgs, 0.22 mmol) and tert-butyl 4-(2-methoxy-4-(4,4,5,5-tetramethyl-1,3,2-dioxaborolan-2-yl)phenyl)piperazine-1-carboxylate (90 mgs, 0.22 mmol), in DME (3 mL) was added 2.0 M aq Na$_2$CO$_3$ (0.3 mL, 0.5 mmol) and Pd(PPh$_3$)$_4$ catalyst (14 mgs, 0.012 mmol). The reaction mixture was heated at 115° C. for 4 hrs. Cooled to rt and to the mixture was added 2-((tetrahydro-2H-pyran-4-yl)oxy)-5-(4,4,5,5-tetramethyl-1,3,2-dioxaborolan-2-yl)benzonitrile (84 mgs, 0.26 mmol), 2.0 M aq Na$_2$CO$_3$ (0.2 mL, 0.37 mmol) and Pd(PPh$_3$)$_4$ (25 mgs, 0.022 mmol) and the reaction mixture was further heated at 1015° C. for 16 hr. The mixture was then concentrated and purified by flash chromatography (5-100% Ethyl acetate/hexanes) to give tert-butyl 4-(4-(4-(3-cyano-4-((tetrahydro-2H-pyran-4- yl)oxy)phenyl)-7-((2-(trimethylsilyl)ethoxy)methyl)-7H-pyrrolo[2,3-d]pyrimidin-6-yl)-2-methoxyphenyl)piperazine-1-carboxylate. LCMS-ESI$^+$ (m/z): [M+H]$^+$ calcd for C$_{40}$H$_{52}$N$_6$O$_6$Si: 741.9. found: 741.3 Step 4: To a solution of tert-butyl 4-(4-(4-(3-cyano-4-((tetrahydro-2H-pyran-4-yl)oxy)phenyl)-7-((2-(trimethylsilyl)ethoxy)methyl)-7H-pyrrolo[2,3-d]pyrimidin-6-yl)-2-methoxyphenyl)piperazine-1-carboxylate (130 mgs, 0.175 mmol) in DCM (2 mL) was added TFA (2 mL) and stirred at room temperature for 2 h. Add 0.7 mL more TFA and stirred at rt for 16 h. The volatiles were removed under reduce pressure and azeotrope three times with acetonitrile. The residue was dissolved in MeOH (2 mL) and treated with ethane-1,2-diamine (0.5 mL) at room temperature for 16 hrs. The mixture was then diluted with acetonitrile/water, stirred at rt for 15 min and the resulting solids were filtered and purified by reverse phase chromatography to give 5-(6-(3-methoxy-4-(piperazin-1-yl)phenyl)-7H-pyrrolo[2,3-d]pyrimidin-4-yl)-2-((tetrahydro-2H-pyran-4-yl)oxy)benzonitrile as TFA salt which was treated with MP carbonate resin in methanol to give the free base. LCMS-ESI$^+$ (m/z): [M+H]$^+$ calcd for C$_{29}$H$_{30}$N$_6$O$_3$ as (M+H)$^+$ 511.6 found: 511.2.

Step 5: To a solution of 5-(6-(3-methoxy-4-(piperazin-1-yl)phenyl)-7H-pyrrolo[2,3-d]pyrimidin-4-yl)-2-((tetrahydro-2H-pyran-4-yl)oxy)benzonitrile (25 mgs, 0.05 mmol), glycolic acid (8 mgs, 0.1 mmol) and HATU (270 mgs, 0.07 mmol) in DMF (0.5 mL) was added DIPEA (0.03 mL, 0.15 mmol) and the resulting solution was stirred at rt for 48 hrs. The crude mixture was concentrated and purified by reverse phase chromatography to give the title compound as TFA salt. LCMS-ESI$^+$ (m/z): [M+H]$^+$ calcd for C$_{31}$H$_{32}$N$_6$O$_5$ as (M+H)$^+$ 569.6. found: 569.2; $^1$H NMR (400 MHz, DMSO-d$_6$) δ 12.86 (s, 1H), 8.83 (s, 1H), 8.60-8.37 (m, 2H), 7.69-7.33 (m, 4H), 6.98 (d, J=8.7 Hz, 1H), 4.98 (dt, J=7.9, 3.9 Hz, 1H), 4.12 (s, 2H), 3.93 (s, 3H), 3.90-3.81 (m, 3H), 3.68-3.41 (m, 6H), 3.03 (m, 4H), 2.12-2.00 (m, 2H), 1.71 (dtd, J=12.3, 8.2, 3.8 Hz, 2H).

Example 135: 5-(6-(3-methoxy-4-(4-(methylsulfonyl)piperazin-1-yl)phenyl)-7H-pyrrolo[2,3-d]pyrimidin-4-yl)-2-((tetrahydro-2H-pyran-4-yl)oxy)benzonitrile

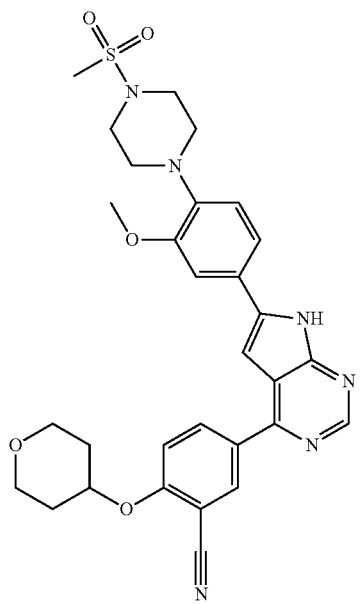 [SMILES: COc1cc(-c2cc3c(-c4ccc(OC5CCOCC5)c(C#N)c4)ncnc3[nH]2)ccc1N1CCN(S(C)(=O)=O)CC1]

To a solution of 5-(6-(3-methoxy-4-(piperazin-1-yl)phenyl)-7H-pyrrolo[2,3-d]pyrimidin-4-yl)-2-((tetrahydro-2H-pyran-4-yl)oxy)benzonitrile (25 mgs, 0.05 mmol) in DCM (1 mL) was added Methane sulfonic anhydride (11 mgs, 0.06 mmol) and DIPEA (0.03 mL, 0.15 mmol) and the resulting cloudy solution was stirred at rt for 48 hrs. The crude mixture was concentrated and purified by reverse phase chromatography to give the title compound as TFA salt. LCMS-ESI$^+$ (m/z): [M+H]$^+$ calcd for C$_{30}$H$_{32}$N$_6$O$_5$S as (M+H)$^+$ 589.7. found: 589.2. $^1$H NMR (400 MHz, DMSO-d$_6$) δ 12.86 (s, 1H), 8.83 (d, J=1.2 Hz, 1H), 8.50 (dt, J=6.9, 1.8 Hz, 2H), 7.77-7.37 (m, 4H), 7.45 (s, 1H), 7.02 (d, J=8.1 Hz, 1H), 4.97 (dt, J=8.0, 4.5 Hz, 2H), 3.92 (s, 3H), 3.87 (m, 2H), 3.56 (ddd, J=11.6, 8.0, 3.0 Hz, 2H), 3.31-3.21 (m, 4H), 3.13 (t, J=4.8 Hz, 4H), 2.93 (s, 3H), 2.13-1.95 (m, 2H), 1.71 (ddp, J=12.3, 8.3, 4.1 Hz, 2H).

Example 136: 5-(6-(3-methoxy-4-morpholinophenyl)-7H-pyrrolo[2,3-d]pyrimidin-4-yl)-2-((tetrahydro-2H-pyran-4-yl)oxy)benzonitrile

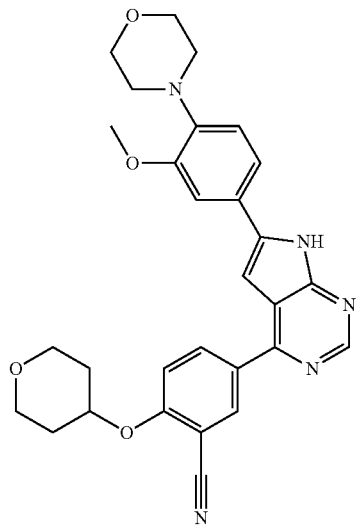 [SMILES: COc1cc(-c2cc3c(-c4ccc(OC5CCOCC5)c(C#N)c4)ncnc3[nH]2)ccc1N1CCOCC1]

Step 1: To a mixture of 4-chloro-6-iodo-7-((2-(trimethylsilyl)ethoxy)methyl)-7H-pyrrolo[2,3-d]pyrimidine (75 mgs, 0.18 mmol) and 4-(2-methoxy-4-(4,4,5,5-tetramethyl-1,3,2-dioxaborolan-2-yl)phenyl)morpholine (64 mgs, 0.20 mmol), in DME (3 mL) was added 2.0 M aq Na$_2$CO$_3$ (0.25 mL, 0.5 mmol), and Pd(PPh$_3$)$_4$ catalyst (11 mgs, 0.009 mmol). The reaction mixture was heated at 110° C. for 5 hrs. Cooled to rt and to the mixture was added 2-((tetrahydro-2H-pyran-4-yl)oxy)-5-(4,4,5,5-tetramethyl-1,3,2-dioxaborolan-2-yl)benzonitrile (72 mgs, 0.22 mmol), 2.0 M aq Na$_2$CO$_3$ (0.2 mL, 0.37 mmol) and Pd(PPh$_3$)$_4$ (21 mgs, 0.018 mmol) and the reaction mixture was further heated at 100° C. for 16 hr. The mixture was then concentrated and purified by flash chromatography (10-75% Ethyl acetate/hexanes) to give 5-(6-(3-methoxy-4-morpholinophenyl)-7-((2-(trimethylsilyl)ethoxy)methyl)-7H-pyrrolo[2,3-d]pyrimidin-4-yl)-2-((tetrahydro-2H-pyran-4-yl)oxy)benzonitrile. LCMS-ESI$^+$ (m/z): [M+H]$^+$ calcd for C$_{35}$H$_{43}$N$_5$O$_5$Si: 642.8. found: 642.3 Step 2: To a solution of 5-(6-(3-methoxy-4-morpholinophenyl)-7-((2-(trimethylsilyl)ethoxy)methyl)-7H-pyrrolo[2,3-d]pyrimidin-4-yl)-2-((tetrahydro-2H-pyran-4-yl)oxy)benzonitrile (77 mgs, 0.12 mmol) in DCM (2 mL) was added TFA (1.5 mL) and stirred at room temperature for 1 h. The volatiles were removed under reduce pressure and azeotrope three times with acetonitrile. The residue was dissolved in MeOH (2 mL) and treated with ethane-1,2-diamine (0.5 mL) at room temperature for 2 h. The crude mixture was concentrated and purified by reverse phase chromatography to give the title compound as TFA salt. LCMS-ESI+ (m/z): [M+H]+ calcd for $C_{29}H_{29}N_5O_4$ as (M+H)+ 512.6. found: 512.2; $^1$H NMR (400 MHz, DMSO-$d_6$) δ 12.78 (s, 1H), 8.81 (s, 1H), 8.51 (m, 2H), 7.73-7.51 (m, 4H), 7.42 (d, J=2.0 Hz, 1H), 6.98 (d, J=8.2 Hz, 1H), 5.09-4.97 (m, 1H), 3.91 (s, 3H), 3.89-3.83 (m, 2H), 3.77-3.68 (m, 4H), 3.56 (ddd, J=11.4, 8.3, 3.1 Hz, 2H), 3.04 (m, 4H), 2.06 (dd, J=9.6, 5.0 Hz, 2H), 1.71 (dtd, J=12.4, 8.2, 3.9 Hz, 2H).

Example 137: 5-(6-(2-methoxy-4-morpholinophenyl)-7H-pyrrolo[2,3-d]pyrimidin-4-yl)-2-((tetrahydro-2H-pyran-4-yl)oxy)benzonitrile

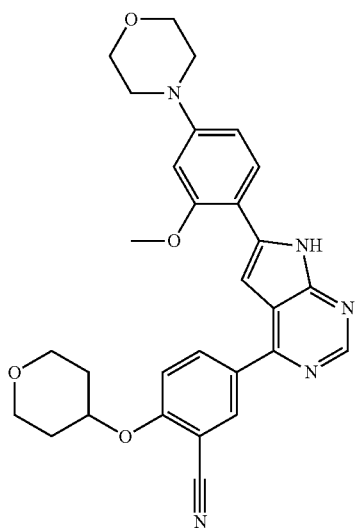 [SMILES: COc1cc(N2CCOCC2)ccc1-c1cc2c(-c3ccc(OC4CCOCC4)c(C#N)c3)ncnc2[nH]1]

Step 1: To a mixture of 4-chloro-6-iodo-7-((2-(trimethylsilyl)ethoxy)methyl)-7H-pyrrolo[2,3-d]pyrimidine (75 mgs, 0.18 mmol) and 4-(3-methoxy-4-(4,4,5,5-tetramethyl-1,3,2-dioxaborolan-2-yl)phenyl)morpholine (64 mgs, 0.20 mmol), in DME (3 mL) was added 2.0 M aq $Na_2CO_3$ (0.25 mL, 0.5 mmol), Pd(PPh$_3$)$_4$ catalyst (11 mgs, 0.009 mmol) and potassium acetate (36 mgs, 0.36 mmol). The reaction mixture was heated at 110° C. for 5 hrs. Cooled to rt and to the mixture was added 2-((tetrahydro-2H-pyran-4-yl)oxy)-5-(4,4,5,5-tetramethyl-1,3,2-dioxaborolan-2-yl)benzonitrile (72 mgs, 0.22 mmol), 2.0 M aq $Na_2CO_3$ (0.2 mL, 0.37 mmol) and Pd(PPh$_3$)$_4$ (21 mgs, 0.018 mmol) and the reaction mixture was further heated at 100° C. for 16 hr. The mixture was then concentrated and purified by flash chromatography (10-75% Ethyl acetate/hexanes) to give 5-(6-(2-methoxy-4-morpholinophenyl)-7-((2-(trimethylsilyl)ethoxy)methyl)-7H-pyrrolo[2,3-d]pyrimidin-4-yl)-2-((tetrahydro-2H-pyran-4-yl)oxy)benzonitrile. LCMS-ESI+ (m/z): [M+H]+ calcd for $C_{35}H_{43}N_5O_5Si$: 642.8. found: 642.3 Step 2: To a solution of 5-(6-(2-methoxy-4-morpholinophenyl)-7-((2-(trimethylsilyl)ethoxy)methyl)-7H-pyrrolo[2,3-d]pyrimidin-4-yl)-2-((tetrahydro-2H-pyran-4-yl)oxy)benzonitrile (43 mgs, 0.066 mmol) in DCM (2 mL) was added TFA (1.5 mL) and stirred at room temperature for 1 h. The volatiles were removed under reduce pressure and azeotrope three times with acetonitrile. The residue was dissolved in MeOH (2 mL) and treated with ethane-1,2-diamine (0.5 mL) at room temperature for 2 h. The crude mixture was concentrated and purified by reverse phase chromatography to give the title compound as TFA salt. LCMS-ESI+ (m/z): [M+H]+ calcd for $C_{29}H_{29}N_5O_4$ as (M+H)+ 512.6. found: 512.2; $^1$H NMR (400 MHz, DMSO-$d_6$) δ 12.78 (s, 1H), 8.75 (s, 1H), 8.46-8.43 (m, 1H), 7.89-7.77 (m, 3H), 7.57 (d, J=9.2 Hz, 1H), 7.20 (d, J=2.0 Hz, 1H), 6.64 (m, 1H), 4.99-4.93 (m, 1H), 3.94 (s, 3H), 3.89-3.83 (m, 2H), 3.79-3.76 (m, 4H), 3.59-3.53 (m, 2H), 3.26-3.23 (m, 4H), 2.10-2.05 (m, 2H), 1.75-1.68 (m, 2H).

Example 138: 2-(cyclopropylmethoxy)-5-(6-(4-(2-(pyrrolidin-1-yl)ethoxy)phenyl)-7H-pyrrolo[2,3-d]pyrimidin-4-yl)benzonitrile

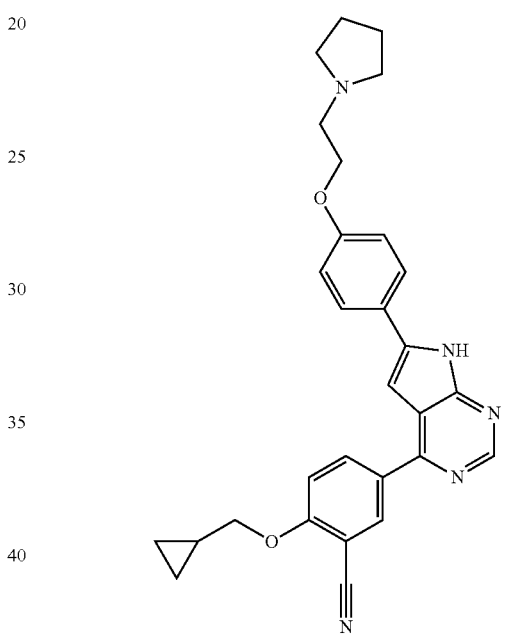

Step 1: To a mixture of 4-chloro-6-(4-(2-(pyrrolidin-1-yl)ethoxy)phenyl)-7-((2-(trimethylsilyl)ethoxy)methyl)-7H-pyrrolo[2,3-d]pyrimidine (75 mgs, 0.18 mmol) and 2-(cyclopropylmethoxy)-5-(4,4,5,5-tetramethyl-1,3,2-dioxaborolan-2-yl)benzonitrile (57 mgs, 0.19 mmol), in DME (3 mL) was added 2.0 M aq $Na_2CO_3$ (0.25 mL, 0.5 mmol), Pd(PPh$_3$)$_4$ catalyst (18 mgs, 0.009 mmol) and potassium acetate (36 mgs, 0.36 mmol). The reaction mixture was heated at 115° C. for 5 hrs. Cooled to rt and to the solids formed were filtered and washed with methanol and dried to give 2-(cyclopropylmethoxy)-5-(6-(4-(2-(pyrrolidin-1-yl)ethoxy)phenyl)-7-((2-(trimethylsilyl)ethoxy)methyl)-7H-pyrrolo[2,3-d]pyrimidin-4-yl)benzonitrile. LCMS-ESI+ (m/z): [M+H]+ calcd for $C_{35}H_{43}N_5O_3Si$: 610.8. found: 610.3.

Step 2: To a solution of 2-(cyclopropylmethoxy)-5-(6-(4-(2-(pyrrolidin-1-yl)ethoxy)phenyl)-7-((2-(trimethylsilyl)ethoxy)methyl)-7H-pyrrolo[2,3-d]pyrimidin-4-yl)benzonitrile in DCM (2 mL) was added TFA (1.5 mL) and stirred at room temperature for 1 h. The volatiles were removed under reduce pressure and azeotrope three times with acetonitrile. The residue was dissolved in MeOH (2 mL) and treated with ethane-1,2-diamine (0.5 mL) at room temperature for 2 h.

The crude mixture was concentrated and purified by reverse phase chromatography to give the title compound as TFA salt. LCMS-ESI⁺ (m/z): [M+H]⁺ calcd for C₂₉H₂₉N₅O₂ as (M+H)⁺ 480.6. found: 480.2; ¹H NMR (400 MHz, DMSO-d₆) δ 12.83 (s, 1H), 10.31 (s, 1H), 8.83 (d, J=3.0 Hz, 1H), 8.54 (d, J=8.4 Hz, 2H), 8.11-8.02 (m, 2H), 7.49-7.38 (m, 2H), 7.23-7.06 (m, 2H), 4.41 (t, J=4.7 Hz, 2H), 4.14 (m, 2H), 3.66-3.49 (m, 4H), 3.17-2.96 (m, 2H), 1.96-1.86 (m, 4H), 1.28-1.22 (m, 1H), 0.65-0.58 (m, 2H), 0.42-0.42 (m, 2H).

Example 139: 2-((1,1-dioxidotetrahydro-2H-thiopyran-4-yl)oxy)-5-(6-(3-methoxy-4-(4-(oxetan-3-yl)piperazin-1-yl)phenyl)-7H-pyrrolo[2,3-d]pyrimidin-4-yl)benzonitrile

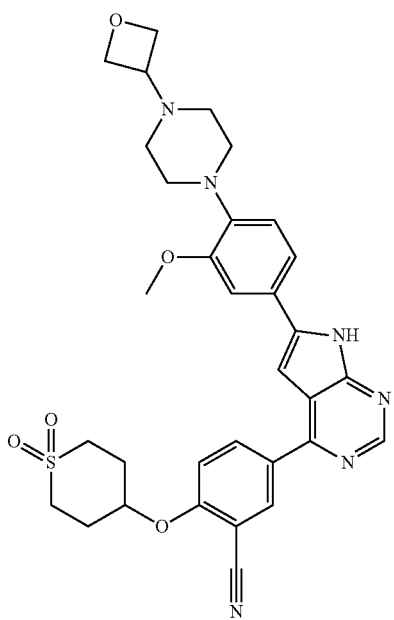 [SMILES: COc1cc(-c2cc3c(-c4ccc(OC5CCS(=O)(=O)CC5)c(C#N)c4)ncnc3[nH]2)ccc1N1CCN(C2COC2)CC1]

Step 1: To a solution of tert-butyl 4-(2-methoxy-4-(4,4,5,5-tetramethyl-1,3,2-dioxaborolan-2-yl)phenyl)piperazine-1-carboxylate (521 mgs, 1.64 mmol) in DCM (8 mL) was added TFA (7 mL) and the reaction mixture was stirred at rt for 15 min. The mixture was then concentrated and azeotrope with acetonitrile and dried to give 1-(2-methoxy-4-(4,4,5,5-tetramethyl-1,3,2-dioxaborolan-2-yl)phenyl)piperazine which was used further without purification.

Step 2: To the suspension of 1-(2-methoxy-4-(4,4,5,5-tetramethyl-1,3,2-dioxaborolan-2-yl)phenyl)piperazine (521 mgs, 1.64 mmol) in THF (10 mL) and DIPEA (1 mL, 5.7 mmol) was added oxetan-3-one (1.05 mL, 16.4 mmol) and stirred at rt for 10 min and then NaBH(OAc)₃ (2.4 g, 11 mmol) was added. The reaction mixture was stirred at 55° C. for 4 h. The reaction mixture was cooled and poured into NaHCO3 solution and extracted with EtOAC and the combined organic leyers were washed with brine and dried (MgSO₄). Filtration, followed by concentration gave 1-(2-methoxy-4-(4,4,5,5-tetramethyl-1,3,2-dioxaborolan-2-yl)phenyl)-4-(oxetan-3-yl)piperazine which was used further without purification. LCMS-ESI⁺ (m/z): [M+H]⁺ calcd for C₂₀H₃₁BN₂O₄ as (M+H)⁺ 375.3. found: 375.2.

Step 3: To a mixture of 4-chloro-6-iodo-7-((2-(trimethylsilyl)ethoxy)methyl)-7H-pyrrolo[2,3-d]pyrimidine (200 mgs, 0.49 mmol) and 1-(2-methoxy-4-(4,4,5,5-tetramethyl-1,3,2-dioxaborolan-2-yl)phenyl)-4-(oxetan-3-yl)piperazine (332 mgs, 0.89 mmol), in DME (7 mL) was added 2.0 M aq Na₂CO₃ (0.7 mL, 1.33 mmol) and Pd(PPh₃)₄ catalyst (28 mgs, 0.024 mmol). The reaction mixture was heated at 115° C. for 5 hrs. The mixture was then concentrated and purified by flash chromatography (30-100% Ethyl acetate/hexanes) to give 4-chloro-6-(3-methoxy-4-(4-(oxetan-3-yl)piperazin-1-yl)phenyl)-7-((2-(trimethylsilyl)ethoxy)methyl)-7H-pyrrolo[2,3-d]pyrimidine. LCMS-ESI⁺ (m/z): [M+H]⁺ calcd for C₂₆H₃₆ClN₅O₃Si as (M+H)⁺ 531.1. found: 531.2.

Step 4: To a solution of 4-chloro-6-(3-methoxy-4-(4-(oxetan-3-yl)piperazin-1-yl)phenyl)-7-((2-(trimethylsilyl)ethoxy)methyl)-7H-pyrrolo[2,3-d]pyrimidine (75 mgs, 0.14 mmol) and 2-((1,1-dioxidotetrahydro-2H-thiopyran-4-yl)oxy)-5-(4,4,5,5-tetramethyl-1,3,2-dioxaborolan-2-yl)benzonitrile (64 mgs, 0.17 mmol), in DME (2 mL) was added 2.0 M aq Na₂CO₃ (0.15 mL, 0.28 mmol) and Pd(PPh₃)₄ catalyst (16 mgs, 0.014 mmol). The reaction mixture was heated at 115° C. for 5 hrs. The mixture was then concentrated and purified by flash chromatography (0-10% MeOH/Ethyl acetate) to give 2-((1,1-dioxidotetrahydro-2H-thiopyran-4-yl)oxy)-5-(6-(3-methoxy-4-(4-(oxetan-3-yl)piperazin-1-yl)phenyl)-7-((2-(trimethylsilyl)ethoxy)methyl)-7H-pyrrolo[2,3-d]pyrimidin-4-yl)benzonitrile. LCMS-ESI⁺ (m/z): [M+H]⁺ calcd for C₃₈H₄₈N₆O₆SSi: 745.9. found: 745.2.

Step 4: To a solution of 2-((1,1-dioxidotetrahydro-2H-thiopyran-4-yl)oxy)-5-(6-(3-methoxy-4-(4-(oxetan-3-yl)piperazin-1-yl)phenyl)-7-((2-(trimethylsilyl)ethoxy)methyl)-7H-pyrrolo[2,3-d]pyrimidin-4-yl)benzonitrile (98 mgs, 0.13 mmol) in DCM (2 mL) was added TFA (2 mL) and stirred at room temperature for 4 hrs. The volatiles were removed under reduce pressure and azeotrope three times with acetonitrile. The residue was dissolved in MeOH (2 mL) and treated with ethane-1,2-diamine (0.5 mL) at room temperature for 16 hrs. The mixture was then diluted with acetonitrile/water, stirred at rt for 15 min and the resulting solids were filtered and purified by reverse phase chromatography (twice) to give the title compound as TFA salt LCMS-ESI⁺ (m/z): [M+H]⁺ calcd for C₃₂H₃₄N₆O₅S as (M+H)⁺ 615.7. found: 615.2; ¹H NMR (400 MHz, DMSO-d₆) δ 12.77 (s, 1H), 8.80 (s, 1H), 8.62-8.47 (m, 2H), 7.66 (d, J=7.0 Hz, 2H), 7.57 (d, J=9.6 Hz, 1H), 7.46 (d, J=1.9 Hz, 1H), 7.06 (d, J=8.5 Hz, 1H), 5.12-5.07 (m, 1H), 4.77 (m 4H), 4.50 (m, 1H), 3.93 (s, 3H), 3.70-3.45 (m, 4H), 3.30-3.17 (m, 4H), 3.15-2.90 (m, 4H), 2.40-2.33 (m, 4H).

329

Example 140: 2-((3,3-difluoropiperidin-4-yl)oxy)-5-(6-(3-methoxy-4-(4-(oxetan-3-yl)piperazin-1-yl)phenyl)-7H-pyrrolo[2,3-d]pyrimidin-4-yl)benzonitrile

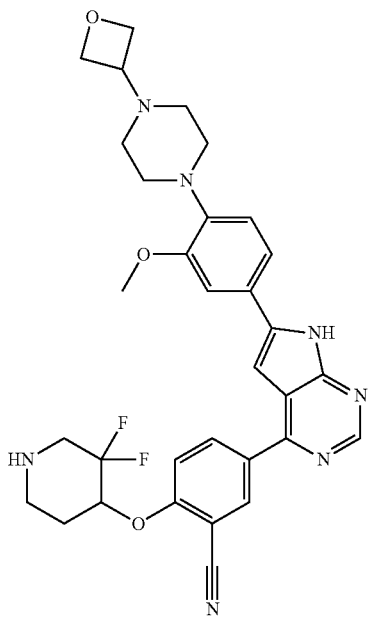 [SMILES: COc1cc(-c2cc3c(-c4ccc(OC5CCNCC5(F)F)c(C#N)c4)ncnc3[nH]2)ccc1N1CCN(C2COC2)CC1]

Step 1: To a mixture of 4-chloro-6-(3-methoxy-4-(4-(oxetan-3-yl)piperazin-1-yl)phenyl)-7-((2-(trimethylsilyl)ethoxy)methyl)-7H-pyrrolo[2,3-d]pyrimidine (1 g, 1.9 mmol) and 2-fluoro-5-(4,4,5,5-tetramethyl-1,3,2-dioxaborolan-2-yl)benzonitrile (563 mgs, 2.28 mmol), in DME was added 2.0 M aq $Na_2CO_3$ (2.6 mL, 5.2 mmol) and $Pd(PPh_3)_4$ catalyst (109 mgs, 0.09 mmol). The reaction mixture was heated at 115° C. for 5 hrs. The mixture was then concentrated and purified by flash chromatography (0-10% MeOH/Ethyl acetate) to give 2-fluoro-5-(6-(3-methoxy-4-(4-(oxetan-3-yl)piperazin-1-yl)phenyl)-7-((2-(trimethylsilyl)ethoxy)methyl)-7H-pyrrolo[2,3-d]pyrimidin-4-yl)benzonitrile. LCMS-ESI⁺ (m/z): [M+H]⁺ calcd for $C_{33}H_{39}FN_6O_3Si$: 615.8. found: 615.3.

Step 2: To a solution of 2-fluoro-5-(6-(3-methoxy-4-(4-(oxetan-3-yl)piperazin-1-yl)phenyl)-7-((2-(trimethylsilyl)ethoxy)methyl)-7H-pyrrolo[2,3-d]pyrimidin-4-yl)benzonitrile (844 mgs, 1.37 mmol) in DCM (8 mL) was added TFA (8 mL) and stirred at room temperature for 1 h. The volatiles were removed under reduce pressure and azeotrope three times with acetonitrile. The residue was dissolved in MeOH (8 mL) and treated with ethane-1,2-diamine (3 mL) at room temperature for 16 hrs. The mixture was then diluted with acetonitrile/water, stirred at rt for 15 min and the resulting solids were filtered and dried to give 2-fluoro-5-(6-(3-methoxy-4-(4-(oxetan-3-yl)piperazin-1-yl)phenyl)-7H-pyrrolo[2,3-d]pyrimidin-4-yl)benzonitrile. LCMS-ESI⁺ (m/z): [M+H]⁺ calcd for $C_{27}H_{25}FN_6O_2$ as (M+H)⁺ 485.5. found: 485.2.

Step 3: A solution of a racemic mixture tert-butyl 3,3-difluoro-4-hydroxypiperidine-1-carboxylate (97 mgs, 0.41 mmol) in 2-Me-THF (9 mL) was stirred in an ice-water bath under an atmosphere of Argon. Potassium tert-butoxide solution (1.0 M, 0.4 mL, 0.41 mmol) was added in a single portion and the mixture was stirred at 0° C. for 40 minutes,

330 and then 2-fluoro-5-(6-(3-methoxy-4-(4-(oxetan-3-yl)piperazin-1-yl)phenyl)-7H-pyrrolo[2,3-d]pyrimidin-4-yl)benzonitrile (100 mgs, 0.21 mmol) was added. The mixture was stirred at 60° C. for 1 hr. After the mixture cooled to room temperature, water was added, and mixture evaporated under reduced pressure to yield the crude tert-butyl 4-(2-cyano-4-(6-(3-methoxy-4-(4-(oxetan-3-yl)piperazin-1-yl)phenyl)-7H-pyrrolo[2,3-d]pyrimidin-4-yl)phenoxy)-3,3-difluoropiperidine-1-carboxylate which was dissolved in DCM (3 mL) and TFA was added (2 mL). The resulting solution was stirred st rt for 16 h. The mixture was then concentrated and purified by reverse phase chromatography to give the title compound as TFA salt. LCMS-ESI⁺ (m/z): [M+H]⁺ calcd for $C_{32}H_{33}F_2N_7O_3$ as (M+H)⁺ 602.7. found: 602.2. ¹H NMR (400 MHz, DMSO-d₆) δ 12.79 (s, 1H), 10.15 (s, 1H), 8.81 (s, 1H), 8.68-8.48 (m, 2H), 7.75-7.60 (m, 3H), 7.47-7.45 (m, 1H), 7.05 (d, J=8.2 Hz, 1H), 5.49-5.41 (m, 1H), 4.91-4.85 (m, 2H), 4.52-4.43 (m, 1H), 3.93 (s, 3H), 3.86-3.74 (m, 2H), 3.64-3.55 (m, 6H), 3.35-3.22 (m, 2H), 3.30-3.20 (m, 4H), 2.41-2.15 (m, 2H).

Example 141: 2-((3,3-difluoro-1-(2-hydroxyacetyl)piperidin-4-yl)oxy)-5-(6-(3-methoxy-4-(4-(oxetan-3-yl)piperazin-1-yl)phenyl)-7H-pyrrolo[2,3-d]pyrimidin-4-yl)benzonitrile

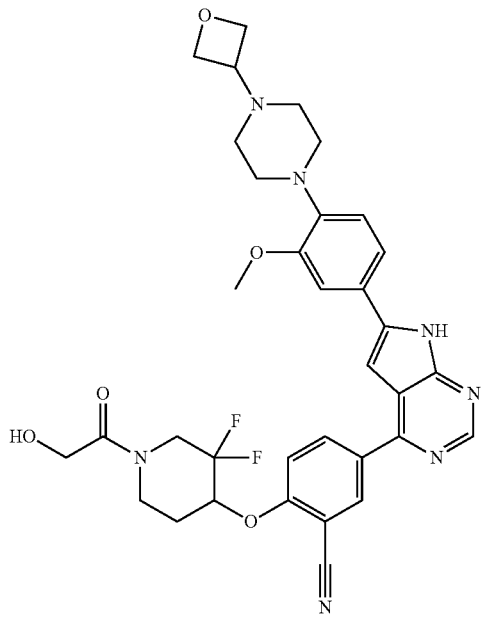 [SMILES: COc1cc(-c2cc3c(-c4ccc(OC5CCN(C(=O)CO)CC5(F)F)c(C#N)c4)ncnc3[nH]2)ccc1N1CCN(C2COC2)CC1]

To a mixture of 2-((3,3-difluoropiperidin-4-yl)oxy)-5-(6-(3-methoxy-4-(4-(oxetan-3-yl)piperazin-1-yl)phenyl)-7H-pyrrolo[2,3-d]pyrimidin-4-yl)benzonitrile (150 mgs, 0.25 mmol), glycolic acid (38 mgs, 0.5 mmol) and HATU (190 mgs, 0.5 mmol) in DMF (2 mL) was added DIPEA (0.2 mL, 1.15 mmol) and the resulting solution was stirred at rt for 3 hrs. The crude mixture was concentrated and purified by reverse phase chromatography to give the title compound as TFA salt. LCMS-ESI⁺ (m/z): [M+H]⁺ calcd for $C_{34}H_{35}F_2N_7O_5$ as (M+H)⁺ 660.7. found: 660.3; ¹H NMR (400 MHz, DMSO-d₆) δ ¹H NMR (400 MHz, DMSO-d₆) δ 12.78 (s, 1H), 10.63 (s, 1H), 8.81 (s, 1H), 8.55 (d, J=8.7 Hz, 2H), 7.75-7.60 (m, 3H), 7.47 (d, J=2.0 Hz, 1H), 7.06 (d, J=8.6 Hz, 1H), 5.45-5.37 (m, 1H), 4.77 (d, J=6.4 Hz, 2H), 4.58-4.45 (m, 1H), 4.19-4.05 (m, 2H), 3.94 (s, 3H), 3.75-3.45 (m, 10H), 3.20-2.95 (m, 4H), 2.20-1.90 (m, 2H).

Example 142: (R)-2-(3-hydroxypyrrolidin-1-yl)-5-(6-(3-methoxy-4-(4-(oxetan-3-yl)piperazin-1-yl)phenyl)-7H-pyrrolo[2,3-d]pyrimidin-4-yl)benzonitrile

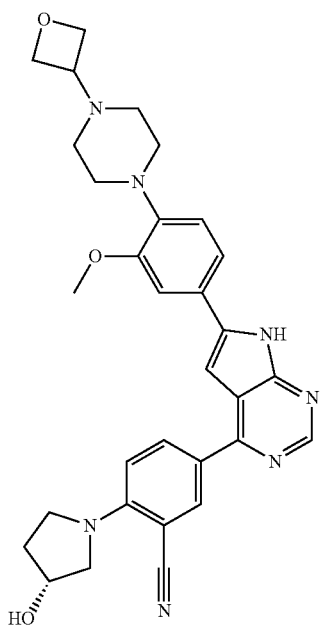 [SMILES: COc1cc(-c2cc3c(-c4ccc(N5CC[C@@H](O)C5)c(C#N)c4)ncnc3[nH]2)ccc1N1CCN(C2COC2)CC1]

To a solution of 2-fluoro-5-(6-(3-methoxy-4-(4-(oxetan-3-yl)piperazin-1-yl)phenyl)-7H-pyrrolo[2,3-d]pyrimidin-4-yl)benzonitrile (55 mgs, 0.114 mmol) in NMP (1 mL) was added (R)-pyrrolidin-3-ol hydrochloride (42 mgs, 0.341 mmol) and DIPEA (0.16 mL, 0.90 mmol) and heated at 150° C. for 16 h. The mixture was then concentrated and purified by reverse phase chromatography to give the title compound as TFA salt. LCMS-ESI+ (m/z): [M+H]+ calcd for $C_{31}H_{33}N_7O_3$ as (M+H)+ 552.7. found: 552.2; $^1$H NMR (400 MHz, DMSO-d$_6$) δ 12.89 (s, 1H), 10.66 (s, 1H), 8.79 (s, 1H), 8.45-8.24 (m, 2H), 7.65 (dt, J=3.8, 2.0 Hz, 2H), 7.45 (d, J=2.0 Hz, 1H), 7.01 (dd, J=34.5, 9.0 Hz, 2H), 4.77 (d, J=6.5 Hz, 2H), 4.55-4.41 (m, 2H), 3.93 (s, 3H), 3.87-3.71 (m, 3H), 3.71-3.40 (m, 7H), 3.18-2.98 (m, 4H), 2.07-1.92 (m, 2H).

Example 143: 5-(6-(3-methoxy-4-(4-(oxetan-3-yl)piperazin-1-yl)phenyl)-7H-pyrrolo[2,3-d]pyrimidin-4-yl)-2-((tetrahydro-2H-pyran-4-yl)oxy)benzonitrile

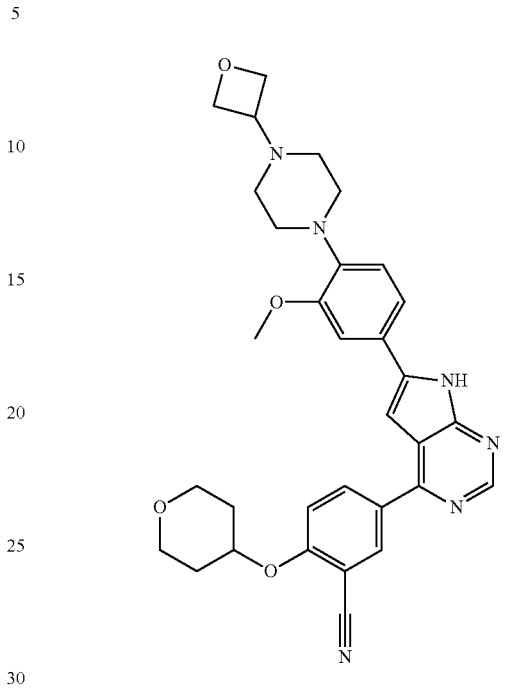

Step 1: To a mixture of 4-chloro-6-(3-methoxy-4-(4-(oxetan-3-yl)piperazin-1-yl)phenyl)-7-((2-(trimethylsilyl)ethoxy)methyl)-7H-pyrrolo[2,3-d]pyrimidine (75 mgs, 0.14 mmol) and 2-((tetrahydro-2H-pyran-4-yl)oxy)-5-(4,4,5,5-tetramethyl-1,3,2-dioxaborolan-2-yl)benzonitrile (56 mgs, 0.17 mmol), in DME (2 mL) was added 2.0 M aq Na$_2$CO$_3$ (0.14 mL, 0.28 mmol) and Pd(PPh$_3$)$_4$ catalyst (16 mgs, 0.014 mmol). The reaction mixture was heated at 115° C. for 16 hrs. The mixture was then concentrated and purified by flash chromatography (0-10% MeOH/Ethyl acetate) to give 5-(6-(3-methoxy-4-(4-(oxetan-3-yl)piperazin-1-yl)phenyl)-7-((2-(trimethylsilyl)ethoxy)methyl)-7H-pyrrolo[2,3-d]pyrimidin-4-yl)-2-((tetrahydro-2H-pyran-4-yl)oxy)benzonitrile. LCMS-ESI+ (m/z): [M+H]+ calcd for $C_{38}H_{48}N_6O_5Si$: 697.9. found: 697.3.

Step 2: To a solution of 5-(6-(3-methoxy-4-(4-(oxetan-3-yl)piperazin-1-yl)phenyl)-7-((2-(trimethylsilyl)ethoxy)methyl)-7H-pyrrolo[2,3-d]pyrimidin-4-yl)-2-((tetrahydro-2H-pyran-4-yl)oxy)benzonitrile (98 mgs, 0.14 mmol) in DCM (2 mL) was added TFA (2 mL) and stirred at room temperature for 4 hrs. The volatiles were removed under reduce pressure and azeotrope three times with acetonitrile. The residue was dissolved in MeOH (2 mL) and treated with ethane-1,2-diamine (0.5 mL) at room temperature for 16 hrs. The mixture was then diluted with acetonitrile/water, stirred at rt for 15 min and the resulting solids were filtered and dried. The solids were then purified by reverse phase chromatography to give the title compound as TFA salt. LCMS-ESI+ (m/z): [M+H]+ calcd for $C_{32}H_{34}N_6O_4$ as (M+H)+ 567.7. found: 567.2; $^1$H NMR (400 MHz, DMSO-d$_6$) δ 12.79 (s, 1H), 8.81 (s, 1H), 8.54-8.39 (m, 2H), 7.69-7.62 (m, 2H), 7.61-7.52 (m, 1H), 7.46 (d, J=1.9 Hz, 1H), 7.05 (d, J=8.8 Hz, 1H), 5.00-4.94 (m, 1H), 4.81-4.73 (m, 4H), 4.55-4.45 (m, 1H), 4.35-4.05 (m, 4H), 3.93 (s, 3H), 3.90-3.75 (m, 4H), 3.64-3.53 (m, 4H), 3.20-2.95 (m, 4H), 2.10-2.02 (m, 2H), 1.75-1.65 (m, 2H).

Example 144: 2-(((3R,4S)-3-fluoropiperidin-4-yl)oxy)-5-(6-(3-methoxy-4-(4-(oxetan-3-yl)piperazin-1-yl)phenyl)-7H-pyrrolo[2,3-d]pyrimidin-4-yl)benzonitrile

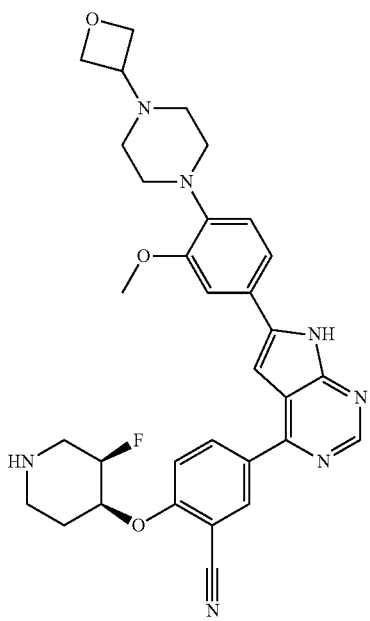 [SMILES: COc1cc(-c2cc3c(-c4ccc(O[C@H]5CCNC[C@H]5F)c(C#N)c4)ncnc3[nH]2)ccc1N1CCN(C2COC2)CC1]

The title compound was prepared in similar manner to Example 140 using (3R,4S)-tert-butyl 3-fluoro-4-hydroxypiperidine-1-carboxylate instead of racemic mixture tert-butyl 3,3-difluoro-4-hydroxypiperidine-1-carboxylate. LCMS-ESI+ (m/z): [M+H]+ calcd for $C_{32}H_{34}FN_7O_3$ as (M+H)+ 584.7. found: 584.2; $^1$H NMR (400 MHz, DMSO-$d_6$) δ 12.78 (s, 1H), 9.06 (s, 1H), 8.81 (s, 2H), 8.70-8.48 (m, 2H), 7.79-7.54 (m, 2H), 7.44 (d, J=2.0 Hz, 1H), 7.05 (d, J=8.6 Hz, 1H), 5.35-5.10 (m, 2H), 4.83-4.75 (m, 4H), 4.59-4.44 (m, 1H), 3.93 (s, 3H), 3.75-3.32 (m, 8H), 3.20-2.95 (m, 4H), 2.21-2.10 (m, 2H).

Example 145: 2-(((3R,4S)-3-fluoro-1-(2-hydroxyacetyl)piperidin-4-yl)oxy)-5-(6-(3-methoxy-4-(4-(oxetan-3-yl)piperazin-1-yl)phenyl)-7H-pyrrolo[2,3-d]pyrimidin-4-yl)benzonitrile

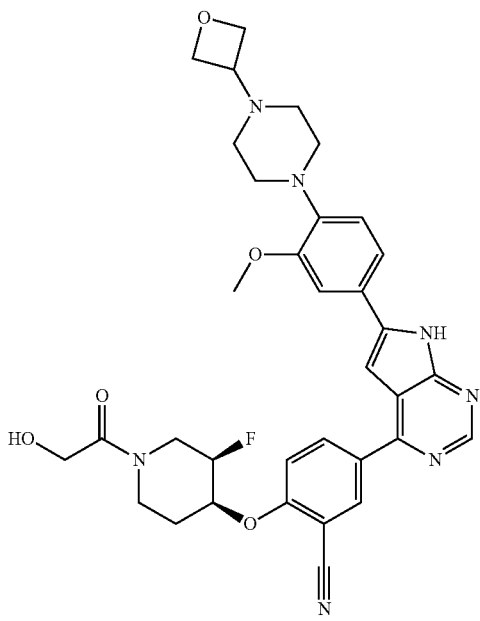 [SMILES: COc1cc(-c2cc3c(-c4ccc(O[C@H]5CCN(C(=O)CO)C[C@H]5F)c(C#N)c4)ncnc3[nH]2)ccc1N1CCN(C2COC2)CC1]

The title compound was prepared in similar manner to Example 141. LCMS-ESI+ (m/z): [M+H]+ calcd for $C_{34}H_{36}FN_7O_5$ as (M+H)+ 642.7. found: 642.3; $^1$H NMR (400 MHz, DMSO-$d_6$) δ 12.79 (s, 1H), 10.67 (s, 1H), 8.82 (s, 1H), 8.63-8.39 (m, 2H), 7.79-7.60 (m, 3H), 7.45 (d, J=2.0 Hz, 1H), 7.06 (d, J=8.8 Hz, 1H), 5.19-4.99 (m, 3H), 4.80-4.74 (m, 2H), 4.58-4.33 (m, 2H), 4.20-4.06 (m, 4H), 3.93 (s, 3H), 3.70-3.30 (m, 6H), 3.20-2.90 (m, 4H), 2.05-1.99 (m, 2H).

Example 146: 5-(8-(4-methoxyphenyl)-9H-purin-6-yl)-2-((tetrahydro-2H-pyran-4-yl)oxy)benzonitrile

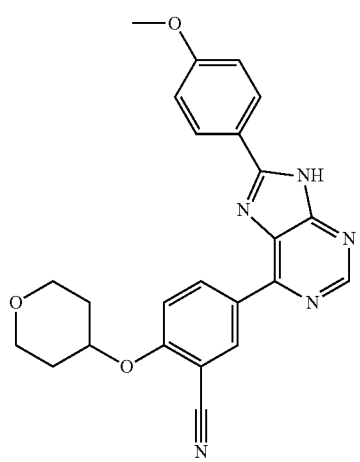 [SMILES: COc1ccc(-c2nc3c(-c4ccc(OC5CCOCC5)c(C#N)c4)ncnc3[nH]2)cc1]

Step 1: To a solution of 8-iodo-6-(phenylthio)-9-(tetrahydro-2H-pyran-2-yl)-9H-purine (400 mgs, 0.913 mmol) and (4-methoxyphenyl)boronic (153 mgs, 0.10 mmol) in dioxane/water (8 mL, 2:1), was added 2.0 M aq $Na_2CO_3$ (1.4 mL, 0.4 mmol), $PdCl_2(PPh_3)_2$ (105 mgs, 0.09 mmol) and the reaction mixture was heated at 105° C. for 16 hrs. After cooled to rt, th reaction mixture was diluted with DCM and filtered thru Celite and washed. The filtrate was then concentrated and the residue was dissolved in 1,4-dioxane (7 mL) and 4.0M HCl dioxane (1 mL) was added. After 15 min at rt, diethylether (50 mL) was added and the solids formed were filtered and washed with ether and dried to give 8-(4-methoxyphenyl)-6-(phenylthio)-9H-purine which was used further without purification. LCMS-ESI+ (m/z): [M+H]+ calcd for $C_{23}H_{22}N_4O_2S$ as (M+H)+ 419.5. found: 419.1.

Step 2: To an 20 mL microwave vial 8-(4-methoxyphenyl)-6-(phenylthio)-9H-purine (50 mgs, 0.15 mmoL), (4-((tetrahydro-2H-pyran-4-yl)oxy)phenyl)boronic acid (44 mgs, 0.18 mmol), CuTC (37 mgs, 0.19 mmol), tri(furan-2-yl)phosphine (TFP) (7 mgs, 0.03 mmol) in 2-Me-THF (6 mL) was added. The mixture was degassed with Argon for 5 minutes. $Pd_2(dba)_3$ (6 mgs, 0.006 mmol) catalyst was added and the solution was heated at 50° C. overnight. After cooling down to room temperature, the crude mixture was concentrated and purified by reverse phase chromatography (twice) to give the title compound as TFA salt. LCMS-ESI+ (m/z): [M+H]+ calcd for $C_{24}H_{21}N_5O_3$ as (M+H)+ 428.5. found: 428.1; $^1$H NMR (400 MHz, DMSO-$d_6$) δ 9.20 (m, 2H), 8.87 (s, 1H), 8.27 (d, J=9.2 Hz, 2H), 7.64 (d, J=8.4 Hz, 1H), 7.19 (d, J=8.8 Hz, 2H), 4.99-4.93 (m, 1H), 3.89 (m, 2H), 3.86 (s, 3H), 3.56-3.45 (m, 2H), 2.15-2.03 (m, 2H), 1.72-1.67 (m, 2H).

Example 147: 4-(3-cyano-4-((tetrahydro-2H-pyran-4-yl)oxy)phenyl)-1H-pyrrolo[2,3-b]pyridine-2-carbonitrile

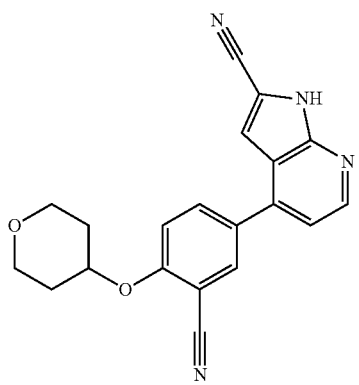 [SMILES: N#Cc1cc2c(-c3ccc(OC4CCOCC4)c(C#N)c3)ccnc2[nH]1]

5-(2-Iodo-1-(phenylsulfonyl)-1H-pyrrolo[2,3-b]pyridin-4-yl)-2-((tetrahydro-2H-pyran-4-yl)oxy)benzonitrile (150 mg, 0.26 mmol) was treated with copper(I) cyanide (103 mg, 1.15 mmol) and [1,1'-bis(diphenylphosphino)ferrocene]dichloropalladium(II)-complex with dichloromethane (31 mg, 0.084 mmol) and the mixture heated to 100° C. for 16 h. Filtration and concentration provided a brown semi-solid, which was taken up in 1 mL THF and 0.4 mL TFE and treated with $Cs_2CO_3$ (250 mg, 0.77 mmol). The mixture was heated at 100° C. in a μ-wave reactor for 35 min. Purification by high performance liquid chromatography provided 4-(3-cyano-4-((tetrahydro-2H-pyran-4-yl)oxy)phenyl)-1H-pyrrolo[2,3-b]pyridine-2-carbonitrile. ES/MS 345.1 (M+H⁺).

Example 148: 5-(2-(3-hydroxyprop-1-yn-1-yl)-1H-pyrrolo[2,3-b]pyridin-4-yl)-2-((tetrahydro-2H-pyran-4-yl)oxy)benzonitrile

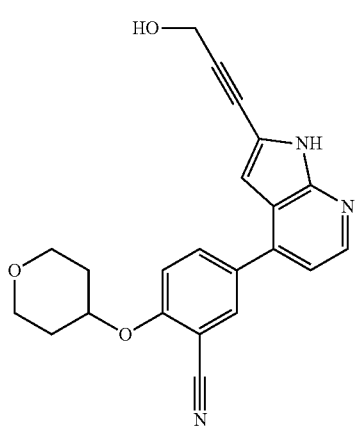 [SMILES: N#Cc1cc(-c2ccnc3[nH]c(C#CCO)cc23)ccc1OC1CCOCC1]

5-(2-Iodo-1-(phenylsulfonyl)-1H-pyrrolo[2,3-b]pyridin-4-yl)-2-((tetrahydro-2H-pyran-4-yl)oxy)benzonitrile (150 mg, 0.26 mmol), propargyl alcohol (36 mg, 0.64 mmol), copper iodide (7.3 mg, 0.038 mmol) and trans-dichlorobis(triphenylphosphine)palladium(II) (18 mg, 0.026 mmol) in 1 mL dioxane and 0.25 mL TEA was stirred at rt for 20 h. The reaction was diluted with DCM, filtered and concentrated to provide a dark semi-solid.

Residue was taken up in 0.5 mL THF and 0.2 mL TFE and treated with $Cs_2CO_3$ (252 mg, 0.77 mmol). The mixture was heated at 100° C. for 30 min, then cooled to rt and filtered and concentrated. Purification by RP-high performance liquid chromatography provided 5-(2-(3-hydroxyprop-1-yn-1-yl)-1H-pyrrolo[2,3-b]pyridin-4-yl)-2-((tetrahydro-2H-pyran-4-yl)oxy)benzonitrile. ES/MS 374.1 (M+H⁺).

Example 149: (R)-2-((1-(2-hydroxyacetyl)pyrrolidin-3-yl)oxy)-5-(2-(4-(2-hydroxypropan-2-yl)phenyl)-1H-pyrrolo[2,3-b]pyridin-4-yl)benzonitrile

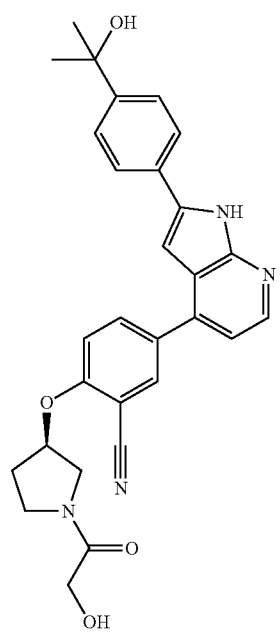 [SMILES: CC(C)(O)c1ccc(-c2cc3c(-c4ccc(O[C@@H]5CCN(C(=O)CO)C5)c(C#N)c4)ccnc3[nH]2)cc1]

Step 1: Preparation of (R)-tert-butyl 3-(2-cyano-4-(2-(4-(2-hydroxypropan-2-yl)phenyl)-1-tosyl-1H-pyrrolo[2,3-b]pyridin-4-yl)phenoxy)pyrrolidine-1-carboxylate: A solution of 2-(4-(4-bromo-1-tosyl-1H-pyrrolo[2,3-b]pyridin-2-yl)phenyl)propan-2-ol (547 mg, 1.127 g) and (R)-tert-butyl 3-(2-cyano-4-(4,4,5,5-tetramethyl-1,3,2-dioxaborolan-2-yl)phenoxy)pyrrolidine-1-carboxylate (467 mg, 1.127 mg) in 10 mL dioxane was treated with aq. $Na_2CO_3$ (1.41 mL, 2.82 mmol, 2M), aq. $NaHCO_3$ (0.563 mL, 0.563 mmol, 1M) and [1,1'-bis(diphenylphosphino)ferrocene]dichloropalladium (II)-complex with dichloromethane (92 mg, 0.113 mmol) and the mixture heated to 80° C. for 20 h. The reaction was cooled to rt and diluted with 70 mL DCM. $MgSO_4$ was added and the reaction stirred for 5 min, filtered and concentrated. Purification by RP HPLC provided (R)-tert-butyl 3-(2-cyano-4-(2-(4-(2-hydroxypropan-2-yl)phenyl)-1-tosyl-1H-pyrrolo[2,3-b]pyridin-4-yl)phenoxy)pyrrolidine-1-carboxylate (932 mg, 119% yield) as a rigid foam contaminated by an unidentified impurity. ES/MS 693.2 (M+H⁺).

Step 2: Preparation of (R)-5-(2-(4-(2-hydroxypropan-2-yl)phenyl)-1-tosyl-1H-pyrrolo[2,3-b]pyridin-4-yl)-2-(pyrrolidin-3-yloxy)benzonitrile: A solution of (R)-tert-butyl 3-(2-cyano-4-(2-(4-(2-hydroxypropan-2-yl)phenyl)-1-tosyl-1H-pyrrolo[2,3-b]pyridin-4-yl)phenoxy)pyrrolidine-1-carboxylate (932 mg, 1.34 mmol) in 10 mL DCM was treated with 10 mL TFA and stirred for 15 min. The reaction was concentrated and the residue partitioned between EtOAc and 2M NaOH. The organic layer was dried with $Na_2SO_4$ and concentrated to provide (R)-5-(2-(4-(2-hydroxypropan-2-yl)phenyl)-1-tosyl-1H-pyrrolo[2,3-b]pyridin-4-yl)-2-(pyrrolidin-3-yloxy)benzonitrile (821 mg, 103% yield). ES/MS 593.2 (M+H+).

Step 3: Preparation of (R)-2-((1-(2-hydroxyacetyl)pyrrolidin-3-yl)oxy)-5-(2-(4-(2-hydroxypropan-2-yl)phenyl)-1H-pyrrolo[2,3-b]pyridin-4-yl)benzonitrile: A solution of (R)-5-(2-(4-(2-hydroxypropan-2-yl)phenyl)-1-tosyl-1H-pyrrolo[2,3-b]pyridin-4-yl)-2-(pyrrolidin-3-yloxy)benzonitrile (153 mg, 0.258 mmol) and glycolic acid (29 mg, 387 mmol) was treated with HATU (118 mg, 0.31 mmol) and TEA (72 µL, 0.52 mmol) and stirred for 30 min. The reaction was partitioned between EtOAc and NaHCO₃ and the organic layer separated, dried and concentrated. The residue was taken up in 1 mL THF and 0.4 mL TFE and treated with Cs₂CO₃ (252 mg, 0.77 mmol) and heated at 100° C. for 30 min in a µ-wave reactor. Purification by RP-high performance liquid chromatography gave (R)-2-((1-(2-hydroxyacetyl)pyrrolidin-3-yl)oxy)-5-(2-(4-(2-hydroxypropan-2-yl)phenyl)-1H-pyrrolo[2,3-b]pyridin-4-yl)benzonitrile. 1H NMR (400 MHz, Acetonitrile-d3) d 13.92 (s, 1H), 8.29 (s, 1H), 8.21-8.09 (m, 2H), 7.92-7.85 (m, 2H), 7.67 (dd, J=8.5, 1.3 Hz, 2H), 7.45 (d, J=5.6 Hz, 1H), 7.38 (dd, J=8.8, 4.0 Hz, 1H), 7.26 (s, 1H), 5.39-5.25 (m, 1H), 4.13 (s, 2H), 4.07 (d, J=5.6 Hz, 1H), 3.88-3.72 (m, 2H), 3.72-3.48 (m, 4H), 2.37 (td, J=8.5, 8.0, 3.6 Hz, 1H), 2.33-2.21 (m, 1H), 1.55 (s, 6H). ES/MS 497.2 (M+H+).

Example 150: (R)-2-((1-(2-hydroxyacetyl)pyrrolidin-3-yl)oxy)-5-(2-(4-(prop-1-en-2-yl)phenyl)-1H-pyrrolo[2,3-b]pyridin-4-yl)benzonitrile

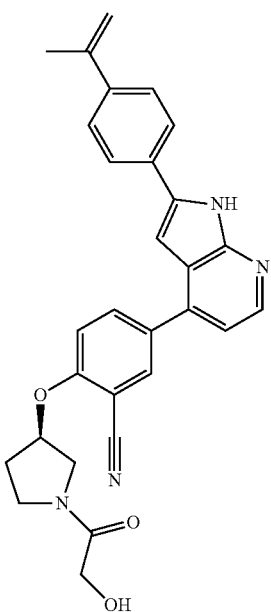 [SMILES: C=C(C)c1ccc(-c2cc3c(-c4ccc(O[C@@H]5CCN(C(=O)CO)C5)c(C#N)c4)ccnc3[nH]2)cc1]

A solution of (R)-2-((1-(2-hydroxyacetyl)pyrrolidin-3-yl)oxy)-5-(2-(4-(2-hydroxypropan-2-yl)phenyl)-1H-pyrrolo[2,3-b]pyridin-4-yl)benzonitrile (128 mg, 258 mmol) in 1 mL THF and 0.4 mL TFE was treated with 0.5 mL TFA and allowed to stand for 20 min. Purification of this mixture by RP high performance liquid chromatography gave (R)-2-((1-(2-hydroxyacetyl)pyrrolidin-3-yl)oxy)-5-(2-(4-(prop-1-en-2-yl)phenyl)-1H-pyrrolo[2,3-b]pyridin-4-yl)benzonitrile. 1H NMR (400 MHz, DMSO-d6) δ 8.80 (d, J=6.1 Hz, 1H), 8.76-8.55 (m, 2H), 8.49-8.30 (m, 2H), 8.24-8.13 (m, 2H), 8.00 (dd, J=6.1, 3.2 Hz, 1H), 7.90 (dd, J=8.9, 3.1 Hz, 1H), 7.79 (d, J=2.3 Hz, 1H), 6.09 (s, 1H), 5.86 (d, J=25.6 Hz, 1H), 5.76 (s, 1H), 4.68 (s, 1H), 4.61 (d, J=5.6 Hz, 1H), 4.46-4.23 (m, 2H), 4.24-4.04 (m, 2H), 2.92 (d, J=7.8 Hz, 1H), 2.82 (s, 1H), 2.73 (s, 3H). ES/MS 479.3 (M+H+).

Example 151: (R)-5-(2-(4-(2-hydroxypropan-2-yl)phenyl)-1H-pyrrolo[2,3-b]pyridin-4-yl)-2-(pyrrolidin-3-yloxy)benzonitrile

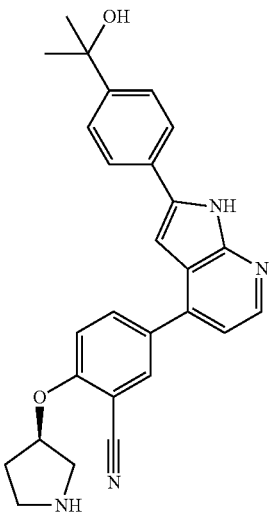 [SMILES: CC(C)(O)c1ccc(-c2cc3c(-c4ccc(O[C@@H]5CCNC5)c(C#N)c4)ccnc3[nH]2)cc1]

(R)-5-(2-(4-(2-hydroxypropan-2-yl)phenyl)-1-tosyl-1H-pyrrolo[2,3-b]pyridin-4-yl)-2-(pyrrolidin-3-yloxy)benzonitrile was prepared using an analogous to Example 149. ES/MS 439.2 (M+H+).

Example 152: 2-((1-(2-aminoacetyl)piperidin-4-yl)oxy)-5-(2-(4-morpholinophenyl)-1H-pyrrolo[2,3-b]pyridin-4-yl)benzonitrile

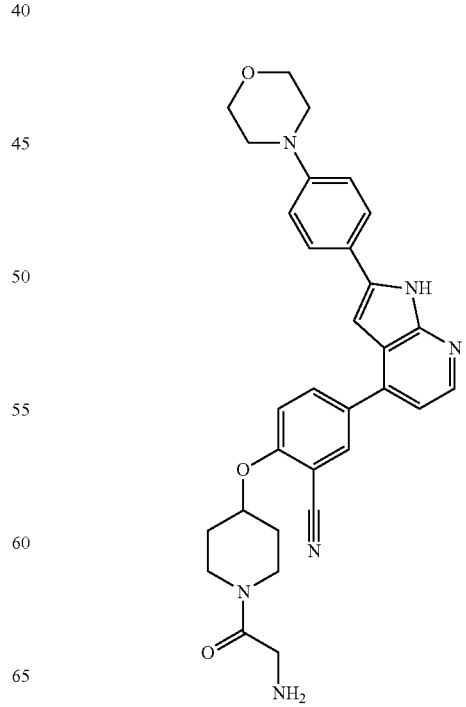

2-((1-(2-Aminoacetyl)piperidin-4-yl)oxy)-5-(2-(4-morpholinophenyl)-1H-pyrrolo[2,3-b]pyridin-4-yl)benzonitrile prepared using the same procedure as Example 149. 1H NMR (400 MHz, DMSO-d6) δ 12.19 (s, 1H), 8.21 (d, J=5.0 Hz, 1H), 8.18-8.06 (m, 2H), 8.00 (s, 3H), 7.86 (d, J=8.8 Hz, 2H), 7.54 (d, J=8.9 Hz, 1H), 7.19 (d, J=5.1 Hz, 1H), 7.01 (d, J=8.7 Hz, 2H), 6.98 (d, J=2 Hz, 1H), 5.05-4.97 (m, 1H), 3.94 (d, J=6.1 Hz, 2H), 3.80-3.72 (m, 1H), 3.74 (t, J=4.8 Hz, 4H), 3.65-3.50 (m, 2H), 3.48-3.34 (m, 1H), 3.18 (t, J=4.9 Hz, 4H), 2.13-1.92 (m, 2H), 1.88-1.66 (m, 2H). ES/MS 537.2 (M+H⁺).

Example 153: 2-((1-acetylazetidin-3-yl)oxy)-5-(2-(4-morpholinophenyl)-1H-pyrrolo[2,3-b]pyridin-4-yl)benzonitrile

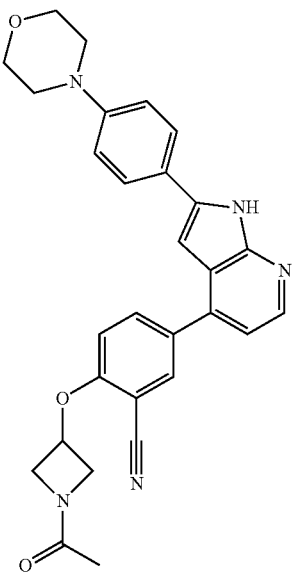 [SMILES: CC(=O)N1CC(Oc2ccc(-c3ccnc4[nH]c(-c5ccc(N6CCOCC6)cc5)cc34)cc2C#N)C1]

2-((1-Acetylazetidin-3-yl)oxy)-5-(2-(4-morpholinophenyl)-1H-pyrrolo[2,3-b]pyridin-4-yl)benzonitrile was prepared using the same procedure as Example 149. ES/MS 494.3 (M+H⁺).

Example 154: 2-((1-(2-hydroxyacetyl)azetidin-3-yl)oxy)-5-(2-(4-morpholinophenyl)-1H-pyrrolo[2,3-b]pyridin-4-yl)benzonitrile

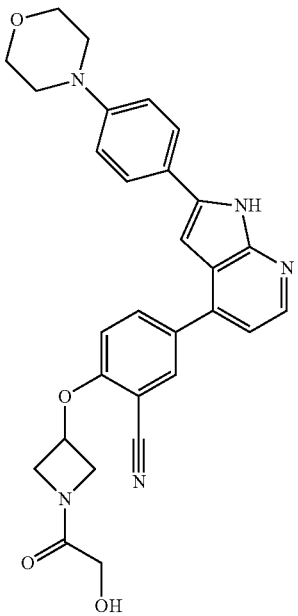 [SMILES: N#Cc1cc(-c2ccnc3[nH]c(-c4ccc(N5CCOCC5)cc4)cc23)ccc1OC1CN(C(=O)CO)C1]

2-((1-(2-hydroxyacetyl)azetidin-3-yl)oxy)-5-(2-(4-morpholinophenyl)-1H-pyrrolo[2,3-b]pyridin-4-yl)benzonitrile was prepared using the same procedure as Example 149. ES/MS 510.3 (M+H⁺).

Example 155: 5-(6-(6-morpholinopyridin-3-yl)-7H-pyrrolo[2,3-d]pyrimidin-4-yl)-2-((tetrahydro-2H-pyran-4-yl)oxy)benzonitrile

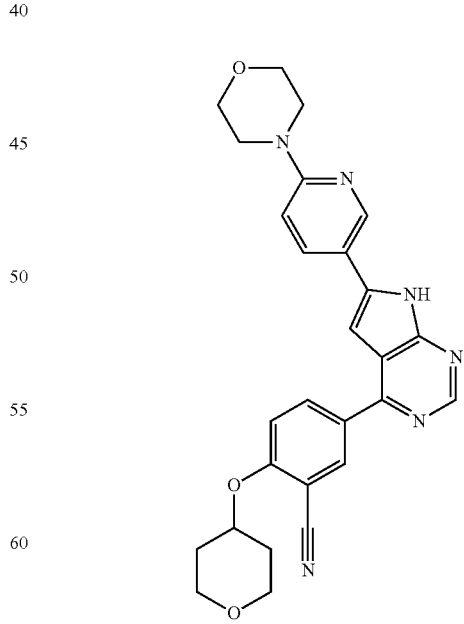

Step 1: Preparation of 5-(6-(6-morpholinopyridin-3-yl)-7-((2-(trimethylsilyl)ethoxy)methyl)-7H-pyrrolo[2,3-d]pyrimidin-4-yl)-2-((tetrahydro-2H-pyran-4-yl)oxy)benzonitrile: A solution of 4-(5-(4-chloro-7-((2-(trimethylsilyl)ethoxy)methyl)-7H-pyrrolo[2,3-d]pyrimidin-6-yl)pyridin-2-yl)morpholine (225 mg, 0.504 mmol), 2-((tetrahydro-2H-pyran-4-yl)oxy)-5-(4,4,5,5-tetramethyl-1,3,2-dioxaborolan-2-yl)benzonitrile (199 mg, 0.605 mmol), aqueous Na₂CO₃ (0.601 mL, 1.20 mmol, 2N) and aqueous NaHCO₃ (0.24 mL, 0.24 mmol, 1N) in 6 mL dioxane was treated with [1,1'-bis(diphenylphosphino)ferrocene]dichloropalladium(II)-complex with dichloromethane (39 mg, 0.048 mmol) and heated to 100° C. for 1 h. The reaction was cooled to rt and diluted with DCM, dried with MgSO₄ and filtered. The residue was purified by silica gel chromatography to provide 5-(6-(6-morpholinopyridin-3-yl)-7-((2-(trimethylsilyl)ethoxy)methyl)-7H-pyrrolo[2,3-d]pyrimidin-4-yl)-2-((tetrahydro-2H-pyran-4-yl)oxy)benzonitrile (119 mg, 64% yield). ES/MS 613.3 (M+H⁺).

Step 2: Preparation of 5-(6-(6-morpholinopyridin-3-yl)-7H-pyrrolo[2,3-d]pyrimidin-4-yl)-2-((tetrahydro-2H-pyran-4-yl)oxy)benzonitrile: 5-(6-(6-Morpholinopyridin-3-yl)-7-((2-(trimethylsilyl)ethoxy)methyl)-7H-pyrrolo[2,3-d]pyrimidin-4-yl)-2-((tetrahydro-2H-pyran-4-yl)oxy)benzonitrile (199 mg, 0.325 mmol), was taken up in 10 mL DCM and 10 mL TFA and stirred for 10 min at rt. The reaction was concentrated under vacuum and the residue taken up in dioxane and concentrated a second time. The residue was dissolved in 10 mL MeOH and treated with 2 mL TEA. After stirring for 30 min at rt, the reaction was concentrated and the residue purified by silica gel chromatography to provide 5-(6-(6-morpholinopyridin-3-yl)-7H-pyrrolo[2,3-d]pyrimidin-4-yl)-2-((tetrahydro-2H-pyran-4-yl)oxy)benzonitrile. δ 1H NMR (400 MHz, DMSO-d6) δ 12.65 (s, 1H), 8.83 (d, J=2.4 Hz, 1H), 8.76 (s, 1H), 8.55-8.50 (m, 2H), 8.21 (dd, J=9.0, 2.5 Hz, 1H), 7.53 (d, J=8.8 Hz, 1H), 7.40 (d, J=1.9 Hz, 1H), 6.97 (d, J=9.0 Hz, 1H), 4.96 (dq, J=8.1, 4.0 Hz, 1H), 3.87 (ddd, J=10.4, 7.5, 4.1 Hz, 2H), 3.70 (t, J=4.8 Hz, 4H), 3.62-3.48 (m, 6H), 2.10-2.00 (m, 2H), 1.71 (dtd, J=12.3, 8.1, 3.8 Hz, 2H). ES/MS 483.3 (M+H⁺).

Example 156: Preparation of 5-(6-(3-fluoro-4-morpholinophenyl)-7H-pyrrolo[2,3-d]pyrimidin-4-yl)-2-((tetrahydro-2H-pyran-4-yl)oxy)benzonitrile

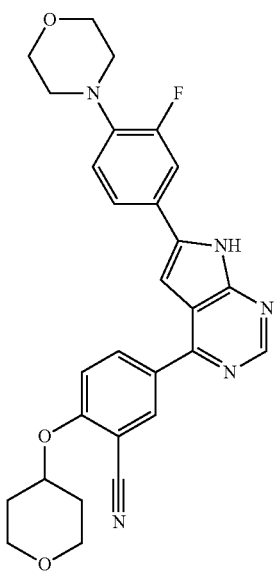 [SMILES: N#Cc1cc(-c2ncnc3[nH]c(-c4ccc(N5CCOCC5)c(F)c4)cc23)ccc1OC1CCOCC1]

5-(6-(3-fluoro-4-morpholinophenyl)-7H-pyrrolo[2,3-d]pyrimidin-4-yl)-2-((tetrahydro-2H-pyran-4-yl)oxy) was prepared in analogous fashion to Example 155. δ 1H NMR (400 MHz, DMSO-d6) δ 12.68 (s, 1H), 8.78 (s, 1H), 8.58-8.51 (m, 2H), 7.93 (dd, J=14.6, 2.0 Hz, 1H), 7.83 (dd, J=8.4, 2.0 Hz, 1H), 7.56-7.44 (m, 2H), 7.12 (t, J=8.9 Hz, 1H), 4.96 (dt, J=8.0, 4.1 Hz, 1H), 3.98-3.82 (m, 3H), 3.75 (t, J=4.6 Hz, 4H), 3.61-3.47 (m, 1H), 3.08 (t, J=4.6 Hz, 4H), 2.05 (d, J=13.7 Hz, 2H), 1.71 (dtd, J=12.3, 8.1, 3.8 Hz, 2H). ES/MS 500.2 (M+H⁺).

Example 157: 2-((1-(2-hydroxyacetyl)piperidin-4-yl)oxy)-5-(6-(4-(4-(oxetan-3-yl)piperazin-1-yl)phenyl)-7H-pyrrolo[2,3-d]pyrimidin-4-yl)benzonitrile

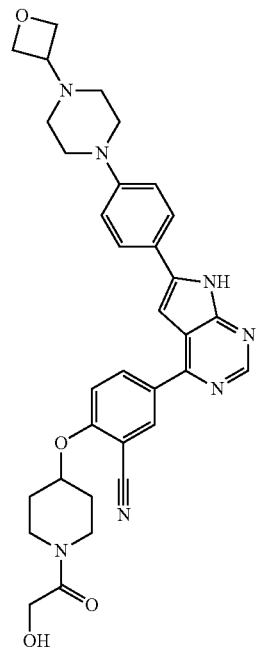 [SMILES: N#Cc1cc(-c2ncnc3[nH]c(-c4ccc(N5CCN(C6COC6)CC5)cc4)cc23)ccc1OC1CCN(C(=O)CO)CC1]

5-(6-(3-fluoro-4-morpholinophenyl)-7H-pyrrolo[2,3-d]pyrimidin-4-yl)-2-((tetrahydro-2H-pyran-4-yl)oxy) was prepared in analogous fashion to Example 155. δ 1H NMR (400 MHz, DMSO-d6) δ 8.78 (s, 1H), 8.53 (d, J=8.4 Hz, 2H), 7.98 (d, J=8.7 Hz, 2H), 7.56 (d, J=8.9 Hz, 1H), 7.38 (d, J=1.9 Hz, 1H), 7.14 (d, J=8.7 Hz, 2H), 5.02 (s, 1H), 4.77 (d, J=6.5 Hz, 4H), 4.43 (s, 1H), 4.12 (s, 2H), 4.10-3.95 (m, 1H), 3.77-3.69 (m, 1H), 3.61-3.45 (m, 3H), 3.37 (s, 1H), 3.25-2.90 (m, 4H), 3.25-2.90 (m, 2H), 2.007-1.94 (m, 2H), 1.81-1.65 (m, 2H). ES/MS 594.2 (M+H⁺).

Example 158: 5-(6-(3-fluoro-4-morpholinophenyl)-7H-pyrrolo[2,3-d]pyrimidin-4-yl)-2-((1-(2-hydroxy-acetyl)piperidin-4-yl)oxy)benzonitrile

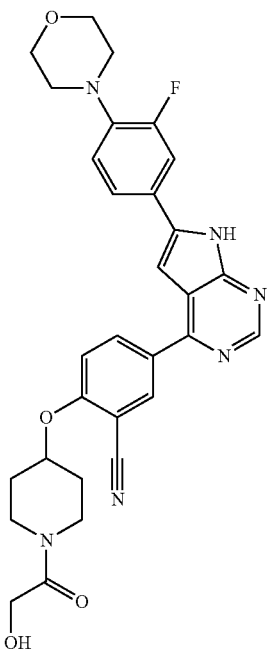 [SMILES: N#Cc1cc(-c2ncnc3[nH]c(-c4ccc(N5CCOCC5)c(F)c4)cc23)ccc1OC1CCN(C(=O)CO)CC1]

5-(6-(3-fluoro-4-morpholinophenyl)-7H-pyrrolo[2,3-d]pyrimidin-4-yl)-2-((1-(2-hydroxyacetyl)piperidin-4-yl)oxy)benzonitrile was prepared in analogous fashion to Example 155. 1H NMR (400 MHz, DMSO-d6) δ 8.81 (s, 1H), 8.53 (d, J=8.2 Hz, 2H), 7.94 (dd, J=14.5, 2.0 Hz, 1H), 7.90-7.79 (m, 1H), 7.56 (d, J=8.8 Hz, 1H), 7.52 (d, J=1.9 Hz, 1H), 7.13 (t, J=8.9 Hz, 1H), 5.03 (s, 1H), 4.12 (s, 2H), 3.78-3.69 (m, 5H), 3.61-3.46 (m, 2H), 3.40-3.32 (m, 1H), 3.12-3.08 (m, 4H), 2.08-7.95 (m, 2H), 1.81-1.66 (m, 2H). ES/MS 557.2 (M+H+).

Example 159: Methyl 4-(4-(3-cyano-4-((1-(2-hydroxyacetyl)piperidin-4-yl)oxy)phenyl)-7H-pyrrolo[2,3-d]pyrimidin-6-yl)benzoate

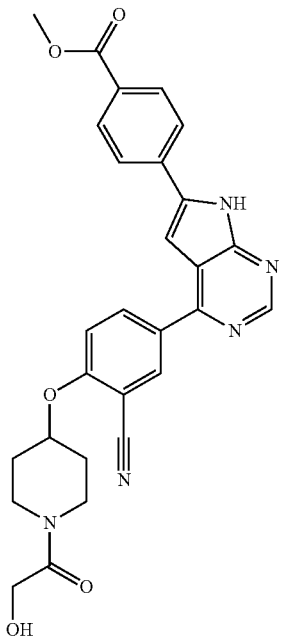

Methyl 4-(4-(3-cyano-4-((1-(2-hydroxyacetyl)piperidin-4-yl)oxy)phenyl)-7H-pyrrolo[2,3-d]pyrimidin-6-yl)benzoate was prepared in analogous fashion to Example 155. 1H NMR (400 MHz, DMSO-d6) δ 12.96 (s, 1H), 8.86 (s, 1H), 8.56 (d, J=6.5 Hz, 2H), 8.23 (d, J=8.2 Hz, 2H), 8.06 (d, J=8.3 Hz, 2H), 7.72 (d, J=1.9 Hz, 1H), 7.57 (d, J=9.7 Hz, 1H), 5.03 (s, 1H), 4.13 (s, 2H), 3.88 (s, 3H), 3.73 (s, 1H), 3.54 (s, 3H), 3.37 (s, 1H), 2.01 (s, 2H), 1.75 (s, 2H). ES/MS 512.2 (M+H+).

Example 160: 2-((1-(2-Hydroxyacetyl)piperidin-4-yl)oxy)-5-(6-(4-(morpholine-4-carbonyl)phenyl)-7H-pyrrolo[2,3-d]pyrimidin-4-yl)benzonitrile

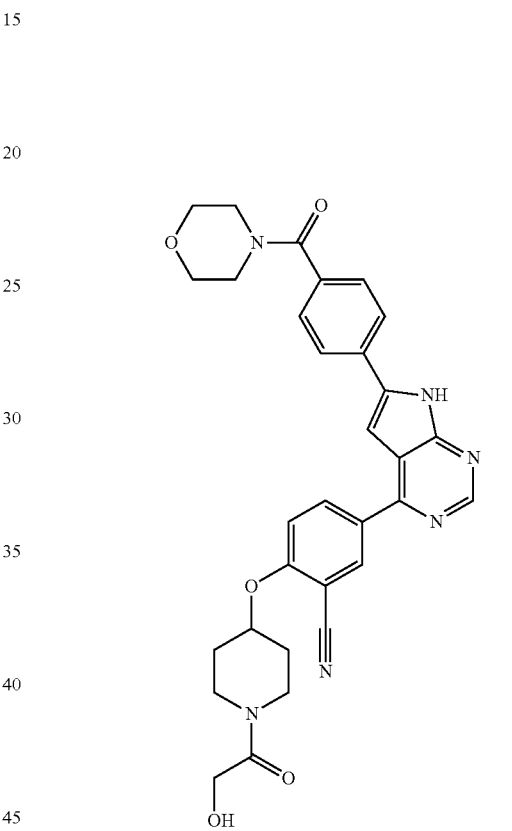

Step 1: Preparation of 4-(4-(3-cyano-4-((1-(2-hydroxyacetyl)piperidin-4-yl)oxy)phenyl)-7-((2-(trimethylsilyl)ethoxy)methyl)-7H-pyrrolo[2,3-d]pyrimidin-6-yl)benzoic acid: A solution of methyl 4-(4-(3-cyano-4-((1-(2-hydroxyacetyl)piperidin-4-yl)oxy)phenyl)-7-((2-(trimethylsilyl)ethoxy)methyl)-7H-pyrrolo[2,3-d]pyrimidin-6-yl)benzoate (1.04 g, 1.62 mmol) in 5 mL THF and 4 mL MeOH was treated with aq. LiOH (2.43 mL, 2.43 mmol, 1.0 M) and the reaction diluted for 2 h. The mixture was diluted with pH 3 citric acid buffer and DCM, and the organic layer was separated, dried with Na2SO4 and concentrated to 4-(4-(3-cyano-4-((1-(2-hydroxyacetyl)piperidin-4-yl)oxy)phenyl)-7-((2-(trimethylsilyl)ethoxy)methyl)-7H-pyrrolo[2,3-d]pyrimidin-6-yl)benzoic acid (1.017 g, 90% Yield). ES/MS 628.2 (M+H+).

Step 2: Preparation of 2-((1-(2-hydroxyacetyl)piperidin-4-yl)oxy)-5-(6-(4-(morpholine-4-carbonyl)phenyl)-7-((2-(trimethylsilyl)ethoxy)methyl)-7H-pyrrolo[2,3-d]pyrimidin-4-yl)benzonitrile: 4-(4-(3-Cyano-4-((1-(2-hydroxyacetyl)piperidin-4-yl)oxy)phenyl)-7-((2-(trimethylsilyl)ethoxy)methyl)-7H-pyrrolo[2,3-d]pyrimidin-6-yl)benzoic acid (150 mg, 0.238 mmol) and morpholine (26 mg, 0.299 mmol) in 3 mL DMF was treated with HATU (118 mg, 0.311 mmol) and DIEA (76 mg, 0.597 mmol) and stirred for 16 h at rt. The mixture was then partitioned between EtOAc and pH 7 phosphate buffe, washed 2 times with 5% LiCl solution, dried with $Na_2SO_4$ and concentrated. Purification by silica gel chromatography provided 2-((1-(2-hydroxyacetyl)piperidin-4-yl)oxy)-5-(6-(4-(morpholine-4-carbonyl)phenyl)-7-((2-(trimethylsilyl)ethoxy)methyl)-7H-pyrrolo[2,3-d]pyrimidin-4-yl)benzonitrile (167 mg, 80% Yield). ES/MS 697.2 (M+H$^+$).

Step 3: Preparation of 2-((1-(2-hydroxyacetyl)piperidin-4-yl)oxy)-5-(6-(4-(morpholine-4-carbonyl)phenyl)-7H-pyrrolo[2,3-d]pyrimidin-4-yl)benzonitrile: A solution of 2-((1-(2-hydroxyacetyl)piperidin-4-yl)oxy)-5-(6-(4-(morpholine-4-carbonyl)phenyl)-7-((2-(trimethylsilyl)ethoxy)methyl)-7H-pyrrolo[2,3-d]pyrimidin-4-yl)benzonitrile (133 mg, 0.191 mmol) in 1 mL THF was diluted with 1N TBAF (1.9 mL, 1.9 mmol) and sealed in a glass vial. Reaction stirred at 70 C for 24 h. The mixture was diluted with EtOAc and brine, filtered and the organic layer concentrated. Purified by reverse phase HPLC to provide 2-((1-(2-hydroxyacetyl)piperidin-4-yl)oxy)-5-(6-(4-(morpholine-4-carbonyl)phenyl)-7H-pyrrolo[2,3-d]pyrimidin-4-yl)benzonitrile. 1H NMR (400 MHz, DMSO-d6) δ 12.98-12.88 (m, 1H), 8.85 (s, 1H), 8.54 (h, J=2.3 Hz, 2H), 8.21-8.07 (m, 2H), 7.64 (d, J=1.9 Hz, 1H), 7.56 (dd, J=11.5, 9.0 Hz, 3H), 5.10-4.99 (m, 1H), 4.13 (s, 2H), 3.71 (d, J=80.1 Hz, 13H), 2.03 (m, 2H), 1.90-1.65 (m, 2H). ES/MS 567.2 (M+H$^+$).

Example 161: 2-((1-(2-Hydroxyacetyl)piperidin-4-yl)oxy)-5-(6-(4-(4-methylpiperazine-1-carbonyl)phenyl)-7H-pyrrolo[2,3-d]pyrimidin-4-yl)benzonitrile

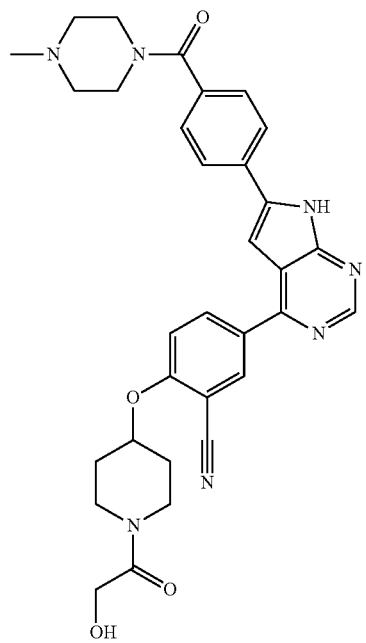 [SMILES: CN1CCN(C(=O)c2ccc(-c3cc4c(-c5ccc(OC6CCN(C(=O)CO)CC6)c(C#N)c5)ncnc4[nH]3)cc2)CC1]

2-((1-(2-Hydroxyacetyl)piperidin-4-yl)oxy)-5-(6-(4-(4-methylpiperazine-1-carbonyl)phenyl)-7H-pyrrolo[2,3-d]pyrimidin-4-yl)benzonitrile was prepared in analogous fashion to Example 160. 1H NMR (400 MHz, Methanol-d4) δ 8.86 (s, 1H), 8.45 (d, J=0.9 Hz, 1H), 8.43 (d, J=2.3 Hz, 1H), 8.12-8.06 (m, 2H), 7.65 (d, J=8.4 Hz, 2H), 7.52 (d, J=8.6 Hz, 1H), 7.43 (s, 1H), 5.04 (dd, J=6.7, 3.4 Hz, 1H), 4.28 (s, 3H), 3.78 (d, J=5.4 Hz, 2H), 3.69 (d, J=9.9 Hz, 1H), 3.62-3.38 (m, 3H), 3.24-3.11 (m, 2H), 3.55-3.45 (m, 1H), 2.97 (s, 4H), 2.10 (d, J=12.5 Hz, 3H), 2.02-1.86 (m, 2H). ES/MS 580.3 (M+H$^+$).

Example 162: 2-((1-(2-Hydroxyacetyl)piperidin-4-yl)oxy)-5-(6-(4-(pyrrolidine-1-carbonyl)phenyl)-7H-pyrrolo[2,3-d]pyrimidin-4-yl)benzonitrile

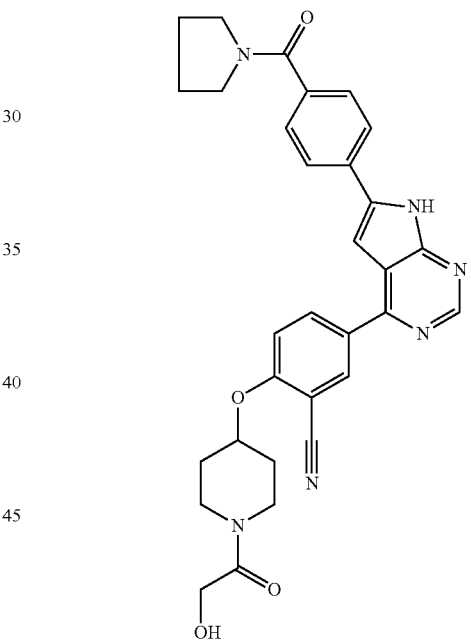

2-((1-(2-Hydroxyacetyl)piperidin-4-yl)oxy)-5-(6-(4-(pyrrolidine-1-carbonyl)phenyl)-7H-pyrrolo[2,3-d]pyrimidin-4-yl)benzonitrile was prepared in analogous fashion to Example 160. 1H NMR (400 MHz, DMSO-d6) δ 12.90 (s, 1H), 8.84 (s, 1H), 8.59-8.51 (m, 2H), 8.17-8.09 (m, 2H), 7.68-7.60 (m, 3H), 7.57 (d, J=9.8 Hz, 1H), 5.09-5.00 (m, 1H), 4.14-4.11 (m, 3H), 3.77-3.69 (m, 1H), 3.64-3.28 (m, 8H), 2.08-1.92 (m, 2H), 1.92-1.61 (m, 6H). ES/MS 551.2 (M+H$^+$).

Example 163: Preparation of 4-(4-(3-Cyano-4-((1-(2-hydroxyacetyl)piperidin-4-yl)oxy)phenyl)-7H-pyrrolo[2,3-d]pyrimidin-6-yl)-N-(oxetan-3-yl)benzamide

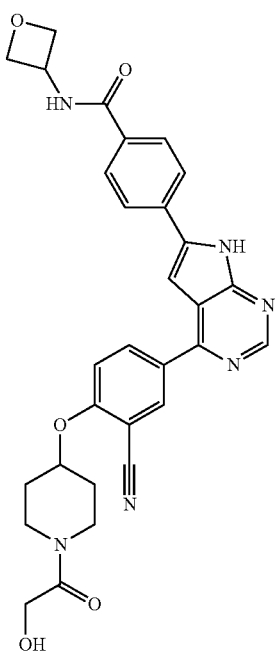 [SMILES: N#Cc1cc(-c2ncnc3[nH]c(-c4ccc(C(=O)NC5COC5)cc4)cc23)ccc1OC1CCN(C(=O)CO)CC1]

4-(4-(3-Cyano-4-((1-(2-hydroxyacetyl)piperidin-4-yl)oxy)phenyl)-7H-pyrrolo[2,3-d]pyrimidin-6-yl)-N-(oxetan-3-yl)benzamide was prepared in analogous fashion to Example 160. 1H NMR (400 MHz, Methanol-d4) δ 8.86 (d, J=5.4 Hz, 1H), 8.45 (d, J=8.2 Hz, 2H), 8.23 (d, J=8.4 Hz, 2H), 8.10 (d, J=8.5 Hz, 2H), 7.53 (s, 1H), 7.42 (s, 1H), 5.07-5.01 (m, 1H), 4.90-4.73 (m, 1H), 4.65-4.50 (m, 2H), 4.29 (s, 2H), 3.91 (dd, J=11.7, 4.4 Hz, 1H), 3.86-3.74 (m, 4H), 3.54-3.46 (m, 1H), 2.15-2.03 (m, 2H), 1.86-2.01 (m, 2H). ES/MS 553.2 (M+H+).

Example 164: 2-(2-Oxaspiro[3.3]heptan-6-yloxy)-5-(6-(4-morpholinophenyl)-7H-pyrrolo[2,3-d]pyrimidin-4-yl)benzonitrile

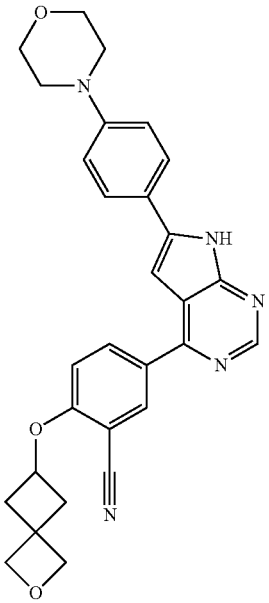 [SMILES: N#Cc1cc(-c2ncnc3[nH]c(-c4ccc(N5CCOCC5)cc4)cc23)ccc1OC1CC2(COC2)C1]

2-(2-)Oxaspiro[3.3]heptan-6-yloxy)-5-(6-(4-morpholinophenyl)-7H-pyrrolo[2,3-d]pyrimidin-4-yl)benzonitrile was prepared in analogous fashion to Example 149. ES/MS 494.2 (M+H+).

Example 165: Ethyl 3-(4-(3-cyano-4-((1-(2-hydroxyacetyl)piperidin-4-yl)oxy)phenyl)-7H-pyrrolo[2,3-d]pyrimidin-6-yl)benzoate

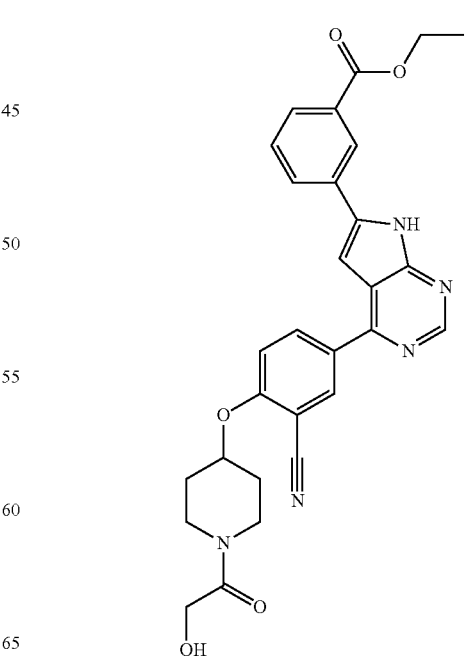

Ethyl 3-(4-(3-cyano-4-((1-(2-hydroxyacetyl)piperidin-4-yl)oxy)phenyl)-7H-pyrrolo[2,3-d]pyrimidin-6-yl)benzoate was prepared in analogous fashion to Example 160. ES/MS 526.2 (M+H$^+$).

Example 166: Preparation of 2-(3,3-Bis(hydroxymethyl)cyclobutoxy)-5-(6-(4-morpholinophenyl)-7H-pyrrolo[2,3-d]pyrimidin-4-yl)benzonitrile

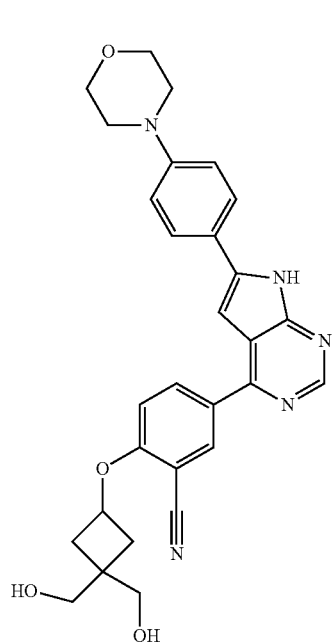 [SMILES: N#Cc1cc(-c2ncnc3[nH]c(-c4ccc(N5CCOCC5)cc4)cc23)ccc1OC1CC(CO)(CO)C1]

2-(3,3-Bis(hydroxymethyl)cyclobutoxy)-5-(6-(4-morpholinophenyl)-7H-pyrrolo[2,3-d]pyrimidin-4-yl)benzonitrile was prepared in analogous fashion to Example 155. 1H NMR (400 MHz, Methanol-d4) δ 8.87 (s, 1H), 8.44-8.28 (m, 2H), 7.86 (d, J=8.8 Hz, 2H), 7.34-7.22 (m, 2H), 7.09 (d, J=8.8 Hz, 2H), 5.09-4.95 (m, 1H), 3.90-3.80 (m, 5H), 3.65 (s, 2H), 3.59 (s, 2H), 3.31-3.26 (m, 4H), 2.59-2.45 (m, 2H), 2.26-2.15 (m, 1H). ES/MS 544.2 (M+H$^+$).

Example 167: 2-((1-(2-Hydroxyacetyl)piperidin-4-yl)oxy)-5-(6-(3-(pyrrolidine-1-carbonyl)phenyl)-7H-pyrrolo[2,3-d]pyrimidin-4-yl)benzonitrile

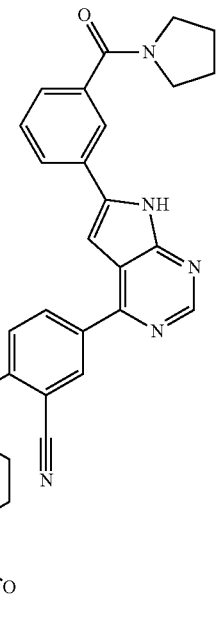

2-((1-(2-Hydroxyacetyl)piperidin-4-yl)oxy)-5-(6-(3-(pyrrolidine-1-carbonyl)phenyl)-7H-pyrrolo[2,3-d]pyrimidin-4-yl)benzonitrile was prepared in analogous fashion to Example 160. $^1$H NMR (400 MHz, DMSO-d6) δ 12.87 (s, 1H), 8.84 (s, 1H), 8.64-8.49 (m, 2H), 8.19 (d, J=1.7 Hz, 1H), 8.15 (d, J=7.9 Hz, 1H), 7.64 (d, J=1.9 Hz, 1H), 7.62-7.44 (m, 3H), 5.09-4.96 (m, 1H), 4.12 (s, 2H), 3.46 (dt, J=28.4, 6.6 Hz, 2H), 3.40-3.31 (m, 1H), 3.19-3.07 (m, 6H), 2.08-1.93 (m, 2H), 1.93-1.65 (m, 6H). ES/MS 553.4 (M+H$^+$).

Example 168: 2-(4-(4-(3-Cyano-4-((tetrahydro-2H-pyran-4-yl)oxy)phenyl)-7H-pyrrolo[2,3-d]pyrimidin-6-yl)phenyl)acetic acid

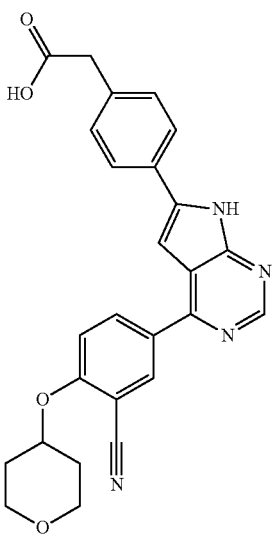 [SMILES: N#Cc1cc(-c2ncnc3[nH]c(-c4ccc(CC(=O)O)cc4)cc23)ccc1OC1CCOCC1]

2-(4-(4-(3-Cyano-4-((tetrahydro-2H-pyran-4-yl)oxy)phenyl)-7H-pyrrolo[2,3-d]pyrimidin-6-yl)phenyl)acetic acid was prepared in analogous fashion to Example 160. δ 1H NMR (400 MHz, DMSO-d6) δ 12.79 (s, 1H), 8.82 (s, 1H), 8.60-8.46 (m, 2H), 8.01 (d, J=8.2 Hz, 2H), 7.55 (d, J=9.7 Hz, 1H), 7.50 (d, J=1.9 Hz, 1H), 7.39 (d, J=8.1 Hz, 2H), 4.97 (dt, J=7.9, 4.0 Hz, 1H), 3.88 (dt, J=10.5, 4.6 Hz, 2H), 3.63 (s, 2H), 3.56 (ddd, J=11.4, 8.2, 3.1 Hz, 2H), 2.05 (d, J=12.8 Hz, 2H), 1.71 (dtd, J=12.3, 8.0, 3.8 Hz, 2H). ES/MS 455.1 (M+H⁺).

Example 169: 2-(2-(4-(2-Methoxypropan-2-yl)phenyl)-1H-pyrrolo[2,3-b]pyridin-4-yl)-5-((tetrahydro-2H-pyran-4-yl)oxy)isonicotinonitrile

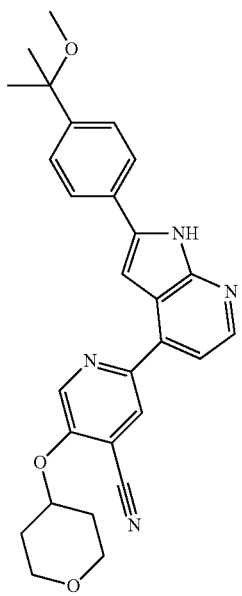 [SMILES: COC(C)(C)c1ccc(-c2cc3c(-c4cc(C#N)c(OC5CCOCC5)cn4)ccnc3[nH]2)cc1]

2-(2-(4-(2-Methoxypropan-2-yl)phenyl)-1H-pyrrolo[2,3-b]pyridin-4-yl)-5-((tetrahydro-2H-pyran-4-yl)oxy)isonicotinonitrile was prepared in analogous fashion to Example 155. 1H NMR (400 MHz, DMSO-d6) δ 12.31 (s, 1H), 9.02 (s, 1H), 8.51 (s, 1H), 8.29 (d, J=5.1 Hz, 1H), 7.96 (d, J=8.4 Hz, 2H), 7.61 (d, J=5 Hz, 1H), 7.52 (d, J=2 Hz, 1H), 7.47 (dd, J=8.4, 2 Hz, 2H), 5.11 (dt, J=8.3, 4.2 Hz, 1H), 3.89 (dt, J=10.3, 4.6 Hz, 2H), 3.59-3.52 (m, 2H), 3.00 (s, 3H), 2.22-2.05 (m, 2H), 1.74 (dq, J=8.6, 4.3 Hz, 2H), 1.47 (s, 6H). ES/MS 469.2 (M+H⁺).

Example 170: 2-(2-(4-(2-Hydroxypropan-2-yl)phenyl)-1H-pyrrolo[2,3-b]pyridin-4-yl)-5-((tetrahydro-2H-pyran-4-yl)oxy)isonicotinonitrile

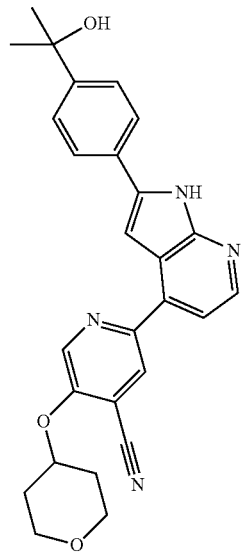 [SMILES: CC(C)(O)c1ccc(-c2cc3c(-c4cc(C#N)c(OC5CCOCC5)cn4)ccnc3[nH]2)cc1]

2-(2-(4-(2-Hydroxypropan-2-yl)phenyl)-1H-pyrrolo[2,3-b]pyridin-4-yl)-5-((tetrahydro-2H-pyran-4-yl)oxy)isonicotinonitrile was prepared in analogous fashion to Example 155. 1H NMR (400 MHz, DMSO-d6) δ 12.26 (s, 1H), 9.02 (s, 1H), 8.51 (s, 1H), 8.28 (d, J=5.1 Hz, 1H), 7.93-7.89 (m, 2H), 7.60 (d, J=5.1 Hz, 1H), 7.58-7.52 (m, 2H), 7.50 (d, J=2.1 Hz, 1H), 5.11 (dt, J=8.3, 4.2 Hz, 1H), 5.05 (s, 1H), 3.89 (dt, J=10.3, 4.6 Hz, 2H), 3.61-3.52 (m, 2H), 2.10 (d, J=13.4 Hz, 2H), 1.73 (dtd, J=12.8, 8.5, 3.9 Hz, 2H), 1.45 (s, 6H). ES/MS 455.3 (M+H⁺).

Example 171: 3-(4-(3-cyano-4-((tetrahydro-2H-pyran-4-yl)oxy)phenyl)-7H-pyrrolo[2,3-d]pyrimidin-6-yl)benzamide

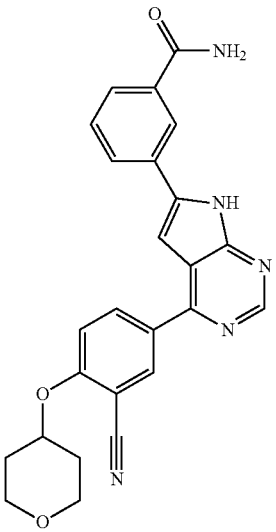 [SMILES: N#Cc1cc(-c2ncnc3[nH]c(-c4cccc(C(N)=O)c4)cc23)ccc1OC1CCOCC1]

3-(4-(3-Cyano-4-((tetrahydro-2H-pyran-4-yl)oxy)phenyl)-7H-pyrrolo[2,3-d]pyrimidin-6-yl)benzamide was prepared in analogous fashion to Example 160. 1H NMR (400 MHz, DMSO-d6) δ 12.81 (s, 1H), 8.82 (s, 1H), 8.60-8.49 (m, 3H), 8.18 (dt, J=7.9, 1.4 Hz, 1H), 8.03 (s, 1H), 7.87 (dt, J=7.8, 1.3 Hz, 1H), 7.66-7.48 (m, 4H), 4.96 (dq, J=8.1, 4.0 Hz, 1H), 3.88 (dt, J=10.5, 4.5 Hz, 2H), 3.56 (ddd, J=11.5, 8.3, 3.1 Hz, 2H), 2.05 (dd, J=10.2, 5.8 Hz, 2H), 1.71 (dtd, J=12.4, 8.2, 3.9 Hz, 2H). ES/MS 440.2 (M+H⁺).

Example 172: 5-(5-fluoro-2-(3-methoxy-4-morpholinophenyl)-1H-pyrrolo[2,3-b]pyridin-4-yl)-2-((tetrahydro-2H-pyran-4-yl)oxy)benzonitrile

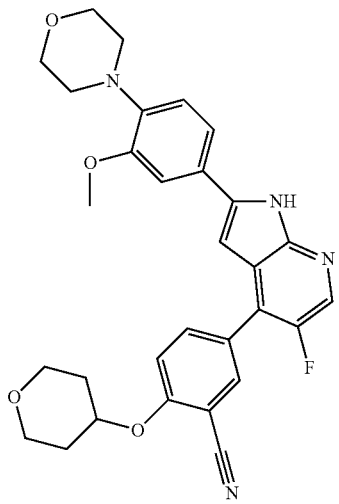 [SMILES: COc1cc(-c2cc3c(-c4ccc(OC5CCOCC5)c(C#N)c4)c(F)cnc3[nH]2)ccc1N1CCOCC1]

Step 1: Preparation of 5-(5-fluoro-2-(3-methoxy-4-morpholinophenyl)-1-tosyl-1H-pyrrolo[2,3-b]pyridin-4-yl)-2-((tetrahydro-2H-pyran-4-yl)oxy)benzonitrile: A solution of 4-(4-(4-chloro-5-fluoro-1-tosyl-1H-pyrrolo[2,3-b]pyridin-2-yl)-2-methoxyphenyl)morpholine (157 mg, 0.477 mol), 2-((tetrahydro-2H-pyran-4-yl)oxy)-5-(4,4,5,5-tetramethyl-1,3,2-dioxaborolan-2-yl)benzonitrile (271 mg, 0.525 mmol) and 1,1'-Bis(diphenylphosphino)ferrocene]dichloropalladium(II) (35 mg, 0.0477 mmol) in 3 mL dioxane was treated with 2N Na₂CO₃ (0.716 mL, 1.4 mmol) and heated to 100° C. for 16 h. The reaction was cooled to rt and partitioned between DCM and brine. The organic layer was dried with MgSO4 and concentrated to provide dark red oil. Purification by silica gel chromatography provided 5-(5-fluoro-2-(3-methoxy-4-morpholinophenyl)-1-tosyl-1H-pyrrolo[2,3-b]pyridin-4-yl)-2-((tetrahydro-2H-pyran-4-yl)oxy)benzonitrile (0.229 mg, 104% yield) as a yellow solid. ES/MS 683.2 (M+H⁺).

Step 2: Preparation of 5-(5-fluoro-2-(3-methoxy-4-morpholinophenyl)-1H-pyrrolo[2,3-b]pyridin-4-yl)-2-((tetrahydro-2H-pyran-4-yl)oxy)benzonitrile: A solution of 5-(5-fluoro-2-(3-methoxy-4-morpholinophenyl)-1-tosyl-1H-pyrrolo[2,3-b]pyridin-4-yl)-2-((tetrahydro-2H-pyran-4-yl)oxy)benzonitrile (339 mg, 0.497 mmol) and Cs2CO3 (484 mg, 1.49 mmol) in 4 mL THF and 2 mL TFE was heated to 100° C. for 1 h. Rxn was cooled to rt, diluted with MeOH, filtered and concentrated. Purification of the residue by RP HPLC provided 5-(5-fluoro-2-(3-methoxy-4-morpholinophenyl)-1H-pyrrolo[2,3-b]pyridin-4-yl)-2-((tetrahydro-2H-pyran-4-yl)oxy)benzonitrile as a yellow solid. ¹H NMR (400 MHz, DMSO-d6) δ 12.32 (s, 1H), 8.23 (d, J=3.0 Hz, 1H), 8.08-7.99 (m, 1H), 7.99-7.80 (m, 1H), 7.63-7.41 (m, 3H), 7.03-6.83 (m, 2H), 4.92 (dp, J=11.2, 3.8 Hz, 1H), 3.94-3.82 (m, 5H), 3.73 (t, J=4.3 Hz, 4H), 3.55 (ddd, J=11.5, 8.6, 3.1 Hz, 2H), 3.08-2.99 (m, 4H), 2.09-2.10 (m, 2H), 1.71 (dtd, J=12.5, 8.3, 3.9 Hz, 2H). ES/MS 529.3 (M+H⁺).

Example 173: 5-(5-fluoro-2-(4-(2-hydroxypropan-2-yl)phenyl)-1H-pyrrolo[2,3-b]pyridin-4-yl)-2-((tetrahydro-2H-pyran-4-yl)oxy)benzonitrile

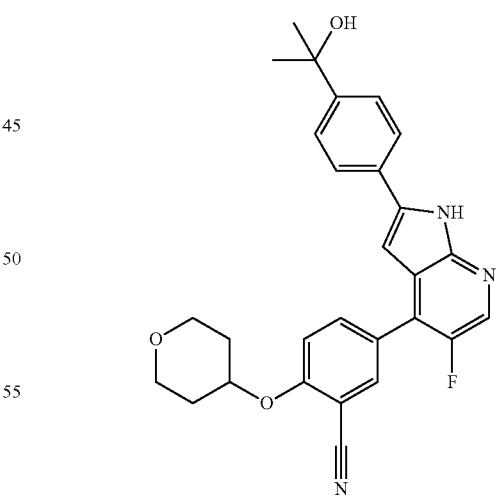

5-(5-Fluoro-2-(4-(2-hydroxypropan-2-yl)phenyl)-1H-pyrrolo[2,3-b]pyridin-4-yl)-2-((tetrahydro-2H-pyran-4-yl)oxy)benzonitrile was prepared in analogous fashion to Example 172. 1H NMR (400 MHz, DMSO-d6) δ 12.35 (s, 1H), 8.25 (d, J=3.0 Hz, 1H), 8.07-8.00 (m, 1H), 7.96 (dd, J=8.7, 2.1 Hz, 1H), 7.93-7.83 (m, 2H), 7.60-7.47 (m, 3H), 6.93 (d, J=2.1 Hz, 1H), 5.05 (s, 1H), 4.93 (dt, J=8.1, 4.1 Hz, 1H), 3.88 (dt, J=11.0, 4.5 Hz, 2H), 3.66-3.50 (m, 2H), 2.05 (d, J=13.5 Hz, 2H), 1.71 (dtd, J=12.4, 8.2, 3.8 Hz, 2H), 1.43 (s, 6H). ES/MS 472.2 (M+H⁺).

Example 174: Preparation of 5-(5-fluoro-2-(4-(2-(pyrrolidin-1-yl)ethoxy)phenyl)-1H-pyrrolo[2,3-b]pyridin-4-yl)-2-((tetrahydro-2H-pyran-4-yl)oxy)benzonitrile Example 175: 5-(6-(1,4-dioxaspiro[4.5]dec-7-en-8-yl)-7H-pyrrolo[2,3-d]pyrimidin-4-yl)-2-((1-(2-hydroxyacetyl)piperidin-4-yl)oxy)benzonitrile

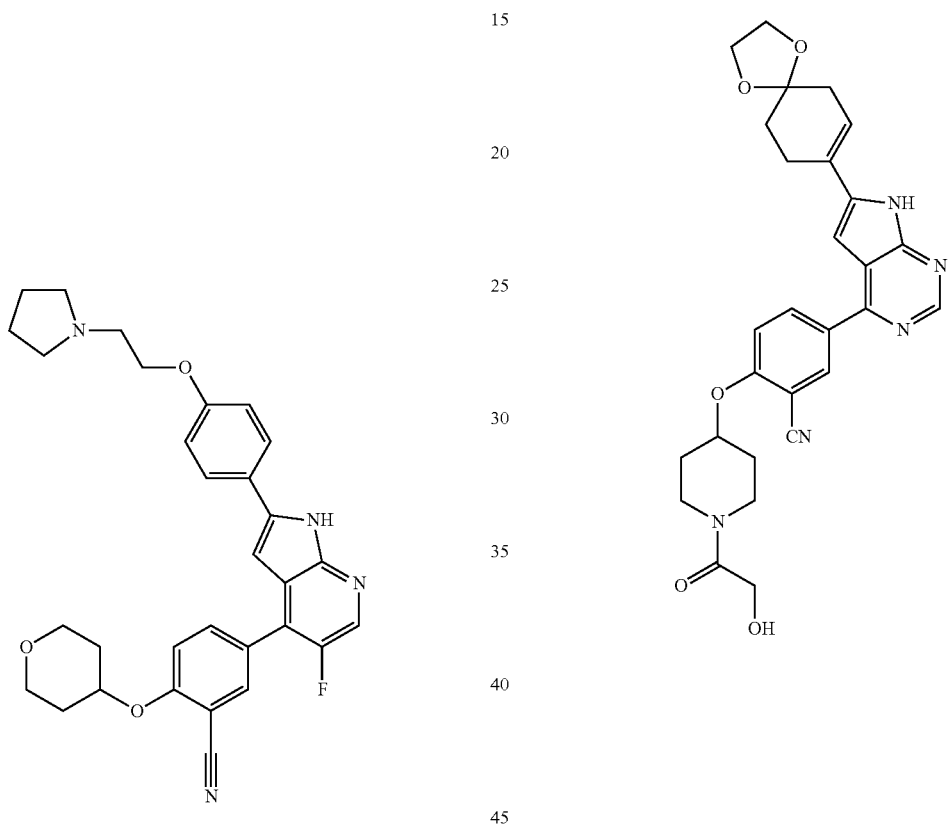

5-(5-Fluoro-2-(4-(2-(pyrrolidin-1-yl)ethoxy)phenyl)-1H-pyrrolo[2,3-b]pyridin-4-yl)-2-((tetrahydro-2H-pyran-4-yl)oxy)benzonitrile was prepared by same method as Example 172. 1H NMR (400 MHz, DMSO-d6) δ 12.32 (d, J=2.2 Hz, 1H), 9.77 (s, 1H), 8.24 (d, J=3.0 Hz, 1H), 8.03 (dd, J=2.3, 1.0 Hz, 1H), 8.00-7.90 (m, 3H), 7.55 (d, J=9.0 Hz, 1H), 7.14-7.03 (m, 2H), 6.90 (d, J=2.1 Hz, 1H), 4.93 (dq, J=8.1, 4.0 Hz, 1H), 4.35 (t, J=5.0 Hz, 2H), 3.89 (dd, J=11.6, 5.3 Hz, 2H), 3.69-3.52 (m, 6H), 3.14 (q, J=10.1, 8.7 Hz, 2H), 2.14-1.94 (m, 4H), 1.95-1.80 (m, 2H), 1.71 (dtd, J=12.4, 8.2, 3.8 Hz, 2H). ES/MS 527.4 (M+H⁺).

A solution of 5-(6-(1,4-dioxaspiro[4.5]dec-7-en-8-yl)-7-((2-(trimethylsilyl)ethoxy)methyl)-7H-pyrrolo[2,3-d]pyrimidin-4-yl)-2-((1-(2-hydroxyacetyl)piperidin-4-yl)oxy)benzonitrile (323 mg, 0.50 mmol) in 1N TBAF solution in THF (5.00 mL 5.00 mmol) was stirred at 60° C. for 16 h. The reaction was cooled to rt and diluted with DCM and sat. NaHCO₃. The organic layer was dried with MgSO₄ and concentrated. The residue was purified by silica gel chromatography to provide 5-(6-(1,4-dioxaspiro[4.5]dec-7-en-8-yl)-7H-pyrrolo[2,3-d]pyrimidin-4-yl)-2-((1-(2-hydroxyacetyl)piperidin-4-yl)oxy)benzonitrile (3 mg, 1.0% yield) as a yellow solid. 1H NMR (400 MHz, Methanol-d4) δ 8.71 (s, 1H), 8.36 (dq, J=5.3, 2.3 Hz, 2H), 7.46 (d, J=9.6 Hz, 1H), 6.76 (s, 1H), 6.41 (s, 1H), 5.05-4.97 (m, 1H), 4.28 (s, 2H), 4.01 (s, 4H), 3.81-3.77 (m, 2H), 3.75-3.61 (m, 3H), 3.55-3.44 (m, 1H), 2.77-2.71 (m, 2H), 2.53-2.49 (m, 2H), 2.14-2.00 (m, 2H), 1.94 (t, J=6.5 Hz, 2H). ES/MS 516.3 (M+H⁺).

Example 176: Preparation of 5-((3,3-difluoro-1-(2-hydroxyacetyl)piperidin-4-yl)oxy)-2-(2-(4-(4-(oxetan-3-yl)piperazin-1-yl)phenyl)-1H-pyrrolo[2,3-b]pyridin-4-yl)isonicotinonitrile

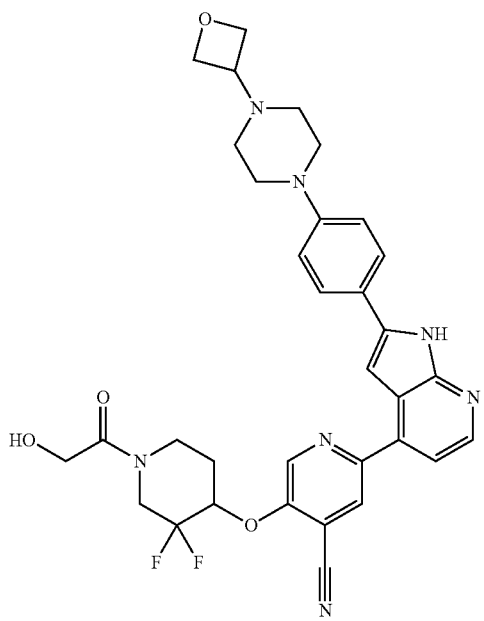 [SMILES: N#Cc1cc(-c2ccnc3[nH]c(-c4ccc(N5CCN(C6COC6)CC5)cc4)cc23)ncc1OC1CCN(C(=O)CO)CC1(F)F]

Step 1: Preparation of 5-((3,3-difluoro-1-(2-hydroxyacetyl)piperidin-4-yl)oxy)-2-(2-(4-(4-(oxetan-3-yl)piperazin-1-yl)phenyl)-1-tosyl-1H-pyrrolo[2,3-b]pyridin-4-yl)isonicotinonitrile: A solution of glycolic acid (45 mg, 0.60 mmol) in 2 mL DMF was treated with HATU (227 mg, 0.60 mmol) followed by 5-((3,3-difluoropiperidin-4-yl)oxy)-2-(2-(4-(4-(oxetan-3-yl)piperazin-1-yl)phenyl)-1-tosyl-1H-pyrrolo[2,3-b]pyridin-4-yl)isonicotinonitrile (217 mg, 0.30 mmol) and TEA (208 uL, 1.0 mmol). After stirring for 2 h, the solution was diluted with EtOAc and 2N $Na_2CO_3$. Organic layer was separated, dried with Na2SO4 and concentrated. Residue purified by silica gel chromatography to provide 5-((3,3-difluoro-1-(2-hydroxyacetyl)piperidin-4-yl)oxy)-2-(2-(4-(4-(oxetan-3-yl)piperazin-1-yl)phenyl)-1-tosyl-1H-pyrrolo[2,3-b]pyridin-4-yl)isonicotinonitrile (71 mg, 30% yield) as a yellow solid. ES/MS 784.3 (M+H⁺).

Step 2: Preparation of 5-((3,3-difluoro-1-(2-hydroxyacetyl)piperidin-4-yl)oxy)-2-(2-(4-(4-(oxetan-3-yl)piperazin-1-yl)phenyl)-1H-pyrrolo[2,3-b]pyridin-4-yl)isonicotinonitrile: A solution of 5-((3,3-difluoropiperidin-4-yl)oxy)-2-(2-(4-(4-(oxetan-3-yl)piperazin-1-yl)phenyl)-1-tosyl-1H-pyrrolo[2,3-b]pyridin-4-yl)isonicotinonitrile (334 mg, 0.43 mmol) and $Cs_2CO_3$ (699 mg, 2.0 mmol) in THF (10 mL) and TFE (4 mL) was stirred at 110° C. for 90 min. The reaction was then diluted with THF and filtered. Filtrate was concentrated and redissolved in MeCN. Purification by RP HPLC provided 5-((3,3-difluoro-1-(2-hydroxyacetyl)piperidin-4-yl)oxy)-2-(2-(4-(4-(oxetan-3-yl)piperazin-1-yl)phenyl)-1H-pyrrolo[2,3-b]pyridin-4-yl)isonicotinonitrile (83 mg, 31% yield) as a yellow solid. $^1$H NMR (400 MHz, DMSO-D6) δ 12.14 (s, 1H), 9.10 (s, 1H), 8.54 (s, 1H), 8.23 (d, J=5.2 Hz, 1H), 7.84 (d, J=8.6 Hz, 2H), 7.58 (d, J=5.1 Hz, 1H), 7.36 (d, J=2.1 Hz, 1H), 7.03 (d, J=8.6 Hz, 2H), 5.50 (d, J=12.8 Hz, 1H), 4.87 (d, J=10.0 Hz, 1H), 4.56 (t, J=6.5 Hz, 2H), 4.47 (t, J=6.1 Hz, 2H), 4.27-4.12 (m, 2H), 3.90-3.75 (m, 2H), 3.71-3.62 (m, 1H), 3.51-3.40 (m, 2H), 3.25 (s, 4H), 2.41 (s, 4H), 2.28-1.98 (m, 2H). ES/MS 630.3 (M+H⁺).

Example 177: 5-(2-(4-(1H-pyrazol-1-yl)phenyl)-1H-pyrrolo[2,3-b]pyridin-4-yl)-2-((tetrahydro-2H-pyran-4-yl)oxy)benzonitrile

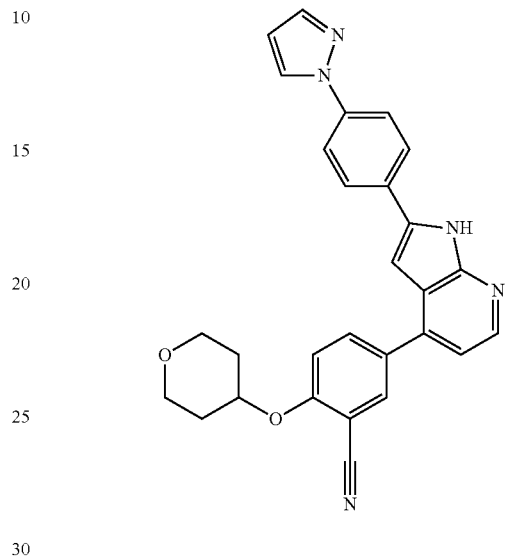

Step 1: Preparation of 5-(2-(4-(1H-pyrazol-1-yl)phenyl)-1-(phenylsulfonyl)-1H-pyrrolo[2,3-b]pyridin-4-yl)-2-((tetrahydro-2H-pyran-4-yl)oxy)benzonitrile: To 5-(2-iodo-1-(phenylsulfonyl)-1H-pyrrolo[2,3-b]pyridin-4-yl)-2-((tetrahydro-2H-pyran-4-yl)oxy)benzonitrile (100 mg, 0.171 mmol) in dioxane (2 mL), (4-(1H-pyrazol-1-yl)phenyl)boronic acid (13 mg, 0.019 mmol), cesium carbonate (166 mg, 0.509 mmol) dissolved in water, and PEPPSI-iPr catalyst (139 mg, 0.204 mmol) were added. The reaction mixture was heated at 85° C. for 3 h. After cooling to room temperature, the reaction mixture was poured into water and extracted with ethyl acetate. The combined organic layers were washed with brine, dried, filtered and concentrated under reduced pressure. The residue was purified by flash column chromatography on silica gel to afford 5-(2-(4-(1H-pyrazol-1-yl)phenyl)-1-(phenylsulfonyl)-1H-pyrrolo[2,3-b]pyridin-4-yl)-2-((tetrahydro-2H-pyran-4-yl)oxy)benzonitrile.

Step 2: Preparation of 5-(2-(4-(1H-pyrazol-1-yl)phenyl)-1H-pyrrolo[2,3-b]pyridin-4-yl)-2-((tetrahydro-2H-pyran-4-yl)oxy)benzonitrile: To a microwave vial, a solution of 5-(2-(4-(1H-pyrazol-1-yl)phenyl)-1-(phenylsulfonyl)-1H-pyrrolo[2,3-b]pyridin-4-yl)-2-((tetrahydro-2H-pyran-4-yl)oxy)benzonitrile (33 mg, 0.055 mmol) in 2-methyltetrahydrofuran (1 mL), 2,2,2-trifluoroethanol (0.5 mL) and cesium carbonate (93 mg, 0.285 mmol) were added. The reaction mixture was heated in a microwave reactor at 110° C. for 45 min. After cooling to room temperature, the mixture was poured into water and extracted with ethyl acetate. The combined organic layers were washed with brine, dried, filtered and concentrated under reduced pressure. The residue was purified via prep HPLC to give the title compound. $^1$H NMR (400 MHz, dmso-d6) δ 12.37 (s, 1H), 8.58 (d, J=2.6 Hz, 1H), 8.27 (d, J=5.0 Hz, 1H), 8.16-8.07 (m, 4H), 7.94 (d, J=8.6 Hz, 2H), 7.77 (d, J=1.7 Hz, 1H), 7.53 (d, J=8.9 Hz, 1H), 7.22 (d, J=5.0 Hz, 2H), 6.57 (m, 1H), 4.97-4.89 (m, 1H), 3.92-3.84 (m, 2H), 3.56 (m, 2H), 2.11-2.00 (m, 2H), 1.77-1.65 (m, 2H). LCMS-ESI+ (m/z): [M+H]+ calcd for C28H23N5O2: 462.2. found: 462.1.

Example 178: 5-(2-(1-(oxetan-3-yl)-2,5-dihydro-1H-pyrrol-3-yl)-1H-pyrrolo[2,3-b]pyridin-4-yl)-2-((tetrahydro-2H-pyran-4-yl)oxy)benzonitrile

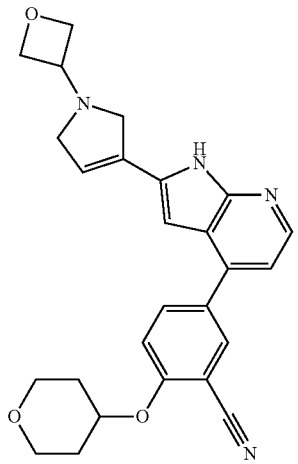 [SMILES: N#Cc1cc(-c2ccnc3[nH]c(C4=CCN(C5COC5)C4)cc23)ccc1OC1CCOCC1]

Step 1: Preparation of tert-butyl 3-(4-(3-cyano-4-((tetrahydro-2H-pyran-4-yl)oxy)phenyl)-1-(phenylsulfonyl)-1H-pyrrolo[2,3-b]pyridin-2-yl)-2,5-dihydro-1H-pyrrole-1-carboxylate: To 5-(2-iodo-1-(phenylsulfonyl)-1H-pyrrolo[2,3-b]pyridin-4-yl)-2-((tetrahydro-2H-pyran-4-yl)oxy)benzonitrile (1100 mg, 1.879 mmol) in dioxane (25 mL), tert-butyl 3-(4,4,5,5-tetramethyl-1,3,2-dioxaborolan-2-yl)-2,5-dihydro-1H-pyrrole-1-carboxylate (554 mg, 1.877 mmol), cesium carbonate (1827 mg, 5.607 mmol) dissolved in water, and PEPPSI-iPr catalyst (139 mg, 0.204 mmol) were added. The reaction mixture was heated at 85° C. for 3 h. After cooling to room temperature, the reaction mixture was poured into water and extracted with ethyl acetate. The combined organic layers were washed with brine, dried, filtered and concentrated under reduced pressure. The residue was purified by flash column chromatography on silica gel to afford tert-butyl 3-(4-(3-cyano-4-((tetrahydro-2H-pyran-4-yl)oxy)phenyl)-1-(phenylsulfonyl)-1H-pyrrolo[2,3-b]pyridin-2-yl)-2,5-dihydro-1H-pyrrole-1-carboxylate.

Step 2: Preparation of 5-(2-(2,5-dihydro-1H-pyrrol-3-yl)-1-(phenylsulfonyl)-1H-pyrrolo[2,3-b]pyridin-4-yl)-2-((tetrahydro-2H-pyran-4-yl)oxy)benzonitrile: Tert-butyl 3-(4-(3-cyano-4-((tetrahydro-2H-pyran-4-yl)oxy)phenyl)-1-(phenylsulfonyl)-1H-pyrrolo[2,3-b]pyridin-2-yl)-2,5-dihydro-1H-pyrrole-1-carboxylate (221 mg, 0.353 mmol) dissolved in dichloromethane (4 mL) was treated with trifluoroacetic acid (200 µL, 2.612 mmol). The reaction mixture was stirred at rt overnight and then concentrated. The residue was dissolved in ethyl acetate and washed with saturated sodium bicarbonate solution. The combined organic layers were washed with brine, dried, filtered and concentrated under reduced pressure to afford 5-(2-(2,5-dihydro-1H-pyrrol-3-yl)-1-(phenylsulfonyl)-1H-pyrrolo[2,3-b]pyridin-4-yl)-2-((tetrahydro-2H-pyran-4-yl)oxy)benzonitrile.

Step 3: Preparation of 5-(2-(1-(oxetan-3-yl)-2,5-dihydro-1H-pyrrol-3-yl)-1-(phenylsulfonyl)-1H-pyrrolo[2,3-b]pyridin-4-yl)-2-((tetrahydro-2H-pyran-4-yl)oxy)benzonitrile: 5-(2-(2,5-dihydro-1H-pyrrol-3-yl)-1-(phenylsulfonyl)-1H-pyrrolo[2,3-b]pyridin-4-yl)-2-((tetrahydro-2H-pyran-4-yl)oxy)benzonitrile (91 mg, 0.173 mmol) dissolved in dichloromethane (2 mL) was treated with 3-oxetanone (10 mg, 0.139 mmol) followed by sodium triacetoxyborohydride (53 mg, 0.252 mmol). The reaction mixture was stirred at rt for 1 h and then concentrated. The residue was dissolved in ethyl acetate and washed with water. The combined organic layers were washed with brine, dried, filtered and concentrated under reduced pressure. The residue was purified by flash column chromatography on silica gel to afford 5-(2-(1-(oxetan-3-yl)-2,5-dihydro-1H-pyrrol-3-yl)-1-(phenylsulfonyl)-1H-pyrrolo[2,3-b]pyridin-4-yl)-2-((tetrahydro-2H-pyran-4-yl)oxy)benzonitrile.

Step 4: Preparation of 5-(2-(1-(oxetan-3-yl)-2,5-dihydro-1H-pyrrol-3-yl)-1H-pyrrolo[2,3-b]pyridin-4-yl)-2-((tetrahydro-2H-pyran-4-yl)oxy)benzonitrile: To a microwave vial, a solution of 5-(2-(1-(oxetan-3-yl)-2,5-dihydro-1H-pyrrol-3-yl)-1-(phenylsulfonyl)-1H-pyrrolo[2,3-b]pyridin-4-yl)-2-((tetrahydro-2H-pyran-4-yl)oxy)benzonitrile (16 mg, 0.027 mmol) in 2-methyltetrahydrofuran (1 mL), 2,2,2-trifluoroethanol (0.5 mL) and cesium carbonate (45 mg, 0.138 mmol) were added. The reaction mixture was heated in a microwave reactor at 110° C. for 45 min. After cooling to room temperature, the mixture was poured into water and extracted with ethyl acetate. The combined organic layers were washed with brine, dried, filtered and concentrated under reduced pressure. The residue was purified via prep HPLC to give the title compound. 1H NMR (400 MHz, dmso-d6) δ 12.37 (s, 1H), 8.32 (d, J=5.0 Hz, 1H), 8.07 (d, J=2.3 Hz, 1H), 8.01 (dd, J=8.8, 2.4 Hz, 1H), 7.52 (d, J=8.9 Hz, 1H), 7.23 (d, J=5.0 Hz, 1H), 6.75 (d, J=1.9 Hz, 1H), 6.53 (s, 1H), 4.96-4.88 (m, 1H), 4.83 (m, 2H), 4.66 (m, 3H), 3.87 (m, 3H), 3.55 (m, 5H), 2.07-1.98 (m, 2H), 1.69 (m, 2H). LCMS-ESI+ (m/z): [M+H]+ calcd for C26H26N4O3: 443.2. found: 443.1.

Example 179: 3-(4-(3-cyano-4-((tetrahydro-2H-pyran-4-yl)oxy)phenyl)-1H-pyrrolo[2,3-b]pyridin-2-yl)-N,N-dimethylacrylamide

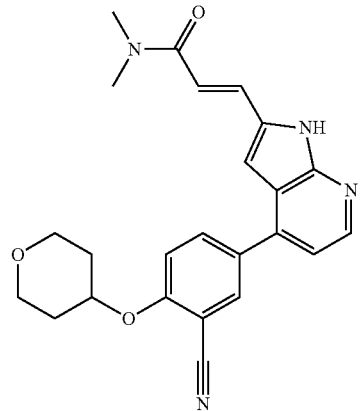 [SMILES: CN(C)C(=O)/C=C/c1cc2c(-c3ccc(OC4CCOCC4)c(C#N)c3)ccnc2[nH]1]

The title compound was synthesized in the same manner as Example 177 starting with 4-bromo-2-iodo-1-tosyl-1H-pyrrolo[2,3-b]pyridine and N,N-dimethyl-3-(4,4,5,5-tetramethyl-1,3,2-dioxaborolan-2-yl)propanamide. 1H NMR (400 MHz, dmso-d6) δ 12.25 (d, J=2.0 Hz, 1H), 8.31 (d, J=5.0 Hz, 1H), 8.10 (d, J=2.3 Hz, 1H), 8.03 (dd, J=8.9, 2.4 Hz, 1H), 7.54-7.48 (m, 1H), 7.45-7.38 (m, 2H), 7.22 (d, J=5.0 Hz, 1H), 7.05 (d, J=1.9 Hz, 1H), 4.92 (m, 1H), 3.87 (m, 2H), 3.16 (s, 3H), 2.93 (s, 3H), 2.03 (m, 2H), 1.69 (m, 2H). LCMS-ESI⁺ (m/z): [M+H]⁺ calcd for C24H24N4O3: 417.2. found: 417.1.

Example 180: Preparation of 5-(2-(1,4-dioxaspiro[4.5]dec-7-en-8-yl)-1H-pyrrolo[2,3-b]pyridin-4-yl)-2-((tetrahydro-2H-pyran-4-yl)oxy)benzonitrile

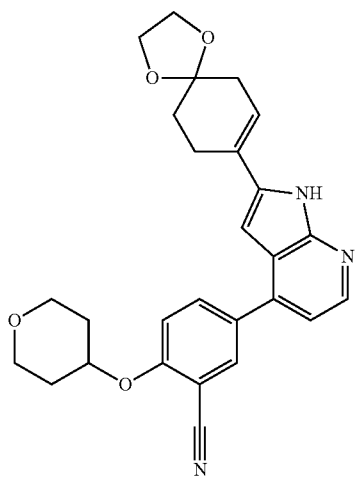 [SMILES: N#Cc1cc(-c2ccnc3[nH]c(C4=CCC5(CC4)OCCO5)cc23)ccc1OC1CCOCC1]

The title compound was synthesized in the same manner as Example 177 starting with 4-bromo-2-iodo-1-tosyl-1H-pyrrolo[2,3-b]pyridine and 4,4,5,5-tetramethyl-2-(1,4-dioxaspiro[4.5]dec-7-en-8-yl)-1,3,2-dioxaborolane. ¹H NMR (400 MHz, dmso-d6) δ 12.00 (s, 1H), 8.23 (d, J=5.2 Hz, 1H), 8.10 (d, J=2.3 Hz, 1H), 8.04 (dd, J=8.8, 2.3 Hz, 1H), 7.50 (d, J=9.0 Hz, 1H), 7.20 (d, J=5.2 Hz, 1H), 6.63 (d, J=1.9 Hz, 1H), 6.45-6.40 (m, 1H), 4.90 (m, 1H), 3.91 (s, 4H), 3.87 (m, 2H), 3.54 (m, 2H), 2.61 (m, 2H), 2.40 (m, 2H), 2.04 (m, 2H), 1.80 (m, 2H), 1.69 (m, 2H). LCMS-ESI⁺ (m/z): [M+H]⁺ calcd for C27H27N3O4: 458.2. found: 458.2.

Example 181: Preparation of 5-(2-(1-methyl-1H-pyrazol-5-yl)-1H-pyrrolo[2,3-b]pyridin-4-yl)-2-((tetrahydro-2H-pyran-4-yl)oxy)benzonitrile

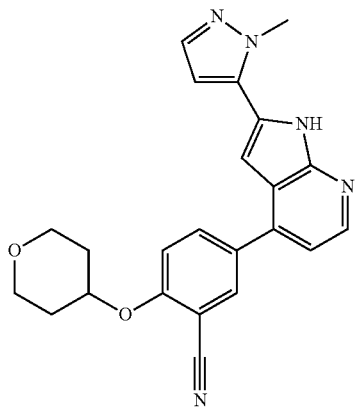 [SMILES: Cn1nccc1-c1cc2c(-c3ccc(OC4CCOCC4)c(C#N)c3)ccnc2[nH]1]

The title compound was synthesized in the same manner as Example 177 starting with 4-bromo-2-iodo-1-tosyl-1H-pyrrolo[2,3-b]pyridine and 1-methyl-5-(4,4,5,5-tetramethyl-1,3,2-dioxaborolan-2-yl)-1H-pyrazole. ¹H NMR (400 MHz, dmso-d6) δ 12.25 (s, 1H), 8.27 (d, J=5.0 Hz, 1H), 8.09 (d, J=2.3 Hz, 1H), 8.05 (dd, J=8.8, 2.4 Hz, 1H), 7.50-7.44 (m, 2H), 7.20 (d, J=5.0 Hz, 1H), 6.88 (m, 1H), 6.74 (d, J=2.0 Hz, 1H), 4.92-4.81 (m, 1H), 4.00 (s, 3H), 3.86-3.77 (m, 2H), 3.50 (m, 2H), 2.04-1.93 (m, 2H), 1.64 (m, 2H). LCMS-ESI⁺ (m/z): [M+H]⁺ calcd for C23H21N5O2: 400.2. found: 400.2.

Example 182: 5-(2-(1-(2-hydroxyacetyl)-2,5-dihydro-1H-pyrrol-3-yl)-1H-pyrrolo[2,3-b]pyridin-4-yl)-2-((tetrahydro-2H-pyran-4-yl)oxy)benzonitrile

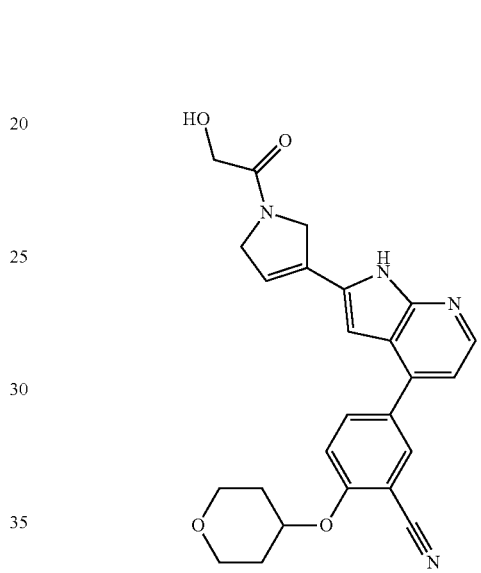

Step 1: Preparation of 5-(2-(1-(2-hydroxyacetyl)-2,5-dihydro-1H-pyrrol-3-yl)-1-(phenylsulfonyl)-1H-pyrrolo[2,3-b]pyridin-4-yl)-2-((tetrahydro-2H-pyran-4-yl)oxy)benzonitrile: 5-(2-(2,5-dihydro-1H-pyrrol-3-yl)-1-(phenylsulfonyl)-1H-pyrrolo[2,3-b]pyridin-4-yl)-2-((tetrahydro-2H-pyran-4-yl)oxy)benzonitrile (102 mg, 0.193 mmol) dissolved in dichloromethane (2 mL) was treated with glycolic acid (23 mg, 0.302 mmol), HATU (110 mg. 0.289 mmol), and N,N-diisopropylethylamine (100 μL, 0.574 mmol). The reaction mixture was stirred at room temperature overnight and then concentrated. The residue was diluted with ethyl acetate and washed with citric acid solution. The combined organic layers were dried over sodium sulfate, filtered, and concentrated to give 5-(2-(1-(2-hydroxyacetyl)-2,5-dihydro-1H-pyrrol-3-yl)-1-(phenylsulfonyl)-1H-pyrrolo[2,3-b]pyridin-4-yl)-2-((tetrahydro-2H-pyran-4-yl)oxy)benzonitrile.

Step 2: Procedures described in step 2 of Example 177 were followed to give to give the title compound. ¹H NMR (400 MHz, dmso-d6) δ 12.24 (d, J=19.2 Hz, 1H), 8.27 (m, 1H), 8.14-8.07 (m, 1H), 8.07-7.99 (m, 1H), 7.56-7.48 (m, 1H), 7.24-7.17 (m, 1H), 6.78-6.60 (m, 1H), 6.56 (d, J=11.9 Hz, 1H), 4.90 (m, 1H), 4.56 (d, J=21.3 Hz, 2H), 4.42-4.30 (m, 2H), 4.09 (d, J=15.0 Hz, 2H), 3.92-3.81 (m, 2H), 3.55 (m, 2H), 2.04 (m, 2H), 1.70 (m, 2H). LCMS-ESI⁺ (m/z): [M+H]⁺ calcd for C25H24N4O4: 445.2. found: 446.0.

Example 183: 5-(6-(6-oxo-1,6-dihydropyridin-3-yl)-7H-pyrrolo[2,3-d]pyrimidin-4-yl)-2-((tetrahydro-2H-pyran-4-yl)oxy)benzonitrile

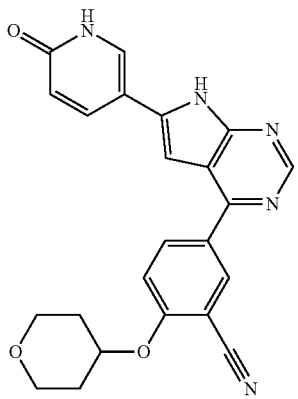 [SMILES: N#Cc1cc(-c2ncnc3[nH]c(-c4ccc(=O)[nH]c4)cc23)ccc1OC1CCOCC1]

Step 1: Preparation of 2-(tert-butoxy)-5-(4,4,5,5-tetramethyl-1,3,2-dioxaborolan-2-yl)pyridine: 5-bromo-2-(tert-butoxy)pyridine (218 mg, 0.947 mmol) dissolved in dioxane (8 mL) was treated with bis pinacolato diboron (480 mg, 1.89 mmol), (1,1'-Bis(diphenylphosphino)ferrocene)palladium (II) dichloride (77 mg, 0.094 mmol), and potassium acetate (278 mg, 2.833 mmol). The reaction mixture was heated at 80° C. for 4 h. After cooling to room temperature, the reaction mixture was filtered. The filtrate was diluted with ethyl acetate and washed with water. The combined organic layers were dried over sodium sulfate, filtered, and concentrated. The residue was purified by flash column chromatography on silica gel to give 2-(tert-butoxy)-5-(4,4,5,5-tetramethyl-1,3,2-dioxaborolan-2-yl)pyridine.

Step 2: 6-(6-(tert-butoxy)pyridin-3-yl)-4-chloro-7-(phenylsulfonyl)-7H-pyrrolo[2,3-d]pyrimidine was synthesized according to procedures described in step 1 of Example 177.

Step 3: Preparation of 5-(6-(6-(tert-butoxy)pyridin-3-yl)-7-(phenylsulfonyl)-7H-pyrrolo[2,3-d]pyrimidin-4-yl)-2-((tetrahydro-2H-pyran-4-yl)oxy)benzonitrile: 6-(6-(tert-butoxy)pyridin-3-yl)-4-chloro-7-(phenylsulfonyl)-7H-pyrrolo[2,3-d]pyrimidine (119 mg, 0.269 mmol) dissolved in dioxane (3 mL) was treated with 2-((tetrahydro-2H-pyran-4-yl)oxy)-5-(4,4,5,5-tetramethyl-1,3,2-dioxaborolan-2-yl)benzonitrile (88 mg, 0.267 mmol), (1,1'-Bis(diphenylphosphino)ferrocene)palladium(II) dichloride (14 mg, 0.017 mmol), and 2M sodium carbonate solution (380 μL, 0.76 mmol). The reaction mixture was heated at 90° C. for 2 h. After cooling to room temperature, the reaction mixture was concentrated. The residue was dissolved in ethyl acetate and washed with water. The combined organic layers were dried over sodium sulfate, filtered, and concentrated. The residue was purified by flash column chromatography on silica gel to give 5-(6-(6-(tert-butoxy)pyridin-3-yl)-7-(phenylsulfonyl)-7H-pyrrolo[2,3-d]pyrimidin-4-yl)-2-((tetrahydro-2H-pyran-4-yl)oxy)benzonitrile.

Step 4: 5-(6-(6-(tert-butoxy)pyridin-3-yl)-7H-pyrrolo[2,3-d]pyrimidin-4-yl)-2-((tetrahydro-2H-pyran-4-yl)oxy)benzonitrile was made according to procedures described in step 2 of Example 177.

Step 5: Preparation of 5-(6-(6-oxo-1,6-dihydropyridin-3-yl)-7H-pyrrolo[2,3-d]pyrimidin-4-yl)-2-((tetrahydro-2H-pyran-4-yl)oxy)benzonitrile: 5-(6-(6-(tert-butoxy)pyridin-3-yl)-7H-pyrrolo[2,3-d]pyrimidin-4-yl)-2-((tetrahydro-2H-pyran-4-yl)oxy)benzonitrile (10 mg, 0.021 mmol) dissolved in dichloromethane (1 mL) was treated with trifluoroacetic acid (30 μL, 0.392 mmol). The reaction mixture was stirred at room temperature for 1 h and then concentrated. The residue was purified via prep HPLC to give 5-(6-(6-oxo-1,6-dihydropyridin-3-yl)-7H-pyrrolo[2,3-d]pyrimidin-4-yl)-2-((tetrahydro-2H-pyran-4-yl)oxy)benzonitrile. $^1$H NMR (400 MHz, dmso-d6) δ 12.55 (s, 1H), 8.76 (s, 1H), 8.50 (m, 2H), 8.18-8.12 (m, 2H), 7.53 (d, J=8.7 Hz, 1H), 7.34 (m, 1H), 6.49 (d, J=9.4 Hz, 2H), 4.99-4.91 (m, 1H), 3.88 (m, 2H), 3.59-3.51 (m, 2H), 2.03 (m, 2H), 1.78-1.63 (m, 2H). LCMS-ESI$^+$ (m/z): [M+H]$^+$ calcd for C23H19N5O3: 414.2. found: 414.1.

Example 184: Preparation of 2-((1-(2-hydroxyacetyl)piperidin-4-yl)oxy)-5-(6-(3-(morpholinomethyl)phenyl)-7H-pyrrolo[2,3-d]pyrimidin-4-yl)benzonitrile

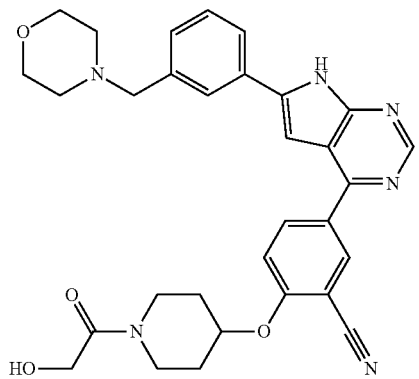 [SMILES: N#Cc1cc(-c2ncnc3[nH]c(-c4cccc(CN5CCOCC5)c4)cc23)ccc1OC1CCN(C(=O)CO)CC1]

The title compound was synthesized in the same manner as Example 177 using 2-((1-(2-hydroxyacetyl)piperidin-4-yl)oxy)-5-(4,4,5,5-tetramethyl-1,3,2-dioxaborolan-2-yl)benzonitrile. $^1$H NMR (400 MHz, dmso-d6) δ 12.90 (s, 1H), 8.85 (s, 1H), 8.52 (m, 2H), 8.16-8.10 (m, 2H), 7.64 (m, 1H), 7.56 (m, 2H), 7.46 (d, J=1.9 Hz, 1H), 5.03 (m, 1H), 4.40 (s, 2H), 4.13 (s, 2H), 3.97 (m, 2H), 3.73-3.64 (m, 4H), 3.19-3.15 (m, 4H), 2.03 (m, 2H), 1.74 (m, 2H). LCMS-ESI$^+$ (m/z): [M+H]$^+$ calcd for C31H32N6O4: 553.3. found: 553.2.

Example 185: Preparation of 5-(6-(4-(pyrrolidine-1-carbonyl)phenyl)-7H-pyrrolo[2,3-d]pyrimidin-4-yl)-2-((tetrahydro-2H-pyran-4-yl)oxy)benzonitrile

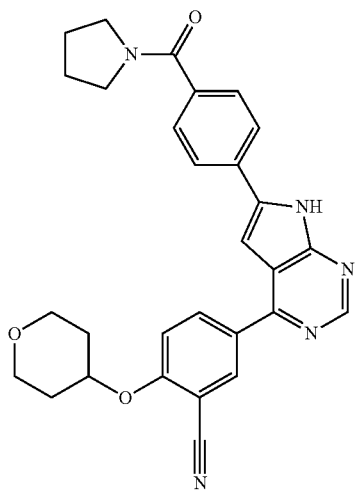 [SMILES: N#Cc1cc(-c2ncnc3[nH]c(-c4ccc(C(=O)N5CCCC5)cc4)cc23)ccc1OC1CCOCC1]

Step 1: Preparation of 4-(4-(3-cyano-4-((tetrahydro-2H-pyran-4-yl)oxy)phenyl)-7-((2-(trimethylsilyl)ethoxy)methyl)-7H-pyrrolo[2,3-d]pyrimidin-6-yl)benzoic acid Methyl 4-(4-(3-cyano-4-((tetrahydro-2H-pyran-4-yl)oxy)phenyl)-7-((2-(trimethylsilyl)ethoxy)methyl)-7H-pyrrolo[2,3-d]pyrimidin-6-yl)benzoate (173 mg, 0.296 mmol) dissolved in tetrahydrofuran (3 mL) and methanol (1 mL) was treated with lithium hydroxide (37 mg, 0.882 mmol) dissolved in water. The reaction mixture was stirred at room temperature overnight and then concentrated. The residue was dissolved in ethyl acetate and washed with 1N HCl solution. The combined organic layers were washed with brine, dried, filtered and concentrated under reduced pressure to afford 4-(4-(3-cyano-4-((tetrahydro-2H-pyran-4-yl)oxy)phenyl)-7-((2-(trimethylsilyl)ethoxy)methyl)-7H-pyrrolo[2,3-d]pyrimidin-6-yl)benzoic acid.

Step 2: Preparation of 5-(6-(4-(pyrrolidine-1-carbonyl)phenyl)-7-((2-(trimethylsilyl)ethoxy)methyl)-7H-pyrrolo[2,3-d]pyrimidin-4-yl)-2-((tetrahydro-2H-pyran-4-yl)oxy)benzonitrile: 4-(4-(3-cyano-4-((tetrahydro-2H-pyran-4-yl)oxy)phenyl)-7-((2-(trimethylsilyl)ethoxy)methyl)-7H-pyrrolo[2,3-d]pyrimidin-6-yl)benzoic acid (165 mg, 0.289 mmol) dissolved in dichloromethane (2 mL) was treated with pyrrolidine (30 µL, 0.363 mmol), HATU (132 mg. 0.347 mmol), and N,N-diisopropylethylamine (150 µL, 0.861 mmol). The reaction mixture was stirred at room temperature for 1 h and concentrated. The residue was diluted with ethyl acetate and washed with water. The combined organic layers were dried over sodium sulfate, filtered, and concentrated. The residue was purified by flash column chromatography on silica gel to give 5-(6-(4-(pyrrolidine-1-carbonyl)phenyl)-7-((2-(trimethylsilyl)ethoxy)methyl)-7H-pyrrolo[2,3-d]pyrimidin-4-yl)-2-((tetrahydro-2H-pyran-4-yl)oxy)benzonitrile.

Step 3: Preparation of 5-(6-(4-(pyrrolidine-1-carbonyl)phenyl)-7H-pyrrolo[2,3-d]pyrimidin-4-yl)-2-((tetrahydro-2H-pyran-4-yl)oxy)benzonitrile: 5-(6-(4-(pyrrolidine-1-carbonyl)phenyl)-7-((2-(trimethylsilyl)ethoxy)methyl)-7H-pyrrolo[2,3-d]pyrimidin-4-yl)-2-((tetrahydro-2H-pyran-4-yl)oxy)benzonitrile (35 mg, 0.056 mmol) dissolved in 2-methyl tetrahydrofuran (1.5 mL) was treated with tetrabutylammonium fluoride solution (1M in THF, 360 µL, 0.360 mmol). The reaction mixture was heated at 70° C. for 4 h. After cooling to room temperature, the reaction mixture was concentrated. The residue was dissolved in ethyl acetate and washed with saturated sodium bicarbonate solution. The combined organic layers were dried over sodium sulfate, filtered, and concentrated. The residue was purified via prep HPLC to give the title compound. $^1$H NMR (400 MHz, dmso-d6) δ 12.91 (s, 1H), 8.84 (s, 1H), 8.54 (m, 2H), 8.12 (d, J=8.2 Hz, 2H), 7.67-7.61 (m, 3H), 7.55 (d, J=9.7 Hz, 1H), 4.97 (m, 1H), 3.91-3.83 (m, 2H), 3.56 (m, 4H), 3.17-3.09 (m, 1H), 2.05 (m, 2H), 1.91-1.78 (m, 4H), 1.72 (m, 2H), 1.56 (m, 1H). LCMS-ESI$^+$ (m/z): [M+H]$^+$ calcd for C29H27N5O3: 494.2. found: 494.2.

Example 186: 5-(6-(4-(morpholine-4-carbonyl)phenyl)-7H-pyrrolo[2,3-d]pyrimidin-4-yl)-2-((tetrahydro-2H-pyran-4-yl)oxy)benzonitrile

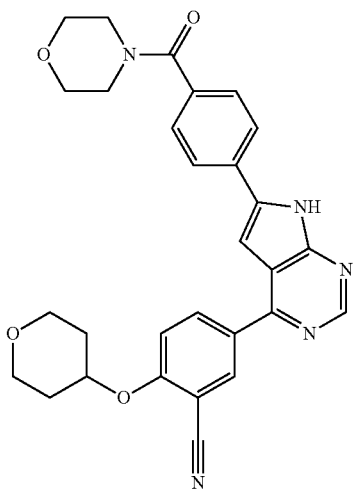 [SMILES: N#Cc1cc(-c2ncnc3[nH]c(-c4ccc(C(=O)N5CCOCC5)cc4)cc23)ccc1OC1CCOCC1]

The title compound was synthesized in the same manner as Example 185 using morpholine. $^1$H NMR (400 MHz, dmso-d6) δ 12.93 (s, 1H), 8.85 (s, 1H), 8.53 (m, 2H), 8.14 (d, J=8.2 Hz, 2H), 7.63 (d, J=1.9 Hz, 1H), 7.55 (m, 3H), 4.97 (dt, J=8.0, 4.0 Hz, 1H), 3.88 (m, 4H), 3.56 (m, 4H), 3.19-3.10 (m, 1H), 3.01 (m, 1H), 2.05 (m, 2H), 1.71 (m, 2H), 1.60-1.49 (m, 1H), 1.29 (m, 1H). LCMS-ESI$^+$ (m/z): [M+H]$^+$ calcd for C29H27N5O4: 510.2. found: 510.2.

Example 187: 5-(6-(4-(4-methylpiperazine-1-carbonyl)phenyl)-7H-pyrrolo[2,3-d]pyrimidin-4-yl)-2-((tetrahydro-2H-pyran-4-yl)oxy)benzonitrile

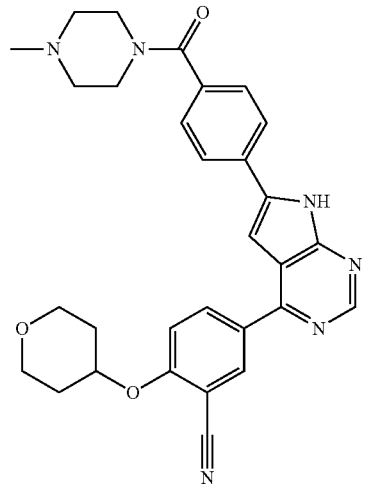 [SMILES: CN1CCN(C(=O)c2ccc(-c3cc4c(-c5ccc(OC6CCOCC6)c(C#N)c5)ncnc4[nH]3)cc2)CC1]

The title compound was synthesized in the same manner as Example 185 using 1-methylpiperazine. $^1$H NMR (400 MHz, dmso-d6) δ 13.70 (s, 1H), 9.65 (s, 1H), 9.37-9.33 (m, 2H), 8.99 (d, J=8.2 Hz, 2H), 8.45 (d, J=1.9 Hz, 1H), 8.38 (m, 3H), 5.82-5.73 (m, 1H), 4.69 (m, 2H), 4.38 (m, 3H), 3.93 (m, 3H), 3.64 (s, 3H), 2.91-2.80 (m, 2H), 2.53 (m, 2H). LCMS-ESI$^+$ (m/z): [M+H]$^+$ calcd for C30H30N6O3: 523.2. found: 523.1.

Example 188: 5-(6-(3,3-dimethyl-2-oxoindolin-6-yl)-7H-pyrrolo[2,3-d]pyrimidin-4-yl)-2-((tetrahydro-2H-pyran-4-yl)oxy)benzonitrile

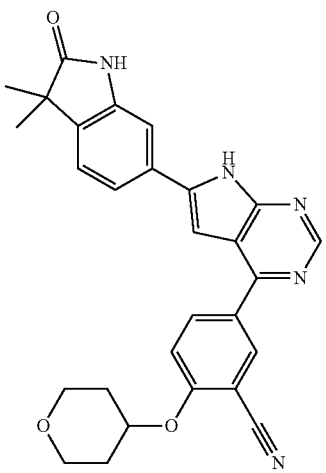 [SMILES: CC1(C)C(=O)Nc2cc(-c3cc4c(-c5ccc(OC6CCOCC6)c(C#N)c5)ncnc4[nH]3)ccc21]

The title compound was synthesized in the same manner as Example 185 starting from coupling of 4-chloro-6-iodo-7-((2-(trimethylsilyl)ethoxy)methyl)-7H-pyrrolo[2,3-d]pyrimidine and 3,3-dimethyl-6-(4,4,5,5-tetramethyl-1,3,2-dioxaborolan-2-yl)indolin-2-one using the following procedure: 4-chloro-6-iodo-7-((2-(trimethylsilyl)ethoxy)methyl)-7H-pyrrolo[2,3-d]pyrimidine (70 mg, 0.171 mmol) dissolved in dimethoxyethane (2 mL) was treated with 3,3-dimethyl-6-(4,4,5,5-tetramethyl-1,3,2-dioxaborolan-2-yl)indolin-2-one (49 mg, 0.171 mmol), tetrakis(triphenylphosphine)palladium(0) (20 mg, 0.017 mmol), and 2M sodium carbonate solution (240 μL, 0.480 mmol). The reaction mixture was heated at 90° C. for 1 h. After cooling to room temperature, the reaction mixture was concentrated. The residue was dissolved in ethyl acetate and washed with water. The combined organic layers were dried over sodium sulfate, filtered, and concentrated. The residue was purified by flash column chromatography on silica gel to give 6-(4-chloro-7-((2-(trimethylsilyl)ethoxy)methyl)-7H-pyrrolo[2,3-d]pyrimidin-6-yl)-3,3-dimethylindolin-2-one. $^1$H NMR (400 MHz, dmso-d6) δ 12.86 (s, 1H), 10.58 (s, 1H), 8.84 (d, J=5.3 Hz, 1H), 8.54-8.46 (m, 2H), 7.81-7.73 (m, 1H), 7.68 (dd, J=7.8, 1.6 Hz, 1H), 7.57 (m, 1H), 7.51-7.45 (m, 1H), 7.42 (m, 1H), 4.96 (m, 1H), 3.89 (m, 2H), 3.17-3.10 (m, 1H), 2.10-2.00 (m, 2H), 1.71 (m, 2H), 1.54 (m, 1H), 1.31 (s, 3H), 1.26 (s, 3H). LCMS-ESI$^+$ (m/z): [M+H]$^+$ calcd for C28H25N5O3: 480.2. found: 480.2.

Example 189: 5-(6-(2,3-dihydro-1H-pyrido[2,3-b][1,4]oxazin-7-yl)-7H-pyrrolo[2,3-d]pyrimidin-4-yl)-2-((tetrahydro-2H-pyran-4-yl)oxy)benzonitrile

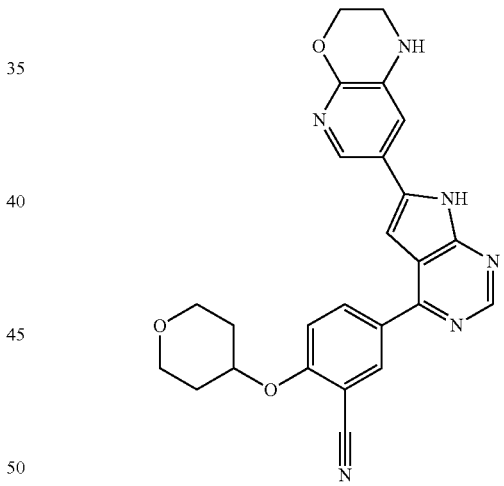

The title compound was synthesized in the same manner as Example 188 using 7-(4,4,5,5-tetramethyl-1,3,2-dioxaborolan-2-yl)-2,3-dihydro-1H-pyrido[2,3-b][1,4]oxazine and 4-chloro-6-iodo-7-((2-(trimethylsilyl)ethoxy)methyl)-7H-pyrrolo[2,3-d]pyrimidine. $^1$H NMR (400 MHz, dmso-d6) δ 12.76 (s, 1H), 8.80 (d, J=1.1 Hz, 1H), 8.51-8.47 (m, 2H), 8.09 (d, J=2.2 Hz, 1H), 7.55 (d, J=9.7 Hz, 1H), 7.48 (d, J=2.2 Hz, 1H), 7.32 (d, J=1.9 Hz, 1H), 4.96 (m, 1H), 4.31 (m, 2H), 3.87 (m, 2H), 3.31 (m, 2H), 3.18-3.10 (m, 1H), 2.05 (m, 2H), 1.70 (m, 2H), 1.55 (m, 1H). LCMS-ESI$^+$ (m/z): [M+H]$^+$ calcd for C25H22N6O3: 455.2. found: 455.2.

Example 190: 5-(6-(2-methylthiazol-5-yl)-7H-pyrrolo[2,3-d]pyrimidin-4-yl)-2-((tetrahydro-2H-pyran-4-yl)oxy)benzonitrile

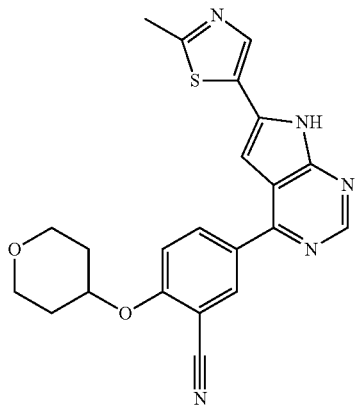 [SMILES: Cc1ncc(-c2cc3c(-c4ccc(OC5CCOCC5)c(C#N)c4)ncnc3[nH]2)s1]

The title compound was synthesized in the same manner as Example 188 using 2-methyl-5-(4,4,5,5-tetramethyl-1,3,2-dioxaborolan-2-yl)thiazole and 4-chloro-6-iodo-7-((2-(trimethylsilyl)ethoxy)methyl)-7H-pyrrolo[2,3-d]pyrimidine. $^1$H NMR (400 MHz, dmso-d6) δ 12.95 (s, 1H), 8.82 (s, 1H), 8.48 (m, 2H), 8.25 (s, 1H), 7.54 (d, J=9.7 Hz, 1H), 7.25 (d, J=1.8 Hz, 1H), 4.95 (m, 1H), 3.87 (m, 2H), 3.18-3.09 (m, 1H), 2.71 (s, 3H), 2.05 (m, 2H), 1.70 (m, 2H), 1.54 (m, 1H). LCMS-ESI$^+$ (m/z): [M+H]$^+$ calcd for C22H19N5O2S: 418.1. found: 418.1.

Example 191: 5-(6-(3,4-dihydro-2H-benzo[b][1,4]oxazin-6-yl)-7H-pyrrolo[2,3-d]pyrimidin-4-yl)-2-((tetrahydro-2H-pyran-4-yl)oxy)benzonitrile

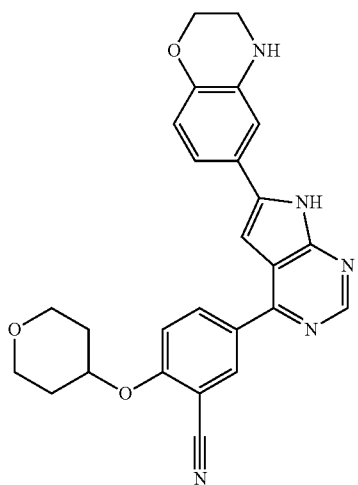 [SMILES: N#Cc1cc(-c2ncnc3[nH]c(-c4ccc5c(c4)NCCO5)cc23)ccc1OC1CCOCC1]

The title compound was synthesized in the same manner as Example 188 using 6-(4,4,5,5-tetramethyl-1,3,2-dioxaborolan-2-yl)-3,4-dihydro-2H-benzo[b][1,4]oxazine and 4-chloro-6-iodo-7-((2-(trimethylsilyl)ethoxy)methyl)-7H-pyrrolo[2,3-d]pyrimidine. $^1$H NMR (400 MHz, dmso-d6) δ 12.73 (s, 1H), 8.80 (s, 1H), 8.47 (s, 2H), 7.56 (d, J=8.8 Hz, 1H), 7.22-7.16 (m, 3H), 6.76 (d, J=8.0 Hz, 1H), 4.96 (m, 1H), 4.16 (m, 2H), 3.56 (m, 2H), 3.31 (m, 2H), 3.18-3.09 (m, 1H), 2.10-1.98 (m, 2H), 1.71 (m, 2H), 1.54 (m, 1H). LCMS-ESI$^+$ (m/z): [M+H]$^+$ calcd for C26H23N5O3: 454.2. found: 454.1.

Example 192: 2-(methylsulfonyl)-5-(2-(4-morpholinophenyl)-1H-pyrrolo[2,3-b]pyridin-4-yl)benzonitrile

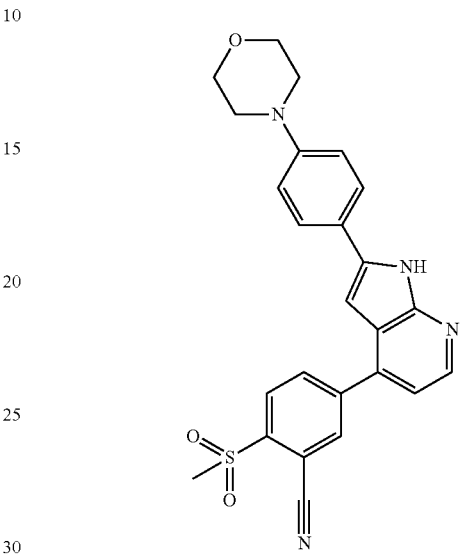

Step 1: To stirring solution of substrate 4-(4-(4-bromo-1-(phenylsulfonyl)-1H-pyrrolo[2,3-b]pyridin-2-yl)phenyl)morpholine (500 mg, 1.0 mmol), 2-fluoro-5-(4,4,5,5-tetramethyl-1,3,2-dioxaborolan-2-yl)benzonitrile (272.6 mg, 1.1 mmol) and PdCl$_2$(PPh$_3$)$_2$ (70 mg, 0.1 mmol) in DMF (6 mL) was added solution of NaHCO$_3$ (253 mg, 3.0 mmol) in 3 mL water.

This solution was stirred at 105° C. for 1 h. The reaction mixture was cooled to room temperature, diluted with dichloromethane and filtered through pad of silica gel and washed with 10% MeOH/DCM. The crude product was adsorbed on silica gel, dried and purified by column chromatography to afford product 2-fluoro-5-(2-(4-morpholinophenyl)-1-(phenylsulfonyl)-1H-pyrrolo[2,3-b]pyridin-4-yl)benzonitrile. LCMS-ESI$^+$ (m/z): [M+H]$^+$ calcd for C$_{30}$H$_{23}$FN$_4$O$_3$S: 539.1. found: 539.2.

Step 2: To the mixture of 2-fluoro-5-(2-(4-morpholinophenyl)-1-(phenylsulfonyl)-1H-pyrrolo[2,3-b]pyridin-4-yl)benzonitrile (150 mg, 0.28 mmol), sodium methanethiolate (39 mg, 0.56 mmol) were added Toluene (2 mL) followed by Water (2 ml) and stirred at RT for 3 h. The solvent was concentrated and the crude was purified by flash column chromatography to afford 2-(methylthio)-5-(2-(4-morpholinophenyl)-1-(phenylsulfonyl)-1H-pyrrolo[2,3-b]pyridin-4-yl)benzonitrile. LCMS-ESI$^+$ (m/z): [M+H]$^+$ calcd for C$_{31}$H$_{26}$N$_4$O$_3$S$_2$: 567.1. found: 567.2.

Step 3: 2-(methylthio)-5-(2-(4-morpholinophenyl)-1-(phenylsulfonyl)-1H-pyrrolo[2,3-b]pyridin-4-yl)benzonitrile (70 mg, 0.12 mmol) was dissolved in dichloromethane (1 mL) and cooled to 0° C. To stirred solution was added a solution of mCPBA (49 mg, 0.28 mmol) in dichloromethane (2 mL) at 0° C. This solution was allowed to warm to RT and stirred for 3 h. The solvent was concentrated and the crude was purified by flash column chromatography to afford 2-(methylsulfonyl)-5-(2-(4-morpholinophenyl)-1-(phenylsulfonyl)-1H-pyrrolo[2,3-b]pyridin-4-yl)benzonitrile. LCMS-ESI+ (m/z): [M+H]+ calcd for $C_{31}H_{26}N_4O_5S_2$: 599.1. found: 599.0.

Step 4: 2-(methylsulfonyl)-5-(2-(4-morpholinophenyl)-1-(phenylsulfonyl)-1H-pyrrolo[2,3-b]pyridin-4-yl)benzonitrile (75 mg, 0.12 mmol) was dissolved in a mixture of trifluoro ethanol, Me-THF (2:1), and added $Cs_2CO_3$ (122 mg, 0.37 mmol). This mixture was heated at 85° C. for 12 h. The reaction mixture was cooled to room temperature, diluted with dichloromethane and poured in to water. The organic layer separated, dried over $Na_2SO_4$ and the solvent was concentrated to dryness. The residue was purified via prep HPLC (5-95% acetonitrile in water, 0.1% trifluoroacetic acid buffer) to isolate 2-(methylsulfonyl)-5-(2-(4-morpholinophenyl)-1H-pyrrolo[2,3-b]pyridin-4-yl)benzonitrile. LCMS-ESI+ (m/z): [M+H]+ calcd for $C_{25}H_{22}N_4O_3S$: 458.1. found: 458.9.

Example 193: 2-(3-hydroxyazetidin-1-yl)-5-(2-(4-morpholinophenyl)-1H-pyrrolo[2,3-b]pyridin-4-yl)benzonitrile

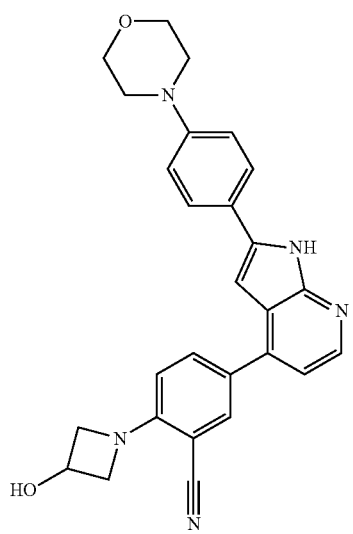 [SMILES: N#Cc1cc(-c2ccnc3[nH]c(-c4ccc(N5CCOCC5)cc4)cc23)ccc1N1CC(O)C1]

The title compound was prepared following similar procedure reported in Example 192 by substituting 2-(methylthio)-5-(2-(4-morpholinophenyl)-1-(phenylsulfonyl)-1H-pyrrolo[2,3-b]pyridin-4-yl)benzonitrile with azetidin-3-ol followed by phenylsulfonyl group deprotection as shown in the example-4 to afford product 2-(3-hydroxyazetidin-1-yl)-5-(2-(4-morpholinophenyl)-1H-pyrrolo[2,3-b]pyridin-4-yl)benzonitrile. LCMS-ESI+ (m/z): [M+H]+ calcd for $C_{27}H_{25}N_5O_2$: 452.2. found: 452.3. 1H NMR (400 MHz, DMSO-$d_6$) δ 12.05 (s, 1H), 8.14 (d, J=5.0 Hz, 1H), 7.94-7.87 (m, 2H), 7.87-7.80 (m, 1H), 7.11 (d, J=5.1 Hz, 1H), 7.05-6.95 (m, 2H), 6.92 (d, J=2.1 Hz, 1H), 6.74 (d, J=8.6 Hz, 1H), 5.76 (d, J=6.3 Hz, 1H), 4.71-4.51 (m, 1H), 4.52-4.29 (m, 2H), 4.01-3.82 (m, 2H), 3.74 (t, J=4.8 Hz, 4H), 3.17 (t, J=4.8 Hz, 4H).

Example 194: 5-(8-((3-morpholinophenyl)amino)-9H-purin-6-yl)-2-((tetrahydro-2H-pyran-4-yl)oxy)benzonitrile

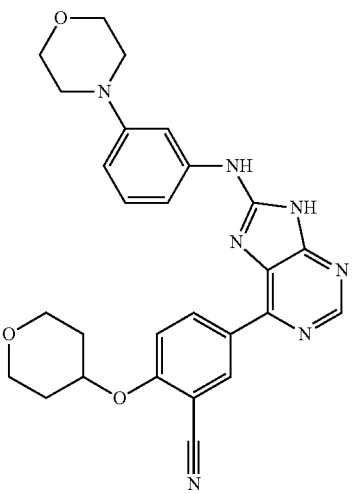 [SMILES: N#Cc1cc(-c2ncnc3[nH]c(Nc4cccc(N5CCOCC5)c4)nc23)ccc1OC1CCOCC1]

Step-1: To the mixture of 8-bromo-6-chloro-9H-purine (100 mg, 0.42 mmol) and 3-morpholinoaniline (76 mg, 0.42 mmol) were added IPA (3 mL) followed by DIPE (0.45 mL) in a 10 mL microwave vial and sealed. The mixture was irradiated at 150° C. for 8 h. The reaction mixture was transferred in to 25 mL round bottom-flask and the solvent concentrated. The crude product was purified by flash column chromatography to afford 6-chloro-N-(3-morpholinophenyl)-9H-purin-8-amine. LCMS-ESI+ (m/z): [M+H]+ calcd for $C_{15}H_{15}ClN_6O$: 330.1. found: 331.2.

Step-2: To stirred mixture of 6-chloro-N-(3-morpholinophenyl)-9H-purin-8-amine (100 mg, 0.3 mmol), 2-((tetrahydro-2H-pyran-4-yl)oxy)-5-(4,4,5,5-tetramethyl-1,3,2-dioxaborolan-2-yl)benzonitrile (120 mg, 0.36 mmol), PEPPSI-iPr catalyst (41.2 mg, 0.06 mmol) in dioxane (6 mL) was added solution of $Cs_2CO_3$ (295 mg, 0.9 mmol) in Water (3 mL) and heated at 105° C. for 12 h. The reaction mixture was cooled to room temperature, diluted with dichloromethane and filtered through pad of silica gel and washed with 10% MeOH/DCM. The solvent was concentrated and the crude product was purified by flash column chromatography to afford 5-(8-((3-morpholinophenyl)amino)-9H-purin-6-yl)-2-((tetrahydro-2H-pyran-4-yl)oxy)benzonitrile. LCMS-ESI+ (m/z): [M+H]+ calcd for $C_{27}H_{27}N_7O_3$: 498.2. found: 498.3. 1H NMR (400 MHz, DMSO-$d_6$) δ 9.94 (s, 1H), 9.09-8.83 (m, 2H), 8.65 (s, 1H), 7.57 (d, J=2.4 Hz, 1H), 7.51 (d, J=9.1 Hz, 2H), 7.20 (t, J=8.1 Hz, 1H), 7.12 (d, J=8.0 Hz, 1H), 6.67 (dd, J=8.0, 2.2 Hz, 1H), 4.93 (dt, J=8.2, 4.3 Hz, 1H), 4.25 (s, 4H), 3.87 (dt, J=10.5, 4.6 Hz, 2H), 3.77 (t, J=4.8 Hz, 4H), 3.54 (ddd, J=11.5, 8.4, 3.0 Hz, 2H), 2.14-1.94 (m, 2H), 1.70 (dtd, J=12.5, 8.3, 3.8 Hz, 2H).

Example 195: (R)-5-(2-(4-morpholinophenyl)-3H-imidazo[4,5-b]pyridin-7-yl)-2-(pyrrolidin-3-yloxy)benzonitrile

Example 196: (R)-2-((1-(2-hydroxyacetyl)pyrrolidin-3-yl)oxy)-5-(2-(4-morpholinophenyl)-3H-imidazo[4,5-b]pyridin-7-yl)benzonitrile

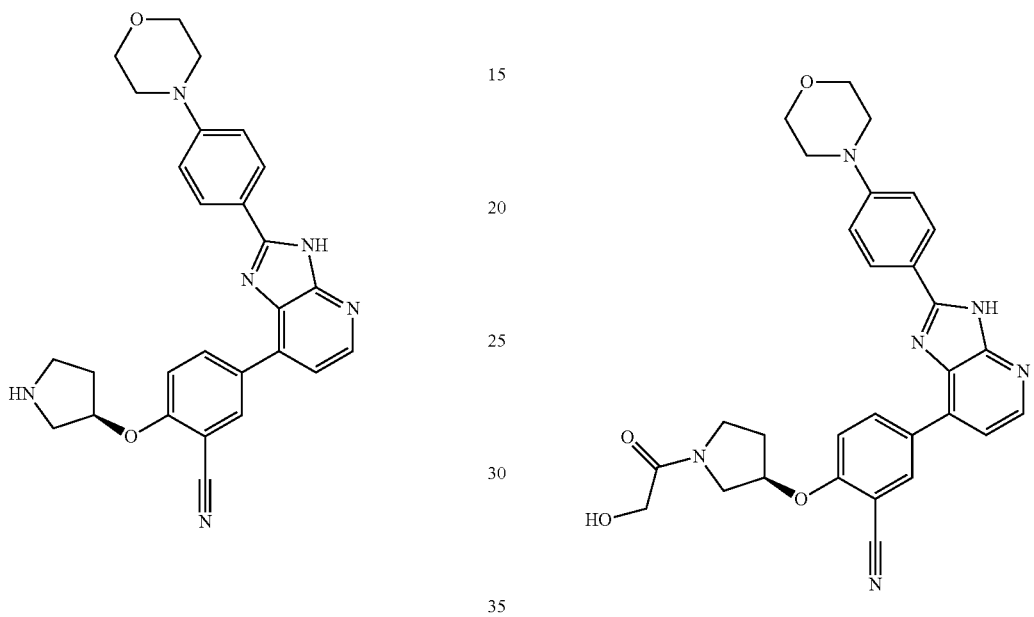

Step 1: To stirred mixture of 4-(4-(7-chloro-3H-imidazo[4,5-b]pyridin-2-yl)phenyl)morpholine (200 mg, 0.63 mmol) (R)-tert-butyl 3-(2-cyano-4-(4,4,5,5-tetramethyl-1,3,2-dioxaborolan-2-yl)phenoxy)pyrrolidine-1-carboxylate (316 mg, 0.76 mmol), PEPPSI-iPr catalyst (86 mg, 0.13 mmol) in dioxane (6 mL) was added solution of $Cs_2CO_3$ (690 mg, 1.9 mmol) in Water (3 mL) and heated at 105° C. for 1 h. The reaction mixture was cooled to room temperature, diluted with dichloromethane and filtered through pad of silica gel and washed with 10% MeOH/DCM. The solvent was concentrated and the crude product was purified by flash column chromatography on silica gel to afford (R)-tert-butyl 3-(2-cyano-4-(2-(4-morpholinophenyl)-3H-imidazo[4,5-b]pyridin-7-yl)phenoxy)pyrrolidine-1-carboxylate. LCMS-ESI$^+$ (m/z): [M+H]$^+$ calcd for $C_{32}H_{34}N_6O_4$: 567.7. found: 567.2.

Step 2: To substrate (R)-tert-butyl 3-(2-cyano-4-(2-(4-morpholinophenyl)-3H-imidazo[4,5-b]pyridin-7-yl)phenoxy)pyrrolidine-1-carboxylate (30 mg, 0.05 mmol), was added premixed solution of 15% HCl in dichloromethane (5 mL) and stirred at room temperature for 2 h. Solvent was removed by vacuum and dried to afford product (R)-5-(2-(4-morpholinophenyl)-3H-imidazo[4,5-b]pyridin-7-yl)-2-(pyrrolidin-3-yloxy)benzonitrile. LCMS-ESI$^+$ (m/z): [M+H]$^+$ calcd for $C_{27}H_{26}N_6O_2$: 467.2. found: 467.1.

To solution of compound (R)-5-(2-(4-morpholinophenyl)-3H-imidazo[4,5-b]pyridin-7-yl)-2-(pyrrolidin-3-yloxy)benzonitrile (30 mg, 0.064 mmol), 2-hydroxyacetic acid (9.8 mg, 0.13 mmol), HATU (48.9 mg, 0.12 mmol) in dichloromethane (3 mL) was added DIPE (134 uL, 0.77 mmol) in a 10 mL microwave vial and sealed. This reaction mixture was stirred at room temperature overnight. The solvent was concentrated and the crude product was purified via prep HPLC (5-95% acetonitrile in water, 0.1% trifluoroacetic acid buffer) to isolate (R)-2-((1-(2-hydroxyacetyl)pyrrolidin-3-yl)oxy)-5-(2-(4-morpholinophenyl)-3H-imidazo[4,5-b]pyridin-7-yl)benzonitrile. LCMS-ESI$^+$ (m/z): [M+H]$^+$ calcd for $C_{29}H_{28}N_6O_4$: 525.2. found: 525.3. $^1$H NMR (400 MHz, DMSO-$d_6$) δ 8.69 (d, J=48.8 Hz, 3H), 8.32 (s, 1H), 8.14 (d, J=8.4 Hz, 2H), 7.68-7.47 (m, 2H), 7.12 (d, J=8.8 Hz, 2H), 5.38 (d, J=30.7 Hz, 1H), 4.13-3.92 (m, 2H), 3.84-3.72 (m, 4H), 3.64-3.56 (m, 3H), 3.27 (t, J=4.9 Hz, 4H), 2.39-2.02 (m, 2H), 1.23 (q, J=7.2, 6.5 Hz, 2H).

Example 197: 5-(2-(4-morpholinophenyl)-3H-imidazo[4,5-b]pyridin-7-yl)-2-(piperidin-4-yloxy)benzonitrile

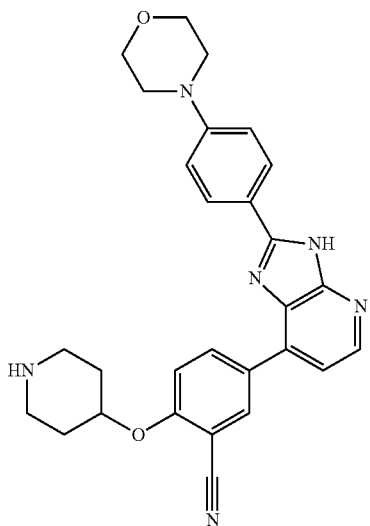 [SMILES: N#Cc1cc(-c2ccnc3[nH]c(-c4ccc(N5CCOCC5)cc4)nc23)ccc1OC1CCNCC1]

To tert-butyl 4-(2-cyano-4-(2-(4-morpholinophenyl)-3-(phenylsulfonyl)-3H-imidazo[4,5-b]pyridin-7-yl)phenoxy)piperidine-1-carboxylate (40 mg, 0.07 mmol), was added premixed solution of 15% HCl in dichloromethane (5 mL) and stirred at room temperature for 2 h. The solvent was removed by vacuum and dried to afford 5-(2-(4-morpholinophenyl)-3H-imidazo[4,5-b]pyridin-7-yl)-2-(piperidin-4-yloxy)benzonitrile LCMS-ESI$^+$ (m/z): [M+H]$^+$ calcd for $C_{28}H_{28}N_6O_2$: 481.2. found: 481.

Example 198: 2-((1-(2-hydroxyacetyl)piperidin-4-yl)oxy)-5-(2-(4-morpholinophenyl)-3H-imidazo[4,5-b]pyridin-7-yl)benzonitrile

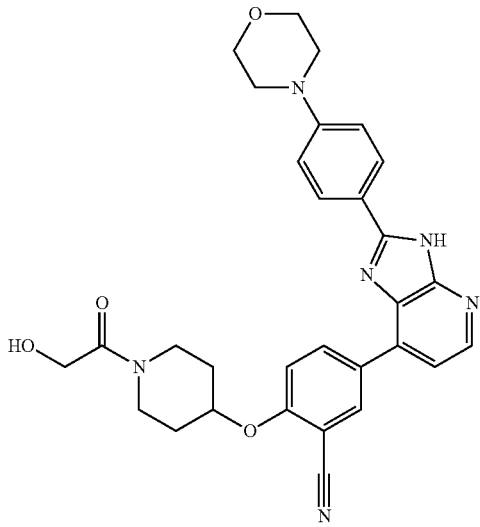 [SMILES: N#Cc1cc(-c2ccnc3[nH]c(-c4ccc(N5CCOCC5)cc4)nc23)ccc1OC1CCN(C(=O)CO)CC1]

To solution of 5-(2-(4-morpholinophenyl)-3H-imidazo[4,5-b]pyridin-7-yl)-2-(piperidin-4-yloxy)benzonitrile (30 mg, 0.062 mmol), 2-hydroxyacetic acid (9.5 mg, 0.13 mmol), HATU (47.5 mg, 0.13 mmol) in dichloromethane (3 mL) was added DIPEA (130 uL, 0.75 mmol) in a 10 mL microwave vial and sealed. This reaction mixture was stirred at room temperature overnight. The solvent was concentrated and the crude product was purified via prep HPLC (5-95% acetonitrile in water, 0.1% trifluoroacetic acid buffer) to isolate 2-((1-(2-hydroxyacetyl)piperidin-4-yl)oxy)-5-(2-(4-morpholinophenyl)-3H-imidazo[4,5-b]pyridin-7-yl)benzonitrile. LCMS-ESI$^+$ (m/z): [M+H]$^+$ calcd for $C_{30}H_{30}N_6O_4$: 539.2. found: 539.3. $^1$H NMR (400 MHz, DMSO-d$_6$) 13.41 (s, 1H), 8.81 (d, J=15.8 Hz, 2H), 8.27 (d, J=5.2 Hz, 1H), 8.12 (d, J=8.6 Hz, 2H), 7.58 (d, J=9.1 Hz, 2H), 7.11 (d, J=8.7 Hz, 2H), 4.99 (s, 1H), 4.55 (t, J=5.5 Hz, 1H), 4.12 (d, J=5.5 Hz, 2H), 3.75 (t, J=4.8 Hz, 5H), 3.53 (d, J=31.5 Hz, 2H), 3.25 (t, J=4.9 Hz, 5H), 1.98 (d, J=7.8 Hz, 2H), 1.72 (d, J=29.3 Hz, 2H).

Example 199: 2-(3-hydroxyazetidin-1-yl)-5-(6-(4-morpholinophenyl)-7H-pyrrolo[2,3-d]pyrimidin-4-yl)benzonitrile

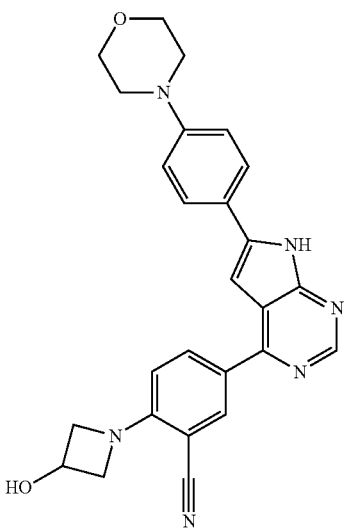 [SMILES: N#Cc1cc(-c2ncnc3[nH]c(-c4ccc(N5CCOCC5)cc4)cc23)ccc1N1CC(O)C1]

Step 1: To stirred mixture of 4-(4-(4-chloro-7-(phenylsulfonyl)-7H-pyrrolo[2,3-d]pyrimidin-6-yl)phenyl)morpholine (100 mg, 0.22 mmol), 2-(3-hydroxyazetidin-1-yl)-5-(4,4,5,5-tetramethyl-1,3,2-dioxaborolan-2-yl)benzonitrile (79.2 mg, 0.26 mmol), PEPPSI-iPr catalyst (30 mg, 0.04 mmol) in dioxane (6 mL) was added solution of Cs$_2$CO$_3$ (214.3 mg, 0.66 mmol) in Water (3 mL) and heated at 95° C. for 1 h. The reaction mixture was cooled to room temperature, diluted with dichloromethane and filtered through pad of silica gel and washed with 10% MeOH/DCM. The solvent was concentrated and the crude product was purified by flash column chromatography on silica gel to afford 2-(3-hydroxyazetidin-1-yl)-5-(6-(4-morpholinophenyl)-7H-pyrrolo[2,3-d]pyrimidin-4-yl)benzonitrile. LCMS-ESI$^+$ (m/z): [M+H]$^+$ calcd for $C_{32}H_{28}N_6O_4S$: 593.2. found: 593.3.

Step 2: 2-(3-hydroxyazetidin-1-yl)-5-(6-(4-morpholinophenyl)-7H-pyrrolo[2,3-d]pyrimidin-4-yl)benzonitrile (100 mg, 0.16 mmol) was dissolved in a mixture of trifluoro ethanol, Me-THF (2:1), and added Cs$_2$CO$_3$ (165 mg, 0.5 mmol). This mixture was heated at 85° C. for 12 h. The reaction mixture was cooled to room temperature, diluted with dichloromethane and poured in to water. The organic layer separated, dried over Na$_2$SO$_4$ and the solvent was concentrated to dryness. The residue was purified via prep HPLC (5-95% acetonitrile in water, 0.1% trifluoroacetic acid buffer) to isolate 2-(3-hydroxyazetidin-1-yl)-5-(6-(4-morpholinophenyl)-7H-pyrrolo[2,3-d]pyrimidin-4-yl)benzonitrile. LCMS-ESI$^+$ (m/z): [M+H]$^+$ calcd for $C_{26}H_{24}N_6O_2$: 453.2. found: 453.3. $^1$H NMR (400 MHz, DMSO-d$_6$) δ 12.59-12.36 (m, 1H), 8.67 (s, 1H), 8.40-8.26 (m, 2H), 7.97-7.84 (m, 2H), 7.26 (s, 1H), 7.09-6.95 (m, 2H), 6.72 (d, J=8.9 Hz, 1H), 5.89-5.65 (m, 1H), 4.60 (s, 1H), 4.52-4.40 (m, 2H), 3.95 (dd, J=8.9, 4.3 Hz, 2H), 3.74 (t, J=4.8 Hz, 4H), 3.20 (t, J=4.9 Hz, 4H).

Example 200: 5-(6-(4-(piperazin-1-yl)phenyl)-7H-pyrrolo[2,3-d]pyrimidin-4-yl)-2-((tetrahydro-2H-pyran-4-yl)oxy)benzonitrile

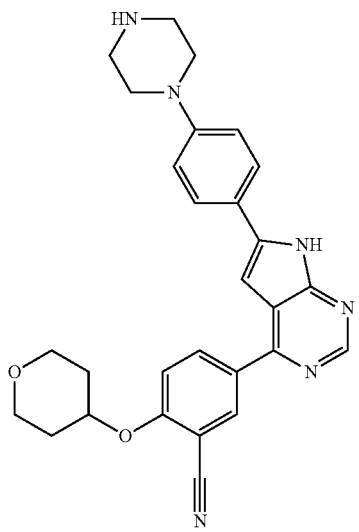 [SMILES: N#Cc1cc(-c2ncnc3[nH]c(-c4ccc(N5CCNCC5)cc4)cc23)ccc1OC1CCOCC1]

Step-1: To stirring solution of 4-chloro-6-iodo-7-(phenylsulfonyl)-7H-pyrrolo[2,3-d]pyrimidine (500 mg, 1.2 mmol), tert-butyl 4-(4-(4,4,5,5-tetramethyl-1,3,2-dioxaborolan-2-yl)phenyl)piperazine-1-carboxylate (462.5 mg, 1.2 mmol), and PdCl$_2$(Ph$_3$P)$_2$ (83.6 mg, 0.11 mmol) in dioxan (12 mL) were added solution of NaHCO$_3$ (300 mg, 3.5 mmol) in water (6 mL). The reaction was stirred at 100° C. for 1 h. The reaction mixture was diluted with dichloromethane, filtered through pad of silica gel washed with 10% MeOH/DCM and the solvent concentrated to dryness. The residue was purified by flash column chromatography on silica gel to afford tert-butyl 4-(4-(4-chloro-7-(phenylsulfonyl)-7H-pyrrolo[2,3-d]pyrimidin-6-yl)phenyl)piperazine-1-carboxylate. LCMS-ESI$^+$ (m/z): [M+H]$^+$ calcd for $C_{27}H_{28}ClN_5O_4S$: 554.2. found: 554.2.

Step-2: To stirred mixture of tert-butyl 4-(4-(4-chloro-7-(phenylsulfonyl)-7H-pyrrolo[2,3-d]pyrimidin-6-yl)phenyl)piperazine-1-carboxylate (400 mg, 0.72 mmol), 2-((tetrahydro-2H-pyran-4-yl)oxy)-5-(4,4,5,5-tetramethyl-1,3,2-dioxaborolan-2-yl)benzonitrile (285 mg, 0.86 mmol), PEPPSI-iPr catalyst (98.3 mg, 0.14 mmol) in dioxane (20 mL) was added solution of Cs$_2$CO$_3$ (704 mg, 2.1 mmol) in Water (10 mL) and heated at 105° C. for 12 h. The reaction mixture was cooled to room temperature, diluted with dichloromethane and filtered through pad of silica gel and washed with 10% MeOH/DCM. The solvent was concentrated and the crude product was purified by flash column chromatography on silica gel to afford tert-butyl 4-(4-(4-(3-cyano-4-((tetrahydro-2H-pyran-4-yl)oxy)phenyl)-7-(phenylsulfonyl)-7H-pyrrolo[2,3-d]pyrimidin-6-yl)phenyl)piperazine-1-carboxylate LCMS-ESI$^+$ (m/z): [M+H]$^+$ calcd for $C_{39}H_{40}N_6O_6S$: 721.2. found: 721.3.

Step-3: To tert-butyl 4-(4-(4-(3-cyano-4-((tetrahydro-2H-pyran-4-yl)oxy)phenyl)-7-(phenylsulfonyl)-7H-pyrrolo[2,3-d]pyrimidin-6-yl)phenyl)piperazine-1-carboxylate (400 mg, 0.55 mmol), was added premixed solution of 15% HCl in dichloromethane (5 mL) and stirred at room temperature for 2 h. Solvent was removed by vacuum and dried to afford 5-(7-(phenylsulfonyl)-6-(4-(piperazin-1-yl)phenyl)-7H-pyrrolo[2,3-d]pyrimidin-4-yl)-2-((tetrahydro-2H-pyran-4-yl)oxy)benzonitrile. LCMS-ESI$^+$ (m/z): [M+H]$^+$ calcd for $C_{34}H_{32}N_6O_4S$: 621.2. found: 621.3.

Step-4: 5-(7-(phenylsulfonyl)-6-(4-(piperazin-1-yl)phenyl)-7H-pyrrolo[2,3-d]pyrimidin-4-yl)-2-((tetrahydro-2H-pyran-4-yl)oxy)benzonitrile was subjected for phenylsulfonyl group deprotection to afford title compound. LCMS-ESI$^+$ (m/z): [M+H]$^+$ calcd for $C_{28}H_{28}N_6O_2$: 481.2. found: 481.3. $^1$H NMR (400 MHz, DMSO-d$_6$) δ 12.70-12.56 (m, 1H), 8.75 (d, J=11.6 Hz, 2H), 8.52 (d, J=8.0 Hz, 2H), 8.03-7.90 (m, 2H), 7.61-7.46 (m, 1H), 7.37 (d, J=2.0 Hz, 1H), 7.18-7.01 (m, 2H), 4.96 (dt, J=8.0, 4.0 Hz, 1H), 3.88 (ddd, J=10.5, 6.0, 4.0 Hz, 2H), 3.56 (ddd, J=11.4, 8.3, 3.1 Hz, 2H), 3.46 (t, J=5.2 Hz, 4H), 3.25 (s, 4H), 2.13-1.97 (m, 2H), 1.71 (dtd, J=12.3, 8.2, 3.9 Hz, 2H).

Example 214-a: 5-(6-(4-(4-(2-hydroxyacetyl)piperazin-1-yl)phenyl)-7H-pyrrolo[2,3-d]pyrimidin-4-yl)-2-((tetrahydro-2H-pyran-4-yl)oxy)benzonitrile

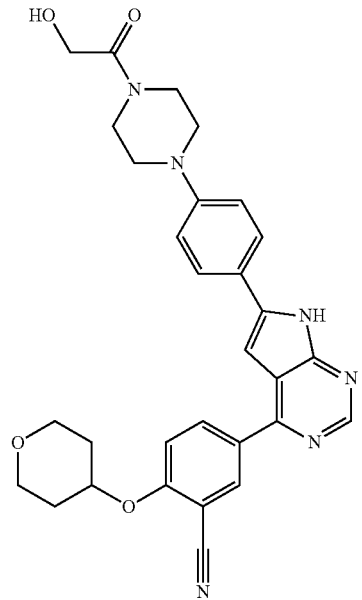 [SMILES: N#Cc1cc(-c2ncnc3[nH]c(-c4ccc(N5CCN(C(=O)CO)CC5)cc4)cc23)ccc1OC1CCOCC1]

5-(7-(phenylsulfonyl)-6-(4-(piperazin-1-yl)phenyl)-7H-pyrrolo[2,3-d]pyrimidin-4-yl)-2-((tetrahydro-2H-pyran-4-yl)oxy)benzonitrile was subjected for glycolic acid coupling followed by phenylsulfonyl group deprotection to afford title compound. LCMS-ESI$^+$ (m/z): [M+H]$^+$ calcd for $C_{30}H_{30}N_6O_4$: 539.2. found: 539.2. $^1$H NMR (400 MHz, Chloroform-d) δ 11.41 (s, 1H), 8.91 (s, 1H), 8.52-8.35 (m, 2H), 7.78 (d, J=8.5 Hz, 2H), 7.18 (d, J=8.9 Hz, 1H), 7.07 (d, J=8.8 Hz, 2H), 7.00-6.91 (m, 1H), 4.87-4.73 (m, 1H), 4.26 (s, 2H), 4.07 (ddd, J=11.2, 7.2, 3.6 Hz, 2H), 3.89 (t, J=5.2

Hz, 2H), 3.74-3.56 (m, 3H), 3.50 (d, J=5.7 Hz, 2H), 3.36 (d, J=5.5 Hz, 4H), 2.17-2.07 (m, 2H), 2.06-1.86 (m, 2H).

Example 215: 5-(6-(4-(4-(methylsulfonyl)piperazin-1-yl)phenyl)-7H-pyrrolo[2,3-d]pyrimidin-4-yl)-2-((tetrahydro-2H-pyran-4-yl)oxy)benzonitrile

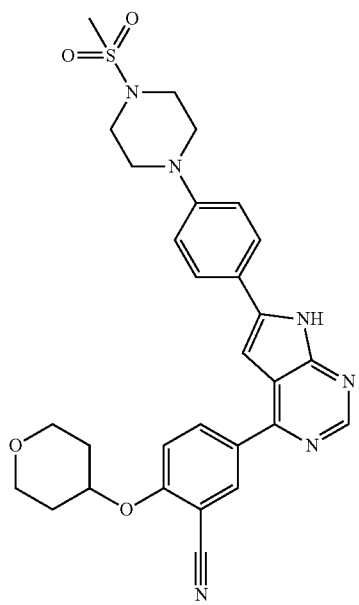 [SMILES: CS(=O)(=O)N1CCN(c2ccc(-c3cc4c(-c5ccc(OC6CCOCC6)c(C#N)c5)ncnc4[nH]3)cc2)CC1]

5-(7-(phenylsulfonyl)-6-(4-(piperazin-1-yl)phenyl)-7H-pyrrolo[2,3-d]pyrimidin-4-yl)-2-((tetrahydro-2H-pyran-4-yl)oxy)benzonitrile was subjected for methanesulfonyl chloride coupling followed by phenylsulfonyl group deprotection to afford title compound. LCMS-ESI$^+$ (m/z): [M+H]$^+$ calcd for $C_{29}H_{30}N_6O_4S$: 559.2. found: 559.2. $^1$H NMR (400 MHz, DMSO-d$_6$) δ 12.58 (d, J=1.9 Hz, 1H), 8.74 (s, 1H), 8.57-8.48 (m, 1H), 8.51 (s, 1H), 7.94 (d, J=8.6 Hz, 2H), 7.53 (d, J=8.8 Hz, 1H), 7.33 (d, J=1.9 Hz, 1H), 7.08 (d, J=8.7 Hz, 2H), 4.95 (dt, J=8.1, 4.2 Hz, 1H), 3.88 (dt, J=10.5, 4.5 Hz, 2H), 3.56 (ddd, J=11.4, 8.3, 3.1 Hz, 2H), 3.37 (t, J=5.1 Hz, 4H), 3.24 (d, J=5.9 Hz, 4H), 2.92 (s, 3H), 2.05 (d, J=13.3 Hz, 2H), 1.71 (dtd, J=12.3, 8.1, 3.8 Hz, 2H).

Example 216: 5-(2-(3,5-dimethylisoxazol-4-yl)-1H-pyrrolo[2,3-b]pyridin-4-yl)-2-((tetrahydro-2H-pyran-4-yl)oxy)benzonitrile

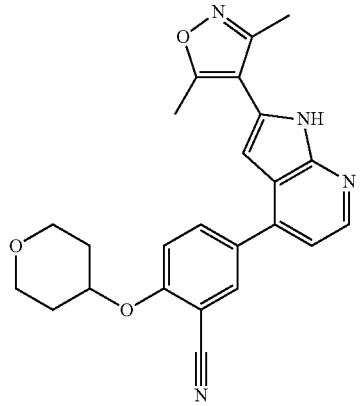 [SMILES: Cc1noc(C)c1-c1cc2c(-c3ccc(OC4CCOCC4)c(C#N)c3)ccnc2[nH]1]

To an appropriate sized microwave vial, 5-(6-iodo-7-(phenylsulfonyl)-7H-pyrrolo[2,3-d]pyrimidin-4-yl)-2-((tetrahydro-2H-pyran-4-yl)oxy)benzonitrile (80 mg, 0.137 mmol), 3,5-dimethyl-4-(4,4,5,5-tetramethyl-1,3,2-dioxaborolan-2-yl)isoxazole (33.8 mg, 0.150 mmol), cesium carbonate (133 mg, 0.41 mmol), dioxane (3 mL) and water (1.5 mL) were added. The mixture was degassed with nitrogen for 10 minutes. PEPPSI-iPr catalyst (8.5 mg, 0.014 mmol) was added and the solution was heated at 105° C. for 2 h. After cooling to room temperature, the mixture was poured into water, and extracted with dichloromethane. The combined organic layers were washed with brine, dried with magnesium sulfate, filtered and concentrated under reduced pressure. The residue 5-(6-(3,5-dimethylisoxazol-4-yl)-7-(phenylsulfonyl)-7H-pyrrolo[2,3-d]pyrimidin-4-yl)-2-((tetrahydro-2H-pyran-4-yl)oxy)benzonitrile was used for next step.

To an appropriate sized microwave vial, the crude material 5-(6-(3,5-dimethylisoxazol-4-yl)-7-(phenylsulfonyl)-7H-pyrrolo[2,3-d]pyrimidin-4-yl)-2-((tetrahydro-2H-pyran-4-yl)oxy)benzonitrile (53 mg, 0.09 mmol) and Cs$_2$CO$_3$ (93 mg, 0.29 mmol) in THF (4 mL) and trifluoro ethanol (2 mL) was heated at 105° C. for 6 h. After cooling down to room temperature, the mixture was poured into water, and extracted with dichloromethane. The combined organic layers were washed with brine, dried with magnesium sulfate, filtered and concentrated under reduced pressure. The residue was purified via prep HPLC (10-95% acetonitrile in water, 0.1% trifluoroacteic acid buffer). Clean fractions poured into a saturated solution of sodium bicarbonate in water and extracted with dichloromethane to yield the product 5-(6-(3,5-dimethylisoxazol-4-yl)-7H-pyrrolo[2,3-d]pyrimidin-4-yl)-2-((tetrahydro-2H-pyran-4-yl)oxy)benzonitrile. $^1$H NMR (400 MHz, DMSO-d6) δ 12.00 (s, 1H), 8.28 (d, J=5.0 Hz, 1H), 8.10 (d, J=2.3 Hz, 1H), 8.06 (dd, J=8.8, 2.4 Hz, 1H), 7.51 (d, J=8.9 Hz, 1H), 7.23 (d, J=5.0 Hz, 1H), 6.71 (s, 1H), 4.90 (tt, J=7.9, 3.9 Hz, 1H), 3.87 (ddd, J=10.4, 5.9, 3.9 Hz, 2H), 3.55 (ddd, J=11.5, 8.3, 3.1 Hz, 2H), 2.51 (s, 3H), 2.33 (s, 3H), 2.12-1.91 (m, 2H), 1.69 (dtd, J=12.4, 8.2, 3.8 Hz, 2H). LCMS-ESI$^+$ (m/z): [M+H]$^+$ calcd for $C_{24}H_{22}N_4O_3$: 415.2. found 415.1.

Example 217: 5-(2-(2-oxo-1,2-dihydropyridin-4-yl)-1H-pyrrolo[2,3-b]pyridin-4-yl)-2-((tetrahydro-2H-pyran-4-yl)oxy)benzonitrile

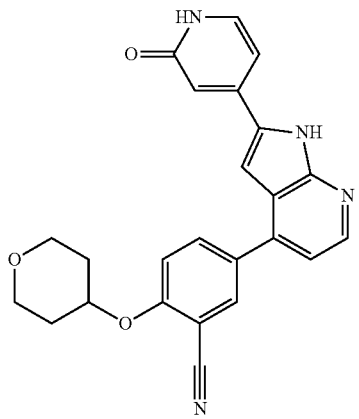 [SMILES: N#Cc1cc(-c2ccnc3[nH]c(-c4cc[nH]c(=O)c4)cc23)ccc1OC1CCOCC1]

To an appropriate sized microwave vial, 5-(2-iodo-1-(phenylsulfonyl)-1H-pyrrolo[2,3-b]pyridin-4-yl)-2-((tetrahydro-2H-pyran-4-yl)oxy)benzonitrile (80 mg, 0.137 mmol), 2-(tert-butoxy)-4-(4,4,5,5-tetramethyl-1,3,2-dioxaborolan-2-yl)pyridine (42 mg, 0.150 mmol), cesium carbonate (133 mg, 0.41 mmol), dioxane (3 mL) and water (1.5 mL) were added. The mixture was degassed with nitrogen for 10 minutes. PEPPSI-iPr catalyst (9 mg, 0.014 mmol) was added and the solution was heated at 105° C. for 2 h. After cooling to room temperature, the mixture was poured into water, and extracted with dichloromethane. The combined organic layers were washed with brine, dried with magnesium sulfate, filtered and concentrated under reduced pressure. The residue 5-(2-(2-(tert-butoxy)pyridin-4-yl)-1-(phenylsulfonyl)-1H-pyrrolo[2,3-b]pyridin-4-yl)-2-((tetrahydro-2H-pyran-4-yl)oxy)benzonitrile was used for next step.

To an appropriate sized microwave vial, the crude material 5-(2-(2-(tert-butoxy)pyridin-4-yl)-1-(phenylsulfonyl)-1H-pyrrolo[2,3-b]pyridin-4-yl)-2-((tetrahydro-2H-pyran-4-yl)oxy)benzonitrile (55 mg, 0.09 mmol) and $Cs_2CO_3$ (88 mg, 0.27 mmol) in THF (4 mL) and 2,2,2-trifluoroethanol (2 mL) was heated at 105° C. for 6 h. After cooling down to room temperature, the mixture was poured into water, and extracted with dichloromethane. The combined organic layers were washed with brine, dried with magnesium sulfate, filtered and concentrated under reduced pressure. The residue 5-(2-(2-(tert-butoxy)pyridin-4-yl)-1H-pyrrolo[2,3-b]pyridin-4-yl)-2-((tetrahydro-2H-pyran-4-yl)oxy)benzonitrile was used for next step.

To a 100 ml round bottle flask, the compound 5-(2-(2-(tert-butoxy)pyridin-4-yl)-1H-pyrrolo[2,3-b]pyridin-4-yl)-2-((tetrahydro-2H-pyran-4-yl)oxy)benzonitrile in TFA (5 mL) was stirred at room temperature for 1 hr. The reaction was concentrated under reduced pressure. The residue was re-dissolved in acetonitrile and then purified via prep HPLC (2-95% acetonitrile in water, 0.1% trifluoroacteic acid buffer) to yield the product 5-(2-(2-oxo-1,2-dihydropyridin-4-yl)-1H-pyrrolo[2,3-b]pyridin-4-yl)-2-((tetrahydro-2H-pyran-4-yl)oxy)benzonitrile. $^1$H NMR (400 MHz, DMSO-$d_6$) δ 12.39 (s, 1H), 11.51 (s, 1H), 8.34 (d, J=5.0 Hz, 1H), 8.15 (d, J=2.3 Hz, 1H), 8.07 (dd, J=8.8, 2.4 Hz, 1H), 7.51 (d, J=9.0 Hz, 1H), 7.40 (d, J=6.9 Hz, 1H), 7.35 (s, 1H), 7.25 (d, J=5.0 Hz, 1H), 6.98 (s, 1H), 6.81 (dd, J=6.9, 1.8 Hz, 1H), 4.92 (tt, J=8.1, 3.9 Hz, 1H), 3.87 (ddd, J=10.5, 5.9, 3.9 Hz, 2H), 3.55 (ddd, J=11.5, 8.3, 3.2 Hz, 2H), 2.11-1.96 (m, 2H), 1.70 (dtd, J=12.3, 8.1, 3.8 Hz, 2H). LCMS-ESI$^+$ (m/z): [M+H]$^+$ calcd for $C_{24}H_{20}N_4O_3$: 413.2. found: 413.1.

Example 218: 5-(6-(4-morpholinophenyl)-7H-pyrrolo[2,3-d]pyrimidin-4-yl)-2-(piperidin-4-yloxy)benzonitrile

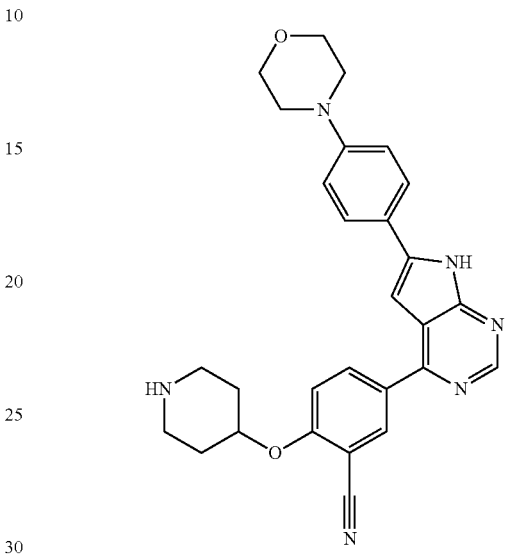

To an appropriate sized microwave vial, 4-bromo-6-iodo-7-(phenylsulfonyl)-7H-pyrrolo[2,3-d]pyrimidine (300 mg, 0.72 mmol), 4-(4-(4,4,5,5-tetramethyl-1,3,2-dioxaborolan-2-yl)phenyl)morpholine (227 mg, 0.79 mmol), sodium bicarbonate (210 mg, 2.1 mmol), 1,4-dioxane (6 mL) and water (3 mL) were added. The mixture was degassed with nitrogen for 10 minutes. Bis(triphenylphosphine)palladium (11) dichloride catalyst (84 mg, 0.07 mmol) was added and the solution heated at 105° C. for 2 h. After cooling to room temperature, the mixture was poured into water, and extracted with dichloromethane. The combined organic layers were washed with brine, dried with magnesium sulfate, filtered and concentrated under reduced pressure. The residue 4-(4-(4-bromo-7-(phenylsulfonyl)-7H-pyrrolo[2,3-d]pyrimidin-6-yl)phenyl)morpholine was used for next step.

To an appropriate sized microwave vial, 4-(4-(4-bromo-7-(phenylsulfonyl)-7H-pyrrolo[2,3-d]pyrimidin-6-yl)phenyl)morpholine (290 mg, 0.64 mmol), tert-butyl 4-(2-cyano-4-(4,4,5,5-tetramethyl-1,3,2-dioxaborolan-2-yl)phenoxy)piperidine-1-carboxylate (300 mg, 0.70 mmol), cesium carbonate (621 mg, 1.9 mmol), 1,4-dioxane (6 mL) and water (3 mL) were added. The mixture was degassed with nitrogen for 10 minutes. PEPPSI-iPr catalyst (43 mg, 0.06 mmol) was added and the solution was heated at 105° C. for 2 h. After cooling to room temperature, the mixture was poured into water, and extracted with dichloromethane. The combined organic layers were washed with brine, dried with magnesium sulfate, filtered and concentrated under reduced pressure. The residue tert-butyl 4-(2-cyano-4-(6-(4-morpholinophenyl)-7-(phenylsulfonyl)-7H-pyrrolo[2,3-d]pyrimidin-4-yl)phenoxy)piperidine-1-carboxylate was used for next step.

To a 100 ml round bottle flask, the compound tert-butyl 4-(2-cyano-4-(6-(4-morpholinophenyl)-7-(phenylsulfonyl)-7H-pyrrolo[2,3-d]pyrimidin-4-yl)phenoxy)piperidine-1-carboxylate (400 mg, 0.56 mmol) in TFA (12 mL) was stirred at room temperature for 1 hr. The reaction was concentrated under reduced pressure. Solids were re-dissolved into DCM and a saturated aqueous solution of $Na_2CO_3$ was added, desired product was extracted with dichloromethane. Organic layer was washed with brine, dried with magnesium sulfate, filtered and concentrated under reduced pressure. The residue 5-(6-(4-morpholinophenyl)-7-(phenylsulfonyl)-7H-pyrrolo[2,3-d]pyrimidin-4-yl)-2-(piperidin-4-yloxy)benzonitrile was used for next step.

To an appropriate sized microwave vial, the crude material 5-(6-(4-morpholinophenyl)-7-(phenylsulfonyl)-7H-pyrrolo[2,3-d]pyrimidin-4-yl)-2-(piperidin-4-yloxy)benzonitrile (100 mg, 0.16 mmol) and $Cs_2CO_3$ (132 mg, 0.4 mmol) in tetrahydrofuran (4 ml) and 2,2,2-trifluoroethanol (2 mL) was heated at 105° C. for 6 h. After cooling down to room temperature, the mixture was poured into water, and extracted with dichloromethane. The combined organic layers were washed with brine, dried with magnesium sulfate, filtered and concentrated under reduced pressure. The residue was purified via prep HPLC (10-95% acetonitrile in water, 0.1% trifluoroacteic acid buffer) to yield the product 5-(6-(4-morpholinophenyl)-7H-pyrrolo[2,3-d]pyrimidin-4-yl)-2-(piperidin-4-yloxy)benzonitrile. $^1H$ NMR (400 MHz, DMSO-$d_6$) δ 12.6 (s, 1H), 8.76 (s, 1H), 8.58-8.40 (m, 2H), 7.94 (d, J=8.8 Hz, 2H), 7.54 (d, J=9.7 Hz, 1H), 7.34 (d, J=2.0 Hz, 1H), 7.05 (d, J=8.7 Hz, 2H), 5.07-5.0 (m, 1H), 3.75 (t, J=4.8 Hz, 4H), 3.31-3.12 (m, 9H), 2.22-2.10 (m, 2H), 2.02-1.87 (m, 2H). LCMS-ESI$^+$ (m/z): [M+H]$^+$ calcd for $C_{28}H_{28}N_6O_2$: 481.2. found: 481.2.

Example 219: 5-(6-(4-(4-methylpiperazin-1-yl)phenyl)-7H-pyrrolo[2,3-d]pyrimidin-4-yl)-2-((tetrahydro-2H-pyran-4-yl)oxy)benzonitrile

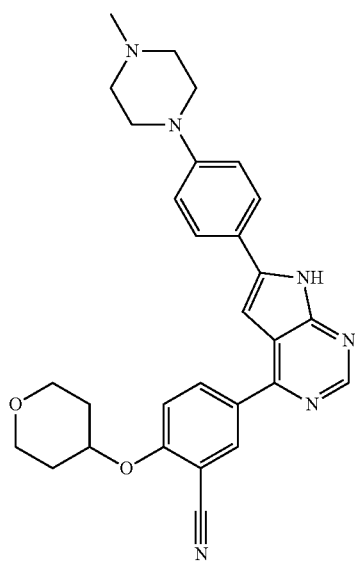

The title compound was prepared following a similar procedure reported in Example 218 using 1-methyl-4-(4-(4,4,5,5-tetramethyl-1,3,2-dioxaborolan-2-yl)phenyl)piperazine and 2-((tetrahydro-2H-pyran-4-yl)oxy)-5-(4,4,5,5-tetramethyl-1,3,2-dioxaborolan-2-yl)benzonitrile. $^1H$ NMR (400 MHz, DMSO-$d_6$) δ 12.5 (s, 1H), 8.73 (s, 1H), 8.55-8.49 (m, 2H), 7.91 (d, J=8.4 Hz, 2H), 7.53 (d, J=8.8 Hz, 1H), 7.30 (s, 1H), 7.03 (d, J=8.5 Hz, 2H), 5.03-4.86 (m, 1H), 3.88 (dt, J=10.9, 4.7 Hz, 2H), 3.56 (ddd, J=11.5, 8.4, 3.0 Hz, 2H), 3.25-3.2 (m, 4H), 2.5-2.42 (m, 4H), 2.21 (s, 3H), 2.05 (q, J=5.7, 4.6 Hz, 2H), 1.79-1.62 (m, 2H). LCMS-ESI$^+$ (m/z): [M+H]$^+$ calcd for $C_{29}H_{30}N_6O_2$: 495.2. found: 495.2.

Example 220: 2-((1-(2-hydroxyacetyl)piperidin-4-yl)oxy)-5-(6-(4-morpholinophenyl)-7H-pyrrolo[2,3-d]pyrimidin-4-yl)benzonitrile

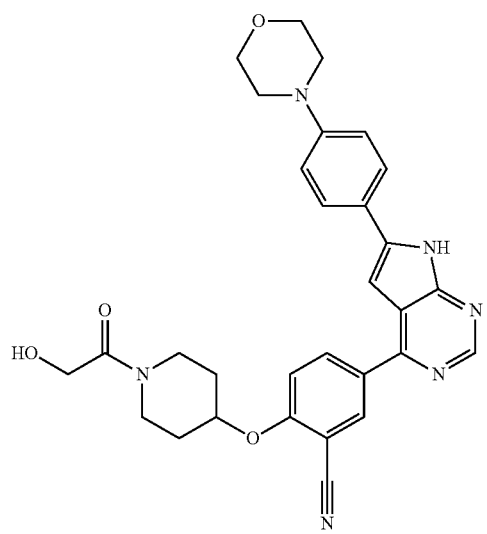 [SMILES: N#Cc1cc(-c2ncnc3[nH]c(-c4ccc(N5CCOCC5)cc4)cc23)ccc1OC1CCN(C(=O)CO)CC1]

Example 218 was followed to synthesize the intermediate 5-(6-(4-morpholinophenyl)-7H-pyrrolo[2,3-d]pyrimidin-4-yl)-2-(piperidin-4-yloxy)benzonitrile.

To a solution of 5-(6-(4-morpholinophenyl)-7H-pyrrolo[2,3-d]pyrimidin-4-yl)-2-(piperidin-4-yloxy)benzonitrile (42 mg, 0.087 mmol), glycolic acid (7 mg, 0.09 mmol), HATU (38 mgs, 0.1 mmol) in DMF (3 mL) was added DIPEA (34 mg, 0.27 mmol) in a 10 mL microwave vial and sealed. This reaction mixture was stirred at room temperature for 2 hrs. Water was added and it was extracted with dichloromethane. Organic layer was dried over $Mg_2SO_4$ and evaporated to dryness. Solids re-dissolved in acetonitrile and purified via preparative HPLC (5-65% acetonitrile in water, 0.1% trifluoroacteic acid buffer). Fractions containing desired product were collected lyophilized to obtain 2-((1-(2-hydroxyacetyl)piperidin-4-yl)oxy)-5-(6-(4-morpholinophenyl)-7H-pyrrolo[2,3-d]pyrimidin-4-yl)benzonitrile. $^1H$ NMR (400 MHz, DMSO-$d_6$) δ 12.77 (s, 1H), 8.80 (s, 1H), 8.56-8.45 (m, 2H), 7.94 (d, J=8.8 Hz, 2H), 7.57 (d, J=9.7 Hz, 1H), 7.37 (d, J=1.9 Hz, 1H), 7.05 (d, J=8.8 Hz, 2H), 5.2-5.05 (m, 2H), 4.12 (s, 2H), 3.74 (q, J=6.2, 5.4 Hz, 4H), 3.6-3.45 (m, 2H), 3.40-3.28 (m, 2H), 3.22 (t, J=4.9 Hz, 4H), 1.99 (d, J=16.5 Hz, 2H), 1.74 (d, J=28.9 Hz, 2H). LCMS-ESI$^+$ (m/z): [M+H]$^+$ calcd for $C_{30}H_{30}N_6O_4$: 539.2. found: 539.2.

Example 221: 5-(6-(4-morpholinophenyl)-7H-pyrrolo[2,3-d]pyrimidin-4-yl)isoindolin-1-one

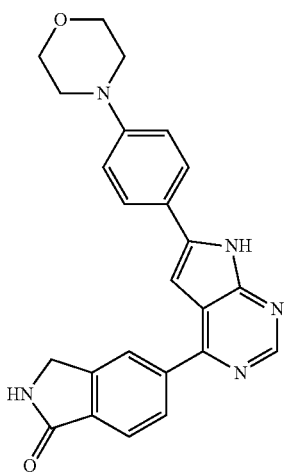 [SMILES: O=C1NCc2cc(-c3ncnc4[nH]c(-c5ccc(N6CCOCC6)cc5)cc34)ccc21]

The title compound was prepared following a similar procedure reported in Example 218 using 5-(4,4,5,5-tetramethyl-1,3,2-dioxaborolan-2-yl)isoindolin-1-one. LCMS-ESI⁺ (m/z): [M+H]⁺ calcd for $C_{24}H_{21}N_5O_2$: 412.2. found 412.2.

Example 223: 5,5'-(7H-pyrrolo[2,3-d]pyrimidine-4,6-diyl)bis(2-((tetrahydro-2H-pyran-4-yl)oxy)benzonitrile)

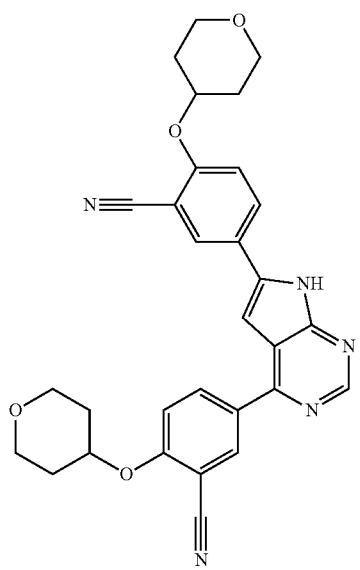 [SMILES: N#Cc1cc(-c2cc3c(-c4ccc(OC5CCOCC5)c(C#N)c4)ncnc3[nH]2)ccc1OC1CCOCC1]

The title compound was prepared following a similar procedure reported in Example 218 using 2-((tetrahydro-2H-pyran-4-yl)oxy)-5-(4,4,5,5-tetramethyl-1,3,2-dioxaborolan-2-yl)benzonitrile. ¹H NMR (400 MHz, DMSO-d₆) δ 12.85 (s, 1H), 8.83 (s, 1H), 8.51 (ddd, J=10.7, 5.9, 2.3 Hz, 3H), 8.30 (dd, J=9.0, 2.4 Hz, 1H), 7.60 (d, J=1.8 Hz, 1H), 7.53 (dd, J=14.0, 9.4 Hz, 2H), 5.02-4.87 (m, 2H), 3.92-3.82 (m, 4H), 3.6-3.51 (m, 4H), 2.13-1.95 (m, 4H), 1.75-1.62 (m, 4H). LCMS-ESI⁺ (m/z): [M+H]⁺ calcd for $C_{30}H_{27}N_5O_4$: 522.2. found 522.2.

Example 224: 5,5'-(7H-pyrrolo[2,3-d]pyrimidine-4,6-diyl)bis(isoindolin-1-one)

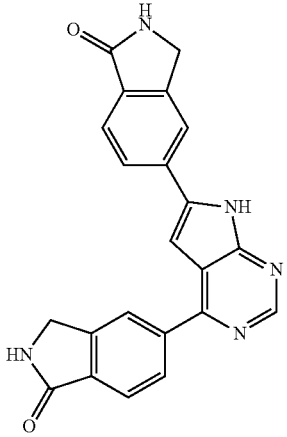 [SMILES: O=C1NCc2cc(-c3cc4c(-c5ccc6c(c5)CNC6=O)ncnc4[nH]3)ccc21]

The title compound was prepared following a similar procedure reported in Example 218 using 5-(4,4,5,5-tetramethyl-1,3,2-dioxaborolan-2-yl)isoindolin-1-one. LCMS-ESI⁺ (m/z): [M+H]⁺ calcd for $C_{22}H_{15}N_5O_2$: 382.1. found 382.2.

Example 225: 5-(2-(2-(tert-butoxy)pyridin-4-yl)-1H-pyrrolo[2,3-b]pyridin-4-yl)-2-((tetrahydro-2H-pyran-4-yl)oxy)benzonitrile

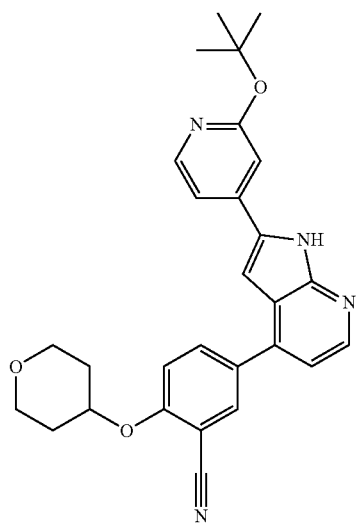 [SMILES: CC(C)(C)Oc1cc(-c2cc3c(-c4ccc(OC5CCOCC5)c(C#N)c4)ccnc3[nH]2)ccn1]

The title compound was prepared following a similar procedure reported in Example 216 using 2-(tert-butoxy)-4-(4,4,5,5-tetramethyl-1,3,2-dioxaborolan-2-yl)pyridine. LCMS-ESI⁺ (m/z): [M+H]⁺ calcd for $C_{28}H_{28}N_4O_3$: 469.2. found 469.2.

Example 226: 5-(6-(4-(2-(pyrrolidin-1-yl)ethoxy)phenyl)-7H-pyrrolo[2,3-d]pyrimidin-4-yl)-2-((tetrahydro-2H-pyran-4-yl)oxy)benzonitrile Example 227: 2-(3-hydroxyazetidin-1-yl)-5-(6-(4-(2-(pyrrolidin-1-yl)ethoxy)phenyl)-7H-pyrrolo[2,3-d]pyrimidin-4-yl)benzonitrile

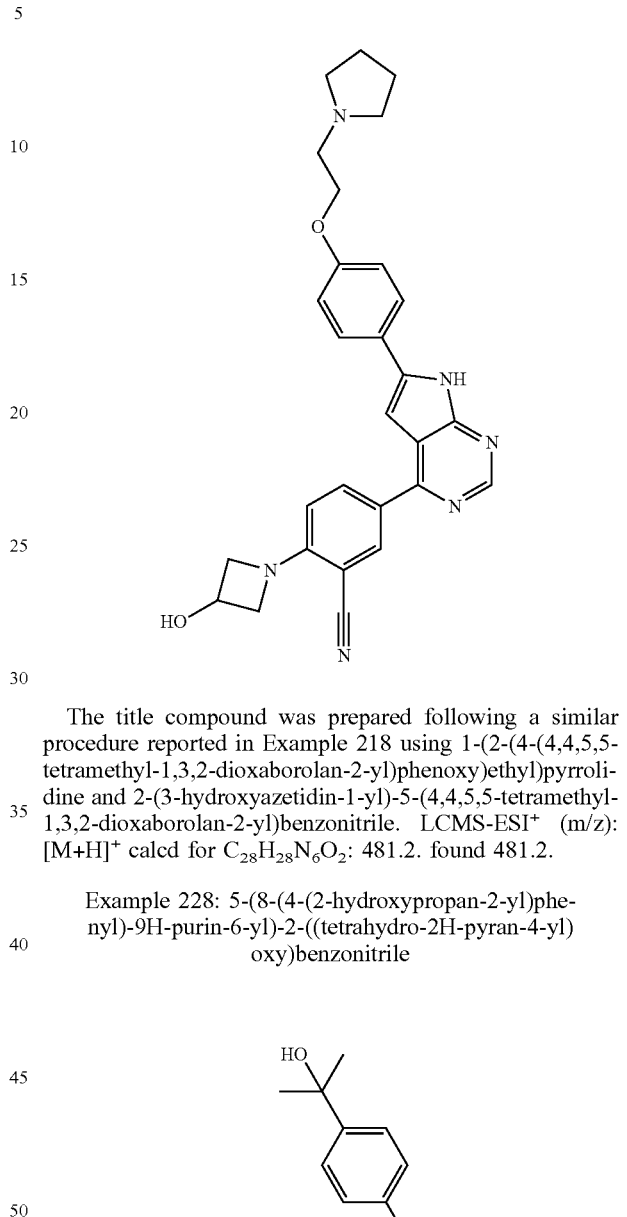

The title compound was prepared following a similar procedure reported in Example 218 using 1-(2-(4-(4,4,5,5-tetramethyl-1,3,2-dioxaborolan-2-yl)phenoxy)ethyl)pyrrolidine and 2-(3-hydroxyazetidin-1-yl)-5-(4,4,5,5-tetramethyl-1,3,2-dioxaborolan-2-yl)benzonitrile. LCMS-ESI$^+$ (m/z): [M+H]$^+$ calcd for C$_{28}$H$_{28}$N$_6$O$_2$: 481.2. found 481.2.

Example 228: 5-(8-(4-(2-hydroxypropan-2-yl)phenyl)-9H-purin-6-yl)-2-((tetrahydro-2H-pyran-4-yl)oxy)benzonitrile

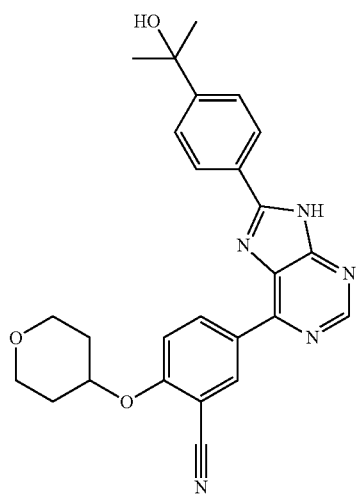

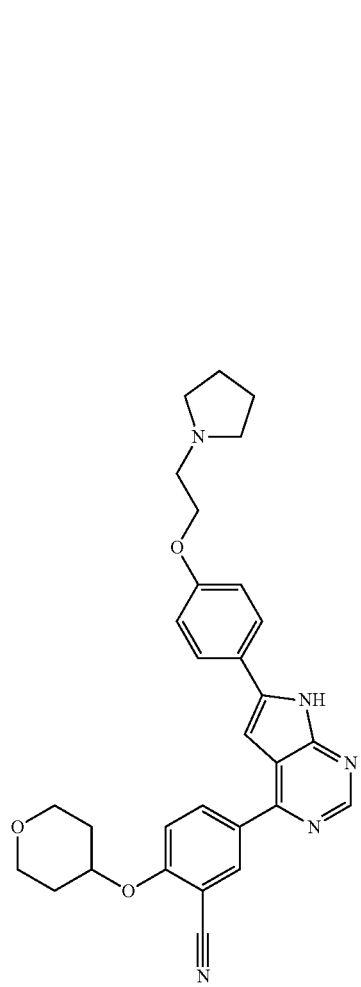 [SMILES: N#Cc1cc(-c2ncnc3[nH]c(-c4ccc(OCCN5CCCC5)cc4)cc23)ccc1OC1CCOCC1]

The title compound was prepared following a similar procedure reported in Example 218 using 1-(2-(4-(4,4,5,5-tetramethyl-1,3,2-dioxaborolan-2-yl)phenoxy)ethyl)pyrrolidine. $^1$H NMR (400 MHz, DMSO-d$_6$) δ 12.6 (s, 1H), 8.74 (s, 1H), 8.53 (d, J=8.8 Hz, 2H), 7.99 (d, J=8.7 Hz, 2H), 7.53 (d, J=8.8 Hz, 1H), 7.36 (s, 1H), 7.05 (d, J=8.7 Hz, 2H), 4.96 (dq, J=8.0, 4.0 Hz, 1H), 4.12 (t, J=5.9 Hz, 2H), 3.94-3.81 (m, 2H), 3.56 (ddd, J=11.5, 8.3, 3.2 Hz, 2H), 2.79 (t, J=5.9 Hz, 2H), 2.56-2.49 (m, 4H), 2.11-1.96 (m, 2H), 1.78-1.61 (m, 6H). LCMS-ESI$^+$ (m/z): [M+H]$^+$ calcd for C$_{30}$H$_{31}$N$_5$O$_3$: 510.3. found 510.2.

To an appropriate sized microwave vial, 5-(2-iodo-1-(phenylsulfonyl)-1H-pyrrolo[2,3-b]pyridin-4-yl)-2-((tetrahydro-2H-pyran-4-yl)oxy)benzonitrile (100 mg, 0.23 mmol), 2-(tert-butoxy)-4-(4,4,5,5-tetramethyl-1,3,2-dioxaborolan-2-yl)pyridine (66 mg, 0.250 mmol), cesium carbonate (222 mg, 0.68 mmol), dioxane (3 mL) and water (1.5 mL) were added. The mixture was degassed with nitrogen for 10 minutes. PEPPSI-iPr catalyst (15 mg, 0.022 mmol) was added and the solution was heated at 105° C. for 2 h. After cooling to room temperature, the mixture was poured into water, and extracted with dichloromethane. The combined organic layers were washed with brine, dried with magnesium sulfate, filtered and concentrated under reduced pressure. The residue 2-(4-(6-(phenylthio)-9-(tetrahydro-2H-pyran-2-yl)-9H-purin-8-yl)phenyl)propan-2-ol was used for next step.

To an appropriate sized microwave vial, 2-(4-(6-(phenylthio)-9-(tetrahydro-2H-pyran-2-yl)-9H-purin-8-yl)phenyl)propan-2-ol (91 mgs, 0.2 mmol), 2-((tetrahydro-2H-pyran-4-yl)oxy)-5-(4,4,5,5-tetramethyl-1,3,2-dioxaborolan-2-yl) benzonitrile (60 mgs, 0.24 mmol) copper(I) thiophene-2-carboxylate (50 mgs, 0.26 mmol), tris(2-furyl)phosphine (8 mgs, 0.03 mmol), tetrahydrofuran was added. The mixture was degassed with nitrogen for 10 minutes. $Pd_2(dba)_3$ (7 mgs, 0.08 mmol) was added and the solution was heated at 50° C. 17 h. After cooling to room temperature, the mixture was poured into a saturated solution of sodium bicarbonate in water, and extracted with dichloromethane. The combined organic layers were washed with brine, dried with magnesium sulfate, filtered and concentrated under reduced pressure. The residue was used for next step.

To a solution of 5-(8-(4-(2-hydroxypropan-2-yl)phenyl)-9-(tetrahydro-2H-pyran-2-yl)-9H-purin-6-yl)-2-((tetrahydro-2H-pyran-4-yl)oxy)benzonitrile (80 mgs, 0.15 mmol) in acetonitrile an acidic aqueous solution (0.1% TFA) was added and the mixture was heated at 55° C. for 20 min. Mixture cooled down to room temperature, poured into an aqueous saturated solution of sodium bicarbonate and extracted with DCM. The combined organic layers were washed with brine, dried with magnesium sulfate, filtered and concentrated under reduced pressure. Solids were re-dissolved in ACN and loaded into Gilson prep-HPLC (10-90% ACN 1% TFA). Clean fractions were diluted with basic saturated aqueous solution of $NaHCO_3$ and extracted with DCM. Organic layer was washed with brine, dried with magnesium sulfate, filtered and concentrated under reduced pressure to yield 5-(8-(4-(2-hydroxypropan-2-yl)phenyl)-9H-purin-6-yl)-2-((tetrahydro-2H-pyran-4-yl)oxy)benzonitrile. $^1$H NMR (400 MHz, DMSO-d$_6$) δ 9.20 (d, J=8.7 Hz, 2H), 8.86 (s, 1H), 8.24 (d, J=8.1 Hz, 2H), 7.75-7.47 (m, 4H), 5.16 (s, 1H), 4.96 (tt, J=8.0, 3.9 Hz, 1H), 3.88 (dt, J=11.5, 4.5 Hz, 2H), 3.56 (ddd, J=11.5, 8.4, 3.1 Hz, 2H), 2.16-1.97 (m, 2H), 1.71 (dtd, J=12.5, 8.3, 3.8 Hz, 2H), 1.47 (s, 6H). LCMS-ESI$^+$ (m/z): [M+H]$^+$ calcd for $C_{26}H_{25}N_5O_3$: 456.2. found 456.2.

Example 229: 2-((1-(2-hydroxyacetyl)piperidin-4-yl)oxy)-5-(6-(4-(2-(pyrrolidin-1-yl)ethoxy)phenyl)-7H-pyrrolo[2,3-d]pyrimidin-4-yl)benzonitrile

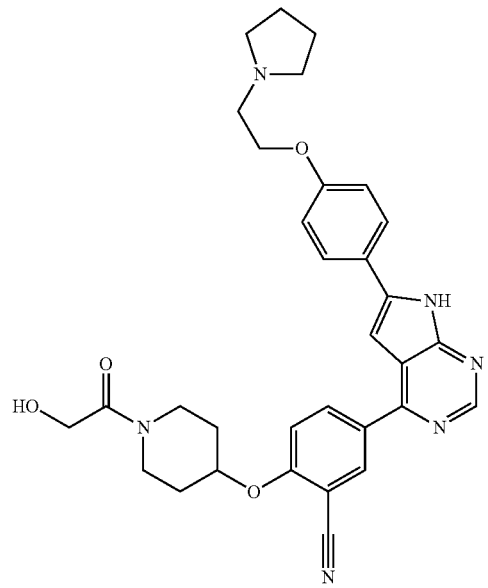 [SMILES: N#Cc1cc(-c2ncnc3[nH]c(-c4ccc(OCCN5CCCC5)cc4)cc23)ccc1OC1CCN(C(=O)CO)CC1]

The title compound was prepared following a similar procedure reported in Example 220 using 1-(2-(4-(4,4,5,5-tetramethyl-1,3,2-dioxaborolan-2-yl)phenoxy)ethyl)pyrrolidine. $^1$H NMR (400 MHz, DMSO-d$_6$) δ 12.62 (s, 1H), 8.76 (d, J=7.3 Hz, 1H), 8.57-8.46 (m, 2H), 8.00 (d, J=8.8 Hz, 2H), 7.55 (d, J=8.8 Hz, 1H), 7.39 (s, 1H), 7.06 (d, J=8.8 Hz, 2H), 5.02-4.98 (m, 3H), 4.55 (t, J=5.5 Hz, 1H), 4.12 (d, J=5.5 Hz, 4H), 3.73 (s, 2H), 3.54 (s, 2H), 3.37 (s, 2H), 2.79 (q, J=5.7 Hz, 2H), 2.57-2.49 (m, 2H), 2.1-2.0 (m, 3H), 1.73 (d, J=30.5 Hz, 3H). LCMS-ESI$^+$ (m/z): [M+H]$^+$ calcd for $C_{32}H_{34}N_6O_4$: 567.3. found 567.2.

Example 230: 5,5'-(7H-pyrrolo[2,3-d]pyrimidine-4,6-diyl)bis(2-(3-hydroxyazetidin-1-yl)benzonitrile)

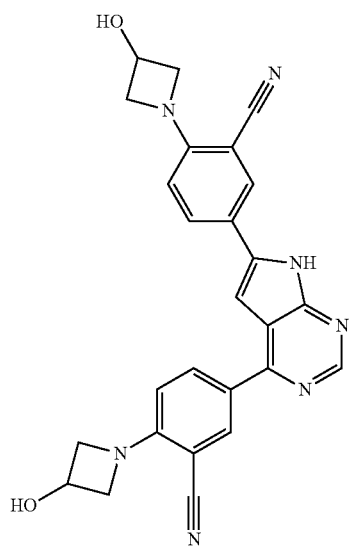 [SMILES: N#Cc1cc(-c2cc3c(-c4ccc(N5CC(O)C5)c(C#N)c4)ncnc3[nH]2)ccc1N1CC(O)C1]

The title compound was prepared following a similar procedure reported in Example 218 using 2-(3-hydroxyazetidin-1-yl)-5-(4,4,5,5-tetramethyl-1,3,2-dioxaborolan-2-yl)benzonitrile. $^1$H NMR (400 MHz, DMSO-$d_6$) δ 12.49 (s, 1H), 8.68 (s, 1H), 8.39-8.26 (m, 2H), 8.22 (d, J=2.2 Hz, 1H), 8.08 (dd, J=8.9, 2.2 Hz, 1H), 7.38 (s, 1H), 6.68 (dd, J=15.9, 8.9 Hz, 2H), 5.78 (dd, J=13.1, 6.3 Hz, 2H), 4.62-4.52 (m, 2H), 4.52-4.39 (m, 4H), 4.02-3.89 (m, 4H). LCMS-ESI$^+$ (m/z): [M+H]$^+$ calcd for $C_{26}H_{21}N_7O_2$: 464.2. found 464.2.

Example 231: 5-(8-(2-methylthiazol-5-yl)-9H-purin-6-yl)-2-((tetrahydro-2H-pyran-4-yl)oxy)benzonitrile

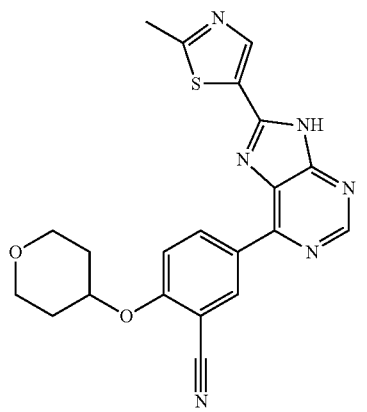 [SMILES: Cc1ncc(-c2nc3c(-c4ccc(OC5CCOCC5)c(C#N)c4)ncnc3[nH]2)s1]

6-chloropyrimidine-4,5-diamine (200 mgs, 1.3 mmol) and 2-methylthiazole-5-carboxylic acid (218 mgs, 1.5 mmol) were dissolved in phosphoryl chloride (4 mL) in a 10 mL microwave vial. The reaction mixture was stirred at 160° C. for 30 min in a microwave reactor. After cooling down to room temperature reaction mixture was diluted with diethylether and solids filtered out. Solids were re-dissolved in dichloromethane and extracted with aqueous saturated solution of sodium bicarbonate. Organic layer was dried over $Mg_2SO_4$ and evaporated under reduced pressure. Solids were suspended in ACN and stirred over 1 hr. Solids were filtered out to yield 5-(6-chloro-9H-purin-8-yl)-2-methylthiazole.

To an appropriate sized microwave vial, 5-(6-chloro-9H-purin-8-yl)-2-methylthiazole (80 mg, 0.137 mmol), 2-((tetrahydro-2H-pyran-4-yl)oxy)-5-(4,4,5,5-tetramethyl-1,3,2-dioxaborolan-2-yl)benzonitrile (42 mg, 0.150 mmol), cesium carbonate (133 mg, 0.41 mmol), dioxane (3 mL) and water (1.5 mL) were added. The mixture was degassed with nitrogen for 10 minutes. PEPPSI-iPr catalyst (9 mg, 0.014 mmol) was added and the solution was heated at 105° C. for 2 h. After cooling to room temperature, the mixture was poured into water, and extracted with dichloromethane. The combined organic layers were washed with brine, dried with magnesium sulfate, filtered and concentrated under reduced pressure. Solids were re-dissolved in ACN and loaded into Gilson prep-HPLC (10-90% ACN 1% TFA). Clean fractions were diluted with basic saturated aqueous solution of $NaHCO_3$ and extracted with DCM. Organic layer was washed with brine, dried with magnesium sulfate, filtered and concentrated under reduced pressure to yield 5-(8-(2-methylthiazol-5-yl)-9H-purin-6-yl)-2-((tetrahydro-2H-pyran-4-yl)oxy)benzonitrile. LCMS-ESI$^+$ (m/z): [M+H]$^+$ calcd for $C_{21}H_{18}N_6O_2S$: 419.1; found 419.2.

Example 232: 5-(8-(4-(4-(oxetan-3-yl)piperazin-1-yl)phenyl)-9H-purin-6-yl)-2-((tetrahydro-2H-pyran-4-yl)oxy)benzonitrile

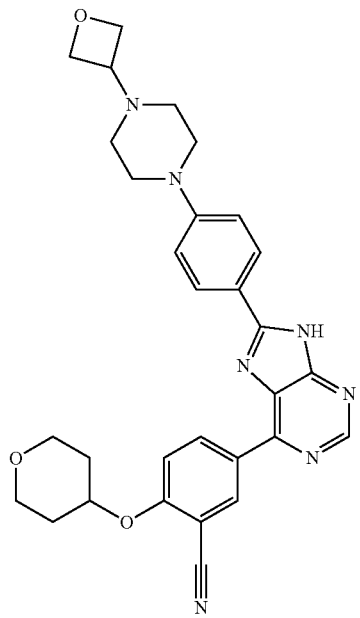

The title compound was prepared following a similar procedure reported in Example 228 using 1-(oxetan-3-yl)-4-(4-(4,4,5,5-tetramethyl-1,3,2-dioxaborolan-2-yl)phenyl)piperazine. $^1$H NMR (400 MHz, DMSO-$d_6$) 13.4 (s, 1H), 9.25-9.11 (m, 2H), 8.77 (s, 1H), 8.15 (d, J=8.6 Hz, 1H), 7.66-7.57 (m, 2H), 7.11 (d, J=8.7 Hz, 2H), 4.94 (dt, J=8.3, 4.2 Hz, 1H), 4.56 (t, J=6.5 Hz, 2H), 4.47 (t, J=6.0 Hz, 2H), 3.87 (dq, J=12.5, 7.8, 6.2 Hz, 2H), 3.62-3.50 (m, 3H), 3.39-3.25 (m, 4H), 2.41 (t, J=5.1 Hz, 4H), 2.10-2.00 (m, 2H), 1.70 (ddt, J=13.9, 9.6, 4.7 Hz, 2H). LCMS-ESI$^+$ (m/z): [M+H]$^+$ calcd for $C_{30}H_{31}N_7O_3$: 538.3. found 538.2.

Example 233: 2-((1-(2-hydroxyacetyl)piperidin-4-yl)oxy)-5-(8-(4-(2-(pyrrolidin-1-yl)ethoxy)phenyl)-9H-purin-6-yl)benzonitrile

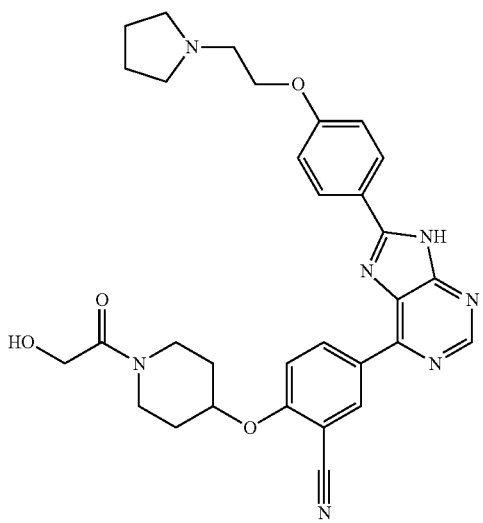 [SMILES: N#Cc1cc(-c2ncnc3[nH]c(-c4ccc(OCCN5CCCC5)cc4)nc23)ccc1OC1CCN(C(=O)CO)CC1]

To an appropriate sized microwave vial, 8-iodo-6-(phenylthio)-9-(tetrahydro-2H-pyran-2-yl)-9H-purine (400 mg, 0.91 mmol), 1-(2-(4-(4,4,5,5-tetramethyl-1,3,2-dioxaborolan-2-yl)phenoxy)ethyl)pyrrolidine (318 mg, 1.0 mmol), sodium bicarbonate (268 mg, 3.0 mmol), dioxane (7 mL) and water (3 mL) were added. The mixture was degassed with nitrogen for 10 minutes. Bis(triphenylphosphine)palladium (II) dichloride (104 mgs, 0.9 mmol) was added and the solution was heated at 105° C. overnight. After cooling to room temperature, the mixture was poured into water, and extracted with dichloromethane. The combined organic layers were washed with brine, dried with magnesium sulfate, filtered and concentrated under reduced pressure. The residue 6-(phenylthio)-8-(4-(2-(pyrrolidin-1-yl)ethoxy)phenyl)-9-(tetrahydro-2H-pyran-2-yl)-9H-purine was used for next step.

6-(phenylthio)-8-(4-(2-(pyrrolidin-1-yl)ethoxy)phenyl)-9-(tetrahydro-2H-pyran-2-yl)-9H-purine (320 mgs, 0.64 mmol) was diluted with ACN, then 1N HCl aqueous solution was added and mixture was stirred at room temperature for 10 min. Aqueous phase was neutralized with saturated aqueous solution of sodium bicarbonate. Mixture was diluted and extracted with dichloromethane. Organic layer was dried with magnesium sulfate and concentrated under reduced pressure to yield 6-chloro-8-(4-(2-(pyrrolidin-1-yl)ethoxy)phenyl)-9H-purine.

To an appropriate sized microwave vial, 6-chloro-8-(4-(2-(pyrrolidin-1-yl)ethoxy)phenyl)-9H-purine (140 mgs, 0.36 mmol), tert-butyl 4-(2-cyano-4-(4,4,5,5-tetramethyl-1,3,2-dioxaborolan-2-yl)phenoxy)piperidine-1-carboxylate (140 mgs, 0.4 mmol) copper(I) thiophene-2-carboxylate (82 mgs, 0.4 mmol), tris(2-furyl)phosphine (12 mgs, 0.05 mmol), THF was added. The mixture was degassed with nitrogen for 10 minutes. Pd$_2$(dba)$_3$ (7 mgs, 0.08 mmol) was added and the solution was heated at 50° C. 17 h. After cooling to room temperature, the mixture was poured into a saturated solution of NaHCO$_3$ in water, and extracted with dichloromethane. The combined organic layers were washed with brine, dried with magnesium sulfate, filtered and concentrated under reduced pressure to give tert-butyl 4-(2-cyano-4-(8-(4-(2-(pyrrolidin-1-yl)ethoxy)phenyl)-9H-purin-6-yl)phenoxy)piperidine-1-carboxylate which was used further without purification.

Boc deprotection of tert-butyl 4-(2-cyano-4-(8-(4-(2-(pyrrolidin-1-yl)ethoxy)phenyl)-9H-purin-6-yl)phenoxy)piperidine-1-carboxylate with acid followed by glycolic acid coupling and purification gave the title compound. $^1$H NMR (400 MHz, DMSO-d$_6$) δ 13.5 (s, 1H), 9.19 (d, J=7.6 Hz, 2H), 8.82 (s, 1H), 8.30-8.20 (m, 2H), 7.66-7.58 (m, 1H), 7.23-7.11 (m, 2H), 5.00 (tt, J=7.3, 3.6 Hz, 1H), 4.55 (t, J=5.5 Hz, 1H), 4.23-4.05 (m, 5H), 3.81-3.72 (m, 1H), 3.62-3.52 (m, 1H), 3.50-3.43 (m, 2H), 2.82 (t, J=5.8 Hz, 2H), 2.53 (ddt, J=7.4, 4.9, 2.4 Hz, 5H), 2.01 (s, 2H), 1.82-1.60 (m, 4H). LCMS-ESI$^+$ (m/z): [M+H]$^+$ calcd for C$_{31}$H$_{33}$N$_7$O$_4$: 568.3. found 568.3.

Example 234: (S)-2-((1-(2-hydroxypropanoyl)piperidin-4-yl)oxy)-5-(8-(4-morpholinophenyl)-9H-purin-6-yl)benzonitrile

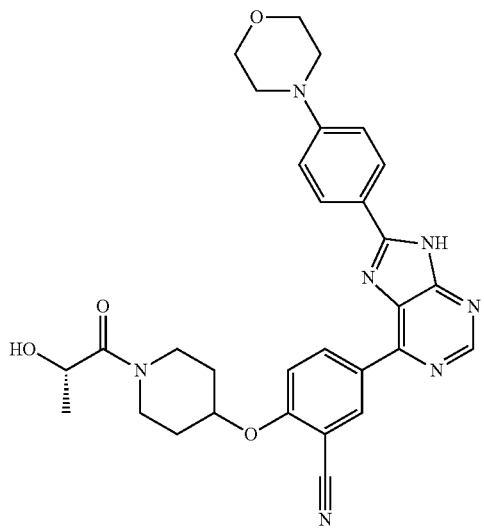 [SMILES: C[C@H](O)C(=O)N1CCC(Oc2ccc(-c3ncnc4[nH]c(-c5ccc(N6CCOCC6)cc5)nc34)cc2C#N)CC1]

The title compound was synthesized dissolving the intermediate tert-butyl 4-(2-cyano-4-(8-(4-(4-(oxetan-3-yl)piperazin-1-yl)phenyl)-9H-purin-6-yl)phenoxy)piperidine-1-carboxylate (700 mgs, 1.2 mmol) (that was synthesized following Example 231 using 4-(4-(oxetan-3-yl)piperazin-1-yl)benzoic acid and tert-butyl 4-(2-cyano-4-(4,4,5,5-tetramethyl-1,3,2-dioxaborolan-2-yl)phenoxy)piperidine-1-carboxylate) in 10 ml of a solution of dichloromethane and TFA (2:1) in a 100 ml round bottle flask and stirred at room temperature for 1 hr. The reaction mixture was concentrated under reduced pressure and solids were re-dissolved into dichloromethane and a saturated aqueous solution of Na$_2$CO$_3$, desired product was extracted with dichloromethane. Organic layer was washed with brine, dried with magnesium sulfate, filtered and concentrated under reduced pressure. The residue 5-(8-(4-(4-(oxetan-3-yl)piperazin-1-yl)phenyl)-9H-purin-6-yl)-2-(piperidin-4-yloxy)benzonitrile was used for next step.

To a solution of 5-(8-(4-(4-(oxetan-3-yl)piperazin-1-yl)phenyl)-9H-purin-6-yl)-2-(piperidin-4-yloxy)benzonitrile (50 mg, 0.104 mmol), (S)-2-hydroxypropanoic acid (11 mg, 0.13 mmol), HATU (43 mgs, 0.11 mmol) in DMF (5 mL) was added 4-methylmorpholine (31 mg, 0.31 mmol) in a 10 mL microwave vial and sealed. This reaction mixture was stirred at room temperature for 2 hrs. Water was added and it was extracted with dichloromethane. Organic layer was dried over Mg₂SO₄ solids were filtered out and organics were evaporated to dryness. Solids re-dissolved in acetonitrile and purified via preparative HPLC (5-65% acetonitrile in water, 0.1% trifluoroacteic acid buffer). Fractions containing desired product were collected diluted with a saturated aqueous solution of sodium bicarbonate and extracted with dichloromethane to obtain (S)-2-((1-(2-hydroxypropanoyl)piperidin-4-yl)oxy)-5-(8-(4-(4-(oxetan-3-yl)piperazin-1-yl)phenyl)-9H-purin-6-yl)benzonitrile. ¹H NMR (400 MHz, DMSO-d₆) δ 13.6 (s, 1H), 9.28-9.21 (m, 2H), 8.81 (s, 1H), 8.17 (d, J=8.6 Hz, 2H), 7.64 (d, J=8.9 Hz, 1H), 7.14 (d, J=8.7 Hz, 2H), 5.12-4.88 (m, 2H), 4.46 (t, J=6.6 Hz, 1H), 3.80-3.71 (m, 5H), 3.61-3.51 (m, 2H), 3.32-3.21 (m, 5H), 2.22-1.9 (m, 2H), 1.82-1.61 (m, 2H), 1.19 (d, J=6.5 Hz, 3H). LCMS-ESI⁺ (m/z): [M+H]⁺ calcd for $C_{30}H_{31}N_7O_4$: 554.3. found 554.2.

Example 235: 5-(2-(4-morpholinophenyl)-1H-pyrrolo[2,3-b]pyridin-4-yl)-2-(oxetan-3-yloxy)benzonitrile

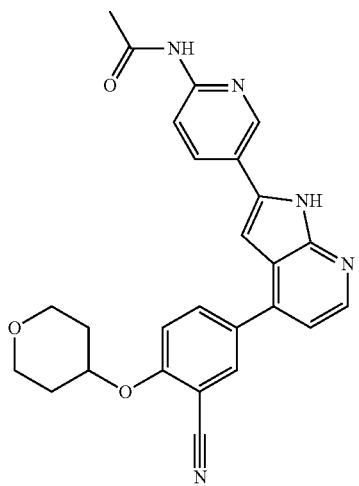 [SMILES: CC(=O)Nc1ccc(-c2cc3c(-c4ccc(OC5CCOCC5)c(C#N)c4)ccnc3[nH]2)cn1]

Step 1: Preparation of 5-bromo-2-(oxetan-3-yloxy)benzonitrile: A solution of 3-hydroxyoxetane (1.33 g, 18 mmol) in N,N-dimethylformamide (36 mL) was stirred in an ice-water bath under an atmosphere of Argon. Sodium hydride (60% dispersion in mineral oil, 0.72 g, 18 mmol) was added in a single portion and the mixture was stirred at 0° C. for 10 minutes, and then the bath was removed. After 30 minutes of stirring at room temperature, to the mixture was added 5-bromo-2-fluorobenzonitrile (3.0 g, 18 mmol) via syringe as a solution in N,N-dimethylformamide (15 mL). The mixture was stirred overnight at 50° C. After the mixture cooled to room temperature, water was added, giving a granular precipitate. It was collected by filtration, washed with water and dried in a vacuum oven over P₂O₅ to provide 5-bromo-2-(oxetan-3-yloxy)benzonitrile. 1H NMR (400 MHz, DMSO-d₆) δ 8.11 (d, J=2.5 Hz, 1H), 7.84 (dd, J=9.0, 2.5 Hz, 1H), 6.90 (d, J=9.0 Hz, 1H), 5.48 (tt, J=5.9, 4.7 Hz, 1H), 4.99 (ddd, J=7.2, 6.0, 1.0 Hz, 2H), 4.61 (ddd, J=7.6, 4.7, 1.0 Hz, 2H).

Step 2: Preparation of 2-(oxetan-3-yloxy)-5-(4,4,5,5-tetramethyl-1,3,2-dioxaborolan-2-yl)benzonitrile: A mixture of 5-bromo-2-(oxetan-3-yloxy)benzonitrile (1.57 g, 6.2 mmol), bis(pinacolato)diboron (3.1 g, 12 mmol), potassium acetate (1.8 g, 19 mmol), and [1,1'-bis(diphenylphosphino)ferrocene]dichloropalladium(II) (0.26 g, 5 mol %) in 1,4-dioxane (20 mL) was heated at 90° C. for 5 hours. The mixture was filtered through a pad of Celite diatomaceous earth, eluting with ethyl acetate. The filtrate was washed once with saturated aqueous sodium chloride solution, dried over anhydrous magnesium sulfate, and concentrated to dryness under reduced pressure. The residue was purified by flash chromatography (silica gel) to provide the putative 2-(oxetan-3-yloxy)-5-(4,4,5,5-tetramethyl-1,3,2-dioxaborolan-2-yl)benzonitrile.

Step 3: Preparation 5-(2-(4-morpholinophenyl)-1-(phenylsulfonyl)-1H-pyrrolo[2,3-b]pyridin-4-yl)-2-(oxetan-3-yloxy)benzonitrile: A mixture of 4-(4-(4-chloro-1-(phenylsulfonyl)-1H-pyrrolo[2,3-b]pyridin-2-yl)phenyl)morpholine (0.15 g, 0.33 mmol), 2-(oxetan-3-yloxy)-5-(4,4,5,5-tetramethyl-1,3,2-dioxaborolan-2-yl)benzonitrile (0.13 g, 0.43 mmol), potassium carbonate (0.11 g, 0.83 mmol), palladium acetate (7 mg, 0.03 mmol), and 2-dicyclohexylphosphino-2',6'-dimethoxybiphenyl (SPhos, 27 mg, 0.66 mmol) was taken up as a suspension in dioxanes (1.5 mL). The mixture was degassed with Argon and then heated at 100° C. block for 300 minutes. After the passage of this interval, water (0.5 mL) was added to the mixture. After another 240 minutes of heating, additional quantities of the boronate (approximately 50 mg), palladium acetate, and SPhos (original stoichiometries) were added. The mixture was heated for 30 minutes in a microwave reactor at 120° C. The crude reaction mixture was purified by flash chromatography (silica gel) to provide 5-(2-(4-morpholinophenyl)-1-(phenylsulfonyl)-1H-pyrrolo[2,3-b]pyridin-4-yl)-2-(oxetan-3-yloxy)benzonitrile. LCMS-ESI⁺ (m/z): [M+H]⁺ calcd for $C_{33}H_{29}N_4O_5S$: 593.2. found: 593.1.

Step 4: Preparation of 5-(2-(4-morpholinophenyl)-1H-pyrrolo[2,3-b]pyridin-4-yl)-2-(oxetan-3-yloxy)benzonitrile: A mixture of 5-(2-(4-morpholinophenyl)-1-(phenylsulfonyl)-1H-pyrrolo[2,3-b]pyridin-4-yl)-2-(oxetan-3-yloxy)benzonitrile (0.16 g, 0.27 mmol) in dioxanes (2 mL) was treated successively with cesium carbonate (0.26, 0.81 mmol) and 2,2,2-trifluoroethanol (1 mL, dropwise). The mixture was heated in a microwave reactor for 30 minutes at 100° C. The resulting suspension was concentrated to dryness under reduced pressure. The residue was taken up in dichloromethane and acidified with trifluoroacetic acid. After concentration, the residue was purified by flash chromatography (silica gel) to provide, after trituration with hot methanol and filtration, 5-(2-(4-morpholinophenyl)-1H-pyrrolo[2,3-b]pyridin-4-yl)-2-(oxetan-3-yloxy)benzonitrile.

LCMS-ESI⁺ (m/z): [M+H]⁺ calcd for $C_{27}H_{25}N_4O_3$: 453.2. found: 453.3. ¹H NMR (400 MHz, DMSO-d₆) δ 12.19 (s, 1H), 8.43-8.19 (m, 2H), 8.12 (dd, J=8.8, 2.3 Hz, 1H), 7.97-7.82 (m, 2H), 7.22 (d, J=5.0 Hz, 1H), 7.17-6.95 (m, 4H), 5.71-5.48 (m, 1H), 5.10-5.03 (m, 2H), 4.75-4.68 (m, 2H), 3.79 (dd, J=6.1, 3.6 Hz, 4H), 3.23 (dd, J=5.9, 3.7 Hz, 4H).

Example 236: N-(5-(4-(3-cyano-4-((tetrahydro-2H-pyran-4-yl)oxy)phenyl)-1H-pyrrolo[2,3-b]pyridin-2-yl)pyridin-2-yl)acetamide

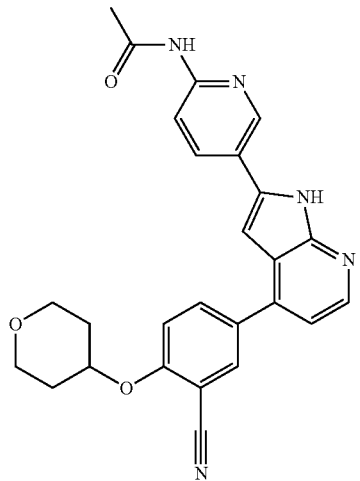 [SMILES: CC(=O)Nc1ccc(-c2cc3c(-c4ccc(OC5CCOCC5)c(C#N)c4)ccnc3[nH]2)cn1]

Step 1: Preparation of N-(5-(4-(3-cyano-4-((tetrahydro-2H-pyran-4-yl)oxy)phenyl)-1-(phenylsulfonyl)-H-pyrrolo[2,3-b]pyridin-2-yl)pyridin-2-yl)acetamide: A mixture of 5-(2-iodo-1-(phenylsulfonyl)-1H-pyrrolo[2,3-b]pyridin-4-yl)-2-((tetrahydro-2H-pyran-4-yl)oxy)benzonitrile (0.28 g, 0.47 mmol), tert-butyl 3-(4-(4,4,5,5-tetramethyl-1,3,2-dioxaborolan-2-yl)-1H-pyrazol-1-yl)azetidine-1-carboxylate (Sigma Aldrich, 0.15 g, 0.57 mmol), cesium carbonate (0.39 g, 1.2 mmol), and bis(triphenylphosphine)palladium(II) dichloride (0.02 g, 0.03 mmol) in 1,4-dioxanes (3 mL) and water (1 mL), was heated for 30 minutes on an 85° C. block. After cooling to room temperature, the mixture was purified via flash chromatography on silica gel to give the desired material. LCMS-ESI+ (m/z): [M+H]+ calcd for $C_{32}H_{28}N_5O_5S$: 594.2. found: 594.5.

Step 2: Preparation of N-(5-(4-(3-cyano-4-((tetrahydro-2H-pyran-4-yl)oxy)phenyl)-1H-pyrrolo[2,3-b]pyridin-2-yl)pyridin-2-yl)acetamide: A mixture of N-(5-(4-(3-cyano-4-((tetrahydro-2H-pyran-4-yl)oxy)phenyl)-1-(phenylsulfonyl)-1H-pyrrolo[2,3-b]pyridin-2-yl)pyridin-2-yl)acetamide (0.28 g, 0.27 mmol) in dioxanes (3 mL) was treated successively with cesium carbonate (0.46, 1.4 mmol) and 2,2,2-trifluoroethanol (1.5 mL, dropwise). The mixture was heated in a microwave reactor for 30 minutes at 100° C. The resulting suspension was concentrated to dryness under reduced pressure. The residue was taken up in dichloromethane and acidified with trifluoroacetic acid. After concentration, the residue was purified by prep HPLC (10-55% acetonitrile in water, 0.1% trifluoroacetic acid buffer) to furnish N-(5-(4-(3-cyano-4-((tetrahydro-2H-pyran-4-yl)oxy)phenyl)-1H-pyrrolo[2,3-b]pyridin-2-yl)pyridin-2-yl)acetamide. LCMS-ESI+ (m/z): [M+H]+ calcd for $C_{26}H_{24}N_5O_3$: 454.2. found: 454.2. $^1$H NMR (400 MHz, DMSO-$d_6$) δ 12.44 (s, 1H), 10.70 (s, 1H), 9.01 (d, J=2.4 Hz, 1H), 8.40 (dd, J=8.8, 2.5 Hz, 1H), 8.33 (d, J=5.0 Hz, 1H), 8.25-8.17 (m, 2H), 8.14 (dd, J=8.8, 2.3 Hz, 1H), 7.58 (d, J=8.9 Hz, 1H), 7.34-7.24 (m, 2H), 4.98 (tt, J=7.9, 3.9 Hz, 1H), 4.13-3.78 (m, 2H), 3.61 (ddd, J=11.5, 8.2, 3.1 Hz, 2H), 2.16 (s, 3H), 2.10 (ddt, J=13.0, 8.5, 4.0 Hz, 2H), 1.76 (dtd, J=12.4, 8.1, 3.8 Hz, 2H).

Example 237: 2-((tetrahydro-2H-pyran-4-yl)oxy)-5-(2-(4-(2,2,2-trifluoroacetyl)phenyl)-1H-pyrrolo[2,3-b]pyridin-4-yl)benzonitrile

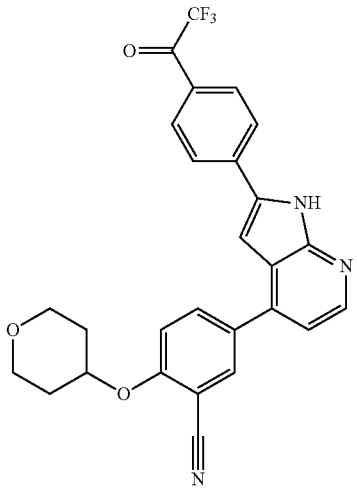 [SMILES: N#Cc1cc(-c2ccnc3[nH]c(-c4ccc(C(=O)C(F)(F)F)cc4)cc23)ccc1OC1CCOCC1]

Step 1: Preparation of 5-(1-(phenylsulfonyl)-2-(4-(2,2,2-trifluoroacetyl)phenyl)-1H-pyrrolo[2,3-b]pyridin-4-yl)-2-((tetrahydro-2H-pyran-4-yl)oxy)benzonitrile: A mixture of 5-(2-iodo-1-(phenylsulfonyl)-1H-pyrrolo[2,3-b]pyridin-4-yl)-2-((tetrahydro-2H-pyran-4-yl)oxy)benzonitrile (0.38 g, 0.65 mmol), 2,2,2-trifluoro-1-(4-(4,4,5,5-tetramethyl-1,3,2-dioxaborolan-2-yl)phenyl)ethanone (Frontier Scientific, 0.23 g, 0.78 mmol), cesium carbonate (0.53 g, 1.6 mmol), and bis(triphenylphosphine)palladium(II) dichloride (0.03 g, 0.04 mmol) in 1,4-dioxanes (3 mL) and water (1 mL), was heated overnight on an 90° C. block. After cooling to room temperature, the mixture was purified via flash chromatography on silica gel to give the desired material. LCMS-ESI+ (m/z): [M+H$_2$O+H]+ calcd for $C_{33}H_{27}F_3N_3O_6S$: 650.2. found: 650.1.

Step 2: Preparation of 2-((tetrahydro-2H-pyran-4-yl)oxy)-5-(2-(4-(2,2,2-trifluoroacetyl)phenyl)-1H-pyrrolo[2,3-b]pyridin-4-yl)benzonitrile: A mixture of 5-(1-(phenylsulfonyl)-2-(4-(2,2,2-trifluoroacetyl)phenyl)-1H-pyrrolo[2,3-b]pyridin-4-yl)-2-((tetrahydro-2H-pyran-4-yl)oxy)benzonitrile (0.41 g, 0.65 mmol) in dioxanes (2 mL) was treated successively with cesium carbonate (0.63, 1.9 mmol) and 2,2,2-trifluoroethanol (1 mL, dropwise). The mixture was heated in a microwave reactor for 30 minutes at 100° C. The resulting suspension was concentrated to dryness under reduced pressure. The residue was taken up in dichloromethane and acidified with trifluoroacetic acid. After concentration, the residue was purified first by flash chromatography (silica gel) and then by prep HPLC (10-60% acetonitrile in water, 0.1% trifluoroacetic acid buffer) to furnish 2-((tetrahydro-2H-pyran-4-yl)oxy)-5-(2-(4-(2,2,2-trifluoroacetyl)phenyl)-1H-pyrrolo[2,3-b]pyridin-4-yl)benzonitrile. LCMS-ESI+ (m/z): [M+H$_2$O+H]+ calcd for $C_{27}H_{23}F_3N_3O_4$: 510.2. found: 510.2. $^1$H NMR (400 MHz, DMSO-$d_6$) δ 12.70 (s, 0.5H), 12.46 (s, 0.5H), 8.47-8.34 (m, 1H), 8.34 (s, 1H), 8.22 (dd, J=9.3, 2.3 Hz, 1H), 8.15 (dt, J=8.9, 2.3 Hz, 2H), 8.08 (d, J=8.5 Hz, 1H), 7.72 (d, J=8.2 Hz, 1H), 7.59 (dd, J=9.0, 3.4 Hz, 1H), 7.31 (dd, J=13.8, 5.0 Hz, 1H), 7.27 (d, J=2.0 Hz, 1H), 4.99 (tq, J=7.9, 3.8 Hz, 1H), 3.94 (dd, J=10.5, 5.9, 3.9 Hz, 2H), 3.76-3.42 (m, 2H), 2.11 (dq, J=15.3, 4.0 Hz, 2H), 1.76 (dtd, J=12.4, 8.3, 3.8 Hz, 2H).

Example 238: Methyl 4-(4-(3-cyano-4-((tetrahydro-2H-pyran-4-yl)oxy)phenyl)-1H-pyrrolo[2,3-b]pyridin-2-yl)benzoate

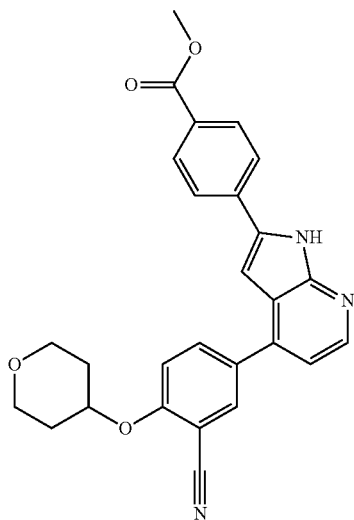 [SMILES: COC(=O)c1ccc(-c2cc3c(-c4ccc(OC5CCOCC5)c(C#N)c4)ccnc3[nH]2)cc1]

Methyl 4-(4-(3-cyano-4-((tetrahydro-2H-pyran-4-yl)oxy)phenyl)-1H-pyrrolo[2,3-b]pyridin-2-yl)benzoate was isolated from the prep HPLC purification of 2-((tetrahydro-2H-pyran-4-yl)oxy)-5-(2-(4-(2,2,2-trifluoroacetyl)phenyl)-1H-pyrrolo[2,3-b]pyridin-4-yl)benzonitrile. LCMS-ESI$^+$ (m/z): [M+H]$^+$ calcd for $C_{27}H_{24}F_3N_3O_4$: 454.2. found: 454.2.

Example 239: 5-(2-(4-morpholinophenyl)-1H-pyrrolo[2,3-b]pyridin-4-yl)-2-((tetrahydro-2H-pyran-3-yl)oxy)benzonitrile

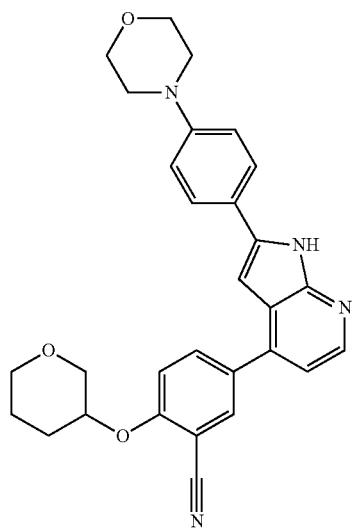 [SMILES: N#Cc1cc(-c2ccnc3[nH]c(-c4ccc(N5CCOCC5)cc4)cc23)ccc1OC1CCCOC1]

Step 1: Preparation of 5-bromo-2-((tetrahydro-2H-pyran-3-yl)oxy)benzonitrile A solution of 3-hydroxytetrahydropyran (Astatech, 2.0 g, 20 mmol) in N,N-dimethylformamide (40 mL) was stirred in an ice-water bath under an atmosphere of Argon. Sodium hydride (60% in mineral oil, 0.79 g, 20 mmol) was added in a single portion. The mixture was stirred at 0° C. for one hour and then the cooling bath was removed. To the mixture was added via syringe 5-bromo-2-fluorobenzonitrile (Matrix Scientific, 3.3 g, 17 mmol) as a solution in N,N-dimethylformamide (20 mL) at room temperature. Mixture was stirred for 3 hours at 50° C. block and then allowed to cool to room temperature. Water was added and the resulting precipitate was collected by filtration, washed with water, dried under house vacuum and then in vacuum oven over $P_2O_5$ to provide the desired material. $^1$H NMR (400 MHz, DMSO-d$_6$) δ 8.04 (d, J=2.5 Hz, 1H), 7.84 (dd, J=9.1, 2.6 Hz, 1H), 7.35 (d, J=9.1 Hz, 1H), 4.64 (m, 1H), 3.82 (m, 1H), 3.63 (m, 3H), 2.05 (m, 1H), 1.83 (m, 2H), 1.57 (m, 1H).

Step 2: Preparation of 2-((tetrahydro-2H-pyran-3-yl)oxy)-5-(4,4,5,5-tetramethyl-1,3,2-dioxaborolan-2-yl)benzonitrile: A mixture of 5-bromo-2-((tetrahydro-2H-pyran-3-yl)oxy)benzonitrile (0.35 g, 1.2 mmol), bis(pinacolato)diboron (0.63 g, 2.5 mmol), potassium acetate (0.37 g, 3.7 mmol), and [1,1'-bis(diphenylphosphino)ferrocene]dichloropalladium(II) complex with dichloromethane (52 mg, 5 mol %) in 1,4-dioxane (5 mL) was heated overnight at 90° C. The reaction mixture was filtered through a pad of Celite diatomaceous earth, and the filtrate was concentrated to dryness under reduced pressure. The crude 2-((tetrahydro-2H-pyran-3-yl)oxy)-5-(4,4,5,5-tetramethyl-1,3,2-dioxaborolan-2-yl)benzonitrile was carried forward without further purification. LCMS-ESI$^+$ (m/z): [M+H]$^+$ calcd for $C_{18}H_{25}BNO_4$: 330.2. found: 330.0.

Step 3: Preparation of 5-(2-(4-morpholinophenyl)-1-(phenylsulfonyl)-1H-pyrrolo[2,3-b]pyridin-4-yl)-2-((tetrahydro-2H-pyran-3-yl)oxy)benzonitrile: A mixture of 4-(4-(4-chloro-1-(phenylsulfonyl)-1H-pyrrolo[2,3-b]pyridin-2-yl)phenyl)morpholine (0.10 g, 0.22 mmol), crude 2-((tetrahydro-2H-pyran-3-yl)oxy)-5-(4,4,5,5-tetramethyl-1,3,2-dioxaborolan-2-yl)benzonitrile (0.41 g, 1.2 mmol), potassium carbonate (0.08 g, 0.55 mmol), palladium acetate (5 mg, 0.02 mmol), and 2-dicyclohexylphosphino-2',6'-dimethoxybiphenyl (SPhos, 18 mg, 0.04 mmol) was taken up as a suspension in dioxanes (5 mL) and water (1 mL). The mixture was heated at 95° C. for 5 hours. After the passage of this interval, PEPPSI-iPr [1,3-Bis(2,6-Diisopropylphenyl)imidazol-2-ylidene](3-chloropyridyl)palladium(II) dichloride (~20 mg) was added. The mixture was heated for 30 minutes in a microwave reactor at 130° C. The crude reaction mixture was purified by flash chromatography (silica gel) to provide 5-(2-(4-morpholinophenyl)-1-(phenylsulfonyl)-1H-pyrrolo[2,3-b]pyridin-4-yl)-2-((tetrahydro-2H-pyran-3-yl)oxy)benzonitrile. LCMS-ESI$^+$ (m/z): [M+H]$^+$ calcd for $C_{35}H_{33}N_4O_5S$: 621.2. found: 621.1.

Step 4: Preparation of 5-(2-(4-morpholinophenyl)-1H-pyrrolo[2,3-b]pyridin-4-yl)-2-((tetrahydro-2H-pyran-3-yl)oxy)benzonitrile: A mixture of 5-(2-(4-morpholinophenyl)-1-(phenylsulfonyl)-1H-pyrrolo[2,3-b]pyridin-4-yl)-2-((tetrahydro-2H-pyran-3-yl)oxy)benzonitrile (0.11 g, 0.17 mmol) in dioxanes (2 mL) was treated successively with cesium carbonate (0.17, 0.52 mmol) and 2,2,2-trifluoroethanol (1 mL, dropwise). The mixture was heated in a microwave reactor for 30 minutes at 100° C. The resulting suspension was concentrated to dryness under reduced pressure. The residue was taken up in dichloromethane and acidified with trifluoroacetic acid. After concentration, the residue was purified first by prep HPLC (10-85% acetonitrile in water, 0.1% trifluoroacetic acid buffer) to furnish 5-(2-(4-morpholinophenyl)-1H-pyrrolo[2,3-b]pyridin-4-yl)-2-((tetrahydro-2H-pyran-3-yl)oxy)benzonitrile. LCMS-ESI$^+$ (m/z): [M+H]$^+$ calcd for $C_{29}H_{29}N_4O_3$: 481.2. found: 481.2.

Example 240: 2-((1,1-dioxidotetrahydro-2H-thiopyran-4-yl)oxy)-5-(6-(4-morpholinophenyl)-7H-pyrrolo[2,3-d]pyrimidin-4-yl)benzonitrile

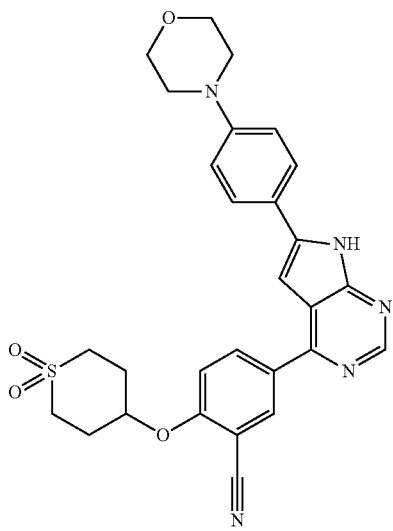 [SMILES: N#Cc1cc(-c2ncnc3[nH]c(-c4ccc(N5CCOCC5)cc4)cc23)ccc1OC1CCS(=O)(=O)CC1]

Step 1: Preparation of 5-bromo-2-((tetrahydro-2H-thiopyran-4-yl)oxy)benzonitrile A solution of tetrahydrothiopyran-4-ol (Sigma Aldrich, 2.0 g, 17 mmol) in N,N-dimethylformamide (DMF, 30 mL) was treated with sodium hydride (60% in mineral oil, 0.68 g, 17 mmol) in a single portion at room temperature. The mixture was stirred for one hour at room temperature before 5-bromo-2-fluorobenzonitrile (2.8 g, 14 mmol) was added in a single portion. An additional volume of DMF (20 mL) was added. The mixture was stirred on a 50° C. heating block for two hours before it was poured onto ice (approximately 100 g), precipitating a solid that was then collected by vacuum filtration and dried in a vacuum oven over phosphorus pentoxide to provide the desired product. $^1$H NMR (400 MHz, DMSO-$d_6$) δ 8.03 (d, J=2.5 Hz, 1H), 7.82 (dd, J=9.1, 2.6 Hz, 1H), 7.31 (d, J=9.1 Hz, 1H), 4.74 (m, 1H), 2.83 (m, 2H), 2.63 (m, 2H), 2.16 (m, 2H), 1.90 (m, 2H).

Step 2: preparation of 5-bromo-2-((1,1-dioxidotetrahydro-2 h-thiopyran-4-yl)oxy)benzonitrile: A solution of 5-bromo-2-((tetrahydro-2H-thiopyran-4-yl)oxy)benzonitrile (1.2 g, 4.0 mmol) in dichloromethane (50 mL) was treated with calcium carbonate (1.6 g, 16 mmol). The resulting suspension was cooled in an ice-water bath. Meta-chloroperbenzoic acid (mCPBA, Sigma Aldrich, <77%, 2.3 g, 10 mmol) was added in a single portion. The mixture was stirred overnight while ice-water bath gradually regained room temperature. The mixture was filtered through a fritted funnel, eluting with dichloromethane. The filtrate was washed twice each with aqueous solutions of 5% sodium bisulfite and saturated sodium hydrogen carbonate. The organics were dried over anhydrous magnesium sulfate, filtered, and concentrated under reduced pressure to provide the desired material. LCMS-ESI$^+$ (m/z): [M+H]$^+$ calcd for $C_{12}H_{13}BrNO_3S$: 330.0. found: 329.9.

Step 3: Preparation of 2-((1,1-dioxidotetrahydro-2H-thiopyran-4-yl)oxy)-5-(4,4,5,5-tetramethyl-1,3,2-dioxaborolan-2-yl)benzonitrile: A solution of 5-bromo-2-((1,1-dioxidotetrahydro-2H-thiopyran-4-yl)oxy)benzonitrile (5.9 g, 18 mmol) in dioxanes (65 mL) was added to a mixture of bis(pinacolato)diboron (9.1 g, 36 mmol), potassium acetate (5.3 g, 54 mmol), and [1,1'-bis(diphenylphosphino)ferrocene]dichloropalladium(II) (1.3 g, 10 mol %). The mixture was heated at 100° C. overnight. The mixture was filtered through a pad of Celite diatomaceous earth and concentrated under reduced pressure. The residue was purified by flash chromatography (silica gel) to provide the desired material. LCMS-ESI$^+$ (m/z): [M+H]$^+$ calcd for $C_{18}H_{25}BNO_5S$: 378.2. found: 378.1.

Step 4: Preparation of 2-((1,1-dioxidotetrahydro-2H-thiopyran-4-yl)oxy)-5-(6-(4-morpholinophenyl)-7H-pyrrolo[2,3-d]pyrimidin-4-yl)benzonitrile: A suspension of 4-(4-(4-chloro-7H-pyrrolo[2,3-d]pyrimidin-6-yl)phenyl)morpholine (61 mg, 0.19 mmol) in DMF (1 mL) was treated with a solution of 2-((1,1-dioxidotetrahydro-2H-thiopyran-4-yl)oxy)-5-(4,4,5,5-tetramethyl-1,3,2-dioxaborolan-2-yl)benzonitrile (0.11 g, 0.29 mmol) in DMF (1.1 mL) and [1,1'-bis(diphenylphosphino)ferrocene]dichloropalladium(II) complex with dichloromethane (14 mg, 10 mol %). Aqueous sodium carbonate solution (2 M, 0.44 mL) was added. The mixture was irradiated in a microwave reactor for 30 minutes at 125° C. Upon cooling the mixture was neutralized by the addition of glacial acetic acid and then purified by flash chromatography (silica gel) to provide, after trituration with warm acetonitrile and filtration, 2-((1,1-dioxidotetrahydro-2H-thiopyran-4-yl)oxy)-5-(6-(4-morpholinophenyl)-7H-pyrrolo[2,3-d]pyrimidin-4-yl)benzonitrile. LCMS-ESI$^+$ (m/z): [M+H]$^+$ calcd for $C_{28}H_{28}N_5O_4S$: 530.2. found: 530.2. $^1$H NMR (400 MHz, DMSO-$d_6$) δ 12.63 (s, 1H), 8.80 (s, 1H), 8.66-8.54 (m, 2H), 7.99 (d, J=8.0 Hz, 2H), 7.60 (d, J=8.0 Hz, 1H), 7.39 (s, 1H), 7.10 (d, J=8.0 Hz, 2H), 5.14 (p, J=4.7 Hz, 1H), 3.80 (m, 4H), 3.28 (m, 8H), 2.39 (m, 4H).

Example 241: 5-(8-(3-fluoro-4-morpholinophenyl)-9H-purin-6-yl)-2-((1-(2-hydroxyacetyl)piperidin-4-yl)oxy)benzonitrile

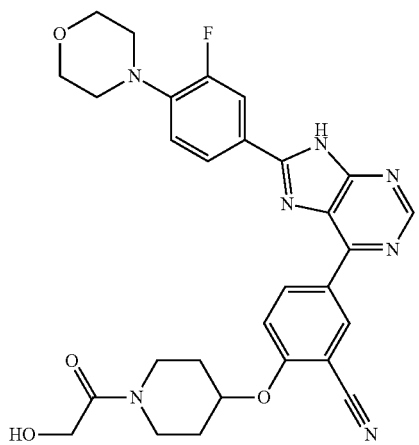 [SMILES: N#Cc1cc(-c2ncnc3[nH]c(-c4ccc(N5CCOCC5)c(F)c4)nc23)ccc1OC1CCN(C(=O)CO)CC1]

Step 1: Preparation of 4-(4-(6-chloro-9H-purin-8-yl)-2-fluorophenyl)morpholine: A mixture of 6-chloro-4,5-diaminopyrimidine (321 mg, 2.2 mmol), 3-fluoro-4-morpholinobenzoic acid (500 mg, 2.2 mmol) and ammonium chloride (713 mg, 6 eq) in POCl$_3$ (7 mL) was heated at 110° C. for 36 h in a sealed tube. The reaction mixture was cooled and the residue was washed several times with ether. The residue was dissolved in DCM and aqueous NaHCO3. The aqueous layer was extracted with DCM. The combined organics were washed with saturated NaHCO₃, brine, and dried (Na2SO4), filtered, and collected to give a solid. LCMS-ESI⁺ (m/z): [M+H]⁺ calcd for $C_{15}H_{13}ClFN_5O$: 334.1. found: 334.2.

Step 2: To a mixture of 5-(8-(3-fluoro-4-morpholinophenyl)-9H-purin-6-yl)-2-(piperidin-4-yloxy)benzonitrile (43 mg, 0.0861 mmol), hydroxyacetic acid (9 mg) and DIPEA (13 mg) in DMF (1.5 mL) was added HATU (39 mg). The reaction mixture was stirred at rt for 16 hrs. The mixture was concentrated to dryness. The residue was purified by silica gel column chromatography eluted 5-15% MeOH in DCM to give the title compound. 1H NMR (400 MHz, DMSO-d6) δ 13.98 (s, 1H), 9.35-9.02 (m, 2H), 8.87 (s, 1H), 8.16-7.94 (m, 2H), 7.64 (d, J=9.1 Hz, 1H), 7.24 (t, J=8.8 Hz, 1H), 5.01 (m, 1H), 4.54 (m, 1H), 4.12 (d, J=5.4 Hz, 2H), 3.76 (m, 5H), 3.67-3.41 (m, 2H), 3.29 (m, 1H), 3.22-3.06 (m, 4H), 2.02 (m, 2H), 1.73 (m, 2H). LCMS-ESI⁺ (m/z): calcd for $C_{29}H_{28}FN_7O_4$: 558.2. found [M+H]⁺: 558.2.

Example 242: 5-(8-(3-fluoro-4-morpholinophenyl)-9H-purin-6-yl)-2-((tetrahydro-2H-pyran-4-yl)oxy)benzonitrile

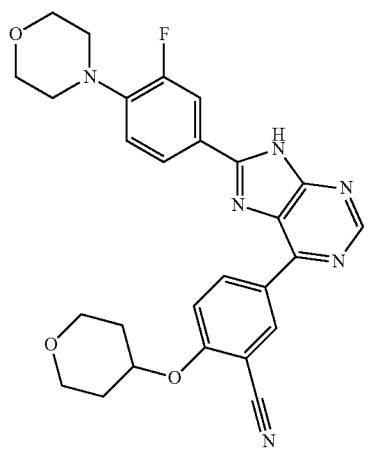 [SMILES: N#Cc1cc(-c2ncnc3[nH]c(-c4ccc(N5CCOCC5)c(F)c4)nc23)ccc1OC1CCOCC1]

A sealed tube containing a suspension of 4-(4-(6-chloro-9H-purin-8-yl)-2-fluorophenyl)morpholine (120 mg, 0.36 mmol) and Pd(PPh₃)₄ (21 mg, 0.018 mmol) in a degassed mixture of dioxane/H₂O (3 mL, 4/1), was preheated at 85° C. for 5 min. Next, K₂CO₃ (124 mg, 0.90 mmol) and 2-((tetrahydro-2H-pyran-4-yl)oxy)-5-(4,4,5,5-tetramethyl-1,3,2-dioxaborolan-2-yl)benzonitrile (178 mg, 0.54 mmol), were added to the mixture and the reaction was additionally heated at 100° C. in the sealed tube for 15 h. Afterwards, the crude material was allowed to reach room temperature. It was concentrated in vacuo, the residue was diluted in MeOH and filtered through a short pad of celite, washing the solids with MeOH. The filtrate was concentrated to dryness. The residue was purified by silica gel column chromatography eluted 5-15% MeOH in DCM to give the title compound. ¹H NMR (400 MHz, DMSO-d6) δ 9.30-9.06 (m, 2H), 8.85 (s, 1H), 8.15-7.88 (m, 2H), 7.61 (d, J=9.1 Hz, 1H), 7.21 (m, 1H), 4.94 (m, 1H), 4.03-3.81 (m, 2H), 3.76 (m, 4H), 3.55 (m, 2H), 3.15 (m, 4H), 2.17-1.97 (m, 2H), 1.70 (m, 2H). LCMS-ESI⁺ (m/z): [M+H]⁺ calcd for $C_{27}H_{25}FN_6O_3$: 501.2. found: 501.2.

Example 243: 5-(8-(6-morpholinopyridin-3-yl)-9H-purin-6-yl)-2-((tetrahydro-2H-pyran-4-yl)oxy)benzonitrile

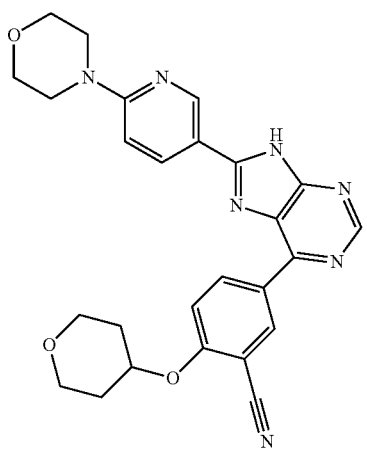 [SMILES: N#Cc1cc(-c2ncnc3[nH]c(-c4ccc(N5CCOCC5)nc4)nc23)ccc1OC1CCOCC1]

Step 1: Preparation of 4-(5-(6-chloro-9H-purin-8-yl)pyridin-2-yl)morpholine: A mixture of 6-chloro-4,5-diaminopyrimidine (347 mg, 2.4 mmol), 500 mg of 6-morpholinonicotinic acid (500 mg, 2.4 mmol), and ammonium chloride (713 mg, 6 eq) in POCl3 (7 mL) was heated at 110 C for 36 hrs in a sealed tube. The reaction mixture was cooled and the residue was washed several times with ether. The residue was dissolved in CH2Cl2 and aqueous NaHCO3. The aqueous layer was extracted with CH2Cl2. A dark solid was suspended in the mixture. Filtration of the mixture gave the crude product as a dark solid. LCMS-ESI⁺ (m/z): [M+H]⁺ calcd for $C_{14}H_{13}ClN_6O$: 317.1. found: 317.2.

Step 2: A sealed tube containing a suspension of 4-(5-(6-chloro-9H-purin-8-yl)pyridin-2-yl)morpholine (120 mg, 0.38 mmol) and Pd(PPh₃)₄ (22 mg, 0.019 mmol) in a degassed mixture of dioxane/H₂O (13 mL, 4/1), was preheated at 85° C. for 5 min. Next, K₂CO₃ (131 mg, 0.947 mmol) and 2-((tetrahydro-2H-pyran-4-yl)oxy)-5-(4,4,5,5-tetramethyl-1,3,2-dioxaborolan-2-yl)benzonitrile (187 mg, 0.57 mmol), were added to the mixture and the reaction was additionally heated at 100° C. in the sealed tube for 15 h. Afterwards, the reaction mixture was allowed to reach room temperature. It was concentrated to dryness. The residue was triturated with MeOH and filtered. The solid was washed with MeOH and DCM several times to give the title compound. 1H NMR (400 MHz, DMSO-d6) δ 9.33-9.12 (m, 2H), 9.04 (d, J=2.3 Hz, 1H), 8.75 (s, 1H), 8.37 (dd, J=9.0, 2.4 Hz, 1H), 7.59 (d, J=9.1 Hz, 1H), 7.02 (d, J=9.0 Hz, 1H), 4.93 (m, 1H), 3.88 (m, 2H), 3.71 (m, 4H), 3.65-3.46 (m, 6H), 2.06 (m, 2H), 1.70 (m, 2H). LCMS-ESI⁺ (m/z): [M+H]⁺ calcd for $C_{26}H_{25}N_7O_3$: 484.2. found: 484.3.

Example 244: 5-(8-(3-fluoro-4-morpholinophenyl)-9H-purin-6-yl)-2-(piperidin-4-yloxy)benzonitrile

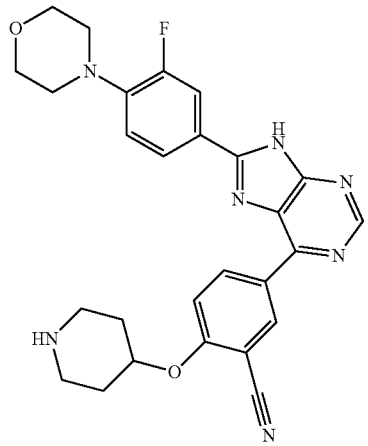 [SMILES: N#Cc1cc(-c2ncnc3[nH]c(-c4ccc(N5CCOCC5)c(F)c4)nc23)ccc1OC1CCNCC1]

A solution of tert-butyl 4-(2-cyano-4-(8-(3-fluoro-4-morpholinophenyl)-9H-purin-6-yl)phenoxy)piperidine-1-carboxylate (200 mgs) in DCM (7 mL) and trifluoroacetic acid (2.5 mL) was stirred at rt for 4 h. The solvent was evaporated under reduced pressure. The reaction mixture was then concentrated to dryness. The residue was purified by silica gel column chromatography eluted 5-15% MeOH in DCM to give the title compound. LCMS-ESI$^+$ (m/z): [M+H]$^+$ calcd for $C_{27}H_{26}FN_7O_2$: 500.2. found: 500.2.

Example 245: tert-butyl 4-(2-cyano-4-(8-(3-fluoro-4-morpholinophenyl)-9H-purin-6-yl)phenoxy)piperidine-1-carboxylate

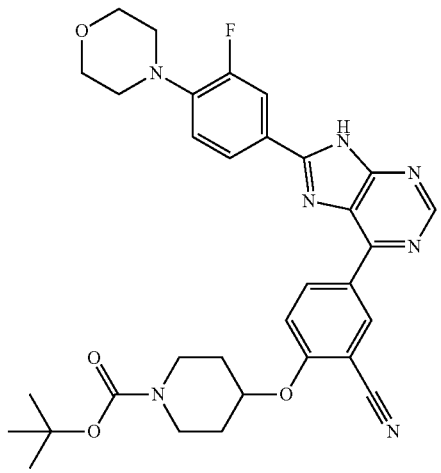 [SMILES: CC(C)(C)OC(=O)N1CCC(Oc2ccc(-c3ncnc4[nH]c(-c5ccc(N6CCOCC6)c(F)c5)nc34)cc2C#N)CC1]

A sealed tube containing a suspension of 4-(4-(6-chloro-9H-purin-8-yl)-2-fluorophenyl)morpholine (230 mg, 0.689 mmol) and Pd(PPh$_3$)$_4$ (40 mg, 0.034 mmol) in a degassed mixture of dioxane/H$_2$O (6 mL, 4/1), was preheated at 85° C. for 5 min. Next, K$_2$CO$_3$ (238 mg, 2 mmol) and tert-butyl 4-(2-cyano-4-(4,4,5,5-tetramethyl-1,3,2-dioxaborolan-2-yl)phenoxy)piperidine-1-carboxylate (443 mg, 1 mmol), were added to the mixture and the reaction was additionally heated at 100° C. in the sealed tube for 15 h. Afterwards, the crude material was allowed to reach room temperature. It was concentrated to dryness. The residue was triturated with MeOH and filtered through a short pad of celite, washing the solids with MeOH. The filtrate was concentrated to dryness and the residue was purified by silica gel column chromatography eluted 0-5% MeOH in DCM to give the title compound. LCMS-ESI$^+$ (m/z): [M+H]$^+$ calcd for $C_{32}H_{34}N_7O_4$: 600.3. found: 600.0.

Example 246: tert-butyl 4-(2-cyano-4-(8-(4-(4-methylpiperazin-1-yl)phenyl)-9H-purin-6-yl)phenoxy)piperidine-1-carboxylate

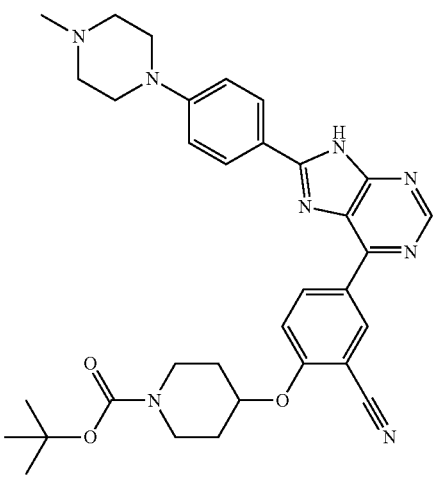 [SMILES: CN1CCN(c2ccc(-c3nc4c(-c5ccc(OC6CCN(C(=O)OC(C)(C)C)CC6)c(C#N)c5)ncnc4[nH]3)cc2)CC1]

Step 1: Preparation of 6-chloro-8-(4-(4-methylpiperazin-1-yl)phenyl)-9H-purine: A mixture of 6-chloro-4,5-diaminopyrimidine (500 mg, 3.5 mmol), 4-(4-methylpiperazin-1-yl) benzoic acid (762 mg, 3.5 mmol) in POCl$_3$ (8 mL) was heated at 110 C for 16 hrs. After it was cooled to room temperature, the residue was washed several times with ether. Then the residue was dissolved in small amount of MeOH, purified by silica gel column using 5-25% of MeOH in CH2Cl2 as eluent to give the product. LCMS-ESI$^+$ (m/z): [M+H]$^+$ calcd for $C_{16}H_{17}ClN_6$: 329.1. found: 329.2.

Step 2: A sealed tube containing a suspension of 6-chloro-8-(4-(4-methylpiperazin-1-yl)phenyl)-9H-purine (210 mg, 0.639 mmol) and Pd(PPh$_3$)$_4$ (37 mg, 0.032 mmol) in a degassed mixture of dioxane/H$_2$O (5 mL, 4/1), was preheated at 85° C. for 5 min. Next, K$_2$CO$_3$ (221 mg, 2 mmol) and tert-butyl 4-(2-cyano-4-(4,4,5,5-tetramethyl-1,3,2-dioxaborolan-2-yl)phenoxy)piperidine-1-carboxylate (410 mg, 0.96 mmol), were added to the mixture and the reaction was additionally heated at 100° C. in the sealed tube for 15 h. Afterwards, the crude material was allowed to reach room temperature. It was concentrated to dryness. The residue was triturated with MeOH and filtered through a short pad of celite, washing the solids with MeOH. The filtrate was concentrated to dryness and the residue purified by silica gel column chromatography eluted 0-5% MeOH in DCM to give the title compound. LCMS-ESI$^+$ (m/z): [M+H]$^+$ calcd for $C_{33}H_{38}N_8O_3$: 595.3. found: 595.2.

Example 247: 5-(8-(4-(4-methylpiperazin-1-yl)phenyl)-9H-purin-6-yl)-2-(piperidin-4-yloxy)benzonitrile

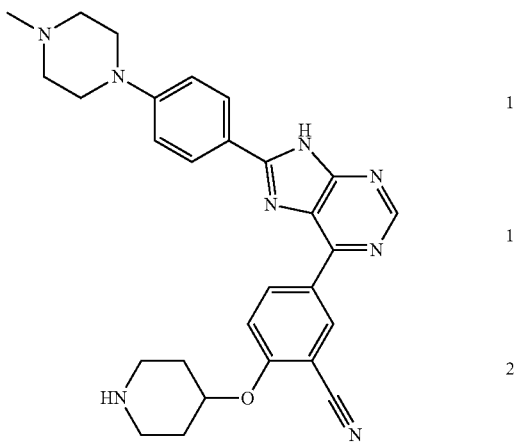

A solution of tert-butyl 4-(2-cyano-4-(8-(4-(4-methylpiperazin-1-yl)phenyl)-9H-purin-6-yl)phenoxy)piperidine-1-carboxylate (230 mg) in DCM (7 mL) and trifluoroacetic acid (2.5 mL) was stirred at rt for 4 h. The solvent was evaporated under reduced pressure. The reaction mixture was then concentrated to dryness, the residue was triturated with EtOAc and filtered. The solid was washed with EtOAc to give the title compound. 1H NMR (400 MHz, DMSO-d6) δ 9.30-9.24 (m, 1H), 9.20-9.09 (m, 1H), 8.85 (s, 1H), 8.18 (d, J=8.6 Hz, 2H), 7.62 (d, J=9.1 Hz, 1H), 7.21 (d, J=8.6 Hz, 2H), 5.01 (s, 1H), 3.33-3.01 (m, 6H), 2.79 (m, 2H), 2.48 (m, 7H), 2.18 (m, 2H), 1.96 (m, 2H). LCMS-ESI⁺ (m/z): [M+H]⁺ calcd for C$_{28}$H$_{30}$N$_8$O: 495.3. found: 495.2.

Example 248: 2-((1-(2,2-difluoroacetyl)piperidin-4-yl)oxy)-5-(8-(4-morpholinophenyl)-9H-purin-6-yl)benzonitrile

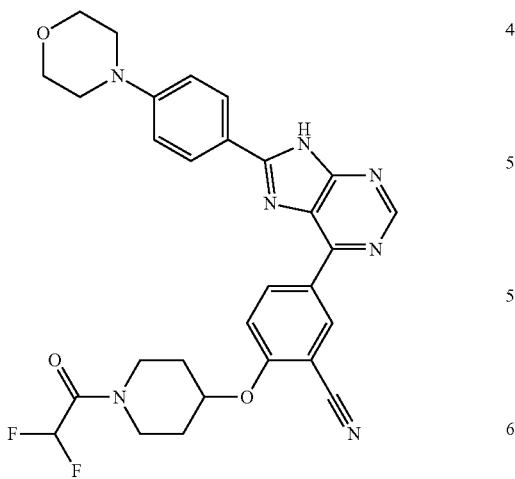

To a mixture of 5-(8-(4-morpholinophenyl)-9H-purin-6-yl)-2-(piperidin-4-yloxy)benzonitrile (25 mg, 0.052 mmol), difluoroacetic acid (5 mg) and DIPEA (8 mg) in DMF (1 mL) was added HATU (24 mg). The reaction mixture was stirred at rt for 16 hrs. The mixture was concentrated to dryness. The residue was triturated with MeOH and filtered. The solid was washed with methanol to give the title compound. 1H NMR (400 MHz, DMSO-d6) δ 9.20 (m, 2H), 8.83 (s, 1H), 8.16 (d, J=8.6 Hz, 2H), 7.74-7.55 (m, 1H), 7.14 (d, J=8.9 Hz, 2H), 6.77 (t, 1H), 5.04 (s, 1H), 3.74 (m, 6H), 3.57 (m, 2H), 3.30 (m, 4H), 2.05 (m, 2H), 1.90-1.63 (m, 2H). LCMS-ESI⁺ (m/z): calcd for C$_{29}$H$_{27}$F2N$_7$O$_3$: 560.2. found [M+H]⁺: 560.2.

Example 249: 2-((1-acetylpiperidin-4-yl)oxy)-5-(8-(4-morpholinophenyl)-9H-purin-6-yl)benzonitrile

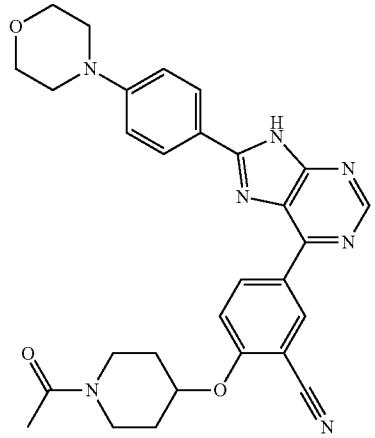 [SMILES: CC(=O)N1CCC(Oc2ccc(-c3ncnc4[nH]c(-c5ccc(N6CCOCC6)cc5)nc34)cc2C#N)CC1]

To a mixture of 5-(8-(4-morpholinophenyl)-9H-purin-6-yl)-2-(piperidin-4-yloxy)benzonitrile (25 mg, 0.052 mmol), acetic acid (5 mg) and DIPEA (8 mg) in DMF (1 mL) was added HATU (24 mg). The reaction mixture was stirred at rt for 16 hrs. The mixture was concentrated to dryness. The residue was triturated with MeOH and filtered. The solid was washed with MeOH to give the title compound. 1H NMR (400 MHz, DMSO-d6) δ 13.81 (s, 1H), 9.19 (m, 2H), 8.83 (s, 1H), 8.16 (d, J=8.6 Hz, 2H), 7.63 (m, 1H), 7.14 (d, J=8.8 Hz, 2H), 5.18-4.85 (m, 1H), 3.87-3.56 (m, 6H), 3.44 (m, 2H), 3.30 (m, 4H), 2.03 (s, 3H), 1.94 (m, 2H), 1.82-1.57 (m, 2H). LCMS-ESI⁺ (m/z): calcd for C$_{29}$H$_{29}$N$_7$O$_3$: 524.2. found [M+H]⁺: 524.2.

Example 250: 2-((1-formylpiperidin-4-yl)oxy)-5-(8-(4-morpholinophenyl)-9H-purin-6-yl)benzonitrile

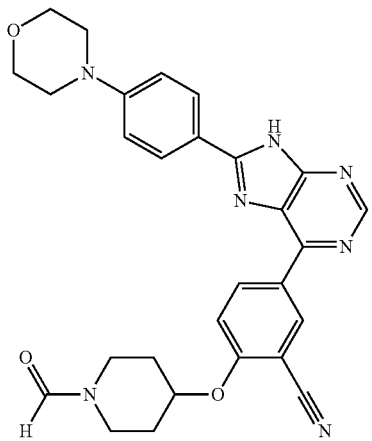 [SMILES: N#Cc1cc(-c2ncnc3[nH]c(-c4ccc(N5CCOCC5)cc4)nc23)ccc1OC1CCN(C=O)CC1]

To a mixture of 5-(8-(4-morpholinophenyl)-9H-purin-6-yl)-2-(piperidin-4-yloxy)benzonitrile (25 mg, 0.052 mmol), formic acid (5 mg) and DIPEA (8 mg) in DMF (1 mL) was added HATU (24 mg). The reaction mixture was stirred at rt for 16 hrs. The mixture was concentrated to dryness. The residue was triturated with methanol and filtered. The solid was washed with methanol to give the title compound. 1H NMR (400 MHz, DMSO-d6) δ 9.18 (m, 2H), 8.83 (s, 1H), 8.17 (d, J=8.6 Hz, 2H), 8.03 (s, 1H), 7.64 (m, 1H), 7.14 (d, J=8.7 Hz, 2H), 5.03 (t, J=5.5 Hz, 1H), 3.52-3.84 (m, 6H), 3.71-3.52 (m, 2H), 3.39 (m, 2H), 3.32 (m, 4H), 2.14-1.88 (m, 2H), 1.72 (m, 2H). LCMS-ESI+ (m/z): calcd for $C_{28}H_{27}N_7O_3$: 510.2. found[M+H]+: 510.3.

Example 251: 2-((1-(2-hydroxyacetyl)piperidin-4-yl)oxy)-5-(8-(4-(4-methylpiperazin-1-yl)phenyl)-9H-purin-6-yl)benzonitrile

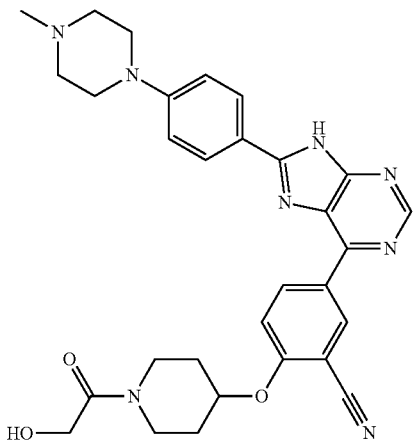 [SMILES: CN1CCN(c2ccc(-c3nc4c(-c5ccc(OC6CCN(C(=O)CO)CC6)c(C#N)c5)ncnc4[nH]3)cc2)CC1]

To a mixture of 5-(8-(4-(4-methylpiperazin-1-yl)phenyl)-9H-purin-6-yl)-2-(piperidin-4-yloxy)benzonitrile (43 mg, 0.0861 mmol), hydroxyacetic acid (9 mg) and DIPEA (13 mg) in DMF (1.5 mL) was added HATU (39 mg). The reaction mixture was stirred at rt for 16 hrs. The mixture was concentrated to dryness. The residue was triturated with methanol and filtered. The solid was washed with methanol to give the title compound. 1H NMR (400 MHz, DMSO-d6) δ 9.23 (m, 1H), 9.16 (m, 1H), 8.85 (s, 1H), 8.19 (d, J=8.6 Hz, 2H), 7.64 (m, 1H), 7.21 (d, J=8.7 Hz, 2H), 5.01 (m, 1H), 4.63-4.48 (m, 1H), 4.12 (d, J=4.5 Hz, 2H), 3.52-3.74 (m, 8H), 3.24-3.03 (m, 5H), 2.74 (s, 3H), 2.01 (m, 2H), 1.88-1.58 (m, 2H). LCMS-ESI+ (m/z): calcd for $C_{30}H_{32}N_8O_3$: 553.3. found [M+H]+: 553.1.

Example 252: 5-(8-(4-(morpholinomethyl)phenyl)-9H-purin-6-yl)-2-((tetrahydro-2H-pyran-4-yl)oxy)benzonitrile

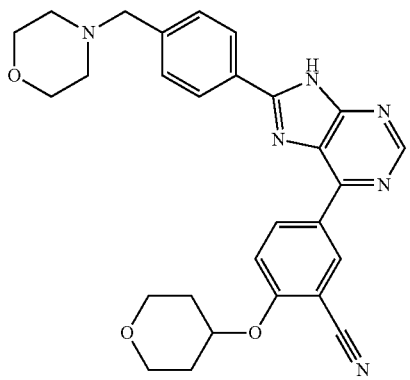 [SMILES: N#Cc1cc(-c2ncnc3[nH]c(-c4ccc(CN5CCOCC5)cc4)nc23)ccc1OC1CCOCC1]

Step 1: 4-(4-(6-chloro-9H-purin-8-yl)benzyl)morpholine: A mixture of 6-chloro-4,5-diaminopyrimidine (327 mg, 2.3 mmol), 4-(morpholinomethyl)benzoic acid (500 mg, 2.3 mmol) and ammonium chloride (725 mg, 6 eq) in POCl3 (7 mL) was heated at 110 C for 36 hrs in a sealed tube. The reaction mixture was cooled and the residue was washed several times with ether. The residue was dissolved in CH2Cl2 and aqueous NaHCO3. The layers were separated and the aqueous was extracted with CH2Cl2. The combined organics were washed with saturated NaHCO3, brine, and dried (Na2SO4), filtered, and collected in vacuo to give the product. LCMS-ESI+ (m/z): [M+H]+ calcd for $C_{16}H_{16}ClN_5O$: 330.1. found: 330.1.

Step 2: A sealed tube containing a suspension of 4-(4-(6-chloro-9H-purin-8-yl)benzyl)morpholine (51 mg) and Pd(PPh3)4 (8 mg) in a degassed mixture of dioxane/H2O (3 mL, 4/1), was preheated at 85° C. for 5 min. Next, K2CO3 (55 mg) and 2-((tetrahydro-2H-pyran-4-yl)oxy)-5-(4,4,5,5-tetramethyl-1,3,2-dioxaborolan-2-yl)benzonitrile (76 mg), were added to the mixture and the reaction was additionally heated at 100° C. in the sealed tube for 15 h. Afterwards, the crude material was allowed to reach room temperature. It was concentrated in vacuo, the residue was diluted in MeOH and filtered through a short pad of celite, washing the solids with MeOH. The filtrate was concentrated to dryness. The residue was purified by silica gel column chromatography eluted 0-10% MeOH in DCM to give the title compound. 1H NMR (400 MHz, DMSO-d6) δ 9.15 (d, J=7.1 Hz, 2H), 8.86 (s, 1H), 8.23 (d, J=8.0 Hz, 2H), 7.56 (m, 3H), 4.94 (m, 1H), 3.88 (m, 2H), 3.68-3.44 (m, 8H), 2.43-2.19 (m, 4H), 2.05 (m, 2H), 1.70 (m, 2H). LCMS-ESI+ (m/z): calcd for $C_{28}H_{28}N_6O_3$: 497.2. found[M+H]+: 497.2.

Example 253: 2-((1-(methylsulfonyl)piperidin-4-yl)oxy)-5-(8-(4-morpholinophenyl)-9H-purin-6-yl)benzonitrile

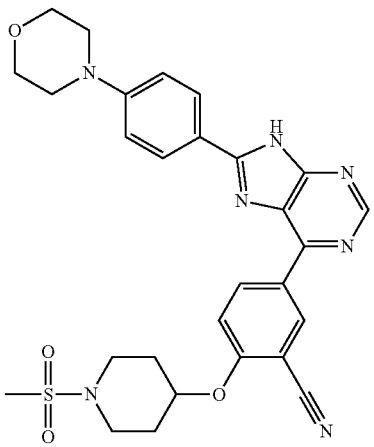 [SMILES: CS(=O)(=O)N1CCC(Oc2ccc(-c3ncnc4[nH]c(-c5ccc(N6CCOCC6)cc5)nc34)cc2C#N)CC1]

Methanesulfonyl chloride (14 mg, 0.013 mmol) was added at 0° C. to a solution of 5-(8-(4-morpholinophenyl)-9H-purin-6-yl)-2-(piperidin-4-yloxy)benzonitrile (30 mg, 0.062 mmol) and N,N-diisopropylethylamine (32 mg, 0.025 mmol) in dichlormethane (1 mL). The reaction mixture was concentrated to dryness. The residue was triturated with EtOAc, filtered to give the title compound. 1H NMR (400 MHz, DMSO-d6) δ 9.18 (d, 2H), 8.83 (s, 1H), 8.25-8.04 (m, 2H), 7.62 (d, J=8.9 Hz, 1H), 7.24-7.02 (m, 2H), 4.95 (m, 1H), 3.75 (m, 4H), 3.31 (m, 8H), 2.92 (s, 3H), 2.08 (m, 2H), 1.89 (m, 2H). LCMS-ESI$^+$ (m/z): calcd for $C_{28}H_{29}N_7O_4S$: 560.2. found [M+H]$^+$: 560.2.

Example 254: 2-((1-formylpiperidin-4-yl)oxy)-5-(8-(4-(4-methylpiperazin-1-yl)phenyl)-9H-purin-6-yl)benzonitrile

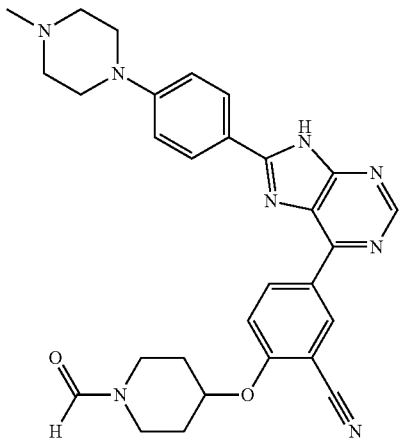 [SMILES: CN1CCN(c2ccc(-c3nc4c(-c5ccc(OC6CCN(C=O)CC6)c(C#N)c5)ncnc4[nH]3)cc2)CC1]

To a mixture of 5-(8-(4-morpholinophenyl)-9H-purin-6-yl)-2-(piperidin-4-yloxy)benzonitrile (25 mg, 0.052 mmol), acetic acid (5 mg) and DIPEA (8 mg) in DMF (1 mL) was added HATU (24 mg). The reaction mixture was stirred at rt for 16 hrs. The reaction mixture was concentrated. The mixture was concentrated to dryness. The residue was purified via HPLC ((20 mL/min, 25-80% MeCN/H$_2$O (0.1% TFA v/v) gradient over 30 min) to give the compound. 1H NMR (400 MHz, DMSO-d6) δ 9.72 (s, 1H), 9.31-9.06 (m, 2H), 8.85 (s, 1H), 8.27-8.12 (m, 2H), 8.03 (s, 1H), 7.64 (d, J=9.2 Hz, 1H), 7.32-7.12 (m, 2H), 5.04 (m, 1H), 4.08 (m, 2H), 3.40 (m, 6H), 3.22-3.01 (m, 4H), 2.98-2.76 (m, 3H), 2.00 (m, 2H), 1.85-1.55 (m, 2H). LCMS-ESI$^+$ (m/z): calcd for $C_{29}H_{30}N_8O_2$: 523.3. found[M+H]$^+$: 523.3.

Example 255: 5-(8-(4-(1-(2,2-difluoroethyl)piperidin-4-yl)phenyl)-9H-purin-6-yl)-2-((1-(2-hydroxyacetyl)piperidin-4-yl)oxy)benzonitrile

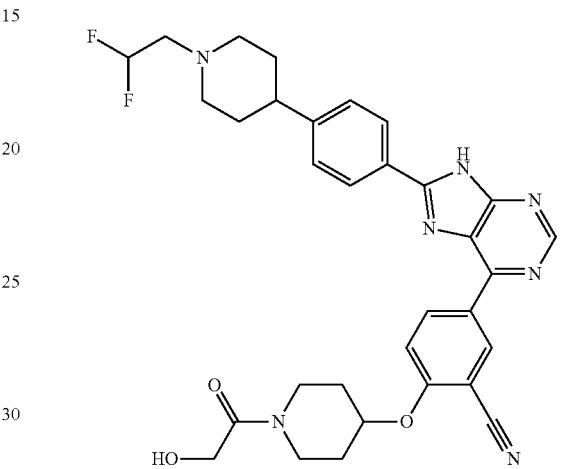

Step 1: A mixture of methyl 4-(piperidin-4-yl)benzoate (1.6 g, 7.3 mmol), 2,2-difluoroethyl trifluoromethanesulfonate (2.03 g, 9.5 mmol), K2CO3 (6.05 g, 44 mmol) in a mixture of MeCN (60 mL) and THF (7 mL) in a sealed tube was heated at 55° C. overnight. The mixture was filtered and the filtrate was concentrated to dryness under reduced pressure to give crude product as a white solid.

Step 2: To a solution of methyl 4-(1-(2,2-difluoroethyl)piperidin-4-yl)benzoate (1.45 g, 5.12 mmol) in MeOH (8 mL), 2M NaOH (7.7 mL, 15.4 mmol) was added. The reaction was heated for 3 hours at 40° C. The solvent was removed under reduced pressure and the solution was diluted with water and neutralized to pH 7 with aqueous 25% HCl. The solution was concentrated to dryness and the residue was purified by silica gel column chromatography eluted 5-20% MeOH in CH2Cl2 to give the product. LCMS-ESI$^+$ (m/z): [M+H]$^+$ calcd for $C_{14}H_{17}F_2N_2O$: 270.1. found: 270.1.

Step 3: A mixture of 4-(1-(2,2-difluoroethyl)piperidin-4-yl)benzoic acid (837 mg), 6-chloro-4,5-diaminopyrimidine (494 mg) in POCl3 (10 mL) was heated at 120 C for 16 hrs. After it was cooled to room temperature, the residue was washed several times with ether. Then the residue was dissolved in small amount of MeOH, purified by silica gel column using 5-25% of MeOH in CH2Cl2 as eluent to give 6-chloro-8-(4-(1-(2,2-difluoroethyl)piperidin-4-yl)phenyl)-9H-purine. LCMS-ESI$^+$ (m/z): [M+H]$^+$ calcd for $C_{18}H_{18}ClF_2N_5$: 378.1. found: 378.2.

Step 4: 5-(8-(4-(1-(2,2-difluoroethyl)piperidin-4-yl)phenyl)-9H-purin-6-yl)-2-(piperidin-4-yloxy)benzonitrile was prepared in a similar manner to Example 246 step 1 and Example 247.

Step 5: To a mixture of 5-(8-(4-(1-(2,2-difluoroethyl)piperidin-4-yl)phenyl)-9H-purin-6-yl)-2-(piperidin-4- yloxy)benzonitrile (70 mg, 0.13 mmol), hydroxyacetic acid (16 mg) and DIPEA (27 mg) in DMF (3 mL) was added HATU (90 mg). The reaction mixture was stirred at rt for 16 hrs. The mixture was concentrated to dryness. The residue was purified via HPLC ((20 mL/min, 20-90% MeCN/H$_2$O (0.1% TFA v/v) gradient over 30 min) to give the title compound. $^1$H NMR (400 MHz, DMSO-d$_6$) 9.30-9.06 (m, 2H), 8.91 (s, 1H), 8.27 (d, J=8.1 Hz, 2H), 7.64 (m, 1H), 7.52 (d, J=7.9 Hz, 2H), 6.79-6.35 (t, 1H), 5.02 (dt, J=7.4, 3.7 Hz, 1H), 4.12 (s, 2H), 3.56 (m, 5H), 3.18 (s, 3H), 2.89 (m, 2H), 2.01 (m, 8H), 1.84-1.59 (m, 2H). LCMS-ESI$^+$ (m/z): calcd for C$_{31}$H$_{32}$F$_2$N$_8$O$_3$: 602.3. found[M+H]$^+$: 602.3.

Example 256: 5-(8-(4-(4-(2-fluoroethyl)-3-methyl-piperazin-1-yl)phenyl)-9H-purin-6-yl)-2-((1-(2-hydroxyacetyl)piperidin-4-yl)oxy)benzonitrile

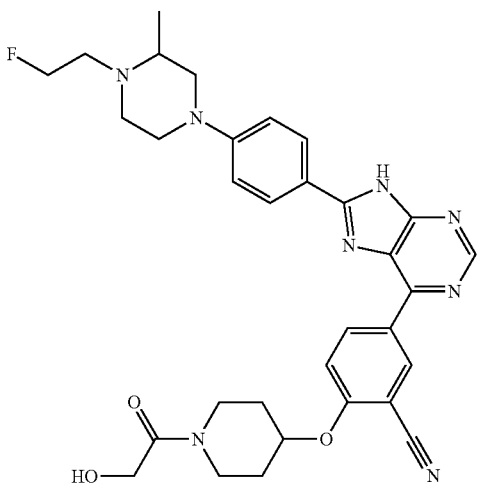 [SMILES: CC1CN(c2ccc(-c3nc4c(-c5ccc(OC6CCN(C(=O)CO)CC6)c(C#N)c5)ncnc4[nH]3)cc2)CCN1CCF]

Step 1: To a solution of ethyl 4-(3-methylpiperazin-1-yl) benzoate (0.6 g) in DMF (20 mL), 1-bromo-2-fluoroethane (0.46 g) and Na$_2$CO$_3$ (0.61 g) were added and heated to 70° C. for 18 h. The reaction was cooled to rt, diluted with EtOAc, and washed twice with NaHCO$_3$ and brine. The organic layer was dried over MgSO$_4$, loaded onto silica, and purified via flash chromatography using EtOAc/Hex gradient 0-50%. The desired fractions were combined and the solvent was removed to give ethyl 4-(4-(2-fluoroethyl)-3-methylpiperazin-1-yl)benzoate.

Step 2: To a solution of ethyl 4-(4-(2-fluoroethyl)-3-methylpiperazin-1-yl)benzoate (782 mg, 2.66 mmol) in MeOH (4 ml), 2M NaOH (4 ml, 48 mmol) was added. The reaction was heated for 3 hours at 40° C. The solvent was removed under reduced pressure and the solution was diluted with water and neutralized to pH 7 with aqueous 25% HCl. The solvents were removed and the residue was purified by silica gel column chromatography with 0-10% MeOH in CH2Cl2 to give 4-(4-(2-fluoroethyl)-3-methylpiperazin-1-yl)benzoic acid. LCMS-ESI$^+$ (m/z): [M+H]$^+$ calcd for C$_{14}$H$_{19}$FN$_2$O$_2$: 267.1. found: 267.1.

Step 3: A mixture of 4-(4-(2-fluoroethyl)-3-methylpiperazin-1-yl)benzoic acid (280 mg), 6-chloro-4,5-diaminopyrimidine (167 mg) in POCl3 (8 mL) was heated at 110° C. for 16 hrs. After it was cooled to room temperature, the mixture was concentrated to remove the remaining POCl3, and then the residue was washed several times with ether. Then the residue was dissolved in small amount of MeOH, purified by silica gel using 5-25% of MeOH in CH2Cl2 as eluent to give 6-chloro-8-(4-(4-(2-fluoroethyl)-3-methylpiperazin-1-yl)phenyl)-9H-purine. LCMS-ESI$^+$ (m/z): [M+H]$^+$ calcd for C$_{18}$H$_{20}$ClFN$_6$: 375.1; found: 375.2.

Step 4: 5-(8-(4-(4-(2-fluoroethyl)-3-methylpiperazin-1-yl)phenyl)-9H-purin-6-yl)-2-(piperidin-4-yloxy)benzonitrile was prepared in a similar manner to Example 246 step 1 and Example 247.

Step 5: To a mixture of 5-(8-(4-(4-(2-fluoroethyl)-3-methylpiperazin-1-yl)phenyl)-9H-purin-6-yl)-2-(piperidin-4-yloxy)benzonitrile (16 mg, 0.03 mmol), hydroxyacetic acid (4 mg) and DIPEA (6 mg) in DMF (0.5 mL) was added HATU (18 mg). The reaction mixture was stirred at rt for 16 hrs. The mixture was concentrated to dryness. The residue was purified via HPLC ((20 mL/min, 20-90% MeCN/H$_2$O (0.1% TFA v/v) gradient over 30 min) to give the title compound. $^1$H NMR (400 MHz, DMSO-d$_6$) δ 9.25 (s, 1H), 9.13 (m, 1H), 8.85 (s, 1H), 8.20 (d, J=8.6 Hz, 2H), 7.93 (s, 1H), 7.64 (m, 1H), 7.24 (d, J=8.6 Hz, 2H), 5.12-4.70 (m, 2H), 4.12 (m, 2H), 0.3.09-3.72 (m, 8H), 2.87 (s, 2H), 2.71 (s, 2H), 2.49 (m, 2H), 2.01 (m, 2H), 1.90-1.60 (m, 2H), 1.37 (m, 3H). LCMS-ESI$^+$ (m/z): calcd for C$_{32}$H$_{35}$FN$_8$O$_3$: 599.3. found[M+H]$^+$: 599.3.

Example 257: 2-((1-(2-hydroxyacetyl)piperidin-4-yl)oxy)-5-(8-(4-(1-(2,2,2-trifluoroethyl)piperidin-4-yl)phenyl)-9H-purin-6-yl)benzonitrile

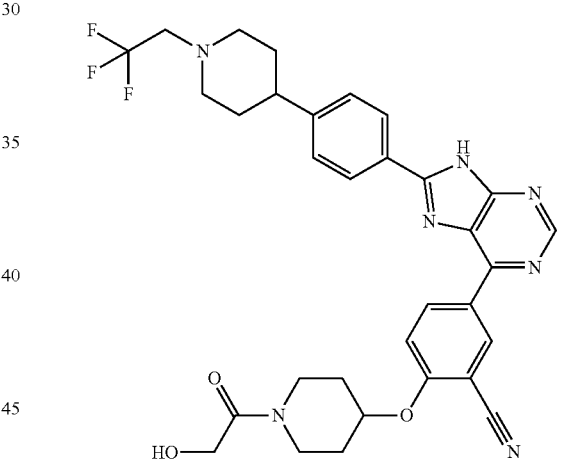

Step 1: A mixture of methyl 4-(piperidin-4-yl)benzoate (1.5 g, 6.8 mmol), 2,2,2-trifluoroethyl trifluoromethanesulfonate (2.06 g, 8.9 mmol), K2CO3 (5.67 g, 41 mmol) in a mixture of MeCN (50 mL) and THF (5 mL) in a sealed tube was heated at 55 C overnight. The mixture filtered and the filtrate was concentrated to dryness under reduced pressure to give methyl 4-(1-(2,2,3-trifluoroethyl)piperidin-4-yl)benzoate as a white solid.

Step 2: To a solution of methyl 4-(1-(2,2,3-trifluoroethyl) piperidin-4-yl)benzoate (1.45 g, 5.12 mmol) in MeOH (8.5 ml), 2M NaOH (8.2 ml, 15.4 mmol) was added. The reaction was heated for 3 hours at 40° C. The solvent was removed under reduced pressure and the solution was diluted with water and neutralized to pH 7 with aqueous 25% HCl. The mixture was concentrated to dryness and the residue was purified by silica gel column m eluent with 5-10% MeOH in CH2Cl2 to give 4-(1-(2,2,2-trifluoroethyl)piperidin-4-yl) benzoic acid. LCMS-ESI$^+$ (m/z): [M+H]$^+$ calcd for C$_{14}$H$_{16}$F$_3$NO$_2$: 287.1. found: 288.1.

Step 3: A mixture of 4-(1-(2,2,2-trifluoroethyl)piperidin-4-yl)benzoic acid (1.5 g), 6-chloro-4,5-diaminopyrimidine (830 mg) in POCl3 (15 mL) was heated at 120° C. for 16 hrs. After it was cooled to room temperature, the residue was washed several times with ether. Then the residue was dissolved in small amount of MeOH, purified by silica gel column, using 5-25% of MeOH in CH2Cl2 as eluent to give 6-chloro-8-(4-(1-(2,2,2-trifluoroethyl)piperidin-4-yl)phenyl)-9H-purine. LCMS-ESI$^+$ (m/z): [M+H]$^+$ calcd for $C_{18}H_{17}ClF_3N_5$: 396.1. found: 396.3.

Step 4: 2-(piperidin-4-yloxy)-5-(8-(4-(1-(2,2,2-trifluoroethyl)piperidin-4-yl)phenyl)-9H-purin-6-yl)benzonitrile benzonitrile was prepared in a similar manner to Example 246 step 1 and Example 247.

Step 5: To a mixture of 2-(piperidin-4-yloxy)-5-(8-(4-(1-(2,2,2-trifluoroethyl)piperidin-4-yl)phenyl)-9H-purin-6-yl)benzonitrile (35 mg, 0.062 mmol), hydroxyacetic acid (8 mg) and DIPEA (13 mg) in DMF (5 mL) was added HATU (38 mg). The reaction mixture was stirred at rt for 16 hrs. The mixture was concentrated to dryness. The residue was purified via HPLC ((20 mL/min, 20-90% MeCN/H$_2$O (0.1% TFA v/v) gradient over 30 min) to give the title compound. $^1$H NMR (400 MHz, DMSO-d$_6$) 9.19 (d, J=8.5 Hz, 2H), 8.90 (s, 1H), 8.30-8.13 (m, 2H), 7.65 (m, 1H), 7.52 (d, J=8.2 Hz, 2H), 5.02 (m, 1H), 4.12 (s, 2H), 3.73 (m, 6H), 3.42 (m, 4H), 3.13 (m, 2H), 2.74-2.54 (m, 2H), 2.02 (m, 2H), 1.90-1.60 (m, 5H). LCMS-ESI$^+$ (m/z): calcd for $C_{32}H_{32}F_3N_7O_3$: 620.3. found [M+H]$^+$: 620.3.

Example 258: 5-(8-(4-(1-(2,2-difluoroethyl)piperidin-4-yl)phenyl)-9H-purin-6-yl)-2-((1-formylpiperidin-4-yl)oxy)benzonitrile

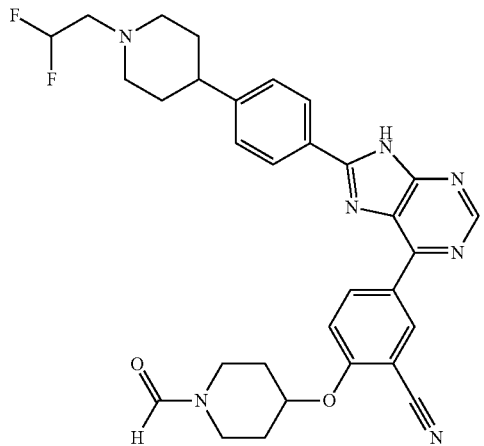 [SMILES: N#Cc1cc(-c2ncnc3[nH]c(-c4ccc(C5CCN(CC(F)F)CC5)cc4)nc23)ccc1OC1CCN(C=O)CC1]

To a mixture of 5-(8-(4-(1-(2,2-difluoroethyl)piperidin-4-yl)phenyl)-9H-purin-6-yl)-2-(piperidin-4-yloxy)benzonitrile (60 mg, 0.11 mmol), formic acid (8 mg) and DIPEA (23 mg) in DMF (2.5 mL) was added HATU (67 mg). The reaction mixture was stirred at rt for 16 hrs. The mixture was concentrated to dryness. The residue was purified via HPLC ((20 mL/min, 20-90% MeCN/H$_2$O (0.1% TFA v/v) gradient over 30 min) to give the title compound. $^1$H NMR (400 MHz, DMSO-d$_6$) δ 9.26-9.07 (m, 2H), 8.91 (s, 1H), 8.27 (d, J=8.1 Hz, 2H), 8.03 (s, 1H), 7.64 (m, 1H), 7.52 (d, J=7.9 Hz, 2H), 6.57 (tt, J=53.6, 4.0 Hz, 1H), 5.04 (m, 1H), 3.40-3.85 (m, 8H), 3.20 (m, 2H), 2.92 (m, 2H), 2.17-1.88 (m, 6H), 1.84-1.57 (m, 2H). LCMS-ESI$^+$ (m/z): calcd for $C_{31}H_{31}F_2N_7O_2$: 572.3. found[M+H]$^+$: 572.3.

Example 259: 2-((1-formylpiperidin-4-yl)oxy)-5-(8-(4-(1-(2,2,2-trifluoroethyl)piperidin-4-yl)phenyl)-9H-purin-6-yl)benzonitrile

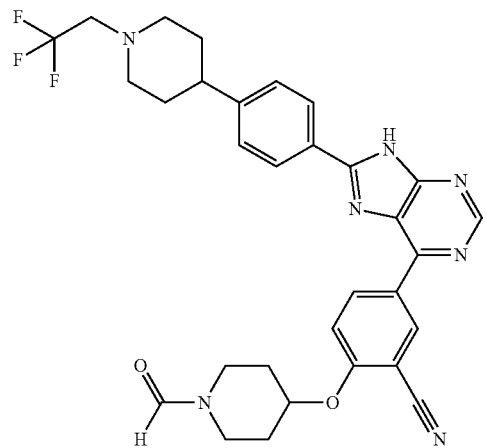 [SMILES: N#Cc1cc(-c2ncnc3[nH]c(-c4ccc(C5CCN(CC(F)(F)F)CC5)cc4)nc23)ccc1OC1CCN(C=O)CC1]

To a mixture of 2-(piperidin-4-yloxy)-5-(8-(4-(1-(2,2,2-trifluoroethyl)piperidin-4-yl)phenyl)-9H-purin-6-yl)benzonitrile (40 mg, 0.071 mmol), formic acid (5 mg) and DIPEA (15 mg) in DMF (1.5 mL) was added HATU (43 mg). The reaction mixture was stirred at rt for 16 hrs. The mixture was concentrated to dryness. The residue was purified via HPLC ((20 mL/min, 20-90% MeCN/H$_2$O (0.1% TFA v/v) gradient over 30 min) to give the title compound. $^1$H NMR (400 MHz, DMSO-d$_6$) 9.27-9.08 (m, 2H), 8.90 (s, 1H), 8.31-8.15 (m, 2H), 8.03 (s, 1H), 7.72-7.58 (m, 1H), 7.52 (d, J=8.2 Hz, 2H), 5.04 (m, 1H), 4.21-3.52 (m, 4H), 3.39 (m, 2H), 3.16 (m, 2H), 2.83-2.55 (m, 4H), 2.01 (m, 2H), 1.91-1.56 (m, 5H). LCMS-ESI$^+$ (m/z): calcd for $C_{31}H_{30}F_3N_7O_2$: 590.2. found [M+H]$^+$: 590.3.

Example 260: Preparation of 5-(8-(4-(1-(2,2-difluoroethyl)piperidin-4-yl)phenyl)-9H-purin-6-yl)-2-(piperidin-4-yloxy)benzonitrile

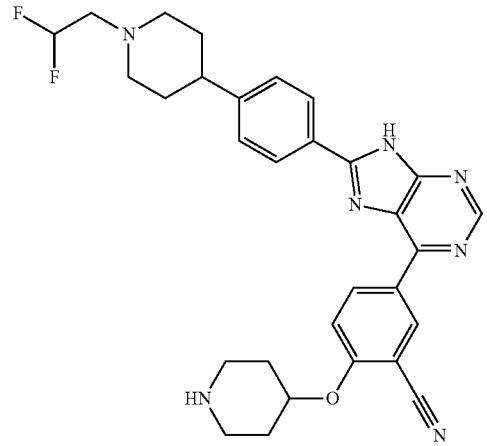 [SMILES: N#Cc1cc(-c2ncnc3[nH]c(-c4ccc(C5CCN(CC(F)F)CC5)cc4)nc23)ccc1OC1CCNCC1]

A solution of tert-butyl 4-(2-cyano-4-(8-(4-(1-(2,2-difluoroethyl)piperidin-4-yl)phenyl)-9H-purin-6-yl)phenoxy) piperidine-1-carboxylate (420 mg) in DCM (14 mL) and trifluoroacetic acid (5 mL) was stirred at rt overnight. The solvent was evaporated under reduced pressure. The reaction mixture was then concentrated to dryness, the residue was purified by silica gel column chromatography eluted 5-15% MeOH in DCM to give the title compound. LCMS-ESI⁺ (m/z): calcd for $C_{30}H_{31}F_2N_7O$: 544.3. found [M+H]⁺: 544.2.

Example 261: 2-(piperidin-4-yloxy)-5-(8-(4-(1-(2,2,2-trifluoroethyl)piperidin-4-yl)phenyl)-9H-purin-6-yl)benzonitrile

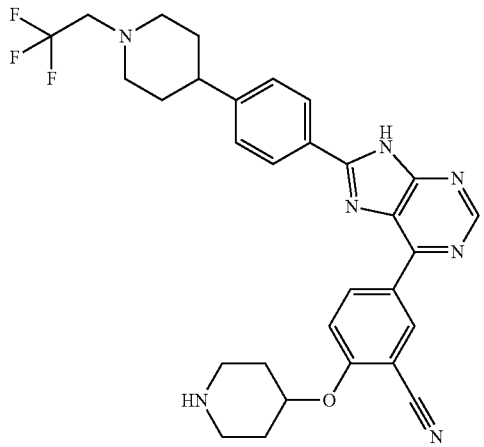 [SMILES: N#Cc1cc(-c2ncnc3[nH]c(-c4ccc(C5CCN(CC(F)(F)F)CC5)cc4)nc23)ccc1OC1CCNCC1]

A solution of tert-butyl 4-(2-cyano-4-(8-(4-(1-(2,2,2-trifluoroethyl)piperidin-4-yl)phenyl)-9H-purin-6-yl)phenoxy)piperidine-1-carboxylate (140 mg) in DCM (5 mL) and trifluoroacetic acid (2 mL) was stirred at rt overnight. The solvent was evaporated under reduced pressure. The residue was purified by silica gel column chromatography eluted 5-15% MeOH in DCM to give the title compound. LCMS-ESI⁺ (m/z): calcd for $C_{30}H_{30}F_3N_7O$: 562.3. found [M+H]⁺: 562.2.

Example 262: 4-(2-cyano-4-(8-(4-morpholinophenyl)-9H-purin-6-yl)phenoxy)piperidine-1-sulfonamide

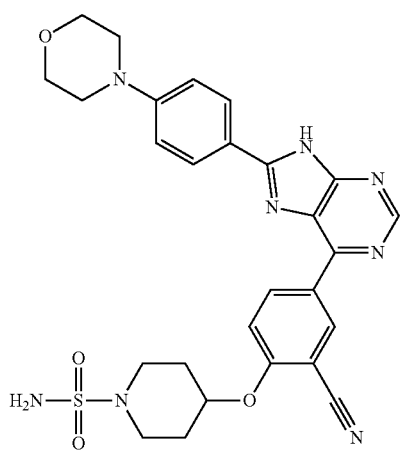 [SMILES: N#Cc1cc(-c2ncnc3[nH]c(-c4ccc(N5CCOCC5)cc4)nc23)ccc1OC1CCN(S(N)(=O)=O)CC1]

5-(8-(4-morpholinophenyl)-9H-purin-6-yl)-2-(piperidin-4-yloxy)benzonitrile (50 mg) and sulfamide (100 mg) in dioxane were heated at reflux for 16 hrs. The reaction was cooled to ambient temperature. The mixture was concentrated to dryness. The residue was purified via HPLC ((20 mL/min, 20-90% MeCN/H₂O (0.1% TFA v/v) gradient over 30 min) to give the title compound. ¹H NMR (400 MHz, DMSO-d₆) δ 9.19 (s, 2H), 8.83 (s, 1H), 8.24-8.07 (m, 2H), 7.63 (m, 1H), 7.23-7.05 (m, 2H), 6.84 (s, 2H), 6.49 (s, 2H), 4.99-4.76 (m, 1H), 3.75 (m, 4H), 3.32 (m, 5H), 3.05 (m, 2H), 2.07 (m, 2H), 1.87 (m, 2H). LCMS-ESI⁺ (m/z): calcd for $C_{27}H_{28}N_8N_4S$: 561.2. found [M+H]⁺: 561.2.

Example 263: 4-(2-cyano-4-(2-(4-(4-(2,2-difluoroethyl)piperazin-1-yl)phenyl)-3H-imidazo[4,5-b]pyridin-7-yl)phenoxy)piperidine-1-sulfonamide

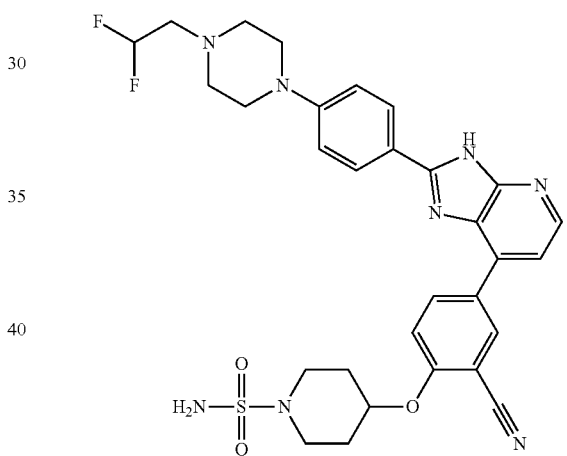

5-(8-(4-(4-(2,2-difluoroethyl)piperazin-1-yl)phenyl)-9H-purin-6-yl)-2-(piperidin-4-yloxy)benzonitrile (30 mg) and sulfamide (53 mg) in dioxane were heated at reflux for 16 hrs. The reaction was cooled to ambient temperature and then concentrated to dryness. The reside was purified via HPLC ((20 mL/min, 20-90% MeCN/H₂O (0.1% TFA v/v) gradient over 30 min) to give the title compound. ¹H NMR (400 MHz, DMSO-d₆) δ 12.65 (s, 1H), 8.77 (s, 1H), 8.52 (m, 2H), 7.95 (d, J=8.6 Hz, 2H), 7.55 (m, 1H), 7.35 (m, 1H), 7.08 (d, J=8.7 Hz, 2H), 6.84 (m, 2H), 6.37 (t, J=55.1 Hz, 1H), 4.89 (m, 1H), 3.16-3.59 (m, 9H), 3.09 (m, 4H), 2.09 (m, 2H), 1.97-1.72 (m, 2H). LCMS-ESI⁺ (m/z): calcd for $C_{29}H_{31}F_2N_9O_3S$: 623.2. found [M+H]⁺: 623.2.

Example 264: 5-(6-(4-(4-(2,2-difluoroethyl)piper-azin-1-yl)phenyl)-7H-pyrrolo[2,3-d]pyrimidin-4-yl)-2-((1-(2-hydroxyacetyl)piperidin-4-yl)oxy)benzonitrile

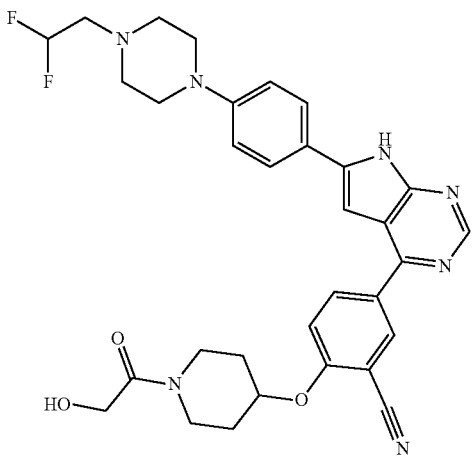 [SMILES: N#Cc1cc(-c2ncnc3[nH]c(-c4ccc(N5CCN(CC(F)F)CC5)cc4)cc23)ccc1OC1CCN(C(=O)CO)CC1]

Step 1: A mixture of 1-(4-bromophenyl)piperazine (5 g, 20.7 mmol), 2,2-difluoroethyl trifluoromethanesulfonate (27 mmol), K2CO3 (17.2 g, 124 mmol) in a mixture of MeCN (60 mL) and THF (7 ml) in a sealed tube was heated at 55° C. for 3 h. The mixture was filtered and the filtrate and concentrated to dryness under reduced pressure to give 1-(4-bromophenyl)-4-(2,2-difluoroethyl)piperazine.

Step 2: Pd(PPh$_3$)$_4$ (715 mg, 0.619 mmol) was added to a mixture of 1-(4-bromophenyl)-4-(2,2-difluoroethyl)pipera-zine (5.7 g, 18.7 mmol), pinacolatodiboron (4.74 g, 18.7 mmol) and potassium carbonate (5.27 g, 38 mmol) in toluene (240 mL) under nitrogen protection. The reaction mixture was refluxed overnight. After the mixture was cooled to room temperature, the solvent was removed under vacuum. To the residue were added water (160 mL) and ethyl acetate (160 mL). The organic phase was collected and the aqueous phase was extracted with ethyl acetate (160 mL×2). The organic phases were combined, dried over anhydrous sodium sulfate, and concentrated to dryness. The residue was purified by silica gel column to give 1-(2,2-difluoroethyl)-4-(4-(4,4,5,5-tetramethyl-1,3,2-dioxaboro-lan-2-yl)phenyl)piperazine.

Step 3: A sealed tube containing a suspension of 4-chloro-6-iodo-7-((2-(trimethylsilyl)ethoxy)methyl)-7H-pyrrolo[2,3-d]pyrimidine (1 g, 2.44 mmol) and Pd-dppf-Cl2 (178 mg, 0.244 mmol) in a degassed mixture of dioxane/H$_2$O (15 mL, 4/1 v/v), was preheated at 85° C. for 5 min. Next, 1 N NaHCO$_3$ (7.3 mL) and 1-(2,2-difluoroethyl)-4-(4-(4,4,5,5-tetramethyl-1,3,2-dioxaborolan-2-yl)phenyl)piperazine (860 mg, 2.44 mmol), were added to the mixture and the reaction was additionally heated at 90° C. in the sealed tube for 15 h. Afterwards, the crude material was allowed to reach room temperature. It was concentrated to dryness. The residue was purified by column chromatography over silica gel column using Hexanes and EtOAc mixtures (from 10 percent to 35 percent of EtOAc) as eluent to give 4-chloro-6-(4-(4-(2,2-difluoroethyl)piperazin-1-yl)phenyl)-7-((2-(trimethylsilyl)ethoxy)methyl)-7H-pyrrolo[2,3-d]pyrimi-dine as a syrup. LCMS-ESI$^+$ (m/z): [M+H]$^+$ calcd for C$_{24}$H$_{32}$ClF$_2$N$_5$OSi: 508.2. found: 508.3.

Step 4: A sealed tube containing a suspension of 4-chloro-6-(4-(4-(2,2-difluoroethyl)piperazin-1-yl)phenyl)-7-((2-(trimethylsilyl)ethoxy)methyl)-7H-pyrrolo[2,3-d]pyrimi-dine (180 mg, 0.354 mmol) and Pd(PPh$_3$)$_4$ (21 mg, 0.018 mmol) in a degassed mixture of dioxane/H$_2$O (2.5 mL, 4/1 v/v), was preheated at 85° C. for 5 min. Next, K$_2$CO$_3$ (122 mg, 0.88 mmol) and tert-butyl 4-(2-cyano-4-(4,4,5,5-tetram-ethyl-1,3,2-dioxaborolan-2-yl)phenoxy)piperidine-1-car-boxylate (182 mg, 0.43 mmol), were added to the mixture and the reaction was additionally heated at 100° C. in the sealed tube for 15 h. Afterwards, the crude material was allowed to reach room temperature. It was concentrated to dryness. The residue was purified by column chromatogra-phy over silica gel column using Hexanes and EtOAc mixtures (from 10 percent to 30 percent of EtOAc) as eluent to tert-butyl 4-(2-cyano-4-(6-(4-(4-(2,2-difluoroethyl)piper-azin-1-yl)phenyl)-7-((2-(trimethylsilyl)ethoxy)methyl)-7H-pyrrolo[2,3-d]pyrimidin-4-yl)phenoxy)piperidine-1-car-boxylate. LCMS-ESI$^+$ (m/z): [M+H]$^+$ calcd for C$_{41}$H$_{53}$F$_2$N$_7$O$_4$Si: 774.4. found: 774.2.

Step 5: 5-(6-(4-(4-(2,2-difluoroethyl)piperazin-1-yl)phe-nyl)-7H-pyrrolo[2,3-d]pyrimidin-4-yl)-2-(piperidin-4-yloxy)benzonitrile was prepared in a similar manner to Example 265.

Step 6: To a mixture of 5-(6-(4-(4-(2,2-difluoroethyl) piperazin-1-yl)phenyl)-7H-pyrrolo[2,3-d]pyrimidin-4-yl)-2-(piperidin-4-yloxy)benzonitrile (30 mg), hydroxyacetic acid (7 mg) and DIPEA (11 mg) in DMF (1.5 mL) was added HATU (34 mg). The reaction mixture was stirred at rt for 16 hrs. The mixture was concentrated to dryness. The residue was purified via HPLC ((20 mL/min, 20-90% MeCN/H$_2$O (0.1% TFA v/v) gradient over 30 min) to give the title compound. $^1$H NMR (400 MHz, DMSO-d$_6$) δ 12.82 (s, 1H), 8.82 (s, 1H), 8.57-8.41 (m, 2H), 7.97 (d, J=8.7 Hz, 2H), 7.58 (m, 1H), 7.41 (m, 1H), 7.11 (d, J=8.7 Hz, 2H), 6.51 (t, J=54.0 Hz, 1H), 5.03 (m, 1H), 4.13 (s, 2H), 3.13-3.73 (m, 15H), 2.00 (m, 2H), 1.74 (m, 2H). LCMS-ESI$^+$ (m/z): calcd for C$_{32}$H$_{33}$F$_2$N$_7$O$_3$: 602.3. found [M+H]$^+$: 602.2.

Example 265: 5-(6-(4-(4-(2,2-difluoroethyl)piper-azin-1-yl)phenyl)-7H-pyrrolo[2,3-d]pyrimidin-4-yl)-2-(piperidin-4-yloxy)benzonitrile

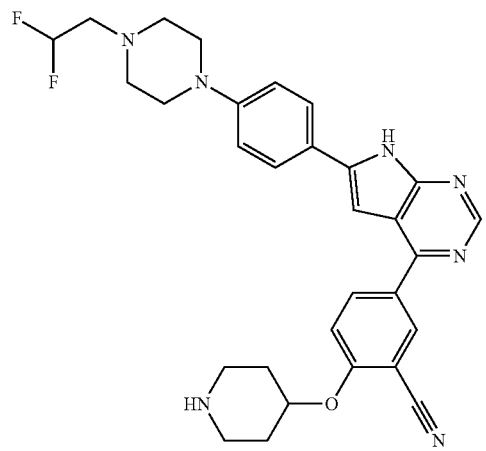

A solution of tert-butyl 4-(2-cyano-4-(6-(4-(4-(2,2-difluo-roethyl)piperazin-1-yl)phenyl)-7-((2-(trimethylsilyl)ethoxy) methyl)-7H-pyrrolo[2,3-d]pyrimidin-4-yl)phenoxy)piperi-dine-1-carboxylate (260 mg) in DCM (7 mL) and trifluoroacetic acid (2.5 mL) was stirred at rt overnight. The solvent was evaporated under reduced pressure. The reaction mixture was then concentrated to dryness, the residue was purified by silica gel column chromatography eluted 5-15% MeOH in DCM to give the title compound.

$^1$H NMR (400 MHz, DMSO-d$_6$) δ 12.64 (s, 1H), 8.76 (s, 1H), 8.69-8.41 (m, 2H), 8.01-7.82 (m, 2H), 7.64-7.44 (m, 1H), 7.34 (d, J=1.9 Hz, 1H), 7.19-6.95 (m, 2H), 6.35 (t, J=54.7 Hz, 1H), 5.03 (m, 1H), 3.22-3.83 (m, 11H), 2.98 (s, 4H), 2.26-2.06 (m, 2H), 2.07-1.84 (m, 2H). LCMS-ESI$^+$ (m/z): calcd for C$_{30}$H$_{31}$F$_2$N$_7$O: 544.3. found [M+H]$^+$: 544.2.

Example 266: 2-((1-(2,2-difluoroacetyl)piperidin-4-yl)oxy)-5-(8-(4-(morpholinomethyl)phenyl)-9H-purin-6-yl)benzonitrile

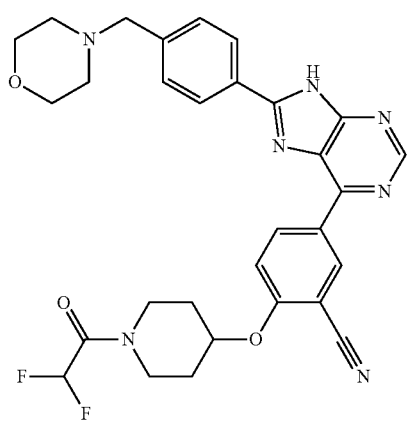 [SMILES: N#Cc1cc(-c2ncnc3[nH]c(-c4ccc(CN5CCOCC5)cc4)nc23)ccc1OC1CCN(C(=O)C(F)F)CC1]

To a mixture of 5-(8-(4-(morpholinomethyl)phenyl)-9H-purin-6-yl)-2-(piperidin-4-yloxy)benzonitrile (29 mg), difluoroacetic acid (9 mg) and DIPEA (10 mg) in DMF (1 mL) was added HATU (29 mg). The reaction mixture was stirred at rt for 16 hrs. The mixture was concentrated to dryness. The residue was purified by HPLC ((20 mL/min, 20-90% MeCN/H$_2$O (0.1% TFA v/v) gradient over 30 min) to give the title compound. $^1$H NMR (400 MHz, DMSO-d$_6$) δ 10.04 (s, 1H), 9.32-9.09 (m, 2H), 8.95 (s, 1H), 8.38 (d, J=8.2 Hz, 2H), 7.75 (d, J=8.1 Hz, 2H), 7.65 (d, J=9.2 Hz, 1H), 6.77 (t, J=52.8 Hz, 1H), 5.06 (m, 1H), 4.45 (s, 2H), 3.06-4.01 (m, 12H), 2.06 (m, 2H), 1.80 (m 2H). LCMS-ESI$^+$ (m/z): calcd for C$_{30}$H$_{29}$F$_2$N$_7$O$_3$: 574.2. found [M+H]$^+$: 574.2.

Example 267: 2-((1-(2,2-difluoroacetyl)piperidin-4-yl)oxy)-5-(8-(4-((dimethylamino)methyl)phenyl)-9H-purin-6-yl)benzonitrile

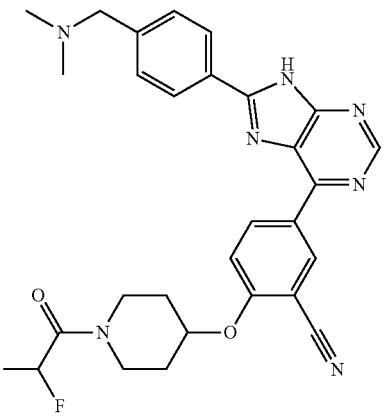

5-(8-(4-((dimethylamino)methyl)phenyl)-9H-purin-6-yl)-2-(piperidin-4-yloxy)benzonitrile was prepared in similar manner starting to Example 241 from 4-((dimethylamino)methyl)benzoic acid Step 2: To a mixture of 5-(8-(4-((dimethylamino)methyl)phenyl)-9H-purin-6-yl)-2-(piperidin-4-yloxy)benzonitrile (29 mg), difluoroacetic acid (9 mg) and DIPEA (10 mg) in DMF (1 mL) was added HATU (29 mg). The reaction mixture was stirred at rt for 16 hrs. The mixture was concentrated to dryness. The residue was purified by HPLC ((20 mL/min, 20-90% MeCN/H$_2$O (0.1% TFA v/v) gradient over 30 min) to give the title compound. LCMS-ESI$^+$ (m/z): calcd for C$_{28}$H$_{27}$F$_2$N$_7$O$_2$: 532.2. found [M+H]$^+$: 532.3.

Example 268: 2-((1-(2,2-difluoroacetyl)piperidin-4-yl)oxy)-5-(8-(4-(4-methylpiperazin-1-yl)phenyl)-9H-purin-6-yl)benzonitrile

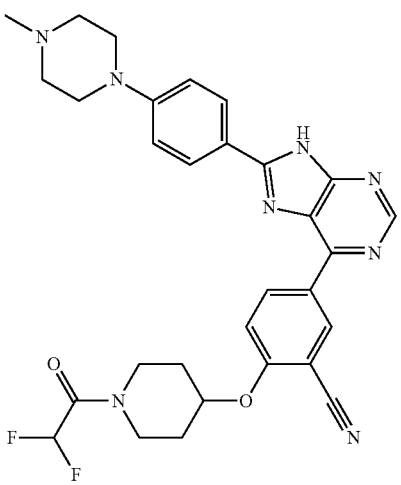 [SMILES: CN1CCN(c2ccc(-c3nc4c(-c5ccc(OC6CCN(C(=O)C(F)F)CC6)c(C#N)c5)ncnc4[nH]3)cc2)CC1]

To a mixture of of 5-(8-(4-morpholinophenyl)-9H-purin-6-yl)-2-(piperidin-4-yloxy)benzonitrile (25 mg, 0.051 mmol), difluoroacetic acid (6 mg) and DIPEA (8 mg) in DMF (1 mL) was added HATU (23 mg). The reaction mixture was stirred at rt for 16 hrs. The mixture was concentrated to dryness. The residue was purified by HPLC ((20 mL/min, 20-90% MeCN/H$_2$O (0.1% TFA v/v) gradient over 30 min) to give the title compound. $^1$H NMR (400 MHz, DMSO-d$_6$) δ 9.73 (s, 1H), 9.31-9.06 (m, 2H), 8.85 (s, 1H), 8.20 (d, J=8.7 Hz, 2H), 7.64 (d, J=9.2 Hz, 1H), 7.23 (d, J=8.8 Hz, 2H), 6.77 (t, J=52.8 Hz, 1H), 5.05 (m, 1H), 4.08 (m, 2H), 3.80-3.40 (m, 6H), 3.13 (m, 4H), 2.96-2.78 (m, 3H), 2.16-1.96 (m, 2H), 1.90-1.64 (m, 2H). LCMS-ESI$^+$ (m/z): calcd for C$_{30}$H$_{30}$F$_2$N$_8$O$_3$: 573.3. found[M+H]$^+$: 573.3.

Example 269: 5-(6-(6-aminopyrazin-2-yl)-7H-pyrrolo[2,3-d]pyrimidin-4-yl)-2-((tetrahydro-2H-pyran-4-yl)oxy)benzonitrile

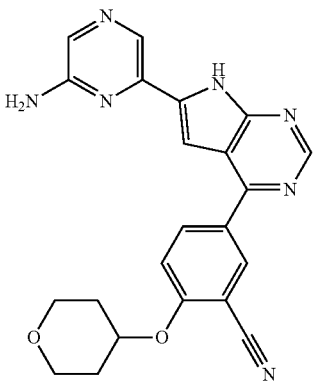 [SMILES: N#Cc1cc(-c2ncnc3[nH]c(-c4cncc(N)n4)cc23)ccc1OC1CCOCC1]

Step 1: A sealed tube containing a suspension of 4-chloro-6-iodo-7-((2-(trimethylsilyl)ethoxy)methyl)-7H-pyrrolo[2,3-d]pyrimidine (135 mg, 0.33 mmol), N,N-di-Boc-6-(4,4,5,5-tetramethyl-1,3,2-dioxaborolan-2-yl)pyrazin-2-amine (139 mg, 0.33 mmol), 1M NaHCO3 solution (1 mL), and Pd-dppfCl$_2$ (24 mg, 0.033 mmol) in a degassed mixture of dioxane/H$_2$O (10 mL, 4/1) was heated at 90° C. for 2 h. The mixture was concentrated to dryness and the residue was purified by silica gel column with 5-30% EtOAc in hexanes to give the two products, tert-butyl (6-(4-chloro-7-((2-(trimethylsilyl)ethoxy)methyl)-7H-pyrrolo[2,3-d]pyrimidin-6-yl)pyrazin-2-yl)carbamate (LCMS-ESI$^+$ (m/z): [M+H]$^+$ calcd for C$_{21}$H$_{29}$ClN$_6$O$_3$Si: 477.2. found: 477.0) and the bis Boc pdt (LCMS-ESI$^+$ (m/z): [M+H]$^+$ calcd for C$_{26}$H$_{37}$ClN$_6$O$_5$Si: 577.2. found: 577.0) as a mixture, which was used for next reaction without further separation.

Step 2: A sealed tube containing a suspension of above product (200 mg, 0.35 mmol) and Pd(PPh$_3$)$_4$ (20 mg, 0.017 mmol) in a degassed mixture of dioxane/H$_2$O (2.5 mL, 4/1), was preheated at 85° C. for 5 min. Next, K$_2$CO$_3$ (120 mg, 0.87 mmol) and 2-((tetrahydro-2H-pyran-4-yl)oxy)-5-(4,4,5,5-tetramethyl-1,3,2-dioxaborolan-2-yl)benzonitrile (137 mg, 0.42 mmol), were added to the mixture and the reaction was additionally heated at 100° C. in the sealed tube for 15 h. Afterwards, the crude material was allowed to reach room temperature. It was concentrated to dryness. The residue was purified by column chromatography over silica gel using CH2Cl2 and MeOH mixtures (from 0-10% of MeOH) as eluent to give tert-butyl (6-(4-(3-cyano-4-(tetrahydro-2H-pyran-4-yl)oxy)phenyl)-7-((2-(trimethylsilyl)ethoxy)methyl)-7H-pyrrolo[2,3-d]pyrimidin-6-yl)pyrazin-2-yl)carbamate as oil. LCMS-ESI$^+$ (m/z): [M+H]$^+$ calcd for C$_{33}$H$_{41}$N$_7$O$_5$Si: 644.3. found: 644.2.

Step 3: A solution of tert-butyl (6-(4-(3-cyano-4-((tetrahydro-2H-pyran-4-yl)oxy)phenyl)-7-((2-(trimethylsilyl)ethoxy)methyl)-7H-pyrrolo[2,3-d]pyrimidin-6-yl)pyrazin-2-yl)carbamate (200 mg) in DCM (6 mL) and trifluoroacetic acid (2.5 mL) was stirred at rt overnight. The solvent was evaporated under reduced pressure. The reaction mixture was then concentrated to dryness, the residue was purified via HPLC (20 mL/min, 20-90% MeCN/H$_2$O (0.1% TFA v/v) gradient over 30 min) to give the title compound. LCMS-ESI$^+$ (m/z): calcd for C$_{22}$H$_{19}$N$_7$O$_2$: 414.2. found [M+H]$^+$: 414.1.

Biological Assay for TBK1 and IKKε:

Enzymatic activity of IKKε and TBK1 was measured using a homogeneous time resolved fluorescence resonance energy transfer (TR-FRET) assay that monitors enzyme dependent phosphorylation of a biotinylated serine/threonine peptide substrate. An increase in the amount of phopshorylated peptide results in an increase in TR-FRET signal. TBK1 and IKKε were expressed and purified as full length recombinant proteins. Detection reagents for the assay were purchased from Cisbio. TBK1 and IKKε enzymes were assayed under initial rate conditions in the presence of 2× Km ATP (40-80 µM) and 1 µM peptide, hepes (pH 7), 0.1 mM orthovanadate, 0.02% NaN3, 0.01% BSA, 10 mM MgCl2, 0.01% (v/v) tritonX, 1 mM dithiothreitol, 0.5% (v/v) DMSO at the following concentrations for each enzyme: TBK1 at 2.5 nM and IKKε at 0.3 nM. After an assay reaction time of 240 minutes at 25° C., reactions were terminated with EDTA.

Amount of phosphorylated peptide was determined by the addition of 125 nM streptavidin XL665 and europium cryptate labeled anti-phospho monoclonal antibody and the resulting TR-FRET signal was recorded on an Envision plate reader (Ex: 340 nm; Em: 615/665 nm; 100 µs delay and 200 µs read window). Data was normalized based on a positive (1 µM Staurosporine) and negative (DMSO) controls and IC50 values calculated from the fit of the dose-response curves to a four-parameter equation. All IC50 values represent geometric mean values of a minimum of four determinations. These assays generally produced results within 3-fold of the reported mean.

Results:

Table 1 below depicts IKKε-IC50 (nM) and TBK1-IC50 (nM) values for the compounds described herein.

TABLE 1

| Examples | Structure | IKKε-IC50 (nM) | TBK1-IC50 (nM) |
|---|---|---|---|
| Example 1 | 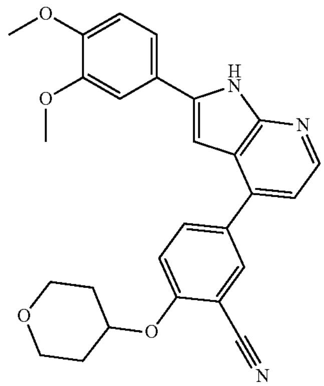 [SMILES: COc1ccc(-c2cc3c(-c4ccc(OC5CCOCC5)c(C#N)c4)ccnc3[nH]2)cc1OC] | 40.97 | 8.19 |
| Example 2 | 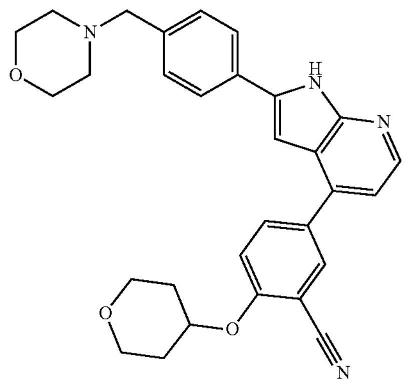 [SMILES: N#Cc1cc(-c2ccnc3[nH]c(-c4ccc(CN5CCOCC5)cc4)cc23)ccc1OC1CCOCC1] | 1.50 | 1.50 |
| Example 3 | 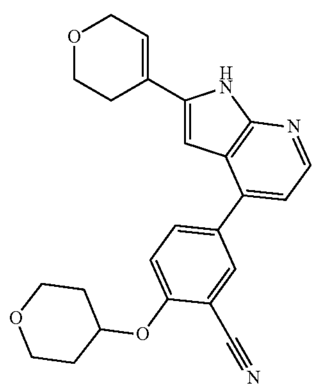 [SMILES: N#Cc1cc(-c2ccnc3[nH]c(C4=CCOCC4)cc23)ccc1OC1CCOCC1] | 10.50 | 3.31 |
| Example 4 | 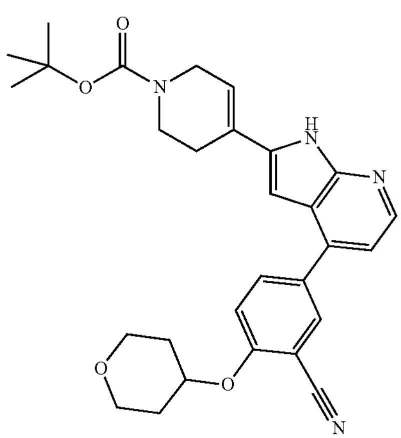 [SMILES: CC(C)(C)OC(=O)N1CC=C(c2cc3c(-c4ccc(OC5CCOCC5)c(C#N)c4)ccnc3[nH]2)CC1] | 43.75 | 16.97 |

TABLE 1-continued

| Examples | Structure | IKKε-IC50 (nM) | TBK1-IC50 (nM) |
|---|---|---|---|
| Example 5 | 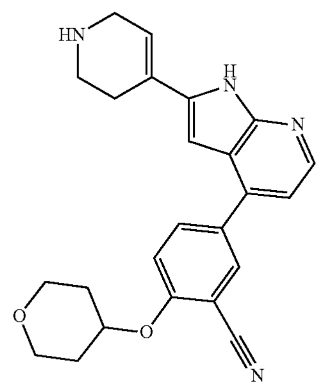 [SMILES: N#Cc1cc(-c2ccnc3[nH]c(C4=CCNCC4)cc23)ccc1OC1CCOCC1] | 39.74 | 29.84 |
| Example 6 | 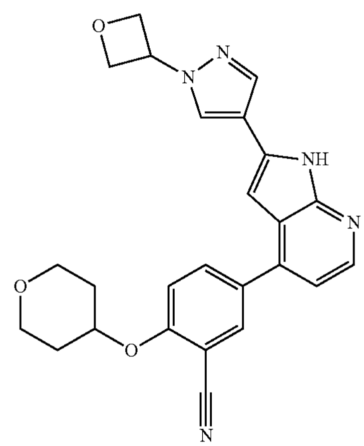 [SMILES: N#Cc1cc(-c2ccnc3[nH]c(-c4cnn(C5COC5)c4)cc23)ccc1OC1CCOCC1] | 4.87 | 3.13 |
| Example 7 | 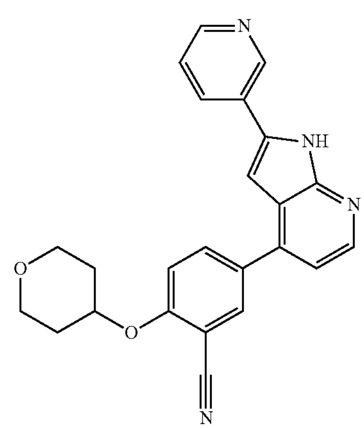 [SMILES: N#Cc1cc(-c2ccnc3[nH]c(-c4cccnc4)cc23)ccc1OC1CCOCC1] | 17.01 | 11.80 |

TABLE 1-continued

| Examples | Structure | IKKε-IC50 (nM) | TBK1-IC50 (nM) |
|---|---|---|---|
| Example 8 | 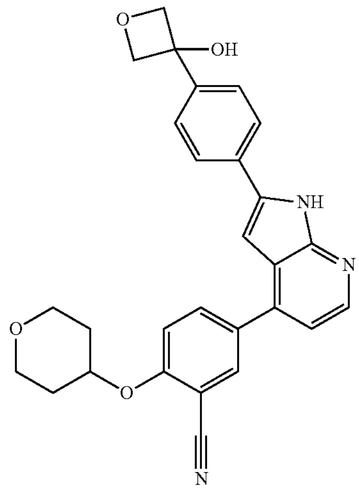 [SMILES: N#Cc1cc(-c2ccnc3[nH]c(-c4ccc(C5(O)COC5)cc4)cc23)ccc1OC1CCOCC1] | 6.99 | 3.09 |
| Example 9 | 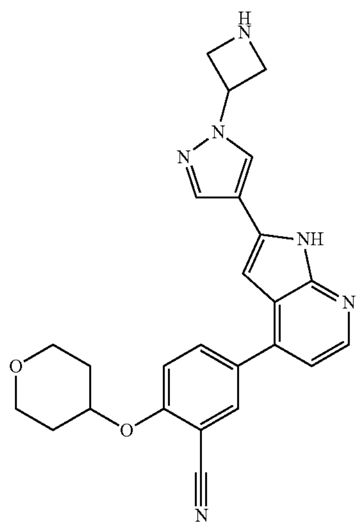 [SMILES: N#Cc1cc(-c2ccnc3[nH]c(-c4cnn(C5CNC5)c4)cc23)ccc1OC1CCOCC1] | 1.41 | 2.38 |
| Example 10 | 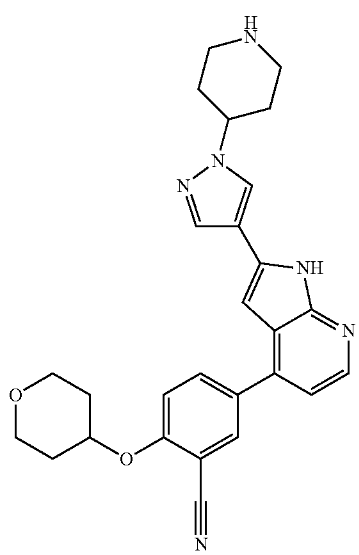 [SMILES: N#Cc1cc(-c2ccnc3[nH]c(-c4cnn(C5CCNCC5)c4)cc23)ccc1OC1CCOCC1] | 1.74 | 1.22 |

TABLE 1-continued

| Examples | Structure | IKKε-IC50 (nM) | TBK1-IC50 (nM) |
|---|---|---|---|
| Example 11 | 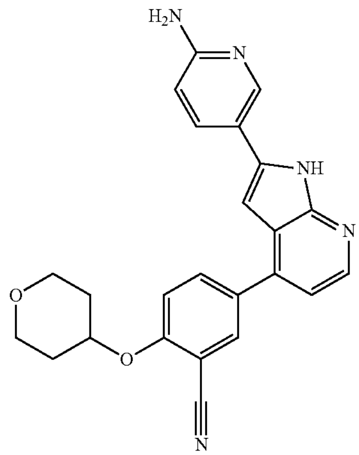 [SMILES: N#Cc1cc(-c2ccnc3[nH]c(-c4ccc(N)nc4)cc23)ccc1OC1CCOCC1] | 9.51 | 5.53 |
| Example 12 | 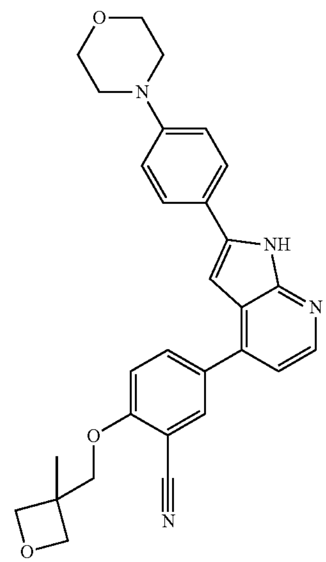 [SMILES: CC1(COc2ccc(-c3ccnc4[nH]c(-c5ccc(N6CCOCC6)cc5)cc34)cc2C#N)COC1] | 40.98 | 14.10 |
| Example 13 | 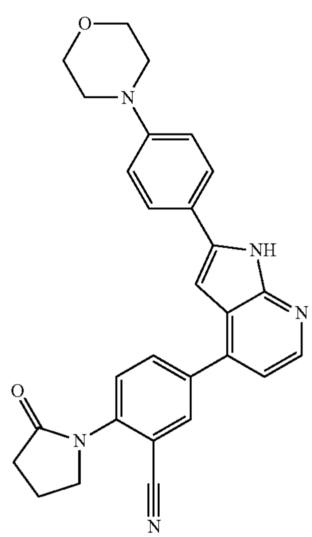 [SMILES: N#Cc1cc(-c2ccnc3[nH]c(-c4ccc(N5CCOCC5)cc4)cc23)ccc1N1CCCC1=O] | 182.11 | 24.86 |

TABLE 1-continued
| Examples | Structure | IKKε-IC50 (nM) | TBK1-IC50 (nM) |
|---|---|---|---|
| Example 14 | 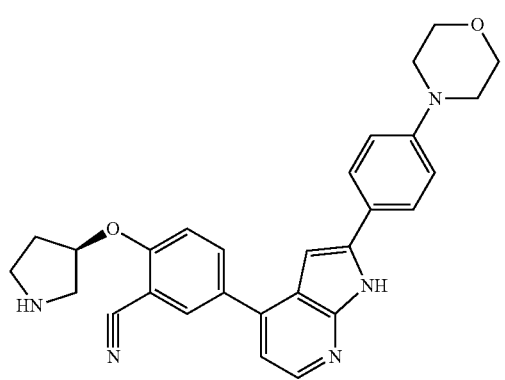 [SMILES: N#Cc1cc(-c2ccnc3[nH]c(-c4ccc(N5CCOCC5)cc4)cc23)ccc1O[C@@H]1CCNC1] | 20.76 | 6.86 |
| Example 15 | 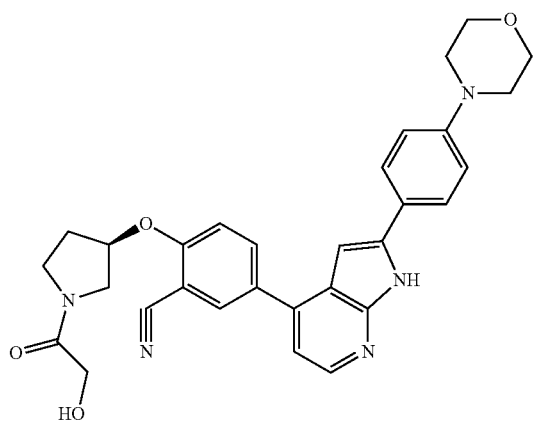 [SMILES: N#Cc1cc(-c2ccnc3[nH]c(-c4ccc(N5CCOCC5)cc4)cc23)ccc1O[C@@H]1CCN(C(=O)CO)C1] | 2.45 | 1.34 |
| Example 16 | 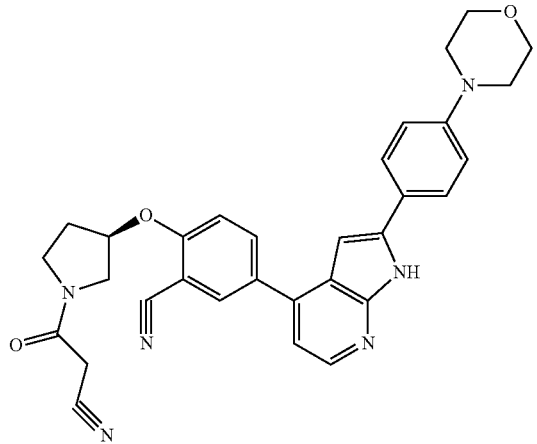 [SMILES: N#CCC(=O)N1CC[C@@H](Oc2ccc(-c3ccnc4[nH]c(-c5ccc(N6CCOCC6)cc5)cc34)cc2C#N)C1] | 13.75 | 4.32 |

TABLE 1-continued

| Examples | Structure | IKKε-IC50 (nM) | TBK1-IC50 (nM) |
|---|---|---|---|
| Example 17 | 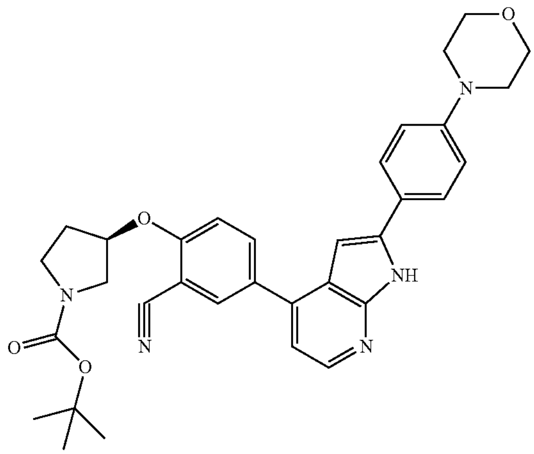 [SMILES: CC(C)(C)OC(=O)N1CC[C@@H](Oc2ccc(-c3ccnc4[nH]c(-c5ccc(N6CCOCC6)cc5)cc34)cc2C#N)C1] | 394.44 | 145.91 |
| Example 18 | 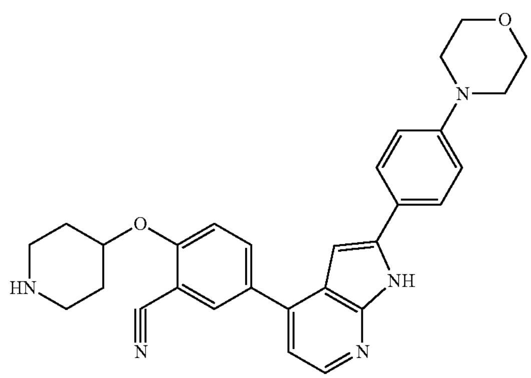 [SMILES: N#Cc1cc(-c2ccnc3[nH]c(-c4ccc(N5CCOCC5)cc4)cc23)ccc1OC1CCNCC1] | 33.23 | 17.12 |
| Example 19 | 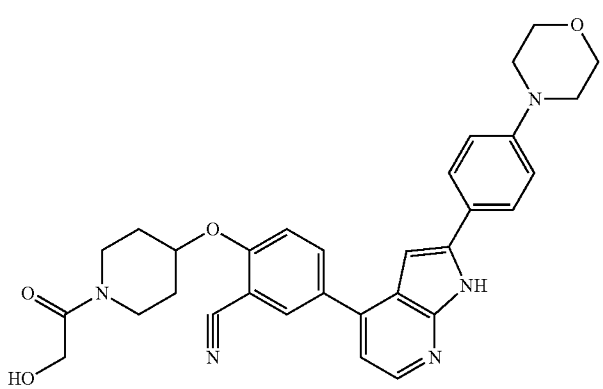 [SMILES: N#Cc1cc(-c2ccnc3[nH]c(-c4ccc(N5CCOCC5)cc4)cc23)ccc1OC1CCN(C(=O)CO)CC1] | 3.72 | 1.90 |

TABLE 1-continued

| Examples | Structure | IKKε-IC50 (nM) | TBK1-IC50 (nM) |
|---|---|---|---|
| Example 20 | 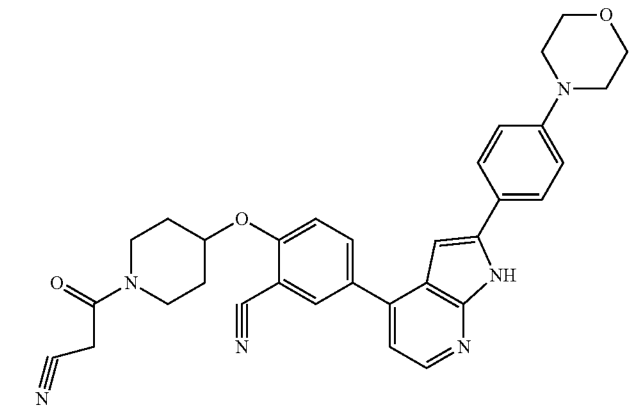 [SMILES: N#CCC(=O)N1CCC(Oc2ccc(-c3ccnc4[nH]c(-c5ccc(N6CCOCC6)cc5)cc34)cc2C#N)CC1] | 27.48 | 9.25 |
| Example 21 | 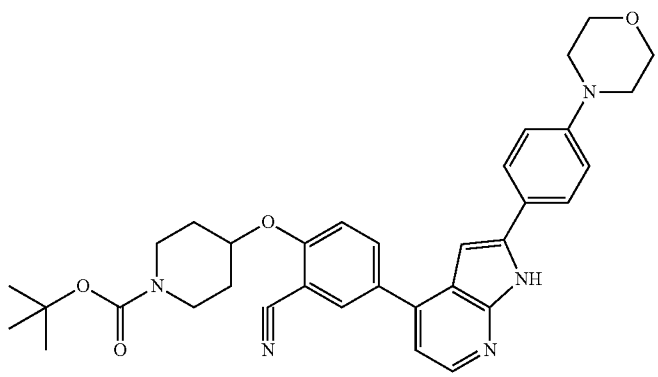 [SMILES: CC(C)(C)OC(=O)N1CCC(Oc2ccc(-c3ccnc4[nH]c(-c5ccc(N6CCOCC6)cc5)cc34)cc2C#N)CC1] | >1000 | 695.93 |
| Example 22 | 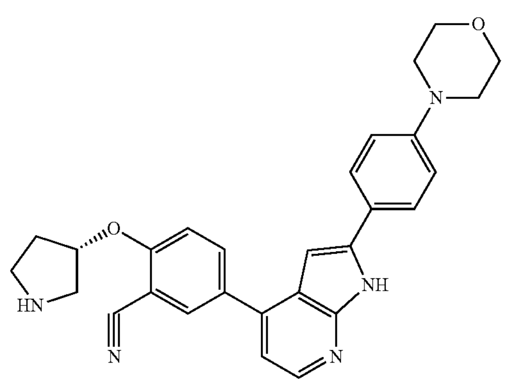 [SMILES: N#Cc1cc(-c2ccnc3[nH]c(-c4ccc(N5CCOCC5)cc4)cc23)ccc1O[C@H]1CCNC1] | 132.40 | 39.61 |
| Example 23 | 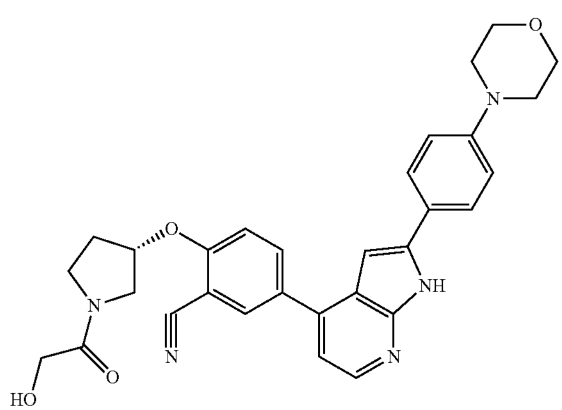 [SMILES: N#Cc1cc(-c2ccnc3[nH]c(-c4ccc(N5CCOCC5)cc4)cc23)ccc1O[C@H]1CCN(C(=O)CO)C1] | 64.94 | 16.22 |

TABLE 1-continued
| Examples | Structure | IKKε-IC50 (nM) | TBK1-IC50 (nM) |
|---|---|---|---|
| Example 24 | 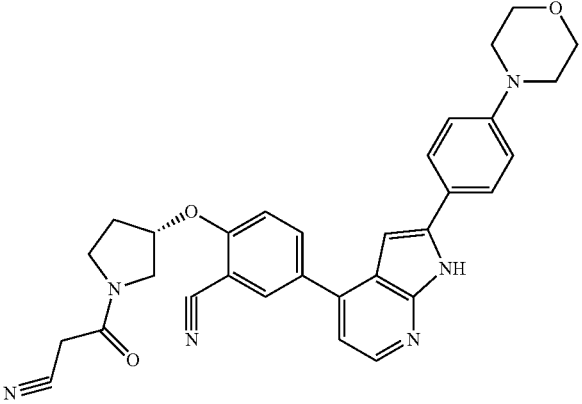 [SMILES: N#CCC(=O)N1CC[C@H](Oc2ccc(-c3ccnc4[nH]c(-c5ccc(N6CCOCC6)cc5)cc34)cc2C#N)C1] | 320.55 | 56.80 |
| Example 25 | 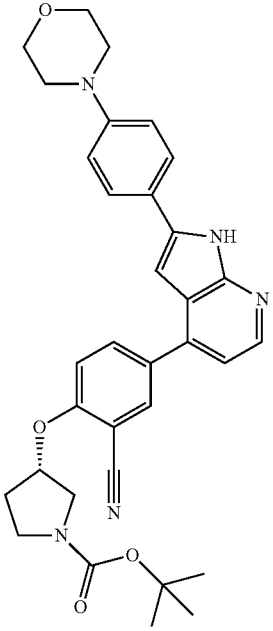 [SMILES: CC(C)(C)OC(=O)N1CC[C@H](Oc2ccc(-c3ccnc4[nH]c(-c5ccc(N6CCOCC6)cc5)cc34)cc2C#N)C1] | 306.34 | 115.01 |
| Example 26 | 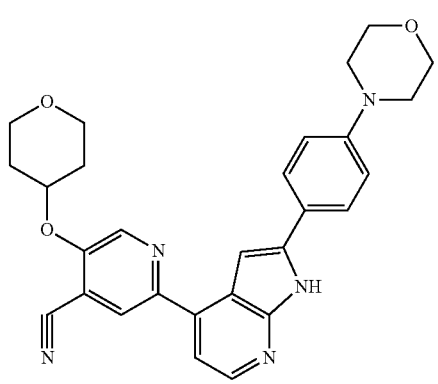 [SMILES: N#Cc1cc(-c2ccnc3[nH]c(-c4ccc(N5CCOCC5)cc4)cc23)ncc1OC1CCOCC1] | 6.84 | 3.43 |

TABLE 1-continued
| Examples | Structure | IKKε-IC50 (nM) | TBK1-IC50 (nM) |
|---|---|---|---|
| Example 27 | 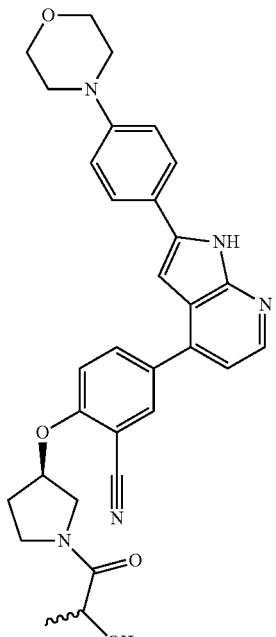 | 13.37 | 6.54 |
| Example 28 | 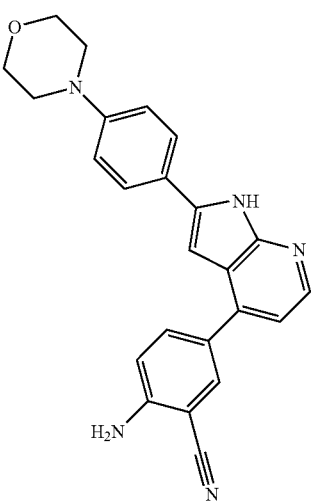 [SMILES: N#Cc1cc(-c2ccnc3[nH]c(-c4ccc(N5CCOCC5)cc4)cc23)ccc1N] | 118.69 | 11.66 |

TABLE 1-continued
| Examples | Structure | IKKε-IC50 (nM) | TBK1-IC50 (nM) |
|---|---|---|---|
| Example 29 | 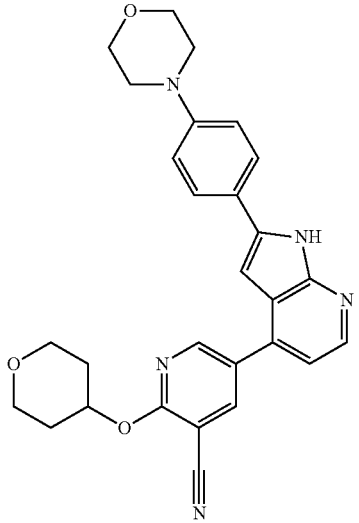 | 241.83 | 14.80 |
| Example 30 | 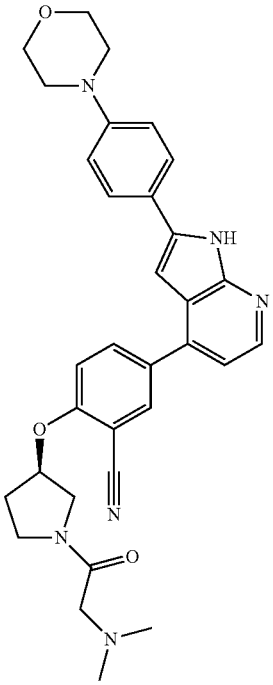 [SMILES: CN(C)CC(=O)N1CC[C@@H](Oc2ccc(-c3ccnc4[nH]c(-c5ccc(N6CCOCC6)cc5)cc34)cc2C#N)C1] | 135.09 | 70.66 |

TABLE 1-continued
| Examples | Structure | IKKε-IC50 (nM) | TBK1-IC50 (nM) |
|---|---|---|---|
| Example 31 | 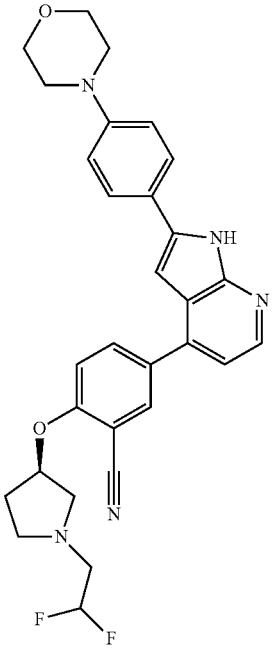 [SMILES: N#Cc1cc(-c2ccnc3[nH]c(-c4ccc(N5CCOCC5)cc4)cc23)ccc1O[C@@H]1CCN(CC(F)F)C1] | 59.23 | 19.05 |
| Example 32 | 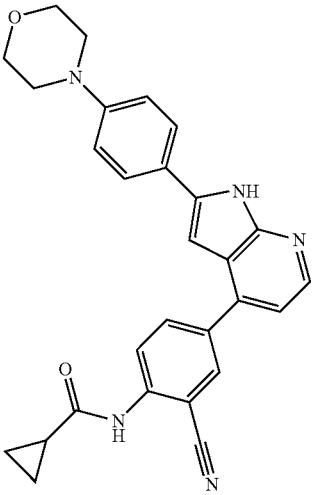 [SMILES: N#Cc1cc(-c2ccnc3[nH]c(-c4ccc(N5CCOCC5)cc4)cc23)ccc1NC(=O)C1CC1] | >1000 | 9.34 |

TABLE 1-continued

| Examples | Structure | IKKε-IC50 (nM) | TBK1-IC50 (nM) |
|---|---|---|---|
| Example 33 | 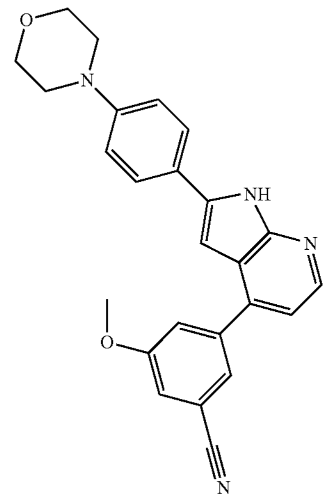 [SMILES: COc1cc(C#N)cc(-c2ccnc3[nH]c(-c4ccc(N5CCOCC5)cc4)cc23)c1] | >1000 | 14.47 |
| Example 34 | 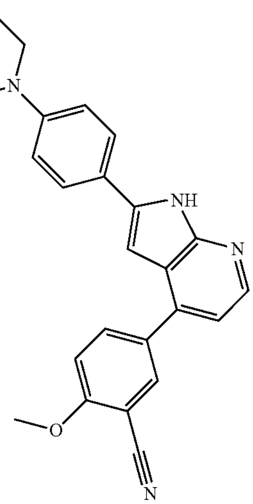 | >1000 | 89.84 |
| Example 35 | 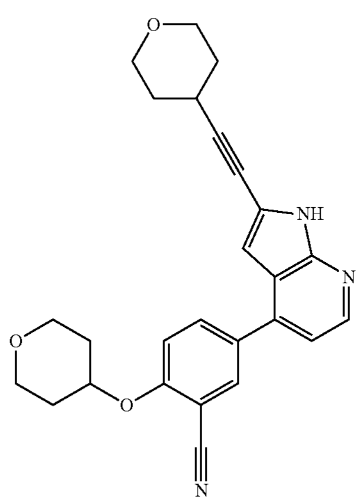 [SMILES: N#Cc1cc(-c2ccnc3[nH]c(C#CC4CCOCC4)cc23)ccc1OC1CCOCC1] | 139.00 | 52.81 |

TABLE 1-continued

| Examples | Structure | IKKε-IC50 (nM) | TBK1-IC50 (nM) |
|---|---|---|---|
| Example 36 | 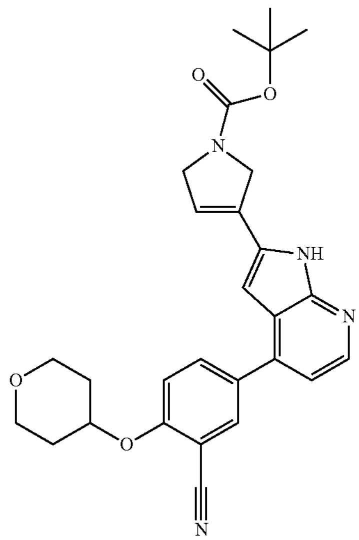 [SMILES: CC(C)(C)OC(=O)N1CC=C(c2cc3c(-c4ccc(OC5CCOCC5)c(C#N)c4)ccnc3[nH]2)C1] | 79.05 | 38.38 |
| Example 37 | 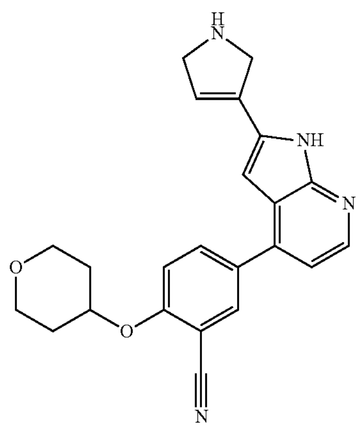 [SMILES: N#Cc1cc(-c2ccnc3[nH]c(C4=CCNC4)cc23)ccc1OC1CCOCC1] | 46.34 | 13.43 |
| Example 38 | 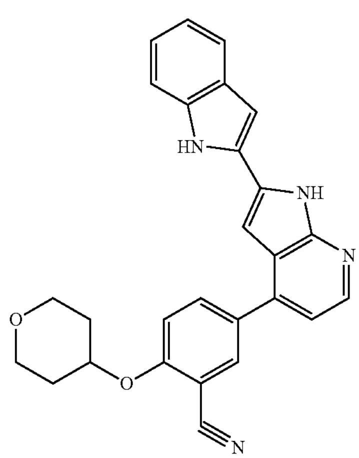 [SMILES: N#Cc1cc(-c2ccnc3[nH]c(-c4cc5ccccc5[nH]4)cc23)ccc1OC1CCOCC1] | 76.75 | 32.48 |

TABLE 1-continued

| Examples | Structure | IKKε-IC50 (nM) | TBK1-IC50 (nM) |
|---|---|---|---|
| Example 39 | 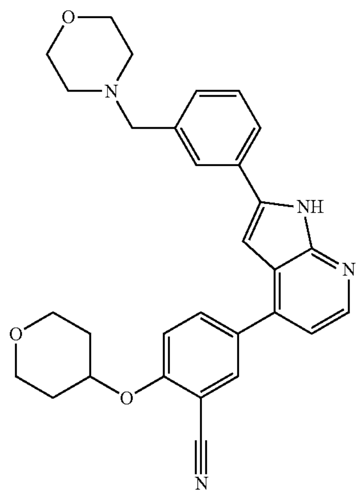 [SMILES: N#Cc1cc(-c2ccnc3[nH]c(-c4cccc(CN5CCOCC5)c4)cc23)ccc1OC1CCOCC1] | 10.73 | 10.14 |
| Example 40 | 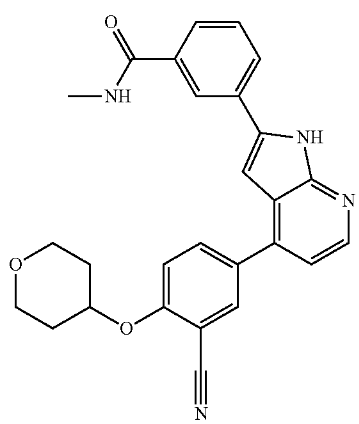 [SMILES: CNC(=O)c1cccc(-c2cc3c(-c4ccc(OC5CCOCC5)c(C#N)c4)ccnc3[nH]2)c1] | 11.05 | 7.98 |
| Example 41 | 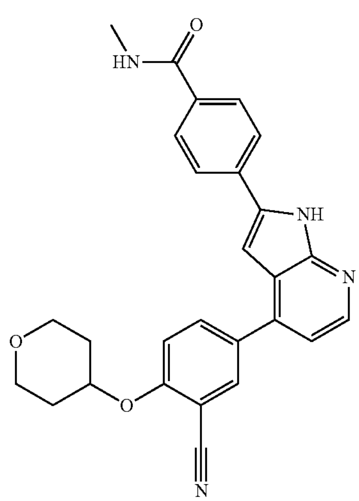 [SMILES: CNC(=O)c1ccc(-c2cc3c(-c4ccc(OC5CCOCC5)c(C#N)c4)ccnc3[nH]2)cc1] | 5.59 | 3.08 |

TABLE 1-continued

| Examples | Structure | IKKε-IC50 (nM) | TBK1-IC50 (nM) |
|---|---|---|---|
| Example 42 | 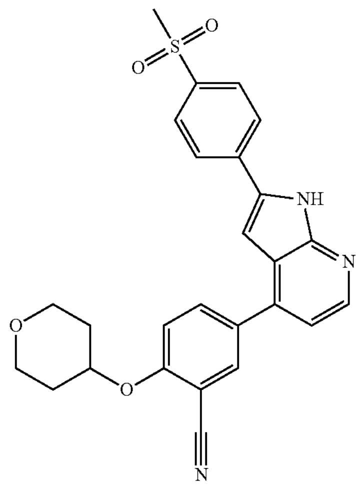 [SMILES: CS(=O)(=O)c1ccc(-c2cc3c(-c4ccc(OC5CCOCC5)c(C#N)c4)ccnc3[nH]2)cc1] | 6.42 | 3.75 |
| Example 43 | 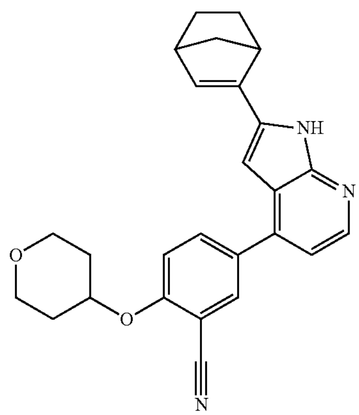 [SMILES: N#Cc1cc(-c2ccnc3[nH]c(C4=CC5CCC4C5)cc23)ccc1OC1CCOCC1] | >1000 | 433.53 |
| Example 44 | 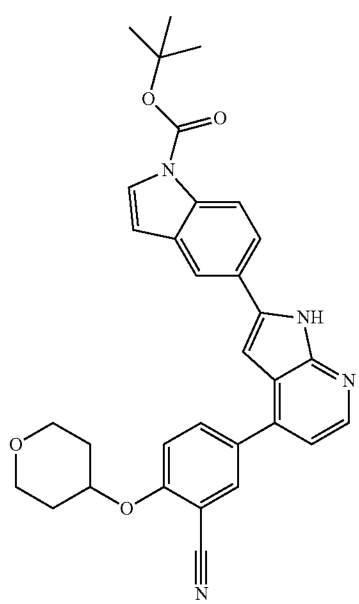 [SMILES: CC(C)(C)OC(=O)n1ccc2cc(-c3cc4c(-c5ccc(OC6CCOCC6)c(C#N)c5)ccnc4[nH]3)ccc21] | >1000 | >1000 |

TABLE 1-continued

| Examples | Structure | IKKε-IC50 (nM) | TBK1-IC50 (nM) |
|---|---|---|---|
| Example 45 | 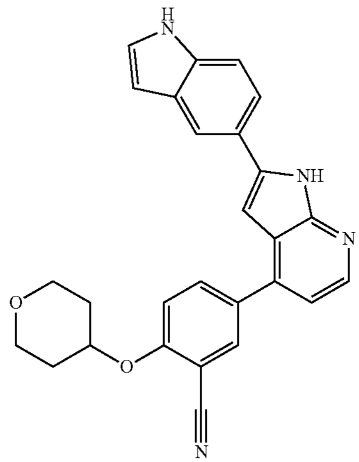 [SMILES: N#Cc1cc(-c2ccnc3[nH]c(-c4ccc5[nH]ccc5c4)cc23)ccc1OC1CCOCC1] | 32.16 | 32.05 |
| Example 46 | 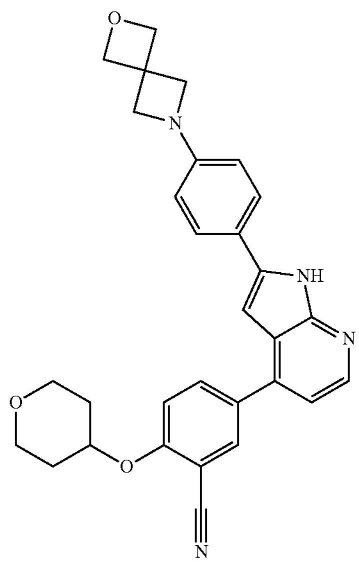 [SMILES: N#Cc1cc(-c2ccnc3[nH]c(-c4ccc(N5CC6(COC6)C5)cc4)cc23)ccc1OC1CCOCC1] | 13.02 | 4.49 |
| Example 47 | 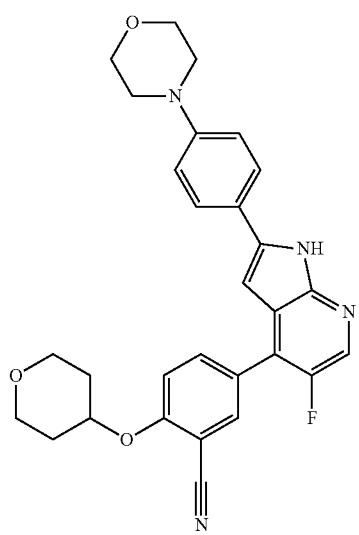 [SMILES: N#Cc1cc(-c2c(F)cnc3[nH]c(-c4ccc(N5CCOCC5)cc4)cc23)ccc1OC1CCOCC1] | 17.46 | 4.05 |

TABLE 1-continued

| Examples | Structure | IKKε-IC50 (nM) | TBK1-IC50 (nM) |
|---|---|---|---|
| Example 48 | 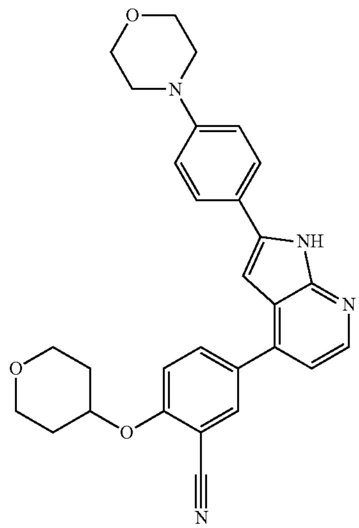 | 11.46 | 3.26 |
| Example 49 | 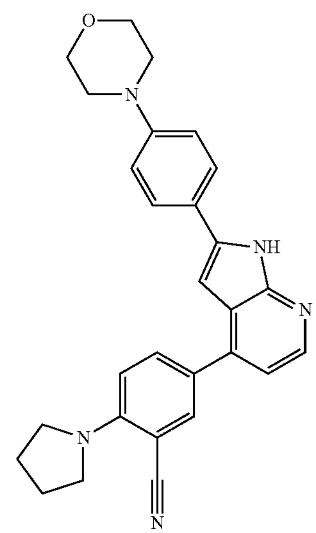 [SMILES: N#Cc1cc(-c2ccnc3[nH]c(-c4ccc(N5CCOCC5)cc4)cc23)ccc1N1CCCC1] | >78.0187 | 7.05 |
| Example 50 | 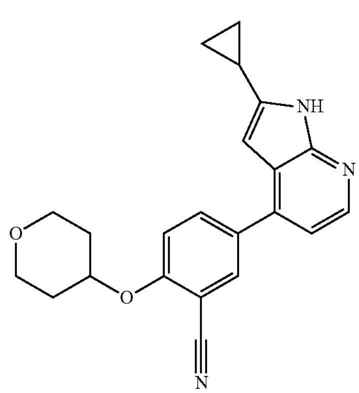 [SMILES: N#Cc1cc(-c2ccnc3[nH]c(C4CC4)cc23)ccc1OC1CCOCC1] | 448.87 | 651.33 |

TABLE 1-continued

| Examples | Structure | IKKε-IC50 (nM) | TBK1-IC50 (nM) |
|---|---|---|---|
| Example 51 | 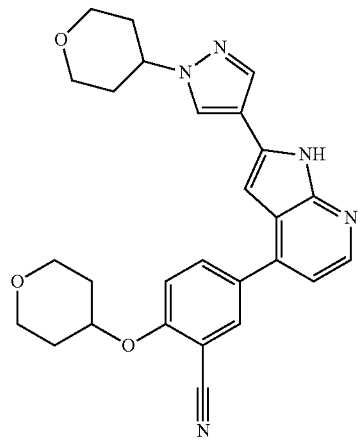 [SMILES: N#Cc1cc(-c2ccnc3[nH]c(-c4cnn(C5CCOCC5)c4)cc23)ccc1OC1CCOCC1] | 2.98 | 3.54 |
| Example 52 | 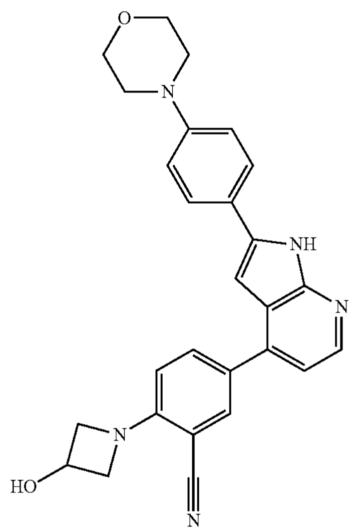 [SMILES: N#Cc1cc(-c2ccnc3[nH]c(-c4ccc(N5CCOCC5)cc4)cc23)ccc1N1CC(O)C1] | 3.33 | 15.55 |
| Example 53 | 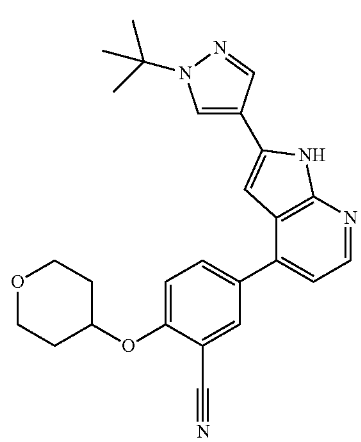 [SMILES: CC(C)(C)n1cc(-c2cc3c(-c4ccc(OC5CCOCC5)c(C#N)c4)ccnc3[nH]2)cn1] | 13.65 | 9.40 |

TABLE 1-continued

| Examples | Structure | IKKε-IC50 (nM) | TBK1-IC50 (nM) |
|---|---|---|---|
| Example 54 | 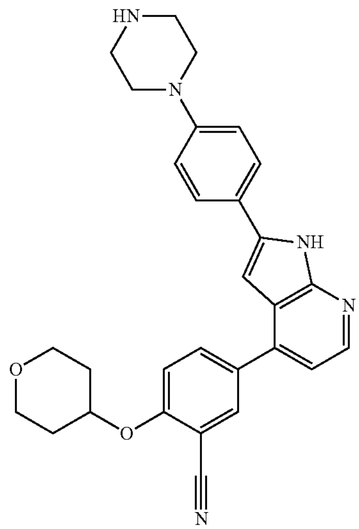 [SMILES: N#Cc1cc(-c2ccnc3[nH]c(-c4ccc(N5CCNCC5)cc4)cc23)ccc1OC1CCOCC1] | 0.81 | 1.28 |
| Example 55 | 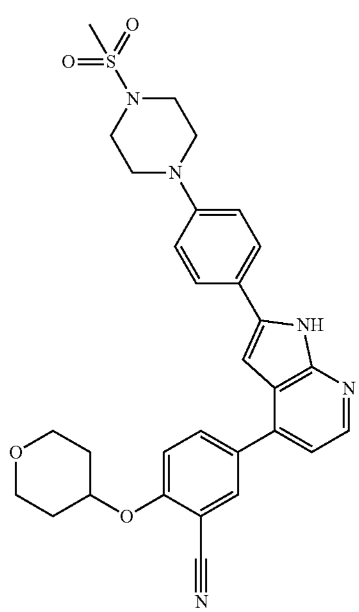 [SMILES: CS(=O)(=O)N1CCN(c2ccc(-c3cc4c(-c5ccc(OC6CCOCC6)c(C#N)c5)ccnc4[nH]3)cc2)CC1] | >1000 | 2.84 |

TABLE 1-continued

| Examples | Structure | IKKε-IC50 (nM) | TBK1-IC50 (nM) |
|---|---|---|---|
| Example 56 | 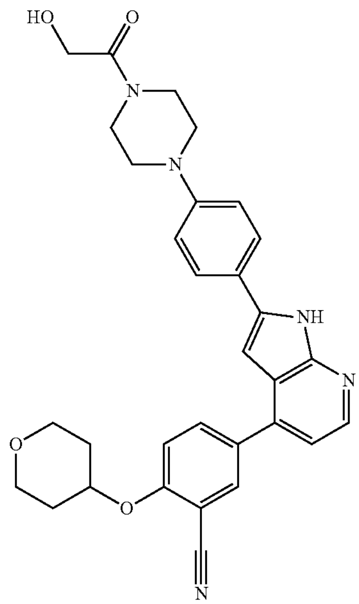 [SMILES: N#Cc1cc(-c2ccnc3[nH]c(-c4ccc(N5CCN(C(=O)CO)CC5)cc4)cc23)ccc1OC1CCOCC1] | 15.85 | 2.02 |
| Example 57 | 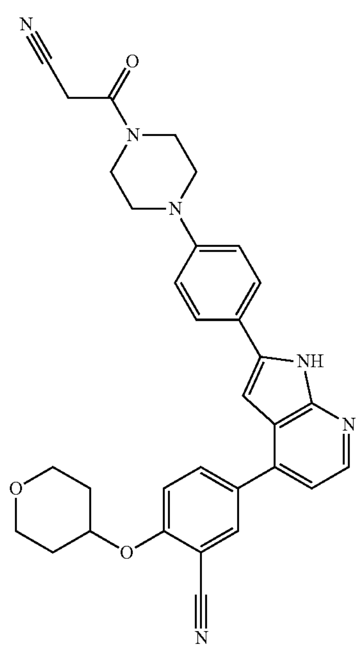 [SMILES: N#CCC(=O)N1CCN(c2ccc(-c3cc4c(-c5ccc(OC6CCOCC6)c(C#N)c5)ccnc4[nH]3)cc2)CC1] | 2.98 | 1.46 |

TABLE 1-continued

| Examples | Structure | IKKε-IC50 (nM) | TBK1-IC50 (nM) |
|---|---|---|---|
| Example 58 | 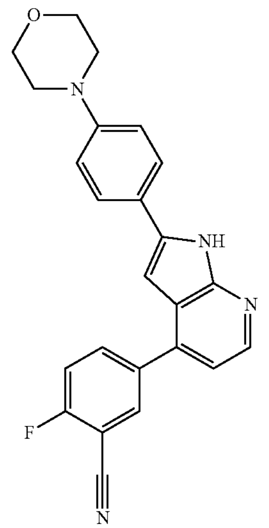 [SMILES: N#Cc1cc(-c2ccnc3[nH]c(-c4ccc(N5CCOCC5)cc4)cc23)ccc1F] | >1000 | 6.06 |
| Example 59 | 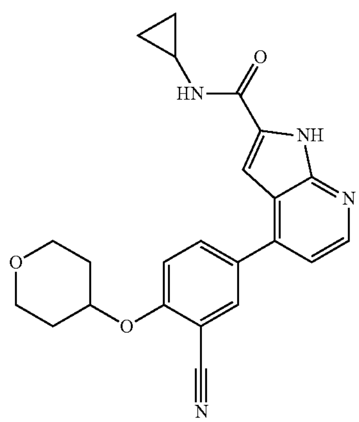 [SMILES: N#Cc1cc(-c2ccnc3[nH]c(C(=O)NC4CC4)cc23)ccc1OC1CCOCC1] | 55.40 | 79.36 |
| Example 60 | 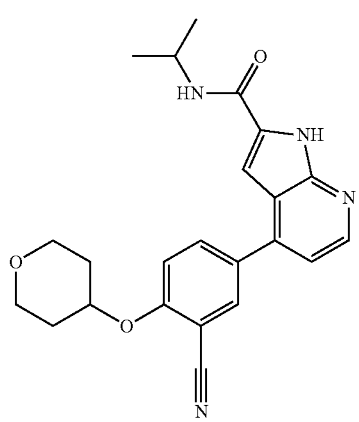 [SMILES: CC(C)NC(=O)c1cc2c(-c3ccc(OC4CCOCC4)c(C#N)c3)ccnc2[nH]1] | 44.48 | 63.75 |

TABLE 1-continued
| Examples | Structure | IKKε-IC50 (nM) | TBK1-IC50 (nM) |
|---|---|---|---|
| Example 61 | 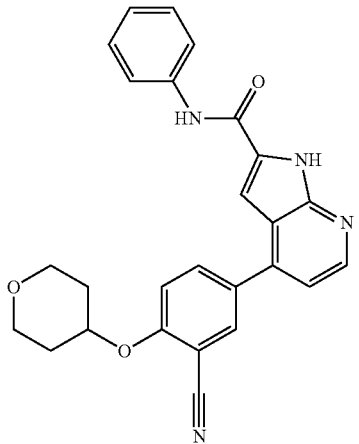 [SMILES: N#Cc1cc(-c2ccnc3[nH]c(C(=O)Nc4ccccc4)cc23)ccc1OC1CCOCC1] | 111.85 | 312.38 |
| Example 62 | 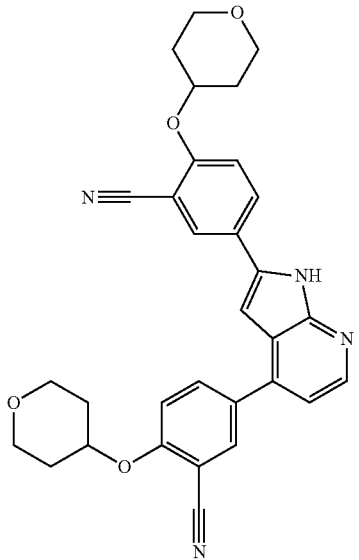 [SMILES: N#Cc1cc(-c2cc3c(-c4ccc(OC5CCOCC5)c(C#N)c4)ccnc3[nH]2)ccc1OC1CCOCC1] | 25.31 | 24.15 |

TABLE 1-continued

| Examples | Structure | IKKε-IC50 (nM) | TBK1-IC50 (nM) |
|---|---|---|---|
| Example 63 | 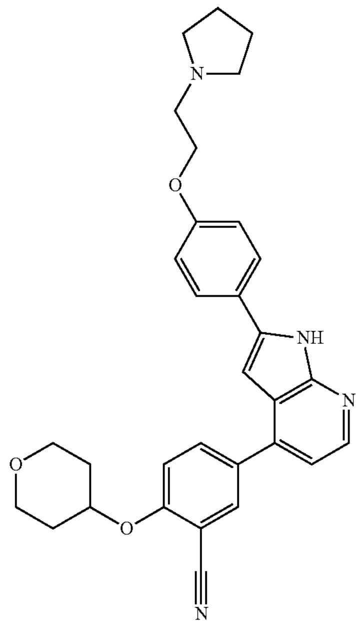 [SMILES: N#Cc1cc(-c2ccnc3[nH]c(-c4ccc(OCCN5CCCC5)cc4)cc23)ccc1OC1CCOCC1] | 0.71 | 1.84 |
| Example 64 | 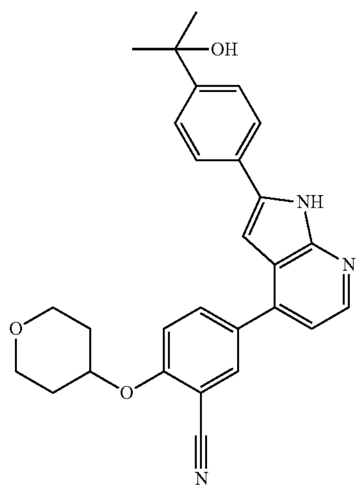 [SMILES: CC(C)(O)c1ccc(-c2cc3c(-c4ccc(OC5CCOCC5)c(C#N)c4)ccnc3[nH]2)cc1] | 4.41 | 2.77 |
| Example 65 | 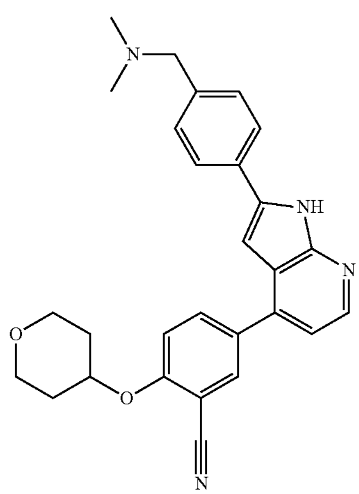 [SMILES: CN(C)Cc1ccc(-c2cc3c(-c4ccc(OC5CCOCC5)c(C#N)c4)ccnc3[nH]2)cc1] | 0.77 | 1.74 |

TABLE 1-continued

| Examples | Structure | IKKε-IC50 (nM) | TBK1-IC50 (nM) |
|---|---|---|---|
| Example 66 | 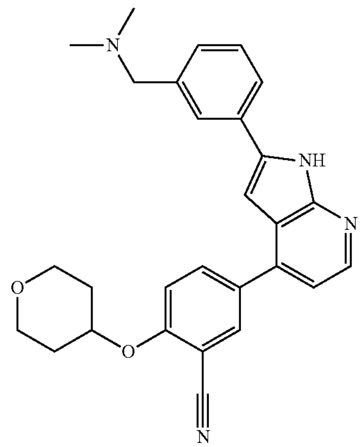 [SMILES: CN(C)Cc1cccc(-c2cc3c(-c4ccc(OC5CCOCC5)c(C#N)c4)ccnc3[nH]2)c1] | 2.32 | 6.12 |
| Example 67 | 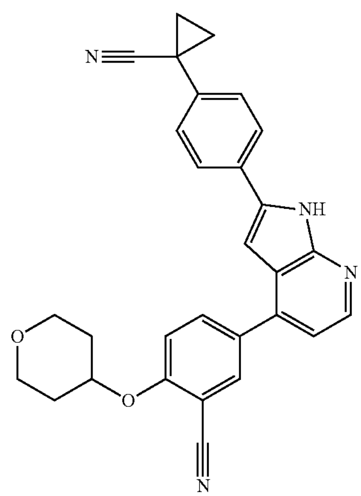 [SMILES: N#Cc1cc(-c2ccnc3[nH]c(-c4ccc(C5(C#N)CC5)cc4)cc23)ccc1OC1CCOCC1] | >1000 | 5.56 |
| Example 68 | 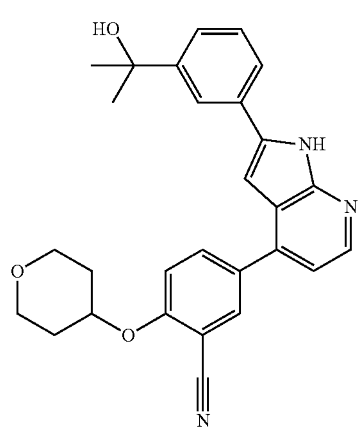 [SMILES: CC(C)(O)c1cccc(-c2cc3c(-c4ccc(OC5CCOCC5)c(C#N)c4)ccnc3[nH]2)c1] | 22.53 | 10.55 |

TABLE 1-continued

| Examples | Structure | IKKε-IC50 (nM) | TBK1-IC50 (nM) |
|---|---|---|---|
| Example 69 | 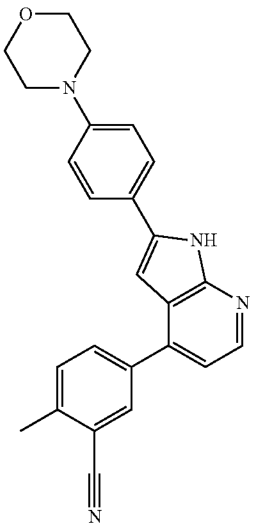 [SMILES: Cc1ccc(-c2ccnc3[nH]c(-c4ccc(N5CCOCC5)cc4)cc23)cc1C#N] | >1000 | 79.70 |
| Example 70 | 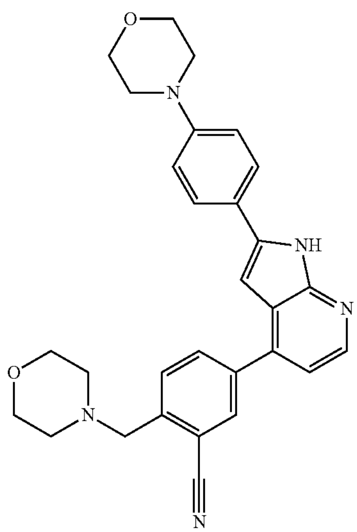 [SMILES: N#Cc1cc(-c2ccnc3[nH]c(-c4ccc(N5CCOCC5)cc4)cc23)ccc1CN1CCOCC1] | 131.76 | 10.48 |
| Example 71 | 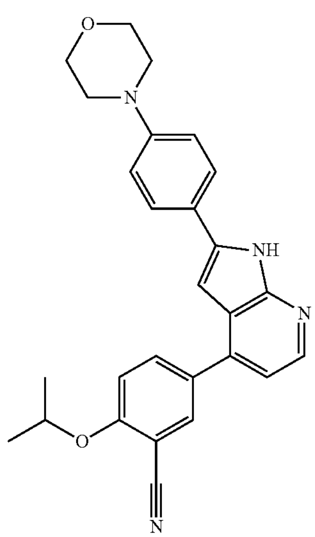 [SMILES: CC(C)Oc1ccc(-c2ccnc3[nH]c(-c4ccc(N5CCOCC5)cc4)cc23)cc1C#N] | 357.61 | 59.33 |

TABLE 1-continued

| Examples | Structure | IKKε-IC50 (nM) | TBK1-IC50 (nM) |
|---|---|---|---|
| Example 72 | 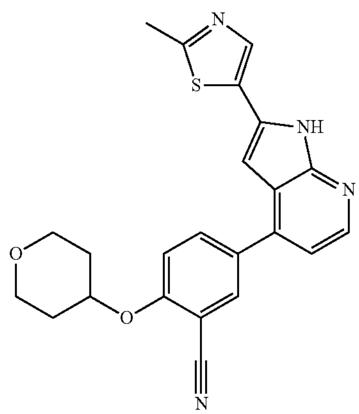 [SMILES: Cc1ncc(-c2cc3c(-c4ccc(OC5CCOCC5)c(C#N)c4)ccnc3[nH]2)s1] | 4.30 | 6.03 |
| Example 73 | 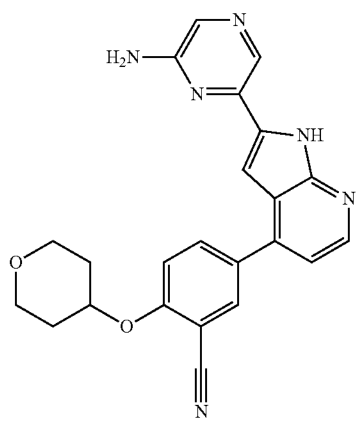 [SMILES: N#Cc1cc(-c2ccnc3[nH]c(-c4cncc(N)n4)cc23)ccc1OC1CCOCC1] | 16.06 | 8.48 |
| Example 74 | 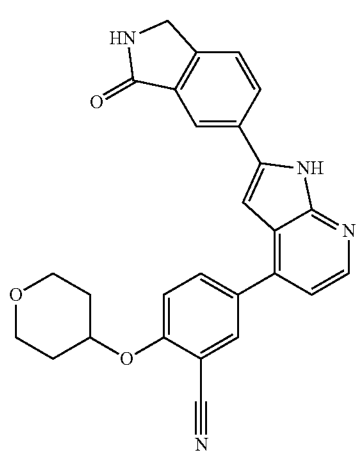 [SMILES: N#Cc1cc(-c2ccnc3[nH]c(-c4ccc5c(c4)C(=O)NC5)cc23)ccc1OC1CCOCC1] | >1000 | 9.62 |

TABLE 1-continued

| Examples | Structure | IKKε-IC50 (nM) | TBK1-IC50 (nM) |
|---|---|---|---|
| Example 75 | 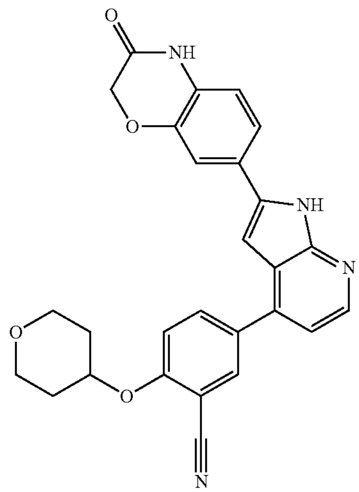 [SMILES: N#Cc1cc(-c2ccnc3[nH]c(-c4ccc5c(c4)OCC(=O)N5)cc23)ccc1OC1CCOCC1] | 10.49 | 6.28 |
| Example 76 | 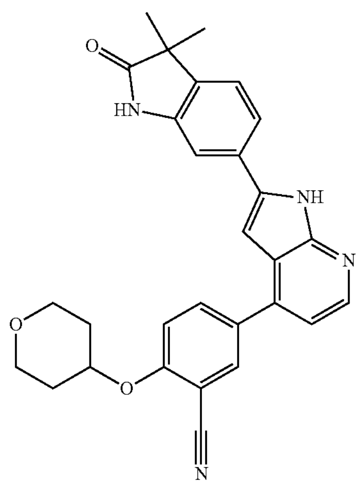 [SMILES: CC1(C)C(=O)Nc2cc(-c3cc4c(-c5ccc(OC6CCOCC6)c(C#N)c5)ccnc4[nH]3)ccc21] | >1000 | 5.76 |
| Example 77 | 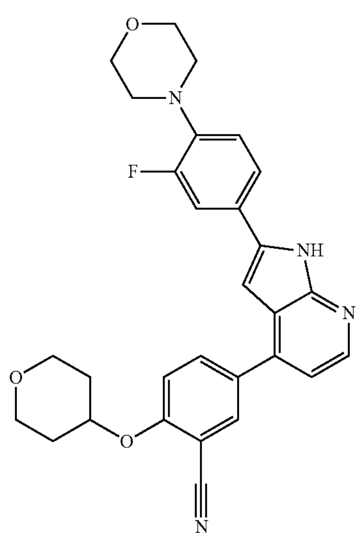 [SMILES: N#Cc1cc(-c2ccnc3[nH]c(-c4ccc(N5CCOCC5)c(F)c4)cc23)ccc1OC1CCOCC1] | 38.05 | 10.91 |

TABLE 1-continued

| Examples | Structure | IKKε-IC50 (nM) | TBK1-IC50 (nM) |
|---|---|---|---|
| Example 78 | 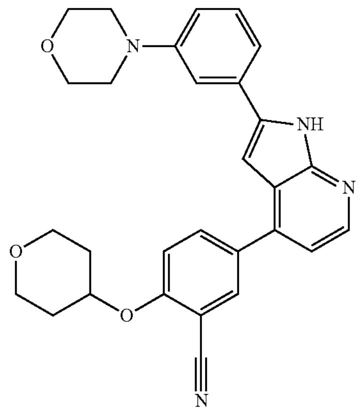 [SMILES: N#Cc1cc(-c2ccnc3[nH]c(-c4cccc(N5CCOCC5)c4)cc23)ccc1OC1CCOCC1] | 40.08 | 25.49 |
| Example 79 | 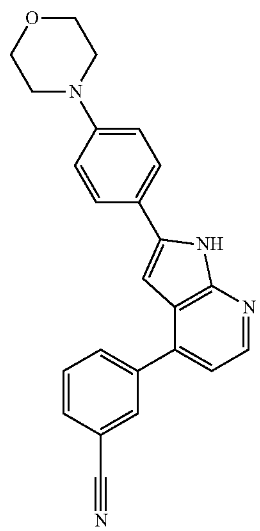 [SMILES: N#Cc1cccc(-c2ccnc3[nH]c(-c4ccc(N5CCOCC5)cc4)cc23)c1] | >1000 | 28.24 |
| Example 80 | 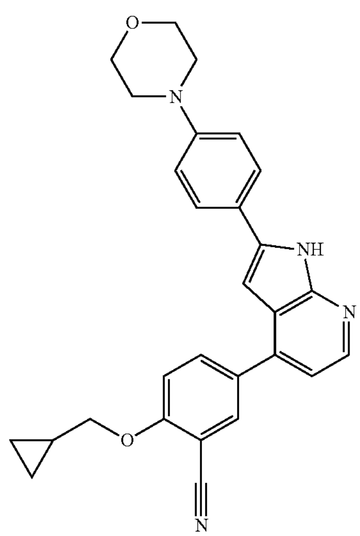 [SMILES: N#Cc1cc(-c2ccnc3[nH]c(-c4ccc(N5CCOCC5)cc4)cc23)ccc1OCC1CC1] | >1000 | 16.83 |

TABLE 1-continued

| Examples | Structure | IKKε-IC50 (nM) | TBK1-IC50 (nM) |
|---|---|---|---|
| Example 81 | 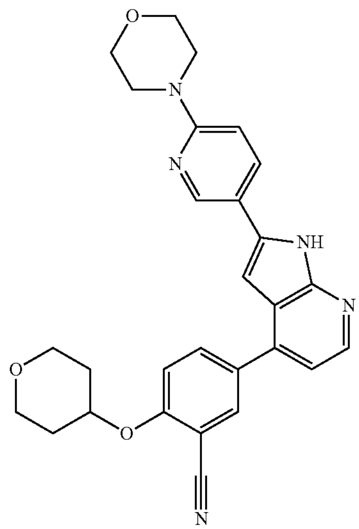 [SMILES: N#Cc1cc(-c2ccnc3[nH]c(-c4ccc(N5CCOCC5)nc4)cc23)ccc1OC1CCOCC1] | 9.90 | 4.10 |
| Example 82 | 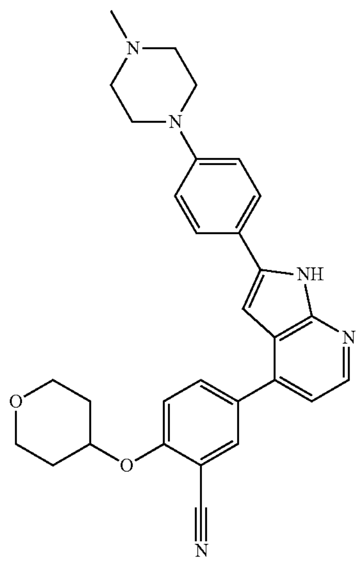 [SMILES: CN1CCN(c2ccc(-c3cc4c(-c5ccc(OC6CCOCC6)c(C#N)c5)ccnc4[nH]3)cc2)CC1] | 0.29 | 0.90 |
| Example 83 | 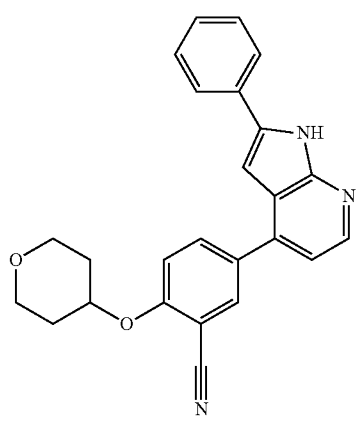 [SMILES: N#Cc1cc(-c2ccnc3[nH]c(-c4ccccc4)cc23)ccc1OC1CCOCC1] | 19.79 | >1000 |

TABLE 1-continued
| Examples | Structure | IKKε-IC50 (nM) | TBK1-IC50 (nM) |
|---|---|---|---|
| Example 84 | 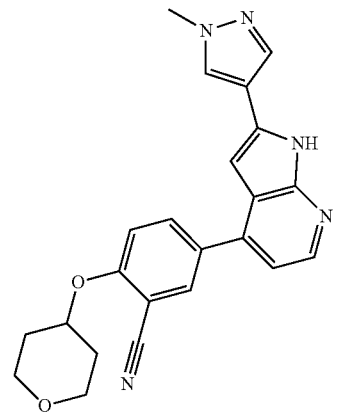 [SMILES: Cn1cc(-c2cc3c(-c4ccc(OC5CCOCC5)c(C#N)c4)ccnc3[nH]2)cn1] | 4.71 | 3.68 |
| Example 85 | 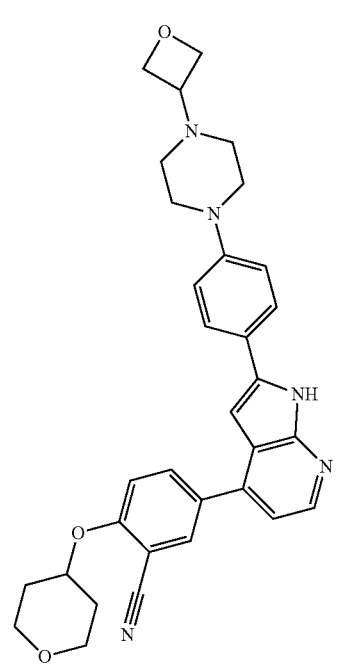 [SMILES: N#Cc1cc(-c2ccnc3[nH]c(-c4ccc(N5CCN(C6COC6)CC5)cc4)cc23)ccc1OC1CCOCC1] | 3.50 | 1.31 |
| Example 86 | 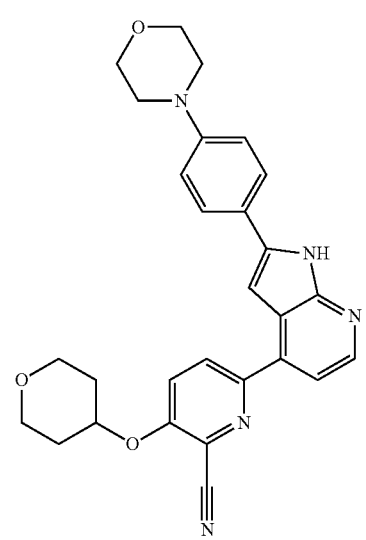 | 13.83 | 3.89 |

TABLE 1-continued
| Examples | Structure | IKKε-IC50 (nM) | TBK1-IC50 (nM) |
|---|---|---|---|
| Example 87 | 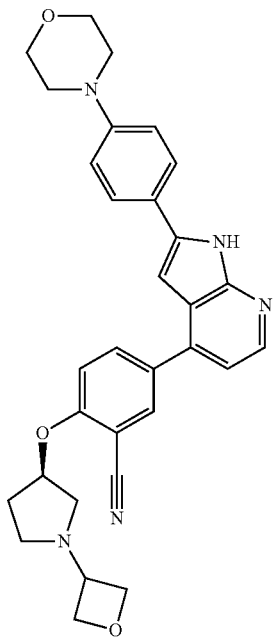 [SMILES: N#Cc1cc(-c2ccnc3[nH]c(-c4ccc(N5CCOCC5)cc4)cc23)ccc1O[C@@H]1CCN(C2COC2)C1] | 62.97 | 26.79 |
| Example 101 | 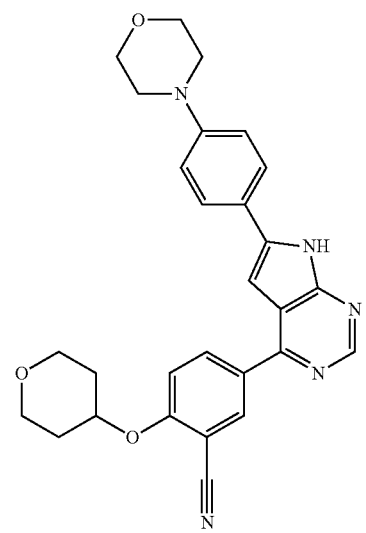 | 8.06 | 1.72 |

TABLE 1-continued

| Examples | Structure | IKKε-IC50 (nM) | TBK1-IC50 (nM) |
|---|---|---|---|
| Example 102 | 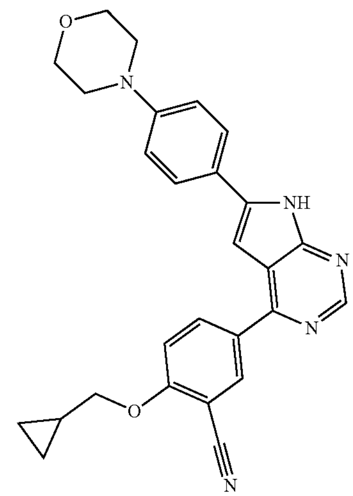 [SMILES: N#Cc1cc(-c2ncnc3[nH]c(-c4ccc(N5CCOCC5)cc4)cc23)ccc1OCC1CC1] | >1000 | >1000 |
| Example 103 | 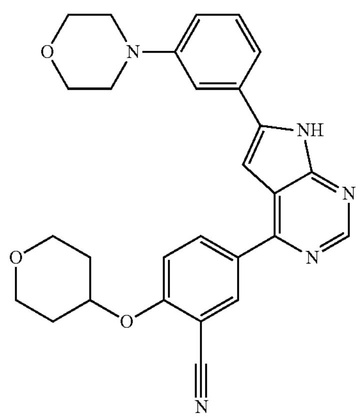 [SMILES: N#Cc1cc(-c2ncnc3[nH]c(-c4cccc(N5CCOCC5)c4)cc23)ccc1OC1CCOCC1] | 18.95 | 2.63 |
| Example 104 | 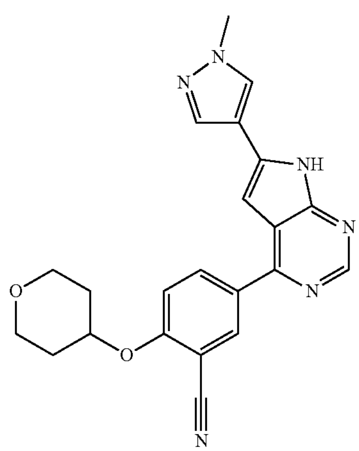 [SMILES: Cn1cc(-c2cc3c(-c4ccc(OC5CCOCC5)c(C#N)c4)ncnc3[nH]2)cn1] | 8.18 | 3.81 |

TABLE 1-continued
| Examples | Structure | IKKε-IC50 (nM) | TBK1-IC50 (nM) |
|---|---|---|---|
| Example 105 | 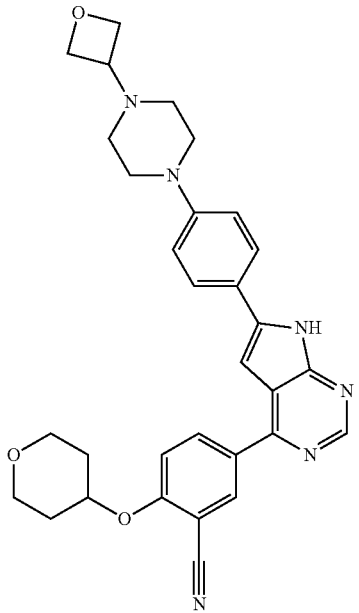 [SMILES: N#Cc1cc(-c2ncnc3[nH]c(-c4ccc(N5CCN(C6COC6)CC5)cc4)cc23)ccc1OC1CCOCC1] | 5.54 | 0.87 |
| Example 106 | 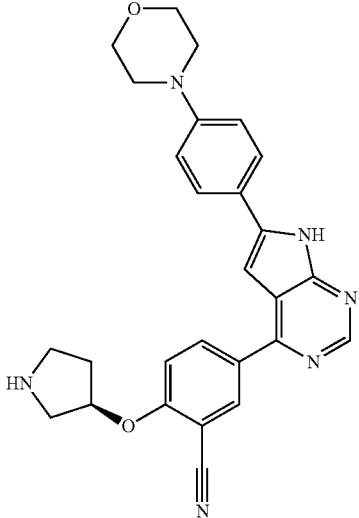 [SMILES: N#Cc1cc(-c2ncnc3[nH]c(-c4ccc(N5CCOCC5)cc4)cc23)ccc1O[C@@H]1CCNC1] | 18.98 | 4.94 |

TABLE 1-continued

| Examples | Structure | IKKε-IC50 (nM) | TBK1-IC50 (nM) |
|---|---|---|---|
| Example 107 | 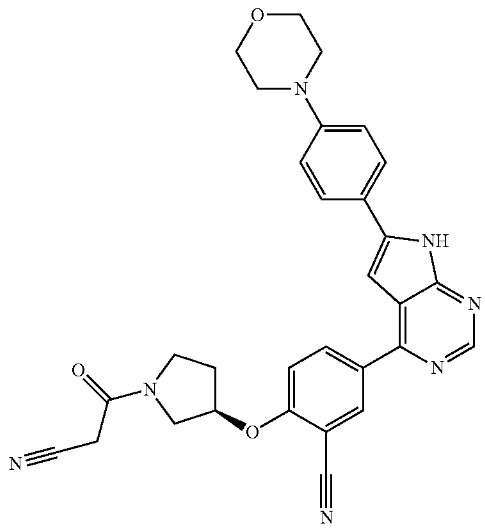 [SMILES: N#CCC(=O)N1CC[C@@H](Oc2ccc(-c3ncnc4[nH]c(-c5ccc(N6CCOCC6)cc5)cc34)cc2C#N)C1] | 11.69 | 2.26 |
| Example 108 | 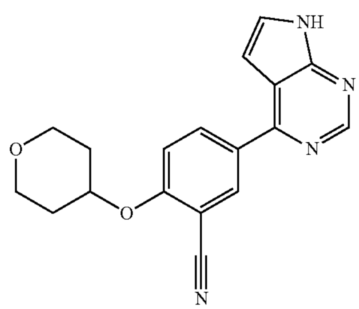 [SMILES: N#Cc1cc(-c2ncnc3[nH]ccc23)ccc1OC1CCOCC1] | 2229.32 | 1408.59 |
| Example 201 | 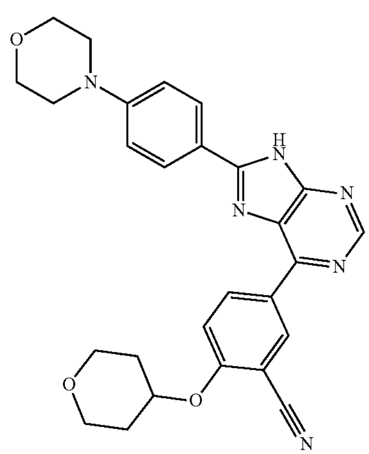 [SMILES: N#Cc1cc(-c2ncnc3[nH]c(-c4ccc(N5CCOCC5)cc4)nc23)ccc1OC1CCOCC1] | 19.74 | 3.00 |

TABLE 1-continued
| Examples | Structure | IKKε-IC50 (nM) | TBK1-IC50 (nM) |
|---|---|---|---|
| Example 202 | 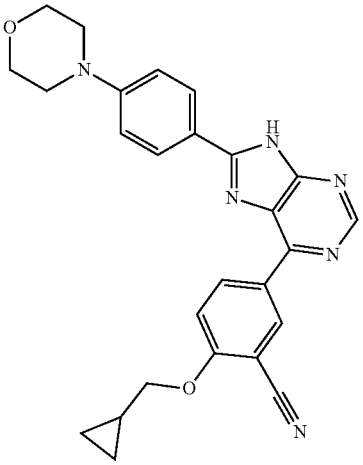 [SMILES: N#Cc1cc(-c2ncnc3[nH]c(-c4ccc(N5CCOCC5)cc4)nc23)ccc1OCC1CC1] | >1000 | >1000 |
| Example 203 | 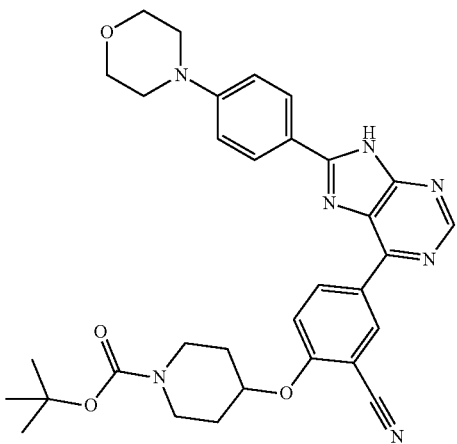 [SMILES: CC(C)(C)OC(=O)N1CCC(Oc2ccc(-c3ncnc4[nH]c(-c5ccc(N6CCOCC6)cc5)nc34)cc2C#N)CC1] | >1000 | >1000 |
| Example 204 | 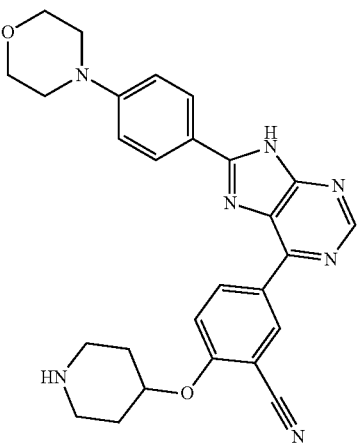 [SMILES: N#Cc1cc(-c2ncnc3[nH]c(-c4ccc(N5CCOCC5)cc4)nc23)ccc1OC1CCNCC1] | 83.70 | 36.83 |

TABLE 1-continued

| Examples | Structure | IKKε-IC50 (nM) | TBK1-IC50 (nM) |
|---|---|---|---|
| Example 205 | 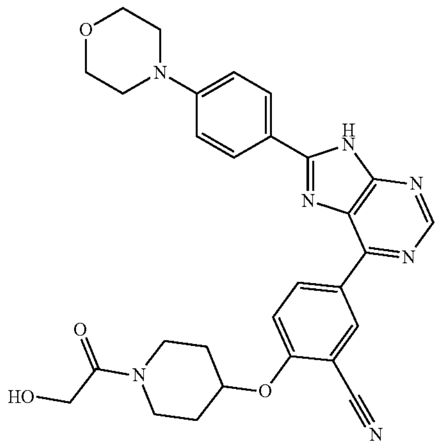 [SMILES: N#Cc1cc(-c2ncnc3[nH]c(-c4ccc(N5CCOCC5)cc4)nc23)ccc1OC1CCN(C(=O)CO)CC1] | 4.71 | 2.07 |
| Example 206 | 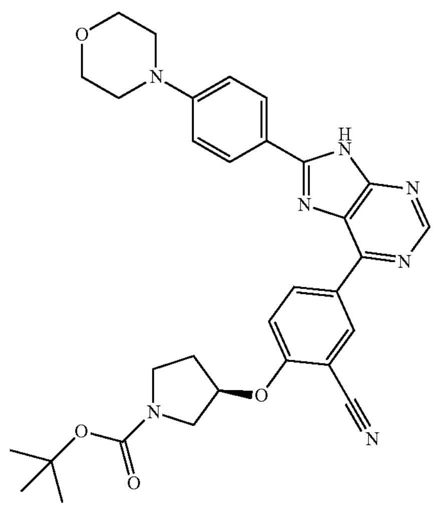 [SMILES: CC(C)(C)OC(=O)N1CC[C@@H](Oc2ccc(-c3ncnc4[nH]c(-c5ccc(N6CCOCC6)cc5)nc34)cc2C#N)C1] | >1000 | >1000 |
| Example 207 | 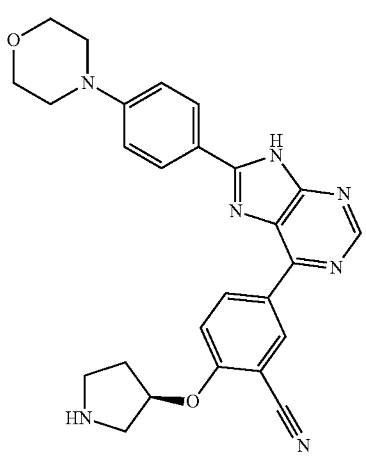 [SMILES: N#Cc1cc(-c2ncnc3[nH]c(-c4ccc(N5CCOCC5)cc4)nc23)ccc1O[C@@H]1CCNC1] | 112.84 | 15.83 |

TABLE 1-continued
| Examples | Structure | IKKε-IC50 (nM) | TBK1-IC50 (nM) |
|---|---|---|---|
| Example 208 | 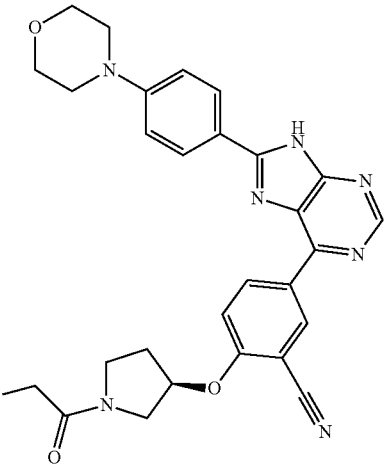 | 7.58 | 1.68 |
| Example 209 | 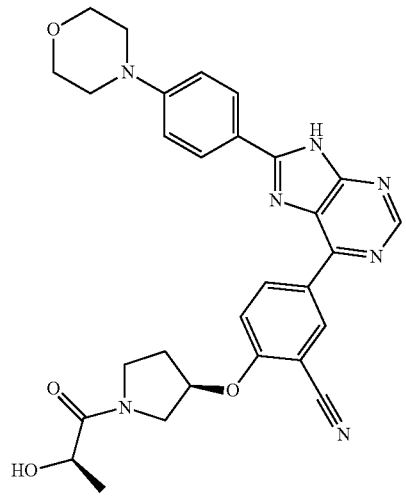 [SMILES: C[C@@H](O)C(=O)N1CC[C@@H](Oc2ccc(-c3ncnc4[nH]c(-c5ccc(N6CCOCC6)cc5)nc34)cc2C#N)C1] | 58.66 | 13.06 |
| Example 210 | 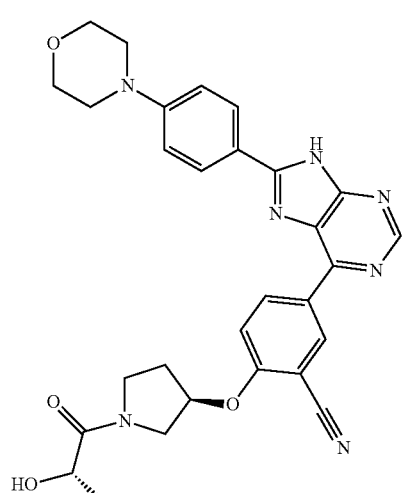 | >875.141 | 38.92 |

TABLE 1-continued

| Examples | Structure | IKKε-IC50 (nM) | TBK1-IC50 (nM) |
|---|---|---|---|
| Example 211 | 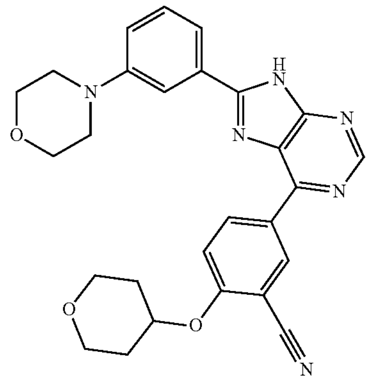 [SMILES: N#Cc1cc(-c2ncnc3[nH]c(-c4cccc(N5CCOCC5)c4)nc23)ccc1OC1CCOCC1] | 25.34 | 9.57 |
| Example 212 | 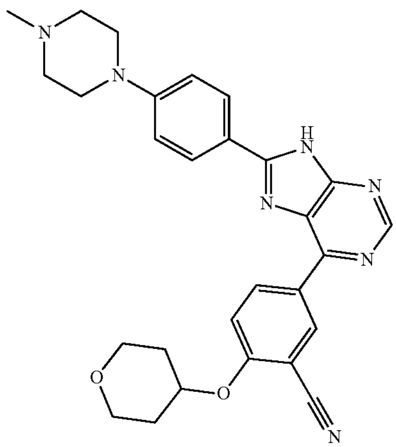 [SMILES: CN1CCN(c2ccc(-c3nc4c(-c5ccc(OC6CCOCC6)c(C#N)c5)ncnc4[nH]3)cc2)CC1] | 1.08 | 1.14 |
| Example 213 | 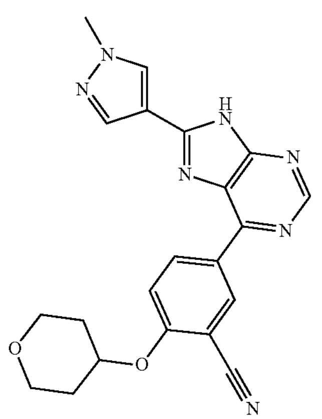 [SMILES: Cn1cc(-c2nc3c(-c4ccc(OC5CCOCC5)c(C#N)c4)ncnc3[nH]2)cn1] | 30.23 | 12.40 |

TABLE 1-continued

| Examples | Structure | IKKε-IC50 (nM) | TBK1-IC50 (nM) |
|---|---|---|---|
| Example 214 | 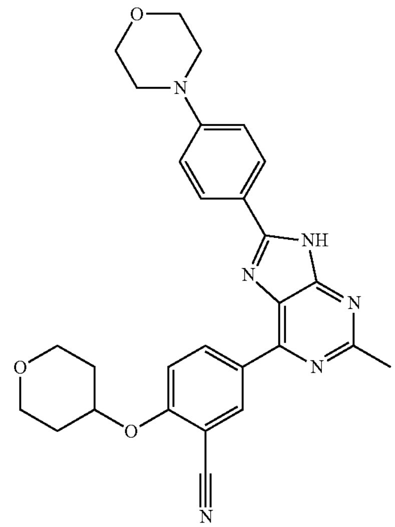 [SMILES: Cc1nc(-c2ccc(OC3CCOCC3)c(C#N)c2)c2nc(-c3ccc(N4CCOCC4)cc3)[nH]c2n1] | >1000 | >1000 |
| Example 301 | 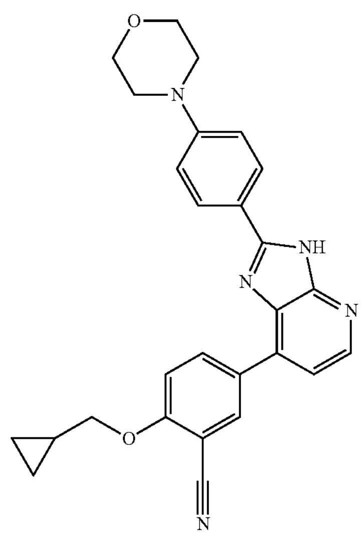 [SMILES: N#Cc1cc(-c2ccnc3[nH]c(-c4ccc(N5CCOCC5)cc4)nc23)ccc1OCC1CC1] | >1000 | 43.53 |
| Example 302 | 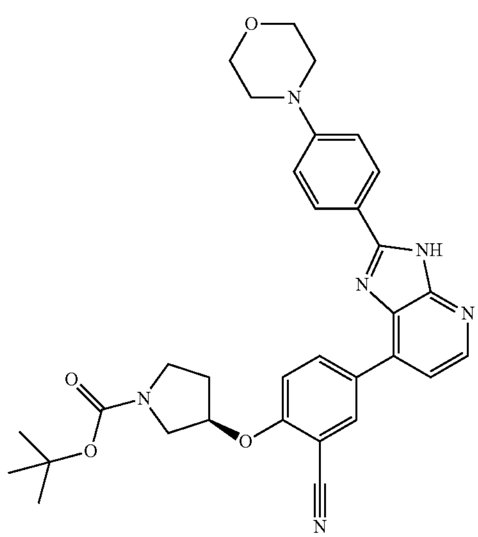 [SMILES: CC(C)(C)OC(=O)N1CC[C@@H](Oc2ccc(-c3ccnc4[nH]c(-c5ccc(N6CCOCC6)cc5)nc34)cc2C#N)C1] | >1000 | >1000 |

TABLE 1-continued
| Examples | Structure | IKKε-IC50 (nM) | TBK1-IC50 (nM) |
|---|---|---|---|
| Example 303 | 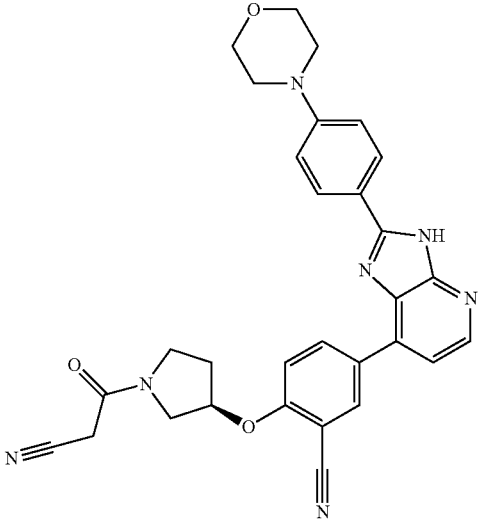 [SMILES: N#CCC(=O)N1CC[C@@H](Oc2ccc(-c3ccnc4[nH]c(-c5ccc(N6CCOCC6)cc5)nc34)cc2C#N)C1] | 7.51 | 4.59 |
| Example 304 | 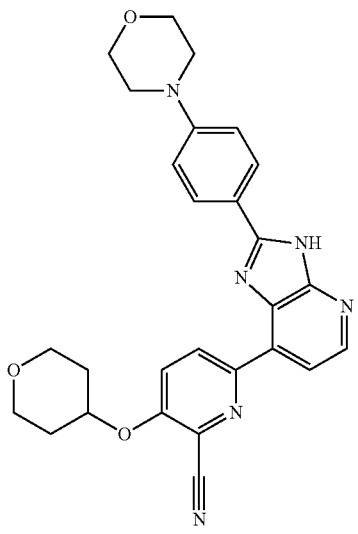 [SMILES: N#Cc1nc(-c2ccnc3[nH]c(-c4ccc(N5CCOCC5)cc4)nc23)ccc1OC1CCOCC1] | 18.59 | 9.25 |
| Example 305 | 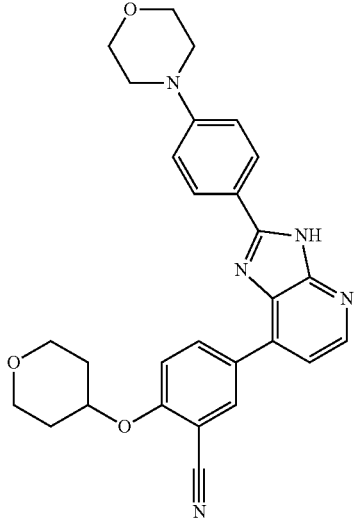 | 10.79 | 3.20 |

TABLE 1-continued

| Examples | Structure | IKKε-IC50 (nM) | TBK1-IC50 (nM) |
|---|---|---|---|
| Example 306 | 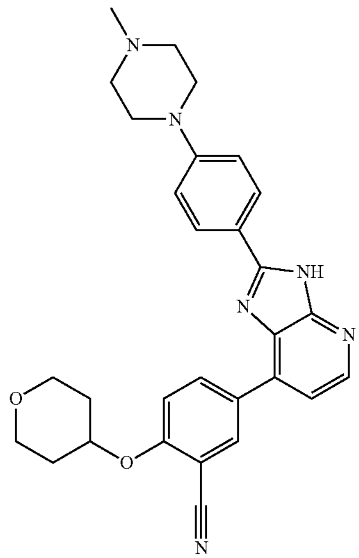 | 1.21 | 1.85 |
| Example 307 | 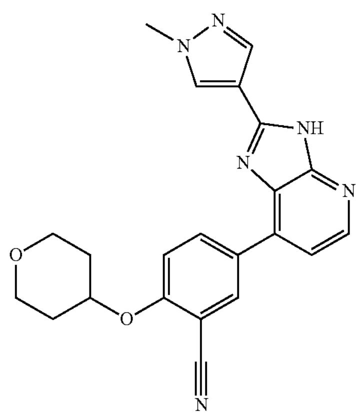 [SMILES: Cn1cc(-c2nc3c(-c4ccc(OC5CCOCC5)c(C#N)c4)ccnc3[nH]2)cn1] | 21.32 | 44.25 |
| Example 308 | 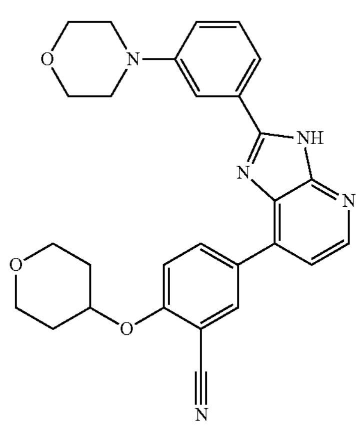 [SMILES: N#Cc1cc(-c2ccnc3[nH]c(-c4cccc(N5CCOCC5)c4)nc23)ccc1OC1CCOCC1] | 18.09 | 25.12 |

TABLE 1-continued

| Examples | Structure | IKKε-IC50 (nM) | TBK1-IC50 (nM) |
|---|---|---|---|
| Example 401 | 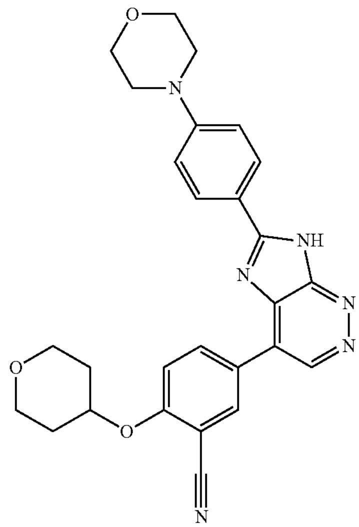 | >1000 | >1000 |
| Example 109 | 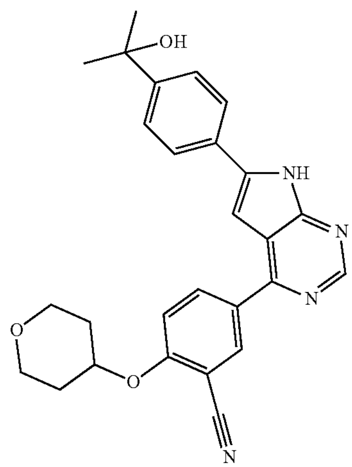 [SMILES: CC(C)(O)c1ccc(-c2cc3c(-c4ccc(OC5CCOCC5)c(C#N)c4)ncnc3[nH]2)cc1] | 4.994 | 0.821 |
| Example 110 | 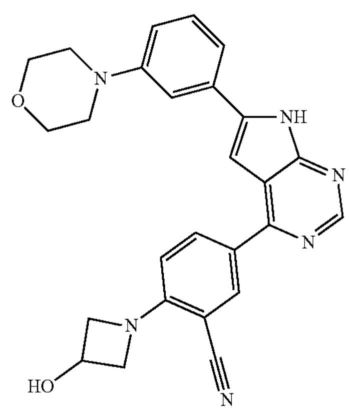 [SMILES: N#Cc1cc(-c2ncnc3[nH]c(-c4cccc(N5CCOCC5)c4)cc23)ccc1N1CC(O)C1] | 57.414 | 12.555 |

TABLE 1-continued

| Examples | Structure | IKKε-IC50 (nM) | TBK1-IC50 (nM) |
|---|---|---|---|
| Example 111 | 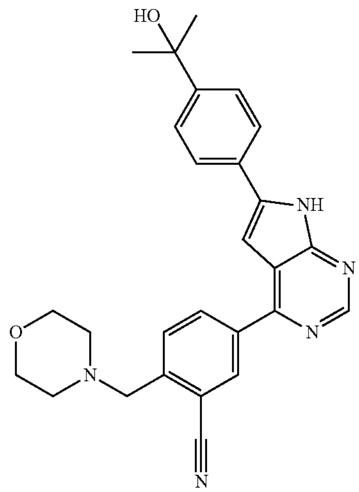 [SMILES: CC(C)(O)c1ccc(-c2cc3c(-c4ccc(CN5CCOCC5)c(C#N)c4)ncnc3[nH]2)cc1] | 279.169 | 36.902 |
| Example 112 | 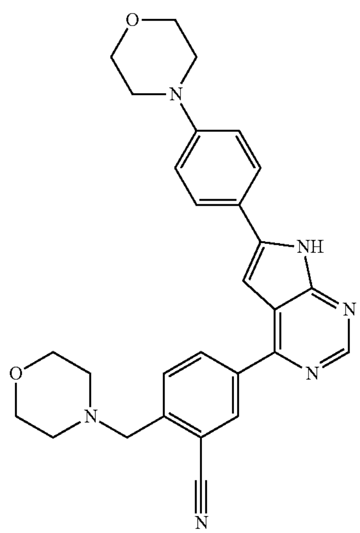 [SMILES: N#Cc1cc(-c2ncnc3[nH]c(-c4ccc(N5CCOCC5)cc4)cc23)ccc1CN1CCOCC1] | 85.032 | 19.61 |
| Example 113 | 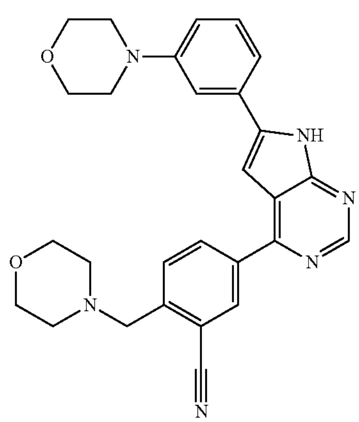 [SMILES: N#Cc1cc(-c2ncnc3[nH]c(-c4cccc(N5CCOCC5)c4)cc23)ccc1CN1CCOCC1] | 1000 | 69.147 |

TABLE 1-continued

| Examples | Structure | IKKε-IC50 (nM) | TBK1-IC50 (nM) |
|---|---|---|---|
| Example 114 | 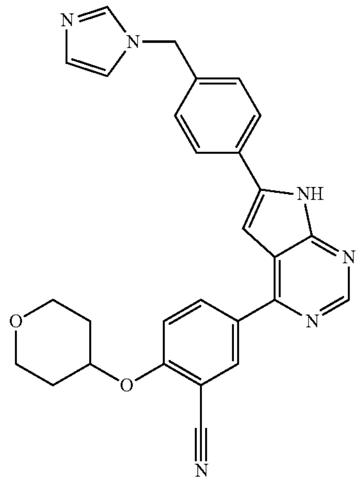 [SMILES: N#Cc1cc(-c2ncnc3[nH]c(-c4ccc(Cn5ccnc5)cc4)cc23)ccc1OC1CCOCC1] | 5.786 | 5.126 |
| Example 115 | 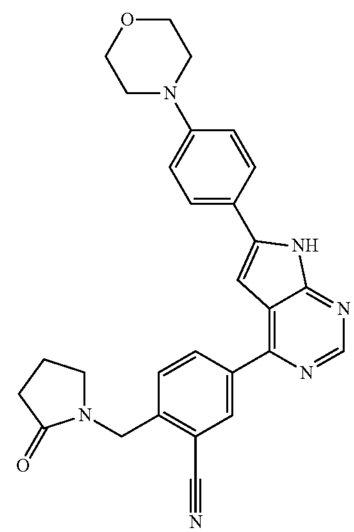 [SMILES: N#Cc1cc(-c2ncnc3[nH]c(-c4ccc(N5CCOCC5)cc4)cc23)ccc1CN1CCCC1=O] | 1000 | 45.673 |
| Example 116 | 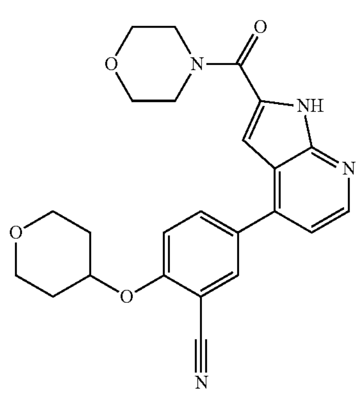 [SMILES: N#Cc1cc(-c2ccnc3[nH]c(C(=O)N4CCOCC4)cc23)ccc1OC1CCOCC1] | 666.941 | 1000 |

TABLE 1-continued
| Examples | Structure | IKKε-IC50 (nM) | TBK1-IC50 (nM) |
|---|---|---|---|
| Example 117 | 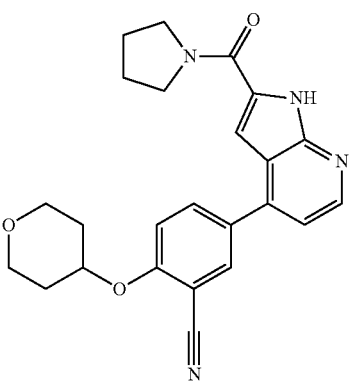 [SMILES: N#Cc1cc(-c2ccnc3[nH]c(C(=O)N4CCCC4)cc23)ccc1OC1CCOCC1] | 261.557 | 383.224 |
| Example 118 | 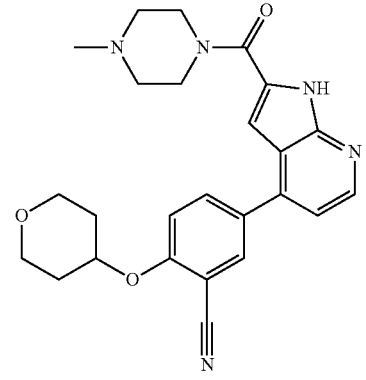 | 291.28 | 1000 |
| Example 119 | 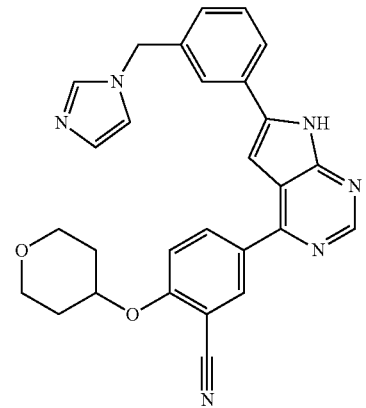 [SMILES: N#Cc1cc(-c2ncnc3[nH]c(-c4cccc(Cn5ccnc5)c4)cc23)ccc1OC1CCOCC1] | 1.224 | 1.234 |

TABLE 1-continued

| Examples | Structure | IKKε-IC50 (nM) | TBK1-IC50 (nM) |
|---|---|---|---|
| Example 120 | 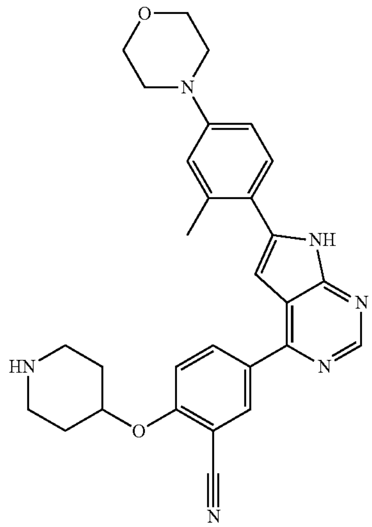 [SMILES: Cc1cc(N2CCOCC2)ccc1-c1cc2c(-c3ccc(OC4CCNCC4)c(C#N)c3)ncnc2[nH]1] | 102.017 | 22.151 |
| Example 121 | 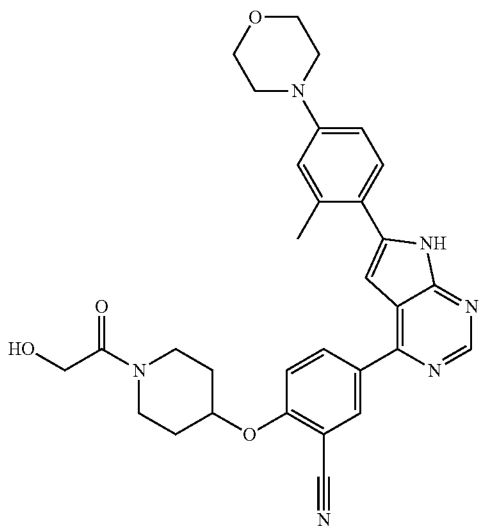 [SMILES: Cc1cc(N2CCOCC2)ccc1-c1cc2c(-c3ccc(OC4CCN(C(=O)CO)CC4)c(C#N)c3)ncnc2[nH]1] | 4.404 | 1.283 |
| Example 122 | 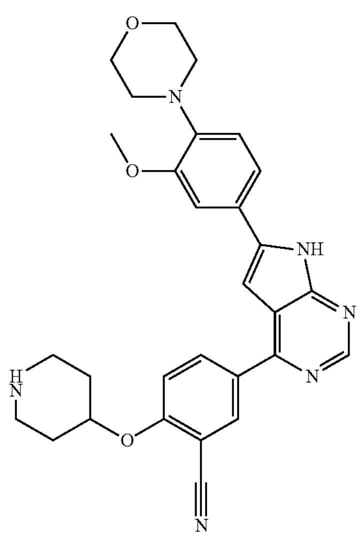 [SMILES: COc1cc(-c2cc3c(-c4ccc(OC5CCNCC5)c(C#N)c4)ncnc3[nH]2)ccc1N1CCOCC1] | 115.373 | 21.201 |

TABLE 1-continued

| Examples | Structure | IKKε-IC50 (nM) | TBK1-IC50 (nM) |
|---|---|---|---|
| Example 123 | 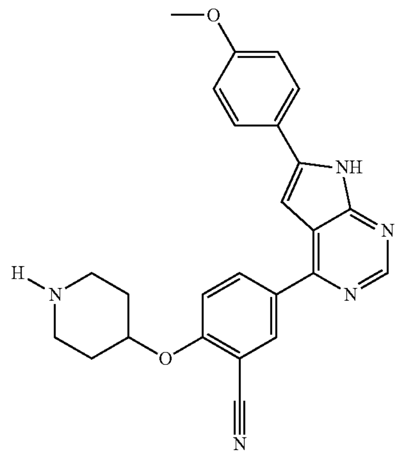 [SMILES: COc1ccc(-c2cc3c(-c4ccc(OC5CCNCC5)c(C#N)c4)ncnc3[nH]2)cc1] | 65.791 | 22.387 |
| Example 124 | 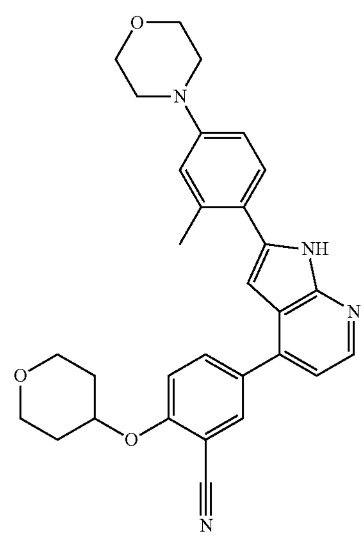 [SMILES: Cc1cc(N2CCOCC2)ccc1-c1cc2c(-c3ccc(OC4CCOCC4)c(C#N)c3)ccnc2[nH]1] | 18.572 | 5.897 |
| Example 125 | 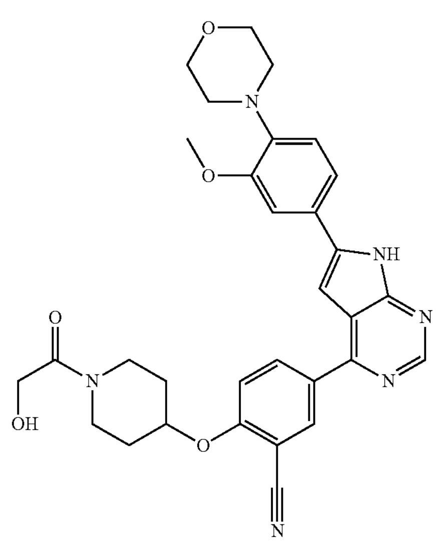 [SMILES: COc1cc(-c2cc3c(-c4ccc(OC5CCN(C(=O)CO)CC5)c(C#N)c4)ncnc3[nH]2)ccc1N1CCOCC1] | 2.619 | 0.9 |

TABLE 1-continued

| Examples | Structure | IKKε-IC50 (nM) | TBK1-IC50 (nM) |
|---|---|---|---|
| Example 126 | 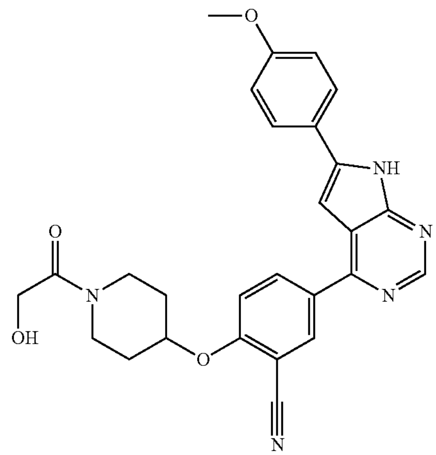 [SMILES: COc1ccc(-c2cc3c(-c4ccc(OC5CCN(C(=O)CO)CC5)c(C#N)c4)ncnc3[nH]2)cc1] | 3.29 | 1.337 |
| Example 127 | 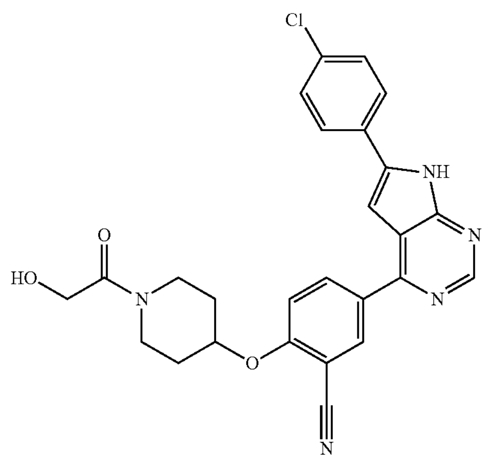 [SMILES: N#Cc1cc(-c2ncnc3[nH]c(-c4ccc(Cl)cc4)cc23)ccc1OC1CCN(C(=O)CO)CC1] | 9.578 | 4.638 |
| Example 128 | 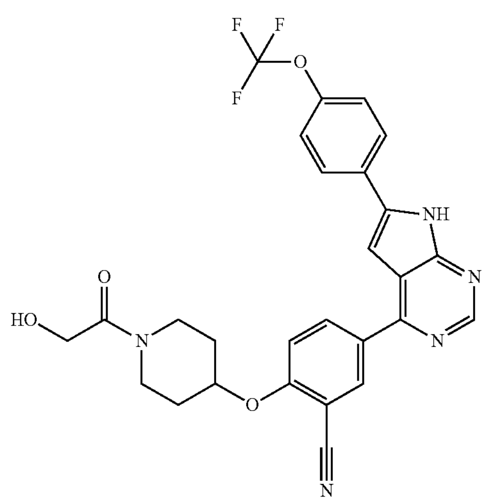 [SMILES: N#Cc1cc(-c2ncnc3[nH]c(-c4ccc(OC(F)(F)F)cc4)cc23)ccc1OC1CCN(C(=O)CO)CC1] | 13.626 | 4.205 |

TABLE 1-continued
| Examples | Structure | IKKε-IC50 (nM) | TBK1-IC50 (nM) |
|---|---|---|---|
| Example 129 | 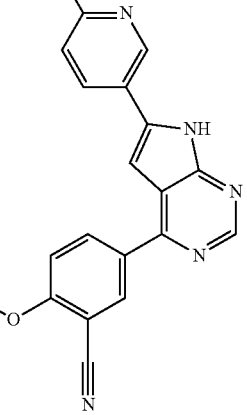 | 17.448 | 2.769 |
| Example 130 | 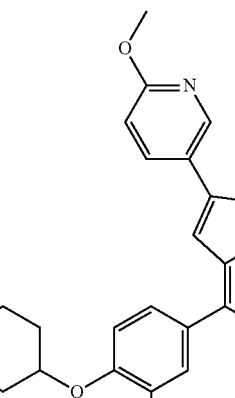 | 10.609 | 5.435 |
| Example 131 | 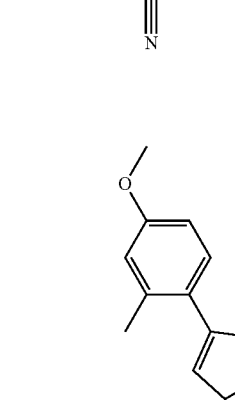 | 12.411 | 5.681 |

TABLE 1-continued
| Examples | Structure | IKKε-IC50 (nM) | TBK1-IC50 (nM) |
|---|---|---|---|
| Example 132 | 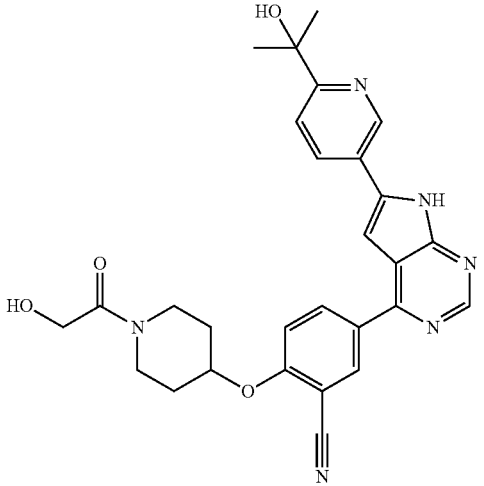 [SMILES: CC(C)(O)c1ccc(-c2cc3c(-c4ccc(OC5CCN(C(=O)CO)CC5)c(C#N)c4)ncnc3[nH]2)cn1] | 8.834 | 3.261 |
| Example 133 | 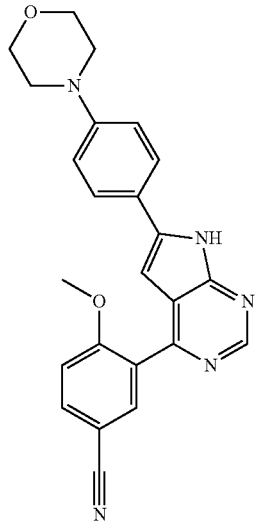 [SMILES: COc1ccc(C#N)cc1-c1ncnc2[nH]c(-c3ccc(N4CCOCC4)cc3)cc12] | 1000 | 1000 |

TABLE 1-continued
| Examples | Structure | IKKε-IC50 (nM) | TBK1-IC50 (nM) |
|---|---|---|---|
| Example 134 | 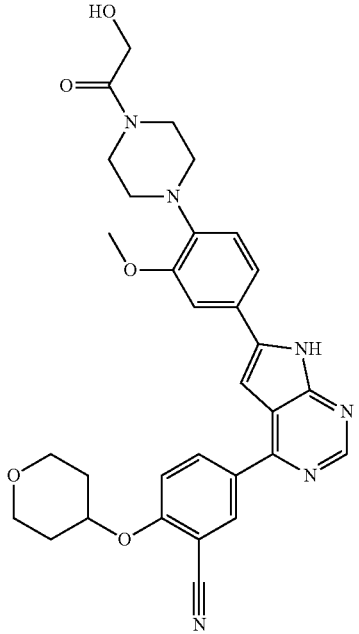 [SMILES: COc1cc(-c2cc3c(-c4ccc(OC5CCOCC5)c(C#N)c4)ncnc3[nH]2)ccc1N1CCN(C(=O)CO)CC1] | 6.09 | 1.088 |
| Example 135 | 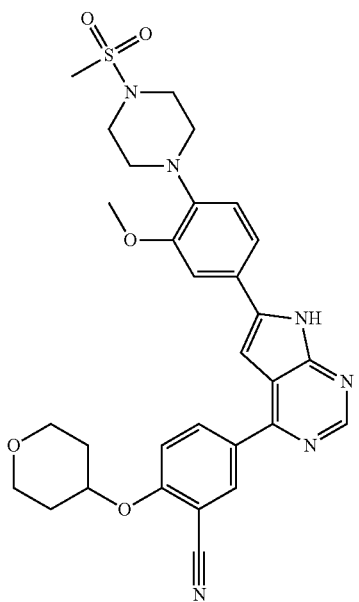 [SMILES: COc1cc(-c2cc3c(-c4ccc(OC5CCOCC5)c(C#N)c4)ncnc3[nH]2)ccc1N1CCN(S(C)(=O)=O)CC1] | 7.374 | 2.282 |

TABLE 1-continued

| Examples | Structure | IKKε-IC50 (nM) | TBK1-IC50 (nM) |
|---|---|---|---|
| Example 136 | 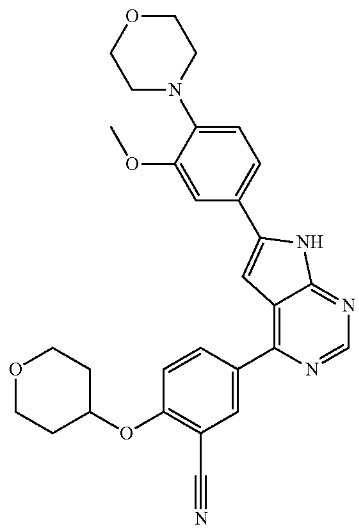 [SMILES: COc1cc(-c2cc3c(-c4ccc(OC5CCOCC5)c(C#N)c4)ncnc3[nH]2)ccc1N1CCOCC1] | 9.233 | 1.002 |
| Example 137 | 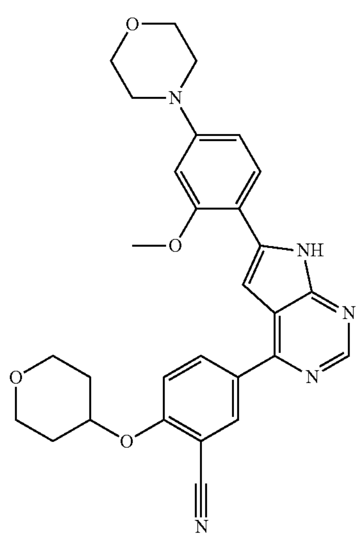 [SMILES: COc1cc(N2CCOCC2)ccc1-c1cc2c(-c3ccc(OC4CCOCC4)c(C#N)c3)ncnc2[nH]1] | 47.469 | 9.783 |

TABLE 1-continued
| Examples | Structure | IKKε-IC50 (nM) | TBK1-IC50 (nM) |
|---|---|---|---|
| Example 138 | 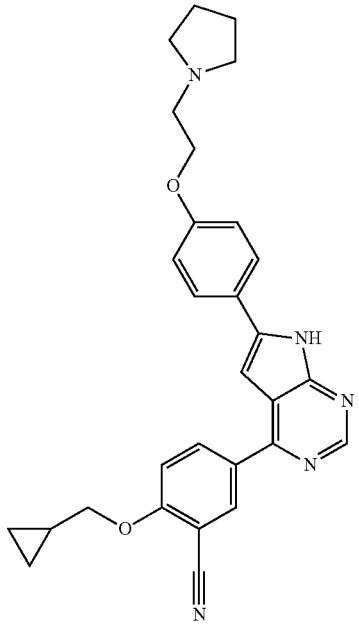 [SMILES: N#Cc1cc(-c2ncnc3[nH]c(-c4ccc(OCCN5CCCC5)cc4)cc23)ccc1OCC1CC1] | 3.905 | 5.885 |
| Example 139 | 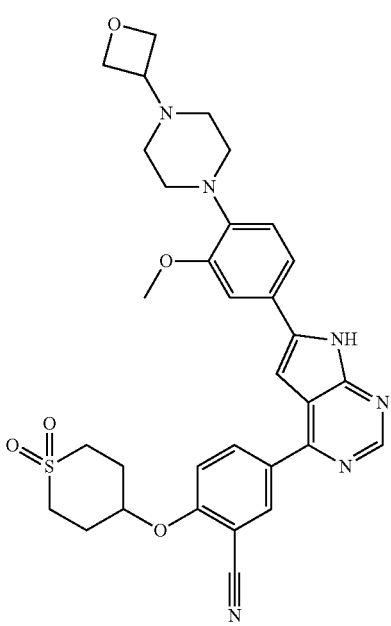 [SMILES: COc1cc(-c2cc3c(-c4ccc(OC5CCS(=O)(=O)CC5)c(C#N)c4)ncnc3[nH]2)ccc1N1CCN(C2COC2)CC1] | 25.04 | 3.679 |

TABLE 1-continued

| Examples | Structure | IKKε-IC50 (nM) | TBK1-IC50 (nM) |
| --- | --- | --- | --- |
| Example 140 | 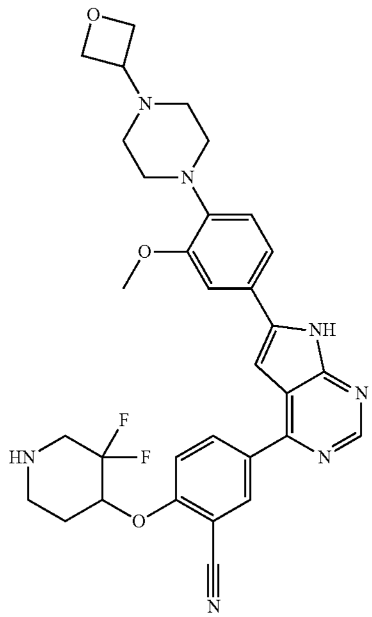 [SMILES: COc1cc(-c2cc3c(-c4ccc(OC5CCNCC5(F)F)c(C#N)c4)ncnc3[nH]2)ccc1N1CCN(C2COC2)CC1] | 32.919 | 3.548 |
| Example 141 | 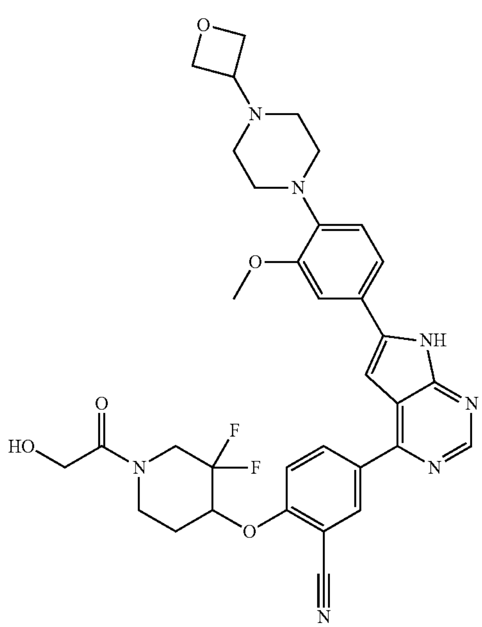 [SMILES: COc1cc(-c2cc3c(-c4ccc(OC5CCN(C(=O)CO)CC5(F)F)c(C#N)c4)ncnc3[nH]2)ccc1N1CCN(C2COC2)CC1] | 0.687 | 0.763 |

TABLE 1-continued
| Examples | Structure | | IKKε-IC50 (nM) | TBK1-IC50 (nM) |
|---|---|---|---|---|
| Example 142 | Chiral 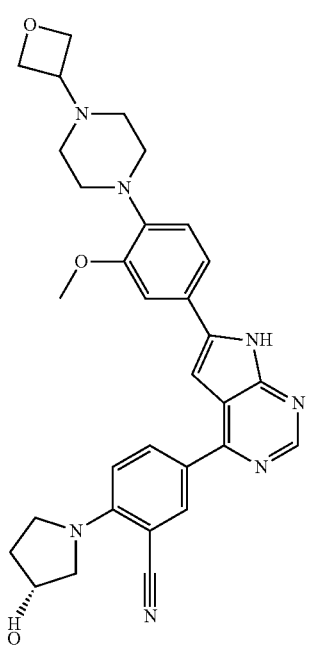 | | 14.659 | 2.032 |
| Example 143 | 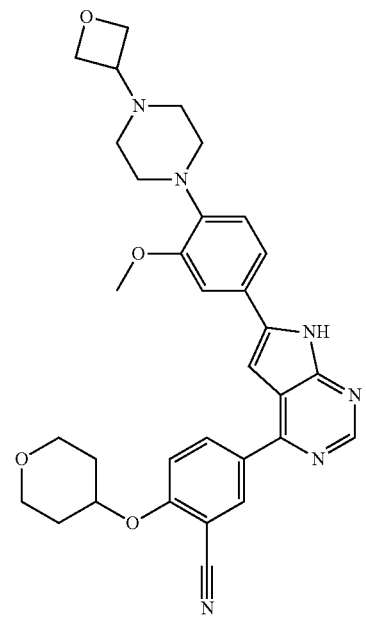 [SMILES: COc1cc(-c2cc3c(-c4ccc(OC5CCOCC5)c(C#N)c4)ncnc3[nH]2)ccc1N1CCN(C2COC2)CC1] | | 6.903 | 1.025 |

TABLE 1-continued
| Examples | Structure | | IKKε-IC50 (nM) | TBK1-IC50 (nM) |
|---|---|---|---|---|
| Example 144 | 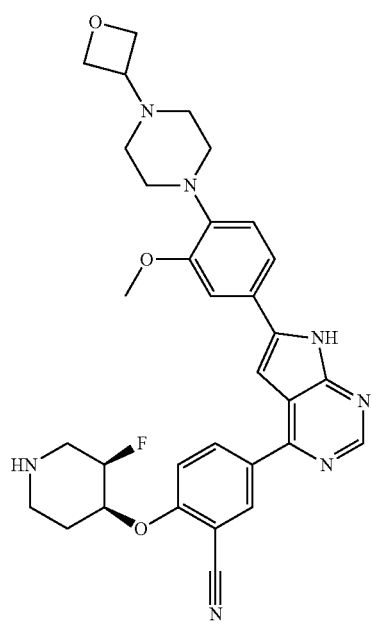 | Chiral | 64.351 | 6.17 |
| Example 145 | 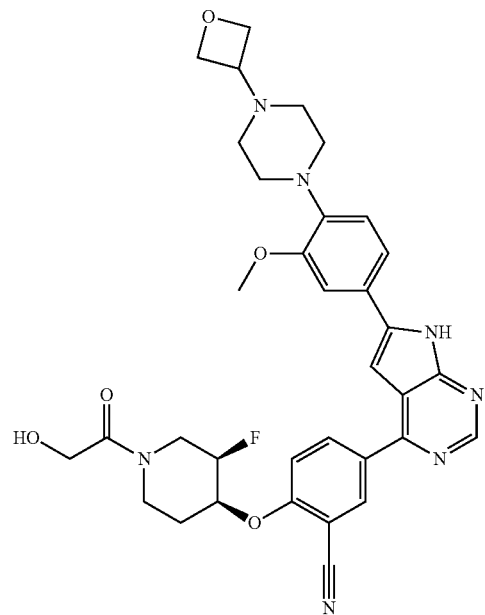 | Chiral | 0.481 | 1.051 |

TABLE 1-continued

| Examples | Structure | IKKε-IC50 (nM) | TBK1-IC50 (nM) |
| --- | --- | --- | --- |
| Example 146 | 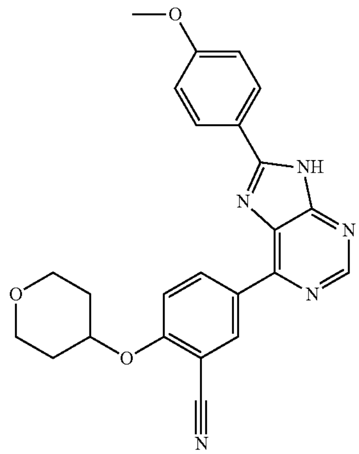 [SMILES: COc1ccc(-c2nc3c(-c4ccc(OC5CCOCC5)c(C#N)c4)ncnc3[nH]2)cc1] | 23.358 | 4.713 |
| Example 147 | 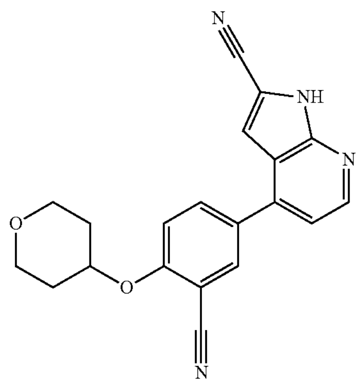 [SMILES: N#Cc1cc2c(-c3ccc(OC4CCOCC4)c(C#N)c3)ccnc2[nH]1] | 1000 | 1000 |
| Example 148 | 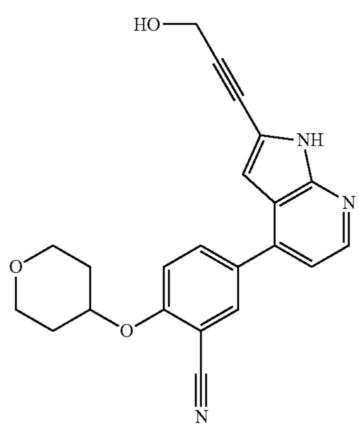 [SMILES: N#Cc1cc(-c2ccnc3[nH]c(C#CCO)cc23)ccc1OC1CCOCC1] | 204.853 | 184.161 |

TABLE 1-continued
| Examples | Structure | IKKε-IC50 (nM) | TBK1-IC50 (nM) |
|---|---|---|---|
| Example 149 | 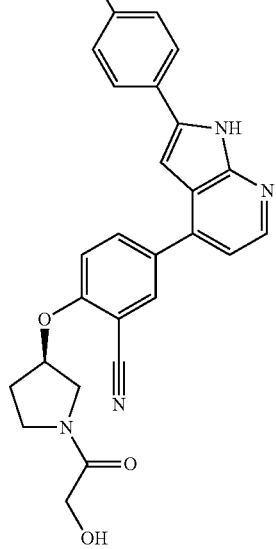 | 2.265 | 1.536 |
| Example 150 | 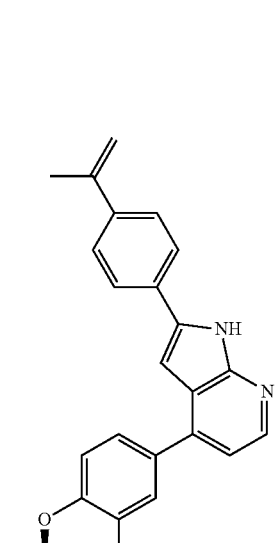 | 18.446 | 11.231 |

TABLE 1-continued
| Examples | Structure | IKKε-IC50 (nM) | TBK1-IC50 (nM) |
|---|---|---|---|
| Example 151 | 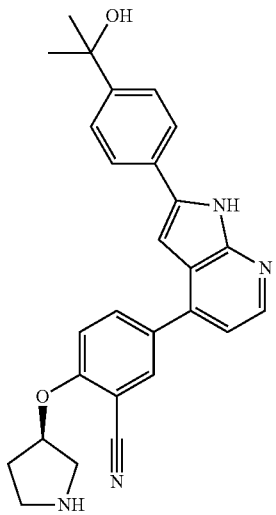 [SMILES: CC(C)(O)c1ccc(-c2cc3c(-c4ccc(O[C@@H]5CCNC5)c(C#N)c4)ccnc3[nH]2)cc1] | 120.407 | 43.017 |
| Example 152 | 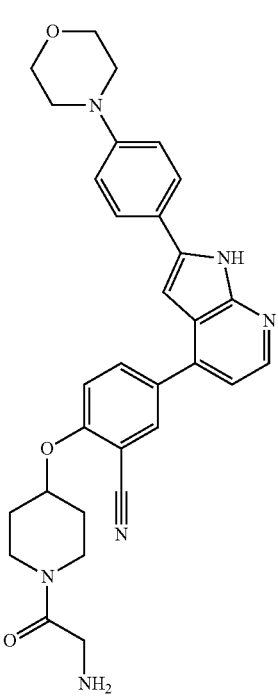 [SMILES: N#Cc1cc(-c2ccnc3[nH]c(-c4ccc(N5CCOCC5)cc4)cc23)ccc1OC1CCN(C(=O)CN)CC1] | 18.41 | 5.956 |

TABLE 1-continued
| Examples | Structure | IKKϵ-IC50 (nM) | TBK1-IC50 (nM) |
|---|---|---|---|
| Example 153 | 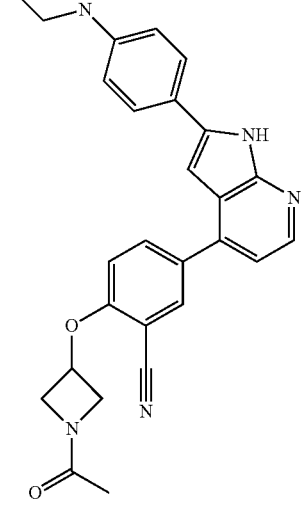 | 195.14 | 51.11 |
| Example 154 | 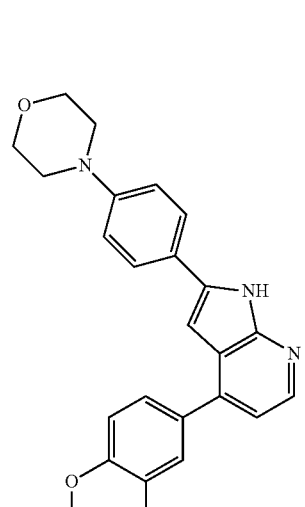 | 145.97 | 32.439 |

TABLE 1-continued
| Examples | Structure | IKKε-IC50 (nM) | TBK1-IC50 (nM) |
|---|---|---|---|
| Example 155 | 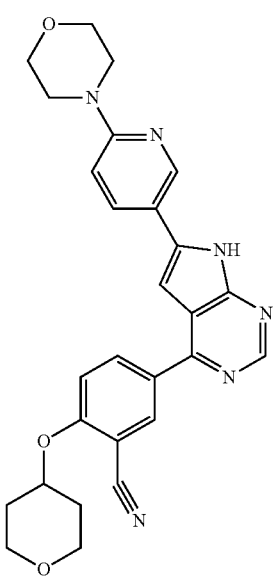 [SMILES: N#Cc1cc(-c2ncnc3[nH]c(-c4ccc(N5CCOCC5)nc4)cc23)ccc1OC1CCOCC1] | 15.198 | 4.391 |
| Example 156 | 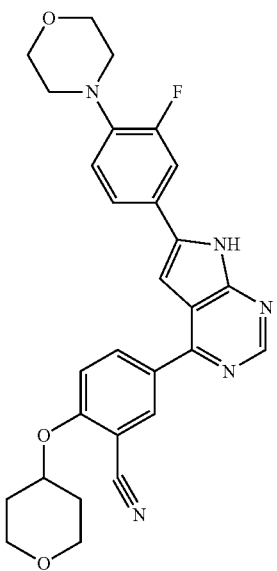 [SMILES: N#Cc1cc(-c2ncnc3[nH]c(-c4ccc(N5CCOCC5)c(F)c4)cc23)ccc1OC1CCOCC1] | 14.281 | 2.776 |

TABLE 1-continued
| Examples | Structure | IKKε-IC50 (nM) | TBK1-IC50 (nM) |
|---|---|---|---|
| Example 157 | 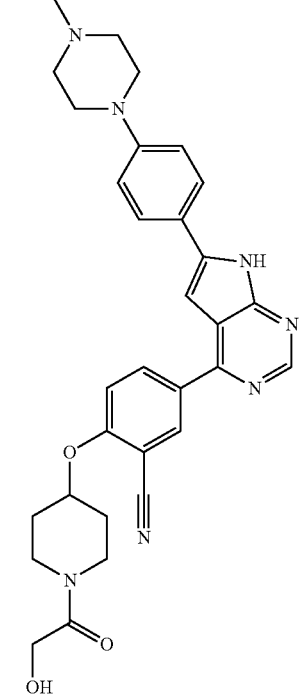 | 1.432 | 0.849 |
| Example 158 | 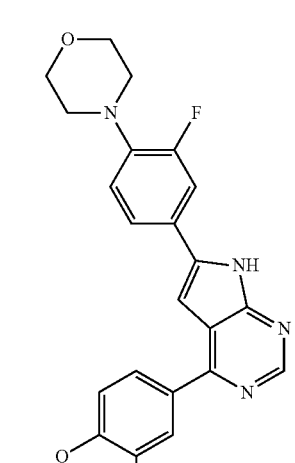 | 2.386 | 1.018 |

TABLE 1-continued
| Examples | Structure | IKKε-IC50 (nM) | TBK1-IC50 (nM) |
|---|---|---|---|
| Example 159 | 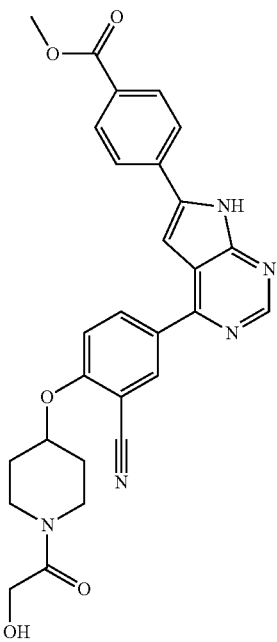 [SMILES: COC(=O)c1ccc(-c2cc3c(-c4ccc(OC5CCN(C(=O)CO)CC5)c(C#N)c4)ncnc3[nH]2)cc1] | 5.095 | 2.168 |
| Example 160 | 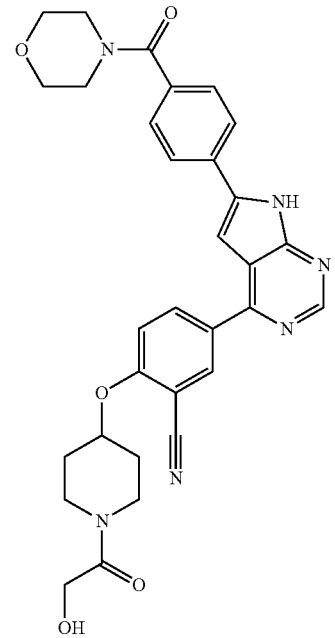 [SMILES: N#Cc1cc(-c2ncnc3[nH]c(-c4ccc(C(=O)N5CCOCC5)cc4)cc23)ccc1OC1CCN(C(=O)CO)CC1] | 2.328 | 1.323 |

TABLE 1-continued

| Examples | Structure | IKKε-IC50 (nM) | TBK1-IC50 (nM) |
| --- | --- | --- | --- |
| Example 161 | 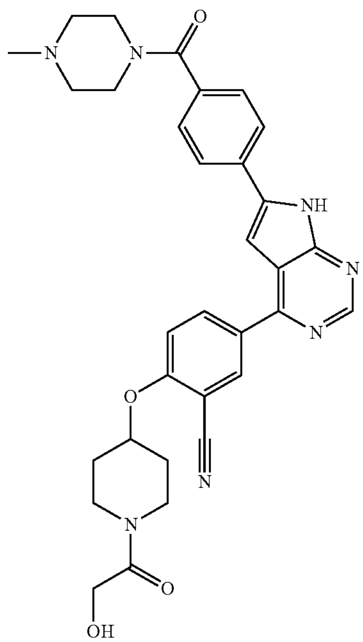 [SMILES: CN1CCN(C(=O)c2ccc(-c3cc4c(-c5ccc(OC6CCN(C(=O)CO)CC6)c(C#N)c5)ncnc4[nH]3)cc2)CC1] | 1.117 | 1.565 |
| Example 162 | 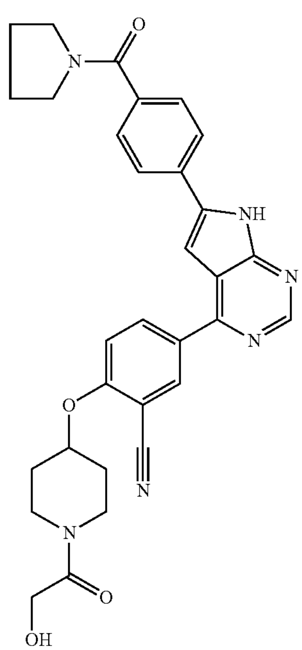 [SMILES: N#Cc1cc(-c2ncnc3[nH]c(-c4ccc(C(=O)N5CCCC5)cc4)cc23)ccc1OC1CCN(C(=O)CO)CC1] | 2.682 | 1.481 |

TABLE 1-continued
| Examples | Structure | IKKe-IC50 (nM) | TBK1-IC50 (nM) |
|---|---|---|---|
| Example 163 | 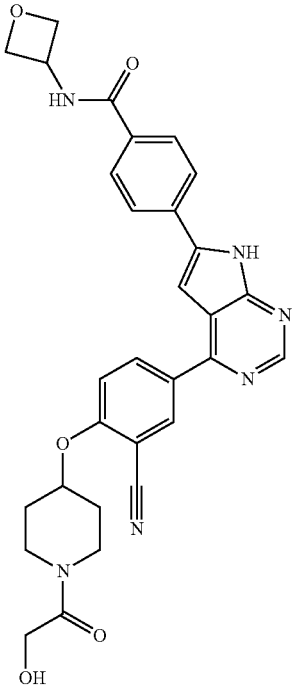 [SMILES: N#Cc1cc(-c2ncnc3[nH]c(-c4ccc(C(=O)NC5COC5)cc4)cc23)ccc1OC1CCN(C(=O)CO)CC1] | 1.797 | 1.781 |
| Example 164 | 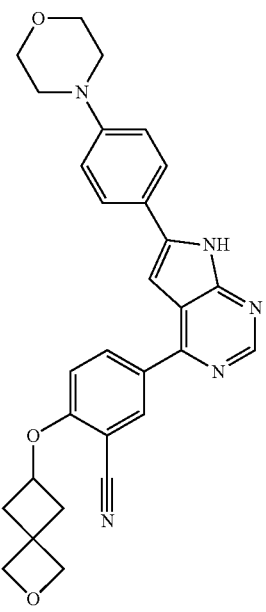 [SMILES: N#Cc1cc(-c2ncnc3[nH]c(-c4ccc(N5CCOCC5)cc4)cc23)ccc1OC1CC2(COC2)C1] | 95.138 | 56.12 |

TABLE 1-continued
| Examples | Structure | IKKε-IC50 (nM) | TBK1-IC50 (nM) |
|---|---|---|---|
| Example 165 | 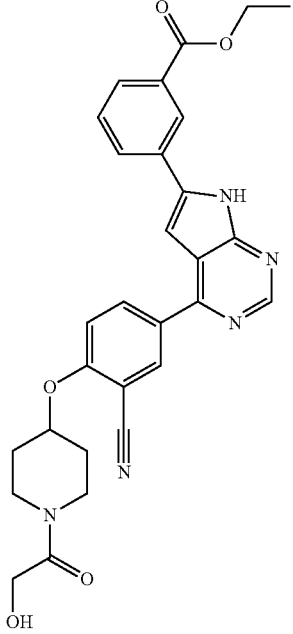 [SMILES: CCOC(=O)c1cccc(-c2cc3c(-c4ccc(OC5CCN(C(=O)CO)CC5)c(C#N)c4)ncnc3[nH]2)c1] | nd | nd |
| Example 166 | 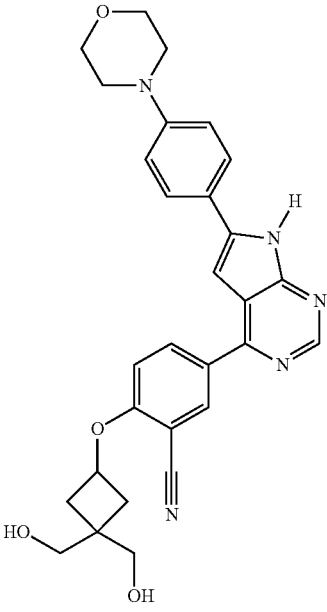 [SMILES: N#Cc1cc(-c2ncnc3[nH]c(-c4ccc(N5CCOCC5)cc4)cc23)ccc1OC1CC(CO)(CO)C1] | 41.85 | 16.232 |

TABLE 1-continued
| Examples | Structure | IKKε-IC50 (nM) | TBK1-IC50 (nM) |
|---|---|---|---|
| Example 167 | 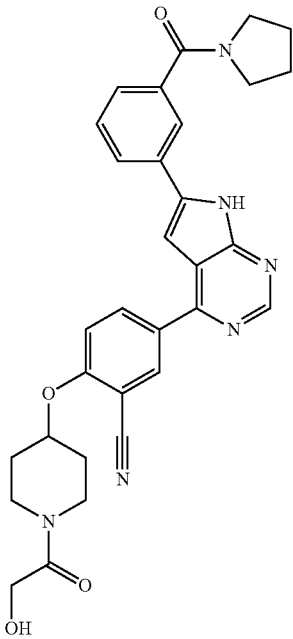 [SMILES: N#Cc1cc(-c2ncnc3[nH]c(-c4cccc(C(=O)N5CCCC5)c4)cc23)ccc1OC1CCN(C(=O)CO)CC1] | 4.142 | 1.865 |
| Example 168 | 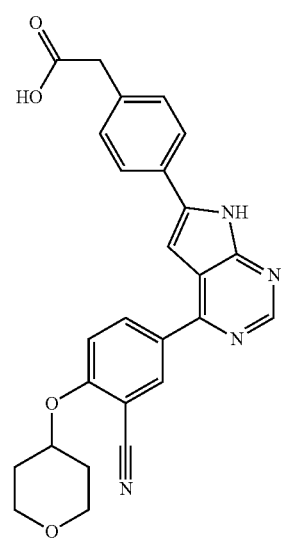 [SMILES: N#Cc1cc(-c2ncnc3[nH]c(-c4ccc(CC(=O)O)cc4)cc23)ccc1OC1CCOCC1] | 15.662 | 13.717 |

TABLE 1-continued

| Examples | Structure | IKKε-IC50 (nM) | TBK1-IC50 (nM) |
|---|---|---|---|
| Example 169 | 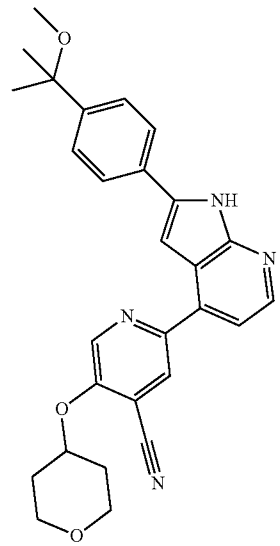 [SMILES: COC(C)(C)c1ccc(-c2cc3c(-c4cc(C#N)c(OC5CCOCC5)cn4)ccnc3[nH]2)cc1] | 13.169 | 4.802 |
| Example 170 | 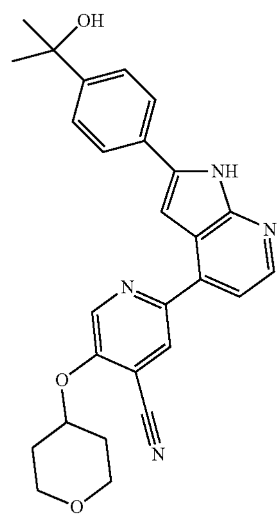 [SMILES: CC(C)(O)c1ccc(-c2cc3c(-c4cc(C#N)c(OC5CCOCC5)cn4)ccnc3[nH]2)cc1] | 8.181 | 3.838 |
| Example 171 | 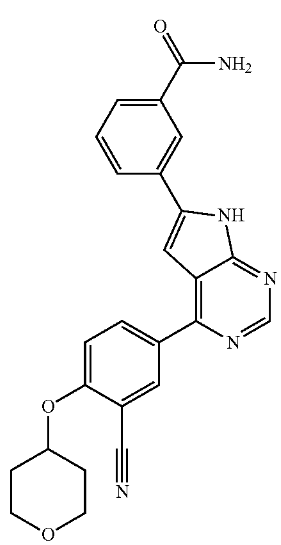 [SMILES: N#Cc1cc(-c2ncnc3[nH]c(-c4cccc(C(N)=O)c4)cc23)ccc1OC1CCOCC1] | 10.608 | 6.399 |

TABLE 1-continued

| Examples | Structure | IKKε-IC50 (nM) | TBK1-IC50 (nM) |
|---|---|---|---|
| Example 172 | 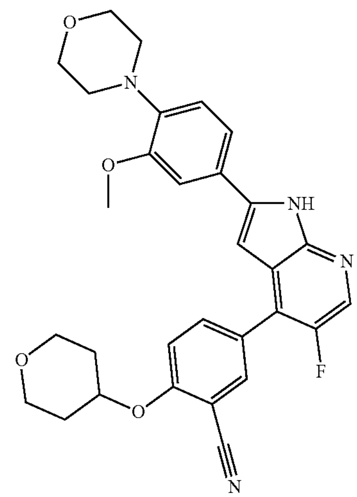 [SMILES: COc1cc(-c2cc3c(-c4ccc(OC5CCOCC5)c(C#N)c4)c(F)cnc3[nH]2)ccc1N1CCOCC1] | 259.919 | 30.224 |
| Example 173 | 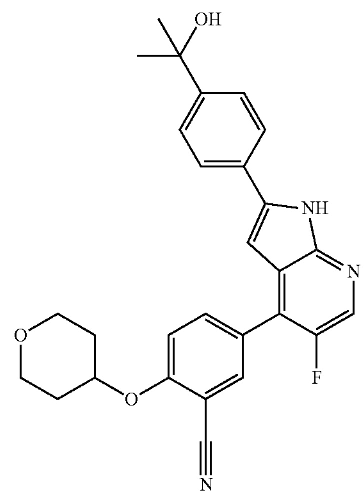 [SMILES: CC(C)(O)c1ccc(-c2cc3c(-c4ccc(OC5CCOCC5)c(C#N)c4)c(F)cnc3[nH]2)cc1] | 114.746 | 15.579 |
| Example 174 | 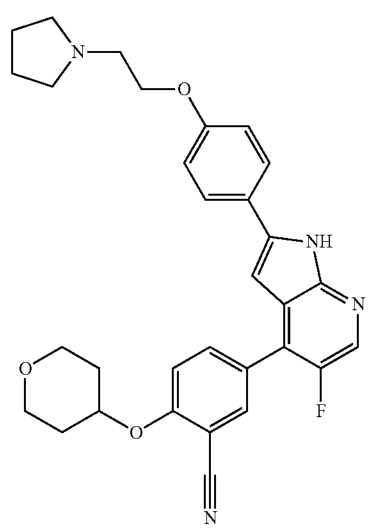 [SMILES: N#Cc1cc(-c2c(F)cnc3[nH]c(-c4ccc(OCCN5CCCC5)cc4)cc23)ccc1OC1CCOCC1] | 8.298 | 6.351 |

TABLE 1-continued
| Examples | Structure | IKKε-IC50 (nM) | TBK1-IC50 (nM) |
|---|---|---|---|
| Example 175 | 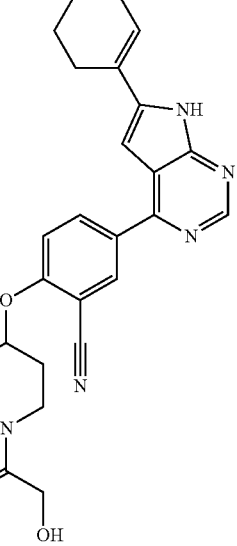 | 5.842 | 1.459 |
| Example 176 | 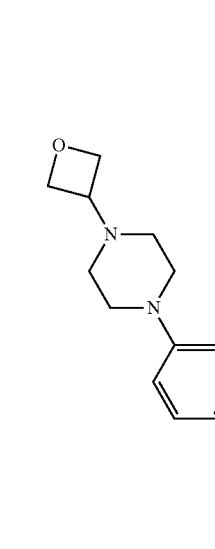 | 1.442 | 1.806 |

TABLE 1-continued

| Examples | Structure | IKKε-IC50 (nM) | TBK1-IC50 (nM) |
|---|---|---|---|
| Example 177 | 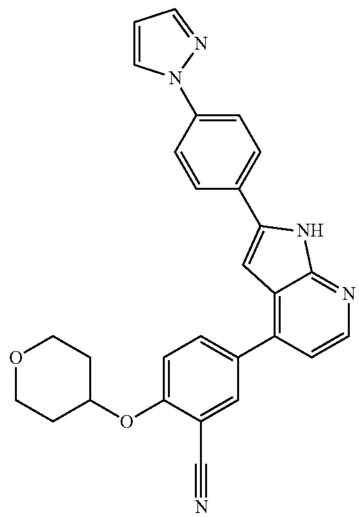 [SMILES: N#Cc1cc(-c2ccnc3[nH]c(-c4ccc(-n5cccn5)cc4)cc23)ccc1OC1CCOCC1] | 1000 | 33.531 |
| Example 178 | 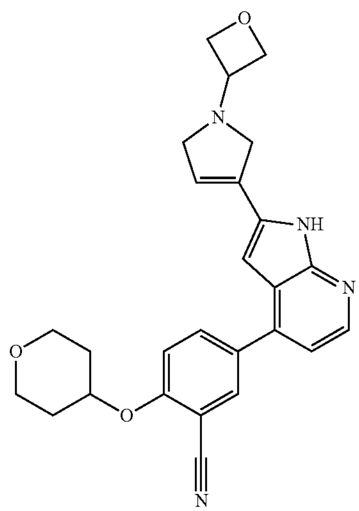 [SMILES: N#Cc1cc(-c2ccnc3[nH]c(C4=CCN(C5COC5)C4)cc23)ccc1OC1CCOCC1] | 18.314 | 7.815 |
| Example 179 | 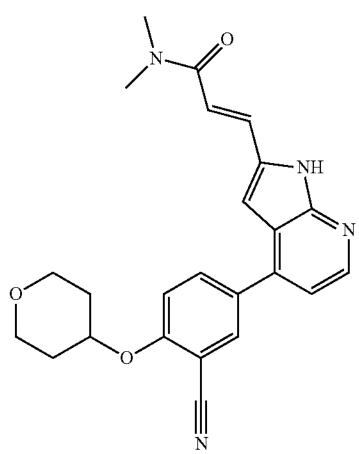 [SMILES: CN(C)C(=O)/C=C/c1cc2c(-c3ccc(OC4CCOCC4)c(C#N)c3)ccnc2[nH]1] | 69.84 | 103.089 |

TABLE 1-continued

| Examples | Structure | IKKε-IC50 (nM) | TBK1-IC50 (nM) |
|---|---|---|---|
| Example 180 | 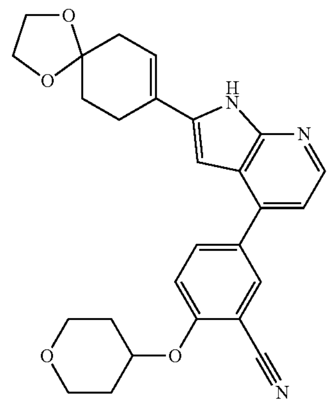 [SMILES: N#Cc1cc(-c2ccnc3[nH]c(C4=CCC5(CC4)OCCO5)cc23)ccc1OC1CCOCC1] | 20.708 | 3.095 |
| Example 181 | 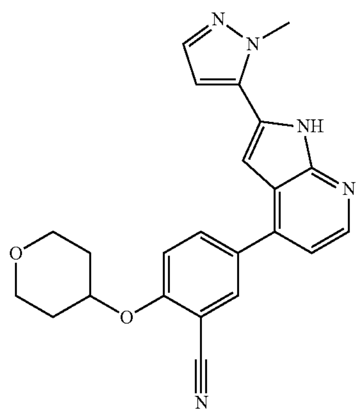 [SMILES: Cn1nccc1-c1cc2c(-c3ccc(OC4CCOCC4)c(C#N)c3)ccnc2[nH]1] | 34.772 | 23.887 |
| Example 182 | 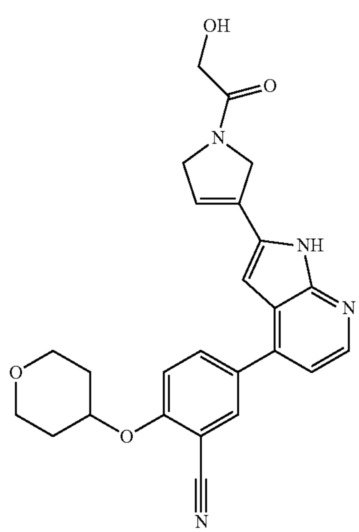 [SMILES: N#Cc1cc(-c2ccnc3[nH]c(C4=CCN(C(=O)CO)C4)cc23)ccc1OC1CCOCC1] | 35.45 | 14.764 |

TABLE 1-continued

| Examples | Structure | IKKε-IC50 (nM) | TBK1-IC50 (nM) |
|---|---|---|---|
| Example 183 | 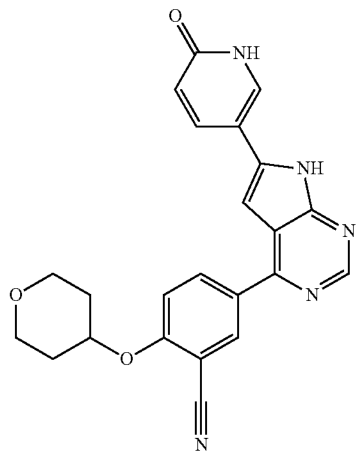 [SMILES: N#Cc1cc(-c2ncnc3[nH]c(-c4ccc(=O)[nH]c4)cc23)ccc1OC1CCOCC1] | 34.731 | 18.873 |
| Example 184 | 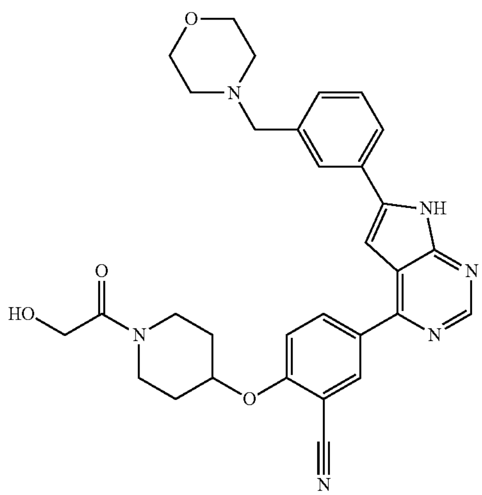 [SMILES: N#Cc1cc(-c2ncnc3[nH]c(-c4cccc(CN5CCOCC5)c4)cc23)ccc1OC1CCN(C(=O)CO)CC1] | 3.429 | 4.987 |
| Example 185 | 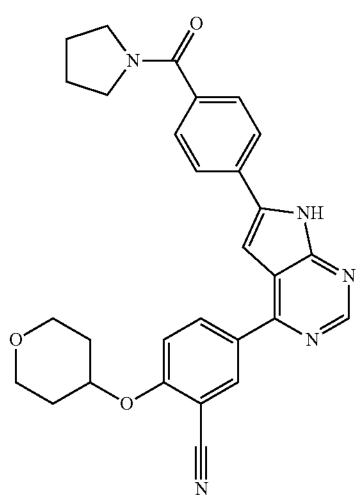 [SMILES: N#Cc1cc(-c2ncnc3[nH]c(-c4ccc(C(=O)N5CCCC5)cc4)cc23)ccc1OC1CCOCC1] | 5.388 | 1.335 |

TABLE 1-continued

| Examples | Structure | IKKε-IC50 (nM) | TBK1-IC50 (nM) |
|---|---|---|---|
| Example 186 | 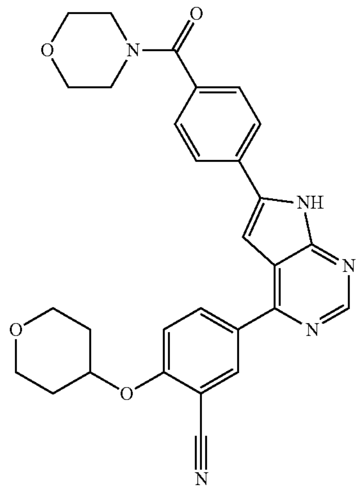 [SMILES: N#Cc1cc(-c2ncnc3[nH]c(-c4ccc(C(=O)N5CCOCC5)cc4)cc23)ccc1OC1CCOCC1] | 4.957 | 1.619 |
| Example 187 | 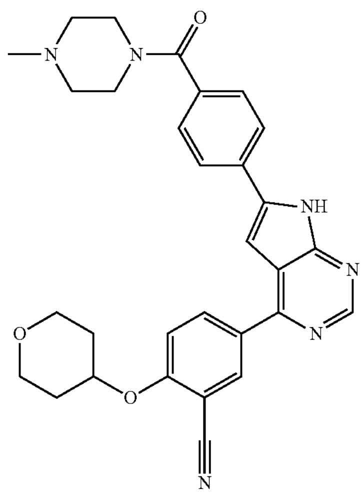 [SMILES: CN1CCN(C(=O)c2ccc(-c3cc4c(-c5ccc(OC6CCOCC6)c(C#N)c5)ncnc4[nH]3)cc2)CC1] | 1.881 | 1.162 |
| Example 188 | 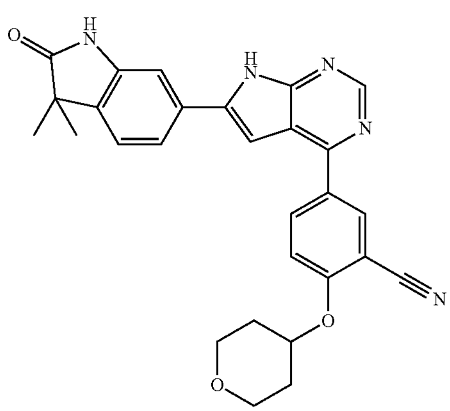 [SMILES: CC1(C)C(=O)Nc2cc(-c3cc4c(-c5ccc(OC6CCOCC6)c(C#N)c5)ncnc4[nH]3)ccc21] | 8.463 | 1.692 |

TABLE 1-continued
| Examples | Structure | IKKε-IC50 (nM) | TBK1-IC50 (nM) |
|---|---|---|---|
| Example 189 | 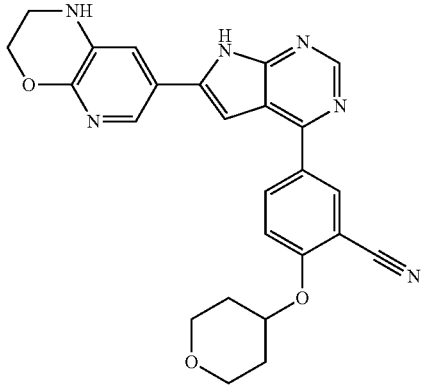 [SMILES: N#Cc1cc(-c2ncnc3[nH]c(-c4cnc5c(c4)NCCO5)cc23)ccc1OC1CCOCC1] | 7.988 | 4.355 |
| Example 190 | 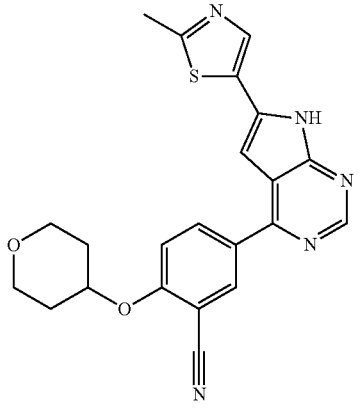 | 14.107 | 7.906 |
| Example 191 | 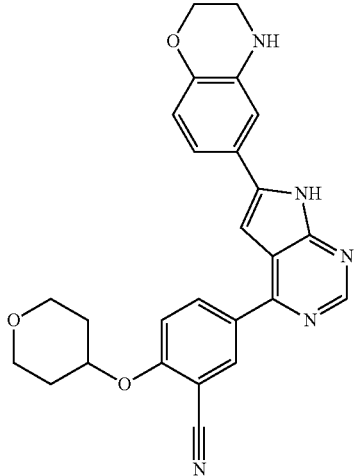 [SMILES: N#Cc1cc(-c2ncnc3[nH]c(-c4ccc5c(c4)NCCO5)cc23)ccc1OC1CCOCC1] | 12.713 | 5.092 |

TABLE 1-continued

| Examples | Structure | IKKε-IC50 (nM) | TBK1-IC50 (nM) |
|---|---|---|---|
| Example 192 | 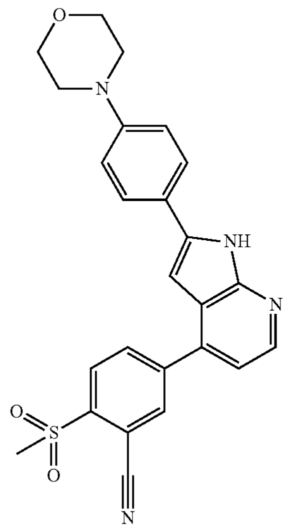 [SMILES: CS(=O)(=O)c1ccc(-c2ccnc3[nH]c(-c4ccc(N5CCOCC5)cc4)cc23)cc1C#N] | 1000 | 275.002 |
| Example 193 | 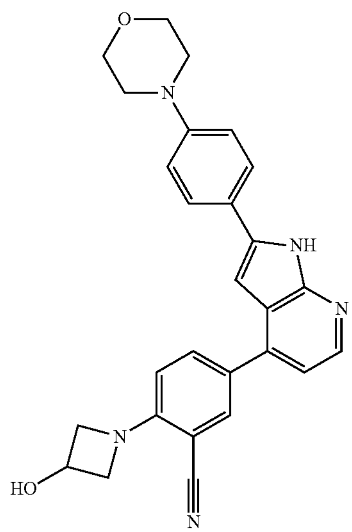 [SMILES: N#Cc1cc(-c2ccnc3[nH]c(-c4ccc(N5CCOCC5)cc4)cc23)ccc1N1CC(O)C1] | 15.522 | 3.327 |
| Example 194 | 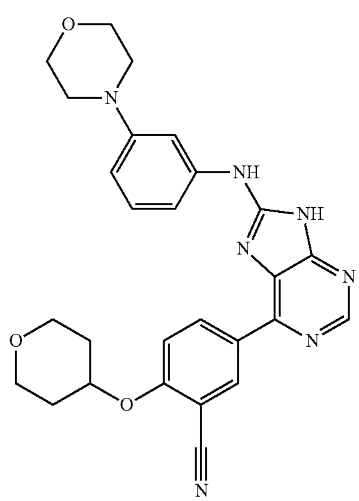 [SMILES: N#Cc1cc(-c2ncnc3[nH]c(Nc4cccc(N5CCOCC5)c4)nc23)ccc1OC1CCOCC1] | 563.741 | 297.65 |

TABLE 1-continued

| Examples | Structure | IKKε-IC50 (nM) | TBK1-IC50 (nM) |
|---|---|---|---|
| Example 195 | 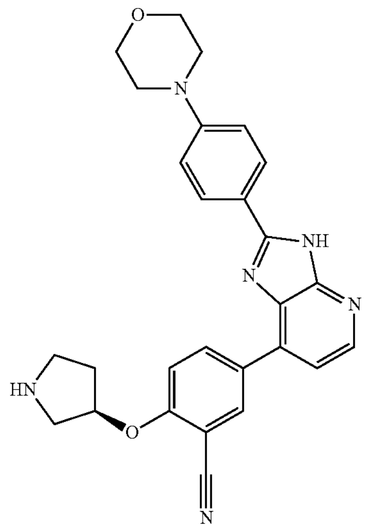 [SMILES: N#Cc1cc(-c2ccnc3[nH]c(-c4ccc(N5CCOCC5)cc4)nc23)ccc1O[C@@H]1CCNC1] | 62.275 | 17.662 |
| Example 196 | 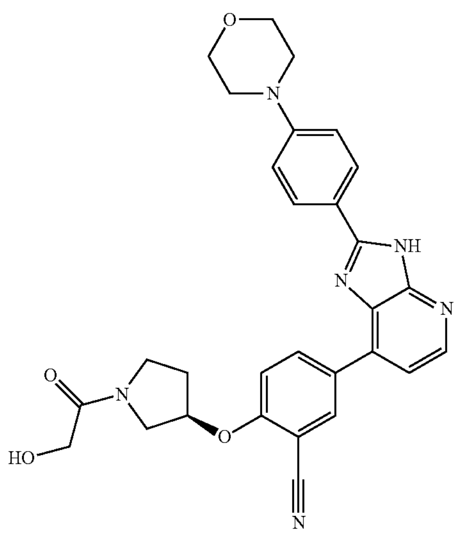 [SMILES: N#Cc1cc(-c2ccnc3[nH]c(-c4ccc(N5CCOCC5)cc4)nc23)ccc1O[C@@H]1CCN(C(=O)CO)C1] | 12.742 | 4.5 |
| Example 197 | 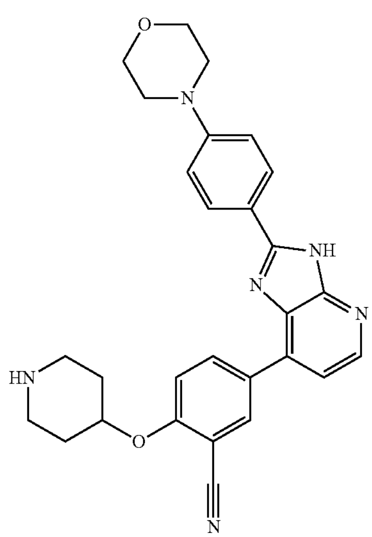 [SMILES: N#Cc1cc(-c2ccnc3[nH]c(-c4ccc(N5CCOCC5)cc4)nc23)ccc1OC1CCNCC1] | 109.242 | 29.15 |

TABLE 1-continued
| Examples | Structure | IKKε-IC50 (nM) | TBK1-IC50 (nM) |
|---|---|---|---|
| Example 198 | 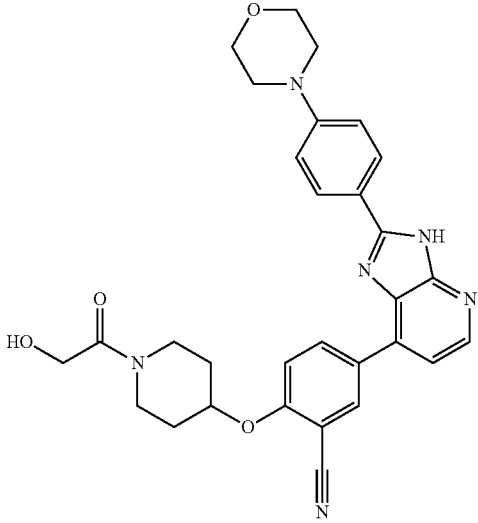 | 3.422 | 2.299 |
| Example 199 | 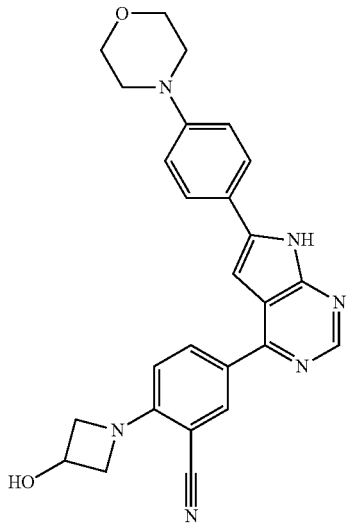 | 1000 | 2.146 |
| Example 200 | 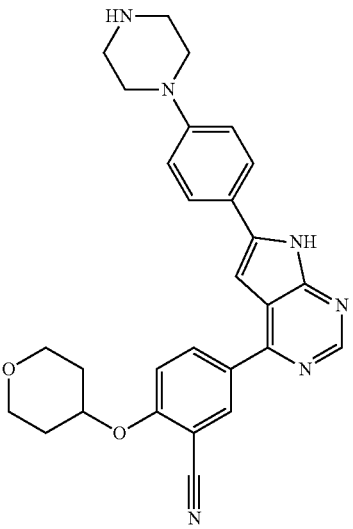 | 1.032 | 0.644 |

TABLE 1-continued
| Examples | Structure | IKKε-IC50 (nM) | TBK1-IC50 (nM) |
|---|---|---|---|
| Example 214 | 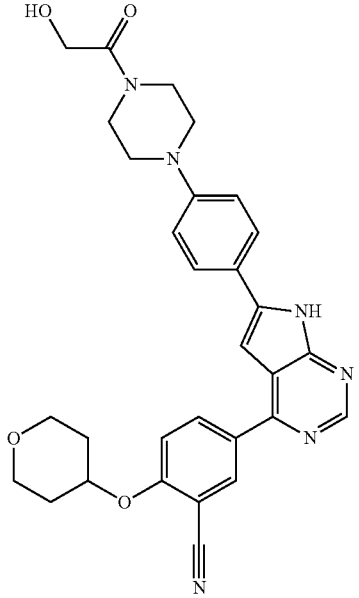 [SMILES: N#Cc1cc(-c2ncnc3[nH]c(-c4ccc(N5CCN(C(=O)CO)CC5)cc4)cc23)ccc1OC1CCOCC1] | 4.43 | 0.762 |
| Example 215 | 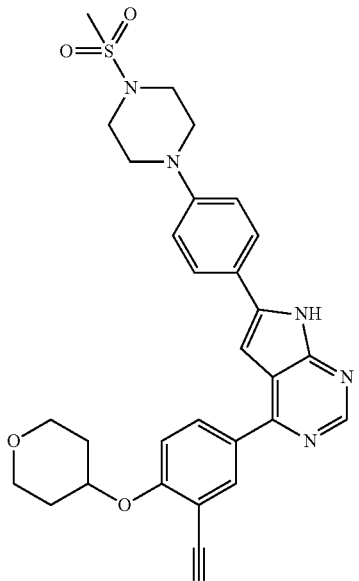 | 3.15 | 1.419 |
| Example 216 | 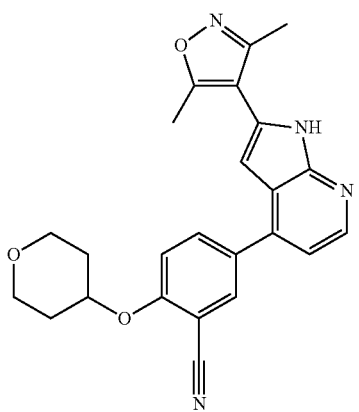 [SMILES: Cc1noc(C)c1-c1cc2c(-c3ccc(OC4CCOCC4)c(C#N)c3)ccnc2[nH]1] | 121.396 | 67.563 |

TABLE 1-continued
| Examples | Structure | IKKε-IC50 (nM) | TBK1-IC50 (nM) |
|---|---|---|---|
| Example 217 | 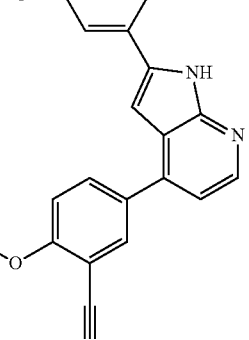 | 34.72 | 19.286 |
| Example 218 | 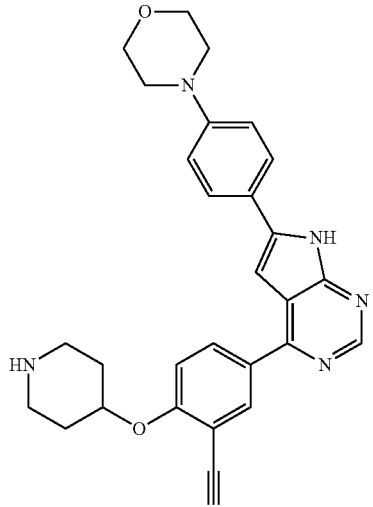 | 139.844 | 31.057 |
| Example 219 | 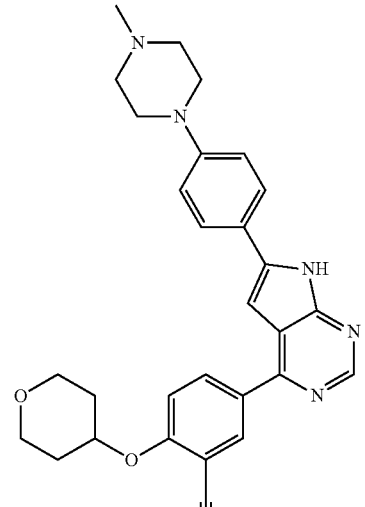 | 3.37 | 2.501 |

TABLE 1-continued
| Examples | Structure | IKKε-IC50 (nM) | TBK1-IC50 (nM) |
|---|---|---|---|
| Example 220 | 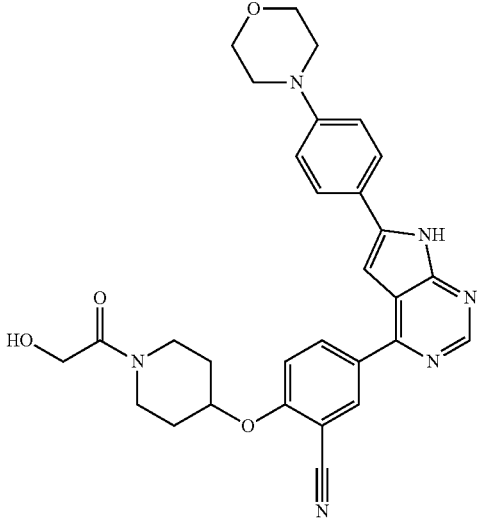 | 1.48 | 0.503 |
| Example 221 | 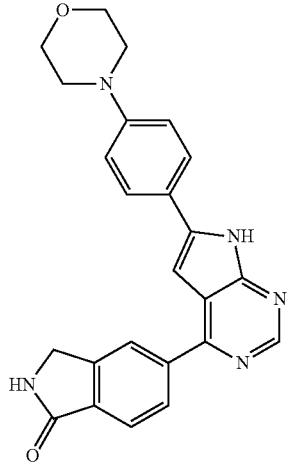 [SMILES: O=C1NCc2cc(-c3ncnc4[nH]c(-c5ccc(N6CCOCC6)cc5)cc34)ccc21] | 1000 | 1000 |
| Example 223 | 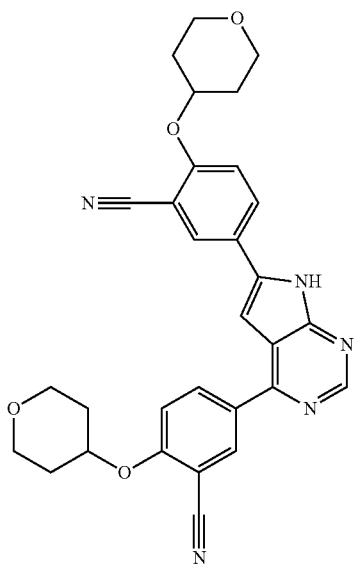 [SMILES: N#Cc1cc(-c2cc3c(-c4ccc(OC5CCOCC5)c(C#N)c4)ncnc3[nH]2)ccc1OC1CCOCC1] | 25.097 | 2.839 |

TABLE 1-continued
| Examples | Structure | IKKε-IC50 (nM) | TBK1-IC50 (nM) |
|---|---|---|---|
| Example 224 | 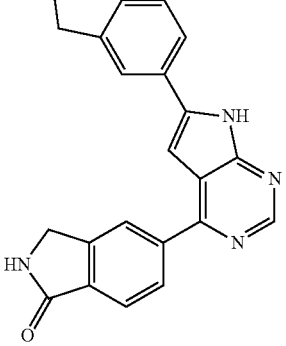 | 1000 | 1000 |
| Example 225 | 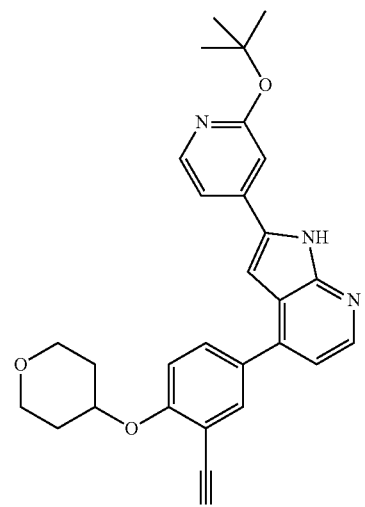 | 1000 | 1000 |
| Example 226 | 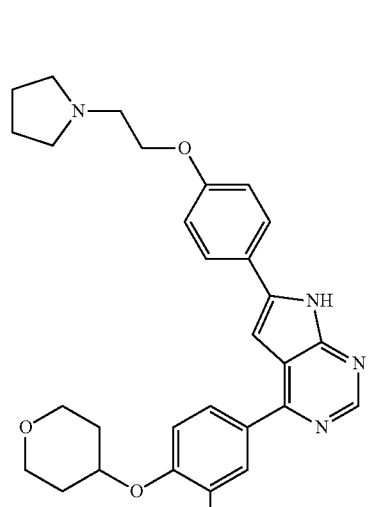 | 1.8 | 1.241 |

TABLE 1-continued
| Examples | Structure | IKKε-IC50 (nM) | TBK1-IC50 (nM) |
|---|---|---|---|
| Example 227 | 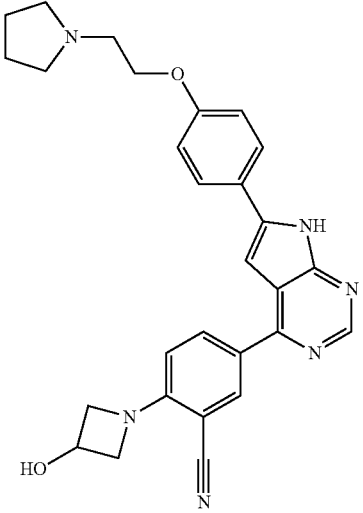 [SMILES: N#Cc1cc(-c2ncnc3[nH]c(-c4ccc(OCCN5CCCC5)cc4)cc23)ccc1N1CC(O)C1] | 70.201 | 42.414 |
| Example 228 | 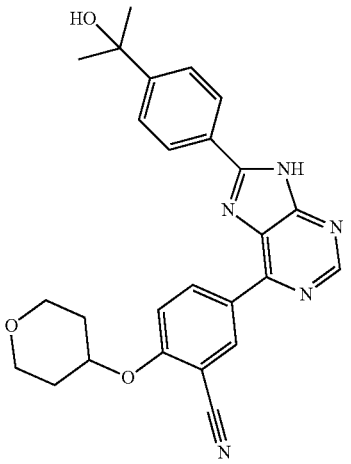 [SMILES: CC(C)(O)c1ccc(-c2nc3c(-c4ccc(OC5CCOCC5)c(C#N)c4)ncnc3[nH]2)cc1] | 14.502 | 1.622 |
| Example 229 | 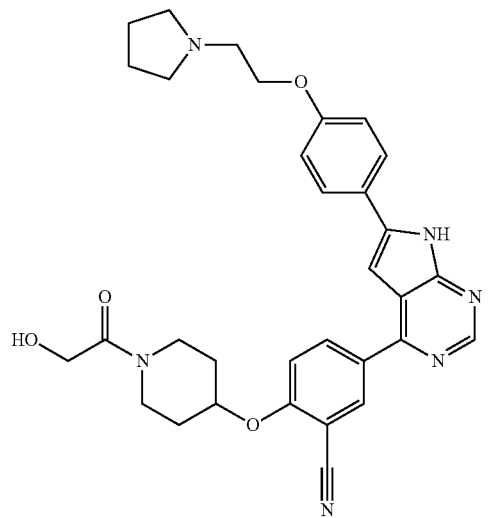 | 0.851 | 1.009 |

TABLE 1-continued

| Examples | Structure | IKKε-IC50 (nM) | TBK1-IC50 (nM) |
|---|---|---|---|
| Example 230 | 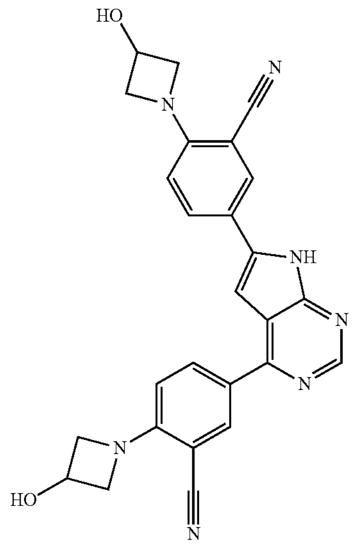 [SMILES: N#Cc1cc(-c2cc3c(-c4ccc(N5CC(O)C5)c(C#N)c4)ncnc3[nH]2)ccc1N1CC(O)C1] | 324.155 | 13.362 |
| Example 231 | 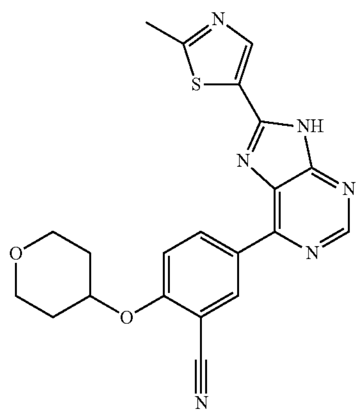 [SMILES: Cc1ncc(-c2nc3c(-c4ccc(OC5CCOCC5)c(C#N)c4)ncnc3[nH]2)s1] | n.d. | 52.756 |
| Example 232 | 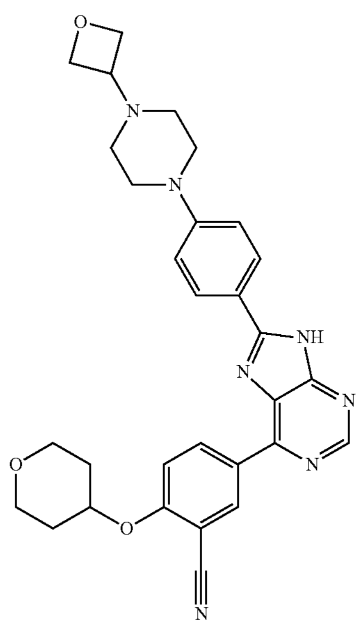 | 15.48 | 4.49 |

TABLE 1-continued

| Examples | Structure | IKKε-IC50 (nM) | TBK1-IC50 (nM) |
|---|---|---|---|
| Example 233 | 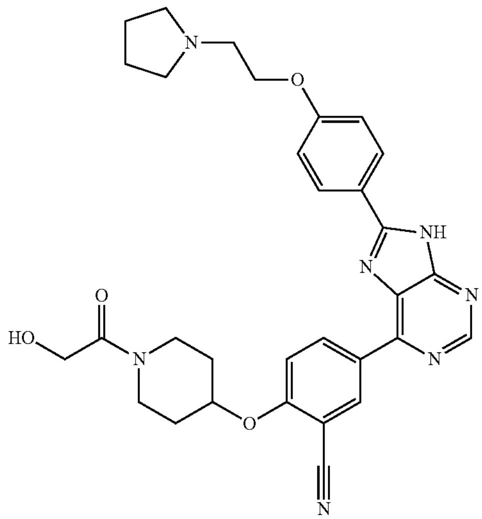 [SMILES: N#Cc1cc(-c2ncnc3[nH]c(-c4ccc(OCCN5CCCC5)cc4)nc23)ccc1OC1CCN(C(=O)CO)CC1] | 2.036 | 3.33 |
| Example 234 | Chiral | 8.642 | 2.341 |
| Example 235 | 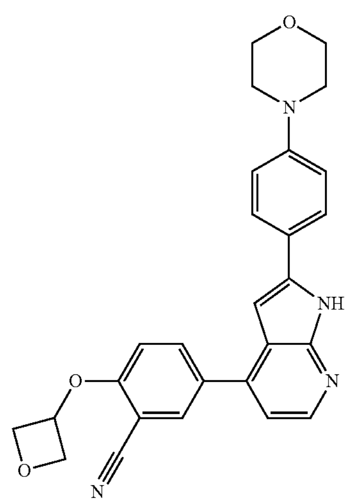 [SMILES: N#Cc1cc(-c2ccnc3[nH]c(-c4ccc(N5CCOCC5)cc4)cc23)ccc1OC1COC1] | 103.085 | 9.266 |

TABLE 1-continued

| Examples | Structure | IKKε-IC50 (nM) | TBK1-IC50 (nM) |
|---|---|---|---|
| Example 236 | 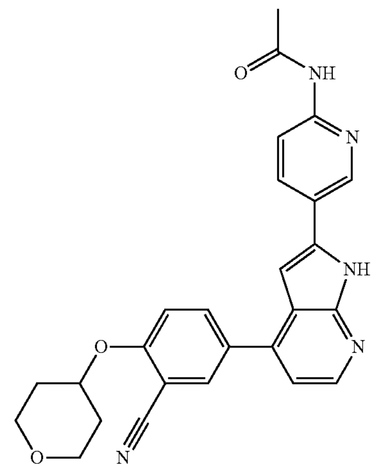 [SMILES: CC(=O)Nc1ccc(-c2cc3c(-c4ccc(OC5CCOCC5)c(C#N)c4)ccnc3[nH]2)cn1] | 7.912 | 15.804 |
| Example 237 | 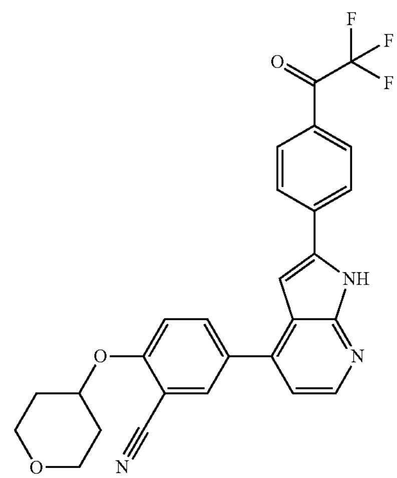 [SMILES: N#Cc1cc(-c2ccnc3[nH]c(-c4ccc(C(=O)C(F)(F)F)cc4)cc23)ccc1OC1CCOCC1] | 29.664 | 11.445 |
| Example 238 | 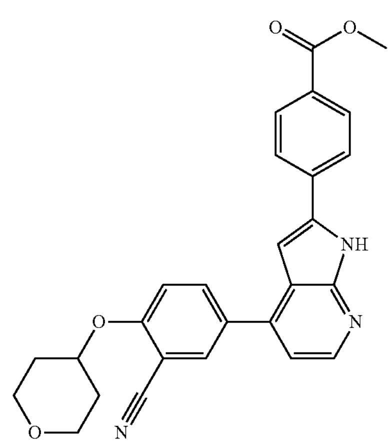 [SMILES: COC(=O)c1ccc(-c2cc3c(-c4ccc(OC5CCOCC5)c(C#N)c4)ccnc3[nH]2)cc1] | 1000 | 268.047 |

TABLE 1-continued

| Examples | Structure | IKKε-IC50 (nM) | TBK1-IC50 (nM) |
|---|---|---|---|
| Example 239 | 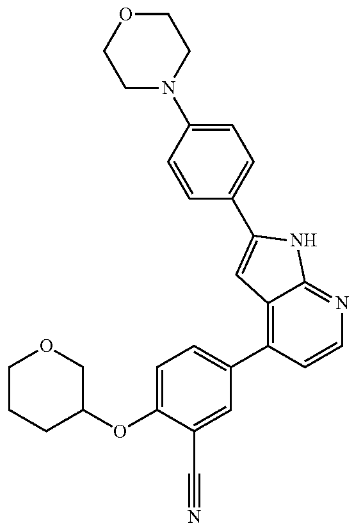 [SMILES: N#Cc1cc(-c2ccnc3[nH]c(-c4ccc(N5CCOCC5)cc4)cc23)ccc1OC1CCCOC1] | 192.838 | 44.693 |
| Example 240 | 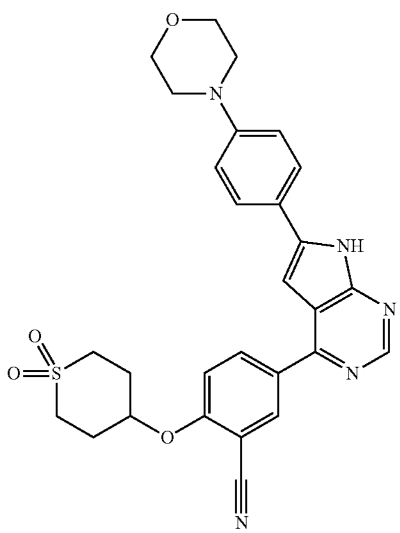 [SMILES: N#Cc1cc(-c2ncnc3[nH]c(-c4ccc(N5CCOCC5)cc4)cc23)ccc1OC1CCS(=O)(=O)CC1] | 33.821 | 3.824 |
| Example 241 | 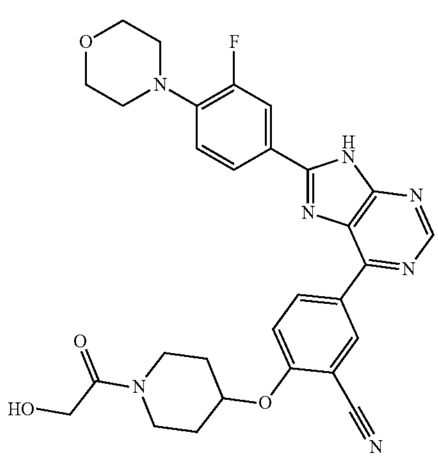 [SMILES: N#Cc1cc(-c2ncnc3[nH]c(-c4ccc(N5CCOCC5)c(F)c4)nc23)ccc1OC1CCN(C(=O)CO)CC1] | 2.637 | 1.299 |

TABLE 1-continued

| Examples | Structure | IKKε-IC50 (nM) | TBK1-IC50 (nM) |
|---|---|---|---|
| Example 242 | 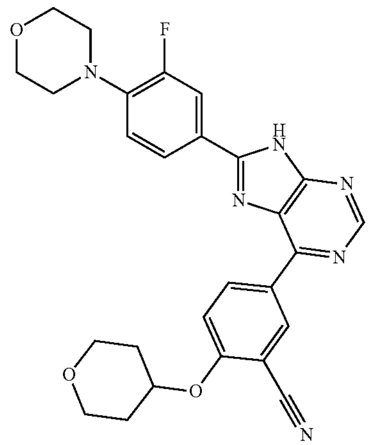 [SMILES: N#Cc1cc(-c2ncnc3[nH]c(-c4ccc(N5CCOCC5)c(F)c4)nc23)ccc1OC1CCOCC1] | 1000 | 3.334 |
| Example 243 | 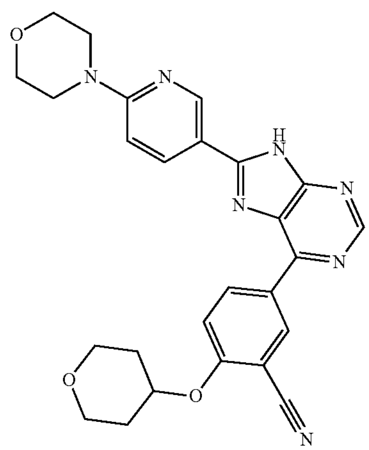 [SMILES: N#Cc1cc(-c2ncnc3[nH]c(-c4ccc(N5CCOCC5)nc4)nc23)ccc1OC1CCOCC1] | 1000 | 11.6 |
| Example 244 | 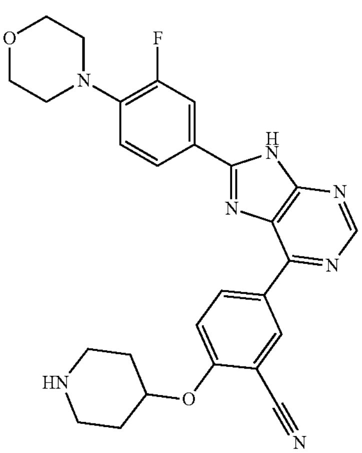 [SMILES: N#Cc1cc(-c2ncnc3[nH]c(-c4ccc(N5CCOCC5)c(F)c4)nc23)ccc1OC1CCNCC1] | 150.934 | 35.847 |

TABLE 1-continued
| Examples | Structure | IKKε-IC50 (nM) | TBK1-IC50 (nM) |
|---|---|---|---|
| Example 245 | 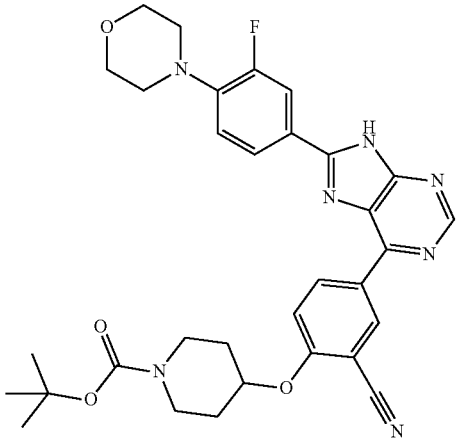 [SMILES: CC(C)(C)OC(=O)N1CCC(Oc2ccc(-c3ncnc4[nH]c(-c5ccc(N6CCOCC6)c(F)c5)nc34)cc2C#N)CC1] | 1000 | 1000 |
| Example 246 | 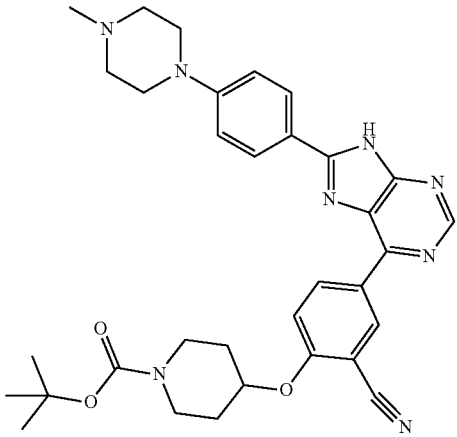 [SMILES: CN1CCN(c2ccc(-c3nc4c(-c5ccc(OC6CCN(C(=O)OC(C)(C)C)CC6)c(C#N)c5)ncnc4[nH]3)cc2)CC1] | 1000 | 1000 |
| Example 247 | 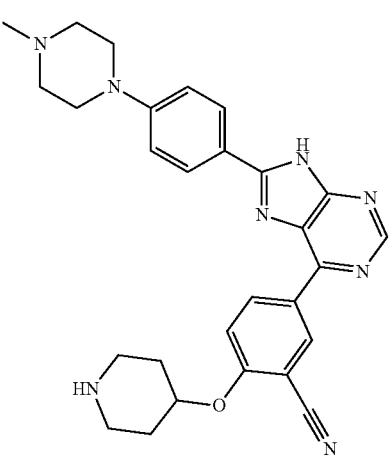 [SMILES: CN1CCN(c2ccc(-c3nc4c(-c5ccc(OC6CCNCC6)c(C#N)c5)ncnc4[nH]3)cc2)CC1] | 16.823 | 11.283 |

TABLE 1-continued

| Examples | Structure | IKKε-IC50 (nM) | TBK1-IC50 (nM) |
|---|---|---|---|
| Example 248 | 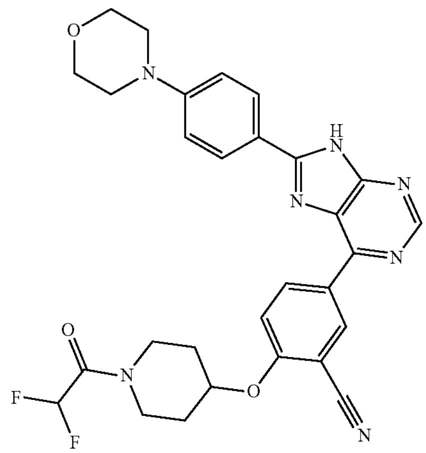 [SMILES: N#Cc1cc(-c2ncnc3[nH]c(-c4ccc(N5CCOCC5)cc4)nc23)ccc1OC1CCN(C(=O)C(F)F)CC1] | 9.823 | 3.631 |
| Example 249 | 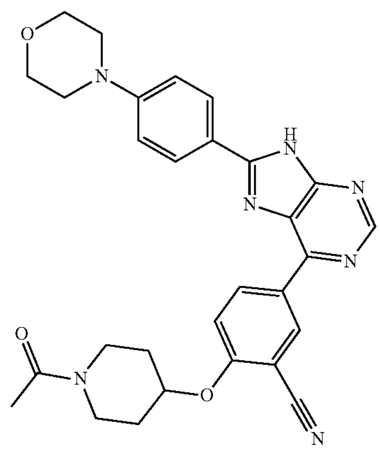 [SMILES: CC(=O)N1CCC(Oc2ccc(-c3ncnc4[nH]c(-c5ccc(N6CCOCC6)cc5)nc34)cc2C#N)CC1] | 14.164 | 6.093 |
| Example 250 | 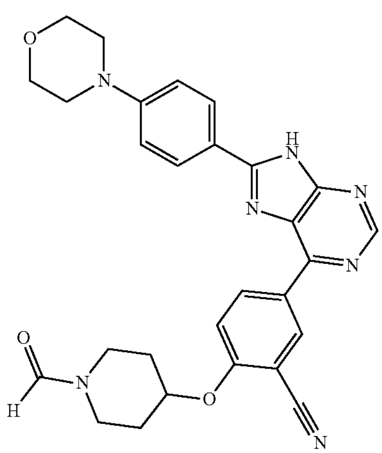 [SMILES: N#Cc1cc(-c2ncnc3[nH]c(-c4ccc(N5CCOCC5)cc4)nc23)ccc1OC1CCN(C=O)CC1] | 9.857 | 2.246 |

TABLE 1-continued

| Examples | Structure | IKKε-IC50 (nM) | TBK1-IC50 (nM) |
|---|---|---|---|
| Example 251 | 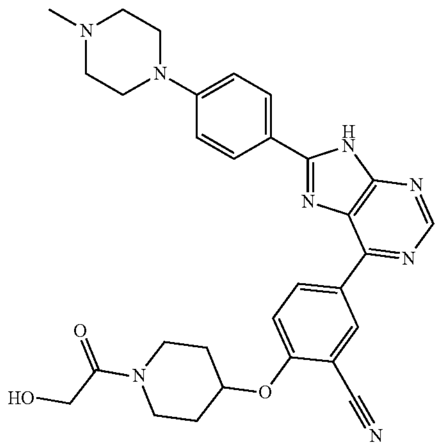 [SMILES: CN1CCN(c2ccc(-c3nc4c(-c5ccc(OC6CCN(C(=O)CO)CC6)c(C#N)c5)ncnc4[nH]3)cc2)CC1] | 0.815 | 0.883 |
| Example 252 | 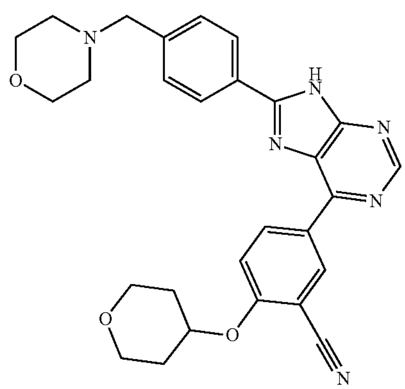 [SMILES: N#Cc1cc(-c2ncnc3[nH]c(-c4ccc(CN5CCOCC5)cc4)nc23)ccc1OC1CCOCC1] | 4.85 | 3.34 |
| Example 253 | 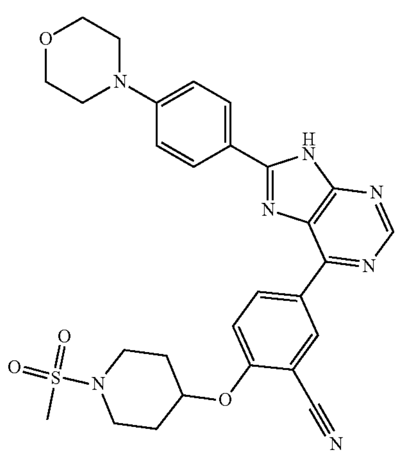 [SMILES: CS(=O)(=O)N1CCC(Oc2ccc(-c3ncnc4[nH]c(-c5ccc(N6CCOCC6)cc5)nc34)cc2C#N)CC1] | 39.809 | 19.783 |

TABLE 1-continued

| Examples | Structure | IKKε-IC50 (nM) | TBK1-IC50 (nM) |
| --- | --- | --- | --- |
| Example 254 | 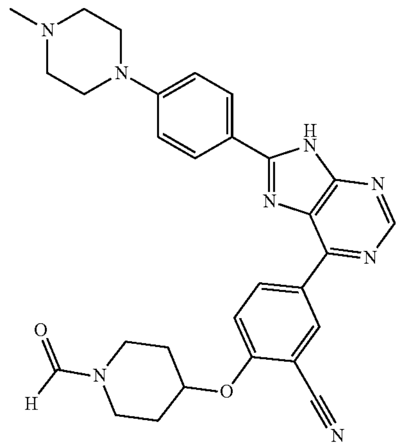 [SMILES: CN1CCN(c2ccc(-c3nc4c(-c5ccc(OC6CCN(C=O)CC6)c(C#N)c5)ncnc4[nH]3)cc2)CC1] | 2.688 | 4.218 |
| Example 255 | 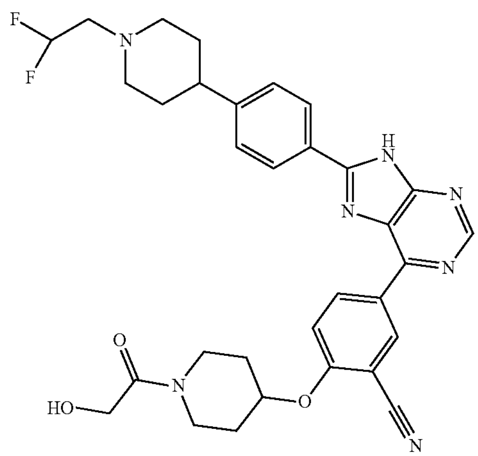 [SMILES: N#Cc1cc(-c2ncnc3[nH]c(-c4ccc(C5CCN(CC(F)F)CC5)cc4)nc23)ccc1OC1CCN(C(=O)CO)CC1] | 3.482 | 1.528 |
| Example 256 | 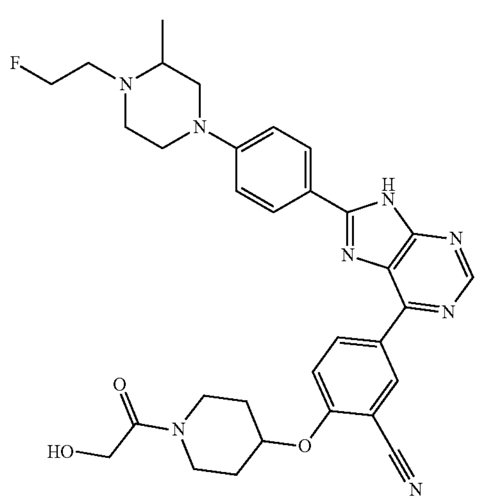 [SMILES: CC1CN(c2ccc(-c3nc4c(-c5ccc(OC6CCN(C(=O)CO)CC6)c(C#N)c5)ncnc4[nH]3)cc2)CCN1CCF] | 1.794 | 2.4 |

TABLE 1-continued
| Examples | Structure | IKKε-IC50 (nM) | TBK1-IC50 (nM) |
|---|---|---|---|
| Example 257 | 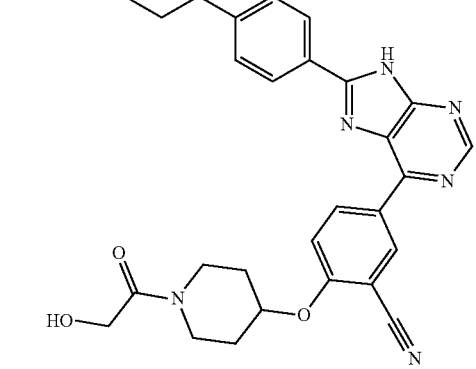 | 13.955 | 3.799 |
| Example 258 | 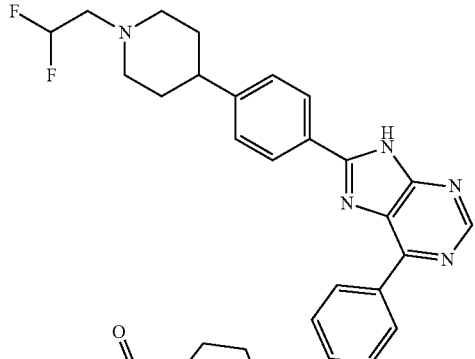 | 12.887 | 6.401 |
| Example 259 | 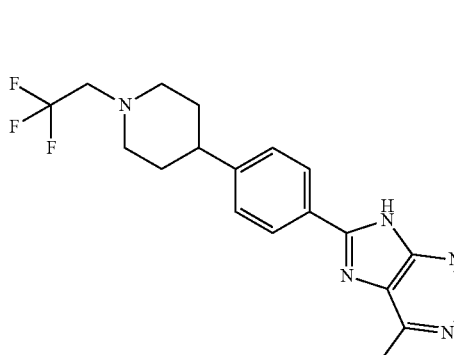 | 45.474 | 12.208 |

TABLE 1-continued

| Examples | Structure | IKKε-IC50 (nM) | TBK1-IC50 (nM) |
|---|---|---|---|
| Example 260 | 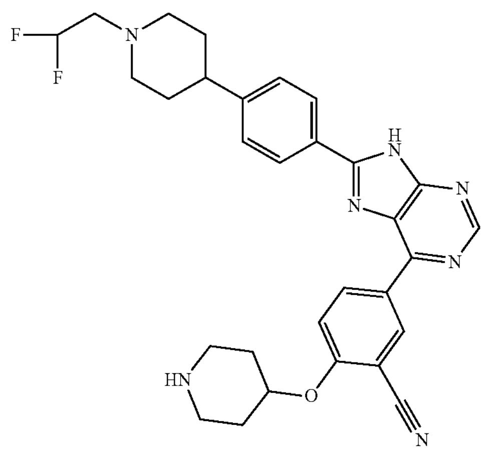 [SMILES: N#Cc1cc(-c2ncnc3[nH]c(-c4ccc(C5CCN(CC(F)F)CC5)cc4)nc23)ccc1OC1CCNCC1] | 84.436 | 26.009 |
| Example 261 | 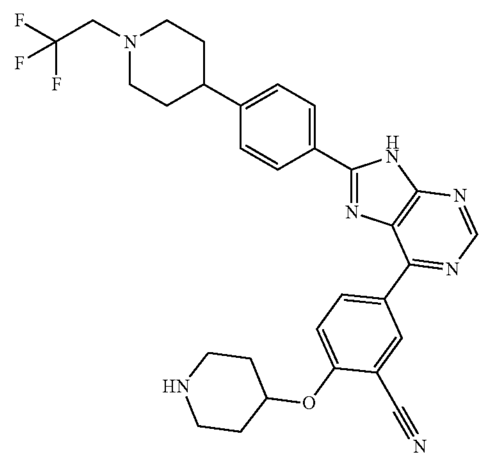 [SMILES: N#Cc1cc(-c2ncnc3[nH]c(-c4ccc(C5CCN(CC(F)(F)F)CC5)cc4)nc23)ccc1OC1CCNCC1] | 96.023 | 37.143 |
| Example 262 | 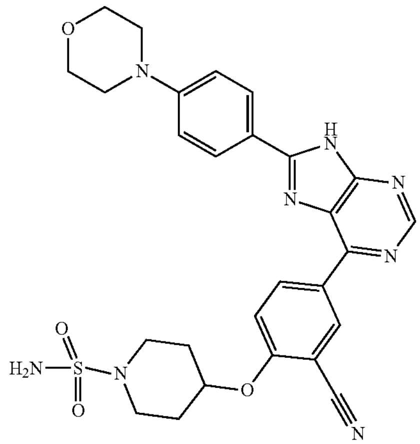 [SMILES: N#Cc1cc(-c2ncnc3[nH]c(-c4ccc(N5CCOCC5)cc4)nc23)ccc1OC1CCN(S(N)(=O)=O)CC1] | 4.224 | 2.078 |

TABLE 1-continued

| Examples | Structure | IKKε-IC50 (nM) | TBK1-IC50 (nM) |
|---|---|---|---|
| Example 263 | 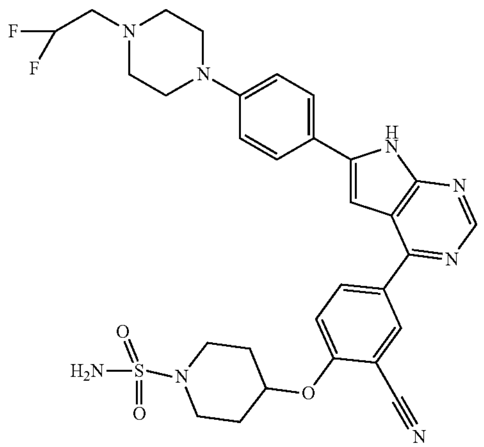 [SMILES: N#Cc1cc(-c2ncnc3[nH]c(-c4ccc(N5CCN(CC(F)F)CC5)cc4)cc23)ccc1OC1CCN(S(N)(=O)=O)CC1] | 6.322 | 3.068 |
| Example 264 | 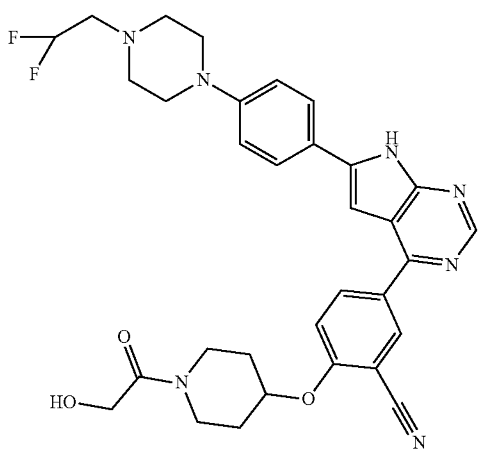 [SMILES: N#Cc1cc(-c2ncnc3[nH]c(-c4ccc(N5CCN(CC(F)F)CC5)cc4)cc23)ccc1OC1CCN(C(=O)CO)CC1] | 2.608 | 0.91 |
| Example 265 | 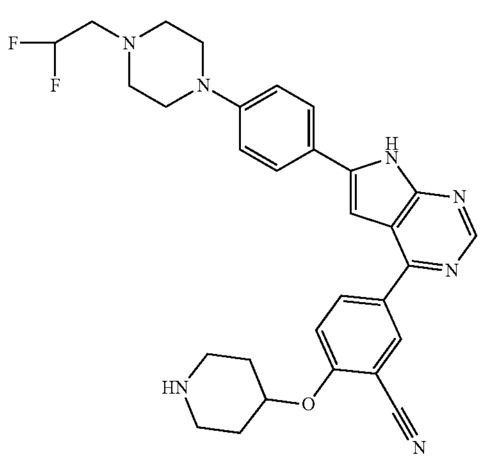 [SMILES: N#Cc1cc(-c2ncnc3[nH]c(-c4ccc(N5CCN(CC(F)F)CC5)cc4)cc23)ccc1OC1CCNCC1] | 58.655 | 16.247 |

TABLE 1-continued

| Examples | Structure | IKKε-IC50 (nM) | TBK1-IC50 (nM) |
|---|---|---|---|
| Example 266 | 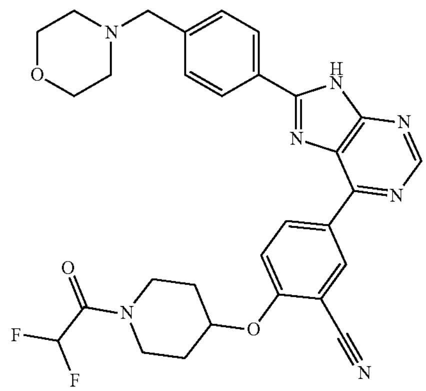 [SMILES: N#Cc1cc(-c2ncnc3[nH]c(-c4ccc(CN5CCOCC5)cc4)nc23)ccc1OC1CCN(C(=O)C(F)F)CC1] | 7.954 | 8.869 |
| Example 267 | 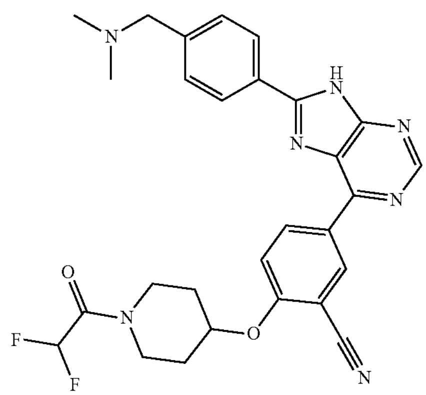 [SMILES: CN(C)Cc1ccc(-c2nc3c(-c4ccc(OC5CCN(C(=O)C(F)F)CC5)c(C#N)c4)ncnc3[nH]2)cc1] | 1000 | 1000 |
| Example 268 | 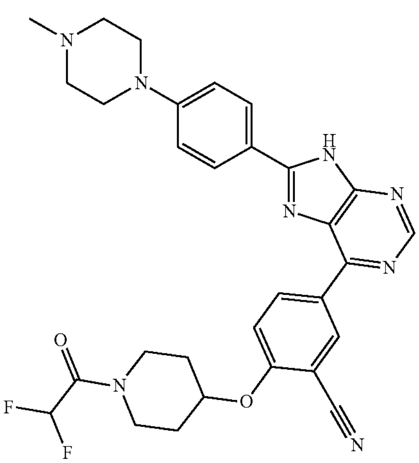 [SMILES: CN1CCN(c2ccc(-c3nc4c(-c5ccc(OC6CCN(C(=O)C(F)F)CC6)c(C#N)c5)ncnc4[nH]3)cc2)CC1] | 2.254 | 3.921 |

TABLE 1-continued

| Examples | Structure | IKKε-IC50 (nM) | TBK1-IC50 (nM) |
|---|---|---|---|
| Example 269 | 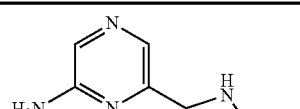 | 47.006 | 32.665 |

While the foregoing description describes specific embodiments and aspects, those with ordinary skill in the art will appreciate that various modifications and alternatives can be developed. Accordingly, the particular embodiments and aspects described above are meant to be illustrative only, and not to limit the scope of the invention, which is to be given the full breadth of the appended claims, and any and all equivalents thereof.

The invention claimed is:

1. A compound of formula (I):

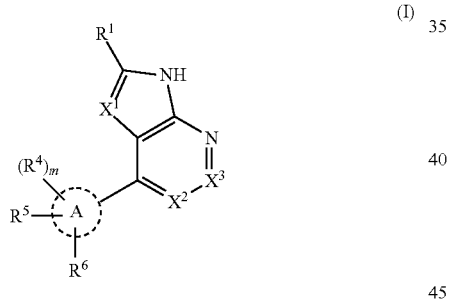

(I)

wherein:

A is a 6 membered aryl or heteroaryl ring;

$X^1$ is $CR^2$ or N;

$X^2$ and $X^3$ are independently $CR^3$ or N, provided that at most only one of $X^2$ and $X^3$ is N;

$R^1$ is selected from the group consisting of $C_{1-6}$ alkyl, $C_{2-6}$ alkenyl, $C_{2-6}$ alkynyl, —$OR^a$, —$C(O)R^a$, —$C(O)OR^a$, —$C(O)NR^aR^b$, —$OC(O)NR^aR^b$, —$NR^aR^b$, —CN, —$NR^aC(O)R^b$, —$NR^aC(O)OR^b$, —$S(O)_{0-2}R^a$, —$S(O)_2 NR^aR^b$, and —$NR^aS(O)_2R^b$, wherein each $C_{1-6}$ alkyl, $C_{2-6}$ alkenyl and $C_{2-6}$ alkynyl is optionally substituted with one to five $R^{20}$ groups;

or $R^1$ has the following structure:

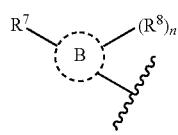

wherein B is selected from the group consisting of $C_{6-10}$ aryl, $C_{3-10}$ cycloalkyl, 5-10 membered heteroaryl and 3-12 membered heterocyclyl;

$R^2$ is selected from the group consisting of $C_{1-6}$ alkyl, $C_{3-10}$ cycloalkyl, 3-12 membered heterocyclyl, $C_{1-6}$ heteroalkyl, $C_{1-6}$ haloalkyl, $C_{2-6}$ alkenyl, $C_{2-6}$ alkynyl, —$NR^aR^b$, halogen, —CN, —$NO_2$, —$OR^a$, —$C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^a$, —$S(O)_2 NR^aR^b$ and —$NR^aS(O)_2R^b$;

each $R^3$ is independently selected from the group consisting of H, $C_{1-6}$ alkyl, $C_{3-10}$ cycloalkyl, 3-12 membered heterocyclyl, $C_{1-6}$ heteroalkyl, $C_{1-6}$ haloalkyl, $C_{2-6}$ alkenyl, $C_{2-6}$ alkynyl, —$NR^aR^b$, halogen, —CN, —$NO_2$, —$OR^a$, —$C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^a$, —$S(O)_2NR^aR^b$ and —$NR^aS(O)_2R^b$;

each $R^4$ is independently selected from the group consisting of H, $C_{1-6}$ alkyl, $C_{1-6}$ heteroalkyl, $C_{1-6}$ haloalkyl, $C_{2-6}$ alkenyl, $C_{2-6}$ alkynyl, —$NR^aR^b$, halogen, —$C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^a$, —$S(O)_2 NR^aR^b$, —$NR^aS(O)_2R^b$, —$N_3$, —CN, —$NO_2$ and —$OR^a$;

$R^5$ is selected from the group consisting of $C_{1-6}$ alkyl, $C_{1-6}$ heteroalkyl, —$NR^aR^b$, halogen, —$C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, $C_{6-10}$ aryl, $C_{3-10}$ cycloalkyl, 5-10 membered heteroaryl, 3-12 membered heterocyclyl and —O—$R^9$ wherein each $C_{1-6}$ alkyl, $C_{1-6}$ heteroalkyl, $C_{6-10}$ aryl, $C_{3-10}$ cycloalkyl, 5-10 membered heteroaryl and 3-12 membered heterocyclyl is optionally substituted with one to five $R^{20}$ groups;

or $R^5$ and one $R^4$ are taken together to form a fused $C_6$ aryl, 5-10 membered heteroaryl, 5-10 membered heterocyclyl or $C_{3-6}$ cycloalkyl, each of which is optionally substituted with one to five $R^{20}$ groups;

$R^6$ is —CN located at the meta (3) position with respect to the point of attachment of the A ring;

$R^7$ is selected from the group consisting of H, $C_{1-6}$ alkyl, $C_{2-6}$ alkenyl, $C_{2-6}$ alkynyl, $C_{1-6}$ heteroalkyl, —$NR^aR^b$, halogen, —$C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, —$NO_2$, —$OR^a$, $C_{6-10}$ aryl, $C_{3-10}$ cycloalkyl, 5-10 membered heteroaryl and 3-12 membered heterocyclyl wherein each $C_{1-6}$ alkyl, $C_{2-6}$ alkenyl, $C_{2-6}$ alkynyl, $C_{1-6}$ heteroalkyl, $C_{6-10}$ aryl, $C_{3-10}$ cycloalkyl, 5-10 membered heteroaryl and 3-12 membered heterocyclyl is optionally substituted with one to five $R^{20}$ groups;

each $R^8$ is independently selected from the group consisting of H, $C_{1-6}$ alkyl, $C_{1-6}$ heteroalkyl, $C_{1-6}$ haloalkyl, $C_{1-6}$ hydroxyalkyl, $C_{2-6}$ alkenyl, $C_{2-6}$ alkynyl, $C_{6-10}$ aryl, $C_{3-10}$ cycloalkyl, 5-10 membered heteroaryl, 3-12 membered heterocyclyl, $-NR^aR^b$, halogen, $-C(O)R^a$, $-C(O)OR^a$, $-C(O)NR^aR^b$, $-OC(O)NR^aR^b$, $-NR^aC(O)R^b$, $-NR^aC(O)OR^b$, $-S(O)_2NR^aR^b$, $-NR^aS(O)_2R^b$, $-N_3$, $-CN$, $-NO_2$ and $-OR^a$, wherein each $C_{1-6}$ alkyl, $C_{1-6}$ heteroalkyl, $C_{6-10}$ aryl, $C_{3-10}$ cycloalkyl, 5-10 membered heteroaryl and 3-12 membered heterocyclyl is optionally substituted with one to five $R^{20}$ groups; or $R^7$ and $R^8$ are taken together to form a fused, spiro or bridged $C_{3-10}$ cycloalkyl or 3-12 membered heterocyclyl, which are optionally substituted with one to five $R^{20}$ groups;

$R^9$ is 3-12 membered heterocyclyl, $C_{6-10}$ aryl, $C_{3-10}$ cycloalkyl, or 5-10 membered heteroaryl, each of which is optionally substituted with one to five $R^{20}$ groups;

n is 0-2;

m is 0-3;

each $R^{20}$ is independently $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, halogen, oxo, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)_2NR^aR^b$, $-NR^aS(O)_2R^b$, $-N_3$, $-CN$, or $-NO_2$, or two $R^{20}$ groups can join together to form a fused, spiro or bridged $C_{3-10}$ cycloalkyl or 3-12 membered heterocyclyl ring, wherein each $C_{1-6}$ alkyl, $C_{3-10}$ cycloalkyl, $C_{1-6}$ heteroalkyl, 3-12 membered heterocyclyl, $C_{6-10}$ aryl, and 5-10 membered heteroaryl is optionally substituted with one to five halogen, oxo, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)_2NR^aR^b$, $-NR^aS(O)_2R^b$, $-N_3$, $-CN$, or $-NO_2$;

each $R^{21}$ is independently $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, hydroxyl, amino, $C_{1-6}$ alkylamino, $-CN$ or halogen; and each $R^a$ and $R^b$ is independently H; or $C_{1-6}$ alkyl, $C_{3-10}$ cycloalkyl, $C_{1-6}$ heteroalkyl, 3-12 membered heterocyclyl, $C_{6-10}$ aryl, or 5-10 membered heteroaryl, each of which is optionally substituted with one to five $R^{21}$; or $R^a$ and $R^b$ together with the atoms to which they are attached form a 3-12 membered heterocyclyl optionally substituted with one to five $R^{21}$ groups;

or a pharmaceutically acceptable salt thereof.

2. The compound of claim 1, or a pharmaceutically acceptable salt thereof, wherein $R^1$ has the structure:

3. The compound of claim 2, or a pharmaceutically acceptable salt thereof, wherein B is selected from the group consisting of phenyl, pyridyl, pyrazolyl, pyrazinyl, pyrrolyl, thiazolyl, dihydropyrrolyl, piperidenyl, pyrrolidenyl, bicyclo[2.2.1]heptenyl, isoindolinonyl, indolyl, cyclopropyl, cyclohexyl, cyclopentyl and benzoxazinonyl.

4. The compound of claim 2, or a pharmaceutically acceptable salt thereof, wherein $R^7$ is selected from the group consisting of amino, 3-7 membered heterocyclyl, $C_{1-6}$ alkylaminocarbonyl, $C_{1-6}$ alkoxycarbonyl, $C_{1-6}$ alkoxy, 5-7 membered heterocyclyl-$C_{1-6}$ alkyl, hydroxyl $C_{1-6}$ alkyl, $C_{1-6}$ alkylsulfonyl-5-7 membered heterocyclyl, 5-7 membered heterocyclyl $C_{1-6}$ alkoxy, 5-7 membered heterocyclyloxy, $C_{1-6}$ alkyl, 5-10 membered heteroaryl, and (4-7 membered heterocyclyl)-4-7 membered heterocyclyl.

5. The compound of claim 2, or a pharmaceutically acceptable salt thereof, wherein $R^7$ is a 5-7 membered heterocyclyl.

6. The compound of claim 1, or a pharmaceutically acceptable salt thereof, wherein $R^1$ is selected from the group consisting of:

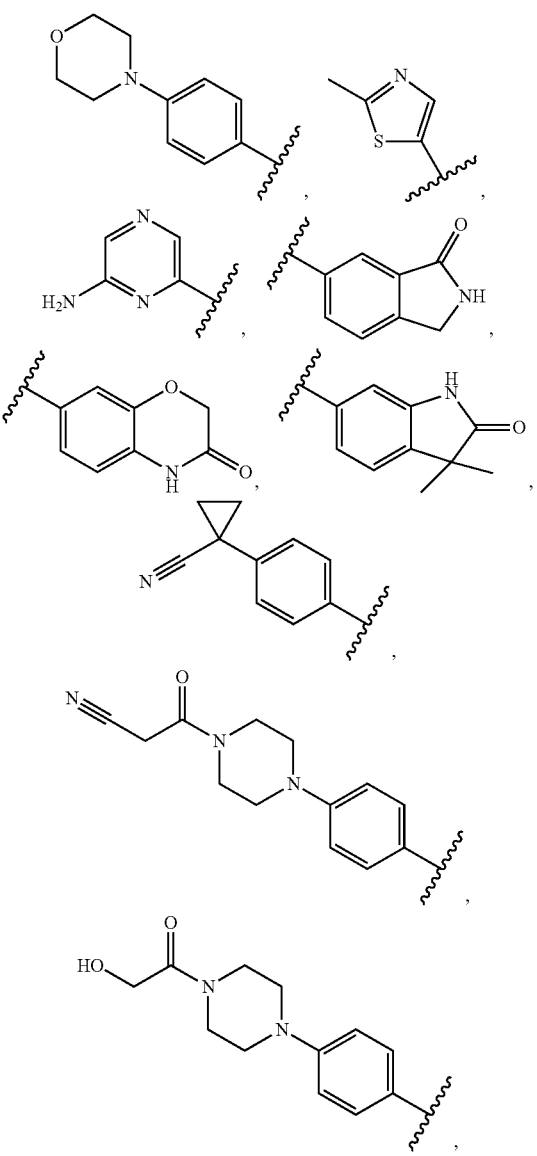

621
-continued
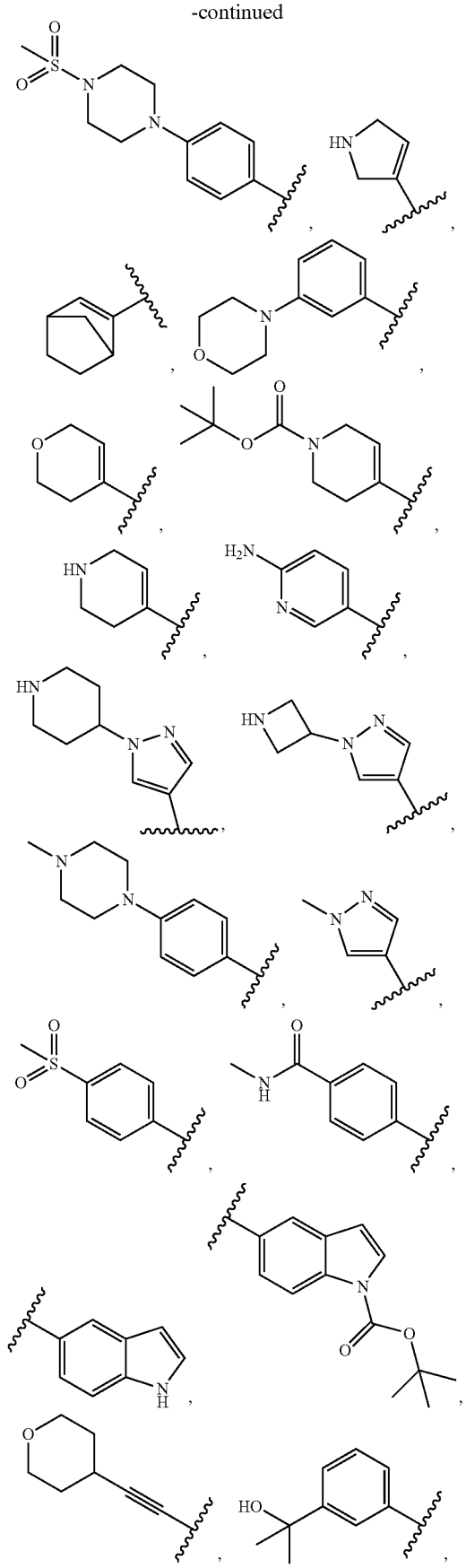
622
-continued
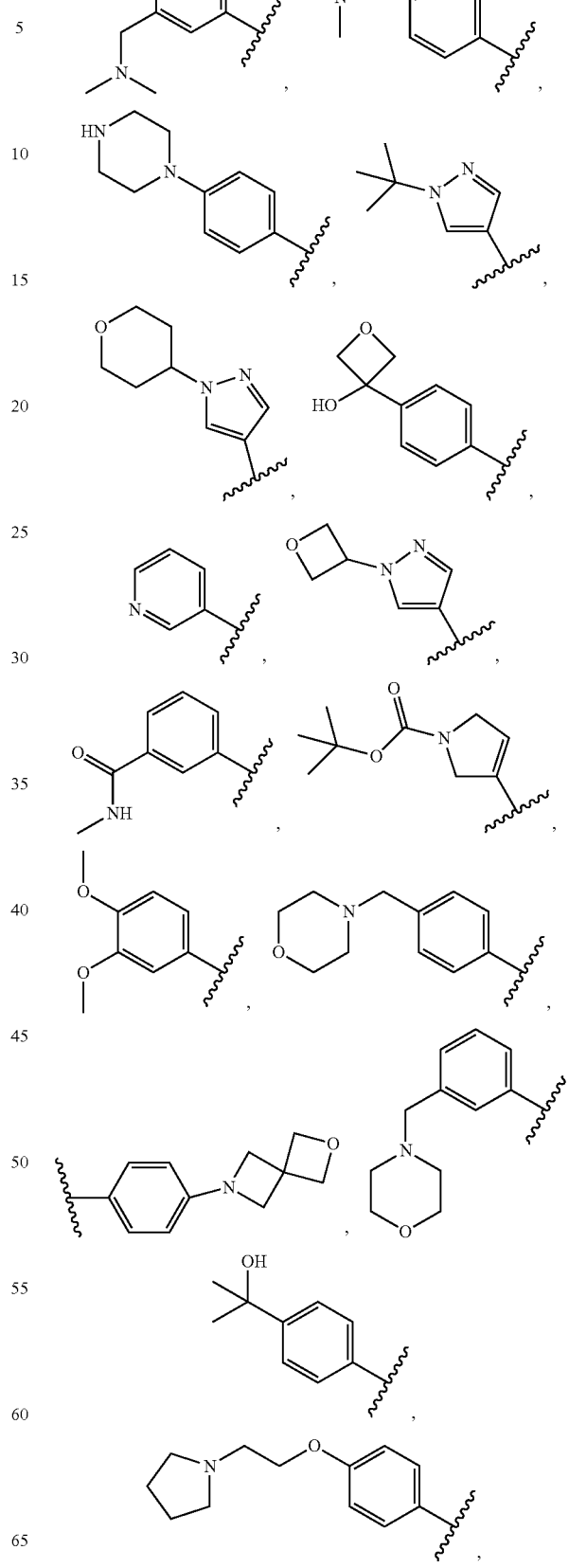

623
-continued
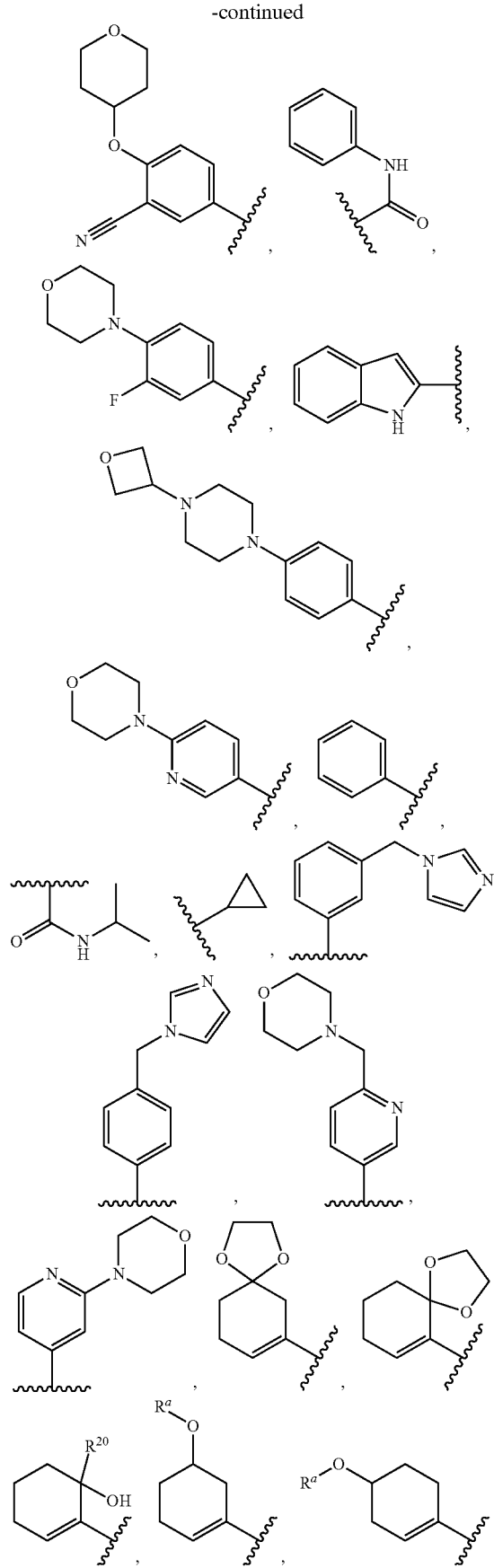
624
-continued
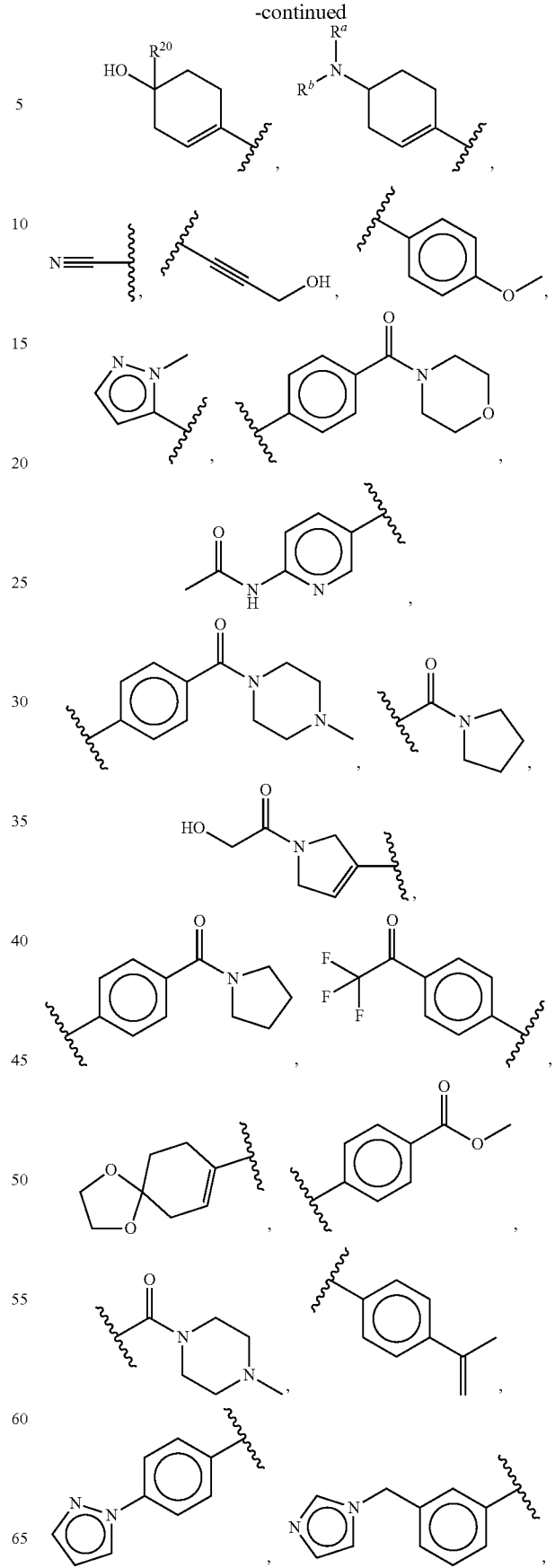

625
-continued
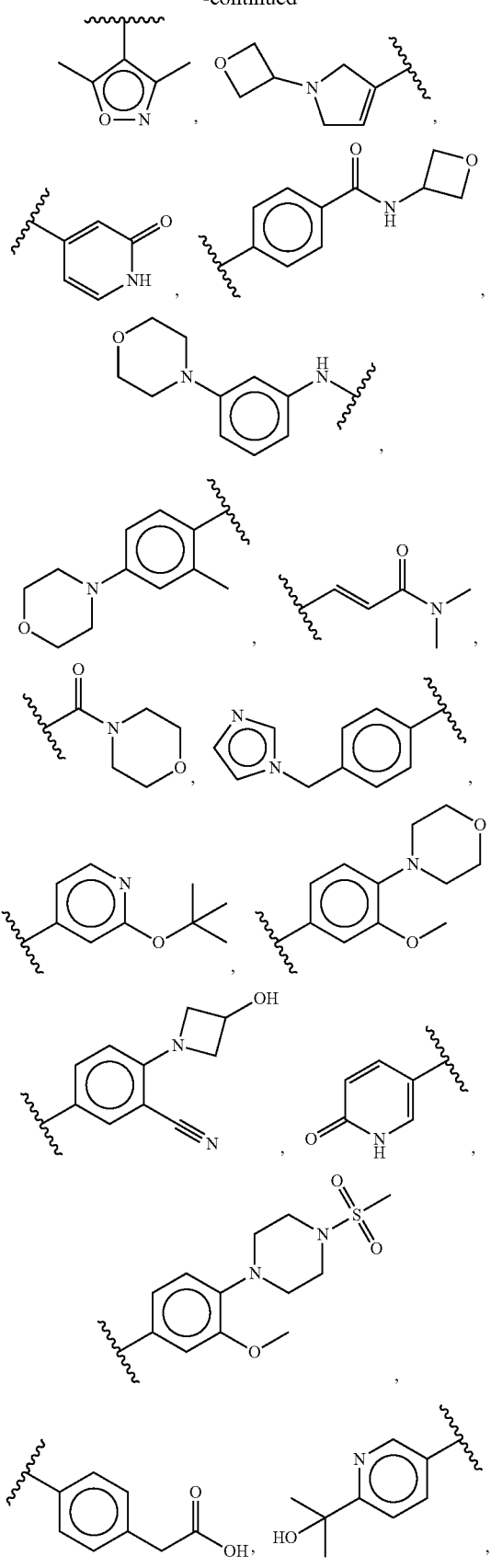
626
-continued
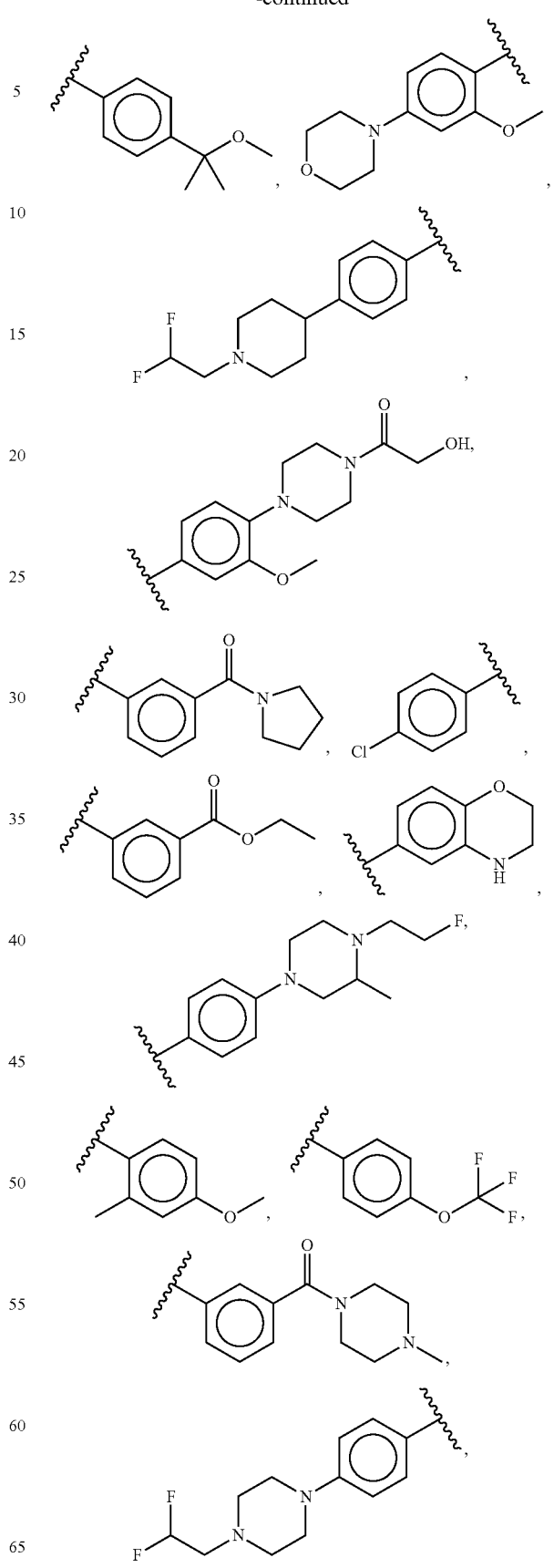

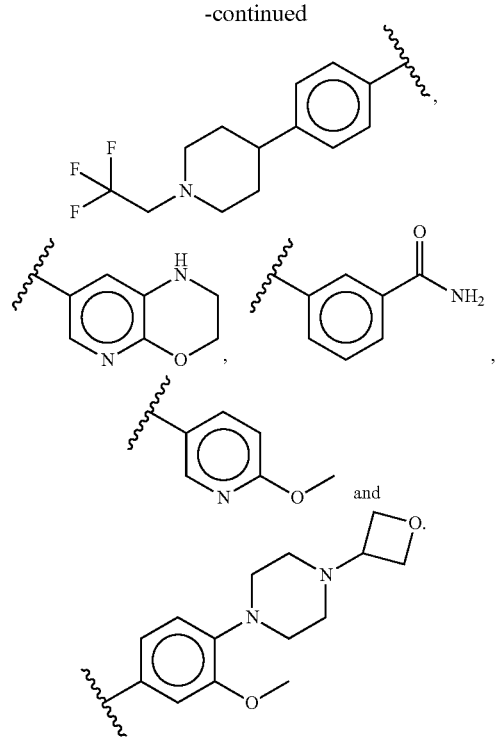
7. The compound of claim 1, or a pharmaceutically acceptable salt thereof, wherein $R^2$, $R^3$ and $R^4$ are each H.
8. The compound of claim 1, or a pharmaceutically acceptable salt thereof, wherein $R^5$ is —$OR^9$.
9. The compound of claim 1, or a pharmaceutically acceptable salt thereof, wherein $R^5$ is selected from the group consisting of:
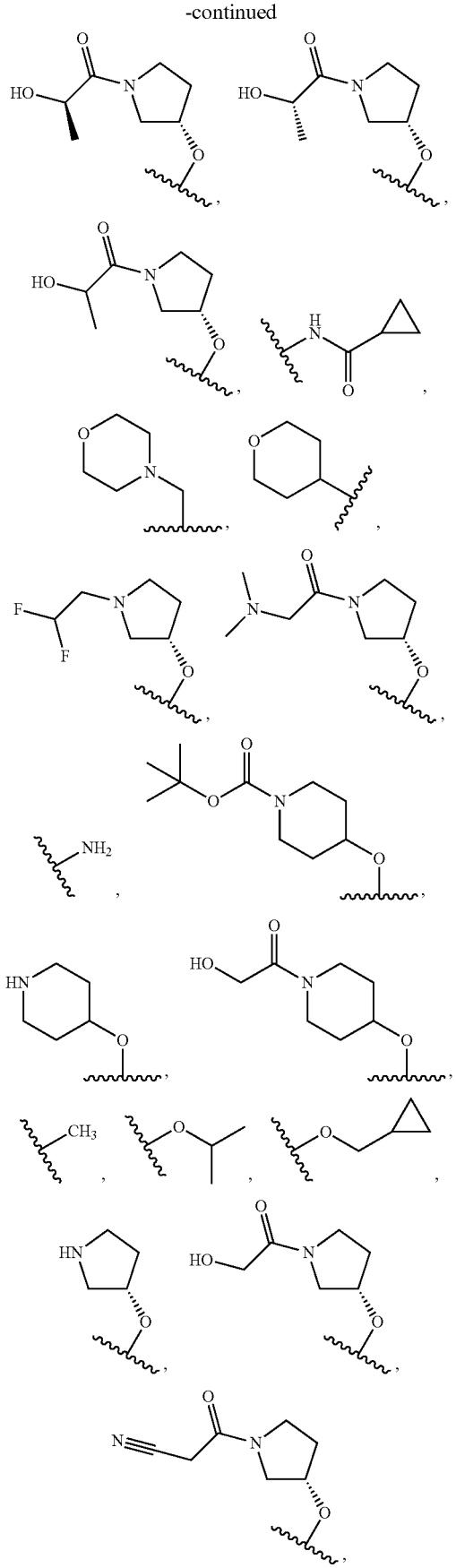

629
-continued

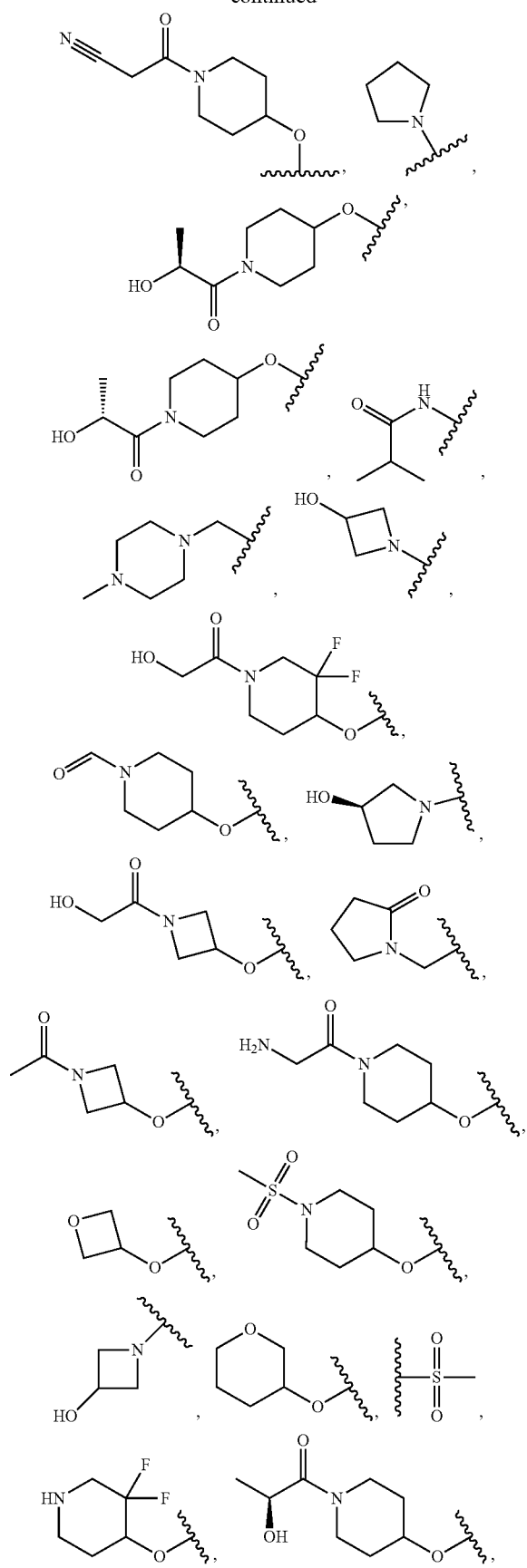

630
-continued

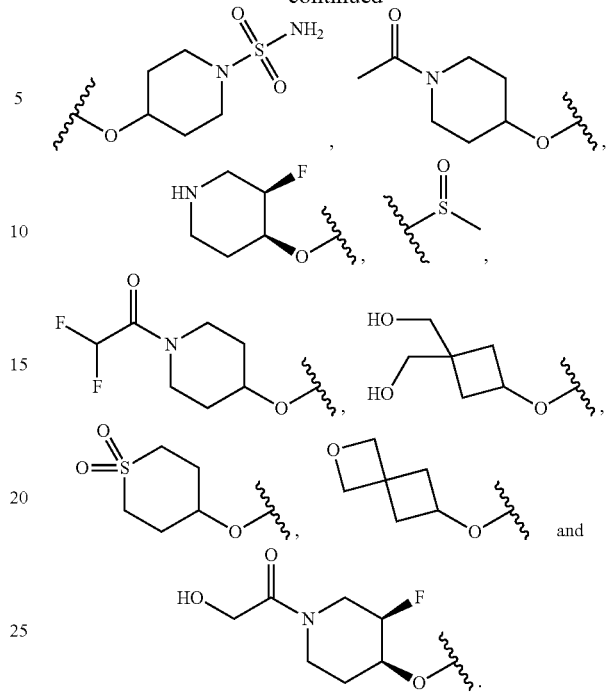

10. The compound of claim 8, or a pharmaceutically acceptable salt thereof, wherein $R^9$ is selected from the group consisting of tetrahydropyranyl, tetrahydrofuranyl, pyrrolidinyl, oxetanylmethyl, 1-(oxetan-3-yl)pyrrolidinyl, oxo-propanylnitrile-pyrrolinyl and piperidinyl.

11. The compound of claim 8, or a pharmaceutically acceptable salt thereof, wherein $R^9$ is:

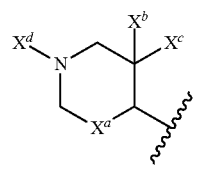

$X^a$ is a bond or $C(R^x)(R^y)$, wherein $R^x$ and $R^y$ are independently selected from the group consisting of H, halo and methyl;

$X^b$ and $X^c$ are independently selected from the group consisting of H, halo and methyl;

$X^d$ is selected from the group consisting of H; or $C_{1-6}$ alkyl, $C_{3-10}$ cycloalkyl, $C_{1-6}$ heteroalkyl, 3-12 membered heterocyclyl, $C_{6-10}$ aryl, and 5-10 membered heteroaryl, each of which is optionally substituted with one to five groups selected from the group consisting of hydroxyl, $C_{1-6}$ alkoxy, amino, —CN, —C(O)H, —C(O)NH$_2$, —C(O)NH($C_{1-6}$ alkyl), —C(O)N($C_{1-6}$ alkyl)$_2$, —COOH, —C(O)$C_{1-6}$ alkyl, —C(O)O$C_{1-6}$ alkyl, and halogen.

12. The compound of claim 11, or a pharmaceutically acceptable salt thereof, wherein $X^b$ is fluoro.

13. The compound of claim 1, or a pharmaceutically acceptable salt thereof, wherein A is phenyl or a 6 membered heteroaryl.

14. The compound of claim 13, or a pharmaceutically acceptable salt thereof, wherein A is phenyl.

15. The compound of claim 1, selected from the group consisting of:
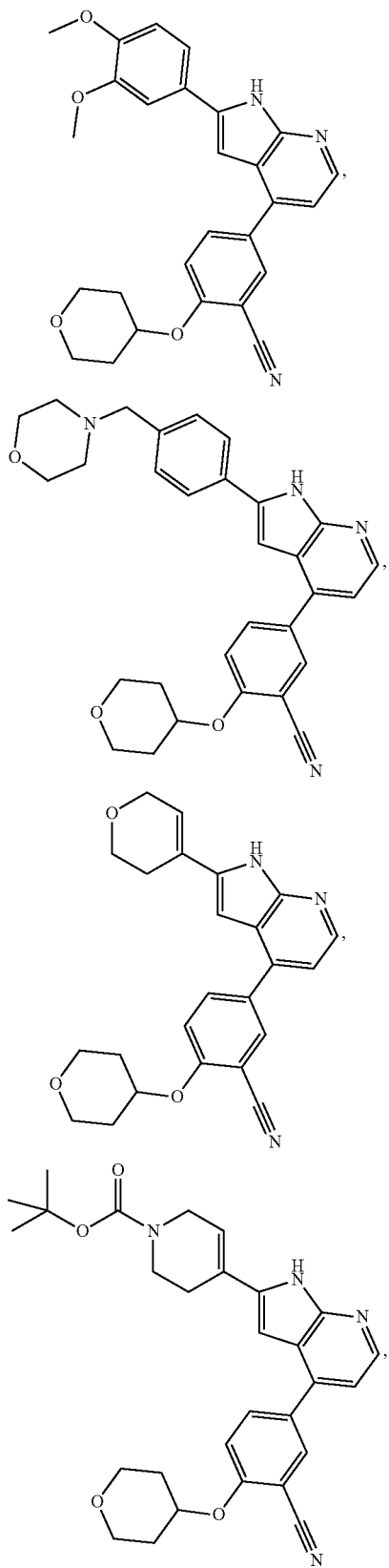
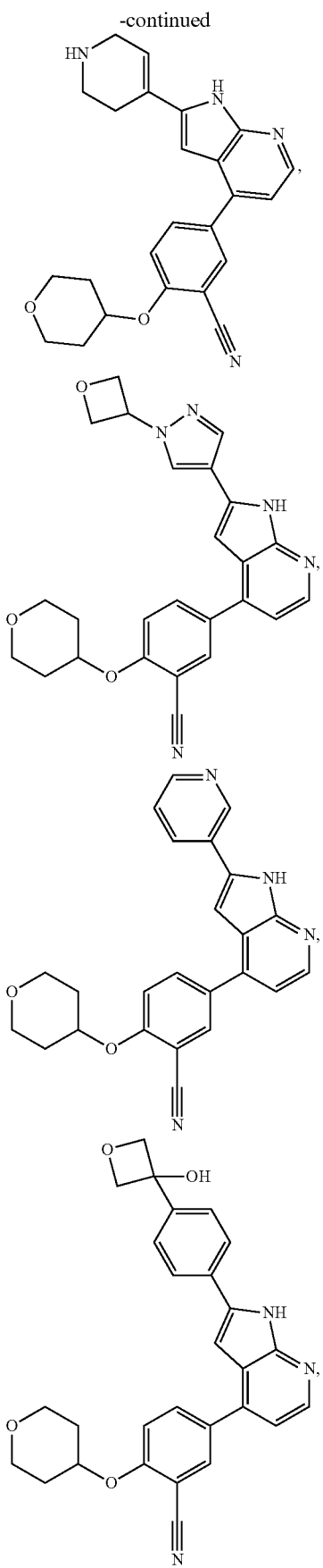

633
-continued
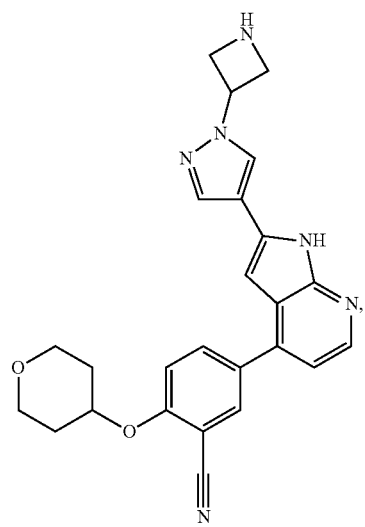
634
-continued
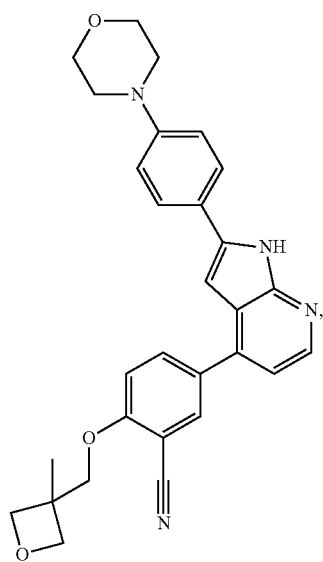
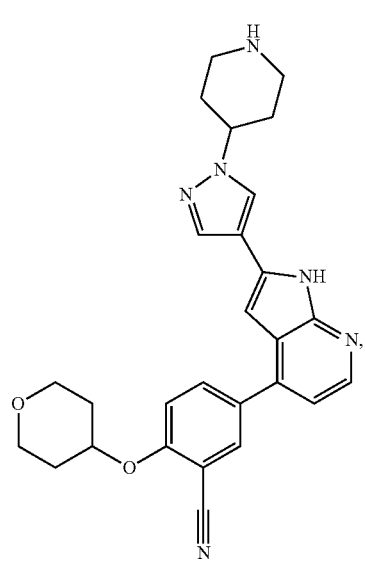
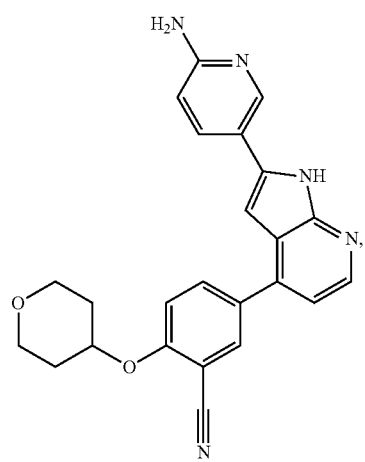
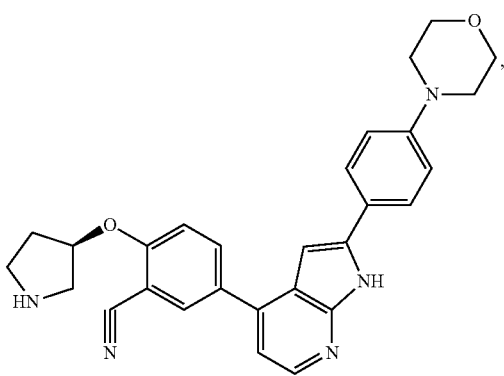

635
-continued
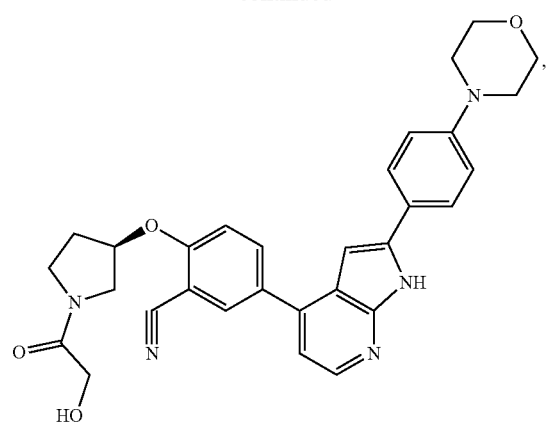
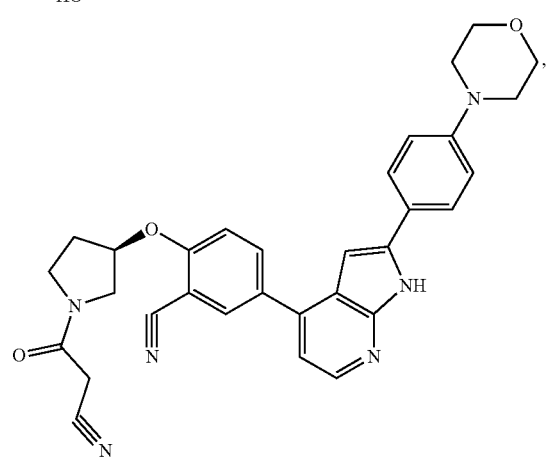
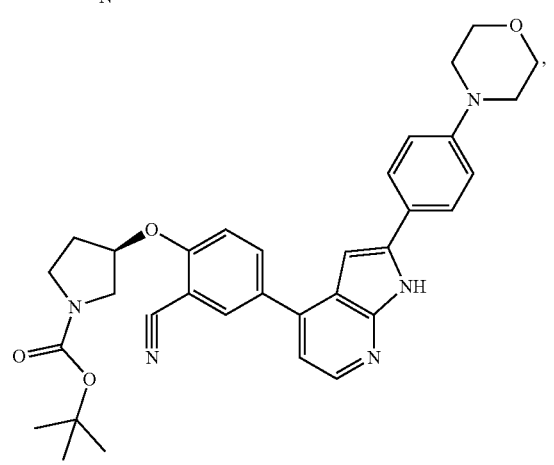
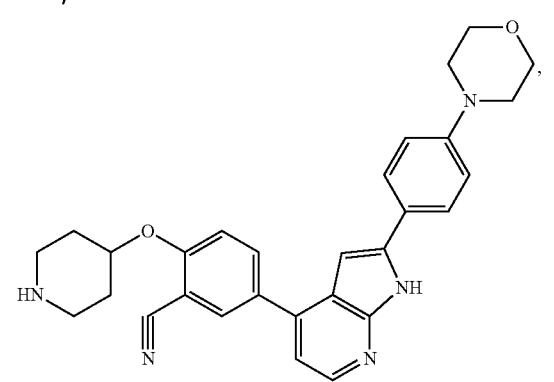
636
-continued
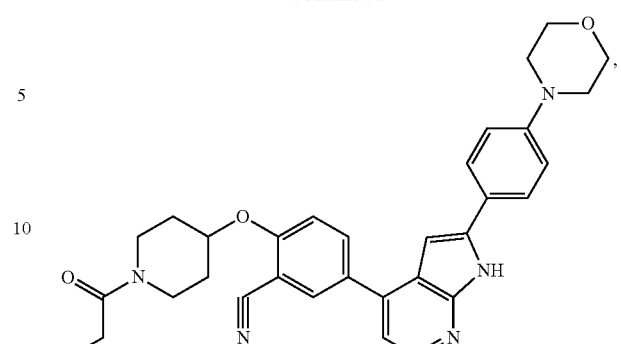
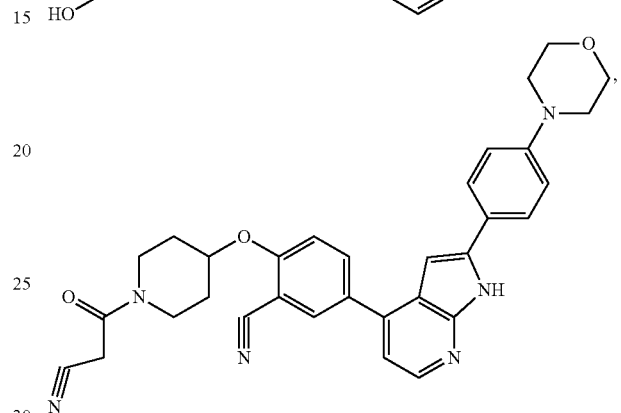
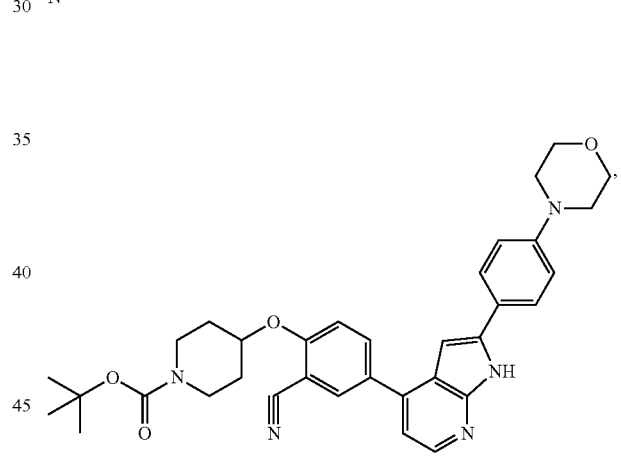
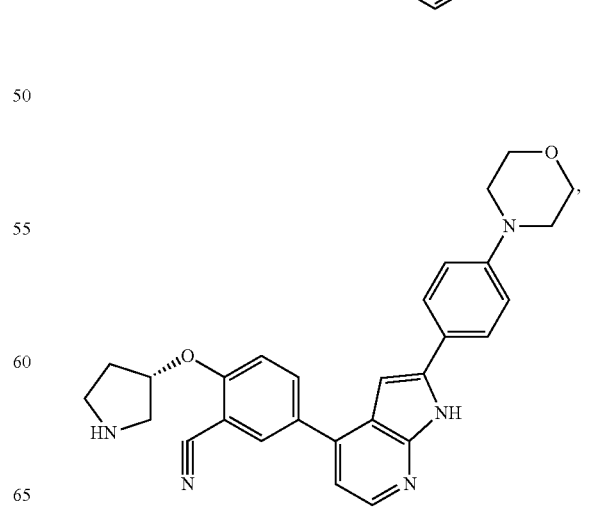

637
-continued
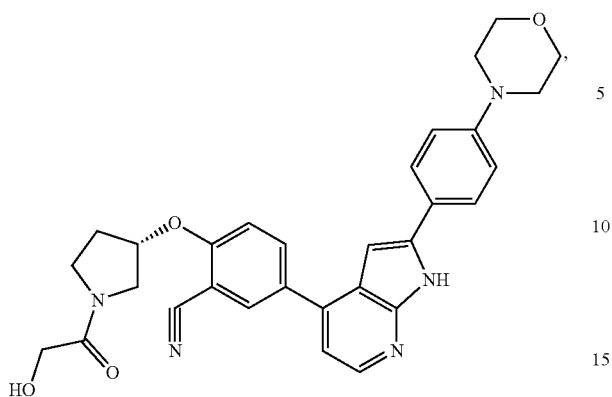
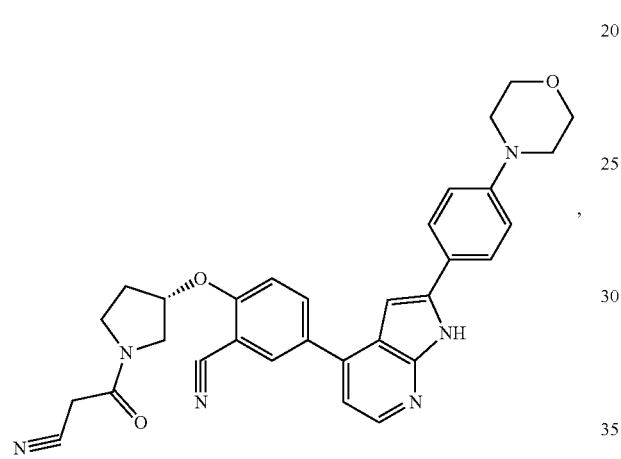
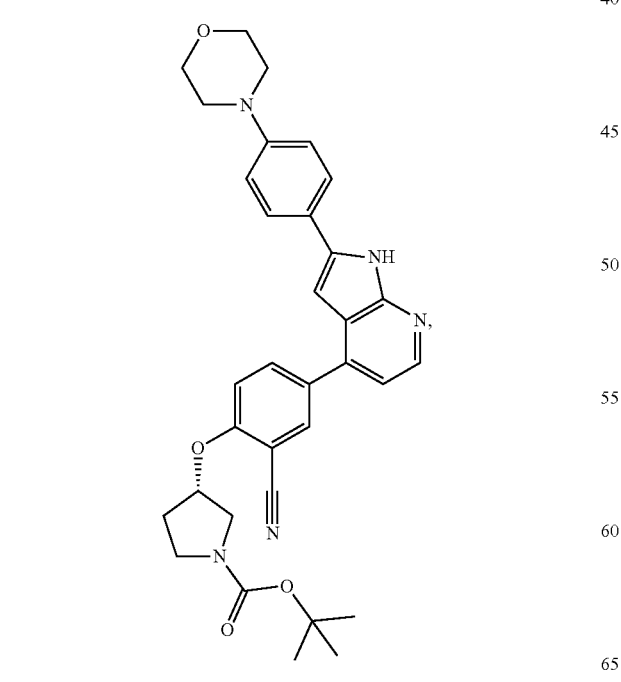
638
-continued
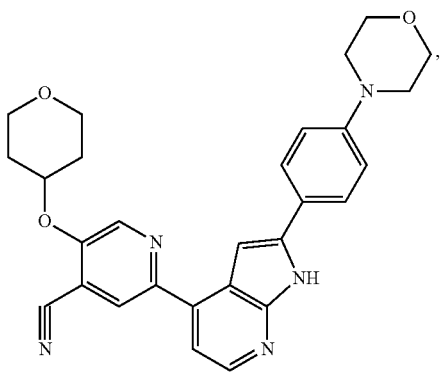
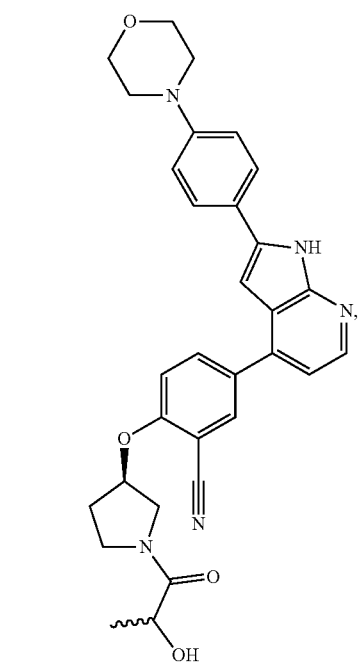
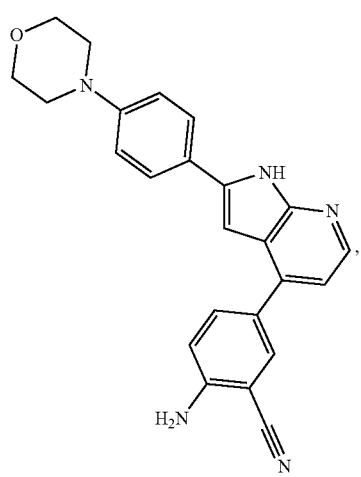

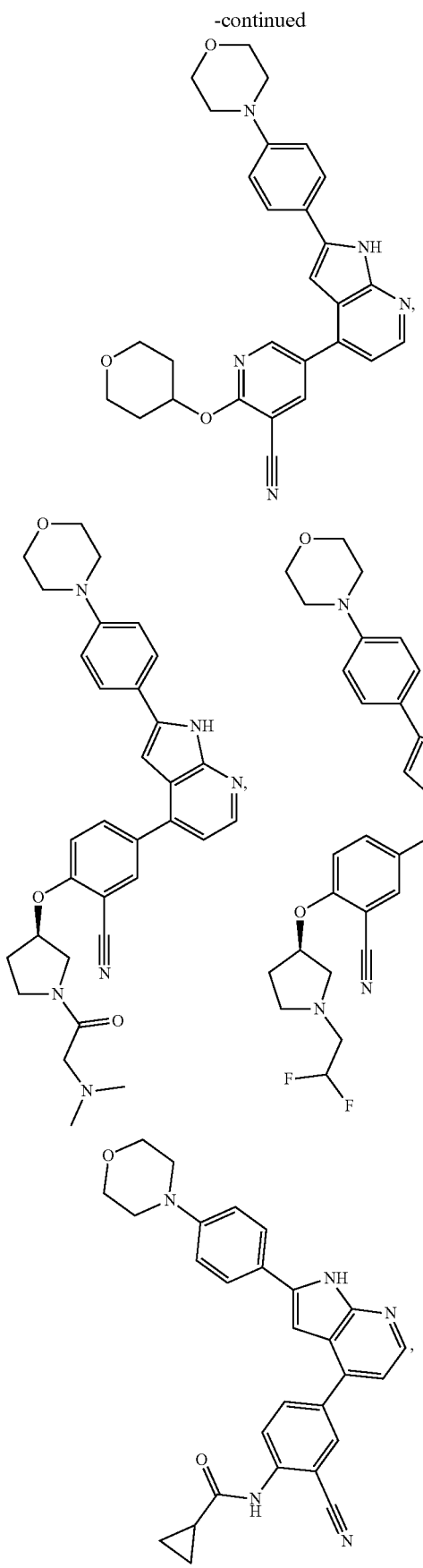
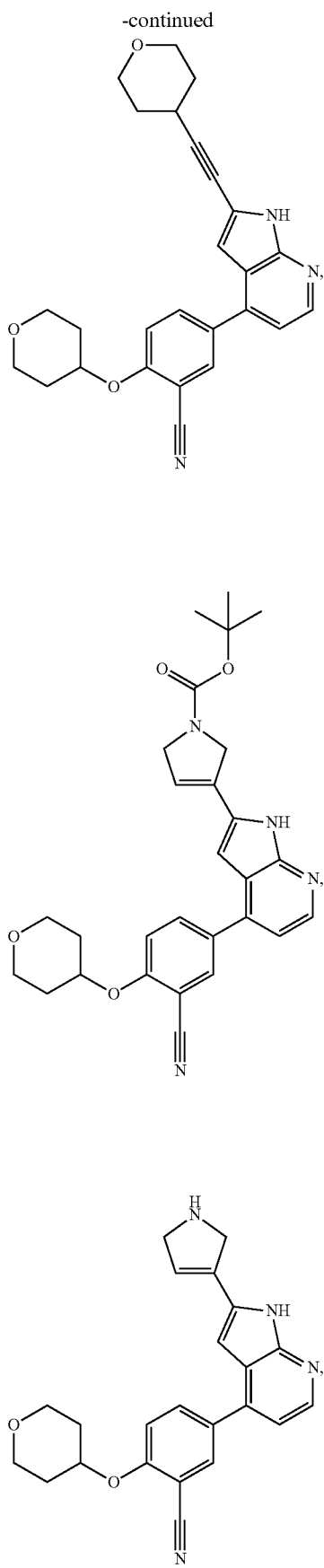

641
-continued
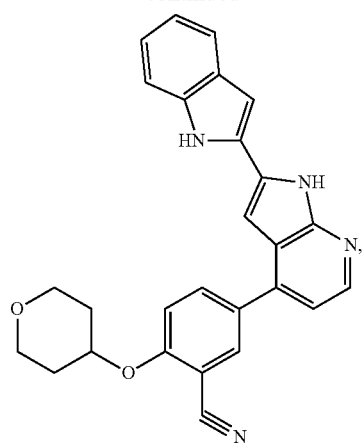
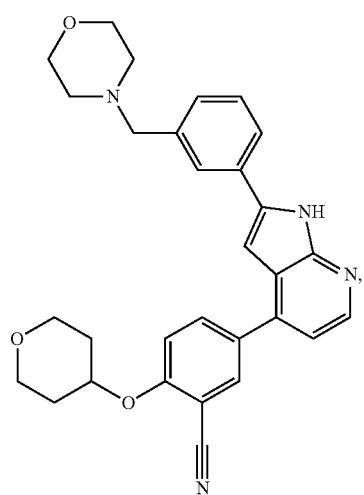
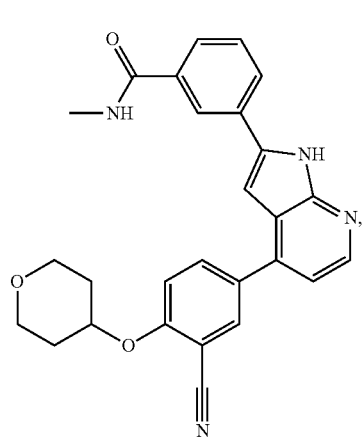
642
-continued
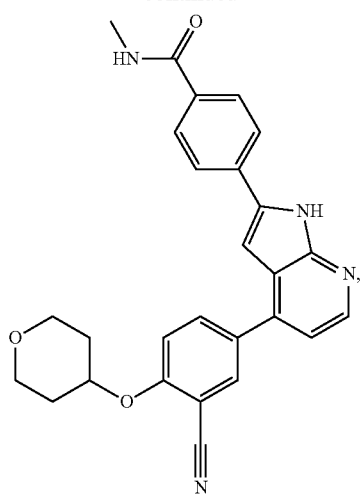
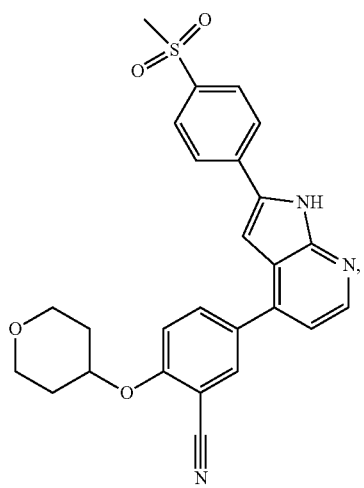
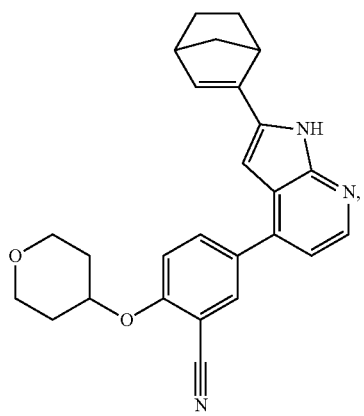

643
-continued
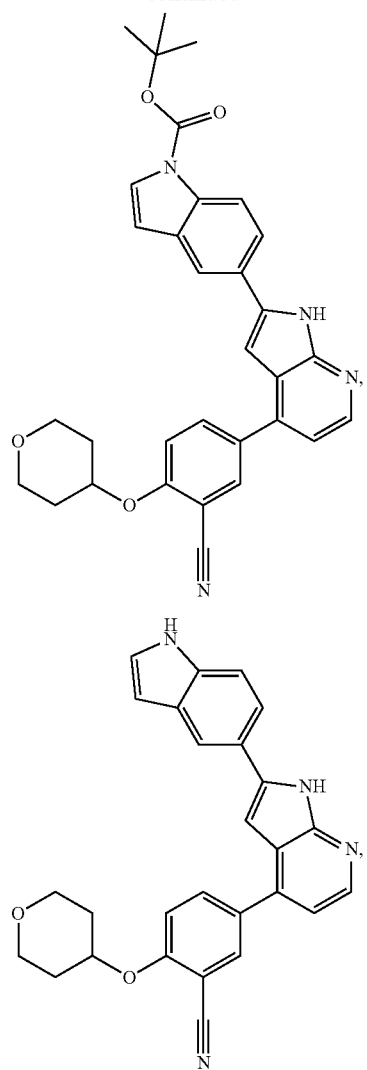
644
-continued
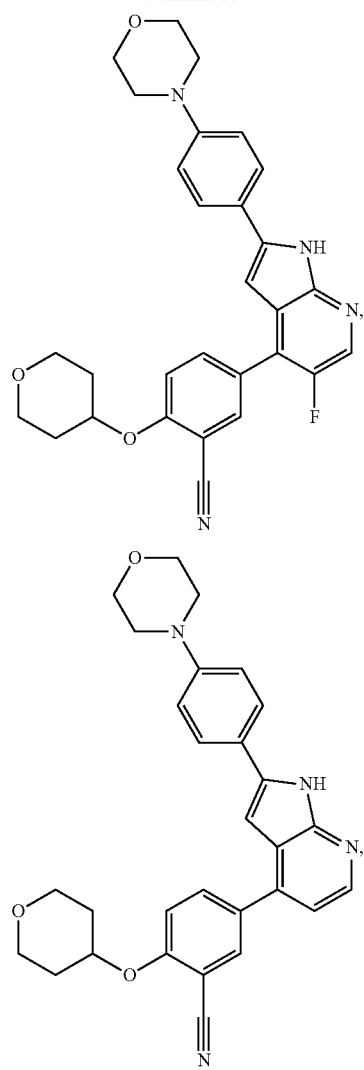
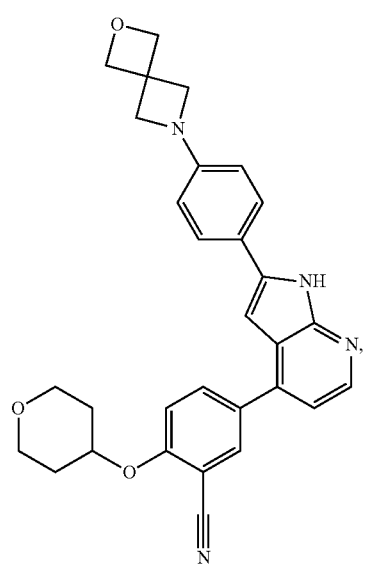
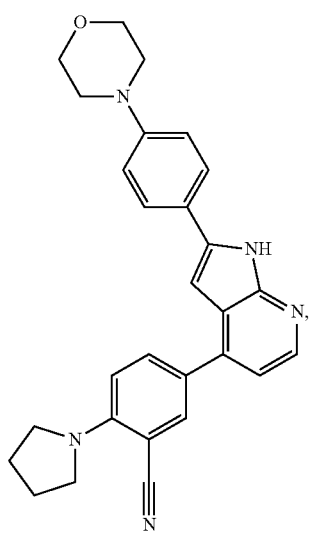

645
-continued
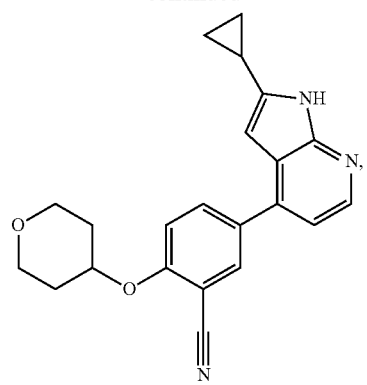
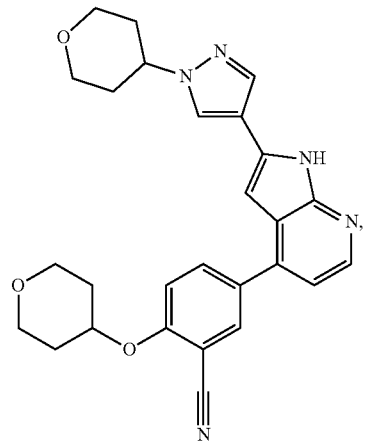
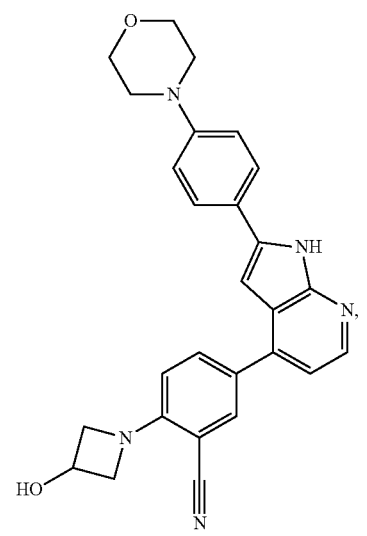
646
-continued
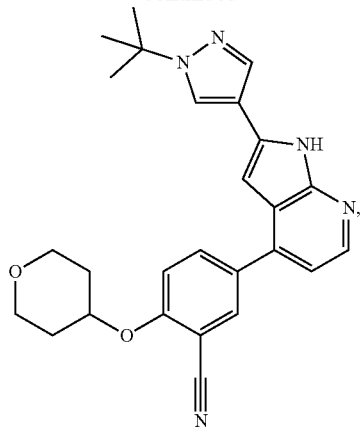
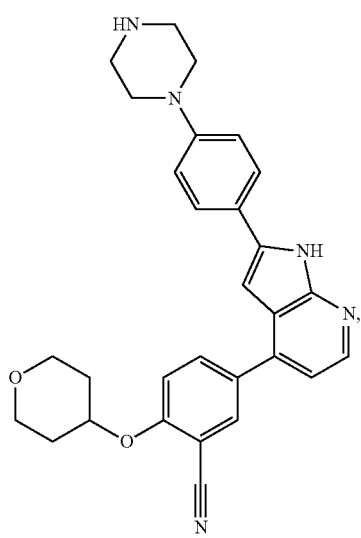
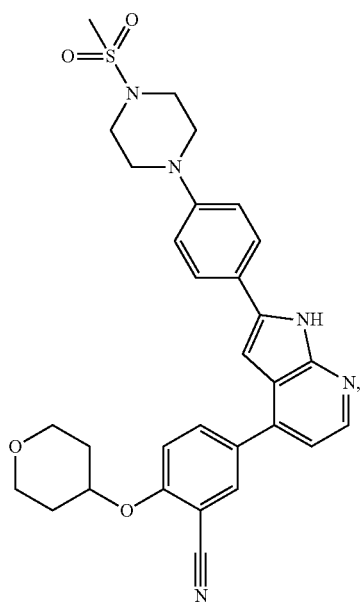

647
-continued
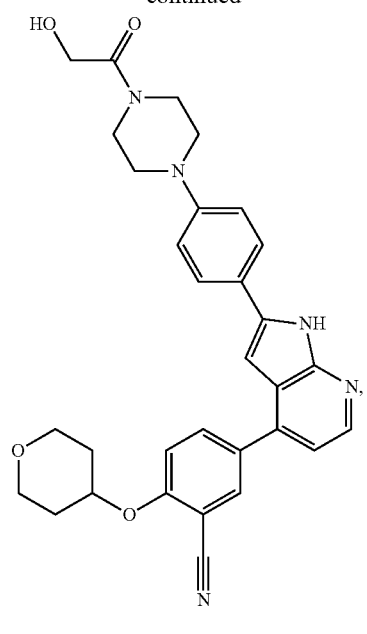
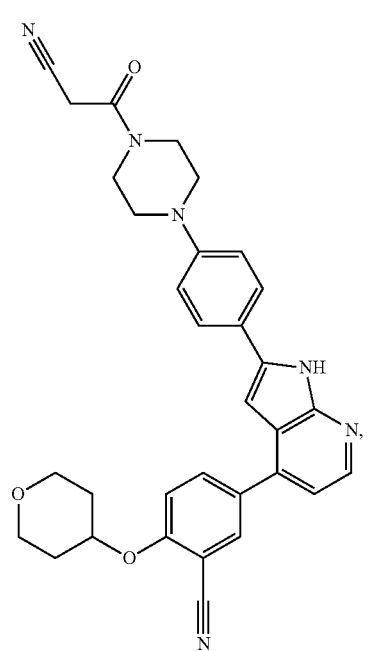
648
-continued
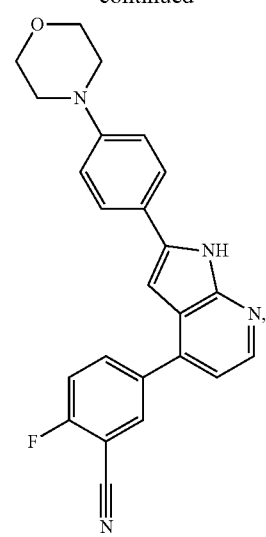
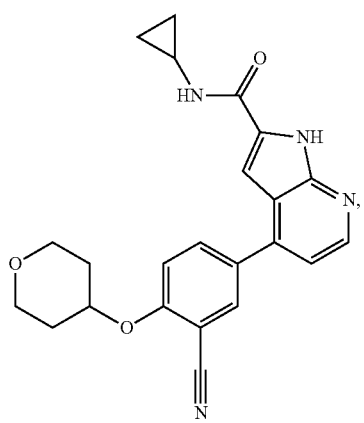
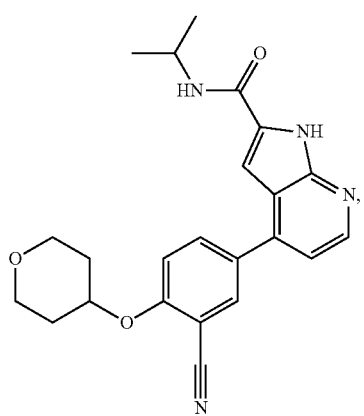

649
-continued
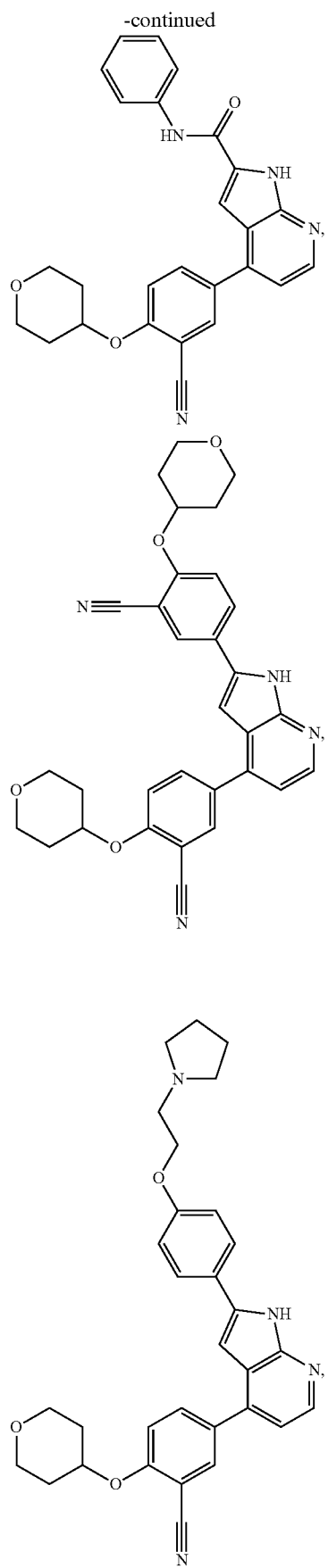
650
-continued
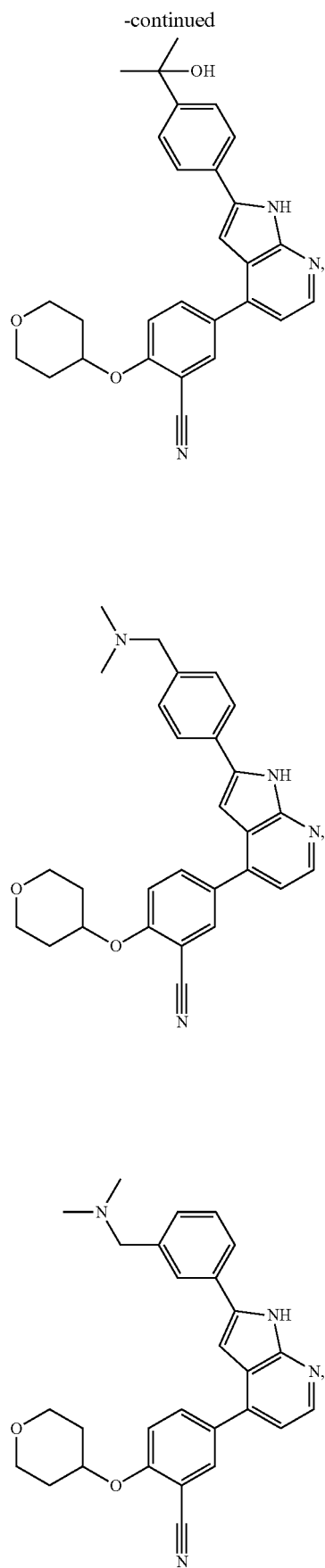

| 651 -continued | 652 -continued |
|---|---|
| 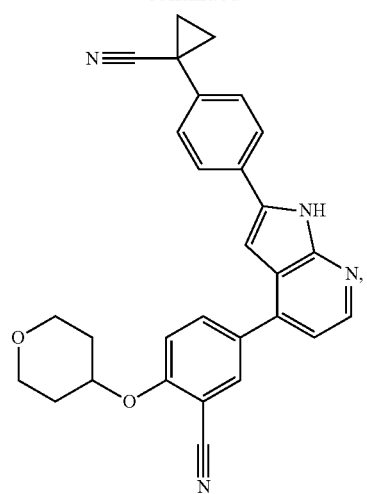 | 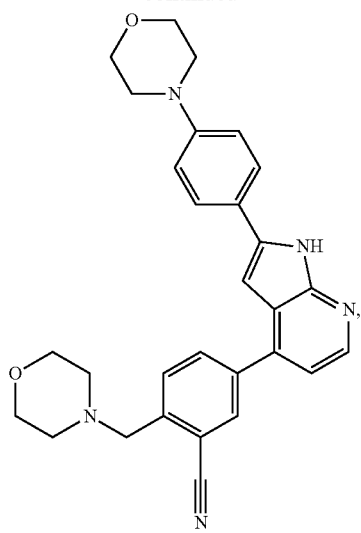 |
| | 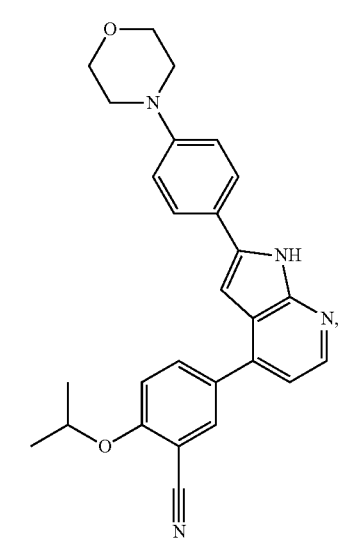 |
| | 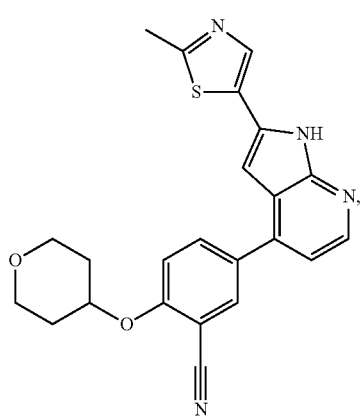 |

653
-continued
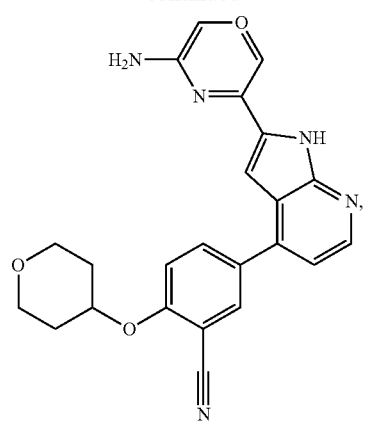
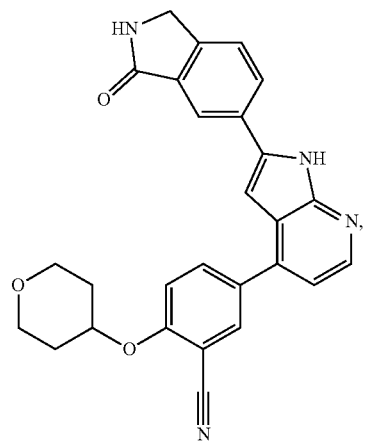
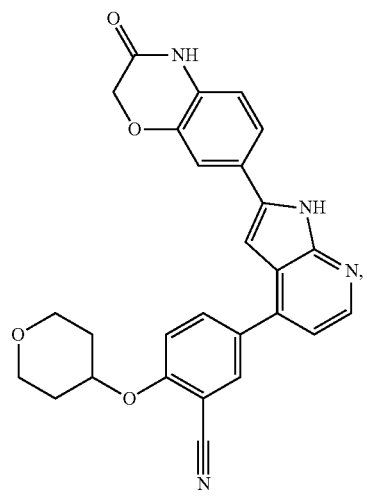
654
-continued
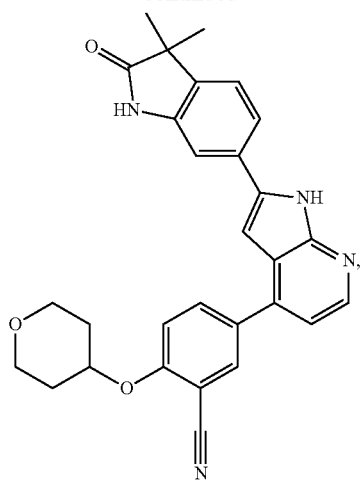
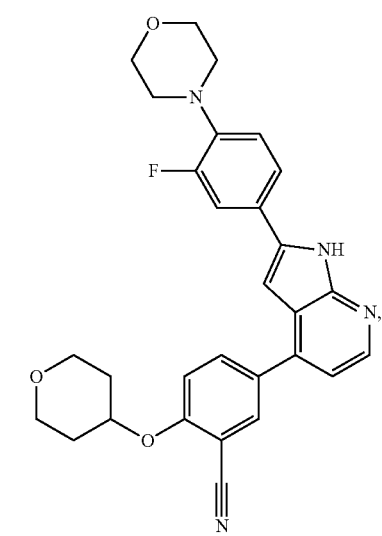
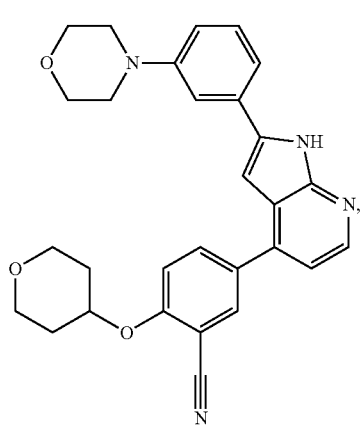

655
-continued
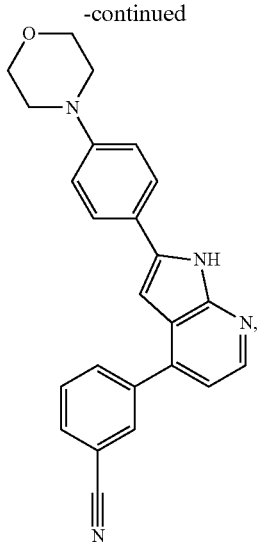
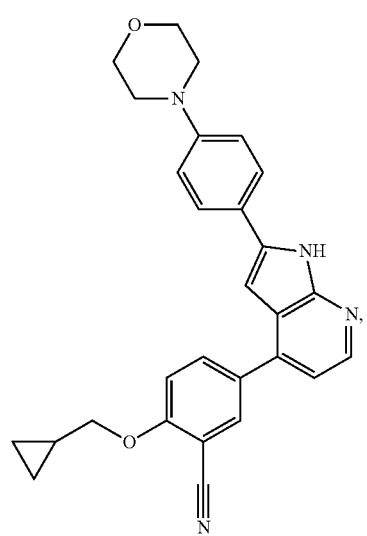
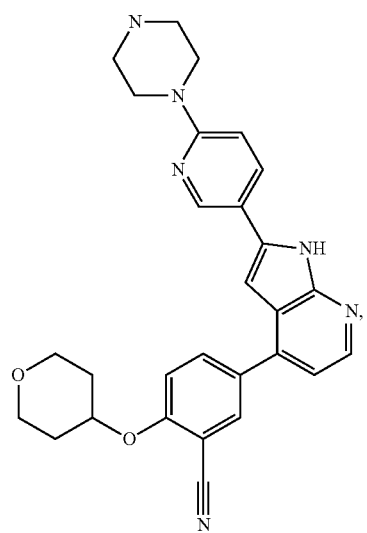
656
-continued
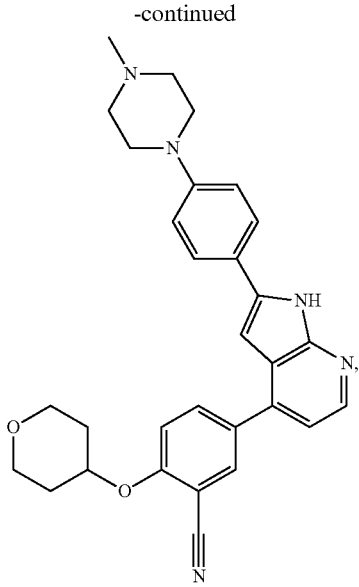
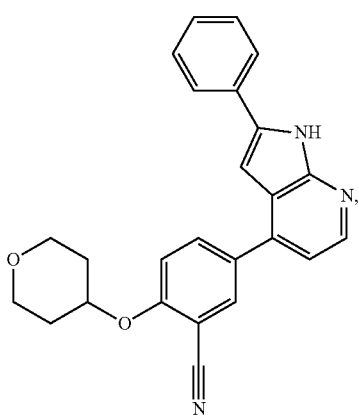
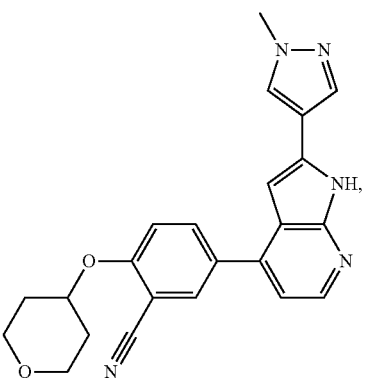

657
-continued
658
-continued
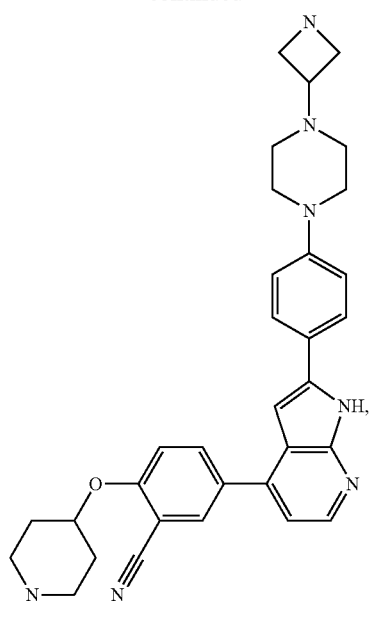
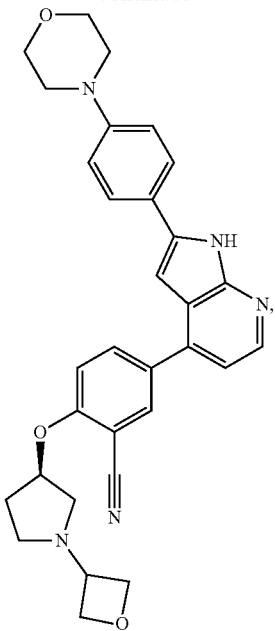
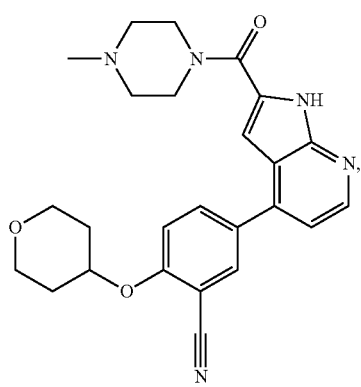
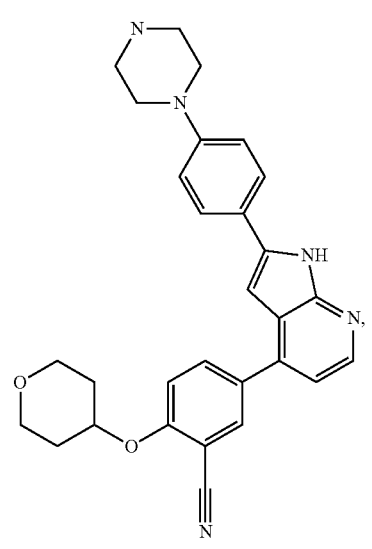

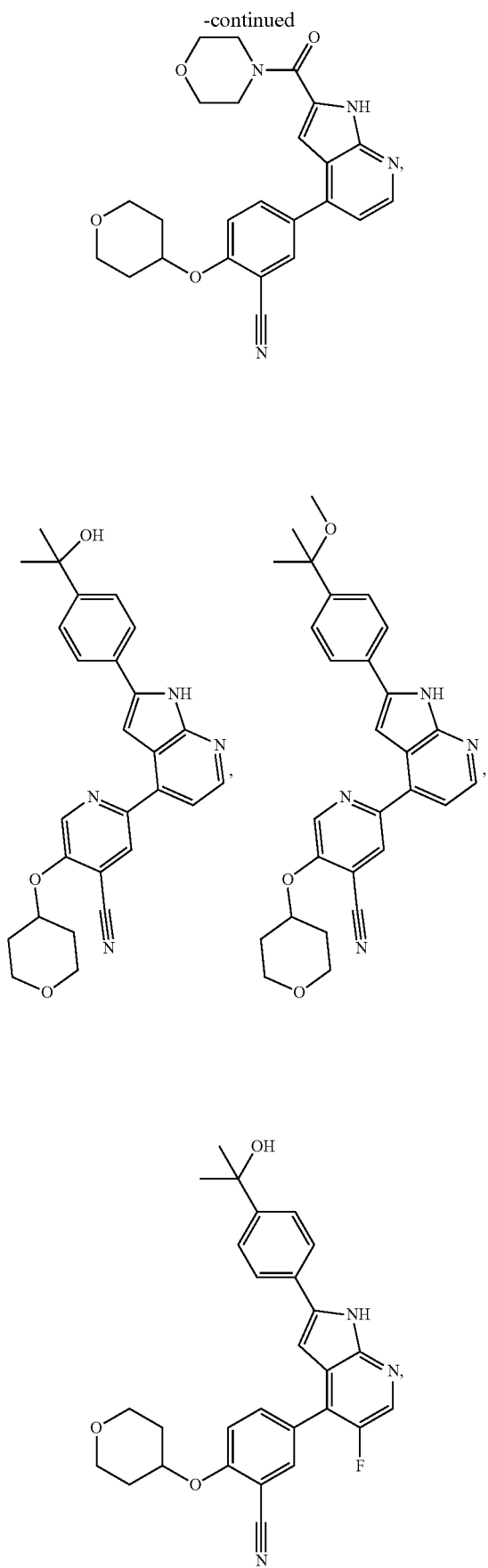

661
-continued
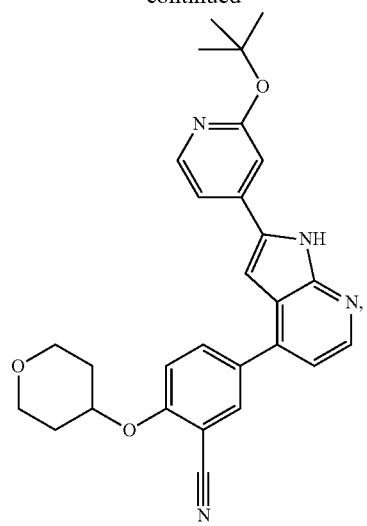
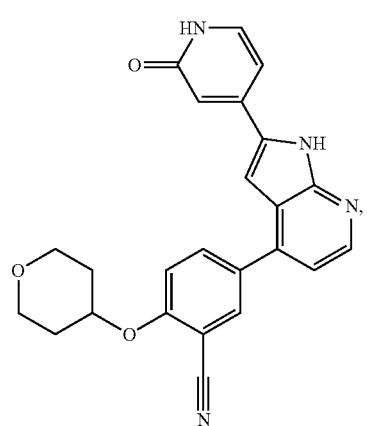
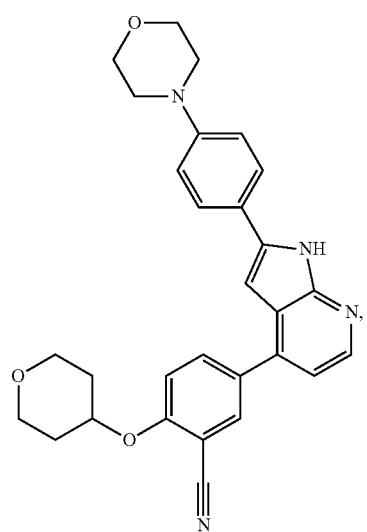
662
-continued
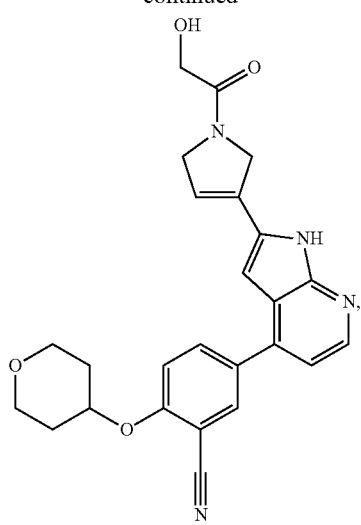
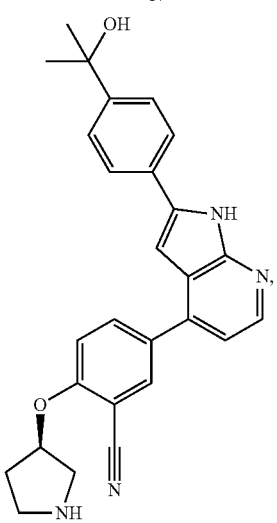
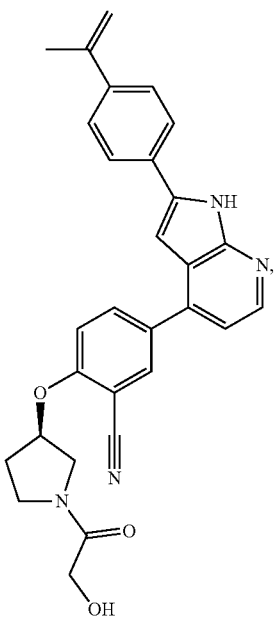

663
-continued
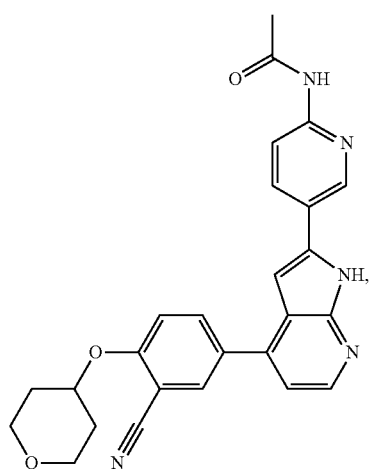
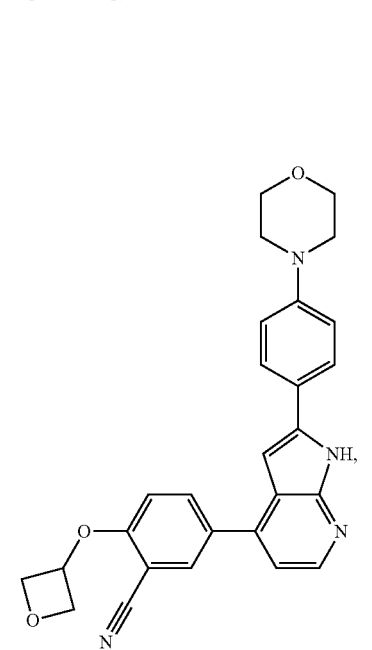
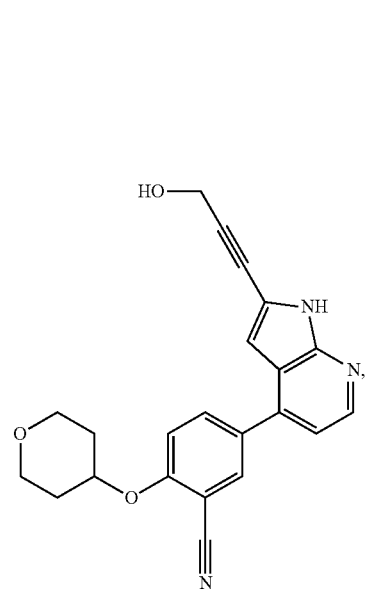
664
-continued
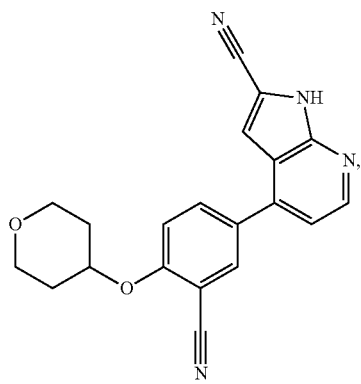
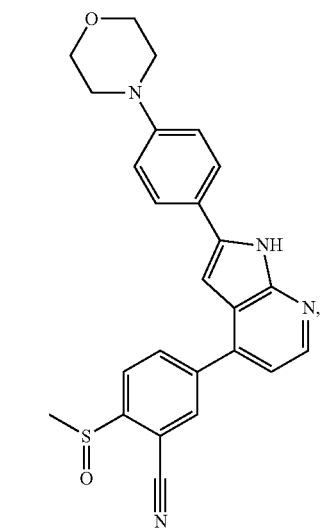
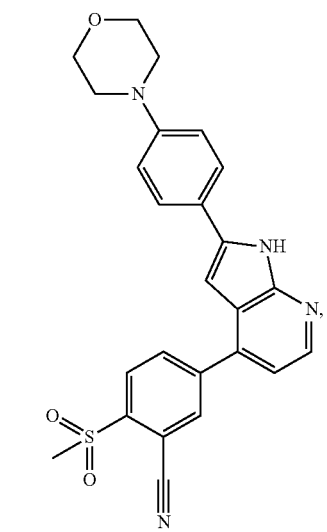

665
-continued
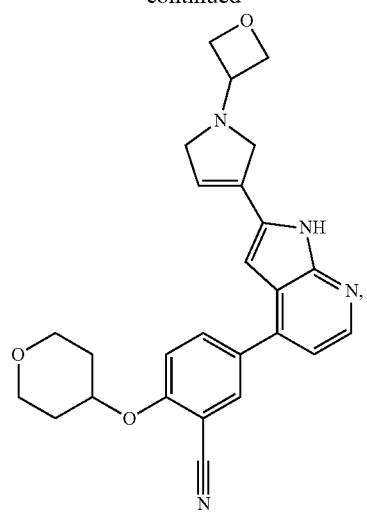
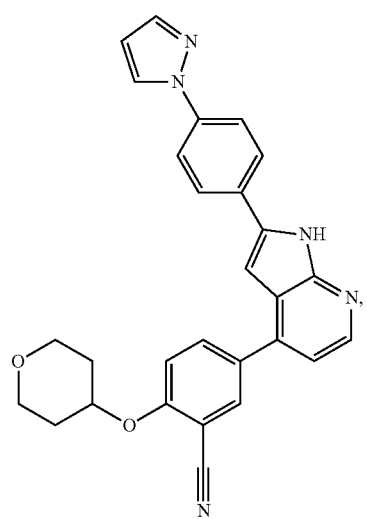 [SMILES: N#Cc1cc(-c2ccnc3[nH]c(-c4ccc(-n5cccn5)cc4)cc23)ccc1OC1CCOCC1]
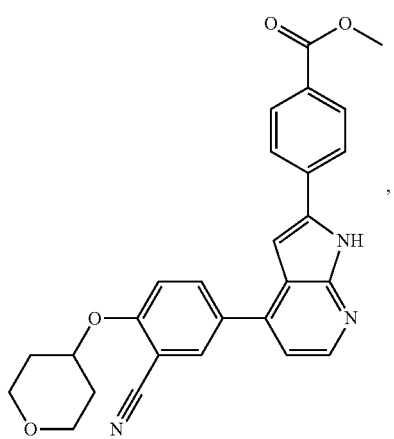
666
-continued
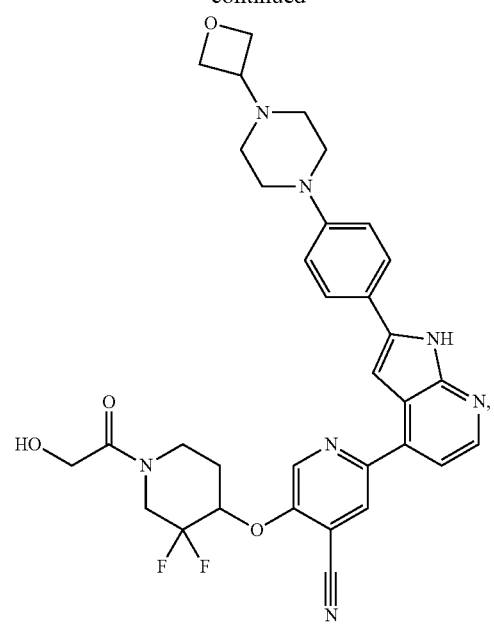
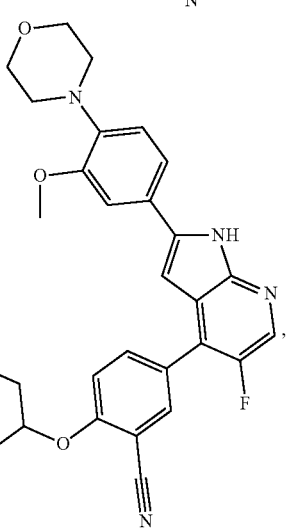
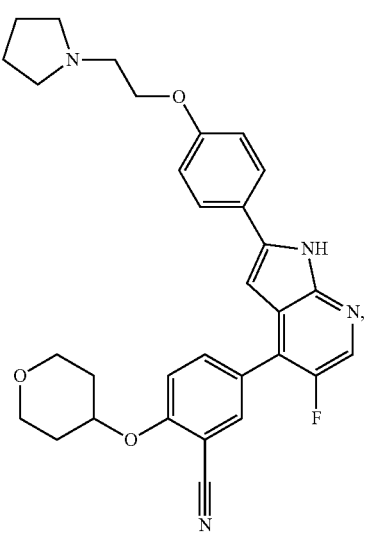

667
-continued
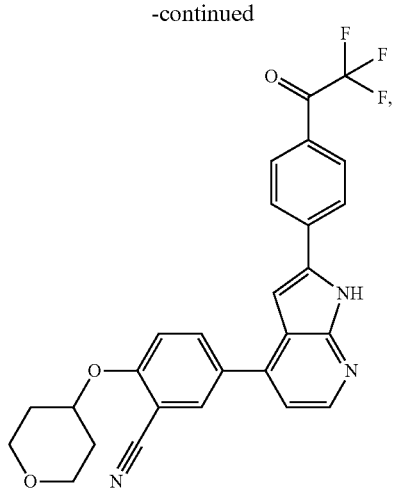
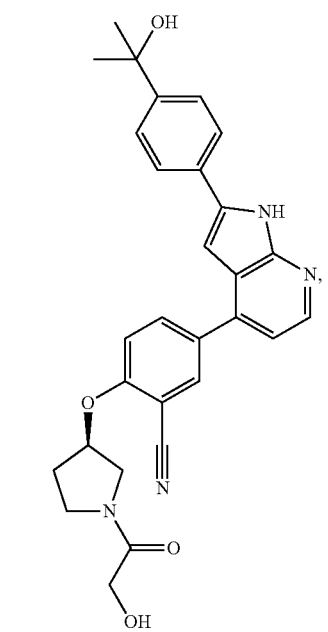
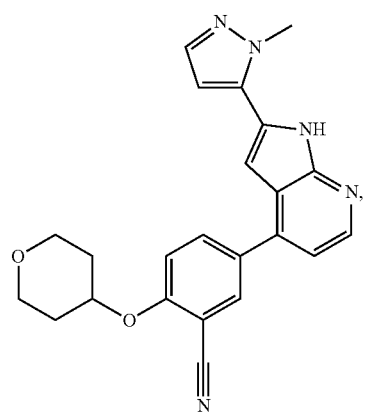
668
-continued
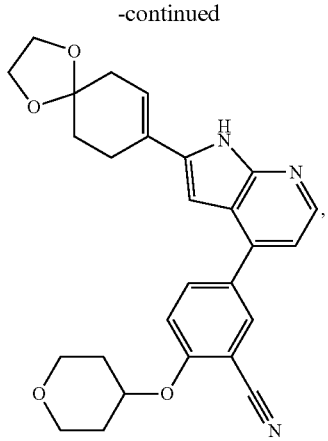
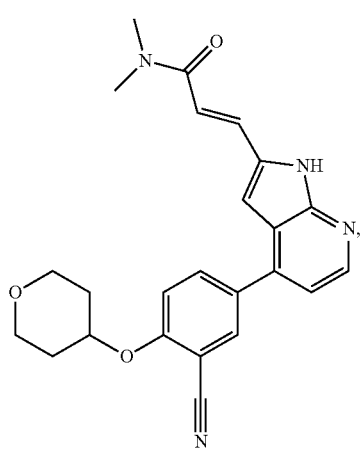
and 669
-continued
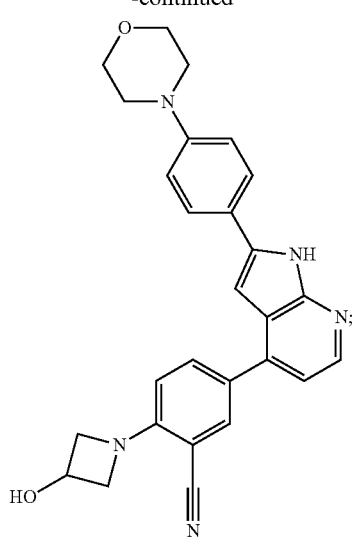
or a pharmaceutically acceptable salt thereof.
16. The compound of claim 1, selected from the group consisting of:
670
-continued
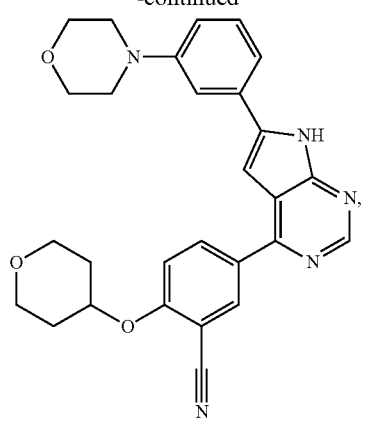
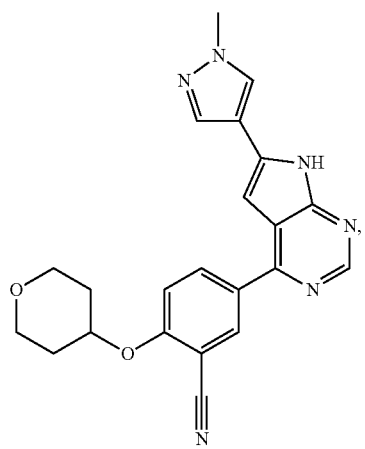
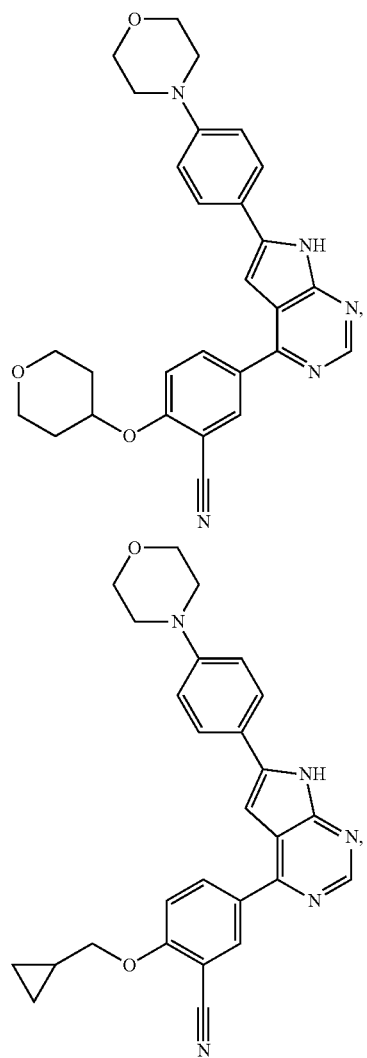
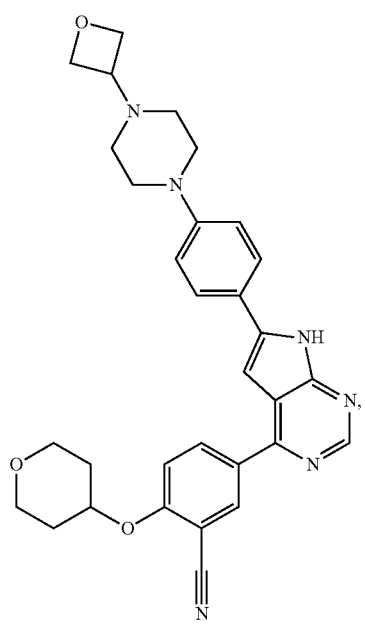

671
-continued
672
-continued
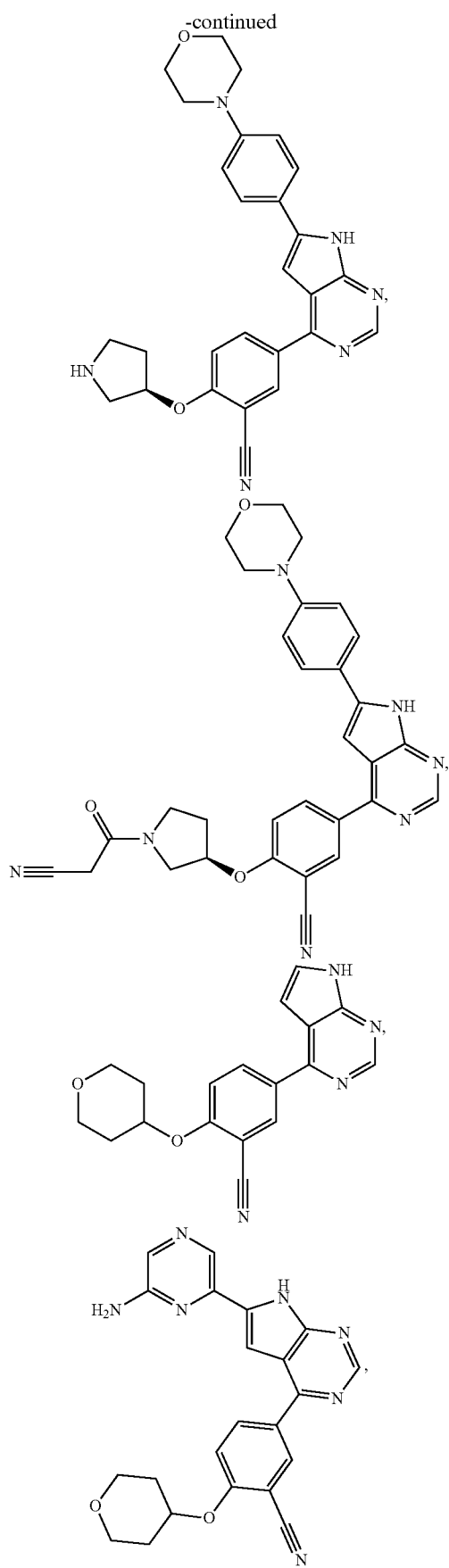

673
-continued
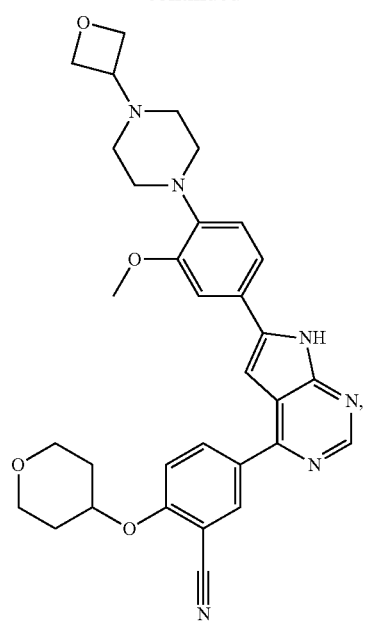
674
-continued
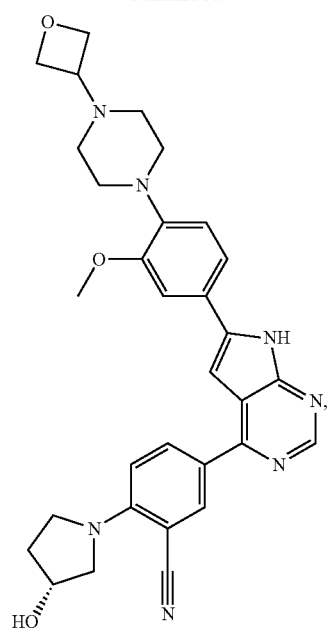
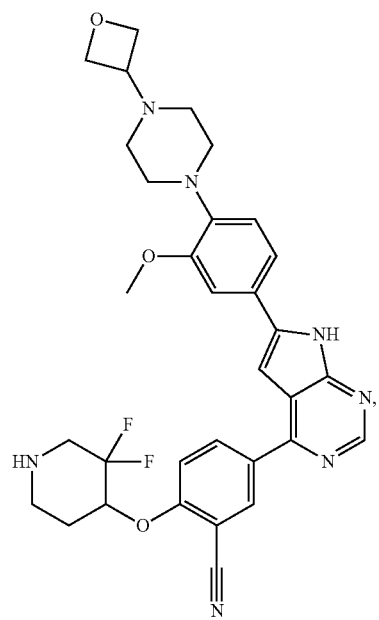
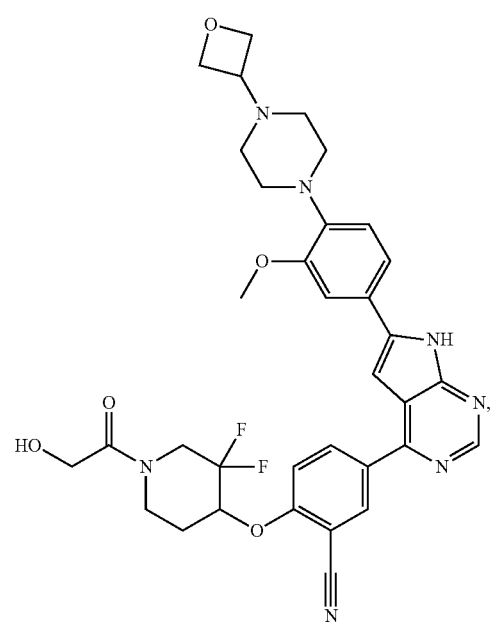

675
-continued
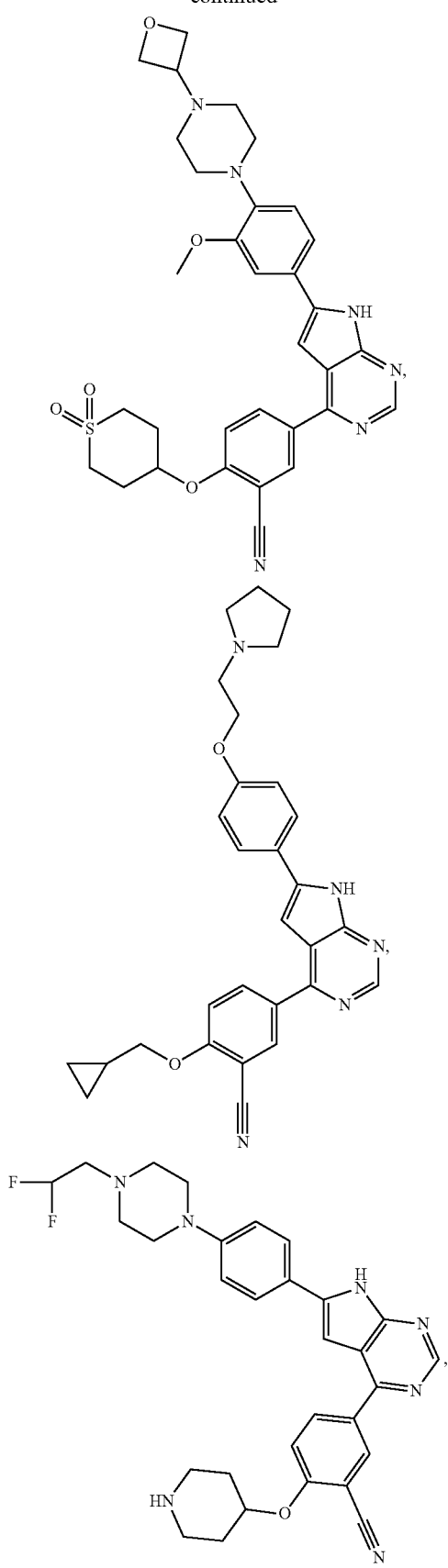
676
-continued
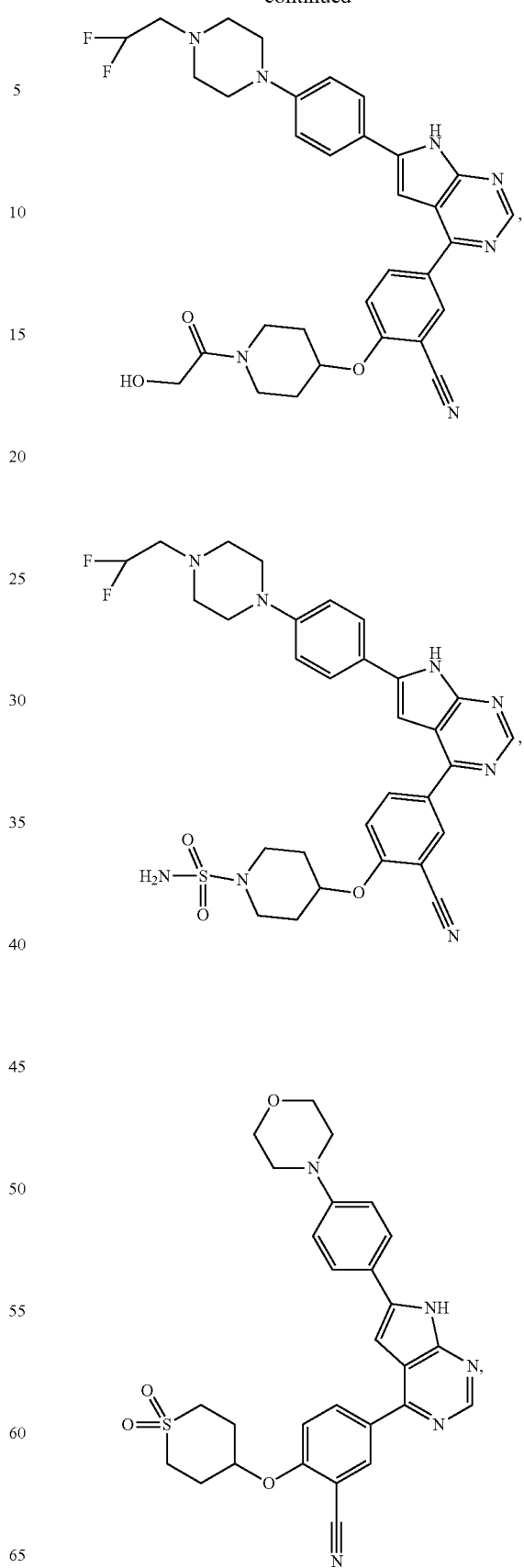

677
-continued
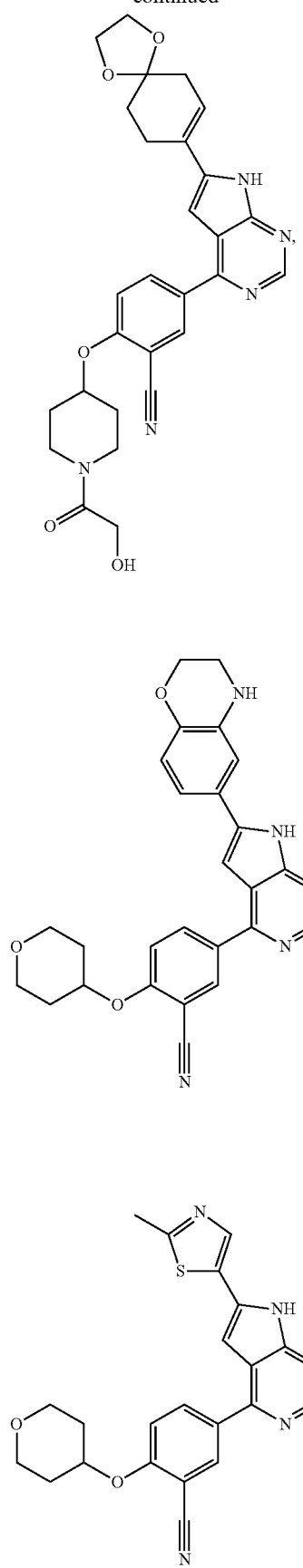
678
-continued
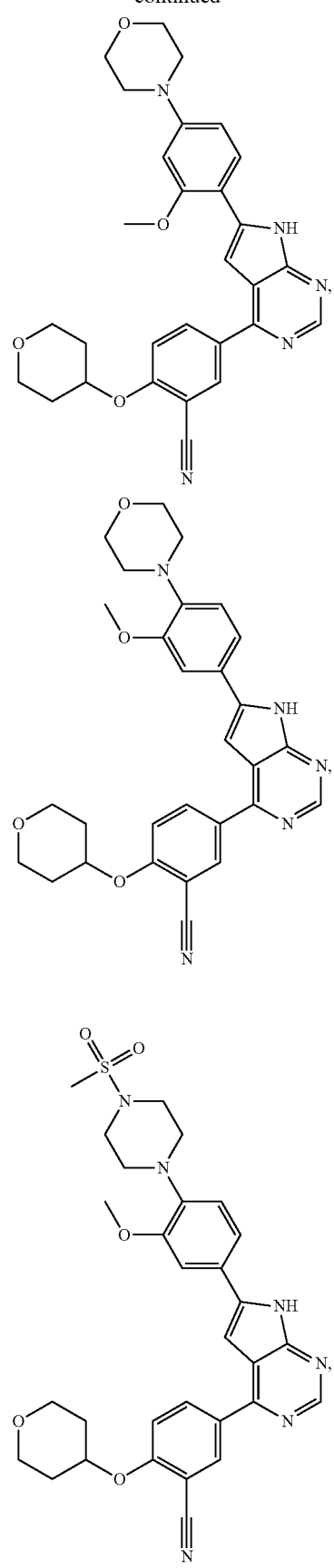

679
-continued
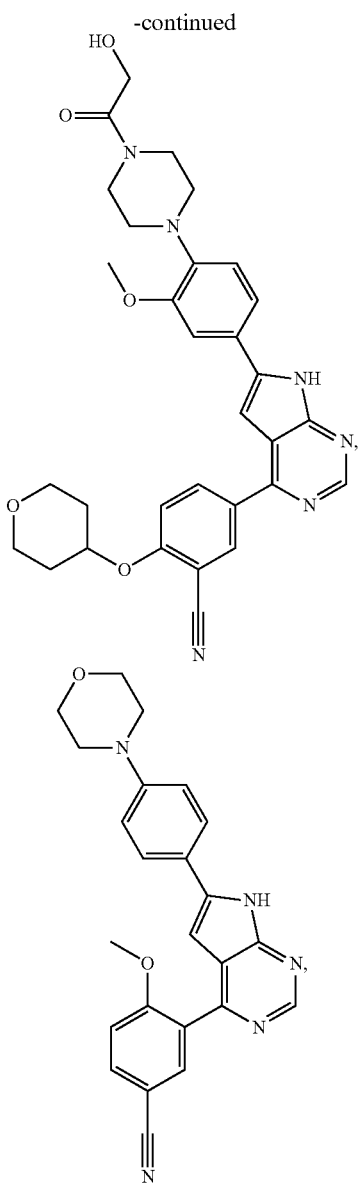
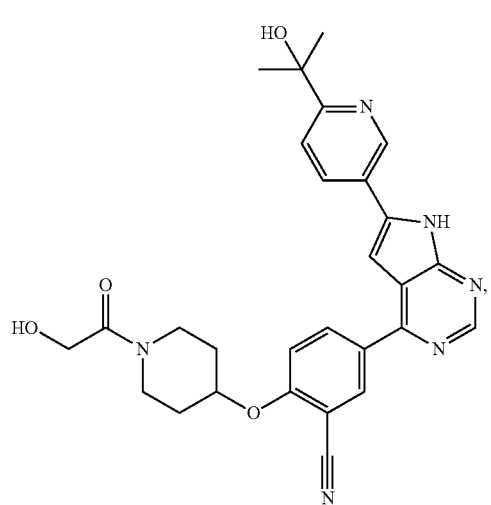
680
-continued
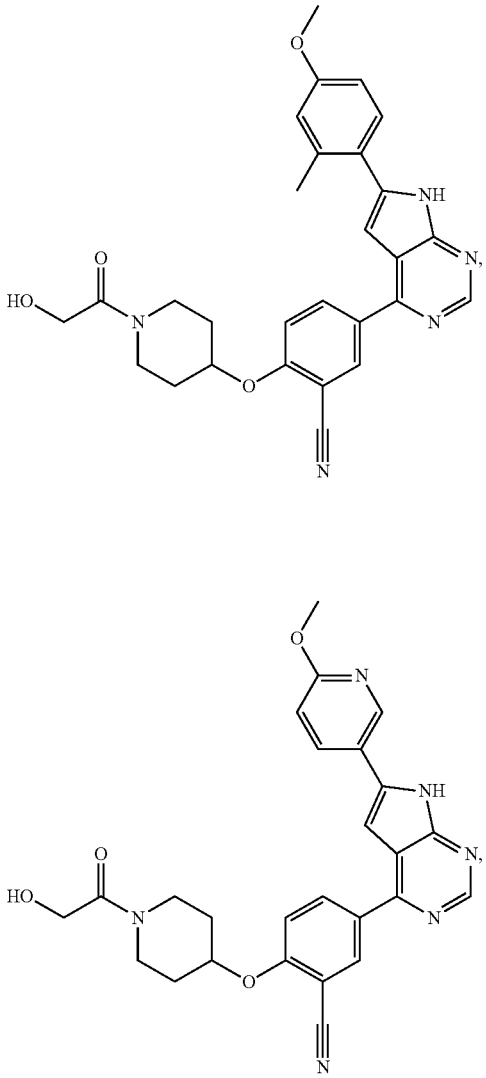
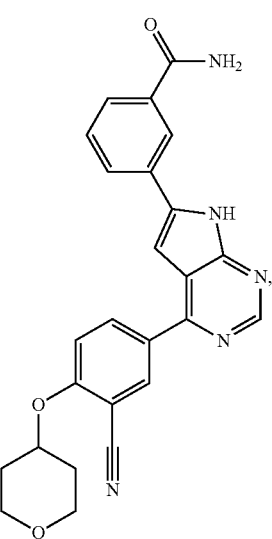

681
-continued
682
-continued
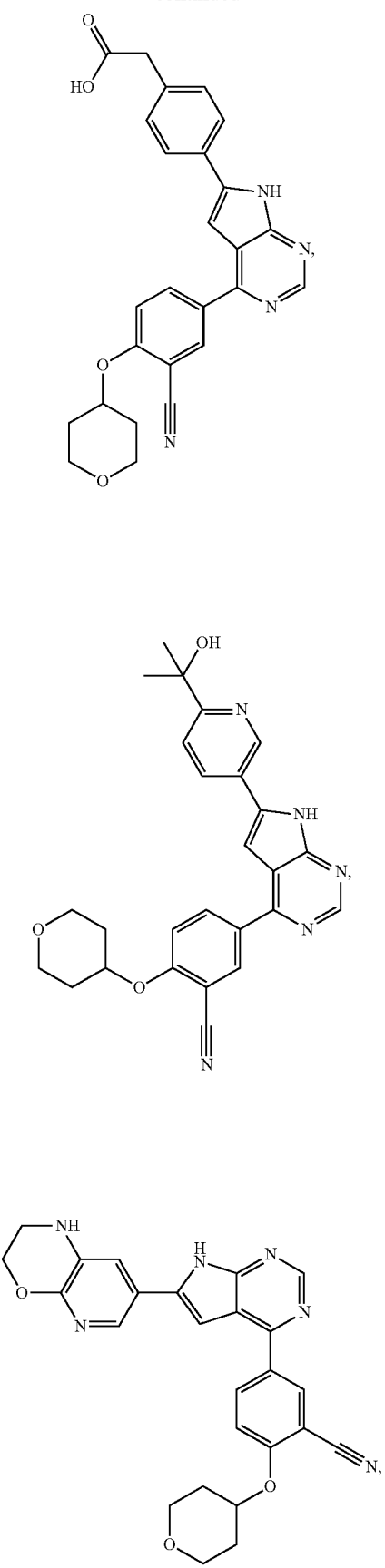
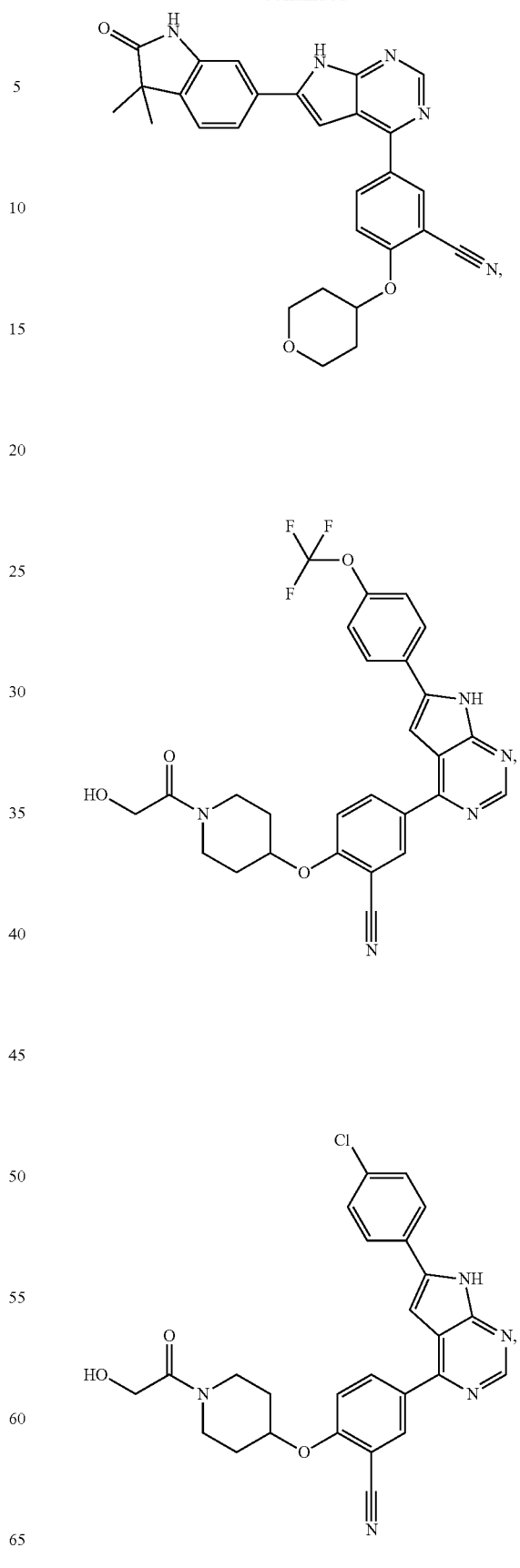

683
-continued
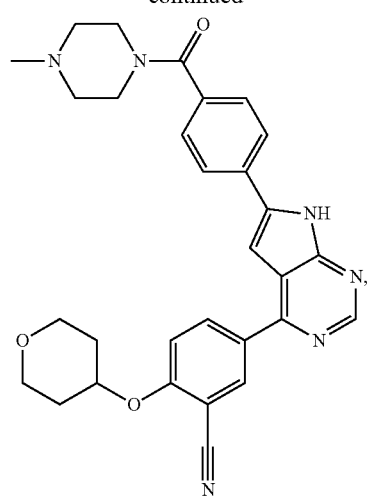
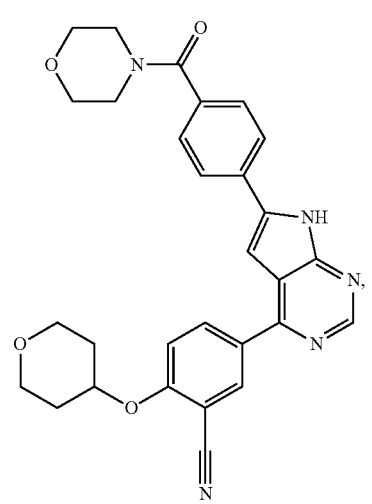
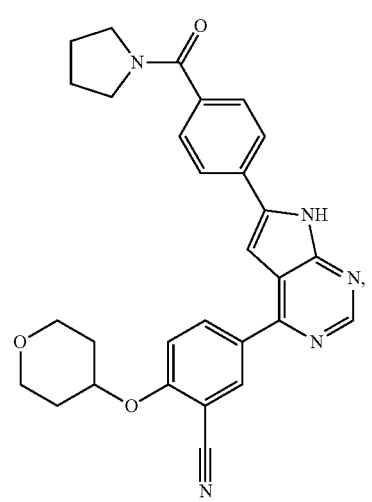
684
-continued
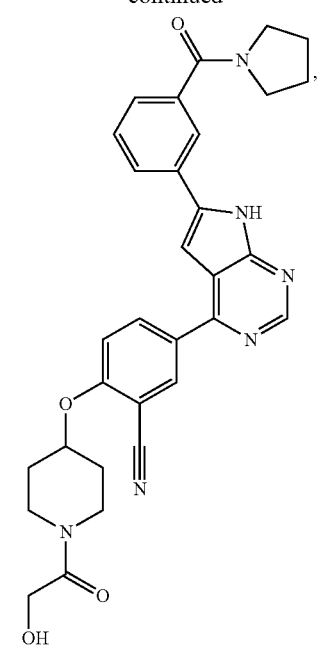
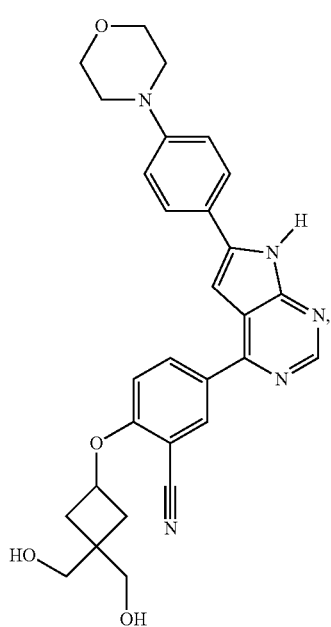

685
-continued
686
-continued
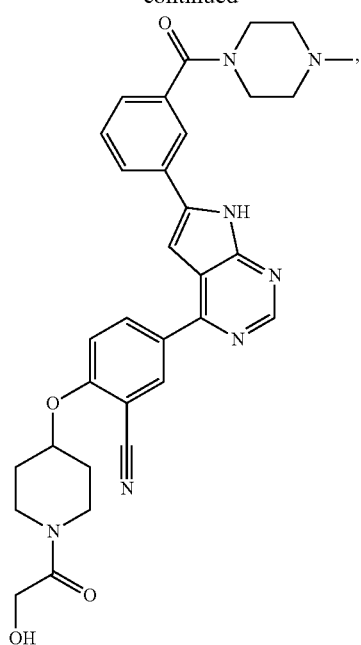
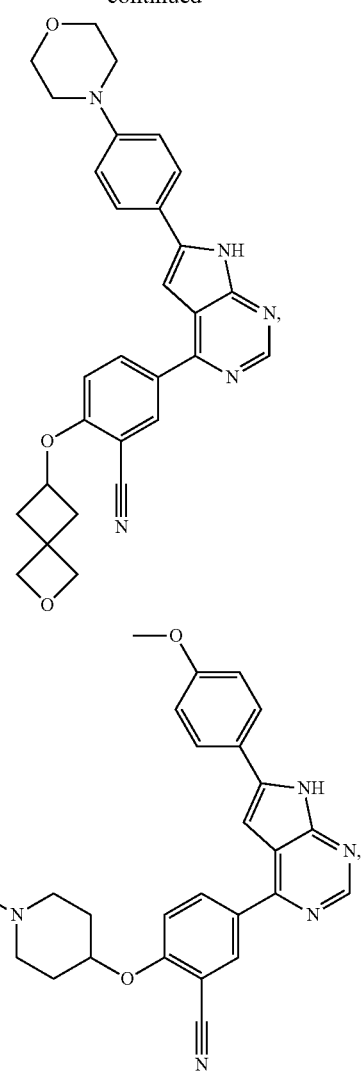
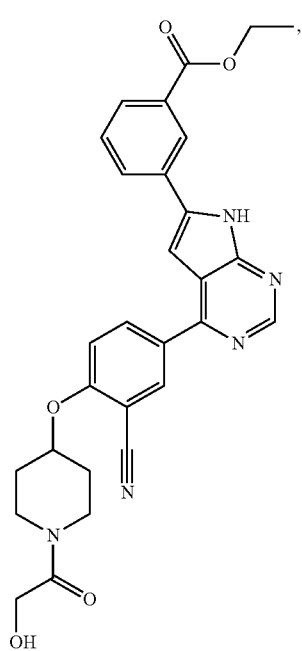

687
-continued
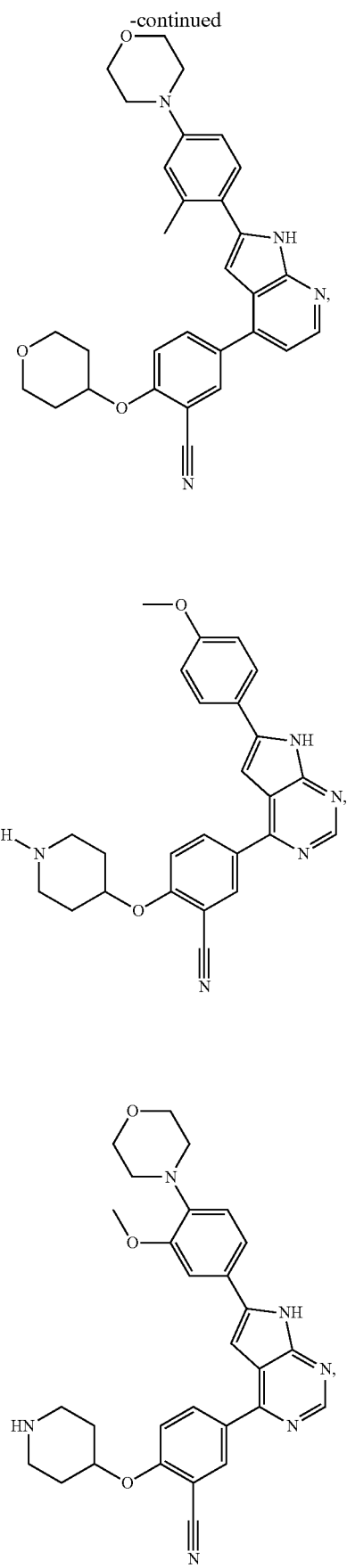
688
-continued
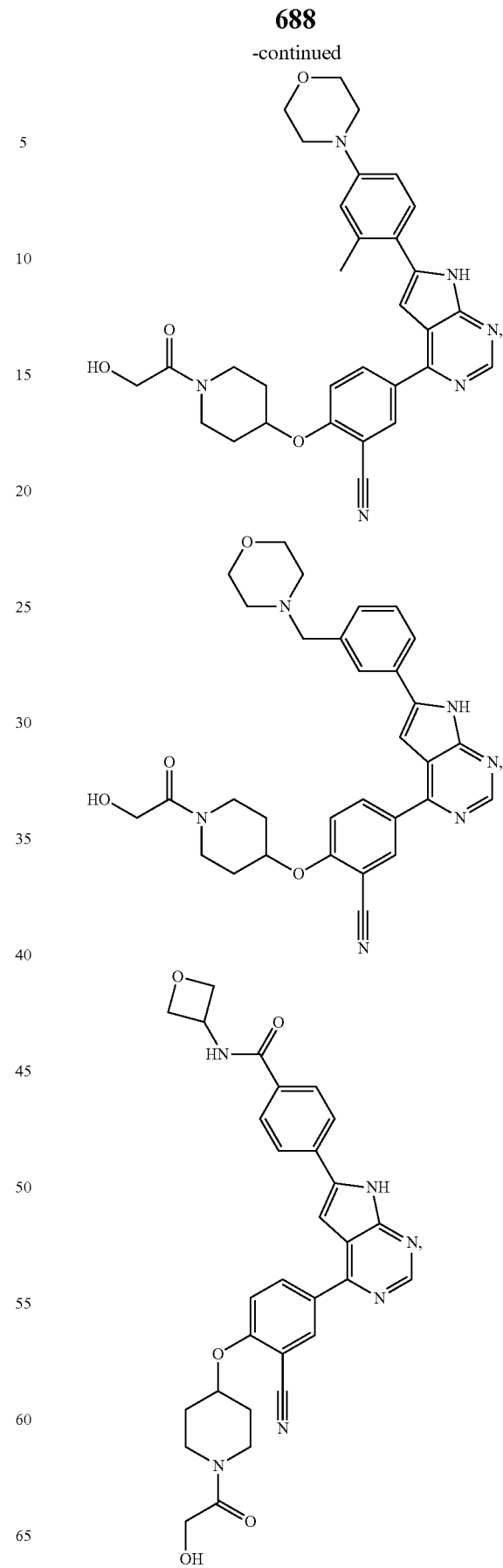

689
-continued
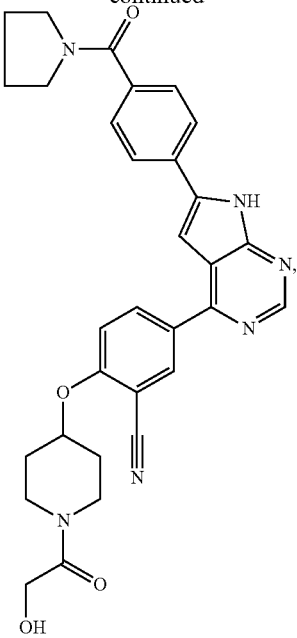
690
-continued
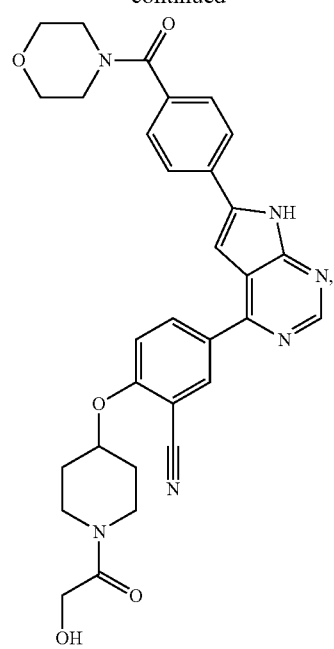
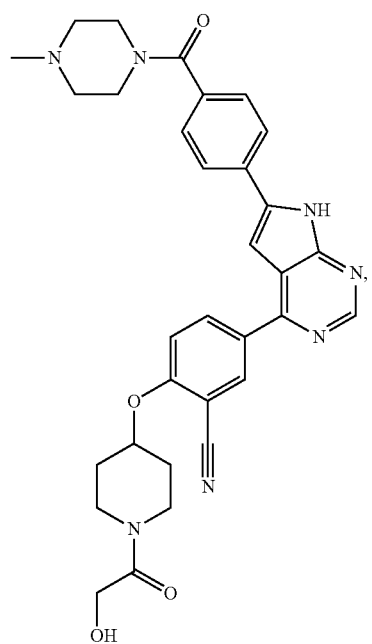
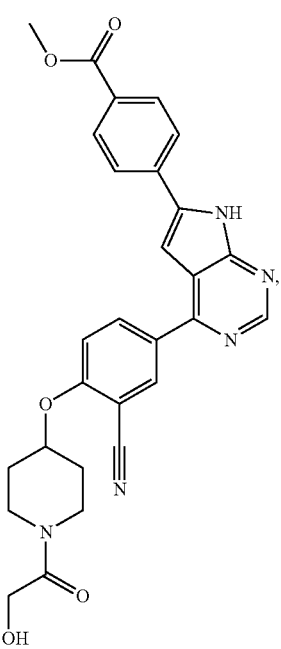

691
-continued
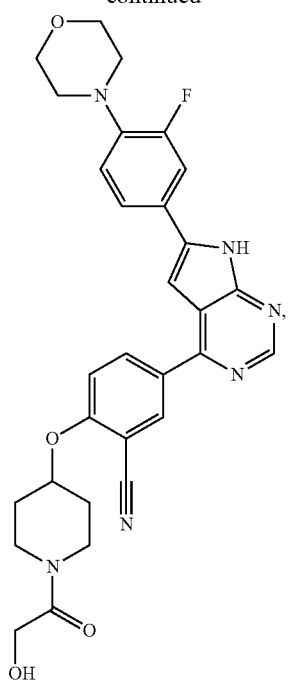
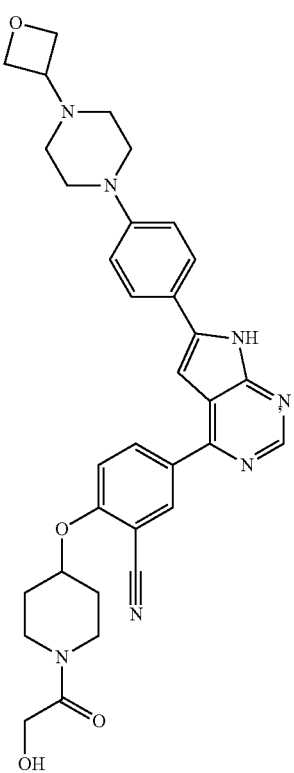
692
-continued
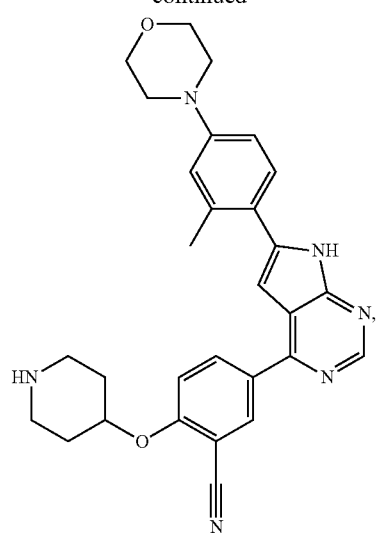
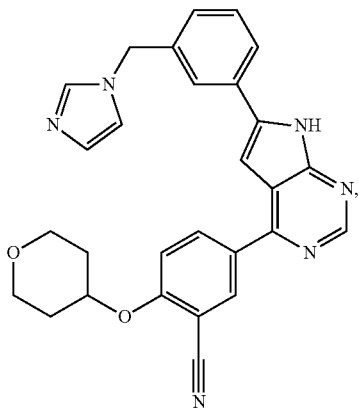
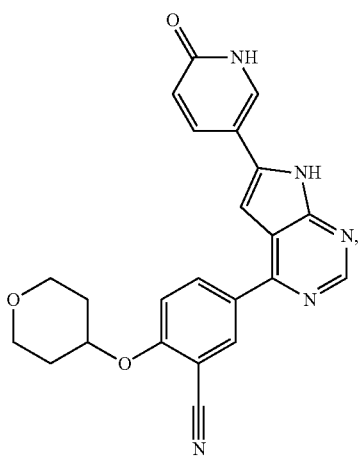

693
-continued
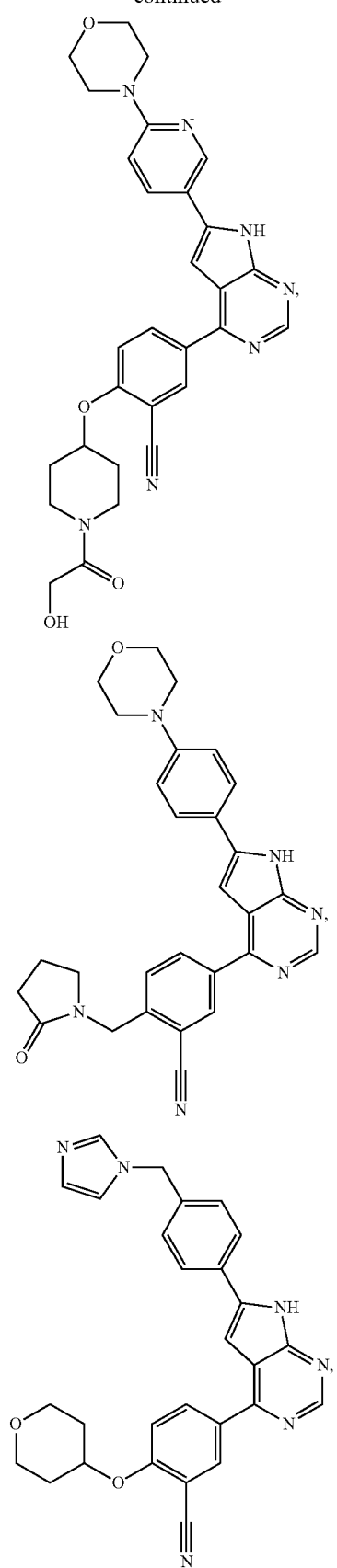
694
-continued
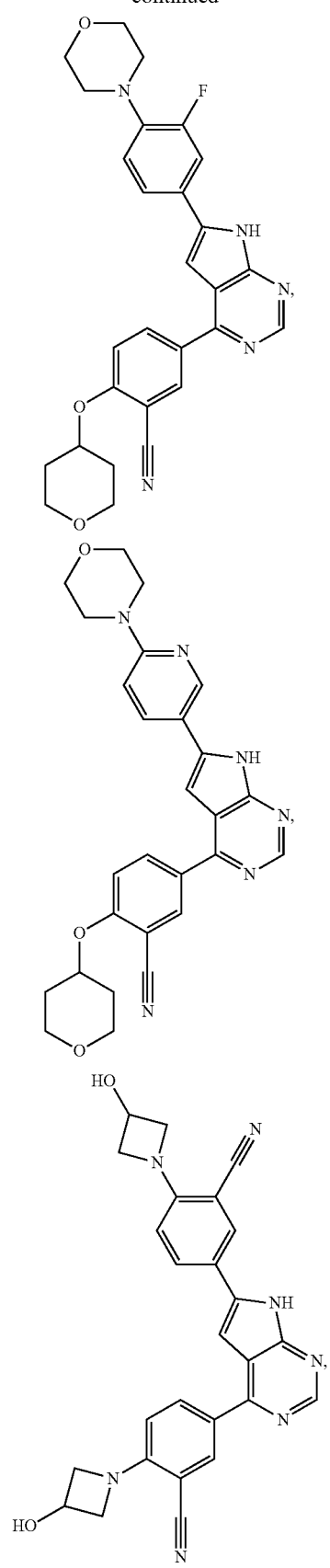

695
-continued
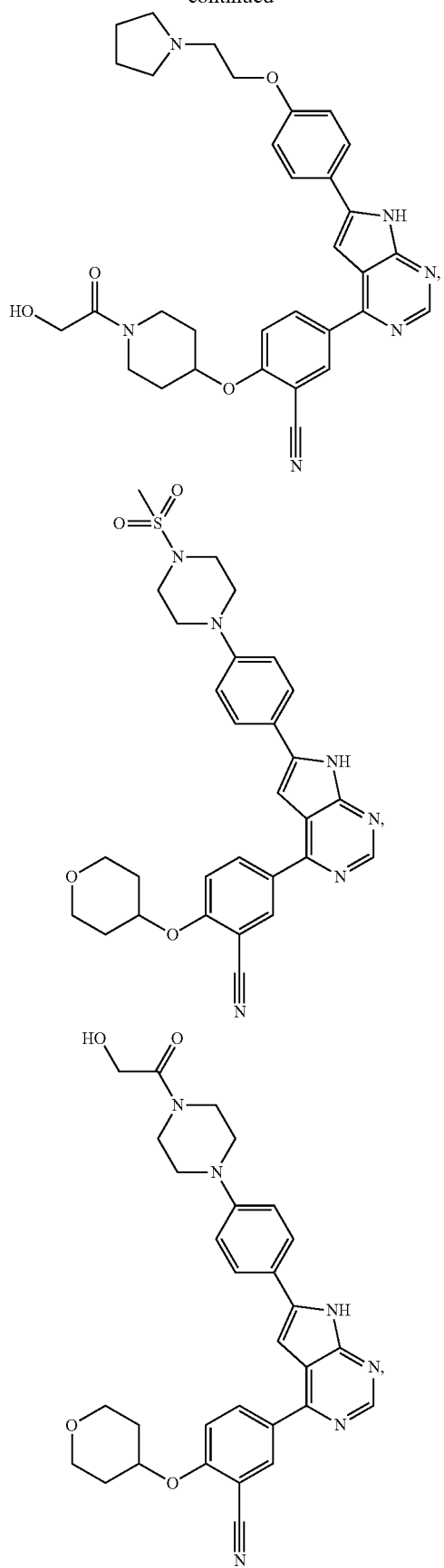
696
-continued
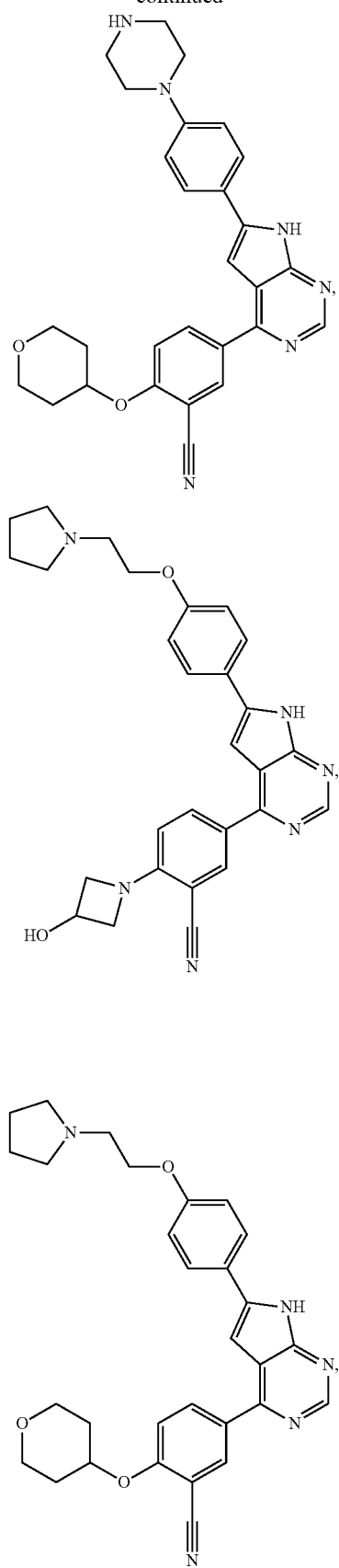

697
-continued
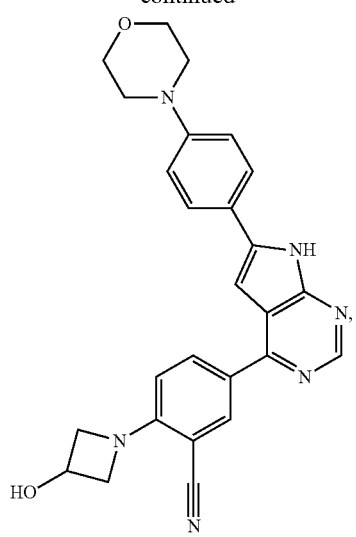
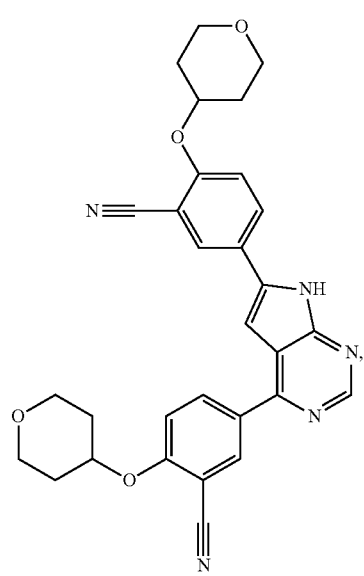
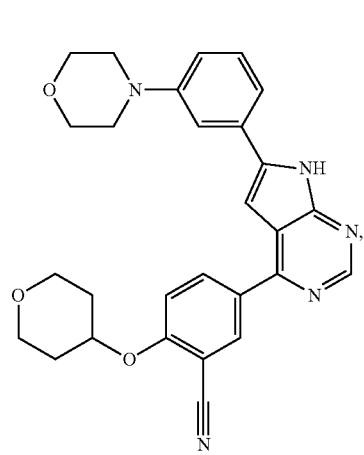
698
-continued
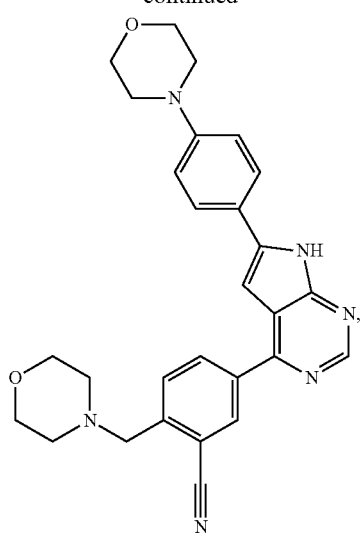
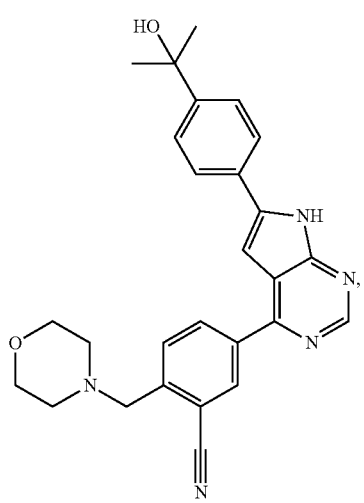
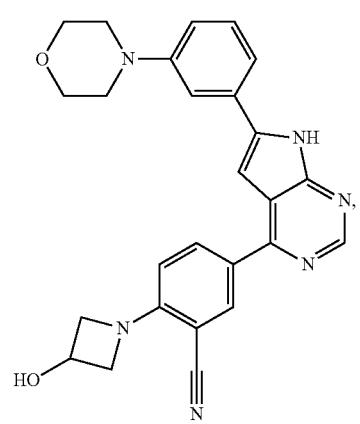

699
-continued
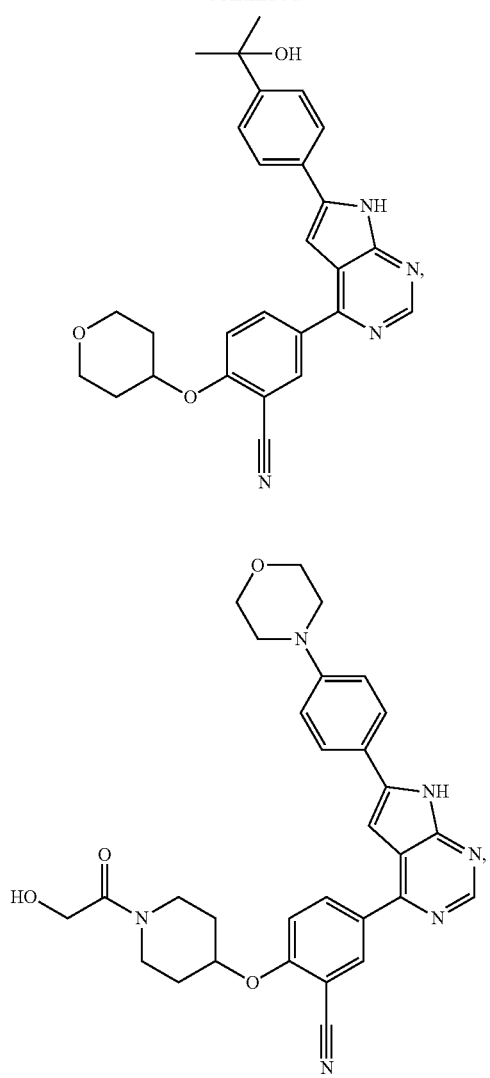
700
-continued
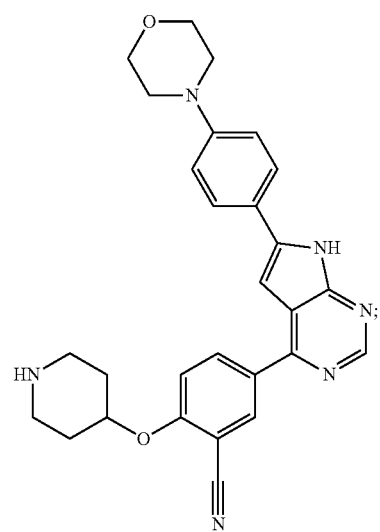
or a pharmaceutically acceptable salt thereof.
17. The compound of claim 1, selected from the group consisting of:
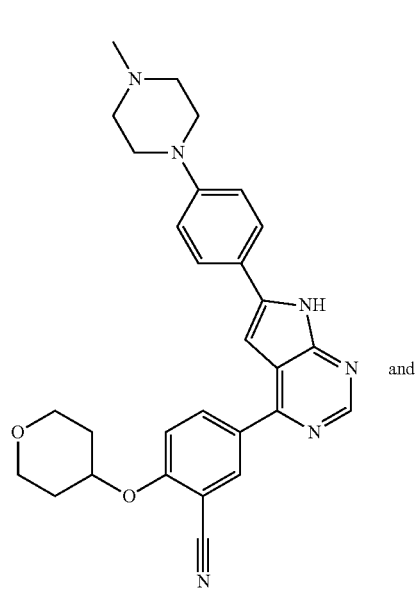
and
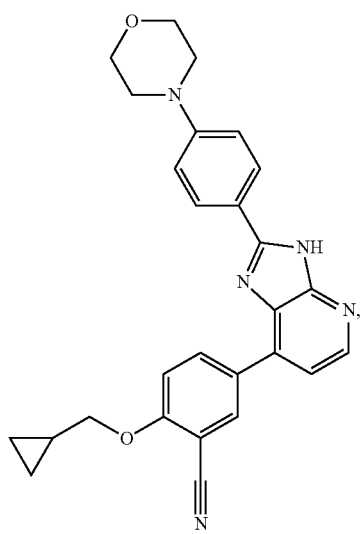

701
-continued
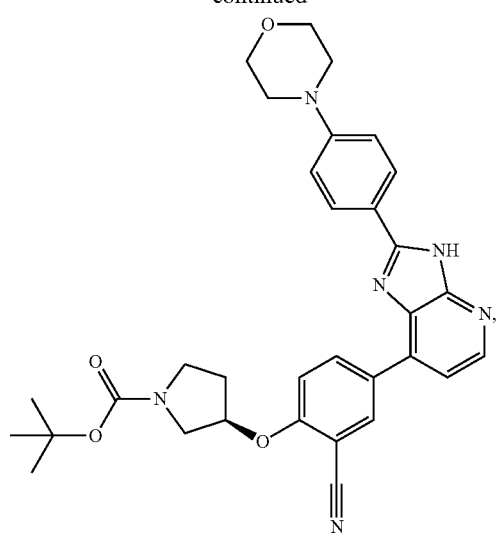
702
-continued
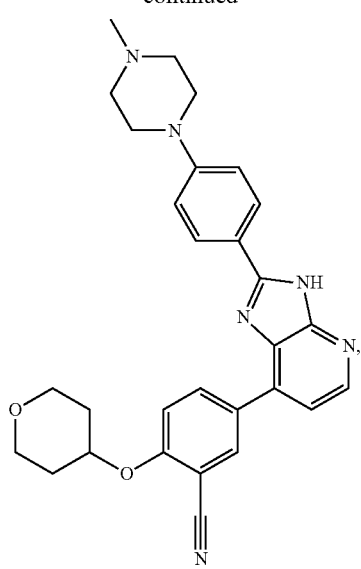
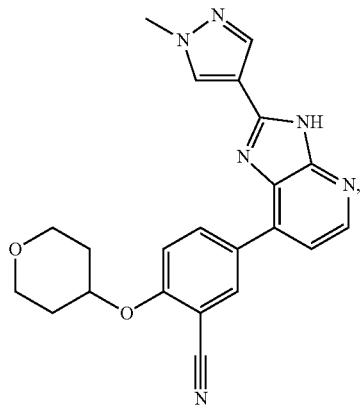
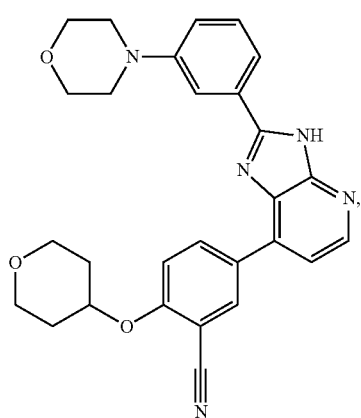

703
-continued
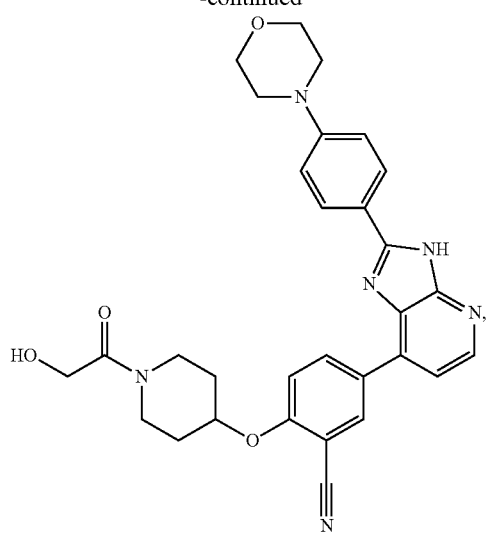
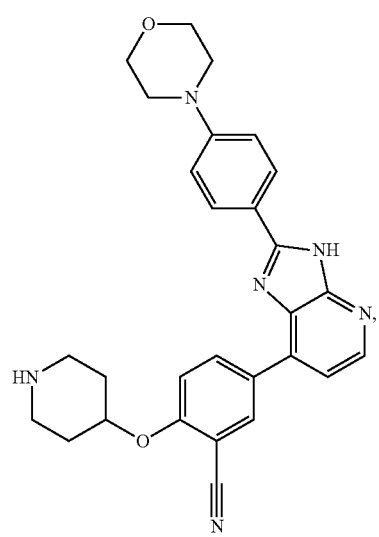
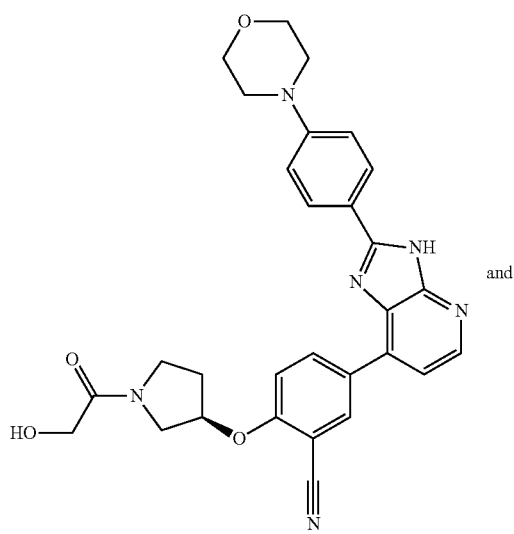
704
-continued
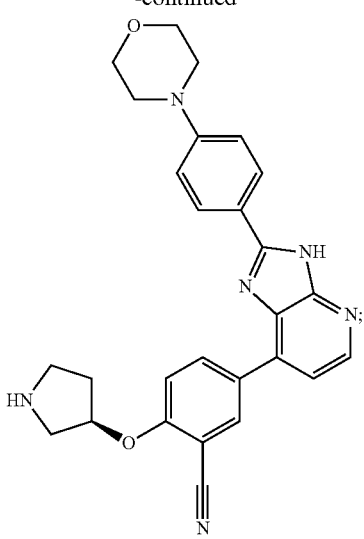
or a pharmaceutically acceptable salt thereof.
18. The compound of claim 1, selected from the group consisting of:
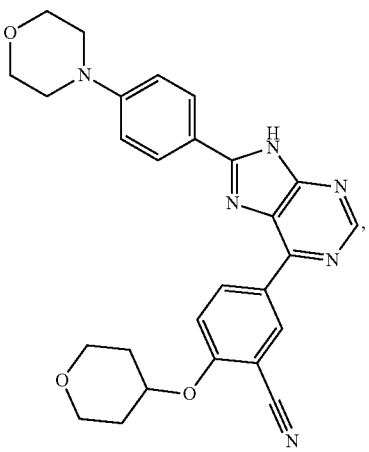
and
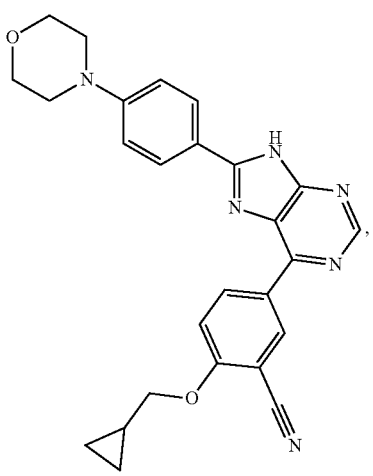

705
-continued
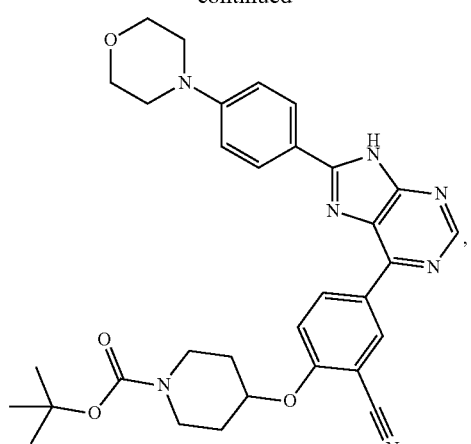
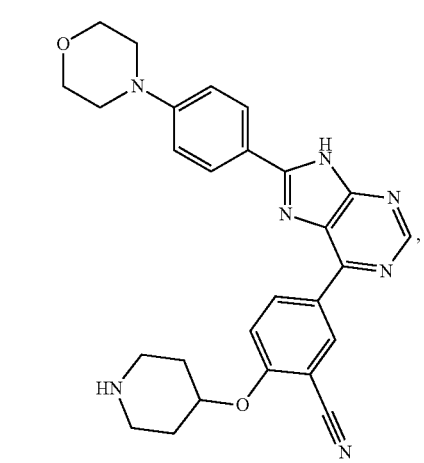
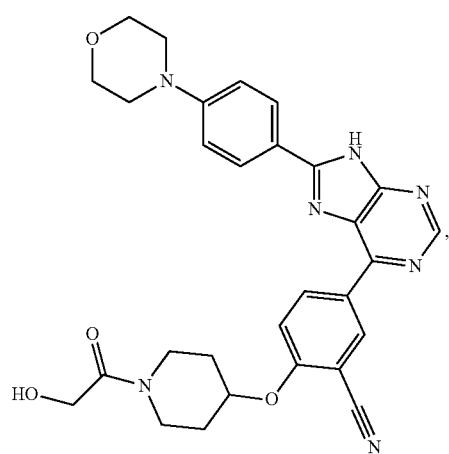
706
-continued
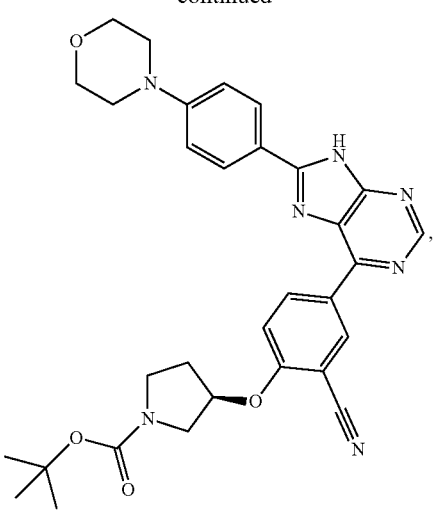
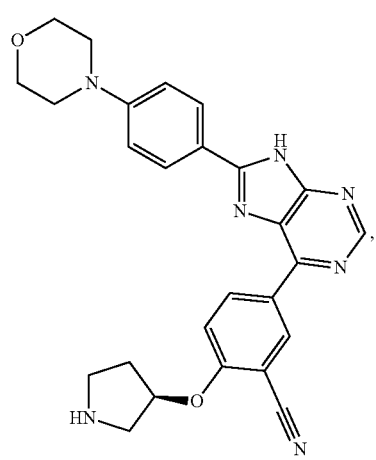
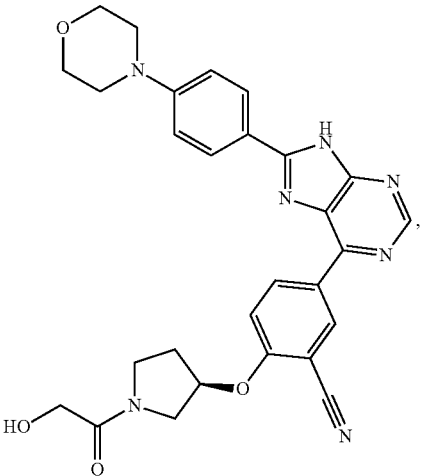

707
-continued
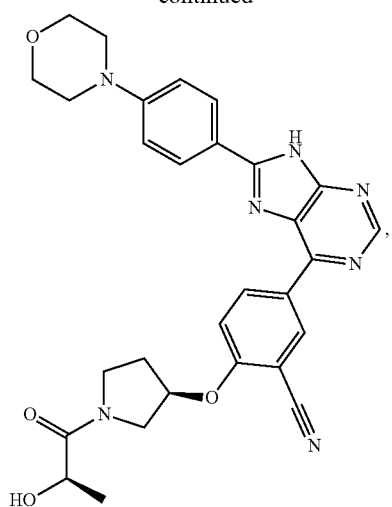
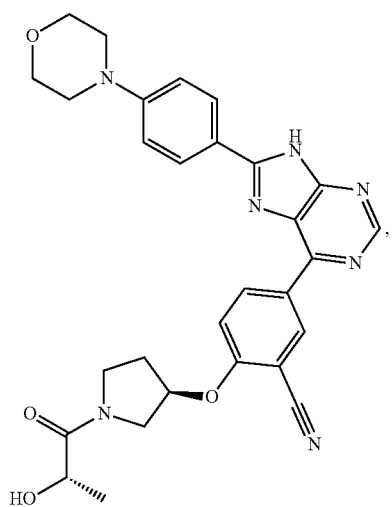
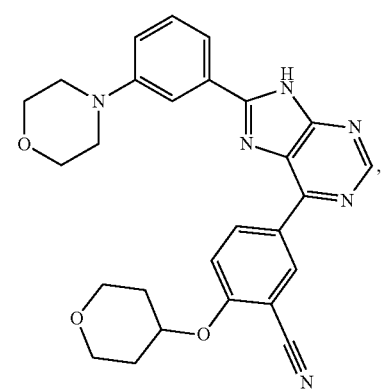
708
-continued
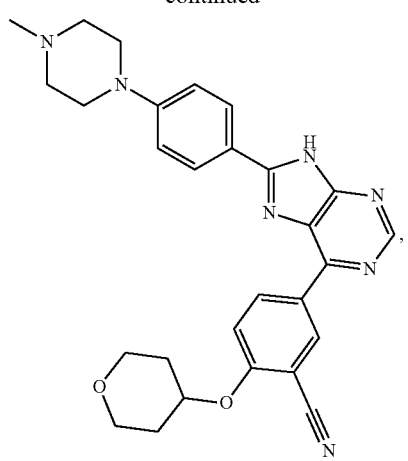
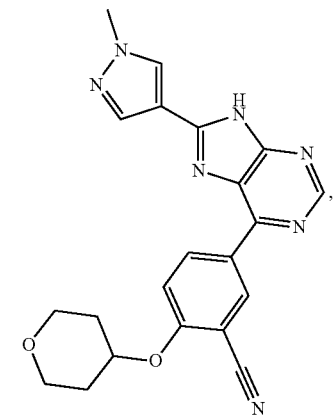
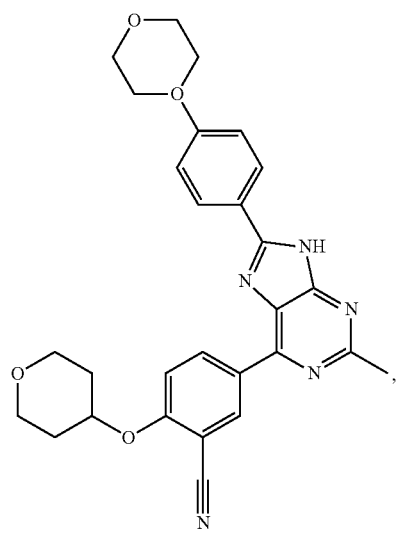

709
-continued
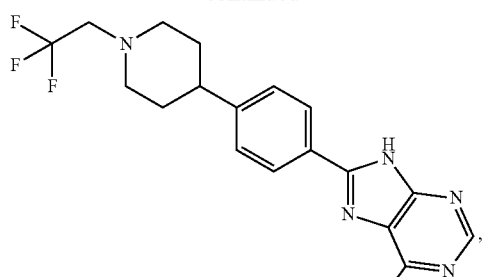
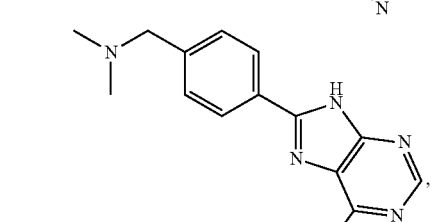
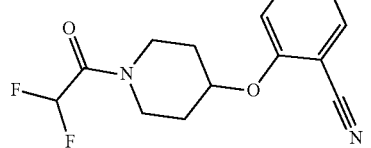
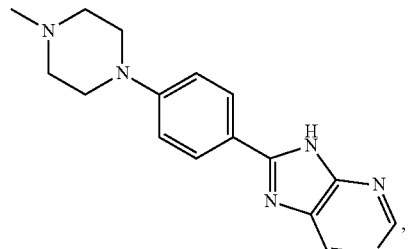
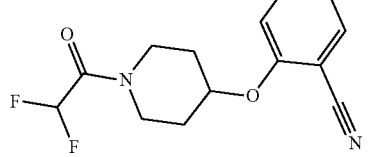
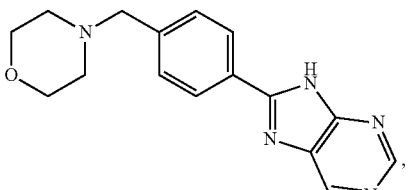
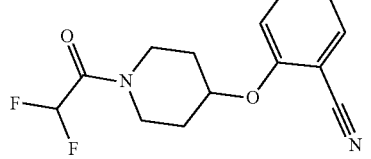
710
-continued
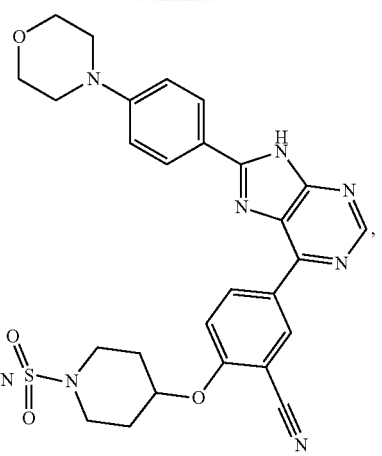
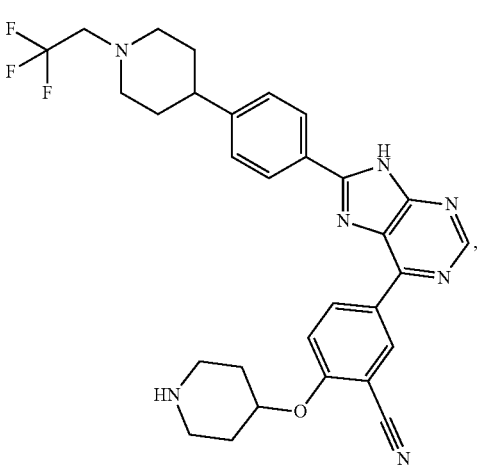
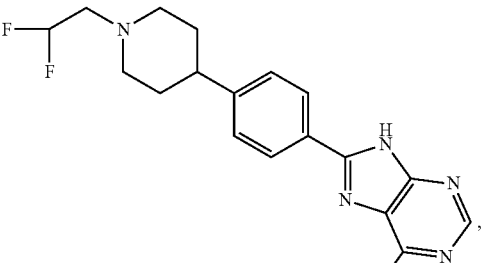
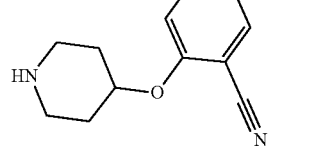

711
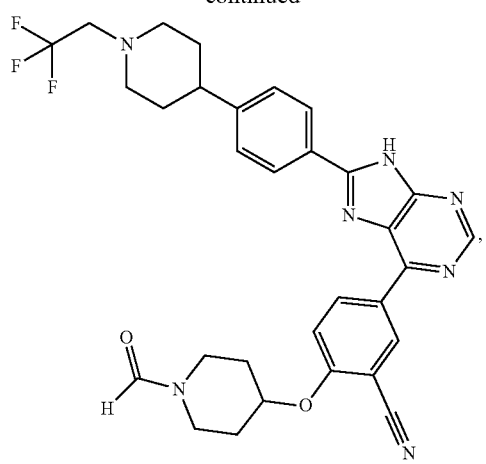
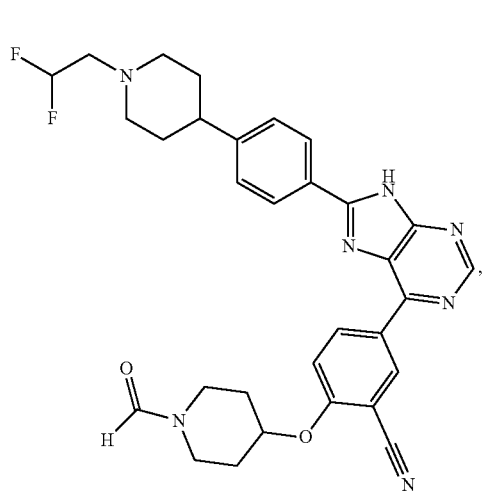
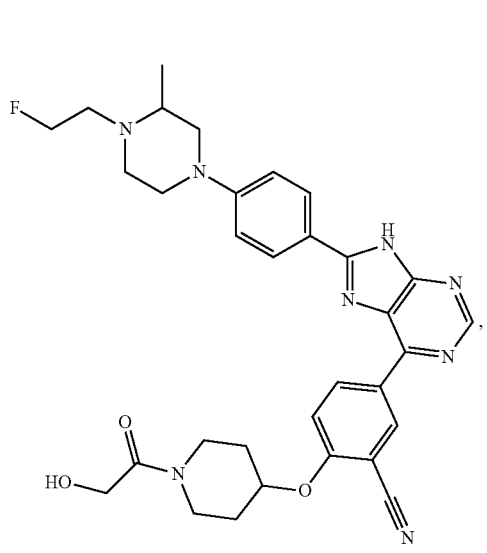
712
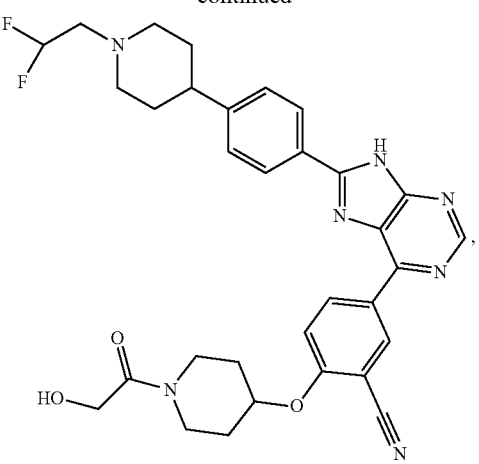
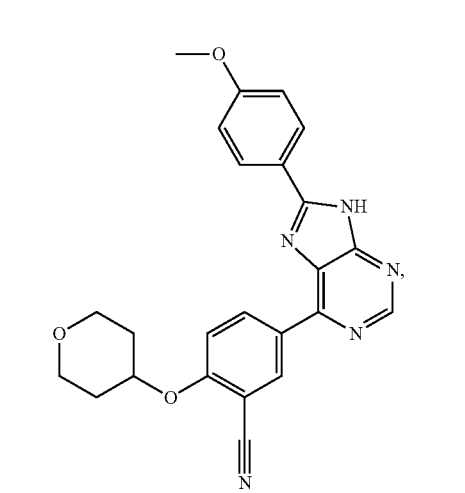
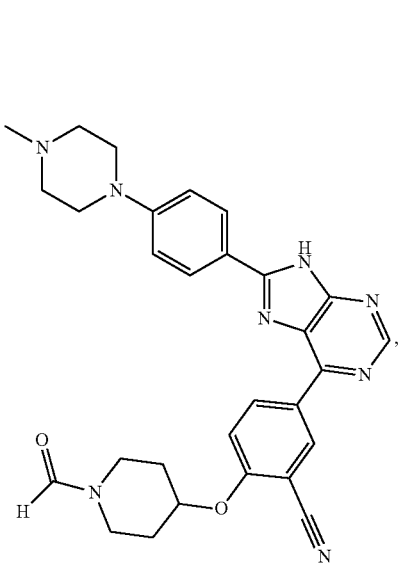

713
-continued
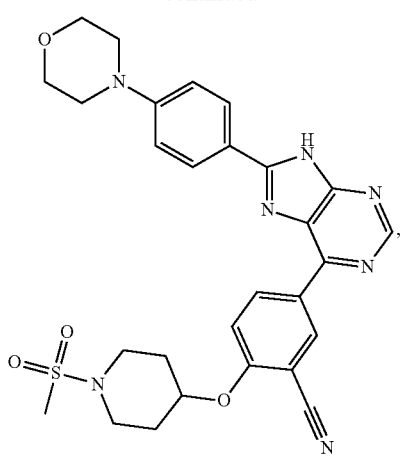
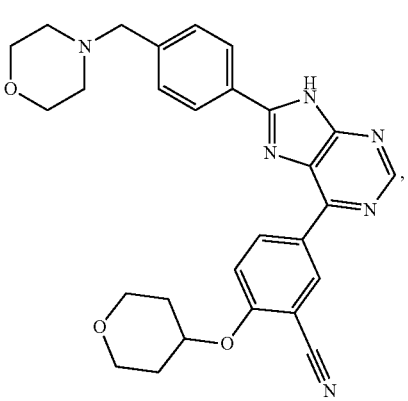
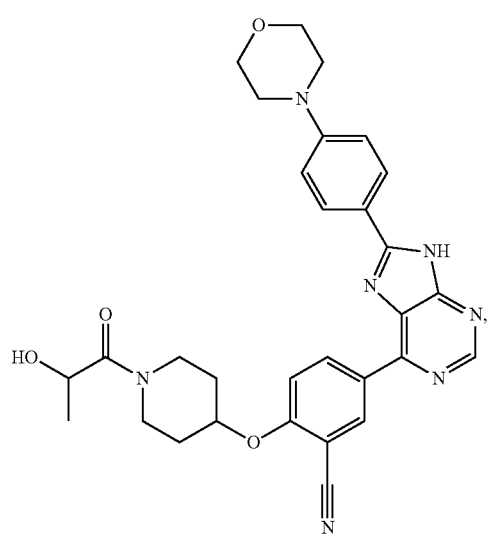
714
-continued
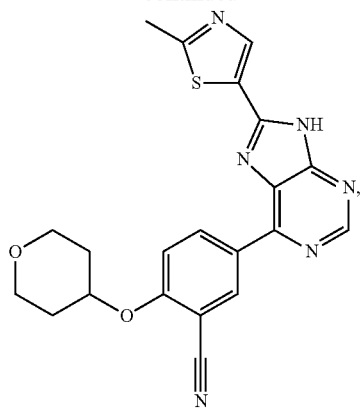
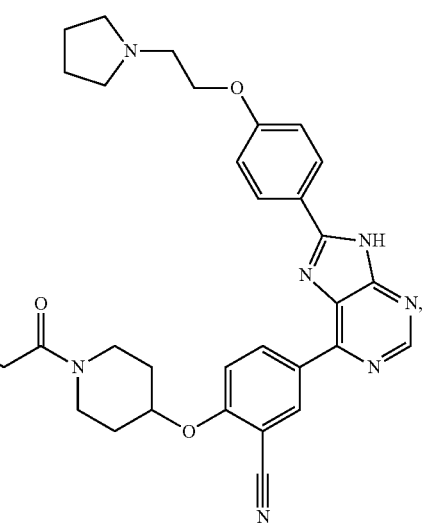
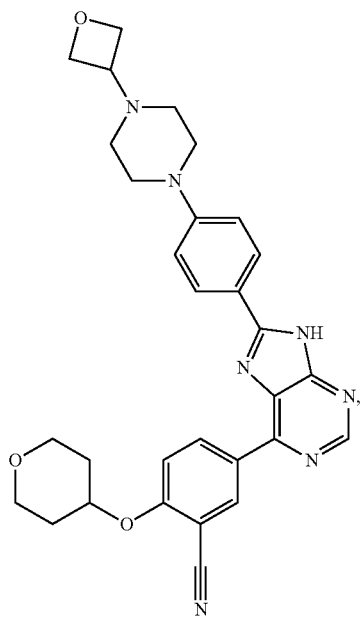

715
-continued
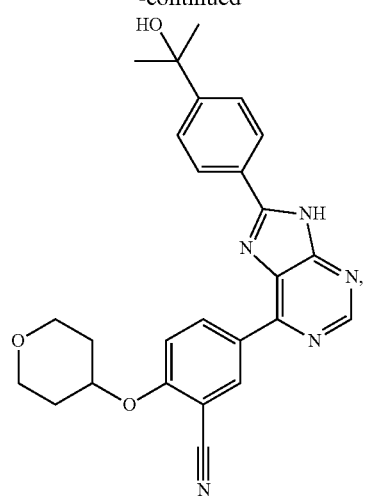
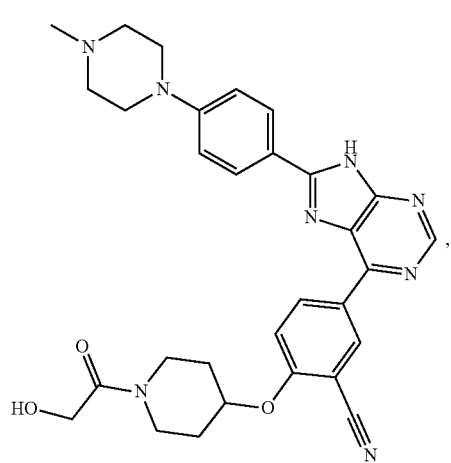
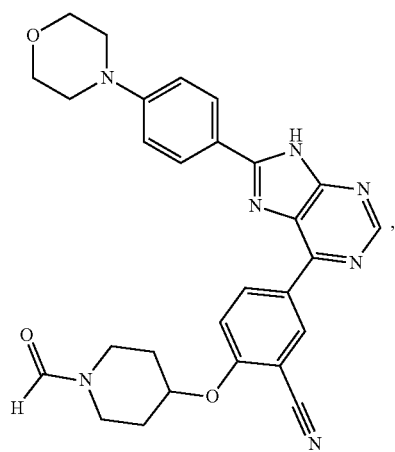
716
-continued
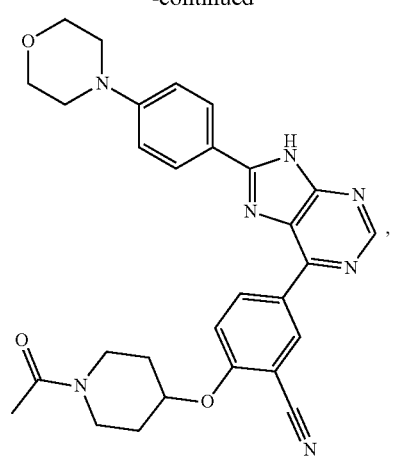
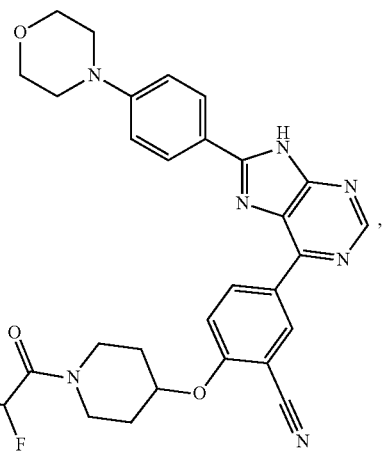
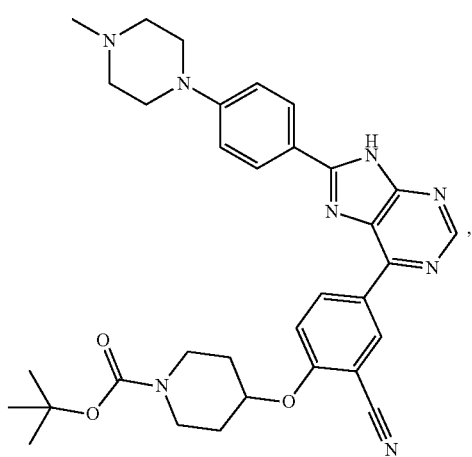

717
-continued
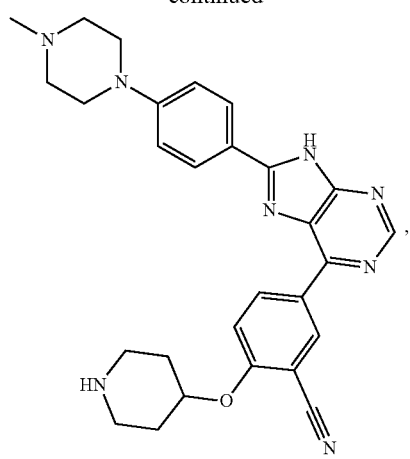
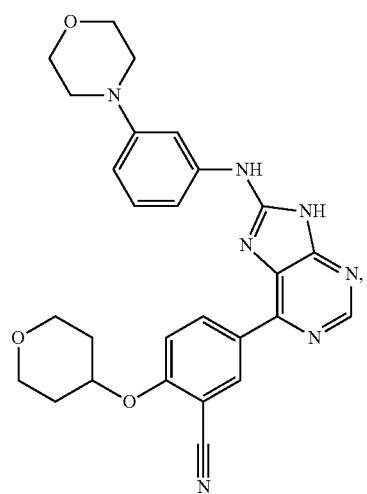
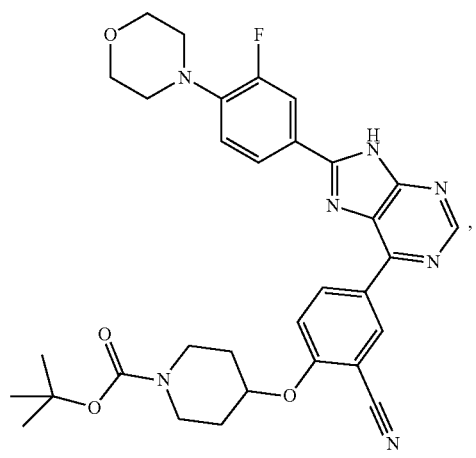
718
-continued
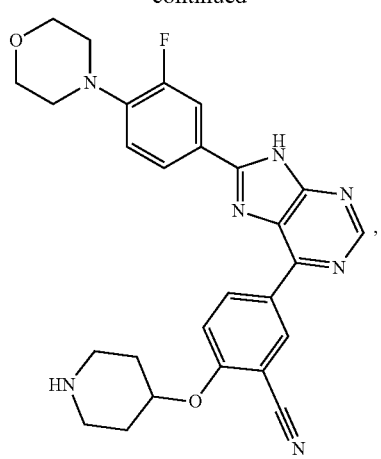
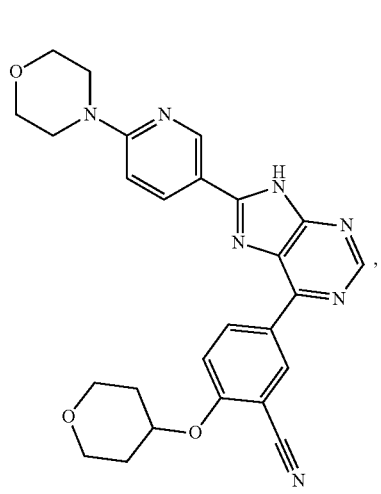
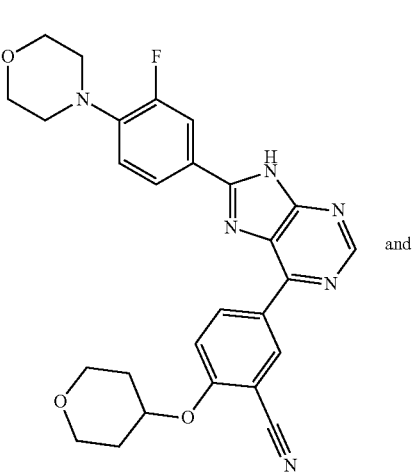
and 719
-continued

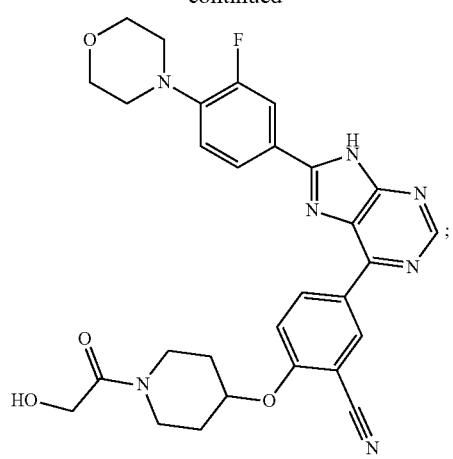

or a pharmaceutically acceptable salt thereof.

19. A pharmaceutical composition comprising the compound of claim 1, or a pharmaceutically acceptable salt thereof, and a pharmaceutically acceptable carrier.

20. A method of treating a subject having a disease or condition responsive to the inhibition of TANK binding kinase 1 (TBK1) or I-Kappa-B kinase (IKKε), comprising administering to the subject a therapeutically effective amount of the compound of claim 1, or a pharmaceutically acceptable salt thereof.

21. The compound of claim 1, selected from the group consisting of:

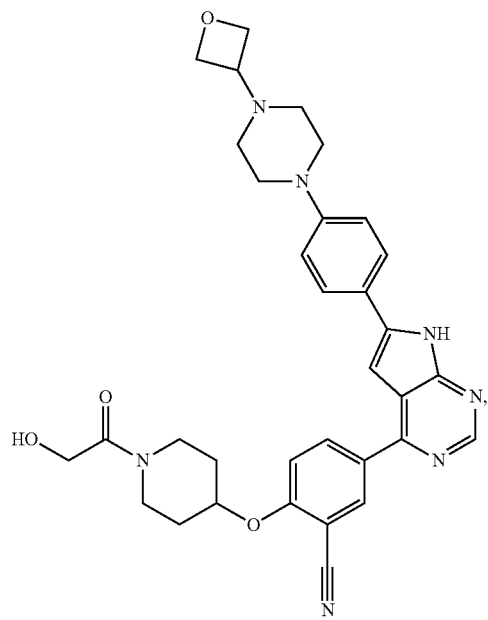

720
-continued

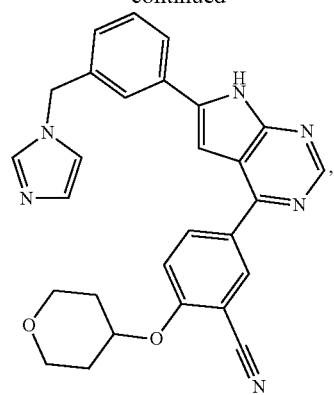

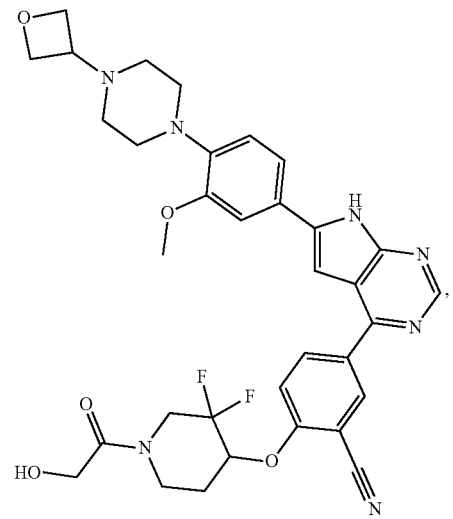

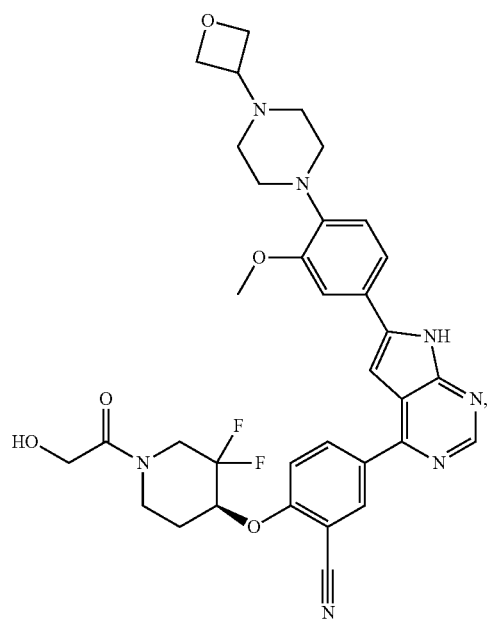

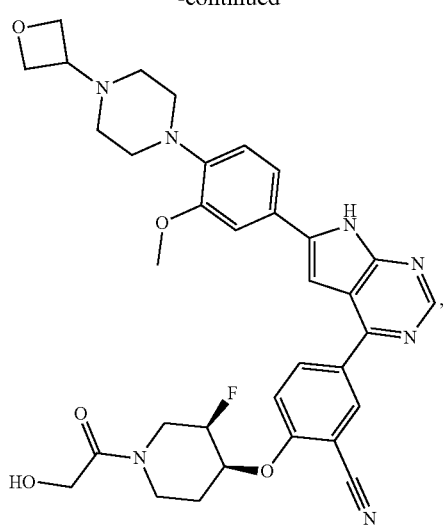
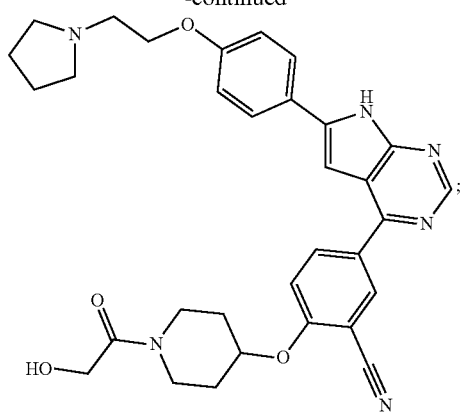
or a pharmaceutically acceptable salt thereof.
22. The compound of claim 21, selected from the group consisting of:
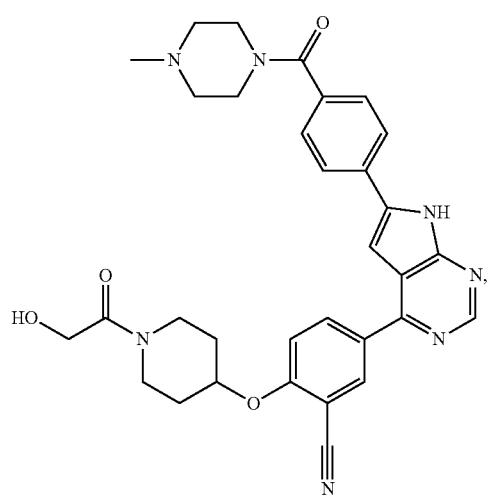
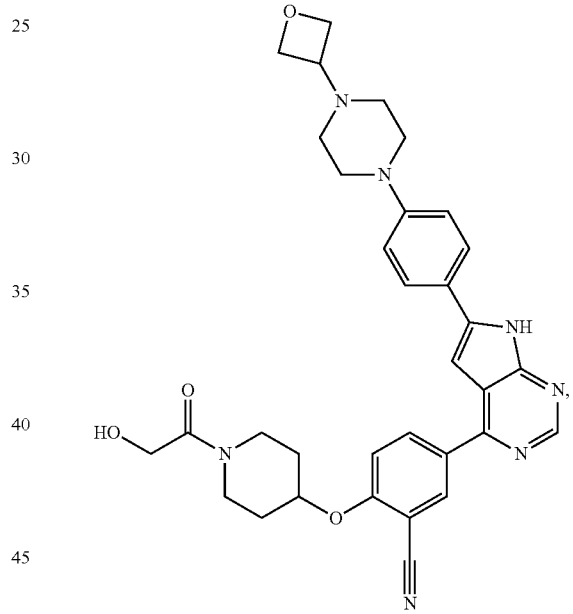
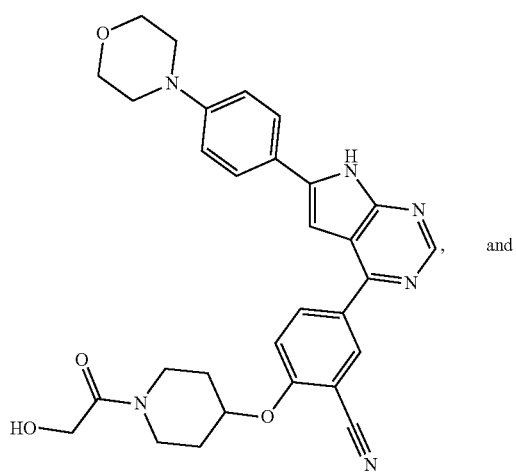
and
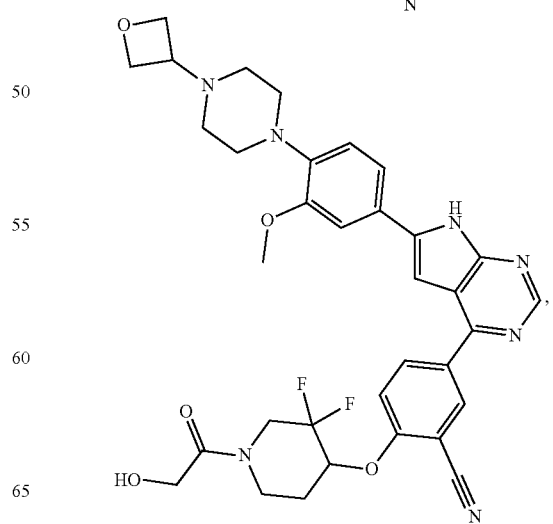

-continued
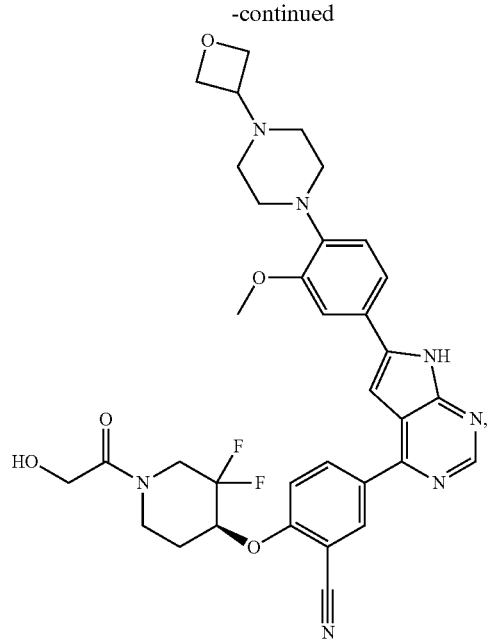
and
23. The compound of claim 22, wherein the compound is
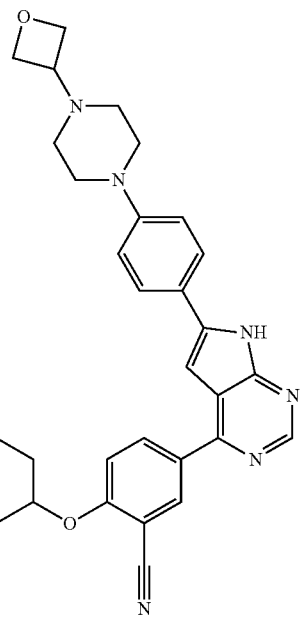
or a pharmaceutically acceptable salt thereof.
24. The compound of claim 22, wherein the compound is
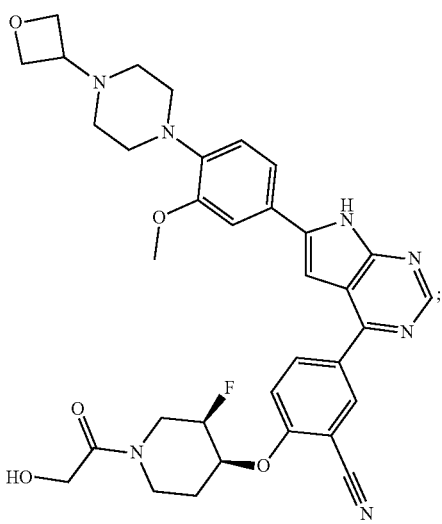 [SMILES: COc1cc(-c2cc3c(-c4ccc(O[C@H]5CCN(C(=O)CO)C[C@H]5F)c(C#N)c4)ncnc3[nH]2)ccc1N1CCN(C2COC2)CC1]
or a pharmaceutically acceptable salt thereof.
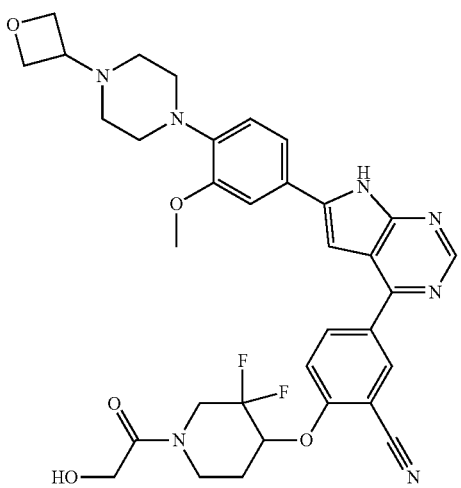 [SMILES: COc1cc(-c2cc3c(-c4ccc(OC5CCN(C(=O)CO)CC5(F)F)c(C#N)c4)ncnc3[nH]2)ccc1N1CCN(C2COC2)CC1]
or a pharmaceutically acceptable salt thereof.

25. The compound of claim 22, wherein the compound is
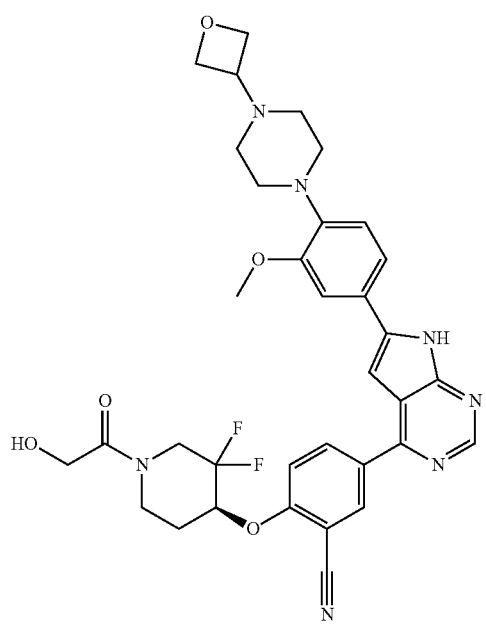 [SMILES: COc1cc(-c2cc3c(-c4ccc(O[C@H]5CCN(C(=O)CO)CC5(F)F)c(C#N)c4)ncnc3[nH]2)ccc1N1CCN(C2COC2)CC1]
or a pharmaceutically acceptable salt thereof.
26. The compound of claim 22, wherein the compound is
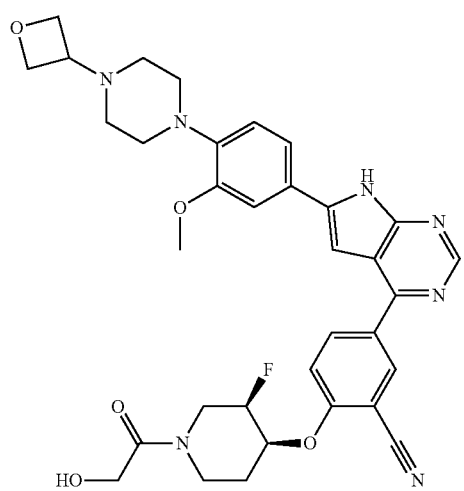 [SMILES: COc1cc(-c2cc3c(-c4ccc(O[C@H]5CCN(C(=O)CO)C[C@H]5F)c(C#N)c4)ncnc3[nH]2)ccc1N1CCN(C2COC2)CC1]
or a pharmaceutically acceptable salt thereof.
27. The compound of claim 1, selected from the group consisting of:
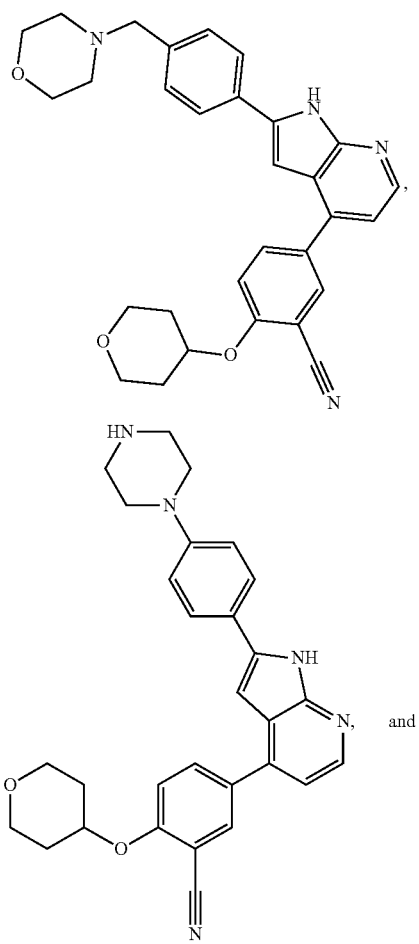
and
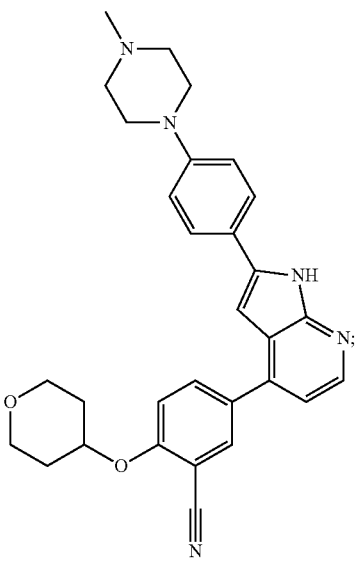
or a pharmaceutically acceptable salt thereof.

28. The compound of claim 27, wherein the compound is
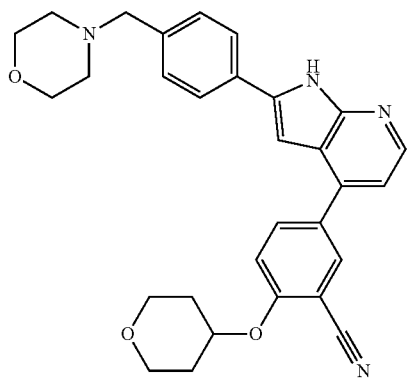 [SMILES: N#Cc1cc(-c2ccnc3[nH]c(-c4ccc(CN5CCOCC5)cc4)cc23)ccc1OC1CCOCC1]
or a pharmaceutically acceptable salt thereof.
29. The compound of claim 27, wherein the compound is
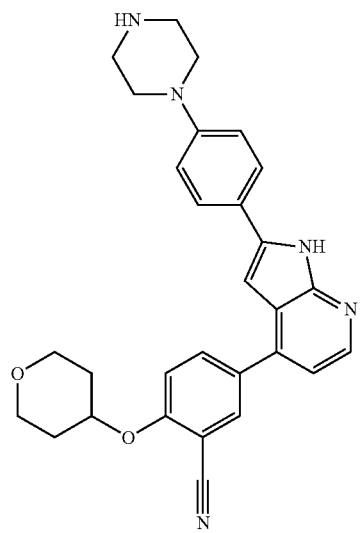
or a pharmaceutically acceptable salt thereof.
30. The compound of claim 27, wherein the compound is
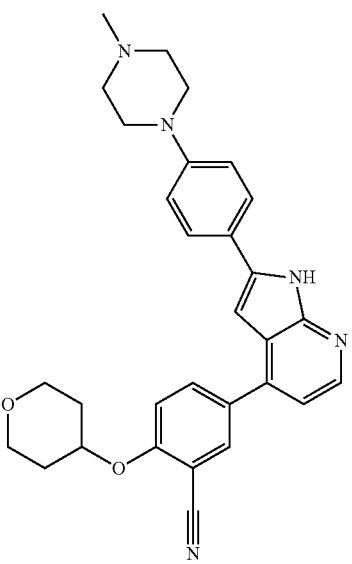 [SMILES: CN1CCN(c2ccc(-c3cc4c(-c5ccc(OC6CCOCC6)c(C#N)c5)ccnc4[nH]3)cc2)CC1]
or a pharmaceutically acceptable salt thereof.
* * * * *